(12) United States Patent
Bursavich et al.

(10) Patent No.: US 11,370,773 B1
(45) Date of Patent: *Jun. 28, 2022

(54) INHIBITING HUMAN INTEGRIN (ALPHA-4) (BETA-7)

(71) Applicant: Morphic Therapeutic, Inc., Waltham, MA (US)

(72) Inventors: Matthew G. Bursavich, Needham, MA (US); Dan Cui, Cambridge, MA (US); James E. Dowling, Lexington, MA (US); Kristopher N. Hahn, Medford, MA (US); Bryce A. Harrison, Framingham, MA (US); Fu-Yang Lin, Sudbury, MA (US); Blaise S. Lippa, Newton, MA (US); Bruce N. Rogers, Belmont, MA (US); Dawn M. Troast, Bedford, MA (US); Cheng Zhong, Belmont, MA (US); Kyle D. Konze, Brooklyn, NY (US); Aleksey I. Gerasyuto, Flemington, NJ (US); Byungchan Kim, West New York, NJ (US); Salma Rafi, Lexington, MA (US); Tyler Day, New York, NY (US); Eugene Hickey, Danbury, CT (US); Evelyne Houang, Queens, NY (US); Robert Zahler, Pennington, NJ (US)

(73) Assignee: Morphic Therapeutic, Inc., Waltham, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/378,282

(22) Filed: Jul. 16, 2021

Related U.S. Application Data

(63) Continuation of application No. PCT/US2020/055986, filed on Oct. 16, 2020.

(60) Provisional application No. 62/916,062, filed on Oct. 16, 2019.

(51) Int. Cl.
*C07D 401/06* (2006.01)
*C07D 213/64* (2006.01)

(52) U.S. Cl.
CPC ......... *C07D 401/06* (2013.01); *C07D 213/64* (2013.01)

(58) Field of Classification Search
CPC .............................. C07D 401/06; C07D 213/64
See application file for complete search history.

(56) References Cited

U.S. PATENT DOCUMENTS

| | | | |
|---|---|---|---|
| 5,721,366 A | 2/1998 | Abood et al. | |
| 5,981,492 A | 11/1999 | Zoller et al. | |
| 6,294,562 B1 | 9/2001 | Stilz et al. | |
| 6,331,552 B1 | 12/2001 | Wehner et al. | |
| 6,645,939 B1 | 11/2003 | Durette et al. | |
| 6,667,334 B1 | 12/2003 | Neises et al. | |
| 6,723,711 B2 | 4/2004 | Biediger et al. | |
| 6,953,798 B1 | 10/2005 | Porter et al. | |
| 6,972,296 B2 | 12/2005 | Biediger et al. | |
| 7,807,167 B2 | 10/2010 | Taylor et al. | |
| 7,972,775 B2 | 7/2011 | Rubin et al. | |
| 9,493,567 B2 | 11/2016 | Lieberburg | |
| 9,873,742 B2 | 1/2018 | Keir et al. | |
| 10,233,245 B2 | 3/2019 | Lieberburg | |
| 10,246,451 B2 | 4/2019 | Biediger et al. | |
| 10,273,542 B2 | 4/2019 | Hackney et al. | |
| 10,494,367 B2 | 12/2019 | Biediger et al. | |
| 10,759,756 B2 | 9/2020 | Bursavich et al. | |
| 11,104,661 B1 | 8/2021 | Bursavich et al. | |
| 11,174,228 B2 | 11/2021 | Bursavich et al. | |
| 2002/0183374 A1 | 12/2002 | Wehner et al. | |
| 2003/0199692 A1 | 10/2003 | Biediger et al. | |
| 2004/0009169 A1 | 1/2004 | Taylor et al. | |
| 2004/0010023 A1 | 1/2004 | Stahle et al. | |
| 2007/0025989 A1 | 2/2007 | Taylor et al. | |
| 2011/0064729 A1 | 3/2011 | Taylor et al. | |
| 2014/0120084 A1 | 5/2014 | Anand et al. | |
| 2015/0152182 A1 | 6/2015 | Taylor et al. | |
| 2017/0306026 A1 | 10/2017 | Taylor et al. | |
| 2018/0086833 A1 | 3/2018 | Hassanali et al. | |
| 2019/0315692 A1 | 10/2019 | Bursavich et al. | |
| 2020/0148773 A1 | 5/2020 | Taylor et al. | |
| 2020/0385352 A1 | 12/2020 | Bursavich et al. | |

FOREIGN PATENT DOCUMENTS

| | | | |
|---|---|---|---|
| EP | | 1213288 A1 | 6/2002 |
| WO | WO-1996/038426 A1 | | 12/1996 |
| WO | WO-98/16524 A1 | | 4/1998 |
| WO | WO-98/16547 A1 | | 4/1998 |
| WO | WO-99/36393 A1 | | 7/1999 |
| WO | WO-2000/000481 A1 | | 1/2000 |
| WO | WO-2000/068188 A1 | | 11/2000 |
| WO | WO-01/21584 A1 | | 3/2001 |
| WO | WO-2002/16328 A1 | | 2/2002 |
| WO | WO-2003/040173 A1 | | 5/2003 |
| WO | WO-03/072040 A2 | | 9/2003 |
| WO | WO-2006/026759 A2 | | 3/2006 |
| WO | WO-2006/126529 A1 | | 11/2006 |
| WO | WO-2006/126637 A1 | | 11/2006 |
| WO | WO-2006/131200 A1 | | 12/2006 |
| WO | WO-2010/091411 A1 | | 8/2010 |
| WO | WO-201 2/135589 A1 | | 10/2012 |
| WO | WO-2016/011940 A1 | | 1/2016 |
| WO | WO-2016/138207 A1 | | 9/2016 |
| WO | WO-2019/200202 A1 | | 10/2019 |
| WO | WO-2020/092375 A1 | | 5/2020 |
| WO | WO-2020/092383 A1 | | 5/2020 |
| WO | WO-2020/092394 A1 | | 5/2020 |
| WO | WO-2020/092401 A1 | | 5/2020 |

(Continued)

OTHER PUBLICATIONS

"Athena Neurosciences Antibody Shows Progress in MS Model," Dow Jones News Service Nov. 14, 1994.

(Continued)

*Primary Examiner* — Patricia L Morris
(74) *Attorney, Agent, or Firm* — Foley Hoag LLP; Dana M. Gordon; Lawrence P. Tardibono

(57) ABSTRACT

Disclosed are small molecule antagonists of human $\alpha_4\beta_7$ integrin, and methods of using them to treat a number of diseases and conditions.

24 Claims, 87 Drawing Sheets

(56) References Cited

FOREIGN PATENT DOCUMENTS

| | | |
|---|---|---|
| WO | WO-2021/076890 A1 | 4/2021 |
| WO | WO-2021/076902 A1 | 4/2021 |

OTHER PUBLICATIONS

Arndt et al., "Peptide derived non-peptidic α4β7-integrin antagonists," Peptides 2002: 4 pages (2002).

Bjorkesten et al., "Surrogate markers and clinical indices, alone or combined, as indicators for endoscopic remission in anti-TNF-treated luminal Crohn's disease," Scandinavian Journal of Gastroenterology, 47(5): 528-537 (2012).

ClinicalTrials.gov, "Study of MORF 057 to Evaluate Single and Multi Ascending Doses in Healthy Volunteers," Identifier: NCT04580745, Publication date: Oct. 8, 2020.

Ferrante et al., "Validation of Endoscopic Activity Scores in Patients With Crohn's Disease Based on a Post Hoc Analysis of Data From SONIC," Gastroenterology, 145: 978-986 (2013).

Form 2 "VLA-4 Antagonists," The Patents Act 1970 (39 of 1970 & The Patent Rule, 2003), Ranbaxy Laboratories Limited 1-19 (2005).

Gottschling et al., "Combinatorial and Rational Strategies to Develop Nonpeptidic α4β7-Integrin Antagonists from Cyclic Peptides," Angew. Chem. Int. Ed., 41(16): 3007-3011 (2002).

International Search Report and Written Opinion for International Application No. PCT/US2019/27141 dated Aug. 16, 2019.

International Search Report and Written Opinion for International Application No. PCT/US2020/055986 dated Feb. 9, 2021.

International Search Report and Written Opinion for International Application No. PCT/US2020/056001 dated Dec. 8, 2020.

Invitation to Pay Additional Fees for International Application No. PCT/US2020/055986 dated Dec. 8, 2020.

Kapp et al., "Integrin modulators: a patent review," Expert Opinion on Therapeutic Patents, 23(10): 1273-1295 (2013).

Kent et al., "A monoclonal antibody to α4-integrin reverses the MR-detectable signs of experimental allergic encephalomyelitis in the Guinea pig," JMRI, 5(5): 535-540 (1995).

Li et al., "α4β7 integrin inhibitors: a patent review," Expert Opinion on Therapeutic Patents, 28(12): 903-917 (2018).

Mangada et al., "Translational Biomarkers for Selective, Oral, Small Molecule α4β7 Inhibitor MORF-057," Morphic Therapeutic, UEG Week 2020 Abstract Submission: 2 pages (2020).

Moskovotz et al., "Defining and Validating Cut-Off's for the Simple Endoscopic Score for Crohn's Disease," Gastroenterology, 132:S1097 (2007).

Notice of Allowance for U.S. Appl. No. 17/072,797 dated Jun. 16, 2021.

Notice of Allowance for U.S. Appl. No. 17/072,797 dated Mar. 3, 2021.

PubChem CID 10162717, "(3S)-3-[2-(3-Benzyl-5-methyl-2-oxopyridin-1-yl)hexanoylamino]-3-(3-fluorophenyl)propanoic acid," Created Oct. 25, 2006.

Pubchem, SID 245847741, Modify Date: Jun. 25, 2015 [retrieved on Jan. 15, 2021]. Retrieved from the Internet <URL:https://pubchem.ncbi.nlm.nih.gov/substance/245847741>.

Sattigeri et al., "Synthesis and biological evaluation of ureido derivatives as VLA-4 antagonists," Ind J Chem 456:2534-2541 (2006).

Sircar et al., "Synthesis and SAR of N-Benzoyl-I-Biphenylalanine Derivatives: Discovery of TR-14035, A Dual a4β7/a4βB1 Integrin Antagonist," Bioorganic & Medicinal Chemistry, 10(6): 2051-2066 (2002).

Stilz et al., "Discovery of an Orally Active Non-Peptide Fibrinogen Receptor Antagonist," J Med Chem 39:2118-2122 (1996).

Tubridy et al., "The effect of anti-α4 integrin antibody on brain lesion activity in MS," Neurology, 53(3): 466-472 (1999).

Wong et al., "Morphic persents positive preclinical data supporting MORF-057 as an oral inhibitor of the α4β7 integrin and potential treatment for inflammatory bowel disease," Morphic Therapeutic, Feb. 14, 2020.

Wong et al., "Morphic therapeutic presents positive preclinical data supporting development of MORF-057 in inflammatory bowel disease at digestive disease week 2020," Morphic Therapeutic, Jun. 29, 2020.

Wong et al., "Preclinical characterization of an oral small molecule inhibitor targeting the integrin A4B7 for the treatment of inflammatory bowel diseases (IBD)," May 20, 2020.

Written Opinion for International Application No. PCT/US2019/058573 dated May 7, 2020.

Extended European Search Report for EP Application No. 19785592.7 dated Nov. 24, 2021.

FIG. 3

| Compounds | a4b7.FP.Mn.CP.Ecto (IC50) [nM] | a4b7.LBA.Mn.CP.886 6MAdCAM (IC50) [nM] | Compounds | a4b7.FP.Mn.CP.Ecto (IC50) [nM] | a4b7.LBA.Mn.CP.8866MAdCAM (IC50) [nM] |
|---|---|---|---|---|---|
| *structure* | B | | *structure* | C | |
| *structure* | A | A | *structure* | A | B |
| *structure* | B | | *structure* | A | |

| Compounds | a4b7.FP.Mn.CP.Ecto (IC$_{50}$) [nM] | a4b7.LBA.Mn.CP.8866MAdCAM (IC$_{50}$) [nM] |
|---|---|---|
|  | B | B |
|  | | |
|  | B | B |

| Compounds | a4b7.FP.Mn.CP.Ecto (IC$_{50}$) [nM] | a4b7.LBA.Mn.CP.8866MAdCAM (IC$_{50}$) [nM] |
|---|---|---|
|  | B | A |
|  | C | |
|  | A | B |

| Compounds | a4b7.FP.Mn. CP.Ecto (IC$_{50}$) [nM] | a4b7.LBA.Mn. CP.8866MAdC AM (IC$_{50}$) [nM] |
|---|---|---|
|  | B | |
|  | B | B |
|  | | |

| Compounds | a4b7.FP.M n.CP.Ecto (IC$_{50}$) [nM] | a4b7.LBA.Mn. CP.8866MAdC AM (IC$_{50}$) [nM] |
|---|---|---|
|  | C | |
|  | B | B |
|  | C | |

| Compounds | a4b7.FP.Mn.CP.Ecto (IC$_{50}$) [nM] | a4b7.LBA.Mn.CP.8866MAdCAM (IC$_{50}$) [nM] |
|---|---|---|
|  | B | B |
|  | | |
|  | B | B |

| Compounds | a4b7.FP.Mn.CP.Ecto (IC$_{50}$) [nM] | a4b7.LBA.Mn.CP.8866MAdCAM (IC$_{50}$) [nM] |
|---|---|---|
|  | B | B |
|  | C | |
|  | B | A |

| Compounds | a4b7.FP.Mn.CP Ecto (IC₅₀) [nM] | a4b7.LBA.Mn.CP.8866MAdCAM (IC₅₀) [nM] |
|---|---|---|
|  | B | |
|  | B | B |
|  | C | |

| Compounds | a4b7.FP.Mn.CP Ecto (IC₅₀) [nM] | a4b7.LBA.Mn.CP.8866MAdCAM (IC₅₀) [nM] |
|---|---|---|
|  | C | |
|  | A | A |
|  | C | |

Figure 4 (cont'd)

| Compounds | a4b7.FP.Mn.CP.Ecto (IC$_{50}$) [nM] | a4b7.LBA.Mn.CP.8866MAdCAM (IC$_{50}$) [nM] |
|---|---|---|
| (structure) | B | B |
| (structure) | C | |
| (structure) | B | B |

| Compounds | a4b7.FP.Mn.CP.Ecto (IC$_{50}$) [nM] | a4b7.LBA.Mn.CP.8866MAdCAM (IC$_{50}$) [nM] |
|---|---|---|
| (structure) | A | B |
| (structure) | C | |
| (structure) | A | B |

Figure 4 (cont'd)

| Compounds | a4b7.FP.Mn.CP.Ecto (IC$_{50}$) [nM] | a4b7.LBA.Mn.CP.8866MAdCAM (IC$_{50}$) [nM] |
|---|---|---|
| [chemical structure] | C | |
| [chemical structure] | B | B |
| [chemical structure] | C | |

| Compounds | a4b7.FP.Mn.CP.Ecto (IC$_{50}$) [nM] | a4b7.LBA.Mn.CP.8866MAdCAM (IC$_{50}$) [nM] |
|---|---|---|
| [chemical structure] | C | |
| [chemical structure] | A | |
| [chemical structure] | C | |

Figure 4 (cont'd)

| Compounds | a4b7.FP.Mn.CP.Ecto (IC$_{50}$) [nM] | a4b7.LBA.Mn.CP.8866MAdCAM (IC$_{50}$) [nM] |
|---|---|---|
| (structure) | B | B |
| (structure) | C | |
| (structure) | A | B |

| Compounds | a4b7.FP.Mn.CP.Ecto (IC$_{50}$) [nM] | a4b7.LBA.Mn.CP.8866MAdCAM (IC$_{50}$) [nM] |
|---|---|---|
| (structure) | B | B |
| (structure) | C | |
| (structure) | B | A |

Figure 4 (cont'd)

| Compounds | a4b7.FP.Mn.CP.Ecto (IC$_{50}$) [nM] | a4b7.LBA.Mn.CP.8866MAdCAM (IC$_{50}$) [nM] |
|---|---|---|
| (structure) | C | |
| (structure) | B | B |
| (structure) | C | |

| Compounds | a4b7.FP.Mn.CP.Ecto (IC$_{50}$) [nM] | a4b7.LBA.Mn.CP.8866MAdCAM (IC$_{50}$) [nM] |
|---|---|---|
| (structure) | C | |
| (structure) | A | A |
| (structure) | C | |

| Compounds | a4b7.FP.Mn.CP.Ecto (IC$_{50}$) [nM] | a4b7.LBA.Mn.CP.8866MAdCAM (IC$_{50}$) [nM] |
|---|---|---|
|  | B | |
|  | B | B |
|  | C | |

| Compounds | a4b7.FP.Mn.CP.Ecto (IC$_{50}$) [nM] | a4b7.LBA.Mn.CP.8866MAdCAM (IC$_{50}$) [nM] |
|---|---|---|
|  | C | |
|  | A | B |
|  | B | |

Figure 4 (cont'd)

| Compounds | a4b7.FP.Mn.CP.Ecto (IC$_{50}$) [nM] | a4b7.LBA.Mn.CP:8866MAdCAM (IC$_{50}$) [nM] |
|---|---|---|
| (structure) | | B |
| (structure) | B | |
| (structure) | B | B |

| Compounds | a4b7.FP.Mn.CP.Ecto (IC$_{50}$) [nM] | a4b7.LBA.Mn.CP:8866MAdCAM (IC$_{50}$) [nM] |
|---|---|---|
| (structure) | A | B |
| (structure) | C | |
| (structure) | B | B |

| Compounds | a4b7.FP.Mn. CP Ecto (IC$_{50}$) [nM] | a4b7.LBA.Mn. CP.8866MAdC AM (IC$_{50}$) [nM] |
|---|---|---|
|  | C | |
|  | B | B |
|  | C | |

| Compounds | a4b7.FP.M n.CP Ecto (IC$_{50}$) [nM] | a4b7.LBA.Mn. CP.8866MAdC AM (IC$_{50}$) [nM] |
|---|---|---|
|  | C | |
|  | A | B |
|  | C | |

| Compounds | a4b7.FP.Mn.CP.Ecto (IC$_{50}$) [nM] | a4b7.LBA.Mn.CP.8866MAdCAM (IC$_{50}$) [nM] |
|---|---|---|
|  | B | B |
|  | | |
|  | B | B |

| Compounds | a4b7.FP.Mn.CP.Ecto (IC$_{50}$) [nM] | a4b7.LBA.Mn.CP.8866MAdCAM (IC$_{50}$) [nM] |
|---|---|---|
|  | B | B |
|  | B | |
|  | B | B |

Figure 4 (cont'd)

| Compounds | a4b7.FP.Mn.CP.Ecto (IC$_{50}$) [nM] | a4b7.LBA.Mn.CP.8866MAdCAM (IC$_{50}$) [nM] |
|---|---|---|
| (structure) | B | B |
| (structure) | C | |
| (structure) | A | B |

| Compounds | a4b7.FP.Mn.CP.Ecto (IC$_{50}$) [nM] | a4b7.LBA.Mn.CP.8866MAdCAM (IC$_{50}$) [nM] |
|---|---|---|
| (structure) | B | B |
| (structure) | C | |
| (structure) | B | |

Figure 4 (cont'd)

| Compounds | a4b7.FP.Mn.CP.Ecto (IC50) [nM] | a4b7.LBA.Mn.CP.8866MAdCAM (IC50) [nM] |
|---|---|---|
| (structure) | C | |
| (structure) | B | B |
| (structure) | C | |

| Compounds | a4b7.FP.Mn.CP.Ecto (IC50) [nM] | a4b7.LBA.Mn.CP.8866MAdCAM (IC50) [nM] |
|---|---|---|
| (structure) | B | |
| (structure) | B | B |
| (structure) | C | |

| Compounds | a4b7.FP.Mn.CP.Ecto (IC$_{50}$) [nM] | a4b7.LBA.Mn.CP.8866MAdCAM (IC$_{50}$) [nM] |
|---|---|---|
|  | C | |
|  | B | A |
|  | C | |

| Compounds | a4b7.FP.Mn.CP.Ecto (IC$_{50}$) [nM] | a4b7.LBA.Mn.CP.8866MAdCAM (IC$_{50}$) [nM] |
|---|---|---|
|  | | |
|  | B | A |
|  | C | |

Figure 4 (cont'd)

| Compounds | a4b7.FP.Mn.CP.Ecto (IC$_{50}$) [nM] | a4b7.LBA.Mn.CP.8866MAdCAM (IC$_{50}$) [nM] |
|---|---|---|
| (structure) | B | A |
| (structure) | B | B |

| Compounds | a4b7.FP.Mn.CP.Ecto (IC$_{50}$) [nM] | a4b7.LBA.Mn.CP.8866MAdCAM (IC$_{50}$) [nM] |
|---|---|---|
| (structure) | B | B |
| (structure) | B | |

| Compounds | a4b7.FP.M n.CP.Ecto (IC50) [nM] | a4b7.LBA.Mn. CP.8866MAdC AM (IC50) [nM] |
|---|---|---|
|  | A | B |
|  | C | |
|  | A | B |

| Compounds | a4b7.FP.Mn. CP.Ecto (IC50) [nM] | a4b7.LBA.Mn. CP.8866MAdC AM (IC50) [nM] |
|---|---|---|
|  | A | A |
|  | C | |
|  | B | A |

Figure 4 (cont'd)

| Compounds | a4b7.FP.Mn.CP.Ecto (IC$_{50}$) [nM] | a4b7.LBA.Mn.CP.8866MAdCAM (IC$_{50}$) [nM] |
|---|---|---|
| (structure) | C | |
| (structure) | B | A |
| (structure) | C | |

| Compounds | a4b7.FP.Mn.CP.Ecto (IC$_{50}$) [nM] | a4b7.LBA.Mn.CP.8866MAdCAM (IC$_{50}$) [nM] |
|---|---|---|
| (structure) | B | |
| (structure) | B | B |
| (structure) | C | |

| Compounds | a4b7.FP.Mn.CP.Ecto (IC$_{50}$) [nM] | a4b7.LBA.Mn.CP.8866MAdCAM (IC$_{50}$) [nM] |
|---|---|---|
|  | B | |
|  | B | B |
|  | B | |

| Compounds | a4b7.FP.Mn.CP.Ecto (IC$_{50}$) [nM] | a4b7.LBA.Mn.CP.8866MAdCAM (IC$_{50}$) [nM] |
|---|---|---|
|  | C | |
|  | B | B |
|  | C | |

| Compounds | a4b7.FP.Mn.CP Ecto (IC$_{50}$) [nM] | a4b7.LBA.Mn.CP.8866MAdC AM (IC$_{50}$) [nM] |
|---|---|---|
|  | A | B |
|  | | |
|  | B | B |

| Compounds | a4b7.FP.Mn.CP Ecto (IC$_{50}$) [nM] | a4b7.LBA.Mn.CP.8866MAdC AM (IC$_{50}$) [nM] |
|---|---|---|
|  | B | B |
|  | | |
|  | A | B |

Figure 4 (cont'd)

| Compounds | a4b7.FP.Mn.CP.Ecto (IC₅₀) [nM] | a4b7.LBA.Mn.CP.8866MAdCAM (IC₅₀) [nM] |
|---|---|---|
| (structure) | C | |
| (structure) | A | A |
| (structure) | C | |

| Compounds | a4b7.FP.Mn.CP.Ecto (IC₅₀) [nM] | a4b7.LBA.Mn.CP.8866MAdCAM (IC₅₀) [nM] |
|---|---|---|
| (structure) | B | |
| (structure) | B | B |
| (structure) | C | |

| Compounds | a4b7.FP.Mn.CP.Ecto (IC$_{50}$) [nM] | a4b7.LBA.Mn.CP.8866MAdCAM (IC$_{50}$) [nM] |
|---|---|---|
|  | B | A |
| | C | |
| | A | B |

| Compounds | a4b7.FP.Mn.CP.Ecto (IC$_{50}$) [nM] | a4b7.LBA.Mn.CP.8866MAdCAM (IC$_{50}$) [nM] |
|---|---|---|
|  | B | B |
| | C | |
| | B | B |

| Compounds | a4b7.FP.Mn.CP.Ecto (IC50) [nM] | a4b7.LBA.Mn.CP.8866MAdCAM (IC50) [nM] |
|---|---|---|
|  | B | B |
|  | C | |

| Compounds | a4b7.FP.Mn.CP.Ecto (IC50) [nM] | a4b7.LBA.Mn.CP.8866MAdCAM (IC50) [nM] |
|---|---|---|
| | | |
|  | B | B |

INHIBITING HUMAN INTEGRIN (ALPHA-4) (BETA-7)

RELATED APPLICATIONS

This application is a continuation of International Application PCT/US20/55986, filed Oct. 16, 2020; which claims benefit of priority to U.S. Provisional Patent Application No. 62/916,062, filed Oct. 16, 2019.

TECHNICAL FIELD

Disclosed are novel compounds and related methods useful for the inhibition of the $\alpha_4\beta_7$ integrin. The compounds and methods disclosed herein are applicable to the development of medicaments for the treatment of $\alpha_4\beta_7$ integrin-mediated conditions, such as inflammatory bowel disease (IBD), ulcerative colitis (UC), and Crohn's disease (CD).

BACKGROUND

Integrins are noncovalently associated $\alpha/\beta$ heterodimeric cell surface receptors involved in numerous cellular processes. Differential expression of integrins can regulate a cell's adhesive properties, allowing different leukocyte populations to be recruited to specific organs in response to different inflammatory signals. The $\alpha_4$ integrins, including $\alpha_4\beta_7$, play a role in lymphocyte migration throughout the gastrointestinal tract. They are expressed on most leukocytes, including B and T lymphocytes, where they mediate cell adhesion via selective binding to its primary ligand, mucosal addressin cell adhesion molecule (MAdCAM). Memory T lymphocytes expressing the $\alpha_4\beta_7$ integrin preferentially migrate into the gastrointestinal tract via firm adhesion to mucosal vascular addressin cell adhesion molecule 1 (MAdCAM-1).

Inhibitors of specific integrin-ligand interactions have been used for the treatment of various diseases. For example, monoclonal antibodies displaying high binding affinity for $\alpha_4\beta_7$ have displayed therapeutic benefits for gastrointestinal auto-inflammatory/autoimmune diseases, such as Crohn's disease, and ulcerative colitis. However, these therapies also have certain undesirable properties for the patient. A monoclonal antibody $\alpha_4\beta_7$ integrin inhibitor is administered by parenteral administration, has a long half-life with inability to rapidly modify exposures, and a reduced activity due to anti-drug antibody formation. Monoclonal antibody therapies can be challenging to manufacture in comparison to small molecule therapies. In addition, some therapies that inhibit $\alpha_4\beta_7$ have also interfered with $\alpha_4\beta_7$ integrin-ligand interactions, thereby resulting in dangerous side effects to the patient. Activity at $\alpha_4\beta_7$ integrin is implicated in emergence of progressive multifocal leukoencephalopathy (PML), a life-threatening and progressive brain infection, in immunosuppressed patients.

There remains a medical need for an effective and safe oral $\alpha_4\beta_7$ integrin inhibitor as an important addition to the therapeutic armamentarium for $\alpha_4\beta_7$ integrin-mediated conditions, such as inflammatory bowel disease (IBD), ulcerative colitis (UC) and Crohn's disease (CD).

SUMMARY

In certain embodiments, the invention relates to compounds of Formula (I):

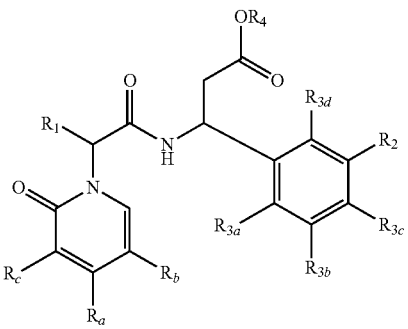

wherein $R_a$, $R_b$, and $R_c$ are independently selected from the group consisting of H, Me, halide, $CF_3$, $C(H)F_2$, $C(F)H_2$, —CN, —$OCF_3$, substituted or unsubstituted ($C_1$-$C_5$)-alkyl, substituted or unsubstituted ($C_1$-$C_5$)-alkoxy, —$CH_2CF_3$, and substituted or unsubstituted —($C_1$-$C_5$)alkylene-N—($R_x$)($R_y$); provided that at least one of $R_a$, $R_b$, and $R_c$ is ($C_1$-$C_5$) alkylene-N—($R_x$)($R_y$);

$R_x$ and $R_y$ are independently selected from the group consisting of H and substituted or unsubstituted ($C_1$-$C_6$)-alkyl; or $R_x$ and $R_y$ taken together with the N to which they are attached form a 4-6 membered ring;

$R_1$ is substituted or unsubstituted ($C_1$-$C_6$)-alkyl, substituted or unsubstituted ($C_1$-$C_4$)-alkylene-($C_3$-$C_6$)-cycloalkyl, or substituted or unsubstituted ($C_1$-$C_4$)-alkylene-($C_1$-$C_4$)-alkoxy;

$R_2$ is

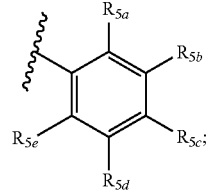

$R_{3a}$ and $R_{3b}$ are independently selected from the group consisting of H, substituted or unsubstituted ($C_1$-$C_5$)-alkyl, substituted or unsubstituted ($C_3$-$C_6$)-cycloalkyl, substituted or unsubstituted 3-6 membered heterocycloalkyl, —OH, —CN, halide, $CF_3$, $C(H)F_2$, $C(F)H_2$, —($C_1$-$C_4$)-alkoxy, —$OCF_3$, and substituted or unsubstituted ($C_1$-$C_4$)-alkylene-($C_1$-$C_4$)-alkoxy; provided that $R_{3a}$ and $R_{3b}$ are not both H;

$R_{3c}$ is selected from the group consisting of H, substituted or unsubstituted ($C_1$-$C_5$)-alkyl, substituted or unsubstituted ($C_3$-$C_6$)-cycloalkyl, substituted or unsubstituted 3-6 membered heterocycloalkyl, hydroxyl, halide, $CF_3$, $C(H)F_2$, $C(F)H_2$, —($C_1$-$C_4$)-alkoxy, —$OCF_3$—CN, and substituted or unsubstituted ($C_1$-$C_4$)-alkylene-($C_1$-$C_4$)-alkoxy;

$R_{3d}$ is selected from the group consisting of H, substituted or unsubstituted ($C_1$-$C_5$)-alkyl, hydroxyl, halide, and —($C_1$-$C_4$)-alkoxy;

$R_4$ is H, or substituted or unsubstituted ($C_1$-$C_4$)-alkyl;

$R_{5a}$, and $R_{5e}$ are independently selected from the group consisting of H, CN, halide, $CF_3$, $C(H)F_2$, $C(F)H_2$, —$CH_2CF_3$, substituted or unsubstituted ($C_3$-$C_6$)-cycloalkyl, substituted or unsubstituted ($C_1$-$C_5$)-alkyl, substituted or unsubstituted 3-6 membered heterocycloalkyl hydroxyl, and ($C_1$-$C_4$)-alkoxy; and $R_{5b}$, $R_{5c}$, and $R_{5d}$ are independently selected from the group consisting of H, CN, halide, $CF_3$, $C(H)F_2$, $C(F)H_2$, —$CH_2CF_3$, substituted or unsubstituted ($C_1$-$C_5$)-alkyl, substituted or unsubstituted ($C_3$-$C_6$)-cycloalkyl, substituted or unsubstituted 3-6 membered heterocycloalkyl, hydroxyl, and ($C_1$-$C_4$)-alkoxy;

or a pharmaceutically acceptable salt thereof.

In some aspects of the invention, a compound of Formula (I) can be a compound wherein one and only one of $R_a$, $R_b$, and $R_c$ is substituted or unsubstituted —($C_1$-$C_5$)alkylene-N—($R_x$)($R_y$); $R_1$ is ($C_1$-$C_6$) alkyl (e.g., isobutyl); $R_{3a}$ and $R_{3b}$ are independently selected from the group consisting of H, ($C_1$-$C_4$)-alkyl (e.g., methyl), halide (e.g., F or Cl), $CF_3$, $C(H)F_2$, and $C(F)H_2$, provided that $R_{3a}$ and $R_{3b}$ are not both H; and $R_4$ is H.

In some examples, a compound of Formula (I) can be a compound wherein one and only one of $R_a$, $R_b$, and $R_c$ is substituted or unsubstituted —($C_1$-$C_5$)alkylene-N—($R_x$)($R_y$); $R_x$ and $R_y$ are each independently unsubstituted ($C_1$-$C_6$)-alkyl (e.g., methyl) or $R_x$ and $R_y$ taken together with the N to which they are attached form a substituted or unsubstituted 4-6 membered heterocyclyl ring; $R_1$ is unsubstituted ($C_1$-$C_6$) alkyl (e.g., isobutyl); $R_{3a}$ and $R_{3b}$ are independently selected from the group consisting of H, unsubstituted ($C_1$-$C_4$)-alkyl (e.g., methyl, ethyl, etc.), halide (e.g., F or Cl), $CF_3$, $C(H)F_2$, and $C(F)H_2$, provided that $R_{3a}$ and $R_{3b}$ are not both H; $R_{3c}$ is selected from the group consisting of: H, F, Cl, hydroxyl, substituted or unsubstituted ($C_1$-$C_4$)-alkyl (e.g., methyl), substituted or unsubstituted ($C_3$-$C_6$)-cycloalkyl (e.g., cyclopropyl), ($C_1$-$C_4$)-alkoxy (e.g., methoxy); $R_{3d}$ is selected from the group consisting of H, halide (e.g., F, or Cl), substituted or unsubstituted ($C_1$-$C_4$)-alkyl (e.g., methyl), and hydroxyl; and $R_4$ is H. In some examples, a compound of Formula (I), Formula (Ia) and/or Formula (Ib) can be a compound wherein one and only one of $R_a$, $R_b$, and $R_c$ is substituted or unsubstituted —($C_1$-$C_5$)alkylene-N—($R_x$)($R_y$); $R_x$ and $R_y$ each independently unsubstituted methyl or $R_x$ and $R_y$ taken together with the N to which they are attached form a substituted or unsubstituted 4-6 membered heterocyclyl ring; $R_1$ is isobutyl; $R_{3a}$ and $R_{3b}$ are independently selected from the group consisting of unsubstituted ($C_1$-$C_4$)-alkyl (e.g., methyl), halide (e.g., F or Cl), $CF_3$, $C(H)F_2$, and $C(F)H_2$, $R_{3c}$ and $R_{3d}$ are both H; and $R_4$ is H. For instance, a compound of Formula (I), Formula (Ia) and/or Formula (Ib) can be a compound wherein $R_1$ is isobutyl; $R_{3a}$ and $R_{3b}$ are independently selected from the group consisting of unsubstituted ($C_1$-$C_4$)-alkyl (e.g., methyl), halide (e.g., F or Cl), $CF_3$, $C(H)F_2$, and $C(F)H_2$, $R_{3c}$ and $R_{3d}$ are both H; $R_4$ is H; and $R_{5a}$ and $R_{5e}$ are each substituted or unsubstituted ($C_1$-$C_4$)-alkyl (e.g., methyl). A compound of Formula (I) can be a compound wherein one and only one of $R_a$, $R_b$, and $R_c$ is substituted or unsubstituted —($C_1$-$C_5$)alkylene-N—($R_x$)($R_y$); $R_x$ and $R_y$ each independently unsubstituted methyl or $R_x$ and $R_y$ taken together with the N to which they are attached form a 4-6 membered heterocyclyl ring optionally substituted with halide (e.g., F); $R_1$ is isobutyl; $R_{3a}$ and $R_{3b}$ are independently selected from the group consisting of unsubstituted ($C_1$-$C_4$)-alkyl (e.g., methyl), halide (e.g., F or Cl), $CF_3$, $C(H)F_2$, and $C(F)H_2$, $R_{3c}$ and $R_{3d}$ are both H; $R_4$ is H; $R_{5a}$ and $R_{5e}$ are each substituted or unsubstituted ($C_1$-$C_4$)-alkyl (e.g., methyl), and $R_{5b}$, $R_{5c}$, and $R_{5d}$ are each independently selected from the group consisting of H, CN, halide (e.g., F, Cl), $CF_3$, $C(H)F_2$, $C(F)H_2$, ($C_1$-$C_5$)-alkyl, hydroxyl, and ($C_1$-$C_4$)-alkoxy. In certain embodiments, the invention relates to a method of treating auto-inflammatory/autoimmune diseases, such as Crohn's disease, and ulcerative colitis; comprising the step of: administering to a subject in need thereof a therapeutically effective amount of any one of the compounds described herein.

In some embodiments, a compound of Formula (I) can be a compound of Formula (Ia):

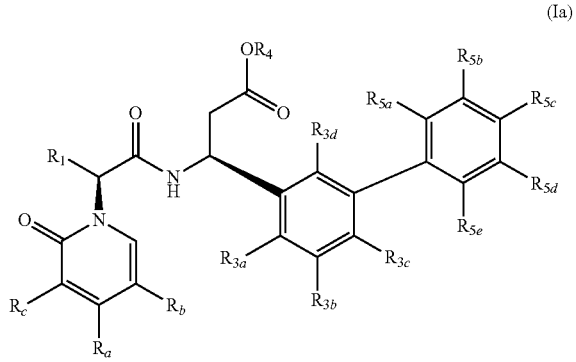

(Ia)

or a pharmaceutically acceptable salt thereof, wherein $R_a$, $R_b$, $R_c$, $R_1$, $R_{3a}$, $R_{3b}$, $R_{3c}$, $R_{3d}$, $R_{5a}$, $R_{5b}$, $R_{5c}$, $R_{5d}$, $R_{5e}$, and $R_4$ in Formula (Ia) are each independently defined as above with respect to Formula (I).

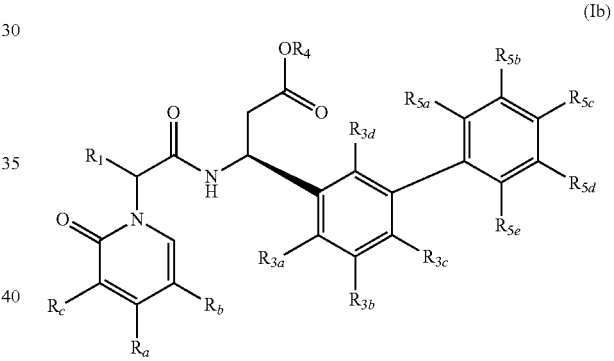

(Ib)

or a pharmaceutically acceptable salt thereof, wherein $R_a$, $R_b$, $R_c$, $R_1$, $R_{3a}$, $R_{3b}$, $R_{3c}$, $R_{3d}$, $R_{5a}$, $R_{5b}$, $R_{5c}$, $R_{5d}$, $R_{5e}$, and $R_4$ in Formula (Ia) are each independently defined as above with respect to Formula (I).

Methods of preparing and isolating the compounds of Formula (I), Formula (Ia) and/or Formula (Ib) are also provided herein.

DETAILED DESCRIPTION

Figure 1:
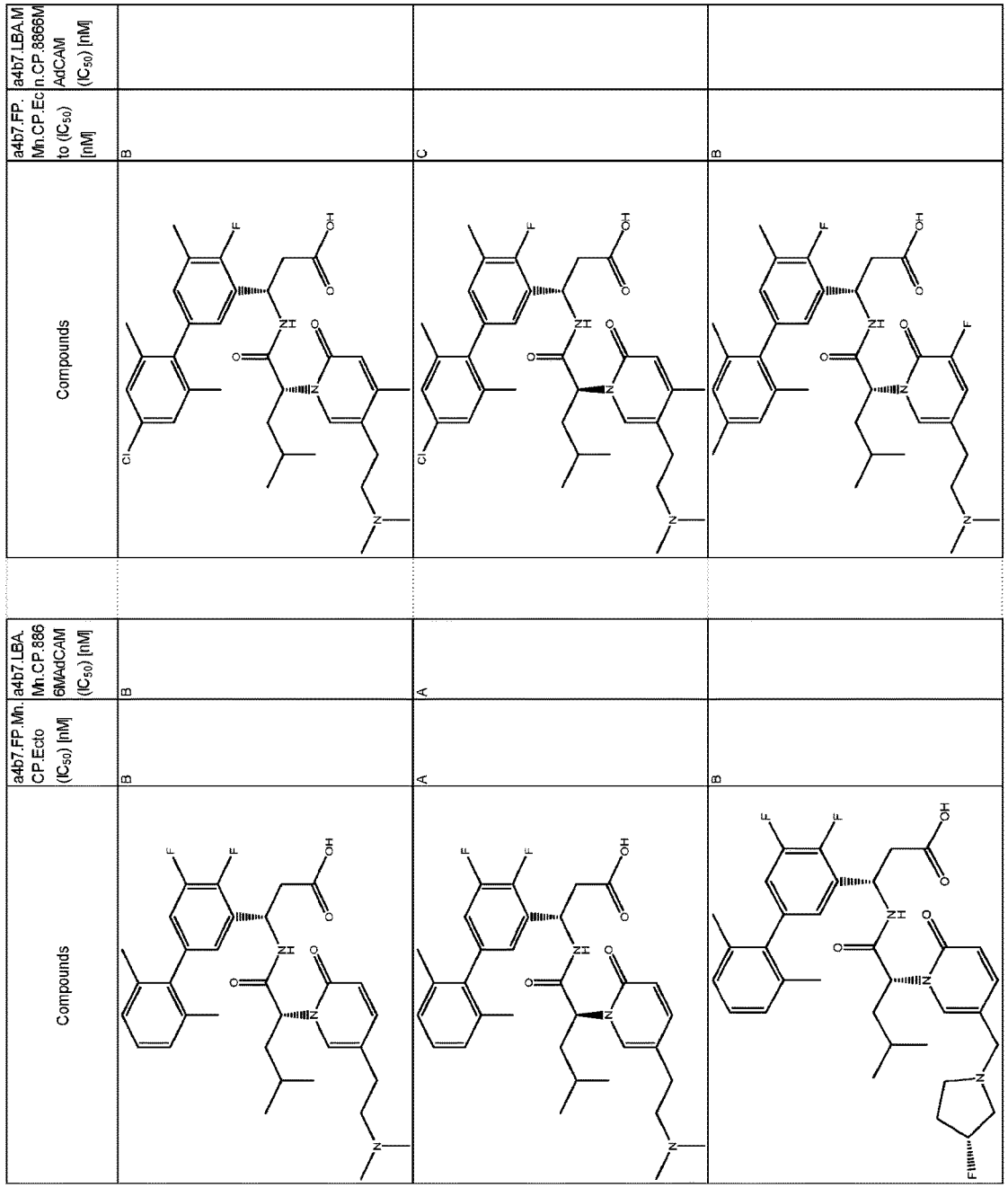
FIG. 1 is a table (Table 1) summarizing in vitro inhibition of $\alpha_4\beta_7$ integrin by exemplary compounds (i.e., data obtained from the fluorescence polarization assay of Example 5, and the ligand binding assay of Example 6).
Figure 1:
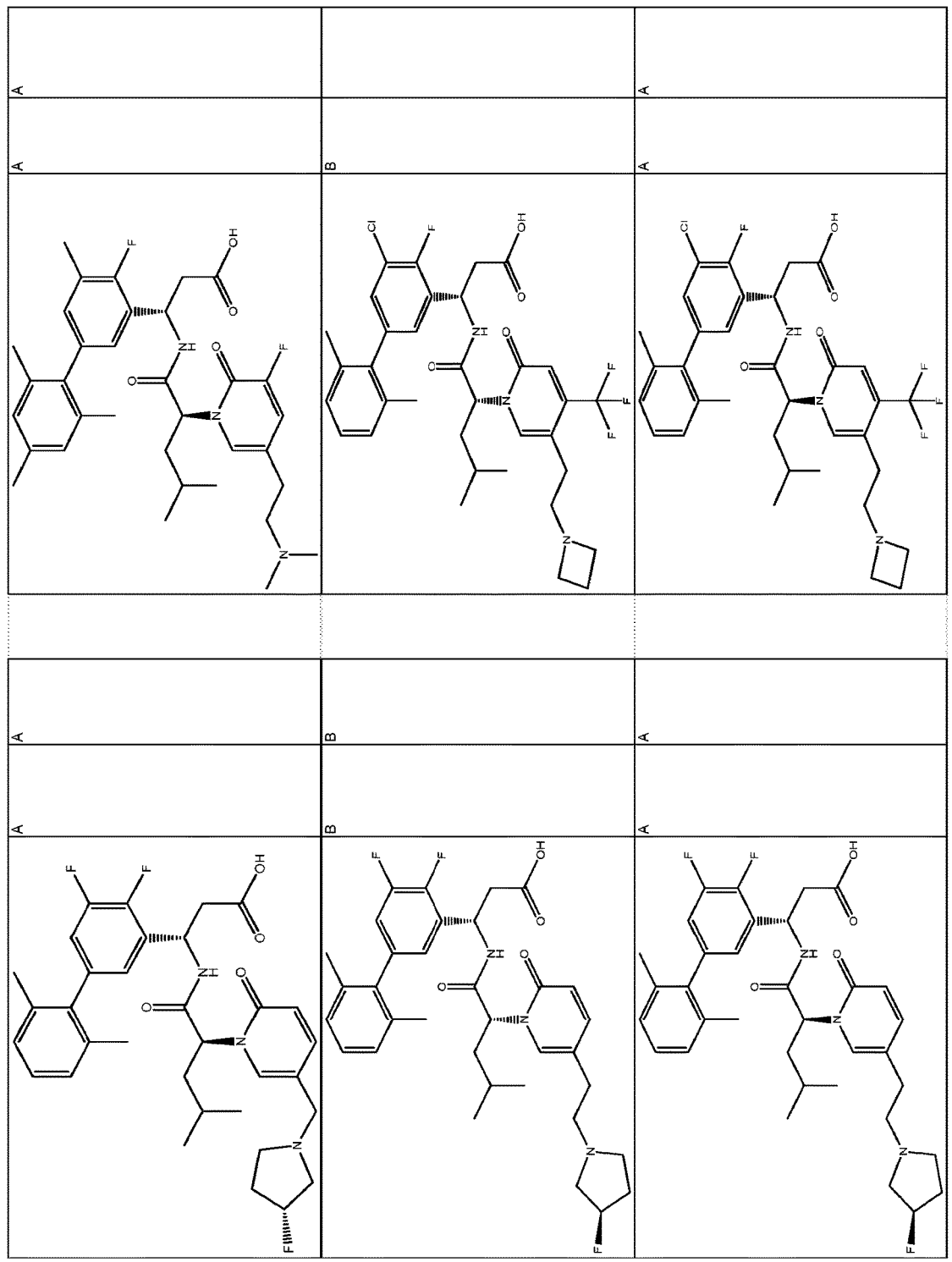
Figure 1:
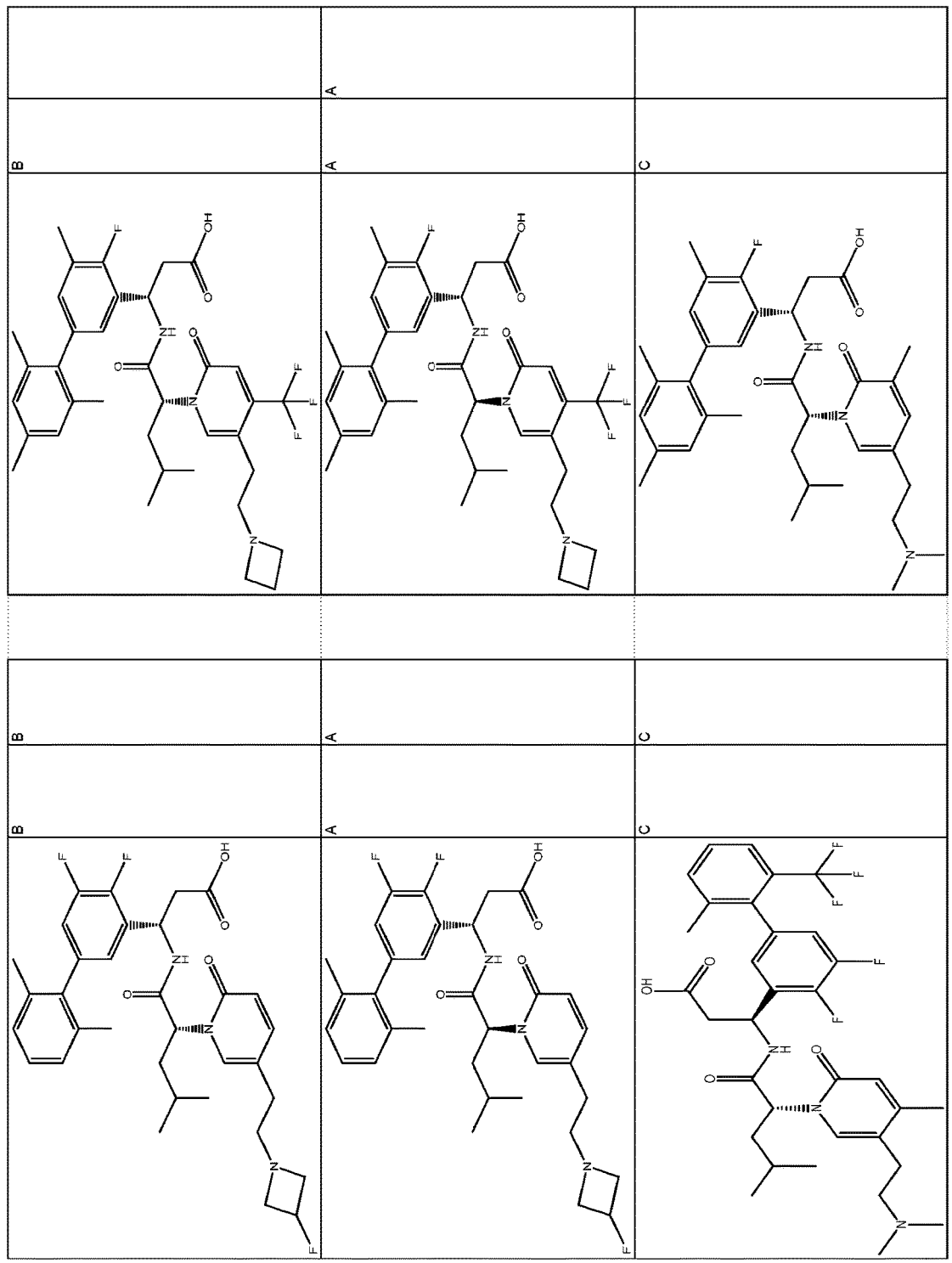
Figure 1:
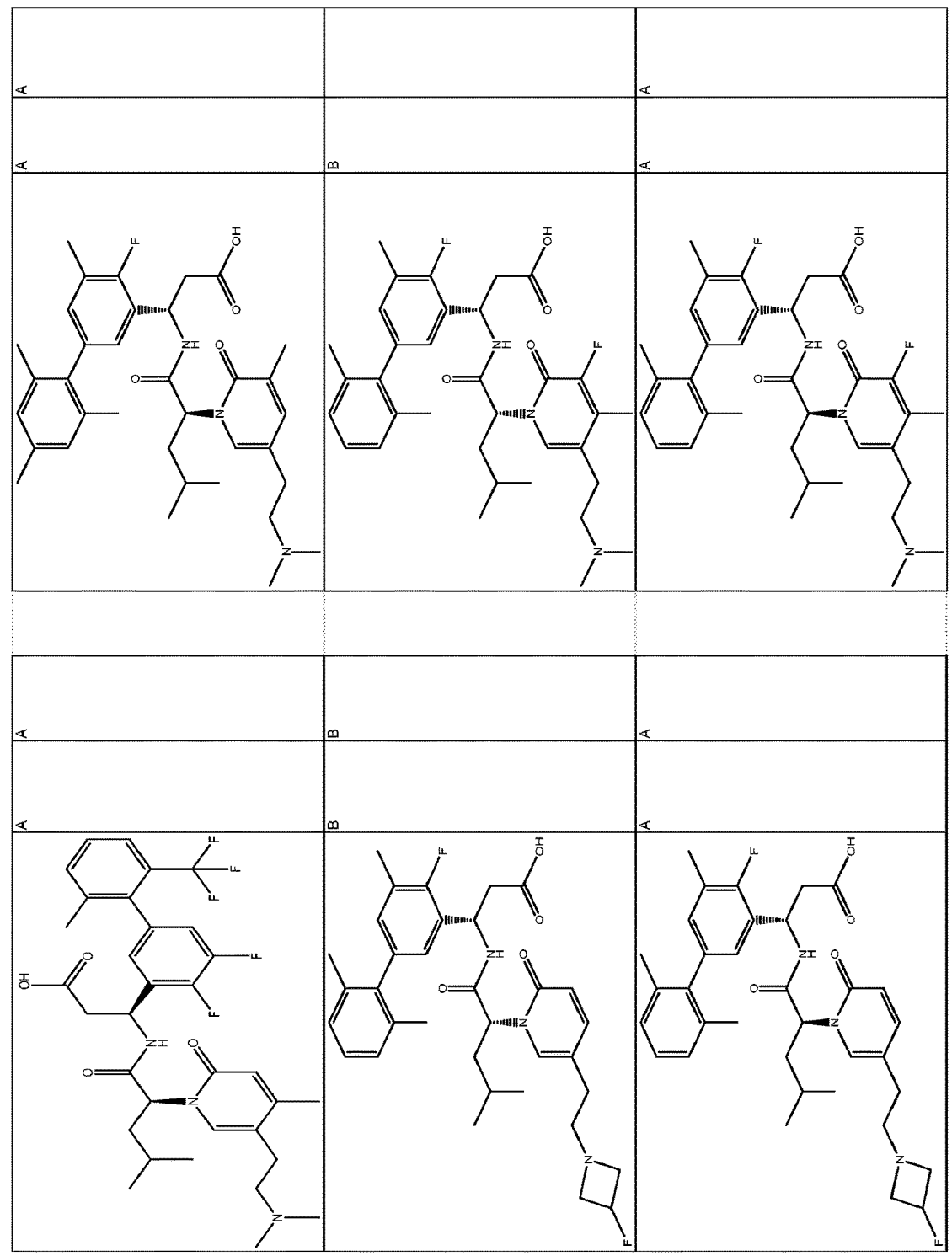
Figure 1:
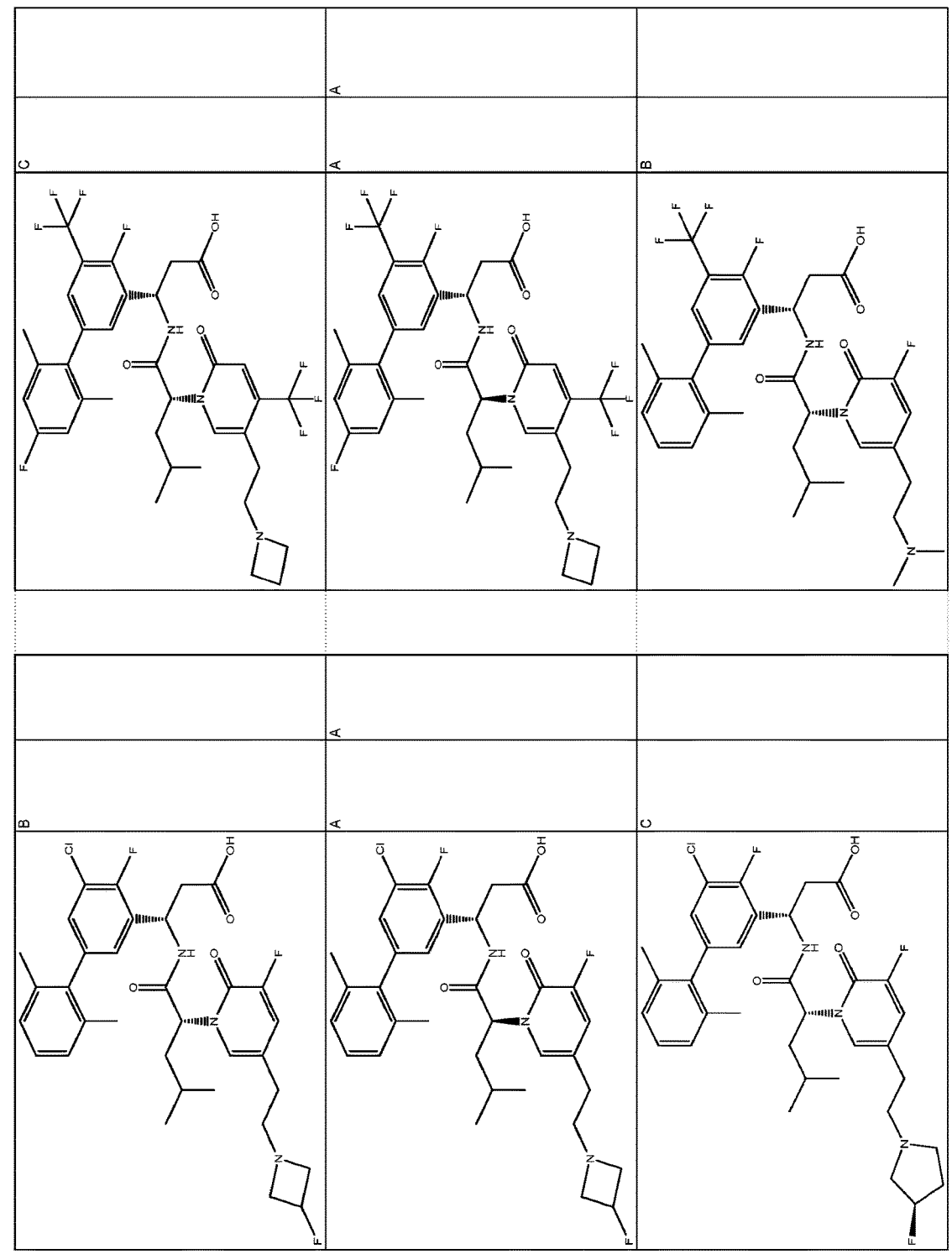
Figure 1:
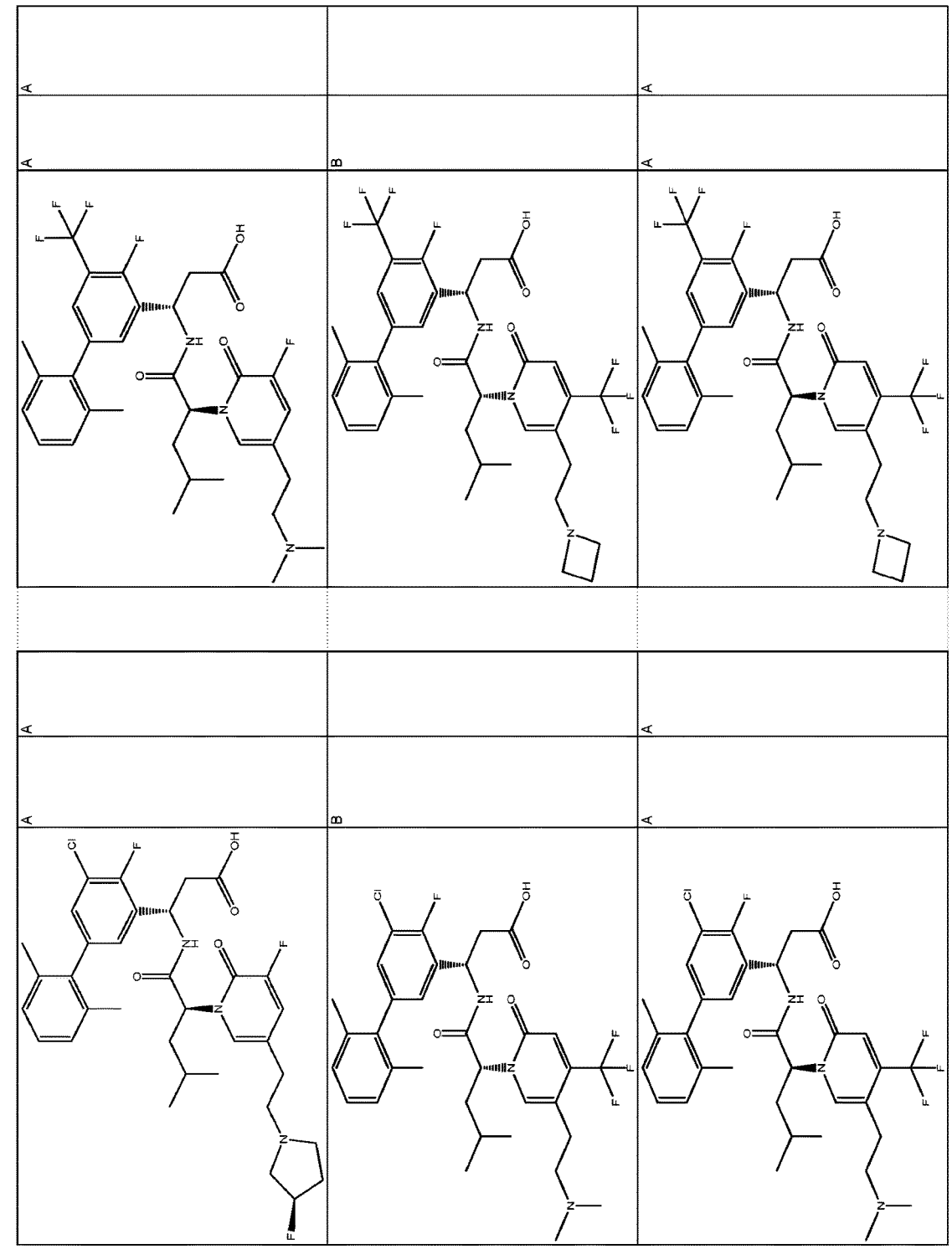
Figure 1:
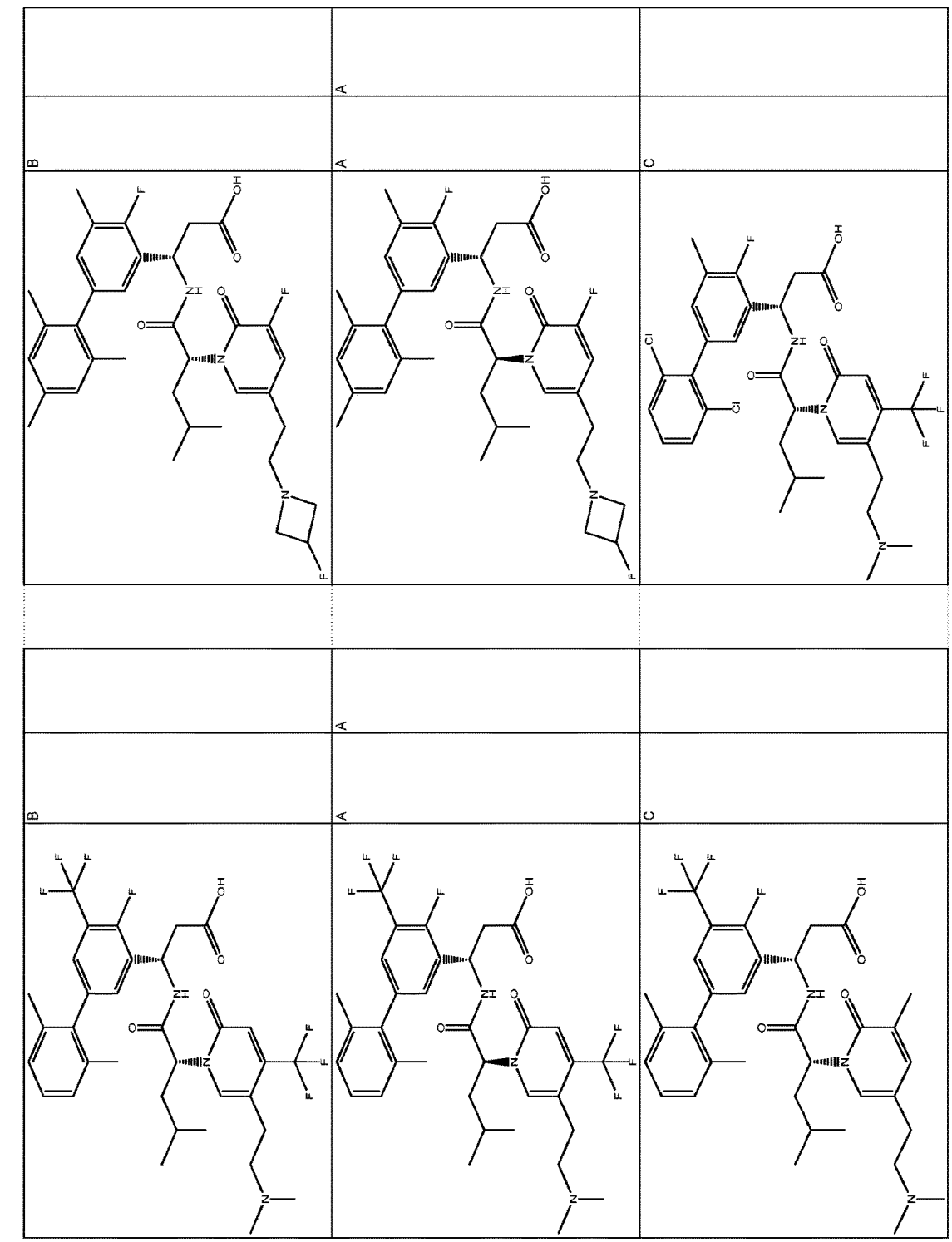
Figure 1:
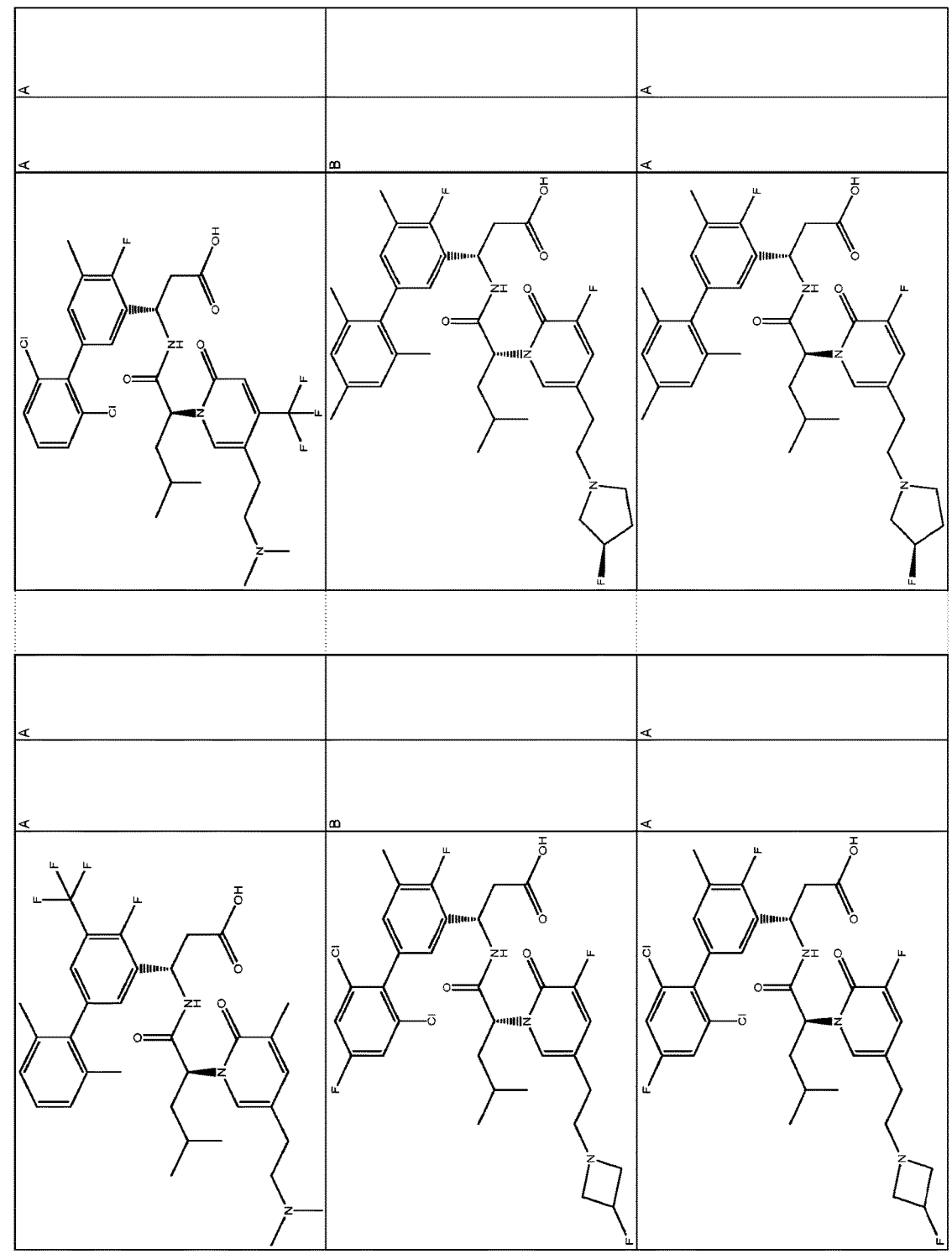
Figure 1:
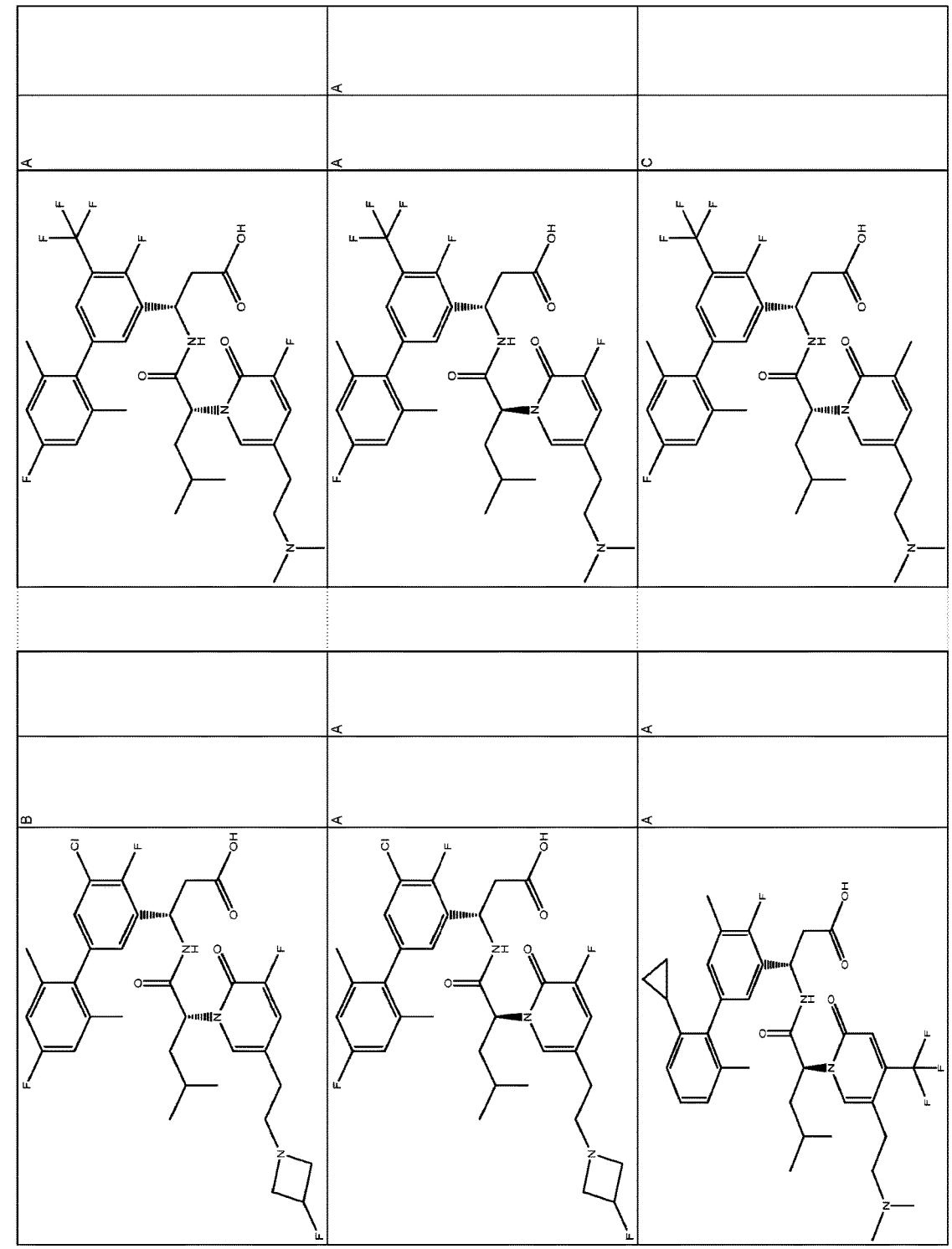
Figure 1:
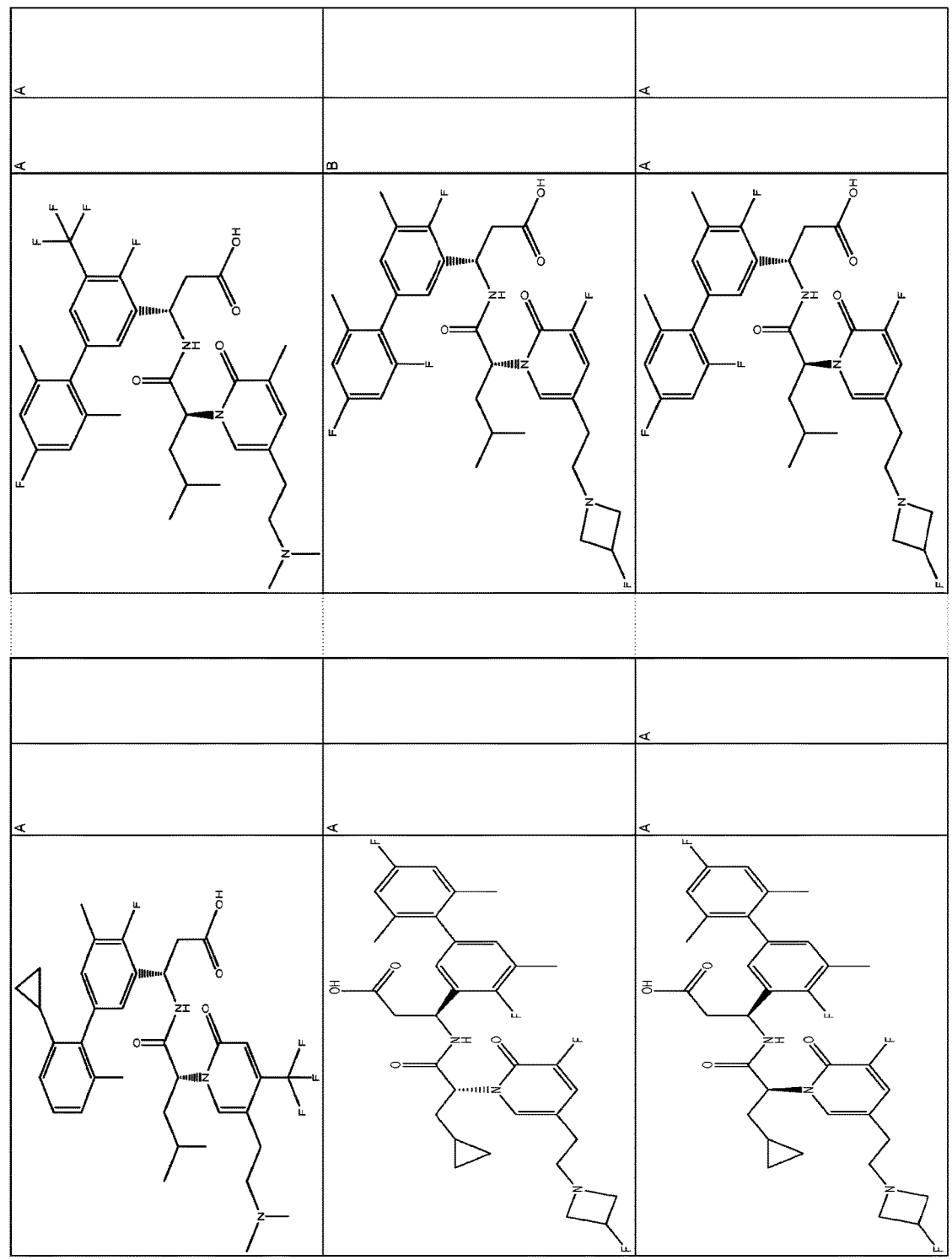
Figure 1:
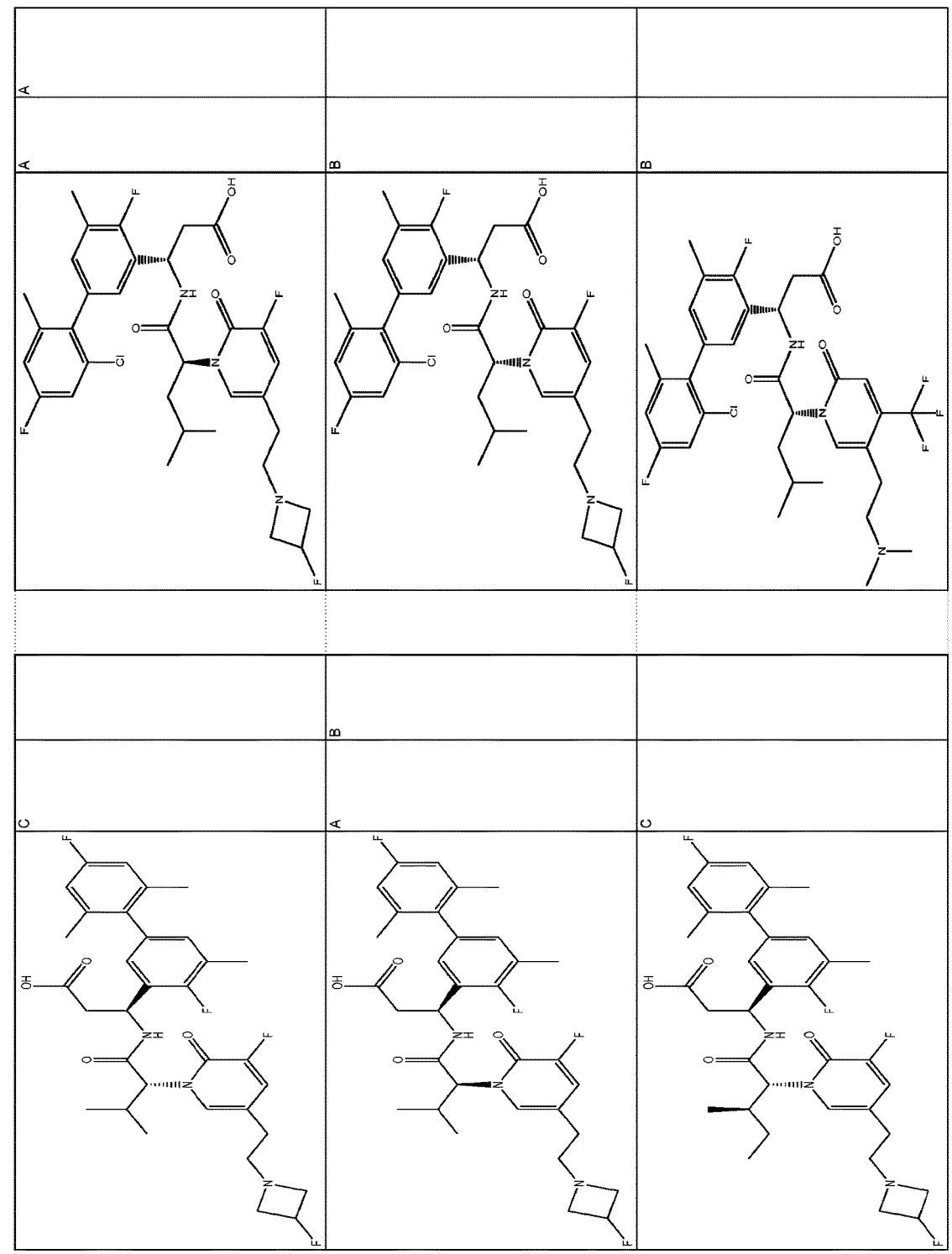
Figure 1:
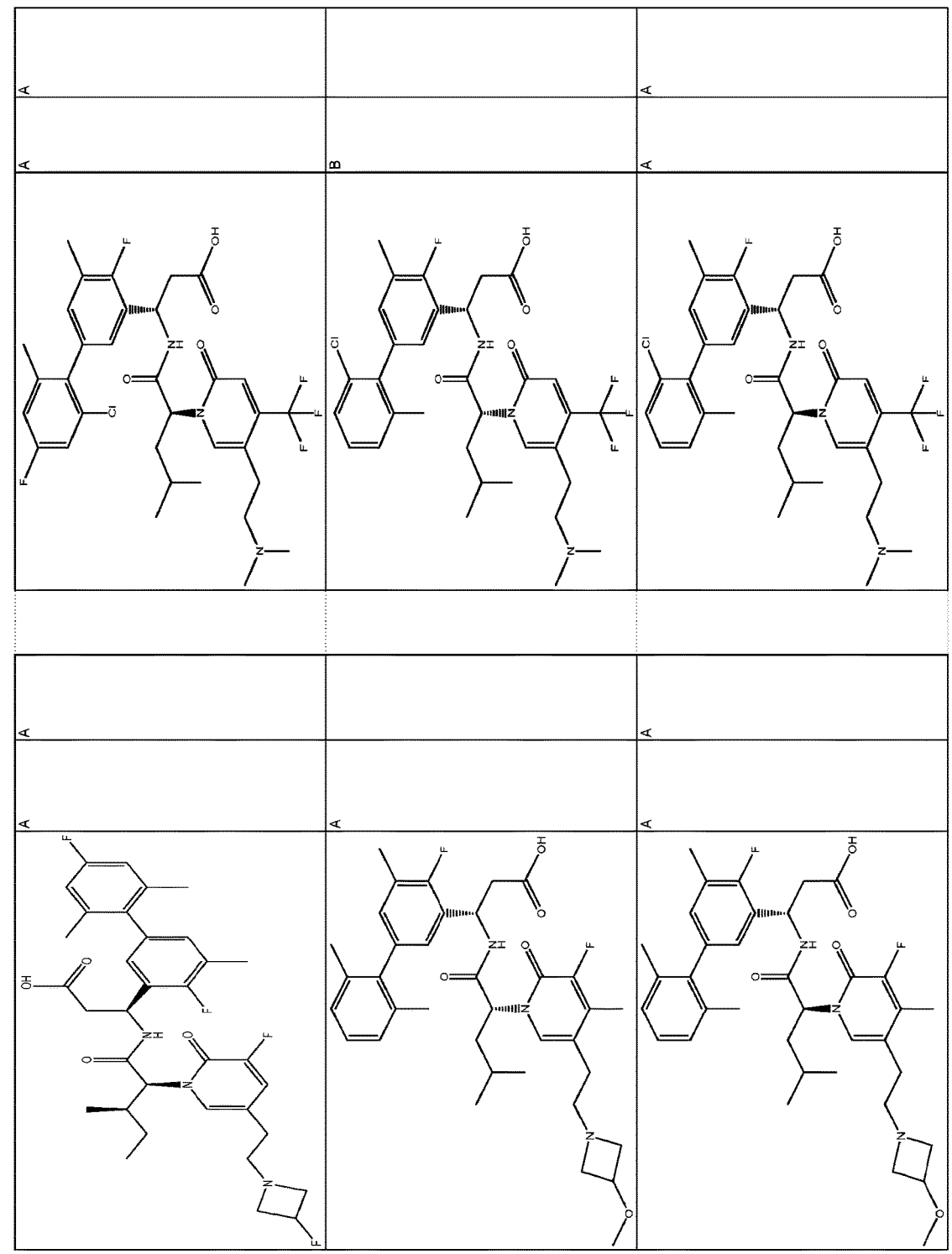
Figure 1:
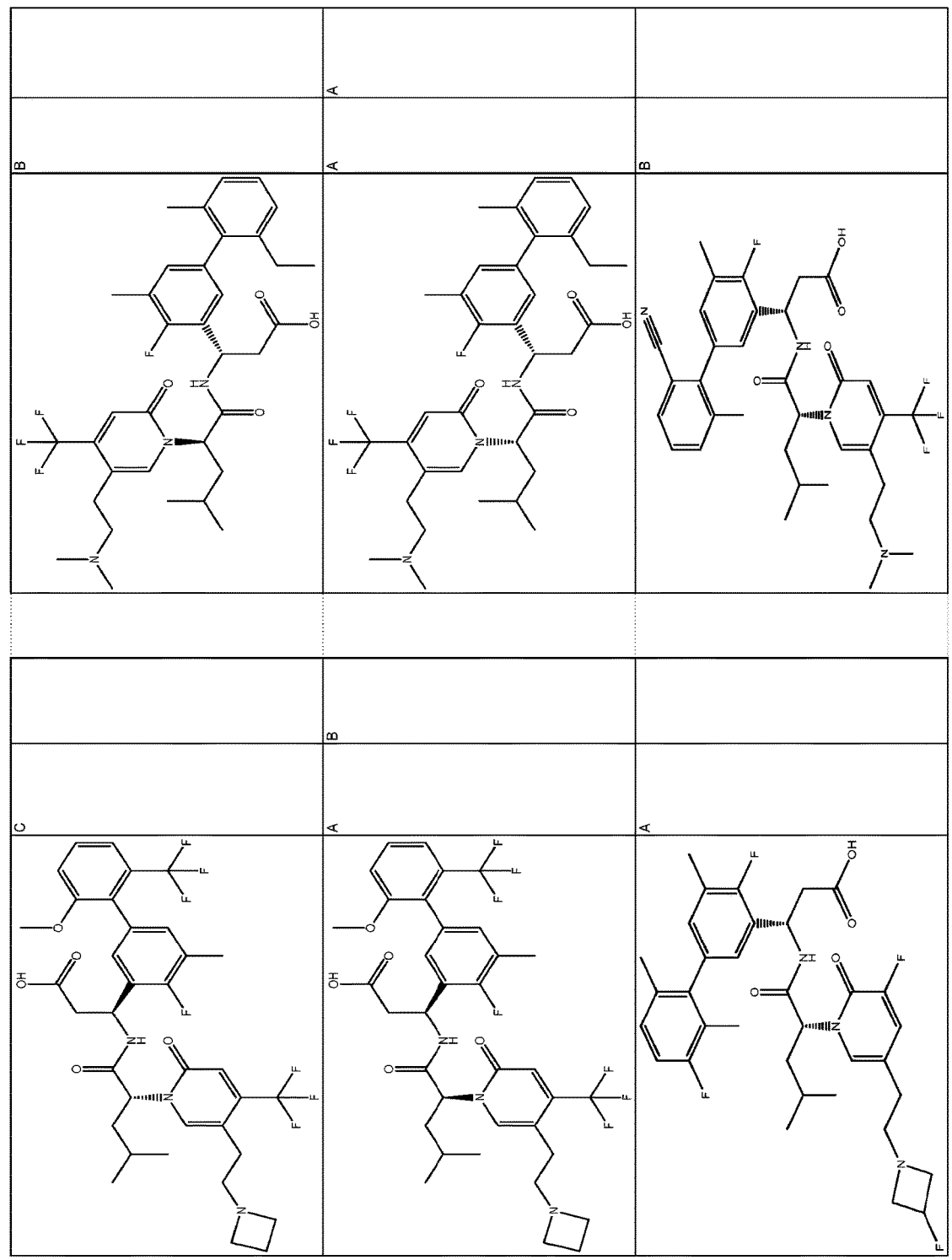
Figure 1:
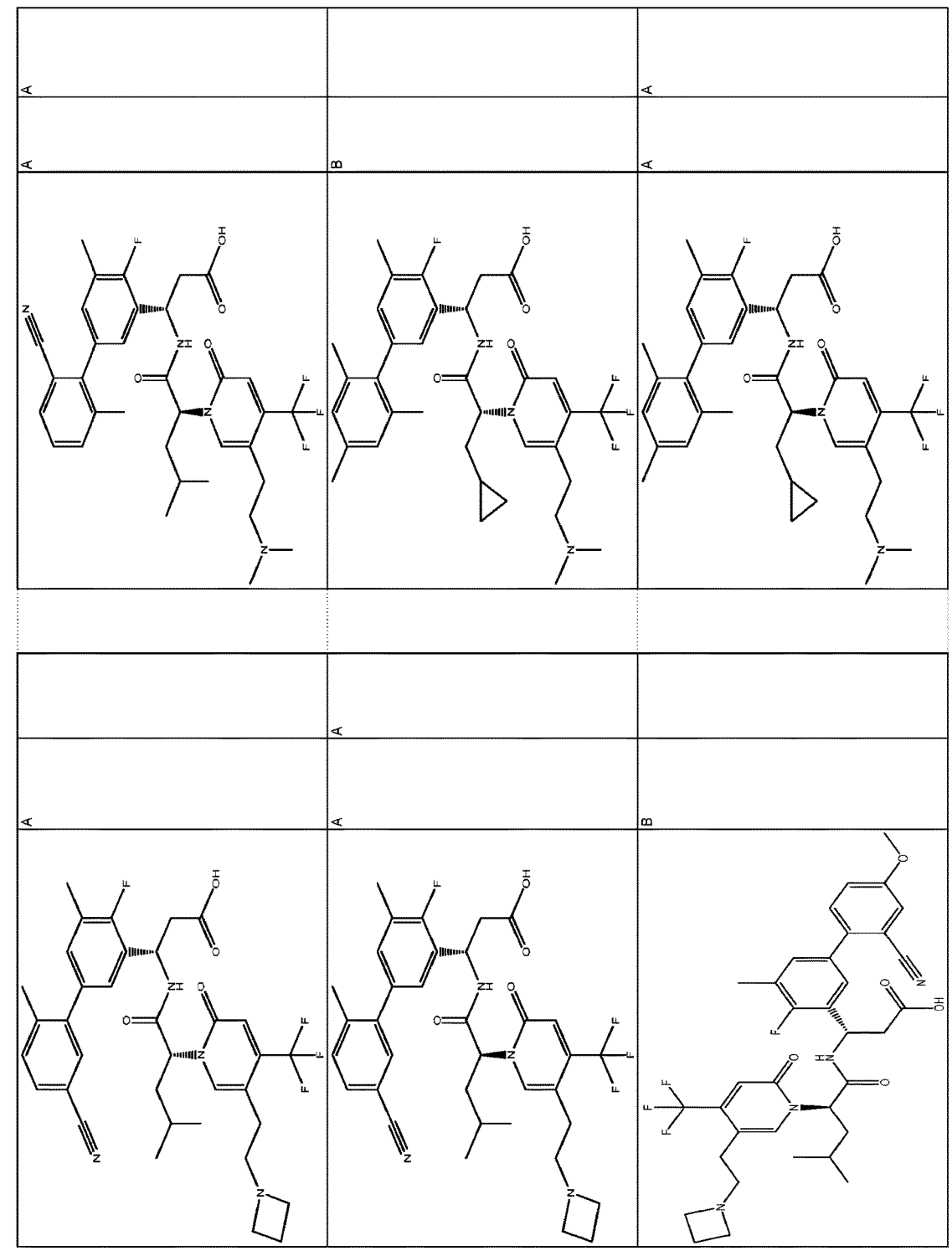
Figure 1:
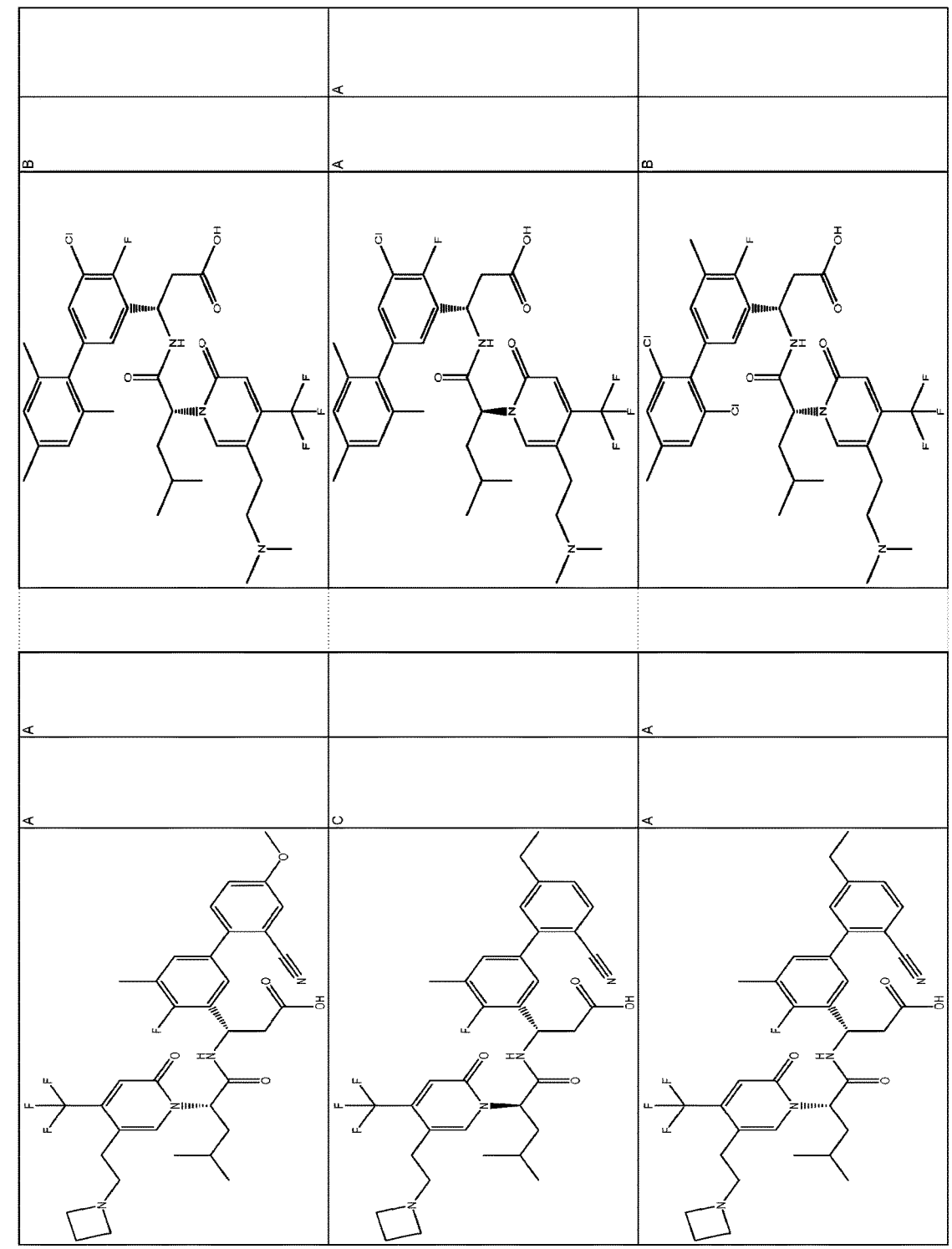
Figure 1:
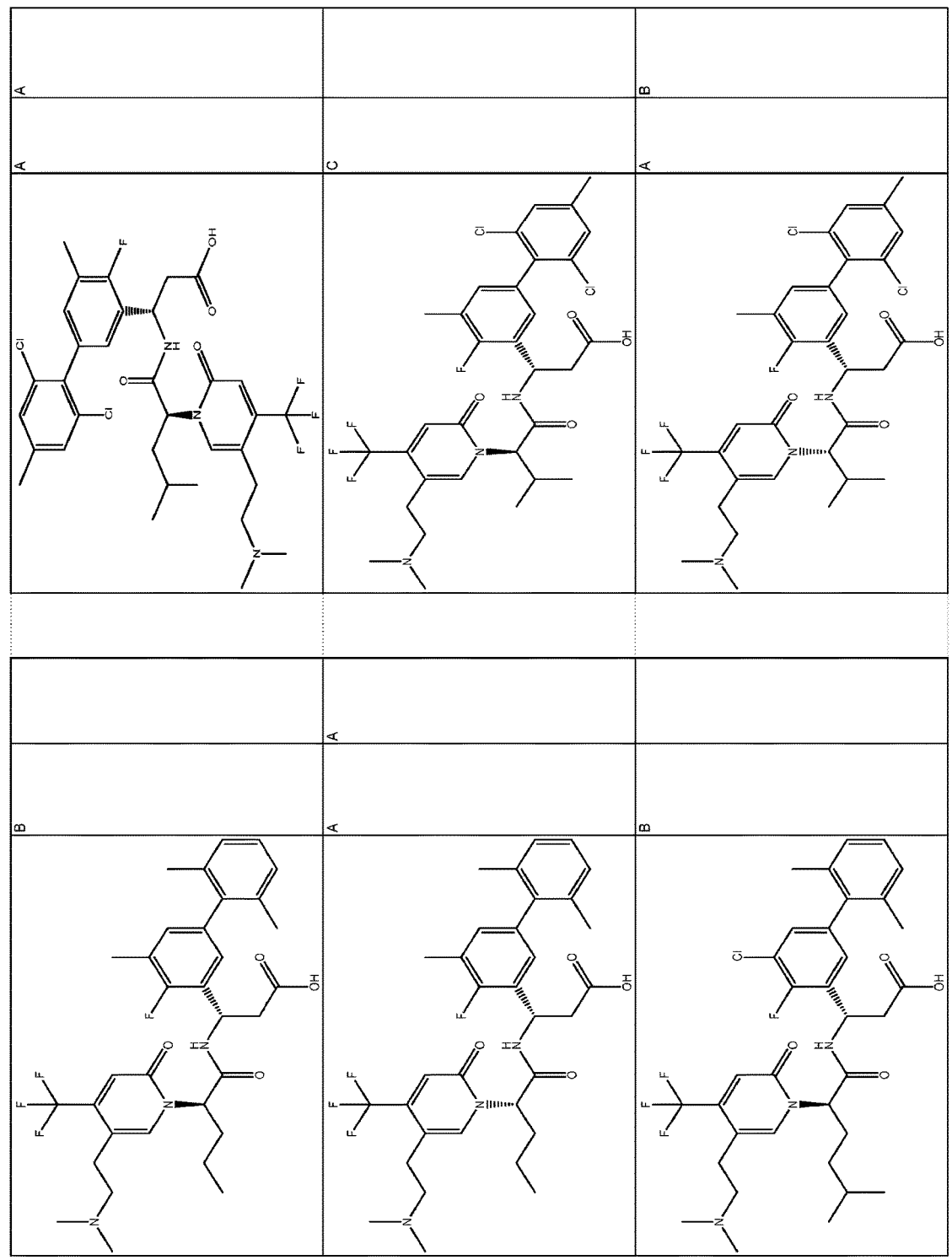
Figure 1:
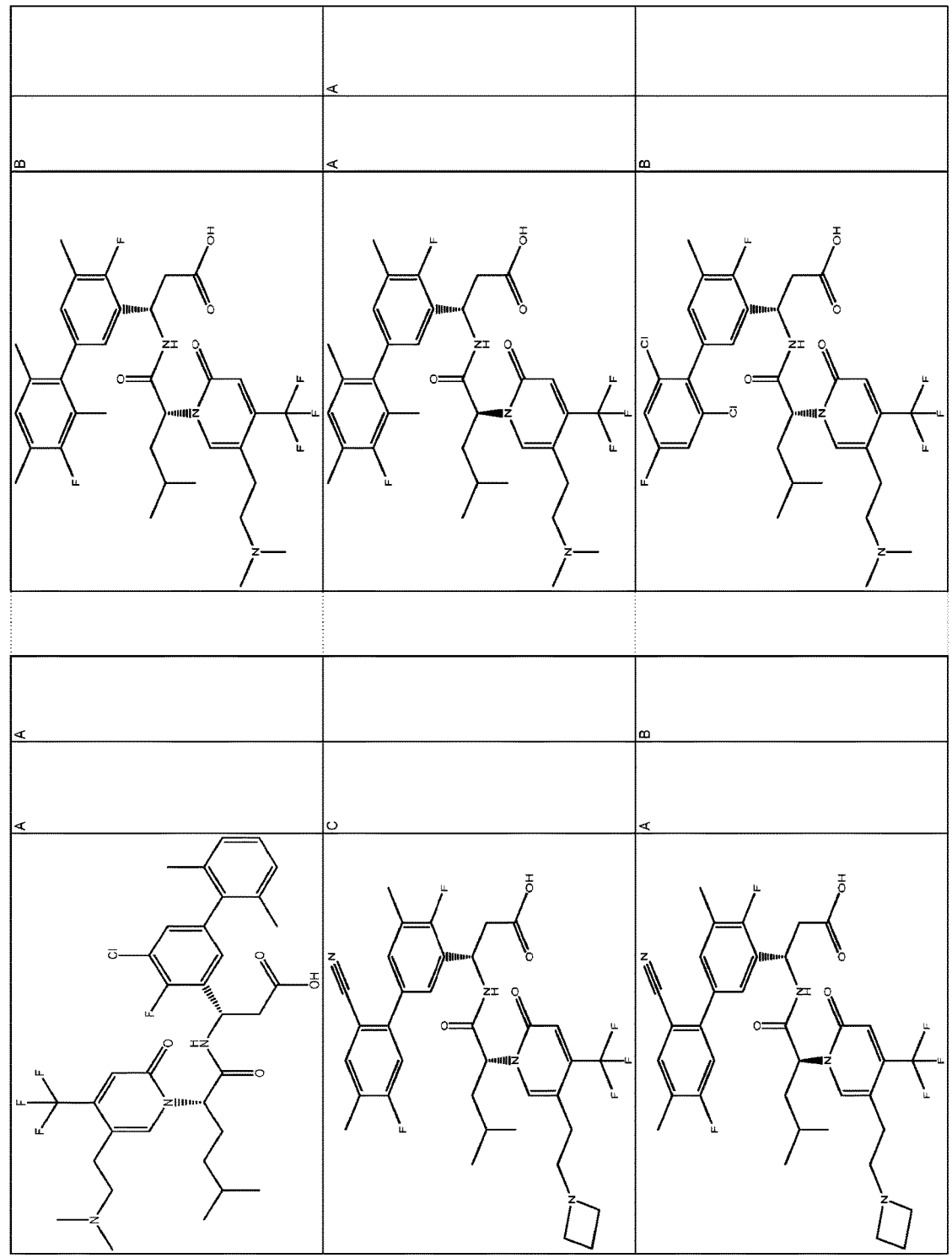
Figure 1:
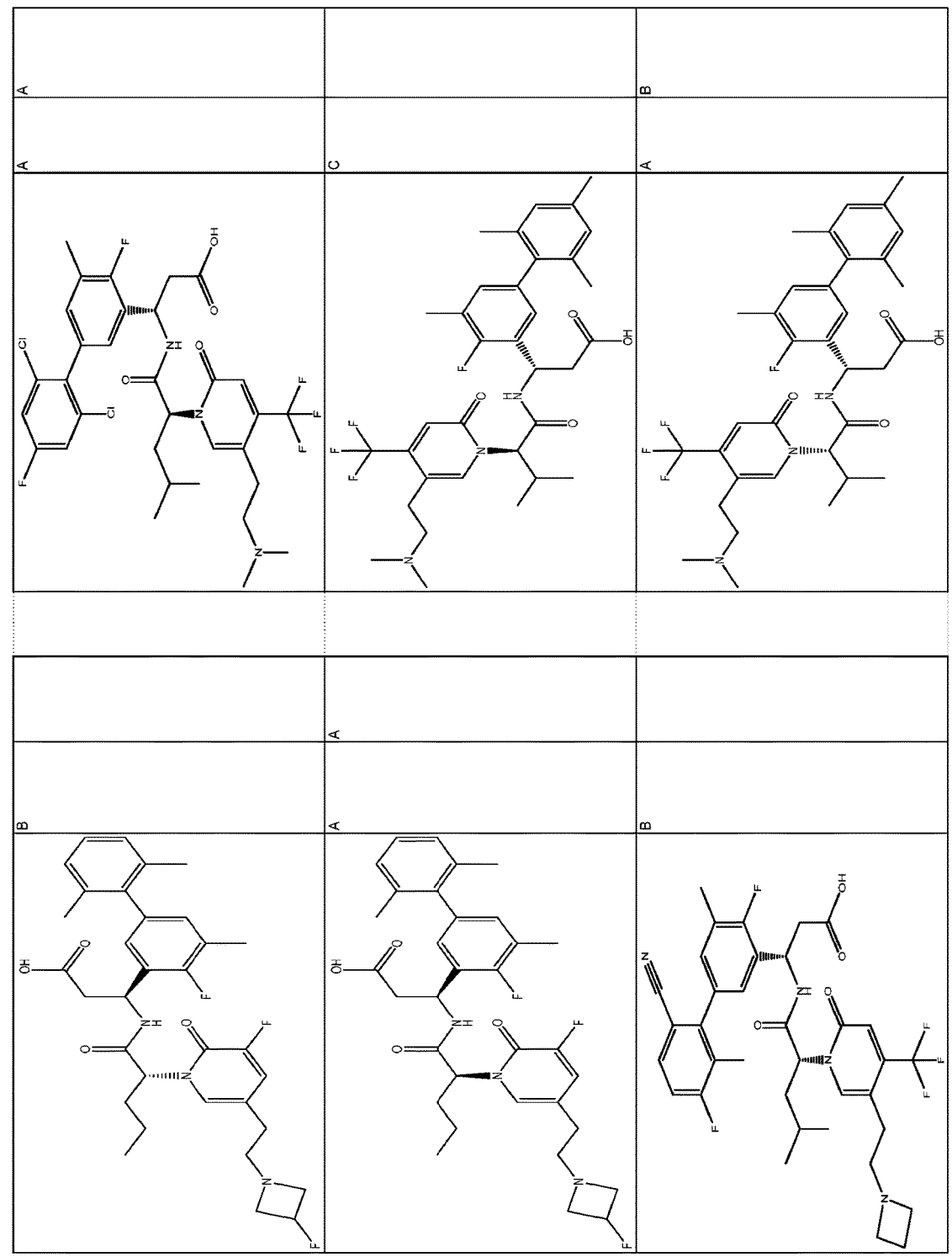
Figure 1:
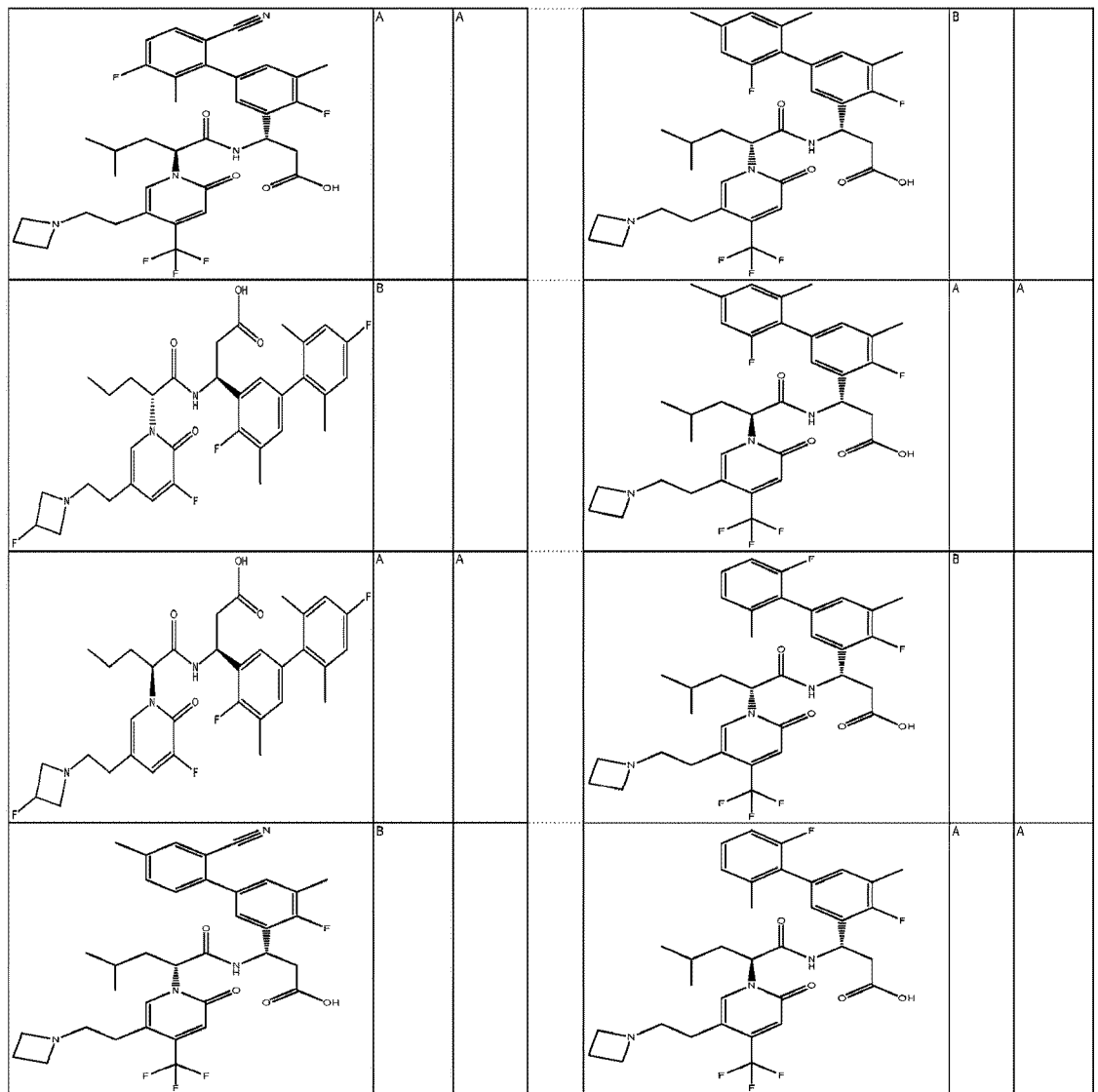
Figure 1:
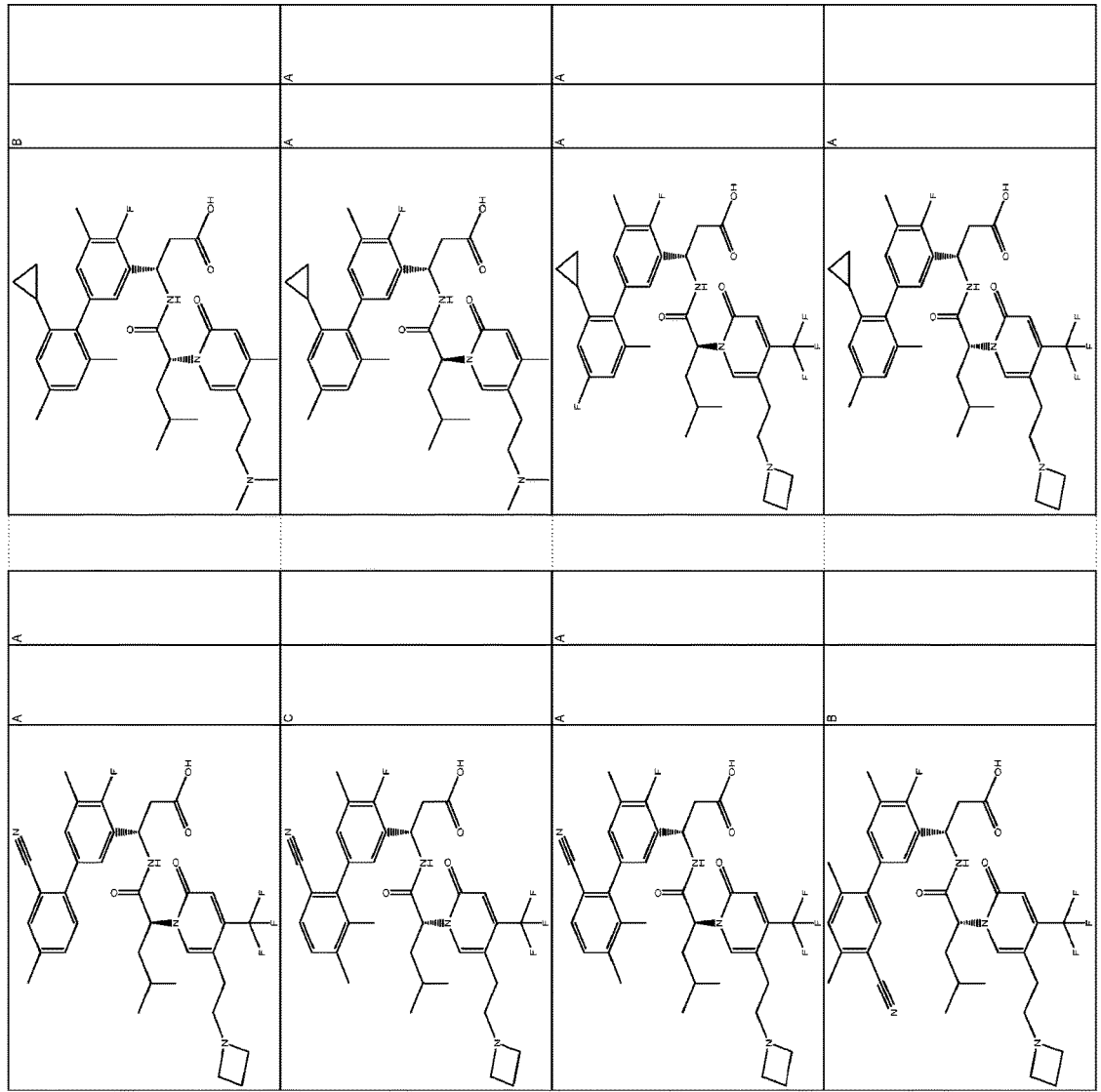
Figure 1:
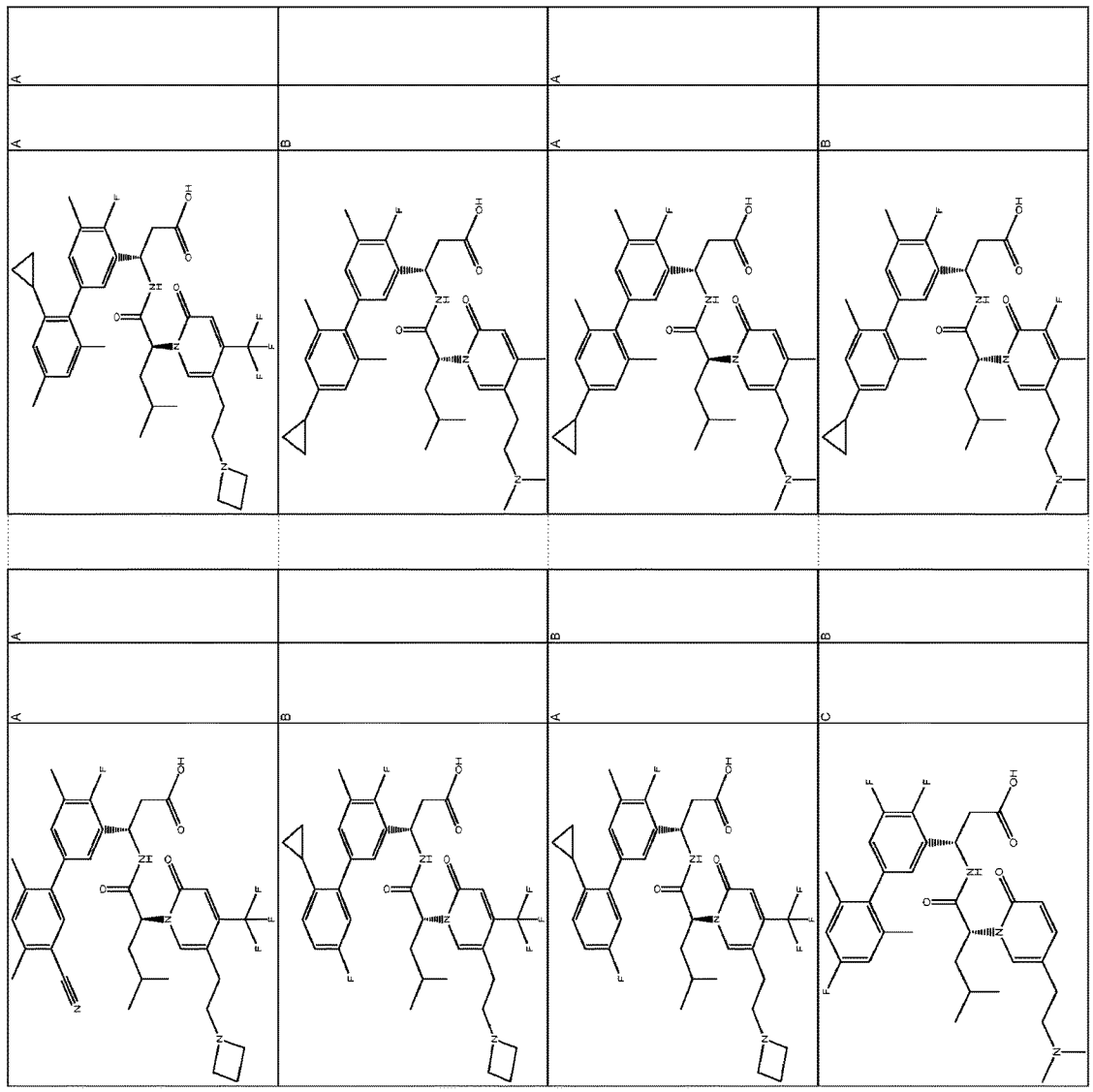
Figure 1:
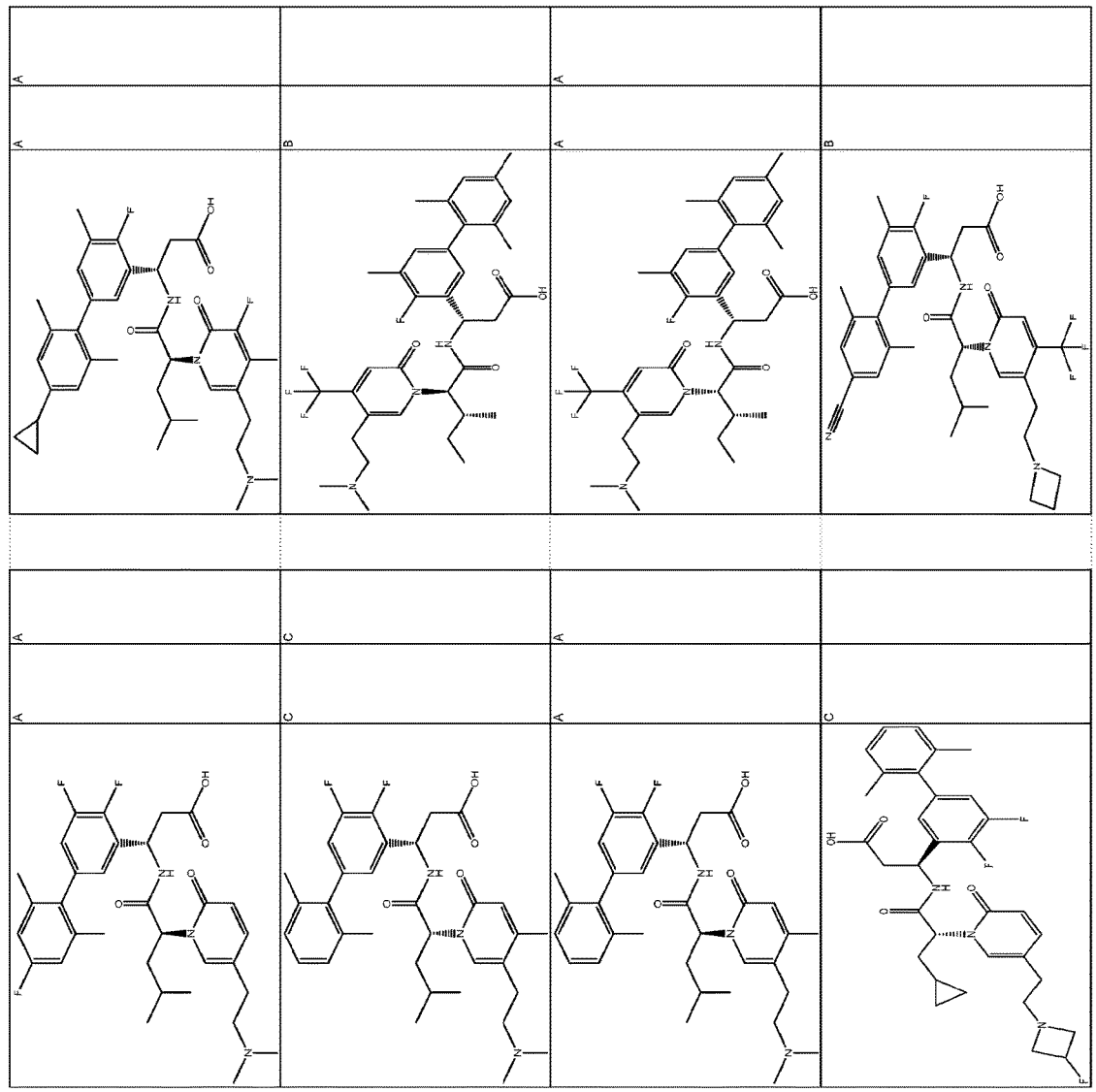
Figure 1:
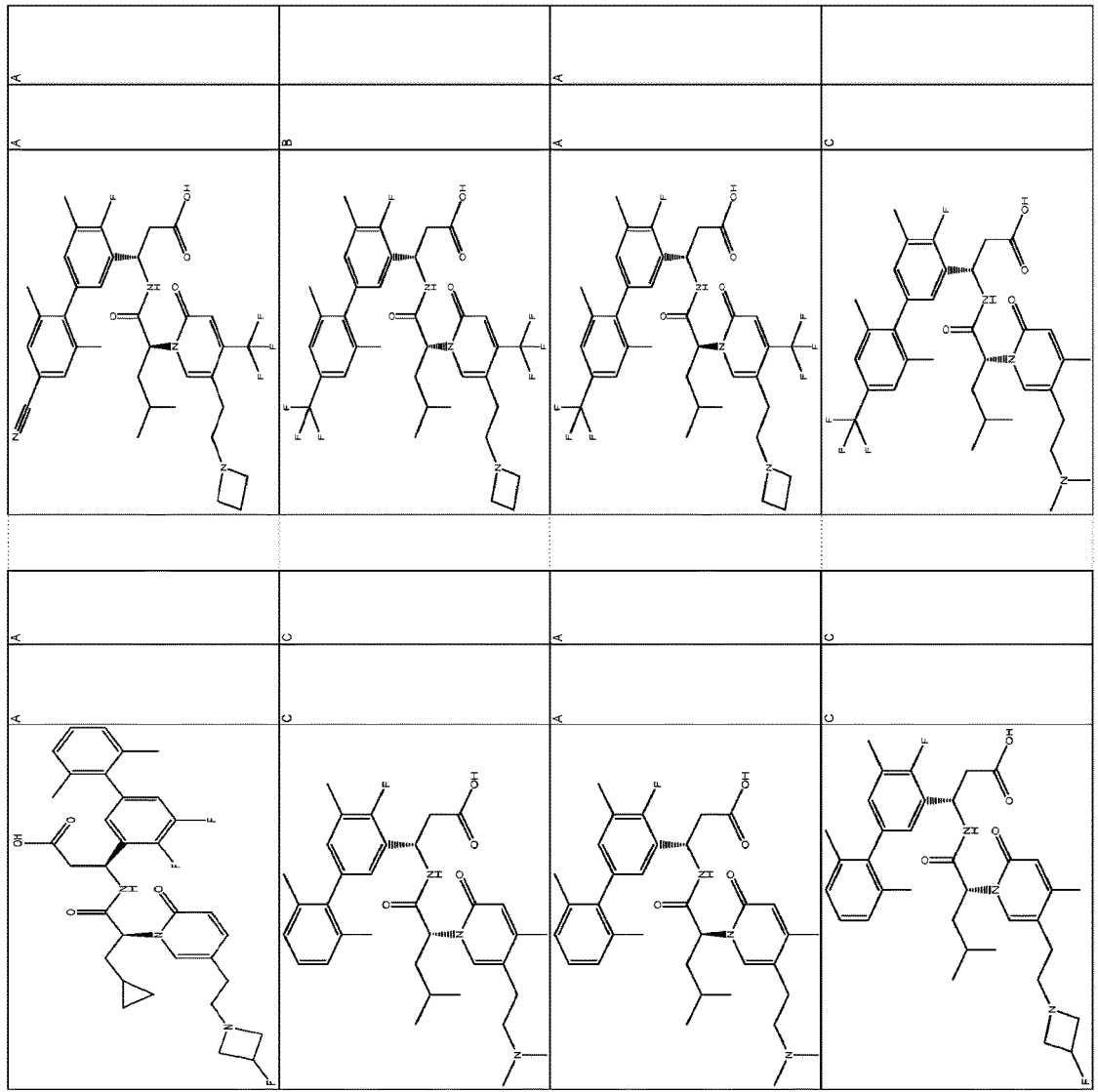
Figure 1:
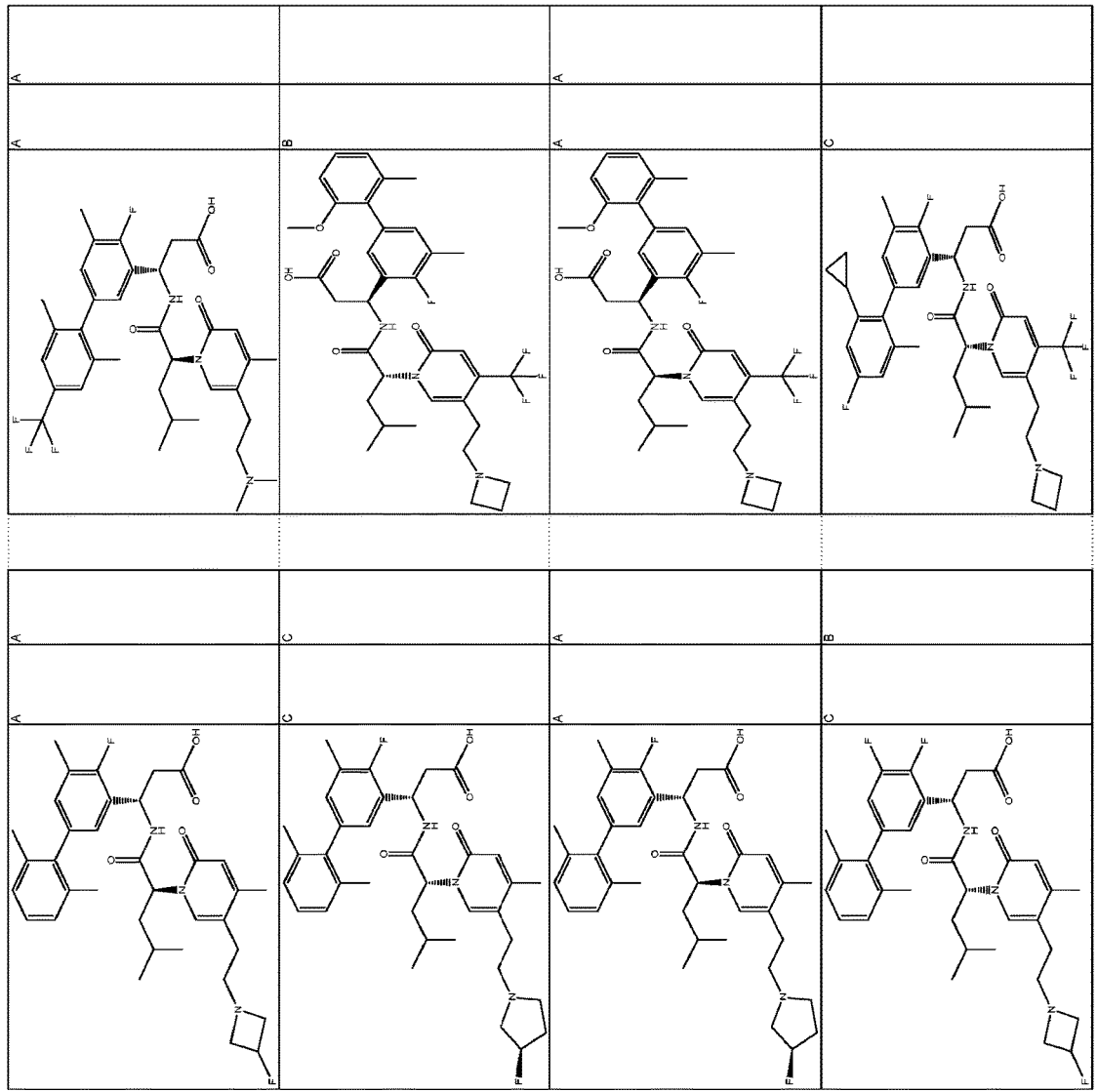
Figure 1:
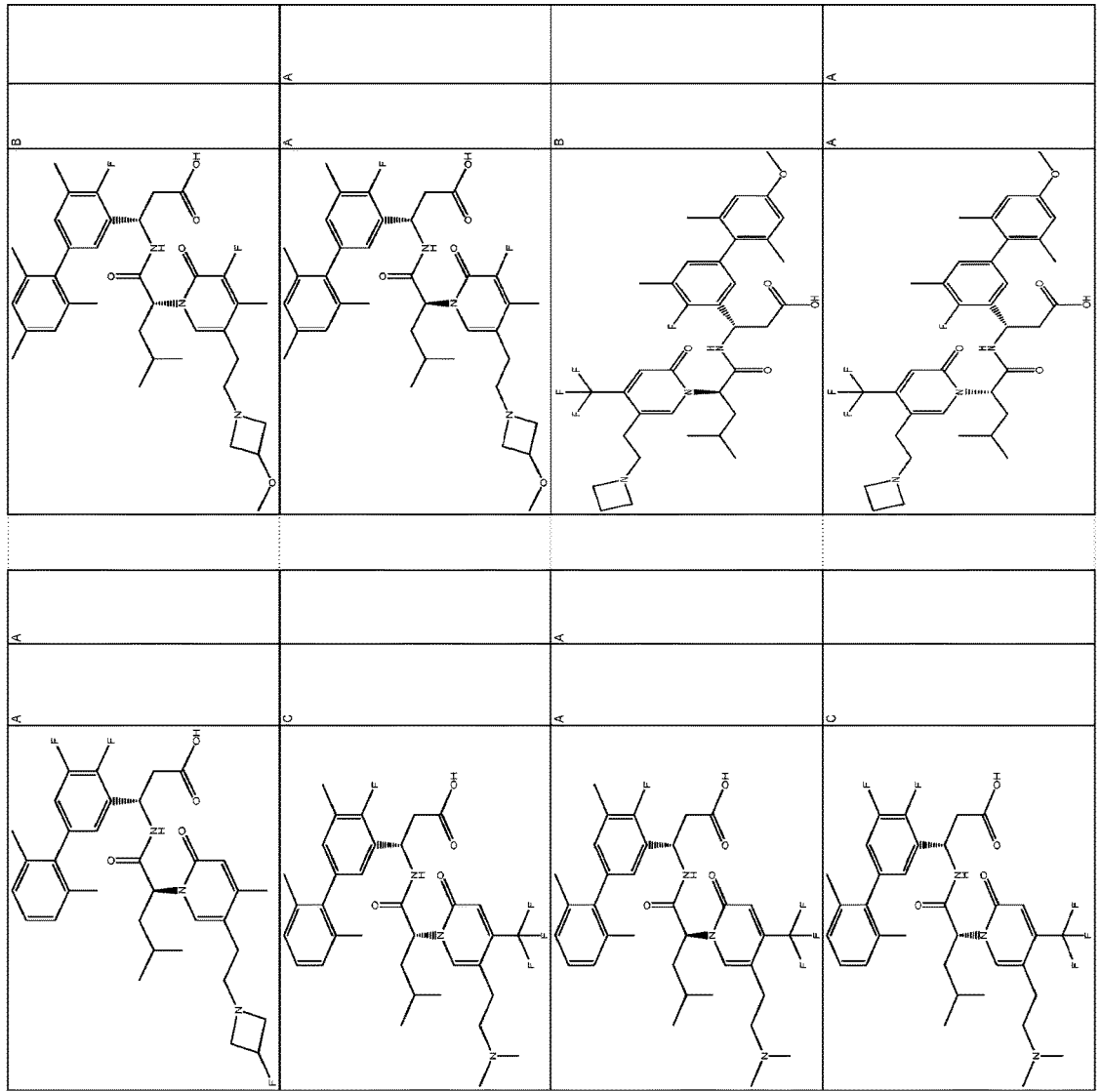
Figure 1:
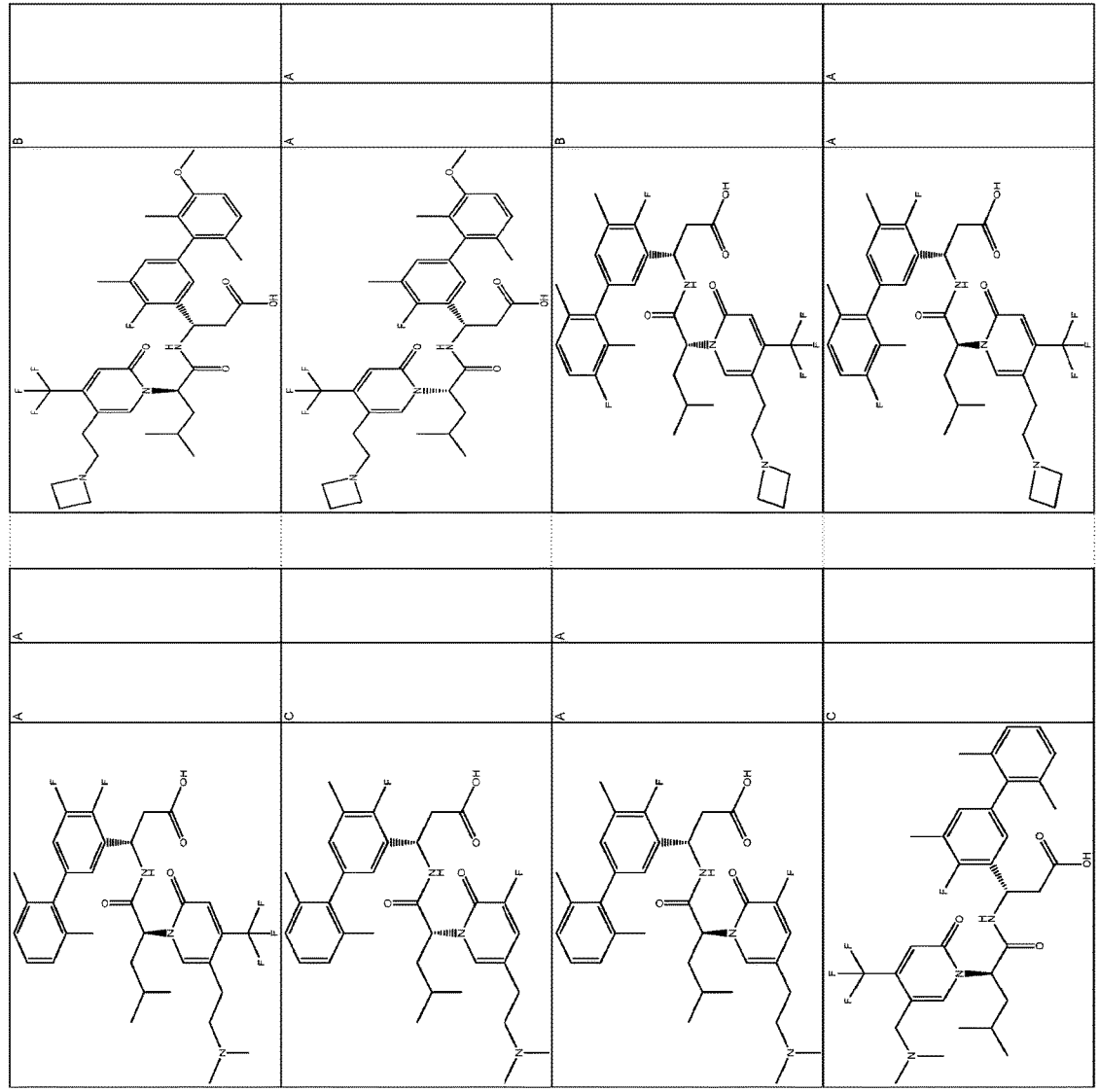
Figure 1:
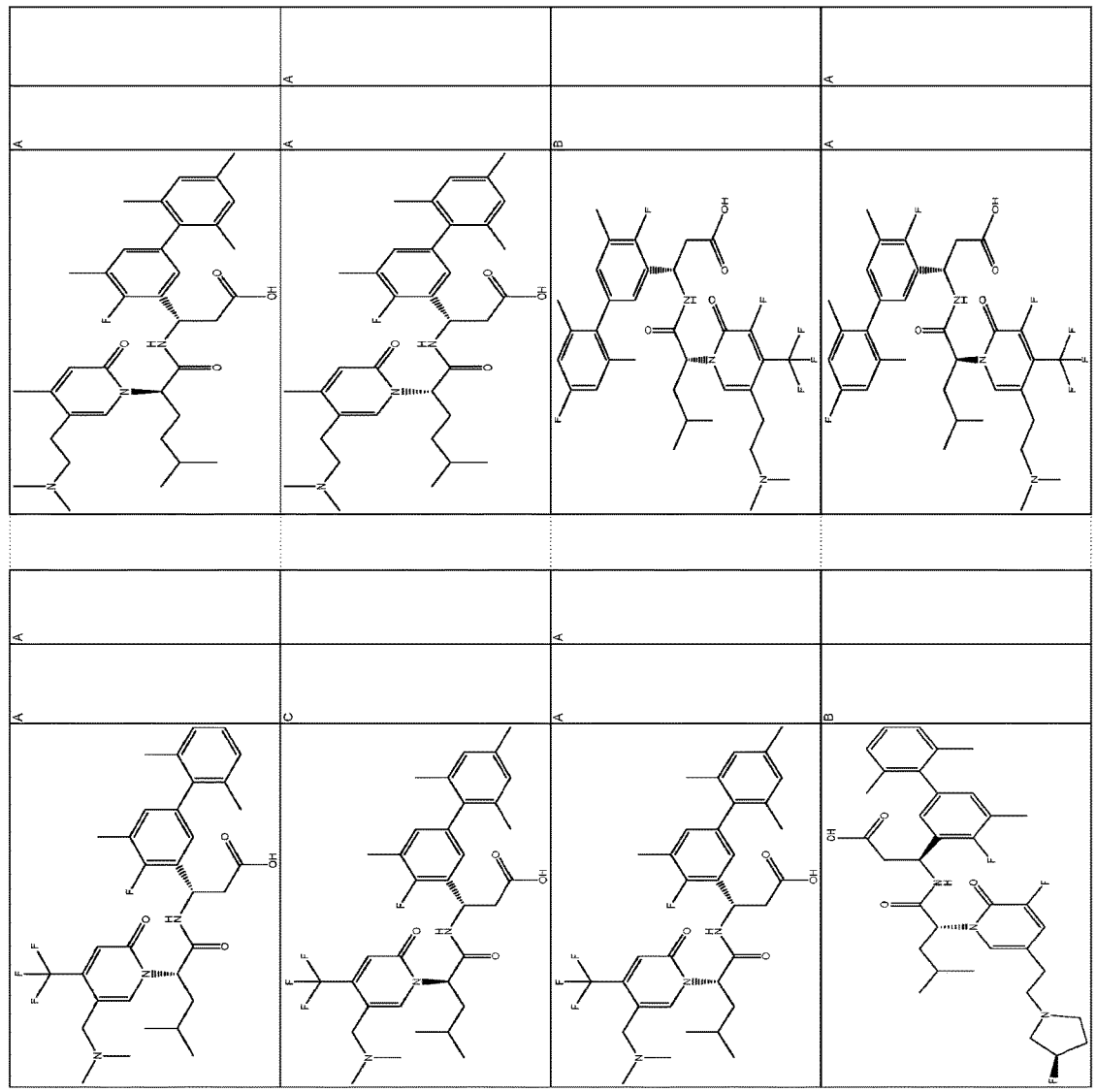
Figure 1:
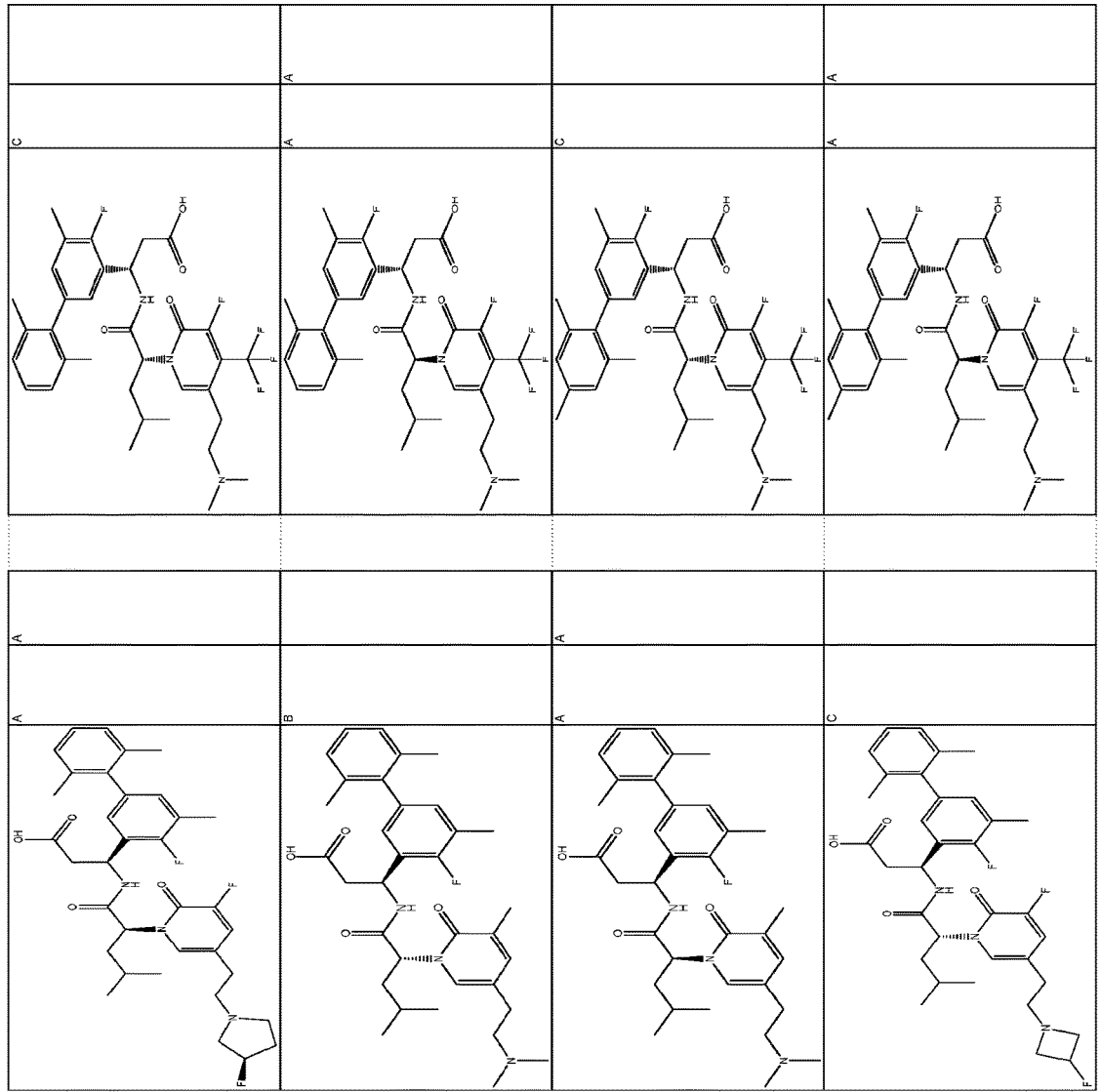
Figure 1:
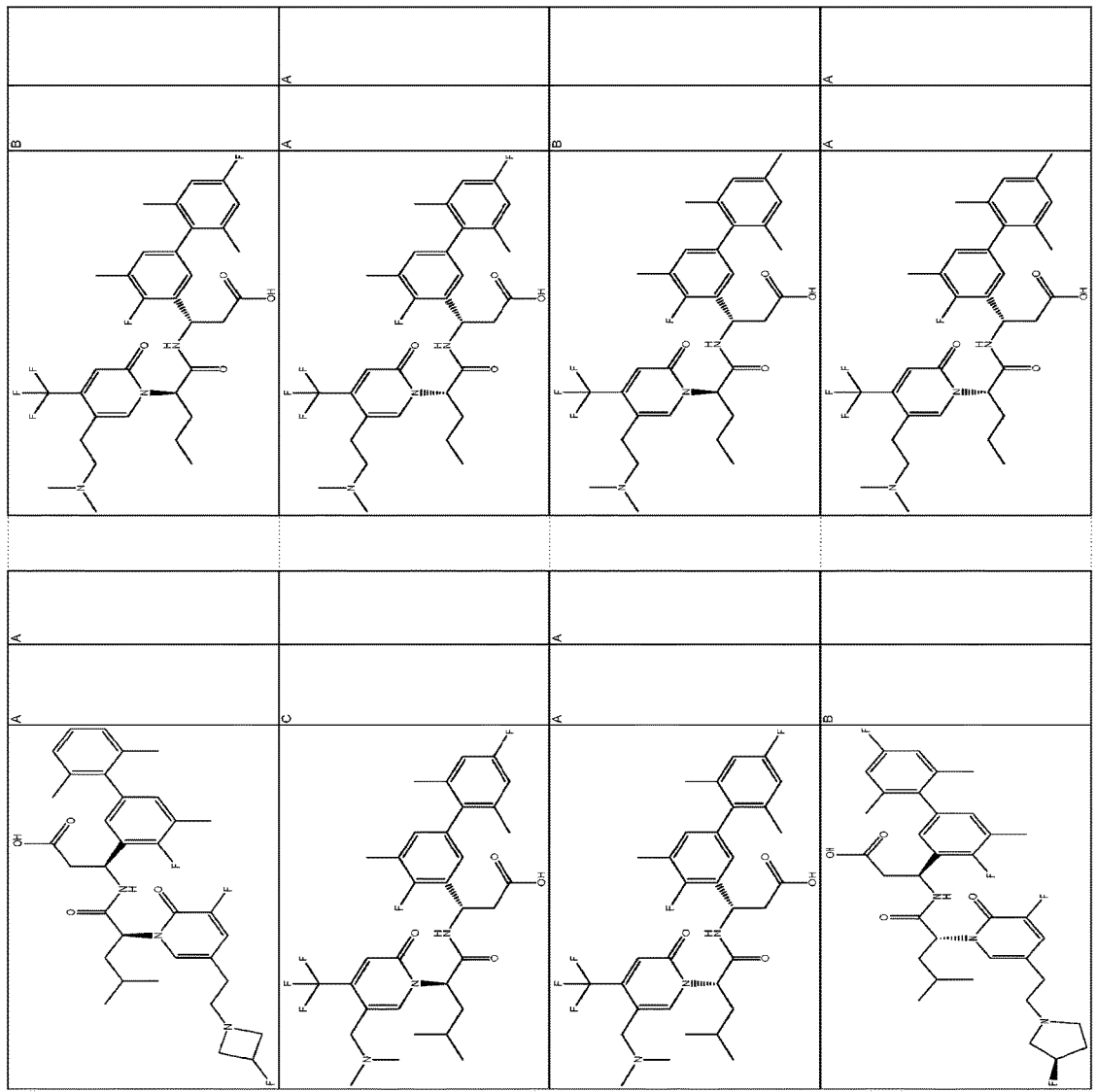
Figure 1:
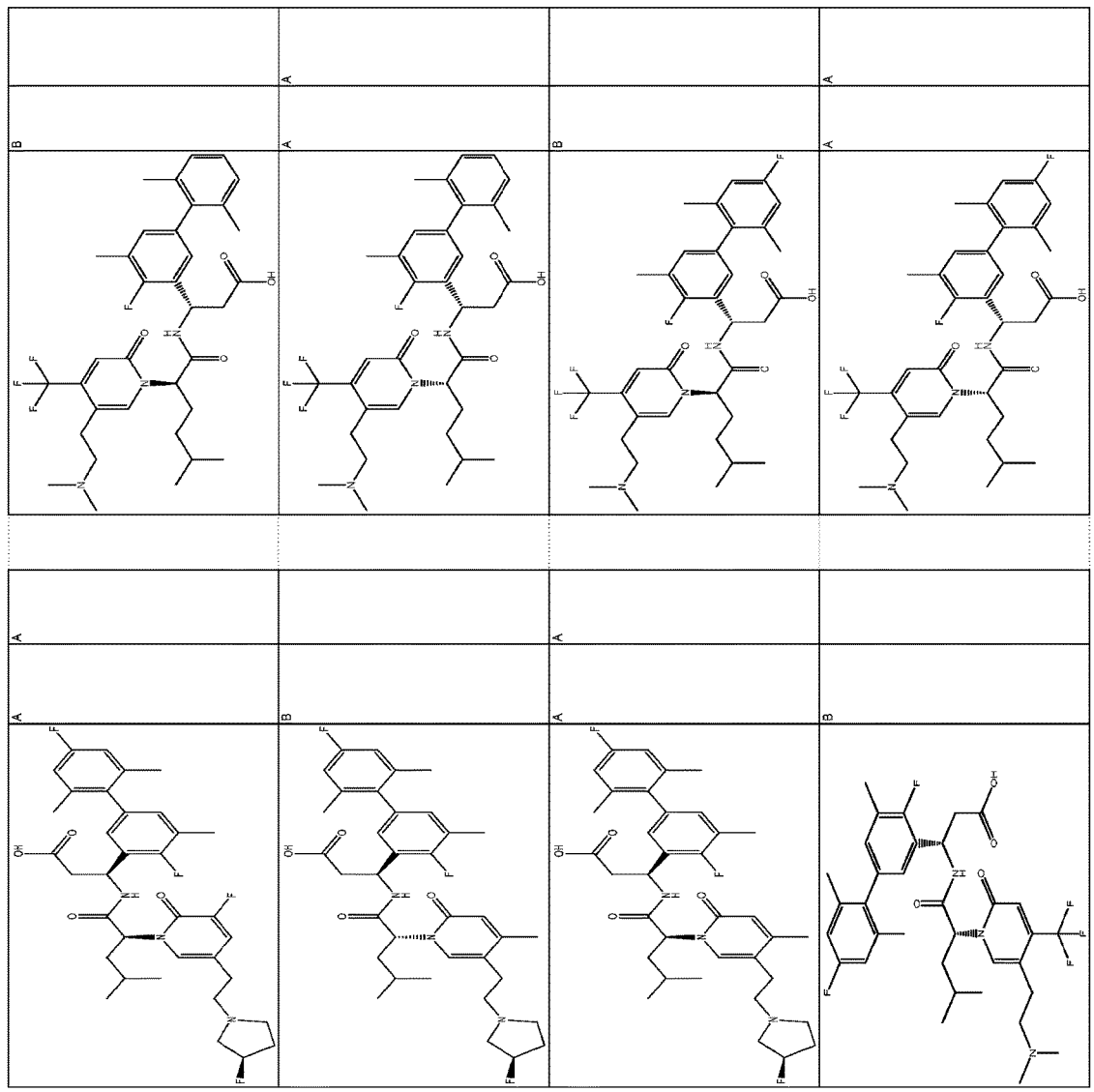
Figure 1:
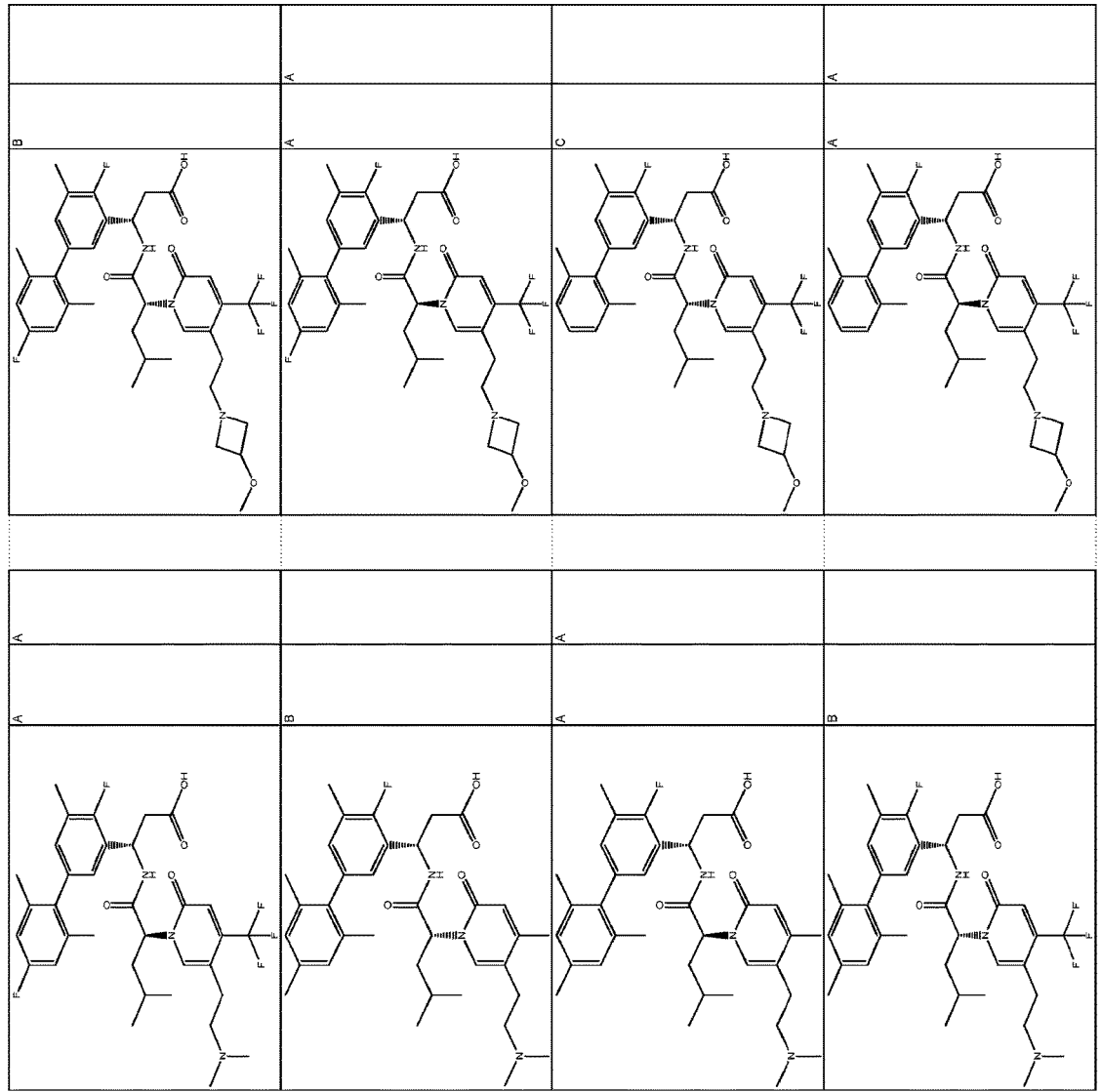
Figure 1:
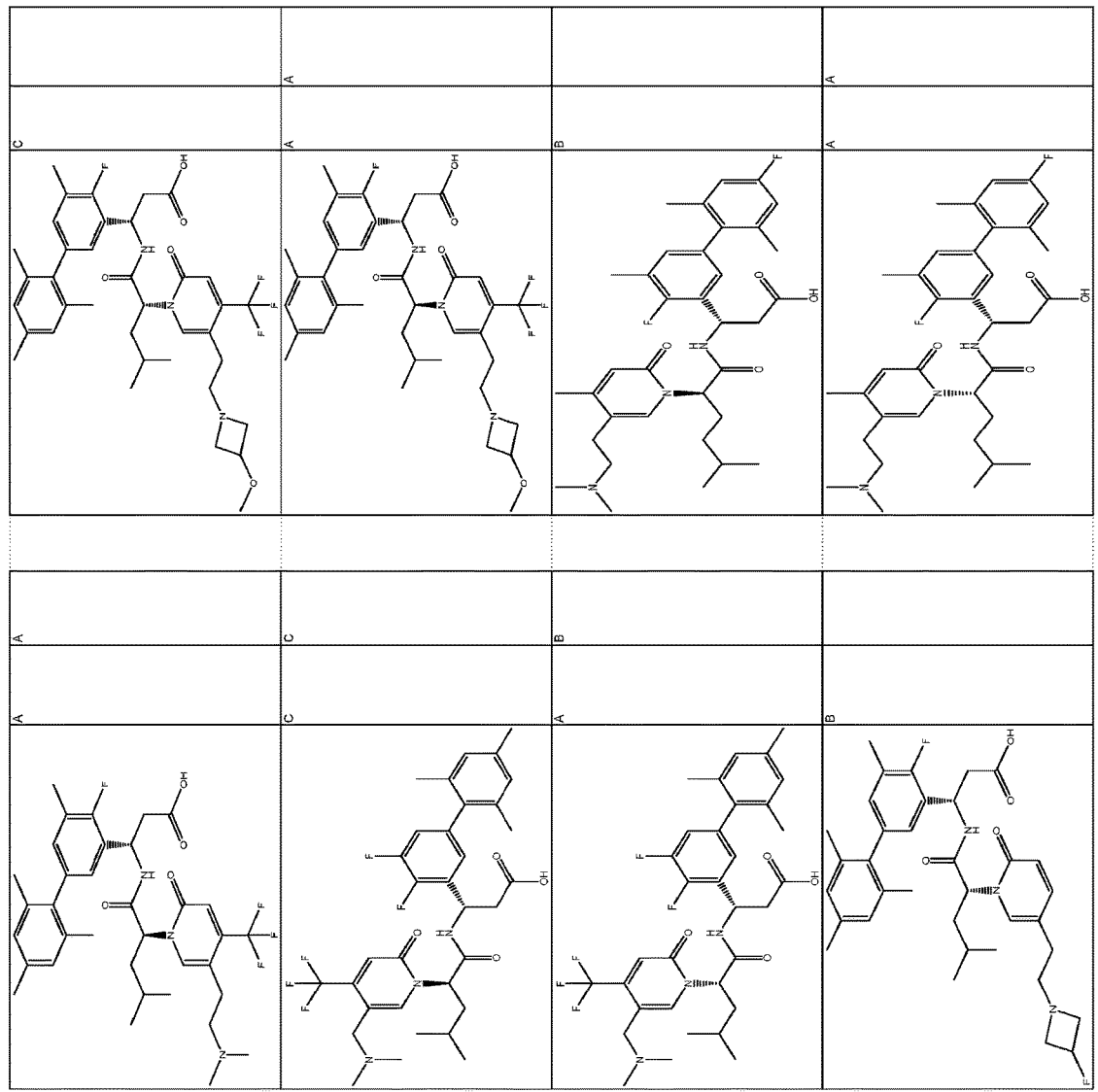
Figure 1:
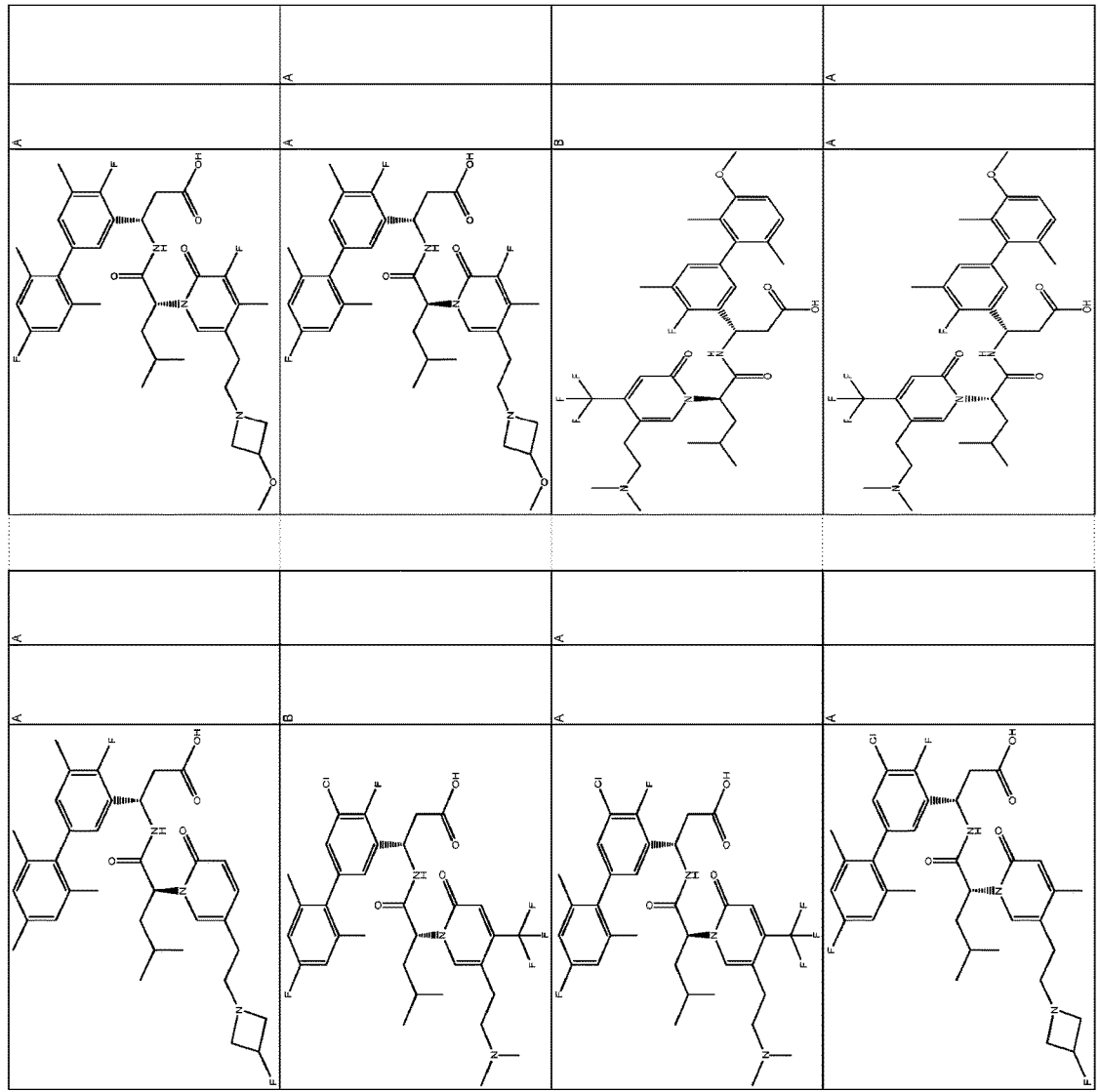
Figure 1:
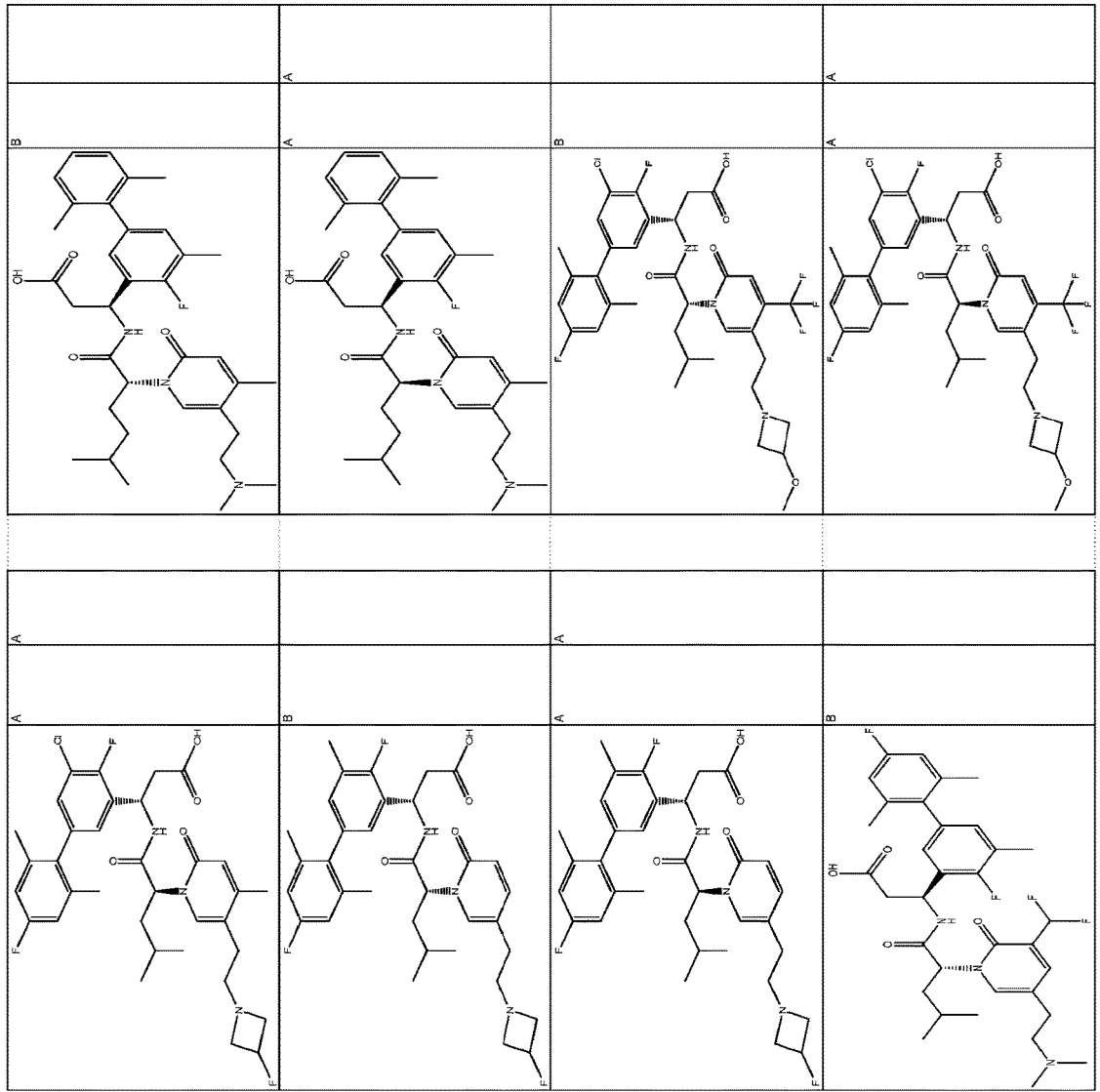
Figure 1:
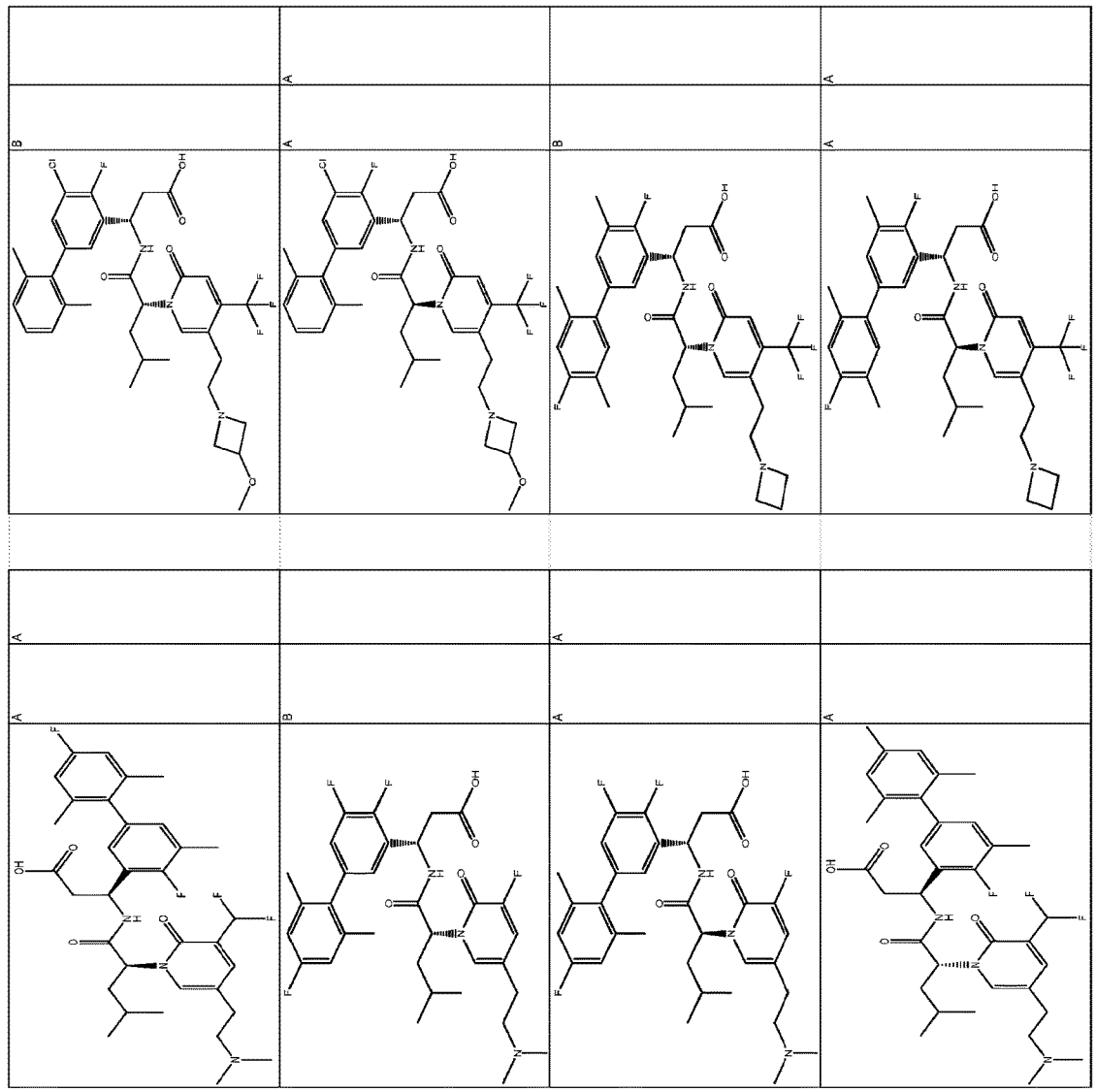
Figure 1:
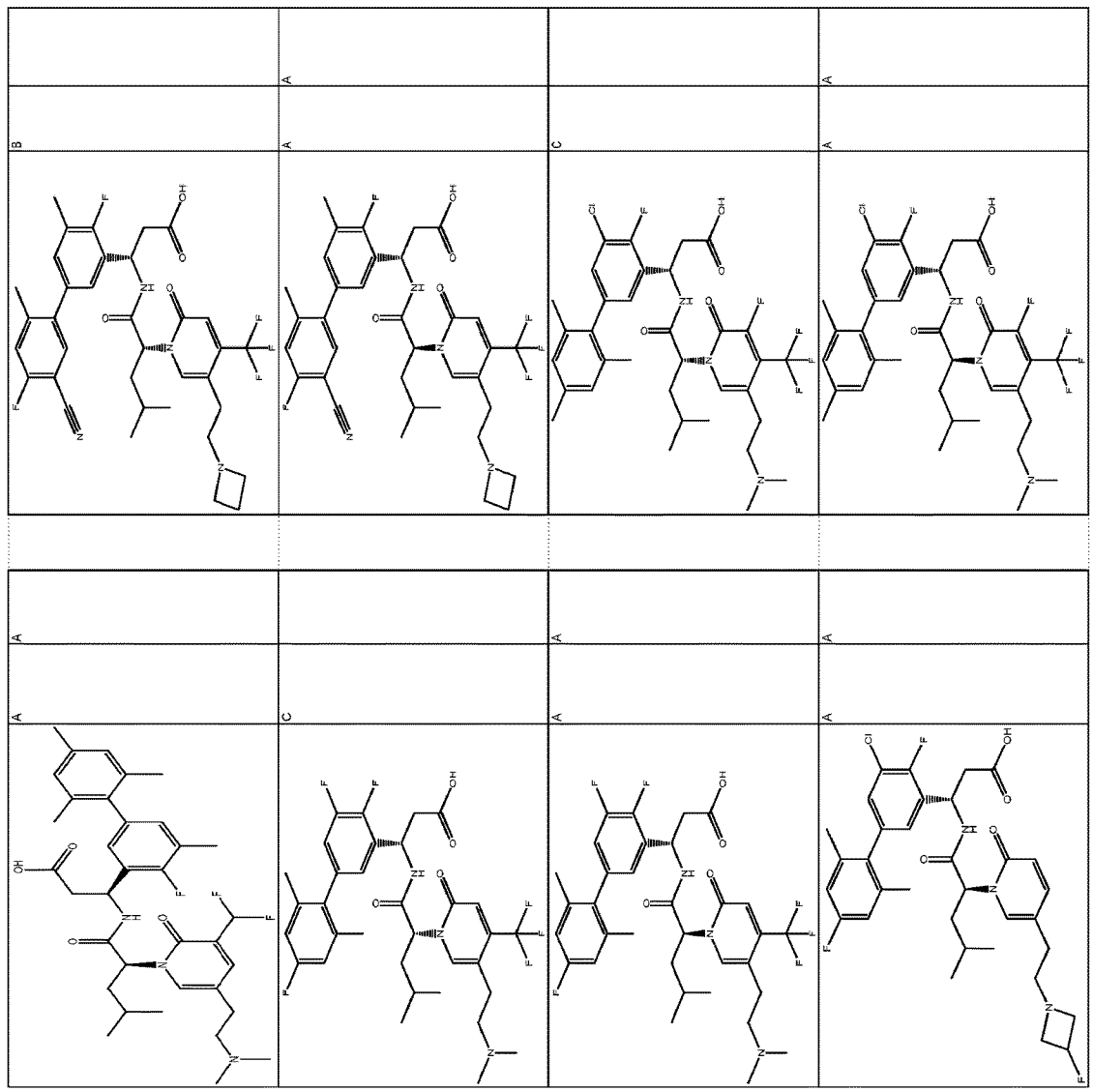
Figure 1:
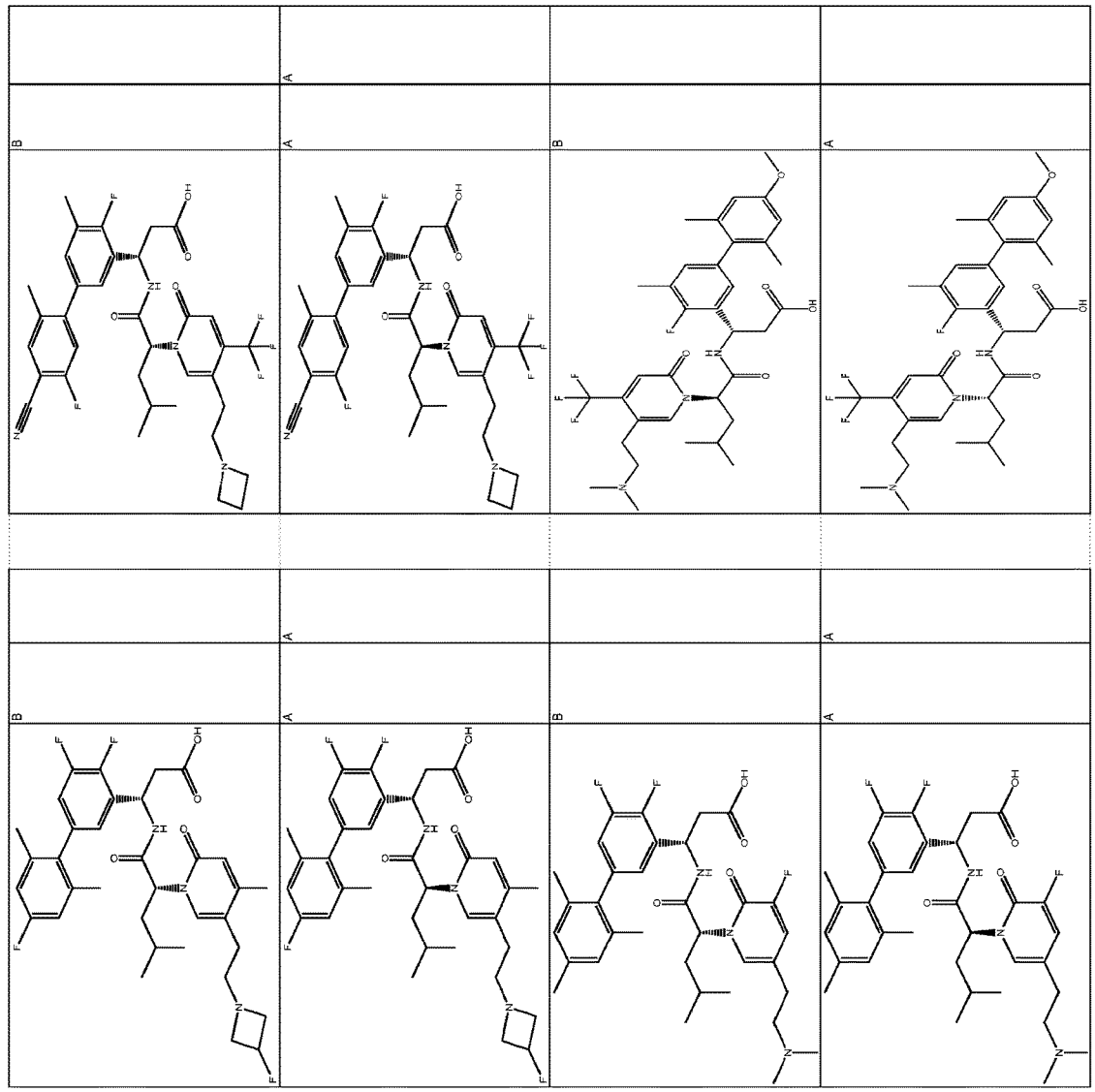
Figure 1:
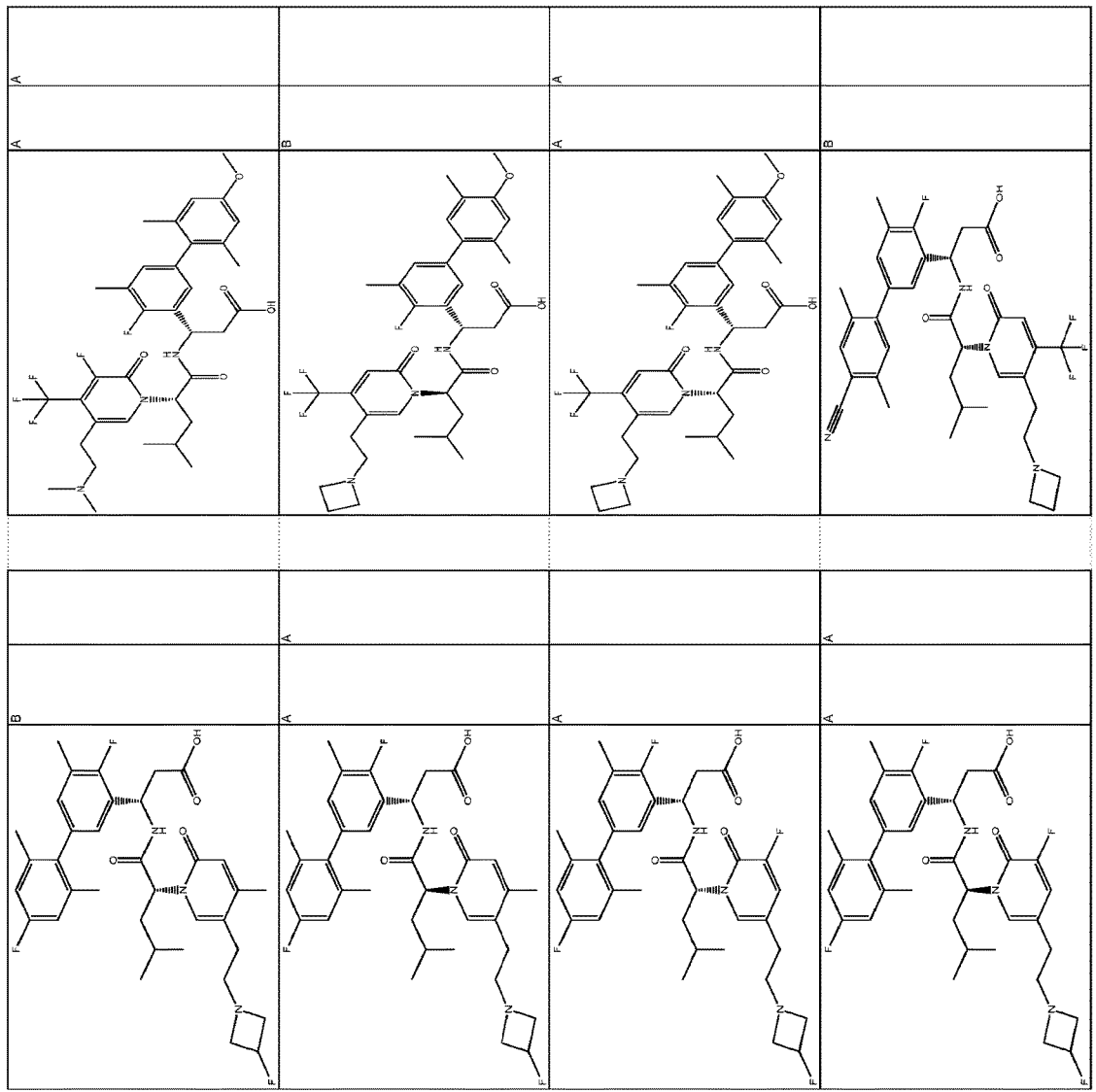
Figure 1:
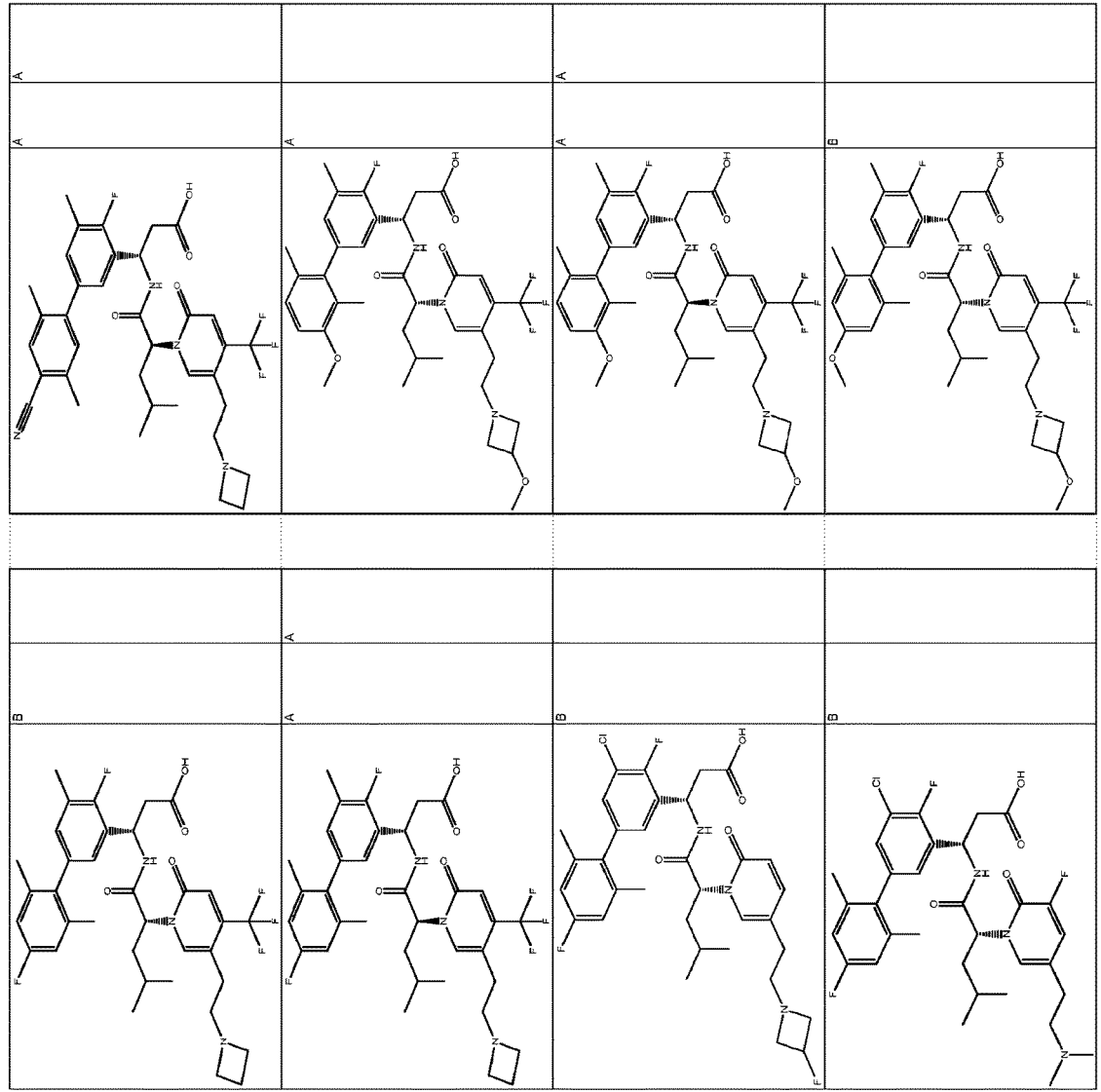
Figure 1:
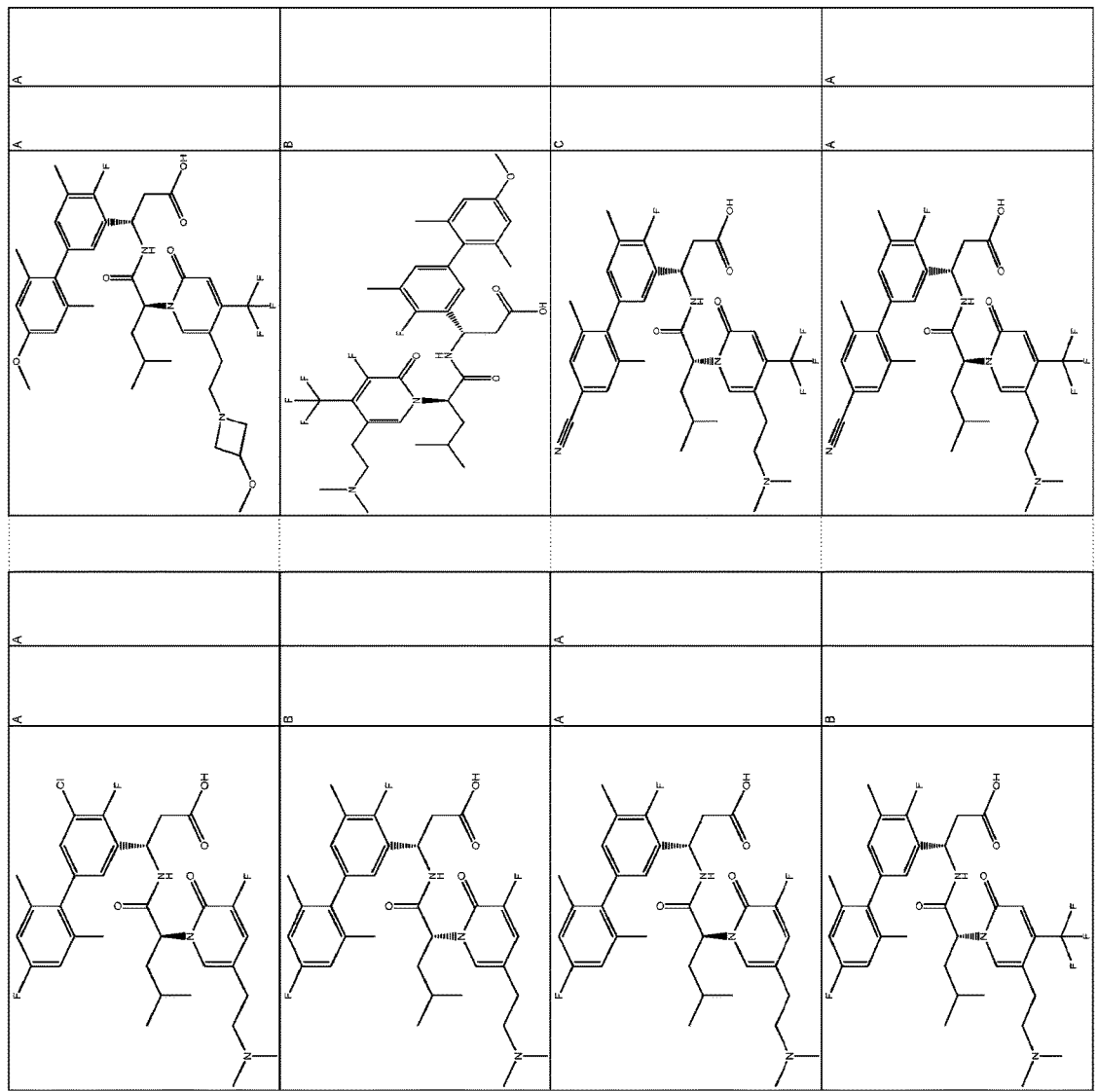
Figure 1:
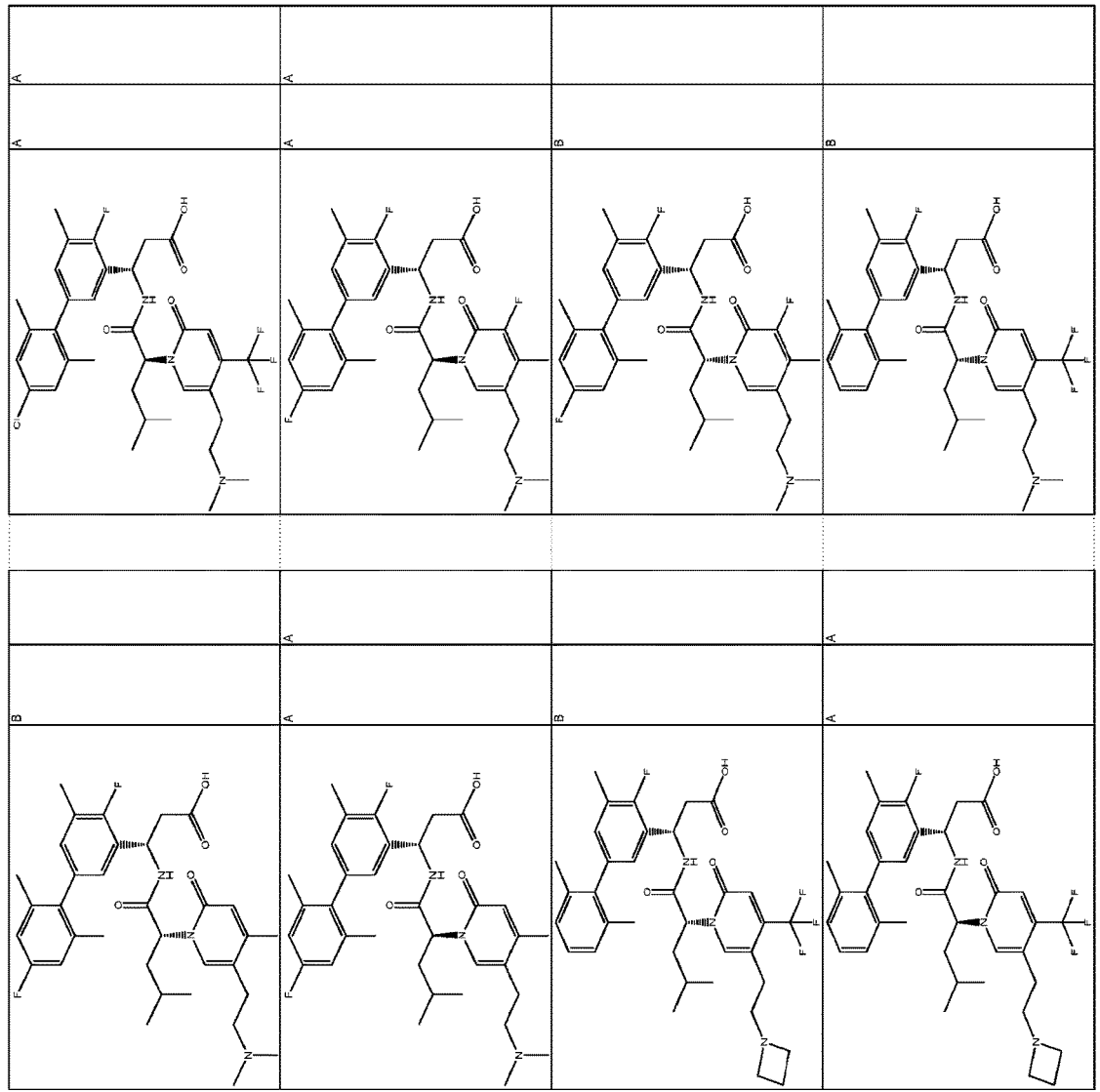

In certain embodiments, the invention relates to compounds that antagonize $\alpha_4\beta_7$ integrin. The compounds will be useful for the treatment of diseases that are treatable by the inhibition of $\alpha_4\beta_7$ integrin (e.g., Crohn's disease (CD), and ulcerative colitis (UC)).

Definitions

For convenience, before further description of the present invention, certain terms employed in the specification, examples and appended claims are collected here. These definitions should be read in light of the remainder of the disclosure and understood as by a person of skill in the art. Unless defined otherwise, all technical and scientific terms used herein have the same meaning as commonly understood by a person of ordinary skill in the art.

In order for the present invention to be more readily understood, certain terms and phrases are defined below and throughout the specification.

The articles "a" and "an" are used herein to refer to one or to more than one (i.e., to at least one) of the grammatical object of the article. By way of example, "an element" means one element or more than one element.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

Certain compounds contained in compositions of the present invention may exist in particular geometric or stereoisomeric forms. In addition, polymers of the present invention may also be optically active. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

If, for instance, a particular enantiomer of compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

Structures depicted herein are also meant to include compounds that differ only in the presence of one or more isotopically enriched atoms. For example, compounds produced by the replacement of a hydrogen with deuterium or tritium, or of a carbon with a $^{13}$C- or $^{14}$C-enriched carbon are within the scope of this invention.

The terms "α4β7", "a4B7", "a4b7", "alpha-4 beta-7" and "alpha 4 beta 7" and the like as used herein all refer to $\alpha_4\beta_7$.

The phrase "pharmaceutically acceptable excipient" or "pharmaceutically acceptable carrier" as used herein means a pharmaceutically acceptable material, composition or vehicle, such as a liquid or solid filler, diluent, excipient, solvent or encapsulating material, involved in carrying or transporting the subject chemical from one organ or portion of the body, to another organ or portion of the body. Each carrier must be "acceptable" in the sense of being compatible with the other ingredients of the formulation, not injurious to the patient, and substantially non-pyrogenic. Some examples of materials which can serve as pharmaceutically acceptable carriers include: (1) sugars, such as lactose, glucose, and sucrose; (2) starches, such as corn starch and potato starch; (3) cellulose, and its derivatives, such as sodium carboxymethyl cellulose, ethyl cellulose, and cellulose acetate; (4) powdered tragacanth; (5) malt; (6) gelatin; (7) talc; (8) excipients, such as cocoa butter; (9) oils, such as peanut oil, cottonseed oil, safflower oil, sesame oil, olive oil, corn oil, and soybean oil; (10) glycols, such as propylene glycol; (11) polyols, such as glycerin, sorbitol, mannitol, and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations. In certain embodiments, pharmaceutical compositions of the present invention are non-pyrogenic, i.e., do not induce significant temperature elevations when administered to a patient.

The term "pharmaceutically acceptable salts" refers to the relatively non-toxic, inorganic and organic acid addition salts of the compound(s). These salts can be prepared in situ during the final isolation and purification of the compound(s), or by separately reacting a purified compound(s) in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, naphthylate, mesylate, glucoheptonate, lactobionate, and laurylsulphonate salts, and the like. (See, for example, Berge et al. (1977) "Pharmaceutical Salts", *J. Pharm. Sci.* 66: 1-19.)

In other cases, the compounds useful in the methods of the present invention may contain one or more acidic functional groups and, thus, are capable of forming pharmaceutically acceptable salts with pharmaceutically acceptable bases. The term "pharmaceutically acceptable salts" in these instances refers to the relatively non-toxic inorganic and organic base addition salts of a compound(s). These salts can likewise be prepared in situ during the final isolation and purification of the compound(s), or by separately reacting the purified compound(s) in its free acid form with a suitable base, such as the hydroxide, carbonate, or bicarbonate of a pharmaceutically acceptable metal cation, with ammonia, or with a pharmaceutically acceptable organic primary, secondary, or tertiary amine. Representative alkali or alkaline earth salts include the lithium, sodium, potassium, calcium, magnesium, and aluminum salts, and the like. Representative organic amines useful for the formation of base addition salts include ethylamine, diethylamine, ethylenediamine, ethanolamine, diethanolamine, piperazine, and the like (see, for example, Berge et al., supra).

A "therapeutically effective amount" (or "effective amount") of a compound with respect to use in treatment, refers to an amount of the compound in a preparation which, when administered as part of a desired dosage regimen (to a mammal, preferably a human) alleviates a symptom, ameliorates a condition, or slows the onset of disease conditions according to clinically acceptable standards for the disorder or condition to be treated or the cosmetic purpose, e.g., at a reasonable benefit/risk ratio applicable to any medical treatment.

The term "prophylactic or therapeutic" treatment is art-recognized and includes administration to the host of one or more of the subject compositions. If it is administered prior to clinical manifestation of the unwanted condition (e.g., disease or other unwanted state of the host animal) then the treatment is prophylactic, (i.e., it protects the host against developing the unwanted condition), whereas if it is administered after manifestation of the unwanted condition, the treatment is therapeutic, (i.e., it is intended to diminish, ameliorate, or stabilize the existing unwanted condition or side effects thereof).

The term "patient" refers to a mammal in need of a particular treatment. In certain embodiments, a patient is a primate, canine, feline, or equine. In certain embodiments, a patient is a human.

An aliphatic chain comprises the classes of alkyl, alkenyl and alkynyl defined below. A straight aliphatic chain is limited to unbranched carbon chain moieties. As used herein, the term "aliphatic group" refers to a straight chain, branched-chain, or cyclic aliphatic hydrocarbon group and includes saturated and unsaturated aliphatic groups, such as an alkyl group, an alkenyl group, or an alkynyl group.

"Alkyl" refers to a fully saturated cyclic or acyclic, branched or unbranched carbon chain moiety having the number of carbon atoms specified, or 1 up to 30 carbon atoms if no specification is made. For example, alkyl of 1 to 8 carbon atoms refers to moieties such as methyl, ethyl, propyl, butyl, pentyl, hexyl, heptyl, and octyl, and those moieties which are positional isomers of these moieties. Alkyl of 10 to 30 carbon atoms includes decyl, undecyl, dodecyl, tridecyl, tetradecyl, pentadecyl, hexadecyl, heptadecyl, octadecyl, nonadecyl, eicosyl, heneicosyl, docosyl, tricosyl and tetracosyl. In certain embodiments, a straight chain or branched chain alkyl has 30 or fewer carbon atoms in its backbone (e.g., $C_1$-$C_{30}$ for straight chains, $C_3$-$C_{30}$ for branched chains), and more preferably 20 or fewer. Alkyl groups may be substituted or unsubstituted. As used herein, "Me" and —$CH_3$ both refer to methyl.

As used herein, the term "alkylene" refers to an alkyl group having the specified number of carbons, for example from 2 to 12 carbon atoms, that contains two points of attachment to the rest of the compound on its longest carbon chain. Non-limiting examples of alkylene groups include methylene —($CH_2$)—, ethylene —($CH_2CH_2$)—, n-propylene —($CH_2CH_2CH_2$)—, isopropylene —($CH_2CH(CH_3)$)—, and the like. Alkylene groups can be cyclic or acyclic, branched or unbranched carbon chain moiety, and may be optionally substituted with one or more substituents.

"Cycloalkyl" means mono- or bicyclic or bridged or spirocyclic, or polycyclic saturated carbocyclic rings, each having from 3 to 12 carbon atoms. Likewise, preferred cycloalkyls have from 3-10 carbon atoms in their ring structure, and more preferably have 3-6 carbons in the ring structure. Cycloalkyl groups may be substituted or unsubstituted.

Unless the number of carbons is otherwise specified, "lower alkyl," as used herein, means an alkyl group, as defined above, but having from one to ten carbons, more preferably from one to six carbon atoms in its backbone structure such as methyl, ethyl, n-propyl, isopropyl, n-butyl, isobutyl, sec-butyl, and tert-butyl. Likewise, "lower alkenyl" and "lower alkynyl" have similar chain lengths. Throughout the application, preferred alkyl groups are lower alkyls. In certain embodiments, a substituent designated herein as alkyl is a lower alkyl.

The term "aryl" as used herein includes 3- to 12-membered substituted or unsubstituted single-ring aromatic groups in which each atom of the ring is carbon (i.e., carbocyclic aryl) or where one or more atoms are heteroatoms (i.e., heteroaryl). Preferably, aryl groups include 5- to 12-membered rings, more preferably 6- to 10-membered rings The term "aryl" also includes polycyclic ring systems having two or more cyclic rings in which two or more carbons are common to two adjoining rings wherein at least one of the rings is aromatic, e.g., the other cyclic rings can be cycloalkyls, cycloalkenyls, cycloalkynyls, aryls, heteroaryls, and/or heterocyclyls. Carbocyclic aryl groups include benzene, naphthalene, phenanthrene, phenol, aniline, and the like. Heteroaryl groups include substituted or unsubstituted aromatic 3- to 12-membered ring structures, more preferably 5- to 12-membered rings, more preferably 5- to 10-membered rings, whose ring structures include one to four heteroatoms. Heteroaryl groups include, for example, pyrrole, furan, thiophene, imidazole, oxazole, thiazole, triazole, pyrazole, pyridine, pyrazine, pyridazine and pyrimidine, and the like. Aryl and heteroaryl can be monocyclic, bicyclic, or polycyclic.

The term "halo", "halide", or "halogen" as used herein means halogen and includes, for example, and without being limited thereto, fluoro, chloro, bromo, iodo and the like, in both radioactive and non-radioactive forms. In a preferred embodiment, halo is selected from the group consisting of fluoro, chloro and bromo.

The terms "heterocyclyl" or "heterocyclic group" refer to 3- to 12-membered ring structures, more preferably 5- to 12-membered rings, more preferably 5- to 10-membered rings, whose ring structures include one to four heteroatoms. Heterocycles can be monocyclic, bicyclic, spirocyclic, or polycyclic. Heterocyclyl groups include, for example, thiophene, thianthrene, furan, pyran, isobenzofuran, chromene, xanthene, phenoxathiin, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring can be substituted at one or more positions with such substituents as described above, as for example, halogen, alkyl, aralkyl, alkenyl, alkynyl, cycloalkyl, hydroxyl, amino, nitro, sulfhydryl, imino, amido, phosphate, phosphonate, phosphinate, carbonyl, carboxyl, silyl, sulfamoyl, sulfinyl, ether, alkylthio, sulfonyl, ketone, aldehyde, ester, a heterocyclyl, an aromatic or heteroaromatic moiety, —$CF_3$, —CN, and the like.

The term "carbonyl" is art-recognized and includes such moieties as can be represented by the formula:

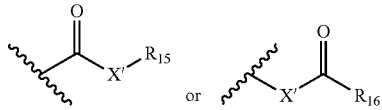

wherein X' is a bond or represents an oxygen or a sulfur, and $R_{15}$ represents a hydrogen, an alkyl, an alkenyl, —$(CH_2)_m$—$R_{10}$ or a pharmaceutically acceptable salt, $R_{16}$ represents a hydrogen, an alkyl, an alkenyl or —$(CH_2)_m$—$R_{10}$, where m and $R_{10}$ are as defined above. Where X' is an oxygen and $R_{15}$ or $R_{16}$ is not hydrogen, the formula represents an "ester." Where X' is an oxygen, and $R_{15}$ is as defined above, the moiety is referred to herein as a carboxyl group, and particularly when $R_{15}$ is a hydrogen, the formula represents a "carboxylic acid". Where X' is an oxygen, and $R_{16}$ is a hydrogen, the formula represents a "formate." On the other hand, where X' is a bond, and $R_{15}$ is not hydrogen, the above formula represents a "ketone" group. Where X' is a bond, and $R_{15}$ is a hydrogen, the above formula represents an "aldehyde" group.

As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described herein above, and for example substituted with one or more substituents selected from alkyl, cycloalkyl, heterocyclylacyl, halogen, OH, OMe, $C(H)F_2$, $C(F)H_2$, $CF_3$, $C(H)_2CF_3$, $SF_5$, $CHFCH_2$amine, $CH_2$amine, and CN. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc.

As used herein, the term "nitro" means —$NO_2$; the term "halogen" designates —F, —Cl, —Br, or —I; the term "hydroxyl" means —OH; and the term "cyano" means —CN.

As used herein, the definition of each expression, e.g., alkyl, m, n, etc., when it occurs more than once in any structure, is intended to be independent of its definition elsewhere in the same structure.

The term "prodrug" as used herein encompasses compounds that, under physiological conditions, are converted into therapeutically active agents. A common method for making a prodrug is to include selected moieties that are hydrolyzed under physiological conditions to reveal the desired molecule. In other embodiments, the prodrug is converted by an enzymatic activity of the host animal.

For purposes of this invention, the chemical elements are identified in accordance with the Periodic Table of the Elements, CAS version, Handbook of Chemistry and Physics, 67th Ed., 1986-87, inside cover.

Exemplary Compounds

In some embodiments, the invention relates to a compound of Formula (I), Formula (Ia), or Formula (Ib):

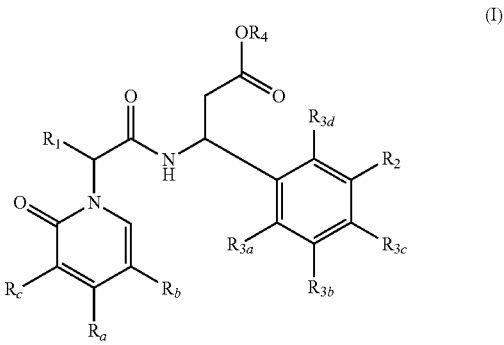

(I)

-continued

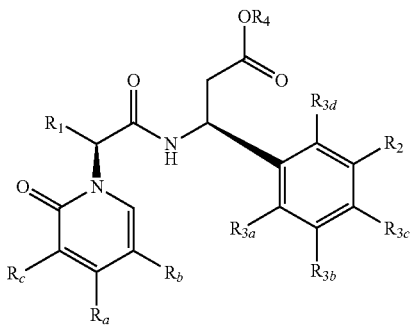

(Ia)

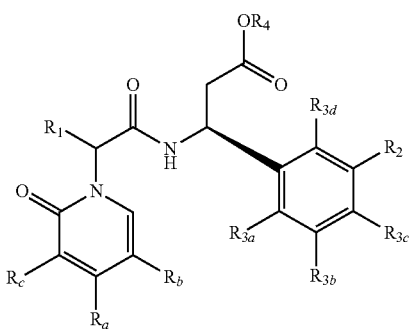

(Ib)

or a pharmceutically acceptable salt thereof;
wherein $R_a$, $R_b$, and $R_c$ are independently selected from the group consisting of H, Me, halide, $CF_3$, $C(H)F_2$, $C(F)H_2$, —CN, —$OCF_3$, substituted or unsubstituted ($C_1$-$C_5$)-alkyl, substituted or unsubstituted ($C_1$-$C_5$)-alkoxy, —$CH_2CF_3$, and substituted or unsubstituted ($C_1$-$C_5$)alkylene-N—($R_x$)($R_y$); provided that at least one of $R_a$, $R_b$, and $R_c$ is —($C_1$-$C_5$) alkylene-N—($R_x$)($R_y$);

$R_x$ and $R_y$ are independently selected from the group consisting of H and substituted or unsubstituted ($C_1$-$C_6$)-alkyl; or $R_x$ and $R_y$ taken together with the N to which they are attached form a 4-6 membered ring;

$R_1$ is substituted or unsubstituted ($C_1$-$C_6$)-alkyl, substituted or unsubstituted ($C_1$-$C_4$)-alkylene-($C_3$-$C_6$)-cycloalkyl, or substituted or unsubstituted ($C_1$-$C_4$)-alkylene-($C_1$-$C_4$)-alkoxy;

$R_2$ is

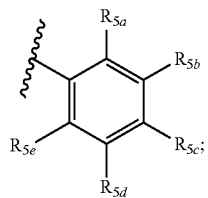

$R_{3a}$ and $R_{3b}$ are independently selected from the group consisting of H, substituted or unsubstituted ($C_1$-$C_5$)-alkyl, substituted or unsubstituted ($C_3$-$C_6$)-cycloalkyl, substituted or unsubstituted 3-6 membered heterocycloalkyl, —OH, —CN, halide, $CF_3$, $C(H)F_2$, $C(F)H_2$, —($C_1$-$C_4$)-alkoxy, —$OCF_3$, and substituted or unsubstituted ($C_1$-$C_4$)-alkylene-($C_1$-$C_4$)-alkoxy; provided that $R_{3a}$ and $R_{3b}$ are not both H;

$R_{3c}$ is selected from the group consisting of H, substituted or unsubstituted ($C_1$-$C_5$)-alkyl, substituted or unsubstituted ($C_3$-$C_6$)-cycloalkyl, substituted or unsubstituted 3-6 membered heterocycloalkyl, hydroxyl, halide, $CF_3$, $C(H)F_2$, $C(F)H_2$, —($C_1$-$C_4$)-alkoxy, —$OCF_3$—CN, and substituted or unsubstituted ($C_1$-$C_4$)-alkylene-($C_1$-$C_4$)-alkoxy;

$R_{3d}$ is selected from the group consisting of H, substituted or unsubstituted ($C_1$-$C_5$)-alkyl, hydroxyl, halide, and —($C_1$-$C_4$)-alkoxy;

$R_4$ is H, or substituted or unsubstituted ($C_1$-$C_4$)-alkyl;

$R_{5a}$, and $R_{5e}$ are independently selected from the group consisting of H, CN, halide, $CF_3$, $C(H)F_2$, $C(F)H_2$, —$CH_2CF_3$, substituted or unsubstituted ($C_3$-$C_6$)-cycloalkyl, substituted or unsubstituted ($C_1$-$C_5$)-alkyl, substituted or unsubstituted 3-6 membered heterocycloalkyl hydroxyl, and ($C_1$-$C_4$)-alkoxy; and $R_{5b}$, $R_{5c}$, and $R_{5d}$ are independently selected from the group consisting of H, CN, halide, $CF_3$, $C(H)F_2$, $C(F)H_2$, —$CH_2CF_3$, substituted or unsubstituted ($C_1$-$C_5$)-alkyl, substituted or unsubstituted ($C_3$-$C_6$)-cycloalkyl, substituted or unsubstituted 3-6 membered heterocycloalkyl, hydroxyl, and ($C_1$-$C_4$)-alkoxy.

In some embodiments, a compound of Formula (Ia) can be a compound wherein: $R_a$ is Me; $R_b$, is substituted or unsubstituted —($C_1$-$C_5$)alkylene-N—($R_x$)($R_y$); $R_x$ and $R_y$ are independently selected from the group consisting of H and substituted or unsubstituted ($C_1$-$C_6$)-alkyl; or $R_x$ and $R_y$ taken together with the N to which they are attached form a 4-6 membered ring; $R_c$ is H; $R_1$ is ($C_1$-$C_6$)-alkyl; $R_{3a}$ is halide; $R_{3b}$ is ($C_1$-$C_5$)-alkyl; $R_{3c}$ is H; $R_{3d}$ is H; $R_4$ is H; $R_{5a}$, and $R_{5e}$ are ($C_1$-$C_5$)-alkyl; and $R_{5b}$, $R_{5c}$, and $R_{5d}$ are independently selected from the group consisting of H, CN, halide, $CF_3$, $C(H)F_2$, $C(F)H_2$, —$CH_2CF_3$, substituted or unsubstituted ($C_1$-$C_5$)-alkyl, substituted or unsubstituted ($C_3$-$C_6$)-cycloalkyl, substituted or unsubstituted 3-6 membered heterocycloalkyl, hydroxyl, and ($C_1$-$C_4$)-alkoxy, or a pharmaceutically acceptable salt thereof.

In some embodiments, a compound of Formula (Ia) can be a compound wherein: $R_a$ is Me; $R_b$, is substituted or unsubstituted —($C_1$-$C_5$)alkylene-N—($R_x$)($R_y$); $R_x$ and $R_y$ are independently selected from the group consisting of H and substituted or unsubstituted ($C_1$-$C_6$)-alkyl; or $R_x$ and $R_y$ taken together with the N to which they are attached form a 4-6 membered ring; $R_c$ is H; $R_1$ is ($C_1$-$C_6$)-alkyl; $R_{3a}$ is halide; $R_{3b}$ is halide; $R_{3c}$ is H; $R_{3d}$ is H; $R_4$ is H; $R_{5a}$, and $R_{5e}$ are ($C_1$-$C_5$)-alkyl; and $R_{5b}$, $R_{5c}$, and $R_{5d}$ are independently selected from the group consisting of H, CN, halide, $CF_3$, $C(H)F_2$, $C(F)H_2$, —$CH_2CF_3$, substituted or unsubstituted ($C_1$-$C_5$)-alkyl, substituted or unsubstituted ($C_3$-$C_6$)-cycloalkyl, substituted or unsubstituted 3-6 membered heterocycloalkyl, hydroxyl, and ($C_1$-$C_4$)-alkoxy, or a pharmaceutically acceptable salt thereof.

In some embodiments, a compound of Formula (Ia) can be a compound wherein: $R_a$ is H; $R_b$, is substituted or unsubstituted —($C_1$-$C_5$)alkylene-N—($R_x$)($R_y$); $R_x$ and $R_y$ are independently selected from the group consisting of H and substituted or unsubstituted ($C_1$-$C_6$)-alkyl; or $R_x$ and $R_y$ taken together with the N to which they are attached form a 4-6 membered ring; $R_c$ is $CH(F)_2$; $R_1$ is ($C_1$-$C_6$)-alkyl; $R_{3a}$ is halide; $R_{3b}$ is ($C_1$-$C_5$)-alkyl; $R_{3c}$ is H; $R_{3d}$ is H; $R_4$ is H; $R_{5a}$, and $R_{5e}$ are ($C_1$-$C_5$)-alkyl; and $R_{5b}$, $R_{5c}$, and $R_{5d}$ are independently selected from the group consisting of H, CN, halide, $CF_3$, $C(H)F_2$, $C(F)H_2$, —$CH_2CF_3$, substituted or unsubstituted ($C_1$-$C_5$)-alkyl, substituted or unsubstituted ($C_3$-$C_6$)-cycloalkyl, substituted or unsubstituted 3-6 membered heterocycloalkyl, hydroxyl, and ($C_1$-$C_4$)-alkoxy, or a pharmaceutically acceptable salt thereof.

In some embodiments, a compound of Formula (Ia) can be a compound wherein: $R_a$ is H; $R_b$, is substituted or unsubstituted —($C_1$-$C_5$)alkylene-N—($R_x$)($R_y$); $R_x$ and $R_y$ are independently selected from the group consisting of H and substituted or unsubstituted ($C_1$-$C_6$)-alkyl; or $R_x$ and $R_y$ taken together with the N to which they are attached form a 4-6 membered ring; $R_c$ is halide; $R_1$ is ($C_1$-$C_6$)-alkyl; $R_{3a}$ is halide; $R_{3b}$ is ($C_1$-$C_5$)-alkyl; $R_{3c}$ is H; $R_{3d}$ is H; $R_4$ is H; $R_{5a}$, and $R_{5e}$ are ($C_1$-$C_5$)-alkyl; and $R_{5b}$, $R_{5c}$ and $R_{5d}$ are independently selected from the group consisting of H, CN, halide, $CF_3$, $C(H)F_2$, $C(F)H_2$, $—CH_2CF_3$, substituted or unsubstituted $(C_1-C_5)$-alkyl, substituted or unsubstituted $(C_3-C_6)$-cycloalkyl, substituted or unsubstituted 3-6 membered heterocycloalkyl, hydroxyl, and $(C_1-C_4)$-alkoxy, or a pharmaceutically acceptable salt thereof.

In some embodiments, a compound of Formula (Ia) can be a compound wherein: $R_a$ is $CF_3$; $R_b$, is substituted or unsubstituted $—(C_1-C_5)$alkylene-N—$(R_x)(R_y)$; $R_x$ and $R_y$ are independently selected from the group consisting of H and substituted or unsubstituted $(C_1-C_6)$-alkyl; or $R_x$ and $R_y$ taken together with the N to which they are attached form a 4-6 membered ring; $R_c$ is H; $R_1$ is $(C_1-C_6)$-alkyl; $R_{3a}$ is halide; $R_{3b}$ is $(C_1-C_5)$-alkyl; $R_{3c}$ is H; $R_{3d}$ is H; $R_4$ is H; $R_{5a}$, and $R_{5e}$ are $(C_1-C_5)$-alkyl; and $R_{5b}$, $R_{5c}$, and $R_{5d}$ are independently selected from the group consisting of H, CN, halide, $CF_3$, $C(H)F_2$, $C(F)H_2$, $—CH_2CF_3$, substituted or unsubstituted $(C_1-C_5)$-alkyl, substituted or unsubstituted $(C_3-C_6)$-cycloalkyl, substituted or unsubstituted 3-6 membered heterocycloalkyl, hydroxyl, and $(C_1-C_4)$-alkoxy, or a pharmaceutically acceptable salt thereof.

In some embodiments, a compound of Formula (Ia) can be a compound wherein: $R_a$ is $CF_3$; $R_b$, is substituted or unsubstituted $—(C_1-C_5)$alkylene-N—$(R_x)(R_y)$; $R_x$ and $R_y$ are independently selected from the group consisting of H and substituted or unsubstituted $(C_1-C_6)$-alkyl; or $R_x$ and $R_y$ taken together with the N to which they are attached form a 4-6 membered ring; $R_c$ is H; $R_1$ is $(C_1-C_6)$-alkyl; $R_{3a}$ is halide; $R_{3b}$ is $CF_3$; $R_{3c}$ is H; $R_{3d}$ is H; $R_4$ is H; $R_{5a}$, and $R_{5e}$ are $(C_1-C_5)$-alkyl; and $R_{5b}$, $R_{5c}$, and $R_{5d}$ are independently selected from the group consisting of H, CN, halide, $CF_3$, $C(H)F_2$, $C(F)H_2$, $—CH_2CF_3$, substituted or unsubstituted $(C_1-C_5)$-alkyl, substituted or unsubstituted $(C_3-C_6)$-cycloalkyl, substituted or unsubstituted 3-6 membered heterocycloalkyl, hydroxyl, and $(C_1-C_4)$-alkoxy, or a pharmaceutically acceptable salt thereof.

In some embodiments, a compound of Formula (Ia) can be a compound wherein: $R_a$ is $CF_3$; $R_b$, is substituted or unsubstituted $—(C_1-C_5)$alkylene-N—$(R_x)(R_y)$; $R_x$ and $R_y$ are independently selected from the group consisting of H and substituted or unsubstituted $(C_1-C_6)$-alkyl; or $R_x$ and $R_y$ taken together with the N to which they are attached form a 4-6 membered ring; $R_c$ is H; $R_1$ is $(C_1-C_6)$-alkyl; $R_{3a}$ is halide; $R_{3b}$ is halide; $R_{3c}$ is H; $R_{3d}$ is H; $R_4$ is H; $R_{5a}$, and $R_{5e}$ are $(C_1-C_5)$-alkyl; and $R_{5b}$, $R_{5c}$, and $R_{5d}$ are independently selected from the group consisting of H, CN, halide, $CF_3$, $C(H)F_2$, $C(F)H_2$, $—CH_2CF_3$, substituted or unsubstituted $(C_1-C_5)$-alkyl, substituted or unsubstituted $(C_3-C_6)$-cycloalkyl, substituted or unsubstituted 3-6 membered heterocycloalkyl, hydroxyl, and $(C_1-C_4)$-alkoxy, or a pharmaceutically acceptable salt thereof.

In some embodiments, a compound of Formula (Ia) can be a compound wherein: $R_a$ is $CF_3$; $R_b$, is substituted or unsubstituted $—(C_1-C_5)$alkylene-N—$(R_x)(R_y)$; $R_x$ and $R_y$ are independently selected from the group consisting of H and substituted or unsubstituted $(C_1-C_6)$-alkyl; or $R_x$ and $R_y$ taken together with the N to which they are attached form a 4-6 membered ring; $R_c$ is H; $R_1$ is $(C_1-C_6)$-alkyl; $R_{3a}$ is halide; $R_{3b}$ is $(C_3-C_6)$-cycloalkyl; $R_{3c}$ is H; $R_{3d}$ is halide; $R_4$ is H; $R_{5a}$, and $R_{5e}$ are $(C_1-C_5)$-alkyl; and $R_{5b}$, $R_{5c}$, and $R_{5d}$ are independently selected from the group consisting of H, CN, halide, $CF_3$, $C(H)F_2$, $C(F)H_2$, $—CH_2CF_3$, substituted or unsubstituted $(C_1-C_5)$-alkyl, substituted or unsubstituted $(C_3-C_6)$-cycloalkyl, substituted or unsubstituted 3-6 membered heterocycloalkyl, hydroxyl, and $(C_1-C_4)$-alkoxy, or a pharmaceutically acceptable salt thereof.

In some embodiments, a compound of Formula (Ia) can be a compound wherein: $R_a$ is $CF_3$; $R_b$ is substituted or unsubstituted $—(C_1-C_5)$alkylene-N—$(R_x)(R_y)$; $R_x$ and $R_y$ are independently selected from the group consisting of H and substituted or unsubstituted $(C_1-C_6)$-alkyl; or Rx and $R_y$ taken together with the N to which they are attached form a 4-6 membered ring; $R_c$ is H; $R_1$ is $(C_1-C_6)$-alkyl; $R_{3a}$ is halide; $R_{3b}$ is $CF_3$; $R_{3c}$ is H; $R_{3d}$ is halide; $R_4$ is H; $R_{5a}$, and $R_{5e}$ are $(C_1-C_5)$-alkyl; and $R_{5b}$, $R_{5c}$, and $R_{5d}$ are independently selected from the group consisting of H, CN, halide, $CF_3$, $C(H)F_2$, $C(F)H_2$, $—CH_2CF_3$, substituted or unsubstituted $(C_1-C_5)$-alkyl, substituted or unsubstituted $(C_3-C_6)$-cycloalkyl, substituted or unsubstituted 3-6 membered heterocycloalkyl, hydroxyl, and $(C_1-C_4)$-alkoxy, or a pharmaceutically acceptable salt thereof.

In some embodiments, a compound of Formula (Ia) can be a compound wherein: $R_a$ is $CF_3$; $R_b$ is substituted or unsubstituted $—(C_1-C_5)$alkylene-N—$(R_x)(R_y)$; R and $R_y$ are independently selected from the group consisting of H and substituted or unsubstituted $(C_1-C_6)$-alkyl; or $R_x$ and $R_y$ taken together with the N to which they are attached form a 4-6 membered ring; $R_c$ is H; $R_1$ is $(C_1-C_6)$-alkyl; $R_{3a}$ is halide; $R_{3b}$ is $(C_1-C_5)$-alkyl; $R_{3c}$ is H; $R_{3d}$ is halide; $R_4$ is H; $R_{5a}$, and $R_{5e}$ are $(C_1-C_5)$-alkyl; and $R_{5b}$, $R_{5c}$ and $R_{5d}$ are independently selected from the group consisting of H, CN, halide, $CF_3$, $C(H)F_2$, $C(F)H_2$, $—CH_2CF_3$, substituted or unsubstituted $(C_1-C_5)$-alkyl, substituted or unsubstituted $(C_3-C_6)$-cycloalkyl, substituted or unsubstituted 3-6 membered heterocycloalkyl, hydroxyl, and $(C_1-C_4)$-alkoxy, or a pharmaceutically acceptable salt thereof.

In some embodiments, a compound of Formula (Ia) can be a compound wherein $R_{5a}$, is halide or $(C_1-C_5)$-alkyl; $R_{5b}$ is H, halide or substituted or unsubstituted $(C_1-C_5)$-alky; $R_{5c}$ is H, halide, substituted or unsubstituted $(C_1-C_5)$-alkyl, or substituted or unsubstituted $(C_3-C_6)$-cycloalkyl; and $R_{5d}$ is selected from the group consisting of H, halide, $CF_3$, $C(H)F_2$, $C(F)H_2$, $—CH_2CF_3$, substituted or unsubstituted $(C_1-C_5)$-alkyl, substituted or unsubstituted $(C_3-C_6)$-cycloalkyl, substituted or unsubstituted 3-6 membered heterocycloalkyl, hydroxyl, and $(C_1-C_4)$-alkoxy; and $R_{5e}$ is halide or $(C_1-C_5)$-alkyl.

In some embodiments, a compound of Formula (I) can be a compound of Formula (Ia), Formula (Ib), Formula (Ic) and/or Formula (Id):

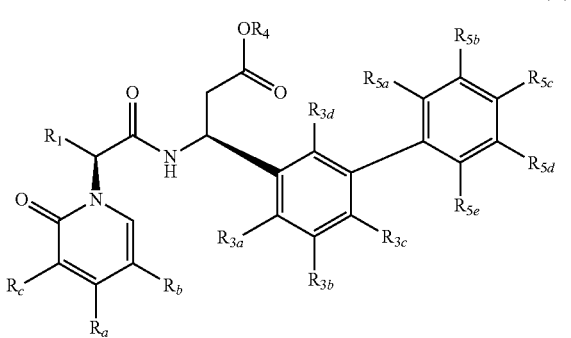

(Ia)

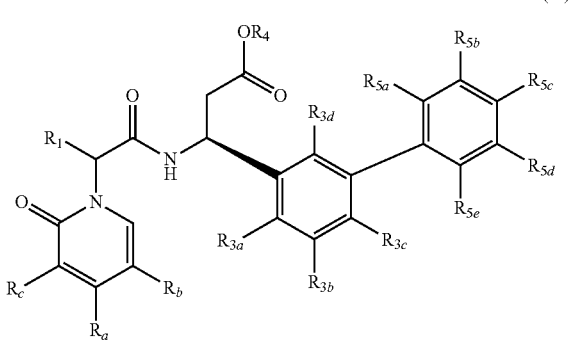

(Ib)

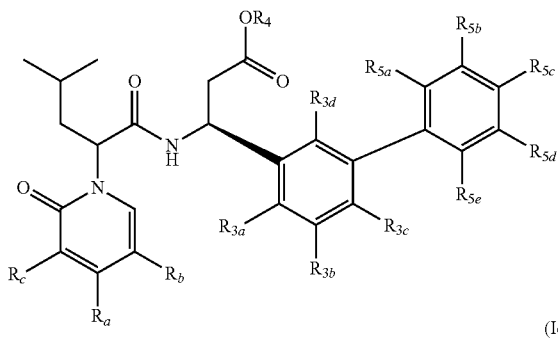

(Ic)

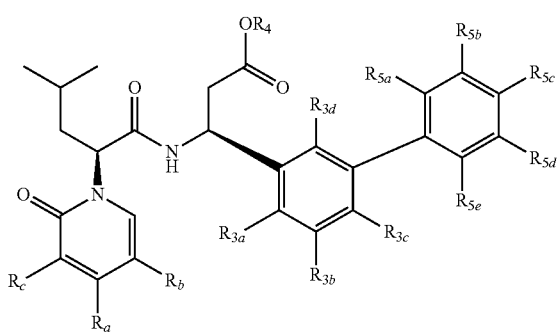

(Id)

wherein $R_a$, $R_b$, $R_c$, $R_1$, $R_{3a}$, $R_{3b}$, $R_{3c}$, $R_{3d}$, $R_{5a}$, $R_{5b}$, $R_{5c}$, $R_{5d}$, $R_{5e}$, and $R_4$ in Formula (Ia), Formula (Ib), Formula (Ic) and Formula (Id) are each independently defined as above with respect to Formula (I).

In some embodiments, a compound of Formula (I) can be a compound of Formula (II), including compounds of Formula (IIa), Formula (IIb) or Formula (IIc):

(II)

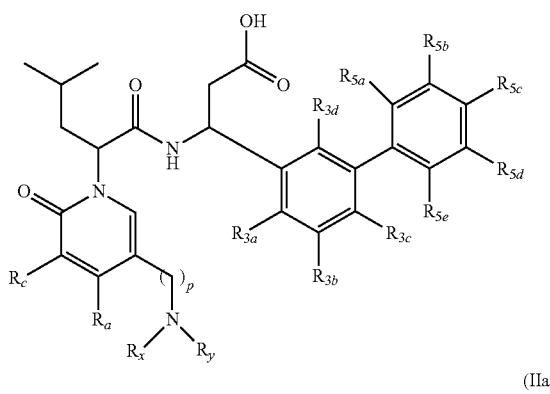

(IIa)

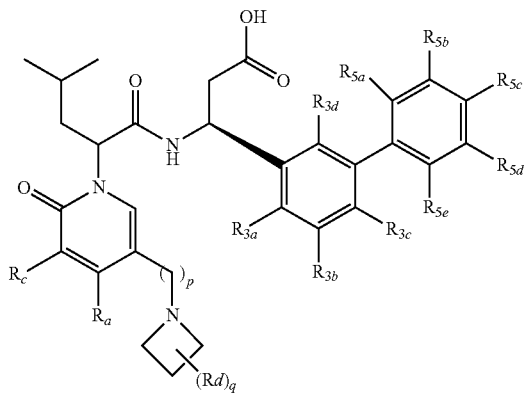

(IIb)

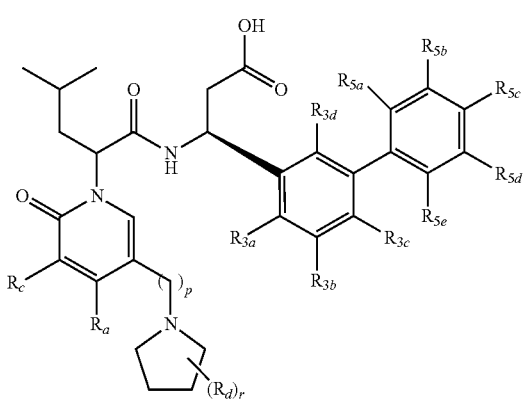

(IIc)

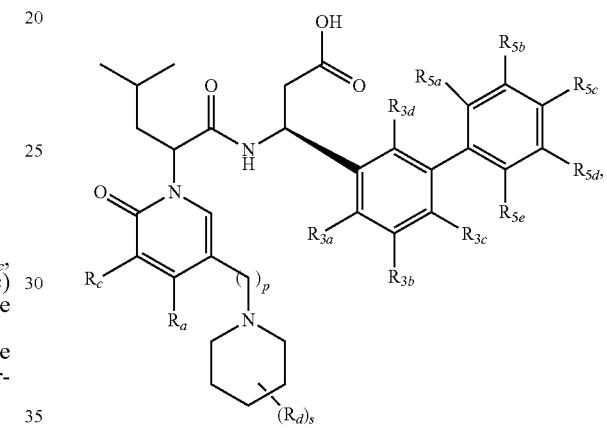

wherein $R_a$, $R_c$, $R_{3a}$, $R_{3b}$, $R_{3c}$, $R_{3d}$, $R_{5a}$, $R_{5b}$, $R_{5c}$ $R_{5d}$, and $R_{ye}$, are as described in Formula (I); p is 1, 2, or 3; q is 0, 1, 2 or 3; r is an 0, 1, 2, 3 or 4; s is 0, 1, 2, 3, 4 or 5; and each Rd is independently selected from the group consisting of halide, ($C_1$-$C_5$)-alkyl, ($C_1$-$C_4$)-alkoxy, —$CF_3$, —$C(H)F_2$, —$OCF_3$, and —CN. In some embodiments, at least one instance of $R_d$ is F or Cl. In some embodiments, at least one instance of $R_d$ is methyl. In some embodiments, at least one instance of $R_d$ is methoxy. In certain embodiments, the invention relates to any one of the aforementioned compounds of Formula (IIa), wherein q is 1. In certain embodiments, the invention relates to any one of the aforementioned compounds of Formula (IIb), wherein r is 1. In certain embodiments, the invention relates to any one of the aforementioned compounds of Formula (IIc), wherein s is 1.

In certain embodiments, the invention relates to any one of the aforementioned compounds, wherein $R_1$ is unsubstituted ($C_1$-$C_6$)-alkyl. In certain embodiments, the invention relates to any one of the aforementioned compounds, wherein $R_1$ is substituted ($C_1$-$C_6$)-alkyl. In certain embodiments, the invention relates to any one of the aforementioned compounds, wherein $R_1$ is substituted or unsubstituted ($C_1$-$C_4$)-alkyl. In certain embodiments, $R_1$ is methyl, ethyl, isopropyl, n-propyl, i-butyl, n-butyl, sec-butyl, or t-butyl. In certain embodiments, the invention relates to any one of the aforementioned compounds, wherein $R_1$ is selected from the group consisting of

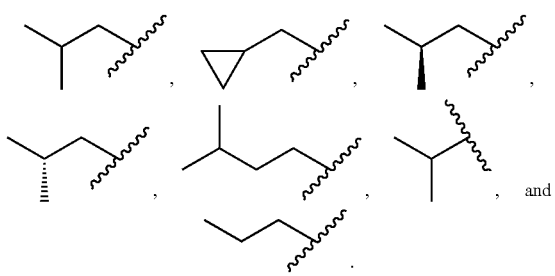

In certain embodiments, the invention relates to any one of the aforementioned compounds, wherein $R_1$ is substituted $(C_1-C_4)$-alkylene-$(C_3-C_6)$-cycloalkyl. In certain embodiments, the invention relates to any one of the aforementioned compounds, wherein $R_1$ is unsubstituted $(C_1-C_4)$-alkylene-$(C_3-C_6)$-cycloalkyl. In certain embodiments, $R_1$ is

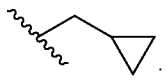 [SMILES: *CC1CC1]

In certain embodiments, the invention relates to any one of the aforementioned compounds, wherein $R_1$ is substituted $(C_1-C_4)$-alkylene-$(C_1-C_4)$-alkoxy. In certain embodiments, the invention relates to any one of the aforementioned compounds, wherein $R_1$ is unsubstituted $(C_1-C_4)$-alkylene-$(C_1-C_4)$-alkoxy. In certain embodiments, $R_1$ is

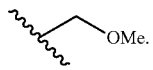

In certain embodiments, the invention relates to any one of the aforementioned compounds, wherein $R_1$ is

In certain embodiments, the invention relates to any one of the aforementioned compounds, wherein $R_1$ is

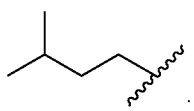 [SMILES: *CCC(C)C]

In certain embodiments, the invention relates to any one of the aforementioned compounds, wherein $R_{3a}$ is H; provided that $R_{3a}$ and $R_{3b}$ are not both H. In certain embodiments, the invention relates to any one of the aforementioned compounds, wherein $R_{3a}$ is unsubstituted $(C_1-C_4)$-alkyl. In certain embodiments, the invention relates to any one of the aforementioned compounds, wherein $R_{3a}$ is substituted $(C_1-C_4)$-alkyl. In certain embodiments, the substituted $(C_1-C_5)$-alkyl, is substituted with a halogen. In certain embodiments, the halogen is Cl or F. In certain embodiments, $R_{3a}$ is methyl, ethyl, isopropyl, n-propyl, i-butyl, n-butyl, or t-butyl. In certain embodiments, the invention relates to any one of the aforementioned compounds, wherein $R_{3a}$ is substituted $(C_3-C_6)$-cycloalkyl. In certain embodiments, the invention relates to any one of the aforementioned compounds, wherein $R_{3a}$ is substituted or unsubstituted $(C_3-C_6)$-cycloalkyl. In certain embodiments, the invention relates to any one of the aforementioned compounds, wherein $R_{3a}$ is cyclopropyl. In certain embodiments, the invention relates to any one of the aforementioned compounds, wherein $R_{3a}$ is halide. In some embodiments, the halide is Cl or F. In certain embodiments, the invention relates to any one of the aforementioned compounds, wherein $R_{3a}$ is $CF_3$. In certain embodiments, the invention relates to any one of the aforementioned compounds, wherein $R_{3a}$ is $C(H)F_2$. In certain embodiments, the invention relates to any one of the aforementioned compounds, wherein $R_{3a}$ is $C(F)H_2$. In certain embodiments, the invention relates to any one of the aforementioned compounds, wherein $R_{3a}$ is substituted —$(C_1-C_4)$-alkoxy. In certain embodiments, the invention relates to any one of the aforementioned compounds, wherein $R_{3a}$ is unsubstituted —$(C_1-C_4)$-alkoxy. In certain embodiments, the invention relates to any one of the aforementioned compounds, wherein $R_{3a}$ is —$OCF_3$. In certain embodiments, the invention relates to any one of the aforementioned compounds, wherein $R_{3a}$ is substituted $(C_1-C_4)$-alkylene-$(C_1-C_4)$-alkoxy. In certain embodiments, the invention relates to any one of the aforementioned compounds, wherein $R_{3a}$ is unsubstituted $(C_1-C_4)$-alkylene-$(C_1-C_4)$-alkoxy. In certain embodiments, $(C_1-C_4)$-alkylene-$(C_1-C_4)$-alkoxy is $CH_2OMe$. In certain embodiments, the invention relates to any one of the aforementioned compounds, wherein $R_{3a}$ is F.

In certain embodiments, the invention relates to any one of the aforementioned compounds, wherein $R_{3b}$ is H; provided that $R_{3a}$ and $R_{3b}$ are not both H. In certain embodiments, the invention relates to any one of the aforementioned compounds, wherein $R_{3b}$ is unsubstituted $(C_1-C_4)$-alkyl. In certain embodiments, the invention relates to any one of the aforementioned compounds, wherein $R_{3b}$ is substituted $(C_1-C_4)$-alkyl. In certain embodiments, the substituted $(C_1-C_5)$-alkyl, is substituted with a halogen. In certain embodiments, the halogen is Cl or F. In certain embodiments, $R_{3b}$ is methyl, ethyl, isopropyl, n-propyl, i-butyl, n-butyl, or t-butyl. In certain embodiments, the invention relates to any one of the aforementioned compounds, wherein $R_{3b}$ is substituted $(C_3-C_6)$-cycloalkyl. In certain embodiments, the invention relates to any one of the aforementioned compounds, wherein $R_{3b}$ is substituted or unsubstituted $(C_3-C_6)$-cycloalkyl. In certain embodiments, the invention relates to any one of the aforementioned compounds, wherein $R_{3b}$ is cyclopropyl. In certain embodiments, the invention relates to any one of the aforementioned compounds, wherein $R_{3b}$ is halide. In some embodiments, the halide is Cl or F. In certain embodiments, the invention relates to any one of the aforementioned compounds, wherein $R_{3b}$ is $CF_3$. In certain embodiments, the invention relates to any one of the aforementioned compounds, wherein $R_{3b}$ is $C(H)F_2$. In certain embodiments, the invention relates to any one of the aforementioned compounds, wherein $R_{3b}$ is $C(F)H_2$. In certain embodiments, the invention relates to any one of the aforementioned compounds, wherein $R_{3b}$ is substituted —$(C_1-C_4)$-alkoxy. In certain embodiments, the invention relates to any one of the aforementioned compounds, wherein $R_{3b}$ is unsubstituted —$(C_1-C_4)$-alkoxy. In certain embodiments, the invention relates to any one of the aforementioned compounds, wherein $R_{3b}$ is —$OCF_3$. In certain embodiments, the invention relates to any one of the aforementioned compounds, wherein $R_{3b}$ is substituted $(C_1-C_4)$-alkylene-$(C_1-C_4)$-alkoxy. In certain embodiments, the invention relates to any one of the aforementioned compounds, wherein $R_{3b}$ is unsubstituted $(C_1-C_4)$-alkylene-$(C_1-C_4)$-alkoxy. In certain embodiments, $(C_1-C_4)$-alkylene-$(C_1-C_4)$-alkoxy is —$CH_2OMe$. In certain embodiments, the invention relates to any one of the aforementioned compounds, wherein $R_{3b}$ is selected from the group consisting of $(C_1-C_4)$-alkylene optionally substituted with one or more halide and $(C_3-C_6)$-cycloalkyl. In certain embodiments, the invention relates to any one of the aforementioned compounds, wherein $R_{3b}$ is selected from the group consisting of methyl, cyclopropyl and $CF_3$. In certain embodiments, the invention relates to any one of the aforementioned compounds, wherein $R_{3b}$ is methyl. In certain embodiments, the invention relates to any one of the aforementioned compounds, wherein $R_{3b}$ is selected from the group consisting of halide, $(C_1-C_4)$-alkylene optionally substituted with one or more halide and $(C_3-C_6)$-cycloalkyl. In certain embodiments, the invention relates to any one of the aforementioned compounds, wherein $R_{3b}$ is selected from the group consisting of F, Cl, methyl, and $CF_3$. In certain embodiments, the invention relates to any one of the aforementioned compounds, wherein $R_{3b}$ is methyl. In certain embodiments, the invention relates to any one of the aforementioned compounds, wherein $R_{3b}$ is F. In certain embodiments, the invention relates to any one of the aforementioned compounds, wherein $R_{3b}$ is Cl. In certain embodiments, the invention relates to any one of the aforementioned compounds, wherein $R_{3b}$ is $CF_3$.

In certain embodiments, $R_{3a}$ and $R_{3b}$ are independently selected from the group consisting of H, $(C_1-C_5)$-alkyl, halide, $CF_3$, $C(H)F_2$, and $C(F)H_2$; provided that $R_{3a}$ and $R_{3b}$ are not both H. For example, $R_{3a}$ and $R_{3b}$ can be independently selected from the group consisting of H, methyl, Cl, F, $CF_3$, $C(H)F_2$, and $C(F)H_2$; provided that $R_{3a}$ and $R_{3b}$ are not both H. In certain embodiments, $R_{3a}$ is halide and $R_{3b}$ is selected from the group consisting of $(C_1-C_4)$-alkylene optionally substituted with one or more halide and $(C_3-C_6)$-cycloalkyl. In certain embodiments, $R_{3a}$ is F and $R_{3b}$ is selected from the group consisting of $(C_1-C_4)$-alkylene optionally substituted with one or more halide and $(C_3-C_6)$-cycloalkyl. In certain embodiments, $R_{3a}$ is F and $R_{3b}$ is selected from the group consisting of methyl, cyclopropyl and $CF_3$. In certain embodiments, $R_{3a}$ is F and $R_{3b}$ is selected from the group consisting of F, Cl, methyl, and $CF_3$. In certain embodiments, $R_{3a}$ is F and $R_{3b}$ is selected from the group consisting of F, Cl, methyl, cyclopropyl and $CF_3$.

In certain embodiments, the invention relates to any one of the aforementioned compounds, wherein $R_{3c}$ is selected from the group consisting of: H, substituted or unsubstituted $(C_1-C_5)$-alkyl, substituted or unsubstituted cyclopropyl, hydroxyl, methoxy, halide, $CF_3$, $C(H)F_2$, $C(F)H_2$, and CN. In certain embodiments, the invention relates to any one of the aforementioned compounds, wherein $R_{3c}$ is H. In certain embodiments, the invention relates to any one of the aforementioned compounds, wherein $R_{3c}$ is unsubstituted $(C_1-C_4)$-alkyl. In certain embodiments, the invention relates to any one of the aforementioned compounds, wherein $R_{3c}$ is substituted $(C_1-C_4)$-alkyl. In certain embodiments, the substituted $(C_1-C_5)$-alkyl, is substituted with a halogen. In certain embodiments, the halogen is Cl or F. In certain embodiments, $R_{3c}$ is methyl, ethyl, isopropyl, n-propyl, i-butyl, n-butyl, or t-butyl. In certain embodiments, the invention relates to any one of the aforementioned compounds, wherein $R_{3c}$ is substituted $(C_3-C_6)$-cycloalkyl. In certain embodiments, the invention relates to any one of the aforementioned compounds, wherein $R_{3c}$ is substituted or unsubstituted $(C_3-C_6)$-cycloalkyl. In certain embodiments, the invention relates to any one of the aforementioned compounds, wherein $R_{3c}$ is cyclopropyl. In certain embodiments, the invention relates to any one of the aforementioned compounds, wherein $R_{3c}$ is halide. In some embodiments, the halide is Cl or F. In certain embodiments, the invention relates to any one of the aforementioned compounds, wherein $R_{3c}$ is $CF_3$. In certain embodiments, the invention relates to any one of the aforementioned compounds, wherein $R_{3c}$ is $C(H)F_2$. In certain embodiments, the invention relates to any one of the aforementioned compounds, wherein $R_{3c}$ is $C(F)H_2$. In certain embodiments, the invention relates to any one of the aforementioned compounds, wherein $R_{3c}$ is substituted —$(C_1-C_4)$-alkoxy. In certain embodiments, the invention relates to any one of the aforementioned compounds, wherein $R_{3c}$ is unsubstituted —$(C_1-C_4)$-alkoxy. In certain embodiments, the invention relates to any one of the aforementioned compounds, wherein $R_{3c}$ is —$OCF_3$. In certain embodiments, the invention relates to any one of the aforementioned compounds, wherein $R_{3c}$ is substituted $(C_1-C_4)$-alkylene-$(C_1-C_4)$-alkoxy. In certain embodiments, the invention relates to any one of the aforementioned compounds, wherein $R_{3c}$ is unsubstituted $(C_1-C_4)$-alkylene-$(C_1-C_4)$-alkoxy. In certain embodiments, $(C_1-C_4)$-alkylene-$(C_1-C_4)$-alkoxy is —$CH_2OMe$.

In certain embodiments, the invention relates to any one of the aforementioned compounds, wherein $R_{3c}$ is H; $R_{3a}$ is halide; and $R_{3b}$ is selected from the group consisting of $(C_1-C_4)$-alkylene optionally substituted with one or more halide and $(C_3-C_6)$-cycloalkyl. In certain embodiments, $R_{3c}$ is H; $R_{3a}$ is F; and $R_{3b}$ is selected from the group consisting of $(C_1-C_4)$-alkylene optionally substituted with one or more halide and $(C_3-C_6)$-cycloalkyl. In certain embodiments, $R_{3c}$ is H; $R_{3a}$ is F; and $R_{3b}$ is selected from the group consisting of methyl, cyclopropyl and $CF_3$. In certain embodiments, $R_{3c}$ is H; $R_{3a}$ is F; $R_{3b}$ is selected from the group consisting of F, Cl, methyl, and $CF_3$. In certain embodiments, $R_{3c}$ is H; $R_{3a}$ is F; $R_{3b}$ is selected from the group consisting of F, Cl, methyl, cyclopropyl and $CF_3$. In certain embodiments, the invention relates to any one of the aforementioned compounds, wherein $R_{3d}$ is selected from the group consisting of H, substituted or unsubstituted $(C_1-C_5)$-alkyl, hydroxyl, halide, methoxy, halide, $CF_3$, $C(H)F_2$, and $C(F)H_2$. In certain embodiments, the invention relates to any one of the aforementioned compounds, wherein $R_{3d}$ H. In certain embodiments, the invention relates to any one of the aforementioned compounds, wherein $R_{3d}$ is unsubstituted $(C_1-C_4)$-alkyl. In certain embodiments, the invention relates to any one of the aforementioned compounds, wherein $R_{3d}$ is substituted $(C_1-C_4)$-alkyl. In certain embodiments, the substituted $(C_1-C_5)$-alkyl, is substituted with a halogen. In certain embodiments, the halogen is F. In certain embodiments, $R_{3d}$ is methyl. In certain embodiments, the invention relates to any one of the aforementioned compounds, wherein $R_{3d}$ is substituted $(C_3-C_6)$-cycloalkyl. In certain embodiments, the invention relates to any one of the aforementioned compounds, wherein $R_{3c}$ is substituted or unsubstituted $(C_3-C_6)$-cycloalkyl. In certain embodiments, the invention relates to any one of the aforementioned compounds, wherein $R_{3d}$ is cyclopropyl. In certain embodiments, the invention relates to any one of the aforementioned compounds, wherein $R_{3d}$ is halide. In some embodiments, the halide is Cl or F In certain embodiments, the invention relates to any one of the aforementioned compounds, wherein $R_{3d}$ is $CF_3$. In certain embodiments, the invention relates to any one of the aforementioned compounds, wherein $R_{3d}$ is $C(H)F_2$. In certain embodiments, the invention relates to any one of the aforementioned compounds, wherein $R_{3d}$ is $C(F)H_2$. In certain embodiments, the invention relates to any one of the aforementioned compounds, wherein $R_{3d}$ is substituted —$(C_1$-$C_4)$-alkoxy. In certain embodiments, the invention relates to any one of the aforementioned compounds, wherein $R_{3d}$ is unsubstituted —$(C_1$-$C_4)$-alkoxy. In certain embodiments, —$(C_1$-$C_4)$-alkoxy is methoxy. In certain embodiments, the invention relates to any one of the aforementioned compounds, wherein $R_{3d}$ is —$OCF_3$. In certain embodiments, the invention relates to any one of the aforementioned compounds, wherein $R_{3d}$ is substituted $(C_1$-$C_4)$-alkylene-$(C_1$-$C_4)$-alkoxy. In certain embodiments, the invention relates to any one of the aforementioned compounds, wherein $R_{3d}$ is unsubstituted $(C_1$-$C_4)$-alkylene-$(C_1$-$C_4)$-alkoxy. In certain embodiments, $(C_1$-$C_4)$-alkylene-$(C_1$-$C_4)$-alkoxy is —$CH_2OMe$.

In some embodiments, $R_{3c}$ and $R_{3d}$ are the same. In some embodiments, $R_{3c}$ and $R_{3d}$ are both H. In some embodiments, $R_{3c}$ and $R_{3d}$ are different. In some embodiments, $R_{3c}$ is H and $R_{3d}$ is H or halide. In some embodiments, $R_{3c}$ is H and $R_{3d}$ is F.

In certain embodiments, the invention relates to any one of the aforementioned compounds, wherein $R_{3c}$ and $R_{3d}$ are both H; $R_{3a}$ is halide; and $R_{3b}$ is selected from the group consisting of $(C_1$-$C_4)$-alkylene optionally substituted with one or more halide and $(C_3$-$C_6)$-cycloalkyl. In certain embodiments, $R_{3c}$ and $R_{3d}$ are both H; $R_{3a}$ is F; and $R_{3b}$ is selected from the group consisting of $(C_1$-$C_4)$-alkylene optionally substituted with one or more halide and $(C_3$-$C_6)$-cycloalkyl. In certain embodiments, $R_{3c}$ and $R_{3d}$ are both H; $R_{3a}$ is F; and $R_{3b}$ is selected from the group consisting of methyl, cyclopropyl and $CF_3$. In certain embodiments, $R_{3c}$ and $R_{3d}$ are both H; $R_{3a}$ is F; $R_{3b}$ is selected from the group consisting of F, Cl, methyl, and $CF_3$. In certain embodiments, $R_{3c}$ and $R_{3d}$ are both H; $R_{3a}$ is F; $R_{3b}$ is selected from the group consisting of F, Cl, methyl, cyclopropyl and $CF_3$.

In certain embodiments, the invention relates to any one of the aforementioned compounds, wherein $R_{3c}$ is H; $R_{3d}$ is F; $R_{3a}$ is halide; and $R_{3b}$ is selected from the group consisting of $(C_1$-$C_4)$-alkylene optionally substituted with one or more halide and $(C_3$-$C_6)$-cycloalkyl. In certain embodiments, $R_{3c}$ is H; $R_{3d}$ is F; $R_{3a}$ is F; and $R_{3b}$ is selected from the group consisting of $(C_1$-$C_4)$-alkylene optionally substituted with one or more halide and $(C_3$-$C_6)$-cycloalkyl. In certain embodiments, $R_{3c}$ is H; $R_{3d}$ is F; $R_{3a}$ is F; and $R_{3b}$ is selected from the group consisting of methyl, cyclopropyl and $CF_3$. In certain embodiments, $R_{3c}$ is H; $R_{3d}$ is F; $R_{3a}$ is F; $R_{3b}$ is selected from the group consisting of F, Cl, methyl, and $CF_3$. In certain embodiments, $R_{3c}$ is H; $R_{3d}$ is F; $R_{3a}$ is F; $R_{3b}$ is selected from the group consisting of F, Cl, methyl, cyclopropyl and $CF_3$.

In certain embodiments, the invention relates to any one of the aforementioned compounds, wherein $R_4$ is H. In certain embodiments, the invention relates to any one of the aforementioned compounds, wherein $R_4$ is substituted $(C_1$-$C_4)$-alkyl. In certain embodiments, the invention relates to any one of the aforementioned compounds, wherein $R_4$ is unsubstituted $(C_1$-$C_4)$-alkyl. In certain embodiments, the invention relates to any one of the aforementioned compounds, wherein $R_4$ is methyl, ethyl, n-propyl, or i-propyl. In certain embodiments, the invention relates to any one of the aforementioned compounds, wherein $R_4$ is methyl or ethyl.

In certain embodiments, $R_{5a}$ is H. In certain embodiments, the invention relates to any one of the aforementioned compounds, wherein $R_{5a}$ is substituted or unsubstituted $(C_1$-$C_4)$-alkyl. In certain embodiments, the invention relates to any one of the aforementioned compounds, wherein $R_{5a}$ is unsubstituted $(C_1$-$C_4)$-alkyl. In certain embodiments, the invention relates to any one of the aforementioned compounds, wherein $R_{5a}$ is substituted $(C_1$-$C_4)$-alkyl. In certain embodiments, the substituted $(C_1$-$C_5)$-alkyl, is substituted with one or more halogen. In certain embodiments, the halogen is Cl or F. In certain embodiments, $R_{5a}$ is methyl, ethyl, isopropyl, n-propyl, i-butyl, n-butyl, or t-butyl. In certain embodiments, $R_{5a}$ is methyl. In certain embodiments, the invention relates to any one of the aforementioned compounds, wherein $R_{5a}$ is halide. In some embodiments, the halide is Cl or F. In certain embodiments, $R_{5a}$ is substituted $(C_3$-$C_6)$-cycloalkyl. In certain embodiments, $R_{5a}$ is unsubstituted $(C_3$-$C_6)$-cycloalkyl. In some embodiments, $(C_3$-$C_6)$-cycloalkyl is cyclopropyl. In certain embodiments, the invention relates to any one of the aforementioned compounds, wherein $R_{5a}$ is $CF_3$. In certain embodiments, the invention relates to any one of the aforementioned compounds, wherein $R_{5a}$ is $C(H)F_2$. In certain embodiments, the invention relates to any one of the aforementioned compounds, wherein $R_{5a}$ is $C(F)H_2$. In certain embodiments, the invention relates to any one of the aforementioned compounds, wherein $R_{5a}$ is $(C_1$-$C_4)$-alkoxy. In some embodiments, $(C_1$-$C_4)$-alkoxy is methoxy. In certain embodiments, the invention relates to any one of the aforementioned compounds, wherein $R_{5a}$ is methoxy. In certain embodiments, the invention relates to any one of the aforementioned compounds, wherein $R_{5a}$ is hydroxyl. In certain embodiments, the invention relates to any one of the aforementioned compounds, wherein $R_{5a}$ is $OCF_3$. In certain embodiments, $R_{5a}$ is CN. In certain embodiments, the invention relates to any one of the aforementioned compounds, wherein $R_{5a}$ is substituted $(C_1$-$C_4)$-alkylene-$(C_1$-$C_4)$-alkoxy. In certain embodiments, the invention relates to any one of the aforementioned compounds, wherein $R_{5a}$ is unsubstituted $(C_1$-$C_4)$-alkylene-$(C_1$-$C_4)$-alkoxy. In certain embodiments, $(C_1$-$C_4)$-alkylene-$(C_1$-$C_4)$-alkoxy is —$CH_2OMe$. In certain embodiments, $R_{5a}$ is $CH_2OH$.

In certain embodiments, the invention relates to any one of the aforementioned compounds, wherein $R_{5b}$ is CN. In certain embodiments, the invention relates to any one of the aforementioned compounds, wherein $R_{5b}$ is unsubstituted $(C_1$-$C_4)$-alkyl. In certain embodiments, the invention relates to any one of the aforementioned compounds, wherein $R_{5b}$ is substituted $(C_1$-$C_4)$-alkyl. In certain embodiments, the substituted $(C_1$-$C_5)$-alkyl, is substituted with a halogen. In certain embodiments, the halogen is Cl or F. In certain embodiments, $R_{5b}$ is methyl, ethyl, isopropyl, n-propyl, i-butyl, n-butyl, or t-butyl. In certain embodiments, $R_{5a}$ is methyl. In certain embodiments, the invention relates to any one of the aforementioned compounds, wherein $R_{5b}$ is halide. In some embodiments, the halide is Cl or F. In certain embodiments, $R_{5b}$ is substituted $(C_3$-$C_6)$-cycloalkyl. In certain embodiments, $R_{5b}$ is unsubstituted $(C_3$-$C_6)$-cycloalkyl. In certain embodiments, the invention relates to any one of the aforementioned compounds, wherein $R_{5b}$ is $CF_3$. In certain embodiments, the invention relates to any one of the aforementioned compounds, wherein $R_{5b}$ is $C(H)F_2$. In certain embodiments, the invention relates to any one of the aforementioned compounds, wherein $R_{5b}$ is $C(F)H_2$. In certain embodiments, the invention relates to any one of the aforementioned compounds, wherein $R_{5b}$ is $(C_1$-$C_4)$-alkoxy. In certain embodiments, the invention relates to any one of the aforementioned compounds, wherein $R_{5b}$ is methoxy. In certain embodiments, the invention relates to any one of the aforementioned compounds, wherein $R_{5b}$ is hydroxyl. In certain embodiments, the invention relates to any one of the aforementioned compounds, wherein $R_{5b}$ is $OCF_3$. In certain embodiments, the invention relates to any one of the aforementioned compounds, wherein $R_{5b}$ is substituted $(C_1$-$C_4)$-alkylene-$(C_1$-$C_4)$-alkoxy. In certain embodiments, the invention relates to any one of the aforementioned compounds, wherein $R_{5b}$ is unsubstituted $(C_1$-$C_4)$-alkylene-$(C_1$-$C_4)$-alkoxy. In certain embodiments, $(C_1$-$C_4)$-alkylene-$(C_1$-$C_4)$-alkoxy is —CH$_2$OMe. In certain embodiments, the invention relates to any one of the aforementioned compounds, wherein $R_{5b}$ is hydrogen.

In certain embodiments, the invention relates to any one of the aforementioned compounds, wherein $R_{5c}$ is CN. In certain embodiments, the invention relates to any one of the aforementioned compounds, wherein $R_{5c}$ is unsubstituted $(C_1$-$C_4)$-alkyl. In certain embodiments, the invention relates to any one of the aforementioned compounds, wherein $R_{5c}$ is substituted $(C_1$-$C_4)$-alkyl. In certain embodiments, the substituted $(C_1$-$C_5)$-alkyl, is substituted with a halogen. In certain embodiments, the halogen is Cl or F. In certain embodiments, $R_{5c}$ is methyl, ethyl, isopropyl, n-propyl, i-butyl, n-butyl, or t-butyl. In certain embodiments, $R_{5c}$ is methyl. In certain embodiments, the invention relates to any one of the aforementioned compounds, wherein $R_{5c}$ is halide. In some embodiments, the halide is Cl or F. In certain embodiments, $R_{5c}$ is substituted $(C_3$-$C_6)$-cycloalkyl. In certain embodiments, $R_{5c}$ is cyclopropyl. In certain embodiments, $R_{5c}$ is unsubstituted $(C_3$-$C_6)$-cycloalkyl. In certain embodiments, the invention relates to any one of the aforementioned compounds, wherein $R_{5c}$ is CF$_3$. In certain embodiments, the invention relates to any one of the aforementioned compounds, wherein $R_{5c}$ is C(H)F$_2$. In certain embodiments, the invention relates to any one of the aforementioned compounds, wherein $R_{5c}$ is C(F)H$_2$. In certain embodiments, the invention relates to any one of the aforementioned compounds, wherein $R_{5c}$ is $(C_1$-$C_4)$-alkoxy. In certain embodiments, the invention relates to any one of the aforementioned compounds, wherein $R_{5c}$ is methoxy. In certain embodiments, the invention relates to any one of the aforementioned compounds, wherein $R_{5c}$ is hydroxyl. In certain embodiments, the invention relates to any one of the aforementioned compounds, wherein $R_{5c}$ is OCF$_3$. In certain embodiments, the invention relates to any one of the aforementioned compounds, wherein $R_{5c}$ is substituted $(C_1$-$C_4)$-alkylene-$(C_1$-$C_4)$-alkoxy. In certain embodiments, the invention relates to any one of the aforementioned compounds, wherein $R_{5c}$ is unsubstituted $(C_1$-$C_4)$-alkylene-$(C_1$-$C_4)$-alkoxy. In certain embodiments, $(C_1$-$C_4)$-alkylene-$(C_1$-$C_4)$-alkoxy is —CH$_2$OMe. In certain embodiments, the invention relates to any one of the aforementioned compounds, wherein $R_{5c}$ is hydrogen.

In certain embodiments, the invention relates to any one of the aforementioned compounds, wherein $R_{5d}$ is CN. In certain embodiments, the invention relates to any one of the aforementioned compounds, wherein $R_{5d}$ is unsubstituted $(C_1$-$C_4)$-alkyl. In certain embodiments, the invention relates to any one of the aforementioned compounds, wherein $R_{5d}$ is substituted $(C_1$-$C_4)$-alkyl. In certain embodiments, the substituted $(C_1$-$C_5)$-alkyl, is substituted with a halogen. In certain embodiments, the halogen is Cl or F. In certain embodiments, $R_{5d}$ is methyl, ethyl, isopropyl, n-propyl, i-butyl, n-butyl, or t-butyl. In certain embodiments, $R_{5d}$ is methyl In certain embodiments, the invention relates to any one of the aforementioned compounds, wherein $R_{5d}$ is halide. In some embodiments, the halide is Cl or F. In certain embodiments, $R_{5d}$ is substituted $(C_3$-$C_6)$-cycloalkyl. In certain embodiments, $R_{5d}$ is unsubstituted $(C_3$-$C_6)$-cycloalkyl. In certain embodiments, the invention relates to any one of the aforementioned compounds, wherein $R_{5d}$ is CF$_3$. In certain embodiments, the invention relates to any one of the aforementioned compounds, wherein $R_{5d}$ is C(H)F$_2$. In certain embodiments, the invention relates to any one of the aforementioned compounds, wherein $R_{5d}$ is C(F)H$_2$. In certain embodiments, the invention relates to any one of the aforementioned compounds, wherein $R_{5d}$ is $(C_1$-$C_4)$-alkoxy. In certain embodiments, the invention relates to any one of the aforementioned compounds, wherein $R_{5d}$ is methoxy. In certain embodiments, the invention relates to any one of the aforementioned compounds, wherein $R_{5d}$ is hydroxyl. In certain embodiments, the invention relates to any one of the aforementioned compounds, wherein $R_{5d}$ is —OCF$_3$. In certain embodiments, the invention relates to any one of the aforementioned compounds, wherein $R_{5d}$ is substituted $(C_1$-$C_4)$-alkylene-$(C_1$-$C_4)$-alkoxy. In certain embodiments, the invention relates to any one of the aforementioned compounds, wherein $R_{5d}$ is unsubstituted $(C_1$-$C_4)$-alkylene-$(C_1$-$C_4)$-alkoxy. In certain embodiments, $(C_1$-$C_4)$-alkylene-$(C_1$-$C_4)$-alkoxy is —CH$_2$OMe. In certain embodiments, the invention relates to any one of the aforementioned compounds, wherein $R_{5d}$ is hydrogen.

In certain embodiments, the invention relates to any one of the aforementioned compounds, wherein $R_{5e}$ is CN. In certain embodiments, the invention relates to any one of the aforementioned compounds, wherein $R_{5e}$ is unsubstituted $(C_1$-$C_4)$-alkyl. In certain embodiments, the invention relates to any one of the aforementioned compounds, wherein $R_{5e}$ is substituted $(C_1$-$C_4)$-alkyl. In certain embodiments, the substituted $(C_1$-$C_5)$-alkyl, is substituted with a halogen. In certain embodiments, the halogen is Cl or F. In certain embodiments, $R_{5e}$ is methyl, ethyl, isopropyl, n-propyl, i-butyl, n-butyl, or t-butyl. In certain embodiments, $R_{5e}$ is methyl. In certain embodiments, the invention relates to any one of the aforementioned compounds, wherein $R_{5e}$ is halide. In some embodiments, the halide is Cl or F. In certain embodiments, $R_{5e}$ is substituted $(C_3$-$C_6)$-cycloalkyl. In certain embodiments, $R_{5e}$ is unsubstituted $(C_3$-$C_6)$-cycloalkyl. In certain embodiments, the invention relates to any one of the aforementioned compounds, wherein $R_{5e}$ is CF$_3$. In certain embodiments, the invention relates to any one of the aforementioned compounds, wherein $R_{5e}$ is C(H)F$_2$. In certain embodiments, the invention relates to any one of the aforementioned compounds, wherein $R_{5e}$ is C(F)H$_2$. In certain embodiments, the invention relates to any one of the aforementioned compounds, wherein $R_{5e}$ is $(C_1$-$C_4)$-alkoxy. In certain embodiments, the invention relates to any one of the aforementioned compounds, wherein $R_{5e}$ is methoxy. In certain embodiments, the invention relates to any one of the aforementioned compounds, wherein $R_{5e}$ is hydroxyl. In certain embodiments, the invention relates to any one of the aforementioned compounds, wherein $R_{5e}$ is —OCF$_3$. In certain embodiments, the invention relates to any one of the aforementioned compounds, wherein $R_{5e}$ is substituted $(C_1$-$C_4)$-alkylene-$(C_1$-$C_4)$-alkoxy. In certain embodiments, the invention relates to any one of the aforementioned compounds, wherein $R_{5e}$ is unsubstituted $(C_1$-$C_4)$-alkylene-$(C_1$-$C_4)$-alkoxy. In certain embodiments, $(C_1$-$C_4)$-alkylene-$(C_1$-$C_4)$-alkoxy is —CH$_2$OMe. In certain embodiments, the invention relates to any one of the aforementioned compounds, wherein $R_{5e}$ is hydrogen.

In certain embodiments, $R_{5b}$ is H. In certain embodiments, the invention relates to any one of the aforementioned compounds, wherein $R_{5b}$ is substituted or unsubstituted $(C_1$-$C_4)$-alkyl. In certain embodiments, the invention relates to any one of the aforementioned compounds, wherein $R_{5b}$ is unsubstituted $(C_1$-$C_4)$-alkyl. In certain embodiments, the invention relates to any one of the aforementioned compounds, wherein $R_{5b}$ is substituted $(C_1-C_4)$-alkyl. In certain embodiments, the substituted $(C_1-C_5)$-alkyl, is substituted with one or more halogen. In certain embodiments, the halogen is Cl or F. In certain embodiments, $R_{5b}$ is methyl, ethyl, isopropyl, n-propyl, i-butyl, n-butyl, or t-butyl. In certain embodiments, the invention relates to any one of the aforementioned compounds, wherein $R_{5b}$ is halide. In some embodiments, the halide is Cl or F. In certain embodiments, $R_{5b}$ is substituted $(C_3-C_6)$-cycloalkyl. In certain embodiments, $R_{5b}$ is unsubstituted $(C_3-C_6)$-cycloalkyl. In some embodiments, $(C_3-C_6)$-cycloalkyl is cyclopropyl. In certain embodiments, the invention relates to any one of the aforementioned compounds, wherein $R_{5b}$ is $CF_3$. In certain embodiments, the invention relates to any one of the aforementioned compounds, wherein $R_{5b}$ is $C(H)F_2$. In certain embodiments, the invention relates to any one of the aforementioned compounds, wherein $R_{5b}$ is $C(F)H_2$. In certain embodiments, the invention relates to any one of the aforementioned compounds, wherein $R_{5a}$ is $(C_1-C_4)$-alkoxy. In some embodiments, $(C_1-C_4)$-alkoxy is methoxy. In certain embodiments, the invention relates to any one of the aforementioned compounds, wherein $R_{5b}$ is methoxy. In certain embodiments, the invention relates to any one of the aforementioned compounds, wherein $R_{5b}$ is hydroxyl. In certain embodiments, the invention relates to any one of the aforementioned compounds, wherein $R_{5b}$ is $OCF_3$. In certain embodiments, $R_{5b}$ is CN. In certain embodiments, the invention relates to any one of the aforementioned compounds, wherein $R_{5b}$ is substituted $(C_1-C_4)$-alkylene-$(C_1-C_4)$-alkoxy. In certain embodiments, the invention relates to any one of the aforementioned compounds, wherein $R_{5b}$ is unsubstituted $(C_1C_4)$-alkylene-$(C_1-C_4)$-alkoxy. In certain embodiments, $(C_1-C_4)$-alkylene-$(C_1-C_4)$-alkoxy is $CH_2OMe$. In certain embodiments, $R_{5b}$ is $CH_2OH$.

In certain embodiments, $R_{5c}$ is H. In certain embodiments, the invention relates to any one of the aforementioned compounds, wherein $R_{5c}$ is substituted or unsubstituted $(C_1-C_4)$-alkyl. In certain embodiments, the invention relates to any one of the aforementioned compounds, wherein $R_{5a}$ is unsubstituted $(C_1-C_4)$-alkyl. In certain embodiments, the invention relates to any one of the aforementioned compounds, wherein $R_{5c}$ is substituted $(C_1-C_4)$-alkyl. In certain embodiments, the substituted $(C_1-C_5)$-alkyl, is substituted with one or more halogen. In certain embodiments, the halogen is Cl or F. In certain embodiments, $R_{5c}$ is methyl, ethyl, isopropyl, n-propyl, i-butyl, n-butyl, or t-butyl. In certain embodiments, the invention relates to any one of the aforementioned compounds, wherein $R_{5c}$ is halide. In some embodiments, the halide is Cl or F. In certain embodiments, $R_{5c}$ is substituted $(C_3-C_6)$-cycloalkyl. In certain embodiments, $R_{5c}$ is unsubstituted $(C_3-C_6)$-cycloalkyl. In some embodiments, $(C_3-C_6)$-cycloalkyl is cyclopropyl. In certain embodiments, the invention relates to any one of the aforementioned compounds, wherein $R_{5c}$ is $CF_3$. In certain embodiments, the invention relates to any one of the aforementioned compounds, wherein $R_{5c}$ is $C(H)F_2$. In certain embodiments, the invention relates to any one of the aforementioned compounds, wherein $R_{5c}$ is $C(F)H_2$. In certain embodiments, the invention relates to any one of the aforementioned compounds, wherein $R_{5c}$ is $(C_1-C_4)$-alkoxy. In some embodiments, $(C_1-C_4)$-alkoxy is methoxy. In certain embodiments, the invention relates to any one of the aforementioned compounds, wherein $R_{5c}$ is methoxy. In certain embodiments, the invention relates to any one of the aforementioned compounds, wherein $R_{5c}$ is hydroxyl. In certain embodiments, the invention relates to any one of the aforementioned compounds, wherein $R_{5c}$ is $OCF_3$. In certain embodiments, $R_{5e}$ is CN. In certain embodiments, the invention relates to any one of the aforementioned compounds, wherein $R_{5a}$ is substituted $(C_1-C_4)$-alkylene-$(C_1-C_4)$-alkoxy. In certain embodiments, the invention relates to any one of the aforementioned compounds, wherein $R_{5c}$ is unsubstituted $(C_1-C_4)$-alkylene-$(C_1-C_4)$-alkoxy. In certain embodiments, $(C_1-C_4)$-alkylene-$(C_1-C_4)$-alkoxy is $—CH_2OMe$. In certain embodiments, $R_{5c}$ is $CH_2OH$.

In certain embodiments, $R_{5d}$ is H. In certain embodiments, the invention relates to any one of the aforementioned compounds, wherein $R_{5d}$ is substituted or unsubstituted $(C_1-C_4)$-alkyl. In certain embodiments, the invention relates to any one of the aforementioned compounds, wherein $R_{5d}$ is unsubstituted $(C_1-C_4)$-alkyl. In certain embodiments, the invention relates to any one of the aforementioned compounds, wherein $R_{5d}$ is substituted $(C_1-C_4)$-alkyl. In certain embodiments, the substituted $(C_1-C_5)$-alkyl, is substituted with one or more halogen. In certain embodiments, the halogen is Cl or F. In certain embodiments, $R_{5d}$ is methyl, ethyl, isopropyl, n-propyl, i-butyl, n-butyl, or t-butyl. In certain embodiments, the invention relates to any one of the aforementioned compounds, wherein $R_{5d}$ is halide. In some embodiments, the halide is Cl or F. In certain embodiments, $R_{5d}$ is substituted $(C_3-C_6)$-cycloalkyl. In certain embodiments, $R_{5d}$ is unsubstituted $(C_3-C_6)$-cycloalkyl. In some embodiments, $(C_3-C_6)$-cycloalkyl is cyclopropyl. In certain embodiments, the invention relates to any one of the aforementioned compounds, wherein $R_{5d}$ is $CF_3$. In certain embodiments, the invention relates to any one of the aforementioned compounds, wherein $R_{5d}$ is $C(H)F_2$. In certain embodiments, the invention relates to any one of the aforementioned compounds, wherein $R_{5d}$ is $C(F)H_2$. In certain embodiments, the invention relates to any one of the aforementioned compounds, wherein $R_{5d}$ is $(C_1-C_4)$-alkoxy. In some embodiments, $(C_1-C_4)$-alkoxy is methoxy. In certain embodiments, the invention relates to any one of the aforementioned compounds, wherein $R_{5d}$ is methoxy. In certain embodiments, the invention relates to any one of the aforementioned compounds, wherein $R_{5d}$ is hydroxyl. In certain embodiments, the invention relates to any one of the aforementioned compounds, wherein $R_{5d}$ is $OCF_3$. In certain embodiments, $R_{5d}$ is CN. In certain embodiments, the invention relates to any one of the aforementioned compounds, wherein $R_{5d}$ is substituted $(C_1-C_4)$-alkylene-$(C_1-C_4)$-alkoxy. In certain embodiments, the invention relates to any one of the aforementioned compounds, wherein $R_{5d}$ is unsubstituted $(C_1-C_4)$-alkylene-$(C_1-C_4)$-alkoxy. In certain embodiments, $(C_1-C_4)$-alkylene-$(C_1-C_4)$-alkoxy is $—CH_2OMe$. In certain embodiments, $R_{5d}$ is $CH_2OH$.

In certain embodiments, $R_{5e}$ is H. In certain embodiments, the invention relates to any one of the aforementioned compounds, wherein $R_{5e}$ is substituted or unsubstituted $(C_1-C_4)$-alkyl. In certain embodiments, the invention relates to any one of the aforementioned compounds, wherein $R_{5e}$ is unsubstituted $(C_1-C_4)$-alkyl. In certain embodiments, the invention relates to any one of the aforementioned compounds, wherein $R_{5e}$ is substituted $(C_1-C_4)$-alkyl. In certain embodiments, the substituted $(C_1-C_5)$-alkyl, is substituted with one or more halogen. In certain embodiments, the halogen is Cl or F. In certain embodiments, $R_{5e}$ is methyl, ethyl, isopropyl, n-propyl, i-butyl, n-butyl, or t-butyl. In certain embodiments, the invention relates to any one of the aforementioned compounds, wherein $R_{5e}$ is halide. In some embodiments, the halide is Cl or F. In certain embodiments, $R_{5e}$ is substituted $(C_3-C_6)$-cycloalkyl. In certain embodiments, $R_{5e}$ is unsubstituted $(C_3-C_6)$-cycloalkyl. In some embodiments, $(C_3-C_6)$-cycloalkyl is cyclopropyl. In certain embodiments, the invention relates to any one of the aforementioned compounds, wherein $R_{5e}$ is $CF_3$. In certain embodiments, the invention relates to any one of the aforementioned compounds, wherein $R_{5e}$ is $C(H)F_2$. In certain embodiments, the invention relates to any one of the aforementioned compounds, wherein $R_{5e}$ is $C(F)H_2$. In certain embodiments, the invention relates to any one of the aforementioned compounds, wherein $R_{5e}$ is $(C_1-C_4)$-alkoxy. In some embodiments, $(C_1-C_4)$-alkoxy is methoxy. In certain embodiments, the invention relates to any one of the aforementioned compounds, wherein $R_{5e}$ is methoxy. In certain embodiments, the invention relates to any one of the aforementioned compounds, wherein $R_{5e}$ is hydroxyl. In certain embodiments, the invention relates to any one of the aforementioned compounds, wherein $R_{5e}$ is $OCF_3$. In certain embodiments, $R_{5e}$ is CN. In certain embodiments, the invention relates to any one of the aforementioned compounds, wherein $R_{5e}$ is substituted $(C_1-C_4)$-alkylene-$(C_1-C_4)$-alkoxy. In certain embodiments, the invention relates to any one of the aforementioned compounds, wherein $R_{5e}$ is unsubstituted $(C_1-C_4)$-alkylene-$(C_1-C_4)$-alkoxy. In certain embodiments, $(C_1-C_4)$-alkylene-$(C_1-C_4)$-alkoxy is —$CH_2OMe$. In certain embodiments, $R_{5e}$ is $CH_2OH$.

In some embodiments, $R_{5a}$ and $R_{5e}$ are identical. For example, $R_{5a}$ and $R_{5e}$ can both be substituted or unsubstituted $(C_1-C_4)$-alkyl. In some examples, $R_{5a}$ and $R_{5e}$ is are both unsubstituted $(C_1-C_4)$-alkyl (e.g., methyl). In some examples, $R_{5a}$ and $R_{5e}$ are both unsubstituted methyl.

In some embodiments, $R_{5b}$ and $R_{5d}$ are identical. For example, $R_{5a}$ and $R_{5e}$ can both be hydrogen.

In some embodiments, $R_{5a}$ and $R_{5e}$ are both substituted, and $R_{5b}$ and $R_{5d}$ are both hydrogen. For example, $R_{5a}$ and $R_{5e}$ can both be (the same or different) substituted or unsubstituted $(C_1-C_4)$-alkyl. In some examples, $R_{5a}$ and $R_{5e}$ can both be unsubstituted $(C_1-C_4)$-alkyl (e.g., methyl) and $R_{5b}$ and $R_{5d}$ are both hydrogen. In some examples, $R_{5a}$ and $R_{5e}$ are both unsubstituted methyl and $R_{5b}$ and $R_{5d}$ are both hydrogen. In some embodiments, $R_{5a}$, and $R_{5e}$ are independently selected from the group consisting of H, CN, halide, $CF_3$, $C(H)F_2$, $C(F)H_2$, $(C_1-C_5)$-alkyl, hydroxyl, and $(C_1-C_4)$-alkoxy.

In some embodiments, $R_{5c}$ is hydrogen, halide (e.g., F), substituted or unsubstituted $(C_1-C_4)$-alkoxy (e.g., methoxy), or substituted or unsubstituted $(C_1-C_4)$-alkyl (e.g., methyl).

In some embodiments, $R_{5a}$ and $R_{ye}$ are both substituted or unsubstituted $(C_1-C_5)$-alkyl, both $R_{5b}$ and $R_{5d}$ are hydrogen and Rye is hydrogen, halide (e.g., F), substituted or unsubstituted $(C_1-C_4)$-alkoxy (e.g., methoxy), or substituted or unsubstituted $(C_1-C_4)$-alkyl (e.g, methyl). For example, $R_{5a}$ and $R_{5e}$ can both be methyl; $R_{5b}$ and $R_{5d}$ are both hydrogen; and $R_{5c}$ is selected from the group consisting of hydrogen, halide (e.g., F), substituted or unsubstituted $(C_1-C_4)$-alkoxy (e.g., methoxy), and substituted or unsubstituted $(C_1-C_4)$-alkyl (e.g, methyl). In some examples, $R_{5a}$ and $R_{5e}$ can both be methyl; $R_{5b}$ and $R_{5d}$ are both hydrogen; and $R_{5e}$ is selected from the group consisting of hydrogen, F, Cl, methoxy, and methyl. In some examples, $R_{5a}$, $R_{5c}$ and $R_{5e}$ are each methyl; and $R_{5b}$ and $R_{5d}$ are both hydrogen. In some embodiments, $R_{5b}$, $R_{5e}$ is, and $R_{5d}$ are independently selected from the group consisting of H, CN, halide, $CF_3$, $C(H)F_2$, $C(F)H_2$, $(C_1-C_5)$-alkyl, hydroxyl, and $(C_1-C_4)$-alkoxy.

In certain embodiments, the invention relates to any one of the aforementioned compounds, wherein $R_a$, $R_b$ and $R_c$ comprise a charged amine. At least one of $R_a$, $R_b$ and $R_c$ can be a substituted or unsubstituted $(C_1-C_5)$alkylene-N—$(R_x)$$(R_y)$; wherein $R_x$ and $R_y$ are independently selected from the group consisting of H, substituted or unsubstituted $(C_1-C_6)$-alkyl, or substituted or unsubstituted $(C_1-C_4)$-alkylene-$(C_1-C_4)$-alkoxy; or $R_x$ and $R_y$ taken together with the N to which they are attached form a substituted or unsubstituted 4-6 membered heterocyclyl ring.

In certain embodiments, the invention relates to any one of the aforementioned compounds, wherein only one of $R_a$, $R_b$ and $R_c$ is a substituted or unsubstituted —$(C_1-C_5)$alkylene-N—$(R_x)$$(R_y)$; wherein $R_x$ and $R_y$ are independently selected from the group consisting of H, substituted or unsubstituted $(C_1-C_6)$-alkyl, or substituted or unsubstituted $(C_1-C_4)$-alkylene-$(C_1-C_4)$-alkoxy. In certain embodiments, the invention relates to any one of the aforementioned compounds, wherein only one of $R_a$, $R_b$ and $R_c$ is a substituted or unsubstituted —$(C_1-C_5)$alkylene-N—$(R_x)$$(R_y)$; wherein $R_x$ and $R_y$ are independently selected from the group consisting of substituted or unsubstituted $(C_1-C_6)$-alkyl, or substituted or unsubstituted $(C_1-C_4)$-alkylene-$(C_1-C_4)$-alkoxy. In certain embodiments, the invention relates to any one of the aforementioned compounds, wherein only one of $R_a$, $R_b$ and $R_c$ is a substituted or unsubstituted $(C_1-C_5)$ alkylene-N—$(R_x)$$(R_y)$; wherein $R_x$ and $R_y$ are independently selected from the group consisting of substituted or unsubstituted $(C_1-C_6)$-alkyl.

In certain embodiments, the invention relates to any one of the aforementioned compounds, wherein only one of $R_a$, $R_b$ and $R_c$ is a substituted or unsubstituted —$(C_1-C_5)$alkylene-N—$(R_x)$$(R_y)$; wherein $R_x$ and $R_y$ taken together with the N to which they are attached form a substituted or unsubstituted 4-6 membered heterocyclyl ring. In certain embodiments, the invention relates to any one of the aforementioned compounds, wherein only one of $R_a$, $R_b$ and $R_c$ is a substituted or unsubstituted $(C_1-C_5)$alkylene-N—$(R_x)$$(R_y)$; wherein $R_x$ and $R_y$ taken together with the N to which they are attached form a 4-6 membered heterocyclyl ring optionally substituted with one or more halide (e.g., F, Cl).

In some embodiments, $R_a$, $R_b$, and $R_c$ are independently selected from the group consisting of H, substituted or unsubstituted $(C_1-C_5)$-alkyl, halide, $CF_3$, $C(H)F_2$, $C(F)H_2$, substituted or unsubstituted $(C_1-C_4)$-alkoxy, —$OCF_3$, and at least one of $R_a$, $R_b$, and $R_c$ is —$(C_1-C_3)$alkylene-N—$(R_x)$$(R_y)$ wherein $R_x$ and $R_y$ are independently selected from the group consisting of H and $(C_1-C_6)$-alkyl; or $R_x$ and $R_y$ taken together with the N to which they are attached form a 4-6 membered heterocyclyl ring optionally substituted with one or more halide (e.g., F, or Cl).

In some embodiments, $R_a$, $R_b$, and $R_c$ are independently selected from the group consisting of H, substituted or unsubstituted $(C_1-C_5)$-alkyl, halide, $CF_3$, $C(H)F_2$, $C(F)H_2$, substituted or unsubstituted $(C_1-C_4)$-alkoxy, —$OCF_3$, and at least one of $R_a$, $R_b$, and $R_c$ is —$(C_1-C_3)$alkylene-N—$(R_x)$$(R_y)$ wherein $R_x$ and $R_y$ are independently selected from the group consisting of $(C_1-C_6)$-alkyl (e.g., methyl); or $R_x$ and $R_y$ taken together with the N to which they are attached form a 4-6 membered heterocyclyl ring optionally substituted with one or more halide (e.g., F, or Cl).

In certain embodiments, the invention relates to any one of the aforementioned compounds, wherein only one of $R_a$, $R_b$ and $R_c$ is selected from the group consisting of

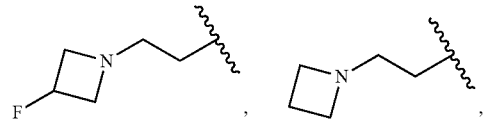

,

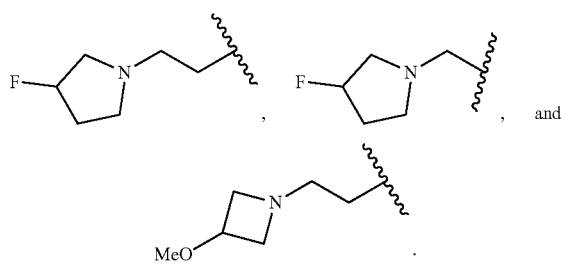

In certain embodiments, the invention relates to any one of the aforementioned compounds, wherein only one of $R_a$, $R_b$ and $R_c$ is selected from the group consisting of:

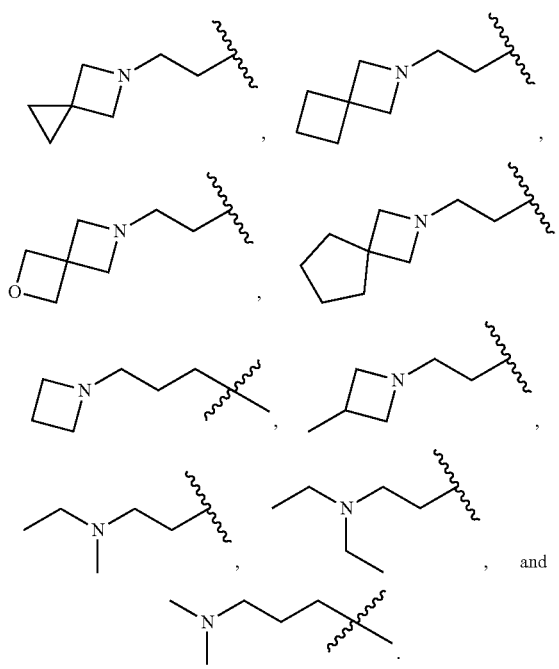

In certain embodiments, the invention relates to any one of the aforementioned compounds, wherein only one of $R_a$, $R_b$ and $R_c$ is selected from the group consisting of:

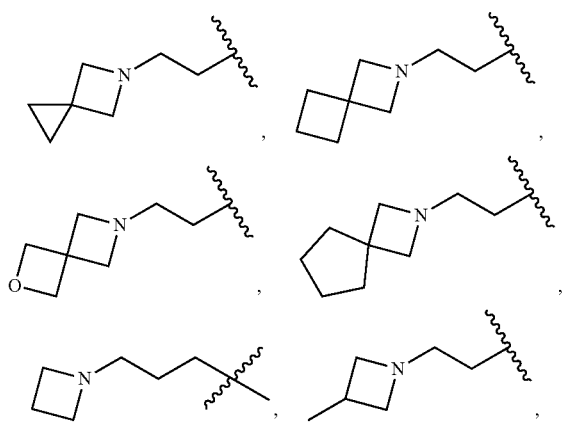

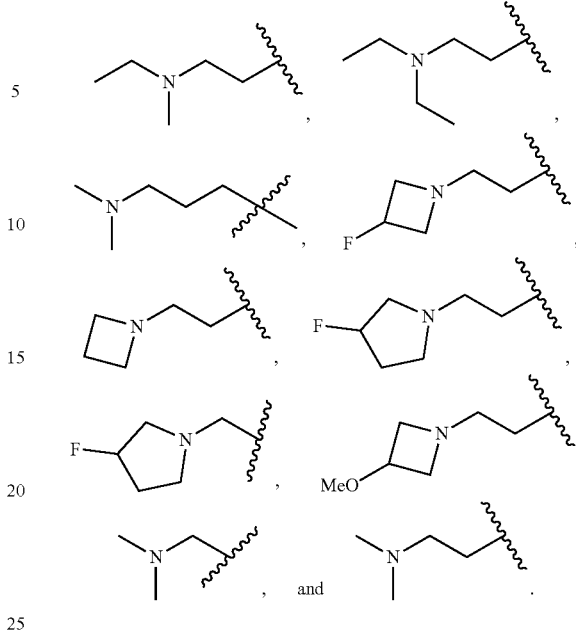

In certain embodiments, the invention relates to any one of the aforementioned compounds, wherein $R_a$ is selected from the group consisting of H, substituted or unsubstituted $(C_1-C_5)$-alkyl, halide, $CF_3$, $C(H)F_2$, $C(F)H_2$, substituted or unsubstituted $(C_1-C_4)$-alkoxy, and $-OCF_3$. In certain embodiments, the invention relates to any one of the aforementioned compounds, wherein $R_a$ is selected from the group consisting of H, substituted or unsubstituted $(C_1-C_5)$-alkyl, halide, $CF_3$, $C(H)F_2$, $C(F)H_2$, substituted or unsubstituted $(C_1-C_4)$-alkoxy, and $-OCF_3$; and one of $R_b$ and $R_c$ is a substituted or unsubstituted $-(C_1-C_5)$alkylene-N—$(R_x)$$(R_y)$; wherein $R_x$ and $R_y$ are independently selected from the group consisting of H, substituted or unsubstituted $(C_1-C_6)$-alkyl, or substituted or unsubstituted $(C_1-C_4)$-alkylene-$(C_1-C_4)$-alkoxy; or $R_x$ and $R_y$ taken together with the N to which they are attached form a substituted or unsubstituted 4-6 membered heterocyclyl ring.

In certain embodiments, the invention relates to any one of the aforementioned compounds, wherein $R_a$ is H. In certain embodiments, the invention relates to any one of the aforementioned compounds, wherein $R_a$ is Me. In certain embodiments, the invention relates to any one of the aforementioned compounds, wherein $R_a$ is halide. In some embodiments, halide is Cl or F. In certain embodiments, the invention relates to any one of the aforementioned compounds, wherein $R_a$ is $CF_3$. In certain embodiments, the invention relates to any one of the aforementioned compounds, wherein $R_a$ is $C(H)F_2$. In certain embodiments, the invention relates to any one of the aforementioned compounds, wherein $R_a$ is $C(F)H_2$. In certain embodiments, the invention relates to any one of the aforementioned compounds, wherein $R_a$ is substituted $(C_1-C_4)$-alkoxy. In certain embodiments, the invention relates to any one of the aforementioned compounds, wherein $R_a$ is unsubstituted $(C_1-C_4)$-alkoxy. In some embodiments, $(C_1-C_4)$-alkoxy is methoxy. In certain embodiments, the invention relates to any one of the aforementioned compounds, wherein $R_a$ is $-OCF_3$. In certain embodiments, the invention relates to any one of the aforementioned compounds, wherein $R_a$ is substituted $-(C_1-C_5)$alkylene-N—$(R_x)$$(R_y)$. In certain embodiments, the invention relates to any one of the aforementioned compounds, wherein $R_a$ is unsubstituted —$(C_1-C_5)$alkylene-N—$(R_x)(R_y)$. In some embodiments, —$(C_1-C_5)$alkylene of —$(C_1-C_5)$alkylene-N—$(R_x)(R_y)$ is substituted with one or more halide or —$(C_1-C_4)$alkyl. In certain embodiments, the invention relates to any one of the aforementioned compounds, wherein —$(C_1-C_5)$alkylene-N—$(R_x)(R_y)$ is —$(C_1-C_4)$alkylene-N—$(R_x)(R_y)$.

In some embodiments, $R_a$ is substituted $(C_1-C_5)$-alkyl, substituted $(C_1-C_4)$-alkoxy, or substituted —$(C_1-C_5)$alkylene-N—$(R_x)(R_y)$, wherein substituted means substituted with halide or $(C_1-C_4)$-alkoxy. In some embodiments, Ra is substituted $(C_1-C_5)$-alkyl, substituted $(C_1-C_4)$-alkoxy, or substituted —$(C_1-C_5)$alkylene-N—$(R_x)(R_y)$, wherein substituted means substituted with F or methoxy. In some embodiments, $R_a$ is selected from the group consisting of

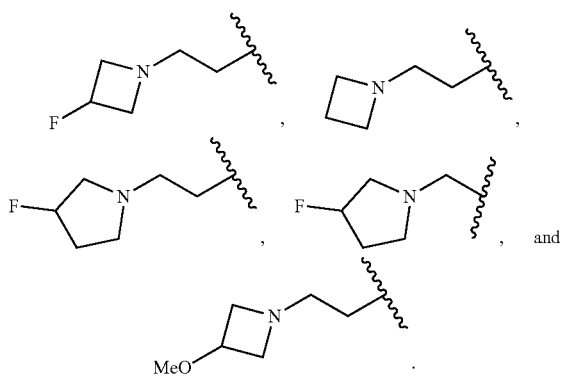

and

In some embodiments, $R_a$

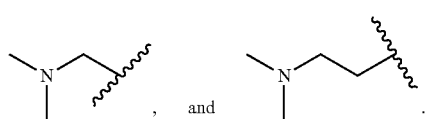

and .

In some embodiments, $R_a$ is

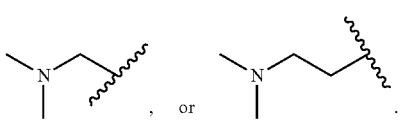

or .

In some embodiments, $R_a$ is $CF_3$.

In certain embodiments, the invention relates to any one of the aforementioned compounds, wherein $R_a$ is selected from the group consisting of H, substituted or unsubstituted $(C_1-C_5)$-alkyl, halide, $CF_3$, $C(H)F_2$, $C(F)H_2$, substituted or unsubstituted $(C_1-C_4)$-alkoxy, and —OCF; and $R_b$ is a substituted or unsubstituted —$(C_1-C_5)$alkylene-N—$(R_x)(R_y)$; wherein $R_x$ and $R_y$ are independently selected from the group consisting of H, substituted or unsubstituted $(C_1-C_6)$-alkyl, or substituted or unsubstituted $(C_1-C_4)$-alkylene-$(C_1-C_4)$-alkoxy; or $R_x$ and $R_y$ taken together with the N to which they are attached form a substituted or unsubstituted 4-6 membered heterocyclyl ring.

In certain embodiments, the invention relates to any one of the aforementioned compounds, wherein $R_b$ is H. In certain embodiments, the invention relates to any one of the aforementioned compounds, wherein $R_b$ is Me. In certain embodiments, the invention relates to any one of the aforementioned compounds, wherein $R_b$ is halide. In some embodiments, halide is Cl or F. In certain embodiments, the invention relates to any one of the aforementioned compounds, wherein $R_b$ is $CF_3$. In certain embodiments, the invention relates to any one of the aforementioned compounds, wherein $R_b$ is $C(H)F_2$. In certain embodiments, the invention relates to any one of the aforementioned compounds, wherein $R_b$ is $C(F)H_2$. In certain embodiments, the invention relates to any one of the aforementioned compounds, wherein $R_b$ is substituted $(C_1-C_4)$-alkoxy. In certain embodiments, the invention relates to any one of the aforementioned compounds, wherein $R_b$ is unsubstituted $(C_1-C_4)$-alkoxy. In some embodiments, $(C_1-C_4)$-alkoxy is methoxy. In certain embodiments, the invention relates to any one of the aforementioned compounds, wherein $R_b$ is —$OCF_3$. In certain embodiments, the invention relates to any one of the aforementioned compounds, wherein $R_b$ is substituted —$(C_1-C_5)$alkylene-N—$(R_x)(R_y)$. In certain embodiments, the invention relates to any one of the aforementioned compounds, wherein $R_b$ is unsubstituted $(C_1-C_5)$alkylene-N—$(R_x)(R_y)$. In some embodiments, —$(C_1-C_5)$alkylene of —$(C_1-C_5)$alkylene-N—$(R_x)(R_y)$ is substituted with one or more halide or —$(C_1-C_4)$alkyl. In certain embodiments, the invention relates to any one of the aforementioned compounds, wherein —$(C_1-C_5)$alkylene-N—$(R_x)(R_y)$ is —$(C_1-C_4)$alkylene-N—$(R_x)(R_y)$.

In some embodiments, $R_b$ is substituted $(C_1-C_5)$-alkyl, substituted $(C_1-C_4)$-alkoxy, or substituted —$(C_1-C_5)$alkylene-N—$(R_x)(R_y)$, wherein substituted means substituted with halide or $(C_1-C_4)$-alkoxy. In some embodiments, $R_b$ is substituted $(C_1-C_5)$-alkyl, substituted $(C_1-C_4)$-alkoxy, or substituted —$(C_1-C_5)$alkylene-N—$(R_x)(R_y)$, wherein substituted means substituted with F or methoxy. In some embodiments, $R_b$ is —$(C_1-C_5)$alkylene-N—$(R_x)(R_y)$ wherein $R_x$ and $R_y$ are each methyl, or wherein $R_x$ and $R_y$ taken together with the N to which they are attached form a 4-6 membered heterocyclyl ring optionally substituted with one or more halide (e.g., F, or Cl). In some embodiments, $R_b$ is —$(C_2-C_3)$alkylene-N—$(R_x)(R_y)$ wherein $R_x$ and $R_y$ are each methyl, or wherein $R_x$ and $R_y$ taken together with the N to which they are attached form a 4-6 membered heterocyclyl ring optionally substituted with one or more halide (e.g., F, or Cl). In some embodiments, $R_b$ is —$(C_2-C_3)$alkylene-N—$(R_x)(R_y)$ wherein $R_x$ and $R_y$ are each methyl, or wherein $R_x$ and $R_y$ taken together with the N to which they are attached form a 4-membered heterocyclyl ring optionally substituted with one or more halide (e.g., F, or Cl). In some embodiments, $R_b$ is —$(C_2-C_3)$alkylene-N—$(R_x)(R_y)$ wherein $R_x$ and $R_y$ are each methyl, or wherein $R_x$ and $R_y$ taken together with the N to which they are attached form a 4-6 membered heterocyclyl ring optionally substituted with one or more halide (e.g., F, or Cl). In some embodiments, $R_b$ is —$(C_2-C_3)$alkylene-N—$(R_x)(R_y)$ wherein $R_x$ and $R_y$ are each methyl, or wherein $R_x$ and $R_y$ taken together with the N to which they are attached form a 4-membered heterocyclyl ring optionally substituted with one or more halide (e.g., F, or Cl).

In certain embodiments, the invention relates to any one of the aforementioned compounds, $R_b$ is

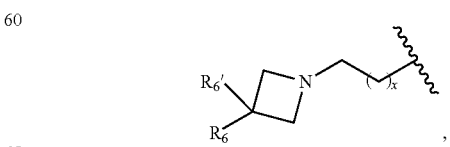

wherein x is 1 or 2; $R_6$ is H and $R_6'$ is $(C_1-C_4)$alkyl optionally substituted with one or more halide (e.g., $CF_3$), or $R_6$ and $R_6'$ together form a substituted or unsubstituted 3-6 member cycloalkyl or heterocycloalkyl. In certain embodiments, the invention relates to any one of the aforementioned compounds, $R_b$ is

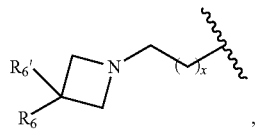

wherein x is 1 or 2; $R_6$ is H and $R_6'$ is $(C_1-C_4)$alkyl optionally substituted with one or more halide (e.g., $CF_3$), or $R_6$ and $R_6'$ together form a 3-6 member cycloalkyl or heterocycloalkyl optionally substituted with halide (e.g., F), $(C_1-C_4)$alkyl (e.g., methyl), $(C_1-C_4)$alkoxy (e.g., methoxy), $(C_3-C_6)$cycloalkyl (e.g., spirocycloprpyl) or $(C_3-C_6)$heterocycloalkyl (e.g., azaspiro[3.3]heptyl). In some embodiments, $R_b$ is selected from the group consisting of

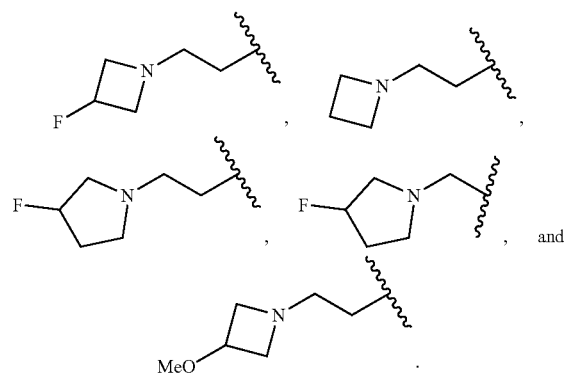

In some embodiments, $R_b$

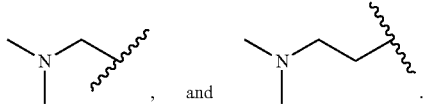

In certain embodiments, the invention relates to any one of the aforementioned compounds, $R_b$ is selected from the group consisting of:

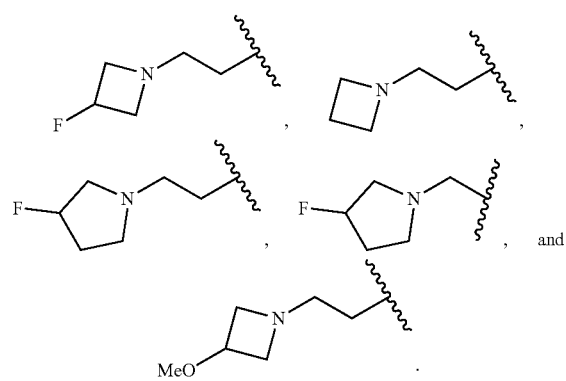

In some embodiments, $R_b$ is

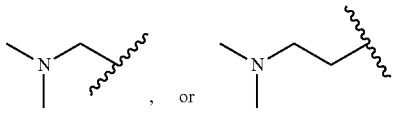

In certain embodiments, the invention relates to any one of the aforementioned compounds, wherein $R_b$ is selected from the group consisting of:

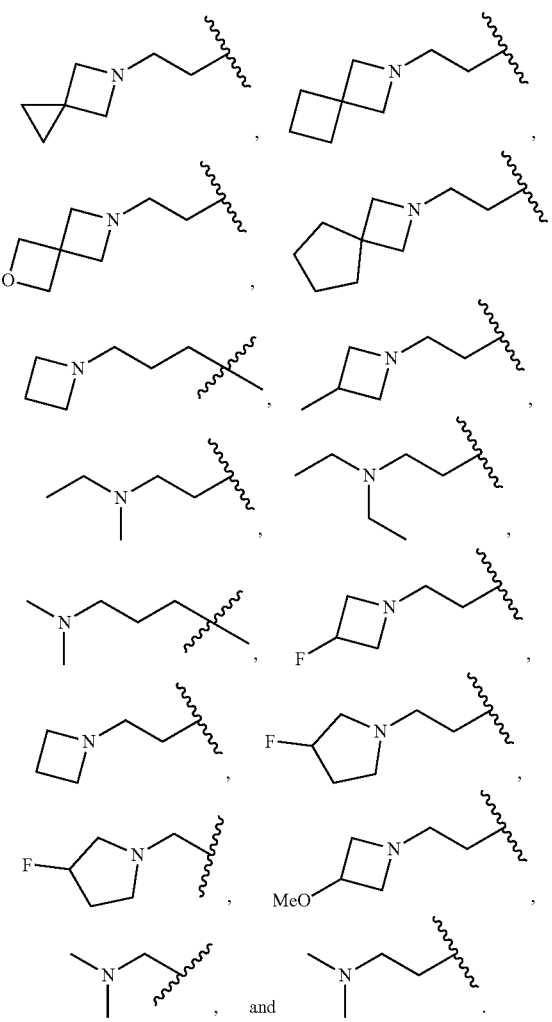

In certain embodiments, the invention relates to any one of the aforementioned compounds, wherein $R_c$ is H. In certain embodiments, the invention relates to any one of the aforementioned compounds, wherein $R_c$ is Me. In certain embodiments, the invention relates to any one of the aforementioned compounds, wherein $R_c$ is halide. In some embodiments, halide is Cl or F. In certain embodiments, the invention relates to any one of the aforementioned compounds, wherein is $CF_3$. In certain embodiments, the invention relates to any one of the aforementioned compounds, wherein $R_c$ is $C(H)F_2$. In certain embodiments, the invention relates to any one of the aforementioned compounds, wherein $R_c$ is $C(F)H_2$. In certain embodiments, the invention relates to any one of the aforementioned compounds, wherein $R_c$ is substituted $(C_1\text{-}C_4)$-alkoxy. In some embodiments, $(C_1\text{-}C_4)$-alkoxy is methoxy. In certain embodiments, the invention relates to any one of the aforementioned compounds, wherein $R_c$ is unsubstituted $(C_1\text{-}C_4)$-alkoxy. In certain embodiments, the invention relates to any one of the aforementioned compounds, wherein $R_c$ is —$OCF_3$. In certain embodiments, the invention relates to any one of the aforementioned compounds, wherein $R_c$ is substituted —$(C_1\text{-}C_5)$alkylene-N—$(R_x)(R_y)$. In certain embodiments, the invention relates to any one of the aforementioned compounds, wherein $R_c$ is unsubstituted —$(C_1\text{-}C_5)$alkylene-N—$(R_x)(R_y)$. In some embodiments, —$(C_1\text{-}C_5)$alkylene of —$(C_1\text{-}C_5)$alkylene-N—$(R_x)(R_y)$ is substituted with one or more halide or $(C_1\text{-}C_4)$alkyl. In certain embodiments, the invention relates to any one of the aforementioned compounds, wherein —$(C_1\text{-}C_5)$alkylene-N—$(R_x)(R_y)$ is —$(C_1\text{-}C_4)$alkylene-N—$(R_x)(R_y)$.

In some embodiments, $R_c$ is substituted $(C_1\text{-}C_5)$-alkyl, substituted $(C_1\text{-}C_4)$-alkoxy, or substituted —$(C_1\text{-}C_5)$alkylene-N—$(R_x)(R_y)$, wherein substituted means substituted with halide or $(C_1\text{-}C_4)$-alkoxy. In some embodiments, $R_c$ is substituted $(C_1\text{-}C_5)$-alkyl, substituted $(C_1\text{-}C_4)$-alkoxy, or substituted —$(C_1\text{-}C_5)$alkylene-N—$(R_x)(R_y)$, wherein substituted means substituted with F or methoxy.

In some embodiments, $R_c$ is selected from the group consisting of

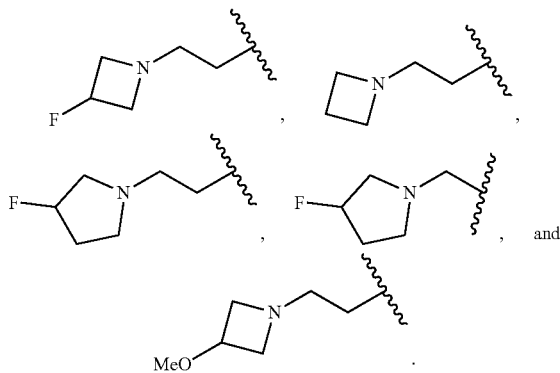

In some embodiments, $R_c$

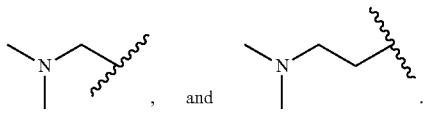

In some embodiments, at least one of $R_a$, $R_b$, and $R_c$ is H.

In some embodiments, at least one of $R_a$, $R_b$, and $R_c$ is a charged amine; and at least one of $R_a$, $R_b$, and $R_c$ is H.

In certain embodiments, the invention relates to any one of the aforementioned compounds, wherein $R_x$ is H. In certain embodiments, the invention relates to any one of the aforementioned compounds, wherein $R_x$ is substituted $(C_1\text{-}C_6)$-alkyl. In certain embodiments, the invention relates to any one of the aforementioned compounds, wherein $R_x$ is unsubstituted $(C_1\text{-}C_6)$-alkyl. In certain embodiments, the invention relates to any one of the aforementioned compounds, wherein $R_x$ is substituted $(C_1\text{-}C_4)$-alkyl. In some embodiments $(C_1\text{-}C_6)$-alkyl is substituted with OMe, CN, or halide. In certain embodiments, the invention relates to any one of the aforementioned compounds, wherein $R_x$ is unsubstituted $(C_1\text{-}C_4)$-alkyl. In certain embodiments, the invention relates to any one of the aforementioned compounds, wherein $R_x$ is $(C_1\text{-}C_4)$-alkylene-$(C_1\text{-}C_4)$-alkoxy. In some embodiments, $(C_1\text{-}C_4)$-alkylene-$(C_1\text{-}C_4)$-alkoxy is —$(CH_2)_2$OMe. In certain embodiments, the invention relates to any one of the aforementioned compounds, wherein $R_x$ is Me.

In certain embodiments, the invention relates to any one of the aforementioned compounds, wherein $R_y$ is H. In certain embodiments, the invention relates to any one of the aforementioned compounds, wherein $R_y$ is substituted $(C_1\text{-}C_6)$-alkyl. In certain embodiments, the invention relates to any one of the aforementioned compounds, wherein $R_y$ is unsubstituted $(C_1\text{-}C_6)$-alkyl. In certain embodiments, the invention relates to any one of the aforementioned compounds, wherein $R_y$ is substituted $(C_1\text{-}C_4)$-alkyl. In some embodiments, $(C_1\text{-}C_6)$-alkyl is substituted with OMe, CN, or halide. In certain embodiments, the invention relates to any one of the aforementioned compounds, wherein $R_y$ is unsubstituted $(C_1\text{-}C_4)$-alkyl. In certain embodiments, the invention relates to any one of the aforementioned compounds, wherein $R_y$ is $(C_1\text{-}C_4)$-alkylene-$(C_1\text{-}C_4)$-alkoxy. In some embodiments, $(C_1\text{-}C_4)$-alkylene-$(C_1\text{-}C_4)$-alkoxy is —$(CH_2)_2$OMe. In certain embodiments, the invention relates to any one of the aforementioned compounds, wherein $R_y$ is Me.

In certain embodiments, the invention relates to any one of the aforementioned compounds, wherein $R_x$ is Me; and $R_y$ is Me.

In certain embodiments, the invention relates to any one of the aforementioned compounds, wherein $R_x$ and $R_y$ taken together with the N to which they are attached form a substituted or unsubstituted 4-6 membered ring. In some embodiments, the 4-6 membered ring is a substituted or unsubstituted heterocycloalkyl. In some embodiments, the substituted 4-6 membered heterocyclealkyl is substituted with halide of $(C_1\text{-}C_6)$alkyl. In some embodiments, the 4-6 membered ring is a substituted or unsubstituted heteroaryl. In some embodiments, the substituted 4-6 membered heteroaryl is substituted with halide of $(C_1\text{-}C_6)$alkyl. In some embodiments, the 4-6 membered ring is selected from

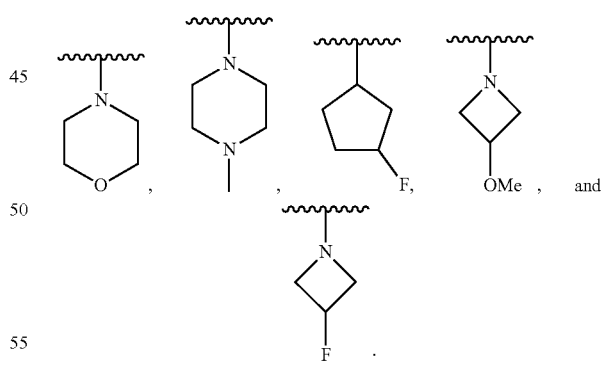

In some embodiments, $R_x$ and $R_y$ taken together with the N to which they are attached form

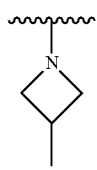 [SMILES: *N1CC(C)C1]

In some embodiments, $R_x$ and $R_y$ taken together with the N to which they are attached form a substituted or unsubstituted 4-6 membered ring of the formula

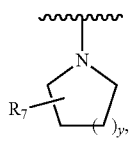

wherein y is 0, 1 or 2; and $R_7$ is H, halide, alkoxy, spirocyclic 3-5 member cycloalkyl, and spirocyclic 3-5 member heterocycloalkyl.

In some embodiments, $R_a$ is $(C_1-C_5)$-alkyl optionally substituted with halide; $R_b$ is —$(C_1-C_5)$alkylene-N—$(R_x)$$(R_y)$ wherein $R_x$ and $R_y$ are each methyl, or wherein $R_x$ and $R_y$ taken together with the N to which they are attached form a 4-5 membered heterocyclyl ring optionally substituted with one or more halide or alkoxy (e.g., methoxy); and $R_c$ is hydrogen, halide or $(C_1-C_5)$-alkyl optionally substituted with halide. In some embodiments, $R_a$ is methyl optionally substituted with halide; $R_b$ is —$(C_2-C_3)$alkylene-N—$(R_x)$$(R_y)$ wherein $R_x$ and $R_y$ are each methyl, or wherein $R_x$ and $R_y$ taken together with the N to which they are attached form a 4-5 membered heterocyclyl ring optionally substituted with one or more halide (e.g., F); and $R_c$ is hydrogen, halide or methyl optionally substituted with halide. In some embodiments, Ra is methyl or $CF_3$; $R_b$ is —$(C_2-C_3)$alkylene-N—$(R_x)(R_y)$ wherein $R_x$ and $R_y$ are each methyl, or wherein $R_x$ and $R_y$ taken together with the N to which they are attached form a 4-5 membered heterocyclyl ring optionally substituted with one or more F or methoxy; and $R_c$ is hydrogen, F, $CH_2F$, $CHF_2$, $CF_3$.

In certain embodiments, the invention relates to a compound of Formula (Ia) or (Ib):

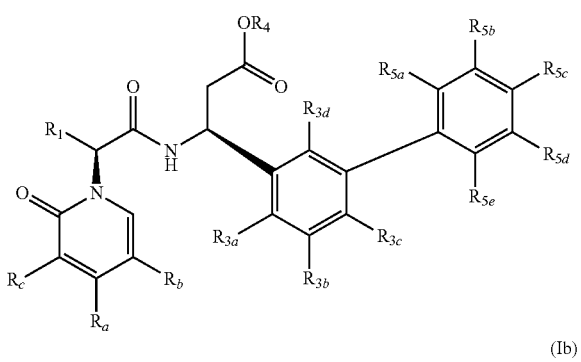

(Ia)

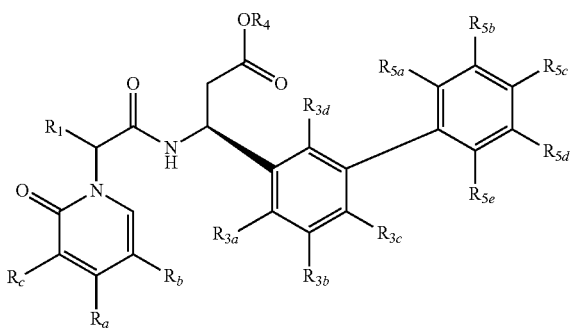

(Ib)

wherein $R_1$, $R_{3c}$, $R_{3d}$, $R_{5a}$, $R_{5b}$, $R_{5c}$, $R_{5d}$, $R_{5e}$, $R_a$, $R_b$, and $R_c$ are as defined above with respect to Formula (I);

$R_4$ is H; and at least one of $R_a$, $R_b$, and $R_c$ is —$(C_1-C_3)$alkylene-N$(R_x)(R_y)$;

$R_x$ and $R_y$ are independently selected from the group consisting of H and methyl; or $R_x$ and $R_y$ taken together with the N to which they are attached form a 4-6 membered ring; and $R_{3a}$, and $R_{3b}$ are each independently selected from the group consisting of methyl and F.

In certain embodiments, the invention relates to any one of the compounds depicted in FIG. 1. In certain embodiments, the invention relates to any one of the compounds depicted in FIG. 2. In certain embodiments, the invention relates to any one of the compounds depicted in FIG. 3. In certain embodiments, the invention relates to any one of the compounds depicted in FIG. 4.

In certain embodiments, a compound is a compound of Formula (I) that is not a compound depicted in FIG. 1. In certain embodiments, a compound is a compound of Formula (I) that is not a compound depicted in FIG. 2. In certain embodiments, a compound is a compound of Formula (I) that is not a compound depicted in FIG. 3. In certain embodiments, a compound is a compound of Formula (I) that is not a compound depicted in FIG. 4. In certain embodiments, a compound is a compound of Formula (I) that is not a compound depicted in FIG. 2, FIG. 3 or FIG. 4.

In certain embodiments, the invention relates to a compound of Formula (Ma):

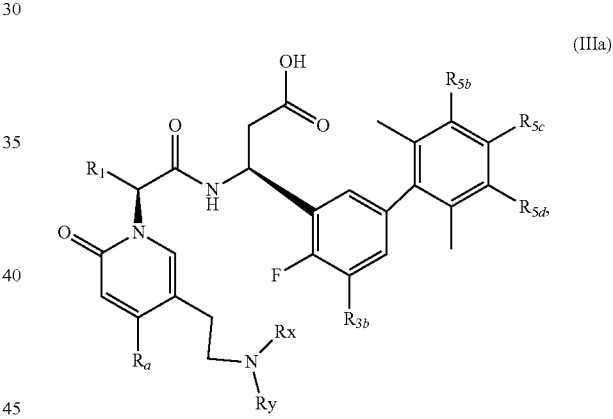

(IIIa)

wherein $R_1$, $R_a$, $R_x$, $R_y$, $R_{3b}$, $R_{5b}$, $R_{5c}$, $R_{5d}$, are as defined above with respect to Formula (I).

In certain embodiments, the invention relates to a compound of Formula (IVa):

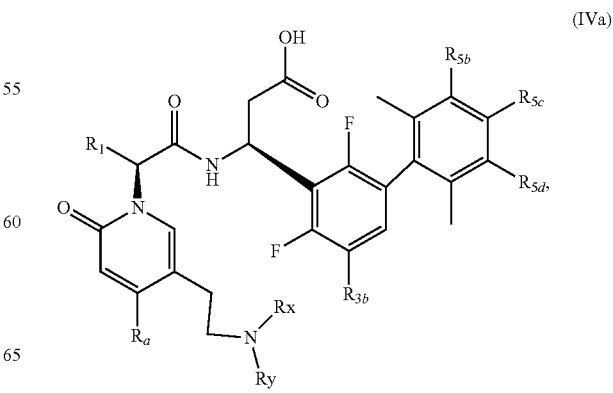

(IVa)

wherein $R_1$, $R_a$, $R_x$, $R_y$, $R_{3b}$, $R_{5b}$, $R_{5c}$, $R_{5d}$, are as defined above with respect to Formula (I).

In certain embodiments, the invention relates to a compound selected from the group consisting of:

(3S)-3-(4,5-difluoro-2',6'-dimethylbiphenyl-3-yl)-3-(2-(5-(2-(3-fluoroazetidine-1-yl)ethyl)-4-methyl-2-oxopyridin-1(2H)-yl)-4-methylpentanamido)propanoic acid;

(3S)-3-(2-(5-(2-(azetidin-1-yl)ethyl)-2-oxo-4-(trifluoromethyl)pyridin-1(2H)-yl)-4-methylpentanamido)-3-(4-fluoro-2',6'-dimethyl-5-(trifluoromethyl)biphenyl-3-yl)propanoic acid;

(3S)-3-(2-(5-(2-(azetidin-1-yl)ethyl)-2-oxo-4-(trifluoromethyl)pyridin-1(2H)-yl)-4-methylpentanamido)-3-(3',4-difluoro-2',5,6'-trimethyl-[1,1'-biphenyl]-3-yl)propanoic acid;

(3S)-3-(2-(5-(2-(azetidin-1-yl)ethyl)-2-oxo-4-(trifluoromethyl)pyridin-1 (2H)-yl)-4-methylpentanamido)-3-(4-fluoro-3'-methoxy-2',5,6'-trimethyl-[1,1'-biphenyl]-3-yl)propanoic acid;

(3S)-3-(4,4'-difluoro-2',5,6'-trimethyl-[1,1'-biphenyl]-3-yl)-3-(2-(5-(2-(dimethylamino)ethyl)-2-oxo-4-(trifluoromethyl)pyridin-1(2H)-yl)-4-methylpentanamido)propanoic acid;

(3S)-3-(5-chloro-4-fluoro-2',6'-dimethyl-[1,1'-biphenyl]-3-yl)-3-(2-(5-(2-(3-methoxyazetidin-1-yl)ethyl)-2-oxo-4-(trifluoromethyl)pyridin-1(2H)-yl)-4-methylpentanamido)propanoic acid;

(3S)-3-(2-(5-(2-(dimethylamino)ethyl)-2-oxo-4-(trifluoromethyl)pyridin-1(2H)-yl)-4-methylpentanamido)-3-(4-fluoro-2',4',5,6'-tetramethylbiphenyl-3-yl)propanoic acid;

(3S)-3-(4,4'-difluoro-2',5,6'-trimethyl-[1,1'-biphenyl]-3-yl)-3-(2-(3-(difluoromethyl)-5-(2-(dimethylamino)ethyl)-2-oxopyridin-1(2H)-yl)-4-methylpentanamido)propanoic acid;

(3S)-3-(2-(5-(2-(dimethylamino)ethyl)-4-methyl-2-oxopyridin-1(2H)-yl)-5-methylhexanamido)-3-(4-fluoro-2',5,6'-trimethylbiphenyl-3-yl)propanoic acid;

(3S)-3-(4-fluoro-2',5,6'-trimethyl-[1,1'-biphenyl]-3-yl)-3-(2-(3-fluoro-5-(2-(3-fluoroazetidine-1-yl)ethyl)-2-oxopyridin-1(2H)-yl)-4-methylpentanamido)propanoic acid; and (3S)-3-(4-fluoro-2',5,6'-trimethyl-[1,1'-biphenyl]-3-yl)-3-(2-(3-fluoro-5-(2-((R)-3-fluoropyrrolidin-1-yl)ethyl)-2-oxopyridin-1(2H)-yl)-4-methylpentanamido)propanoic acid.

or a pharmaceutically acceptable salt thereof.

In certain embodiments, the invention relates to a compound selected from the group consisting of:

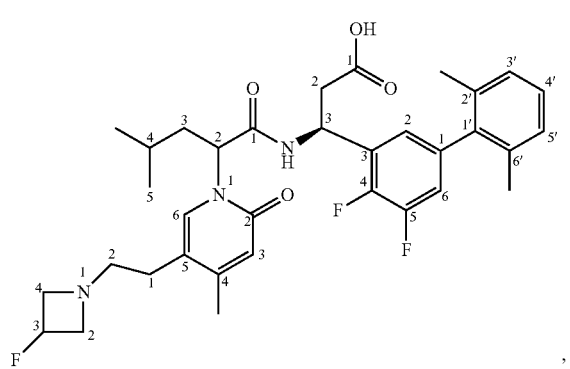

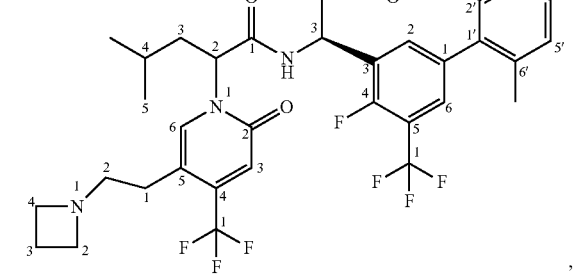

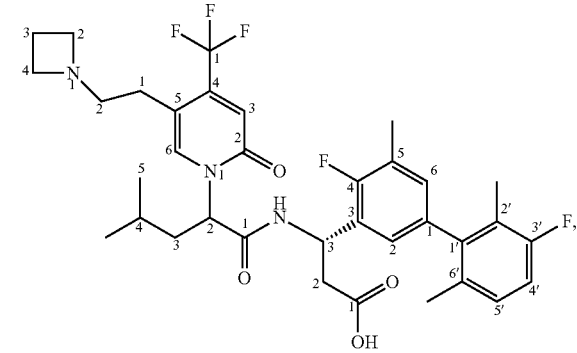

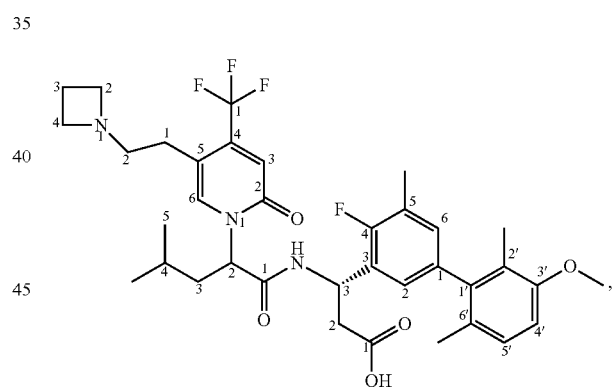

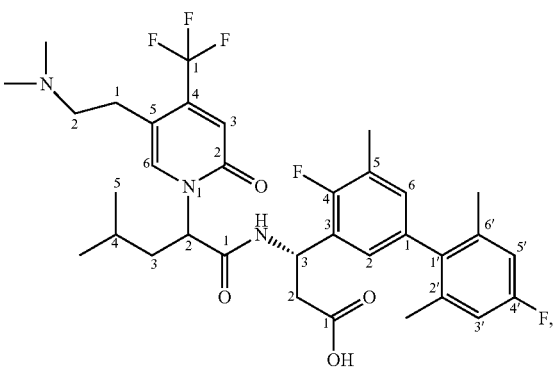

-continued
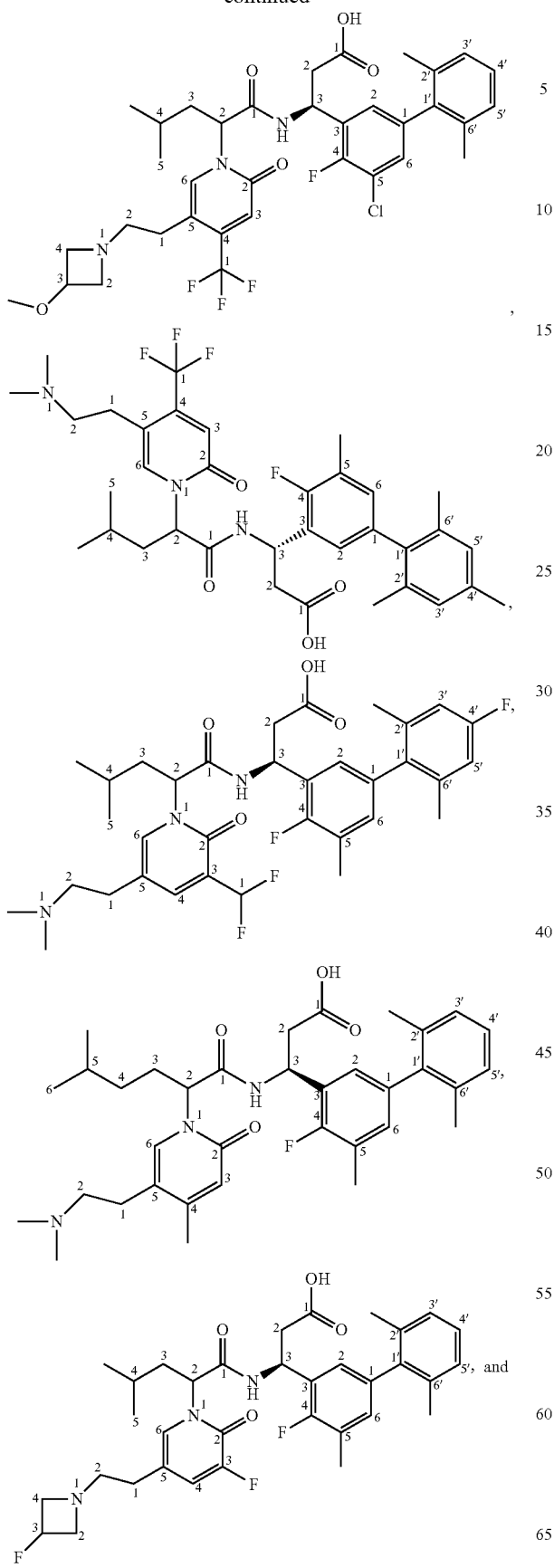
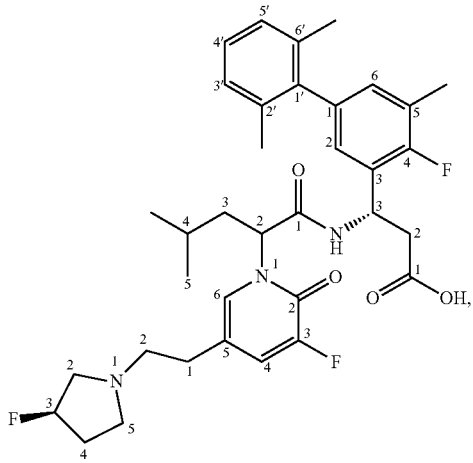
or a pharmaceutically acceptable salt thereof.
In certain embodiments, the invention relates to a compound selected from the group consisting of:
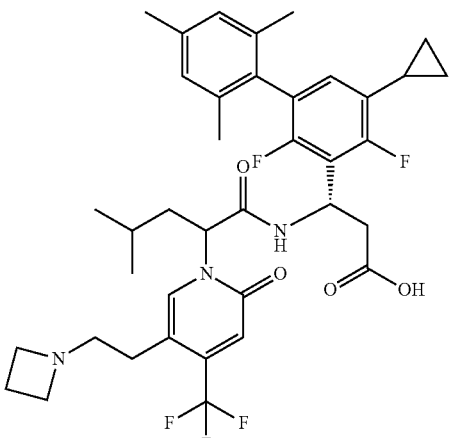
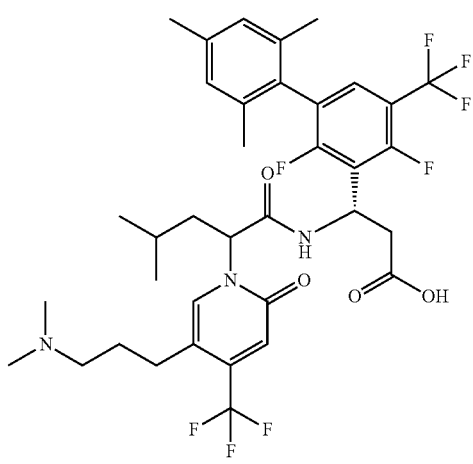

-continued
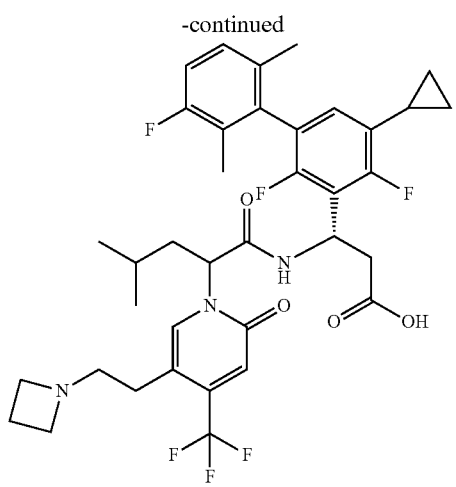
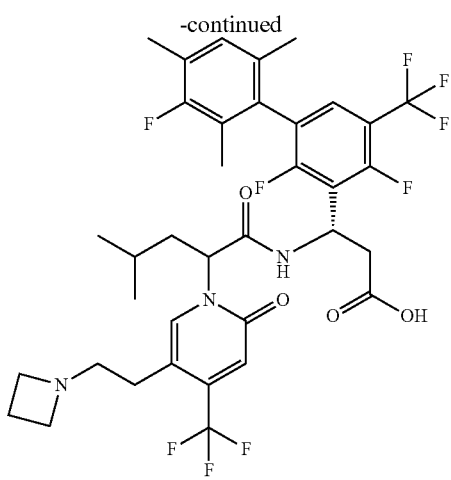
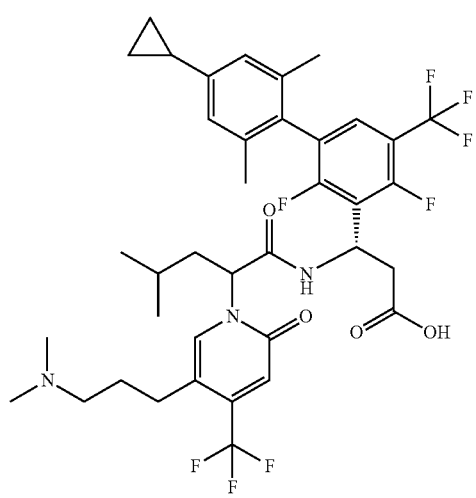
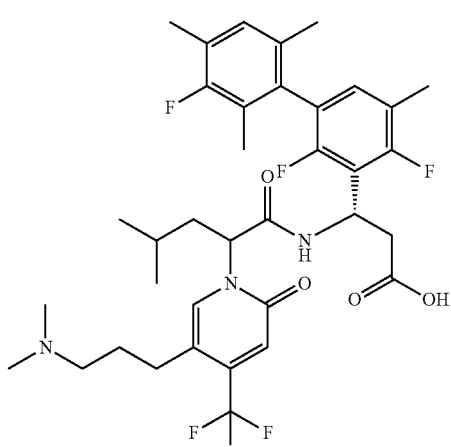
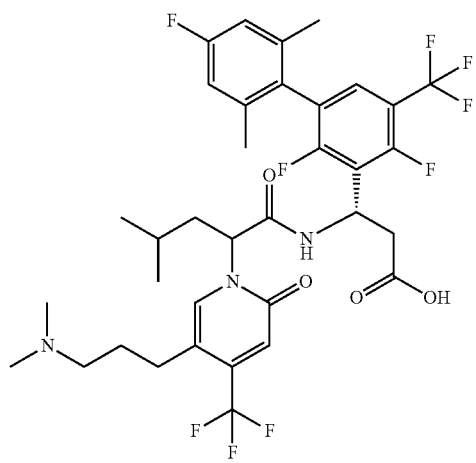
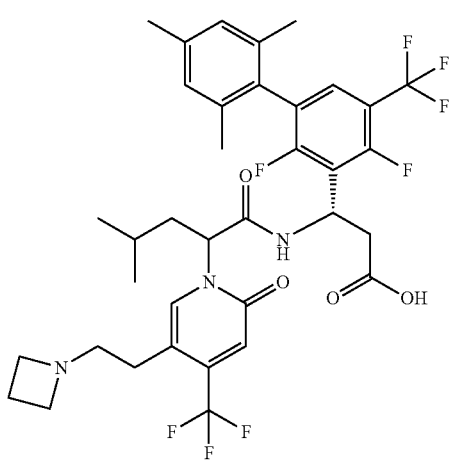

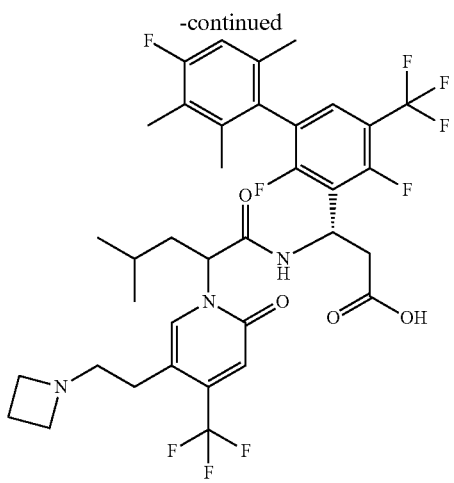

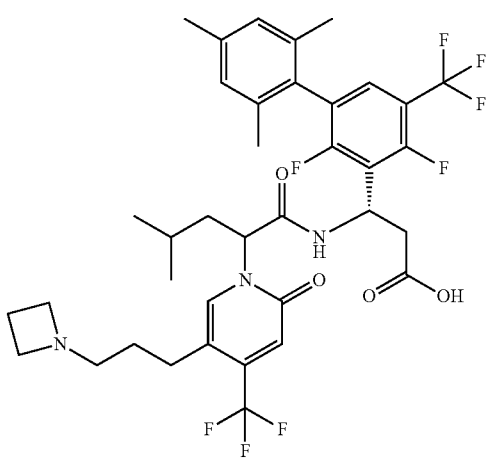

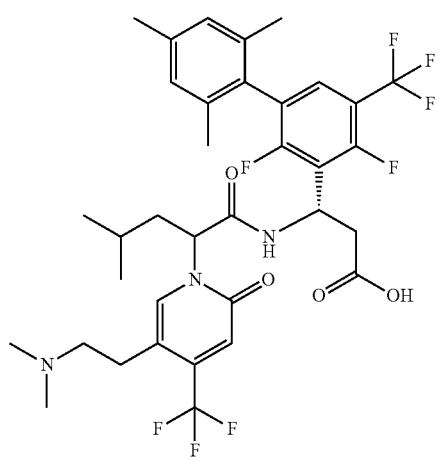

In certain embodiments, the invention relates to a compound selected from the group consisting of:

(S)-3-(4,5-difluoro-2',6'-dimethyl-[1,1'-biphenyl]-3-yl)-3-((S)-2-(5-(2-(3-fluoroazetidine-1-yl)ethyl)-4-methyl-2-oxopyridin-1(2H)-yl)-4-methylpentanamido)propanoic acid;

(S)-3-((S)-2-(5-(2-(azetidin-1-yl)ethyl)-2-oxo-4-(trifluoromethyl)pyridin-1(2H)-yl)-4-methylpentanamido)-3-(4-fluoro-2',6'-dimethyl-5-(trifluoromethyl)-[1,1'-biphenyl]-3-yl)propanoic acid;

(S)-3-((S)-2-(5-(2-(azetidin-1-yl)ethyl)-2-oxo-4-(trifluoromethyl)pyridin-1(2H)-yl)-4-methylpentanamido)-3-(3',4-difluoro-2',5,6'-trimethyl-[1,1'-biphenyl]-3-yl)propanoic acid;

(S)-3-((S)-2-(5-(2-(azetidin-1-yl)ethyl)-2-oxo-4-(trifluoromethyl)pyridin-1 (2H)-yl)-4-methylpentanamido)-3-(4-fluoro-3'-methoxy-2',5,6'-trimethyl-[1,1'-biphenyl]-3-yl)propanoic acid;

(S)-3-(4,4'-difluoro-2',5,6'-trimethyl-[1,1'-biphenyl]-3-yl)-3-((S)-2-(5-(2-(dimethylamino)ethyl)-2-oxo-4-(trifluoromethyl)pyridin-1(2H)-yl)-4-methylpentanamido)propanoic acid;

(S)-3-(5-chloro-4-fluoro-2',6'-dimethyl-[1,1'-biphenyl]-3-yl)-3-((S)-2-(5-(2-(3-methoxyazetidin-1-yl)ethyl)-2-oxo-4-(trifluoromethyl)pyridin-1(2H)-yl)-4-methylpentanamido)propanoic acid;

(S)-3-((S)-2-(5-(2-(dimethylamino)ethyl)-2-oxo-4-(trifluoromethyl)pyridin-1(2H)-yl)-4-methylpentanamido)-3-(4-fluoro-2',4',5,6'-tetramethyl-[1,1'-biphenyl]-3-yl)propanoic acid;

(S)-3-(4,4'-difluoro-2',5,6'-trimethyl-[1,1'-biphenyl]-3-yl)-3-((S)-2-(3-(difluoromethyl)-5-(2-(dimethylamino)ethyl)-2-oxopyridin-1(2H)-yl)-4-methylpentanamido)propanoic acid;

(S)-3-((S)-2-(5-(2-(dimethylamino)ethyl)-4-methyl-2-oxopyridin-1(2H)-yl)-5-methylhexanamido)-3-(4-fluoro-2',5,6'-trimethyl-[1,1'-biphenyl]-3-yl)propanoic acid;

(S)-3-(4-fluoro-2',5,6'-trimethyl-[1,1'-biphenyl]-3-yl)-3-((S)-2-(3-fluoro-5-(2-(3-fluoroazetidine-1-yl)ethyl)-2-oxopyridin-1(2H)-yl)-4-methylpentanamido)propanoic acid; and (S)-3-(4-fluoro-2',5,6'-trimethyl-[1,1'-biphenyl]-3-yl)-3-((S)-2-(3-fluoro-5-(2-((R)-3-fluoropyrrolidin-1-yl)ethyl)-2-oxopyridin-1(2H)-yl)-4-methylpentanamido)propanoic acid;

or a pharmaceutically acceptable salt thereof.

In certain embodiments, the invention relates to a compound selected from the group consisting of:

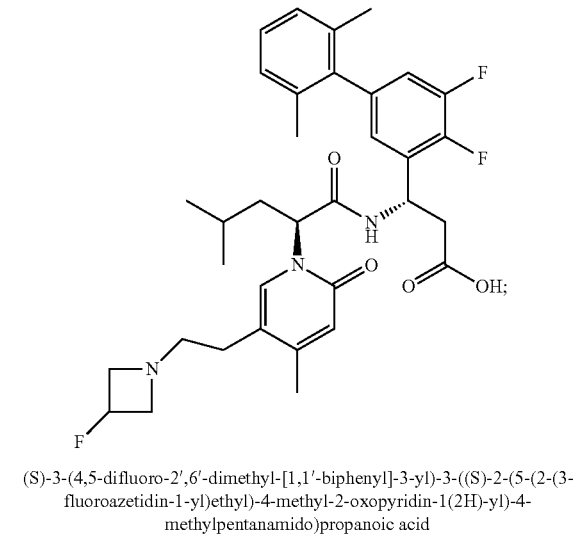

(S)-3-(4,5-difluoro-2',6'-dimethyl-[1,1'-biphenyl]-3-yl)-3-((S)-2-(5-(2-(3-fluoroazetidin-1-yl)ethyl)-4-methyl-2-oxopyridin-1(2H)-yl)-4-methylpentanamido)propanoic acid

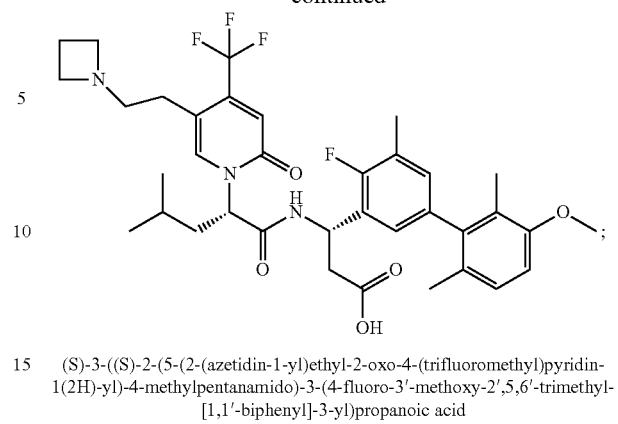

(S)-3-((S)-2-(5-(2-(azetidin-1-yl)ethyl-2-oxo-4-(trifluoromethyl)pyridin-1(2H)-yl)-4-methylpentanamido)-3-(4-fluoro-3'-methoxy-2',5,6'-trimethyl-[1,1'-biphenyl]-3-yl)propanoic acid

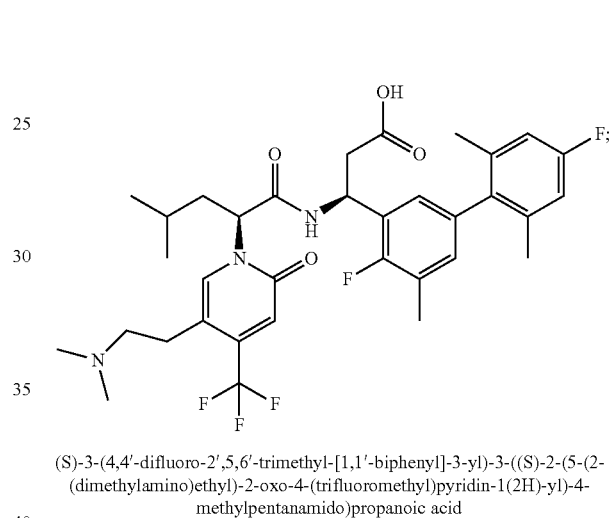

(S)-3-(4,4'-difluoro-2',5,6'-trimethyl-[1,1'-biphenyl]-3-yl)-3-((S)-2-(5-(2-(dimethylamino)ethyl)-2-oxo-4-(trifluoromethyl)pyridin-1(2H)-yl)-4-methylpentanamido)propanoic acid

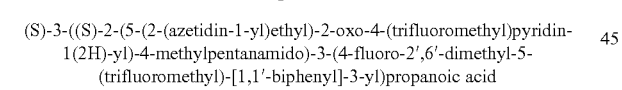

(S)-3-((S)-2-(5-(2-(azetidin-1-yl)ethyl)-2-oxo-4-(trifluoromethyl)pyridin-1(2H)-yl)-4-methylpentanamido)-3-(4-fluoro-2',6'-dimethyl-5-(trifluoromethyl)-[1,1'-biphenyl]-3-yl)propanoic acid

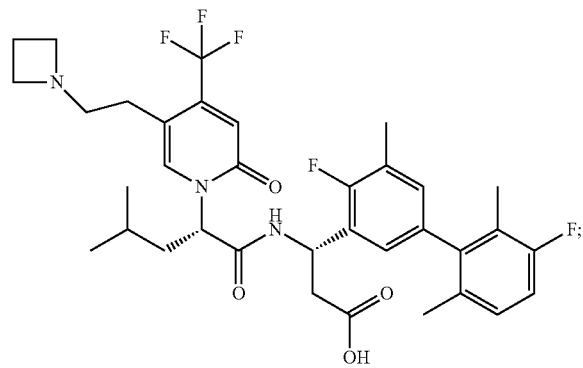

(S)-3-((S)-2-(5-(2-azetidin-1-yl)ethyl)-2-oxo-4-(trifluoromethyl)pyridin-1(2H)-yl)-4-methylpentanamido)-3-(3',4-difluoro-2',5,6'-trimethyl-[1,1'-biphenyl]-3-yl)propanoic acid

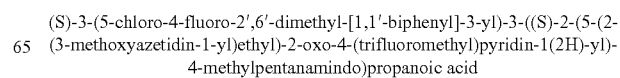

(S)-3-(5-chloro-4-fluoro-2',6'-dimethyl-[1,1'-biphenyl]-3-yl)-3-((S)-2-(5-(2-(3-methoxyazetidin-1-yl)ethyl)-2-oxo-4-(trifluoromethyl)pyridin-1(2H)-yl)-4-methylpentanamido)propanoic acid -continued

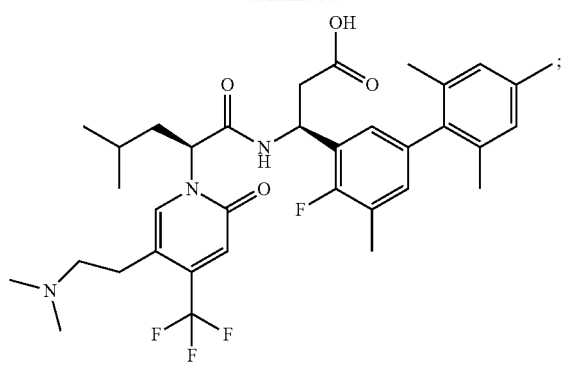

(S)-3-((S)-2-(5-(2-(dimethylamino)ethyl)-2-oxo-4-(trifluoromethyl)pyridin-1(2H)-yl)-4-methylpentanamido)-3-(4-fluoro-2',4',5,6'-tetramethyl-[1,1'-biphenyl]-3-yl)propanoic acid

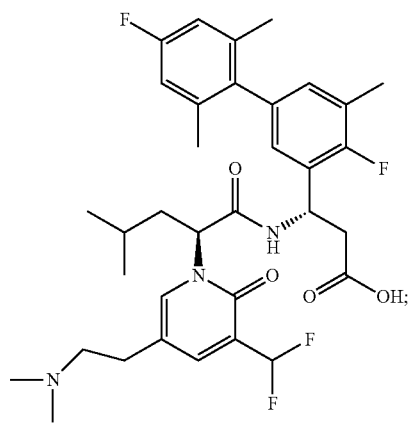

(S)-3-(4,4'-difluoro-2',5,6'-trimethyl-[1,1'-biphenyl]-3-yl)-3-((S)-2-(3-(difluoromethyl)-5-(2-(dimethylamino)ethyl)-2-oxopyridin-1(2H)-yl)-4-methylpentanamido)propanoic acid

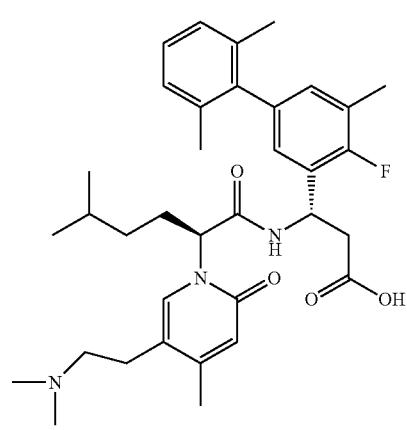

(S)-3-((S)-2-(5-(2-(dimethylamino)ethyl)-4-methyl-2-oxopyridin-1(2H)-yl)-5-methylhexanamido)-3-(4-fluoro-2',5,6'-trimethyl-[1,1'-biphenyl]-3-yl)propanoic acid -continued

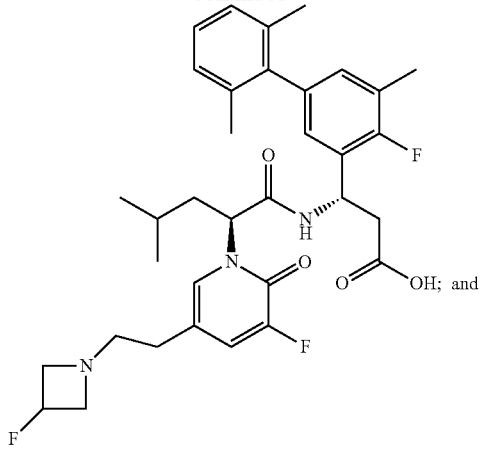

(S)-3-(4-fluoro-2',5,6'-trimethyl-[1,1'-biphenyl]-3-yl)-3-((S)-2-(3-fluoro-5-(2-(3-fluoroazetidin-1-yl)ethyl)-2-oxopyridin-1(2H)-yl)-4-methylpentanamido)propanoic acid

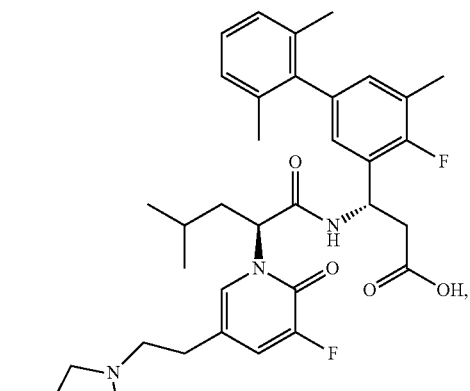

(S)-3-(4-fluoro-2',5,6'-trimethyl-[1,1'-biphenyl]-3-yl)-3-((S)-2-(3-fluoro-5-(2-((R)-3-fluoropyrrolidin-1-yl)ethyl)-2-oxopyridin-1(2H)-yl)-4-methylpentanamido)propanoic acid or a pharmaceutically acceptable salt thereof.

In certain embodiments, the invention relates to any one of the aforementioned compounds, wherein the compound is in the form of a pharmaceutically acceptable salt.

In certain embodiments, the invention relates to a compound selected from the group consisting of:

| Structure | Name |
|---|---|
| 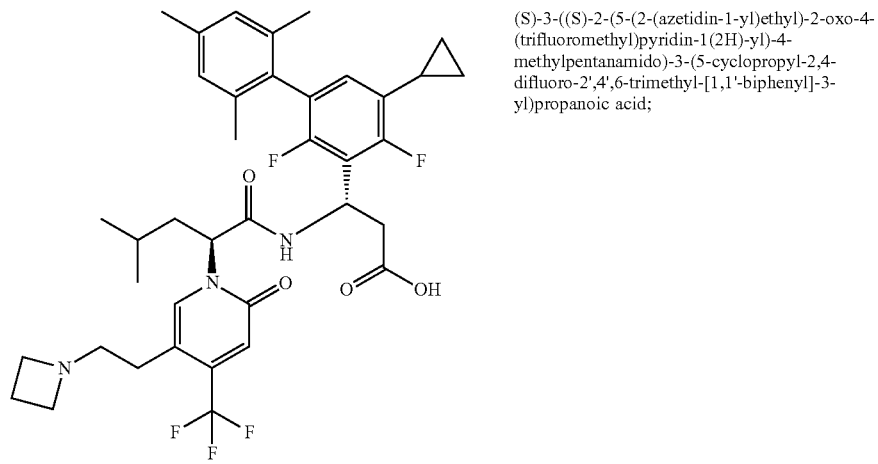 | (S)-3-((S)-2-(5-(2-(azetidin-1-yl)ethyl)-2-oxo-4-(trifluoromethyl)pyridin-1(2H)-yl)-4-methylpentanamido)-3-(5-cyclopropyl-2,4-difluoro-2',4',6-trimethyl-[1,1'-biphenyl]-3-yl)propanoic acid; |
| 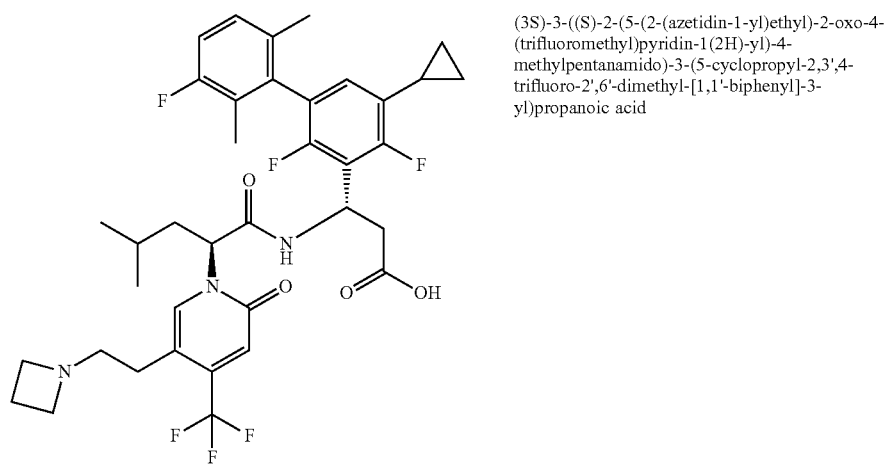 | (3S)-3-((S)-2-(5-(2-(azetidin-1-yl)ethyl)-2-oxo-4-(trifluoromethyl)pyridin-1(2H)-yl)-4-methylpentanamido)-3-(5-cyclopropyl-2,3',4-trifluoro-2',6'-dimethyl-[1,1'-biphenyl]-3-yl)propanoic acid |
| 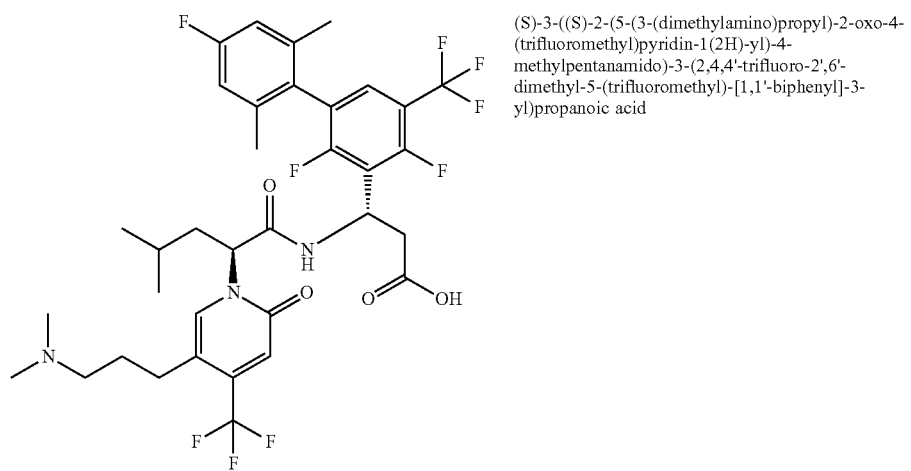 | (S)-3-((S)-2-(5-(3-(dimethylamino)propyl)-2-oxo-4-(trifluoromethyl)pyridin-1(2H)-yl)-4-methylpentanamido)-3-(2,4,4'-trifluoro-2',6'-dimethyl-5-(trifluoromethyl)-[1,1'-biphenyl]-3-yl)propanoic acid |

-continued

| Structure | Name |
|---|---|
| 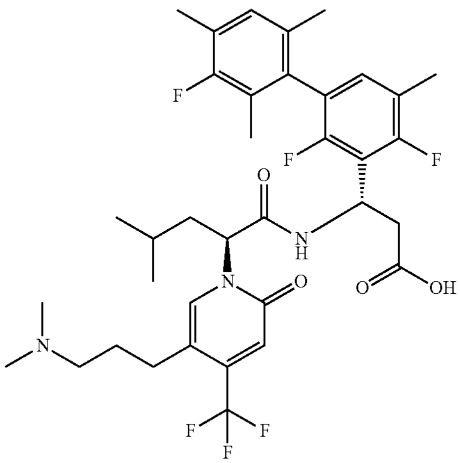 | (3S)-3-((S)-2-(5-(3-(dimethylamino)propyl)-2-oxo-4-(trifluoromethyl)pyridin-1(2H)-yl)-4-methylpentanamido)-3-(2,3',4-trifluoro-2',4',5,6'-tetramethyl-[1,1'-biphenyl]-3-yl)propanoic acid |
| 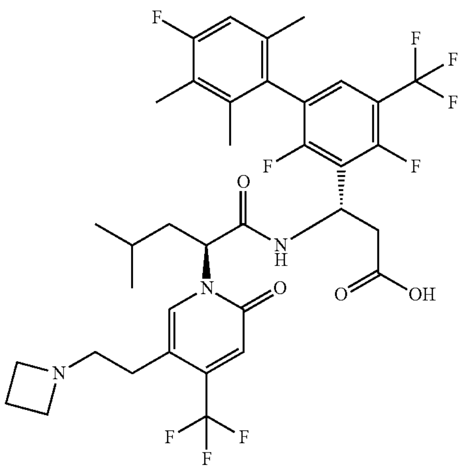 [SMILES: Cc1cc(F)c(C)c(C)c1-c1cc(C(F)(F)F)c(F)c([C@H](CC(=O)O)NC(=O)[C@H](CC(C)C)n2cc(CCN3CCC3)c(C(F)(F)F)cc2=O)c1F] | (3S)-3-((S)-2-(5-(2-(azetidin-1-yl)ethyl)-2-oxo-4-(trifluoromethyl)pyridin-1(2H)-yl)-4-methylpentanamido)-3-(2,4,4'-trifluoro-2',3',6'-trimethyl-5-(trifluoromethyl)-[1,1'-biphenyl]-3-yl)propanoic acid |
| 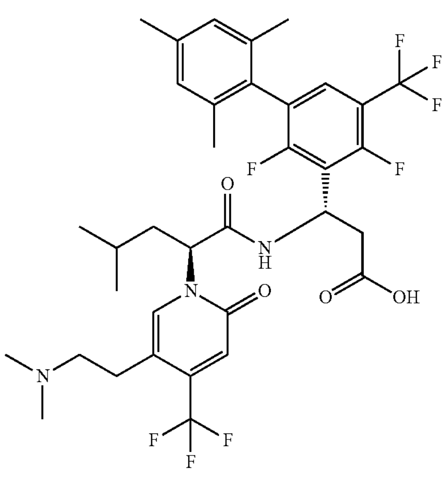 [SMILES: Cc1cc(C)c(-c2cc(C(F)(F)F)c(F)c([C@H](CC(=O)O)NC(=O)[C@H](CC(C)C)n3cc(CCN(C)C)c(C(F)(F)F)cc3=O)c2F)c(C)c1] | (S)-3-(2,4-difluoro-2',4',6'-trimethyl-5-(trifluoromethyl)-[1,1'-biphenyl]-3-yl)-3-((S)-2-(5-(2-(dimethylamino)ethyl)-2-oxo-4-(trifluoromethyl)pyridin-1(2H)-yl)-4-methylpentanamido)propanoic acid |

| Structure | Name |
|---|---|
| 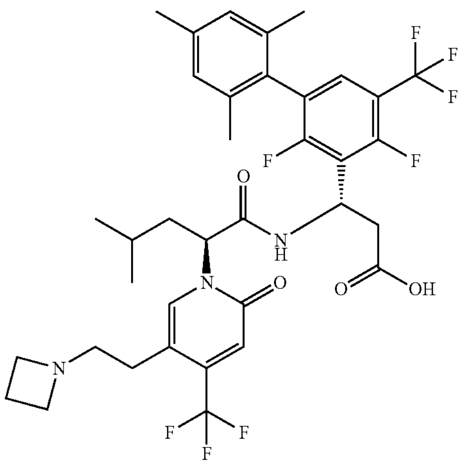 [SMILES: Cc1cc(C)c(-c2cc(C(F)(F)F)c(F)c([C@H](CC(=O)O)NC(=O)[C@H](CC(C)C)n3cc(CCN4CCC4)c(C(F)(F)F)cc3=O)c2F)c(C)c1] | (S)-3-((S)-2-(5-(2-(azetidin-1-yl)ethyl)-2-oxo-4-(trifluoromethyl)pyridin-1(2H)-yl)-4-methylpentanamido)-3-(2,4-difluoro-2',4',6'-trimethyl-5-(trifluoromethyl)-[1,1'-biphenyl]-3-yl)propanic acid |
| 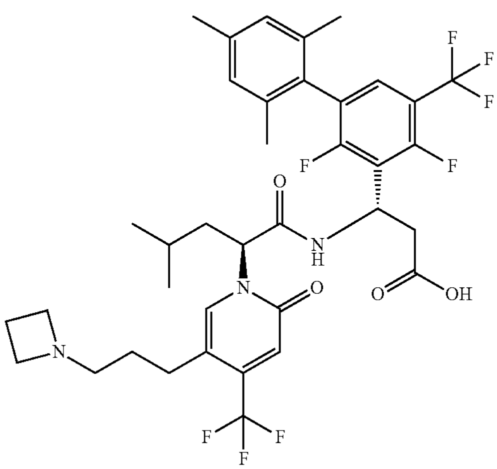 [SMILES: Cc1cc(C)c(-c2cc(C(F)(F)F)c(F)c([C@H](CC(=O)O)NC(=O)[C@H](CC(C)C)n3cc(CCCN4CCC4)c(C(F)(F)F)cc3=O)c2F)c(C)c1] | (S)-3-((S)-2-(5-(3-(azetidin-1-yl)propyl)-2-oxo-4-(trifluoromethyl)pyridin-1(2H)-yl)-4-methylpentanamido)-3-(2,4-difluoro-2',4',6'-trimethyl-5-(trifluoromethyl)-[1,1'-biphenyl]-3-yl)propanoic acid |
| 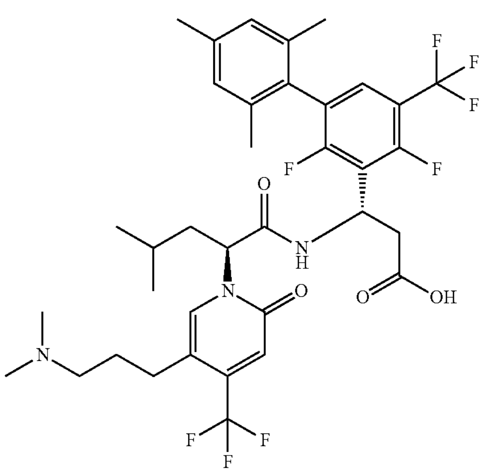 [SMILES: Cc1cc(C)c(-c2cc(C(F)(F)F)c(F)c([C@H](CC(=O)O)NC(=O)[C@H](CC(C)C)n3cc(CCCN(C)C)c(C(F)(F)F)cc3=O)c2F)c(C)c1] | (S)-3-(2,4-difluoro-2',4',6'-trimethyl-5-(trifluoromethyl)-[1,1'-biphenyl]-3-yl)-3-((S)-2-(5-(3-(dimethylamino)propyl)-2-oxo-4-(trifluoromethyl)pyridin-1(2H)-yl)-4-methylpentanamido)propanoic acid |

| Structure | Name |
|---|---|
| (structure) | (S)-3-(4'-cyclopropyl-2,4-difluoro-2',6'-dimethyl-5-(trifluoromethyl)-[1,1'-biphenyl]-3-yl)-3-((S)-2-(5-(3-(dimethylamino)propyl)-2-oxo-4-(trifluoromethyl)pyridin-1(2H)-yl)-4-methylpentanamido)propanoic acid |
| (structure) | (3S)-3-((S)-2-(5-(2-(azetidin-1-yl)ethyl)-2-oxo-4-(trifluoromethyl)pyridin-1(2H)-yl)-4-methylpentanamido)-3-(2,3',4-trifluoro-2',4',6'-trimethyl-5-(trifluoromethyl)-[1,1'-biphenyl]-3-yl)propanoic acid |

Exemplary Pharmaceutical Compositions

Compounds of Formula (I) can be formulated in various pharmaceutical compositions. A compound of Formula (I) (including compounds of Formula (Ia) and Formula (Ib) as provided herein), as well as pharmaceutically acceptable salts thereof, may be the active pharmaceutical ingredient (API) combined with one or more other ingredients to form a drug substance pharmaceutical composition. The drug substance (DS) pharmaceutical composition can comprise the API (i.e., a compound of Formula (I) or pharmaceutically acceptable salt thereof) and one or more pharmaceutically acceptable carriers, diluents, and/or excipients. The carrier(s), diluent(s) or excipient(s) can be selected to be compatible with the other ingredients of the formulation and appropriately safe and effective for an intended therapy. A desired weight concentration of the compound of Formula (I) as the active pharmaceutical ingredient (API) can be combined with the other inactive ingredients to form a drug substance (DS) in a formulation batch. Pharmaceutically acceptable compositions can be formulated for administration by an appropriate route, for example by the oral delivery (including as a capsule or tablet) in unit dosage forms. Such compositions may be prepared by bringing into association the active pharmaceutical ingredient (API) comprising a compound of Formula (I) with the carrier(s) or excipient(s).

In certain embodiments, the invention provides a pharmaceutical composition formulated for oral delivery of an $\alpha_4\beta_7$ integrin inhibitor, the composition comprising the $\alpha_4\beta_7$ integrin inhibitor compound of formula (I) as an API and a pharmaceutically acceptable carrier formulated for oral therapeutic administration of the $\alpha_4\beta_7$ integrin inhibitor compound.

In certain embodiments, the invention provides a pharmaceutical composition comprising the compound of Formula (I), or a pharmaceutically acceptable salt thereof as the active pharmaceutical ingredient (API).

In certain embodiments, the invention provides a pharmaceutical composition comprising the compound of Formula (Ia), or a pharmaceutically acceptable salt thereof as the active pharmaceutical ingredient (API).

In certain embodiments, the invention provides a pharmaceutical composition comprising the compound of Formula (Ib), or a pharmaceutically acceptable salt thereof as the active pharmaceutical ingredient (API).

In certain embodiments, the invention provides a pharmaceutical composition comprising the compound (3S)-3-(4,5-difluoro-2',6'-dimethylbiphenyl-3-yl)-3-(2-(5-(2-(3-fluoroazetidine-1-yl)ethyl)-4-methyl-2-oxopyridin-1(2H)-yl)-4-methylpentanamido)propanoic acid or a pharmaceutically acceptable salt thereof as the active pharmaceutical ingredient (API).

In certain embodiments, the invention provides a pharmaceutical composition comprising the compound (3S)-3-(2-(5-(2-(azetidin-1-yl)ethyl)-2-oxo-4-(trifluoromethyl)pyridin-1(2H)-yl)-4-methylpentanamido)-3-(4-fluoro-2',6'-dimethyl-5-(trifluoromethyl)biphenyl-3-yl)propanoic acid or a pharmaceutically acceptable salt thereof as the active pharmaceutical ingredient (API).

In certain embodiments, the invention provides a pharmaceutical composition comprising the compound (3S)-3-(2-(5-(2-(azetidin-1-yl)ethyl)-2-oxo-4-(trifluoromethyl)pyridin-1(2H)-yl)-4-methylpentanamido)-3-(3',4-difluoro-2',5',6'-trimethyl-[1,1'-biphenyl]-3-yl)propanoic acid or a pharmaceutically acceptable salt thereof as the active pharmaceutical ingredient (API).

In certain embodiments, the invention provides a pharmaceutical composition comprising the compound (3S)-3-(2-(5-(2-(azetidin-1-yl)ethyl)-2-oxo-4-(trifluoromethyl)pyridin-1(2H)-yl)-4-methylpentanamido)-3-(4-fluoro-3'-methoxy-2',5',6'-trimethyl-[1,1'-biphenyl]-3-yl)propanoic acid or a pharmaceutically acceptable salt thereof as the active pharmaceutical ingredient (API).

In certain embodiments, the invention provides a pharmaceutical composition comprising the compound (3S)-3-(4,4'-difluoro-2',5',6'-trimethyl-[1,1'-biphenyl]-3-yl)-3-(2-(5-(2-(dimethylamino)ethyl)-2-oxo-4-(trifluoromethyl)pyridin-1(2H)-yl)-4-methylpentanamido)propanoic acid or a pharmaceutically acceptable salt thereof as the active pharmaceutical ingredient (API).

In certain embodiments, the invention provides a pharmaceutical composition comprising the compound (3S)-3-(5-chloro-4-fluoro-2',6'-dimethyl-[1,1'-biphenyl]-3-yl)-3-(2-(5-(2-(3-methoxyazetidin-1-yl)ethyl)-2-oxo-4-(trifluoromethyl)pyridin-1(2H)-yl)-4-methylpentanamido)propanoic acid or a pharmaceutically acceptable salt thereof as the active pharmaceutical ingredient (API).

In certain embodiments, the invention provides a pharmaceutical composition comprising the compound (3S)-3-(2-(5-(2-(dimethylamino)ethyl)-2-oxo-4-(trifluoromethyl)pyridin-1(2H)-yl)-4-methylpentanamido)-3-(4-fluoro-2',4',5',6'-tetramethylbiphenyl-3-yl)propanoic acid or a pharmaceutically acceptable salt thereof as the active pharmaceutical ingredient (API).

In certain embodiments, the invention provides a pharmaceutical composition comprising the compound (3S)-3-(4,4'-difluoro-2',5',6'-trimethyl-[1,1'-biphenyl]-3-yl)-3-(2-(3-(difluoromethyl)-5-(2-(dimethylamino)ethyl)-2-oxopyridin-1(2H)-yl)-4-methylpentanamido)propanoic acid or a pharmaceutically acceptable salt thereof as the active pharmaceutical ingredient (API).

In certain embodiments, the invention provides a pharmaceutical composition comprising the compound (3S)-3-(2-(5-(2-(dimethylamino)ethyl)-4-methyl-2-oxopyridin-1(2H)-yl)-5-methylhexanamido)-3-(4-fluoro-2',5',6'-trimethylbiphenyl-3-yl)propanoic acid or a pharmaceutically acceptable salt thereof as the active pharmaceutical ingredient (API).

In certain embodiments, the invention provides a pharmaceutical composition comprising the compound (3S)-3-(4-fluoro-2',5',6'-trimethyl-[1,1'-biphenyl]-3-yl)-3-(2-(3-fluoro-5-(2-(3-fluoroazetidine-1-yl)ethyl)-2-oxopyridin-1(2H)-yl)-4-methylpentanamido)propanoic acid or a pharmaceutically acceptable salt thereof as the active pharmaceutical ingredient (API).

In certain embodiments, the invention provides a pharmaceutical composition comprising the compound (3S)-3-(4-fluoro-2',5',6'-trimethyl-[1,1'-biphenyl]-3-yl)-3-(2-(3-fluoro-5-(2-((R)-3-fluoropyrrolidin-1-yl)ethyl)-2-oxopyridin-1(2H)-yl)-4-methylpentanamido)propanoic acid or a pharmaceutically acceptable salt thereof as the active pharmaceutical ingredient (API).

In certain embodiments, the invention provides a pharmaceutical composition comprising the compound (S)-3-(4,5-difluoro-2',6'-dimethyl-[1,1'-biphenyl]-3-yl)-3-((S)-2-(5-(2-(3-fluoroazetidine-1-yl)ethyl)-4-methyl-2-oxopyridin-1(2H)-yl)-4-methylpentanamido)propanoic acid or a pharmaceutically acceptable salt thereof as the active pharmaceutical ingredient (API).

In certain embodiments, the invention provides a pharmaceutical composition comprising the compound (S)-3-((S)-2-(5-(2-(azetidin-1-yl)ethyl)-2-oxo-4-(trifluoromethyl)pyridin-1(2H)-yl)-4-methylpentanamido)-3-(4-fluoro-2',6'-dimethyl-5-(trifluoromethyl)-[1,1'-biphenyl]-3-yl)propanoic acid or a pharmaceutically acceptable salt thereof as the active pharmaceutical ingredient (API).

In certain embodiments, the invention provides a pharmaceutical composition comprising the compound (S)-3-((S)-2-(5-(2-(azetidin-1 yl)ethyl)-2-oxo-4-(trifluoromethyl)pyridin-1 (2H)-yl)-4-methylpentanamido)-3-(3',4-difluoro-2',5',6'-trimethyl-[1,1'-biphenyl]-3-yl)propanoic acid or a pharmaceutically acceptable salt thereof as the active pharmaceutical ingredient (API).

In certain embodiments, the invention provides a pharmaceutical composition comprising the compound (S)-3-((S)-2-(5-(2-(azetidin-1-yl)ethyl)-2-oxo-4-(trifluoromethyl)pyridin-1 (2H)-yl)-4-methylpentanamido)-3-(4-fluoro-3'-methoxy-2',5',6'-trimethyl-[1,1'-biphenyl]-3-yl)propanoic acid or a pharmaceutically acceptable salt thereof as the active pharmaceutical ingredient (API).

In certain embodiments, the invention provides a pharmaceutical composition comprising the compound (S)-3-(4,4'-difluoro-2',5',6'-trimethyl-[1,1'-biphenyl]-3-yl)-3-((S)-2-(5-(2-(dimethylamino)ethyl)-2-oxo-4-(trifluoromethyl)pyridin-1(2H)-yl)-4-methylpentanamido)propanoic acid or a pharmaceutically acceptable salt thereof as the active pharmaceutical ingredient (API).

In certain embodiments, the invention provides a pharmaceutical composition comprising the compound (S)-3-((S)-2-(5-(2-(dimethylamino)ethyl)-2-oxo-4-(trifluoromethyl)pyridin-1(2H)-yl)-4-methylpentanamido)-3-(4-fluoro-2',4',5',6'-tetramethyl-[1,1'-biphenyl]-3-yl)propanoic Acid or a pharmaceutically acceptable salt thereof as the active pharmaceutical ingredient (API).

In certain embodiments, the invention provides a pharmaceutical composition comprising the compound (S)-3-(4,4'-difluoro-2',5',6'-trimethyl-[1,1'-biphenyl]-3-yl)-3-((S)-2-(3-(difluoromethyl)-5-(2-(dimethylamino)ethyl)-2-oxopyridin-1(2H)-yl)-4-methylpentanamido)propanoic acid or a pharmaceutically acceptable salt thereof as the active pharmaceutical ingredient (API).

In certain embodiments, the invention provides a pharmaceutical composition comprising the compound (S)-3-((S)-2-(5-(2-(dimethylamino)ethyl)-4-methyl-2-oxopyridin-1(2H)-yl)-5-methylhexanamido)-3-(4-fluoro-2',5,6'-trimethyl-[1,1'-biphenyl]-3-yl)propanoic acid or a pharmaceutically acceptable salt thereof as the active pharmaceutical ingredient (API).

In certain embodiments, the invention provides a pharmaceutical composition comprising the compound (S)-3-(4-fluoro-2',5,6'-trimethyl-[1,1'-biphenyl]-3-yl)-3-((S)-2-(3-fluoro-5-(2-(3-fluoroazetidine-1-yl)ethyl)-2-oxopyridin-1(2H)-yl)-4-methylpentanamido)propanoic acid or a pharmaceutically acceptable salt thereof as the active pharmaceutical ingredient (API).

In certain embodiments, the invention provides a pharmaceutical composition comprising the compound (S)-3-(4-fluoro-2',5,6'-trimethyl-[1,1'-biphenyl]-3-yl)-3-((S)-2-(3-fluoro-5-(2-((R)-3-fluoropyrrolidin-1-yl)ethyl)-2-oxopyridin-1 (2H)-yl)-4-methylpentanamido)propanoic acid or a pharmaceutically acceptable salt thereof as the active pharmaceutical ingredient (API).

In certain embodiments, the invention relates to a pharmaceutical composition comprising a compound selected from the group consisting of:

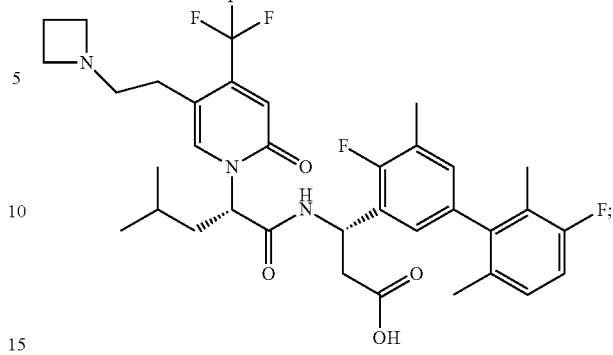

(S)-3-((S)-2-(5-(2-(azetidin-1-yl)ethyl)-2-oxo-4-(trifluoromethyl)pyridin-1(2H)-yl)-4-methylpentanamido)-3-(3',4-difluoro-2',5',6'-trimethyl-[1,1'-biphenyl]-3-yl)propanoic acid

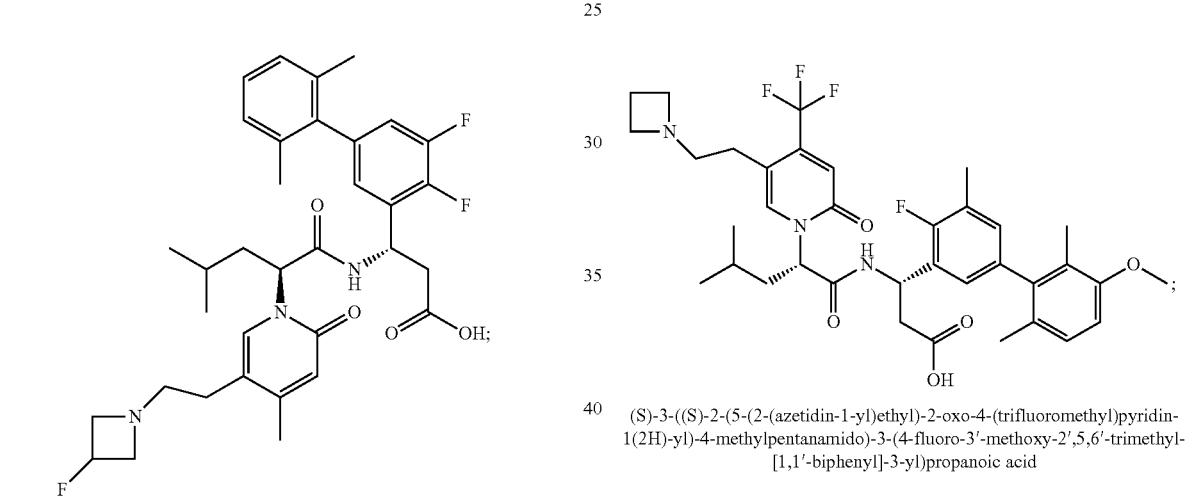

(S)-3-(4,5-difluoro-2',6'-dimethyl-[1,1'-biphenyl]-3-yl)-3-((S)-2-(5-(2-(3-fluoroazetidin-1-yl)ethyl)-4-methyl-2-oxopyridin-1(2H)-yl)-4-methylpentanamido)propanoic acid (S)-3-((S)-2-(5-(2-(azetidin-1-yl)ethyl)-2-oxo-4-(trifluoromethyl)pyridin-1(2H)-yl)-4-methylpentanamido)-3-(4-fluoro-3'-methoxy-2',5,6'-trimethyl-[1,1'-biphenyl]-3-yl)propanoic acid

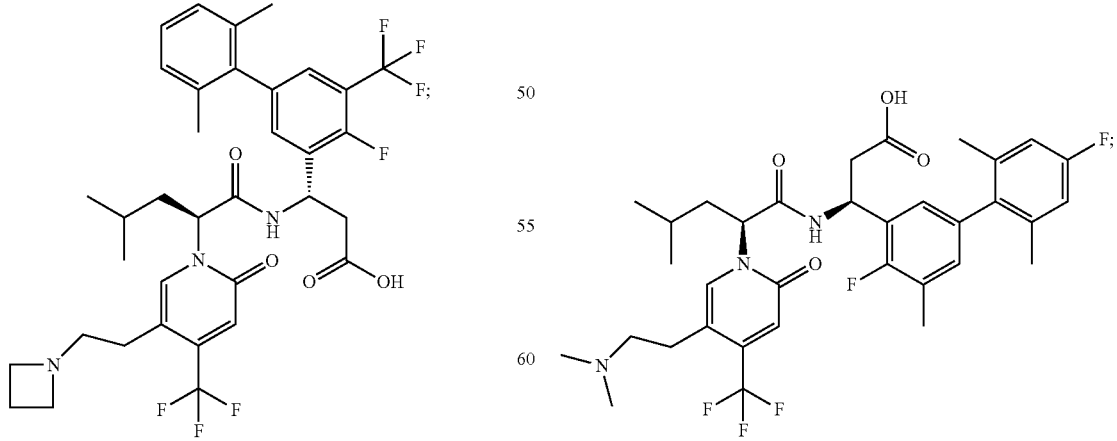

(S)-3-((S)-2-(5-(2-(azetidin-1-yl)ethyl)-2-oxo-4-(trifluoromethyl)pyridin-1(2H)-yl)-4-methylpentanamido)-3-(4-fluoro-2',6'-dimethyl-5-(trifluoromethyl)-[1,1'-biphenyl]-3-yl)propanoic acid (S)-3-(4,4'-difluoro-2',5,6'-trimethyl-[1,1'-biphenyl]-3-yl)-3-((S)-2-(5-(2-(dimethylamino)ethyl)-2-oxo-4-(trifluoromethyl)pyridin-1(2H)-yl)-4-methylpentanamido)propanoic acid -continued

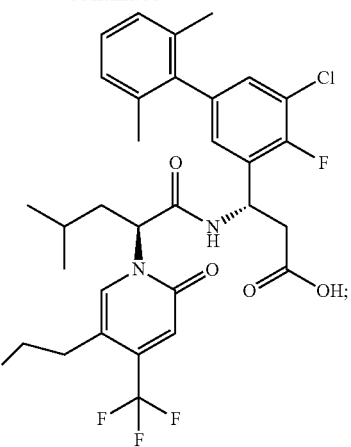

(S)-3-(5-chloro-4-fluoro-2',6'-dimethyl-[1,1'-biphenyl]-3-yl)-3-((S)-2-(5-(2-(3-methoxyazetidin-1-yl)ethyl)-2-oxo-4-(trifluoromethyl)pyridin-1(2H)-yl)-4-methylpentanamindo)propanoic acid

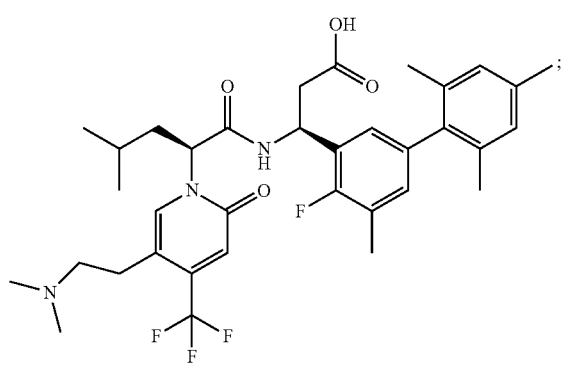

(S)-3-((S)-2-(5-(2-(dimethylamino)ethyl)-2-oxo-4-(trifluoromethyl)pyridin-1(2H)-yl)-4-methylpentanamido)-3-(4-fluoro-2',4',5,6'-tetramethyl-[1,1'-biphenyl]-3-yl)propanoic acid

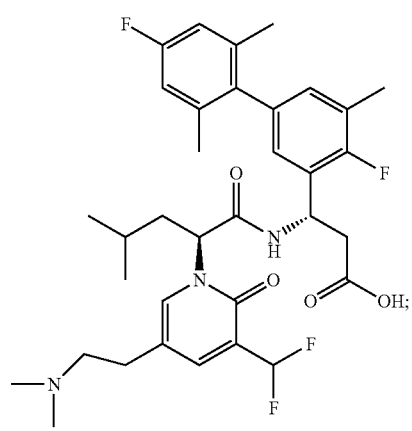

(S)-3-(4,4'-difluoro-2',5,6'-trimethyl-[1,1'-biphenyl]-3-yl)-3-((S)-2-(3-(difluoromethyl)-5-(2-(dimethylamino)ethyl)-2-oxopyridin-1(2H)-yl)-4-methylpentanamido)propanoic acid -continued

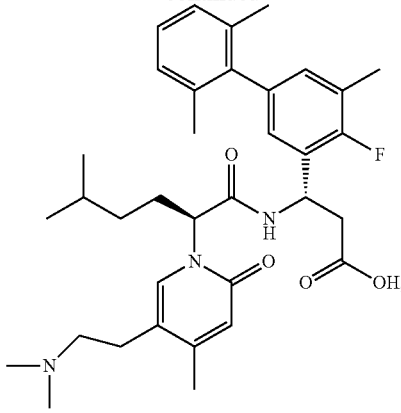

(S)-3-((S)-2-(5-(2-(dimethylamino)ethyl)-4-methyl-2-oxopyridin-1(2H)-yl)-5-methylhexanamido)-3-(4-fluoro-2',5,6'-trimethyl-[1,1'-biphenyl]-3-yl)propanoic acid

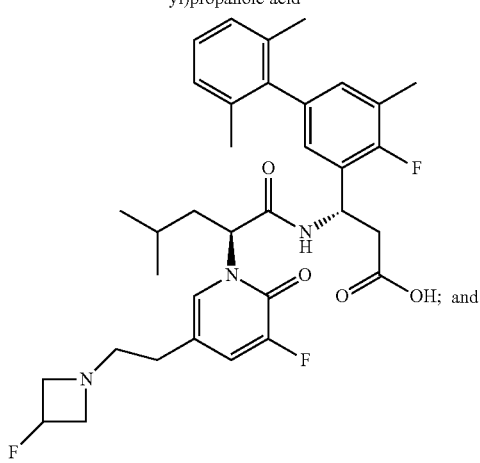

(S)-3-(4-fluoro-2',5,6'-trimethyl-[1,1'-biphenyl]-3-yl)-3-((S)-2-(3-fluoro-5-(2-(3-fluoroazetidin-1-yl)ethyl)-2-oxopyridin-1(2H)-yl)-4-methylpentanamido)propanoic acid

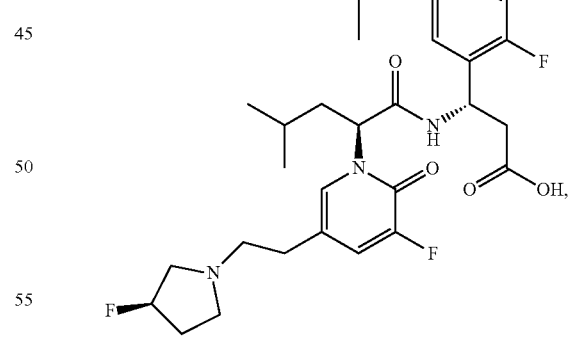

(S)-3-(4-fluoro-2',5,6'-trimethyl-[1,1'-biphenyl]-3-yl)-3-((S)-2-(3-fluoro-5-(2-((R)-3-fluoropyrrolidin-1-yl)ethyl)-2-oxopyridin-1(2H)-yl)-4-methylpentanamido)propanoic acid pharmaceutically acceptable salt thereof.

In certain embodiments, the invention relates to a pharmaceutical composition comprising a compound selected from the group consisting of, or a pharmaceutically acceptable salt thereof as the active pharmaceutical ingredient (API):

| Structure | Name |
|---|---|
| 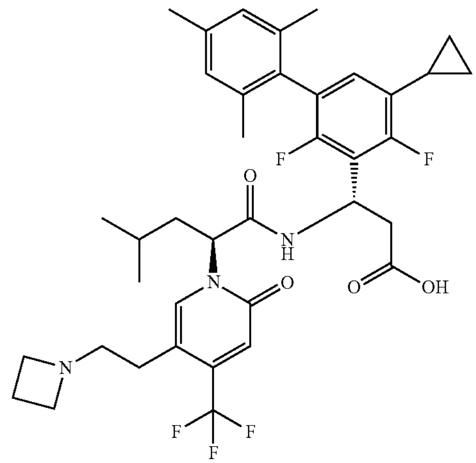 [SMILES: Cc1cc(C)c(-c2cc(C3CC3)c(F)c([C@H](CC(=O)O)NC(=O)[C@H](CC(C)C)n3cc(CCN4CCC4)c(C(F)(F)F)cc3=O)c2F)c(C)c1] | (S)-3-((S)-2-(5-(2-(azetidin-1-yl)ethyl)-2-oxo-4-(trifluoromethyl)pyridin-1(2H)-yl)-4-methylpentanamido)-3-(5-cyclopropyl-2,4-difluoro-2',4',6'-trimethyl-[1,1'-biphenyl]-3-yl)propanoic acid; |
| 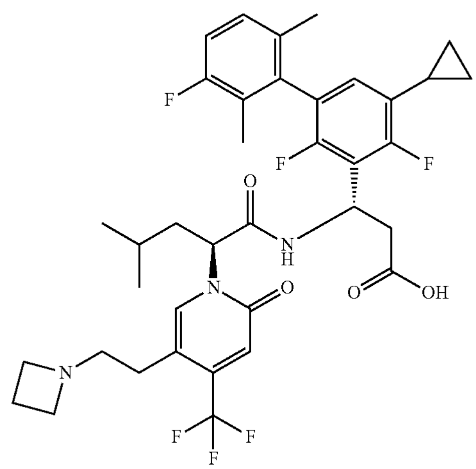 [SMILES: Cc1ccc(F)c(C)c1-c1cc(C2CC2)c(F)c([C@H](CC(=O)O)NC(=O)[C@H](CC(C)C)n2cc(CCN3CCC3)c(C(F)(F)F)cc2=O)c1F] | (3S)-3-((S)-2-(5-(2-(azetidin-1-yl)ethyl)-2-oxo-4-(trifluoromethyl)pyridin-1(2H)-yl)-4-methylpentanamido)-3-(5-cyclopropyl-2,3',4-trifluoro-2',6'-dimethyl-[1,1'-biphenyl]-3-yl)propanoic acid |
| 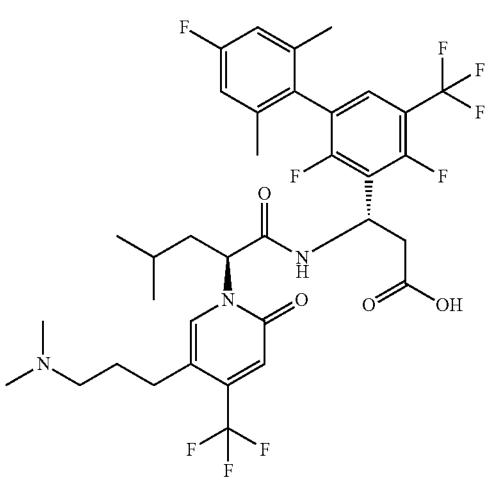 [SMILES: Cc1cc(F)cc(C)c1-c1cc(C(F)(F)F)c(F)c([C@H](CC(=O)O)NC(=O)[C@H](CC(C)C)n2cc(CCCN(C)C)c(C(F)(F)F)cc2=O)c1F] | (S)-3-((S)-2-(5-(3-(dimethylamino)propyl)-2-oxo-4-(trifluoromethyl)pyridin-1(2H)-yl)-4-methylpentanamido)-3-(2,4,4'-trifluoro-2',6'-dimethyl-5-(trifluoromethyl)-[1,1'-biphenyl]-3-yl)propanoic acid |

| Structure | Name |
|---|---|
| 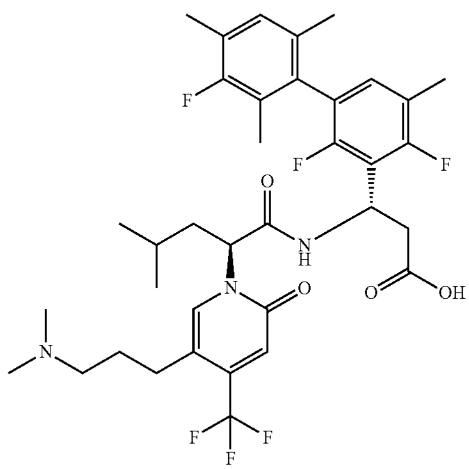 [SMILES: Cc1cc(C)c(-c2cc(C)c(F)c([C@H](CC(=O)O)NC(=O)[C@H](CC(C)C)n3cc(CCCN(C)C)c(C(F)(F)F)cc3=O)c2F)c(C)c1F] | (3S)-3-((S)-2-(5-(3-(dimethylamino)propyl)-2-oxo-4-(trifluoromethyl)pyridin-1(2H)-yl)-4-methylpentanamido)-3-(2,3',4-trifluoro-2',4',5,6'-tetramethyl-[1,1'-biphenyl]-3-yl)propanoic acid |
| 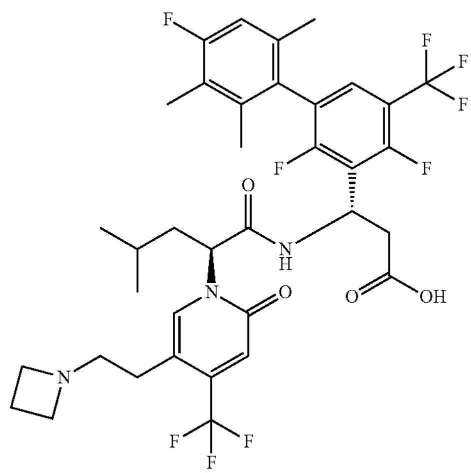 [SMILES: Cc1cc(F)c(C)c(C)c1-c1cc(C(F)(F)F)c(F)c([C@H](CC(=O)O)NC(=O)[C@H](CC(C)C)n2cc(CCN3CCC3)c(C(F)(F)F)cc2=O)c1F] | (3S)-3-((S)-2-(5-(2-(azetidin-1-yl)ethyl)-2-oxo-4-(trifluoromethyl)pyridin-1(2H)-yl)-4-methylpentanamido)-3-(2,4,4'-trifluoro-2',3',6'-trimethyl-5-(trifluoromethyl)-[1,1'-biphenyl]-3-yl)propanoic acid |
| 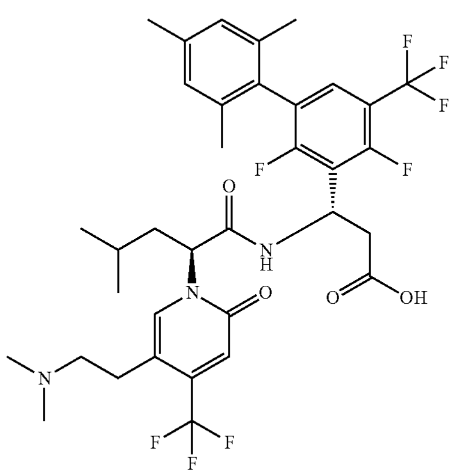 [SMILES: Cc1cc(C)c(-c2cc(C(F)(F)F)c(F)c([C@H](CC(=O)O)NC(=O)[C@H](CC(C)C)n3cc(CCN(C)C)c(C(F)(F)F)cc3=O)c2F)c(C)c1] | (S)-3-(2,4-difluoro-2',4',6'-trimethyl-5-(trifluoromethyl)-[1,1'-biphenyl]-3-yl)-3-((S)-2-(5-(2-(dimethylamino)ethyl)-2-oxo-4-(trifluoromethyl)pyridin-1(2H)-yl)-4-methylpentanamido)propanoic acid |

| Structure | Name |
|---|---|
| 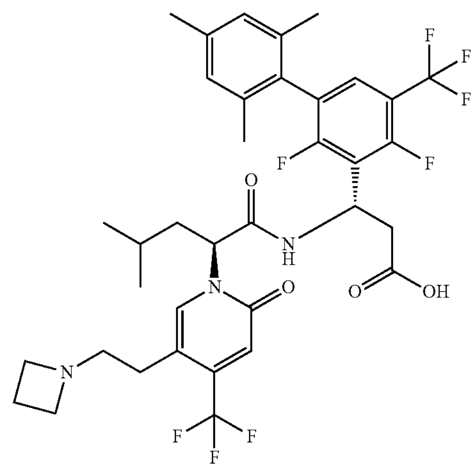 [SMILES: Cc1cc(C)c(-c2cc(C(F)(F)F)c(F)c([C@H](CC(=O)O)NC(=O)[C@H](CC(C)C)n3cc(CCN4CCC4)c(C(F)(F)F)cc3=O)c2F)c(C)c1] | (S)-3-((S)-2-(5-(2-(azetidin-1-yl)ethyl)-2-oxo-4-(trifluoromethyl)pyridin-1(2H)-yl)-4-methylpentanamido)-3-(2,4-difluoro-2',4',6'-trimethyl-5-(trifluoromethyl)-[1,1'-biphenyl]-3-yl)propanoic acid |
| 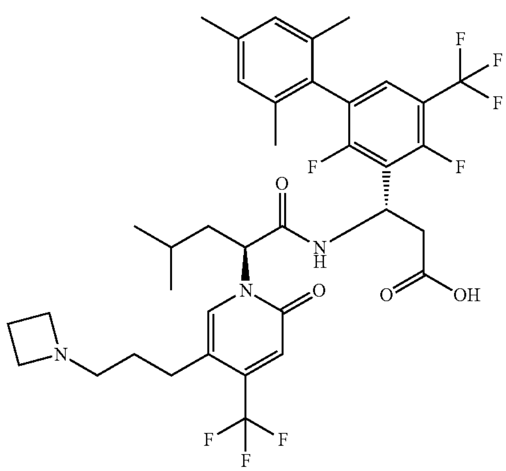 [SMILES: Cc1cc(C)c(-c2cc(C(F)(F)F)c(F)c([C@H](CC(=O)O)NC(=O)[C@H](CC(C)C)n3cc(CCCN4CCC4)c(C(F)(F)F)cc3=O)c2F)c(C)c1] | (S)-3-((S)-2-(5-(3-(azetidin-1-yl)propyl)-2-oxo-4-(trifluoromethyl)pyridin-1(2H)-yl)-4-methylpentanamido)-3-(2,4-difluoro-2',4',6'-trimethyl-5-(trifluoromethyl)-[1,1'-biphenyl]-3-yl)propanoic acid |
| 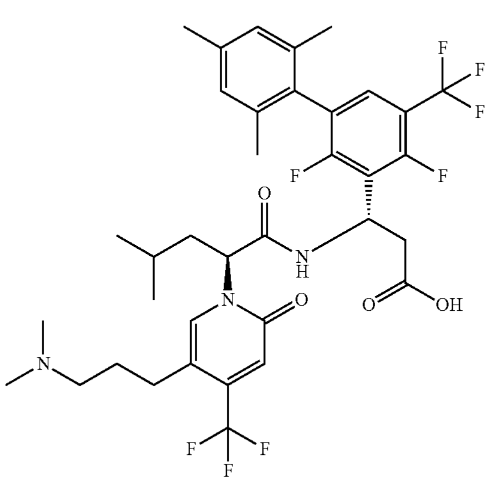 [SMILES: Cc1cc(C)c(-c2cc(C(F)(F)F)c(F)c([C@H](CC(=O)O)NC(=O)[C@H](CC(C)C)n3cc(CCCN(C)C)c(C(F)(F)F)cc3=O)c2F)c(C)c1] | (S)-3-(2,4-difluoro-2',4',6'-trimethyl-5-(trifluoromethyl)-[1,1'-biphenyl]-3-yl)-3-((S)-2-(5-(3-(dimethylamino)propyl)-2-oxo-4-(trifluoromethyl)pyridin-1(2H)-yl)-4-methylpentanamido)propanoic acid |

| Structure | Name |
|---|---|
| 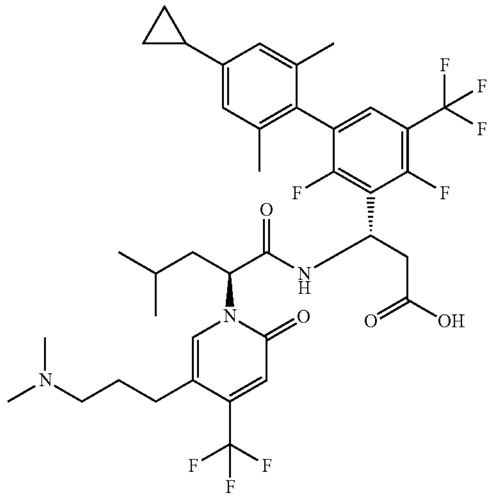 [SMILES: Cc1cc(C2CC2)cc(C)c1-c1cc(C(F)(F)F)c(F)c([C@H](CC(=O)O)NC(=O)[C@H](CC(C)C)n2cc(CCCN(C)C)c(C(F)(F)F)cc2=O)c1F] | (S)-3-(4'-cyclopropyl-2,4-difluoro-2',6'-dimethyl-5-trifluoromethyl)-[1,1'-biphenyl]-3-yl)-3-((S)-2-(5-(3-(dimethylamino)propyl)-2-oxo-4-(trifluoromethyl)pyridin-1(2H)-yl)-4-methylpentanamido)propanoic acid |
| 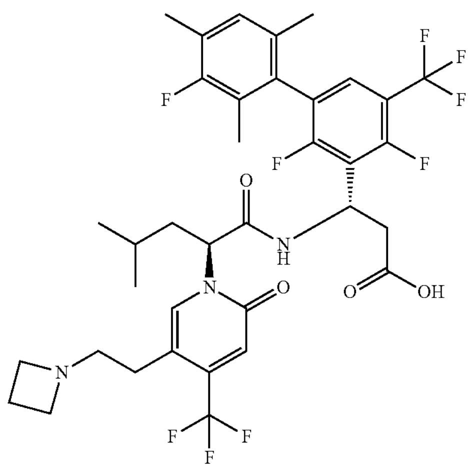 [SMILES: Cc1cc(C)c(-c2cc(C(F)(F)F)c(F)c([C@H](CC(=O)O)NC(=O)[C@H](CC(C)C)n3cc(CCN4CCC4)c(C(F)(F)F)cc3=O)c2F)c(C)c1F] | (3S)-3-((S)-2-(5-(2-(azetidin-1-yl)ethyl)-2-oxo-4-(trifluoromethyl)pyridin-1(2H)-yl)-4-methylpentanamido)-3-(2,3',4-trifluoro-2',4',6'-trimethyl-5-(trifluoromethyl)-[1,1'-biphenyl]-3-yl)propanoic acid. |

Pharmaceutically acceptable compositions comprising the compound of Formula (I) can be prepared by various procedures. For example, the compounds of Formula (I) can be formulated with suitable excipients, diluents, or carriers, and formed into tablets, or capsules, and other suitable dosage forms.

Pharmaceutical compositions can be provided in unit dose forms containing a predetermined amount of API comprising a compound of Formula (I) per unit dose. Such a unit may contain, a desired amount of a compound of the Formula (I) or pharmaceutically acceptable salt thereof, depending on the condition being treated, the route of administration and the age, weight and condition of the patient. Such unit doses may therefore be administered at a desired dose interval. The concentration of active compound in the drug composition will depend on various applicable parameters and considerations such as the absorption, inactivation and excretion rates of the drug as well as other factors known to those of skill in the art. It is to be noted that dosage values will also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed composition. The active ingredient can be administered at once, or can be divided into a number of smaller doses to be administered at varying intervals of time.

In certain embodiments, the mode of administration of the active compound is oral. Oral compositions will generally include an inert diluent or an edible carrier. They can be enclosed in gelatin capsules or compressed into tablets. For the purpose of oral therapeutic administration, the active compound can be incorporated with excipients and used in the form of tablets, troches or capsules. Pharmaceutically compatible binding agents, and/or adjuvant materials can be included as part of the composition. Pharmaceutical compositions comprising a compound of Formula (I) formulated for oral delivery can be prepared in a unit dosage form, such as a capsule at a desired dosage strength of the compound of Formula (I). For oral administration in liquid form, the oral drug components can be combined with any oral, non-toxic, pharmaceutically acceptable inert carrier such as ethanol, glycerol, water and the like. For oral administration in the form of a tablet or capsule, the compound of Formula (I) can be combined with an oral, non-toxic, pharmaceutically acceptable, inert carrier. Other examples of excipients, diluents, and carriers that are suitable for such formulations include the following: fillers and extenders such as starch, and sugars; and binding agents such as cellulose derivatives. Moreover, when desired or necessary, suitable binders, lubricants, disintegrating agents and coloring agents can also be incorporated into the mixture. Suitable binders include starch, natural sugars, natural and synthetic gums, and the like. Lubricants and/or glidants can be used in these dosage forms.

The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. When the dosage unit form is a capsule, it can contain, in addition to material of the above type, a liquid carrier such as a fatty oil. In addition, unit dosage forms can contain various other materials that modify the physical form of the dosage unit, for example, coatings of sugar, or other enteric agents.

The compound can be administered as a component of an elixir, suspension, syrup, wafer, or the like. A syrup can contain, in addition to the active compound(s), sucrose or sweetener as a sweetening agent and certain preservatives, dyes and colorings and flavors.

The compounds can be formulated as solutions appropriate for parenteral administration, for example, by intramuscular, subcutaneous or intravenous routes. For example, a compound of Formula (I) can be dissolved in a suitable buffer. A pharmaceutical composition comprising a desired concentration of a compound of Formula (I) can be formulated as an injectable drug solution in (useful, e.g., in preclinical animal studies).

Exemplary Methods

Compounds inhibiting $\alpha_4\beta_7$ are useful for development of medicaments to treat ulcerative colitis and Crohn's disease patients. Ulcerative colitis (UC) and Crohn's disease (CD) patients suffer from autoimmune inflammation in the digestive tract and for many of these patients, the $CD4^+$ memory T cells drive the progression and flare ups of the disease via their ability to secrete pro-inflammatory, effector cytokines within the gut, impacting the surrounding immune cells and tissue. The progression and flare ups of these disease conditions are believed to include extravasation of T cells leaving the blood to enter tissue in the gut leading to inflammatory conditions found in UC and CD via integrin related mechanisms. The inhibition of $\alpha_4\beta_7$ can disrupt this mechanism, thereby preventing the localization of T cells to the tissue and effectively treating and preventing disease such as UC and CD. T cell homing to the gut requires surface expression of integrin $\alpha_4\beta_7$ and chemokine receptor CCR9. While CCR9 is utilized by the cell to migrate against the gradient of CCL25 expressed in the small intestine, $\alpha_4\beta_7$ is a tethering molecule which binds the ligand, mucosal addressin cell adhesion molecule 1 (MAdCAM-1). Integrin $\alpha_4\beta_7$ binds MAdCAM-1 with high affinity facilitating rolling and firm adhesion of cells followed by extravasation into tissue.

Pharmaceutical compositions can comprise compounds that inhibit the $\alpha_4\beta_7$ integrin on inflammatory cells that enables adhesion of these cells to mucosal addressin cell adhesion molecule-1 (MAdCAM-1), and inhibiting or preventing these cells from entering the gut lamina propria and gut associated lymphoid tissue.

Compounds of Formula (I) were evaluated using a fluorescent polarization (FP) assay, as described in Example 5. FP assays are used to evaluate potency of compounds on purified protein. The FP assays consists of measuring purified integrin $\alpha\beta$ heterodimer ecto domains or headpiece binding to surrogate or truncated ligands. Results of the FP assay for exemplary compounds of Formula (I) are provided herein.

Compounds of Formula (I) were further evaluated using a Ligand binding assay (LBA) as described in Example 6 to examine compound potency of free ligand binding to receptors expressed on cells. The MAdCAM ligand binding assay uses flow cytometry to measure the binding of fluorescently-labeled MAdCAM-1-Fc to RPMI 8866 cells in the presence of Mn++. This assay assesses the binding of compounds to native full-length receptors on the cell surface. One advantage of the MAdCAM ligand binding assay is its ability to quantify and discriminate the activity of potent compounds that exceed the FP assay's functional sensitivity limit [~10 nM in Mn]. Ligand binding assays (LBA) are used to examine compound potency and selectivity of free ligand binding to receptors expressed on cells.

In some embodiments, compounds of the invention can be selected from one or more of the following numbered embodiments:

1. A compound of Formula (I):

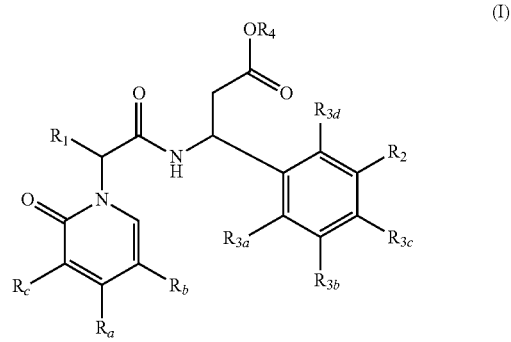

wherein $R_a$, $R_b$, and $R_c$ are independently selected from the group consisting of H, Me, halide, $CF_3$, $C(H)F_2$, $C(F)H_2$, and —$(C_1-C_5)$alkylene-N—$(R_x)(R_y)$; provided that at least one of $R_a$, $R_b$, and $R_c$ is —$(C_1-C_5)$alkylene-N—$(R_x)(R_y)$;

$R_x$ and $R_y$ are independently selected from the group consisting of H and substituted or unsubstituted $(C_1-C_6)$-alkyl; or $R_x$ and $R_y$ taken together with the N to which they are attached form a 4-6 membered ring;

$R_1$ is substituted or unsubstituted $(C_1-C_6)$-alkyl, substituted or unsubstituted $(C_1-C_4)$-alkylene-$(C_3-C_6)$-cycloalkyl, or substituted or unsubstituted $(C_1-C_4)$-alkylene-$(C_1-C_4)$-alkoxy;

$R_2$ is

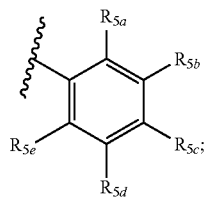

$R_{3a}$ and $R_{3b}$ are independently selected from the group consisting of H, substituted or unsubstituted ($C_1$-$C_5$)-alkyl, substituted or unsubstituted ($C_3$-$C_6$)-cycloalkyl, substituted or unsubstituted 3-6 membered heterocycloalkyl, —OH, —CN, halide, $CF_3$, $C(H)F_2$, $C(F)H_2$, —($C_1$-$C_4$)-alkoxy, —$OCF_3$, and substituted or unsubstituted ($C_1$-$C_4$)-alkylene-($C_1$-$C_4$)-alkoxy; provided that $R_{3a}$ and $R_{3b}$ are not both H; $R_{3c}$, and $R_{3d}$ are H;

$R_4$ is H, or substituted or unsubstituted ($C_1$-$C_4$)-alkyl;

$R_{5a}$, and $R_{5e}$ are independently selected from the group consisting of H, CN, halide, $CF_3$, $C(H)F_2$, $C(F)H_2$, substituted or unsubstituted ($C_3$-$C_6$)-cycloalkyl, substituted or unsubstituted ($C_1$-$C_5$)-alkyl, hydroxyl, and ($C_1$-$C_4$)-alkoxy; and $R_{5b}$, $R_{5c}$, and $R_{5d}$ are independently selected from the group consisting of H, CN, halide, $CF_3$, $C(H)F_2$, $C(F)H_2$, substituted or unsubstituted ($C_1$-$C_5$)-alkyl, substituted or unsubstituted ($C_3$-$C_6$)-cycloalkyl, substituted or unsubstituted 3-6 membered heterocycloalkyl, hydroxyl, and ($C_1$-$C_4$)-alkoxy;

or a pharmaceutically acceptable salt thereof.

2. The compound of embodiment 1, wherein $R_1$ is methyl, ethyl, n-propyl, iso-propyl, n-butyl, iso-butyl, sec-butyl, or t-butyl.

3. The compound of embodiment 2, wherein $R_1$ is iso-butyl.

4. The compound of embodiment 1, wherein $R_1$ is

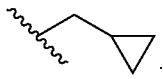

5. The compound of embodiment 1, wherein $R_1$ is

6. The compound of any one of embodiments 1-5, wherein $R_{3a}$ and $R_{3b}$ are independently selected from the group consisting of halide, substituted or unsubstituted ($C_1$-$C_5$)-alkyl, substituted or unsubstituted ($C_3$-$C_6$)-cycloalkyl, substituted or unsubstituted ($C_1$-$C_4$)-alkoxy, $CF_3$, $C(H)F_2$, and $C(F)H_2$.

7. The compound of embodiment 6, wherein $R_{3a}$ and $R_{3b}$ are independently selected from the group consisting of halide and ($C_1$-$C_4$)-alkyl.

8. The compound of embodiment 7, wherein halide is Cl or F.

9. The compound of embodiment 7 or 8, wherein ($C_1$-$C_4$)-alkyl is methyl.

10. The compound of any one of embodiments 1-7, wherein $R_{3a}$ is methyl; and $R_{3b}$ is F.

11. The compound of any one of embodiments 1-7, wherein $R_{3a}$ is F; and $R_{3b}$ is methyl.

12. The compound of any one of embodiments 1-11, wherein $R_4$ is H.

13. The compound of any one of embodiments 1-11, wherein $R_4$ is methyl, ethyl, n-propyl, iso-propyl.

14. The compound of any one of embodiments 1-13, wherein $R_{5a}$ and $R_{5e}$ are independently selected from the group consisting of halide, $CF_3$, $C(H)F_2$, $C(F)H_2$, and substituted or unsubstituted ($C_1$-$C_4$)-alkyl.

15. The compound of any one of embodiments 1-14, wherein $R_{5a}$ is halide.

16. The compound of embodiment 15, wherein $R_{5a}$ is F or Cl.

17. The compound of any one of embodiments 1-14, wherein $R_{5a}$ is $CF_3$.

18. The compound of any one of embodiments 1-14, wherein $R_{5a}$ is $C(H)F_2$.

19. The compound of any one of embodiments 1-14, wherein $R_{5a}$ is $C(F)H_2$.

20. The compound of any one of embodiments 1-14, wherein $R_{5a}$ is unsubstituted ($C_1$-$C_4$)-alkyl.

21. The compound of embodiment 20, wherein $R_{5a}$ is methyl.

22. The compound of any one of embodiments 1-14, wherein $R_{5a}$ is substituted ($C_1$-$C_5$)-alkyl, substituted with at least one halide.

23. The compound of any one of embodiments 1-14, wherein $R_{5a}$ is unsubstituted ($C_1$-$C_4$)-alkoxy.

24. The compound of embodiment 23, wherein $R_{5a}$ is OMe.

25. The compound of any one of embodiments 1-24, wherein $R_{5e}$ is halide.

26. The compound of embodiment 25, wherein $R_{5e}$ is F or Cl.

27. The compound of any one of embodiments 1-24, wherein $R_{5e}$ is $CF_3$.

28. The compound of any one of embodiments 1-24, wherein $R_{5e}$ is $C(H)F_2$.

29. The compound of any one of embodiments 1-24, wherein $R_{5e}$ is $C(F)H_2$.

30. The compound of any one of embodiments 1-24, wherein $R_{5e}$ is unsubstituted ($C_1$-$C_4$)-alkyl.

31. The compound of embodiment 30, wherein $R_{5e}$ is methyl.

32. The compound of any one of embodiments 1-24, wherein $R_{5e}$ is substituted ($C_1$-$C_5$)-alkyl, substituted with at least one halide.

33. The compound of any one of embodiments 1-24, wherein $R_{5e}$ is unsubstituted ($C_1$-$C_4$)-alkoxy.

34. The compound of embodiment 33, wherein $R_{5e}$ is OMe.

35. The compound of any one of embodiments 1-34, wherein $R_{5b}$, $R_{5c}$, and $R_{5d}$ are independently selected from the group consisting of H, halide, $CF_3$, $C(H)F_2$, $C(F)H_2$, substituted or unsubstituted ($C_1$-$C_5$)-alkyl, and substituted or unsubstituted ($C_1$-$C_4$)-alkoxy.

36. The compound of any one of embodiments 1-35, wherein $R_{5b}$ is H.

37. The compound of any one of embodiments 1-35, wherein $R_{5b}$ is halide.

38. The compound of embodiment 37, wherein $R_{5b}$ is Cl or F.

39. The compound of any one of embodiments 1-35, wherein $R_{5b}$ is $CF_3$.

40. The compound of any one of embodiments 1-35, wherein $R_{5b}$ is $C(H)F_2$.
41. The compound of any one of embodiments 1-35, wherein $R_{5b}$ is $C(F)H_2$.
42. The compound of any one of embodiments 1-35, wherein $R_{5b}$ is unsubstituted $(C_1$-$C_4)$-alkyl.
43. The compound of embodiment 37, wherein $R_{5b}$ is methyl.
44. The compound of any one of embodiments 1-35, wherein $R_{5b}$ is unsubstituted $(C_1$-$C_4)$-alkoxy.
45. The compound of embodiment 44, wherein $R_{5b}$ is OMe.
46. The compound of any one of embodiments 1-35, wherein $R_{5b}$ is unsubstituted $(C_3$-$C_6)$-cycloalkyl.
47. The compound of embodiment 46, wherein $R_{5b}$ is cyclopropyl.
48. The compound of any one of embodiments 1-47, wherein $R_{5c}$ is H.
49. The compound of any one of embodiments 1-47, wherein $R_{5c}$ is halide.
50. The compound of embodiment 49, wherein $R_{5c}$ is Cl or F.
51. The compound of any one of embodiments 1-47, wherein $R_{5c}$ is $CF_3$.
52. The compound of any one of embodiments 1-47, wherein $R_{5c}$ is $C(H)F_2$.
53. The compound of any one of embodiments 1-47, wherein $R_{5c}$ is $C(F)H_2$.
54. The compound of any one of embodiments 1-47, wherein $R_{5c}$ is unsubstituted $(C_1$-$C_4)$-alkyl.
55. The compound of embodiment 54, wherein $R_{5c}$ is methyl.
56. The compound of any one of embodiments 1-47, wherein $R_{5c}$ is unsubstituted $(C_1$-$C_4)$-alkoxy.
57. The compound of embodiment 56, wherein $R_{5c}$ is OMe.
58. The compound of any one of embodiments 1-47, wherein $R_{5c}$ is unsubstituted $(C_3$-$C_6)$-cycloalkyl.
59. The compound of embodiment 58, wherein $R_{5b}$ is cyclopropyl.
60. The compound of any one of embodiments 1-59, wherein $R_{5d}$ is H.
61. The compound of any one of embodiments 1-59, wherein $R_{5d}$ is halide.
62. The compound of embodiment 61, wherein $R_{5d}$ is Cl or F.
63. The compound of any one of embodiments 1-59, wherein $R_{5d}$ is $CF_3$.
64. The compound of any one of embodiments 1-59, wherein $R_{5d}$ is $C(H)F_2$.
65. The compound of any one of embodiments 1-59, wherein $R_{5d}$ is $C(F)H_2$.
66. The compound of any one of embodiments 1-59, wherein $R_{5d}$ is unsubstituted $(C_1$-$C_4)$-alkyl.
67. The compound of embodiment 66, wherein $R_{5d}$ is methyl.
68. The compound of any one of embodiments 1-67, wherein $R_{5d}$ is unsubstituted $(C_1$-$C_4)$-alkoxy.
69. The compound of embodiment 68, wherein $R_{5d}$ is OMe.
70. The compound of any one of embodiments 1-67, wherein $R_{5d}$ is unsubstituted $(C_3$-$C_6)$-cycloalkyl.
71. The compound of embodiment 70, wherein $R_{5d}$ is cyclopropyl.
72. The compound of any one of embodiments 1-35, wherein $R_{5b}$, and $R_{5d}$ are each H.
73. The compound of any one of embodiments 1-72, wherein $R_a$ is H.
74. The compound of any one of embodiments 1-72, wherein $R_a$ is Me.
75. The compound of any one of embodiments 1-72, wherein $R_a$ is halide.
76. The compound of embodiment 75, wherein $R_a$ is Cl or F.
77. The compound of any one of embodiments 1-72, wherein $R_a$ is $CF_3$.
78. The compound of any one of embodiments 1-72, wherein $R_a$ is $C(H)F_2$.
79. The compound of any one of embodiments 1-72, wherein $R_a$ is $C(F)H_2$.
80. The compound of any one of embodiments 1-72, wherein $R_a$ is unsubstituted —$(C_1$-$C_3)$alkylene-N—$(R_x)(R_y)$.
81. The compound of any one of embodiments 1-72, wherein $R_a$ is substituted —$(C_1$-$C_3)$alkylene-N—$(R_x)(R_y)$, substituted with F or OMe.
82. The compound of any one of embodiments 1-81, wherein $R_b$ is H.
83. The compound of any one of embodiments 1-81, wherein $R_b$ is Me.
84. The compound of any one of embodiments 1-81, wherein $R_b$ is halide.
85. The compound of embodiment 84, wherein $R_b$ is Cl or F.
86. The compound of any one of embodiments 1-81, wherein $R_b$ is $CF_3$.
87. The compound of any one of embodiments 1-81, wherein $R_b$ is $C(H)F_2$.
88. The compound of any one of embodiments 1-81, wherein $R_b$ is $C(F)H_2$.
89. The compound of any one of embodiments 1-81, wherein $R_b$ is unsubstituted —$(C_1$-$C_3)$alkylene-N—$(R_x)(R_y)$.
90. The compound of any one of embodiments 1-81, wherein $R_b$ is substituted —$(C_1$-$C_3)$alkylene-N—$(R_x)(R_y)$, substituted with F or OMe.
91. The compound of any one of embodiments 1-90, wherein $R_c$ is H.
92. The compound of any one of embodiments 1-90, wherein $R_c$ is Me.
93. The compound of any one of embodiments 1-90, wherein $R_c$ is halide.
94. The compound of embodiment 93, wherein $R_c$ is Cl or F.
95. The compound of any one of embodiments 1-90, wherein $R_c$ is $CF_3$.
96. The compound of any one of embodiments 1-90, wherein $R_c$ is $C(H)F_2$.
97. The compound of any one of embodiments 1-90, wherein $R_c$ is $C(F)H_2$.
98. The compound of any one of embodiments 1-90, wherein $R_c$ is unsubstituted —$(C_1$-$C_3)$alkylene-N—$(R_x)(R_y)$.
99. The compound of any one of embodiments 1-90, wherein $R_c$ is substituted —$(C_1$-$C_3)$alkylene-N—$(R_x)(R_y)$, substituted with F or OMe.
100. The compound of any one of embodiments 1-99, wherein $R_x$ is H.
101. The compound of any one of embodiments 1-99, wherein $R_x$ is unsubstituted $(C_1$-$C_6)$-alkyl.
102. The compound of any one of embodiments 1-100, wherein $R_y$ is H.

103. The compound of any one of embodiments 1-100, wherein $R_y$ is unsubstituted ($C_1$-$C_6$)-alkyl.
104. The compound of any one of embodiments 1-72, 80-81, 89-90, and 98-99, wherein $R_x$ and $R_y$ taken together with the N to which they are attached form a unsubstituted 4-6 membered ring.
105. The compound of any one of embodiments 1-72, 80-81, 89-90, and 98-99, wherein $R_x$ and $R_y$ taken together with the N to which they are attached form a substituted 4-6 membered ring, substituted with at least one halide, substituted or unsubstituted ($C_1$-$C_4$) alkyl, or OMe.
106. The compound of embodiment 104 or 105, wherein the 4-6 membered ring is a 3-6 membered heterocycloalkyl.
107. The compound of embodiment 104 or 105, wherein the 4-6 membered ring is a 4-5 membered heterocycloalkyl.
108. The compound of embodiment 1, wherein the compound is a compound of Formula (Ia):

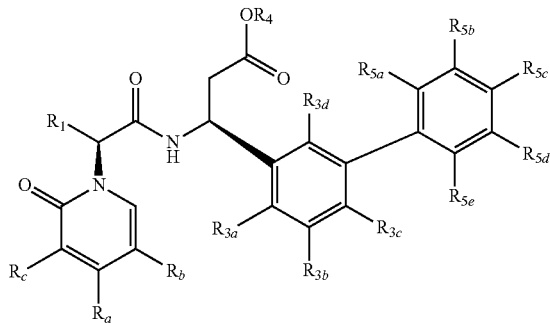

(Ia)

wherein
at least one of $R_a$, $R_b$, and $R_c$ is —($C_1$-$C_3$)alkylene-N($R_x$)($R_y$);
$R_x$ and $R_y$ are independently selected from the group consisting of H and methyl; or
$R_x$ and $R_y$ taken together with the N to which they are attached form a substituted or unsubstituted 4-6 membered ring; and
$R_{3a}$, and $R_{3b}$ are each independently selected from the group consisting of methyl and F.
109. The compound of embodiment 108, wherein $R_{5a}$, and $R_{5e}$ are independently unsubstituted ($C_1$-$C_4$) alkyl.
110. The compound of embodiment 108 or 109, wherein $R_b$ is unsubstituted —($C_1$-$C_3$)alkylene-N($R_x$)($R_y$).
111. The compound of embodiment 1 or 108, wherein $R_a$ is selected from the group consisting of H, C(H)F$_2$, CF$_3$, and Me.
112. The compound of embodiment 1 or 108, wherein $R_b$ is selected from the group consisting of

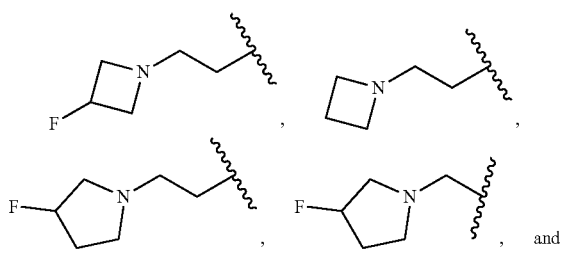

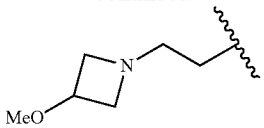

113. The compound of embodiment 1 or 108, wherein $R_b$ is selected from the group consisting of

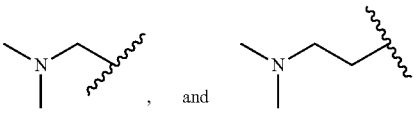

114. The compound of embodiment 1 or 108, wherein $R_c$ is H or F.
115. The compound of any one of embodiments 1 and 108-114, wherein $R_1$ is selected from the group consisting of

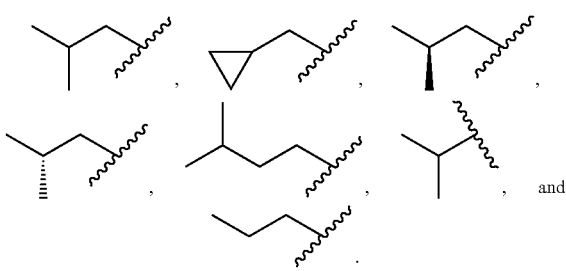

116. The compound of any one of embodiments 108-115, wherein $R_{5a}$ is CF$_3$.
117. The compound of any one of embodiments 108-115, wherein $R_{5a}$ is C(H)F$_2$.
118. The compound of any one of embodiments 108-115, wherein $R_{5a}$ is C(F)H$_2$.
119. The compound of any one of embodiments 108-115, wherein $R_{5a}$ is methyl.
120. The compound of any one of embodiments 108-115, wherein $R_{5a}$ is OMe.
121. The compound of any one of embodiments 108-115, wherein $R_{5a}$ is F or Cl.
122. The compound of any one of embodiments 108-121, wherein $R_{5b}$ is H.
123. The compound of any one of embodiments 108-121, wherein $R_{5b}$ is CF$_3$.
124. The compound of any one of embodiments 108-121, wherein $R_{5b}$ is C(H)F$_2$.
125. The compound of any one of embodiments 108-121, wherein $R_{5b}$ is C(F)H$_2$.
126. The compound of any one of embodiments 108-121, wherein $R_{5b}$ is methyl.
127. The compound of any one of embodiments 108-121, wherein $R_{5b}$ is OMe.
128. The compound of any one of embodiments 108-121, wherein $R_{5b}$ is F or Cl.
129. The compound of any one of embodiments 108-128, wherein $R_{5c}$ is H.
130. The compound of any one of embodiments 108-128, wherein $R_{5c}$ is CF$_3$.
131. The compound of any one of embodiments 108-128, wherein $R_{5c}$ is C(H)F$_2$.

132. The compound of any one of embodiments 108-128, wherein $R_{5c}$ is C(F)H$_2$.
133. The compound of any one of embodiments 108-128, wherein $R_{5c}$ is methyl.
134. The compound of any one of embodiments 108-128, wherein $R_{5c}$ is OMe.
135. The compound of any one of embodiments 108-128, wherein $R_{5c}$ is F or Cl.
136. The compound of any one of embodiments 108-135, wherein $R_{5d}$ is H.
137. The compound of any one of embodiments 108-135, wherein $R_{5d}$ is CF$_3$.
138. The compound of any one of embodiments 108-135, wherein $R_{5d}$ is C(H)F$_2$.
139. The compound of any one of embodiments 108-135, wherein $R_{5d}$ is C(F)H$_2$.
140. The compound of any one of embodiments 108-135, wherein $R_{5d}$ is methyl.
141. The compound of any one of embodiments 108-135, wherein $R_{5d}$ is OMe.
142. The compound of any one of embodiments 108-135, wherein $R_{5d}$ is F or Cl.
143. The compound of any one of embodiments 108-142, wherein $R_{5e}$ is CF$_3$.
144. The compound of any one of embodiments 108-142, wherein $R_{5e}$ is C(H)F$_2$.
145. The compound of any one of embodiments 108-142, wherein $R_{5e}$ is C(F)H$_2$.
146. The compound of any one of embodiments 108-142, wherein $R_{5e}$ is methyl.
147. The compound of any one of embodiments 108-142, wherein $R_{5e}$ is OMe.
148. The compound of any one of embodiments 108-142, wherein $R_{5e}$ is F or Cl.
149. The compound of any one of embodiments 1, and 108-121, wherein at least one of $R_{5b}$, $R_{5c}$, and $R_{5d}$ is H.
150. The compound of any one of embodiments 1, and 108-121, wherein at least two of $R_{5b}$, $R_{5c}$, and $R_{5d}$ is H.
151. The compound of any one of embodiments 1, and 108-121, wherein $R_{5b}$, $R_{5c}$, and $R_{5d}$ are H.
152. The compound of any one of embodiments 1, and 108-151, wherein $R_{3a}$ is H.
153. The compound of any one of embodiments 1, and 108-151, wherein $R_{3a}$ is methyl.
154. The compound of any one of embodiments 1, and 108-151, wherein $R_{3a}$ is halide.
155. The compound of any one of embodiments 1, and 108-151, wherein $R_{3a}$ is CF$_3$.
156. The compound of any one of embodiments 1, and 108-151, wherein $R_{3a}$ is C(H)F$_2$.
157. The compound of any one of embodiments 1, and 108-151, wherein $R_{3a}$ is C(F)H$_2$.
158. The compound of any one of embodiments 1, and 108-151, wherein $R_{3a}$ is OMe.
159. The compound of any one of embodiments 1, and 108-158, wherein $R_{3b}$ is H.
160. The compound of any one of embodiments 1, and 108-158, wherein $R_{3b}$ is methyl.
161. The compound of any one of embodiments 1, and 108-158, wherein $R_{3b}$ is halide.
162. The compound of any one of embodiments 1, and 108-158, wherein $R_{3b}$ is CF$_3$.
163. The compound of any one of embodiments 1, and 108-158, wherein $R_{3b}$ is C(H)F$_2$.
164. The compound of any one of embodiments 1, and 108-158, wherein $R_{3b}$ is C(F)H$_2$.
165. The compound of any one of embodiments 1, and 108-158, wherein $R_{3b}$ is OMe.
166. The compound of any one of embodiments 1, and 108-158, wherein $R_{3b}$ is OCF$_3$.
167. The compound of any one of embodiments 1, and 108-158, wherein $R_{3b}$ is cyclopropyl.
168. The compound of any one of embodiments 108-151, wherein $R_{3a}$ is methyl and $R_{3b}$ is F.
169. The compound of any one of embodiments 108-151, wherein $R_{3a}$ is F and $R_{3b}$ is methyl.
170. The compound of embodiment 1, wherein the compound is selected from any one of the compounds of FIG. 1, or an enantiomer thereof.
171. The compound of embodiment 1, wherein the compound is a compound of Formula (Ic)

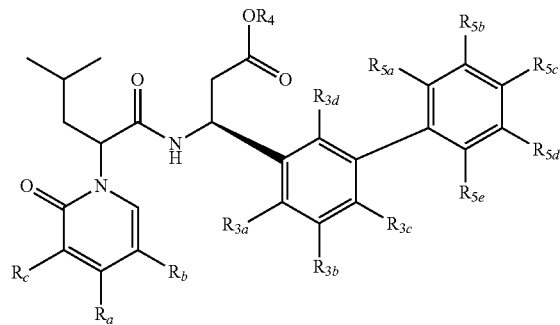

or a pharmaceutically acceptable salt thereof, wherein
$R_a$, $R_b$, and $R_c$ are independently selected from the group consisting of H, substituted or unsubstituted (C$_1$-C$_5$)-alkyl, halide, CF$_3$, C(H)F$_2$, C(F)H$_2$, substituted or unsubstituted (C$_1$-C$_4$)-alkoxy, —OCF$_3$, and substituted or unsubstituted —(C$_1$-C$_5$)alkylene-N—(R$_x$)(R$_y$); provided that one of $R_a$, $R_b$, and $R_c$ is —(C$_1$-C$_5$)alkylene-N—(R$_x$)(R$_y$);
$R_x$ and $R_y$ are independently selected from the group consisting of H, substituted or unsubstituted (C$_1$-C$_6$)-alkyl, or substituted or unsubstituted (C$_1$-C$_4$)-alkylene-(C$_1$-C$_4$)-alkoxy; or $R_x$ and $R_y$ taken together with the N to which they are attached form a substituted or unsubstituted 4-6 membered heterocyclyl ring;
$R_{3a}$ and $R_{3b}$ are independently selected from the group consisting of H, substituted or unsubstituted (C$_1$-C$_5$)-alkyl, substituted or unsubstituted (C$_3$-C$_6$)-cycloalkyl, substituted or unsubstituted 3-6 membered heterocycloalkyl, —OH, —CN, halide, CF$_3$, C(H)F$_2$, C(F)H$_2$, —(C$_1$-C$_4$)-alkoxy, —OCF$_3$, and substituted or unsubstituted (C$_1$-C$_4$)-alkylene-(C$_1$-C$_4$)-alkoxy; provided that $R_{3a}$ and $R_{3b}$ are not both H;
$R_{3c}$ is selected from the group consisting of H, substituted or unsubstituted (C$_1$-C$_5$)-alkyl, substituted or unsubstituted (C$_3$-C$_6$)-cycloalkyl, substituted or unsubstituted 3-6 membered heterocycloalkyl, hydroxyl, halide, CF$_3$, C(H)F$_2$, C(F)

H₂, —(C₁-C₄)-alkoxy, —OCF₃—CN, and substituted or unsubstituted (C₁-C₄)-alkylene-(C₁-C₄)-alkoxy;

$R_{3d}$ is selected from the group consisting of H, substituted or unsubstituted (C₁-C₅)-alkyl, hydroxyl, halide, and —(C₁-C₄)-alkoxy;

$R_{5a}$, and $R_{5e}$ are independently selected from the group consisting of H, CN, halide, CF₃, C(H)F₂, C(F)H₂, substituted or unsubstituted (C₁-C₅)-alkyl, hydroxyl, and (C₁-C₄)-alkoxy; and $R_{5b}$, $R_{5c}$, and $R_{5d}$ are independently selected from the group consisting of H, CN, halide, CF₃, C(H)F₂, C(F)H₂, substituted or unsubstituted (C₁-C₅)-alkyl, hydroxyl, and (C₁-C₄)-alkoxy;

or a pharmaceutically acceptable salt thereof.

172. A compound selected from the group consisting of:
(3S)-3-(4,5-difluoro-2',6'-dimethylbiphenyl-3-yl)-3-(2-(5-(2-(3-fluoroazetidine-1-yl)ethyl)-4-methyl-2-oxopyridin-1(2H)-yl)-4-methylpentanamido)propanoic acid;
(3S)-3-(2-(5-(2-(azetidin-1-yl)ethyl)-2-oxo-4-(trifluoromethyl)pyridin-1(2H)-yl)-4-methylpentanamido)-3-(4-fluoro-2',6'-dimethyl-5-(trifluoromethyl)biphenyl-3-yl)propanoic Acid;
(3S)-3-(2-(5-(2-(azetidin-1-yl)ethyl)-2-oxo-4-(trifluoromethyl)pyridin-1(2H)-yl)-4-methylpentanamido)-3-(3',4-difluoro-2',5,6'-trimethyl-[1,1'-biphenyl]-3-yl)propanoic Acid;
(3S)-3-(2-(5-(2-(azetidin-1-yl)ethyl)-2-oxo-4-(trifluoromethyl)pyridin-1(2H)-yl)-4-methylpentanamido)-3-(4-fluoro-3'-methoxy-2',5,6'-trimethyl-[1,1'-biphenyl]-3-yl)propanoic acid;
(3S)-3-(4,4'-difluoro-2',5,6'-trimethyl-[1,1'-biphenyl]-3-yl)-3-(2-(5-(2-(dimethylamino)ethyl)-2-oxo-4-(trifluoromethyl)pyridin-1(2H)-yl)-4-methylpentanamido)propanoic acid;
(3S)-3-(5-chloro-4-fluoro-2',6'-dimethyl-[1,1'-biphenyl]-3-yl)-3-(2-(5-(2-(3-methoxyazetidin-1-yl)ethyl)-2-oxo-4-(trifluoromethyl)pyridin-1(2H)-yl)-4-methylpentanamido)propanoic acid;
(3S)-3-(2-(5-(2-(dimethylamino)ethyl)-2-oxo-4-(trifluoromethyl)pyridin-1(2H)-yl)-4-methylpentanamido)-3-(4-fluoro-2',4',5,6'-tetramethylbiphenyl-3-yl)propanoic Acid;
(3S)-3-(4,4'-difluoro-2',5,6'-trimethyl-[1,1'-biphenyl]-3-yl)-3-(2-(3-(difluoromethyl)-5-(2-(dimethylamino)ethyl)-2-oxopyridin-1(2H)-yl)-4-methylpentanamido)propanoic acid;
(3S)-3-(2-(5-(2-(dimethylamino)ethyl)-4-methyl-2-oxopyridin-1(2H)-yl)-5-methylhexanamido)-3-(4-fluoro-2',5,6'-trimethylbiphenyl-3-yl)propanoic Acid;
(3S)-3-(4-fluoro-2',5,6'-trimethyl-[1,1'-biphenyl]-3-yl)-3-(2-(3-fluoro-5-(2-(3-fluoroazetidine-1-yl)ethyl)-2-oxopyridin-1(2H)-yl)-4-methylpentanamido)propanoic acid;
(3S)-3-(4-fluoro-2',5,6'-trimethyl-[1,1'-biphenyl]-3-yl)-3-(2-(3-fluoro-5-(2-((R)-3-fluoropyrrolidin-1-yl)ethyl)-2-oxopyridin-1(2H)-yl)-4-methylpentanamido)propanoic acid; and
(3S)-3-(5-chloro-4-fluoro-2',6'-dimethyl-[1,1'-biphenyl]-3-yl)-3-(2-(5-(2-(3-methoxyazetidin-1-yl)ethyl)-2-oxo-4-(trifluoromethyl)pyridin-1(2H)-yl)-4-methylpentanamido)propanoic acid,
or a pharmaceutically acceptable salt thereof.

173. The compound of embodiment 1, wherein the compound is the compound:

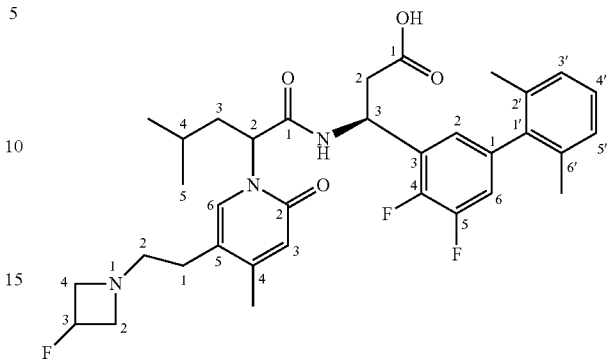

or a pharmaceutically acceptable salt thereof.

174. The compound of embodiment 1, wherein the compound is the compound:

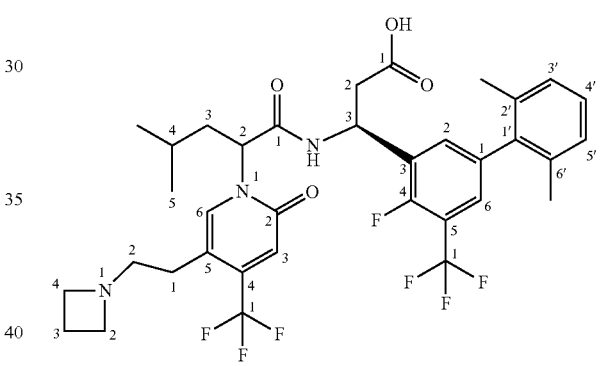

or a pharmaceutically acceptable salt thereof.

175. The compound of embodiment 1, wherein the compound is the compound:

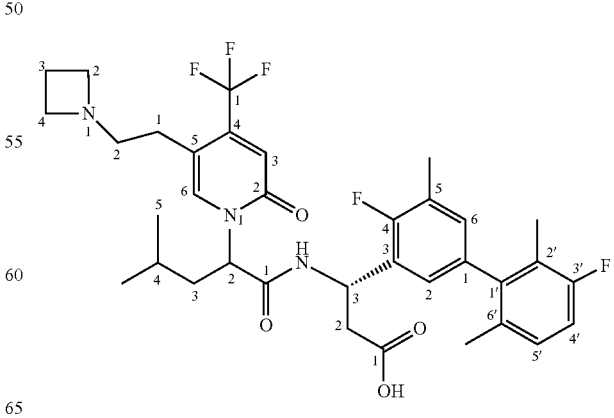

or a pharmaceutically acceptable salt thereof.

176. The compound of embodiment 1, wherein the compound is the compound:

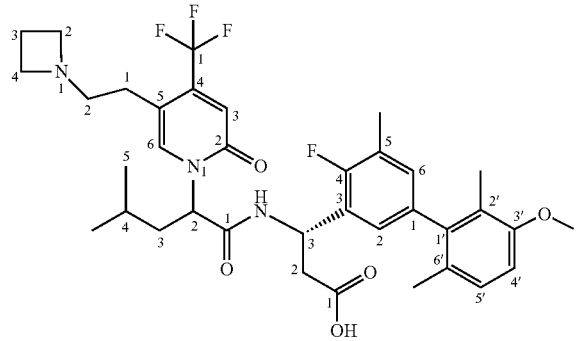

or a pharmaceutically acceptable salt thereof.

177. The compound of embodiment 1, wherein the compound is the compound:

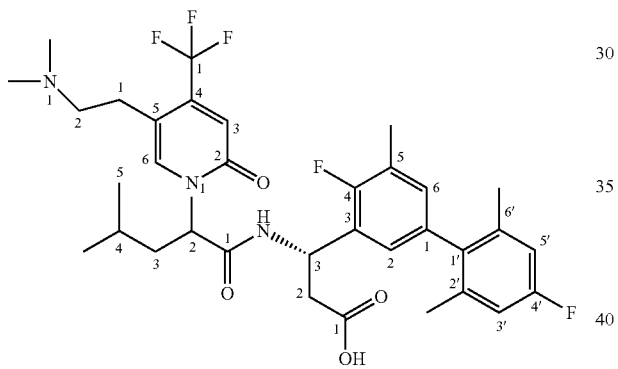

or a pharmaceutically acceptable salt thereof.

178. The compound of embodiment 1, wherein the compound is the compound:

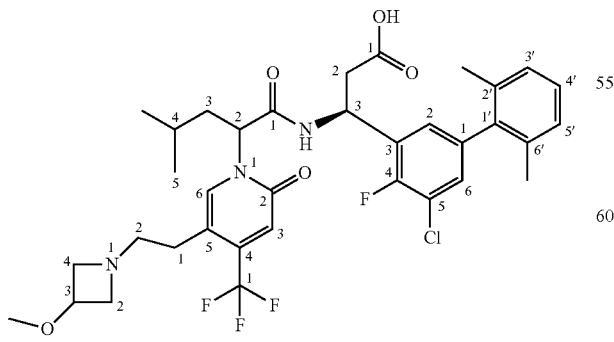

or a pharmaceutically acceptable salt thereof.

179. The compound of embodiment 1, wherein the compound is the compound:

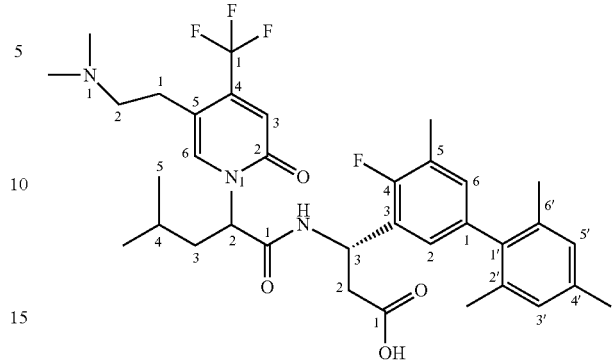

or a pharmaceutically acceptable salt thereof.

180. The compound of embodiment 1, wherein the compound is the compound:

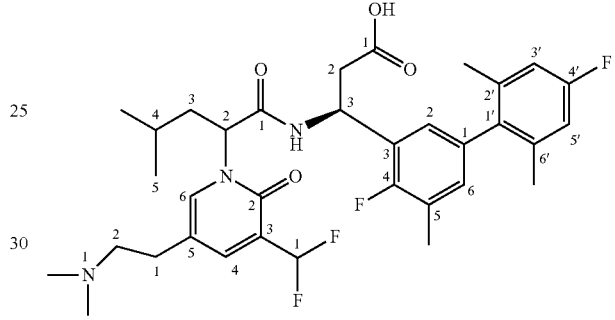

or a pharmaceutically acceptable salt thereof.

181. The compound of embodiment 1, wherein the compound is the compound:

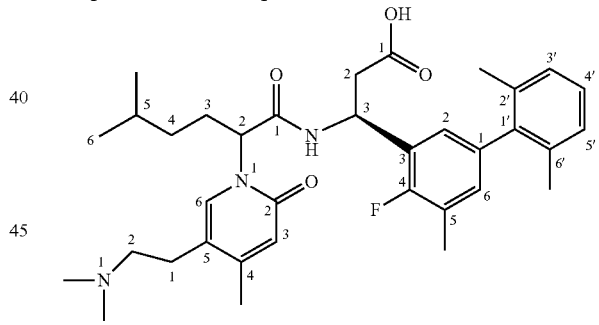

or a pharmaceutically acceptable salt thereof.

182. The compound of embodiment 1, wherein the compound is the compound:

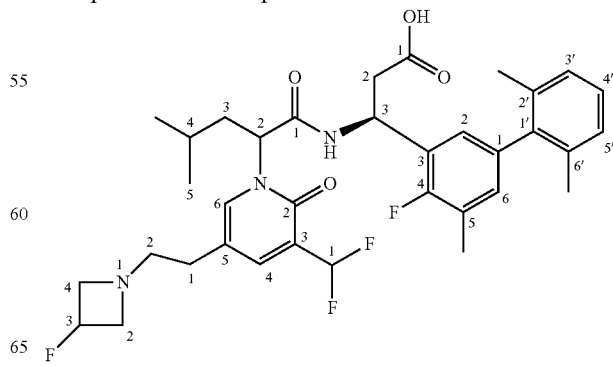

or a pharmaceutically acceptable salt thereof.

183. The compound of embodiment 1, wherein the compound is the compound:

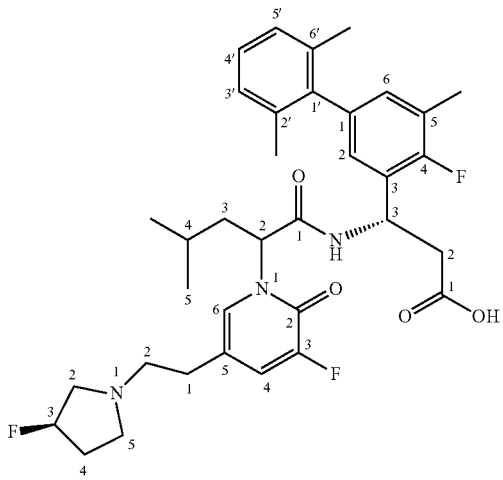 [SMILES: Cc1cc(-c2c(C)cccc2C)cc([C@H](CC(=O)O)NC(=O)C(CC(C)C)n2cc(CCN3CC[C@@H](F)C3)cc(F)c2=O)c1F]

or a pharmaceutically acceptable salt thereof.

184. The compound of embodiment 1, wherein the compound is the compound:

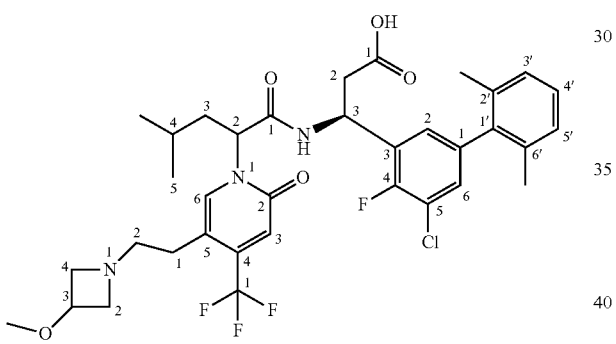

or a pharmaceutically acceptable salt thereof.

185. The compound of embodiment 1, wherein the compound is (3S)-3-(4,5-difluoro-2',6'-dimethylbiphenyl-3-yl)-3-(2-(5-(2-(3-fluoroazetidine-1-yl)ethyl)-4-methyl-2-oxopyridin-1(2H)-yl)-4-methylpentanamido) propanoic acid, or a pharmaceutically acceptable salt thereof.

186. The compound of embodiment 1, wherein the compound is (3S)-3-(2-(5-(2-(azetidin-1-yl)ethyl)-2-oxo-4-(trifluoromethyl)pyridin-1(2H)-yl)-4-methylpentanamido)-3-(4-fluoro-2',6'-dimethyl-5-(trifluoromethyl) biphenyl-3-yl)propanoic Acid, or a pharmaceutically acceptable salt thereof.

187. The compound of embodiment 1, wherein the compound is (3S)-3-(2-(5-(2-(azetidin-1-yl)ethyl)-2-oxo-4-(trifluoromethyl)pyridin-1(2H)-yl)-4-methylpentanamido)-3-(3',4-difluoro-2',5,6'-trimethyl-[1,1'-biphenyl]-3-yl)propanoic acid, or a pharmaceutically acceptable salt thereof.

188. The compound of embodiment 1, wherein the compound is (3S)-3-(2-(5-(2-(azetidin-1-yl)ethyl)-2-oxo-4-(trifluoromethyl)pyridin-1(2H)-yl)-4-methylpentanamido)-3-(4-fluoro-3'-methoxy-2',5,6'-trimethyl-[1,1'-biphenyl]-3-yl)propanoic Acid, or a pharmaceutically acceptable salt thereof.

189. The compound of embodiment 1, wherein the compound is (3S)-3-(4,4'-difluoro-2',5,6'-trimethyl-[1,1'-biphenyl]-3-yl)-3-(2-(5-(2-(dimethylamino)ethyl)-2-oxo-4-(trifluoromethyl)pyridin-1(2H)-yl)-4-methylpentanamido)propanoic acid, or a pharmaceutically acceptable salt thereof.

190. The compound of embodiment 1, wherein the compound is (3S)-3-(5-chloro-4-fluoro-2',6'-dimethyl-[1,1'-biphenyl]-3-yl)-3-(2-(5-(2-(3-methoxyazetidin-1-yl)ethyl)-2-oxo-4-(trifluoromethyl)pyridin-1(2H)-yl)-4-methylpentanamido)propanoic acid, or a pharmaceutically acceptable salt thereof.

191. The compound of embodiment 1, wherein the compound is (3S)-3-(2-(5-(2-(dimethylamino)ethyl)-2-oxo-4-(trifluoromethyl)pyridin-1(2H)-yl)-4-methylpentanamido)-3-(4-fluoro-2',4',5,6'-tetramethylbiphenyl-3-yl)propanoic Acid, or a pharmaceutically acceptable salt thereof.

192. The compound of embodiment 1, wherein the compound is (3S)-3-(4,4'-difluoro-2',5,6'-trimethyl-[1,1'-biphenyl]-3-yl)-3-(2-(3-(difluoromethyl)-5-(2-(dimethylamino)ethyl)-2-oxopyridin-1(2H)-yl)-4-methylpentanamido)propanoic acid, or a pharmaceutically acceptable salt thereof.

193. The compound of embodiment 1, wherein the compound is (3S)-3-(2-(5-(2-(dimethylamino)ethyl)-4-methyl-2-oxopyridin-1(2H)-yl)-5-methylhexanamido)-3-(4-fluoro-2',5,6'-trimethylbiphenyl-3-yl)propanoic Acid, or a pharmaceutically acceptable salt thereof.

194. The compound of embodiment 1, wherein the compound is (3S)-3-(4-fluoro-2',5,6'-trimethyl-[1,1'-biphenyl]-3-yl)-3-(2-(3-fluoro-5-(2-(3-fluoroazetidine-1-yl)ethyl)-2-oxopyridin-1(2H)-yl)-4-methylpentanamido) propanoic acid, or a pharmaceutically acceptable salt thereof.

195. The compound of embodiment 1, wherein the compound is (3S)-3-(4-fluoro-2',5,6'-trimethyl-[1,1'-biphenyl]-3-yl)-3-(2-(3-fluoro-5-(2-((R)-3-fluoropyrrolidin-1-yl)ethyl)-2-oxopyridin-1(2H)-yl)-4-methylpentanamido)propanoic acid, or a pharmaceutically acceptable salt thereof.

196. The compound of embodiment 1, wherein the compound is (3S)-3-(5-chloro-4-fluoro-2',6'-dimethyl-[1,1'-biphenyl]-3-yl)-3-(2-(5-(2-(3-methoxyazetidin-1-yl)ethyl)-2-oxo-4-(trifluoromethyl)pyridin-1(2H)-yl)-4-methylpentanamido)propanoic acid, or a pharmaceutically acceptable salt thereof.

197. The compound of embodiment 1, wherein the compound is (S)-3-(4,5-difluoro-2',6'-dimethyl-[1,1'-biphenyl]-3-yl)-3-((S)-2-(5-(2-(3-fluoroazetidine-1-yl) ethyl)-4-methyl-2-oxopyridin-1(2H)-yl)-4-methylpentanamido)propanoic acid, or a pharmaceutically acceptable salt thereof.

198. The compound of embodiment 1, wherein the compound is (S)-3-((S)-2-(5-(2-(azetidin-1-yl)ethyl)-2-oxo-4-(trifluoromethyl)pyridin-1(2H)-yl)-4-methyl-pentanamido)-3-(4-fluoro-2',6'-dimethyl-5-(trifluoromethyl)-[1,1'-biphenyl]-3-yl)propanoic Acid, or a pharmaceutically acceptable salt thereof.

199. The compound of embodiment 1, wherein the compound is (S)-3-((S)-2-(5-(2-(azetidin-1-yl)ethyl)-2-oxo-4-(trifluoromethyl)pyridin-1(2H)-yl)-4-methyl-pentanamido)-3-(3',4-difluoro-2',5,6'-trimethyl-[1,1'-biphenyl]-3-yl)propanoic acid, or a pharmaceutically acceptable salt thereof.

200. The compound of embodiment 1, wherein the compound is (S)-3-((S)-2-(5-(2-(azetidin-1-yl)ethyl)-2-oxo-4-(trifluoromethyl)pyridin-1(2H)-yl)-4-methylpentanamido)-3-(4-fluoro-3'-methoxy-2',5,6'-trimethyl-[1,1'-biphenyl]-3-yl)propanoic Acid, or a pharmaceutically acceptable salt thereof.

201. The compound of embodiment 1, wherein the compound is (S)-3-(4,4'-difluoro-2',5,6'-trimethyl-[1,1'-biphenyl]-3-yl)-3-((S)-2-(5-(2-(dimethylamino)ethyl)-2-oxo-4-(trifluoromethyl)pyridin-1(2H)-yl)-4-methylpentanamido)propanoic acid, or a pharmaceutically acceptable salt thereof.

202. The compound of embodiment 1, wherein the compound is (S)-3-(5-chloro-4-fluoro-2',6'-dimethyl-[1,1'-biphenyl]-3-yl)-3-((S)-2-(5-(2-(3-methoxyazetidin-1-yl)ethyl)-2-oxo-4-(trifluoromethyl)pyridin-1(2H)-yl)-4-methylpentanamido)propanoic acid, or a pharmaceutically acceptable salt thereof.

203. The compound of embodiment 1, wherein the compound is (S)-3-((S)-2-(5-(2-(dimethylamino)ethyl)-2-oxo-4-(trifluoromethyl)pyridin-1(2H)-yl)-4-methylpentanamido)-3-(4-fluoro-2',4',5,6'-tetramethyl-[1,1'-biphenyl]-3-yl)propanoic acid, or a pharmaceutically acceptable salt thereof.

204. The compound of embodiment 1, wherein the compound is (S)-3-(4,4'-difluoro-2',5,6'-trimethyl-[1,1'-biphenyl]-3-yl)-3-((S)-2-(3-(difluoromethyl)-5-(2-(dimethylamino)ethyl)-2-oxopyridin-1(2H)-yl)-4-methylpentanamido)propanoic acid, or a pharmaceutically acceptable salt thereof.

205. The compound of embodiment 1, wherein the compound is (S)-3-((S)-2-(5-(2-(dimethylamino)ethyl)-4-methyl-2-oxopyridin-1(2H)-yl)-5-methylhexanamido)-3-(4-fluoro-2',5,6'-trimethyl-[1,1'-biphenyl]-3-yl)propanoic Acid, or a pharmaceutically acceptable salt thereof.

206. The compound of embodiment 1, wherein the compound is (S)-3-(4-fluoro-2',5,6'-trimethyl-[1,1'-biphenyl]-3-yl)-3-((S)-2-(3-fluoro-5-(2-(3-fluoroazetidine-1-yl)ethyl)-2-oxopyridin-1(2H)-yl)-4-methylpentanamido)propanoic acid, or a pharmaceutically acceptable salt thereof.

207. The compound of embodiment 1, wherein the compound is (S)-3-(4-fluoro-2',5,6'-trimethyl-[1,1'-biphenyl]-3-yl)-3-((S)-2-(3-fluoro-5-(2-((R)-3-fluoropyrrolidin-1-yl)ethyl)-2-oxopyridin-1(2H)-yl)-4-methylpentanamido)propanoic acid, or a pharmaceutically acceptable salt thereof.

208. The compound of embodiment 1, wherein the compound is (S)-3-(5-chloro-4-fluoro-2',6'-dimethyl-[1,1'-biphenyl]-3-yl)-3-((S)-2-(5-(2-(3-methoxyazetidin-1-yl)ethyl)-2-oxo-4-(trifluoromethyl)pyridin-1(2H)-yl)-4-methylpentanamido)propanoic acid, or a pharmaceutically acceptable salt thereof.

209. A pharmaceutical composition, comprising a compound of any one of embodiments 1-208; and a pharmaceutically acceptable excipient.

210. A method of inhibiting $\alpha_4\beta_7$ integrin in a cell, comprising contacting the cell with a compound of any one of embodiments 1-208 under conditions effective to reduce the adhesion of the cell to MAdCAM-1.

211. A method of reducing the adhesion of a cell comprising an $\alpha_4\beta_7$ integrin to MAdCAM-1, the method comprising contacting the cell with a compound of any one of embodiments 1-208 under conditions effective to reduce the adhesion of the cell to MAdCAM-1.

212. A method of treating inflammatory bowel disease, ulcerative colitis, or Crohn's disease, comprising administering to a subject in need thereof a therapeutically effective amount of a compound of any one of embodiments 1-208

In some embodiments, compounds of the invention can be a compound of Formula (I):

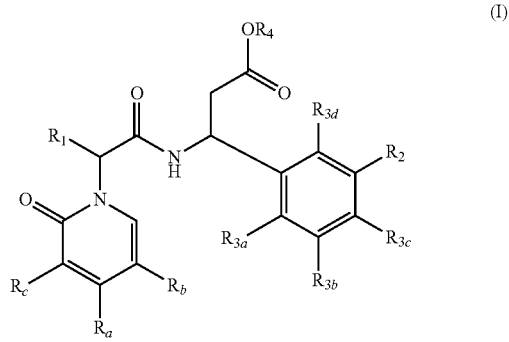

wherein $R_a$, $R_b$, and $R_c$ are independently selected from the group consisting of H, Me, halide, $CF_3$, $C(H)F_2$, $C(F)H_2$, and —$(C_1-C_5)$alkylene-N—$(R_x)(R_y)$; provided that at least one of $R_a$, $R_b$, and $R_c$ is —$(C_1-C_5)$alkylene-N—$(R_x)(R_y)$;

$R_x$ and $R_y$ are independently selected from the group consisting of H and substituted or unsubstituted $(C_1-C_6)$-alkyl; or $R_x$ and $R_y$ taken together with the N to which they are attached form a 4-6 membered ring;

$R_1$ is methyl, ethyl, n-propyl, iso-propyl, n-butyl, iso-butyl, sec-butyl, or t-butyl;

$R_2$ is

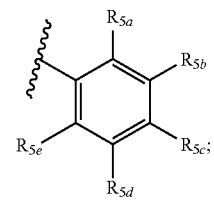

$R_{3a}$ and $R_{3b}$ are independently selected from the group consisting of halide, substituted or unsubstituted $(C_1-C_5)$-alkyl, substituted or unsubstituted $(C_3-C_6)$-cycloalkyl, substituted or unsubstituted $(C_1-C_4)$-alkoxy, $CF_3$, $C(H)F_2$, and $C(F)H_2$;

$R_{3c}$, and $R_{3d}$ are H;

$R_4$ is H;

$R_{5a}$ is methyl;

$R_{5b}$ is selected from the group consisting of H, CN, halide, $CF_3$, $C(H)F_2$, $C(F)H_2$, substituted or unsubstituted $(C_1-C_5)$-alkyl, substituted or unsubstituted $(C_3-C_6)$-cycloalkyl, substituted or unsubstituted 3-6 membered heterocycloalkyl, hydroxyl, and $(C_1-C_4)$-alkoxy;

$R_{5c}$ is methyl;

$R_{5d}$ is H;

$R_{5e}$ is selected from the group consisting of H, CN, halide, $CF_3$, $C(H)F_2$, $C(F)H_2$, substituted or unsubstituted $(C_3-C_6)$-cycloalkyl, substituted or unsubstituted $(C_1-C_5)$-alkyl, hydroxyl, and $(C_1-C_4)$-alkoxy;

or a pharmaceutically acceptable salt thereof.

In some embodiments, compounds of the invention can be a compound of Formula (Ia):

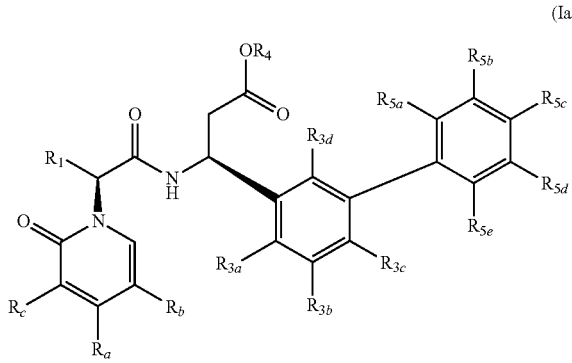
(Ia)

wherein $R_a$, $R_b$, and $R_c$ are independently selected from the group consisting of H, Me, halide, $CF_3$, $C(H)F_2$, $C(F)H_2$, and —($C_1$-$C_5$)alkylene-N—($R_x$)($R_y$); provided that at least one of $R_a$, $R_b$, and Re is —($C_1$-$C_5$)alkylene-N—($R_x$)($R_y$);

at least one of $R_a$, $R_b$, and $R_c$ is —($C_1$-$C_3$)alkylene-N($R_x$)($R_y$);

$R_x$ and $R_y$ are independently selected from the group consisting of H and methyl; or $R_x$ and $R_y$ taken together with the N to which they are attached form a substituted or unsubstituted 4-6 membered ring;

$R_1$ is substituted or unsubstituted ($C_1$-$C_6$)-alkyl, substituted or unsubstituted ($C_1$-$C_4$)-alkylene-($C_3$-$C_6$)-cycloalkyl, or substituted or unsubstituted ($C_1$-$C_4$)-alkylene-($C_1$-$C_4$)-alkoxy;

$R_2$ is

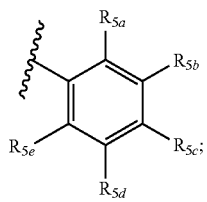

$R_{3a}$, and $R_{3b}$ are each independently selected from the group consisting of methyl and F, and $R_{3a}$ is halide;

$R_{3c}$, and $R_{3d}$ are H;

$R_4$ is H, or substituted or unsubstituted ($C_1$-$C_4$)-alkyl;

$R_{5a}$ is selected from the group consisting of H, CN, halide, $CF_3$, $C(H)F_2$, $C(F)H_2$, substituted or unsubstituted ($C_3$-$C_6$)-cycloalkyl, substituted or unsubstituted ($C_1$-$C_5$)-alkyl, hydroxyl, and ($C_1$-$C_4$)-alkoxy; and $R_{5b}$, and $R_{5c}$ are independently selected from the group consisting of H, CN, halide, $CF_3$, $C(H)F_2$, $C(F)H_2$, substituted or unsubstituted ($C_1$-$C_5$)-alkyl, substituted or unsubstituted ($C_3$-$C_6$)-cycloalkyl, substituted or unsubstituted 3-6 membered heterocycloalkyl, hydroxyl, and ($C_1$-$C_4$)-alkoxy; and $R_{5d}$ is H;

$R_{5e}$ is methyl;

or a pharmaceutically acceptable salt thereof.

In some embodiments, compounds of the invention can be a compound of Formula (Ic)

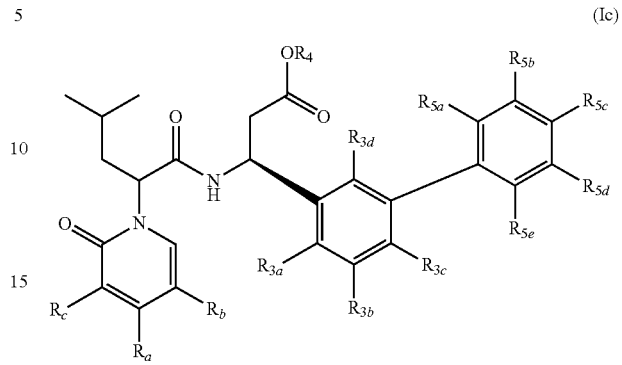
(Ic)

wherein $R_a$, $R_b$, and $R_c$ are independently selected from the group consisting of H, substituted or unsubstituted ($C_1$-$C_5$)-alkyl, halide, $CF_3$, $C(H)F_2$, $C(F)H_2$, substituted or unsubstituted ($C_1$-$C_4$)-alkoxy, —$OCF_3$, and substituted or unsubstituted —($C_1$-$C_5$)alkylene-N—($R_x$)($R_y$); provided that one of $R_a$, $R_b$, and $R_c$ is —($C_1$-$C_5$)alkylene-N—($R_x$)($R_y$);

$R_x$ and $R_y$ are independently selected from the group consisting of H, substituted or unsubstituted ($C_1$-$C_6$)-alkyl, or substituted or unsubstituted ($C_1$-$C_4$)-alkylene-($C_1$-$C_4$)-alkoxy; or $R_x$ and $R_y$ taken together with the N to which they are attached form a substituted or unsubstituted 4-6 membered heterocyclyl ring;

$R_{3a}$ is halide and $R_{3b}$ is selected from the group consisting of H, substituted or unsubstituted ($C_1$-$C_5$)-alkyl, substituted or unsubstituted ($C_3$-$C_6$)-cycloalkyl, substituted or unsubstituted 3-6 membered heterocycloalkyl, —OH, —CN, halide, $CF_3$, $C(H)F_2$, $C(F)H_2$, —($C_1$-$C_4$)-alkoxy, —$OCF_3$, and substituted or unsubstituted ($C_1$-$C_4$)-alkylene-($C_1$-$C_4$)-alkoxy;

$R_{3c}$ is H, substituted or unsubstituted ($C_1$-$C_5$)-alkyl, substituted or unsubstituted ($C_3$-$C_6$)-cycloalkyl, substituted or unsubstituted 3-6 membered heterocycloalkyl, hydroxyl, halide, $CF_3$, $C(H)F_2$, $C(F)H_2$, —($C_1$-$C_4$)-alkoxy, —$OCF_3$— CN, and substituted or unsubstituted ($C_1$-$C_4$)-alkylene-($C_1$-$C_4$)-alkoxy;

$R_{3d}$ is selected from the group consisting of H, substituted or unsubstituted ($C_1$-$C_5$)-alkyl, hydroxyl, halide, and —($C_1$-$C_4$)-alkoxy;

$R_{5a}$, and $R_{5e}$ are independently selected from the group consisting of H, CN, halide, $CF_3$, $C(H)F_2$, $C(F)H_2$, substituted or unsubstituted ($C_1$-$C_5$)-alkyl, hydroxyl, and ($C_1$-$C_4$)-alkoxy; and $R_{5b}$, $R_{5c}$, and $R_{5d}$ are independently selected from the group consisting of H, CN, halide, $CF_3$, $C(H)F_2$, $C(F)H_2$, substituted or unsubstituted ($C_1$-$C_5$)-alkyl, hydroxyl, and ($C_1$-$C_4$)-alkoxy;

or a pharmaceutically acceptable salt thereof.

In some embodiments, compounds of the invention can be a compound (3S)-3-(2-(5-(2-(dimethylamino)ethyl)-2-oxo-4-(trifluoromethyl)pyridin-1(2H)-yl)-4-methylpentanamido)-3-(2-fluoro-3-methyl-5-((S)-2-methylpiperidin-1-yl)phenyl)propanoic acid

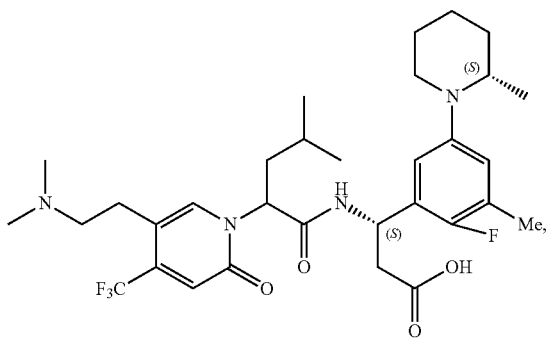

or a pharmaceutically acceptable salt thereof.

In certain embodiments, the invention relates to any one of the aforementioned methods, wherein the subject is a mammal. In certain embodiments, the invention relates to any one of the aforementioned methods, wherein the subject is human.

EXAMPLES

The invention now being generally described, it will be more readily understood by reference to the following examples, which are included merely for purposes of illustration of certain aspects and embodiments of the present invention, and are not intended to limit the invention.

Examples 1-4 describe the synthesis of certain compounds presented in FIG. 1, including compounds of Formula (Ia) and Formula (Ib). Compounds in FIG. 1 can be prepared as a mixture of diastereomeric compounds (e.g., as disclosed in Examples 1-4) having a (3S) configuration (i.e., at the stereocenter beta to the carboxylic acid moiety), and a mixture of diastereomers at the chiral center covalently bound to the pyridone ring nitrogen atom of Formula (I) (e.g., as shown in Formula (Ib)).

In FIG. 1, compounds having greater activity in the fluorescence polarization (FP) assay of Example 5 are shown with the stereochemistry of Formula (Ia). Example 5 describes a fluorescence polarization (FP) assay. Example 6 describes a ligand binding (LB) assay. Example 7 describes a cell adhesion (CA) assay.

Additional Embodiments

In some embodiments, a compound can be selected from one or more of the enumerated embodiments provided below:
1. A compound of Formula (I):

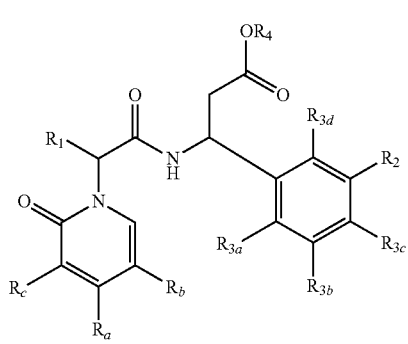

wherein
$R_a$, $R_b$, and $R_c$ are independently selected from the group consisting of H, Me, halide, $CF_3$, $C(H)F_2$, $C(F)H_2$, and —$(C_1-C_5)$alkylene-N—$(R_x)(R_y)$; provided that at least one of $R_a$, $R_b$, and $R_c$ is —$(C_1-C_5)$alkylene-N—$(R_x)(R_y)$;

$R_x$ and $R_y$ are independently selected from the group consisting of H and substituted or unsubstituted $(C_1-C_6)$-alkyl; or $R_x$ and $R_y$ taken together with the N to which they are attached form a 4-6 membered ring;

$R_1$ is substituted or unsubstituted $(C_1-C_6)$-alkyl, substituted or unsubstituted $(C_1-C_4)$-alkylene-$(C_3-C_6)$-cycloalkyl, or substituted or unsubstituted $(C_1-C_4)$-alkylene-$(C_1-C_4)$-alkoxy;

$R_2$ is

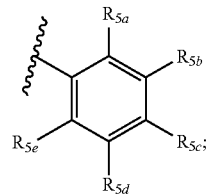

$R_{3a}$ and $R_{3b}$ are independently selected from the group consisting of H, substituted or unsubstituted $(C_1-C_5)$-alkyl, substituted or unsubstituted $(C_3-C_6)$-cycloalkyl, substituted or unsubstituted 3-6 membered heterocycloalkyl, —OH, —CN, halide, $CF_3$, $C(H)F_2$, $C(F)H_2$, —$(C_1-C_4)$-alkoxy, —$OCF_3$, and substituted or unsubstituted $(C_1-C_4)$-alkylene-$(C_1-C_4)$-alkoxy; provided that $R_{3a}$ and $R_{3b}$ are not both H;

$R_{3c}$ and $R_{3d}$ are H;

$R_4$ is H, or substituted or unsubstituted $(C_1-C_4)$-alkyl;

$R_{5a}$ and $R_{5e}$ are independently selected from the group consisting of H, CN, halide, $CF_3$, $C(H)F_2$, $C(F)H_2$, substituted or unsubstituted $(C_3-C_6)$-cycloalkyl, substituted or unsubstituted $(C_1-C_5)$-alkyl, hydroxyl, and $(C_1-C_4)$-alkoxy; and $R_{5b}$, $R_{5c}$, and $R_{5d}$ are independently selected from the group consisting of H, CN, halide, $CF_3$, $C(H)F_2$, $C(F)H_2$, substituted or unsubstituted $(C_1-C_5)$-alkyl, substituted or unsubstituted $(C_3-C_6)$-cycloalkyl, substituted or unsubstituted 3-6 membered heterocycloalkyl, hydroxyl, and $(C_1-C_4)$-alkoxy;

or a pharmaceutically acceptable salt thereof.

2. The compound of embodiment 1, wherein $R_1$ is methyl, ethyl, n-propyl, iso-propyl, n-butyl, iso-butyl, sec-butyl, or t-butyl.

3. The compound of embodiment 2, wherein $R_1$ is iso-butyl.

4. The compound of embodiment 1, wherein $R_1$ is

5. The compound of embodiment 1, wherein $R_1$ is

6. The compound of any one of embodiments 1-5, wherein $R_{3a}$ and $R_{3b}$ are independently selected from the group consisting of halide, substituted or unsubstituted $(C_1-C_5)$- alkyl, substituted or unsubstituted $(C_3-C_6)$-cycloalkyl, substituted or unsubstituted $(C_1-C_4)$-alkoxy, $CF_3$, $C(H)F_2$, and $C(F)H_2$.

7. The compound of embodiment 6, wherein $R_{3a}$ and $R_{3b}$ are independently selected from the group consisting of halide and $(C_1-C_4)$-alkyl.

8. The compound of embodiment 7, wherein halide is Cl or F.

9. The compound of embodiment 7 or 8, wherein $(C_1-C_4)$-alkyl is methyl.

10. The compound of any one of embodiments 1-7, wherein $R_{3a}$ is methyl; and $R_{3b}$ is F.

11. The compound of any one of embodiments 1-7, wherein $R_{3a}$ is F; and $R_{3b}$ is methyl.

12. The compound of any one of embodiments 1-11, wherein $R_4$ is H.

13. The compound of any one of embodiments 1-11, wherein $R_4$ is methyl, ethyl, n-propyl, iso-propyl.

14. The compound of any one of embodiments 1-13, wherein $R_{5a}$ and $R_{5e}$ are independently selected from the group consisting of halide, $CF_3$, $C(H)F_2$, $C(F)H_2$, and substituted or unsubstituted $(C_1-C_4)$-alkyl.

15. The compound of any one of embodiments 1-14, wherein $R_{5a}$ is halide.

16. The compound of embodiment 15, wherein $R_{5a}$ is F or Cl.

17. The compound of any one of embodiments 1-14, wherein $R_{5a}$ is $CF_3$.

18. The compound of any one of embodiments 1-14, wherein $R_{5a}$ is $C(H)F_2$.

19. The compound of any one of embodiments 1-14, wherein $R_{5a}$ is $C(F)H_2$.

20. The compound of any one of embodiments 1-14, wherein $R_{5a}$ is unsubstituted $(C_1-C_4)$-alkyl.

21. The compound of embodiment 20, wherein $R_{5a}$ is methyl.

22. The compound of any one of embodiments 1-14, wherein $R_{5a}$ is substituted $(C_1-C_5)$-alkyl, substituted with at least one halide.

23. The compound of any one of embodiments 1-14, wherein $R_{5a}$ is unsubstituted $(C_1-C_4)$-alkoxy.

24. The compound of embodiment 23, wherein $R_{5a}$ is OMe.

25. The compound of any one of embodiments 1-24, wherein $R_{5e}$ is halide.

26. The compound of embodiment 25, wherein $R_{5e}$ is F or Cl.

27. The compound of any one of embodiments 1-24, wherein $R_{5e}$ is $CF_3$.

28. The compound of any one of embodiments 1-24, wherein $R_{5e}$ is $C(H)F_2$.

29. The compound of any one of embodiments 1-24, wherein $R_{5e}$ is $C(F)H_2$.

30. The compound of any one of embodiments 1-24, wherein $R_{5e}$ is unsubstituted $(C_1-C_4)$-alkyl.

31. The compound of embodiment 30, wherein $R_{5e}$ is methyl.

32. The compound of any one of embodiments 1-24, wherein $R_{5e}$ is substituted $(C_1-C_5)$-alkyl, substituted with at least one halide.

33. The compound of any one of embodiments 1-24, wherein $R_{5e}$ is unsubstituted $(C_1-C_4)$-alkoxy.

34. The compound of embodiment 33, wherein $R_{5e}$ is OMe.

35. The compound of any one of embodiments 1-34, wherein $R_{5b}$, $R_{5c}$, and $R_{5d}$ are independently selected from the group consisting of H, halide, $CF_3$, $C(H)F_2$, $C(F)H_2$, substituted or unsubstituted $(C_1-C_5)$-alkyl, and substituted or unsubstituted $(C_1-C_4)$-alkoxy.

36. The compound of any one of embodiments 1-35, wherein $R_{5b}$ is H.

37. The compound of any one of embodiments 1-35, wherein $R_{5b}$ is halide.

38. The compound of embodiment 37, wherein $R_{5b}$ is Cl or F.

39. The compound of any one of embodiments 1-35, wherein $R_{5b}$ is $CF_3$.

40. The compound of any one of embodiments 1-35, wherein $R_{5b}$ is $C(H)F_2$.

41. The compound of any one of embodiments 1-35, wherein $R_{5b}$ is $C(F)H_2$.

42. The compound of any one of embodiments 1-35, wherein $R_{5b}$ is unsubstituted $(C_1-C_4)$-alkyl.

43. The compound of embodiment 37, wherein $R_{5b}$ is methyl.

44. The compound of any one of embodiments 1-35, wherein $R_{5b}$ is unsubstituted $(C_1-C_4)$-alkoxy.

45. The compound of embodiment 44, wherein $R_{5b}$ is OMe.

46. The compound of any one of embodiments 1-35, wherein $R_{5b}$ is unsubstituted $(C_3-C_6)$-cycloalkyl.

47. The compound of embodiment 46, wherein $R_{5b}$ is cyclopropyl.

48. The compound of any one of embodiments 1-47, wherein $R_{5c}$ is H.

49. The compound of any one of embodiments 1-47, wherein $R_{5c}$ is halide.

50. The compound of embodiment 49, wherein $R_{5c}$ is Cl or F.

51. The compound of any one of embodiments 1-47, wherein $R_{5c}$ is $CF_3$.

52. The compound of any one of embodiments 1-47, wherein $R_{5c}$ is $C(H)F_2$.

53. The compound of any one of embodiments 1-47, wherein $R_{5c}$ is $C(F)H_2$.

54. The compound of any one of embodiments 1-47, wherein $R_{5c}$ is unsubstituted $(C_1-C_4)$-alkyl.

55. The compound of embodiment 54, wherein $R_{5c}$ is methyl.

56. The compound of any one of embodiments 1-47, wherein $R_{5c}$ is unsubstituted $(C_1-C_4)$-alkoxy.

57. The compound of embodiment 56, wherein $R_{5c}$ is OMe.

58. The compound of any one of embodiments 1-47, wherein $R_{5c}$ is unsubstituted $(C_3-C_6)$-cycloalkyl.

59. The compound of embodiment 58, wherein $R_{5b}$ is cyclopropyl.

60. The compound of any one of embodiments 1-59, wherein $R_{5d}$ is H.

61. The compound of any one of embodiments 1-59, wherein $R_{5d}$ is halide.

62. The compound of embodiment 61, wherein $R_{5d}$ is Cl or F.

63. The compound of any one of embodiments 1-59, wherein $R_{5d}$ is $CF_3$.

64. The compound of any one of embodiments 1-59, wherein $R_{5d}$ is $C(H)F_2$.

65. The compound of any one of embodiments 1-59, wherein $R_{5d}$ is $C(F)H_2$.

66. The compound of any one of embodiments 1-59, wherein $R_{5d}$ is unsubstituted $(C_1-C_4)$-alkyl.

67. The compound of embodiment 66, wherein $R_{5d}$ is methyl.

68. The compound of any one of embodiments 1-67, wherein $R_{5d}$ is unsubstituted $(C_1-C_4)$-alkoxy.

69. The compound of embodiment 68, wherein $R_{5d}$ is OMe.

70. The compound of any one of embodiments 1-67, wherein $R_{5d}$ is unsubstituted $(C_3-C_6)$-cycloalkyl.

71. The compound of embodiment 70, wherein $R_{5d}$ is cyclopropyl.
72. The compound of any one of embodiments 1-35, wherein $R_{5b}$, and $R_{5d}$ are each H.
73. The compound of any one of embodiments 1-72, wherein $R_a$ is H.
74. The compound of any one of embodiments 1-72, wherein $R_a$ is Me.
75. The compound of any one of embodiments 1-72, wherein $R_a$ is halide.
76. The compound of embodiment 75, wherein $R_a$ is Cl or F.
77. The compound of any one of embodiments 1-72, wherein $R_a$ is $CF_3$.
78. The compound of any one of embodiments 1-72, wherein $R_a$ is $C(H)F_2$.
79. The compound of any one of embodiments 1-72, wherein $R_a$ is $C(F)H_2$.
80. The compound of any one of embodiments 1-72, wherein $R_a$ is unsubstituted —$(C_1$-$C_3)$alkylene-N—$(R_x)(R_y)$.
81. The compound of any one of embodiments 1-72, wherein $R_a$ is substituted —$(C_1$-$C_3)$alkylene-N—$(R_x)(R_y)$, substituted with F or OMe.
82. The compound of any one of embodiments 1-81, wherein $R_b$ is H.
83. The compound of any one of embodiments 1-81, wherein $R_b$ is Me.
84. The compound of any one of embodiments 1-81, wherein $R_b$ is halide.
85. The compound of embodiment 84, wherein $R_b$ is Cl or F.
86. The compound of any one of embodiments 1-81, wherein $R_b$ is $CF_3$.
87. The compound of any one of embodiments 1-81, wherein $R_b$ is $C(H)F_2$.
88. The compound of any one of embodiments 1-81, wherein $R_b$ is $C(F)H_2$.
89. The compound of any one of embodiments 1-81, wherein $R_b$ is unsubstituted —$(C_1$-$C_3)$alkylene-N—$(R_x)(R_y)$.
90. The compound of any one of embodiments 1-81, wherein $R_b$ is substituted —$(C_1$-$C_3)$alkylene-N—$(R_x)(R_y)$, substituted with F or OMe.
91. The compound of any one of embodiments 1-90, wherein $R_c$ is H.
92. The compound of any one of embodiments 1-90, wherein $R_c$ is Me.
93. The compound of any one of embodiments 1-90, wherein $R_c$ is halide.
94. The compound of embodiment 93, wherein $R_c$ is Cl or F.
95. The compound of any one of embodiments 1-90, wherein $R_c$ is $CF_3$.
96. The compound of any one of embodiments 1-90, wherein $R_c$ is $C(H)F_2$.
97. The compound of any one of embodiments 1-90, wherein $R_c$ is $C(F)H_2$.
98. The compound of any one of embodiments 1-90, wherein $R_c$ is unsubstituted —$(C_1$-$C_3)$alkylene-N—$(R_x)(R_y)$.
99. The compound of any one of embodiments 1-90, wherein $R_c$ is substituted —$(C_1$-$C_3)$alkylene-N—$(R_x)(R_y)$, substituted with F or OMe.
100. The compound of any one of embodiments 1-99, wherein $R_x$ is H.
101. The compound of any one of embodiments 1-99, wherein $R_x$ is unsubstituted $(C_1$-$C_6)$-alkyl.
102. The compound of any one of embodiments 1-100, wherein $R_y$ is H.
103. The compound of any one of embodiments 1-100, wherein $R_y$ is unsubstituted $(C_1$-$C_6)$-alkyl.
104. The compound of any one of embodiments 1-72, 80-81, 89-90, and 98-99, wherein Rx and $R_y$ taken together with the N to which they are attached form a unsubstituted 4-6 membered ring.
105. The compound of any one of embodiments 1-72, 80-81, 89-90, and 98-99, wherein Rx and $R_y$ taken together with the N to which they are attached form a substituted 4-6 membered ring, substituted with at least one halide, substituted or unsubstituted $(C_1$-$C_4)$ alkyl, or OMe.
106. The compound of embodiment 104 or 105, wherein the 4-6 membered ring is a 3-6 membered heterocycloalkyl.
107. The compound of embodiment 104 or 105, wherein the 4-6 membered ring is a 4-5 membered heterocycloalkyl.
108. The compound of embodiment 1, wherein the compound is a compound of Formula (Ia):

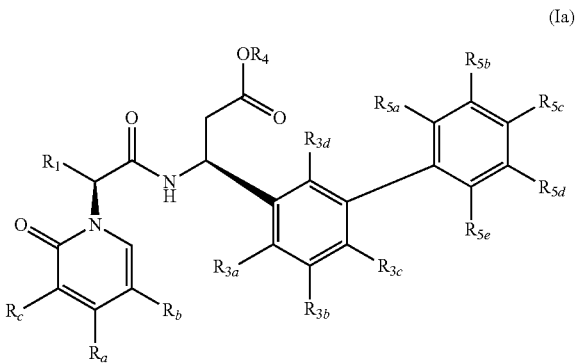

wherein
at least one of $R_a$, $R_b$, and $R_c$ is —$(C_1$-$C_3)$alkylene-N$(R_x)(R_y)$;
$R_x$ and $R_y$ are independently selected from the group consisting of H and methyl; or $R_x$ and $R_y$ taken together with the N to which they are attached form a substituted or unsubstituted 4-6 membered ring; and
$R_{3a}$, and $R_{3b}$ are each independently selected from the group consisting of methyl and F.
109. The compound of embodiment 108, wherein $R_{5a}$, and $R_{5e}$ are independently unsubstituted $(C_1$-$C_4)$ alkyl.
110. The compound of embodiment 108 or 109, wherein $R_b$ is unsubstituted —$(C_1$-$C_3)$alkylene-N$(R_x)(R_y)$.
111. The compound of embodiment 1 or 108, wherein $R_a$ is selected from the group consisting of H, $C(H)F_2$, $CF_3$, and Me.
112. The compound of embodiment 1 or 108, wherein $R_b$ is selected from the group consisting of

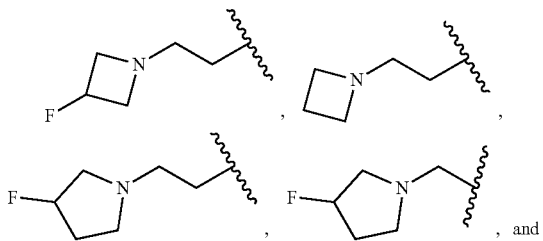

, and

-continued

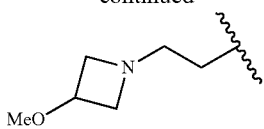

113. The compound of embodiment 1 or 108, wherein $R_b$ is selected from the group consisting of

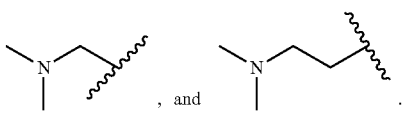

, and

114. The compound of embodiment 1 or 108, wherein $R_c$ is H or F.
115. The compound of any one of embodiments 1 and 108-114, wherein $R_1$ is selected from the group consisting of

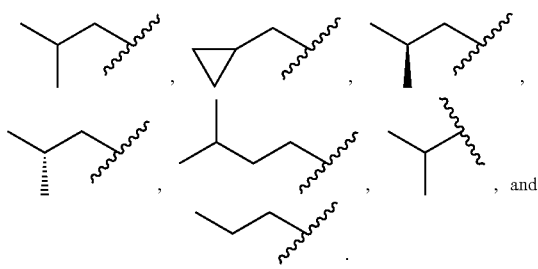

, and

116. The compound of any one of embodiments 108-115, wherein $R_{5a}$ is $CF_3$.
117. The compound of any one of embodiments 108-115, wherein $R_{5a}$ is $C(H)F_2$.
118. The compound of any one of embodiments 108-115, wherein $R_{5a}$ is $C(F)H_2$.
119. The compound of any one of embodiments 108-115, wherein $R_{5a}$ is methyl.
120. The compound of any one of embodiments 108-115, wherein $R_{5a}$ is OMe.
121. The compound of any one of embodiments 108-115, wherein $R_{5a}$ is F or Cl.
122. The compound of any one of embodiments 108-121, wherein $R_{5b}$ is H.
123. The compound of any one of embodiments 108-121, wherein $R_{5b}$ is $CF_3$.
124. The compound of any one of embodiments 108-121, wherein $R_{5b}$ is $C(H)F_2$.
125. The compound of any one of embodiments 108-121, wherein $R_{5b}$ is $C(F)H_2$.
126. The compound of any one of embodiments 108-121, wherein $R_{5b}$ is methyl.
127. The compound of any one of embodiments 108-121, wherein $R_{5b}$ is OMe.
128. The compound of any one of embodiments 108-121, wherein $R_{5b}$ is F or Cl.
129. The compound of any one of embodiments 108-128, wherein $R_{5c}$ is H.
130. The compound of any one of embodiments 108-128, wherein $R_{5c}$ is $CF_3$.
131. The compound of any one of embodiments 108-128, wherein $R_{5c}$ is $C(H)F_2$.
132. The compound of any one of embodiments 108-128, wherein $R_{5c}$ is $C(F)H_2$.
133. The compound of any one of embodiments 108-128, wherein $R_{5c}$ is methyl.
134. The compound of any one of embodiments 108-128, wherein $R_{5c}$ is OMe.
135. The compound of any one of embodiments 108-128, wherein $R_{5c}$ is F or Cl.
136. The compound of any one of embodiments 108-135, wherein $R_{5d}$ is H.
137. The compound of any one of embodiments 108-135, wherein $R_{5d}$ is $CF_3$.
138. The compound of any one of embodiments 108-135, wherein $R_{5d}$ is $C(H)F_2$.
139. The compound of any one of embodiments 108-135, wherein $R_{5d}$ is $C(F)H_2$.
140. The compound of any one of embodiments 108-135, wherein $R_{5d}$ is methyl.
141. The compound of any one of embodiments 108-135, wherein $R_{5d}$ is OMe.
142. The compound of any one of embodiments 108-135, wherein $R_{5d}$ is F or Cl.
143. The compound of any one of embodiments 108-142, wherein $R_{5e}$ is $CF_3$.
144. The compound of any one of embodiments 108-142, wherein $R_{5e}$ is $C(H)F_2$.
145. The compound of any one of embodiments 108-142, wherein $R_{5e}$ is $C(F)H_2$.
146. The compound of any one of embodiments 108-142, wherein $R_{5e}$ is methyl.
147. The compound of any one of embodiments 108-142, wherein $R_{5e}$ is OMe.
148. The compound of any one of embodiments 108-142, wherein $R_{5e}$ is F or Cl.
149. The compound of any one of embodiments 1, and 108-121, wherein at least one of $R_{5b}$, $R_{5c}$, and $R_{5d}$ is H.
150. The compound of any one of embodiments 1, and 108-121, wherein at least two of $R_{5b}$, $R_{5c}$, and $R_{5d}$ is H.
151. The compound of any one of embodiments 1, and 108-121, wherein $R_{5b}$, $R_{5c}$, and $R_{5d}$ are H.
152. The compound of any one of embodiments 1, and 108-151, wherein $R_{3a}$ is H.
153. The compound of any one of embodiments 1, and 108-151, wherein $R_{3a}$ is methyl.
154. The compound of any one of embodiments 1, and 108-151, wherein $R_{3a}$ is halide.
155. The compound of any one of embodiments 1, and 108-151, wherein $R_{3a}$ is $CF_3$.
156. The compound of any one of embodiments 1, and 108-151, wherein $R_{3a}$ is $C(H)F_2$.
157. The compound of any one of embodiments 1, and 108-151, wherein $R_{3a}$ is $C(F)H_2$.
158. The compound of any one of embodiments 1, and 108-151, wherein $R_{3a}$ is OMe.
159. The compound of any one of embodiments 1, and 108-158, wherein $R_{3b}$ is H.
160. The compound of any one of embodiments 1, and 108-158, wherein $R_{3b}$ is methyl.
161. The compound of any one of embodiments 1, and 108-158, wherein $R_{3b}$ is halide.
162. The compound of any one of embodiments 1, and 108-158, wherein $R_{3b}$ is $CF_3$.
163. The compound of any one of embodiments 1, and 108-158, wherein $R_{3b}$ is $C(H)F_2$.
164. The compound of any one of embodiments 1, and 108-158, wherein $R_{3b}$ is $C(F)H_2$.

165. The compound of any one of embodiments 1, and 108-158, wherein $R_{3b}$ is OMe.
166. The compound of any one of embodiments 1, and 108-158, wherein $R_{3b}$ is $OCF_3$.
167. The compound of any one of embodiments 1, and 108-158, wherein $R_{3b}$ is cyclopropyl.
168. The compound of any one of embodiments 108-151, wherein $R_{3a}$ is methyl and $R_{3b}$ is F.
169. The compound of any one of embodiments 108-151, wherein $R_{3a}$ is F and $R_{3b}$ is methyl.
170. The compound of embodiment 1, wherein the compound is selected from any one of the compounds of FIG. 1, or an enantiomer thereof.
171. The compound of embodiment 1, wherein the compound is a compound of Formula (Ic)

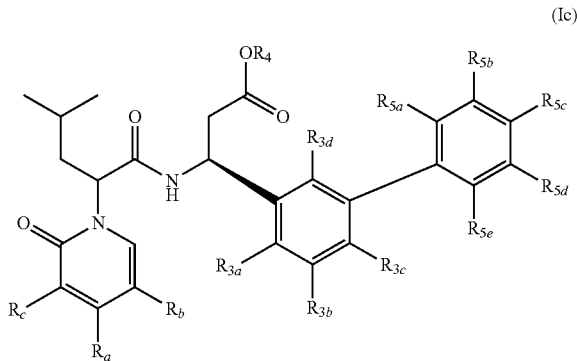

(Ic)

or a pharmaceutically acceptable salt thereof, wherein $R_a$, $R_b$, and $R_c$ are independently selected from the group consisting of H, substituted or unsubstituted ($C_1$-$C_5$)-alkyl, halide, $CF_3$, $C(H)F_2$, $C(F)H_2$, substituted or unsubstituted ($C_1$-$C_4$)-alkoxy, —$OCF_3$, and substituted or unsubstituted —($C_1$-$C_5$)alkylene-N—($R_x$)($R_y$); provided that one of $R_a$, $R_b$, and $R_c$ is —($C_1$-$C_5$)alkylene-N—($R_x$)($R_y$);

$R_x$ and $R_y$ are independently selected from the group consisting of H, substituted or unsubstituted ($C_1$-$C_6$)-alkyl, or substituted or unsubstituted ($C_1$-$C_4$)-alkylene-($C_1$-$C_4$)-alkoxy; or $R_x$ and $R_y$ taken together with the N to which they are attached form a substituted or unsubstituted 4-6 membered heterocyclyl ring;

$R_{3a}$ and $R_{3b}$ are independently selected from the group consisting of H, substituted or unsubstituted ($C_1$-$C_5$)-alkyl, substituted or unsubstituted ($C_3$-$C_6$)-cycloalkyl, substituted or unsubstituted 3-6 membered heterocycloalkyl, —OH, —CN, halide, $CF_3$, $C(H)F_2$, $C(F)H_2$, —($C_1$-$C_4$)-alkoxy, —$OCF_3$, and substituted or unsubstituted ($C_1$-$C_4$)-alkylene-($C_1$-$C_4$)-alkoxy; provided that $R_{3a}$ and $R_{3b}$ are not both H;

$R_{3c}$ is selected from the group consisting of H, substituted or unsubstituted ($C_1$-$C_5$)-alkyl, substituted or unsubstituted ($C_3$-$C_6$)-cycloalkyl, substituted or unsubstituted 3-6 membered heterocycloalkyl, hydroxyl, halide, $CF_3$, $C(H)F_2$, $C(F)H_2$, —($C_1$-$C_4$)-alkoxy, —$OCF_3$—CN, and substituted or unsubstituted ($C_1$-$C_4$)-alkylene-($C_1$-$C_4$)-alkoxy;

$R_{3d}$ is selected from the group consisting of H, substituted or unsubstituted ($C_1$-$C_5$)-alkyl, hydroxyl, halide, and —($C_1$-$C_4$)-alkoxy;

$R_{5a}$, and $R_{5e}$ are independently selected from the group consisting of H, CN, halide, $CF_3$, $C(H)F_2$, $C(F)H_2$, substituted or unsubstituted ($C_1$-$C_5$)-alkyl, hydroxyl, and ($C_1$-$C_4$)-alkoxy; and $R_{5b}$, $R_{5c}$, and $R_{5d}$ are independently selected from the group consisting of H, CN, halide, $CF_3$, $C(H)F_2$, $C(F)H_2$, substituted or unsubstituted ($C_1$-$C_5$)-alkyl, hydroxyl, and ($C_1$-$C_4$)-alkoxy;

or a pharmaceutically acceptable salt thereof.

172. A compound selected from the group consisting of:

(3S)-3-(4,5-difluoro-2',6'-dimethylbiphenyl-3-yl)-3-(2-(5-(2-(3-fluoroazetidine-1-yl)ethyl)-4-methyl-2-oxopyridin-1(2H)-yl)-4-methylpentanamido)propanoic acid;

(3S)-3-(2-(5-(2-(azetidin-1-yl)ethyl)-2-oxo-4-(trifluoromethyl)pyridin-1(2H)-yl)-4-methylpentanamido)-3-(4-fluoro-2',6'-dimethyl-5-(trifluoromethyl)biphenyl-3-yl) propanoic Acid;

(3S)-3-(2-(5-(2-(azetidin-1-yl)ethyl)-2-oxo-4-(trifluoromethyl)pyridin-1(2H)-yl)-4-methylpentanamido)-3-(3',4-difluoro-2',5',6'-trimethyl-[1,1'-biphenyl]-3-yl)propanoic Acid;

(3S)-3-(2-(5-(2-(azetidin-1-yl)ethyl)-2-oxo-4-(trifluoromethyl)pyridin-1(2H)-yl)-4-methylpentanamido)-3-(4-fluoro-3'-methoxy-2',5',6'-trimethyl-[1,1'-biphenyl]-3-yl) propanoic acid;

(3S)-3-(4,4'-difluoro-2',5',6'-trimethyl-[1,1'-biphenyl]-3-yl)-3-(2-(5-(2-(dimethylamino)ethyl)-2-oxo-4-(trifluoromethyl)pyridin-1(2H)-yl)-4-methylpentanamido)propanoic acid;

(3S)-3-(5-chloro-4-fluoro-2',6'-dimethyl-[1,1'-biphenyl]-3-yl)-3-(2-(5-(2-(3-methoxyazetidin-1-yl)ethyl)-2-oxo-4-(trifluoromethyl)pyridin-1(2H)-yl)-4-methylpentanamido)propanoic acid;

(3S)-3-(2-(5-(2-(dimethylamino)ethyl)-2-oxo-4-(trifluoromethyl)pyridin-1(2H)-yl)-4-methylpentanamido)-3-(4-fluoro-2',4',5',6'-tetramethylbiphenyl-3-yl)propanoic Acid;

(3S)-3-(4,4'-difluoro-2',5',6'-trimethyl-[1,1'-biphenyl]-3-yl)-3-(2-(3-(difluoromethyl)-5-(2-(dimethylamino)ethyl)-2-oxopyridin-1(2H)-yl)-4-methylpentanamido)propanoic acid;

(3S)-3-(2-(5-(2-(dimethylamino)ethyl)-4-methyl-2-oxopyridin-1(2H)-yl)-5-methylhexanamido)-3-(4-fluoro-2',5',6'-trimethylbiphenyl-3-yl)propanoic Acid;

(3S)-3-(4-fluoro-2',5',6'-trimethyl-[1,1'-biphenyl]-3-yl)-3-(2-(3-fluoro-5-(2-(3-fluoroazetidine-1-yl)ethyl)-2-oxopyridin-1(2H)-yl)-4-methylpentanamido)propanoic acid;

(3S)-3-(4-fluoro-2',5',6'-trimethyl-[1,1'-biphenyl]-3-yl)-3-(2-(3-fluoro-5-(2-((R)-3-fluoropyrrolidin-1-yl)ethyl)-2-oxopyridin-1(2H)-yl)-4-methylpentanamido)propanoic acid; and (3S)-3-(5-chloro-4-fluoro-2',6'-dimethyl-[1,1'-biphenyl]-3-yl)-3-(2-(5-(2-(3-methoxyazetidin-1-yl)ethyl)-2-oxo-4-(trifluoromethyl)pyridin-1(2H)-yl)-4-methylpentanamido)propanoic acid, or a pharmaceutically acceptable salt thereof.

173. The compound of embodiment 1, wherein the compound is the compound:

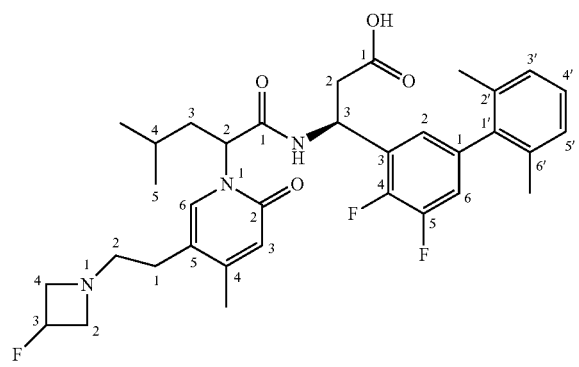 [SMILES: Cc1cc(=O)n(C(CC(C)C)C(=O)N[C@@H](CC(=O)O)c2cc(-c3c(C)cccc3C)cc(F)c2F)cc1CCN1CC(F)C1]

or a pharmaceutically acceptable salt thereof.

174. The compound of embodiment 1, wherein the compound is the compound:

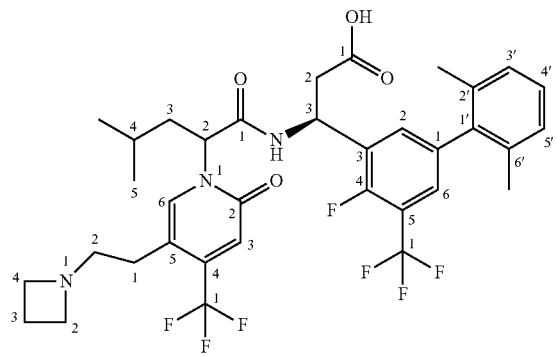 [SMILES: Cc1cccc(C)c1-c1cc([C@H](CC(=O)O)NC(=O)C(CC(C)C)n2cc(CCN3CCC3)c(C(F)(F)F)cc2=O)c(F)c(C(F)(F)F)c1]

or a pharmaceutically acceptable salt thereof.

175. The compound of embodiment 1, wherein the compound is the compound:

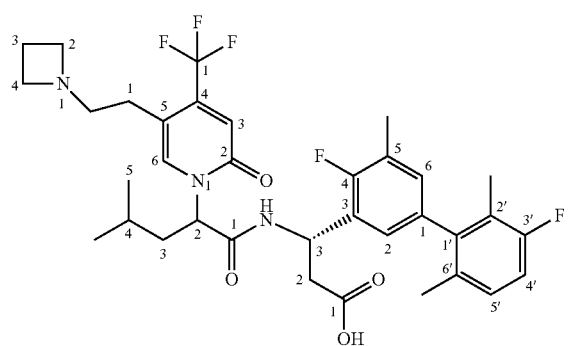

or a pharmaceutically acceptable salt thereof.

176. The compound of embodiment 1, wherein the compound is the compound:

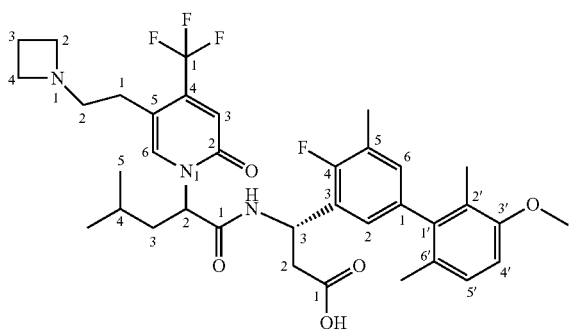

or a pharmaceutically acceptable salt thereof.

177. The compound of embodiment 1, wherein the compound is the compound:

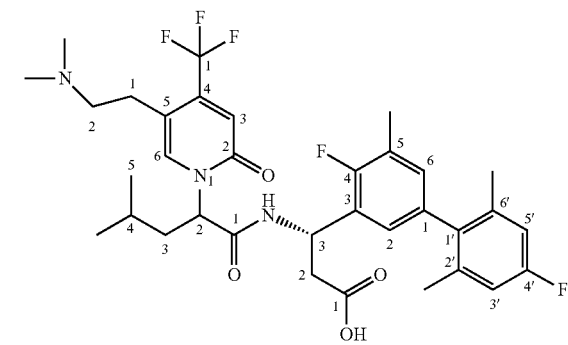

or a pharmaceutically acceptable salt thereof.

178. The compound of embodiment 1, wherein the compound is the compound:

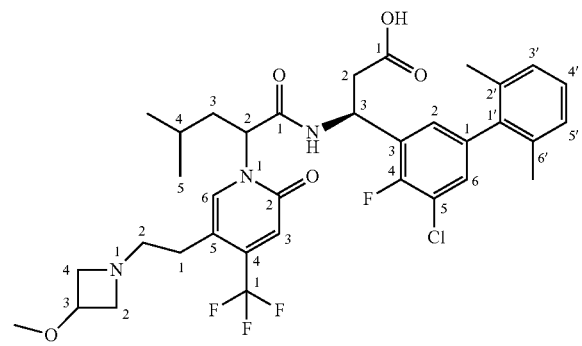 [SMILES: COC1CN(CCc2cn(C(CC(C)C)C(=O)N[C@@H](CC(=O)O)c3cc(-c4c(C)cccc4C)cc(Cl)c3F)c(=O)cc2C(F)(F)F)C1]

or a pharmaceutically acceptable salt thereof.

179. The compound of embodiment 1, wherein the compound is the compound:

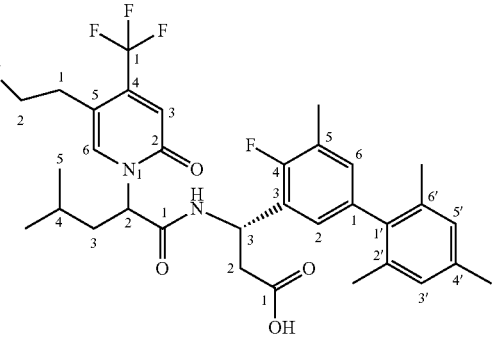

or a pharmaceutically acceptable salt thereof.

180. The compound of embodiment 1, wherein the compound is the compound:

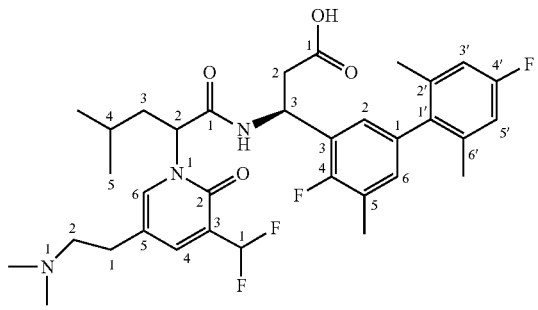 [SMILES: Cc1cc(-c2c(C)cc(F)cc2C)cc([C@H](CC(=O)O)NC(=O)C(CC(C)C)n2cc(CCN(C)C)cc(C(F)F)c2=O)c1F]

or a pharmaceutically acceptable salt thereof.

181. The compound of embodiment 1, wherein the compound is the compound:

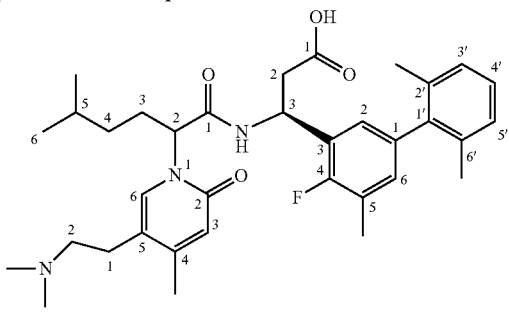

or a pharmaceutically acceptable salt thereof.

182. The compound of embodiment 1, wherein the compound is the compound:

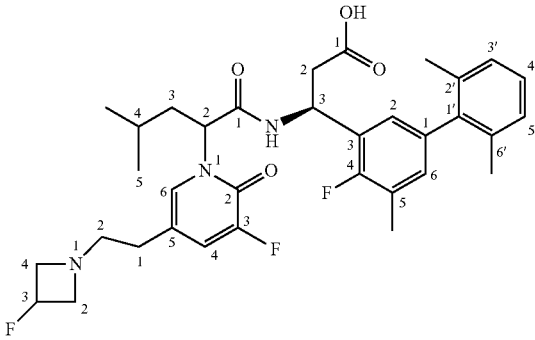 [SMILES: Cc1cc(-c2c(C)cccc2C)cc([C@H](CC(=O)O)NC(=O)C(CC(C)C)n2cc(CCN3CC(F)C3)cc(F)c2=O)c1F]

or a pharmaceutically acceptable salt thereof.

183. The compound of embodiment 1, wherein the compound is the compound:

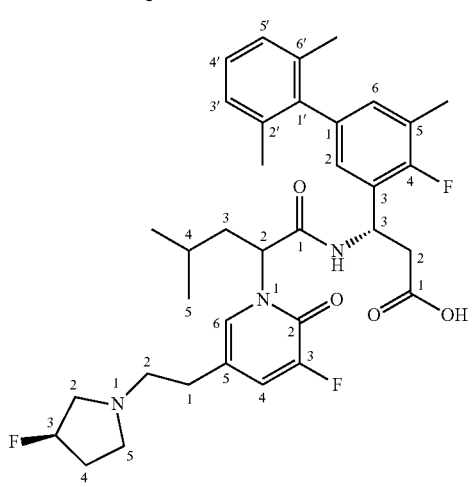

or a pharmaceutically acceptable salt thereof.

184. The compound of embodiment 1, wherein the compound is the compound:

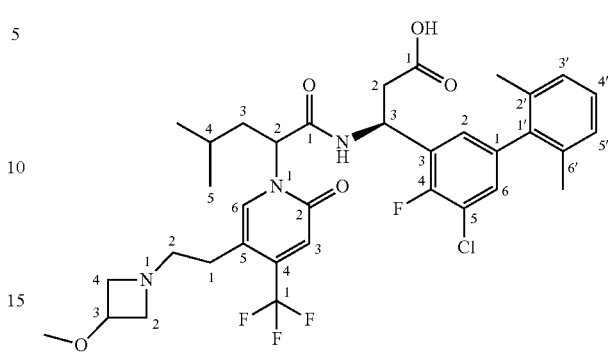

or a pharmaceutically acceptable salt thereof.

185. The compound of embodiment 1, wherein the compound is (3S)-3-(4,5-difluoro-2',6'-dimethylbiphenyl-3-yl)-3-(2-(5-(2-(3-fluoroazetidine-1-yl)ethyl)-4-methyl-2-oxopyridin-1(2H)-yl)-4-methylpentanamido)propanoic acid, or a pharmaceutically acceptable salt thereof.

186. The compound of embodiment 1, wherein the compound is (3S)-3-(2-(5-(2-(azetidin-1-yl)ethyl)-2-oxo-4-(trifluoromethyl)pyridin-1(2H)-yl)-4-methylpentanamido)-3-(4-fluoro-2',6'-dimethyl-5-(trifluoromethyl) biphenyl-3-yl)propanoic Acid, or a pharmaceutically acceptable salt thereof.

187. The compound of embodiment 1, wherein the compound is (3S)-3-(2-(5-(2-(azetidin-1-yl)ethyl)-2-oxo-4-(trifluoromethyl)pyridin-1(2H)-yl)-4-methylpentanamido)-3-(3',4-difluoro-2',5,6'-trimethyl-[1,1'-biphenyl]-3-yl)propanoic Acid, or a pharmaceutically acceptable salt thereof.

188. The compound of embodiment 1, wherein the compound is (3S)-3-(2-(5-(2-(azetidin-1-yl)ethyl)-2-oxo-4-(trifluoromethyl)pyridin-1(2H)-yl)-4-methylpentanamido)-3-(4-fluoro-3'-methoxy-2',5,6'-trimethyl-[1,1'-biphenyl]-3-yl)propanoic Acid, or a pharmaceutically acceptable salt thereof.

189. The compound of embodiment 1, wherein the compound is (3S)-3-(4,4'-difluoro-2',5,6'-trimethyl-[1,1'-biphenyl]-3-yl)-3-(2-(5-(2-(dimethylamino)ethyl)-2-oxo-4-(trifluoromethyl)pyridin-1(2H)-yl)-4-methylpentanamido)propanoic acid, or a pharmaceutically acceptable salt thereof.

190. The compound of embodiment 1, wherein the compound is (3S)-3-(5-chloro-4-fluoro-2',6'-dimethyl-[1,1'-biphenyl]-3-yl)-3-(2-(5-(2-(3-methoxyazetidin-1-yl) ethyl)-2-oxo-4-(trifluoromethyl)pyridin-1(2H)-yl)-4-methylpentanamido)propanoic acid, or a pharmaceutically acceptable salt thereof.

191. The compound of embodiment 1, wherein the compound is (3S)-3-(2-(5-(2-(dimethylamino)ethyl)-2-oxo-4-(trifluoromethyl)pyridin-1(2H)-yl)-4-methylpentanamido)-3-(4-fluoro-2',4',5,6'-tetramethylbiphenyl-3-yl) propanoic Acid, or a pharmaceutically acceptable salt thereof.

192. The compound of embodiment 1, wherein the compound is (3S)-3-(4,4'-difluoro-2',5,6'-trimethyl-[1,1'-biphenyl]-3-yl)-3-(2-(3-(difluoromethyl)-5-(2-(dimethylamino)ethyl)-2-oxopyridin-1(2H)-yl)-4-methylpentanamido)propanoic acid, or a pharmaceutically acceptable salt thereof.

193. The compound of embodiment 1, wherein the compound is (3S)-3-(2-(5-(2-(dimethylamino)ethyl)-4-methyl-2-oxopyridin-1(2H)-yl)-5-methylhexanamido)-3-(4-fluoro-2',5,6'-trimethylbiphenyl-3-yl)propanoic Acid, or a pharmaceutically acceptable salt thereof.

194. The compound of embodiment 1, wherein the compound is (3S)-3-(4-fluoro-2',5,6'-trimethyl-[1,1'-biphenyl]-3-yl)-3-(2-(3-fluoro-5-(2-(3-fluoroazetidine-1-yl)ethyl)-2-oxopyridin-1(2H)-yl)-4-methylpentanamido)propanoic acid, or a pharmaceutically acceptable salt thereof.

195. The compound of embodiment 1, wherein the compound is (3S)-3-(4-fluoro-2',5,6'-trimethyl-[1,1'-biphenyl]-3-yl)-3-(2-(3-fluoro-5-(2-((R)-3-fluoropyrrolidin-1-yl)ethyl)-2-oxopyridin-1(2H)-yl)-4-methylpentanamido)propanoic acid, or a pharmaceutically acceptable salt thereof.

196. The compound of embodiment 1, wherein the compound is (3S)-3-(5-chloro-4-fluoro-2',6'-dimethyl-[1,1'-biphenyl]-3-yl)-3-(2-(5-(2-(3-methoxyazetidin-1-yl)ethyl)-2-oxo-4-(trifluoromethyl)pyridin-1(2H)-yl)-4-methylpentanamido)propanoic acid, or a pharmaceutically acceptable salt thereof.

197. The compound of embodiment 1, wherein the compound is (S)-3-(4,5-difluoro-2',6'-dimethyl-[1,1'-biphenyl]-3-yl)-3-((S)-2-(5-(2-(3-fluoroazetidine-1-yl)ethyl)-4-methyl-2-oxopyridin-1(2H)-yl)-4-methylpentanamido)propanoic acid, or a pharmaceutically acceptable salt thereof.

198. The compound of embodiment 1, wherein the compound is (S)-3-((S)-2-(5-(2-(azetidin-1-yl)ethyl)-2-oxo-4-(trifluoromethyl)pyridin-1(2H)-yl)-4-methylpentanamido)-3-(4-fluoro-2',6'-dimethyl-5-(trifluoromethyl)-[1,1'-biphenyl]-3-yl)propanoic Acid, or a pharmaceutically acceptable salt thereof.

199. The compound of embodiment 1, wherein the compound is (S)-3-((S)-2-(5-(2-(azetidin-1-yl)ethyl)-2-oxo-4-(trifluoromethyl)pyridin-1(2H)-yl)-4-methylpentanamido)-3-(3',4-difluoro-2',5,6'-trimethyl-[1,1'-biphenyl]-3-yl)propanoic Acid, or a pharmaceutically acceptable salt thereof.

200. The compound of embodiment 1, wherein the compound is (S)-3-((S)-2-(5-(2-(azetidin-1-yl)ethyl)-2-oxo-4-(trifluoromethyl)pyridin-1(2H)-yl)-4-methylpentanamido)-3-(4-fluoro-3'-methoxy-2',5,6'-trimethyl-[1,1'-biphenyl]-3-yl)propanoic Acid, or a pharmaceutically acceptable salt thereof.

201. The compound of embodiment 1, wherein the compound is (S)-3-(4,4'-difluoro-2',5,6'-trimethyl-[1,1'-biphenyl]-3-yl)-3-((S)-2-(5-(2-(dimethylamino)ethyl)-2-oxo-4-(trifluoromethyl)pyridin-1(2H)-yl)-4-methylpentanamido)propanoic acid, or a pharmaceutically acceptable salt thereof.

202. The compound of embodiment 1, wherein the compound is (S)-3-(5-chloro-4-fluoro-2',6'-dimethyl-[1,1'-biphenyl]-3-yl)-3-((S)-2-(5-(2-(3-methoxyazetidin-1-yl)ethyl)-2-oxo-4-(trifluoromethyl)pyridin-1(2H)-yl)-4-methylpentanamido)propanoic acid, or a pharmaceutically acceptable salt thereof.

203. The compound of embodiment 1, wherein the compound is (S)-3-((S)-2-(5-(2-(dimethylamino)ethyl)-2-oxo-4-(trifluoromethyl)pyridin-1(2H)-yl)-4-methylpentanamido)-3-(4-fluoro-2',4',5,6'-tetramethyl-[1,1'-biphenyl]-3-yl)propanoic Acid, or a pharmaceutically acceptable salt thereof.

204. The compound of embodiment 1, wherein the compound is (S)-3-(4,4'-difluoro-2',5,6'-trimethyl-[1,1'-biphenyl]-3-yl)-3-((S)-2-(3-(difluoromethyl)-5-(2-(dimethylamino)ethyl)-2-oxopyridin-1(2H)-yl)-4-methylpentanamido)propanoic acid, or a pharmaceutically acceptable salt thereof.

205. The compound of embodiment 1, wherein the compound is (S)-3-((S)-2-(5-(2-(dimethylamino)ethyl)-4-methyl-2-oxopyridin-1(2H)-yl)-5-methylhexanamido)-3-(4-fluoro-2',5,6'-trimethyl-[1,1'-biphenyl]-3-yl)propanoic Acid, or a pharmaceutically acceptable salt thereof.

206. The compound of embodiment 1, wherein the compound is (S)-3-(4-fluoro-2',5,6'-trimethyl-[1,1'-biphenyl]-3-yl)-3-((S)-2-(3-fluoro-5-(2-(3-fluoroazetidine-1-yl)ethyl)-2-oxopyridin-1(2H)-yl)-4-methylpentanamido)propanoic acid, or a pharmaceutically acceptable salt thereof.

207. The compound of embodiment 1, wherein the compound is (S)-3-(4-fluoro-2',5,6'-trimethyl-[1,1'-biphenyl]-3-yl)-3-((S)-2-(3-fluoro-5-(2-((R)-3-fluoropyrrolidin-1-yl)ethyl)-2-oxopyridin-1(2H)-yl)-4-methylpentanamido)propanoic acid, or a pharmaceutically acceptable salt thereof.

208. The compound of embodiment 1, wherein the compound is (S)-3-(5-chloro-4-fluoro-2',6'-dimethyl-[1,1'-biphenyl]-3-yl)-3-((S)-2-(5-(2-(3-methoxyazetidin-1-yl)ethyl)-2-oxo-4-(trifluoromethyl)pyridin-1(2H)-yl)-4-methylpentanamido)propanoic acid, or a pharmaceutically acceptable salt thereof.

209. A pharmaceutical composition, comprising a compound of any one of embodiments 1-208; and a pharmaceutically acceptable excipient.

210. A method of inhibiting $\alpha_4\beta_7$ integrin in a cell, comprising contacting the cell with a compound of any one of embodiments 1-208 under conditions effective to reduce the adhesion of the cell to MAdCAM-1.

211. A method of reducing the adhesion of a cell comprising an $\alpha_4\beta_7$ integrin to MAdCAM-1, the method comprising contacting the cell with a compound of any one of embodiments 1-208 under conditions effective to reduce the adhesion of the cell to MAdCAM-1.

212. A method of treating inflammatory bowel disease, ulcerative colitis, or Crohn's disease, comprising administering to a subject in need thereof a therapeutically effective amount of a compound of any one of embodiments 1-208

In some embodiments, the following compound of Formula (I):

wherein $R_a$, $R_b$, and $R_c$ are independently selected from the group consisting of H, Me, halide, $CF_3$, $C(H)F_2$, $C(F)H_2$, and —$(C_1$-$C_5)$alkylene-N—$(R_x)(R_y)$; provided that at least one of $R_a$, $R_b$, and $R_c$ is —$(C_1$-$C_5)$alkylene-N—$(R_x)(R_y)$;

$R_x$ and $R_y$ are independently selected from the group consisting of H and substituted or unsubstituted ($C_1$-$C_6$)-alkyl; or $R_x$ and $R_y$ taken together with the N to which they are attached form a 4-6 membered ring;

$R_1$ is methyl, ethyl, n-propyl, iso-propyl, n-butyl, iso-butyl, sec-butyl, or t-butyl;

$R_2$ is

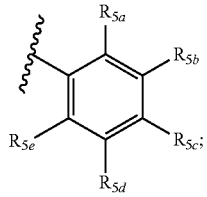

$R_{3a}$ and $R_{3b}$ are independently selected from the group consisting of H, ($C_1$-$C_5$)-alkyl, ($C_3$-$C_6$)-cycloalkyl, substituted or unsubstituted 3-6 membered heterocycloalkyl, —OH, —CN, halide, $CF_3$, $C(H)F_2$, $C(F)H_2$, —($C_1$-$C_4$)-alkoxy, —$OCF_3$, and substituted or unsubstituted ($C_1$-$C_4$)-alkylene-($C_1$-$C_4$)-alkoxy; provided that $R_{3a}$ and $R_{3b}$ are not both H;

$R_{3c}$, and $R_{3d}$ are H;

$R_4$ is H;

$R_{5a}$, and $R_{5e}$ are independently methyl;

$R_{5b}$, and $R_{5c}$ are independently selected from the group consisting of H, CN, halide, $CF_3$, $C(H)F_2$, $C(F)H_2$, substituted or unsubstituted ($C_1$-$C_5$)-alkyl, substituted or unsubstituted ($C_3$-$C_6$)-cycloalkyl, substituted or unsubstituted 3-6 membered heterocycloalkyl, hydroxyl, and ($C_1$-$C_4$)-alkoxy;

$R_{5d}$ is H; and wherein the compound of Formula (I) is selected from the group consisting of:

a. (S)-3-(4,5-difluoro-2',6'-dimethyl-[1,1'-biphenyl]-3-yl)-3-((S)-2-(5-(2-(3-fluoroazetidine-1-yl)ethyl)-4-methyl-2-oxopyridin-1(2H)-yl)-4-methylpentanamido)propanoic acid;

b. (S)-3-((S)-2-(5-(2-(azetidin-1-yl)ethyl)-2-oxo-4-(trifluoromethyl)pyridin-1(2H)-yl)-4-methylpentanamido)-3-(4-fluoro-2',6'-dimethyl-5-(trifluoromethyl)-[1,1'-biphenyl]-3-yl)propanoic Acid;

c. (S)-3-((S)-2-(5-(2-(azetidin-1-yl)ethyl)-2-oxo-4-(trifluoromethyl)pyridin-1(2H)-yl)-4-methylpentanamido)-3-(3',4-difluoro-2',5,6'-trimethyl-[1,1'-biphenyl]-3-yl)propanoic Acid;

d. (S)-3-((S)-2-(5-(2-(azetidin-1-yl)ethyl)-2-oxo-4-(trifluoromethyl)pyridin-1(2H)-yl)-4-methylpentanamido)-3-(4-fluoro-3'-methoxy-2',5,6'-trimethyl-[1,1'-biphenyl]-3-yl)propanoic acid;

e. (S)-3-(4,4'-difluoro-2',5,6'-trimethyl-[1,1'-biphenyl]-3-yl)-3-((S)-2-(5-(2-(dimethylamino)ethyl)-2-oxo-4-(trifluoromethyl)pyridin-1(2H)-yl)-4-methylpentanamido)propanoic acid;

f. (S)-3-(5-chloro-4-fluoro-2',6'-dimethyl-[1,1'-biphenyl]-3-yl)-3-((S)-2-(5-(2-(3-methoxyazetidin-1-yl)ethyl)-2-oxo-4-(trifluoromethyl)pyridin-1(2H)-yl)-4-methylpentanamido)propanoic acid;

g. (S)-3-((S)-2-(5-(2-(dimethylamino)ethyl)-2-oxo-4-(trifluoromethyl)pyridin-1(2H)-yl)-4-methylpentanamido)-3-(4-fluoro-2',4',5,6'-tetramethyl-[1,1'-biphenyl]-3-yl)propanoic Acid;

h. (S)-3-(4,4'-difluoro-2',5,6'-trimethyl-[1,1'-biphenyl]-3-yl)-3-((S)-2-(3-(difluoromethyl)-5-(2-(dimethylamino)ethyl)-2-oxopyridin-1(2H)-yl)-4-methylpentanamido)propanoic acid;

i. (S)-3-((S)-2-(5-(2-(dimethylamino)ethyl)-4-methyl-2-oxopyridin-1(2H)-yl)-5-methylhexanamido)-3-(4-fluoro-2',5,6'-trimethyl-[1,1'-biphenyl]-3-yl)propanoic Acid;

j. (S)-3-(4-fluoro-2',5,6'-trimethyl-[1,1'-biphenyl]-3-yl)-3-((S)-2-(3-fluoro-5-(2-(3-fluoroazetidine-1-yl)ethyl)-2-oxopyridin-1(2H)-yl)-4-methylpentanamido)propanoic acid; and k. (S)-3-(4-fluoro-2',5,6'-trimethyl-[1,1'-biphenyl]-3-yl)-3-((S)-2-(3-fluoro-5-(2-((R)-3-fluoropyrrolidin-1-yl)ethyl)-2-oxopyridin-1(2H)-yl)-4-methylpentanamido)propanoic acid;

or a pharmaceutically acceptable salt thereof.

In some embodiments, wherein the compound is (S)-3-(4,5-difluoro-2',6'-dimethyl-[1,1'-biphenyl]-3-yl)-3-((S)-2-(5-(2-(3-fluoroazetidine-1-yl)ethyl)-4-methyl-2-oxopyridin-1(2H)-yl)-4-methylpentanamido)propanoic acid, or a pharmaceutically acceptable salt thereof.

In some embodiments, wherein the compound is (S)-3-((S)-2-(5-(2-(azetidin-1-yl)ethyl)-2-oxo-4-(trifluoromethyl)pyridin-1(2H)-yl)-4-methylpentanamido)-3-(4-fluoro-2',6'-dimethyl-5-(trifluoromethyl)-[1,1'-biphenyl]-3-yl)propanoic Acid, or a pharmaceutically acceptable salt thereof.

In some embodiments, wherein the compound is (S)-3-((S)-2-(5-(2-(azetidin-1-yl)ethyl)-2-oxo-4-(trifluoromethyl)pyridin-1(2H)-yl)-4-methylpentanamido)-3-(3',4-difluoro-2',5,6'-trimethyl-[1,1'-biphenyl]-3-yl)propanoic Acid, or a pharmaceutically acceptable salt thereof.

In some embodiments, wherein the compound is (S)-3-((S)-2-(5-(2-(azetidin-1-yl)ethyl)-2-oxo-4-(trifluoromethyl)pyridin-1(2H)-yl)-4-methylpentanamido)-3-(4-fluoro-3'-methoxy-2',5,6'-trimethyl-[1,1'-biphenyl]-3-yl)propanoic Acid, or a pharmaceutically acceptable salt thereof.

In some embodiments, wherein the compound is (S)-3-(4,4'-difluoro-2',5,6'-trimethyl-[1,1'-biphenyl]-3-yl)-3-((S)-2-(5-(2-(dimethylamino)ethyl)-2-oxo-4-(trifluoromethyl)pyridin-1(2H)-yl)-4-methylpentanamido)propanoic acid, or a pharmaceutically acceptable salt thereof.

In some embodiments, wherein the compound is (S)-3-(5-chloro-4-fluoro-2',6'-dimethyl-[1,1'-biphenyl]-3-yl)-3-((S)-2-(5-(2-(3-methoxyazetidin-1-yl)ethyl)-2-oxo-4-(trifluoromethyl)pyridin-1(2H)-yl)-4-methylpentanamido)propanoic acid, or a pharmaceutically acceptable salt thereof.

In some embodiments, wherein the compound is (S)-3-((S)-2-(5-(2-(dimethylamino)ethyl)-2-oxo-4-(trifluoromethyl)pyridin-1(2H)-yl)-4-methylpentanamido)-3-(4-fluoro-2',4',5,6'-tetramethyl-[1,1'-biphenyl]-3-yl)propanoic Acid, or a pharmaceutically acceptable salt thereof.

In some embodiments, wherein the compound is (S)-3-(4,4'-difluoro-2',5,6'-trimethyl-[1,1'-biphenyl]-3-yl)-3-((S)-2-(3-(difluoromethyl)-5-(2-(dimethylamino)ethyl)-2-oxopyridin-1(2H)-yl)-4-methylpentanamido)propanoic acid, or a pharmaceutically acceptable salt thereof.

In some embodiments, wherein the compound is (S)-3-((S)-2-(5-(2-(dimethylamino)ethyl)-4-methyl-2-oxopyridin-1(2H)-yl)-5-methylhexanamido)-3-(4-fluoro-2',5,6'-trimethyl-[1,1'-biphenyl]-3-yl)propanoic Acid, or a pharmaceutically acceptable salt thereof.

In some embodiments, wherein the compound is (S)-3-(4-fluoro-2',5,6'-trimethyl-[1,1'-biphenyl]-3-yl)-3-((S)-2-(3-fluoro-5-(2-(3-fluoroazetidine-1-yl)ethyl)-2-oxopyridin-1(2H)-yl)-4-methylpentanamido)propanoic acid, or a pharmaceutically acceptable salt thereof.

In some embodiments, wherein the compound is (S)-3-(4-fluoro-2',5,6'-trimethyl-[1,1'-biphenyl]-3-yl)-3-((S)-2-(3-fluoro-5-(2-((R)-3-fluoropyrrolidin-1-yl)ethyl)-2-oxopyridin-1(2H)-yl)-4-methylpentanamido)propanoic acid, or a pharmaceutically acceptable salt thereof.

In some embodiments, a pharmaceutical composition comprising a compound of Formula (I) as the active pharmaceutical ingredient:

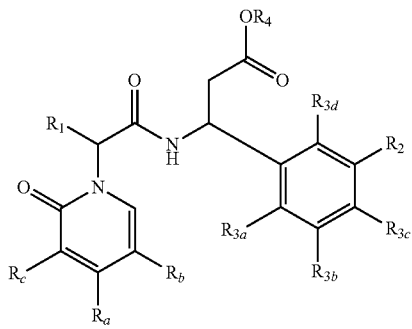
(I)

wherein $R_a$, $R_b$, and $R_c$ are independently selected from the group consisting of H, Me, halide, $CF_3$, $C(H)F_2$, $C(F)H_2$, and —$(C_1$-$C_5)$alkylene-N—$(R_x)(R_y)$; provided that at least one of $R_a$, $R_b$, and $R_c$ is —$(C_1$-$C_5)$alkylene-N—$(R_x)(R_y)$;

$R_x$ and $R_y$ are independently selected from the group consisting of H and substituted or unsubstituted $(C_1$-$C_6)$-alkyl; or $R_x$ and $R_y$ taken together with the N to which they are attached form a 4-6 membered ring;

$R_1$ is methyl, ethyl, n-propyl, iso-propyl, n-butyl, iso-butyl, sec-butyl, or t-butyl;

$R_2$ is

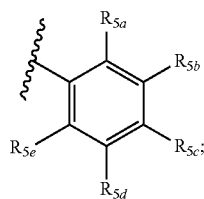

$R_{3a}$ and $R_{3b}$ are independently selected from the group consisting of H, substituted or unsubstituted $(C_1$-$C_5)$-alkyl, substituted or unsubstituted $(C_3$-$C_6)$-cycloalkyl, substituted or unsubstituted 3-6 membered heterocycloalkyl, —OH, —CN, halide, $CF_3$, $C(H)F_2$, $C(F)H_2$, —$(C_1$-$C_4)$-alkoxy, —$OCF_3$, and substituted or unsubstituted $(C_1$-$C_4)$-alkylene-$(C_1$-$C_4)$-alkoxy; provided that $R_{3a}$ and $R_{3b}$ are not both H;

$R_{3c}$, and $R_{3d}$ are H;

$R_4$ is H;

$R_{5a}$, and $R_{5e}$ are independently methyl;

$R_{5b}$, and $R_{5c}$ are independently selected from the group consisting of H, CN, halide, $CF_3$, $C(H)F_2$, $C(F)H_2$, substituted or unsubstituted $(C_1$-$C_5)$-alkyl, substituted or unsubstituted $(C_3$-$C_6)$-cycloalkyl, substituted or unsubstituted 3-6 membered heterocycloalkyl, hydroxyl, and $(C_1$-$C_4)$-alkoxy;

$R_{5d}$ is H; and wherein the compound of Formula (I) is selected from the group consisting of:

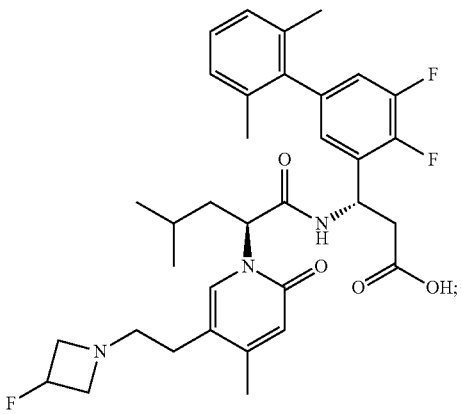

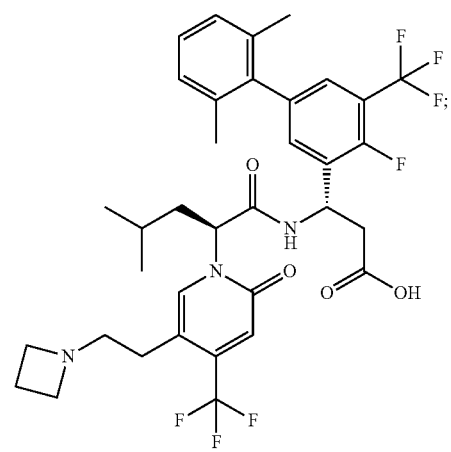 [SMILES: Cc1cccc(C)c1-c1cc([C@H](CC(=O)O)NC(=O)[C@H](CC(C)C)n2cc(CCN3CCC3)c(C(F)(F)F)cc2=O)c(F)c(C(F)(F)F)c1]

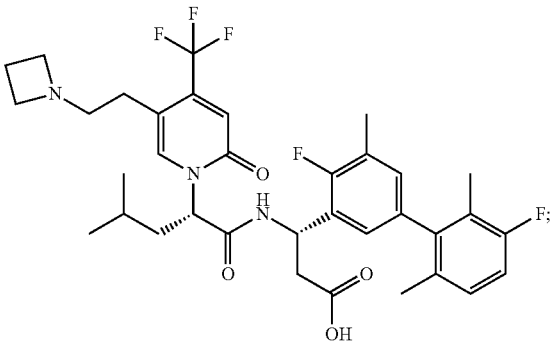 [SMILES: Cc1cc(-c2c(C)ccc(F)c2C)cc([C@H](CC(=O)O)NC(=O)[C@H](CC(C)C)n2cc(CCN3CCC3)c(C(F)(F)F)cc2=O)c1F]

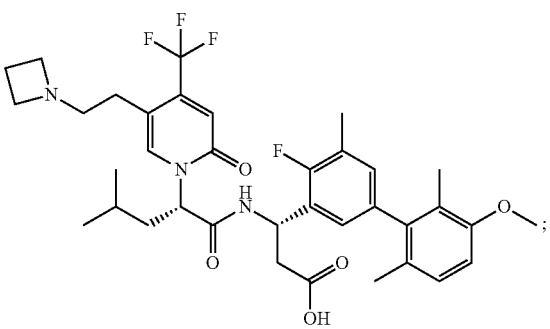 [SMILES: COc1ccc(C)c(-c2cc(C)c(F)c([C@H](CC(=O)O)NC(=O)[C@H](CC(C)C)n3cc(CCN4CCC4)c(C(F)(F)F)cc3=O)c2)c1C]

113
-continued
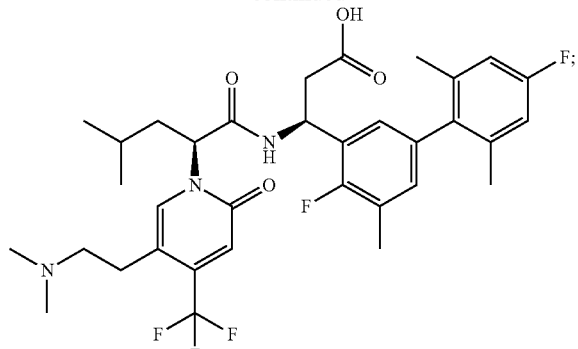
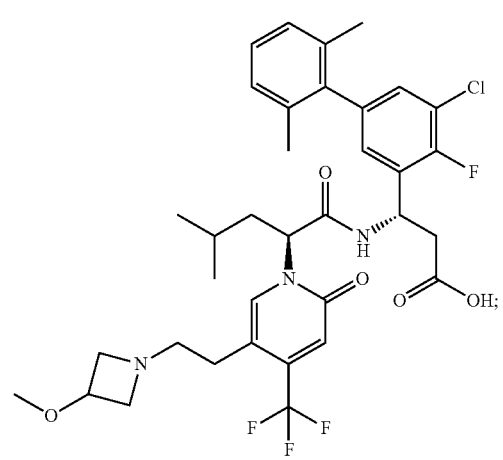 [SMILES: CCC[C@@H](C(=O)N[C@@H](CC(=O)O)c1cc(-c2c(C)cccc2C)cc(Cl)c1F)n1cc(CCN2CC(OC)C2)c(C(F)(F)F)cc1=O]
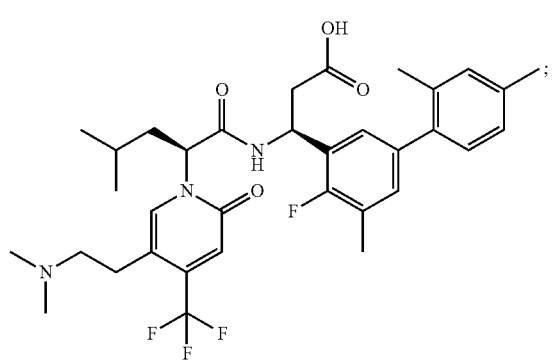
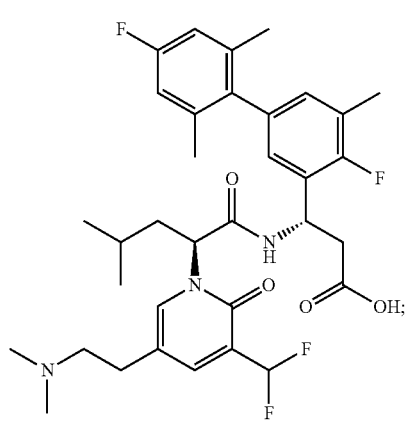
114
-continued
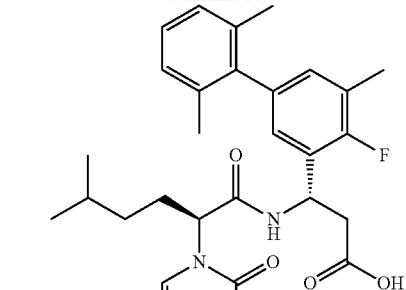
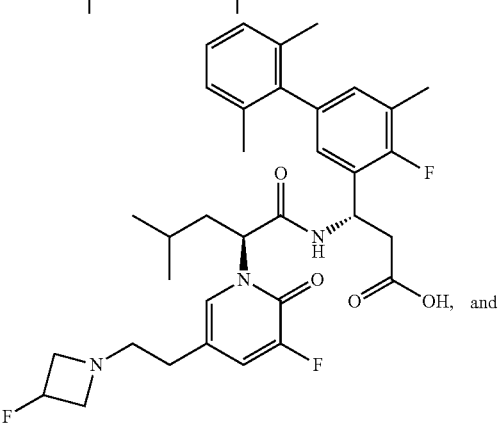
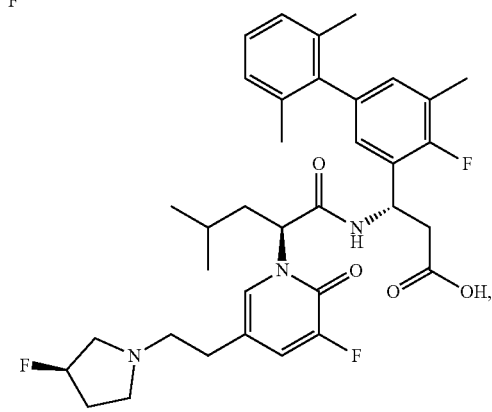
or a pharmaceutically acceptable salt thereof.
In some embodiments, wherein the compound is
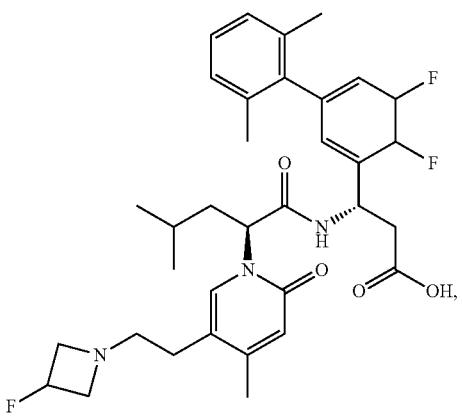
or a pharmaceutically acceptable salt thereof.

115

In some embodiments, wherein the compound is

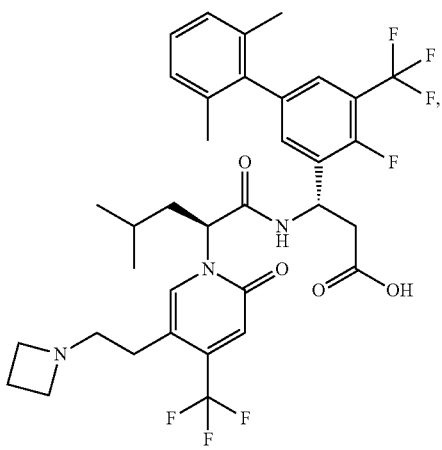

or a pharmaceutically acceptable salt thereof.

In some embodiments, wherein the compound is

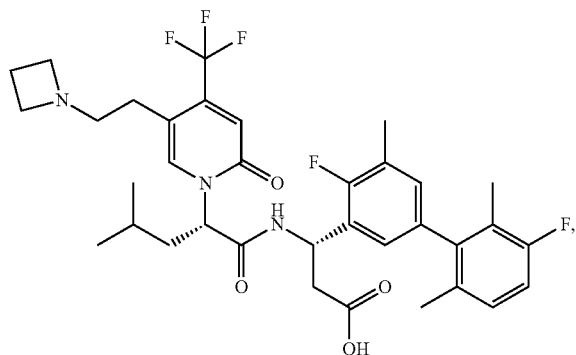

or a pharmaceutically acceptable salt thereof.

In some embodiments, wherein the compound is

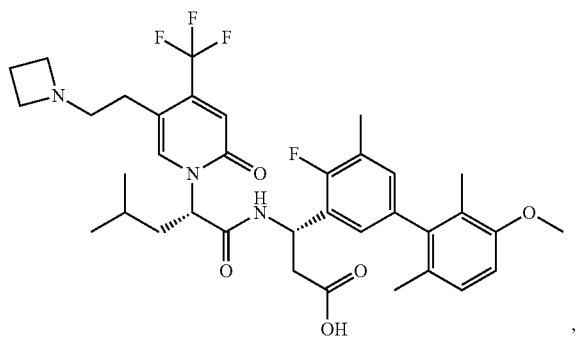

or a pharmaceutically acceptable salt thereof.

116

In some embodiments, wherein the compound is

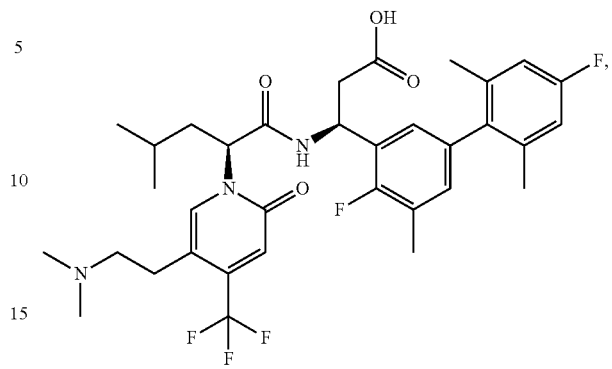

or a pharmaceutically acceptable salt thereof.

In some embodiments, wherein the compound is

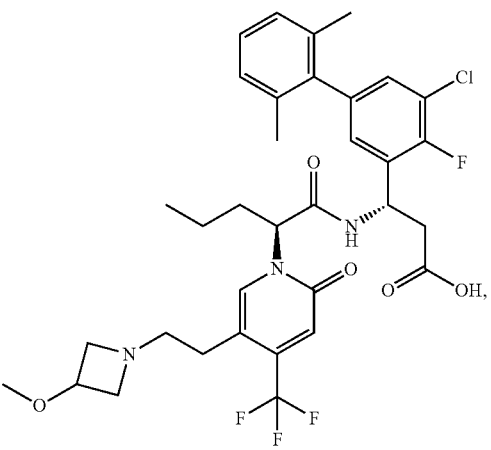

or a pharmaceutically acceptable salt thereof.

In some embodiments, wherein the compound is

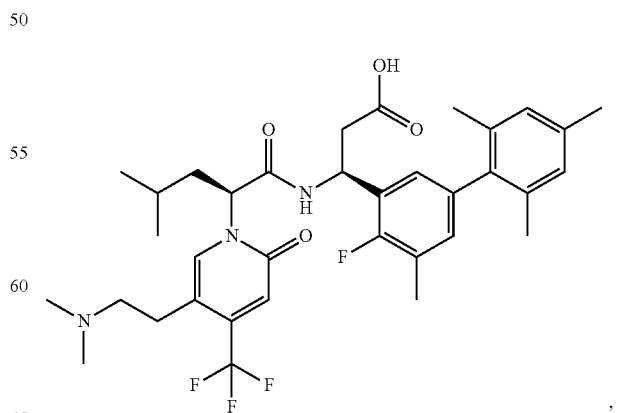

or a pharmaceutically acceptable salt thereof.

In some embodiments, wherein the compound is

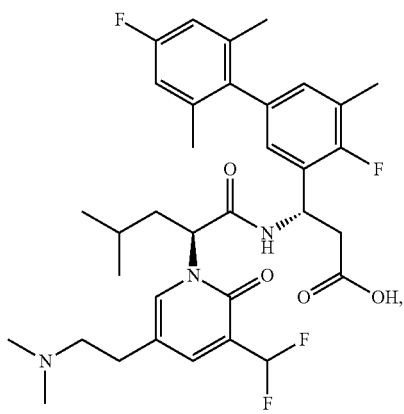

or a pharmaceutically acceptable salt thereof.

In some embodiments, wherein the compound is

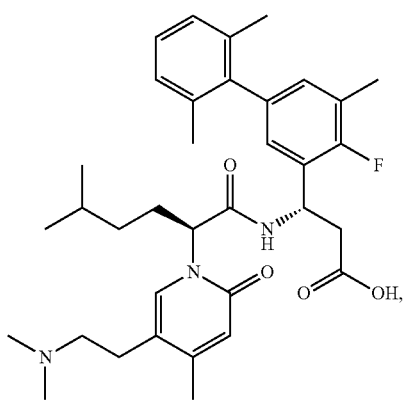

or a pharmaceutically acceptable salt thereof.

In some embodiments, wherein the compound is

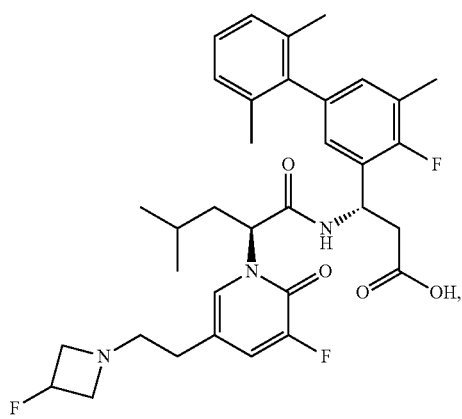 [SMILES: Cc1cc(-c2c(C)cccc2C)cc([C@H](CC(=O)O)NC(=O)[C@H](CC(C)C)n2cc(CCN3CC(F)C3)cc(F)c2=O)c1F]

or a pharmaceutically acceptable salt thereof.

In some embodiments, wherein the compound is

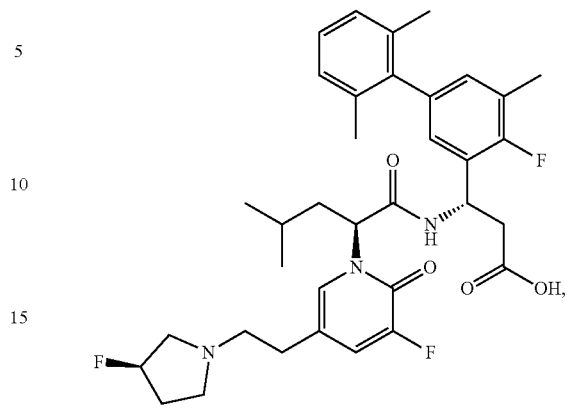

or a pharmaceutically acceptable salt thereof.

In some embodiments, a compound of Formula (Ia):

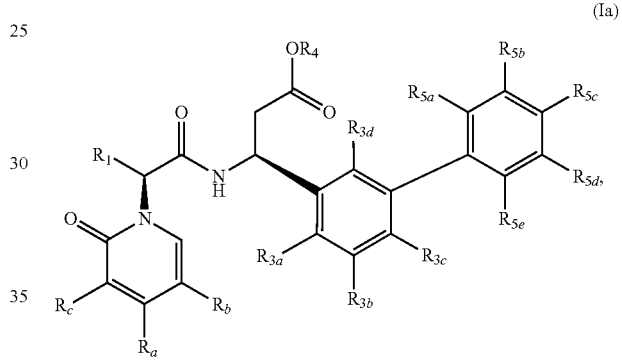

(Ia)

wherein:
$R_a$, is $CF_3$;
$R_b$ is substituted or unsubstituted —($C_1$-$C_5$)alkylene-N—$(R_x)(R_y)$;
$R_x$ and $R_y$ are independently substituted or unsubstituted ($C_1$-$C_6$)-alkyl; or Rx and $R_y$ taken together with the N to which they are attached form a 4-6 membered ring;
$R_c$ is H;
$R_1$ is substituted or unsubstituted ($C_1$-$C_6$)-alkyl;
$R_2$ is

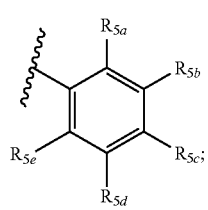

$R_{3a}$ and $R_{3b}$ are independently selected from the group consisting of H, substituted or unsubstituted ($C_1$-$C_5$)-alkyl, substituted or unsubstituted ($C_3$-$C_6$)-cycloalkyl, substituted or unsubstituted 3-6 membered heterocycloalkyl, —OH, —CN, halide, $CF_3$, $C(H)F_2$, $C(F)H_2$, —($C_1$-$C_4$)-alkoxy, —$OCF_3$, and substituted or unsubstituted ($C_1$-$C_4$)-alkylene-($C_1$-$C_4$)-alkoxy; provided that $R_{3a}$ and $R_{3b}$ are not both H;

$R_{3c}$ is H;
$R_{3d}$ is halide;
$R_4$ is H;
$R_{5a}$, and $R_{5e}$ are each independently selected from ($C_1$-$C_5$)-alkyl; and
$R_{5b}$, $R_{5c}$, and $R_{5d}$ are independently selected from the group consisting of H, CN, halide, $CF_3$, $C(H)F_2$, $C(F)H_2$, —$CH_2CF_3$, substituted or unsubstituted ($C_1$-$C_5$)-alkyl, substituted or unsubstituted ($C_3$-$C_6$)-cycloalkyl, substituted or unsubstituted 3-6 membered heterocycloalkyl, hydroxyl, and ($C_1$-$C_4$)-alkoxy;
wherein the compound of Formula (I) is selected from the group consisting of:

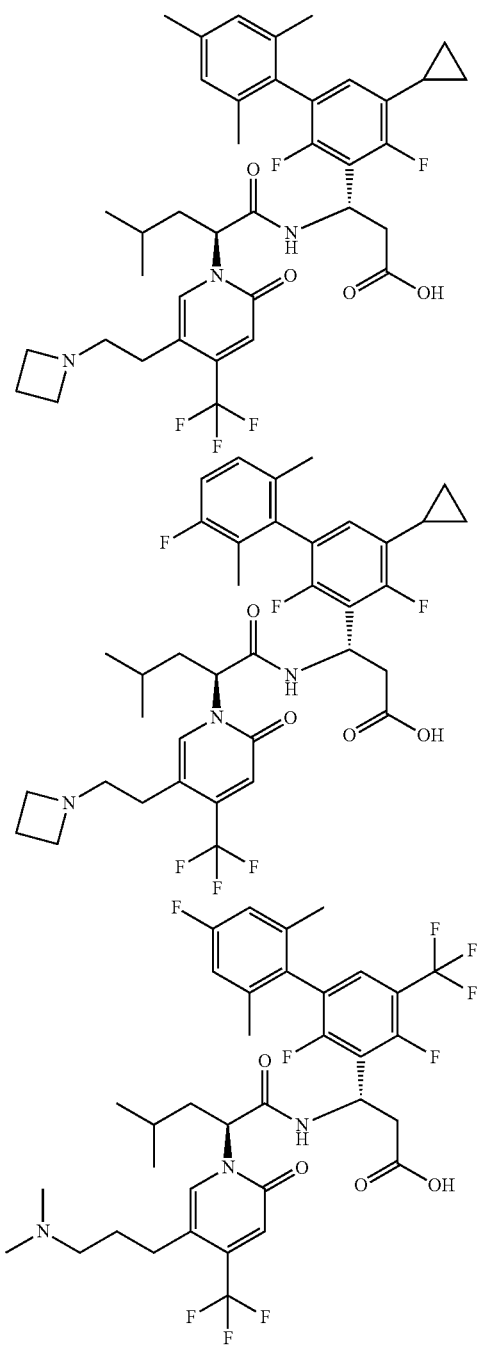

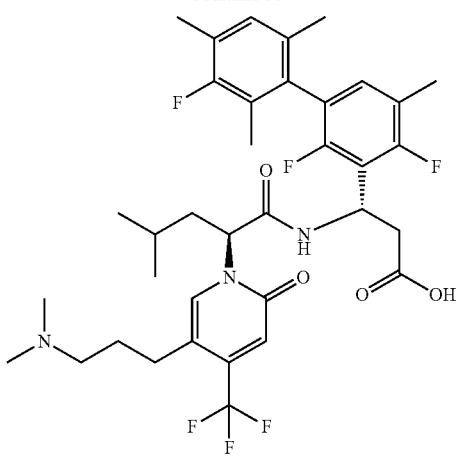

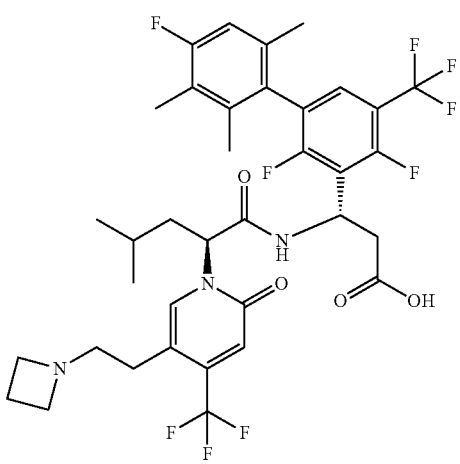

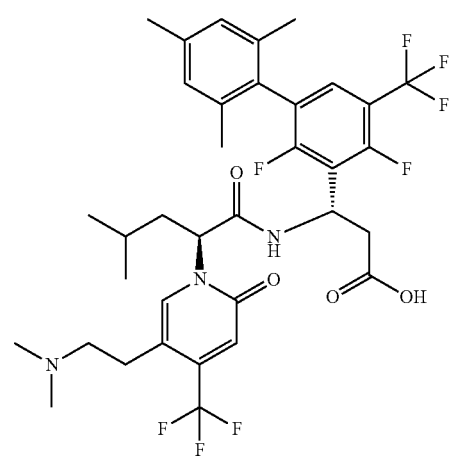

121
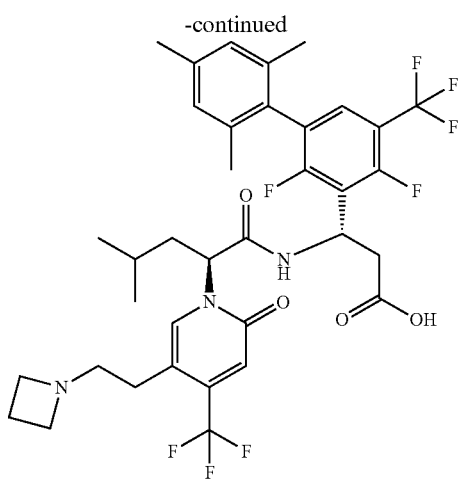
122
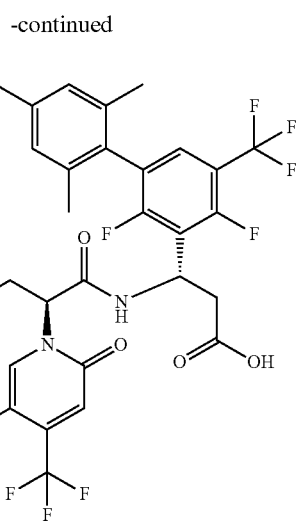
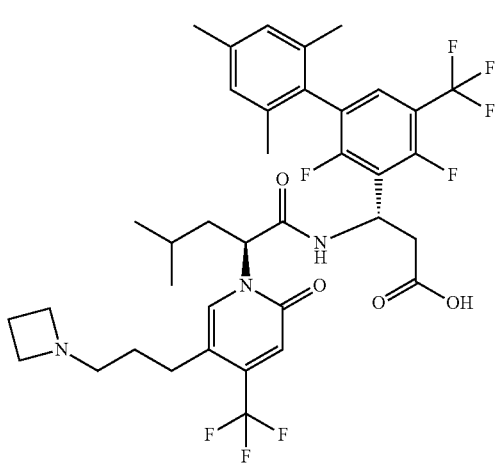
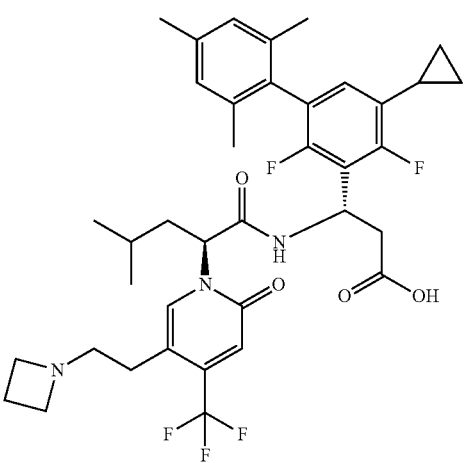
In some embodiments, wherein the compound is
or a pharmaceutically acceptable salt thereof.

In some embodiments, wherein the compound is

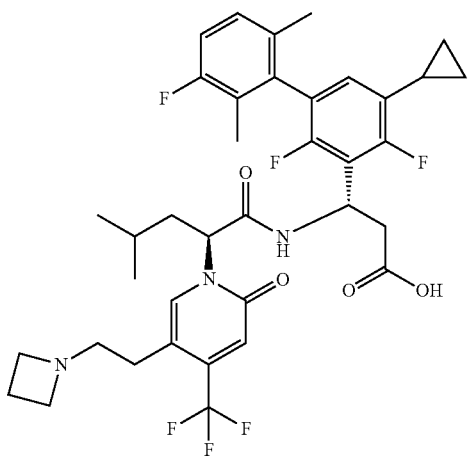

or a pharmaceutically acceptable salt thereof.

In some embodiments, wherein the compound is

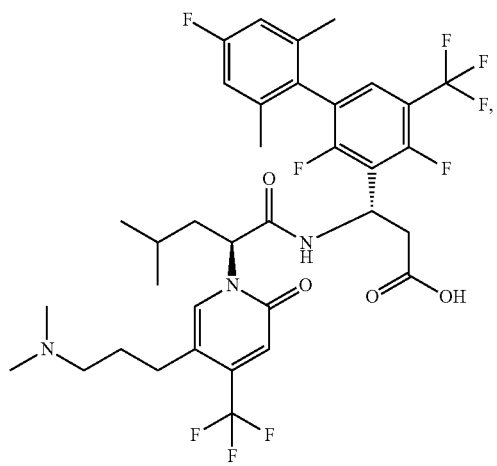 [SMILES: Cc1cc(F)cc(C)c1-c1cc(C(F)(F)F)c(F)c([C@H](CC(=O)O)NC(=O)[C@H](CC(C)C)n2cc(CCCN(C)C)c(C(F)(F)F)cc2=O)c1F]

or a pharmaceutically acceptable salt thereof.

In some embodiments, wherein the compound is

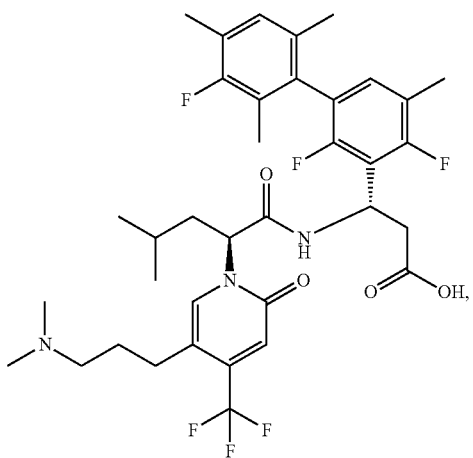 [SMILES: Cc1cc(C)c(-c2cc(C)c(F)c([C@H](CC(=O)O)NC(=O)[C@H](CC(C)C)n3cc(CCCN(C)C)c(C(F)(F)F)cc3=O)c2F)c(C)c1F]

or a pharmaceutically acceptable salt thereof.

In some embodiments, wherein the compound is

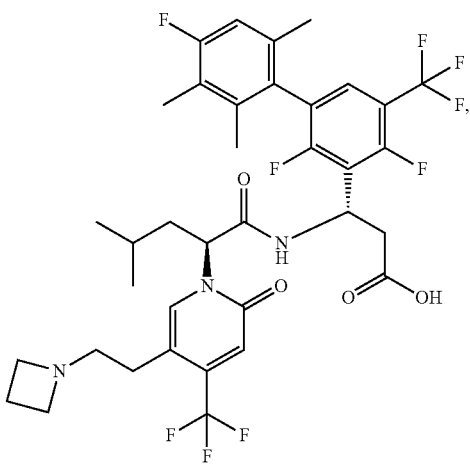 [SMILES: Cc1cc(F)c(C)c(C)c1-c1cc(C(F)(F)F)c(F)c([C@H](CC(=O)O)NC(=O)[C@H](CC(C)C)n2cc(CCN3CCC3)c(C(F)(F)F)cc2=O)c1F]

or a pharmaceutically acceptable salt thereof.

In some embodiments, wherein the compound is

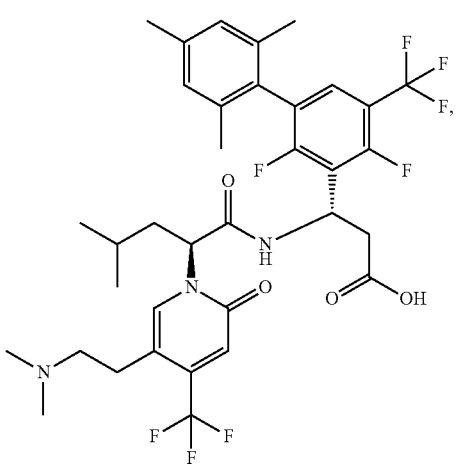 [SMILES: Cc1cc(C)c(-c2cc(C(F)(F)F)c(F)c([C@H](CC(=O)O)NC(=O)[C@H](CC(C)C)n3cc(CCN(C)C)c(C(F)(F)F)cc3=O)c2F)c(C)c1]

or a pharmaceutically acceptable salt thereof.

In some embodiments, wherein the compound is

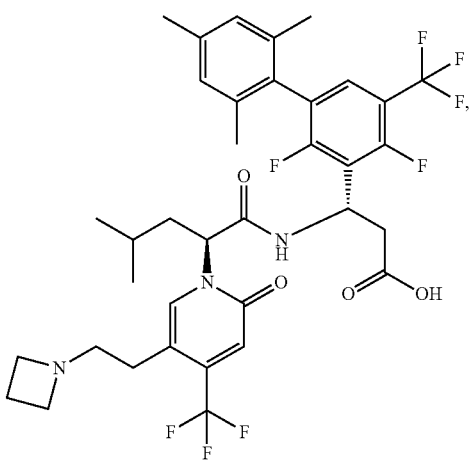 [SMILES: Cc1cc(C)c(-c2cc(C(F)(F)F)c(F)c([C@H](CC(=O)O)NC(=O)[C@H](CC(C)C)n3cc(CCN4CCC4)c(C(F)(F)F)cc3=O)c2F)c(C)c1]

or a pharmaceutically acceptable salt thereof.

125

In some embodiments, wherein the compound is

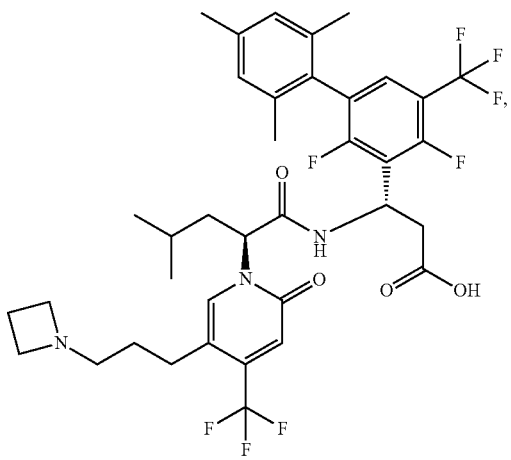 [SMILES: Cc1cc(C)c(-c2cc(C(F)(F)F)c(F)c([C@H](CC(=O)O)NC(=O)[C@H](CC(C)C)n3cc(CCCN4CCC4)c(C(F)(F)F)cc3=O)c2F)c(C)c1]

or a pharmaceutically acceptable salt thereof.

In some embodiments, wherein the compound is

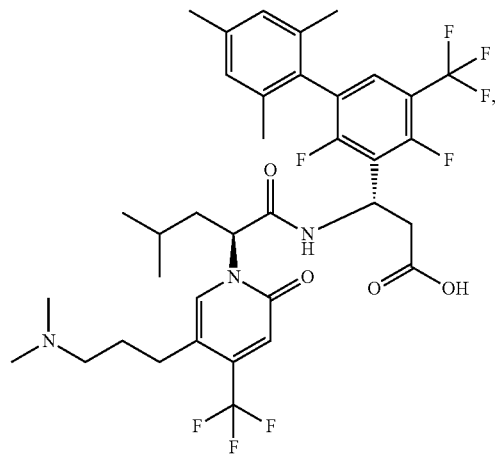 [SMILES: Cc1cc(C)c(-c2cc(C(F)(F)F)c(F)c([C@H](CC(=O)O)NC(=O)[C@H](CC(C)C)n3cc(CCCN(C)C)c(C(F)(F)F)cc3=O)c2F)c(C)c1]

or a pharmaceutically acceptable salt thereof.

In some embodiments, wherein the compound is

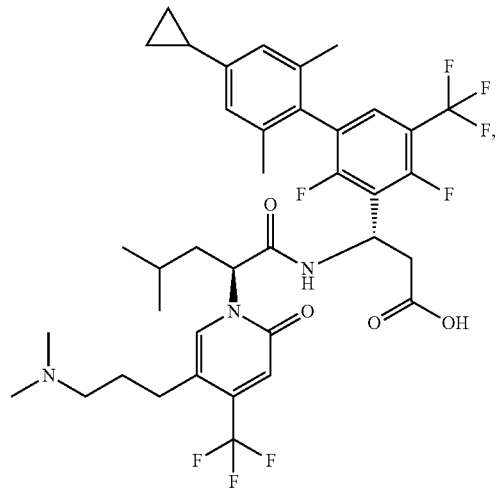 [SMILES: Cc1cc(C2CC2)cc(C)c1-c1cc(C(F)(F)F)c(F)c([C@H](CC(=O)O)NC(=O)[C@H](CC(C)C)n2cc(CCCN(C)C)c(C(F)(F)F)cc2=O)c1F]

or a pharmaceutically acceptable salt thereof.

126

In some embodiments, wherein the compound is

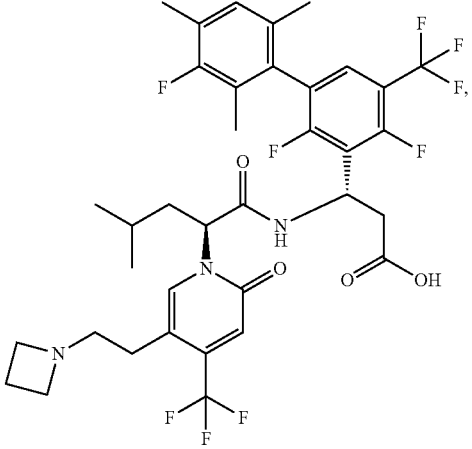 [SMILES: Cc1cc(C)c(-c2cc(C(F)(F)F)c(F)c([C@H](CC(=O)O)NC(=O)[C@H](CC(C)C)n3cc(CCN4CCC4)c(C(F)(F)F)cc3=O)c2F)c(C)c1F]

or a pharmaceutically acceptable salt thereof.

In some embodiments, a pharmaceutical composition comprising a compound of the present application or a pharmaceutically acceptable salt thereof as the active pharmaceutical ingredient. In some embodiments, the invention relates to a compound of Formula (I), Formula (Ia), or Formula (Ib):

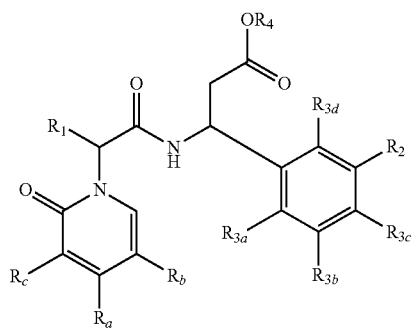

(I)

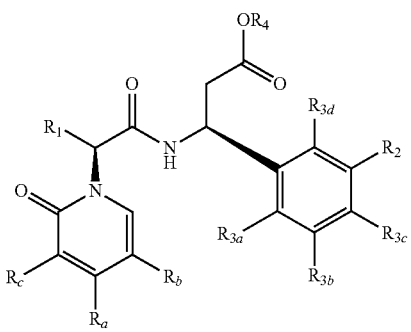

(Ia)

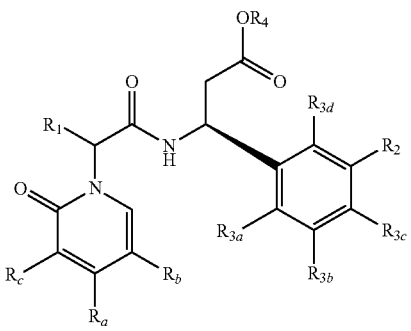

(Ib)

or a pharmaceutically acceptable salt thereof;

wherein $R_a$, $R_b$, and $R_c$ are independently selected from the group consisting of H, Me, halide, $CF_3$, $C(H)F_2$, $C(F)H_2$, —CN, —$OCF_3$, substituted or unsubstituted ($C_1$-$C_5$)-alkyl, ($C_1$-$C_5$)-alkoxy, —$CH_2CF_3$, and substituted or unsubstituted —($C_1$-$C_5$)alkylene-N—($R_x$)($R_y$); provided that at least one of $R_a$, $R_b$, and $R_c$ is —($C_1$-$C_5$)alkylene-N—($R_x$)($R_y$), wherein the substituted ($C_1$-$C_5$)-alkyl is substituted with halide, amino, or ($C_1$-$C_4$)-alkylamino; and the substituted —($C_1$-$C_5$)alkylene-N—($R_x$)($R_y$) is substituted with halide or ($C_1$-$C_4$)-alkoxy;

$R_x$ and $R_y$ are independently selected from the group consisting of H and ($C_1$-$C_6$)-alkyl; or $R_x$ and $R_y$ taken together with the N to which they are attached form a 4-6 membered ring;

$R_1$ is ($C_1$-$C_6$)-alkyl, ($C_1$-$C_4$)-alkylene-($C_3$-$C_6$)-cycloalkyl, or ($C_1$-$C_4$)-alkylene-($C_1$-$C_4$)-alkoxy;

$R_2$ is

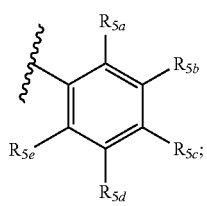

$R_{3a}$ and $R_{3b}$ are independently selected from the group consisting of H, ($C_1$-$C_5$)-alkyl, ($C_3$-$C_6$)-cycloalkyl, 3-6 membered heterocycloalkyl, —OH, —CN, halide, $CF_3$, $C(H)F_2$, $C(F)H_2$, —($C_1$-$C_4$)-alkoxy, —$OCF_3$, and ($C_1$-$C_4$)-alkylene-($C_1$-$C_4$)-alkoxy; provided that $R_{3a}$ and $R_{3b}$ are not both H;

$R_{3c}$ is selected from the group consisting of H, ($C_1$-$C_5$)-alkyl, ($C_3$-$C_6$)-cycloalkyl, 3-6 membered heterocycloalkyl, hydroxyl, halide, $CF_3$, $C(H)F_2$, $C(F)H_2$, —($C_1$-$C_4$)-alkoxy, —$OCF_3$—CN, and ($C_1$-$C_4$)-alkylene-($C_1$-$C_4$)-alkoxy;

$R_{3d}$ is selected from the group consisting of H, ($C_1$-$C_5$)-alkyl, hydroxyl, halide, and —($C_1$-$C_4$)-alkoxy;

$R_4$ is H, or ($C_1$-$C_4$)-alkyl;

$R_{5a}$, and $R_{5e}$ are independently selected from the group consisting of H, CN, halide, $CF_3$, $C(H)F_2$, $C(F)H_2$, —$CH_2CF_3$, ($C_3$-$C_6$)-cycloalkyl, ($C_1$-$C_5$)-alkyl, 3-6 membered heterocycloalkyl hydroxyl, and ($C_1$-$C_4$)-alkoxy; and $R_{5b}$, $R_{5c}$, and $R_{5d}$ are independently selected from the group consisting of H, CN, halide, $CF_3$, $C(H)F_2$, $C(F)H_2$, —$CH_2CF_3$, ($C_1$-$C_5$)-alkyl, ($C_3$-$C_6$)-cycloalkyl, 3-6 membered heterocycloalkyl, hydroxyl, and ($C_1$-$C_4$)-alkoxy.

In one embodiment of the above Formula (Ib), the compound is not a compound recited in FIG. 1.

Figure 2:
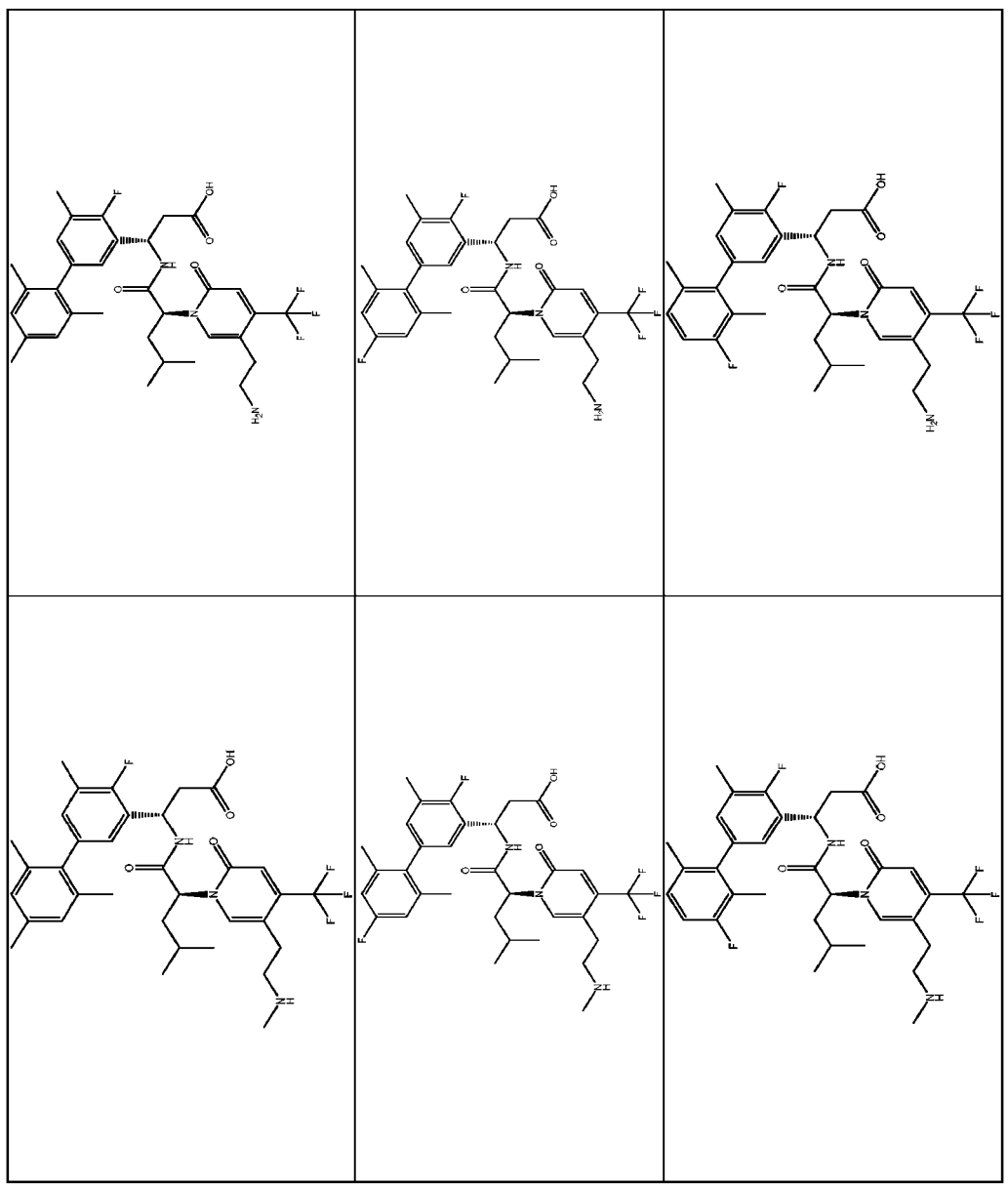
FIG. 2 is a table (Table 2) providing additional exemplary compounds.
Figure 2:
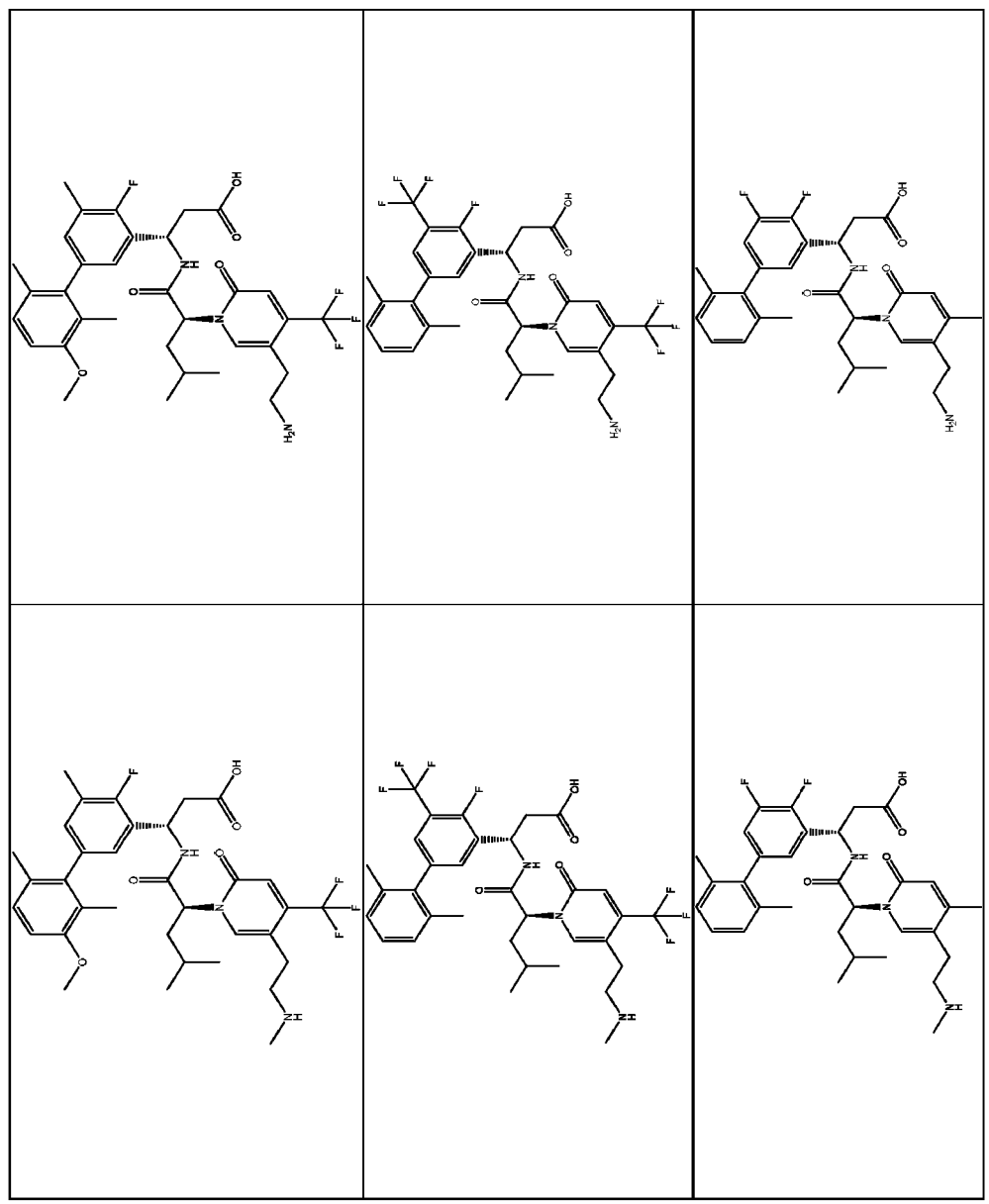
Figure 2:
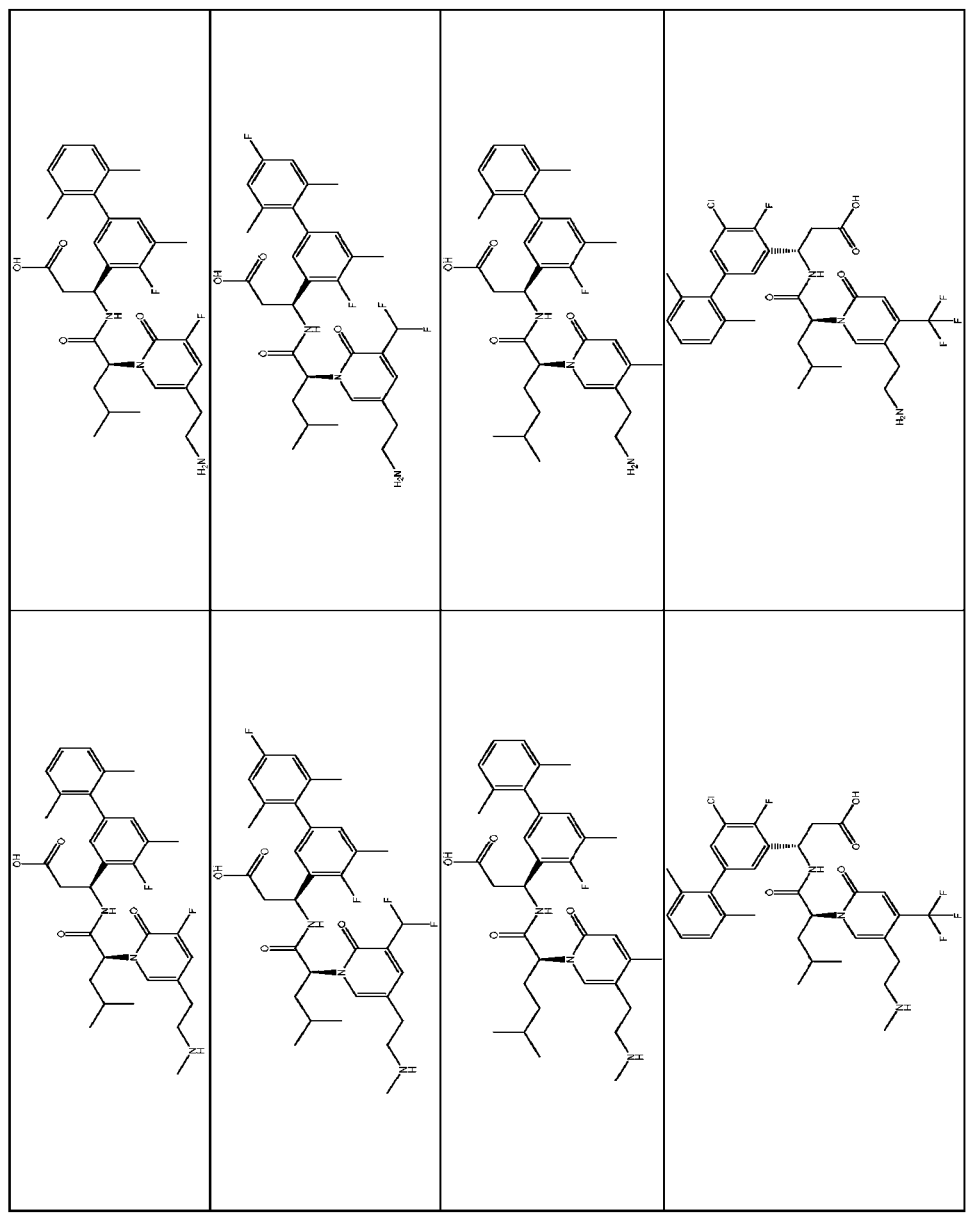
Figure 2:
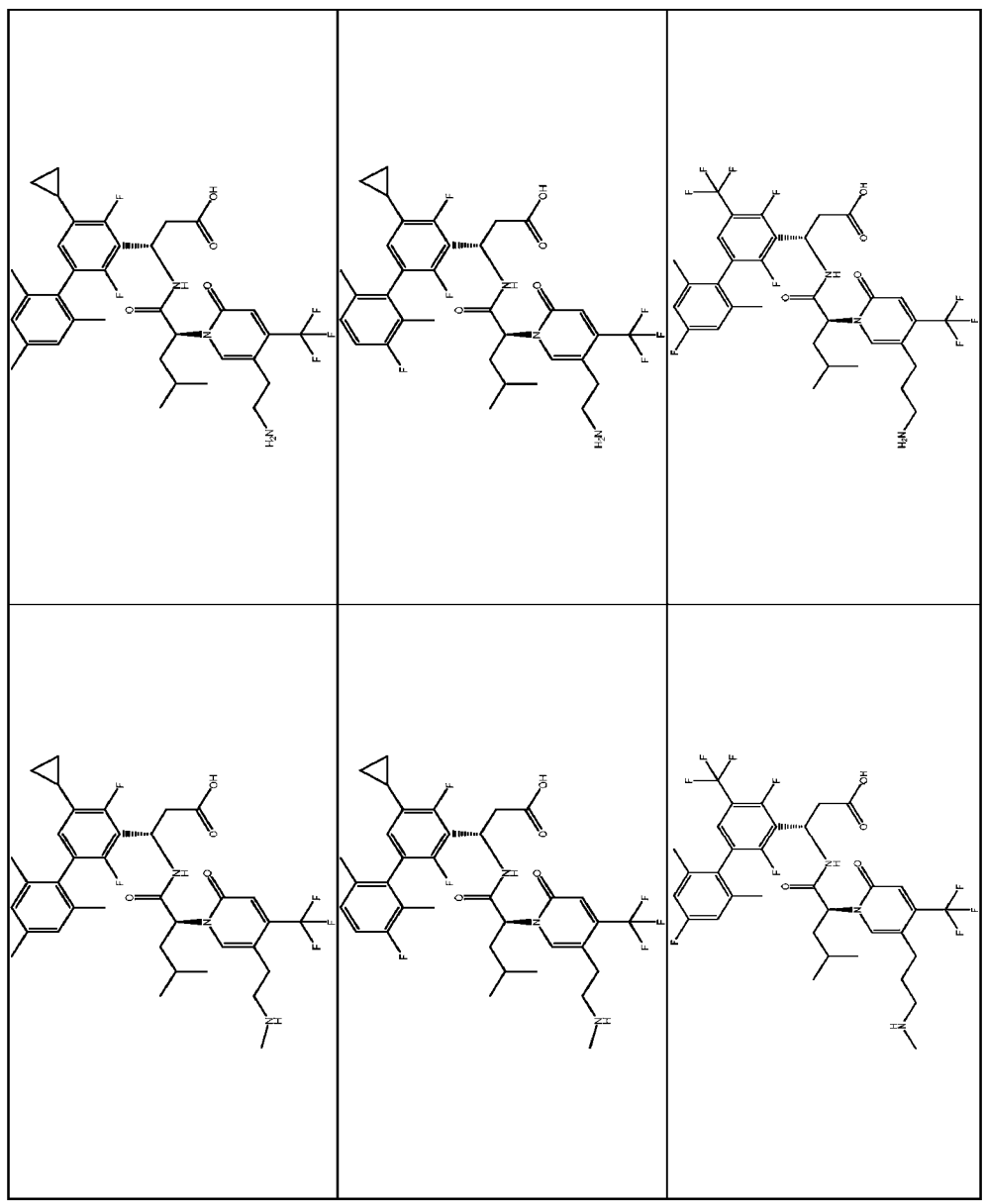
Figure 2:
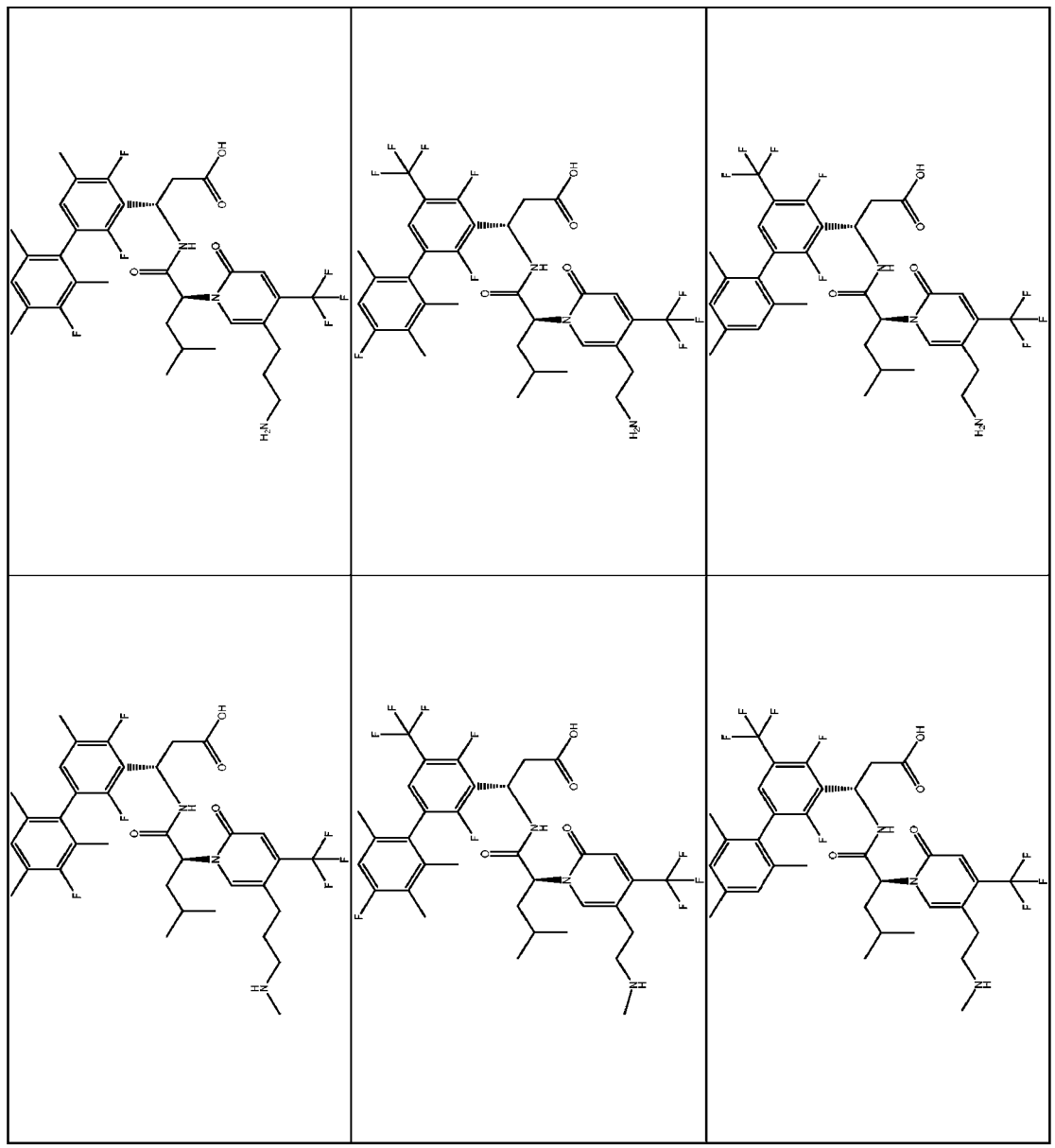
Figure 2:
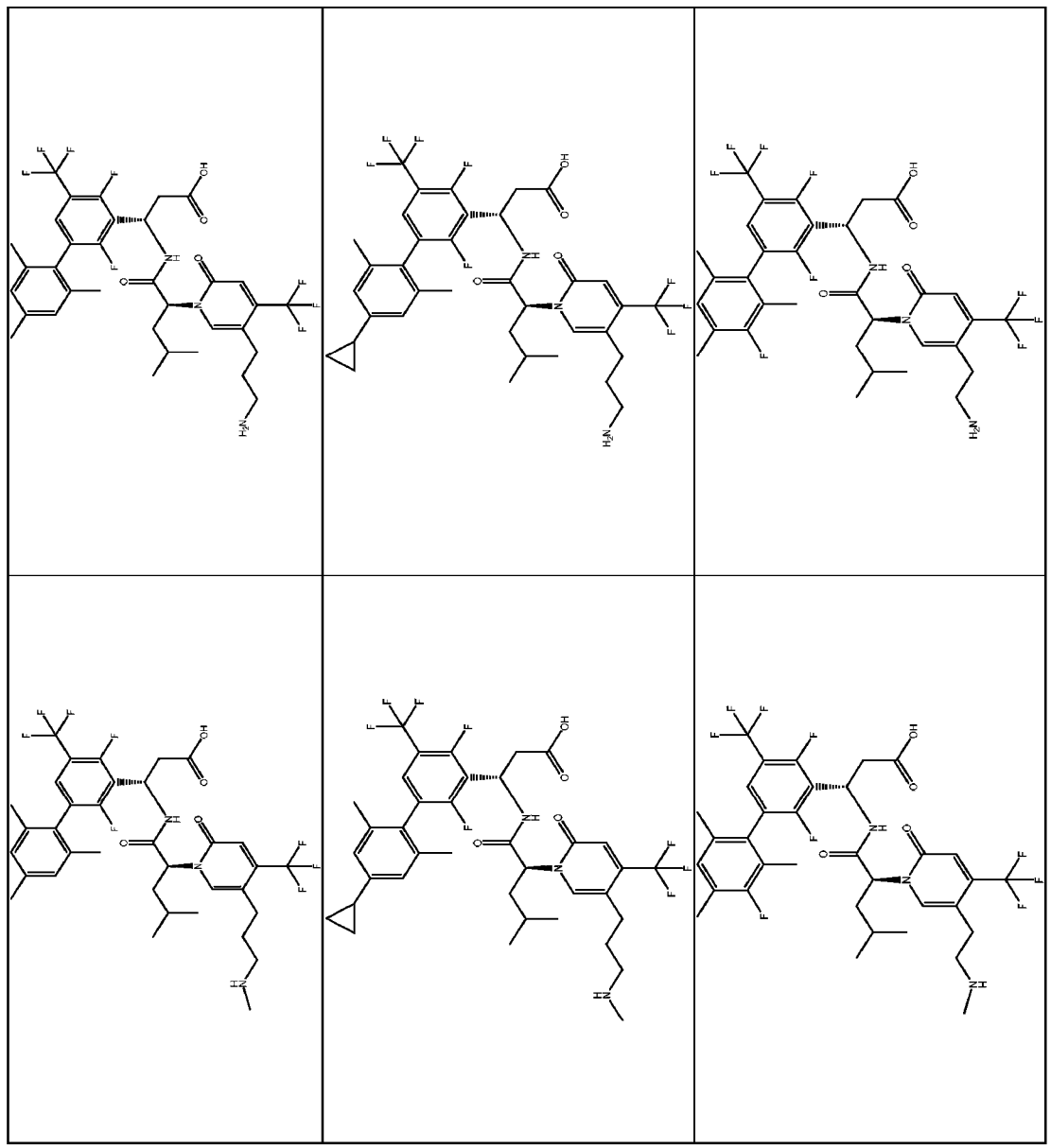

In one embodiment of the above Formula (Ib), the compound is a compound recited in FIGS. 2 and/or 3.

In some embodiments, the invention relates to a compound of Formula (I), Formula (Ia), or Formula (Ib):

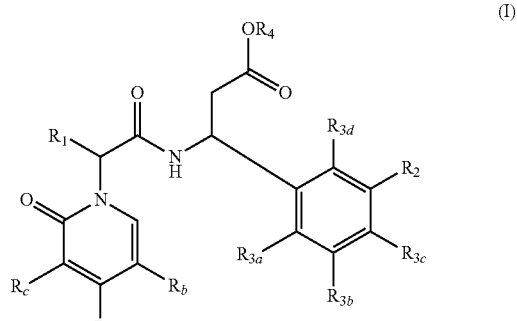

(I)

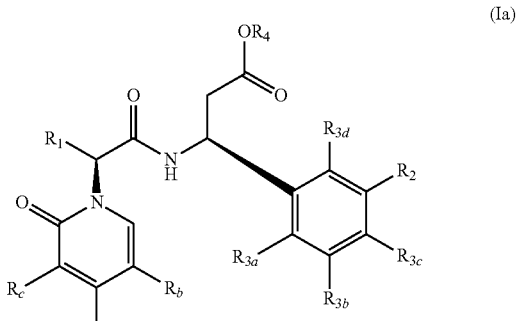

(Ia)

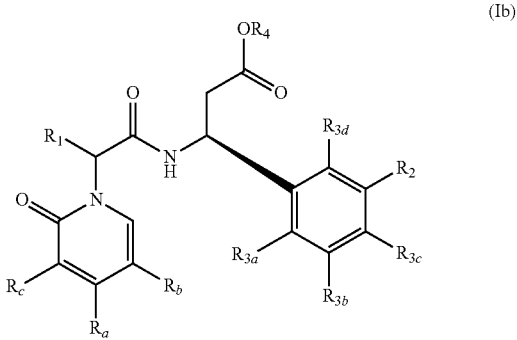

(Ib)

or a pharmaceutically acceptable salt thereof;
wherein
$R_a$, $R_b$, and $R_c$ are independently selected from the group consisting of H, Me, halide, $CF_3$, $C(H)F_2$, $C(F)H_2$, —CN, —$OCF_3$, substituted or unsubstituted ($C_1$-$C_5$)-alkyl, ($C_1$-$C_5$)-alkoxy, —$CH_2CF_3$, and substituted or unsubstituted —($C_1$-$C_5$)alkylene-N—($R_x$)($R_y$); provided that at least one of $R_a$, $R_b$, and $R_c$ is —($C_1$-$C_5$)alkylene-N—($R_x$)($R_y$), wherein the substituted ($C_1$-$C_5$)-alkyl is substituted with halide, amino, or ($C_1$-$C_4$)-alkylamino; and the substituted —($C_1$-$C_5$)alkylene-N—($R_x$)($R_y$) is substituted with halide, ($C_1$-$C_5$)-alkyl, ($C_1$-$C_5$)-alkyl-$OCH_3$, ($C_1$-$C_4$)-haloalkyl, ($C_3$-$C_6$)-cycloalkyl, ($C_1$-$C_4$)-alkoxy, or heterocyclyl;

$R_x$ and $R_y$ are independently selected from the group consisting of H and ($C_1$-$C_6$)-alkyl; or $R_x$ and $R_y$ taken together with the N to which they are attached form a 4-6 membered ring;

$R_1$ is substituted or unsubstituted ($C_1$-$C_6$)-alkyl, ($C_1$-$C_4$)-alkylene-($C_3$-$C_6$)-cycloalkyl, or ($C_1$-$C_4$)-alkylene-($C_1$-$C_4$)-alkoxy, wherein the substituted ($C_1$-$C_6$)-alkyl is substituted with halide or ($C_3$-$C_6$)-cycloalkyl;

$R_2$ is

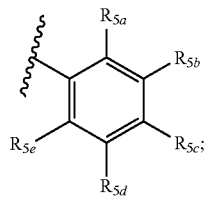

$R_{3a}$ and $R_{3b}$ are independently selected from the group consisting $(C_1$-$C_5)$-alkyl, $(C_3$-$C_6)$-cycloalkyl, 3-6 membered heterocycloalkyl, —OH, —CN, halide, $CF_3$, $C(H)F_2$, $C(F)H_2$, —$(C_1$-$C_4)$-alkoxy, —$OCF_3$, and $(C_1$-$C_4)$-alkylene-$(C_1$-$C_4)$-alkoxy; provided that $R_{3a}$ and $R_{3b}$ are not both H;

$R_{3c}$ is selected from the group consisting of H, $(C_1$-$C_5)$-alkyl, $(C_3$-$C_6)$-cycloalkyl, 3-6 membered heterocycloalkyl, hydroxyl, halide, $CF_3$, $C(H)F_2$, $C(F)H_2$, —$(C_1$-$C_4)$-alkoxy, —$OCF_3$—CN, and substituted or unsubstituted $(C_1$-$C_4)$-alkylene-$(C_1$-$C_4)$-alkoxy;

$R_{3d}$ is selected from the group consisting of H, $(C_1$-$C_5)$-alkyl, hydroxyl, halide, and —$(C_1$-$C_4)$-alkoxy;

$R_4$ is H, or $(C_1$-$C_4)$-alkyl;

$R_{5a}$, and $R_{5e}$ are independently selected from the group consisting of H, CN, halide, $CF_3$, $C(H)F_2$, $C(F)H_2$, —$CH_2CF_3$, $(C_3$-$C_6)$-cycloalkyl $(C_1$-$C_5)$-alkyl, 3-6 membered heterocycloalkyl hydroxyl, and $(C_1$-$C_4)$-alkoxy; and $R_{5b}$, $R_{5c}$, and $R_{5d}$ are independently selected from the group consisting of H, CN, halide, $CF_3$, $C(H)F_2$, $C(F)H_2$, —$CH_2CF_3$, $(C_1$-$C_5)$-alkyl, $(C_3$-$C_6)$-cycloalkyl, 3-6 membered heterocycloalkyl, hydroxyl, and $(C_1$-$C_4)$-alkoxy.

In one embodiment of the above Formula (Ib), the compound is not a compound recited in FIG. 1.

In one embodiment of the above Formula (Ib), the compound is a compound recited in FIGS. 2 and/or 3.

In some embodiments, a compound of Formula (I) can be a compound of Formula (Ib),

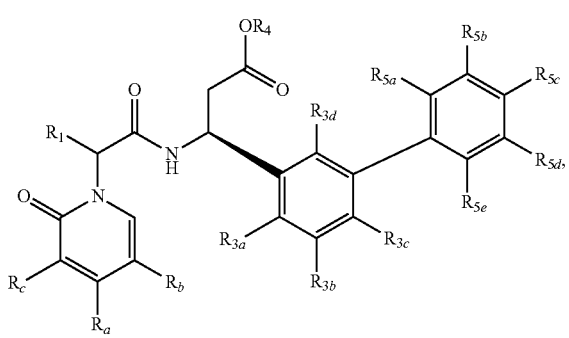

(Ib)

wherein $R_a$ is selected from the group consisting of hydrogen, and $(C_1$-$C_5)$-alkyl optionally substituted with halide;

$R_b$ is —$(C_1$-$C_5)$alkylene-N—$(R_x)(R_y)$;

$R_x$ and $R_y$ are independently selected from the group consisting of $(C_1$-$C_6)$-alkyl; or $R_x$ and $R_y$ taken together with the N to which they are attached form a 4-6 membered ring optionally substituted with halide or $(C_1$-$C_4)$-alkoxy;

$R_c$ are is selected from the group consisting of hydrogen and $(C_1$-$C_5)$-alkyl optionally substituted with halide;

$R_1$ is $(C_1$-$C_6)$-alkyl;

$R_{3a}$ is halide;

$R_{3b}$ is selected from the group consisting of $(C_1$-$C_5)$-alkyl optionally substituted with halide, and $(C_3$-$C_6)$-cycloalkyl;

$R_{3c}$ is hydrogen;

$R_{3a}$ is selected from the group consisting of H and halide;

$R_4$ is hydrogen;

$R_{5a}$, and $R_{5e}$ are each $(C_1$-$C_5)$-alkyl; and $R_{5b}$, $R_{5c}$, and $R_{5d}$ are independently selected from the group consisting of H, CN, halide, $(C_1$-$C_5)$-alkyl optionally substituted with halide (e.g., $CF_3$, $C(H)F_2$, $C(F)H_2$, —$CH_2CF_3$), $(C_3$-$C_6)$-cycloalkyl, 3-6 membered heterocycloalkyl, hydroxyl, and $(C_1$-$C_4)$-alkoxy.

In some embodiments, a compound of Formula (I) can be a compound of Formula (Ia),

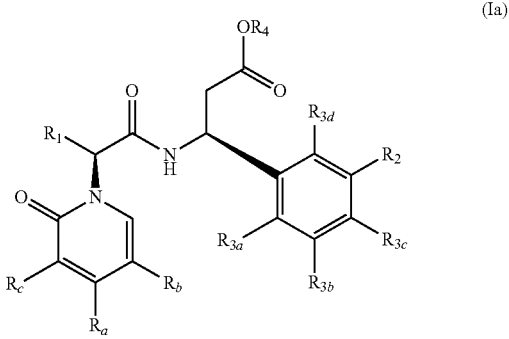

(Ia)

wherein $R_a$ is selected from the group consisting of hydrogen, and methyl optionally substituted with halide;

$R_b$ is —$(C_1$-$C_5)$alkylene-N—$(R_x)(R_y)$;

$R_x$ and $R_y$ are independently selected from the group consisting of methyl and ethyl; or $R_x$ and $R_y$ taken together with the N to which they are attached form a 4-5 membered ring optionally substituted with F or methoxy;

$R_c$ are is selected from the group consisting of hydrogen and methyl optionally substituted with halide;

$R_1$ is selected from the group consisting of isobutyl and isopentyl;

$R_{3a}$ is F;

$R_{3b}$ is selected from the group consisting of $(C_1$-$C_5)$-alkyl optionally substituted with F, and $(C_3$-$C_6)$-cycloalkyl;

$R_{3c}$ is hydrogen;

$R_{3d}$ is selected from the group consisting of H and F;

$R_4$ is hydrogen;

$R_{5a}$, and $R_{5e}$ are each methyl;

$R_{5b}$ and $R_{5d}$ are independently selected from the group consisting of H, F, methyl and methoxy; and $R_{5c}$ is selected from the group consisting of F, methyl and cyclopropyl.

In some embodiments, a compound of Formula (I) can be a compound of Formula (Ia),

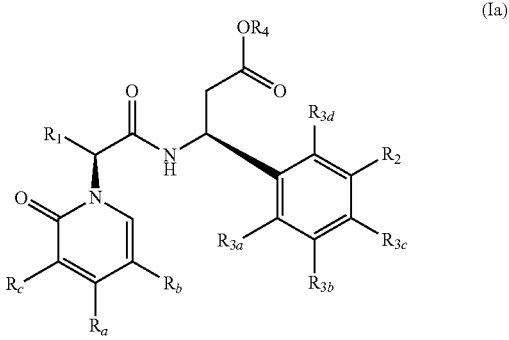

(Ia)

wherein $R_a$ is selected from the group consisting of hydrogen, and methyl optionally substituted with halide;

$R_b$ is —$(C_1$-$C_5)$alkylene-N—$(R_x)(R_y)$;

$R_x$ and $R_y$ are methyl; or $R_x$ and $R_y$ taken together with the N to which they are attached form a 4-5 membered ring optionally substituted with F or methoxy;

$R_c$ are is selected from the group consisting of hydrogen and methyl optionally substituted with halide;

$R_1$ is selected from the group consisting of isobutyl and isopentyl;

$R_{3a}$ is F;

$R_{3b}$ is selected from the group consisting of $(C_1$-$C_5)$-alkyl optionally substituted with F, and $(C_3$-$C_6)$-cycloalkyl;

$R_{3c}$ is hydrogen;

$R_{3d}$ is F;

$R_4$ is hydrogen;

$R_{5a}$, and $R_{5e}$ are each methyl;

$R_{5b}$ and $R_{5a}$ are independently selected from the group consisting of H, F, methyl and methoxy; and $R_{5c}$ is selected from the group consisting of F, methyl and cyclopropyl.

In some embodiments, a compound of Formula (I) can be a compound of Formula (Ia):

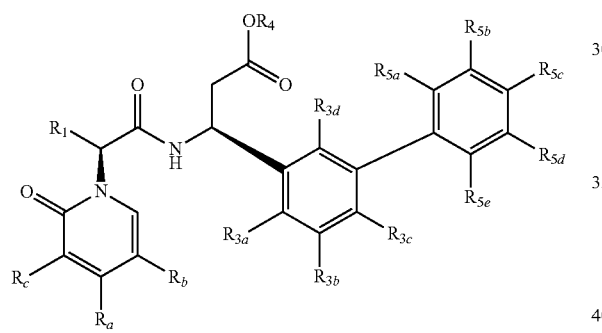

(Ia)

or a pharmaceutically acceptable salt thereof, wherein $R_a$, $R_b$, $R_c$, $R_1$, $R_{3a}$, $R_{3b}$, $R_{3c}$, $R_{3d}$, $R_{5a}$, $R_{5b}$, $R_{5c}$, $R_{5d}$, $R_{5e}$, and $R_4$ in Formula (Ia) are each independently defined as above with respect to Formula (I), and provided that the compound of Formula (Ia) is not a compound selected from the group consisting of:

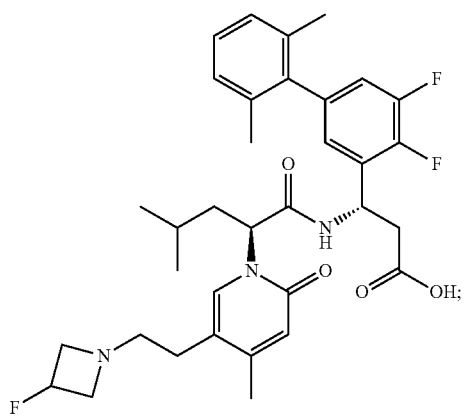

-continued

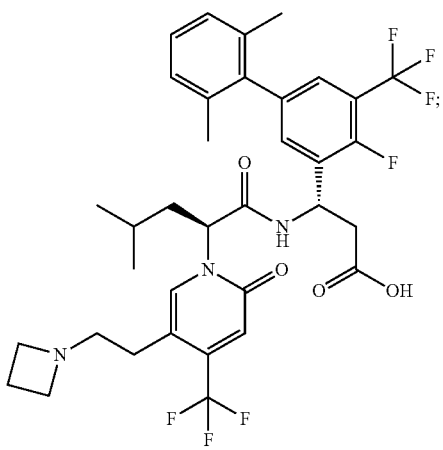

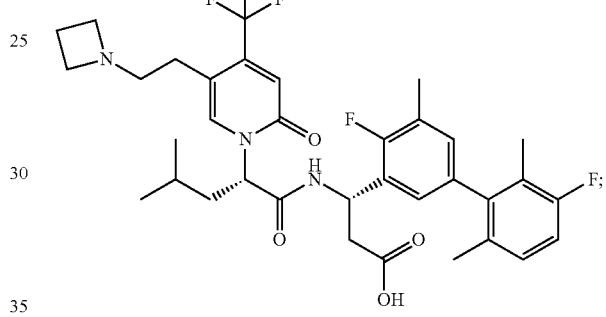

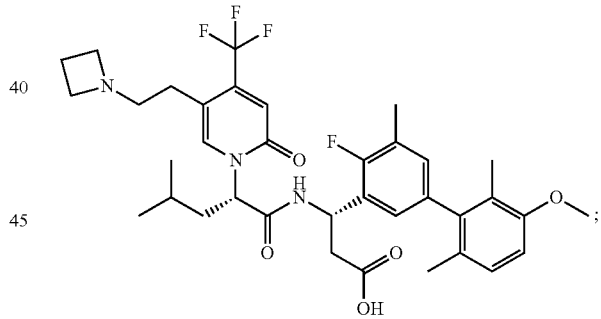

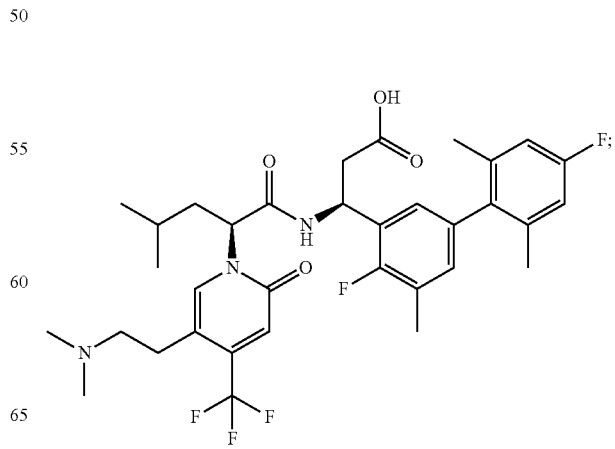

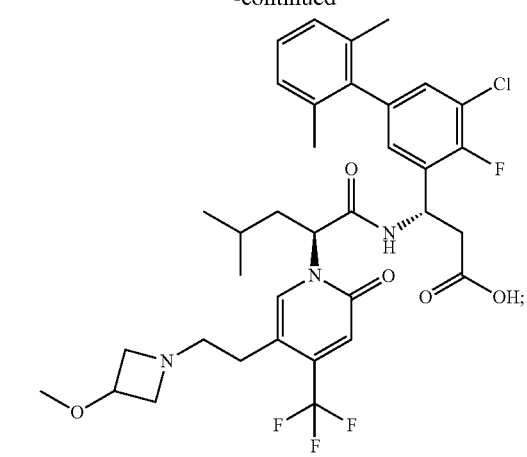
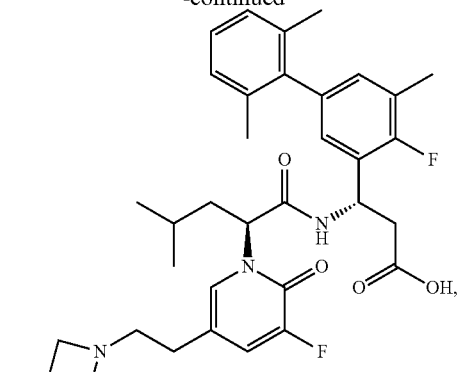
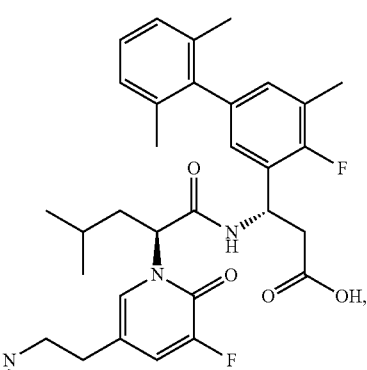
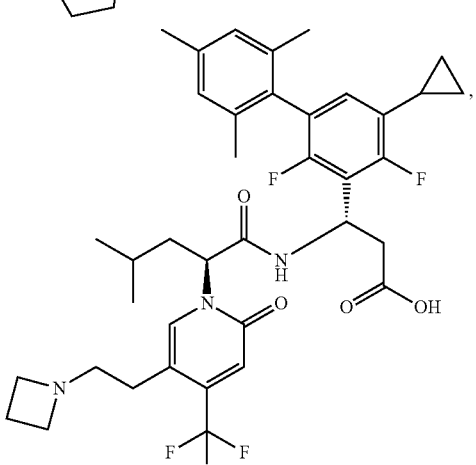
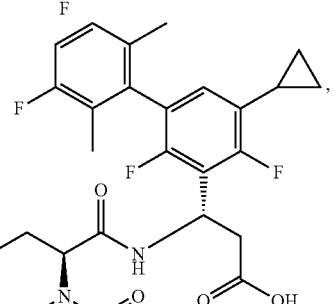
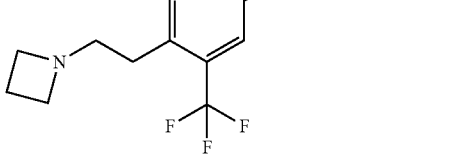

135
-continued
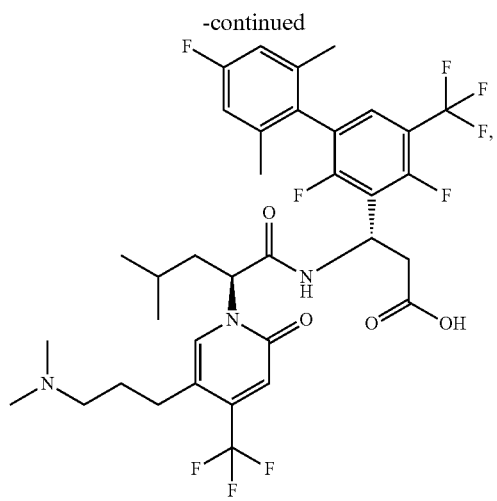
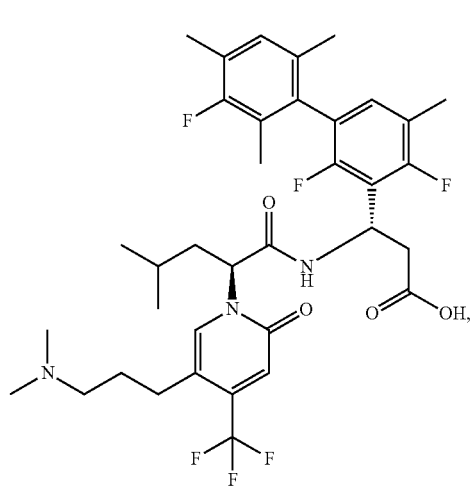
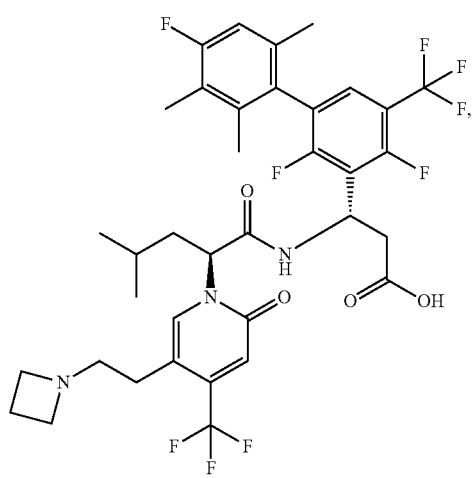
136
-continued
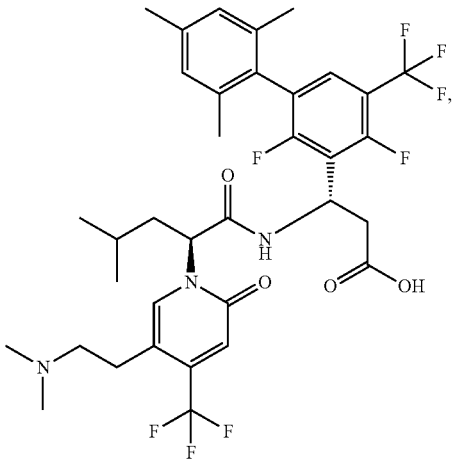
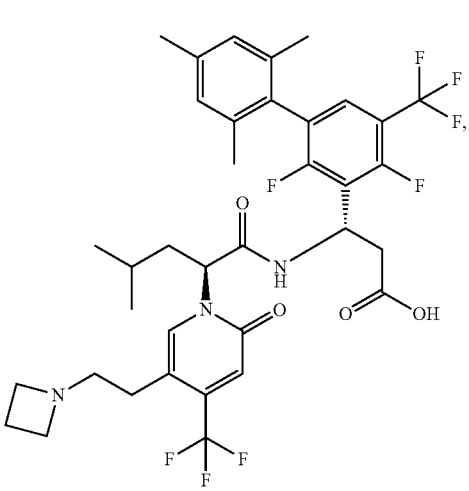
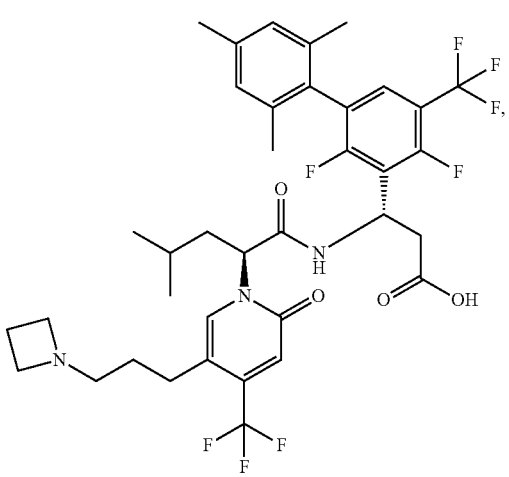

-continued

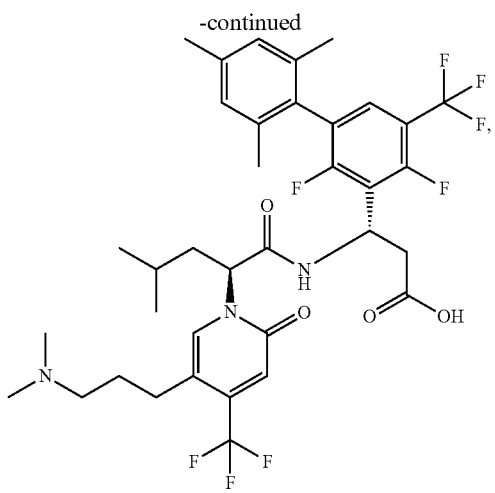

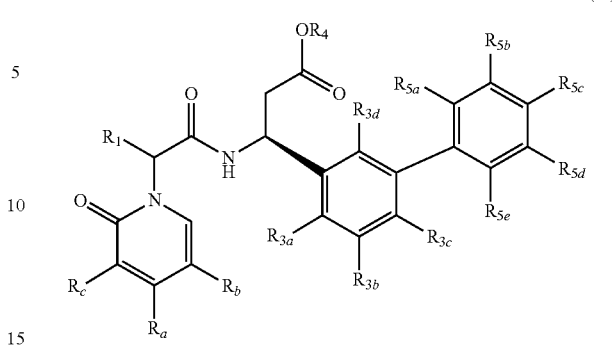

or a pharmaceutically acceptable salt thereof, wherein $R_a$, $R_b$, $R_c$, $R_1$, $R_{3a}$, $R_{3b}$, $R_{3c}$, $R_{3d}$, $R_{5a}$, $R_{5b}$, $R_{5c}$, $R_{5d}$, $R_{5e}$, and $R_4$ in Formula (Ia) are each independently defined as above with respect to Formula (I), and provided that the compound of Formula (Ia) is not a compound selected from the group consisting of:

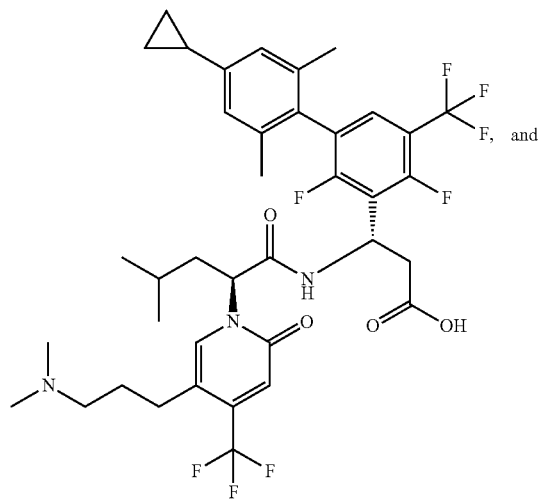

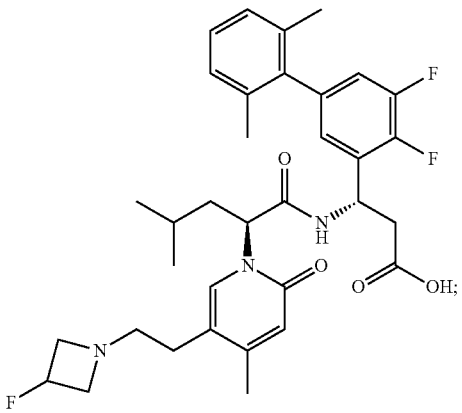

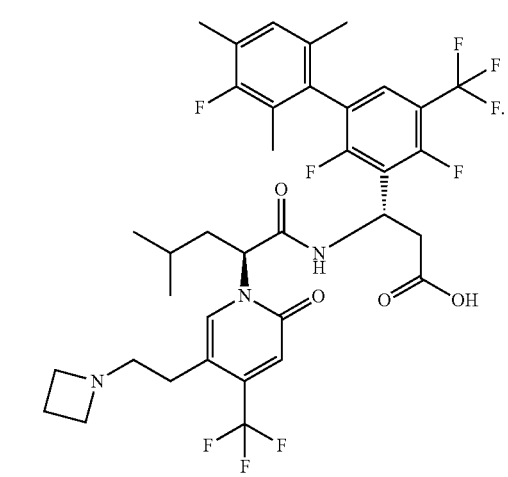

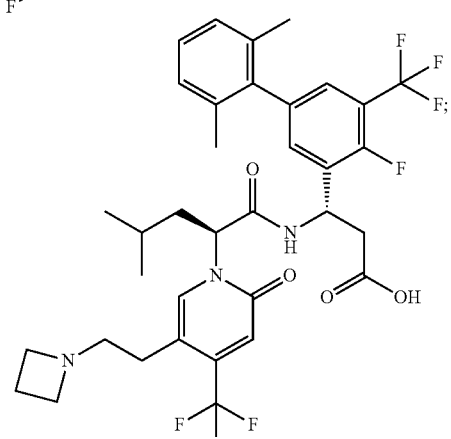

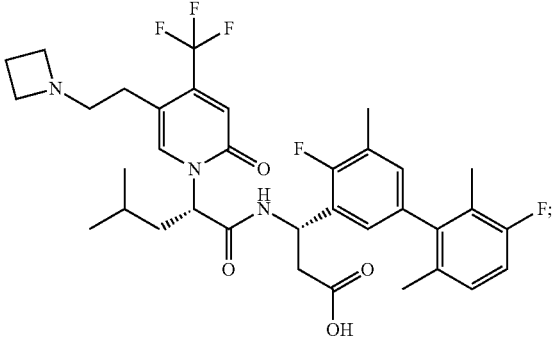

In some embodiments, a compound of Formula (I) can be a compound of Formula (Ib):

139
-continued
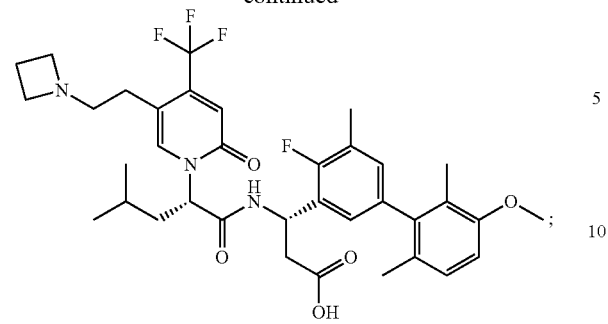
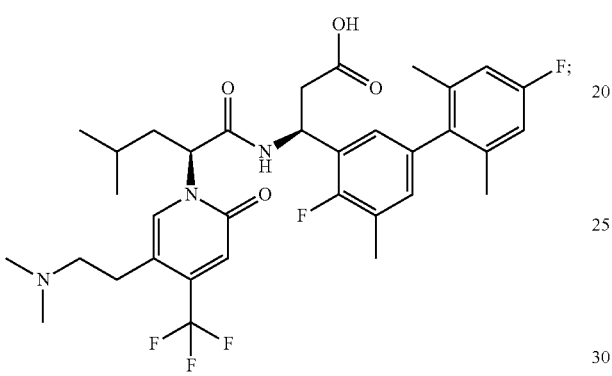
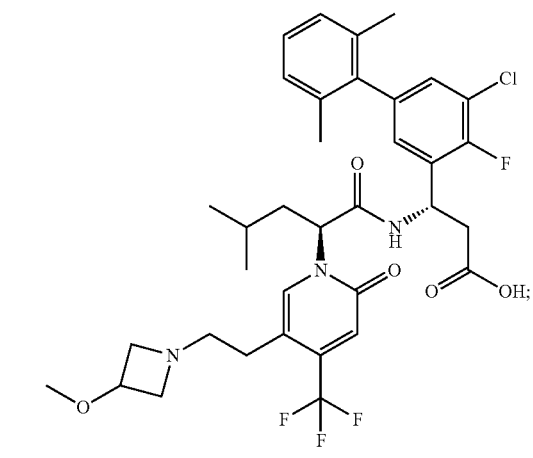
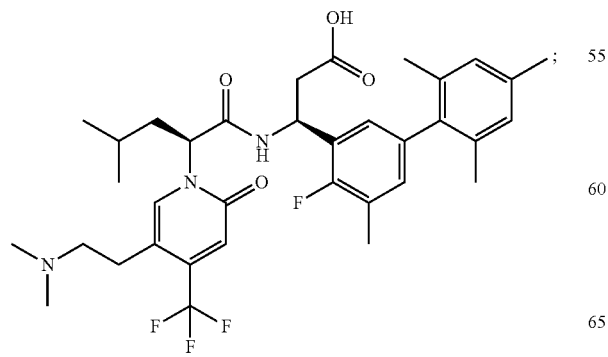
140
-continued
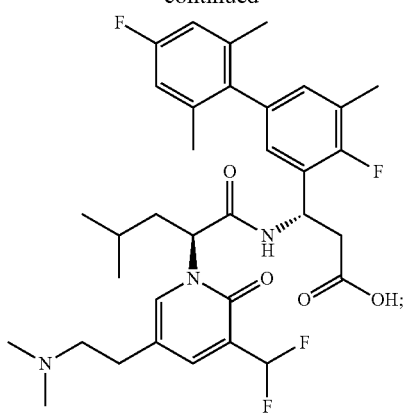
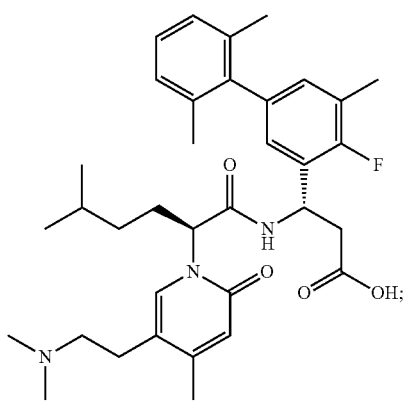
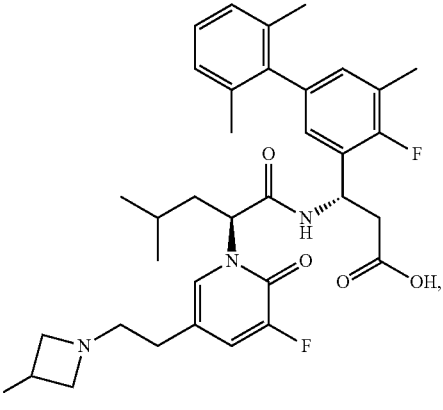
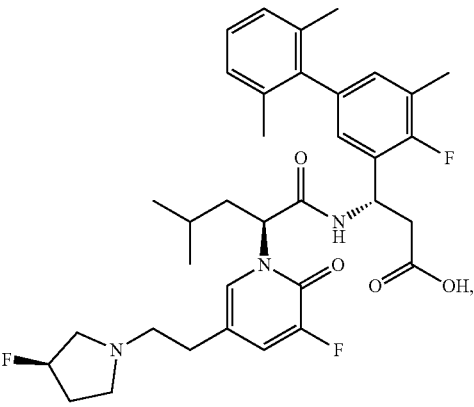

141
-continued
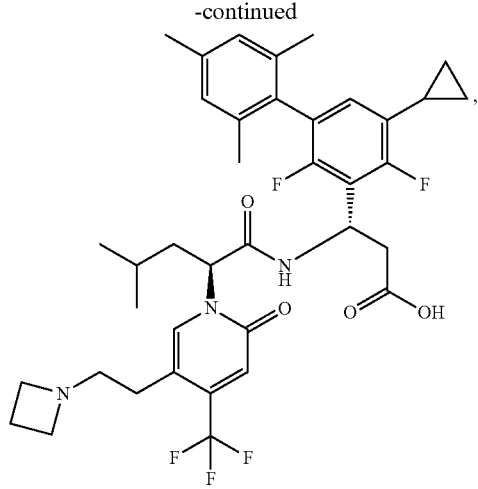
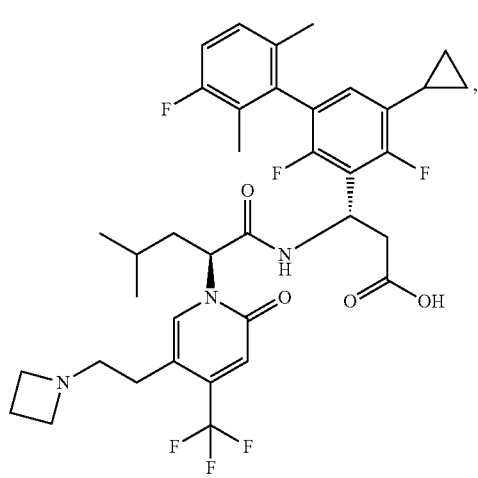
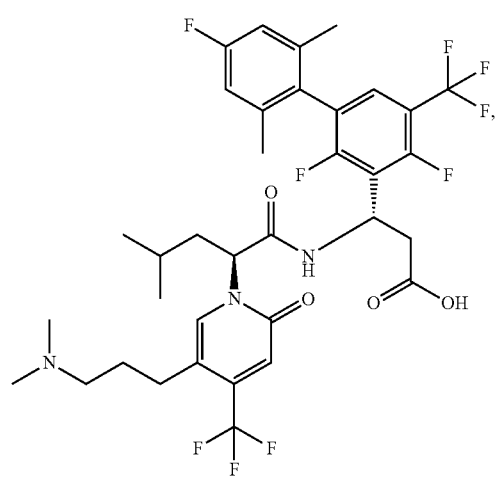
142
-continued
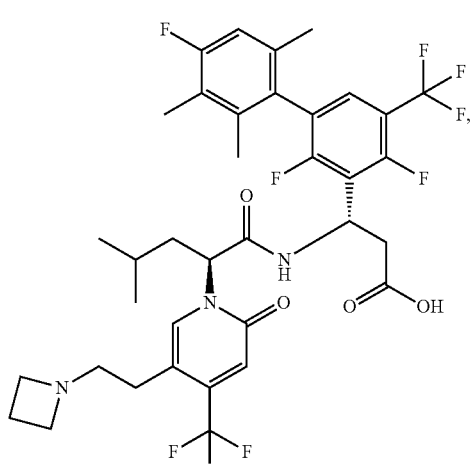
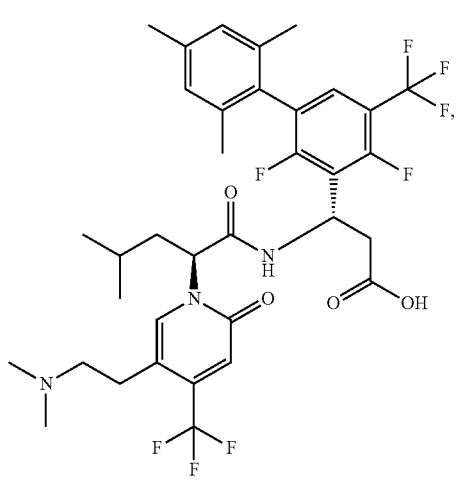

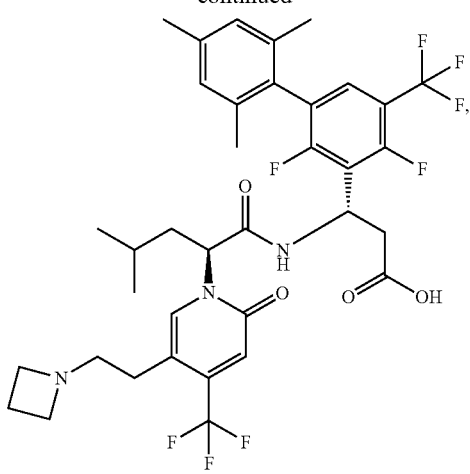

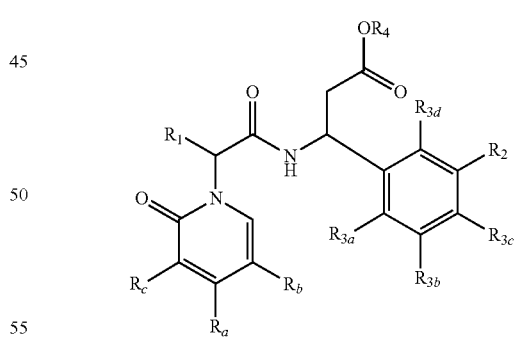

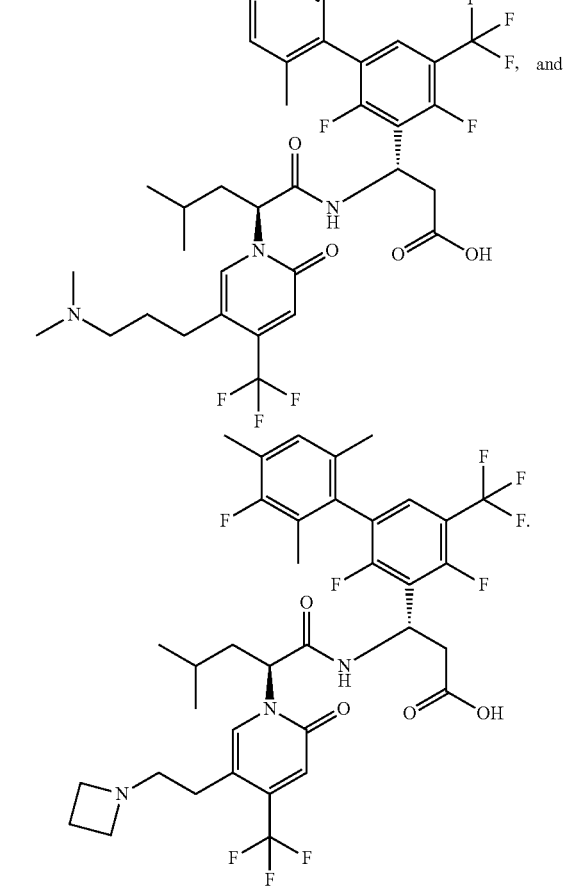

In some embodiments, a compound can be a compound of Formula (I)

$$(I)$$

wherein $R_a$, $R_b$, and $R_c$ are independently selected from the group consisting of H, Me, halide, $CF_3$, $C(H)F_2$, $C(F)H_2$, and —($C_1$-$C_5$)alkylene-N—($R_x$)($R_y$); provided that at least one of $R_a$, $R_b$, and $R_c$ is —($C_1$-$C_5$)alkylene-N—($R_x$)($R_y$);

$R_x$ and $R_y$ are independently selected from the group consisting of H and substituted or unsubstituted ($C_1$-$C_6$)-alkyl; or $R_x$ and $R_y$ taken together with the N to which they are attached form a 4-6 membered ring;

$R_1$ is methyl, ethyl, n-propyl, iso-propyl, n-butyl, iso-butyl, sec-butyl, or t-butyl;

145

$R_2$ is

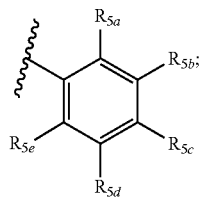

$R_{3a}$ and $R_{3b}$ are independently selected from the group consisting of H, $(C_1-C_5)$-alkyl, $(C_3-C_6)$-cycloalkyl, substituted or unsubstituted 3-6 membered heterocycloalkyl, —OH, —CN, halide, $CF_3$, $C(H)F_2$, $C(F)H_2$, —$(C_1-C_4)$-alkoxy, —$OCF_3$, and substituted or unsubstituted $(C_1-C_4)$-alkylene-$(C_1-C_4)$-alkoxy; provided that $R_{3a}$ and $R_{3b}$ are not both H;

$R_{3c}$, and $R_{3d}$ are H;

$R_4$ is H;

$R_{5a}$, and $R_{5e}$ are independently methyl;

$R_{5b}$, and $R_{5c}$ are independently selected from the group consisting of H, CN, halide, $CF_3$, $C(H)F_2$, $C(F)H_2$, substituted or unsubstituted $(C_1-C_5)$-alkyl, substituted or unsubstituted $(C_3-C_6)$-cycloalkyl, substituted or unsubstituted 3-6 membered heterocycloalkyl, hydroxyl, and $(C_1-C_4)$-alkoxy;

$R_{5d}$ is H; and provided the compound of Formula (I) is not a compound selected from the group consisting of:

a. (S)-3-(4,5-difluoro-2',6'-dimethyl-[1,1'-biphenyl]-3-yl)-3-((S)-2-(5-(2-(3-fluoroazetidine-1-yl)ethyl)-4-methyl-2-oxopyridin-1(2H)-yl)-4-methylpentanamido)propanoic acid;
b. (S)-3-((S)-2-(5-(2-(azetidin-1-yl)ethyl)-2-oxo-4-(trifluoromethyl)pyridin-1(2H)-yl)-4-methylpentanamido)-3-(4-fluoro-2',6'-dimethyl-5-(trifluoromethyl)-[1,1'-biphenyl]-3-yl)propanoic Acid;
c. (S)-3-((S)-2-(5-(2-(azetidin-1-yl)ethyl)-2-oxo-4-(trifluoromethyl)pyridin-1(2H)-yl)-4-methylpentanamido)-3-(3',4-difluoro-2',5',6'-trimethyl-[1,1'-biphenyl]-3-yl)propanoic Acid;
d. (S)-3-((S)-2-(5-(2-(azetidin-1-yl)ethyl)-2-oxo-4-(trifluoromethyl)pyridin-1(2H)-yl)-4-methylpentanamido)-3-(4-fluoro-3'-methoxy-2',5',6'-trimethyl-[1,1'-biphenyl]-3-yl)propanoic acid;
e. (S)-3-(4,4'-difluoro-2',5',6'-trimethyl-[1,1'-biphenyl]-3-yl)-3-((S)-2-(5-(2-(dimethylamino)ethyl)-2-oxo-4-(trifluoromethyl)pyridin-1(2H)-yl)-4-methylpentanamido)propanoic acid;
f. (S)-3-(5-chloro-4-fluoro-2',6'-dimethyl-[1,1'-biphenyl]-3-yl)-3-((S)-2-(5-(2-(3-methoxyazetidin-1-yl)ethyl)-2-oxo-4-(trifluoromethyl)pyridin-1(2H)-yl)-4-methylpentanamido)propanoic acid;
g. (S)-3-((S)-2-(5-(2-(dimethylamino)ethyl)-2-oxo-4-(trifluoromethyl)pyridin-1(2H)-yl)-4-methylpentanamido)-3-(4-fluoro-2',4',5',6'-tetramethyl-[1,1'-biphenyl]-3-yl)propanoic Acid;
h. (S)-3-(4,4'-difluoro-2',5',6'-trimethyl-[1,1'-biphenyl]-3-yl)-3-((S)-2-(3-(difluoromethyl)-5-(2-(dimethylamino)ethyl)-2-oxopyridin-1(2H)-yl)-4-methylpentanamido)propanoic acid;

146 i. (S)-3-((S)-2-(5-(2-(dimethylamino)ethyl)-4-methyl-2-oxopyridin-1(2H)-yl)-5-methylhexanamido)-3-(4-fluoro-2',5',6'-trimethyl-[1,1'-biphenyl]-3-yl)propanoic Acid;
j. (S)-3-(4-fluoro-2',5',6'-trimethyl-[1,1'-biphenyl]-3-yl)-3-((S)-2-(3-fluoro-5-(2-(3-fluoroazetidine-1-yl)ethyl)-2-oxopyridin-1(2H)-yl)-4-methylpentanamido)propanoic acid; and
k. (S)-3-(4-fluoro-2',5',6'-trimethyl-[1,1'-biphenyl]-3-yl)-3-((S)-2-(3-fluoro-5-(2-((R)-3-fluoropyrrolidin-1-yl)ethyl)-2-oxopyridin-1(2H)-yl)-4-methylpentanamido)propanoic acid;

or a pharmaceutically acceptable salt thereof.

In some embodiments, a compound can be a compound of Formula (Ia)

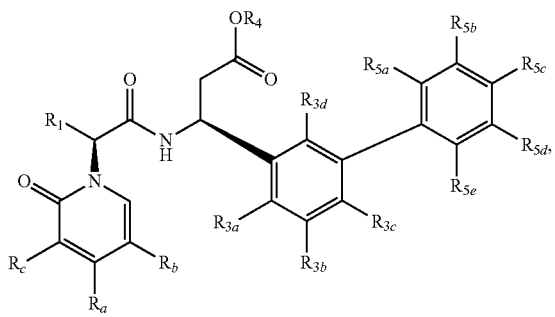

(Ia)

wherein:

$R_a$, is $CF_3$;

$R_b$ is substituted or unsubstituted —$(C_1-C_5)$alkylene-N—$(R_x)(R_y)$;

$R_x$ and $R_y$ are independently substituted or unsubstituted $(C_1-C_6)$-alkyl; or Rx and $R_y$ taken together with the N to which they are attached form a 4-6 membered ring;

$R_c$ is H;

$R_1$ is substituted or unsubstituted $(C_1-C_6)$-alkyl;

$R_{3a}$ and $R_{3b}$ are independently selected from the group consisting of H, substituted or unsubstituted $(C_1-C_5)$-alkyl, substituted or unsubstituted $(C_3-C_6)$-cycloalkyl, substituted or unsubstituted 3-6 membered heterocycloalkyl, —OH, —CN, halide, $CF_3$, $C(H)F_2$, $C(F)H_2$, —$(C_1-C_4)$-alkoxy, —$OCF_3$, and substituted or unsubstituted $(C_1-C_4)$-alkylene-$(C_1-C_4)$-alkoxy; provided that $R_{3a}$ and $R_{3b}$ are not both H;

$R_{3c}$ is H;

$R_{3d}$ is halide;

$R_4$ is H;

$R_{5a}$, and $R_{5e}$ are each independently selected from $(C_1-C_5)$-alkyl; and $R_{5b}$, $R_{5c}$, and $R_{5d}$ are independently selected from the group consisting of H, CN, halide, $CF_3$, $C(H)F_2$, $C(F)H_2$, —$CH_2CF_3$, substituted or unsubstituted $(C_1-C_5)$-alkyl, substituted or unsubstituted $(C_3-C_6)$-cycloalkyl, substituted or unsubstituted 3-6 membered heterocycloalkyl, hydroxyl, and $(C_1-C_4)$-alkoxy;

or a pharmaceutically acceptable salt thereof;

provided the compound of Formula (Ia) is not selected from the group consisting of:
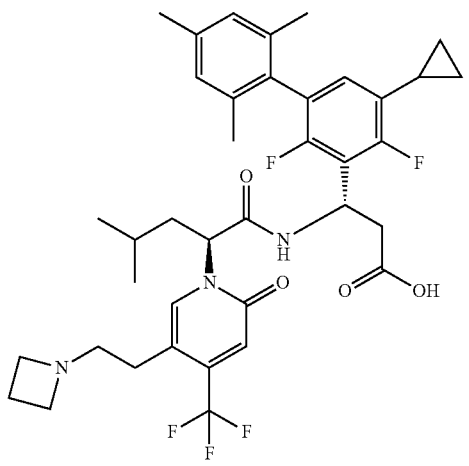
,
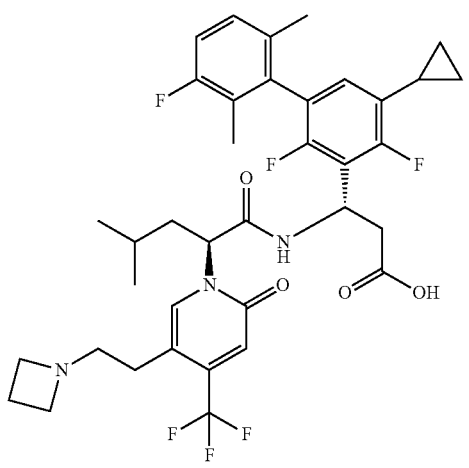
,
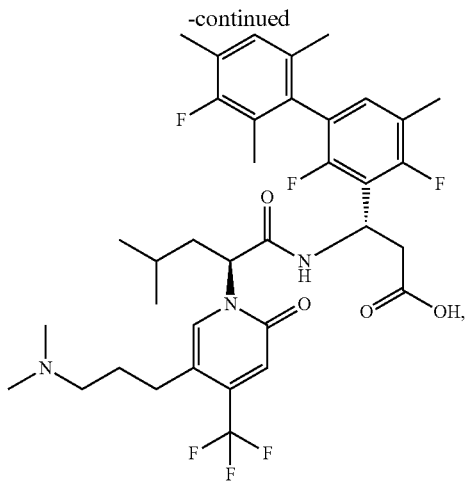
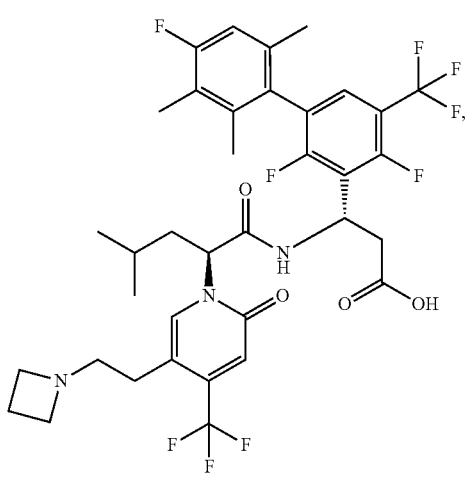
,
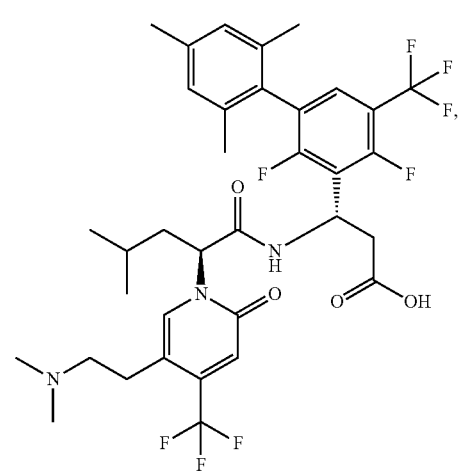

149
-continued

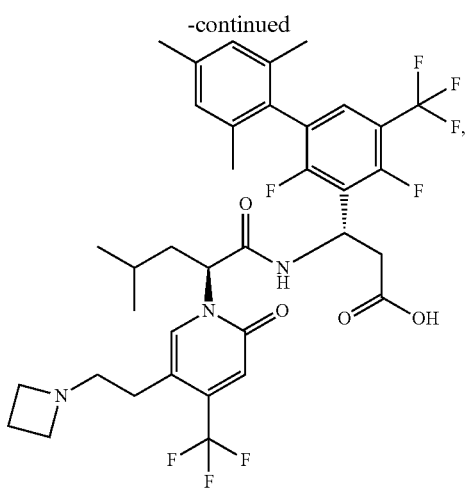

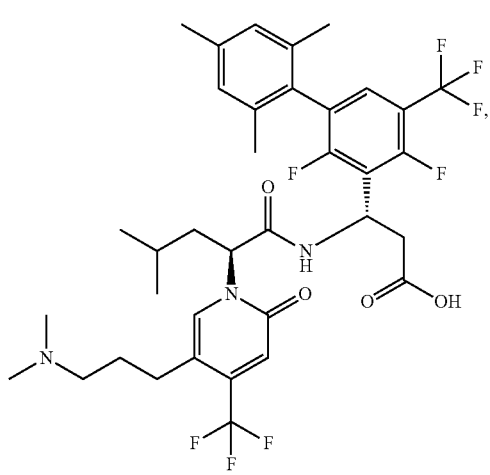

150
-continued

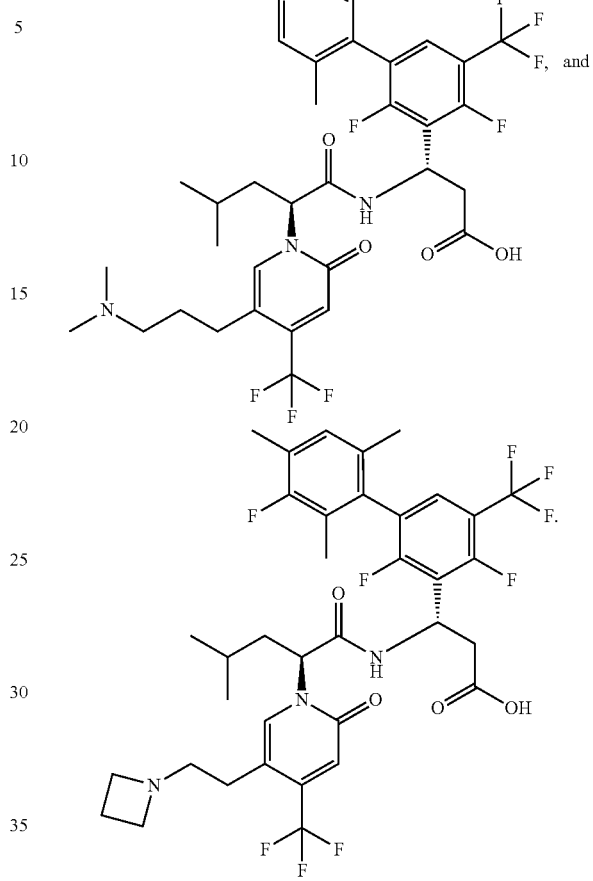

In some embodiments, a compound can be a compound of Formula (Ib)

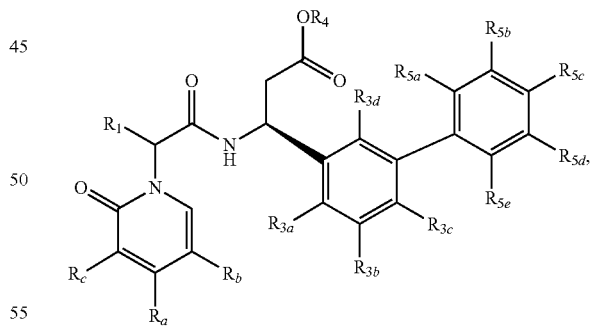

(Ib)

wherein:
$R_a$, is $CF_3$;
$R_b$ is substituted or unsubstituted —($C_1$-$C_5$)alkylene-N—($R_x$)($R_y$);
$R_x$ and $R_y$ are independently substituted or unsubstituted ($C_1$-$C_6$)-alkyl; or Rx and Ry taken together with the N to which they are attached form a 4-6 membered ring;
$R_c$ is H;
$R_1$ is substituted or unsubstituted ($C_1$-$C_6$)-alkyl;

$R_{3a}$ and $R_{3b}$ are independently selected from the group consisting of H, substituted or unsubstituted $(C_1-C_5)$-alkyl, substituted or unsubstituted $(C_3-C_6)$-cycloalkyl, substituted or unsubstituted 3-6 membered heterocycloalkyl, —OH, —CN, halide, $CF_3$, $C(H)F_2$, $C(F)H_2$, —$(C_1-C_4)$-alkoxy, —$OCF_3$, and substituted or unsubstituted $(C_1-C_4)$-alkylene-$(C_1-C_4)$-alkoxy; provided that $R_{3a}$ and $R_{3b}$ are not both H;

$R_{3c}$ is H;

$R_{3d}$ is halide;

$R_4$ is H;

$R_{5a}$, and $R_{5e}$ are each independently selected from $(C_1-C_5)$-alkyl; and $R_{5b}$, $R_{5c}$, and $R_{5d}$ are independently selected from the group consisting of H, CN, halide, $CF_3$, $C(H)F_2$, $C(F)H_2$, —$CH_2CF_3$, substituted or unsubstituted $(C_1-C_5)$-alkyl, substituted or unsubstituted $(C_3-C_6)$-cycloalkyl, substituted or unsubstituted 3-6 membered heterocycloalkyl, hydroxyl, and $(C_1-C_4)$-alkoxy;

or a pharmaceutically acceptable salt thereof;

provided the compound of Formula (Ib) is not selected from the group consisting of:

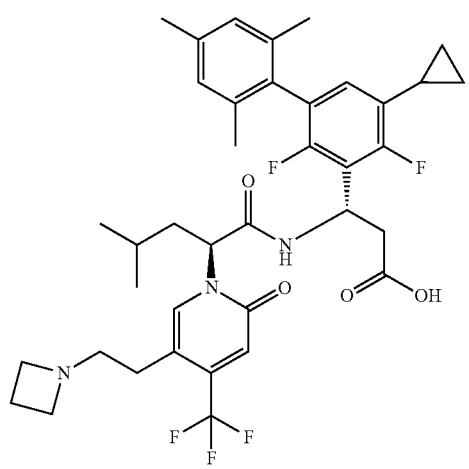

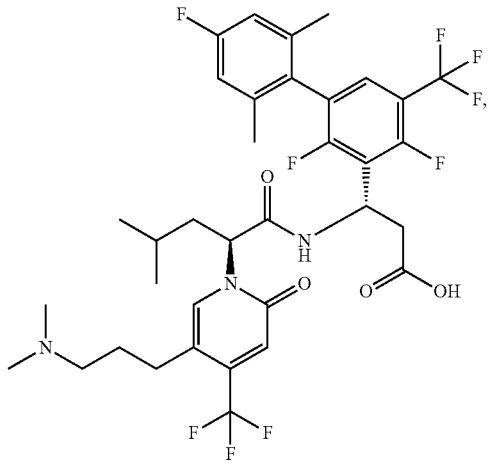

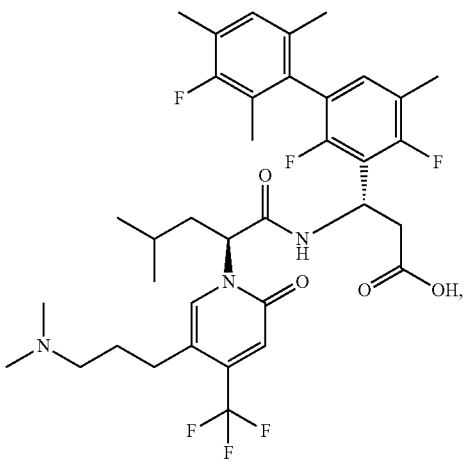

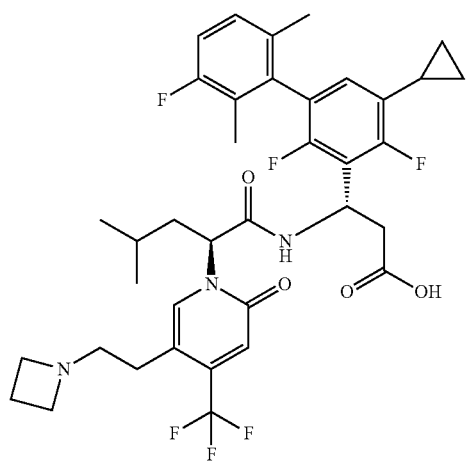

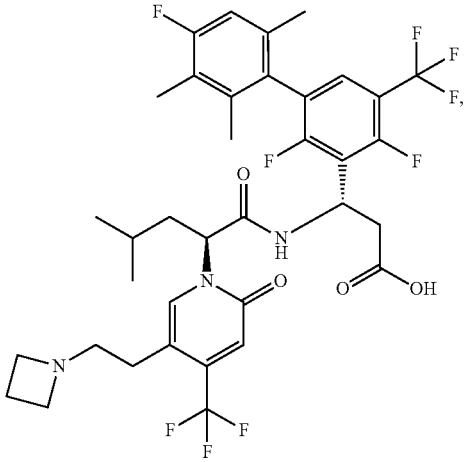

153
-continued

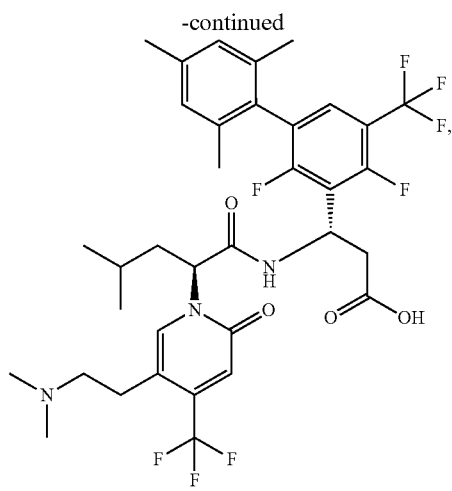

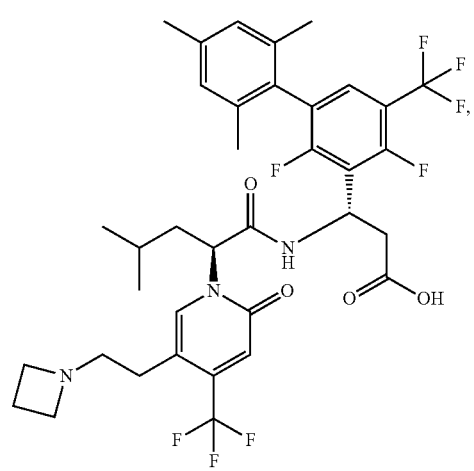

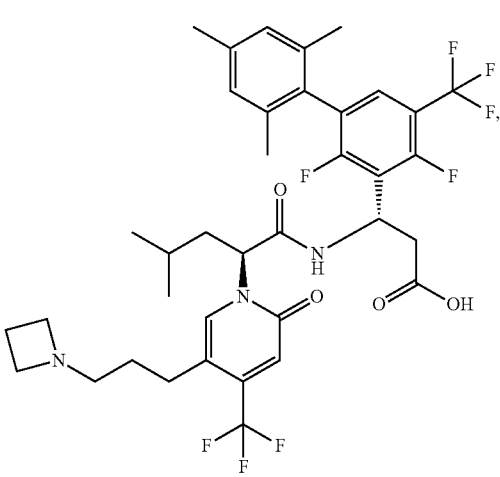

154
-continued

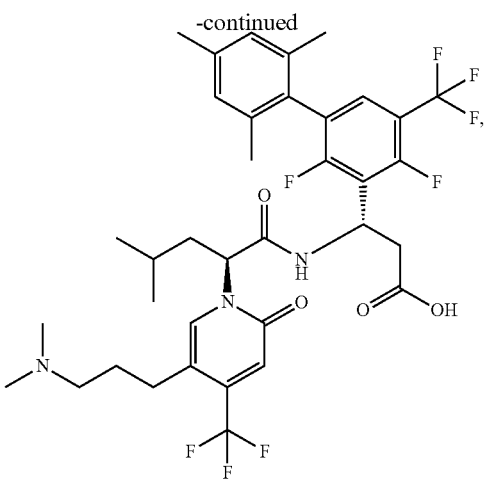

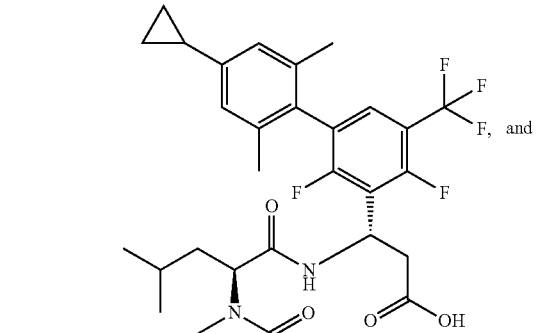

Example 1. General Schemes for the Synthesis of $\alpha_4\beta_7$ Inhibitors

β-Amino Acid Synthesis

The synthesis of β-amino acids can be achieved using well known procedures described in the literature, such as but not limited to "Enantioselective Synthesis of β-Amino Acids," Second Edition, Editors: Eusebio Juaristi, Vadim A. Soloshonok, First published: 27 Jan. 2005, John Wiley & Sons, Inc.; Ellman et. Al Acc. Chem. Res. 2002. 35, 984-995; Franklin A. Davis and Bang-Chi Chen Chem. Soc.

Rev., 1998, 27, 13-18; Jacobsen, M. F.; Skrydstrup, T. J. Org. Chem. 2003, 68, 7122; Tang, T. P.; Ellman, J. A. J. Org. Chem. 2002, 67, 7819; and Tang, T. P.; Ellman, J. A. J. Org. Chem. 1999, 64, 12.

Reductive Aminations

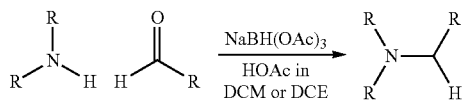

Procedure A: A mixture of amine (1 equiv.), aldehyde (1.2 equiv.) in DCM (1-2 mL/mmol amine) was stirred at room temperature for 30 min. Then NaBH(OAc)$_3$ (1.5 equiv.) was added portion-wise and stirred at room temperature overnight. The solvent was concentrated in vacuo and the residue was purified by silica gel chromatography to provide the desired amine.

Procedure B: A mixture of aldehyde (1 equiv.), amine (1.05-2 equiv.) in DCE (3-4 mL/mmol of aldehyde) was stirred at room temperature for 10-30 mins. Then NaBH(OAc)$_3$ (3-4 equiv.) was added portion-wise and stirred at room temperature 1-16 until complete by LC/MS. The solvent was concentrated in vacuo and the residue was purified by silica gel chromatography to provide the desired amine.

Procedure C: A mixture of aldehyde (1 equiv.), AcOH (1.2 equiv), amine (1.05-2 equiv.) in DCM (2-3 mL/mmol aldehyde) and MeOH (0.5 mL/mmol aldehyde) was stirred at room temperature for 15-30 mins Then NaBH(OAc)$_3$ (2 equiv.) was added portion-wise and stirred at room temperature 1-16 until complete by LC/MS. The solvent was concentrated in vacuo and the residue was purified by silica gel chromatography to provide the desired amine.

Alkylations

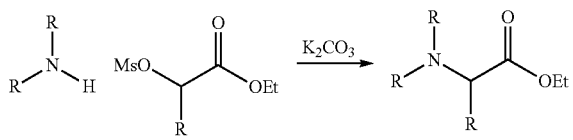

Procedure A: To a solution of amine (1 equiv.) in MeCN (3-4 mL/mmol amine) was added mesylate (1.5 equiv.) and K$_2$CO$_3$ (3 equiv.). The reaction mixture was stirred at 80° C. for 16 hours. The reaction mixture was concentrated in vacuo and the residue was purified by reverse phase HPLC to give the alkylated product.

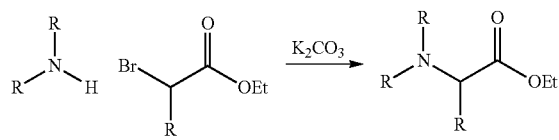

Procedure B: To a solution of amine (1 equiv.) in MeCN (3-4 mL/mmol amine) was added alkylbromide (2 equiv.) and K$_2$CO$_3$ (2 equiv.). The reaction mixture was stirred at 80° C. for 16 hours. The reaction mixture was concentrated in vacuo and the residue was purified by reverse phase HPLC to give the alkylated product.

Phenol Deprotections

A mixture of methoxypyridine (1 equiv.) in 44% HBr/AcOH (10 mL/mmol of substrate) was heated at 55-75° C. for 5-16 hours until complete by LCMS. The reaction was concentrated in vacuo and the residue purified by reverse phase HPLC to give the phenol product.

Wittig Reactions

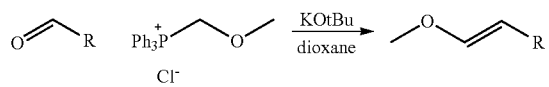

Procedure A: A mixture of (methoxymethyl)triphenylphosphonium chloride (1.5 equiv.), t-BuOK (2.5 equiv.) in dioxane (2 mL/mmol phosphonium salt) was stirred at room temperature for 15 minutes. Then aldehyde (1 equiv.) in THF (1 mL/mmol aldehyde) was added. The mixture was stirred for 2-16 h at room temperature. The reaction mixture was worked up (diluted with water and extracted with EtOAc; combined extracts dried over Na$_2$SO$_4$, filtered and concentrated) and purified by silica gel chromatography to give the enol ether product.

Procedure B: A mixture of (methoxymethyl)triphenylphosphonium chloride (1.1 equiv.), t-BuOK (2.5 equiv.) in THF (4 mL/mmol phosphonium salt) was stirred at 0° C. for 1 h. Then aldehyde (1 equiv.) in THF (2 mL/mmol aldehyde) was added. The mixture was stirred for 16 h at room temperature. The reaction mixture was worked up (diluted with water and extracted with EtOAc; combined extracts dried over Na$_2$SO$_4$, filtered, and concentrated) and purified by silica gel chromatography to give the enol ether product.

Enol Ether to Aldehyde

Procedure A: Enol ether (1 equiv.) was treated with TFA (2 mL/mmol) at room temperature for 4 hours. The solvent was removed in vacuo to provide the desired aldehyde.

Procedure B: Enol ether (1 equiv.) was treated with HCOOH (2 mL/mmol) at 70° C. for 2 hours. The solvent was removed in vacuo to provide the desired aldehyde.

Procedure C: To a solution of enol ether (1 equiv.) in DCM (15 mL/mmol enol ether) was added TFA (2 mL/mmol) and water (0.25 mL/mmol enol ether). The reaction was stirred at 45° C. for 18 h. The reaction was worked up (quenched with NaHCO$_3$, extracted with DCM; combined extracts dried over Na$_2$SO$_4$, filtered, and concentrated) to provide the desired aldehyde.

Stille Reaction

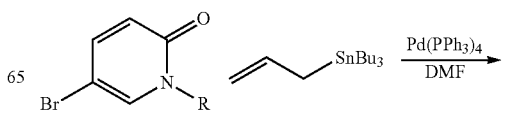

-continued

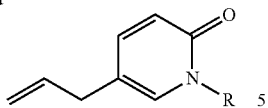

To a solution of arylbromide (1 equiv.) and allylstannane (1.2 equiv.) under $N_2$ in DMF (3 mL/mmol arylbromide) was added $Pd(PPh_3)_4$ (0.1 equiv.). The reaction was stirred at 100° C. for 16 hours. The reaction was concentration in vacuo then diluted with EtOAc, poured into 20% aq. KF and stirred for 1 h and extracted. The combined organic layers were dried over $Na_2SO_4$, filtered and concentrated, and purified by silica gel chromatography to provide the desired product.

Alkene to Aldehyde

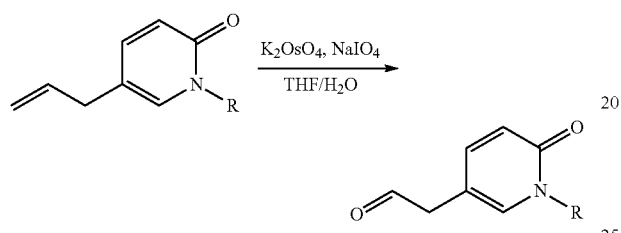

To a solution of alkene (1 equiv.) in $THF/H_2O$ (1:1) (10 mL/mmol of alkene) at 0° C. was added $K_2OsO_4\cdot 2H_2O$ (0.01 equiv.). The mixture was stirred at 0° C. for 5 min then $NaIO_4$ (3 equiv.) in $H_2O$ (1 mL/mmol alkene) was added dropwise and stirred at 0° C. for 1 h then warmed to room temperature and stirred until complete by LCMS. The reaction was worked up (dilute with water and extract with EtOAc; combined organic layers were dried over $Na_2SO_4$, filtered, and concentrated) to give the desired aldehyde.

Ester to Acid

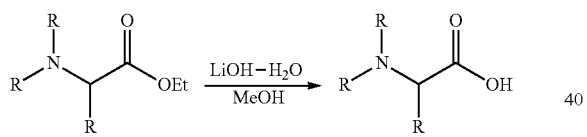

The ester (1 equiv.) was treated with $LiOH-H_2O$ (3-5 equiv.) in MeOH (1-3 mL/mmol ester) and water (1-3 mL/mmol ester) at room temperature for 1-5 h. The reaction was acidified with 1N HCl to pH=3 and concentrated. The residue was purified by prep HPLC to give the desired carboxylic acid product.

Amine Protection

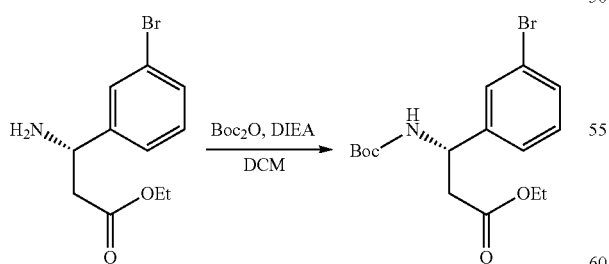

A mixture of amine (1 equiv.), DIEA (3 equiv.), and $Boc_2O$ (2 equiv.) was stirred in DCM (5 mL/mmole amine) at room temperature for 16 h until complete by LCMS. The reaction was worked up (wash with 0.5 N HCl, sat. $NaHCO_3$, brine, extract with DCM; combined organic layers were dried over $Na_2SO_4$, filtered, and concentrated) and purified by silica gel chromatography.

Preparation of Arylborane

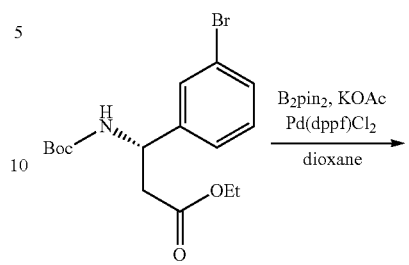

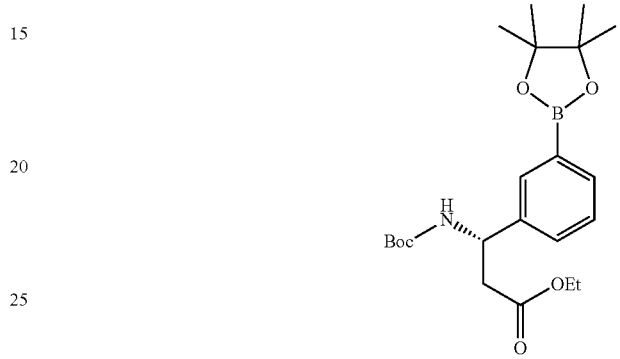

A mixture of arylbromide (1 equiv.), $B_2pin_2$ (1.2 equiv.), $Pd(dppf)Cl_2$ (0.05 equiv.), and KOAc (3 equiv.) in dioxane (10 mL/mmol arylbromide) was stirred at 110° C. for 2-5 h under $N_2$ until complete by LCMS. The reaction was filtered, concentrated in vacuo, and purified by silica gel chromotography to provide the desired arylborane.

Suzuki Coupling

"Palladium-Catalyzed Cross-Coupling Reactions of Organoboron Compounds" N. Miyaura; A. Suzuki *Chem. Rev.* 1995, 957, 2457-2483.

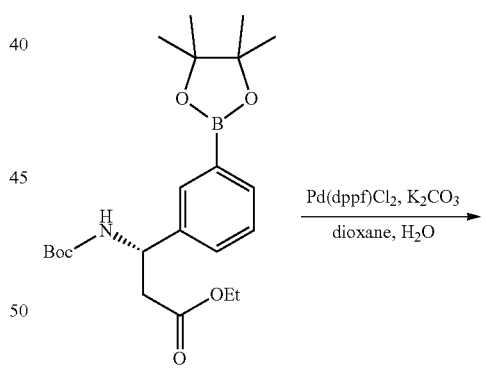

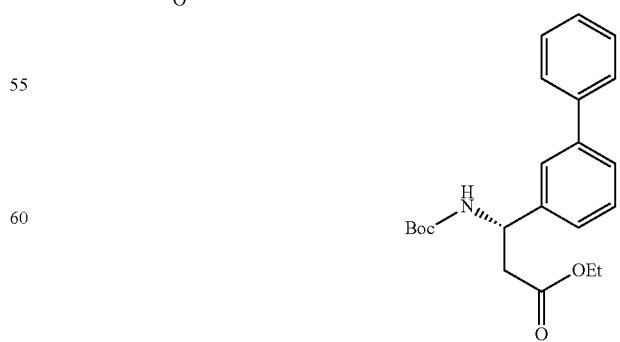

Procedure A: To a solution of arylborane (1 equiv.) in dioxane (10 mL/mmol arylborane) was added arylbromide (1.2 equiv.), Pd(dppf)Cl₂ (0.1 equiv.), K₂CO₃ (2 equiv.), and water (2 mL/mmol). The reaction was stirred at 110° C. for 3 h under N₂. The reaction was worked up (washed with brine and extracted with EtOAc; combined extracts dried over Na₂SO₄, filtered, and concentrated) and purified by silica gel chromatography to provide the desired biaryl product.

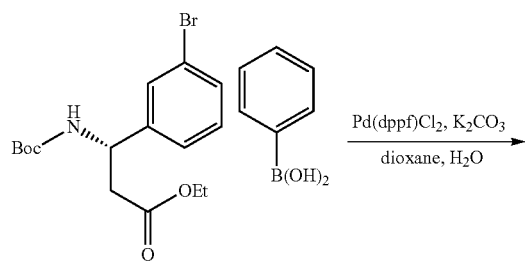

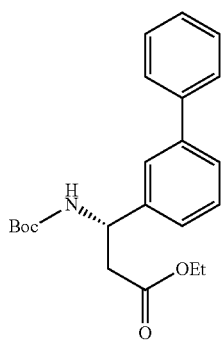

Procedure B: To a solution of arylbromide (1 equiv.) and arylborane (1.1 equiv.) in dioxane (10 mL/mmol arylbromide) was added K₂CO₃ (2 equiv.) in water (2 mL/mmol) and Pd(dppf)Cl₂ (0.1 equiv.). The reaction was stirred at 110° C. for 2 h under N₂. The reaction was worked up (washed with brine and extracted with EtOAc; combined extracts dried over Na₂SO₄, filtered, and concentrated) and purified by silica gel chromatography to provide the desired biaryl product.

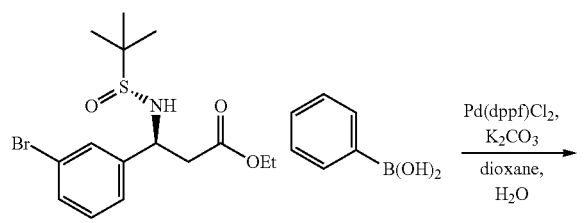

Procedure C: A mixture of arylbromide (1 equiv.), arylborane (2.0 equiv), K₂CO₃ (3 equiv.), and Pd(dppf)Cl₂ (0.05 equiv.) in dioxane (10 mL/mmol arylbromide) and water (1 mL/mmol) was stirred at 110° C. for 2 h under N₂ until complete by LCMS. The reaction was worked up (washed with brine and extracted with EtOAc; combined extracts dried over Na₂SO₄, filtered, and concentrated) and purified by silica gel chromatography to provide the desired biaryl product.

Boc Deprotection

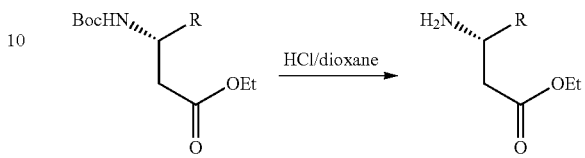

Boc-protected amine (1 equiv.) in DCM (4 mL/mmol amine) was added 4M HCl-dioxane (12 equiv.). The reaction was stirred for 1-2 h until complete by LCMS. The reaction was concentrated in vacuo to give the desired amine.

t-butylsulfinyl Deprotection

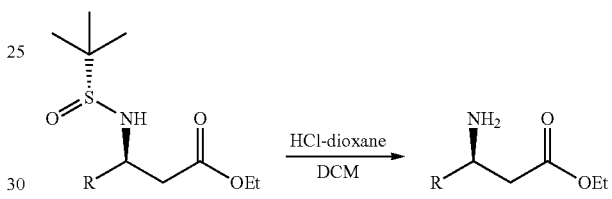

To a solution of t-butylsulfinylamine (1 equiv.) in DCM (0.5 mL/mmol amine) was added 4M HCl-dioxane (1.7 equiv.). The reaction was stirred for 0.5-1 h until complete by LCMS. The reaction was concentrated and purified by prep HPLC to give the desired amine.

Amide Bond Formation

"Peptide Coupling Reagents, More than a Letter Soup" A. El-Faham, F. Albericio *Chem. Rev.* 2011, 111, 11, 6557-6602; "Amide bond formation and peptide coupling" C. A. G. N. Montalbetti; V. Falque *Tetrahedron* 2005, 61, 10827-10852.

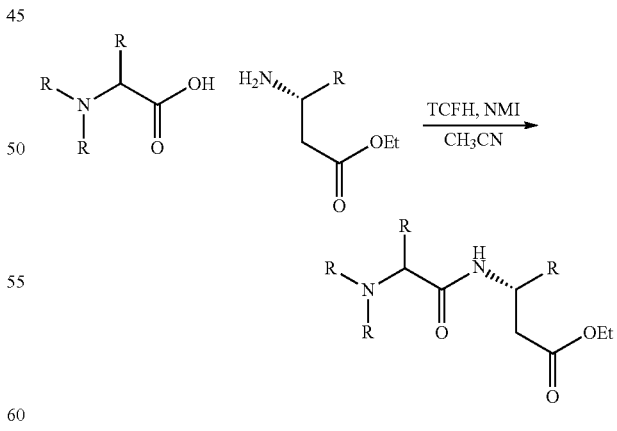

A mixture of amine (1 equiv.), carboxylic acid (1 equiv.), TCFH (2 equiv.), and NMI (4 equiv.) in CH₃CN (10 mL/mmol amine) was stirred at room temperature for 1-2 h until complete by LCMS. The reaction was concentrated in vacuo and purified by silica gel chromatography to give the desired amide product.

Ester Hydrolysis

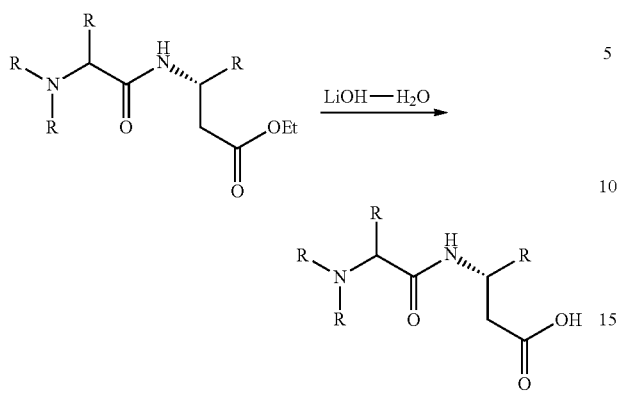

The ester (1 equiv.) was treated with LiOH—H₂O (3-5 equiv.) in MeOH (1-3 mL/mmol ester) and water (1-3 mL/mmol ester) at room temperature for 1-5 h. The reaction was acidified with 1N HCl to pH=4-5 and concentrated. The residue was purified by prep HPLC to give the desired carboxylic acid product.

Analytical Methods

LCMS Analytical Methods

Final compounds were analyzed using LC/MS conditions, with UV detector monitoring at 214 nm and 254 nm, and mass spectrometry scanning 110-800 amu in ESI+ ionization mode.

LC/MS A: column: XBridge C18, 4.6×50 mm, 3.5 µm; mobile phase: A water (10 mM ammonium hydrogen carbonate), B CH₃CN; gradient: 5%-95% B in 1.4 min, then 1.6 min hold; flow rate: 1.8 mL/min; oven temperature 50° C.

LC/MS B: column: SunFire C18, 4.6×50 mm, 3.5 µm; mobile phase: A water (0.01% TFA), B CH₃CN; gradient: 5%-95% B in 1.5 min, then 1.5 min hold; flow rate: 2.0 mL/min; oven temperature 50° C.

LC/MS C: column: XBridge C18, 4.6×50 mm, 3.5 µm; mobile phase: A water (10 mM ammonium hydrogen carbonate), B CH3CN; gradient: 5%-95% B in 1.5 min, then 1.5 min hold; flow rate: 1.8 mL/min; oven temperature 50° C.

LC/MS D: column: Poroshell 120 EC-C138, 4.6×30 mm, 2.7 µm; mobile phase: A water (0.01% TFA), B CH₃CN (0.01% TFA); gradient: 5%-95% B in 1.2 min, then 1.8 min hold; flow rate: 2.2 mL/min; oven temperature 50° C.

Example 2A. Preparation of Intermediates

Preparation of Ethyl (S)-3-(5-bromo-2-fluoro-3-methylphenyl)-3-(((tert-butoxycarbonyl)amino)propanoate Step 1: 5-bromo-2-fluoro-3-methylbenzaldehyde

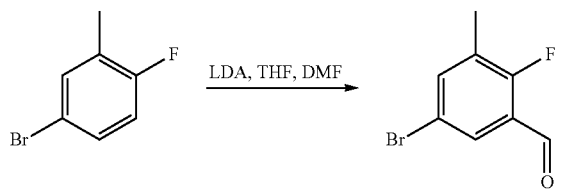

To a mixture of 4-bromo-1-fluoro-2-methylbenzene (10.0 g, 52.9 mmol, 1.0 eq) in anhydrous THF (100.0 mL) under nitrogen atmosphere at −78° C. was added Lithium diisopropylamide (2.0 M, 39.7 mL, 79.4 mmol, 1.5 eq) dropwise over the period of 10 mins and stirred at −78° C. for 1 hour. DMF (15.0 mL) was added dropwise and the mixture was stirred at −78° C. for 2 hours. LCMS showed that the reaction was completed. The reaction mixture was quenched with a saturated NH₄Cl solution (aq) (100 mL) at 0° C., extracted with EtOAc (100 mL×2). The organic layer was washed with brine (100 mL), dried over anhydrous Na₂SO₄, filtered and concentrated in vacuo. The residue obtained was purified by silica gel column (pet ether:EtOAc 9:1) to provide 5-bromo-2-fluoro-3-methylbenzaldehyde as a white solid (8.0 g). Yield 70% (ESI 218.9 [M+H]⁺).

Step 2: (R,E)-N-(5-bromo-2-fluoro-3-methylbenzylidene)-2-methylpropane-2-sulfinamide

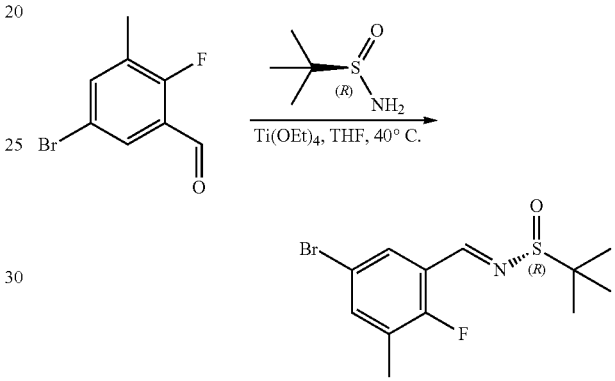

To a mixture of 5-bromo-2-fluoro-3-methylbenzaldehyde (8.0 g, 36.9 mmol, 1.00 eq) and (R)-2-methylpropane-2-sulfinamide (5.4 g, 44.3 mmol, 1.2 eq) in anhydrous THF (80 mL) under nitrogen atmosphere was added Ti(OEt)₄ (12.6 g, 55.4 mmol, 1.50 eq) dropwise at room temperature with the temperature maintained below 30° C. The reaction mixture was warmed to 40° C. and stirred for 1 hour. LCMS showed that the reaction was completed. Water (80 mL) and EtOAc (80 mL) was added into the mixture and stirred at room temperature for 5 mins. The mixture was filtered and washed with EtOAc (50 mL). The filtrate was separated. The organic layer was washed with water (100 mL) and brine (100 mL), dried over anhydrous Na₂SO₄, filtered and concentrated in vacuo to give crude product (R,E)-N-(5-bromo-2-fluoro-3-methylbenzylidene)-2-methylpropane-2-sulfinamide as a yellow solid (12.0 g, crude) which was used in the next step without further purification. Yield 100% (ESI 320.0 [M+H]⁺).

Step 3: Ethyl (S)-3-(5-bromo-2-fluoro-3-methylphenyl)-3-(((R)-tert-butylsulfinyl)amino)propanoate

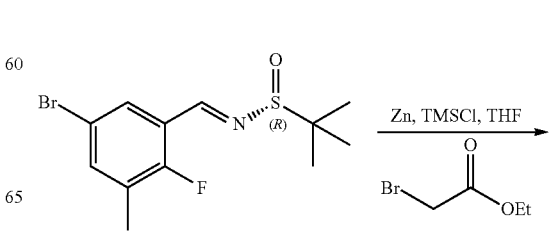

-continued

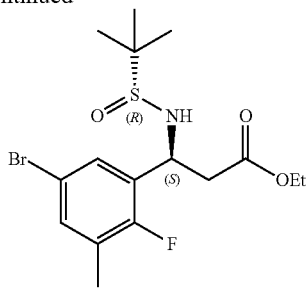

To a mixture of Zn (12.2 g, 187.5 mmol, 5.0 eq) in anhydrous THF (200 mL) under nitrogen atmosphere was added chlorotrimethylsilane (0.8 g, 7.5 mmol, 0.2 eq) dropwise at room temperature. The mixture was stirred at 60° C. for 1 hour under nitrogen atmosphere and cooled to 20-30° C. Ethyl 2-bromoacetate (1.57 g, 9.4 mmol, 0.25 eq) was added dropwise at 20-30° C. When the reaction mixture started to be exothermic, the rest of ethyl 2-bromoacetate (14.4 g, 86.3 mmol, 2.3 eq) was added dropwise during which time the reaction mixture was kept at 50-60° C. After the completion of the addition, the reaction mixture was stirred at 60° C. for 1 hour under nitrogen atmosphere. The reaction mixture was cooled to 0° C., (R,E)-N-(5-bromo-2-fluoro-3-methylbenzylidene)-2-methylpropane-2-sulfinamide (12.0 g, 37.5 mmol) in anhydrous THF (30 mL) was added dropwise and stirred at 25° C. for 1 hour. LCMS showed that the reaction was completed. MTBE (150 mL) and a solution of citric acid (3 g) in water (100 mL) were added into the mixture. The mixture was separated. The aqueous layer was extracted with MTBE (150 mL×2). The combined organic phase was washed with brine (200 mL), dried over anhydrous Na$_2$SO$_4$, filtered and concentrated in vacuo. The residue was purified by silica gel column (pet ether:EtOAc 3:1) to provide ethyl (S)-3-(5-bromo-2-fluoro-3-methylphenyl)-3-(((R)-tert-butylsulfinyl)amino)propanoate (9.0 g). Yield 59% (ESI 408.0 [M+H]$^+$).

Step 4: Ethyl (S)-3-amino-3-(5-bromo-2-fluoro-3-methylphenyl)propanoate

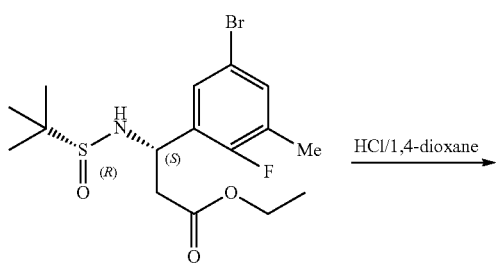

To a solution of ethyl (S)-3-(5-bromo-2-fluoro-3-methylphenyl)-3-(((R)-tert-butylsulfinyl)amino)propanoate (8.0 g, 19.6 mmol, 1.00 eq) in DCM (20 mL) was added HCl-dioxane (4 M, 20 mL, 80.0 mmol, 4.08 eq) and stirred at room temperature for 4 hours. LCMS showed that the reaction was completed. The mixture was filtered and concentrated in vacuo to give crude product ethyl (S)-3-amino-3-(5-bromo-2-fluoro-3-methylphenyl)propanoate as a yellow oil (8.0 g) used in the next step without further purification. Yield 100% (ESI 304.2 [M+H]$^+$).

Step 5: Ethyl (S)-ethyl 3-(5-bromo-2-fluoro-3-methylphenyl)-3-(tert-butoxycarbonylamino)propanoate

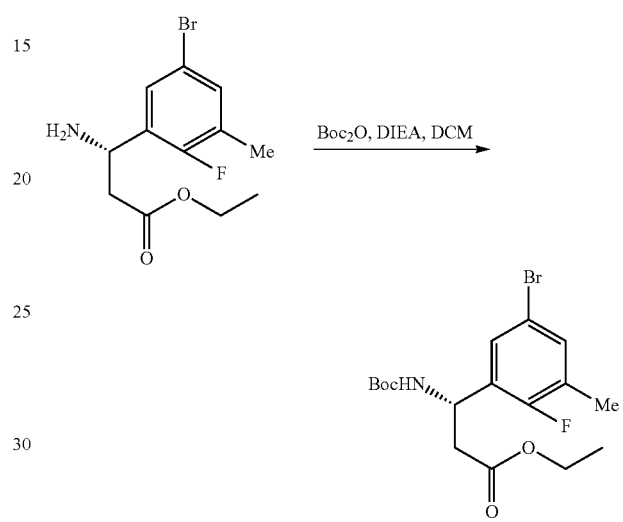

To a solution of ethyl (S)-3-amino-3-(5-bromo-2-fluoro-3-methylphenyl)propanoate (8.0 g, 19.6 mmol, 1.00 eq) in DCM (100 mL) was added DIEA (7.6 g, 59.0 mmol, 3.00 eq) and Boc$_2$O (8.6 g, 39.2 mmol, 2.00 eq). The reaction mixture was stirred at room temperature for 16 hours. LCMS showed that the reaction was completed. The reaction mixture was diluted with DCM (200 mL) and washed with 0.5 N HCl (50 mL×3), saturated NaHCO$_3$ (50 mL) and brine (50 mL). The organic phase was dried over Na$_2$SO$_4$, filtered and concentrated in vacuo. The residue was purified by silica gel column (pet ether:EtOAc 3:1) to provide ethyl (S)-3-(5-bromo-2-fluoro-3-methylphenyl)-3-((tert-butoxycarbonyl)amino)propanoate as a brown oil (6.0 g). Yield 75% (ESI 404.1 (M+H)$^+$).

Preparation of Ethyl (S)-3-((tert-butoxycarbonyl)amino)-3-(2-fluoro-3-methyl-5-(4,4,5,5-tetramethyl-1,3,2-dioxaborolan-2-yl)phenyl)propanoate

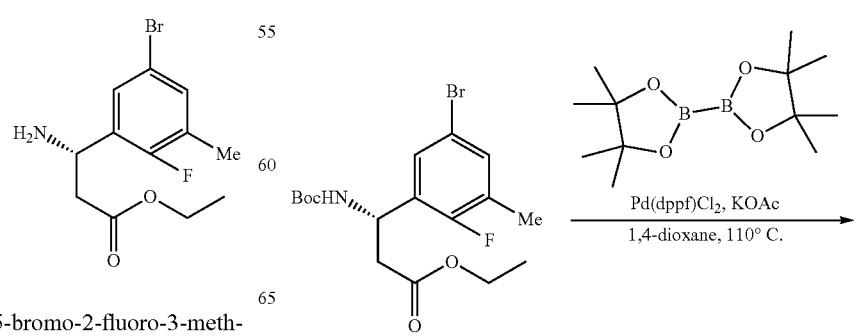

-continued

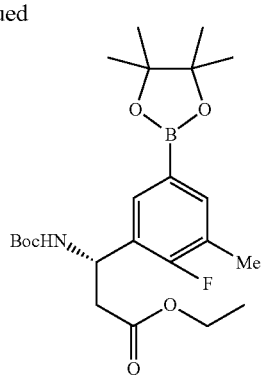

A mixture of ethyl (S)-3-(5-bromo-2-fluoro-3-methylphenyl)-3-((tert-butoxycarbonyl)amino)propanoate (1.0 g, 2.48 mmol, 1.0 eq), bis(pinacolato)diboron (756.28 mg, 2.98 mmol, 1.2 eq), Pd(dppf)Cl$_2$ (90.65 mg, 0.13 mmol, 0.05 eq) and KOAc (729.12 mg, 7.44 mmol, 3.0 eq) in 1,4-dioxane (20 mL) was stirred at 110° C. for 3 hours under nitrogen atmosphere. The reaction mixture was cooled to room temperature, filtered and concentrated in vacuo. The residue was purified by silica gel column (petroleum ether:EtOAc 2:1) to give (S)-ethyl 3-(tert-butoxycarbonylamino)-3-(2-fluoro-3-methyl-5-(4,4,5,5-tetramethyl-1,3,2-dioxaborolan-2-yl)phenyl)propanoate as a colorless oil (1.0 g). Yield 89% (ESI 452.2 (M+H)$^+$).

Preparation of Ethyl (S)-3-amino-3-(2',4-difluoro-5,6'-dimethyl-[1,1'-biphenyl]-3-yl)propanoate Step 1: Ethyl (S)-3-((tert-butoxycarbonyl)amino)-3-(2',4-difluoro-5,6'-dimethyl-[1,1'-biphenyl]-3-yl)propanoate

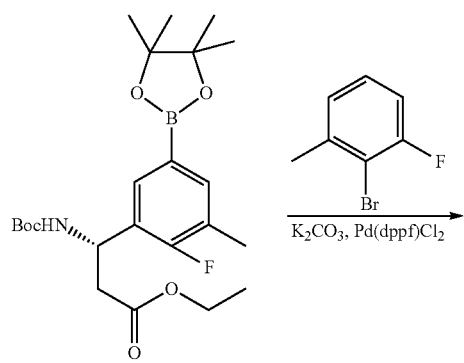

To a solution of ethyl (S)-3-((tert-butoxycarbonyl)amino)-3-(2-fluoro-3-methyl-5-(4,4,5,5-tetramethyl-1,3,2-dioxaborolan-2-yl)phenyl)propanoate (300 mg, 0.66 mmol, 1.0 eq) in dioxane (5 mL) was added 2-bromo-1-fluoro-3-methylbenzene (150 mg, 0.79 mmol, 1.2 eq), Pd(dppf)Cl$_2$ (48 mg, 0.066 mmol, 0.1 eq), K$_2$CO$_3$ (182 mg, 1.32 mmol, 2.0 eq) and water (1 mL). The reaction mixture was stirred at 110° C. for 3 hours under nitrogen atmosphere. Water (10 mL) was added and the solution was extracted with EtOAc (20 mL×3). The combined organic phases were washed with brine (100 mL), dried over anhydrous Na$_2$SO$_4$, filtered and concentrated in vacuo. The residue was purified by silica gel column (petroleum ether:EtOAc 8:1) to provide ethyl (S)-3-((tert-butoxycarbonyl)amino)-3-(2',4-difluoro-5,6'-dimethyl-[1,1'-biphenyl]-3-yl)propanoate as a colorless oil (210 mg). Yield 73% (ESI 334.1 [M+H−100]$^+$).

Step 2: Ethyl (S)-3-amino-3-(2',4-difluoro-5,6'-dimethyl-[1,1'-biphenyl]-3-yl)propanoate

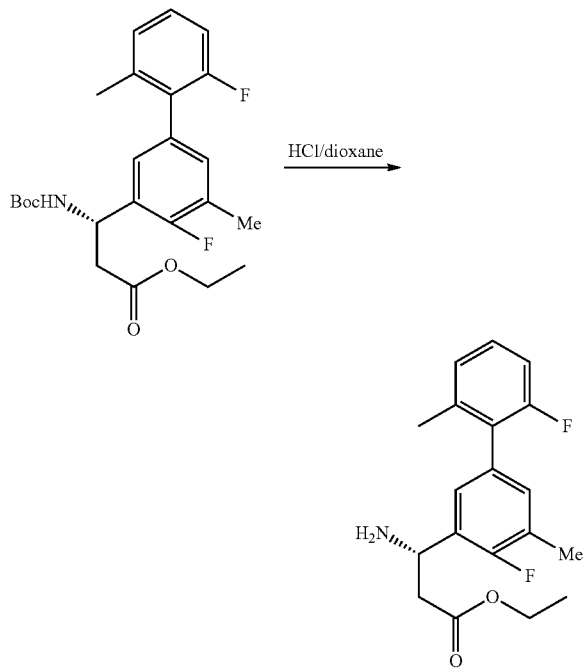

To a stirred solution of ethyl (S)-3-((tert-butoxycarbonyl)amino)-3-(2',4-difluoro-5,6'-dimethyl-[1,1'-biphenyl]-3-yl)propanoate (210 mg, 0.48 mmol, 1.0 eq) in DCM (2 mL) was added HCl-dioxane (4 M, 3.0 mL, 6.0 mmol, 12.5 eq). The mixture was stirred at room temperature for 2 hours. LCMS showed that the reaction was completed. The mixture was concentrated in vacuo to provide ethyl (S)-3-amino-3-(2',4-difluoro-5,6'-dimethyl-[1,1'-biphenyl]-3-yl)propanoate as a colorless oil (160 mg). Yield 99% (ESI 334.1 [M+H]$^+$).

Preparation of Ethyl (S)-3-amino-3-(2'-cyano-4-fluoro-5,6'-dimethyl-[1,1'-biphenyl]-3-yl)propanoate Hydrochloride Step 1: Ethyl (S)-3-((tert-butoxycarbonyl)amino)-3-(2'-cyano-4-fluoro-5,6'-dimethyl-[1,1'-biphenyl]-3-yl)propanoate

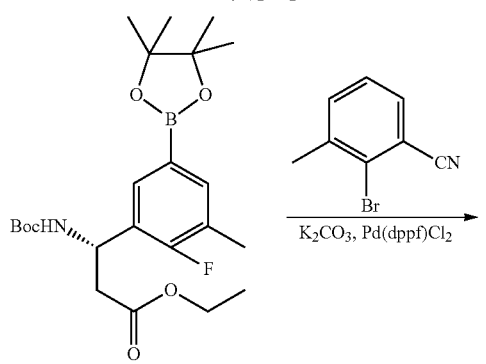

-continued

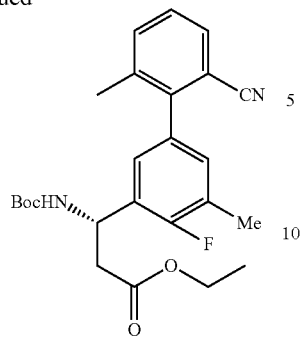

To a solution of ethyl (S)-3-((tert-butoxycarbonyl)amino)-3-(2-fluoro-3-methyl-5-(4,4,5,5-tetramethyl-1,3,2-dioxaborolan-2-yl)phenyl)propanoate (350 mg, 0.77 mmol, 1.0 eq) in dioxane (10 mL) was added 2-bromo-3-methylbenzonitrile (226 mg, 1.16 mmol, 1.5 eq), Pd(dppf)Cl$_2$ (56 mg, 0.077 mmol), K$_2$CO$_3$ (193 mg, 1.4 mmol, 1.8 eq) and water (2 mL). The reaction mixture was stirred at 110° C. for 3 hours under nitrogen atmosphere. Water (20 mL) was added and the solution was extracted with EtOAc (20 mL×3). The combined organic phases were washed with brine (50 mL), dried over anhydrous Na$_2$SO$_4$, filtered and concentrated in vacuo. The residue was purified by silica gel column (petroleum ether:EtOAc 4:1) to provide ethyl (S)-3-((tert-butoxycarbonyl)amino)-3-(2'-cyano-4-fluoro-5,6'-dimethyl-[1,1'-biphenyl]-3-yl)propanoate as a colorless oil (260 mg). Yield 76% (ESI 341.1 [M+H−100]$^+$).

Step 2: Ethyl (S)-3-amino-3-(2'-cyano-4-fluoro-5,6'-dimethyl-[1,1'-biphenyl]-3-yl)propanoate Hydrochloride

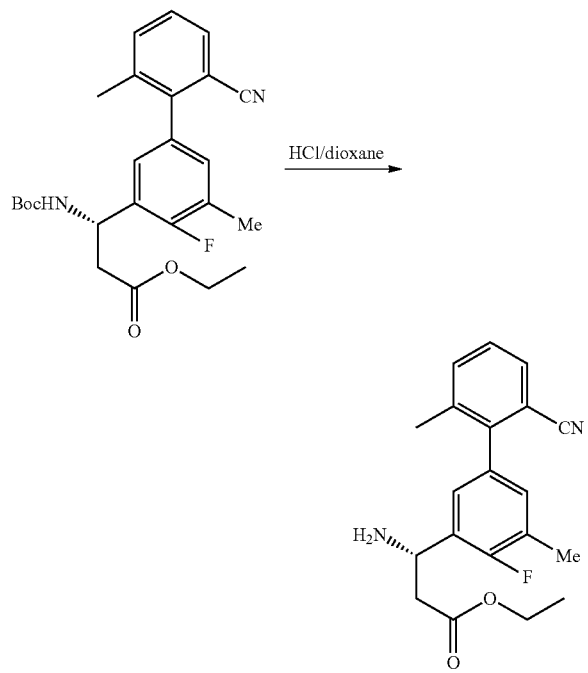

To a stirred solution of ethyl (S)-3-((tert-butoxycarbonyl)amino)-3-(2'-cyano-4-fluoro-5,6'-dimethyl-[1,1'-biphenyl]-3-yl)propanoate (230 mg, 0.52 mmol, 1.0 eq) in DCM (2 mL) was added HCl-dioxane (4 M, 2.0 mL, 4.0 mmol, 7.7 eq). The mixture was stirred at room temperature for 1 hour. LCMS showed that the reaction was completed. The mixture was concentrated in vacuo to provide ethyl (S)-3-amino-3-(2'-cyano-4-fluoro-5,6'-dimethyl-[1,1'-biphenyl]-3-yl)propanoate hydrochloride as a yellow oil (180 mg). Yield 91% (ESI 341.1 [M+H]$^+$).

Preparation of Ethyl (S)-3-amino-3-(2'-chloro-4-fluoro-5,6'-dimethyl-[1,1'-biphenyl]-3-yl)propanoate Step 1: Ethyl (S)-3-((tert-butoxycarbonyl)amino)-3-(2'-chloro-4-fluoro-5,6'-dimethyl-[1,1'-biphenyl]-3-yl)propanoate

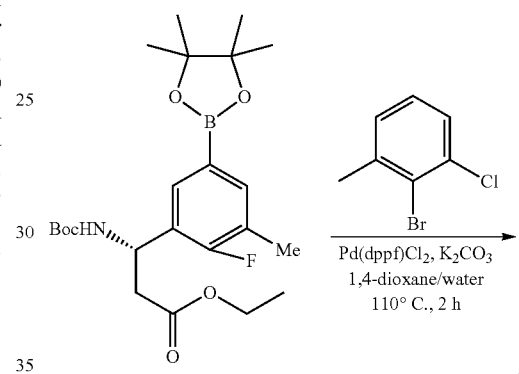

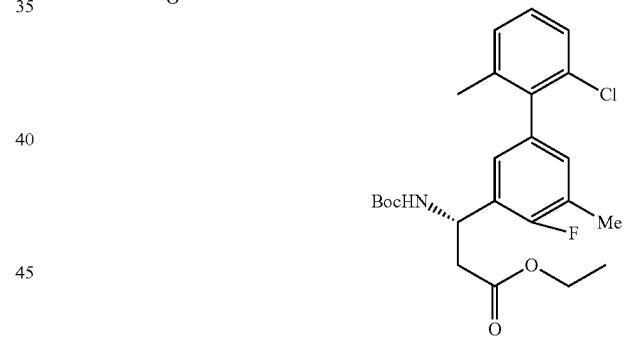

A mixture of ethyl (S)-3-((tert-butoxycarbonyl)amino)-3-(2-fluoro-3-methyl-5-(4,4,5,5-tetramethyl-1,3,2-dioxaborolan-2-yl)phenyl)propanoate (1.0 g, 2.22 mmol, 1.00 eq), 2-bromo-1-chloro-3-methylbenzene (543 mg, 2.66 mmol, 1.20 eq), K$_2$CO$_3$ (613 mg, 4.44 mmol, 2.0 eq) and Pd(dppf)Cl$_2$ (81 mg, 0.11 mmol, 0.05 eq) in dioxane (10 mL) and H$_2$O (2 mL) was stirred at 110° C. for 2 hours under nitrogen atmosphere. Water (30 mL) was added and the solution was extracted with EtOAc (30 mL×3). The combined organic phases were washed with brine (100 mL), dried over anhydrous Na$_2$SO$_4$, filtered and concentrated in vacuo. The residue was purified by silica gel column (petroleum ether:EtOAc 2:1) to provide ethyl (S)-3-((tert-butoxycarbonyl)amino)-3-(2'-chloro-4-fluoro-5,6'-dimethyl-[1,1'-biphenyl]-3-yl)propanoate as a colorless oil (800 mg). Yield 80% (ESI 450.18 [M+H]$^+$).

Step 2: Ethyl (S)-3-amino-3-(2'-chloro-4-fluoro-5,6'-dimethyl-[1,1'-biphenyl]-3-yl)propanoate

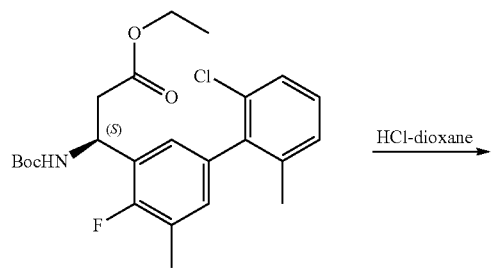

To a mixture of ethyl (S)-3-((tert-butoxycarbonyl)amino)-3-(2'-chloro-4-fluoro-5,6'-dimethyl-[1,1'-biphenyl]-3-yl)propanoate (300 mg, 0.67 mmol, 1.00 eq) in DCM (9 mL) was added HCl-dioxane (4 M, 9.0 mL, 36.0 mmol, 53.73 eq) and stirred at room temperature for 1 hour. LCMS showed that the reaction was completed. The mixture was concentrated in vacuo to provide ethyl (S)-3-amino-3-(2'-chloro-4-fluoro-5,6'-dimethyl-[1,1'-biphenyl]-3-yl)propanoate as a white solid (200 mg) used directly in the next reaction without further purification. Yield 86% (ESI 350.1[M+H]$^+$).

Preparation of Ethyl (S)-3-amino-3-(2'-cyclopropyl-4-fluoro-5,6'-dimethyl-[1,1'-biphenyl]-3-yl)propanoate Step 1: Ethyl (S)-3-((tert-butoxycarbonyl)amino)-3-(2'-cyclopropyl-4-fluoro-5,6'-dimethyl-[1,1'-biphenyl]-3-yl)propanoate

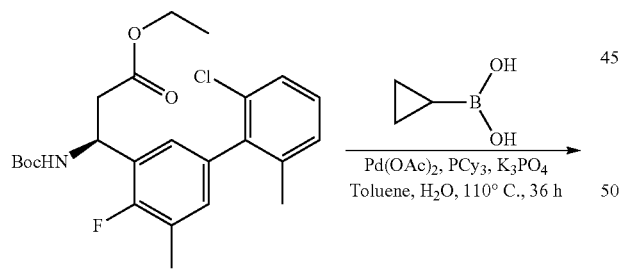

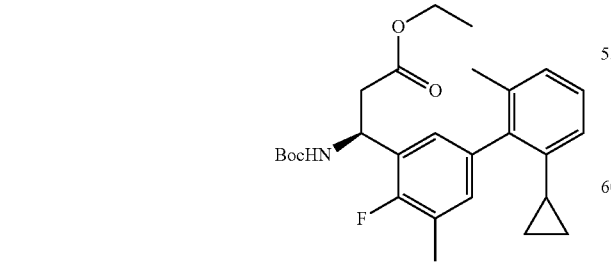

A mixture of ethyl (S)-3-((tert-butoxycarbonyl)amino)-3-(2'-chloro-4-fluoro-5,6'-dimethyl-[1,1'-biphenyl]-3-yl)propanoate (500 mg, 1.12 mmol, 1.00 eq), cyclopropylboronic acid (116 mg, 1.35 mmol, 1.20 eq), K$_3$PO$_4$ (475 mg, 2.24 mmol, 2.00 eq), PCy$_3$ (31 mg, 0.11 mmol, 0.10 eq) and Pd(OAc)$_2$ (11 mg, 0.11 mmol, 0.10 eq) in dioxane (10 mL) and H$_2$O (2 mL) was stirred at 110° C. for 36 hours under nitrogen atmosphere. Water (30 mL) was added and the solution was extracted with EtOAc (30 mL×3). The combined organic phases were washed with brine (20 mL), dried over anhydrous Na$_2$SO$_4$, filtered and concentrated in vacuo. The residue was purified by silica gel column (petroleum ether:EtOAc 2:1) to provide ethyl (S)-3-((tert-butoxycarbonyl)amino)-3-(2'-cyclopropyl-4-fluoro-5,6'-dimethyl-[1,1'-biphenyl]-3-yl)propanoate as a colorless oil (400 mg). Yield 79% (ESI 456.2 [M+H]$^+$).

Step 2: Ethyl (S)-3-amino-3-(2'-cyclopropyl-4-fluoro-5,6'-dimethyl-[1,1'-biphenyl]-3-yl)propanoate

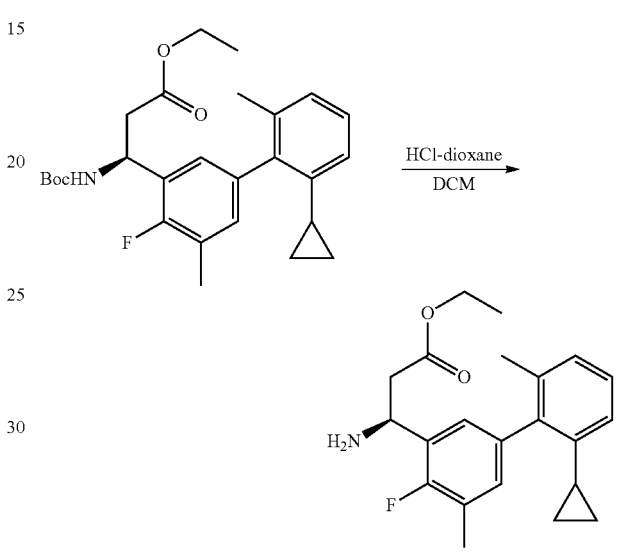

To a mixture of ethyl (S)-3-((tert-butoxycarbonyl)amino)-3-(2'-cyclopropyl-4-fluoro-5,6'-dimethyl-[1,1'-biphenyl]-3-yl)propanoate (400 mg, 0.88 mmol, 1.0 eq) in DCM (9 mL) was added HCl-dioxane (4 M, 9.0 mL, 36.0 mmol, 40.9 eq) and stirred at room temperature for 1 hour. LCMS showed that the reaction was completed. The mixture was concentrated in vacuo to provide ethyl (S)-3-amino-3-(2'-cyclopropyl-4-fluoro-5,6'-dimethyl-[1,1'-biphenyl]-3-yl)propanoate as a white solid (300 mg) used directly in the next reaction without further purification. Yield 96% (ESI 356.2 [M+H]$^+$).

Preparation of Ethyl (S)-3-amino-3-(4-fluoro-4'-methoxy-2',5,6'-trimethyl-[1,1'-biphenyl]-3-yl)propanoate Hydrochloride Step 1: Ethyl (S)-3-amino-3-(2'-ethyl-4-fluoro-5,6'-dimethyl-[1,1'-biphenyl]-3-yl)propanoate Hydrochloride

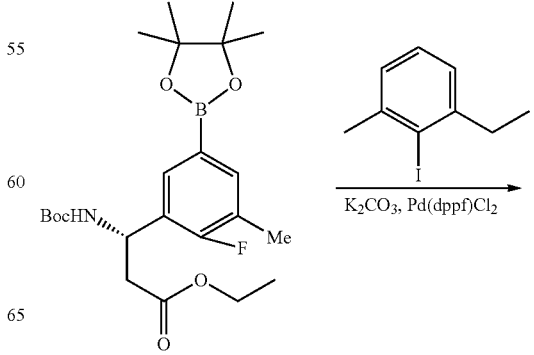

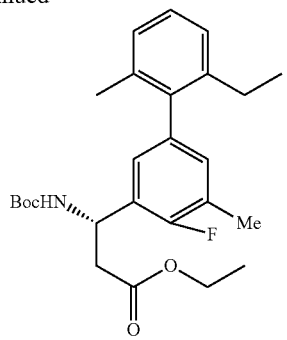

To a solution of ethyl (S)-3-((tert-butoxycarbonyl)amino)-3-(2-fluoro-3-methyl-5-(4,4,5,5-tetramethyl-1,3,2-dioxaborolan-2-yl)phenyl)propanoate (350 mg, 0.77 mmol, 1.0 eq) in dioxane (10 mL) was added 1-ethyl-2-iodo-3-methylbenzene (286 mg, 1.16 mmol, 1.5 eq), Pd(dppf)Cl$_2$ (56 mg, 0.077 mmol, 0.1 eq), K$_2$CO$_3$ (193 mg, 1.4 mmol, 1.8 eq) and water (2 mL). The reaction mixture was stirred at 110° C. for 3 hours under nitrogen atmosphere. Water (10 mL) was added and the solution was extracted with EtOAc (20 mL×3). The combined organic phases were washed with brine (60 mL), dried over anhydrous Na$_2$SO$_4$, filtered and concentrated in vacuo. The residue was purified by silica gel column (petroleum ether:EtOAc 4:1) to provide ethyl (S)-3-((tert-butoxycarbonyl)amino)-3-(2'-ethyl-4-fluoro-5,6'-dimethyl-[1,1'-biphenyl]-3-yl)propanoate as a colorless oil (240 mg). Yield 70% (ESI 344.2 [M+H−100]$^+$).

Step 2: Ethyl (S)-3-amino-3-(2'-ethyl-4-fluoro-5,6'-dimethyl-[1,1'-biphenyl]-3-yl)propanoate Hydrochloride

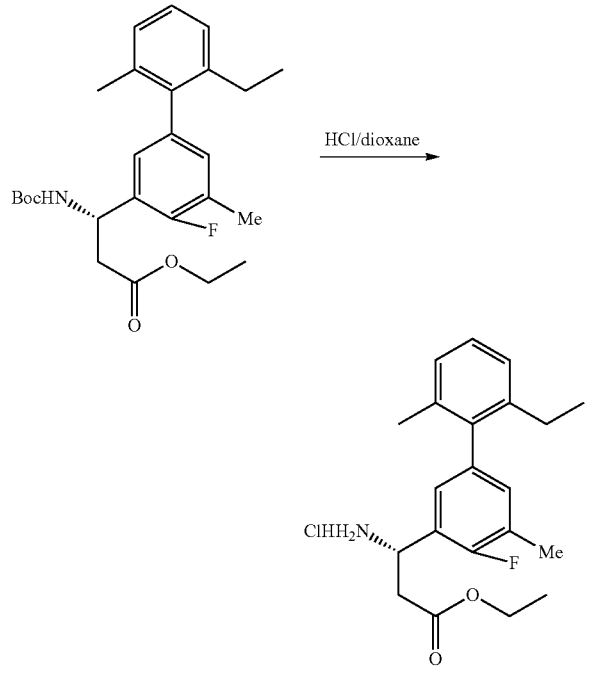

To a stirred solution of ethyl (S)-3-((tert-butoxycarbonyl)amino)-3-(2'-ethyl-4-fluoro-5,6'-dimethyl-[1,1'-biphenyl]-3-yl)propanoate (210 mg, 0.47 mmol, 1.0 eq) in DCM (2 mL) was added HCl-dioxane (4 M, 3.0 mL, 6.0 mmol, 12.8 eq). The mixture was stirred at room temperature for 1 hour. LCMS showed that the reaction was completed. The mixture was concentrated in vacuo to provide ethyl (S)-3-amino-3-(2'-ethyl-4-fluoro-5,6'-dimethyl-[1,1'-biphenyl]-3-yl)propanoate hydrochloride as a colorless oil (170 mg). Yield 94% (ESI 344.1 [M+H]$^+$).

Preparation of (S)-ethyl 3-amino-3-(4-fluoro-2'-methoxy-5,6'-dimethylbiphenyl-3-yl)propanoate Step 1: Ethyl (S)-3-(((R)-tert-butylsulfinyl)amino)-3-(4-fluoro-2',4',5,6'-tetramethyl-[1,1'-biphenyl]-3-yl)propanoate

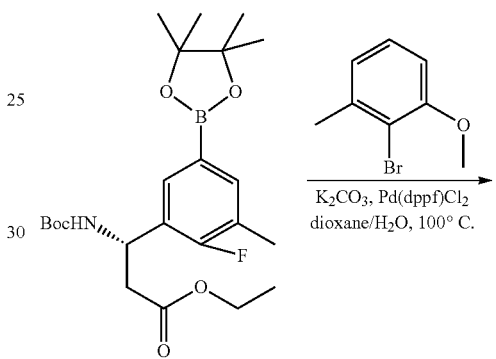

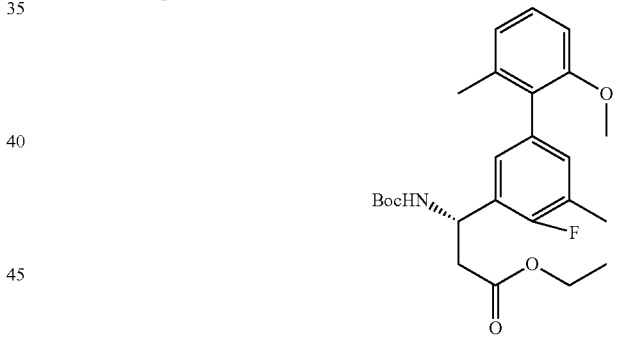

A mixture of (S)-ethyl 3-(tert-butoxycarbonylamino)-3-(2-fluoro-3-methyl-5-(4,4,5,5-tetramethyl-1,3,2-dioxaborolan-2-yl)phenyl)propanoate (1 g, 2.22 mmol, 1.0 eq), 2-bromo-1-methoxy-3-methylbenzene (666 mg, 3.33 mmol, 1.5 eq), K$_2$CO$_3$ (919 mg, 6.66 mmol, 3.0 eq) and Pd(dppf)Cl$_2$ (162 mg, 0.222 mmol, 0.1 eq) in dioxane (15 mL) and H$_2$O (1.5 mL) was stirred at 100° C. under nitrogen atmosphere for 3 hours. LCMS showed the reaction was completed. The reaction mixture was cooled to room temperature. Water (50 mL) was added and the mixture was extracted with EtOAc (50 mL×3). The combined organic layers were washed with brine (100 mL), dried over Na$_2$SO$_4$, filtered and concentrated in vacuo. The residue was purified by silica gel column (pet ether:EtOAc 2:1) to provide (S)-ethyl 3-(tert-butoxycarbonylamino)-3-(4-fluoro-2'-methoxy-5,6'-dimethylbiphenyl-3-yl)propanoate as a yellow oil (0.96 g). Yield 97% (ESI 346.1 [M+H]$^+$).

Step 2: (S)-ethyl 3-amino-3-(4-fluoro-2'-methoxy-5, 6'-dimethylbiphenyl-3-yl)propanoate

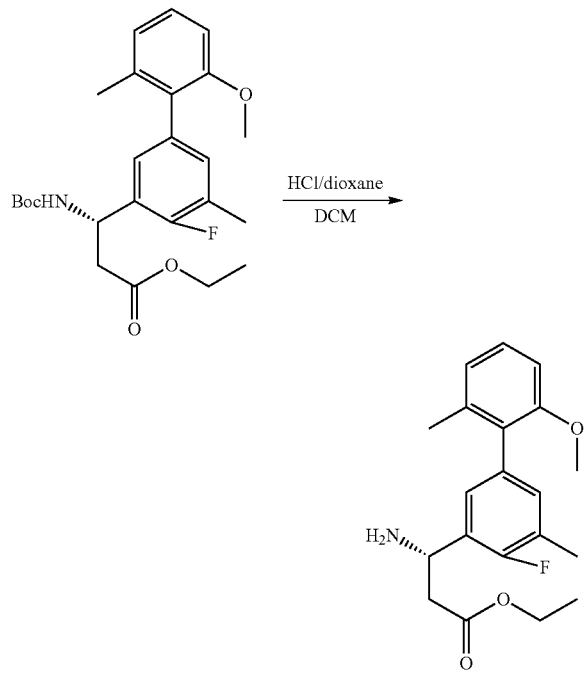

To a stirred solution of (S)-ethyl 3-(tert-butoxycarbonylamino)-3-(4-fluoro-2'-methoxy-5,6'-dimethylbiphenyl-3-yl)propanoate (0.96 g, 2.15 mmol, 1.0 eq) in DCM (7 mL) was added HCl-dioxane (4 M, 2.15 mL, 4 eq) and stirred at 25° C. for 2 hours. LCMS showed that the reaction was completed. The mixture was concentrated in vacuo and the residue was purified by reverse phase HPLC on a C18/40 g column (A: water 10 mM $NH_4HCO_3$, B: MeOH, 0~100%) to provide (S)-ethyl 3-amino-3-(4-fluoro-2'-methoxy-5,6'-dimethylbiphenyl-3-yl)propanoate as a yellow oil (0.6 g). Yield 81% (ESI 346.1 $[M+H]^+$).

Preparation of (S)-ethyl 3-amino-3-(4-fluoro-2'-methoxy-5-methyl-6'-(trifluoromethyl)biphenyl-3-yl)propanoate Step 1:
1-methoxy-2-nitro-3-(trifluoromethyl)benzene

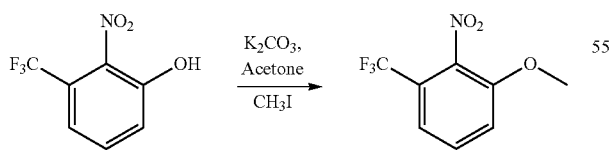

To a mixture of 2-nitro-3-(trifluoromethyl)phenol (1.5 g, 7.25 mmol, 1.0 eq) in acetone (20 mL) was added $K_2CO_3$ (3 g, 21.75 mmol, 3 eq) and $CH_3I$ (5.15 g, 36.25 mmol, 5 eq) and stirred at room temperature for 16 hours. LCMS showed that the reaction was completed. The reaction mixture was filtered, washed with EtOAc (20 mL). The filtrate was concentrated in vacuo and the residue was purified by silica gel column (pet ether:EtOAc 2:1) to provide 1-methoxy-2-nitro-3-(trifluoromethyl)benzene as a white solid (1.3 g). Yield 81%.

Step 2: 2-methoxy-6-(trifluoromethyl)aniline

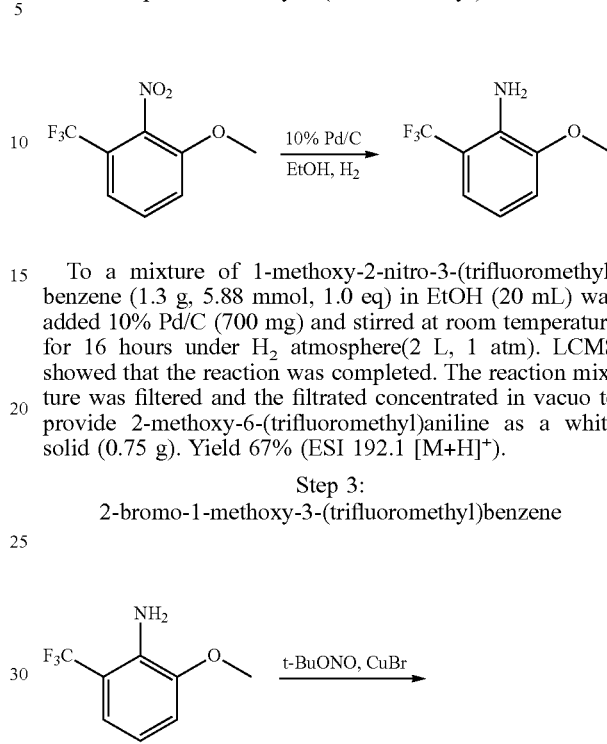

To a mixture of 1-methoxy-2-nitro-3-(trifluoromethyl)benzene (1.3 g, 5.88 mmol, 1.0 eq) in EtOH (20 mL) was added 10% Pd/C (700 mg) and stirred at room temperature for 16 hours under $H_2$ atmosphere(2 L, 1 atm). LCMS showed that the reaction was completed. The reaction mixture was filtered and the filtrated concentrated in vacuo to provide 2-methoxy-6-(trifluoromethyl)aniline as a white solid (0.75 g). Yield 67% (ESI 192.1 $[M+H]^+$).

Step 3: 2-bromo-1-methoxy-3-(trifluoromethyl)benzene

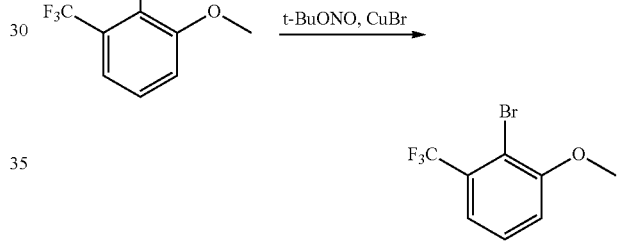

To a mixture of 2-methoxy-6-(trifluoromethyl)aniline (700 mg, 3.66 mmol, 1.0 eq) in MeCN (15 mL) was added t-BuONO (565 mg, 5.49 mmol, 1.5 eq) and CuBr (628 mg, 4.39 mmol, 1.2 eq). The mixture was stirred at 60° C. for 2 hours. LCMS showed that the reaction was completed. The reaction mixture was concentrated in vacuo and the residue was purified by silica gel column (pet ether:EtOAc 10:1) to provide 2-bromo-1-methoxy-3-(trifluoromethyl)benzene as a colorless oil (400 mg). Yield 43%.

Step 4: (S)-ethyl 3-(tert-butoxycarbonylamino)-3-(4-fluoro-2'-methoxy-5-methyl-6'-(trifluoromethyl)biphenyl-3-yl)propanoate

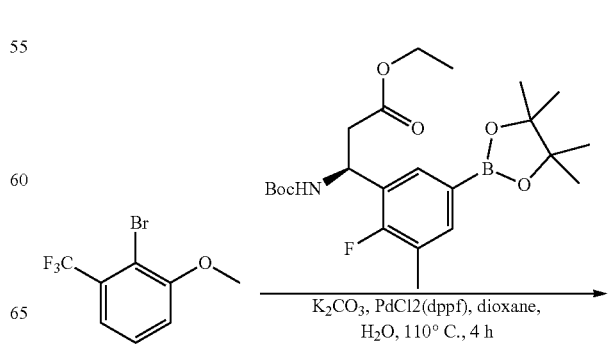

-continued

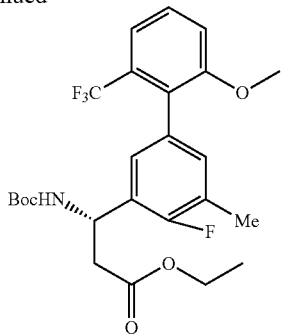

A mixture of 2-bromo-1-methoxy-3-(trifluoromethyl) benzene (400 mg, 1.57 mmol, 1.00 eq), (S)-ethyl 3-(tert-butoxycarbonylamino)-3-(2-fluoro-3-methyl-5-(4,4,5,5-tetramethyl-1,3,2-dioxaborolan-2-yl)phenyl)propanoate (708 mg, 1.57 mmol, 1.0 eq), K$_2$CO$_3$ (650 mg, 4.71 mmol, 3.0 eq) and Pd(dppf)Cl$_2$ (115 mg, 0.157 mmol, 0.1 eq) in dioxane (8 mL) and H$_2$O (0.8 mL) was stirred at 110° C. for 4 hours under nitrogen atmosphere. LCMS showed that the reaction was completed. The mixture was cooled to room temperature. Water (30 mL) was added and the mixture was extracted with EtOAc (30 mL×3). The combined organic phases was washed with brine (30 mL), dried over anhydrous Na$_2$SO$_4$, filtered and concentrated in vacuo. The residue was purified by silica gel column (pet ether:EtOAc 10:1) to provide (S)-ethyl 3-(tert-butoxycarbonylamino)-3-(4-fluoro-2'-methoxy-5-methyl-6'-(trifluoromethyl)biphenyl-3-yl)propanoate (400 mg) as a colorless oil. Yield 51% (ESI 400.1 [M-Boc]$^+$).

Step 5: (S)-ethyl 3-amino-3-(4-fluoro-2'-methoxy-5-methyl-6'-(trifluoromethyl)biphenyl-3-yl)propanoate

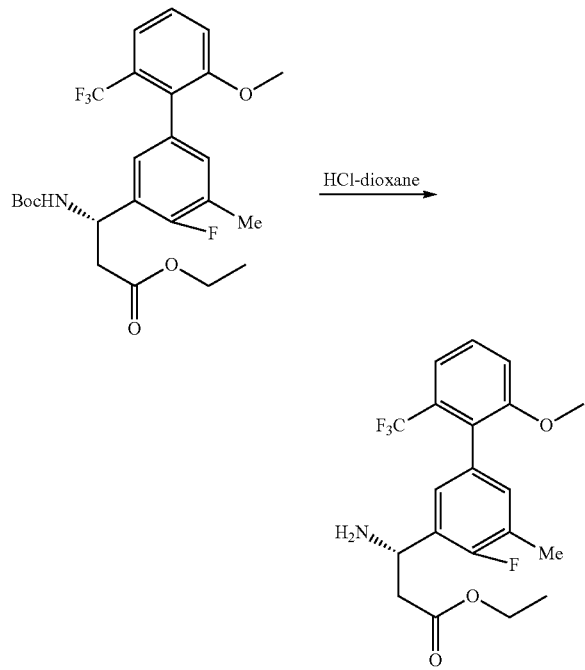

To a stirred solution of (S)-ethyl 3-(tert-butoxycarbonylamino)-3-(4-fluoro-2'-methoxy-5-methyl-6'-(trifluoromethyl)biphenyl-3-yl)propanoate (400 mg, 0.8 mmol, 1.00 eq) in DCM (6 mL) was added HCl-dioxane (4 M, 0.8 mL, 3.2 mmol, 4 eq) and stirred at room temperature for 2 hours. LCMS showed that the reaction was completed. The mixture was concentrated in vacuo and the residue was purified by reverse phase HPLC on a C18/120 g column (A: water 10 mM NH$_4$HCO$_3$, B: MeOH, 0~100%) to provide (S)-ethyl 3-amino-3-(4-fluoro-2'-methoxy-5-methyl-6'-(trifluoromethyl)biphenyl-3-yl)propanoate (280 mg) as a colorless oil. Yield 87% (ESI 400.1 [M+H]$^+$).

Preparation of (S)-ethyl 3-amino-3-(2',6'-dichloro-4-fluoro-5-methylbiphenyl-3-yl)propanoate Step 1: (S)-ethyl 3-(tert-butoxycarbonylamino)-3-(2',6'-dichloro-4-fluoro-5-methylbiphenyl-3-yl)propanoate

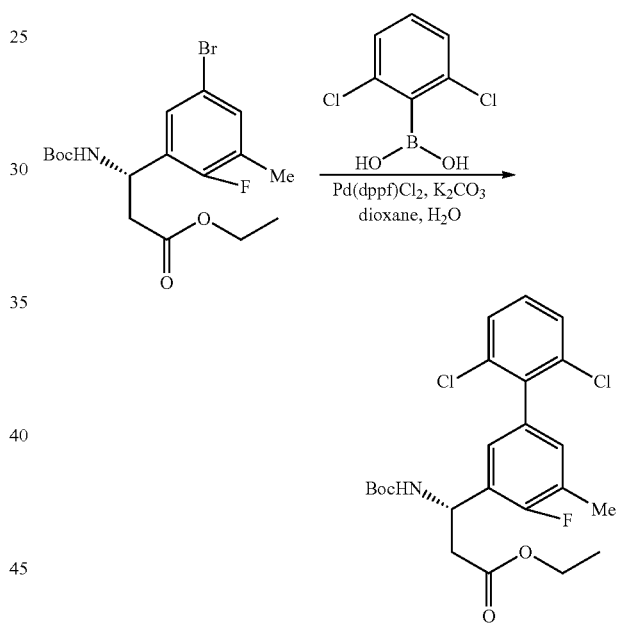

To a mixture of methyl (S)-ethyl 3-(5-bromo-2-fluoro-3-methylphenyl)-3-(tert-butoxycarbonylamino)propanoate (0.5 g, 1.29 mmol, 1 eq) and 2,6-dichlorophenylboronic acid (0.26 g, 1.36 mmol, 1.1 eq) in dioxane (10 mL) was added a solution of K$_2$CO$_3$ (0.34 g, 2.48 mmol, 2 eq) in H$_2$O (2 mL) and Pd(dppf)Cl$_2$ (90 mg, 0.124 mmol, 0.1 eq). The mixture was heated to 110° C. for 2 hours under nitrogen atmosphere. The mixture was cooled to room temperature. Water (20 mL) was added and the solution was extracted with EtOAc (20 mL×3). The combined organic phases were concentrated in vacuo and the residue was purified by silica gel column (pet ether:EtOAc 1:1) to provide (S)-ethyl 3-(tert-butoxycarbonylamino)-3-(2',6'-dichloro-4-fluoro-5-methylbiphenyl-3-yl)propanoate a colorless oil (0.550 g). Yield 94% (ESI 470.4 [M+H]$^+$).

Step 2: (S)-methyl 3-amino-3-(2',6'-dichloro-4-fluoro-5-methylbiphenyl-3-yl)propanoate

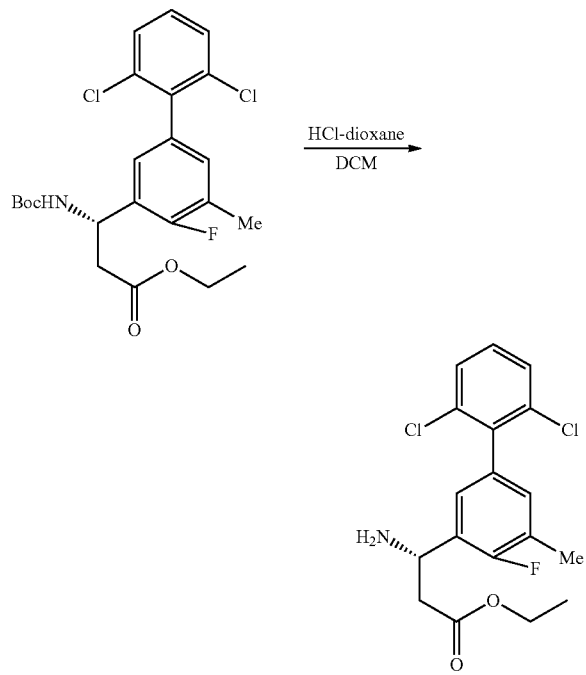

To a mixture of methyl (S)-ethyl 3-(tert-butoxycarbonylamino)-3-(2',6'-dichloro-4-fluoro-5-methylbiphenyl-3-yl)propanoate (0.55 g, 1.21 mmol, 1 eq) in DCM (6 mL) was added HCl-dioxane (4 M, 3 mL, 12 mmol, 10 eq). The mixture was stirred at room temperature for 1 hour. LCMS showed that the reaction was completed. The mixture was concentrated in vacuo to give crude product (S)-ethyl 3-amino-3-(2',6'-dichloro-4-fluoro-5-methylbiphenyl-3-yl)propanoate as a white solid (0.42 g) used directly in the next reaction without further purification. Yield 98% (ESI 370.3 [M+H]$^+$).

Preparation of Ethyl (S)-3-amino-3-(2',4-difluoro-4',5,6'-trimethyl-[1,1'-biphenyl]-3-yl)propanoate Step 1: 2-fluoro-4,6-dimethylaniline

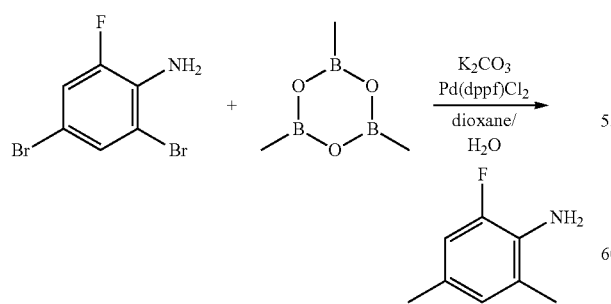

A mixture of 2,4-dibromo-6-fluoroaniline (5.0 g, 18.59 mmol, 1.0 eq), 2,4,6-trimethyl-1,3,5,2,4,6-trioxatriborinane (3.5 M in THF, 21.2 mL, 74.36 mmol, 4.0 eq), Pd(dppf)Cl$_2$ (680 mg, 0.93 mmol, 0.05 eq) and K$_2$CO$_3$ (7.71 g, 55.78 mmol, 3.0 eq) in dioxane (60 mL) and H$_2$O (8 mL) was stirred at 110° C. for 12 hours under nitrogen atmosphere. The mixture was cooled to room temperature. Water (30 mL) was added and the solution was extracted with EtOAc (35 mL×3). The combined organic phases were washed with brine (20 mL), dried over anhydrous Na$_2$SO$_4$, filtered and concentrated in vacuo. The residue was purified by silica gel column (petroleum ether:EtOAc 20:1) to provide 2-fluoro-4,6-dimethylaniline as a yellow oil (2.16 g). Yield 83.5% (ESI 140.2 [M+H]$^+$).

Step 2: 2-bromo-1-fluoro-3,5-dimethylbenzene

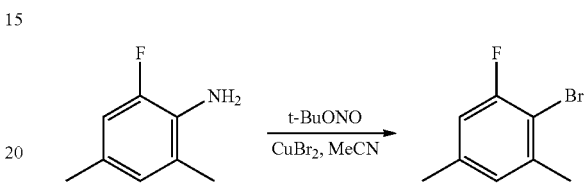

To a stirred solution of 2-fluoro-4,6-dimethylaniline (1.0 g, 7.2 mmol, 1.0 eq) and CuBr$_2$ (4.8 g, 21.6 mmol, 3.0 eq) in MeCN (7 mL) was added tert-Butyl nitrite (1.68 g, 14.4 mmol, 2.0 eq) and stirred at 60° C. for 1 hour under nitrogen atmosphere. LCMS showed that the reaction was completed. The mixture was filtered and concentrated in vacuo. The residue was purified by silica gel column (petroleum ether) to provide 2-bromo-1-fluoro-3,5-dimethylbenzene as a yellow oil (560 mg). Yield 38%.

Step 3: Ethyl (S)-3-((tert-butoxycarbonyl)amino)-3-(2',4-difluoro-4',5,6'-trimethyl-[1,1'-biphenyl]-3-yl)propanoate

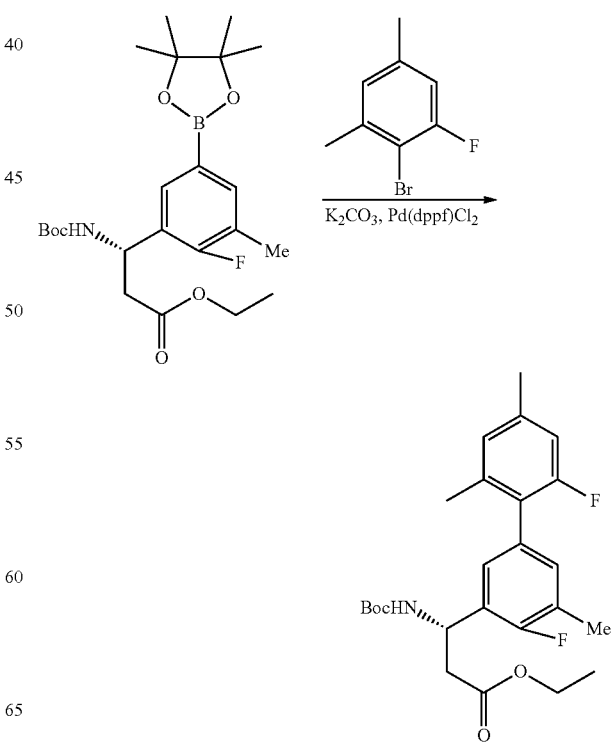

A mixture of ethyl (S)-3-((tert-butoxycarbonyl)amino)-3-(2-fluoro-3-methyl-5-(4,4,5,5-tetramethyl-1,3,2-dioxaborolan-2-yl)phenyl)propanoate (556 mg, 1.23 mmol, 1.0 eq), 2-bromo-1-fluoro-3,5-dimethylbenzene (250 mg, 1.23 mmol, 1.0 eq), Pd(dppf)Cl$_2$ (45 mg, 0.062 mmol, 0.05 eq) and K$_2$CO$_3$ (510 mg, 3.69 mmol, 3.0 eq) in dioxane (6 mL) and water (2 mL) was stirred at 110° C. for 2 hours under nitrogen atmosphere. Water (35 mL) was added and the solution was extracted with EtOAc (25 mL×3). The combined organic phases were washed with brine (50 mL), dried over anhydrous Na$_2$SO$_4$, filtered and concentrated in vacuo. The residue was purified by silica gel column (petroleum ether:EtOAc 7:1) to provide ethyl (S)-3-((tert-butoxycarbonyl)amino)-3-(2',4-difluoro-4',5,6'-trimethyl-[1,1'-biphenyl]-3-yl)propanoate as a yellow oil (365 mg). Yield 66% (ESI 348.1 [M+H−100]$^+$).

Step 4: Ethyl (S)-3-amino-3-(2',4-difluoro-4',5,6'-trimethyl-[1,1'-biphenyl]-3-yl)propanoate

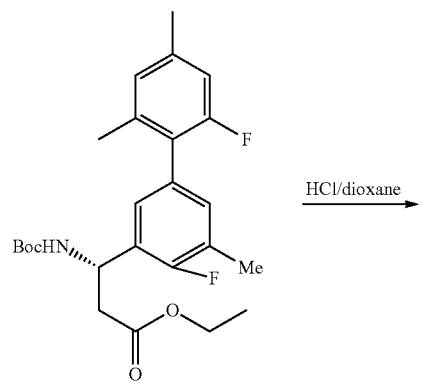

HCl/dioxane

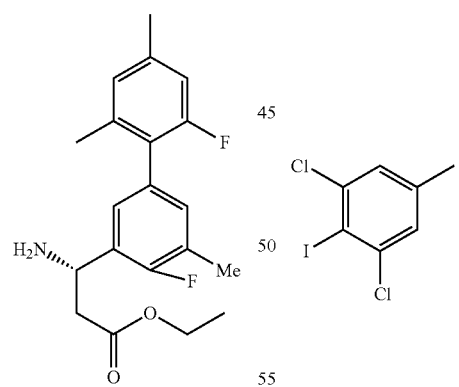

To a stirred solution of ethyl (S)-3-((tert-butoxycarbonyl)amino)-3-(2',4-difluoro-4',5,6'-trimethyl-[1,1'-biphenyl]-3-yl)propanoate (720 mg, 1.29 mmol, 1.0 eq) in DCM (2 mL) was added HCl-dioxane (4 M, 2.0 mL, 4.0 mmol, 3.1 eq) and stirred at room temperature for 1 hour. LCMS showed that the reaction was completed. The mixture was concentrated in vacuo to provide ethyl (S)-3-amino-3-(2',4-difluoro-4',5,6'-trimethyl-[1,1'-biphenyl]-3-yl)propanoate as a yellow oil (450 mg). Yield 93% (ESI 348.1 [M+H]$^+$).

Preparation of (S)-ethyl 3-amino-3-(2',6'-dichloro-4-fluoro-4',5-dimethylbiphenyl-3-yl)propanoate Step 1: 1,3-dichloro-2-iodo-5-methylbenzene

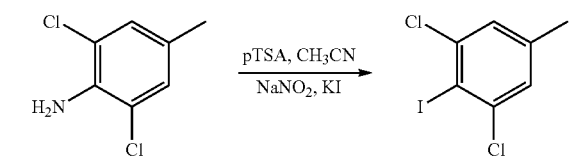

To a mixture of 2,6-dichloro-4-methylaniline (2.5 g, 14.3 mmol, 1.0 eq) in acetonitrile (10 mL) and water (1 mL) was added 4-methylbenzenesulfonic acid (9.8 g, 57.1 mmol, 4 eq) and stirred at 0° C. for 10 mins. A solution of NaNO$_2$ (2.0 g, 28.6 mmol, 2 eq) in H$_2$O (2 mL) was added dropwise and the mixture was stirred at 0° C. for 30 mins. Then a solution of potassium iodide (3.0 g, 17.9 mmol, 1.5 eq) in H$_2$O (2 mL) was added and heated to 50° C. for 2 hours under nitrogen atmosphere. Water (20 mL) was added and the solution was extracted with EtOAc (20 mL×3). The combined organic phases were concentrated in vacuo and the residue was purified by silica gel column (pet ether:EtOAc 1:1) to give 1,3-dichloro-2-iodo-5-methylbenzene as a colorless oil (1.8 g). Yield 44.2% (ESI 286.9[M+H]$^+$).

Step 2: (S)-ethyl 3-(tert-butoxycarbonylamino)-3-(2',6'-dichloro-4-fluoro-4',5-dimethylbiphenyl-3-yl)propanoate

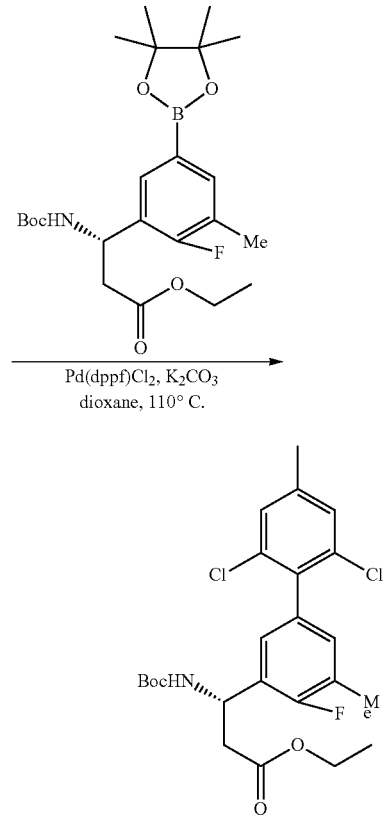

To a mixture of methyl (S)-ethyl 3-(tert-butoxycarbonylamino)-3-(2-fluoro-3-methyl-5-(4,4,5,5-tetramethyl-1,3,2-dioxaborolan-2-yl)phenyl)propanoate (1.5 g, 3.43 mmol, 1 eq) and 1,3-dichloro-2-iodo-5-methylbenzene (2.0 g, 6.86 mmol, 2 eq) in dioxane (10 mL) was added a solution of $K_2CO_3$ (1.9 g, 13.72 mmol, 4 eq) in $H_2O$ (2 mL) and Pd(dppf)Cl$_2$ (250 mg, 0.343 mmol, 0.1 eq). The mixture was heated to 110° C. for 2 hours under nitrogen atmosphere. Water (20 mL) was added and the solution was extracted with EtOAc (20 mL×3). The combined organic phases were concentrated in vacuo and the residue was purified by silica gel column (pet ether:EtOAc 1:1) to give methyl (S)-ethyl 3-(tert-butoxycarbonylamino)-3-(2',6'-dichloro-4-fluoro-4',5-dimethylbiphenyl-3-yl)propanoate as a colorless oil (1.3 g). Yield 78.3% (ESI 484.4 [M+H]$^+$).

Step 3: (S)-ethyl 3-amino-3-(2',6'-dichloro-4-fluoro-4',5-dimethylbiphenyl-3-yl)propanoate

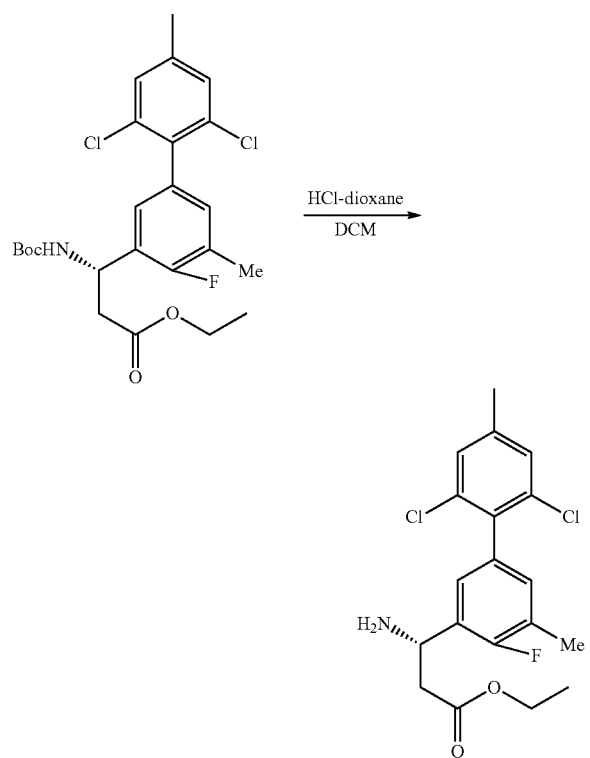

To a mixture of methyl (S)-ethyl 3-(tert-butoxycarbonylamino)-3-(2',6'-dichloro-4-fluoro-4',5-dimethylbiphenyl-3-yl)propanoate (1.3 g, 2.76 mmol, 4 eq) in DCM (6 mL) was added HCl-dioxane (4 M, 3 mL, 12 mmol, 4.3 eq). The mixture was stirred at room temperature for 1 hour. LCMS showed that the reaction was completed. The mixture was concentrated in vacuo to give crude (S)-ethyl 3-amino-3-(2',6'-dichloro-4-fluoro-4',5-dimethylbiphenyl-3-yl)propanoate as a white solid (1.0 g) used directly in the next reaction without further purification. Yield 91% (ESI 384.3 [M+H]$^+$).

Preparation of Ethyl (S)-3-amino-3-(4-fluoro-2',5,6'-trimethyl-[1,1'-biphenyl]-3-yl)propanoate Step 1: Ethyl (S)-3-(((R)-tert-butylsulfinyl)amino)-3-(4-fluoro-2',5,6'-trimethyl-[1,1'-biphenyl]-3-yl)propanoate

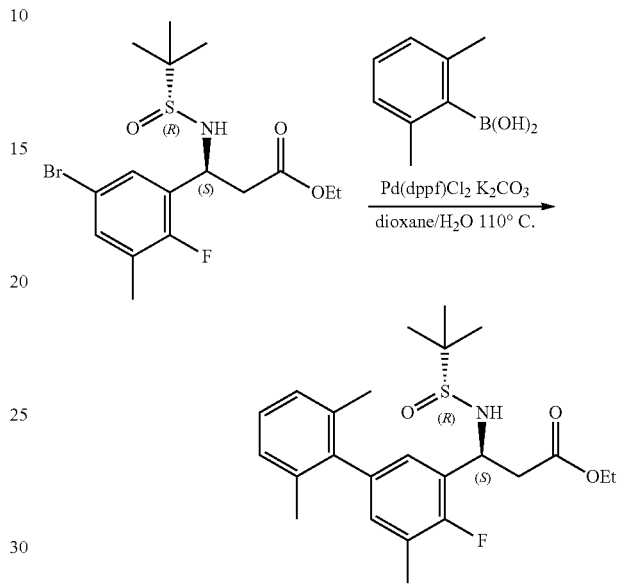

A mixture of ethyl (S)-3-(5-bromo-2-fluoro-3-methylphenyl)-3-(((R)-tert-butylsulfinyl)amino)propanoate (4.0 g, 9.8 mmol, 1.00 eq), (2,6-dimethylphenyl)boronic acid (2.9 g, 19.6 mmol, 2.00 eq), $K_2CO_3$ (4.1 g, 29.4 mmol, 3.0 eq), Pd(dppf)Cl$_2$ (717 mg, 0.98 mmol, 0.05 eq) in dioxane (24 mL) and $H_2O$ (9 mL) was stirred at 110° C. for 2 hours under nitrogen atmosphere. LCMS showed that the reaction was completed. The mixture was cooled to room temperature. Water (30 mL) was added and the solution was extracted with EtOAc (30 mL×3). The combined organic phases were washed with brine (30 mL), dried over anhydrous $Na_2SO_4$, filtered and concentrated in vacuo. The residue was purified by silica gel column (pet ether:EtOAc 1:1) to provide ethyl (S)-3-(((R)-tert-butylsulfinyl)amino)-3-(4-fluoro-2',5,6'-trimethyl-[1,1'-biphenyl]-3-yl)propanoate (4.0 g) as a yellow oil. Yield 94% (ESI 434.1 [M+H]$^+$).

Step 2: Ethyl (S)-3-amino-3-(4-fluoro-2',5,6'-trimethyl-[1,1'-biphenyl]-3-yl)propanoate

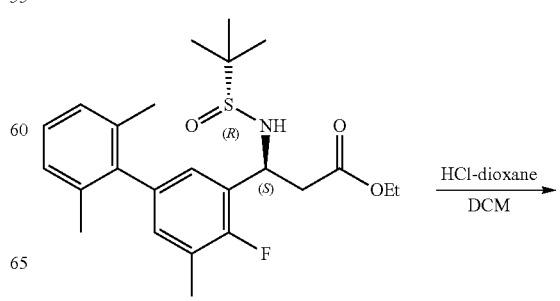

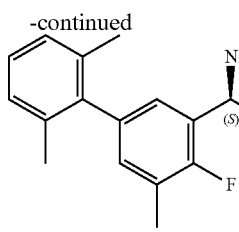

To a stirred solution of ethyl (S)-3-(((R)-tert-butylsulfinyl)amino)-3-(4-fluoro-2',5,6'-trimethyl-[1,1'-biphenyl]-3-yl)propanoate (4.0 g, 9.2 mmol, 1.00 eq) in DCM (6 mL) was added HCl-dioxane (4 M, 4 mL, 16.0 mmol, 1.7 eq). The mixture was stirred at room temperature for 30 mins. LCMS showed that the reaction was completed. The mixture was concentrated in vacuo and the residue was purified by reverse phase HPLC on a C18/120 g column (A: water 10 mM $NH_4HCO_3$, B: MeOH, 0~100%) to provide ethyl (S)-3-amino-3-(4-fluoro-2',5,6'-trimethyl-[1,1'-biphenyl]-3-yl)propanoate (2.0 g) as a colorless oil. Yield 61% (ESI 330.1 $[M+H]^+$).

Preparation of Ethyl (S)-3-amino-3-(4,4'-difluoro-2',5,6'-trimethyl-[1,1'-biphenyl]-3-yl)propanoate Step 1: Ethyl (S)-3-(((R)-tert-butylsulfinyl)amino)-3-(4,4'-difluoro-2',5,6'-trimethyl-[1,1'-biphenyl]-3-yl)propanoate

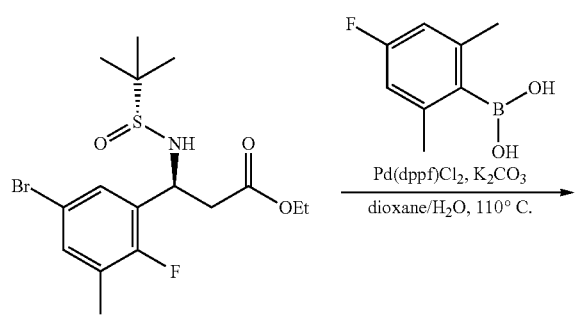

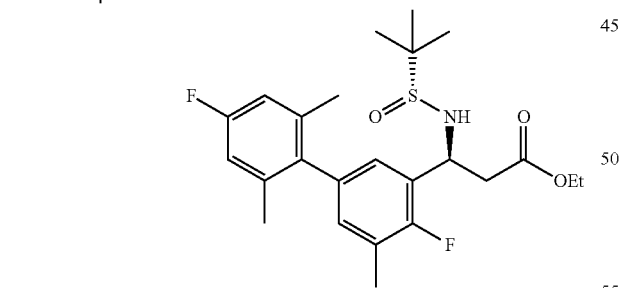

A mixture of ethyl (S)-3-(5-bromo-2-fluoro-3-methylphenyl)-3-(((R)-tert-butylsulfinyl)amino)propanoate (6.0 g, 14.7 mmol, 1.00 eq), (4-fluoro-2,6-dimethylphenyl)boronic acid (3.7 g, 22.1 mmol, 1.5 eq), $K_2CO_3$ (6.1 g, 44.1 mmol, 3.0 eq) and Pd(dppf)Cl$_2$ (1.1 g, 1.47 mmol, 0.01 eq) in dioxane (50 mL) and $H_2O$ (5 mL) was stirred at 110° C. under nitrogen atmosphere for 1 hour. LCMS showed that the reaction was completed. The mixture was cooled to room temperature. Water (50 mL) was added and the solution was extracted with EtOAc (50 mL×3). The combined organic phases were washed with brine (30 mL), dried over anhydrous $Na_2SO_4$, filtered and concentrated in vacuo. The residue was purified by silica gel column (pet ether:EtOAc 1:1) to provide ethyl (S)-3-(((R)-tert-butylsulfinyl)amino)-3-(4,4'-difluoro-2',5,6'-trimethyl-[1,1'-biphenyl]-3-yl)propanoate as a yellow oil (5.5 g). Yield 83% (ESI 452.0 $(M+H)^+$)

Step 2: Ethyl (S)-3-amino-3-(4,4'-difluoro-2',5,6'-trimethyl-[1,1'-biphenyl]-3-yl)propanoate

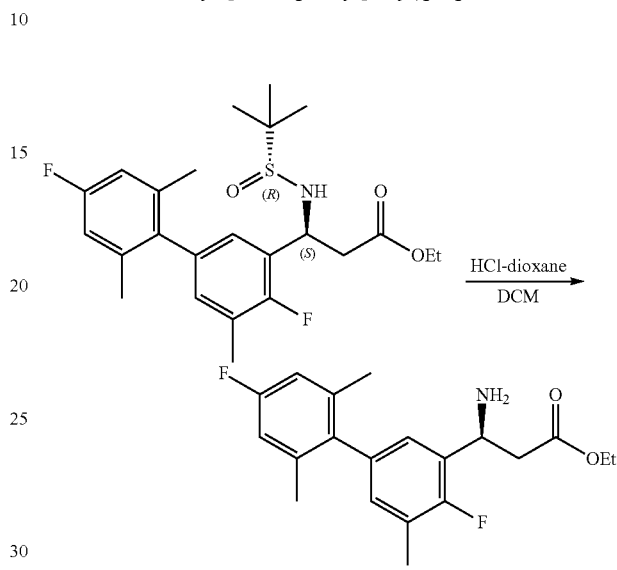

To the solution of ethyl (S)-3-(((R)-tert-butylsulfinyl)amino)-3-(4,4'-difluoro-2',5,6'-trimethyl-[1,1'-biphenyl]-3-yl)propanoate (5.5 g, 12.2 mmol, 1.00 eq) in DCM (6 mL) was added HCl-dioxane (4M, 6 mL, 24.0 mmol, 1.97 eq) and stirred at room temperature for 1 hour. The mixture was concentrated in vacuo and the residue was purified by reverse phase HPLC on a C18/120 g column (A: water/ 0.01% TFA, B: MeOH, 0~100%) to provide ethyl (S)-3-amino-3-(4,4'-difluoro-2',5,6'-trimethyl-[1,1'-biphenyl]-3-yl)propanoate as a yellow solid (4.0 g). Yield 95% (ESI 348.1 $(M+H)^+$).

Preparation of Ethyl (S)-3-amino-3-(4'-chloro-4-fluoro-2',5,6'-trimethyl-[1,1'-biphenyl]-3-yl)propanoate Step 1: 2-(4-chloro-2,6-dimethylphenyl)-4,4,5,5-tetramethyl-1,3,2-dioxaborolane

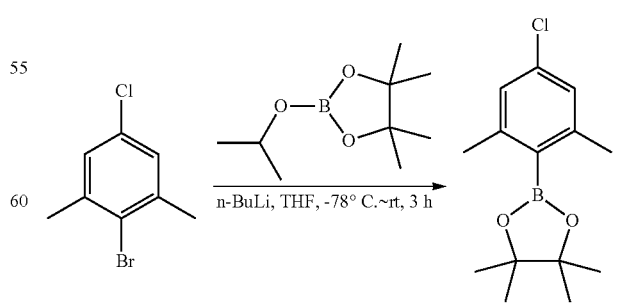

To a solution of 2-bromo-5-chloro-1,3-dimethylbenzene (4.0 g, 18.2 mmol, 1.0 eq) in anhydrous THF (40 mL) under nitrogen atmosphere was added n-BuLi (2 N, 11.0 mL, 22.0 mmol, 1.2 eq) at −78° C. The reaction mixture was stirred at −78° C. for 40 mins and 2-isopropoxy-4,4,5,5-tetramethyl-1,3,2-dioxaborolane (5.1 g, 27.5 mmol, 1.5 eq) in anhydrous THF (40 mL) was added and stirred at −78° C. for 3 hours. After completion, a saturated NH₄Cl solution (aq) (100 mL) was added. The mixture was extracted with EtOAc (100 mL×3). The combined organic layers were washed with brine (50 mL), dried over anhydrous Na₂SO₄, filtered and concentrated in vacuo. The residue obtained was purified by silica gel (petroleum ether:EtOAc 2:1) to give the desired 2-(4-chloro-2,6-dimethylphenyl)-4,4,5,5-tetramethyl-1,3,2-dioxaborolane as a white solid (4.4 g). Yield 90%.

Step 2: Ethyl (S)-3-amino-3-(4'-chloro-4-fluoro-2',5,6'-trimethyl-[1,1'-biphenyl]-3-yl)propanoate

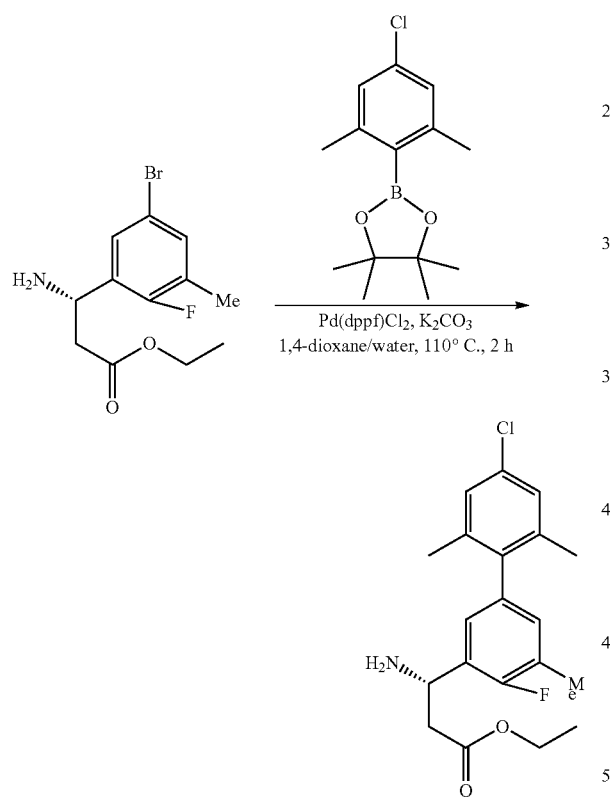

A mixture of ethyl (S)-3-amino-3-(5-bromo-2-fluoro-3-methylphenyl)propanoate (500 mg, 1.7 mmol, 1.0 eq), 2-(4-chloro-2,6-dimethylphenyl)-4,4,5,5-tetramethyl-1,3,2-dioxaborolane (544 mg, 2.04 mmol, 1.2 eq), Pd(dppf)Cl₂ (62 mg, 0.085 mmol, 0.05 eq) and K₂CO₃ (704 mg, 5.1 mmol, 3.0 eq) in 1,4-dioxane (10 mL) and water (2 mL) was stirred at 110° C. for 2 hours under nitrogen atmosphere. Water (20 mL) was added and the solution was extracted with EtOAc (30 mL×3). The combined organic layers were washed with brine (20 mL), dried over anhydrous Na₂SO₄, filtered and concentrated in vacuo. The residue was purified by silica gel column (petroleum ether:EtOAc 1:2) to provide ethyl (S)-3-amino-3-(4'-chloro-4-fluoro-2',5,6'-trimethyl-[1,1'-biphenyl]-3-yl)propanoate as a colorless oil (250 mg). Yield 41% (ESI 364.2 [M+H]⁺).

Preparation of Ethyl (S)-3-amino-3-(4-fluoro-2',4',5,6'-tetramethyl-[1,1'-biphenyl]-3-yl)propanoate Step 1: Ethyl (S)-3-(((R)-tert-butylsulfinyl)amino)-3-(4-fluoro-2',4',5,6'-tetramethyl-[1,1'-biphenyl]-3-yl)propanoate

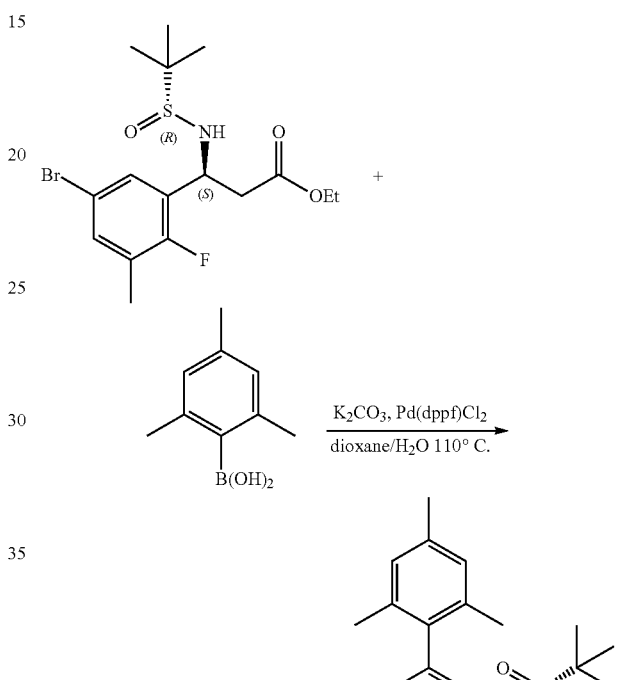

A mixture of ethyl (S)-3-(5-bromo-2-fluoro-3-methylphenyl)-3-(((R)-tert-butylsulfinyl)amino)propanoate (3.8 g, 9.3 mmol, 1.0 eq), mesitylboronic acid (3.05 g, 18.6 mmol, 2.0 eq), K₂CO₃ (3.85 g, 27.9 mmol, 3.0 eq) and Pd(dppf)Cl₂ (340 mg, 0.465 mmol, 0.05 eq) in Dioxane (30 mL) and H₂O (5 mL) was stirred at 110° C. under nitrogen atmosphere for 2 hours. LCMS showed the reaction was complete. The reaction mixture was cooled to room temperature. Water (80 mL) was added and the mixture was extracted with EtOAc (100 mL×3). The combined organic layers were washed with brine (150 mL), dried over Na₂SO₄, filtered and concentrated in vacuo. The residue was purified by silica gel column (pet ether:EtOAc 1:1) to provide ethyl (S)-3-(((R)-tert-butylsulfinyl)amino)-3-(4-fluoro-2',4',5,6'-tetramethyl-[1,1'-biphenyl]-3-yl)propanoate as a yellow oil (3.1 g). Yield 75% (ESI 448.2 [M+H]⁺).

187

Step 2: Ethyl (S)-3-amino-3-(4-fluoro-2',4',5,6'-tetramethyl-[1,1'-biphenyl]-3-yl)propanoate

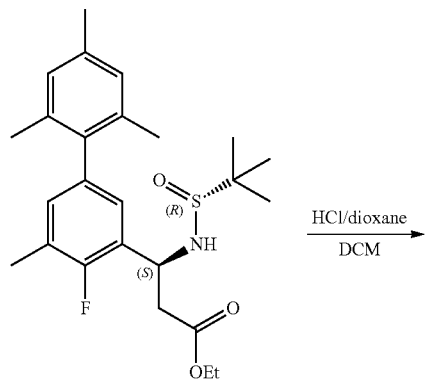

To a stirred solution of ethyl (S)-3-(((R)-tert-butylsulfinyl)amino)-3-(4-fluoro-2',4',5,6'-tetramethyl-[1,1'-biphenyl]-3-yl)propanoate (3.1 g, 6.94 mmol, 1.0 eq) in DCM (7 mL) was added HCl-dioxane (4 M, 6.8 mL, 3.9 eq) and stirred at 25° C. for 2 hours. LCMS showed that the reaction was completed. The mixture was concentrated in vacuo and the residue was purified by reverse phase HPLC on a C18/40 g column (A: water 10 mM $NH_4HCO_3$, B: MeOH, 0~100%) to provide (S)-ethyl 3-amino-3-(4-fluoro-2',4',5,6'-tetramethylbiphenyl-3-yl)propanoate as a yellow oil (1.6 g). Yield 67% (ESI 344.2 $[M+H]^+$).

Example: Preparation of ethyl (S)-3-amino-3-(4-fluoro-2',5,6'-trimethyl-4'-(trifluoromethyl)-[1,1'-biphenyl]-3-yl)propanoate Hydrochloride

Step 1: 2,6-dimethyl-4-(trifluoromethyl)aniline

188

A mixture of 2,6-dibromo-4-(trifluoromethyl)aniline (638 mg, 2.00 mmol, 1.0 eq), 2,4,6-trimethyl-1,3,5,2,4,6-trioxatriborinane (3.5 M in THF, 3.43 mL, 12.00 mmol, 6.0 eq), $K_2CO_3$ (1.10 g, 7.96 mmol, 3.98 eq) and Pd(dppf)Cl$_2$ (245 mg, 0.30 mmol, 0.15 eq) in dioxane (6 mL) and water (1 mL) was stirred at 90° C. for 8 hours under nitrogen atmosphere. The mixture was filtered through a pad of Celite, washed with ethyl acetate (100 mL) and the filtrate was concentrated in vacuo. The residue was purified by silica gel column (petroleum ether:EtOAc 20:1) to provide 2,6-dimethyl-4-(trifluoromethyl)aniline as a colorless oil (1.63 g). Yield 48% (ESI 190.1 $(M+H)^+$).

Step 2: 2-bromo-1,3-dimethyl-5-(trifluoromethyl)benzene

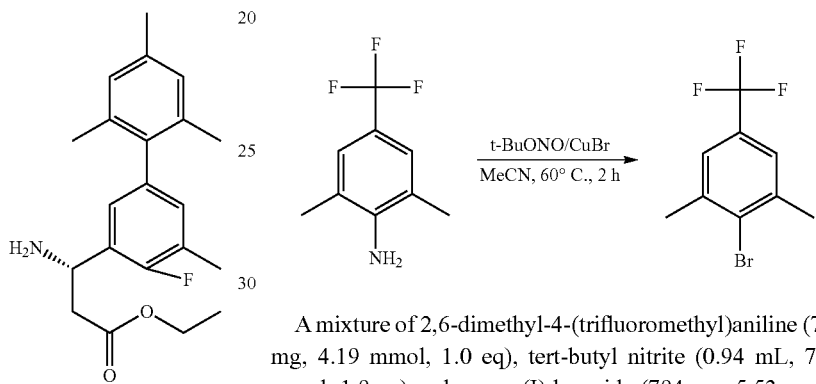

A mixture of 2,6-dimethyl-4-(trifluoromethyl)aniline (793 mg, 4.19 mmol, 1.0 eq), tert-butyl nitrite (0.94 mL, 7.84 mmol, 1.9 eq) and copper(I) bromide (794 mg, 5.53 mmol, 1.3 eq) in anhydrous acetonitrile (16 mL) was stirred at 60° C. for 2 hours under nitrogen atmosphere. LCMS showed that the reaction was completed. The mixture was filtered through a pad of Celite and the filtrate was concentrated in vacuo. The residue was purified by silica gel column (petroleum ether:EtOAc 6:1) to provide 2-bromo-1,3-dimethyl-5-(trifluoromethyl)benzene as a colorless oil (975 mg). Yield 46%. $^1$H NMR (400 MHz, DMSO-$d_6$) δ: 7.55 (s, 2H), 2.42 (s, 6H).

Step 3: Ethyl (S)-3-((tert-butoxycarbonyl)amino)-3-(4-fluoro-2',5,6'-trimethyl-4'-(trifluoromethyl)-[1,1'-biphenyl]-3-yl)propanoate

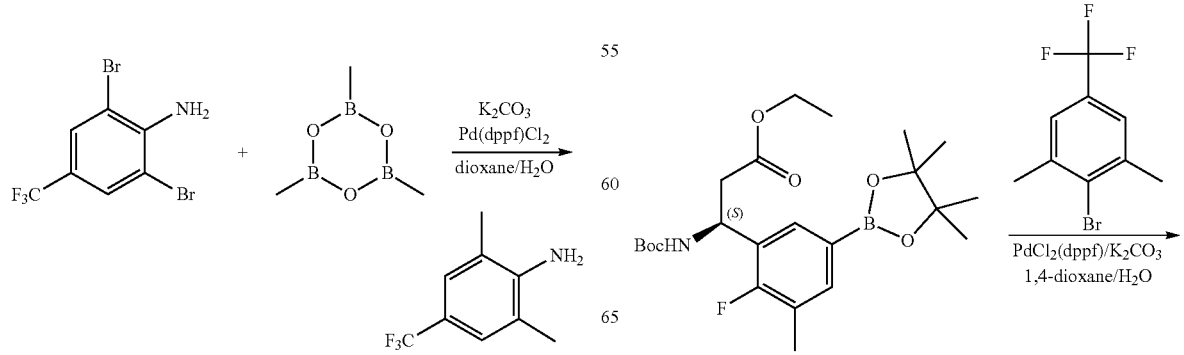

189

-continued

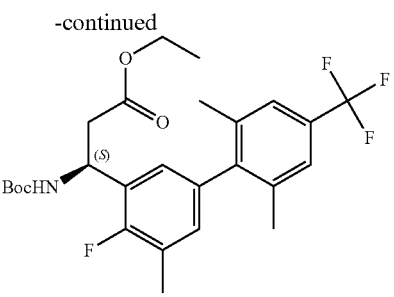

To a solution of ethyl (S)-3-((tert-butoxycarbonyl)amino)-3-(2-fluoro-3-methyl-5-(4,4,5,5-tetramethyl-1,3,2-dioxaborolan-2-yl)phenyl)propanoate (519 mg, 1.15 mmol, 1.0 eq) in dioxane (36 mL) was added 2-bromo-1,3-dimethyl-5-(trifluoromethyl)benzene (306 mg, 1.21 mmol, 1.1 eq), Pd(dppf)Cl$_2$ (188 mg, 0.23 mmol, 0.2 eq), K$_2$CO$_3$ (477 mg, 3.45 mmol, 3.0 eq) and water (3.6 mL). The reaction mixture was stirred at 110° C. for 18 hours under nitrogen atmosphere. The mixture was filtered and concentrated in vacuo. The residue was purified by silica gel column (petroleum ether:EtOAc 6:1) to provide ethyl (S)-3-((tert-butoxycarbonyl)amino)-3-(4-fluoro-2',5,6'-trimethyl-4'-(trifluoromethyl)-[1,1'-biphenyl]-3-yl)propanoate as a light brown oil (308 mg). Yield 54%. (ESI 398.1 [M+H−100]$^+$).

Step 5: Ethyl (S)-3-amino-3-(4-fluoro-2',5,6'-trimethyl-4'-(trifluoromethyl)-[1,1'-biphenyl]-3-yl)propanoate Hydrochloride

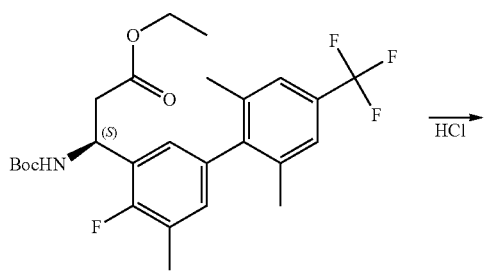

To a stirred solution of ethyl (S)-3-((tert-butoxycarbonyl)amino)-3-(4-fluoro-2',5,6'-trimethyl-4'-(trifluoromethyl)-[1,1'-biphenyl]-3-yl)propanoate (308 mg, 0.62 mmol, 1.0 eq) in DCM (4 mL) was added HCl-dioxane (4 M, 4.0 mL, 16.0 mmol, 25.8 eq). The mixture was stirred at room temperature for 2 hours. LCMS showed that the reaction was completed. The mixture was concentrated in vacuo to provide ethyl (S)-3-amino-3-(4-fluoro-2',5,6'-trimethyl-4'-(trifluoromethyl)-[1,1'-biphenyl]-3-yl)propanoate hydrochloride as a yellow oil (260 mg). Yield 97% (ESI 398.1 [M+H]$^+$).

190

Preparation of Ethyl (S)-3-amino-3-(4'-cyclopropyl-4-fluoro-2',5,6'-trimethyl-[1,1'-biphenyl]-3-yl)propanoate Step 1: 4-cyclopropyl-2,6-dimethylaniline

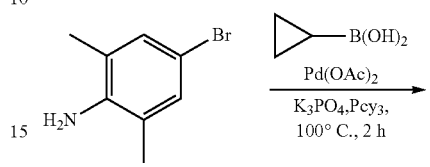

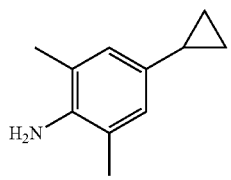

To a mixture of 4-bromo-2,6-dimethylaniline (2.0 g, 10.0 mmol, 1.0 eq), cyclopropylboronic acid (1.03 g, 12.0 mmol, 1.2 eq) in toluene (15 mL) under nitrogen atmosphere was added a solution of K$_3$PO$_4$ (4.2 g, 20.0 mmol, 2.0 eq) in H$_2$O (3 mL), PCy$_3$ (280.0 mg, 1.0 mmol, 0.1 eq) and Pd(OAc)$_2$ (224.0 mg, 1.0 mmol, 0.1 eq). The mixture was stirred at 100° C. for 4 hours under nitrogen atmosphere. Water (30 mL) was added and the solution was extracted with EtOAc (30 mL×3). The combined organic layers were washed with brine (50 mL), dried over anhydrous Na$_2$SO$_4$, filtered and concentrated in vacuo. The residue was purified by silica gel column (petroleum ether:EtOAc 2:1) to provide 4-cyclopropyl-2,6-dimethylaniline (0.8 g) used in the next step without further purification. Yield 93% (ESI 162.2 [M+H]$^+$).

Step 2: 2-bromo-5-cyclopropyl-1,3-dimethylbenzene

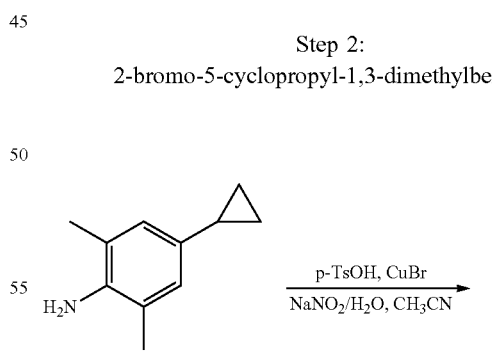

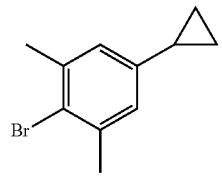

To a mixture of 4-cyclopropyl-2,6-dimethylaniline (800.0 mg, 4.9 mmol, 1.0 eq) in ACN (10 mL) and H₂O (1 mL) was added p-toluenesulphonic acid (3.4 g, 19.8 mmol, 4.0 eq). The mixture was stirred at 0° C. for 10 mins under nitrogen atmosphere. A solution of NaNO₂ (685.0 mg, 9.93 mmol, 2.0 eq) in H₂O (2 mL) was added dropwise and the mixture was stirred 0° C. for 30 mins. CuBr (4.4 g, 19.8 mmol, 4.0 eq) was added to the reaction mixture and stirred at room temperature for 4 hours. Water (50 mL) was added and the solution was extracted with DCM (50 mL×3). The combined organic layers were washed with brine (50 mL), dried over anhydrous Na₂SO₄, filtered and concentrated in vacuo. The residue was purified by silica gel column (petroleum ether: EtOAc 19:1) to provide 2-bromo-5-cyclopropyl-1,3-dimethylbenzene as a yellow oil (800.0 mg) used in the next step without further purification. Yield 49% (ESI 225.1 (M+H)⁺, 227.1 (M+H)⁺).

butoxycarbonyl)amino)-3-(2-fluoro-3-methyl-5-(4,4,5,5-tetramethyl-1,3,2-dioxaborolan-2-yl)phenyl)propanoate (1.6 g, 3.6 mmol, 1.0 eq) in 1,4-dioxane (10 mL) under nitrogen atmosphere was added a solution of K₂CO₃ (1.0 g, 7.2 mmol, 2.0 eq) in H₂O (1 mL) and Pd(dppf)Cl₂ (260 mg, 0.36 mmol, 0.1 eq). The mixture was stirred at 110° C. for 2 hours under nitrogen atmosphere. Water (30 mL) was added and the solution was extracted with EtOAc (50 mL×3). The combined organic phases were washed with brine (50 mL), dried over anhydrous Na₂SO₄, filtered and concentrated in vacuo. The residue was purified by silica gel column (petroleum ether:EtOAc 19:1) to provide ethyl (S)-3-((tert-butoxycarbonyl)amino)-3-(4'-cyclopropyl-4-fluoro-2',5,6'-trimethyl-[1,1'-biphenyl]-3-yl)propanoate as a brown oil (500 mg). Yield 30% (ESI 370.1 [M−100+H]⁺).

Step 3: Ethyl (S)-3-((tert-butoxycarbonyl)amino)-3-(4'-cyclopropyl-4-fluoro-2',5,6'-trimethyl-[1,1'-biphenyl]-3-yl)propanoate Step 4: Ethyl (S)-3-amino-3-(4'-cyclopropyl-4-fluoro-2',5,6'-trimethyl-[1,1'-biphenyl]-3-yl)propanoate Hydrochloride

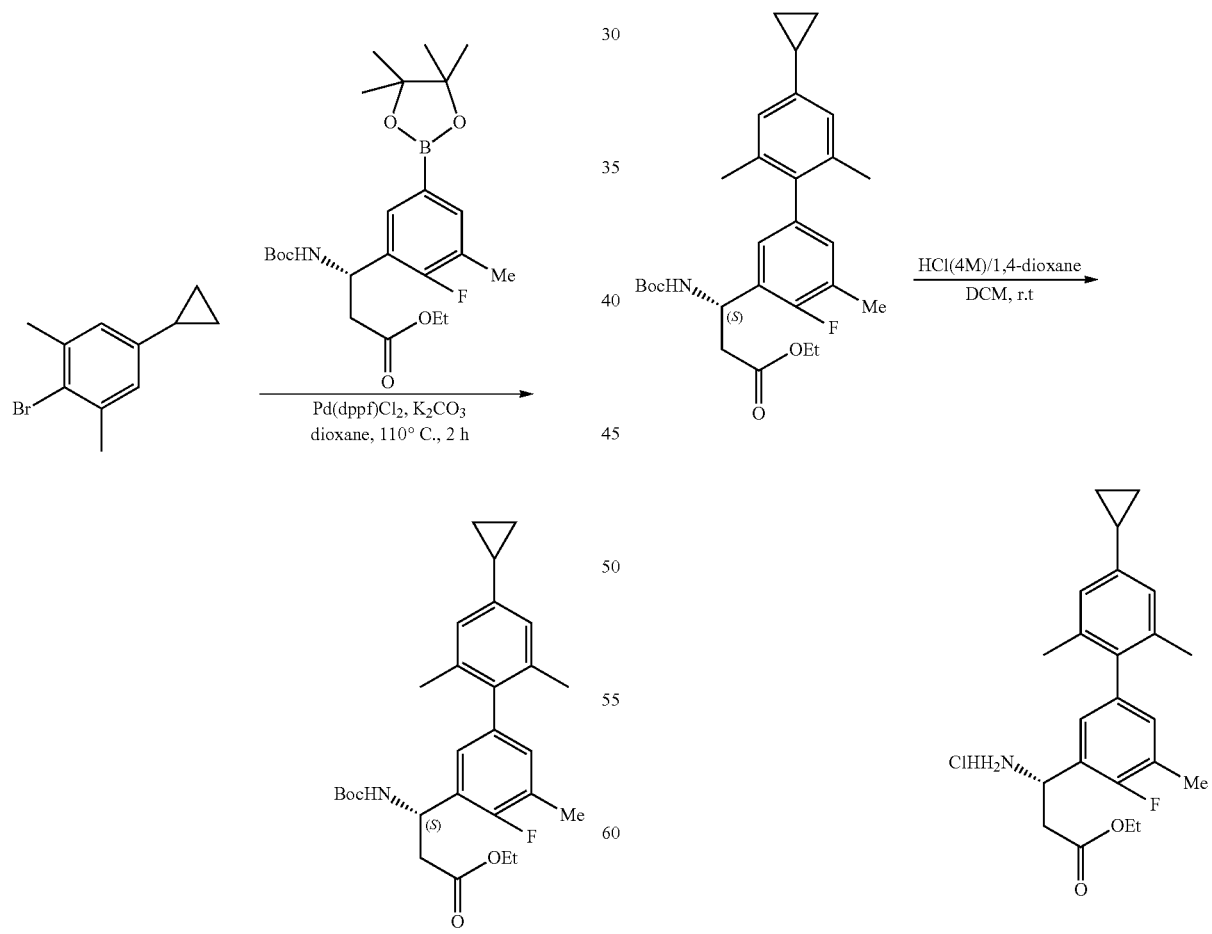

To a mixture of 2-bromo-5-cyclopropyl-1,3-dimethylbenzene (800 mg, 3.6 mmol, 1.0 eq) and ethyl (S)-3-((tert- To a stirred solution of ethyl (S)-3-((tert-butoxycarbonyl)amino)-3-(4'-cyclopropyl-4-fluoro-2',5,6'-trimethyl-[1,1'-biphenyl]-3-yl)propanoate (900 mg, 1.91 mmol, 1.0 eq) in DCM (5 mL) was added HCl-dioxane (4 M, 5.0 mL, 20.0 mmol, 10.47 eq) and stirred at room temperature for 1 hour. LCMS showed that the reaction was completed. The mixture was concentrated in vacuo to provide ethyl (S)-3-amino-3-(4'-cyclopropyl-4-fluoro-2',5,6'-trimethyl-[1,1'-biphenyl]-3-yl)propanoate hydrochloride as a green-yellow foam (710 mg). Yield 91% (ESI 370.2 [M+H]+).

Preparation of Ethyl (S)-3-amino-3-(4-fluoro-4'-methoxy-2',5,6'-trimethyl-[1,1'-biphenyl]-3-yl)propanoate Hydrochloride Step 1: Ethyl (S)-3-((tert-butoxycarbonyl)amino)-3-(4-fluoro-4'-methoxy-2',5,6'-trimethyl-[1,1'-biphenyl]-3-yl)propanoate stirred at 110° C. for 3 hours under nitrogen atmosphere. Water (10 mL) was added and the solution was extracted with EtOAc (20 mL×3). The combined organic layers were washed with brine (60 mL), dried over anhydrous Na$_2$SO$_4$, filtered and concentrated in vacuo. The residue was purified by silica gel column (petroleum ether:EtOAc 7:1) to provide ethyl (S)-3-((tert-butoxycarbonyl)amino)-3-(4-fluoro-4'-methoxy-2',5,6'-trimethyl-[1,1'-biphenyl]-3-yl)propanoate as a colorless oil (230 mg). Yield 65% (ESI 360.2 [M+H−100]+).

Step 2: Ethyl (S)-3-amino-3-(4-fluoro-4'-methoxy-2',5,6'-trimethyl-[1,1'-biphenyl]-3-yl)propanoate Hydrochloride

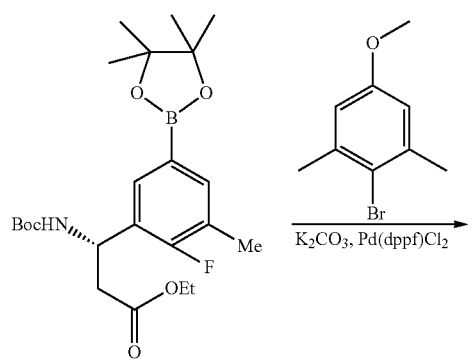

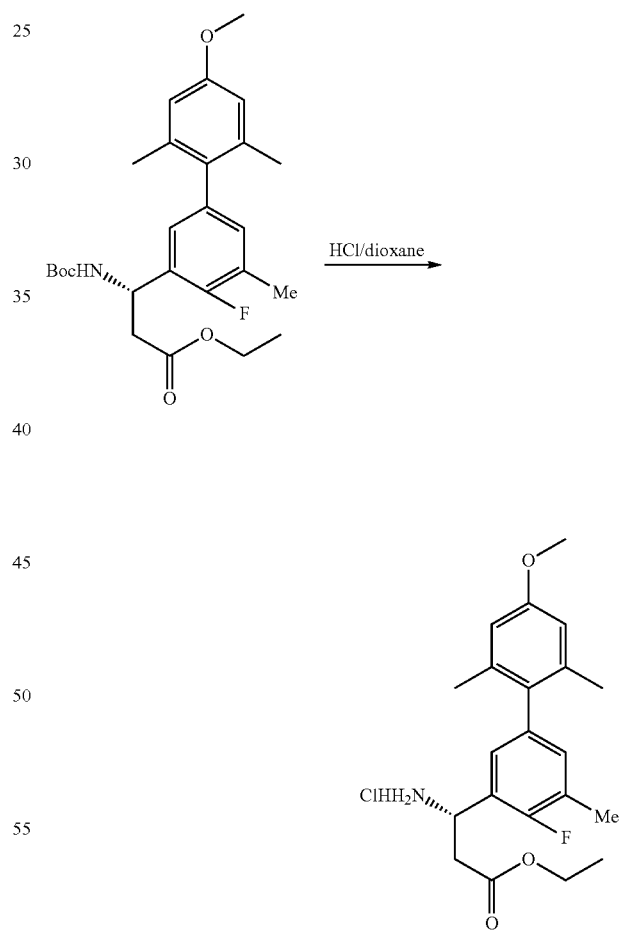

To a solution of ethyl (S)-3-((tert-butoxycarbonyl)amino)-3-(2-fluoro-3-methyl-5-(4,4,5,5-tetramethyl-1,3,2-dioxaborolan-2-yl)phenyl)propanoate (350 mg, 0.77 mmol, 1.0 eq) in dioxane (10 mL) was added 2-bromo-5-methoxy-1,3-dimethylbenzene (166 mg, 0.77 mmol, 1.0 eq), Pd(dppf)Cl$_2$ (56 mg, 0.077 mmol, 0.1 eq), K$_2$CO$_3$ (213 mg, 1.54 mmol, 2.0 eq) and water (2 mL). The reaction mixture was To a stirred solution of ethyl (S)-3-((tert-butoxycarbonyl)amino)-3-(4-fluoro-4'-methoxy-2',5,6'-trimethyl-[1,1'-biphenyl]-3-yl)propanoate (200 mg, 0.43 mmol, 1.0 eq) in DCM (7 mL) was added HCl-dioxane (4 M, 2.0 mL, 4.0 mmol, 9.3 eq). The mixture was stirred at room temperature for 1 hour. LCMS showed that the reaction was completed.

The mixture was concentrated in vacuo to provide ethyl (S)-3-amino-3-(4-fluoro-4'-methoxy-2',5,6'-trimethyl-[1,1'-biphenyl]-3-yl)propanoate hydrochloride as a yellow oil (160 mg). Yield 93% (ESI 360.2 [M+H]⁺).

Preparation of Ethyl (S)-3-amino-3-(4'-cyano-4-fluoro-2',5,6'-trimethyl-[1,1'-biphenyl]-3-yl)propanoate Step 1: Ethyl (S)-3-((tert-butoxycarbonyl)amino)-3-(4'-cyano-4-fluoro-2',5,6'-trimethyl-[1,1'-biphenyl]-3-yl)propanoate

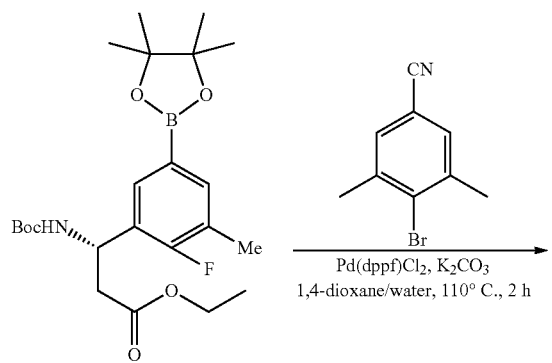

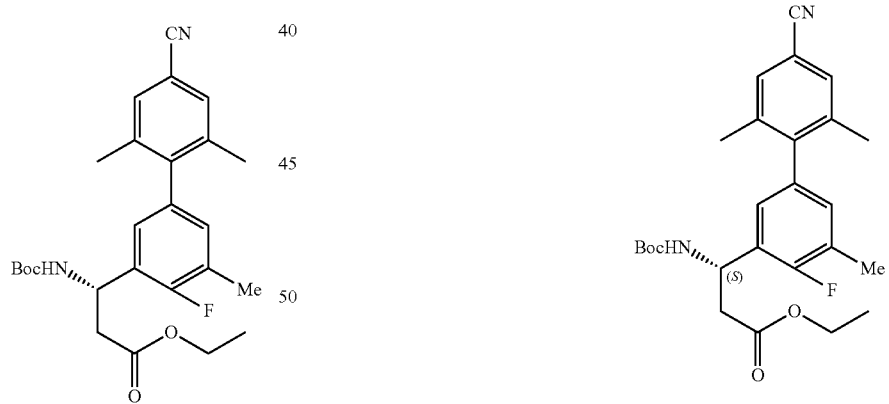

A mixture of ethyl (S)-3-((tert-butoxycarbonyl)amino)-3-(2-fluoro-3-methyl-5-(4,4,5,5-tetramethyl-1,3,2-dioxaborolan-2-yl)phenyl)propanoate (450 mg, 1 mmol, 1.0 eq), 4-bromo-3,5-dimethylbenzonitrile (316 mg, 1.5 mmol, 1.5 eq), Pd(dppf)Cl₂ (37 mg, 0.05 mmol, 0.05 eq) and K₂CO₃ (414 mg, 3 mmol, 3.0 eq) in 1,4-dioxane (8 mL) and water (2 mL) was stirred at 110° C. for 2 hours under nitrogen atmosphere. Water (10 mL) was added and the solution was extracted with EtOAc (20 mL×3). The combined organic layers were washed with brine (20 mL), dried over anhydrous Na₂SO₄, filtered and concentrated in vacuo. The residue was purified by silica gel column (petroleum ether: EtOAc 1:1) to provide ethyl (S)-3-((tert-butoxycarbonyl)amino)-3-(4'-cyano-4-fluoro-2',5,6'-trimethyl-[1,1'-biphenyl]-3-yl)propanoate as a colorless oil (320 mg). Yield 70% (ESI 455.2 [M+H]⁺).

Step 2: Ethyl (S)-3-amino-3-(4'-cyano-4-fluoro-2',5,6'-trimethyl-[1,1'-biphenyl]-3-yl)propanoate To a stirred solution of ethyl (S)-3-((tert-butoxycarbonyl)amino)-3-(4'-cyano-4-fluoro-2',5,6'-trimethyl-[1,1'-biphenyl]-3-yl)propanoate (320 mg, 0.7 mmol, 1.0 eq) in DCM (2 mL) was added HCl-dioxane (4 M, 2.0 mL, 4.0 mmol, 5.7 eq). The mixture was stirred at room temperature for 2 hours. LCMS showed that the reaction was completed. The mixture was concentrated in vacuo to provide ethyl (S)-3-amino-3-(4'-cyano-4-fluoro-2',5,6'-trimethyl-[1,1'-biphenyl]-3-yl)propanoate as a colorless oil (250 mg). Yield 100% (ESI 355.1 [M+H]⁺).

197

Preparation of Ethyl (S)-3-amino-3-(4'-((dimethylamino)methyl)-4-fluoro-2',5',6'-trimethyl-[1,1'-biphenyl]-3-yl)propanoate Step 1: Ethyl (S)-3-((tert-butoxycarbonyl)amino)-3-(4-fluoro-4'-formyl-2',5',6'-trimethyl-[1,1'-biphenyl]-3-yl)propanoate

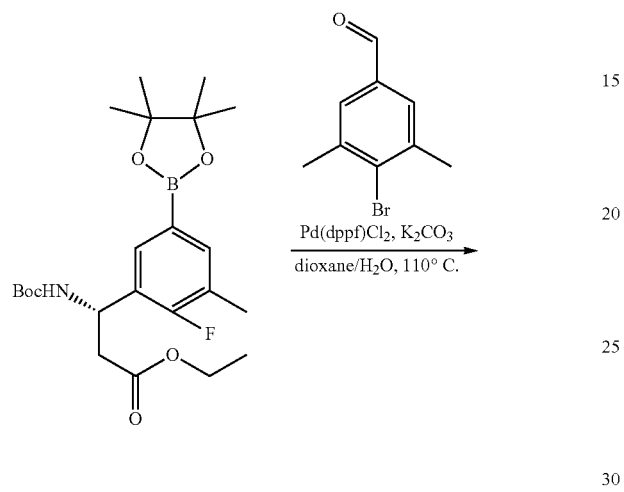

198

(4-fluoro-4'-formyl-2',5',6'-trimethyl-[1,1'-biphenyl]-3-yl)propanoate as a yellow oil (300 mg). Yield 64% (ESI 358.1 [M+H−100]⁺)

Step 2: Ethyl (S)-3-((tert-butoxycarbonyl)amino)-3-(4'-((dimethylamino)methyl)-4-fluoro-2',5',6'-trimethyl-[1,1'-biphenyl]-3-yl)propanoate

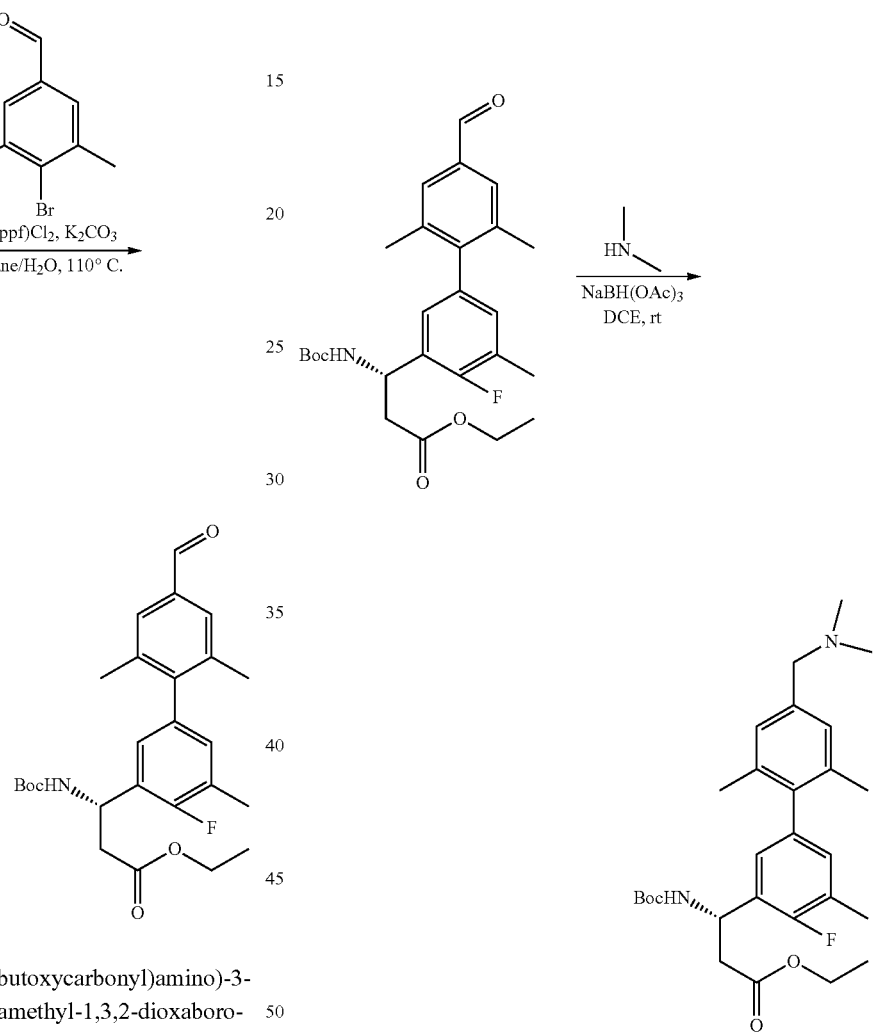

A mixture of ethyl (S)-3-((tert-butoxycarbonyl)amino)-3-(2-fluoro-3-methyl-5-(4,4,5,5-tetramethyl-1,3,2-dioxaborolan-2-yl)phenyl)propanoate (465 mg, 1.03 mmol, 1.1 eq), 4-bromo-3,5-dimethylbenzaldehyde (200 mg, 0.93 mmol, 1.0 eq), K₂CO₃ (259 mg, 1.87 mmol, 2.0 eq) and 1,1'-Bis(diphenylphosphino) ferrocene-palladium(II)dichloride dichloromethane complex (68 mg, 0.09 mmol, 0.1 eq) in dioxane (10 mL) and H₂O (1 mL) was stirred at 80° C. for 3 hours under nitrogen atmosphere. LCMS showed that the reaction was completed. The mixture was cooled to room temperature. Water (50 mL) was added and the solution was extracted with EtOAc (50 mL×3). The combined organic layers were washed with brine (100 mL), dried over anhydrous Na₂SO₄, filtered and concentrated in vacuo. The residue was purified by silica gel column (pet ether:EtOAc 1:3) to provide ethyl (S)-3-((tert-butoxycarbonyl)amino)-3-

A mixture of ethyl (S)-3-((tert-butoxycarbonyl)amino)-3-(4-fluoro-4'-formyl-2',5',6'-trimethyl-[1,1'-biphenyl]-3-yl)propanoate (1.3 g, 2.8 mmol, 1.0 eq) and dimethylamine hydrochloride (233 mg, 2.9 mmol, 1.05 eq) in DCE (10 mL) was stirred at room temperature for 30 mins. Sodium triacetoxyborohydride (1.2 g, 5.6 mmol, 2.0 eq) was added and stirred at room temperature for 16 hours. The solvent was removed in vacuo and the residue was purified by silica gel column (DCM:MeOH 9:1) to provide ethyl (S)-3-((tert-butoxycarbonyl)amino)-3-(4'-((dimethylamino)methyl)-4-fluoro-2',5',6'-trimethyl-[1,1'-biphenyl]-3-yl)propanoate as a yellow oil (800 mg). Yield 58.7% (ESI 487.2 (M+H)⁺).

199

Step 3: Ethyl (S)-3-amino-3-(4'-((dimethylamino)methyl)-4-fluoro-2',5,6'-trimethyl-[1,1'-biphenyl]-3-yl)propanoate

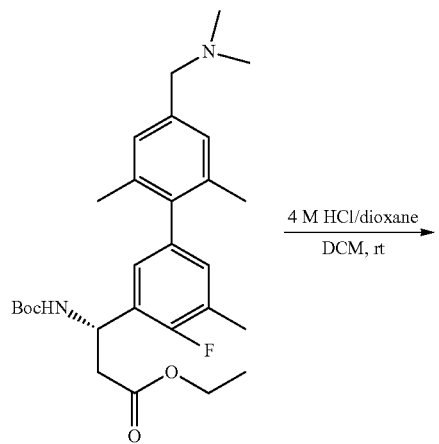

To a stirred solution of ethyl (S)-3-((tert-butoxycarbonyl)amino)-3-(4'-((dimethylamino)methyl)-4-fluoro-2',5,6'-trimethyl-[1,1'-biphenyl]-3-yl)propanoate (800 mg, 1.64 mmol, 1.0 eq) in DCM (10 mL) was added HCl-dioxane (4 M, 3 mL, 12.0 mmol) and stirred at room temperature for 1 hour. LCMS showed that the reaction was completed. The mixture was concentrated in vacuo and the residue was purified by reverse phase on a C18/40 g column (A: water 10 mM NH$_4$HCO$_3$, B: MeOH, 0~100%) to provide ethyl (S)-3-amino-3-(4'-((dimethylamino)methyl)-4-fluoro-2',5,6'-trimethyl-[1,1'-biphenyl]-3-yl)propanoate as a white solid (600 mg). Yield 94% (ESI 387.2 (M+H)$^+$).

200

Preparation of Ethyl (S)-3-amino-3-(4-fluoro-4'-((3-fluoroazetidine-1-yl)methyl)-2',5,6'-trimethyl-[1,1'-biphenyl]-3-yl)propanoate Step 1: Ethyl (S)-3-((tert-butoxycarbonyl)amino)-3-(4-fluoro-4'-((3-fluoroazetidine-1-yl)methyl)-2',5,6'-trimethyl-[1,1'-biphenyl]-3-yl)propanoate

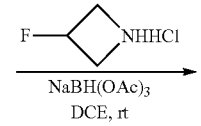

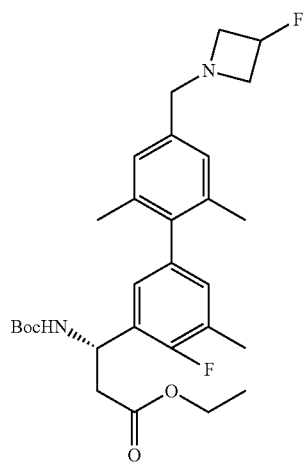

A mixture of ethyl (S)-3-((tert-butoxycarbonyl)amino)-3-(4-fluoro-4'-formyl-2',5,6'-trimethyl-[1,1'-biphenyl]-3-yl)propanoate (1.3 g, 2.8 mmol, 1.0 eq) and 3-fluoroazetidine hydrochloride (233 mg, 2.9 mmol, 1.05 eq) in DCM (10 mL) was stirred at room temperature for 30 mins. Sodium triacetoxyborohydride (1.2 g, 5.6 mmol, 2.0 eq) was added and stirred at room temperature for 16 hours. The solvent was removed in vacuo and the residue was purified by silica gel column (DCM:MeOH 9:1) to provide ethyl (S)-3-(((R)-tert-butylsulfinyl)amino)-3-(4-fluoro-4'-((3-fluorocyclobutyl)methyl)-2',5,6'-trimethyl-[1,1'-biphenyl]-3-yl)propanoate as yellow oil (800 mg). Yield 54.7% (ESI 517.2 [M+H]$^+$).

Step 2: Ethyl (S)-3-amino-3-(4-fluoro-4'-((3-fluoroazetidine-1-yl)methyl)-2',5,6'-trimethyl-[1,1'-biphenyl]-3-yl)propanoate

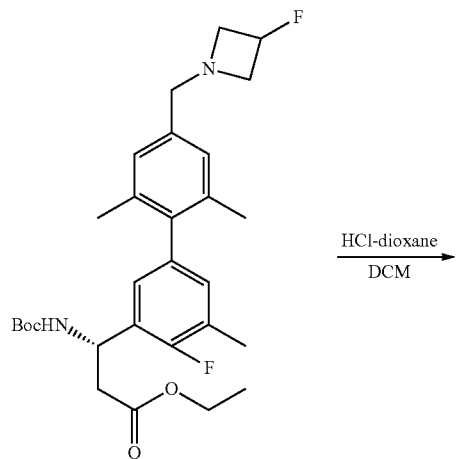

To a solution of ethyl (S)-3-((tert-butoxycarbonyl)amino)-3-(4-fluoro-4'-((3-fluoroazetidine-1-yl)methyl)-2',5,6'-trimethyl-[1,1'-biphenyl]-3-yl)propanoate (800 mg, 1.5 mmol, 1.0 eq) in DCM (10 mL) was added HCl-dioxane (4M, 10.0 mL, 40.0 mmol, 26.7 eq) and stirred at room temperature for 1 hour. The mixture was concentrated in vacuo and the residue was purified by reverse phase HPLC on a C18/120 g column (A: water/0.01% TFA, B: MeOH, 0~100%) to provide ethyl (S)-3-amino-3-(4-fluoro-4'-((3-fluoroazetidine-1-yl)methyl)-2',5,6'-trimethyl-[1,1'-biphenyl]-3-yl)propanoate as a white solid (500 mg). Yield 78% (ESI 417.1 [M+H]$^+$).

Preparation of Ethyl (S)-3-amino-3-(2'-cyclopropyl-4-fluoro-4',5,6'-trimethyl-[1,1'-biphenyl]-3-yl)propanoate

Step 1: 2-bromo-1-chloro-3,5-dimethylbenzene

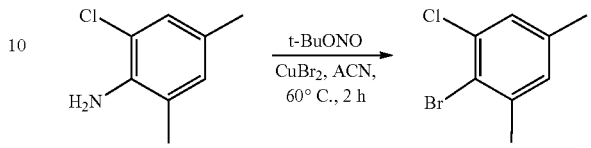

To a mixture of 2-chloro-4,6-dimethylaniline (3.0 g, 19.3 mmol, 1.00 eq) and CuBr$_2$ (21.5 g, 96.5 mmol, 5.00 eq) in ACN (50 mL) was added t-BuONO (5.96 g, 58.9 mmol, 3.00 eq) and stirred at 60° C. for 2 hours under nitrogen atmosphere. The mixture was filtered through a pad of Celite and the filtrate was concentrated in vacuo. The residue was purified by silica gel column (pet ether 100%) to give compound 2-bromo-1-chloro-3,5-dimethylbenzene as colorless oil (2.8 g). Yield: 67% (ESI 220 [M+H]+).

Step 2: Ethyl (S)-3-((tert-butoxycarbonyl)amino)-3-(2'-chloro-4-fluoro-4',5,6'-trimethyl-[1,1'-biphenyl]-3-yl)propanoate

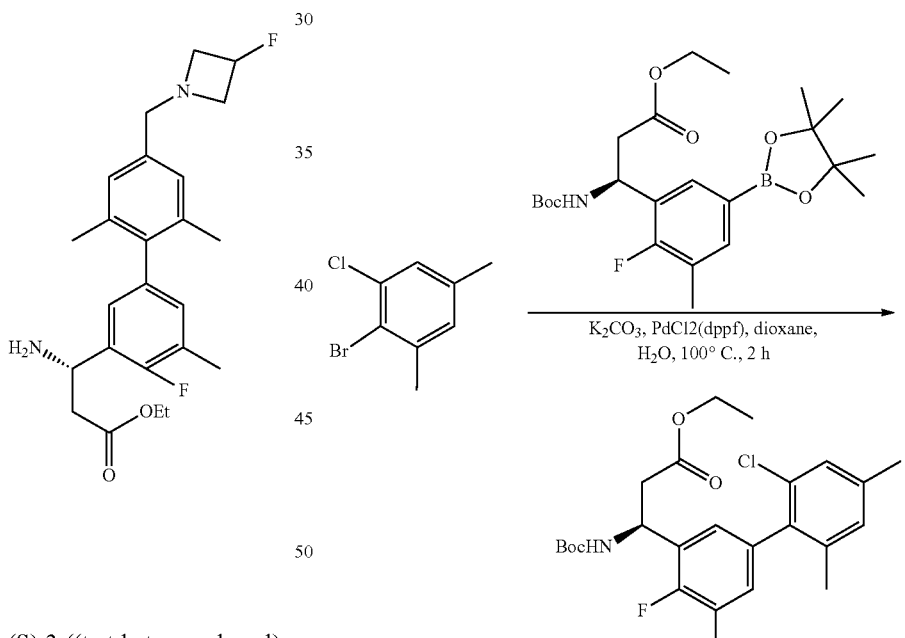

To a mixture of 2-bromo-1-chloro-3,5-dimethylbenzene (483 mg, 2.2 mmol, 1.10 eq), ethyl (S)-3-((tert-butoxycarbonyl)amino)-3-(2-fluoro-3-methyl-5-(4,4,5,5-tetramethyl-1,3,2-dioxaborolan-2-yl)phenyl)propanoate (902 mg, 2.0 mmol, 1.00 eq) in dioxane (10 mL) under nitrogen atmosphere was added a solution of K$_2$CO$_3$ (552 mg, 4.0 mmol, 2.00 eq) in H$_2$O (5 mL) and Pd(dppf)Cl$_2$ (146 mg, 0.2 mmol, 0.10 eq). The mixture was stirred at 100° C. for 2 hours under nitrogen atmosphere. Water (30 mL) was added and the solution was extracted with EtOAc (30 mL×3). The combined organic layers were washed with brine (70 mL), dried over anhydrous Na$_2$SO$_4$, filtered and concentrated in vacuo. The residue was purified by silica gel column (pet ether:EtOAc 10:1) to provide ethyl (S)-3-((tert-butoxycarbonyl)amino)-3-(2'-chloro-4-fluoro-4',5,6'-trimethyl-[1,1'-biphenyl]-3-yl)propanoate as colorless oil (880 mg). Yield 95% (ESI 364 [M−100+]+).

Step 3: Ethyl (S)-3-((tert-butoxycarbonyl)amino)-3-(2'-cyclopropyl-4-fluoro-4',5,6'-trimethyl-[1,1'-biphenyl]-3-yl)propanoate

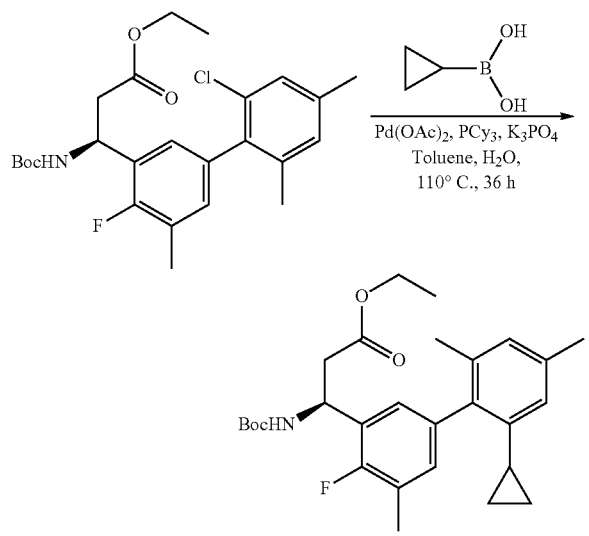

To a solution of ethyl (S)-3-((tert-butoxycarbonyl)amino)-3-(2'-chloro-4-fluoro-4',5,6'-trimethyl-[1,1'-biphenyl]-3-yl)propanoate (880 mg, 1.9 mmol, 1.00 eq), cyclopropylboronic acid (327 mg, 3.8 mmol, 2.00 eq) in toluene (10 mL) under nitrogen atmosphere was added a solution of K$_3$PO$_4$ (807 mg, 3.8 mmol, 2.00 eq) in H$_2$O (2 mL), Pd(OAc)$_2$ (43 mg, 0.19 mmol, 0.10 eq) and PCy$_3$ (107 mg, 0.38 mmol, 0.20 eq). The mixture was stirred at 110° C. for 36 hours under nitrogen atmosphere. Water (30 mL) was added and the solution was extracted with EtOAc (30 mL×3). The combined organic layers were washed with brine (70 mL), dried over anhydrous Na$_2$SO$_4$, filtered and concentrated in vacuo. The residue was purified by silica gel column (pet ether EtOAc 2:1) to provide ethyl (S)-3-((tert-butoxycarbonyl)amino)-3-(2'-cyclopropyl-4-fluoro-4',5,6'-trimethyl-[1,1'-biphenyl]-3-yl)propanoate as a gray solid (625 mg). Yield 70% (ESI 370 [M−100+]+).

Step 4: Ethyl (S)-3-amino-3-(2'-cyclopropyl-4-fluoro-4',5,6'-trimethyl-[1,1'-biphenyl]-3-yl)propanoate Hydrochloride

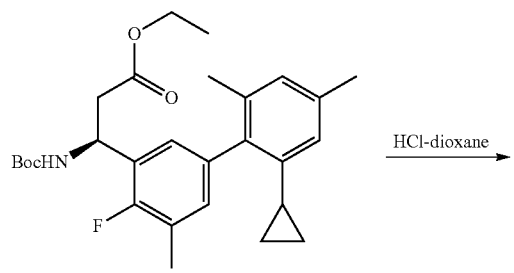

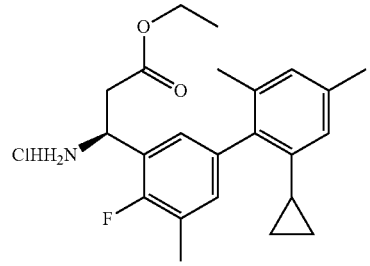

To a solution of ethyl (S)-3-((tert-butoxycarbonyl)amino)-3-(2'-cyclopropyl-4-fluoro-4',5,6'-trimethyl-[1,1'-biphenyl]-3-yl)propanoate (250 mg, 0.53 mmol, 1.00 eq) in 1,4-dioxane (6 mL) was added HCl-dioxane (4M 4.0 mL, 16.0 mmol, 30.2 eq). The mixture was stirred at room temperature for 1 hour. LCMS showed that the reaction was completed. The mixture was concentrated in vacuo to provide ethyl (S)-3-amino-3-(2'-cyclopropyl-4-fluoro-4',5,6'-trimethyl-[1,1'-biphenyl]-3-yl)propanoate hydrochloride as a white solid (215 mg), used directly in the next reaction without further purification. Yield 100% (ESI 370 [M+H]+).

Preparation of Ethyl (S)-3-amino-3-(3',4-difluoro-2',5,6'-trimethyl-[1,1'-biphenyl]-3-yl)propanoate Step 1: 2-bromo-6-fluoro-3-methylbenzaldehyde

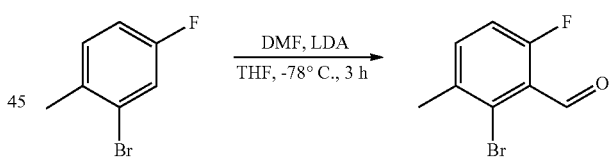

To a mixture of 2-bromo-4-fluoro-1-methylbenzene (5.0 g, 26.5 mmol, 1.00 eq) in anhydrous THF (50 mL) under nitrogen atmosphere was added lithium diisopropylamide (2.0 M, 14.6 mL, 29.2 mmol, 1.10 eq) at −78° C. and stirred at −78° C. for 1 hour. DMF (3.87 g, 53 mmol, 2.00 eq) was added to the reaction mixture at −78° C. and stirred at −78° C. for 0.5 hour, then slowly warmed to room temperature and stirred for 2 hours. The reaction was quenched with water (20 mL), extracted with EtOAc (50 mL×3). The combined organic layers were washed with brine (20 mL×3), dried over anhydrous Na$_2$SO$_4$, filtered and concentrated in vacuo to give the crude product 2-bromo-6-fluoro-3-methylbenzaldehyde as a brown liquid (4.2 g). Yield 73%. $^1$H NMR (400 MHz, MeOD) δ 10.02 (s, 1H), 7.45-7.17 (m, 1H), 7.05-7.00 (m, 1H), 2.26 (s, 3H).

Step 2: (2-bromo-6-fluoro-3-methylphenyl)methanol

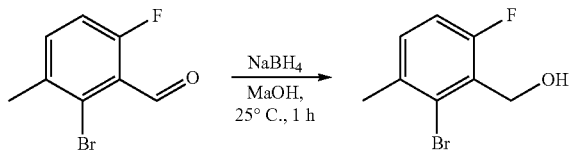

To a mixture of 2-bromo-6-fluoro-3-methylbenzaldehyde (3.0 g, 13.8 mmol, 1.00 eq) in MeOH (30 mL) under nitrogen atmosphere was added NaBH$_4$ (1.5 g, 41.4 mmol, 3.00 eq) at 0° C. and stirred at room temperature for 2 hours. The mixture was quenched with water (50 mL), extracted with EtOAc (50 mL×3). The combined organic phase was washed with brine (80 mL), dried over anhydrous Na$_2$SO$_4$, filtered and concentrated in vacuo. The residue was purified by silica gel column (pet ether:EtOAc 10:1) to provide (2-bromo-6-fluoro-3-methylphenyl)methanol as a white solid (2.7 g). Yield 90%

Step 3: (2-bromo-3-(bromomethyl)-4-fluoro-1-methylbenzene

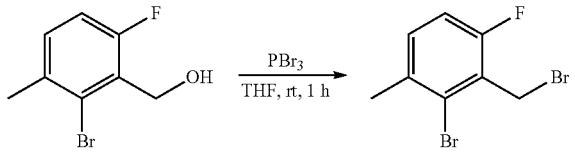

To a mixture of (2-bromo-6-fluoro-3-methylphenyl)methanol (3.2 g, 14.6 mmol, 1.00 eq) in THF (50 mL) under nitrogen atmosphere was added PBr$_3$ (3 mL, 29.2 mmol, 2.00 eq) at room temperature and stirred for 1 hour. The reaction mixture was concentrated in vacuo and the residue was purified by silica gel column (pet ether:EtOAc 99:1) to provide 2-bromo-3-(bromomethyl)-4-fluoro-1-methylbenzene as a white solid (3.58 g). Yield 90% $^1$H NMR (400 MHz, MeOD) δ 7.33-7.30 (m, 1H), 7.09-7.04 (m, 1H), 4.72 (d, J=2.0 Hz, 2H), 2.40 (s, 3H).

Step 4: 2-bromo-4-fluoro-1,3-dimethylbenzene

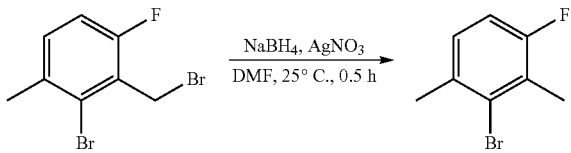

To a mixture of 2-bromo-3-(bromomethyl)-4-fluoro-1-methylbenzene (2.0 g, 7.09 mmol, 1.00 eq) in DMF (20 mL) was added NaBH$_4$ (0.536 g, 14.18 mmol, 2.00 eq) and AgNO$_3$ (2.4 g, 14.18 mmol, 2.00 eq) at room temperature. The reaction was stirred at room temperature for 0.5 hour. The mixture was quenched with water (50 mL) and extracted with EtOAc (50 mL×3). The combined organic layers were washed with brine (100 mL), dried over anhydrous Na$_2$SO$_4$, filtered and concentrated in vacuo. The residue was purified by silica gel column (DCM 100%) to provide 2-bromo-4-fluoro-1,3-dimethylbenzene as colorless oil (1.00 g). Yield 69% $^1$H NMR (400 MHz, CDCl$_3$) δ 7.09-7.01 (m, 1H), 6.90 (t, J=8.7 Hz, 1H), 2.37 (s, 3H), 2.34 (d, J=2.4 Hz, 3H).

Step 5: Ethyl (S)-3-((tert-butoxycarbonyl)amino)-3-(3',4-difluoro-2',5,6'-trimethyl-[1,1'-biphenyl]-3-yl)propanoate

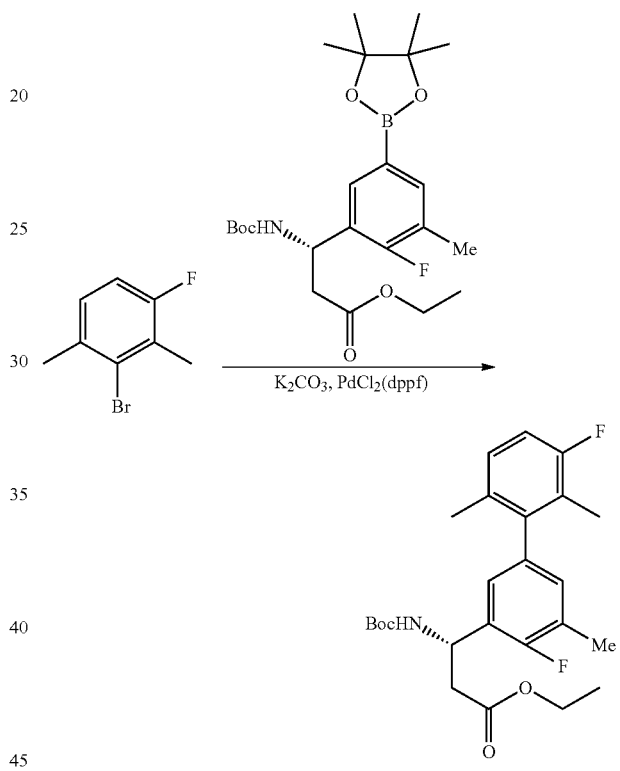

To a mixture of 2-bromo-4-fluoro-1,3-dimethylbenzene (800 mg, 3.93 mmol, 1.00 eq), ethyl (S)-3-((tert-butoxycarbonyl)amino)-3-(2-fluoro-3-methyl-5-(4,4,5,5-tetramethyl-1,3,2-dioxaborolan-2-yl)phenyl)propanoate (1.77 g, 3.93 mmol, 1.00 eq) in dioxane (12 mL) under nitrogen atmosphere was added a solution of K$_2$CO$_3$ (1.08 g, 7.86 mmol, 2.00 eq) in H$_2$O (2 mL) and Pd(dppf)Cl$_2$ (658 mg, 0.39 mmol, 0.10 eq). The mixture was stirred at 100° C. for 2 hours under nitrogen atmosphere. Water (30 mL) was added and the solution was extracted with EtOAc (30 mL×3). The combined organic layers were washed with brine (70 mL), dried over anhydrous Na$_2$SO$_4$, filtered and concentrated in vacuo. The residue was purified by reverse phase HPLC on a C18/40 g column (A: water 10 mM NH$_4$HCO$_3$, B: MeOH, 0~100%) to provide ethyl (S)-3-((tert-butoxycarbonyl)amino)-3-(3',4-difluoro-2',5,6'-trimethyl-[1,1'-biphenyl]-3-yl)propanoate as colorless oil (1.2 g). Yield 68% (ESI 348.1 [M−100+]$^+$).

Step 6: Ethyl (S)-3-amino-3-(3',4-difluoro-2',5,6'-trimethyl-[1,1'-biphenyl]-3-yl)propanoate hydrochloride

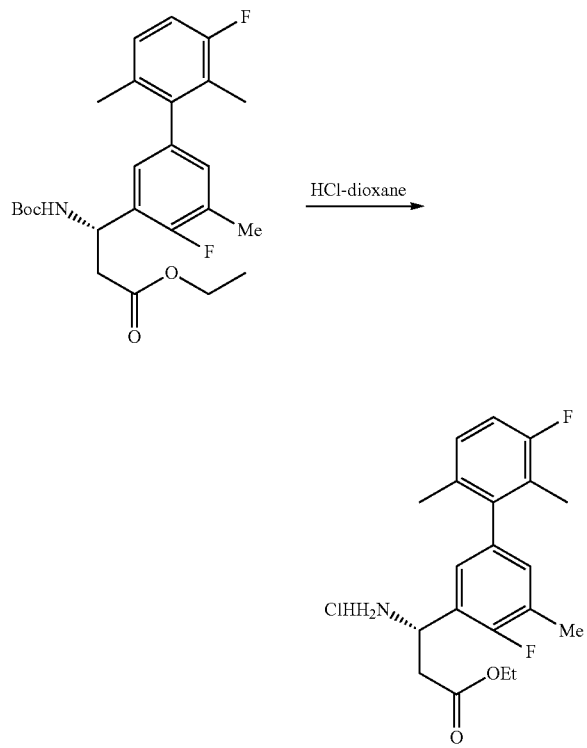

To a mixture of product ethyl (S)-3-((tert-butoxycarbonyl)amino)-3-(3',4-difluoro-2',5,6'-trimethyl-[1,1'-biphenyl]-3-yl)propanoate (1.2 g, 2.68 mmol, 1.00 eq) in 1,4-dioxane (6 mL) was added HCl-dioxane (4M 4.0 mL, 16.0 mmol, 5.97 eq). The mixture was stirred at room temperature for 1 hour. LCMS showed that the reaction was completed. The mixture was concentrated in vacuo to provide ethyl (S)-3-amino-3-(3',4-difluoro-2',5,6'-trimethyl-[1,1'-biphenyl]-3-yl)propanoate hydrochloride (1.0 g crude) used directly in the next reaction without further purification. (ESI 348.2 [M+H]$^+$).

Preparation of (S)-ethyl 3-amino-3-(4-fluoro-3'-methoxy-2',5,6'-trimethylbiphenyl-3-yl)propanoate

Step 1: 1-bromo-2,4-dimethyl-3-nitrobenzene

To a mixture of 1,3-dimethyl-2-nitrobenzene (10 g, 66 mmol, 1.0 eq) in DCM (100 mL) was added FeBr$_3$ (390 mg, 211.32 mmol, 0.02 eq) and Fe (1.12 g, 20 mmol, 0.3 eq). Br$_2$ (11.6 g, 72.6 mmol, 1.1 eq) was added dropwise and stirred at 60° C. for 16 hours. The reaction mixture was concentrated in vacuo and the residue was purified by silica gel column (pet ether) to provide 1-bromo-2,4-dimethyl-3-nitrobenzene as a white solid (10 g). Yield 66%.

Step 2: 1-methoxy-2,4-dimethyl-3-nitrobenzene

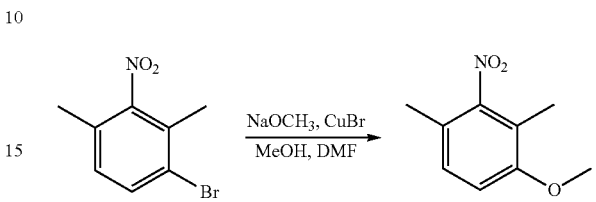

To a mixture of 1-bromo-2,4-dimethyl-3-nitrobenzene (8 g, 35 mmol, 1.0 eq) in MeOH (80 mL) and DMF (80 mL) was added NaOCH$_3$ (5.67 g, 105 mmol, 3 eq) and CuBr (1 g, 7 mmol, 0.2 eq) at room temperature. The mixture was stirred at 110° C. for 16 hours. The reaction mixture was filtered. The filtrate was diluted with water (100 mL), extracted with EtOAc (100 mL×3). The combined organic layers were washed with brine (100 mL), dried over anhydrous Na$_2$SO$_4$, filtered and concentrated in vacuo. The residue was purified by silica gel column (100% pet ether) to provide 1-methoxy-2,4-dimethyl-3-nitrobenzene as a colorless oil (5.8 g). Yield 91% (ESI 182.2 [M+H]$^+$).

Step 3: 3-methoxy-2,6-dimethylaniline

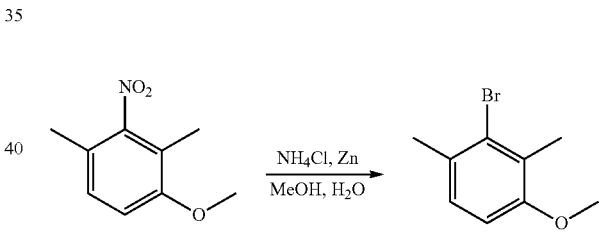

To a mixture of 1-methoxy-2,4-dimethyl-3-nitrobenzene (5.8 g, 32 mmol, 1.0 eq) in MeOH (60 mL) and H$_2$O (6 mL) at 0° C. was added NH$_4$Cl (5.18 g, 96 mmol, 3.0 eq) and Zn (20.8 g, 320 mmol, 10 eq). The mixture was stirred at room temperature for 4 hours. LCMS showed that the reaction was completed. The reaction mixture was filtered and concentrated in vacuo. The residue was purified by silica gel column (pet ether:EtOAc 1:1) to provide 3-methoxy-2,6-dimethylaniline as yellow oil (2.8 g). Yield 58% (ESI 152.2[M+H]$^+$).

Step 4: 2-bromo-4-methoxy-1,3-dimethylbenzene

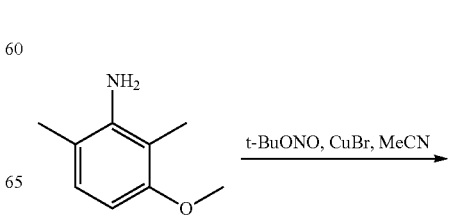

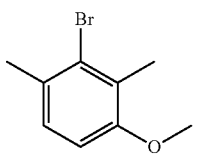

To a mixture of 3-methoxy-2,6-dimethylaniline (2 g, 13.24 mmol, 1.0 eq) in MeCN (30 mL) was added t-BuONO (2.06 g, 20 mmol, 1.5 eq) at 0° C., then CuBr(2.27 g, 15.89 mmol, 1.2 eq) was added. The mixture was stirred at 60° C. for 2 hours. LCMS showed that the reaction was completed. The reaction mixture was concentrated in vacuo and purified by silica gel column (pet ether) to provide 2-bromo-4-methoxy-1,3-dimethylbenzene as a colorless oil (800 mg). Yield 28%.

Step 5: (S)-ethyl 3-(tert-butoxycarbonylamino)-3-(4-fluoro-3'-methoxy-2',5,6'-trimethylbiphenyl-3-yl)propanoate

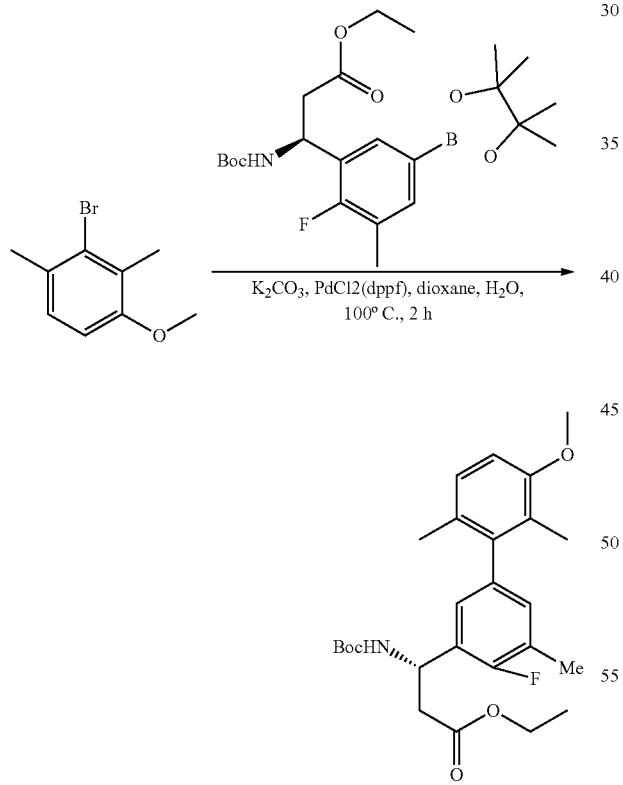

A mixture of 2-bromo-4-methoxy-1,3-dimethylbenzene (700 mg, 3.27 mmol, 1.00 eq), (S)-ethyl 3-(tert-butoxycarbonylamino)-3-(2-fluoro-3-methyl-5-(4,4,5,5-tetramethyl-1,3,2-dioxaborolan-2-yl)phenyl)propanoate (1.47 g, 3.27 mmol, 1.0 eq), $K_2CO_3$ (1.35 g, 9.81 mmol, 3 eq) and Pd(dppf)$Cl_2$ (239 mg, 0.327 mmol, 0.1 eq) in dioxane (10 mL) and $H_2O$ (1 mL) was stirred at 110° C. for 4 hours under nitrogen atmosphere. LCMS showed that the reaction was completed. The mixture was cooled to room temperature. Water (30 mL) was added and the solution was extracted with EtOAc (30 mL×3). The combined organic layers were washed with brine (30 mL), dried over anhydrous $Na_2SO_4$, filtered and concentrated in vacuo. The residue was purified by silica gel column (pet ether:EtOAc 5:1) to provide (S)-ethyl 3-(tert-butoxycarbonylamino)-3-(4-fluoro-3'-methoxy-2',5,6'-trimethylbiphenyl-3-yl)propanoate (1 g) as a colorless oil. Yield 67% (ESI 360.1 [M-Boc+1]$^+$).

Step 6: (S)-ethyl 3-amino-3-(4-fluoro-3'-methoxy-2',5,6'-trimethylbiphenyl-3-yl)propanoate

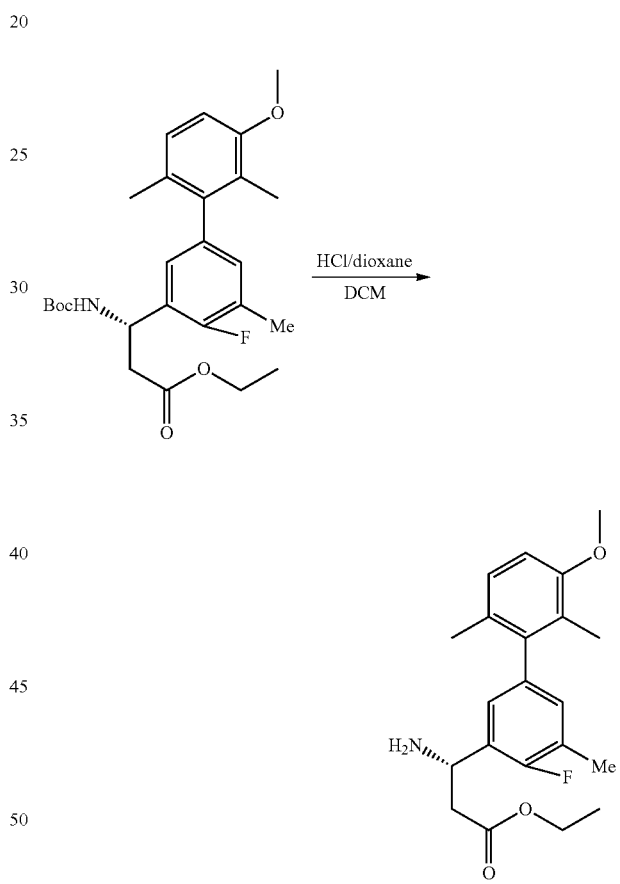

To a stirred solution of (S)-ethyl 3-(tert-butoxycarbonylamino)-3-(4-fluoro-3'-methoxy-2',5,6'-trimethylbiphenyl-3-yl)propanoate (1 g, 2.18 mmol, 1.00 eq) in DCM (8 mL) was added HCl-dioxane (4 M, 2.18 mL, 8.72 mmol, 4 eq). The mixture was stirred at room temperature for 2 hours. LCMS showed that the reaction was completed. The mixture was concentrated in vacuo and the residue was purified by reverse phase HPLC on a C18/80 g column (A: water 10 mM $NH_4HCO_3$, B: MeOH, 0~100%) to provide (S)-ethyl 3-amino-3-(4-fluoro-3'-methoxy-2',5,6'-trimethylbiphenyl-3-yl)propanoate (600 mg) as a colorless oil. Yield 77% (ESI 360.1 [M+H]$^+$).

Preparation of Ethyl (S)-3-amino-3-(6'-cyano-4-fluoro-2',3',5-trimethyl-[1,1'-biphenyl]-3-yl)propanoate Step 1: Ethyl (S)-3-(((R)-tert-butylsulfinyl)amino)-3-(6'-cyano-4-fluoro-2',3',5-trimethyl-[1,1'-biphenyl]-3-yl)propanoate

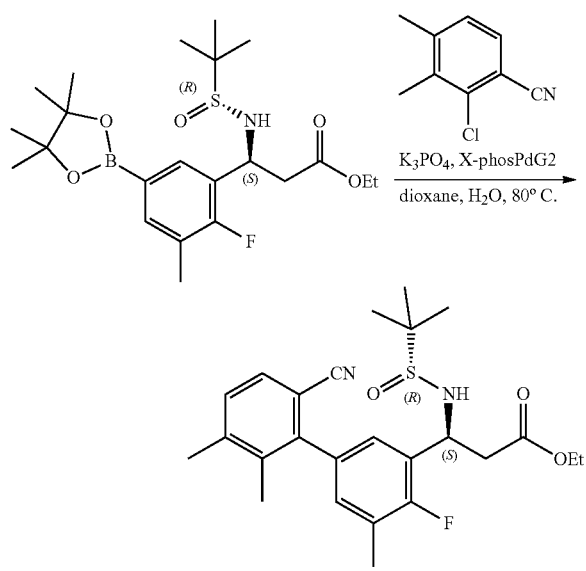

A mixture of ethyl (S)-3-(((R)-tert-butylsulfinyl)amino)-3-(2-fluoro-3-methyl-5-(4,4,5,5-tetramethyl-1,3,2-dioxaborolan-2-yl)phenyl)propanoate (1.7 g, 3.6 mmol, 2.0 eq), 2-chloro-3,4-dimethylbenzonitrile (300 mg, 1.8 mmol, 1.0 eq), K₃PO₄ (1.2 g, 5.4 mmol, 3.0 eq) and XPhosPdG2 (140 mg, 0.18 mmol, 0.1 eq) in dioxane (30 mL) and H₂O (3 mL) was stirred at 80° C. for 2 hours under nitrogen atmosphere. LCMS showed that the reaction was completed. The mixture was cooled to room temperature. Water (20 mL) was added and the solution was extracted with EtOAc (20 mL×3). The combined organic layers were washed with brine (50 mL), dried over anhydrous Na₂SO₄, filtered and concentrated in vacuo. The residue was purified by silica gel column (pet ether:EtOAc 1:1) to provide ethyl (S)-3-(((R)-tert-butylsulfinyl)amino)-3-(6'-cyano-4-fluoro-2',3',5-trimethyl-[1,1'-biphenyl]-3-yl)propanoate (500 mg) as a yellow oil. Yield 60% (ESI 459.3 [M+H]⁺).

Step 2: Ethyl (S)-3-amino-3-(6'-cyano-4-fluoro-2',3',5-trimethyl-[1,1'-biphenyl]-3-yl)propanoate

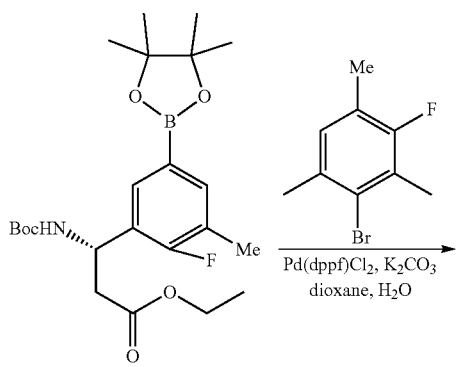

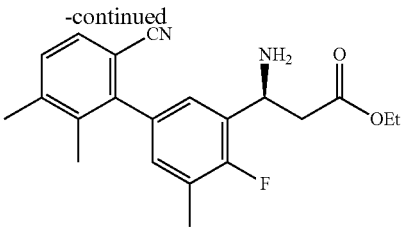

To a stirred solution of ethyl (S)-3-(((R)-tert-butylsulfinyl)amino)-3-(6'-cyano-4-fluoro-2',3',5-trimethyl-[1,1'-biphenyl]-3-yl)propanoate (500 mg, 1.1 mmol, 1.0 eq) in DCM (10 mL) was added HCl-dioxane (4 M, 10 mL, 40.0 mmol, 36.4 eq). The mixture was stirred at room temperature for 1 hour. LCMS showed that the reaction was completed. The mixture was concentrated in vacuo and the residue was purified by reverse phase HPLC on a C18/40 g column (A: water 10 mM NH₄HCO₃, B: MeOH, 0~100%) to provide ethyl (S)-3-amino-3-(6'-cyano-4-fluoro-2',3',5-trimethyl-[1,1'-biphenyl]-3-yl)propanoate (200 mg) as a colorless oil. Yield 51.8% (ESI 355.2 [M+H]⁺).

Preparation of (S)-ethyl 3-amino-3-(3',4-difluoro-2',4',5,6'-tetramethylbiphenyl-3-yl)propanoate Step 1: (S)-ethyl 3-(tert-butoxycarbonylamino)-3-(3',4-difluoro-2',4',5,6'-tetramethylbiphenyl-3-yl)propanoate

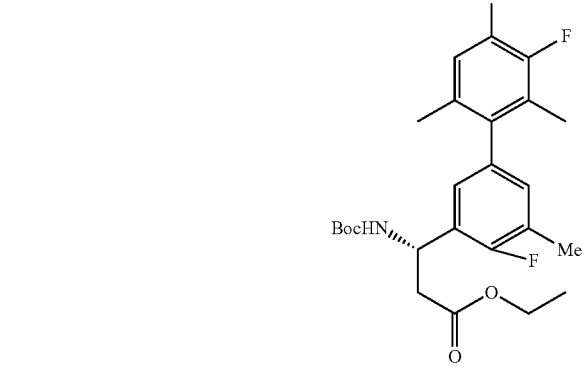

To a mixture of (S)-ethyl 3-(tert-butoxycarbonylamino)-3-(2-fluoro-3-methyl-5-(4,4,5,5-tetramethyl-1,3,2-dioxaborolan-2-yl)phenyl)propanoate (500 mg, 1.14 mmol, 1 eq) and 2-bromo-4-fluoro-1,3,5-trimethylbenzene (309 mg, 1.43 mmol, 1.2 eq) in dioxane (10 mL) was added a solution of K₂CO₃ (314.6 mg, 2.28 mmol, 2 eq) in H₂O (2 mL) and Pd(dppf)Cl₂ (80 mg, 0.11 mmol, 0.1 eq). The mixture was heated to 110° C. for 2 hours under nitrogen atmosphere. Water (20 mL) was added and the solution was extracted with EtOAc (20 mL×3). The combined organic layers were concentrated in vacuo and the residue was purified by silica gel column (pet ether:EtOAc 1:1) to give methyl (S)-ethyl 3-(tert-butoxycarbonylamino)-3-(3',4-difluoro-2',4',5,6'-tetramethylbiphenyl-3-yl)propanoate as a colorless oil (500 mg). Yield 97.8% (ESI 461.5 [M+H]⁺).

Step 2: (S)-ethyl 3-amino-3-(3',4-difluoro-2',4',5,6'-tetramethylbiphenyl-3-yl)propanoate

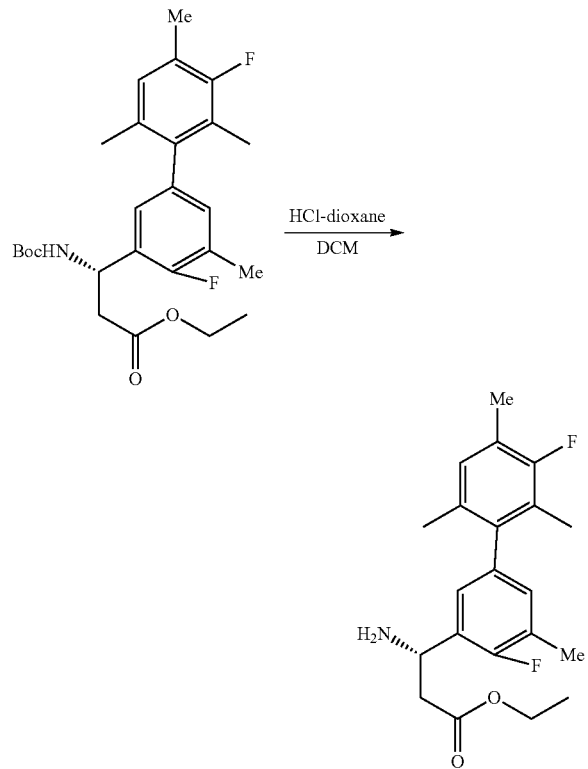

To a mixture of methyl (S)-methyl 3-(tert-butoxycarbonylamino)-3-(3',4-difluoro-2',4',5,6'-tetramethylbiphenyl-3-yl)propanoate (500 mg, 1.12 mmol, 1 eq) in DCM (6 mL) was added HCl-dioxane (4 M, 3 mL, 12 mmol, 10 eq). The mixture was stirred at room temperature for 1 hour. LCMS showed that the reaction was completed. The mixture was concentrated in vacuo to give crude product (S)-ethyl 3-amino-3-(3',4-difluoro-2',4',5,6'-tetramethylbiphenyl-3-yl)propanoate as a white solid (300 mg) used directly in the next reaction without further purification. Yield 77% (ESI 361.4 s [M+H]⁺).

Preparation of Ethyl (S)-3-(5-bromo-3-chloro-2-fluorophenyl)-3-(((R)-tert-butylsulfinyl)amino)propanoate Step 1: (R,E)-N-(5-bromo-3-chloro-2-fluorobenzylidene)-2-methylpropane-2-sulfinamide

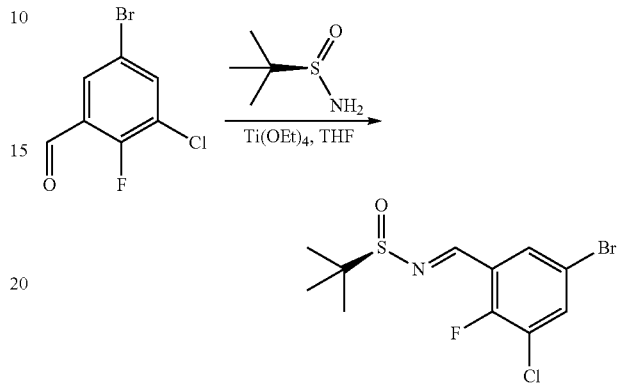

To a mixture of 5-bromo-3-chloro-2-fluorobenzaldehyde (10.0 g, 42.2 mmol, 1.00 eq) and (R)-2-methylpropane-2-sulfinamide (5.6 g, 46.4 mmol, 1.1 eq) in anhydrous THF (100 mL) under nitrogen atmosphere was added Ti(OEt)₄ (14.4 g, 63.3 mmol, 1.50 eq) dropwise at room temperature and the temperature maintained below 30° C. The reaction mixture was warmed to 35° C. and stirred for 1 hour. LCMS showed that the reaction was completed. Water (100 mL) and EtOAc (100 mL) were added into the mixture and stirred at room temperature for 5 mins. The mixture was filtered and washed with EtOAc (50 mL). The filtrate was separated. The organic layer was washed with brine (100 mL), dried over anhydrous Na₂SO₄, filtered and concentrated in vacuo. The residue was purified by silica gel column (pet ether:EtOAc 4:1) to provide (R,E)-N-(5-bromo-3-chloro-2-fluorobenzylidene)-2-methylpropane-2-sulfinamide as a yellow oil (14.0 g). Yield 98% (ESI 341.9 (M+H)⁺).

Step 2: Ethyl (S)-3-(5-bromo-3-chloro-2-fluorophenyl)-3-(((R)-tert-butylsulfinyl)amino)propanoate

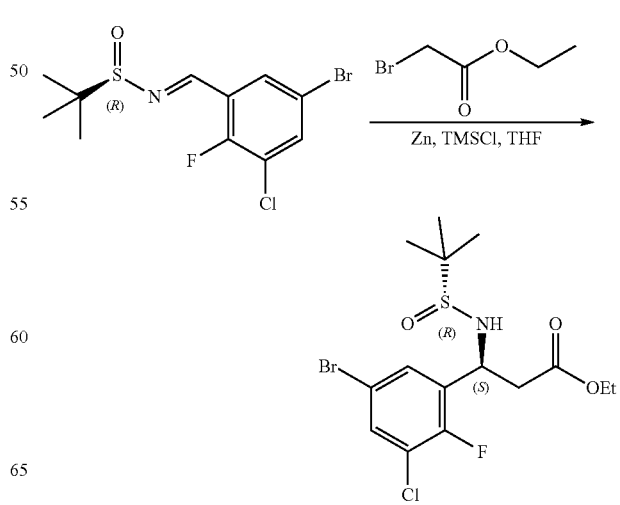

To a mixture of Zn (13.0 g, 205.5 mmol, 5.00 eq) in anhydrous THF (200 mL) under nitrogen atmosphere was added chlorotrimethylsilane (888 mg, 8.22 mmol, 0.2 eq) dropwise at room temperature and stirred at 50° C. under nitrogen atmosphere for 1 hour. The mixture was cooled to 20-30° C. Ethyl 2-bromoacetate (17.1 g, 102.7 mmol, 2.50 eq) was added dropwise at room temperature under nitrogen atmosphere and stirred at 60° C. under for 1 hour. The reaction mixture was cooled to room temperature. A solution of (R,E)-N-(5-bromo-3-chloro-2-fluorobenzylidene)-2-methylpropane-2-sulfinamide (14.0 g, 41.1 mmol, 1.00 eq) in anhydrous THF (20 mL) was added dropwise into the mixture at room temperature under nitrogen atmosphere and stirred at room temperature for 1 hour. LCMS showed that the reaction was completed. Water (100 mL) and EtOAc (100 mL) was added into the mixture and stirred at room temperature for 5 mins. The mixture was filtered. The filtrate was extracted with EtOAc (100 mL). The combined organic layers were washed with water (30 mL) and brine (30 mL), dried over anhydrous Na$_2$SO$_4$, filtered and concentrated in vacuo. The residue was purified by silica gel column (pet ether:EtOAc 4:1) to provide ethyl (S)-3-(5-bromo-3-chloro-2-fluorophenyl)-3-(((R)-tert-butylsulfinyl)amino)propanoate as a yellow oil (12.0 g). Yield 73% (ESI 429.9 (M+H)$^+$).

Preparation of Ethyl (S)-3-amino-3-(5-chloro-4-fluoro-2',6'-dimethyl-[1,1'-biphenyl]-3-yl)propanoate Step 1: Ethyl (S)-3-(((R)-tert-butylsulfinyl)amino)-3-(5-chloro-4-fluoro-2',6'-dimethyl-[1,1'-biphenyl]-3-yl)propanoate

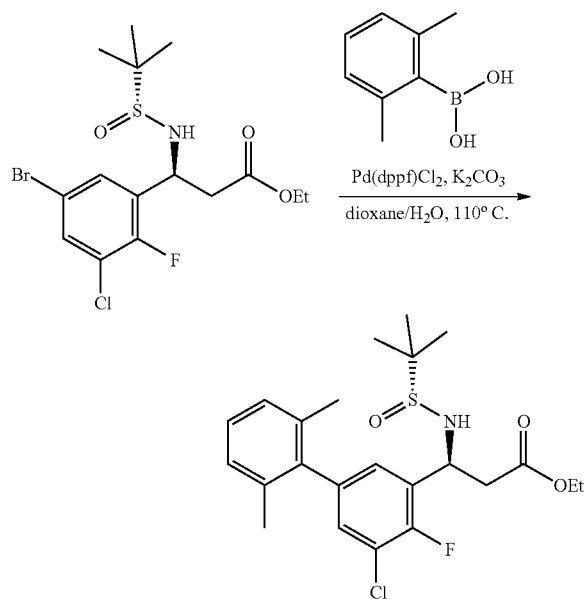

A mixture of ethyl (S)-3-(5-bromo-3-chloro-2-fluorophenyl)-3-(((R)-tert-butylsulfinyl)amino)propanoate (4.0 g, 9.6 mmol, 1.00 eq), K$_2$CO$_3$ (8.0 g, 57.6 mmol, 2.0 eq) Pd(dppf)Cl$_2$ (1.4 g, 1.9 mmol, 0.1 eq) and (2,6-dimethylphenyl)boronic acid (2.8 g, 19.2 mmol, 2.00 eq) in dioxane (40 mL) and H$_2$O (4 mL) was stirred at 80° C. for 16 hours under nitrogen atmosphere. The reaction mixture was cooled to room temperature and poured into 50 mL of water and extracted with EtOAc (50 mL×3). The combined organic layers were washed with brine (100 mL), dried over anhydrous Na$_2$SO$_4$, filtered and concentrated in vacuo. The residue was purified by silica gel column (pet ether:EtOAc 10:1) to provide ethyl (S)-3-(((R)-tert-butylsulfinyl)amino)-3-(5-chloro-4-fluoro-2',6'-dimethyl-[1,1'-biphenyl]-3-yl)propanoate as a yellow oil (3.0 g). Yield 71% (ESI 454.1 (M+H)$^+$)

Step 2: Ethyl (S)-3-amino-3-(5-chloro-4-fluoro-2',6'-dimethyl-[1,1'-biphenyl]-3-yl)propanoate

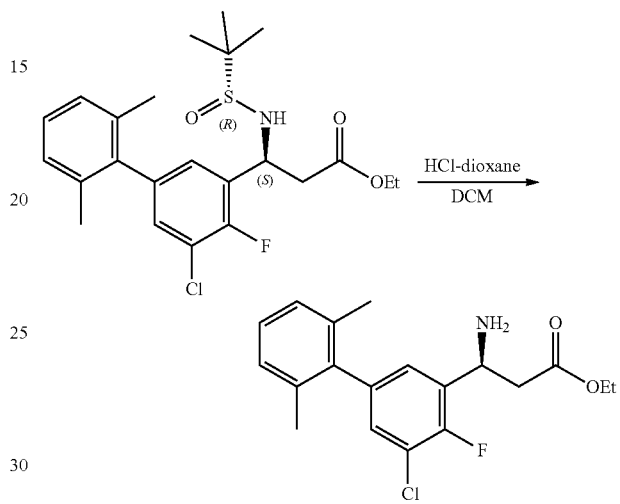

To a mixture of ethyl (S)-3-(((R)-tert-butylsulfinyl)amino)-3-(5-chloro-4-fluoro-2',6'-dimethyl-[1,1'-biphenyl]-3-yl)propanoate (3.0 g, 43.66 mmol, 1.0 eq) in DCM (20 mL) was added HCl-dioxane (4 M, 20 mL, 80 mmol, 1.8 eq). The mixture was stirred at room temperature for 1 hour. LCMS showed that the reaction was completed. The mixture was concentrated in vacuo and the residue was purified by reverse phase HPLC on a C18/120 g column (A: water 10 mM NH$_4$HCO$_3$, B: MeOH, 0~100%) to provide ethyl (S)-3-amino-3-(5-chloro-4-fluoro-2',6'-dimethyl-[1,1'-biphenyl]-3-yl)propanoate as a white solid (1.8 g). Yield 78% (ESI 350.0 [M+H]$^+$).

Preparation of Ethyl (S)-3-amino-3-(5-chloro-4,4'-difluoro-2',6'-dimethyl-[1,1'-biphenyl]-3-yl)propanoate Step 1: Ethyl (S)-3-(((R)-tert-butylsulfinyl)amino)-3-(5-chloro-4,4'-difluoro-2',6'-dimethyl-[1,1'-biphenyl]-3-yl)propanoate

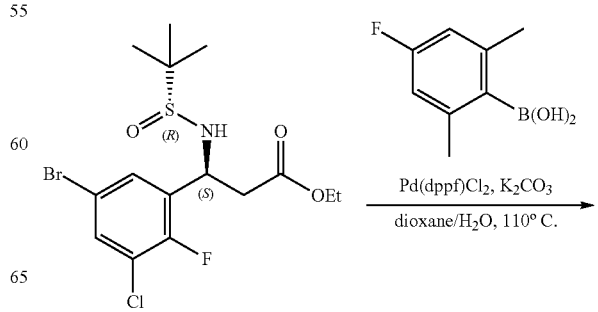

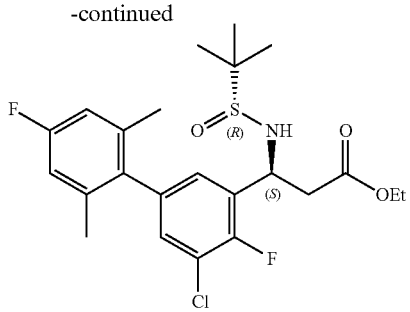

To a mixture of ethyl (S)-3-(5-bromo-3-chloro-2-fluorophenyl)-3-(((R)-tert-butylsulfinyl)amino)propanoate (2.0 g, 4.66 mmol, 1.0 eq) and (4-fluoro-2,6-dimethylphenyl)boronic acid (940 mg, 5.59 mmol, 1.2 eq) in dioxane (20 mL) was added a solution of $K_2CO_3$ (1.3 g, 9.32 mmol, 2.0 eq) in $H_2O$ (2 mL) and Pd(dppf)Cl$_2$ (341 mg, 0.47 mmol, 0.1 eq). The mixture was heated to 110° C. for 2 hours under nitrogen atmosphere. The reaction mixture was cooled to room temperature and poured into water (50 mL) and extracted with EtOAc (50 mL×3). The combined organic layers were washed with brine (100 mL) and dried over anhydrous $Na_2SO_4$, filtered and concentrated in vacuo. The residue was purified by silica gel column (pet ether:EtOAc 1:1) to provide ethyl (S)-3-(((R)-tert-butylsulfinyl)amino)-3-(5-chloro-4,4'-difluoro-2',6'-dimethyl-[1,1'-biphenyl]-3-yl)propanoate as a colorless oil (1.2 g). Yield 54% (ESI 472.1 [M+H]$^+$).

Step 2: Ethyl (S)-3-amino-3-(5-chloro-4,4'-difluoro-2',6'-dimethyl-[1,1'-biphenyl]-3-yl)propanoate

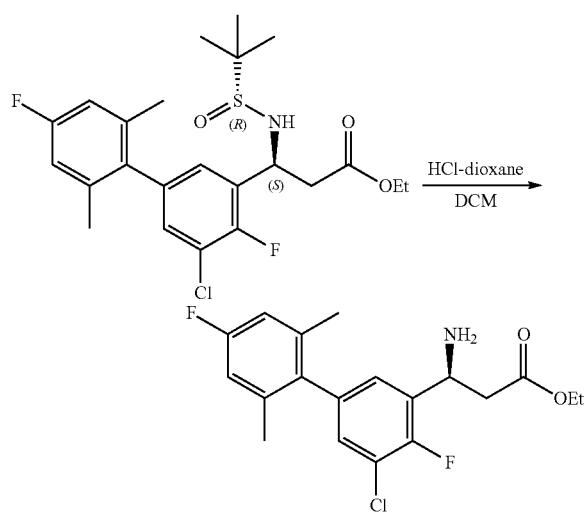

To a mixture of ethyl (S)-3-(((R)-tert-butylsulfinyl)amino)-3-(5-chloro-4,4'-difluoro-2',6'-dimethyl-[1,1'-biphenyl]-3-yl)propanoate (1.2 g, 2.54 mmol, 1.0 eq) in DCM (6 mL) was added HCl-dioxane (4 M, 3 mL, 12 mmol, 4.7 eq). The mixture was stirred at room temperature for 1 hour. LCMS showed that the reaction was completed. The mixture was concentrated in vacuo and the residue was purified by reverse phase HPLC on a C18/80 g column (A: water 0.01% TFA, B: MeOH, 0~100%) to provide ethyl (S)-3-amino-3-(5-chloro-4,4'-difluoro-2',6'-dimethyl-[1,1'-biphenyl]-3-yl)propanoate as a white solid (900 mg). Yield 96% (ESI 368.1 [M+H]$^+$).

Preparation of Ethyl (S)-3-amino-3-(5-chloro-4-fluoro-2',4',6'-trimethyl-[1,1'-biphenyl]-3-yl)propanoate Step 1: Ethyl (S)-3-(((R)-tert-butylsulfinyl)amino)-3-(5-chloro-4-fluoro-2',4',6'-trimethyl-[1,1'-biphenyl]-3-yl)propanoate

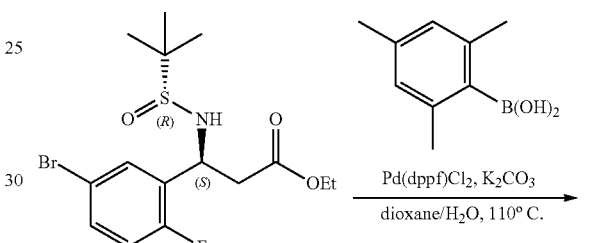

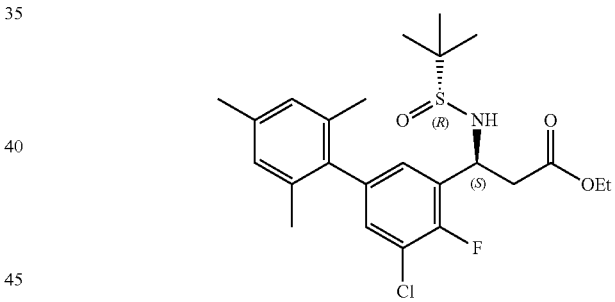

A mixture of ethyl (S)-3-(5-bromo-3-chloro-2-fluorophenyl)-3-(((R)-tert-butylsulfinyl)amino)propanoate (2.0 g, 4.66 mmol, 1.0 eq), mesitylboronic acid (1.5 g, 9.33 mmol, 2.0 eq), $K_2CO_3$ (1.29 g, 9.32 mmol, 2.0 eq) and Pd(dppf)Cl$_2$ (341 mg, 0.466 mmol, 0.1 eq) in dioxane (20 mL) and $H_2O$ (2 mL) was stirred at 110° C. under nitrogen atmosphere overnight. After completion and cooling to room temperature, the reaction mixture was poured into water (50 mL), extracted with EtOAc (50 mL×3). The combined organic layers were washed with brine (100 mL) and dried over anhydrous $Na_2SO_4$, filtered and concentrated in vacuo. The residue was purified by silica gel column (pet ether:EtOAc 1:1) to provide ethyl (S)-3-(((R)-tert-butylsulfinyl)amino)-3-(5-chloro-4-fluoro-2',4',6'-trimethyl-[1,1'-biphenyl]-3-yl)propanoate as a yellow oil (1.9 g). Yield 87% (ESI 468 (M+H)$^+$).

Step 2: Ethyl (S)-3-amino-3-(5-chloro-4-fluoro-2',4',6'-trimethyl-[1,1'-biphenyl]-3-yl)propanoate

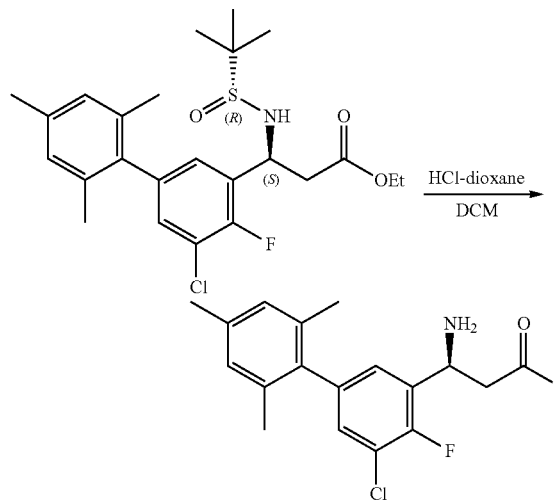

To a mixture of ethyl (S)-3-(((R)-tert-butylsulfinyl)amino)-3-(5-chloro-4-fluoro-2',4',6'-trimethyl-[1,1'-biphenyl]-3-yl)propanoate (1.9 g, 4.06 mmol, 1.0 eq) in DCM (20 mL) was added HCl-dioxane (4 M, 3 mL, 12 mmol, 3.0 eq). The mixture was stirred at room temperature for 1 hour. LCMS showed that the reaction was completed. The mixture was concentrated in vacuo and the residue was purified by reverse phase HPLC on a C18/120 g column (A: water 10 mM NH$_4$HCO$_3$, B: MeOH, 0~100%) to provide ethyl (S)-3-amino-3-(5-chloro-4-fluoro-2',4',6'-trimethyl-[1,1'-biphenyl]-3-yl)propanoate as a white solid (1.3 g). Yield 88% (ESI 364.1 (M+H)$^+$).

Preparation of Ethyl (S)-3-(5-bromo-2,3-difluorophenyl)-3-(((R)-tert-butylsulfinyl)amino)propanoate Step 1: (R,E)-N-(5-bromo-2,3-difluorobenzylidene)-2-methylpropane-2-sulfinamide

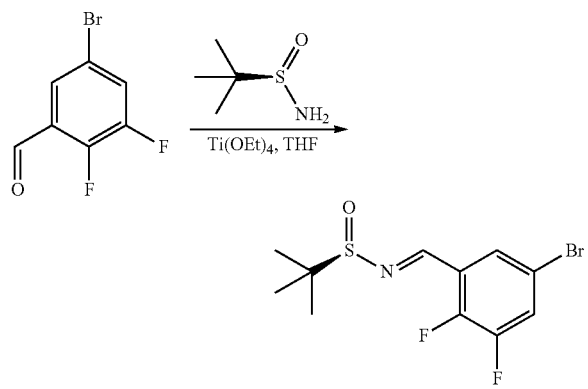

To a mixture of 5-bromo-2,3-difluorobenzaldehyde (4.5 g, 20.36 mmol, 1.0 eq) and (R)-2-methylpropane-2-sulfinamide (2.7 g, 22.40 mmol, 1.1 eq) in anhydrous THF (50 mL) under nitrogen atmosphere was added Ti(OEt)$_4$ (9.3 g, 40.72 mmol, 2.0 eq) dropwise at room temperature while maintaining the temperature below 30° C. The reaction mixture was warmed to 35° C. and stirred for 1 hour. LCMS showed that the reaction was completed. Water (50 mL) and EtOAc (50 mL) was added into the mixture and stirred at room temperature for 10 mins. The mixture was filtered and washed with EtOAc (50 mL). The filtrate was separated. The organic layer was washed with water (70 mL) and brine (70 mL), dried over anhydrous Na$_2$SO$_4$, filtered and concentrated in vacuo. The residue was purified by silica gel column (pet ether:EtOAc 4:1) to provide (R,E)-N-(5-bromo-2,3-difluorobenzylidene)-2-methylpropane-2-sulfinamide as a yellow oil (6.0 g). Yield 91% (ESI 325.9 (M+H)$^+$).

Step 2: Ethyl (S)-3-(5-bromo-2,3-difluorophenyl)-3-(((R)-tert-butylsulfinyl)amino)propanoate

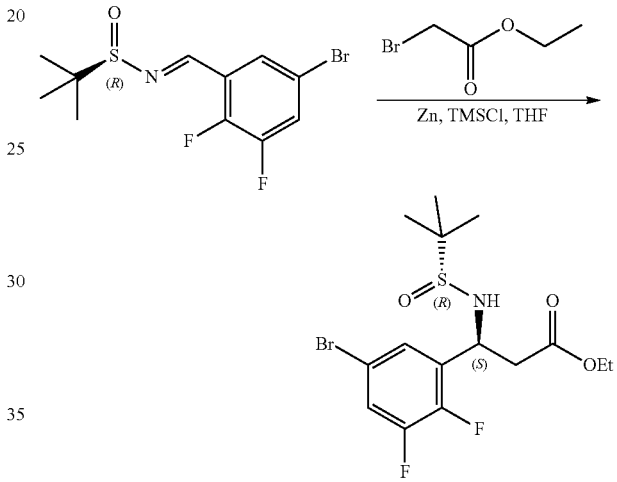

To a mixture of Zn (3.2 g, 49.2 mmol, 4.00 eq) in anhydrous THF (20 mL) under nitrogen atmosphere was added chlorotrimethylsilane (267 mg, 2.46 mmol, 0.2 eq) dropwise at room temperature. The mixture was stirred at 50° C. for 1 hour under nitrogen atmosphere and cooled to 20-30° C. Ethyl 2-bromoacetate (5.1 g, 30.75 mmol, 2.50 eq) was added dropwise at room temperature under nitrogen atmosphere and then stirred at 60° C. for 1 hour under nitrogen atmosphere. The reaction mixture was cooled to room temperature. A solution of (R,E)-N-(5-bromo-2,3-difluorobenzylidene)-2-methylpropane-2-sulfinamide (4.0 g, 12.3 mmol, 1.00 eq) in anhydrous THF (5 mL) was added dropwise into the mixture at room temperature under nitrogen atmosphere and stirred at room temperature for 1 hour. LCMS showed that the reaction was completed. Water (150 mL) and EtOAc (150 mL) were added into the mixture and stirred at room temperature for 10 mins. The mixture was filtered and washed with EtOAc (50 mL). The filtrate was separated. The organic layer was washed with water (100 mL) and brine (100 mL), dried over anhydrous Na$_2$SO$_4$, filtered and concentrated in vacuo. The residue was purified by silica gel column (pet ether:EtOAc 3:1) to provide ethyl (S)-3-(5-bromo-2,3-difluorophenyl)-3-(((R)-tert-butylsulfinyl)amino)propanoate as a colorless oil (2.7 g). Yield 53% (ESI 412.0 (M+H)$^+$).

221

Preparation of Ethyl (S)-3-amino-3-(4,5-difluoro-2',6'-dimethyl-[1,1'-biphenyl]-3-yl)propanoate Step 1: Ethyl (S)-3-(((R)-tert-butylsulfinyl)amino)-3-(4,5-difluoro-2',6'-dimethyl-[1,1'-biphenyl]-3-yl)propanoate

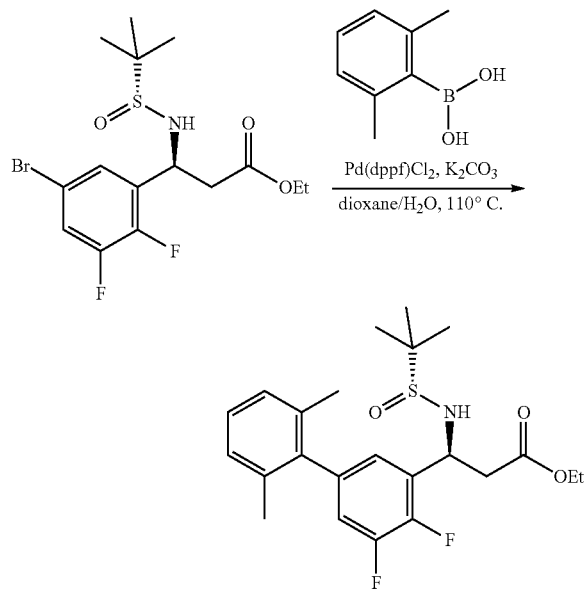

A mixture of ethyl (S)-3-(5-bromo-2,3-difluorophenyl)-3-(((R)-tert-butylsulfinyl)amino)propanoate (1.0 g, 2.4 mmol, 1.00 eq), K$_2$CO$_3$ (664 mg, 4.8 mmol, 2.0 eq) Pd(dppf)Cl$_2$ (175 mg, 0.24 mmol, 0.1 eq) and (2,6-dimethylphenyl)boronic acid (720 mg, 4.8 mmol, 2.00 eq) in dioxane (12 mL) and H$_2$O (1.2 mL) was stirred at 110° C. under nitrogen atmosphere for 2 hours. LCMS showed that the reaction was completed. The reaction mixture was poured into 50 mL of water and extracted with EtOAc (50 mL×3). The combined organic layers were washed with brine (100 mL), dried over anhydrous Na$_2$SO$_4$, filtered and concentrated in vacuo. The residue was purified by silica gel column (pet ether:EtOAc 2:1) to give desired product ethyl (S)-3-(((R)-tert-butylsulfinyl)amino)-3-(4,5-difluoro-2',6'-dimethyl-[1,1'-biphenyl]-3-yl)propanoate as a yellow oil (900 mg). Yield 85% (ESI 438.1 (M+H)$^+$).

Step 2: Ethyl (S)-3-amino-3-(4,5-difluoro-2',6'-dimethyl-[1,1'-biphenyl]-3-yl)propanoate

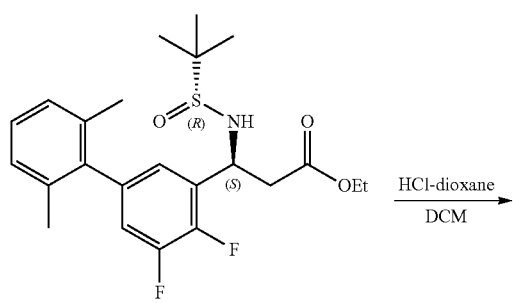

222

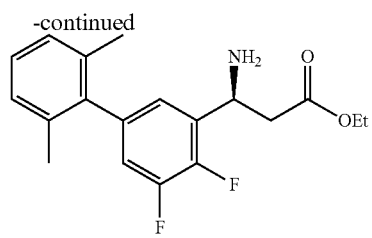

To a mixture of ethyl (S)-3-(((R)-tert-butylsulfinyl)amino)-3-(4,5-difluoro-2',6'-dimethyl-[1,1'-biphenyl]-3-yl)propanoate (900 mg, 2.06 mmol, 1.0 eq) in DCM (4 mL) was added HCl-dioxane (4 M, 2 mL, 8.0 mmol, 3.88 eq). The mixture was stirred at room temperature for 1 hour. LCMS showed that the reaction was completed. The mixture was concentrated in vacuo and the residue was purified by reverse phase HPLC on a C18/40 g column (A: water/0.01% TFA, B: MeOH, 0~100%) to provide ethyl (S)-3-amino-3-(4,5-difluoro-2',6'-dimethyl-[1,1'-biphenyl]-3-yl)propanoate as a light yellow solid (800 mg). Yield 90% (ESI 334.1 [M+H]$^+$).

Preparation of Ethyl (S)-3-amino-3-(4,4',5-trifluoro-2',6'-dimethyl-[1,1'-biphenyl]-3-yl)propanoate Step 1: Ethyl (S)-3-(((R)-tert-butylsulfinyl)amino)-3-(4,4',5-trifluoro-2',6'-dimethyl-[1,1'-biphenyl]-3-yl)propanoate

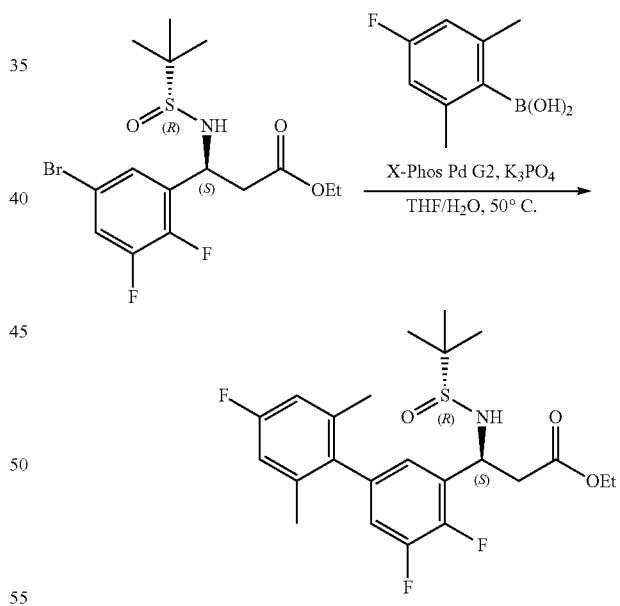

A mixture of ethyl (S)-3-(5-bromo-2,3-difluorophenyl)-3-(((R)-tert-butylsulfinyl)amino)propanoate (1.1 g, 2.68 mmol, 1.00 eq), K$_3$PO$_4$ (1.7 g, 8.04 mmol, 3.00 eq), X-Phos Pd G2 (212 mg, 0.27 mmol, 0.10 eq) and (4-fluoro-2,6-dimethylphenyl)boronic acid (900 mg, 5.36 mmol, 2.00 eq) in THF (10 mL) and H$_2$O (2 mL) was stirred at 50° C. under nitrogen atmosphere for 2 hours. LCMS showed that the reaction was completed. The reaction mixture was poured into 50 mL of water and extracted with EtOAc (50 mL×3). The combined organic layers were washed with brine (100 mL), dried over anhydrous Na$_2$SO$_4$, filtered and concentrated in vacuo. The residue was purified by silica gel column (pet ether:EtOAc 1:1) to provide ethyl (S)-3-(((R)-tert-butylsulfinyl)amino)-3-(4,4',5-trifluoro-2',6'-dimethyl-[1,1'-biphenyl]-3-yl)propanoate as a brown oil (1 g). Yield 82% (ESI 456.1 (M+H)$^+$)

Step 2: Ethyl (S)-3-amino-3-(4,4',5-trifluoro-2',6'-dimethyl-[1,1'-biphenyl]-3-yl)propanoate

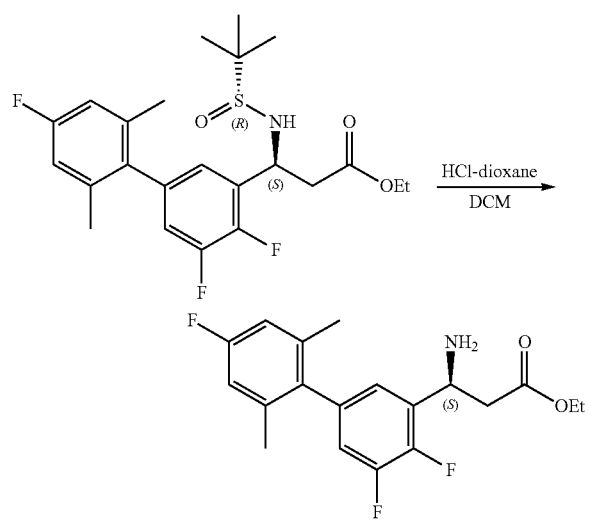

To a mixture of ethyl (S)-3-(((R)-tert-butylsulfinyl) amino)-3-(4,4',5-trifluoro-2',6'-dimethyl-[1,1'-biphenyl]-3-yl)propanoate (1.0 g, 2.2 mmol, 1.0 eq) in DCM (4 mL) was added HCl-dioxane (4 M, 2 mL, 4.0 mmol, 1.8 eq). The mixture was stirred at room temperature for 1 hour. LCMS showed that the reaction was completed. The mixture was concentrated in vacuo and the residue was purified by reverse phase HPLC on a C18/80 g column (A: water 10 mM NH$_4$HCO$_3$, B: MeOH, 0~100%) to provide ethyl (S)-3-amino-3-(4,4',5-trifluoro-2',6'-dimethyl-[1,1'-biphenyl]-3-yl)propanoate as a white solid (750 mg). Yield 97% (ESI 352.1 [M+H]$^+$).

Preparation of Ethyl (S)-3-amino-3-(4,5-difluoro-2', 4',6'-trimethyl-[1,1'-biphenyl]-3-yl)propanoate Scheme:

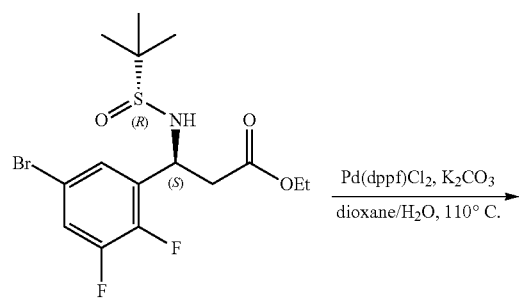

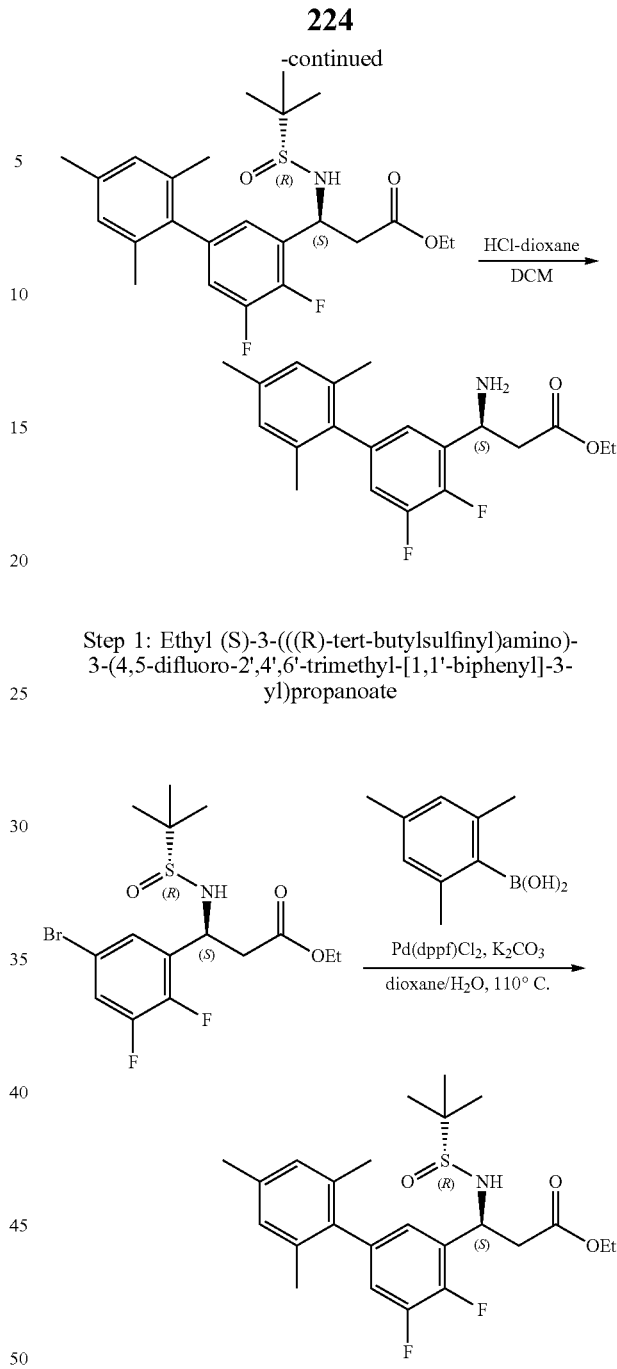

Step 1: Ethyl (S)-3-(((R)-tert-butylsulfinyl)amino)-3-(4,5-difluoro-2',4',6'-trimethyl-[1,1'-biphenyl]-3-yl)propanoate A mixture of ethyl (S)-3-(5-bromo-2,3-difluorophenyl)-3-(((R)-tert-butylsulfinyl)amino)propanoate (1.5 g, 3.65 mmol, 1.0 eq), mesitylboronic acid (1.2 g, 7.30 mmol, 2.0 eq), K$_2$CO$_3$ (1.5 g, 10.95 mmol, 3.0 eq) and Pd(dppf)Cl$_2$ (267 mg, 0.365 mmol, 0.1 eq) in dioxane (10 mL) and H$_2$O (1 mL) was stirred at 110° C. under nitrogen atmosphere for 1 hour. LCMS showed that the reaction was completed. The mixture was cooled to room temperature, poured into water (30 mL), extracted with EtOAc (30 mL×3). The combined organic layers were washed with brine (100 mL), dried over anhydrous Na$_2$SO$_4$, filtered and concentrated in vacuo. The residue was purified by silica gel column (pet ether:EtOAc 2:1) to provide ethyl (S)-3-(((R)-tert-butylsulfinyl)amino)-3-(4,5-difluoro-2',4',6'-trimethyl-[1,1'-biphenyl]-3-yl)propanoate as a yellow oil (1.4 g). Yield 85% (ESI 452.2 (M+H)$^+$).

Step 2: Ethyl (S)-3-amino-3-(4,5-difluoro-2',4',6'-trimethyl-[1,1'-biphenyl]-3-yl)propanoate

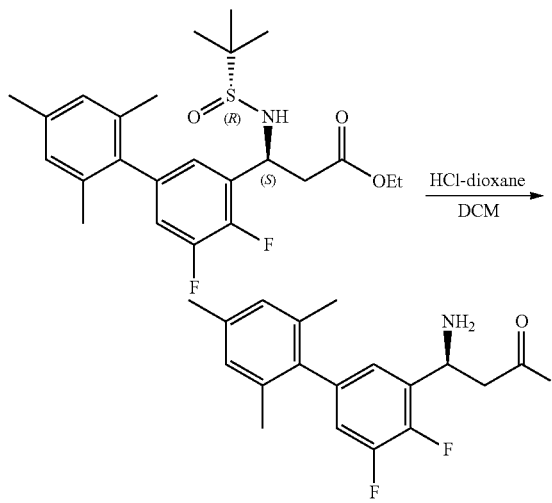

To a mixture of ethyl (S)-3-(((R)-tert-butylsulfinyl)amino)-3-(4,5-difluoro-2',4',6'-trimethyl-[1,1'-biphenyl]-3-yl)propanoate (1.4 g, 3.1 mmol, 1.0 eq) in DCM (20 mL) was added HCl-dioxane (4 M, 2 mL, 8.0 mmol, 2.58 eq). The mixture was stirred at room temperature for 1 hour. LCMS showed that the reaction was completed. The mixture was concentrated in vacuo and the residue was purified by reverse phase HPLC on a C18/120 g column (A: water/0.01% TFA, B: MeOH, 0~100%) to provide ethyl (S)-3-amino-3-(4,5-difluoro-2',4',6'-trimethyl-[1,1'-biphenyl]-3-yl)propanoate as a light yellow solid (1.0 g). Yield 93% (ESI 348.1 (M+H)$^+$).

Preparation of Ethyl (S)-3-(5-bromo-2-fluoro-3-(trifluoromethyl)phenyl)-3-(((R)-tert-butylsulfinyl)amino)propanoate

Step 1: 5-bromo-2-fluoro-3-(trifluoromethyl)benzaldehyde

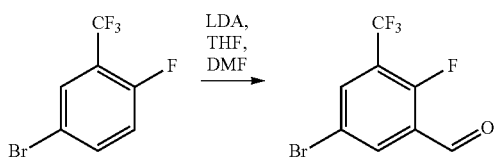 [SMILES: Fc1ccc(Br)cc1C(F)(F)F ; O=Cc1cc(Br)cc(C(F)(F)F)c1F]

To a solution of 4-bromo-1-fluoro-2-(trifluoromethyl)benzene (10.0 g, 41.15 mmol, 1.00 eq) in anhydrous THF (50 mL) under nitrogen atmosphere at −78° C. was added Lithium diisopropylamide (2.0 M, 30.9 mL, 61.73 mmol, 1.50 eq) dropwise and stirred at −78° C. for 1 hour under nitrogen atmosphere. DMF (15 mL) was added dropwise and the mixture was stirred at −78° C. for 1 hour. The mixture was quenched with 1M HCl aqueous solution (30 mL) and extracted with EtOAc (30 mL×3). The combined organic layers were washed with brine (50 mL), dried over anhydrous Na$_2$SO$_4$, filtered and concentrated in vacuo. The residue obtained was purified by silica gel column (pet ether:EtOAc 20:1) to provide 5-bromo-2-fluoro-3-(trifluoromethyl)benzaldehyde as a white solid (8.0 g). Yield 72%. $^1$H NMR (400 MHz, CDCl$_3$) δ 10.34 (s, 1H), 8.19 (dd, J=5.4, 2.4 Hz, 1H), 7.98 (dd, J=6.1, 2.5 Hz, 1H).

Step 2: (R,E)-N-(5-bromo-2-fluoro-3-(trifluoromethyl)benzylidene)-2-methylpropane-2-sulfinamide

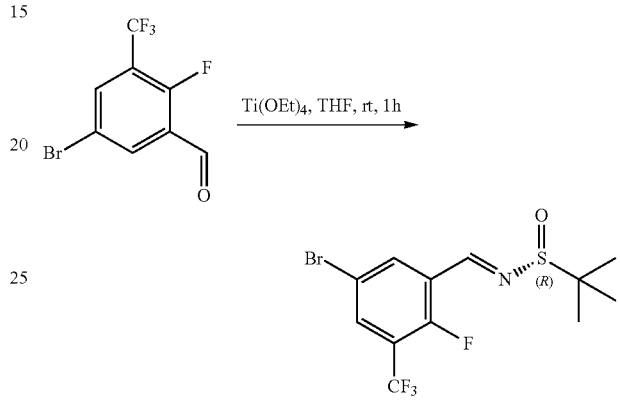

To a mixture of 5-bromo-2-fluoro-3-(trifluoromethyl)benzaldehyde (8.0 g, 29.50 mmol, 1.00 eq) and (R)-2-methylpropane-2-sulfinamide (3.9 g, 32.45 mmol, 1.1 eq) in anhydrous THF (100 mL) under nitrogen atmosphere was added Ti(OEt)$_4$ (13.0 g, 59.00 mmol, 2.00 eq) dropwise at room temperature and maintained the temperature below 30° C. The reaction mixture was stirred at room temperature for 1 hour under nitrogen atmosphere. LCMS showed that the reaction was completed. Water (100 mL) and EtOAc (100 mL) was added into the mixture and stirred at room temperature for 5 mins. The mixture was filtered and washed with EtOAc (50 mL). The filtrate was separated. The organic layer was washed with water (50 mL) and brine (50 mL), dried over anhydrous Na$_2$SO$_4$, filtered and concentrated in vacuo. The residue was purified by silica gel column (pet ether:EtOAc 5:1) to provide (R,E)-N-(5-bromo-2-fluoro-3-(trifluoromethyl)benzylidene)-2-methylpropane-2-sulfinamide as a yellow oil (8.0 g). Yield 72% (ESI 373.9 (M+H)$^+$).

Step 3: Ethyl (S)-3-(5-bromo-2-fluoro-3-(trifluoromethyl)phenyl)-3-(((R)-tert-butylsulfinyl)amino)propanoate

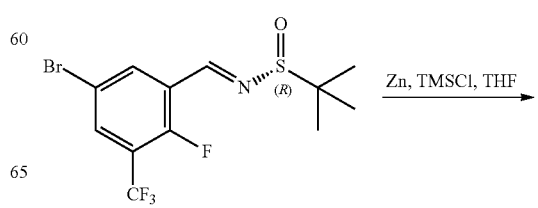

227

-continued

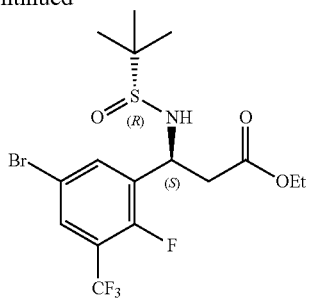

To a mixture of Zn (5.6 g, 85.6 mmol, 4.00 eq) in anhydrous THF (100 mL) under nitrogen atmosphere was added chlorotrimethylsilane (465 mg, 4.28 mmol, 0.2 eq) dropwise at room temperature. The mixture was stirred at 45° C. for 1 hour under nitrogen atmosphere and cooled to 20-30° C. Ethyl 2-bromoacetate (8.9 g, 53.5 mmol, 2.50 eq) was added dropwise at room temperature. The reaction mixture was stirred at 50° C. for 1 hour under nitrogen atmosphere and then cooled to room temperature. A solution of (R,E)-N-(5-bromo-2-fluoro-3-(trifluoromethyl)benzylidene)-2-methylpropane-2-sulfinamide (8.0 g, 21.4 mmol, 1.00 eq) in anhydrous THF (10 mL) was added dropwise into the mixture at room temperature under nitrogen atmosphere. The mixture was stirred at room temperature for 1 hour. LCMS showed that the reaction was completed. Water (100 mL) and EtOAc (100 mL) was added into the mixture and stirred at room temperature for 5 mins. The mixture was filtered and washed with EtOAc (100 mL). The filtrate was separated. The organic layer was washed with water (100 mL) and brine (100 mL), dried over anhydrous Na$_2$SO$_4$, filtered and concentrated in vacuo. The residue was purified by silica gel column (pet ether:EtOAc 4:1) to provide ethyl (S)-3-(5-bromo-2-fluoro-3-(trifluoromethyl) phenyl)-3-(((R)-tert-butylsulfinyl)amino)propanoate as a colorless oil (6.3 g). Yield 64% (ESI 462.0 (M+H)$^+$).

Preparation of Ethyl (S)-ethyl 3-amino-3-(4-fluoro-2',6'-dimethyl-5-(trifluoromethyl)biphenyl-3-yl)propanoate Step 1: Ethyl (S)-3-(((R)-tert-butylsulfinyl)amino)-3-(4-fluoro-2',6'-dimethyl-5-(trifluoromethyl)-[1,1'-biphenyl]-3-yl)propanoate

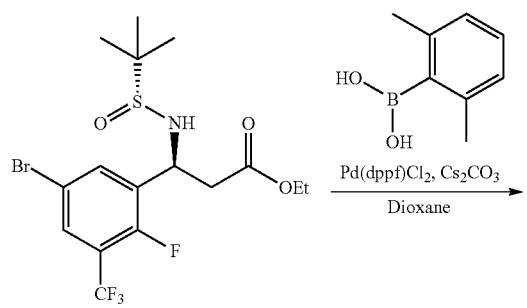

228

-continued

To a solution of ethyl (S)-3-(5-bromo-2-fluoro-3-(trifluoromethyl)phenyl)-3-(((R)-tert-butylsulfinyl)amino)propanoate (3 g, 6.49 mmol) and (2,6-dimethylphenyl)boronic acid (1.46 g, 9.73 mmol) in Dioxane (24 mL) was added a solution of Cs2CO3 (4.23 g, 12.98 mmol) in Water (8 mL). The reaction was purged with N2 for 5 min, followed by addition of PdCl2(dppf) (0.712 g, 0.973 mmol) and another N2 purge for 1 min. The reaction was stirred at 70 C for 4 hours. The reaction mixture was diluted into 250 mL EtOAc, then washed with 1N HCl (250 mL), Sat. NaHCO$_3$ (205 mL) and Brine (250 mL). The residue was concentrated and purified by silica gel chromatography to provide ethyl (S)-3-(((R)-tert-butylsulfinyl)amino)-3-(4-fluoro-2',6'-dimethyl-5-(trifluoromethyl)-[1,1'-biphenyl]-3-yl)propanoate (2.71 g). Yield 86% (ESI 488 (M++H)$^+$).

Step 2: (S)-ethyl 3-amino-3-(4-fluoro-2',6'-dimethyl-5-(trifluoromethyl)biphenyl-3-yl)propanoate

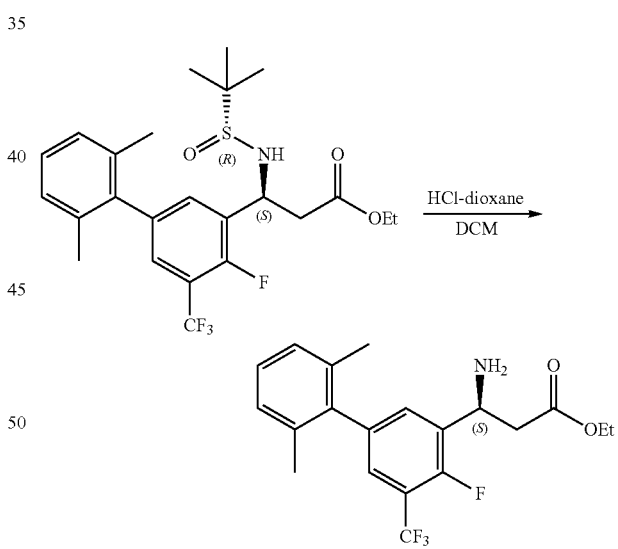

To a solution of (S)-ethyl 3-((R)-1,1-dimethylethylsulfinamido)-3-(4-fluoro-2',6'-dimethyl-5-(trifluoromethyl)biphenyl-3-yl)propanoate (0.93 g, 1.9 mmol, 1.00 eq) in DCM (8 mL) was added HCl-dioxane (4M, 1.9 mL, 7.6 mmol, 4 eq) and stirred at room temperature for 2 hours. The mixture was concentrated in vacuo and the residue was purified by reverse phase HPLC on a C18/120 g column (A: water/ 0.01% TFA, B: MeOH, 0~100%) to provide (R)-ethyl 3-amino-3-(4-fluoro-2',6'-dimethyl-5-(trifluoromethyl)biphenyl-3-yl)propanoate as a yellow solid (0.6 g). Yield 82% (ESI 384.1 (M+H)$^+$).

229

Preparation of Ethyl (S)-3-amino-3-(4,4'-difluoro-2',6'-dimethyl-5-(trifluoromethyl)-[1,1'-biphenyl]-3-yl)propanoate Step 1: Ethyl (S)-3-(((R)-tert-butylsulfinyl)amino)-3-(4,4'-difluoro-2',6'-dimethyl-5-(trifluoromethyl)-[1,1'-biphenyl]-3-yl)propanoate

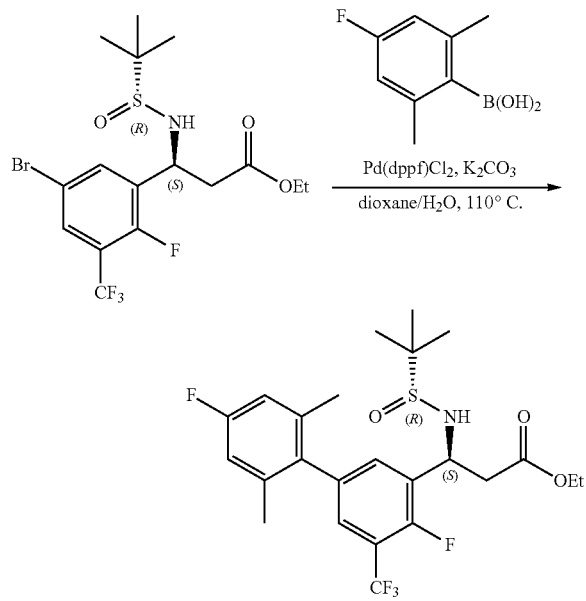

A mixture of ethyl (S)-3-(5-bromo-2-fluoro-3-(trifluoromethyl)phenyl)-3-(((R)-tert-butylsulfinyl)amino)propanoate (2.0 g, 4.3 mmol, 1.00 eq), K₂CO₃ (1.8 g, 12.9 mmol, 3.00 eq), Pd(dppf)Cl₂ (315 mg, 0.43 mmol, 0.10 eq) and (4-fluoro-2,6-dimethylphenyl)boronic acid (1.1 g, 6.45 mmol, 1.50 eq) in dioxane (50 mL) and H₂O (5 mL) was stirred at 110° C. for 2 hours under nitrogen atmosphere. LCMS showed that the reaction was completed. The reaction mixture was poured into 50 mL of water, extracted with EtOAc (50 mL×3). The combined organic layers were washed with brine (15 mL), dried over anhydrous Na₂SO₄, filtered and concentrated in vacuo. The residue was purified by silica gel column (pet ether:EtOAc 3:1) to provide ethyl (S)-3-(((R)-tert-butylsulfinyl)amino)-3-(4,4'-difluoro-2',6'-dimethyl-5-(trifluoromethyl)-[1,1'-biphenyl]-3-yl)propanoate as a colorless oil (1.4 g). Yield 64% (ESI 506.0 (M+H)⁺)

Step 2: Ethyl (S)-3-amino-3-(4,4'-difluoro-2',6'-dimethyl-5-(trifluoromethyl)-[1,1'-biphenyl]-3-yl)propanoate

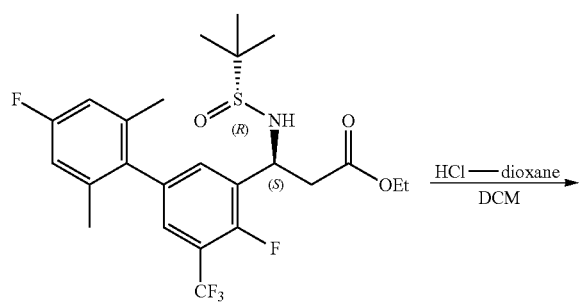

230

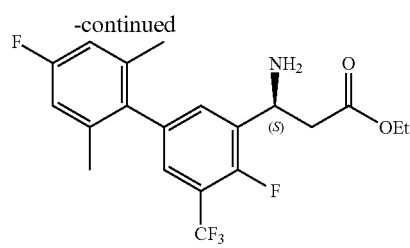

To a mixture of ethyl (S)-3-(((R)-tert-butylsulfinyl)amino)-3-(4,4'-difluoro-2',6'-dimethyl-5-(trifluoromethyl)-[1,1'-biphenyl]-3-yl)propanoate (1.4 g, 2.77 mmol, 1.0 eq) in DCM (10 mL) was added HCl-dioxane (4 M, 6 mL, 24.0 mmol, 8.66 eq). The mixture was stirred at room temperature for 1 hour. LCMS showed that the reaction was completed. The mixture was concentrated in vacuo and the residue was purified by reverse phase HPLC on a C18/120 g column (A: water/0.01% TFA, B: MeOH, 0~100%) to provide ethyl (S)-3-amino-3-(4,4'-difluoro-2',6'-dimethyl-5-(trifluoromethyl)-[1,1'-biphenyl]-3-yl)propanoate as a colorless oil (880 mg). Yield 79% (ESI 402.1 [M+H]⁺).

Preparation of (S)-ethyl 3-amino-3-(4-fluoro-2',3',5,6'-tetramethylbiphenyl-3-yl)propanoate Step 1: (S)-ethyl 3-(tert-butoxycarbonylamino)-3-(4-fluoro-2',3',5,6'-tetramethylbiphenyl-3-yl)propanoate

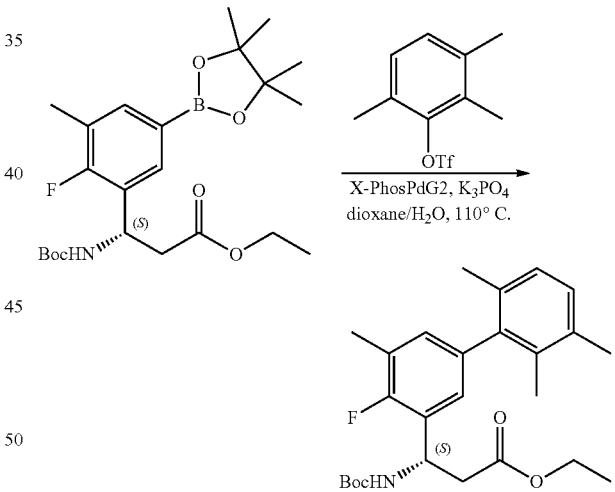

To a mixture of (S)-ethyl 3-(tert-butoxycarbonylamino)-3-(2-fluoro-3-methyl-5-(4,4,5,5-tetramethyl-1,3,2-dioxaborolan-2-yl)phenyl)propanoate (3.0 g, 6.7 mmol), 2,3,6-trimethylphenyl trifluoromethanesulfonate (2.2 g, 8.0 mmol) and K₃PO₄ (4.3 g, 20.1 mmol) in dioxane (30 mL) and H₂O (3 mL) was added X-Phos Pd G2 (550 mg, 0.7 mmol). The mixture was heated to 110° C. for 1 hr under nitrogen atmosphere. Water (50 mL) was added and the solution was extracted with EtOAc (60 mL×3). The combined organic phases were concentrated in vacuo and the residue was purified by silica gel column (pet ether:EtOAc 2:1) to provide (S)-ethyl 3-(tert-butoxycarbonylamino)-3-(4-fluoro-2',3',5,6'-tetramethylbiphenyl-3-yl)propanoate as a dark solid (1.7 g). Yield 57% (ESI 344.1 [M+H−100]⁺).

Step 2: (S)-ethyl 3-amino-3-(4-fluoro-2',3',5,6'-tetramethylbiphenyl-3-yl)propanoate

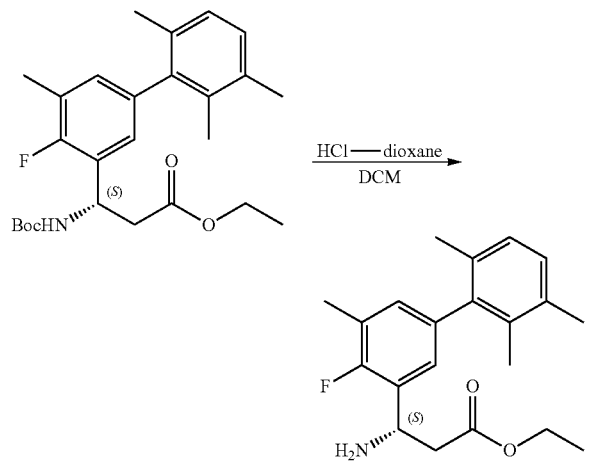

To a mixture of (S)-ethyl 3-(tert-butoxycarbonylamino)-3-(4-fluoro-2',3',5,6'-tetramethylbiphenyl-3-yl)propanoate (1.7 g, 3.8 mmol) in DCM (2 mL) was added HCl-dioxane (4M, 5 mL, 20.0 mmol) and the mixture was stirred at rt for 30 minutes. The mixture was concentrated in vacuo and the residue was purified by reverse phase HPLC on a C18/120 g column (A: water 10 mM $NH_4HCO_3$, B: $CH_3CN$, 0~100%) to provide (S)-ethyl 3-amino-3-(4-fluoro-2',3',5,6'-tetramethylbiphenyl-3-yl)propanoate as a colorless oil (1.0 g). Yield 76% (ESI 344.1 [M+H]$^+$).

Preparation of Ethyl (S)-3-amino-3-(4-fluoro-2',4',6'-trimethyl-5-(trifluoromethyl)-[1,1'-biphenyl]-3-yl)propanoate

Step 1: Ethyl (S)-3-(((R)-tert-butylsulfinyl)amino)-3-(2-fluoro-5-(4,4,5,5-tetramethyl-1,3,2-dioxaborolan-2-yl)-3-(trifluoromethyl)phenyl)propanoate

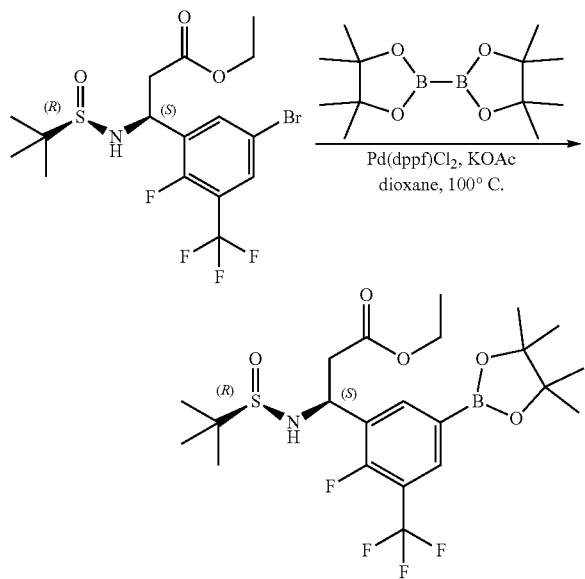

A mixture of ethyl (S)-3-(5-bromo-2-fluoro-3-(trifluoromethyl)phenyl)-3-(((R)-tert-butylsulfinyl)amino)propanoate (2.8 g, 6.1 mmol), KOAc (1.8 g, 18.3 mmol), Pd(dppf)Cl$_2$ (446 mg, 0.61 mmol) and (4,4,4',4',5,5,5',5'-octamethyl-2,2'-bi(1,3,2-dioxaborolane) (2.3 g, 9.15 mmol) in dioxane (30 mL) was stirred at 100° C. for 2 hours under nitrogen. The reaction mixture was poured into 50 mL of water and extracted with EtOAc (20 mL×3). The combined organic layers were washed with brine (10 mL), dried over anhydrous Na$_2$SO$_4$, filtered and the filtrate concentrated in vacuo. The residue was purified by silica gel column (pet ether:EtOAc 3:1) to provide ethyl (S)-3-(((R)-tert-butylsulfinyl)amino)-3-(2-fluoro-5-(4,4,5,5-tetramethyl-1,3,2-dioxaborolan-2-yl)-3-(trifluoromethyl)phenyl)propanoate as a colorless oil (2.6 g). Yield 84% (ESI 510.1 (M+H)$^+$)

Step 2: Ethyl (S)-3-(((R)-tert-butylsulfinyl)amino)-3-(3',4-difluoro-2',6'-dimethyl-5-(trifluoromethyl)-[1,1'-biphenyl]-3-yl)propanoate

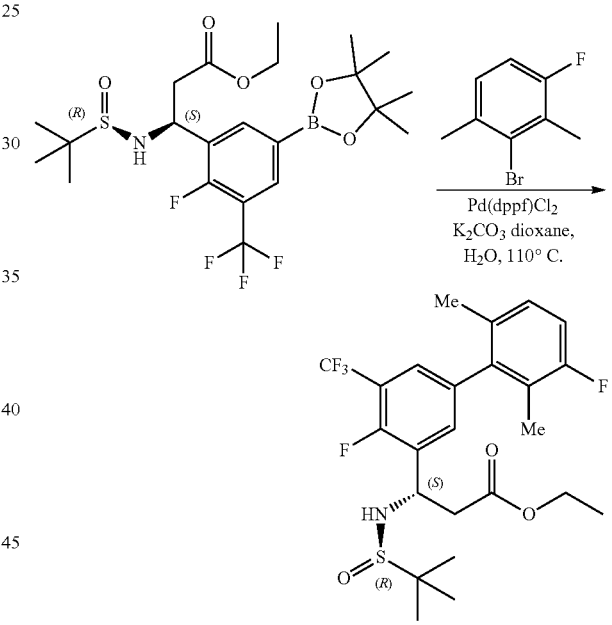

A mixture of ethyl (S)-3-(((R)-tert-butylsulfinyl)amino)-3-(2-fluoro-5-(4,4,5,5-tetramethyl-1,3,2-dioxaborolan-2-yl)-3-(trifluoromethyl)phenyl)propanoate (600 mg, 1.2 mmol), K$_2$CO$_3$ (497 mg, 3.6 mmol), Pd(dppf)Cl$_2$ (88 mg, 0.12 mmol) and 2-bromo-4-fluoro-1,3-dimethylbenzene (363.6 mg, 1.8 mmol) in dioxane (6 mL) and H$_2$O (0.6 mL) was stirred at 110° C. under nitrogen for 2 hours. The reaction mixture was poured into 20 mL of water and extracted with EtOAc (20 mL×3). The combined organic layers were washed with brine (5 mL), dried over anhydrous Na$_2$SO$_4$, filtered and the filtrate was concentrated in vacuo. The residue was purified by silica gel column (pet ether: EtOAc 3:1) to provide ethyl (S)-3-(((R)-tert-butylsulfinyl)amino)-3-(3',4-difluoro-2',6'-dimethyl-5-(trifluoromethyl)-[1,1'-biphenyl]-3-yl)propanoate as a colorless oil (460 mg). Yield 77% (ESI 506.1 (M+H)$^+$)

Step 3: Ethyl (S)-3-amino-3-(3',4-difluoro-2',6'-dimethyl-5-(trifluoromethyl)-[1,1'-biphenyl]-3-yl)propanoate

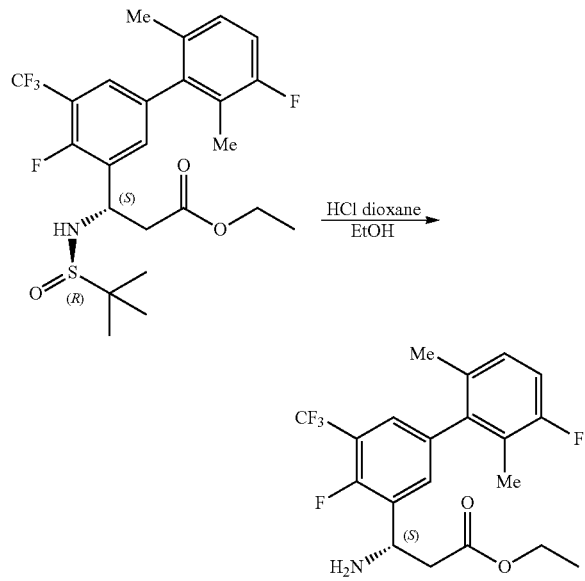

To a mixture of ethyl (S)-3-(((R)-tert-butylsulfinyl)amino)-3-(3',4-difluoro-2',6'-dimethyl-5-(trifluoromethyl)-[1,1'-biphenyl]-3-yl)propanoate (460 mg, 0.91 mmol) in EtOH (5 mL) was added HCl-dioxane (4 M, 2 mL, 8.0 mmol). The mixture was stirred at room temperature for 1 hour. The mixture was concentrated in vacuo and the residue was purified by reverse phase HPLC on a C18/40 g column (A: water/0.05% TFA, B: MeOH, 0~100%) to provide ethyl (S)-3-amino-3-(3',4-difluoro-2',6'-dimethyl-5-(trifluoromethyl)-[1,1'-biphenyl]-3-yl)propanoate as a colorless oil (230 mg). Yield 63% (ESI 402.1 [M+H]$^+$).

Preparation of Ethyl (S)-3-amino-3-(4-fluoro-2',4',6'-trimethyl-5-(trifluoromethyl)-[1,1'-biphenyl]-3-yl)propanoate

Step 1: ((S)-ethyl 3-((R)-1,1-dimethylethylsulfinamido)-3-(4-fluoro-3'-methoxy-2',6'-dimethyl-5-(trifluoromethyl)biphenyl-3-yl)propanoate

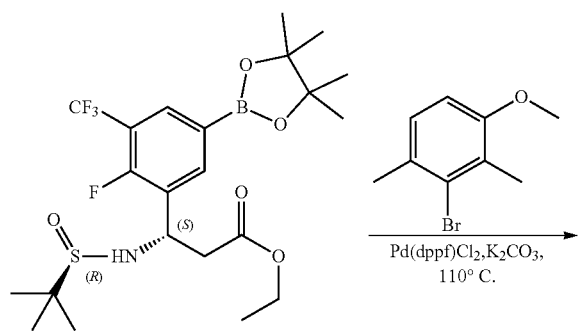

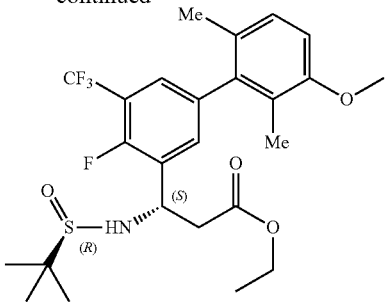

A mixture of (S)-ethyl 3-((R)-1,1-dimethylethylsulfinamido)-3-(2-fluoro-5-(4,4,5,5-tetramethyl-1,3,2-dioxaborolan-2-yl)-3-(trifluoromethyl)phenyl)propanoate (600 mg, 1.18 mmol), K$_2$CO$_3$ (488 mg, 3.54 mmol), Pd(dppf)Cl$_2$ (43 mg, 0.06 mmol) and 2-bromo-4-methoxy-1,3-dimethylbenzene (300 mg, 1.42 mmol) in dioxane (10 mL) and H$_2$O (1 mL) was stirred at 110° C. under nitrogen atmosphere for 1 hour. The reaction mixture was poured into 50 mL of water and extracted with EtOAc (50 mL×3). The combined organic layers were washed with brine (100 mL), dried over anhydrous Na$_2$SO$_4$, filtered and the filtrate was concentrated in vacuo. The residue was purified by silica gel column (pet ether:EtOAc 3:2) to provide (S)-ethyl 3-((R)-1,1-dimethylethylsulfinamido)-3-(4-fluoro-3'-methoxy-2',6'-dimethyl-5-(trifluoromethyl)biphenyl-3-yl)propanoate as a colorless oil (400 mg). Yield 65% (ESI 518.3 (M+H)$^+$)

Step 2: (S)-ethyl 3-amino-3-(4-fluoro-3'-methoxy-2',6'-dimethyl-5-(trifluoromethyl)biphenyl-3-yl)propanoate

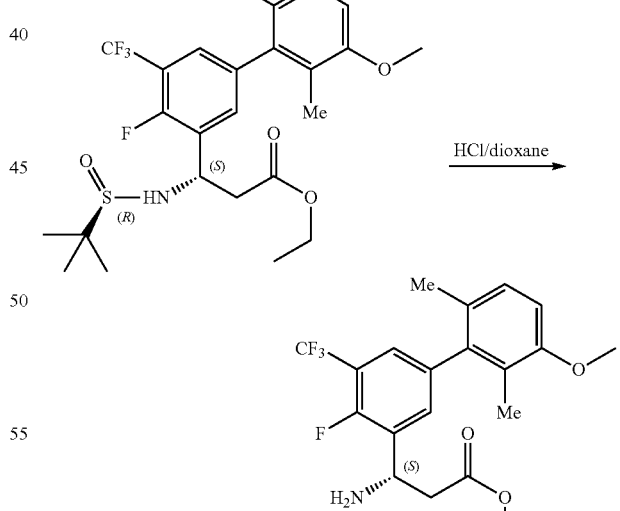

To a mixture of (S)-ethyl 3-((R)-1,1-dimethylethylsulfinamido)-3-(4-fluoro-3'-methoxy-2',6'-dimethyl-5-(trifluoromethyl)biphenyl-3-yl)propanoate (400 mg, 0.77 mmol) in DCM (2 mL) was added HCl-dioxane (4 M, 1 mL, 4.0 mmol). The mixture was stirred at room temperature for 1 hour. The mixture was concentrated in vacuo and the residue was purified by reverse phase HPLC on a C18/40 g column (A: water 10 mM NH$_4$HCO$_3$, B: CH$_3$CN, 0~100%) to provide (S)-ethyl 3-amino-3-(4-fluoro-3'-methoxy-2',6'-dimethyl-5-(trifluoromethyl)biphenyl-3-yl)propanoate (200 mg). Yield 63% (ESI 414.1 [M+H]$^+$).

Preparation of Ethyl (S)-3-amino-3-(4-fluoro-2',4',6'-trimethyl-5-(trifluoromethyl)-[1,1'-biphenyl]-3-yl)propanoate Step 1: 2,3,6-trimethylphenyl trifluoromethanesulfonate

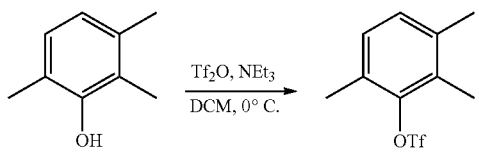

To a mixture of 2,3,6-trimethylphenol (5 g, 36.8 mmol), NEt$_3$ (9.3 g, 92.0 mmol) in DCM (100 mL) was added Tf$_2$O (15.6 g, 55.2 mmol) at 0° C. dropwise and stirred at room temperature for 3 hours. The reaction mixture was poured into 100 mL of water and extracted with DCM (100×3 mL×3). The combined organic layers were washed with brine (100 mL), dried over anhydrous Na$_2$SO$_4$, filtered and the filtrate was concentrated in vacuo. The residue was purified by silica gel column (pet ether) to provide 2,3,6-trimethylphenyl trifluoromethanesulfonate as a colorless oil (8 g). Yield 80% (ESI 269.3 (M+H)$^+$).

Step 2: (S)-ethyl 3-((R)-1,1-dimethylethylsulfinamido)-3-(4-fluoro-2',3',6'-trimethyl-5-(trifluoromethyl)biphenyl-3-yl)propanoate

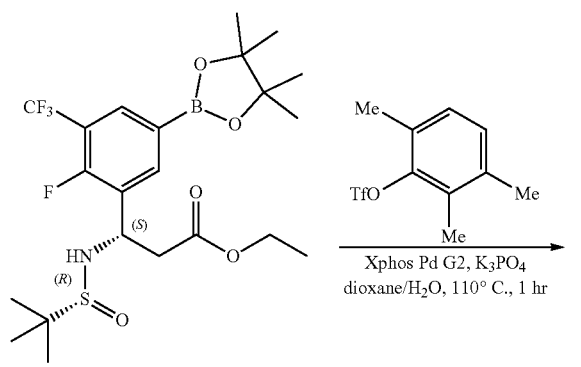

To a mixture of (S)-ethyl 3-((R)-1,1-dimethylethylsulfinamido)-3-(2-fluoro-5-(4,4,5,5-tetramethyl-1,3,2-dioxaborolan-2-yl)-3-(trifluoromethyl)phenyl)propanoate (400 mg, 0.79 mmol), 2,3,6-trimethylphenyl trifluoromethanesulfonate (253 mg, 0.94 mmol) and K$_3$PO$_4$ (502 mg, 2.37 mmol) in dioxane (10 mL) and H$_2$O (1 mL) was added Xphos Pd G2 (63 mg, 0.08 mmol). The mixture was heated to 110° C. for 30 mins under nitrogen atmosphere. Water (20 mL) was added and the solution was extracted with EtOAc (20 mL×3). The combined organic phases were concentrated in vacuo and the residue was purified by silica gel column (pet ether:EtOAc 2:1) to provide (S)-ethyl 3-((R)-1,1-dimethylethylsulfinamido)-3-(4-fluoro-2',3',6'-trimethyl-5-(trifluoromethyl)biphenyl-3-yl)propanoate as a dark solid (300 mg). Yield 76% (ESI 502.1 [M−100+]$^+$).

Step 3: (S)-ethyl 3-amino-3-(4-fluoro-2',3',6'-trimethyl-5-(trifluoromethyl)biphenyl-3-yl)propanoate

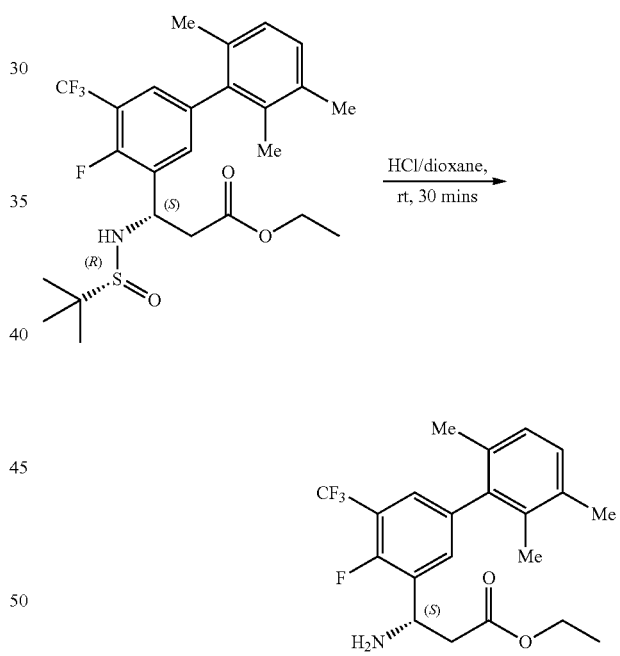

To a mixture of (S)-ethyl 3-((R)-1,1-dimethylethylsulfinamido)-3-(4-fluoro-2',3',6'-trimethyl-5-(trifluoromethyl)biphenyl-3-yl)propanoate (300 mg, 0.6 mmol) in DCM (1 mL) was added HCl-dioxane (4N, 1 mL, 2.5 mmol) and the mixture was stirred at room temperature for 0.5 hr. The mixture was concentrated in vacuo and the residue was purified by reverse phase HPLC on a C18/40 g column (A: water 10 mM NH$_4$HCO$_3$, B: CH$_3$CN, 0~100%) to provide (S)-ethyl 3-amino-3-(4-fluoro-2',3',6'-trimethyl-5-(trifluoromethyl)biphenyl-3-yl)propanoate as a colorless oil (170 mg). Yield 71% (ESI 398.1 (M+H)$^+$).

237

Preparation of Ethyl (S)-3-amino-3-(4-fluoro-2',4', 6'-trimethyl-5-(trifluoromethyl)-[1,1'-biphenyl]-3-yl)propanoate Step 1: (S)-ethyl 3-((R)-1,1-dimethylethylsulfinamido)-3-(4-fluoro-2',4',6'-trimethyl-5-(trifluoromethyl)biphenyl-3-yl)propanoate

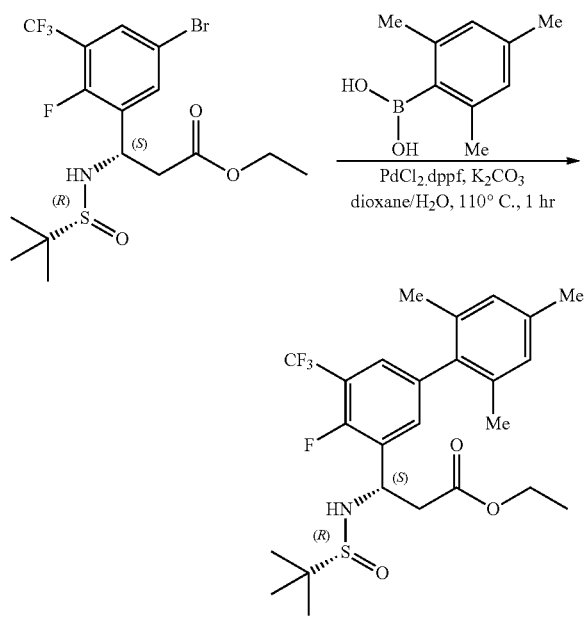

To a mixture of (S)-ethyl 3-(5-bromo-2-fluoro-3-(trifluoromethyl)phenyl)-3-((R)-1,1-dimethylethylsulfinamido)propanoate (461 mg, 1.0 mmol), mesitylboronic acid (197 mg, 1.2 mmol) and K₂CO₃ (414 mg, 3.0 mmol) in dioxane (10 mL) and H₂O (1 mL) was added Pd(dppf)Cl₂ (73 mg, 0.1 mmol). The mixture was heated to 110° C. for 2 hrs under nitrogen atmosphere. Water (20 mL) was added and the mixture was extracted with EtOAc (20 mL×3). The combined organic phases were concentrated in vacuo and the residue was purified by silica gel column (pet ether:EtOAc 2:1) to provide (S)-ethyl 3-((R)-1,1-dimethylethylsulfinamido)-3-(4-fluoro-2',4',6'-trimethyl-5-(trifluoromethyl)biphenyl-3-yl)propanoate as a dark solid (400 mg). Yield 80% (ESI 502.1 [M−100+]⁺).

Step 2: (S)-ethyl 3-amino-3-(4-fluoro-2',4',6'-trimethyl-5-(trifluoromethyl)biphenyl-3-yl)propanoate

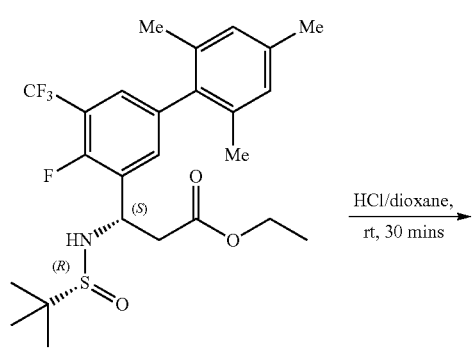

238

-continued

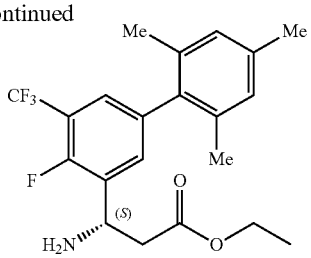

To a mixture of (S)-ethyl 3-((R)-1,1-dimethylethylsulfinamido)-3-(4-fluoro-2',4',6'-trimethyl-5-(trifluoromethyl) biphenyl-3-yl)propanoate (400 mg, 0.8 mmol) in DCM (1 mL) and EtOH (2 mL) was added HCl-dioxane (4M, 2 mL, 8 mmol) and stirred at rt for 0.5 hr. The mixture was concentrated in vacuo to provide the product as a yellow oil (350 mg, crude). (ESI 398.1 [M+H]⁺).

Preparation of Ethyl (3S)-3-amino-3-(2,4,4'-trifluoro-2',3',6'-trimethyl-5-(trifluoromethyl)-[1,1'-biphenyl]-3-yl)propanoate Step 1: 2,6-dibromo-4-fluoro-3-methylaniline

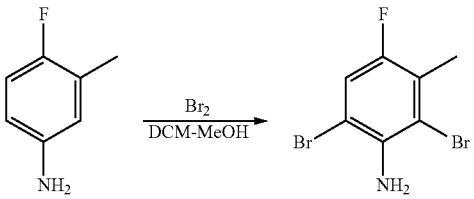

To a mixture of 4-fluoro-3-methylaniline (50.0 g, 400 mmol) in MeOH (120 mL) and DCM (120 mL) was added bromine (52 mL, 1.0 mol) dropwise at room temperature over 1.5 hour and stirred at room temperature for 4 hours. 1N Na₂S₂O₃ aqueous solution (300 mL) and ethyl acetate (500 mL) was added and stirred for 10 mins, then carefully basified with 1N Na₂CO₃ aqueous solution (300 mL). The organic layer was separated and the aqueous layer was extracted with ethyl acetate (2×100 mL). The combined organic layers were washed with 1N Na₂S₂O₃ aqueous solution (300 mL) and brine (200 mL) dried over Na₂SO₄, filtered and concentrated in vacuo to provide 2,6-dibromo-4-fluoro-3-methylaniline as a white solid (80 g). Yield 70.7% (ESI 284.0[M+H]⁺).

Step 2: 4-fluoro-2,3,6-trimethylaniline

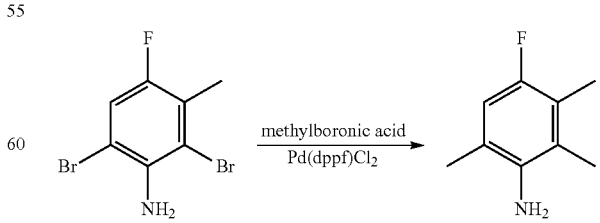

To a solution of ethyl 2,6-dibromo-4-fluoro-3-methylaniline (50.0 g, 273 mmol) in dioxane (500.0 mL) and water (50 mL) was added methylboronic acid (49.0 g, 819 mmol), K$_2$CO$_3$ (111.0 g, 819 mmol) and 1,1'-Bis(diphenylphosphino) ferrocene-palladium(II)dichloride dichloromethane complex (10.0 g, 13.65 mmol). The mixture was stirred at 110° C. overnight. The reaction was poured into water (500 mL) and extracted with Ethyl Acetate (500 mL). The combined organic layers were dried over anhydrous sodium sulfate, filtered and concentrated in vacuo. The residue was purified by silica gel column (pet ether:EtOAc 1:5) to provide 4-fluoro-2,3,6-trimethylaniline as a colorless oil (20.0 g). Yield 47.6% (ESI 154.3 (M+H)$^+$)

Step 3: 2-bromo-5-fluoro-1,3,4-trimethylbenzene

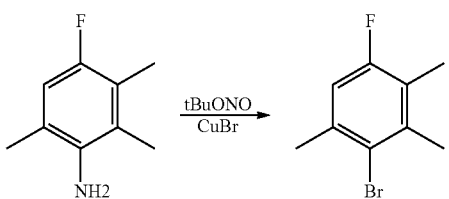

To a mixture of 4-fluoro-2,3,6-trimethylaniline (3.8 g, 24.8 mmol) in MeCN (30 mL) was added t-BuONO (3.8 g, 37.2 mmol) at 0° C., then CuBr(4.3 g, 29.7 mmol) was added. The mixture was stirred at 60° C. for 2 hours. The reaction mixture was concentrated in vacuo and the residue was purified by silica gel column (pet ether) to provide 2-bromo-5-fluoro-1,3,4-trimethylbenzene as a colorless oil (1.3 g). Yield 33.9%.

Step 4: Ethyl (3S)-3-(((R)-tert-butylsulfinyl)amino)-3-(2,4,4'-trifluoro-2',3',6'-trimethyl-5-(trifluoromethyl)-[1,1'-biphenyl]-3-yl)propanoate

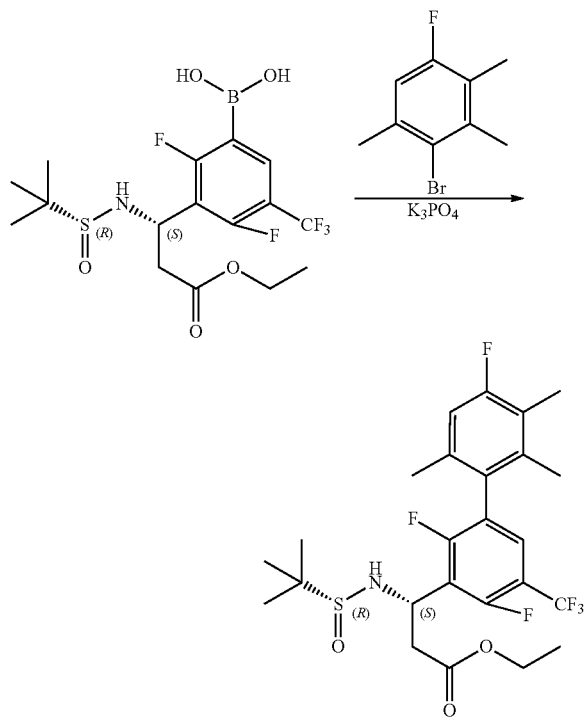

A mixture of (3-((S)-1-(((R)-tert-butylsulfinyl)amino)-3-ethoxy-3-oxopropyl)-2,4-difluoro-5-(trifluoromethyl)phenyl)boronic acid (1.5 g, 3.3 mmol), 2-bromo-5-fluoro-1,3,4-trimethylbenzene (950 mg, 4.3 mmol), K$_3$PO$_4$ (2.1 g, 9.9 mmol), X-Phos Pd G2 (285 mg, 0.33 mmol) in dioxane (10 mL) and H$_2$O (2 mL) was stirred at 110° C. for 2 h under N2 atmosphere. The mixture was poured into water (100 mL) and extracted with EtOAc (100 mL×3). The combined organic layers were dried over anhydrous sodium sulfate, filtered and concentrated in vacuo. The residue was purified by silica gel column (pet ether:EtOAc 1:1) to provide ethyl (3S)-3-(((R)-tert-butylsulfinyl)amino)-3-(2,4,4'-trifluoro-2',3',6'-trimethyl-5-(trifluoromethyl)-[1,1'-biphenyl]-3-yl)propanoate (380 mg) as a yellow oil. Yield 21.3% (ESI 538.0 (M+H)$^+$).

Step 5: Ethyl (3S)-3-amino-3-(2,4,4'-trifluoro-2',3',6'-trimethyl-5-(trifluoromethyl)-[1,1'-biphenyl]-3-yl)propanoate

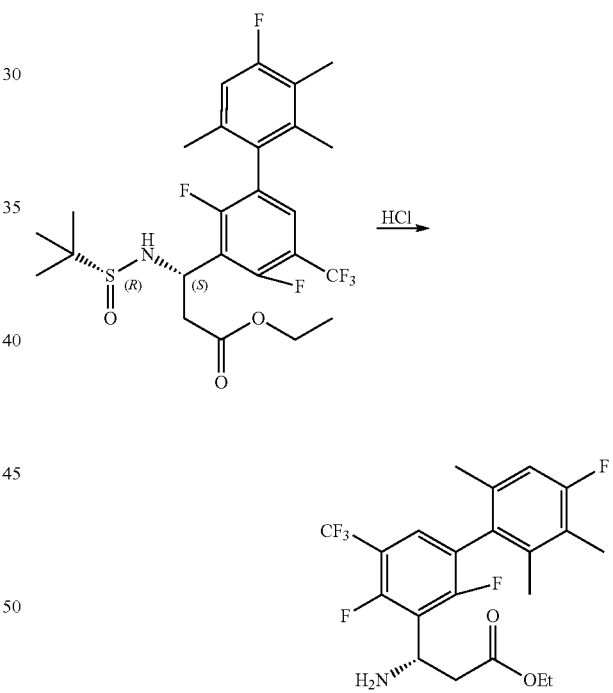

To a solution of ethyl (3S)-3-(((R)-tert-butylsulfinyl)amino)-3-(2,4,4'-trifluoro-2',3',6'-trimethyl-5-(trifluoromethyl)-[1,1'-biphenyl]-3-yl)propanoate (380 mg, 0.70 mmol) in DCM (5 mL) was added HCl-dioxane (4 M, 5 mL) and stirred at room temperature for 1 hour. The mixture was concentrated in vacuo to provide ethyl (3S)-3-amino-3-(2,4,4'-trifluoro-2',3',6'-trimethyl-5-(trifluoromethyl)-[1,1'-biphenyl]-3-yl)propanoate as a yellow oil (340 mg) used directly in the next step without further purification. Yield 100% (ESI 434.2 [M+H]$^+$).

Preparation of Ethyl (3S)-3-amino-3-(3'-cyclopropyl-2,4-difluoro-2',6'-dimethyl-5-(trifluoromethyl)-[1,1'-biphenyl]-3-yl)propanoate Step 1: 3-bromo-2,6-dimethylaniline

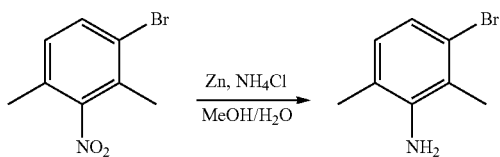

To a mixture of 1-bromo-2,4-dimethyl-3-nitrobenzene (3.0 g, 13.0 mmol) in MeOH (30 mL) and H₂O (3 mL) at 0° C. was added NH₄Cl (2.1 g, 39.0 mmol) and Zn (8.5 g, 130.0 mmol). The mixture was stirred at room temperature for 20 hours. The reaction mixture was filtered and the filtrate was concentrated in vacuo. The residue was purified by silica gel column (pet ether:EtOAc 3:2) to provide 3-bromo-2,6-dimethylaniline as a brown solid (2.0 g). Yield 77% (ESI 200.1 [M+H]⁺).

Step 2: 3-cyclopropyl-2,6-dimethylaniline

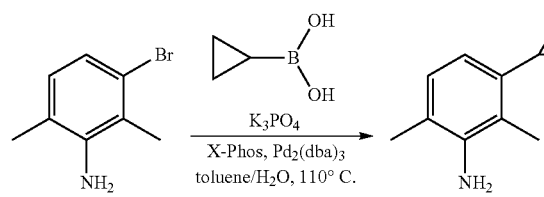

A mixture of 3-bromo-2,6-dimethylaniline (1.5 g, 7.5 mmol), cyclopropylboronic acid (3.2 g, 37.5 mmol), X-Phos (357.5 mg, 0.75 mmol), Pd₂(dba)₃ (343.4 mg, 0.38 mmol) and K₃PO₄ (4.8 g, 22.5 mmol) in 1,4-dioxane (10 mL) and water (1 mL) was stirred at 110° C. for overnight under nitrogen atmosphere. The reaction mixture was cooled to room temperature, filtered through a pad of Celite and the filtrate was concentrated in vacuo. The residue was purified by silica gel column (petroleum ether:EtOAc 5:1) to provide 3-cyclopropyl-2,6-dimethylaniline as a colorless oil (1.1 g). Yield 91% (ESI 162.2 [M+H]⁺).

Step 3: 1-cyclopropyl-3-iodo-2,4-dimethylbenzene

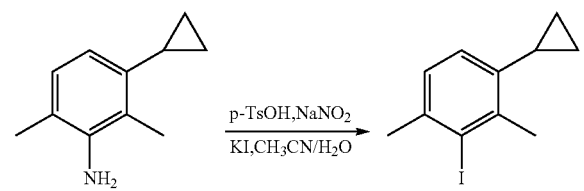

To a mixture of 3-cyclopropyl-2,6-dimethylaniline (1.1 g, 6.8 mmol) in CH₃CN (10 mL) and H₂O (1 mL) was added p-toluenesulphonic acid (5.9 g, 34.0 mmol). The mixture was stirred at 0° C. for 10 mins under under nitrogen atmosphere. A solution of NaNO₂ (703.8 mg, 10.2 mmol) in H₂O (2 mL) was added dropwise and the mixture was stirred 0° C. for 1 hour. Then KI (3.4 g, 20.4 mmol) was added to the reaction mixture and stirred at 0° C. for 2 hours. After completion, water (20 mL) was added and the solution was extracted with EtOAc (20 mL×3). The combined organic phases were washed with brine (20 mL), dried over anhydrous Na₂SO₄, filtered and concentrated in vacuo. The residue was purified by silica gel column (petroleum ether) to provide 1-cyclopropyl-3-iodo-2,4-dimethylbenzene as a colorless oil (240 mg) used without further purification. Yield 13%. ¹H NMR (400 MHz, CDCl₃) δ 6.98 (d, J=7.8 Hz, 1H), 6.93 (d, J=7.8 Hz, 1H), 2.63 (s, 3H), 2.44 (s, 3H), 1.94-1.85 (m, 1H), 0.95-0.86 (m, 2H), 0.62-0.55 (m, 2H).

Step 4: Ethyl (3S)-3-(((R)-tert-butylsulfinyl)amino)-3-(3'-cyclopropyl-2,4-difluoro-2',6'-dimethyl-5-(trifluoromethyl)-[1,1'-biphenyl]-3-yl)propanoate

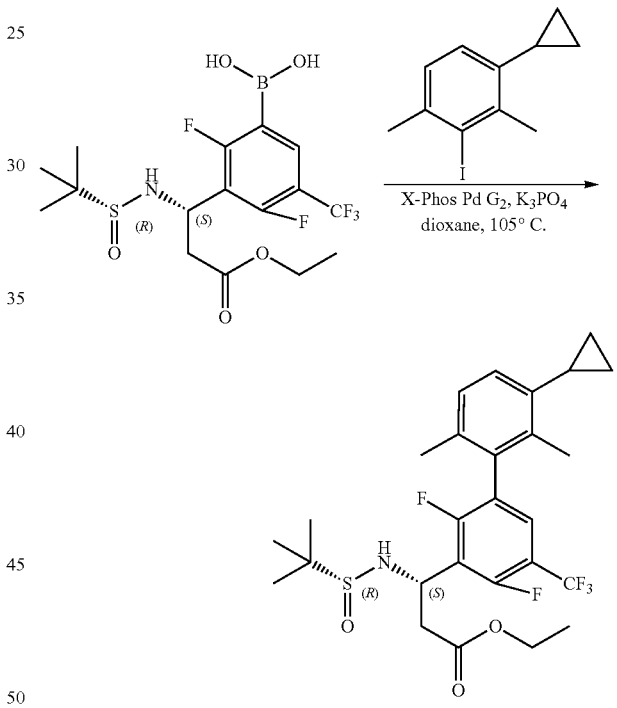

A mixture of (3-((S)-1-(((R)-tert-butylsulfinyl)amino)-3-ethoxy-3-oxopropyl)-2,4-difluoro-5-(trifluoromethyl)phenyl)boronic acid (350 mg, 0.79 mmol), 1-cyclopropyl-3-iodo-2,4-dimethylbenzene (240 mg, 0.88 mmol), X-Phos Pd G2 (62.1 mg, 0.08 mmol) and K₃PO₄ (503.1 mg, 2.37 mmol) in 1,4-dioxane (10 mL) and water (1 mL) was stirred at 105° C. for 1 hour under nitrogen atmosphere. The reaction mixture was cooled to room temperature, filtered through a pad of Celite and the filtrate was concentrated in vacuo. The residue was purified by silica gel column (petroleum ether: EtOAc 3:2) to provide ethyl (3S)-3-(((R)-tert-butylsulfinyl)amino)-3-(3'-cyclopropyl-2,4-difluoro-2',6'-dimethyl-5-(trifluoromethyl)-[1,1'-biphenyl]-3-yl)propanoate as a brown oil (270 mg). Yield 63% (ESI 546.2 [M+H]⁺).

Step 5: Ethyl (3S)-3-amino-3-(3'-cyclopropyl-2,4-difluoro-2',6'-dimethyl-5-(trifluoromethyl)-[1,1'-biphenyl]-3-yl)propanoate

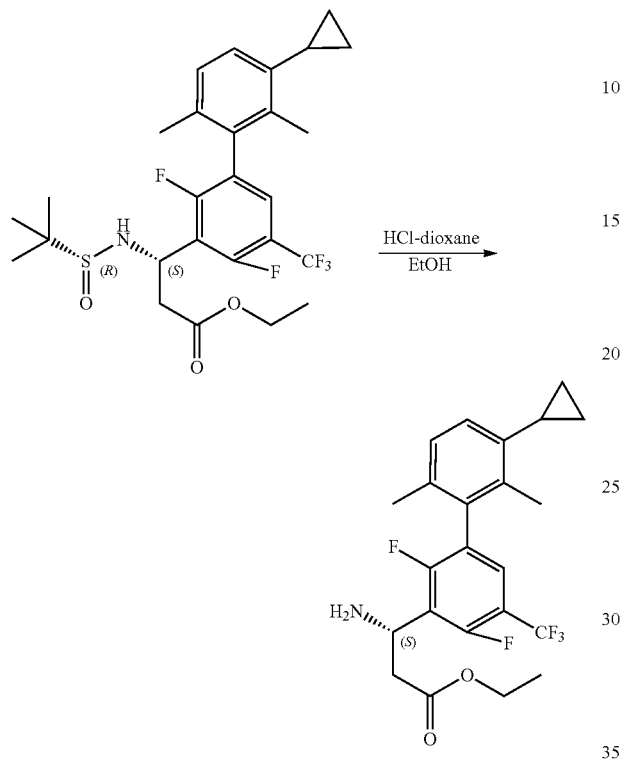

To a mixture of ethyl (3S)-3-(((R)-tert-butylsulfinyl)amino)-3-(3'-cyclopropyl-2,4-difluoro-2',6'-dimethyl-5-(trifluoromethyl)-[1,1'-biphenyl]-3-yl)propanoate (270.0 mg, 049 mmol) in EtOH (2 mL) was added HCl-dioxane (4 M, 2 mL, 8.0 mmol). The mixture was stirred at room temperature for 1 hour. The mixture was concentrated in vacuo to provide ethyl (3S)-3-amino-3-(3'-cyclopropyl-2,4-difluoro-2',6'-dimethyl-5-(trifluoromethyl)-[1,1'-biphenyl]-3-yl)propanoate as a colorless oil (210.0 mg), used without further purification. Yield 96% (ESI 442.2 [M+H]$^+$).

Preparation of (3S)-ethyl 3-amino-3-(3'-cyclopropoxy-2,4-difluoro-2',6'-dimethyl-5-(trifluoromethyl)biphenyl-3-yl)propanoate

Step 1: 2-bromo-4-cyclopropoxy-1,3-dimethylbenzene

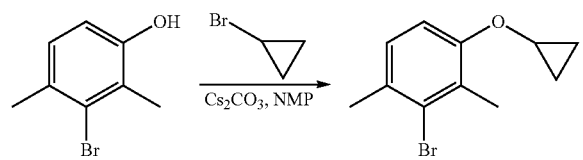

A mixture of 3-bromo-2,4-dimethylphenol (1.0 g, 4.98 mmol), bromocyclopropane (3.0 g, 24.8 mmol) and Cs$_2$CO$_3$ (4.9 g, 14.9 mmol) in NMP (20 mL) was stirred at 140° C. for 20 hours. The mixture was cooled to room temperature and poured into NH$_4$Cl (aq.) (20 mL). The solution was extracted with EtOAc (200 mL×3). The combined organic layer was washed with brine (20 mL×2), dried over anhydrous Na$_2$SO$_4$, filtered and concentrated in vacuo. The residue was purified by silica gel column (pet ether) to provide 2-bromo-4-cyclopropoxy-1,3-dimethylbenzene as a colorless oil (1.0 g). Yield 83%. $^1$H NMR (400 MHz, CDCl$_3$) δ 7.07 (d, J=8.4 Hz, 1H), 7.04 (d, J=8.6 Hz, 1H), 3.75-3.65 (m, 1H), 2.35 (s, 3H), 2.27 (s, 3H), 0.79-0.73 (m, 4H).

Step 2: (3S)-ethyl 3-(3'-cyclopropoxy-2,4-difluoro-2',6'-dimethyl-5-(trifluoromethyl)biphenyl-3-yl)-3-((R)-1,1-dimethylethylsulfinamido)propanoate

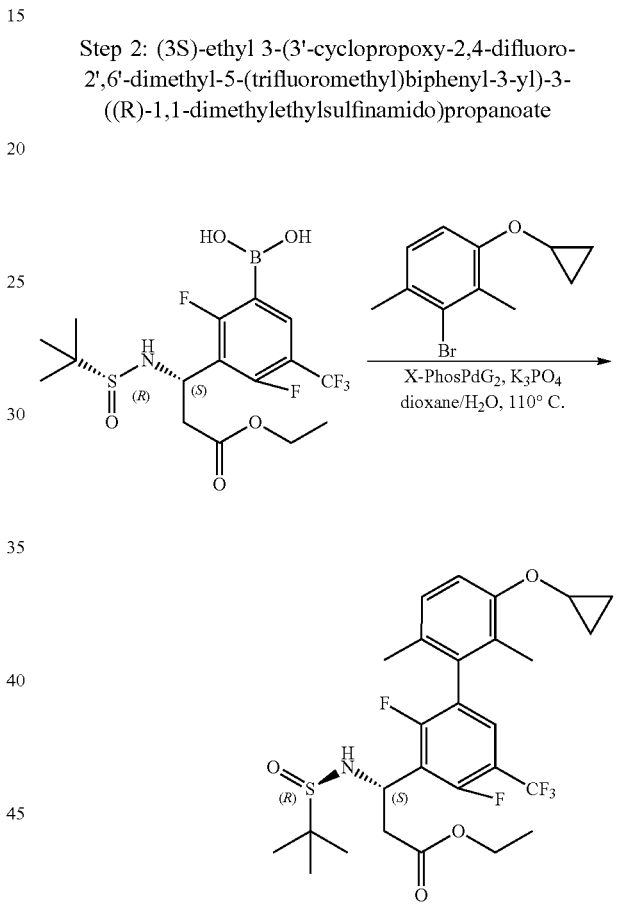

To a mixture of 3-((S)-1-((R)-1,1-dimethylethylsulfinamido)-3-ethoxy-3-oxopropyl)-2,4-difluoro-5-(trifluoromethyl)phenylboronic acid (400 mg, 0.9 mmol), 2-bromo-4-cyclopropoxy-1,3-dimethylbenzene (260 mg, 1.1 mmol) and K$_3$PO$_4$ (636 mg, 3.0 mmol) in dioxane (5 mL) and H$_2$O (0.5 mL) was added X-Phos Pd G2 (79 mg, 0.1 mmol). The mixture was heated to 110° C. for 1 hr under nitrogen atmosphere. Water (10 mL) was added and the solution was extracted with EtOAc (20 mL×3). The combined organic phases were concentrated in vacuo and the residue was purified by silica gel column (pet ether:EtOAc 2:1) to provide (3S)-ethyl 3-(3'-cyclopropoxy-2,4-difluoro-2',6'-dimethyl-5-(trifluoromethyl)biphenyl-3-yl)-3-((R)-1,1-dimethylethylsulfinamido)propanoate as a dark solid (300 mg). Yield 59% (ESI 562.1 [M+H]$^+$).

245

Step 3: (3S)-ethyl 3-amino-3-(3'-cyclopropoxy-2,4-difluoro-2',6'-dimethyl-5-(trifluoromethyl)biphenyl-3-yl)propanoate

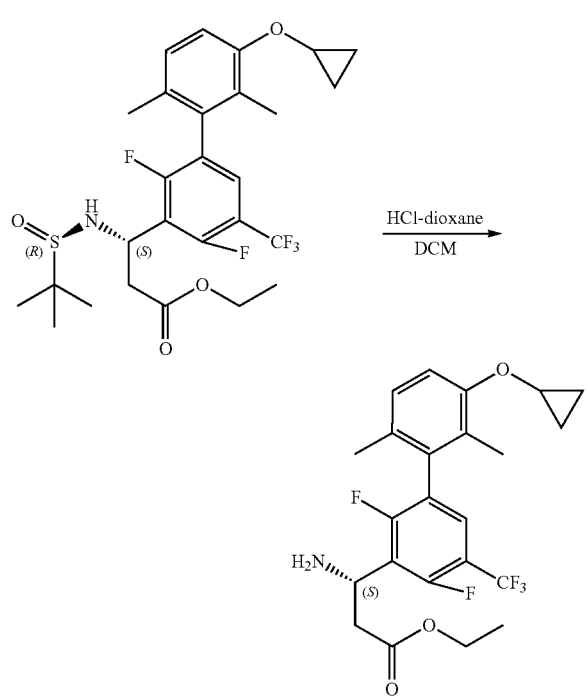

To a mixture of (3S)-ethyl 3-(3'-cyclopropoxy-2,4-difluoro-2',6'-dimethyl-5-(trifluoromethyl)biphenyl-3-yl)-3-((R)-1,1-dimethylethylsulfinamido)propanoate (300 mg, 0.53 mmol) in DCM (1 mL) was added 4M HCl-dioxane (0.5 mL, 2.0 mmol). The mixture was stirred at rt for 0.5 hr. The mixture was concentrated in vacuo and the residue was purified by reverse phase on a C18/120 g column (A: water 10 mM $NH_4HCO_3$, B: $CH_3CN$, 0~100%) to provide (3S)-ethyl 3-amino-3-(3'-cyclopropoxy-2,4-difluoro-2',6'-dimethyl-5-(trifluoromethyl)biphenyl-3-yl)propanoate as a colorless oil (150 mg). Yield 62% (ESI 458.1 [M+H]$^+$).

Preparation of Ethyl (S)-3-amino-3-(2,4-difluoro-2',6'-dimethyl-4',5-bis(trifluoromethyl)-[1,1'-biphenyl]-3-yl)propanoate Step 1: Ethyl (S)-3-(((R)-tert-butylsulfinyl)amino)-3-(2,4-difluoro-2',6'-dimethyl-4',5-bis(trifluoromethyl)-[1,1'-biphenyl]-3-yl)propanoate

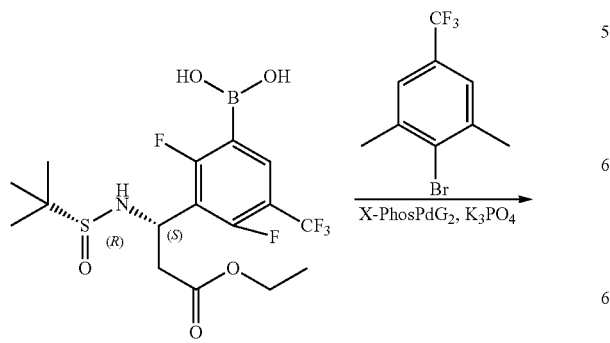

246

-continued

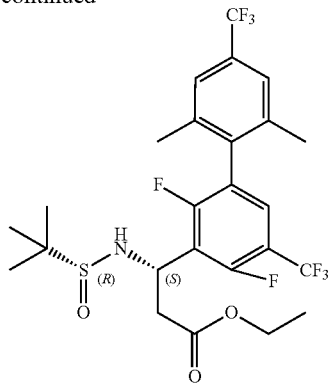

A mixture of (3-((S)-1-(((R)-tert-butylsulfinyl)amino)-3-ethoxy-3-oxopropyl)-2,4-difluoro-5-(trifluoromethyl)phenyl)boronic acid (900 mg, 2.0 mmol), $K_3PO_4$ (1.06 g, 5.0 mmol), X-Phos Pd G2 (157 mg, 0.2 mmol) and 2-bromo-1,3-dimethyl-5-(trifluoromethyl)benzene (607 mg, 2.4 mmol) in dioxane (20 mL) and $H_2O$ (2 mL) was stirred at 100° C. under nitrogen atmosphere for 2 hours. The reaction mixture was poured into 50 mL of water and extracted with EtOAc (50×3 mL×3). The combined organic layers were washed with brine (100 mL), dried over anhydrous $Na_2SO_4$, filtered and the filtrate was concentrated in vacuo. The residue was purified by silica gel column (pet ether:EtOAc 3:2) to provide ethyl (S)-3-(((R)-tert-butylsulfinyl)amino)-3-(2,4-difluoro-2',6'-dimethyl-4',5-bis(trifluoromethyl)-[1,1'-biphenyl]-3-yl)propanoate as a yellow solid (730 mg). Yield 63.6% (ESI 574.2 (M+H)$^+$)

Step 2: Ethyl (S)-3-amino-3-(2,4-difluoro-2',6'-dimethyl-4',5-bis(trifluoromethyl)-[1,1'-biphenyl]-3-yl)propanoate

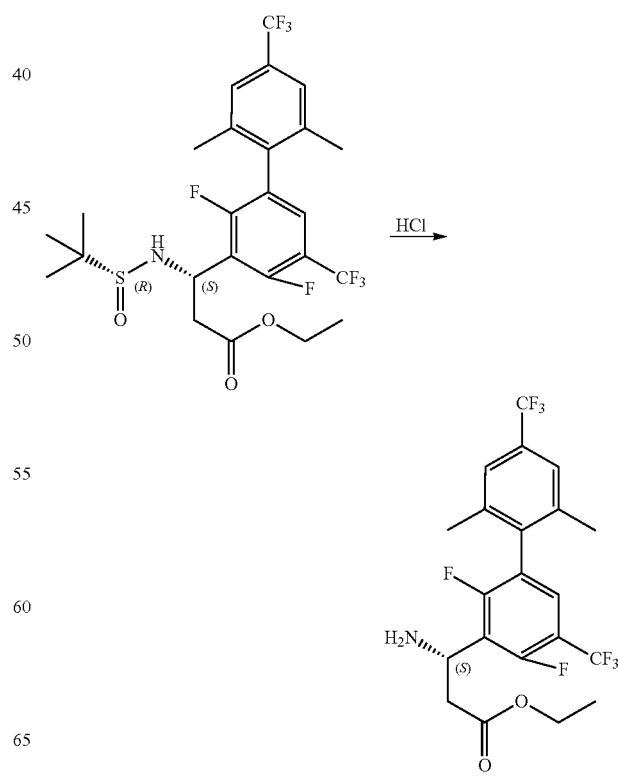

To a mixture of ethyl (S)-3-(((R)-tert-butylsulfinyl)amino)-3-(2,4-difluoro-2',6'-dimethyl-4',5-bis(trifluoromethyl)-[1,1'-biphenyl]-3-yl)propanoate (730 mg, 1.27 mmol) in DCM (4 mL) was added HCl-dioxane (4 M, 1 mL, 4.0 mmol). The mixture was stirred at room temperature for 1 hour. The mixture was concentrated in vacuo and the residue was purified by reverse phase HPLC on a C18/40 g column (A: water 10 mM $NH_4HCO_3$, B: $CH_3CN$, 0~100%) to provide ethyl (S)-3-amino-3-(2,4-difluoro-2',6'-dimethyl-4',5-bis(trifluoromethyl)-[1,1'-biphenyl]-3-yl)propanoate (280 mg). Yield 47% (ESI 470.0 $[M+H]^+$).

Preparation of Ethyl (S)-3-(3-bromo-5-cyclopropyl-2,6-difluorophenyl)-3-(((R)-tert-butylsulfinyl)amino)propanoate Step 1: 5-cyclopropyl-2,4-difluoroaniline

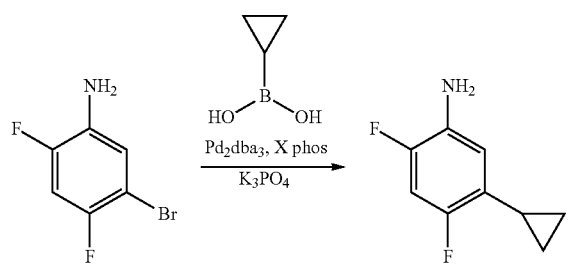

To a solution of 5-bromo-2,4-difluoroaniline (15.0 g, 72.1 mmol) in Toluene (50 mL) and $H_2O$ (55 mL) under nitrogen atmosphere at room temperature was added X-phos (1.7 g, 3.6 mmol), $Pd_2dba_3$ (3.3 g, 3.6 mmol), cyclopropylboronic acid (12.4 g, 144.2 mmol) and $K_3PO_4$ (30.9 g, 144.2 mmol) and stirred at 100° C. for 16 hours under nitrogen atmosphere. The reaction was filtered and washed with EtOAc (50 mL). The filtrate was concentrated in vacuo and the residue was purified by silica gel column (pet ether:EtOAc 10:1) to provide 5-cyclopropyl-2,4-difluoroaniline as white solids (12.0 g). Yield 92% (ESI 170.2 $(M+H)^+$).

Step 2: 1-bromo-5-cyclopropyl-2,4-difluorobenzene

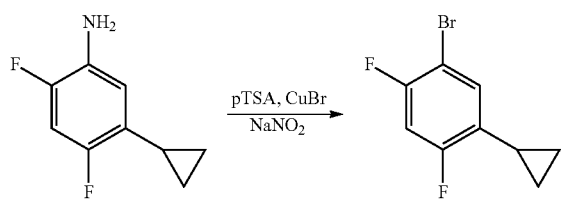

To a mixture of 5-cyclopropyl-2,4-difluoroaniline (12.0 g, 71.0 mmol) and CuBr (25.5 g, 177.5 mmol) in ACN (200 mL) and $H_2O$ (40 mL) at 0° C. was added p-Toluenesulfonic acid (54.0 g, 284.0 mmol) and then stirred for 1 hour. To the mixture was added a solution of $NaNO_2$ (7.3 g, 106.5 mmol) in $H_2O$ (20 mL) dropwise. The mixture was extracted with EtOAc (80 mL×3). The organic layer was washed with brine, dried over $Na_2SO_4$, filtered and concentrated in vacuo. The residue was purified by silica gel column (pet ether) to provide 1-bromo-5-cyclopropyl-2,4-difluorobenzene (7.0 g, yield: 42%) as a colorless oil.

Step 3: 3-bromo-5-cyclopropyl-2,6-difluorobenzaldehyde

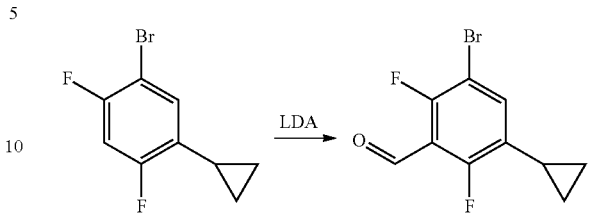

To a solution of 1-bromo-5-cyclopropyl-2,4-difluorobenzene(7.0 g, 30.0 mmol) in THF (50 mL) at −78° C. was added LDA (22.6 mL, 45.2 mmol) dropwise and stirred at −78° C. for 1 h. Then DMF (5 mL) was added dropwise and stirred at −78° C. for another 1 h. The reaction mixture was warmed to r.t. and quenched with saturated $NH_4Cl$ (20 mL) aqeuous solution and stirred at room temperature for 30 mins. The mixture was extracted with EtOAc(100 mL×3). The organic layer was washed with brine, dried over $Na_2SO_4$, filtered and concentrated in vacuo to provide 3-bromo-5-cyclopropyl-2,6-difluorobenzaldehyde as a yellow oil without further purification (6.5 g, yield: 88%).

Step 4: (R,E)-N-(3-bromo-5-cyclopropyl-2,6-difluorobenzylidene)-2-methylpropane-2-sulfinamide

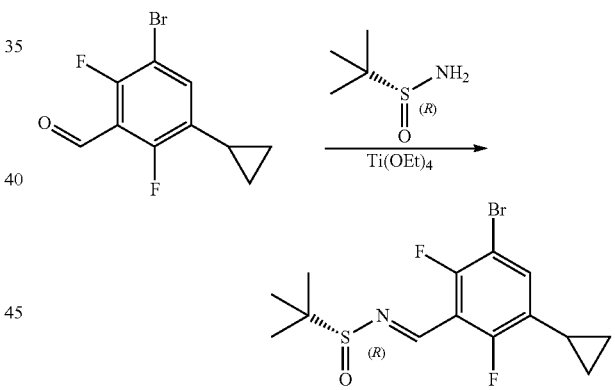

To a mixture of 3-bromo-5-cyclopropyl-2,6-difluorobenzaldehyde (7.3 g, 29.4 mmol) and (R)-2-methylpropane-2-sulfinamide (4.3 g, 35.3 mmol) in anhydrous THE (50 mL) under nitrogen atmosphere was added Ti(OEt)$_4$ (10.0 g, 44.1 mmol) dropwise at room temperature. During which the temperature was maintained below 30° C. The reaction mixture was stirred at room temperature for 1 hour under nitrogen atmosphere. Water (100 mL) and EtOAc (100 mL) was added into the mixture and stirred at room temperature for 5 mins. The mixture was filtered and washed with EtOAc (50 mL). The organic layer was washed with water (50 mL) and brine (50 mL), dried over anhydrous $Na_2SO_4$, filtered and concentrated in vacuo. The residue was purified by silica gel column (pet ether:EtOAc 5:1) to provide (R,E)-N-(3-bromo-5-cyclopropyl-2,6-difluorobenzylidene)-2-methylpropane-2-sulfinamide as a yellow oil (6.3 g). Yield 61% (ESI 364.0 $(M+H)^+$, 366.0 $(M+2+H)^+$).

Step 5: Ethyl (S)-3-(3-bromo-5-cyclopropyl-2,6-difluorophenyl)-3-(((R)-tert-butylsulfinyl)amino)propanoate

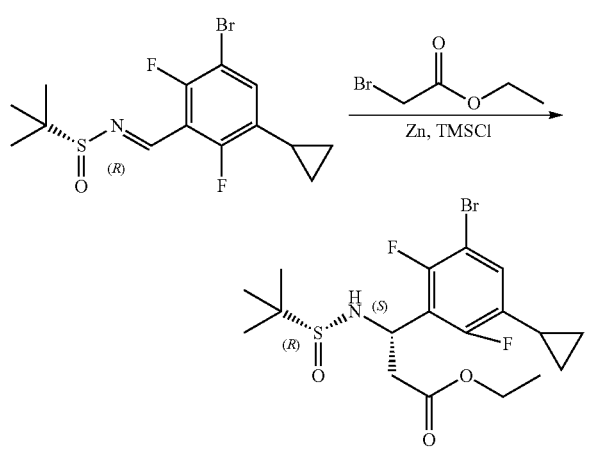

To a mixture of Zn (10.0 g, 149.3 mmol) in anhydrous THF (100 mL) under nitrogen atmosphere was added chlorotrimethylsilane (1.0 g, 9.8 mmol) dropwise at room temperature. The mixture was stirred at 50° C. for 1 hour under nitrogen atmosphere. This mixture was then cooled to 20-30° C. Ethyl 2-bromoacetate (12.4 g, 74.3 mmol) was added dropwise at room temperature and the mixture was stirred at 50° C. for 1 hour under nitrogen atmosphere. The reaction mixture was cooled to room temperature. A solution of (R,E)-N-(3-bromo-5-cyclopropyl-2,6-difluorobenzylidene)-2-methylpropane-2-sulfinamide (9.0 g, 24.7 mmol) in anhydrous THF (10 mL) was added dropwise into the mixture at room temperature and the mixture was stirred at room temperature for 1 hour. Water (100 mL) and EtOAc (100 mL) was added into the mixture and stirred at room temperature for 5 mins. The mixture was filtered and washed with EtOAc (100 mL×2). The organic layer was washed with water (100 mL) and brine (100 mL), dried over anhydrous Na$_2$SO$_4$, filtered and the filtrate was concentrated in vacuo. The residue was purified by silica gel column (pet ether:EtOAc 2:1) to provide ethyl (S)-3-(3-bromo-5-cyclopropyl-2,6-difluorophenyl)-3-(((R)-tert-butylsulfinyl)amino)propanoate as a colorless oil (7.1 g). Yield 78% (ESI 452.0 (M+H)$^+$, 454.0 (M+2++H)$^+$).

Preparation of Ethyl (S)-3-amino-3-(5-cyclopropyl-2,4-difluoro-2',6'-dimethyl-[1,1'-biphenyl]-3-yl)propanoate

Step 1: Ethyl (S)-3-(((R)-tert-butylsulfinyl)amino)-3-(5-cyclopropyl-2,4-difluoro-2',6'-dimethyl-[1,1'-biphenyl]-3-yl)propanoate

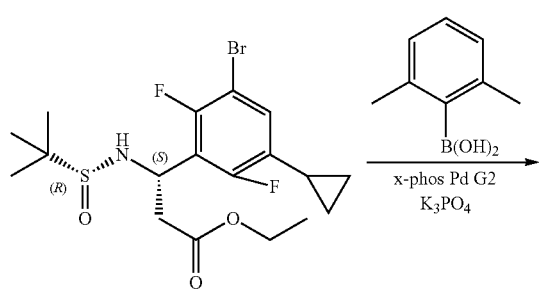

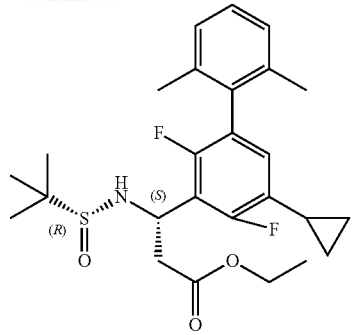

A mixture of ethyl (S)-3-(3-bromo-5-cyclopropyl-2,6-difluorophenyl)-3-(((R)-tert-butylsulfinyl)amino)propanoate (800.0 mg, 1.77 mmol), (2,6-dimethylphenyl)boronic acid (380.0 mg, 2.3 mmol), X-Phos Pd G2 (133.0 mg, 0.17 mmol) and K$_3$PO$_4$ (1.1 g, 5.31 mmol) in Toluene (7 mL) and H$_2$O (0.7 mL) was stirred at 100° C. for 4 hours under a nitrogen atmosphere. The reaction was concentrated in vacuo and the residue purified by silica gel column (pet ether:EtOAc=3:1) to provide ethyl (S)-3-(((R)-tert-butylsulfinyl)amino)-3-(5-cyclopropyl-2,4-difluoro-2',6'-dimethyl-[1,1'-biphenyl]-3-yl)propanoate (700.0 mg, Yield 83%) as a light yellow foam (ESI 478.2 [M+H]$^+$).

Step 2: Ethyl (S)-3-amino-3-(5-cyclopropyl-2,4-difluoro-2',6'-dimethyl-[1,1'-biphenyl]-3-yl)propanoate

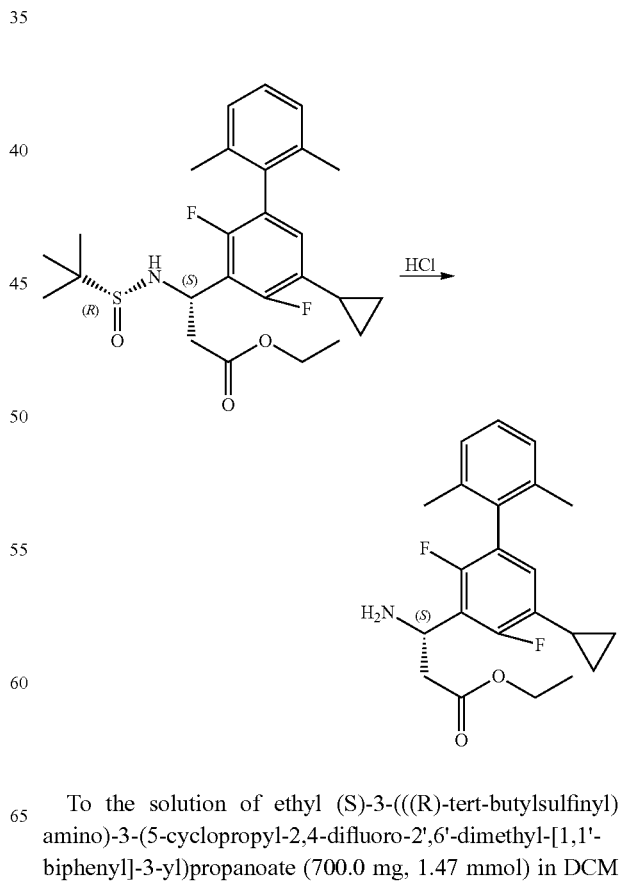

To the solution of ethyl (S)-3-(((R)-tert-butylsulfinyl)amino)-3-(5-cyclopropyl-2,4-difluoro-2',6'-dimethyl-[1,1'-biphenyl]-3-yl)propanoate (700.0 mg, 1.47 mmol) in DCM (8 mL) was added HCl-dioxane (4M, 1.9 mL, 7.6 mmol) and stirred at room temperature for 1 hour. The mixture was concentrated in vacuo and the residue was purified by reverse phase HPLC on a C18/120 g column (A: water/ 0.01% TFA, B: MeOH, 0~100%) to provide ethyl (S)-3-amino-3-(5-cyclopropyl-2,4-difluoro-2',6'-dimethyl-[1,1'-biphenyl]-3-yl)propanoate hydrochloride as a yellow solid (500 mg). Yield 91% (ESI 374.2 (M+H)$^+$).

Preparation of Ethyl (S)-3-amino-3-(5-cyclopropyl-2,4-difluoro-2',4',6'-trimethyl-[1,1'-biphenyl]-3-yl)propanoate Step 1: (S)-ethyl 3-(5-cyclopropyl-2,4-difluoro-2',4',6'-trimethylbiphenyl-3-yl)-3-((R)-1,1-dimethylethylsulfinamido)propanoate

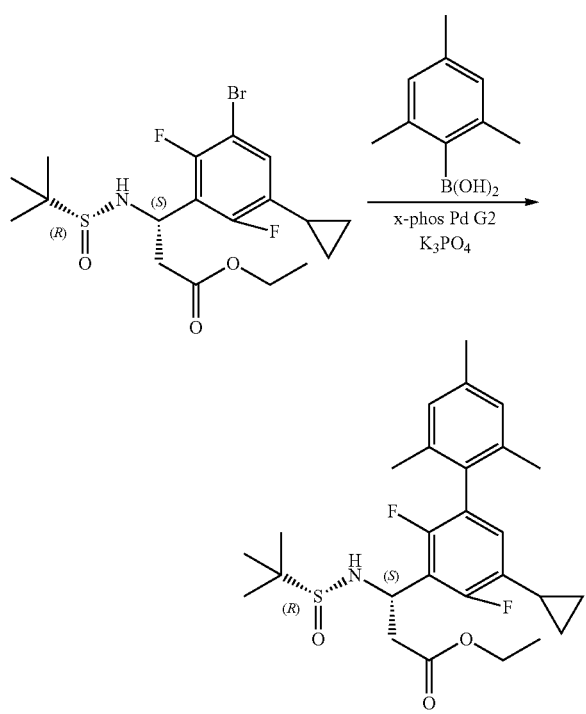

To a mixture of (S)-ethyl 3-(3-bromo-5-cyclopropyl-2,6-difluorophenyl)-3-((R)-1,1-dimethylethylsulfinamido)propanoate (600 mg, 1.3 mmol), mesitylboronic acid (246 mg, 1.5 mmol) and K$_3$PO$_4$ (848 mg, 43.0 mmol) in dioxane (10 mL) and H$_2$O (1 mL) was added X-Phos Pd G2 (79 mg, 0.1 mmol). The mixture was heated to 110° C. for 2 hrs under a nitrogen atmosphere. Water (20 mL) was added and the solution was extracted with EtOAc (20 mL×3). The combined organic phases were concentrated in vacuo and the residue was purified by silica gel column (pet ether:EtOAc 2:1) to provide (S)-ethyl 3-(5-cyclopropyl-2,4-difluoro-2',4',6'-trimethylbiphenyl-3-yl)-3-((R)-1,1-dimethylethylsulfinamido)propanoate as a dark solid (400 mg). Yield 80% (ESI 492.1 [M−100+]$^+$).

Step 2: Ethyl (S)-3-amino-3-(5-cyclopropyl-2,4-difluoro-2',4',6'-trimethyl-[1,1'-biphenyl]-3-yl)propanoate

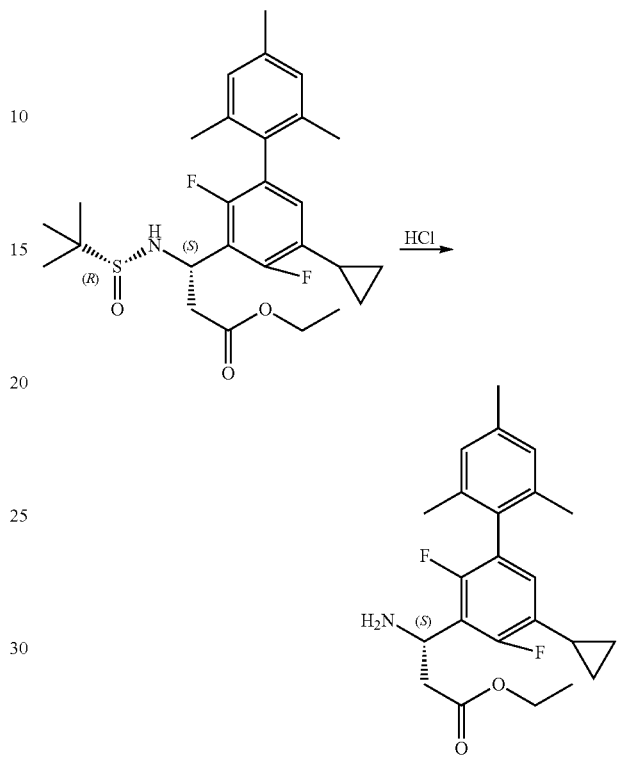

To a mixture of (S)-ethyl 3-(5-cyclopropyl-2,4-difluoro-2',4',6'-trimethylbiphenyl-3-yl)-3-((R)-1,1-dimethylethylsulfinamido)propanoate (550 mg, 1.12 mmol) in DCM (1 mL) and EtOH (2 mL) was added 4M HCl-dioxane (2 mL, 5.0 mmol) and the mixture was stirred at rt for 0.5 hr. Then the mixture was concentrated in vacuo to provide ethyl (S)-3-amino-3-(5-cyclopropyl-2,4-difluoro-2',4',6'-trimethyl-[1,1'-biphenyl]-3-yl)propanoate as a yellow oil (360 mg, crude) used directly in the next reaction. (ESI 388.1 (M+H)$^+$).

Preparation of Ethyl (S)-3-amino-3-(5-cyclopropyl-2,4,4'-trifluoro-2',6'-dimethyl-[1,1'-biphenyl]-3-yl)propanoate Step 1: Ethyl (S)-3-(((R)-tert-butylsulfinyl)amino)-3-(5-cyclopropyl-2,4,4'-trifluoro-2',6'-dimethyl-[1,1'-biphenyl]-3-yl)propanoate

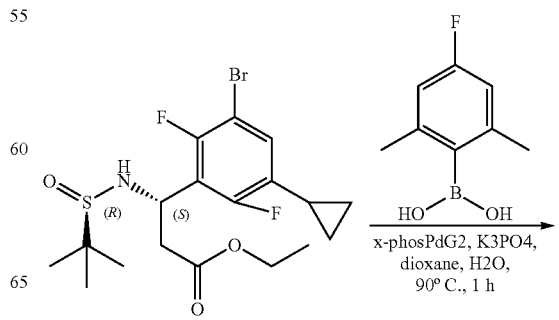

-continued

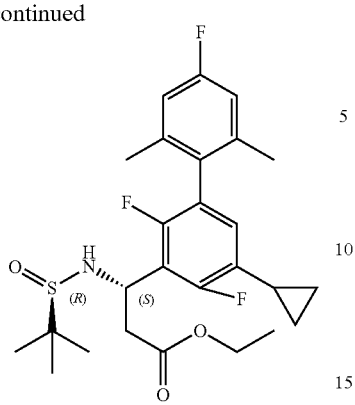

To a mixture of ethyl (S)-3-(3-bromo-5-cyclopropyl-2,6-difluorophenyl)-3-(((R)-tert-butylsulfinyl)amino)propanoate (700 mg, 1.55 mmol), 4-fluoro-2,6-dimethylphenylboronic acid (260 mg, 1.55 mmol), and K$_3$PO$_4$ (657 mg, 3.1 mmol) in 1,4-dioxane (5 mL) and water (0.5 mL) was added X-Phos Pd G2 (117 mg, 0.16 mmol). The mixture was stirred at 90° C. for 1 hour. The solvent was concentrated in vacuo and the residue was purified by silica gel column (petroleum ether:EtOAc 5:1) to provide ethyl (S)-3-(((R)-tert-butylsulfinyl)amino)-3-(5-cyclopropyl-2,4,4'-trifluoro-2',6'-dimethyl-[1,1'-biphenyl]-3-yl)propanoate as a pale yellow oil (420.0 mg). Yield 54.6% (ESI 496.2 (M+H)$^+$).

Step 2: Ethyl (S)-3-amino-3-(5-cyclopropyl-2,4,4'-trifluoro-2',6'-dimethyl-[1,1'-biphenyl]-3-yl)propanoate

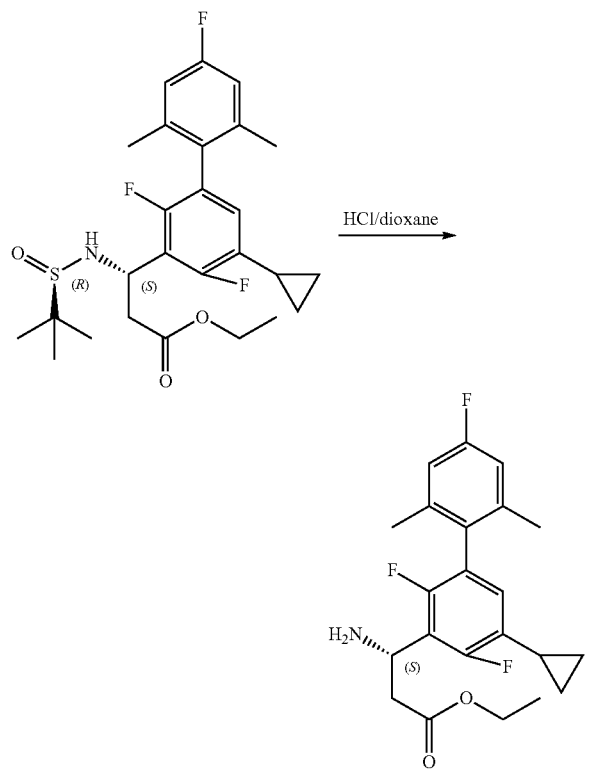

A mixture of ethyl (S)-3-(((R)-tert-butylsulfinyl)amino)-3-(5-cyclopropyl-2,4,4'-trifluoro-2',6'-dimethyl-[1,1'-biphenyl]-3-yl)propanoate (420 mg, 0.85 mmol) in HCl-dioxane (4 M, 3 mL, 12 mmol) was stirred at room temperature for 1 hour. The mixture was concentrated in vacuo to provide ethyl (S)-ethyl 3-amino-3-(5-cyclopropyl-2,4,4'-trifluoro-2',6'-dimethylbiphenyl-3-yl)propanoate as a colorless oil (290 mg) used without further purification. Yield 87.4% (ESI 392.1 [M+H]$^+$).

Preparation of Ethyl (3S)-3-amino-3-(5-cyclopropyl-2,3',4-trifluoro-2',6'-dimethyl-[1,1'-biphenyl]-3-yl)propanoate Step 1: Ethyl (S)-3-(((R)-tert-butylsulfinyl)amino)-3-(3-cyclopropyl-2,6-difluoro-5-(4,4,5,5-tetramethyl-1,3,2-dioxaborolan-2-yl)phenyl)propanoate

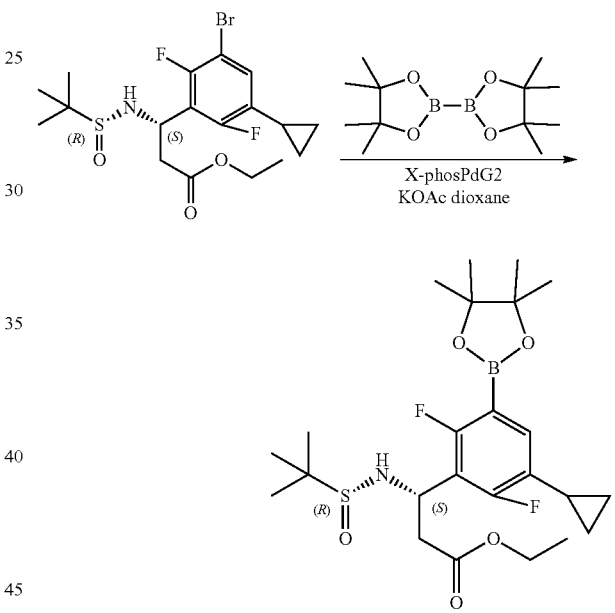

A mixture of ethyl (S)-3-(3-bromo-5-cyclopropyl-2,6-difluorophenyl)-3-(((R)-tert-butylsulfinyl)amino)propanoate (800 mg, 1.8 mmol), KOAc (529 mg, 5.4 mmol), Xphos-PdG$_2$ (142 mg, 0.18 mmol) and 4,4,4',4',5,5,5',5'-octamethyl-2,2'-bi(1,3,2-dioxaborolane) (686 mg, 2.7 mmol) in dioxane (10 mL) was stirred at 110° C. for 2 hours under a nitrogen atmosphere. The reaction mixture was poured into 15 mL of water and extracted with EtOAc (15×3 mL×3). The combined organic layers were washed with brine (5 mL), dried over anhydrous Na$_2$SO$_4$, filtered and the filtrate was concentrated in vacuo. The residue was purified by silica gel column (pet ether:EtOAc 3:1) to provide ethyl (S)-3-(((R)-tert-butylsulfinyl)amino)-3-(3-cyclopropyl-2,6-difluoro-5-(4,4,5,5-tetramethyl-1,3,2-dioxaborolan-2-yl)phenyl)propanoate as a colorless oil (500 mg). Yield 56% (ESI 500.2 (M+H)$^+$)

Step 2: Ethyl (3S)-3-(((R)-tert-butylsulfinyl)amino)-3-(5-cyclopropyl-2,3',4-trifluoro-2',6'-dimethyl-[1,1'-biphenyl]-3-yl)propanoate

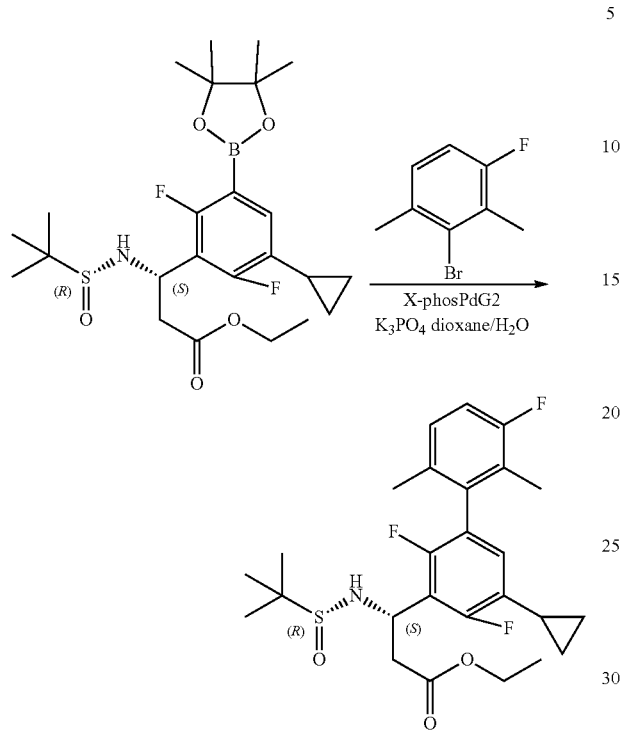

A mixture of ethyl (S)-3-(((R)-tert-butylsulfinyl)amino)-3-(3-cyclopropyl-2,6-difluoro-5-(4,4,5,5-tetramethyl-1,3,2-dioxaborolan-2-yl)phenyl)propanoate (500 mg, 1.0 mmol), K₃PO₄ (636 mg, 3.0 mmol), Xphos-PdG₂ (78.7 mg, 0.1 mmol) and 2-bromo-4-fluoro-1,3-dimethylbenzene (263 mg, 1.3 mmol) in dioxane (10 mL) and H₂O (1 mL) was stirred at 110° C. for 2 hours under a nitrogen atmosphere. The reaction mixture was poured into 15 mL of water and extracted with EtOAc (15×3 mL×3). The combined organic layers were washed with brine (5 mL), dried over anhydrous Na₂SO₄, filtered and the filtrate was concentrated in vacuo. The residue was purified by silica gel column (pet ether: EtOAc 3:1) to provide ethyl (3S)-3-(((R)-tert-butylsulfinyl)amino)-3-(5-cyclopropyl-2,3',4-trifluoro-2',6'-dimethyl-[1,1'-biphenyl]-3-yl)propanoate as a colorless oil (200 mg). Yield 40% (ESI 496.2 (M+H)⁺)

Step 3: Ethyl (3S)-3-amino-3-(5-cyclopropyl-2,3',4-trifluoro-2',6'-dimethyl-[1,1'-biphenyl]-3-yl)propanoate

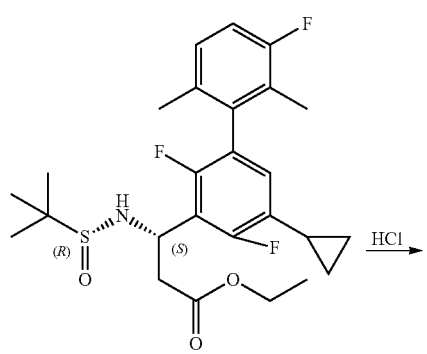

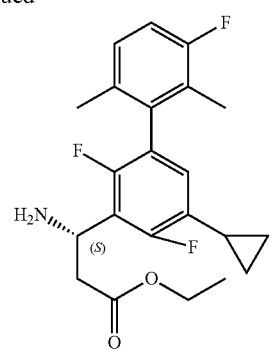

To a mixture of ethyl (3S)-3-(((R)-tert-butylsulfinyl)amino)-3-(5-cyclopropyl-2,3',4-trifluoro-2',6'-dimethyl-[1,1'-biphenyl]-3-yl)propanoate (200 mg, 0.4 mmol) in EtOH (2 mL) was added HCl-dioxane (4 M, 2 mL, 8.0 mmol). The mixture was stirred at room temperature for 1 hour. The mixture was concentrated in vacuo and the residue was purified by reverse phase HPLC on a C18/40 g column (A: water/0.01% TFA, B: MeOH, 0~100%) to provide ethyl (3S)-3-amino-3-(5-cyclopropyl-2,3',4-trifluoro-2',6'-dimethyl-[1,1'-biphenyl]-3-yl)propanoate oil (120 mg). Yield 76% (ESI 392.2 [M+H]⁺).

Example 2B. Preparation of Intermediates

Preparation of 2-(5-((dimethylamino)methyl)-2-oxopyridin-1(2H)-yl)-4-methylpentanoic acid Step 1: 5-((dimethylamino)methyl)pyridin-2(1H)-one

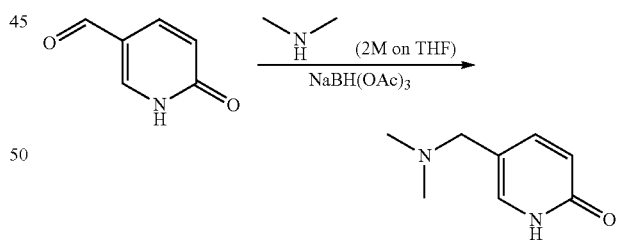

A mixture of 6-oxo-1,6-dihydropyridine-3-carbaldehyde (2 g, 16.2 mmol), dimethylamine (2M in THF, 4 mL) in DCM (10 mL) was stirred at room temperature for 30 mins. Then NaBH(OAc)₃ (5.2 g, 24.39 mmol) was added portionwise and stirred at room temperature overnight. The solvent was concentrated in vacuo and the residue purified by reverse phase HPLC (Eluent A: water 10 mM NH₄HCO₃, Eluent B: MeOH, gradient A→B 0~100%) to provide 5-((dimethylamino)methyl)pyridin-2(1H)-one as a yellow oil (1 g). Yield 41% (ESI 153 (M+H)⁺).

Step 2: Ethyl 2-(5-((dimethylamino)methyl)-2-oxopyridin-1(2H)-yl)-4-methylpentanoate

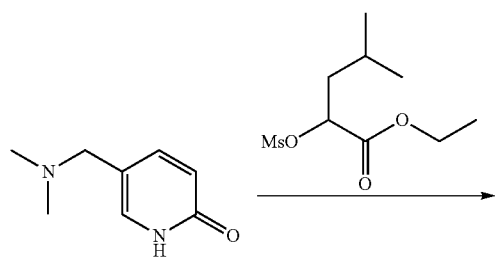

A mixture of 5-((dimethylamino)methyl)pyridin-2(1H)-one (500 mg, 3.28 mmol), $K_2CO_3$ (1.36 g, 9.86 mmol) and ethyl 4-methyl-2-(methylsulfonyloxy)pentanoate (1.17 g, 4.93 mmol) in $CH_3CN$ (20 mL) was stirred at 70° C. overnight. The solvent was concentrated in vacuo and the residue was purified by silica gel column (pet ether:EtOAc 1:2) to provide ethyl 2-(5-((dimethylamino)methyl)-2-oxopyridin-1(2H)-yl)-4-methylpentanoate as a yellow oil (300 mg). Yield 31% (ESI 295 $(M+H)^+$).

Step 3: 2-(5-((dimethylamino)methyl)-2-oxopyridin-1(2H)-yl)-4-methylpentanoic Acid

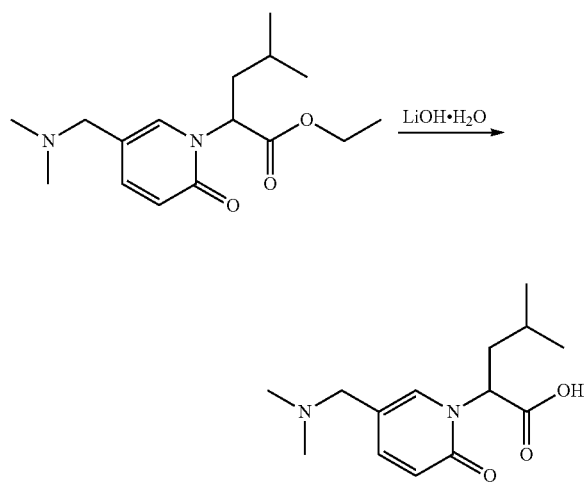

Ethyl 2-(5-((dimethylamino)methyl)-2-oxopyridin-1(2H)-yl)-4-methylpentanoate (300 mg, 1.02 mmol) was treated with $LiOH-H_2O$ (120 mg, 3.02 mmol) in methanol (2 mL) and water (1 mL) at room temperature for 2 hours. The reaction was acidified with 1N HCl to pH=3. The solvent was removed in vacuo and the residue was purified by preparatory-HPLC A conditions (30-80% MeCN) to provide 2-(5-((dimethylamino)methyl)-2-oxopyridin-1(2H)-yl)-4-methylpentanoic acid as a white solid (100 mg). Yield 37% (ESI 267 $(M+H)^+$).

Preparation of 2-(4-((dimethylamino)methyl)-2-oxopyridin-1(2H)-yl)-4-methylpentanoic acid

Step 1: 2-oxo-2,3-dihydropyridine-4-carbaldehyde

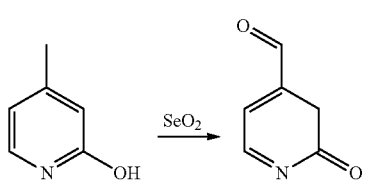

A mixture of 4-methylpyridin-2-ol (3 g, 27.5 mmol) and $SeO_2$ (4 g, 35.8 mmol) in dioxane (40 mL) was refluxed under $N_2$ atmosphere overnight and filtered. The filtrate was removed in vacuo and the residue was purified by silica gel column (DCM:MeOH=1:10) to provide 2-oxo-2,3-dihydropyridine-4-carbaldehyde as a yellow oil (300 mg). Yield 9% (ESI 124 $(M+H)^+$)

Step 2: 4-((dimethylamino)methyl)pyridin-2(1H)-one

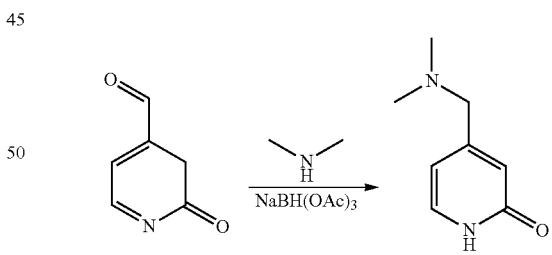

A mixture of 2-oxo-2,3-dihydropyridine-4-carbaldehyde (300 mg, 2.4 mmol), dimethylamine (2M in THF, 6 mL) in DCM (5 mL) was stirred at room temperature for 30 minutes. $NaBH(OAc)_3$ (775.6 mg, 3.65 mmol) was added portion-wise and stirred at room temperature overnight. The solvent was concentrated in vacuo and the residue was purified by reverse phase HPLC (Eluent A: water 10 mM $NH_4HCO_3$, Eluent B: MeOH, gradient A→B 0~100%) to provide 4-((dimethylamino)methyl)pyridin-2(1H)-one as a yellow oil (150 mg). Yield 41% (ESI 153 $(M+H)^+$).

Step 3: Ethyl 2-(4-((dimethylamino)methyl)-2-oxopyridin-1(2H)-yl)-4-methylpentanoate

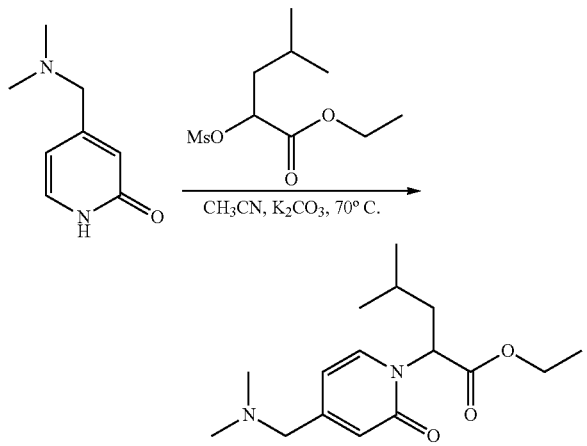

A mixture of 4-((dimethylamino)methyl)pyridin-2(1H)-one (150 mg, 0.98 mmol), K$_2$CO$_3$ (409 mg, 2.96 mmol) and ethyl 4-methyl-2-(methylsulfonyloxy)pentanoate (350 mg, 1.47 mmol) in CH$_3$CN (5 mL) was stirred at 70° C. overnight. The solvent was concentrated in vacuo and the residue was purified by silica gel column (pet ether:EtOAc 1:2) to provide ethyl 2-(4-((dimethylamino)methyl)-2-oxopyridin-1(2H)-yl)-4-methylpentanoate as a yellow oil (100 mg). Yield 35% (ESI 295 (M+H)$^+$).

Step 4: 2-(4-((dimethylamino)methyl)-2-oxopyridin-1(2H)-yl)-4-methylpentanoic Acid

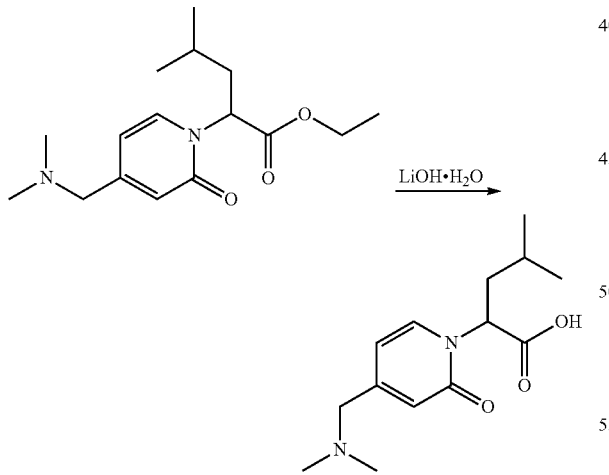

Ethyl 2-(4-((dimethylamino)methyl)-2-oxopyridin-1(2H)-yl)-4-methylpentanoate (100 mg, 0.33 mmol) was treated with LiOH—H$_2$O (40 mg, 1.01 mmol) in methanol (2 mL) and water (1 mL) at room temperature for 2 hours. The solvent was removed in vacuo and the residue was purified by preparatory-HPLC A (30-80% MeCN) to provide 2-(4-((dimethylamino)methyl)-2-oxopyridin-1(2H)-yl)-4-methylpentanoic acid as a white solid (80 mg). Yield 90% (ESI 267 (M+H)$^+$).

Preparation of Acid 3: 2-(5-((3,3-difluoroazetidine-1-yl)methyl)-2-oxopyridin-1(2H)-yl)-4-methylpentanoic Acid

Step 1: 5-((3,3-difluoroazetidine-1-yl)methyl)pyridin-2(1H)-one

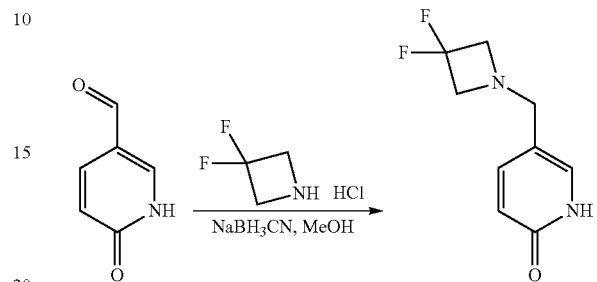

A mixture of 6-oxo-1,6-dihydropyridine-3-carbaldehyde (153 mg, 1.24 mmol) and 3,3-difluoroazetidine hydrochloride (193 mg, 1.49 mmol) in MeOH (3 mL) was stirred at room temperature for 30 mins. NaBH$_3$CN (231 mg, 3.73 mmol) was added and stirred at room temperature for 1 hour. The solvent was removed in vacuo to provide the crude 5-((3,3-difluoroazetidine-1-yl)methyl)pyridin-2(1H)-one as white solid (248 mg) used without further purification. (ESI 201.1 (M+H)$^+$).

Step 2: Ethyl 2-(5-((3,3-difluoroazetidine-1-yl)methyl)-2-oxopyridin-1(2H)-yl)-4-methylpentanoate

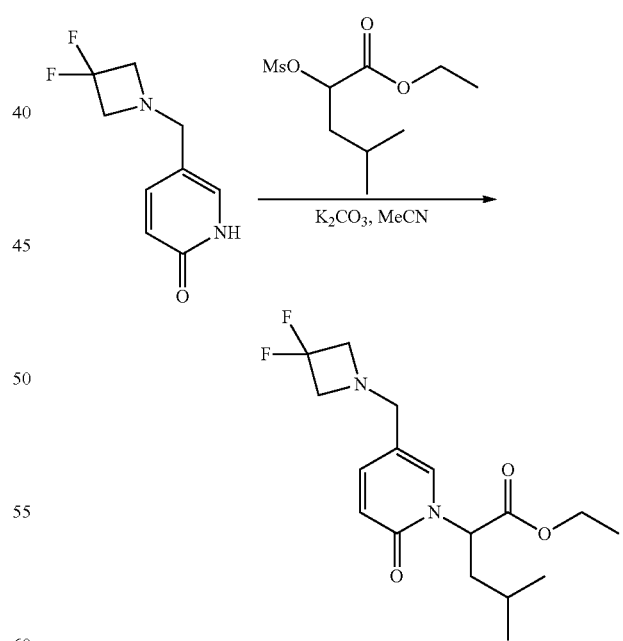

A mixture of 5-((3,3-difluoroazetidine-1-yl)methyl)pyridin-2(1H)-one (248 mg, 1.24 mmol), ethyl 4-methyl-2-(methylsulfonyloxy)pentanoate (443 mg, 1.86 mmol) and K$_2$CO$_3$ (514 mg, 3.72 mmol) in MeCN (5 mL) was stirred at 80° C. overnight. The mixture was filtered and washed with MeCN (5 mL). The filtrate was concentrated in vacuo and the residue was purified by silica gel column (petroleum ether:EtOAc 2:1) to provide ethyl 2-(5-((3,3-difluoroazetidine-1-yl)methyl)-2-oxopyridin-1(2H)-yl)-4-methylpentanoate as a colorless oil (150 mg). Yield 36% (ESI 343.1 (M+H)⁺).

Step 3: 2-(5-((3,3-difluoroazetidine-1-yl)methyl)-2-oxopyridin-1(2H)-yl)-4-methylpentanoic acid

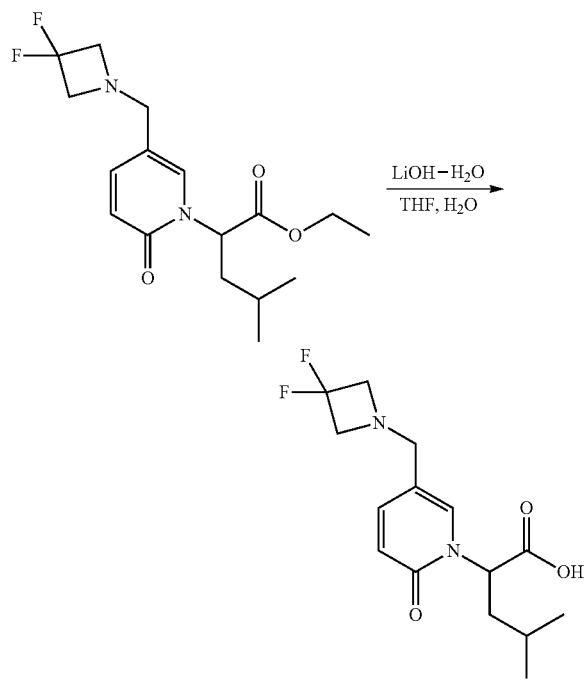

Ethyl 2-(5-((3,3-difluoroazetidine-1-yl)methyl)-2-oxopyridin-1(2H)-yl)-4-methylpentanoate (151 mg, 0.44 mmol) was treated with LiOH—H₂O (28 mg, 0.66 mmol) in THF (3 mL) and H₂O (0.5 mL) at room temperature for 30 mins. The mixture was acidified to pH 4-5 with 1N HCl. The mixture was concentrated in vacuo to provide 2-(5-((3,3-difluoroazetidine-1-yl)methyl)-2-oxopyridin-1(2H)-yl)-4-methylpentanoic acid as white solid (138 mg) used without further purification. Yield 100% (ESI 315.1 (M+H)⁺).

Preparation of 4-methyl-2-(5-(morpholinomethyl)-2-oxopyridin-1(2H)-yl)pentanoic Acid Step 1: Ethyl 2-(5-formyl-2-oxopyridin-1(2H)-yl)-4-methylpentanoate

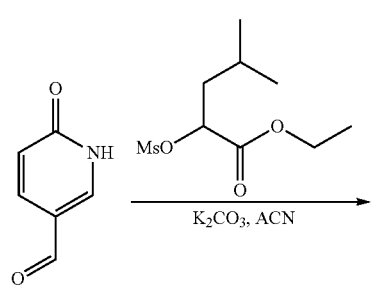

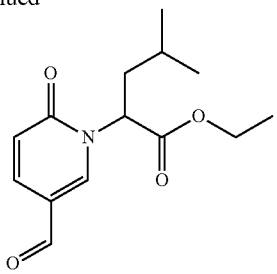

A mixture of 6-oxo-1,6-dihydropyridine-3-carbaldehyde (400 mg, 3.2 mmol), ethyl 4-methyl-2-(methylsulfonyloxy)pentanoate (1 g, 4.2 mmol) and K₂CO₃ (1.1 g, 8 mmol) in MeCN (10 mL) was stirred at 80° C. overnight. The mixture was filtered and washed with MeCN (5 mL). The filtrate was concentrated in vacuo and purified by silica gel column (pet ether:EtOAc 4:1) to provide ethyl 2-(5-formyl-2-oxopyridin-1(2H)-yl)-4-methylpentanoate as a colorless oil (650 mg). Yield 70% (ESI 266.3 (M+H)⁺).

Step 2: Ethyl 2-(5-((3-fluoroazetidine-1-yl)methyl)-2-oxopyridin-1(2H)-yl)-4-methylpentanoate

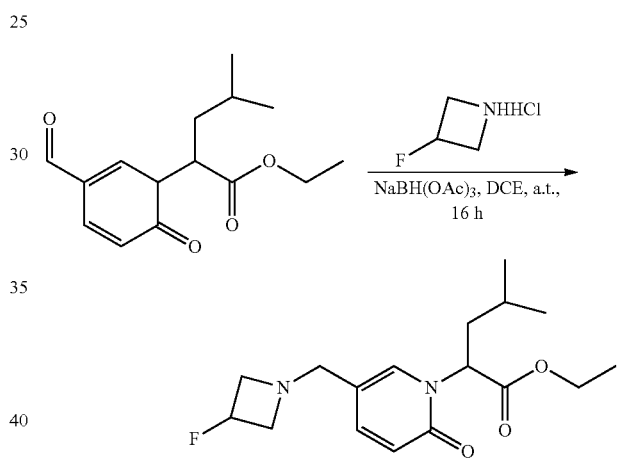

A mixture of ethyl 2-(5-formyl-2-oxopyridin-1(2H)-yl)-4-methylpentanoate (300 mg, 1.13 mmol) and 3-fluoroazetidine hydrochloride (251 mg, 2.26 mmol) in DCE (4 mL) was stirred at room temperature for 30 mins. Sodium triacetoxyborohydride (959 mg, 4.52 mmol) was added and stirred at room temperature overnight. The mixture was concentrated in vacuo and purified by silica gel column (DCM:MeOH 10:1) to provide ethyl 2-(5-((3-fluoroazetidine-1-yl)methyl)-2-oxopyridin-1(2H)-yl)-4-methylpentanoate as a colorless oil (264 mg). Yield 72% (ESI 325.2 (M+H)⁺).

Step 3: 2-(5-((3-fluoroazetidine-1-yl)methyl)-2-oxopyridin-1(2H)-yl)-4-methylpentanoic Acid

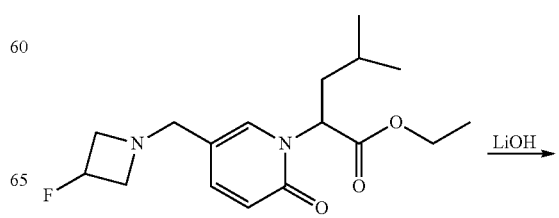

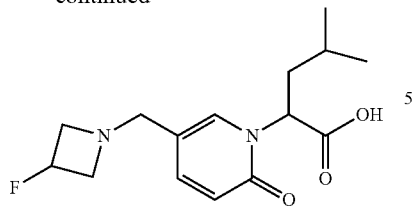

Ethyl 2-(5-((3-fluoroazetidine-1-yl)methyl)-2-oxopyridin-1(2H)-yl)-4-methylpentanoate (264 mg, 0.81 mmol) was treated with LiOH—H$_2$O (171 mg, 4 mmol) in EtOH (4 mL) and H$_2$O (1 mL) at room temperature for 2 hours. The mixture was acidified to pH 4~5 with 1N HCl. The mixture was concentrated in vacuo and purified by silica gel column (DCM:MeOH 10:1) to provide 2-(5-((3-fluoroazetidine-1-yl)methyl)-2-oxopyridin-1(2H)-yl)-4-methylpentanoic acid as a white solid (217 mg). Yield 90% (ESI 297.1 (M+H)$^+$).

Preparation of 4-methyl-2-(5-(morpholinomethyl)-2-oxopyridin-1(2H)-yl)pentanoic Acid Step 1: Ethyl 4-methyl-2-(5-(morpholinomethyl)-2-oxopyridin-1(2H)-yl)pentanoate

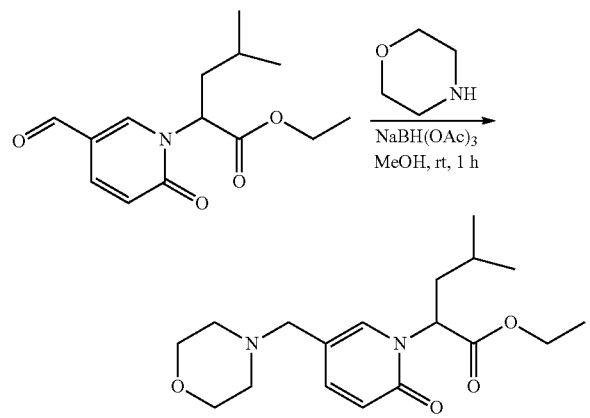

A mixture of ethyl 2-(5-formyl-2-oxopyridin-1(2H)-yl)-4-methylpentanoate (300 mg, 1.13 mmol) and morpholine (147 mg, 1.70 mmol) in DCE (5 mL) was stirred at room temperature for 30 mins. NaBH(OAc)$_3$ (715 mg, 3.39 mmol) was added and stirred at room temperature for 1 hour. The solvent was removed in vacuo and the residue purified by silica gel column (DCM:MeOH 2:1) to provide ethyl 4-methyl-2-(5-(morpholinomethyl)-2-oxopyridin-1(2H)-yl)pentanoate as yellow oil (150 mg). Yield 39% (ESI 337.2 (M+H)$^+$).

Step 2: 4-methyl-2-(5-(morpholinomethyl)-2-oxopyridin-1(2H)-yl)pentanoic Acid

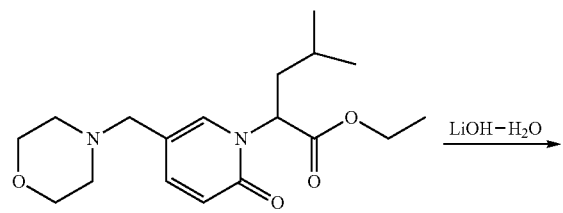

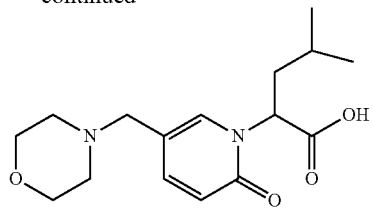

Ethyl 4-methyl-2-(5-(morpholinomethyl)-2-oxopyridin-1(2H)-yl)pentanoate (150 mg, 0.45 mmol) was treated with LiOH—H$_2$O (56 mg, 1.34 mmol) in THF (3 mL) and H$_2$O (0.5 mL) at room temperature for 2 hours. The mixture was acidified to pH 4-5 with 1N HCl. The mixture was concentrated in vacuo and the residue was purified by reverse phase HPLC on a C18/40 g column (A: water 10 mM NH$_4$HCO$_3$, B: MeOH, 0~100%) to provide 4-methyl-2-(5-(morpholinomethyl)-2-oxopyridin-1(2H)-yl)pentanoic acid as white solid (110 mg). Yield 80% (ESI 309.3 (M+H)$^+$).

Preparation of 2-(5-(2-(dimethylamino)ethyl)-2-oxopyridin-1(2H)-yl)-4-methylpentanoic acid Step 1: Ethyl 2-(5-(((R)-3-fluoropyrrolidin-1-yl)methyl)-2-oxopyridin-1(2H)-yl)-4-methylpentanoate

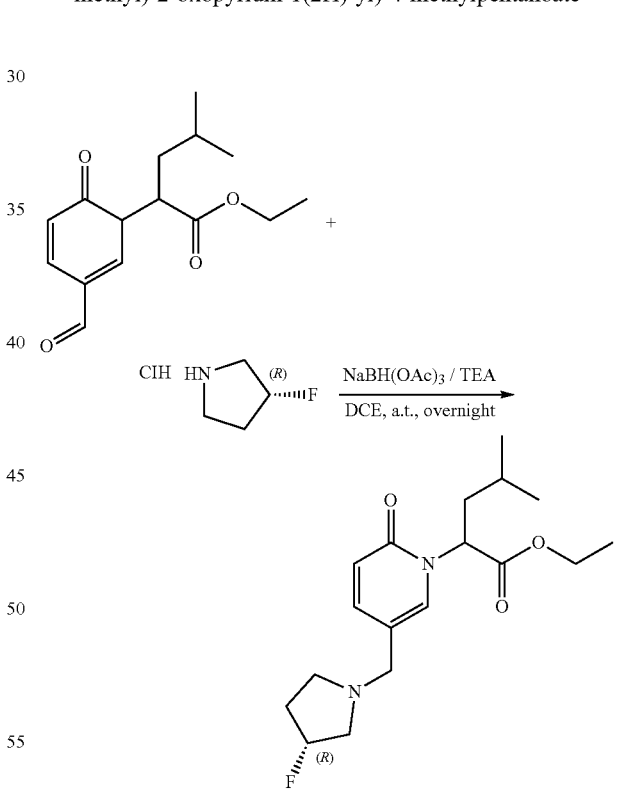

A mixture of ethyl 2-(5-formyl-2-oxopyridin-1(2H)-yl)-4-methylpentanoate (300 mg, 1.13 mmol), (R)-3-fluoropyrrolidin hydrochloride (284 mg, 2.26 mmol) and triethylamine (0.31 mL, 2.26 mmol) in DCE (10 mL) was stirred at room temperature for 30 mins. Sodium triacetoxyborohydride (959 mg, 4.52 mmol) was added and stirred at room temperature overnight. The mixture was concentrated in vacuo and purified by silica gel column (DCM:MeOH 10:1) to provide ethyl 2-(5-(((R)-3-fluoropyrrolidin-1-yl)methyl)-

2-oxopyridin-1(2H)-yl)-4-methylpentanoate as a colorless oil (237 mg). Yield 62% (ESI 339.2 (M+H)⁺).

Step 2: 2-(5-(((R)-3-fluoropyrrolidin-1-yl)methyl)-2-oxopyridin-1(2H)-yl)-4-methylpentanoic Acid

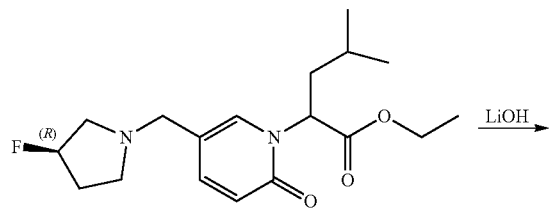

Ethyl 2-(5-(((R)-3-fluoropyrrolidin-1-yl)methyl)-2-oxopyridin-1(2H)-yl)-4-methylpentanoate (426 mg, 1.13 mmol) was treated with LiOH—H₂O (237 mg, 5.65 mmol) in EtOH (6 mL) and H₂O (0.6 mL) at room temperature for 2 hours. The mixture was acidified to pH 4-5 with 1N HCl. The mixture was concentrated in vacuo and the residue purified by silica gel column (DCM:MeOH 10:1) to provide 2-(5-(((R)-3-fluoropyrrolidin-1-yl)methyl)-2-oxopyridin-1(2H)-yl)-4-methylpentanoic acid as a white solid (348 mg). Yield 99% (ESI 311.1 (M+H)⁺).

Preparation of 2-(5-(3-(dimethylamino)azetidin-1-yl)-4-methyl-2-oxopyridin-1(2H)-yl)-4-methylpentanoic Acid Step 1: Ethyl 2-(5-bromo-4-methyl-2-oxopyridin-1(2H)-yl)-4-methylpentanoate

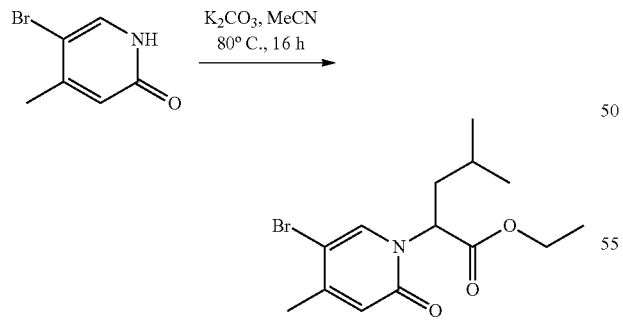

A mixture of 5-bromo-4-methylpyridin-2(1H)-one (3.0 g, 16 mmol, 1.0 eq), K₂CO₃ (4.4 g, 32 mmol, 2.0 eq) and ethyl 4-methyl-2-((methylsulfonyl)oxy)pentanoate (5.7 g, 24 mmol, 1.5 eq) in CH₃CN (50 mL) was stirred at 80° C. for 16 h. LCMS showed the reaction was completed. The mixture was filtered and washed with CH₃CN (20 mL). The filtrate was concentrated in vacuo and the residue was purified by silica gel column (pet ether:EtOAc 3:1) to provide ethyl 2-(5-bromo-4-methyl-2-oxopyridin-1(2H)-yl)-4-methylpentanoate as a yellow oil (4.5 g). Yield 85% (ESI 330 (M+H)⁺). ¹H NMR (500 MHz, CDCl₃) δ 7.46 (s, 1H), 6.49 (d, J=0.6 Hz, 1H), 5.67 (dd, J=10.6, 5.3 Hz, 1H), 4.20 (qd, J=7.1, 0.8 Hz, 2H), 2.24 (d, J=0.8 Hz, 3H), 1.97-1.93 (m, 1H), 1.87-1.80 (m, 1H), 1.51-1.43 (m, 1H), 1.27 (t, J=7.1 Hz, 3H), 0.95 (t, J=6.3 Hz, 6H).

Step 2: Ethyl 2-(5-(3-(dimethylamino)azetidin-1-yl)-4-methyl-2-oxopyridin-1(2H)-yl)-4-methylpentanoate

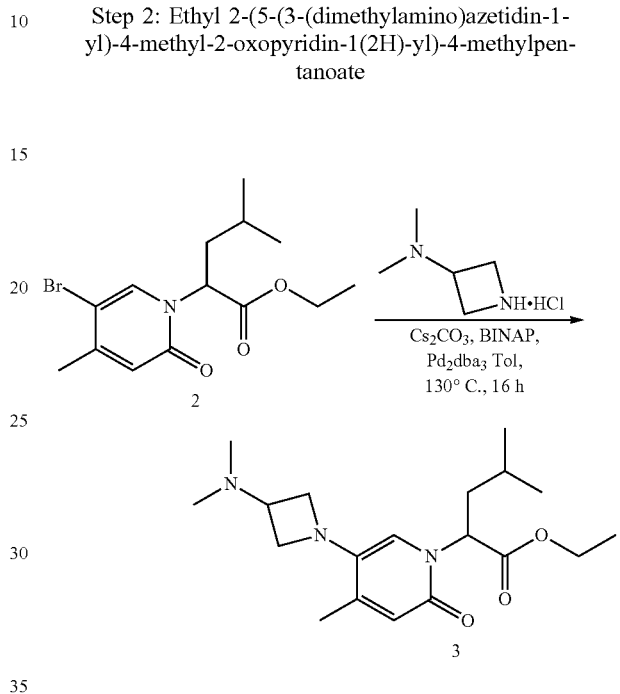

To a solution of ethyl 2-(5-bromo-4-methyl-2-oxopyridin-1(2H)-yl)-4-methylpentanoate (2.0 g, 6.06 mmol, 1.0 eq), N,N-dimethylazetidin-3-amine dihydrochloride (1.57 g, 9.07 mmol, 1.5 eq), and CsCO₃ (8.0 g, 24.5 mmol, 4.0 eq) in toluene (50 mL) was added BINAP (376 mg, 0.606 mmol, 0.1 eq) and Pd₂dba₃ (250 mg, 0.27 mmol, 0.05 eq) under N₂ and then heated to 120° C. for 3 h. LCMS showed the reaction was completed. The mixture was filtered and washed with both EtOAc (20 mL) and EtOH (20 mL). The filtrate was concentrated in vacuo and the residue was purified by silica gel column (pet ether:EtOAc 1:1) to provide ethyl 2-(5-(3-(dimethylamino)azetidin-1-yl)-4-methyl-2-oxopyridin-1(2H)-yl)-4-methylpentanoate (1.4 g). Yield 66% (ESI 350 (M+H)⁺).

Step 3: 2-(5-(3-(dimethylamino)azetidin-1-yl)-4-methyl-2-oxopyridin-1(2H)-yl)-4-methylpentanoic Acid

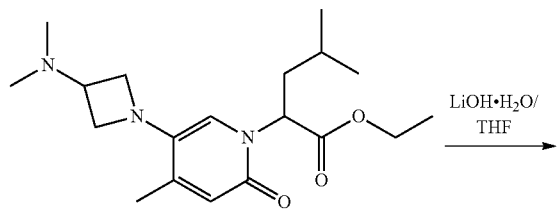

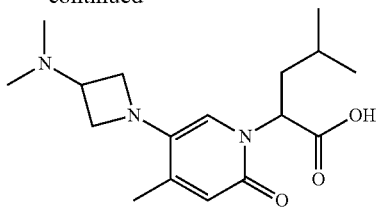

Ethyl 2-(5-(3-(dimethylamino)azetidin-1-yl)-4-methyl-2-oxopyridin-1(2H)-yl)-4-methylpentanoate(1.4 g, 4.0 mmol, 1.0 eq) was treated with LiOH—H₂O (840 mg, 20.0 mmol, 5.0 eq) in THF (20 mL) and water (6 mL) at room temperature for 2 hours. The MeOH was removed and the aqueous material acidified with 1N HCl to pH 4. The mixture was purified by reverse phase HPLC in neutral condition (A: water, B: MeOH, 60% B) to provide 2-(5-(3-(dimethylamino)azetidin-1-yl)-4-methyl-2-oxopyridin-1(2H)-yl)-4-methylpentanoic acid as a white solid (800 mg). Yield 62% (ESI 322 (M+H)⁺). 1H-NMR (400 MHz, MeOD) δ 6.75 (s, 1H), 6.31 (s, 1H), 5.45-5.38 (m, 1H), 3.87-3.28 (m, 2H), 3.24 (s, 3H), 3.17-2.42 (m, 6H), 2.19-2.06 (m, 3H), 1.24-1.19 (m, 1H), 0.85-0.74 (m, 6H).

Preparation of 2-(5-((dimethylamino)methyl)-2-oxo-4-(trifluoromethyl)pyridin-1(2H)-yl)-4-methylpentanoic Acid Step 1: 1-(6-methoxy-4-(trifluoromethyl)pyridin-3-yl)-N,N-dimethylmethanamine

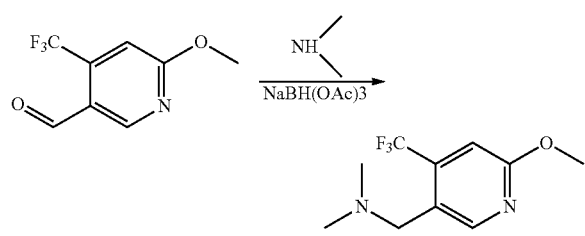

A mixture of 6-methoxy-4-(trifluoromethyl)nicotinaldehyde (0.5 g, 2.44 mmol), dimethylamine (2.0 M in THF, 1.5 mL, 2.92 mmol) in DCE (10 mL) was stirred at room temperature for 15 mins. NaBH(OAc)₃ (1.03 g, 4.88 mmol) was added and stirred at room temperature for 3 hours. The solvent was removed in vacuo and the residue purified by silica gel column (DCM:MeOH 10:1) to provide 1-(6-methoxy-4-(trifluoromethyl)pyridin-3-yl)-N,N-dimethylmethanamine as yellow oil (220 mg). Yield 38% (ESI 235.1 (M+H)⁺).

Step 2: 5-((dimethylamino)methyl)-4-(trifluoromethyl)pyridin-2-ol

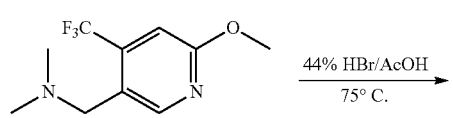

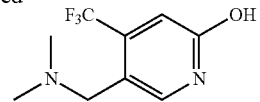

A mixture of 1-(6-methoxy-4-(trifluoromethyl)pyridin-3-yl)-N,N-dimethylmethanamine (220 mg, 0.94 mmol) in 33% HBr/AcOH (10 mL) was heated at 75° C. for 16 hours. The solvent was removed in vacuo and the residue was purified by reverse phase HPLC on a C18/40 g column (A: water 10 mM NH₄HCO₃, B: MeOH, 0~100%) to provide 5-((dimethylamino)methyl)-4-(trifluoromethyl)pyridin-2-ol as a red solid (180 mg). Yield 87% (ESI 221.1 (M+H)⁺).

Step 3: Ethyl 2-(5-((dimethylamino)methyl)-2-oxo-4-(trifluoromethyl)pyridin-1(2)-yl)-4-methylpentanoate

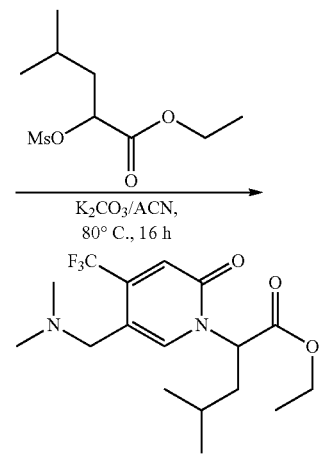

A mixture of 5-((dimethylamino)methyl)-4-(trifluoromethyl)pyridin-2-ol (150 mg, 0.68 mmol), ethyl 4-methyl-2-(methylsulfonyloxy)pentanoate (194 mg, 0.816 mmol) and K₂CO₃ (281.5 mg, 2.04 mmol) in MeCN (10 mL) was stirred at 80° C. overnight. The solvent was removed in vacuo and the residue was purified by reverse phase HPLC on a C18/40 g column (A: water 10 mM NH₄HCO₃, B: MeOH, 0~100%) to provide ethyl 2-(5-((dimethylamino)methyl)-2-oxo-4-(trifluoromethyl)pyridin-1(2H)-yl)-4-methylpentanoate (170 mg). Yield 68% (ESI 363.1 (M+H)⁺).

Step 4: 2-(5-((dimethylamino)methyl)-2-oxo-4-(trifluoromethyl)pyridin-1(2H)-yl)-4-methylpentanoic Acid -continued

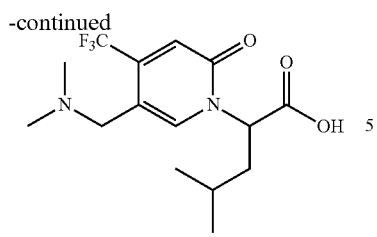

Ethyl 2-(5-((dimethylamino)methyl)-2-oxo-4-(trifluoromethyl)pyridin-1(2H)-yl)-4-methylpentanoate (170 mg, 0.47 mmol) was treated with LiOH—H$_2$O (98.7 mg, 2.35 mmol) in MeOH (10 mL) and H$_2$O (2 mL) at room temperature for 2 hours. The mixture was acidified to pH 4-5 with 1N HCl and purified by reverse phase HPLC on a C18/40 g column (A: water 10 mM NH$_4$HCO$_3$, B: MeOH, 0~100%) to provide 2-(5-((dimethylamino)methyl)-2-oxo-4-(trifluoromethyl)pyridin-1(2H)-yl)-4-methylpentanoic acid as white solid (120 mg). Yield 76% (ESI 335.2 (M+H)$^+$).

Preparation of 2-(5-(2-(dimethylamino)ethyl)-2-oxopyridin-1(2H)-yl)-4-methylpentanoic acid Step 1: 5-(2-methoxyvinyl)pyridin-2(1H)-one

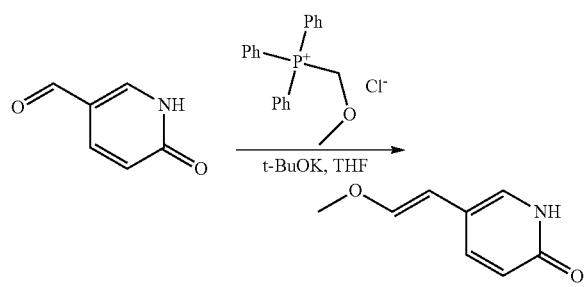

A mixture of (methoxymethyl)triphenylphosphonium chloride (12.5 g, 36.6 mmol), t-BuOK (6.83 g, 61 mmol) in dioxane (60 mL) was stirred at room temperature for 15 minutes. Then 6-oxo-1,6-dihydropyridine-3-carbaldehyde (3 g, 24.4 mmol) in 20 mL THF was added. The mixture was stirred for 16 h at room temperature. To the reaction mixture was added 80 mL water. The mixture was extracted with EtOAc (80 mL×2) and the aqueous phase concentrated in vacuo. The residue was purified by reverse phase HPLC (Eluent A: water 10 mM NH$_4$HCO$_3$, Eluent B: MeOH, gradient A→B 0~100%) to provide 5-(2-methoxyvinyl)pyridin-2(1H)-one as a red oil (1.3 g). Yield 35% (ESI 152.2 (M+H)$^+$).

Step 2: 2-(6-oxo-1,6-dihydropyridin-3-yl)acetaldehyde

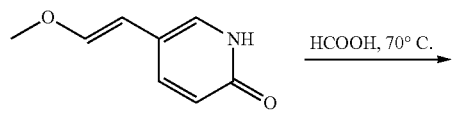

-continued

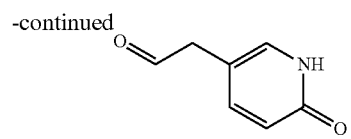

5-(2-methoxyvinyl)pyridin-2(1H)-one (1.2 g, 7.95 mmol) was treated with HCOOH (20 mL) at 70° C. for 2 hours. The solvent was removed in vacuo to provide the crude product 2-(6-oxo-1,6-dihydropyridin-3-yl)acetaldehyde as a red oil (0.8 g, crude). (ESI 138.3 (M+H)$^+$).

Step 3: 5-(2-(dimethylamino)ethyl)pyridin-2(1H)-one

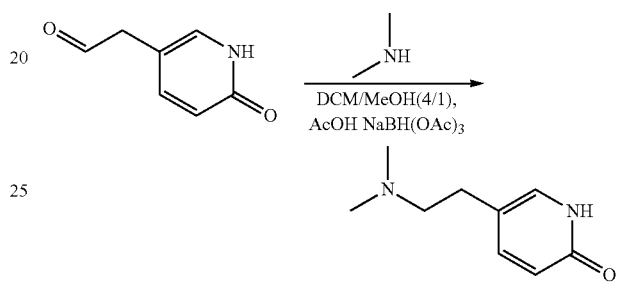

A mixture of methyl 2-(6-oxo-1,6-dihydropyridin-3-yl)acetaldehyde (750 mg, 5.47 mmol), AcOH (394 mg, 6.56 mmol) and dimethylamine (40% in water) (1.23 g, 10.94 mmol) in DCM (10 mL) and MeOH (2.5 mL) was stirred at room temperature for 30 minutes then NaBH(OAc)$_3$ (2.32 g, 10.94 mmol) was added. The mixture was stirred at room temperature overnight. The solvent was removed in vacuo and the residue was purified by silica gel column (DCM:MeOH 2:1) to provide 5-(2-(dimethylamino)ethyl)pyridin-2(1H)-one as yellow oil (500 mg). Yield 55% (ESI 167.2 (M+H)$^+$).

Step 4: Ethyl 2-(5-(2-(dimethylamino)ethyl)-2-oxopyridin-1(2H)-yl)-4-methylpentanoate

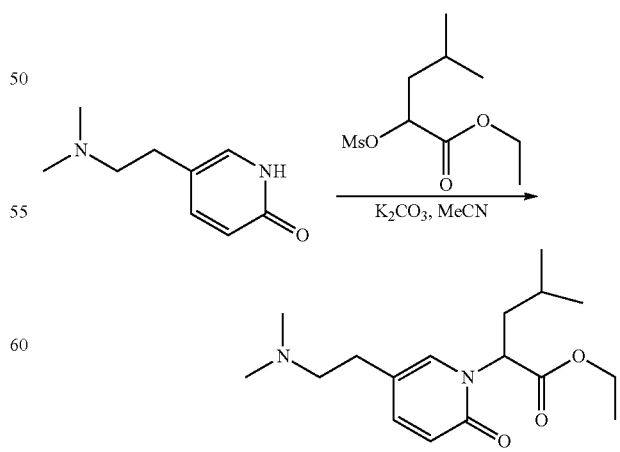

A mixture of methyl 5-(2-(dimethylamino)ethyl)pyridin-2(1H)-one (500 mg, 3 mmol), ethyl 4-methyl-2-(methylsulfonyloxy)pentanoate (1.07 g, 4.5 mmol) and K₂CO₃ (828 mg, 6 mmol) in MeCN (15 mL) was stirred at 70° C. overnight. The solvent was removed in vacuo and the residue was purified by silica gel column (DCM:MeOH 1:2) to provide methyl ethyl 2-(5-(2-(dimethylamino)ethyl)-2-oxopyridin-1(2H)-yl)-4-methylpentanoate as a white solid (100 mg). Yield 11% (ESI 309.2 (M+H)⁺).

Step 5: 2-(5-(2-(dimethylamino)ethyl)-2-oxopyridin-1(2H)-yl)-4-methylpentanoic Acid

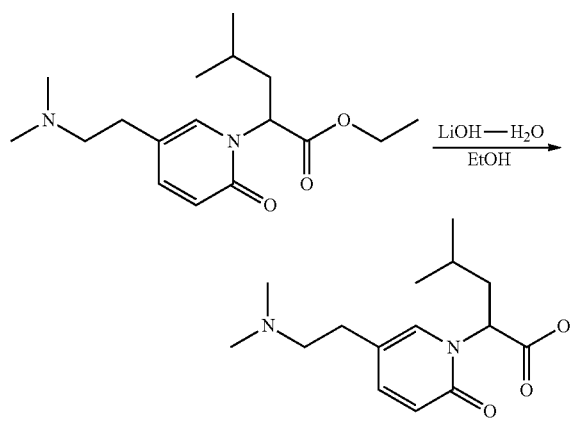

Ethyl 2-(5-(2-(dimethylamino)ethyl)-2-oxopyridin-1(2H)-yl)-4-methylpentanoate (100 mg, 0.32 mmol) was treated with LiOH—H₂O (54 mg, 1.28 mmol) in EtOH (3 mL) and H₂O (1 mL) at room temperature for 2 hours. The reaction mixture was acidified to pH 4-5 with 1 N HCl. The solvent was removed in vacuo and the residue was purified by reverse phase HPLC (Eluent A: water 10 mM NH₄HCO₃, Eluent B: MeOH, gradient A→B 0~100%) to provide 2-(5-(2-(dimethylamino)ethyl)-2-oxopyridin-1(2H)-yl)-4-methylpentanoic acid as white solids (70 mg). Yield 78% (ESI 281.2 (M+H)⁺).

Preparation of 2-(4-(2-(dimethylamino)ethyl)-2-oxopyridin-1(2H)-yl)-4-methylpentanoic acid Step 1: Ethyl 2-(4-bromo-2-oxopyridin-1(2H)-yl)-4-methylpentanoate

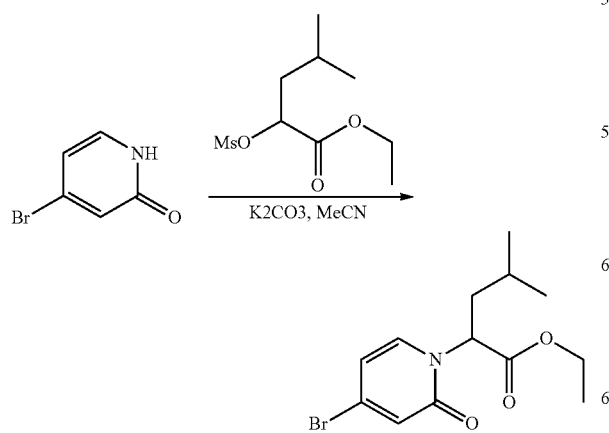

A mixture of 4-bromopyridin-2(1H)-one (1.2 g, 6.94 mmol), K₂CO₃ (1.92 g, 13.88 mmol) and ethyl 4-methyl-2-(methylsulfonyloxy)pentanoate (1.98 g, 8.33 mmol) in CH₃CN (20 mL) was stirred at 80° C. overnight. The solvent was concentrated in vacuo and the residue was purified by silica gel column (pet ether:EtOAc 1:1) to give ethyl 2-(4-bromo-2-oxopyridin-1(2H)-yl)-4-methylpentanoate as a yellow oil (1.6 g). Yield 73% (ESI 316.1 (M+H)⁺).

Step 2: Ethyl 2-(4-(2-(benzyloxycarbonylamino)ethyl)-2-oxopyridin-1(2H)-yl)-4-methylpentanoate

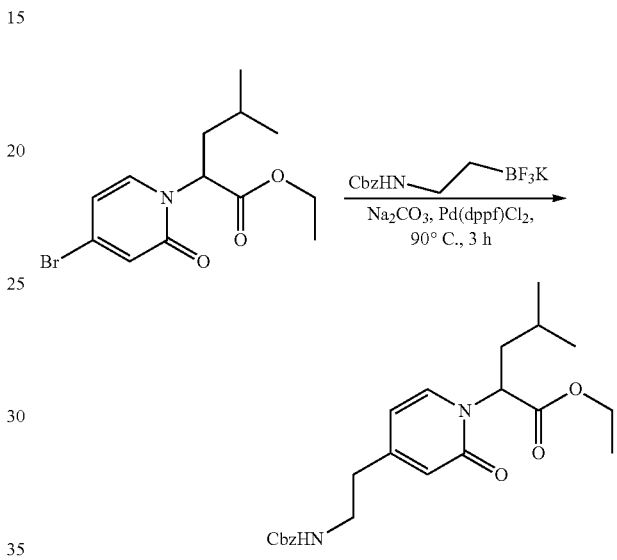

A mixture of ethyl 2-(4-bromo-2-oxopyridin-1(2H)-yl)-4-methylpentanoate (1.6 g, 5.0 mmol), potassium benzyl N-[2-(trifluorobutryl)ethyl]carbamate (1.71 g, 6 mmol), Pd(dppf)Cl₂ (366 mg, 0.5 mmol) and Na₂CO₃ (1.06 g, 10 mmol) in 1,4-dioxane (20 mL) and H₂O (10 mL) was stirred at 90° C. under N₂ atmosphere for 4 hours. The reaction was concentrated and purified by reverse phase HPLC on a C18/40 g column (A: water/0.01% TFA, B: MeOH, 0~100%) to provide ethyl 2-(4-(2-(benzyloxycarbonylamino)ethyl)-2-oxopyridin-1(2H)-yl)-4-methylpentanoate as a yellow oil (700 mg). Yield 35% (ESI 415.1 (M+H)⁺).

Step 3: Ethyl 2-(4-(2-aminoethyl)-2-oxopyridin-1(2H)-yl)-4-methylpentanoate

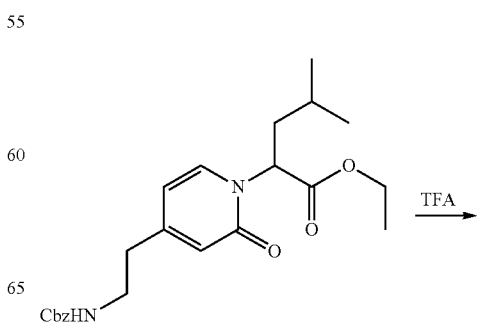

-continued

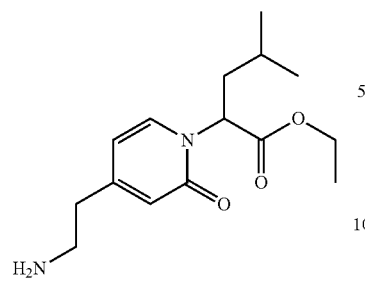

Ethyl 2-(4-(2-(benzyloxycarbonylamino)ethyl)-2-oxopyridin-1(2H)-yl)-4-methylpentanoate (0.7 g, 1.7 mmol) was treated with TFA (10 mL) at 50° C. for 4 hours. The solvent was removed in vacuo and the residue was purified by reverse phase HPLC on a C18/40 g column (A: water 10 mM NH$_4$HCO$_3$, B: MeOH, 0~100%) to provide ethyl 2-(4-(2-aminoethyl)-2-oxopyridin-1(2H)-yl)-4-methylpentanoate as a red oil (0.4 g). Yield 84%. (ESI 281.2 (M+H)$^+$).

Step 4: Ethyl 2-(4-(2-(dimethylamino)ethyl)-2-oxopyridin-1(2H)-yl)-4-methylpentanoate

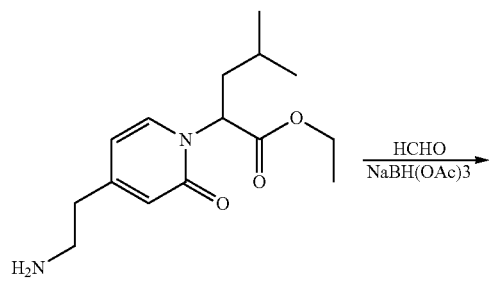

To a mixture of ethyl 2-(4-(2-aminoethyl)-2-oxopyridin-1(2H)-yl)-4-methylpentanoate (400 mg, 1.43 mmol) in MeOH (10 mL) was added HCHO (37% in H$_2$O, 1 mL) and stirred at room temperature for 5 mins. NaBH(OAc)$_3$ (1.21 g, 5.72 mmol) was added and stirred at room temperature for 1 hour. The solvent was removed in vacuo and the residue was purified by reverse phase HPLC on a C18/40 g column (A: water 10 mM NH$_4$HCO$_3$, B: MeOH, 0~100%) to provide ethyl 2-(4-(2-(dimethylamino)ethyl)-2-oxopyridin-1(2H)-yl)-4-methylpentanoate as yellow oil (400 mg). Yield 91% (ESI 309.2 (M+H)$^+$).

Step 5: 2-(4-(2-(dimethylamino)ethyl)-2-oxopyridin-1(2H)-yl)-4-methylpentanoic Acid

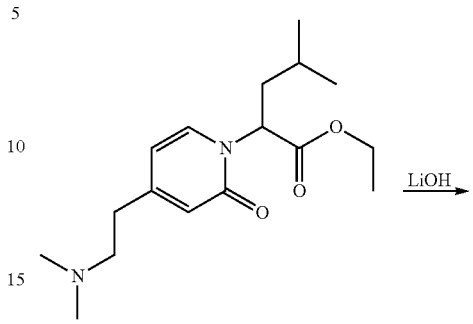

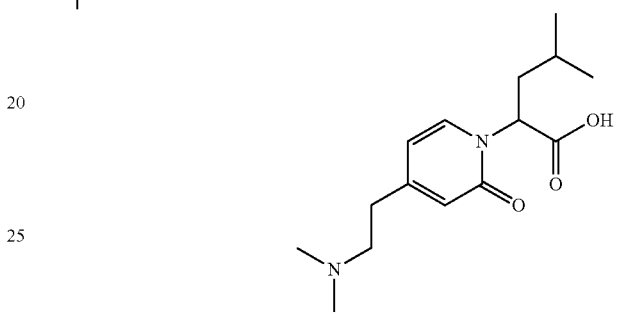

Ethyl 2-(4-(2-(dimethylamino)ethyl)-2-oxopyridin-1(2H)-yl)-4-methylpentanoate (400 mg, 1.3 mmol) was treated with LiOH—H$_2$O (218 mg, 5.2 mmol) in MeOH (4 mL) and H$_2$O (1 mL) at room temperature for 1 hour. The mixture was acidified to pH 4~5 with 1N HCl. The mixture was concentrated in vacuo and the residue was purified by reverse phase HPLC on a C18/40 g column (A: water/0.01% TFA, B: MeOH, 0~100%) to give 2-(4-(2-(dimethylamino)ethyl)-2-oxopyridin-1(2H)-yl)-4-methylpentanoic acid as white solid (310 mg). Yield 85% (ESI 281.2 (M+H)$^+$).

Preparation of 2-(3-(2-(dimethylamino)ethyl)-2-oxopyridin-1(2H)-yl)-4-methylpentanoic acid Step 1: Ethyl 2-(3-bromo-2-oxopyridin-1(2H)-yl)-4-methylpentanoate

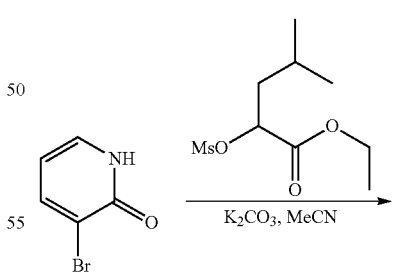

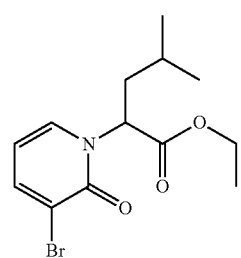

A mixture of 3-bromopyridin-2(1H)-one (1 g, 5.78 mmol), K₂CO₃ (1.6 g, 11.56 mmol) and ethyl 4-methyl-2-(methylsulfonyloxy)pentanoate (1.65 g, 6.94 mmol) in CH₃CN (20 mL) was stirred at 80° C. overnight. The solvent was concentrated in vacuo and purified by silica gel column (petroleum ether:EtOAc 1:1) to provide ethyl 2-(3-bromo-2-oxopyridin-1(2H)-yl)-4-methylpentanoate as a white solid (1.6 g). Yield 88% (ESI 316.1 (M+H)⁺).

Step 2: Ethyl 2-(3-(2-(benzyloxycarbonylamino)ethyl)-2-oxopyridin-1(2H)-yl)-4-methylpentanoate

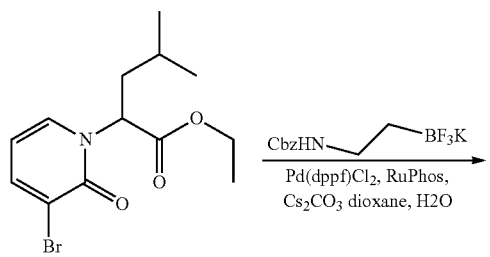

A mixture of ethyl 2-(3-bromo-2-oxopyridin-1(2H)-yl)-4-methylpentanoate (1 g, 3.17 mmol), potassium benzyl N-[2-(trifluoroboryl)ethyl]carbamate (1.08 g, 3.8 mmol), Pd(dppf)Cl₂ (36 mg, 0.16 mmol), Cs₂CO₃ (2 g, 6.34 mmol) and RuPhos (144 mg, 0.32 mmol) in 1,4-dioxane (20 mL) and H₂O (10 mL) was stirred at 110° C. for 2 hours. The reaction was concentrated and purified by reverse phase HPLC on a C18/40 g column (A: water/0.01% TFA, B: MeOH, 0~100%) to give ethyl 2-(3-(2-(benzyloxycarbonylamino)ethyl)-2-oxopyridin-1(2H)-yl)-4-methylpentanoate as a yellow oil (1.1 g). Yield 84% (ESI 415.2 (M+H)⁺).

Step 3: Ethyl 2-(3-(2-aminoethyl)-2-oxopyridin-1(2H)-yl)-4-methylpentanoate

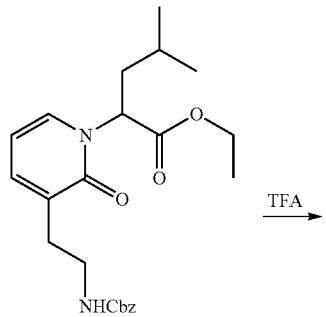

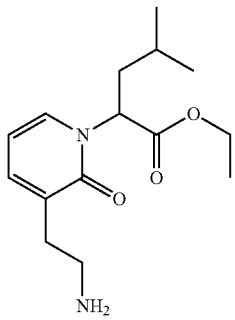

Ethyl 2-(3-(2-(benzyloxycarbonylamino)ethyl)-2-oxopyridin-1(2H)-yl)-4-methylpentanoate (1.07 g, 2.58 mmol) was treated with TFA (20 mL) at 50° C. for 4 hours. The solvent was removed in vacuo and the residue purified by reverse phase HPLC on a C18/40 g column (A: water 10 mM NH4HCO₃, B: MeOH, 0~100%) to provide ethyl 2-(3-(2-aminoethyl)-2-oxopyridin-1(2H)-yl)-4-methylpentanoate as a yellow oil (0.6 g). Yield 83%. (ESI 281.2 (M+H)⁺).

Step 4: Ethyl 2-(3-(2-(dimethylamino)ethyl)-2-oxopyridin-1(2H)-yl)-4-methylpentanoate

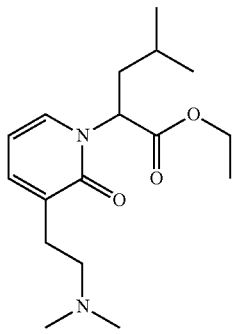

To a mixture of ethyl 2-(3-(2-aminoethyl)-2-oxopyridin-1(2H)-yl)-4-methylpentanoate (600 mg, 2.14 mmol) in MeOH (10 mL) was added HCHO (37% in H₂O, 1 mL). The mixture was stirred at room temperature for 5 mins. NaBH(OAc)₃ (1.81 g, 8.56 mmol) was added and stirred at room temperature for 1 hour. The solvent was removed in vacuo and the residue purified by reverse phase HPLC on a C18/40 g column (A: water 10 mM NH4HCO₃, B: MeOH, 0~100%) to provide ethyl 2-(3-(2-(dimethylamino)ethyl)-2-oxopyridin-1(2H)-yl)-4-methylpentanoate as yellow oil (600 mg). Yield 91% (ESI 309.2 (M+H)⁺).

Step 5: 2-(3-(2-(dimethylamino)ethyl)-2-oxopyridin-1(2H)-yl)-4-methylpentanoic Acid

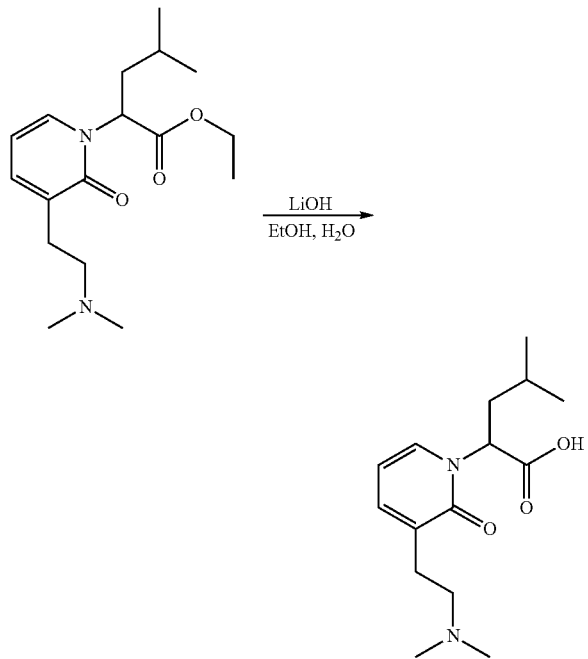

Ethyl 2-(3-(2-(dimethylamino)ethyl)-2-oxopyridin-1(2H)-yl)-4-methylpentanoate (600 mg, 1.95 mmol) was treated with LiOH monohydrate (328 mg, 7.8 mmol) in EtOH (4 mL) and H$_2$O (1 mL) at room temperature for 1 hour. The mixture was acidified to pH 4-5 with 1N HCl aqueous solution. The mixture was concentrated in vacuo and the residue purified by reverse phase HPLC on a C18/40 g column (A: water/0.01% TFA, B: MeOH, 0~100%) to give 2-(3-(2-(dimethylamino)ethyl)-2-oxopyridin-1(2H)-yl)-4-methylpentanoic acid as white solid (500 mg). Yield 92% (ESI 281.2 (M+H)$^+$).

Preparation of Acid 9: 2-(5-(2-(3-fluoroazetidine-1-yl)ethyl)-2-oxopyridin-1(2H)-yl)-4-methylpentanoic Acid Step 1: 5-(2-(azetidin-1-yl)ethyl)pyridin-2(1H)-one

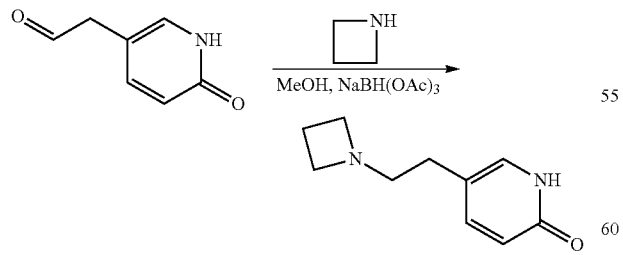

A mixture of methyl 2-(6-oxo-1,6-dihydropyridin-3-yl)acetaldehyde (1.0 g, 7.29 mmol) and azetidine (416 mg, 7.30 mmol) in MeOH (10 mL) was stirred at room temperature for 30 mins. NaBH(OAc)$_3$ (4.6 g, 21.9 mmol) was added and stirred at room temperature for 1 hour. The solvent was removed in vacuo and the residue purified by silica gel column (DCM:MeOH 2:1) to provide 5-(2-(azetidin-1-yl)ethyl)pyridin-2(1H)-one as yellow oil (800 mg). Yield 62% (ESI 179.1 (M+H)$^+$).

Step 2: Ethyl 2-(5-(2-(azetidin-1-yl)ethyl)-2-oxopyridin-1(2H)-yl)-4-methylpentanoate

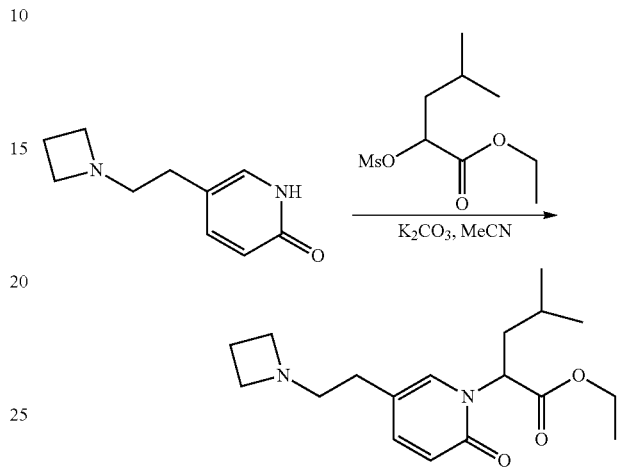

A mixture of 5-(2-(azetidin-1-yl)ethyl)pyridin-2(1H)-one (800 mg, 4.49 mmol), ethyl 4-methyl-2-(methylsulfonyloxy)pentanoate (2.2 g, 6.74 mmol) and K$_2$CO$_3$ (1.8 g, 13.47 mmol) in MeCN (40 mL) was stirred at 80° C. overnight. The mixture was filtered and washed with MeCN (5 mL). The filtrate was concentrated in vacuo and the residue purified by reverse phase HPLC on a C18/80 g column (A: water/0.01% TFA, B: MeOH, 0~100%) to provide ethyl 2-(5-(2-(azetidin-1-yl)ethyl)-2-oxopyridin-1(2H)-yl)-4-methylpentanoate as a colorless oil (600 mg). Yield 42% (ESI 321.2 (M+H)$^+$).

Step 3: 2-(5-(2-(azetidin-1-yl)ethyl)-2-oxopyridin-1(2H)-yl)-4-methylpentanoic Acid

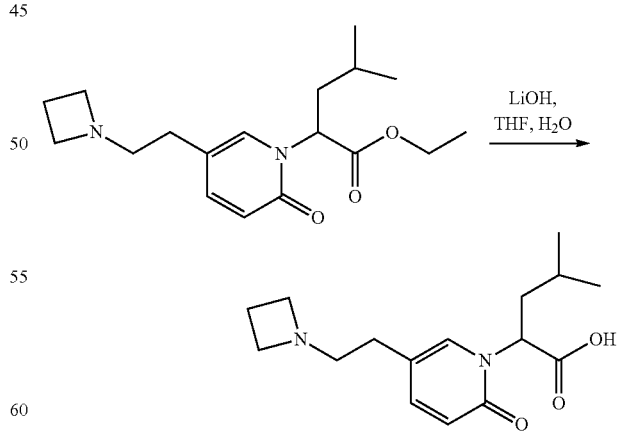

Ethyl 2-(5-(2-(azetidin-1-yl)ethyl)-2-oxopyridin-1(2H)-yl)-4-methylpentanoate (600 mg, 1.88 mmol) was treated with LiOH—H$_2$O (394 mg, 9.40 mmol) in THF (10 mL) and H$_2$O (2 mL) at room temperature for 1 hour. The mixture was acidified to pH 4~5 with 1N HCl. The mixture was concentrated in vacuo and the residue purified by reverse phase HPLC on a C18/40 g column (A: water 10 mM NH₄HCO₃, B: MeOH, 0~100%) to provide 2-(5-(2-(azetidin-1-yl)ethyl)-2-oxopyridin-1(2H)-yl)-4-methylpentanoic acid as red solid (150 mg). Yield 27% (ESI 293.2 (M+H)$^+$).

Preparation of 2-(5-(2-(3-fluoroazetidine-1-yl)ethyl)-2-oxopyridin-1(2H)-yl)-4-methylpentanoic Acid Step 1: 5-(2-(3-fluoroazetidine-1-yl)ethyl)pyridin-2(1H)-one

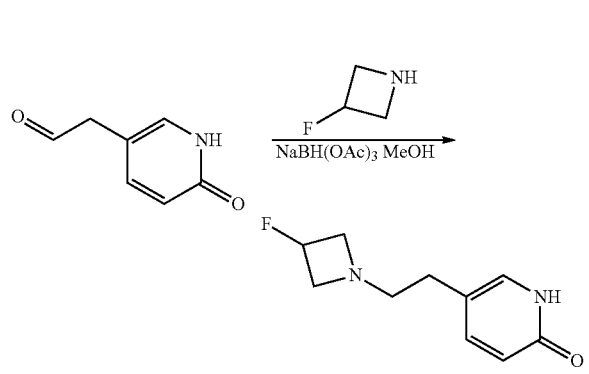

A mixture of 2-(6-oxo-1,6-dihydropyridin-3-yl)acetaldehyde (1.5 g, 11 mmol), AcOH (0.8 g, 13.2 mmol) and 3-fluoroazetidine hydrochloride (1.47 g, 13.2 mmol) in MeOH (30 mL) was stirred at room temperature for 30 mins. NaBH(OAc)₃ (4.66 g, 22 mmol) was added and stirred at room temperature for 3 hours. The solvent was removed in vacuo and the residue was purified by reverse phase HPLC on a C18/120 g column (A: water 10 mM NH₄HCO₃, B: MeOH, 0~100%) to provide 5-(2-(3-fluoroazetidine-1-yl)ethyl)pyridin-2(1H)-one as a yellow oil (2 g, crude). (ESI 197.2 (M+H)$^+$).

Step 2: Ethyl 2-(5-(2-(3-fluoroazetidine-1-yl)ethyl)-2-oxopyridin-1(2H)-yl)-4-methylpentanoate

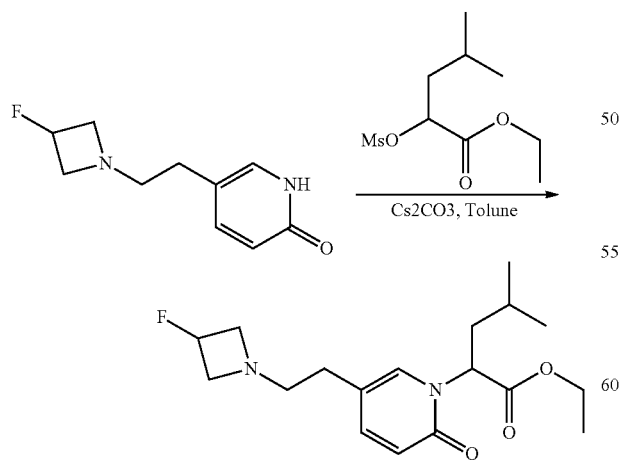

A mixture of 5-(2-(3-fluoroazetidine-1-yl)ethyl)pyridin-2(1H)-one (1.9 g, 9.7 mmol), ethyl 4-methyl-2-(methylsulfonyloxy)pentanoate (3.45 g, 14.5 mmol) and Cs₂CO₃ (9.5 g, 29.1 mmol) in toluene (40 mL) was stirred 110° C. overnight. The solvent was removed in vacuo and the residue purified by reverse phase HPLC on a C18/120 g column (A: water 10 mM NH₄HCO₃, B: MeOH, 0~100%) to provide ethyl 2-(5-(2-(3-fluoroazetidine-1-yl)ethyl)-2-oxopyridin-1(2H)-yl)-4-methylpentanoate as a yellow oil (650 mg). Yield 20% (ESI 339.1 (M+H)$^+$).

Step 3: 2-(5-(2-(3-fluoroazetidine-1-yl)ethyl)-2-oxopyridin-1(2H)-yl)-4-methylpentanoic Acid

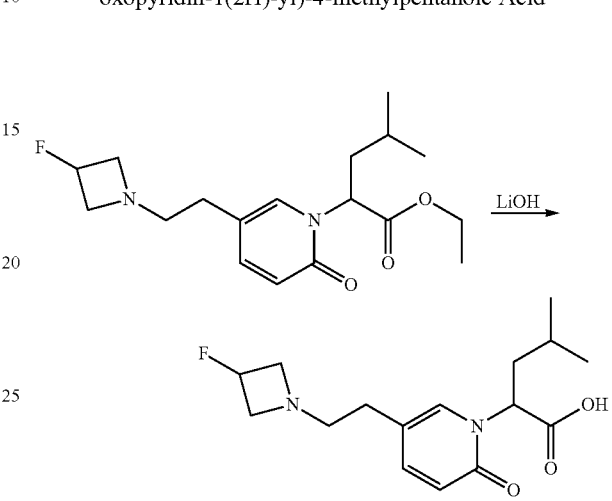

Ethyl 2-(5-(2-(3-fluoroazetidine-1-yl)ethyl)-2-oxopyridin-1(2H)-yl)-4-methylpentanoate (650 mg, 1.92 mmol) was treated with LiOH—H₂O (322 mg, 7.68 mmol) in MeOH (10 mL) and H₂O (2.5 mL) at room temperature for 2 hours. The mixture was acidified to pH 4~5 with 1N HCl, purified by reverse phase HPLC on a C18/40 g column (A: water 10 mM NH₄HCO₃, B: MeOH, 0~100%) to provide 2-(5-(2-(3-fluoroazetidine-1-yl)ethyl)-2-oxopyridin-1(2H)-yl)-4-methylpentanoic acid as a white solid (350 mg). Yield 59% (ESI 311.2 (M+H)$^+$).

Preparation of 3-cyclopropyl-2-(5-(2-(3-fluoroazetidine-1-yl)ethyl)-2-oxopyridin-1(2H)-yl)propanoic Acid Step 1: (S)-2-bromo-3-cyclopropylpropanoic Acid

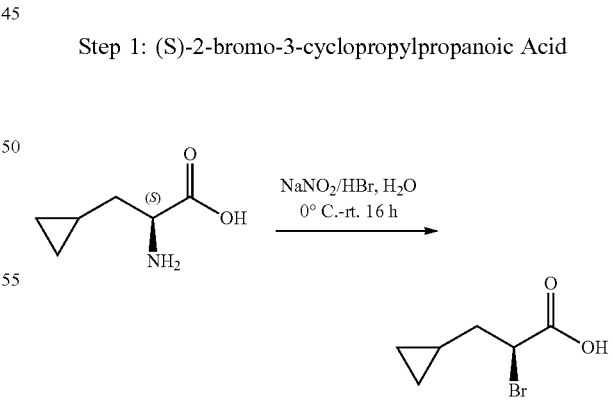

To a solution of (S)-2-amino-3-cyclopropylpropanoic acid (5.0 g, 38.7 mmol) in H₂O (50 mL) was added 40% HBr (60 mL). The reaction mixture was stirred at 0° C. for 10 min. A solution of sodium nitrite (4.5 g, 24 mmol) in H₂O (10 mL) was added. The reaction mixture was stirred at 0° C. for 30 min and warmed to room temperature overnight.

The reaction mixture was extracted with EtOAc (100 mL×3). The organic layer was washed with brine (100 mL) and dried over Na$_2$SO$_4$, filtered and concentrated in vacuo to provide (S)-2-bromo-3-cyclopropylpropanoic acid as a colorless oil used directly in the next reaction without further purification (5.0 g). Yield 74% (ESI 194 (M+H)$^+$).

Step 2: Ethyl (S)-2-bromo-3-cyclopropylpropanoate

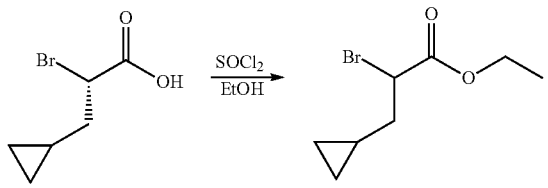

To a solution of (S)-2-bromo-3-cyclopropylpropanoic acid (1 g, 5.2 mmol) in EtOH (20 mL) was added SOCl$_2$ (1.8 g, 15.6 mmol) and stirred at ambient temperature for 2 hours. The solvent was removed in vacuo to provide ethyl 2-bromo-3-cyclopropylpropanoate as a white solid (1.2 g, crude) used directly in the next reaction. (ESI 221.0 (M+H)$^+$).

Step 3: Ethyl 3-cyclopropyl-2-(5-(2-(3-fluoroazetidine-1-yl)ethyl)-2-oxopyridin-1(2H)-yl)propanoate

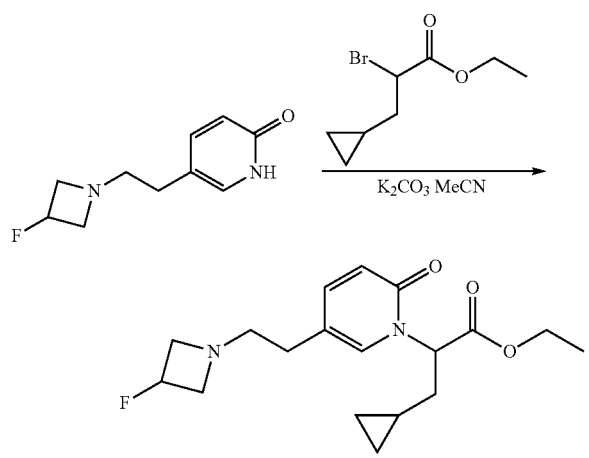

A mixture of ethyl 2-bromo-3-cyclopropylpropanoate (800 mg, 3.64 mmol), 5-(2-(3-fluoroazetidine-1-yl)ethyl)pyridin-2(1H)-one (1.07 g, 5.46 mmol) and K$_2$CO$_3$ (1.5 g, 10.92 mmol) in MeCN (10 mL) was stirred at 80° C. overnight. The mixture was filtered and washed with MeCN (10 mL). The filtrate was concentrated in vacuo and the residue was purified by silica gel column (petroleum ether:EtOAc 2:1) to provide ethyl 3-cyclopropyl-2-(5-(2-(3-fluoroazetidine-1-yl)ethyl)-2-oxopyridin-1(2H)-yl)propanoate as a colorless oil (400 mg). Yield 32% (ESI 337.2 (M+H)$^+$).

Step 4: 3-cyclopropyl-2-(5-(2-(3-fluoroazetidine-1-yl)ethyl)-2-oxopyridin-1(2H)-yl)propanoic acid

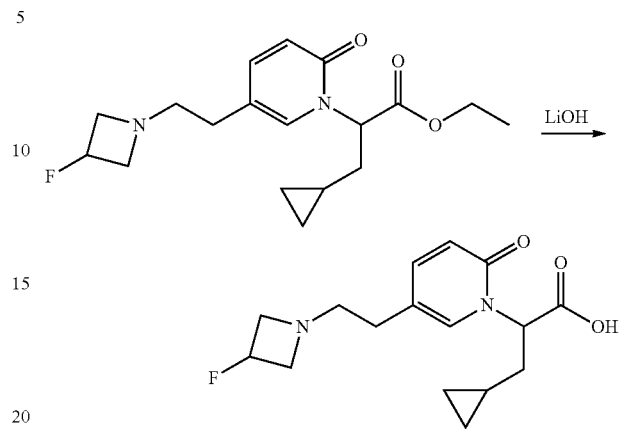

Ethyl 3-cyclopropyl-2-(5-(2-(3-fluoroazetidine-1-yl)ethyl)-2-oxopyridin-1(2H)-yl)propanoate (400 mg, 1.20 mmol) was treated with LiOH—H$_2$O (201 mg, 4.80 mmol) in EtOH (4 mL) and H$_2$O (1 mL) at room temperature for 2 hours. The mixture was acidified to pH 4-5 with 1N HCl. The mixture was concentrated in vacuo and the residue was purified by silica gel column (DCM:MeOH 10:1) to provide 3-cyclopropyl-2-(5-(2-(3-fluoroazetidine-1-yl)ethyl)-2-oxopyridin-1(2H)-yl)propanoic acid as a white solid (310 mg). Yield 85% (ESI 309.15 (M+H)$^+$).

Preparation of 2-(5-(2-((R)-3-fluoropyrrolidin-1-yl)ethyl)-2-oxopyridin-1(2H)-yl)-4-methylpentanoic Acid Step 1: Ethyl 2-(5-bromo-2-oxopyridin-1(2H)-yl)-4-methylpentanoate

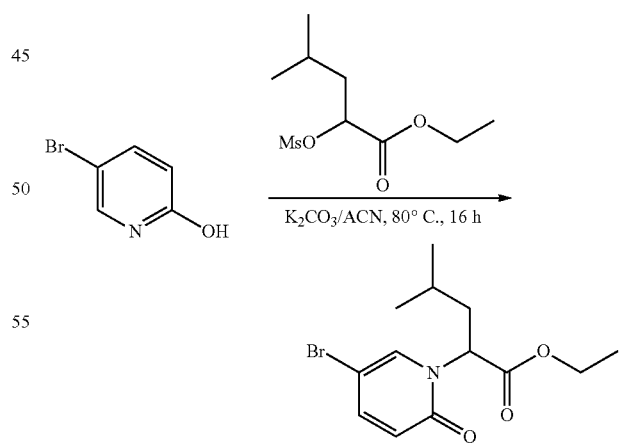

A mixture of 5-bromopyridin-2-ol (12.0 g, 69.0 mmol), K$_2$CO$_3$ (19.1 g, 138.0 mmol) and ethyl 4-methyl-2-(methylsulfonyloxy)pentanoate (18.5 g, 77.7 mmol) in CH$_3$CN (230 mL) was stirred at 80° C. overnight. The solvent was concentrated in vacuo and the residue was purified by silica gel column (pet ether:EtOAc 1:2) to provide ethyl 2-(5- bromo-2-oxopyridin-1(2H)-yl)-4-methylpentanoate as a yellow oil (13.0 g). Yield 60% (ESI 316.0 (M+H)+).

Step 2: Ethyl 2-(5-allyl-2-oxopyridin-1(2H)-yl)-4-methylpentanoate

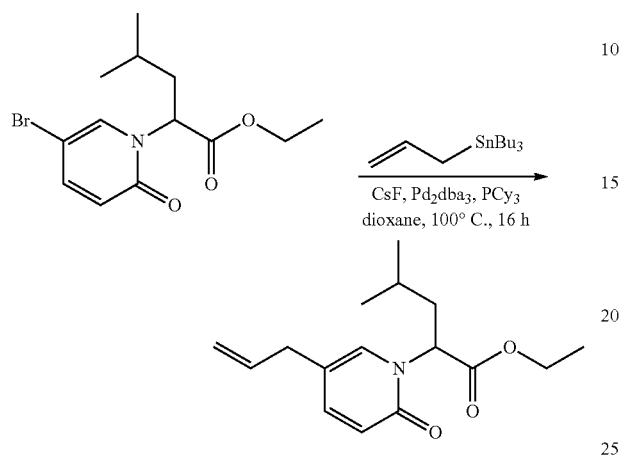

A mixture of ethyl 2-(5-bromo-2-oxopyridin-1(2H)-yl)-4-methylpentanoate (13.0 g, 41.1 mmol), allyltributylstannane (14.9 g, 45.1 mmol), Pd$_2$dba$_3$ (1.8 g, 2.06 mmol), PCy$_3$ (1.1 g, 4.11 mmol) and CsF (12.5 g, 82.2 mmol) in anhydrous dioxane (50 mL) was stirred under N$_2$ at 100° C. for 16 h. The mixture was cooled to room temperature and quenched with saturated NH$_4$Cl solution (100 mL) and extracted with EtOAc (100 mL). The aqueous layer was extracted with EtOAc (200 mL×2). The combined organic layers were washed with brine (100 mL), dried over anhydrous Na$_2$SO$_4$, filtered and concentrated in vacuo. The residue was purified by silica gel column (pet ether:EtOAc 19:1) to provide ethyl 2-(5-allyl-2-oxopyridin-1(2H)-yl)-4-methylpentanoate as a yellow solid (7.1 g). Yield 62% (ESI 278.1 (M+H)+).

Step 3: Ethyl 4-methyl-2-(2-oxo-5-(2-oxoethyl)pyridin-1(2H)-yl)pentanoate

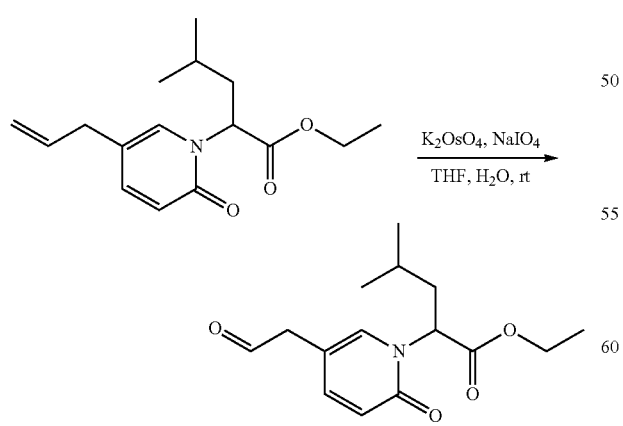

To a solution of ethyl 2-(5-allyl-2-oxopyridin-1(2H)-yl)-4-methylpentanoate (7.1 g, 25.6 mmol) in THF/H$_2$O (80 mL/30 mL) was added a solution of K$_2$OsO$_4$·2H$_2$O (94.0 mg, 0.26 mmol) in H$_2$O (4 mL) and stirred at room temperature for 1 h. A solution of NaIO$_4$ (10.8 g, 51.2 mmol) in H$_2$O (20 mL) was added and stirred at room temperature for 2 h. LCMS showed the reaction was completed. The reaction mixture was diluted with 100 mL of water and extracted with EtOAc (120 mL×3). The combined organic phase was dried over anhydrous Na$_2$SO$_4$, filtered and concentrated in vacuo to give the crude product ethyl 4-methyl-2-(2-oxo-5-(2-oxoethyl)pyridin-1(2H)-yl)pentanoate as a yellow oil (7.0 g, crude) used directly in the next reaction without further purification. (ESI 280.3 (M+H)+).

Step 4: Ethyl 2-(5-(2-((R)-3-fluoropyrrolidin-1-yl)ethyl)-2-oxopyridin-1(2H)-yl)-4-methylpentanoate

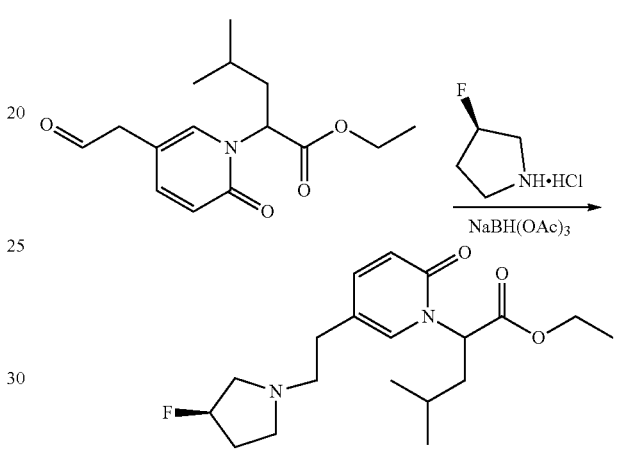

To a mixture of ethyl 4-methyl-2-(2-oxo-5-(2-oxoethyl)pyridin-1(2H)-yl)pentanoate (7.0 g, 25.0 mmol) in DCE (70 mL) at 25° C. was added (R)-3-fluoropyrrolidine hydrochloride (2.7 g, 25.0 mmol) and stirred at 25° C. for 30 mins. Then NaBH(OAc)$_3$ (10.6 g, 50.0 mmol) was added at 5° C. and stirred at 25° C. for 16 hours. The mixture was concentrated in vacuo and the residue was purified by silica gel column (DCM:MeOH 19:1) to give compound ethyl 2-(5-(2-((R)-3-fluoropyrrolidin-1-yl)ethyl)-2-oxopyridin-1(2H)-yl)-4-methylpentanoate (1.3 g) as a yellow oil. Yield: 15% (ESI 353.2 (M+H)+).

Step 5: 2-(5-(2-((R)-3-fluoropyrrolidin-1-yl)ethyl)-2-oxopyridin-1(2H)-yl)-4-methylpentanoic Acid

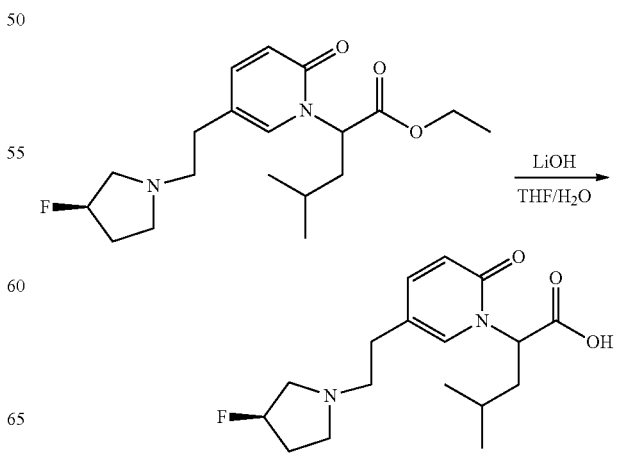

Ethyl 2-(5-(2-((R)-3-fluoropyrrolidin-1-yl)ethyl)-2-oxopyridin-1(2H)-yl)-4-methylpentanoate (1.3 g, 3.69 mmol) was treated with LiOH—H$_2$O (775.0 mg, 18.4 mmol) in MeOH (12 mL) and water (5 mL) at room temperature for 2 hours. The MeOH was removed in vacuo, acidified with 1N HCl to pH=5. The residue was purified by reverse phase HPLC on a C18/120 g column (A: water, B: MeOH, 0~100%) to provide 2-(5-(2-((R)-3-fluoropyrrolidin-1-yl)ethyl)-2-oxopyridin-1(2H)-yl)-4-methylpentanoic acid as a white solid (1.03 g). Yield 86% (ESI 325.1 (M+H)$^+$).

Preparation of 2-(5-(2-(dimethylamino)ethyl)-4-methyl-2-oxopyridin-1(2H)-yl)-4-methylpentanoic Acid Step 1: (E)-2-methoxy-5-(2-methoxyvinyl)-4-methylpyridine

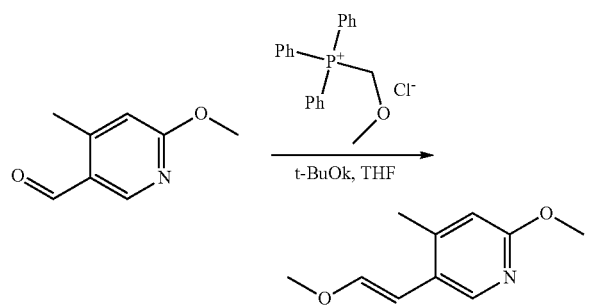

A mixture of (methoxymethyl)triphenyl phosphonium chloride (8.5 g, 24.8 mmol) and t-BuOK (4.6 g, 41.3 mmol) in THF (40 mL) was stirred at room temperature for 20 mins. 6-methoxy-4-methylnicotinaldehyde (2.5 g, 16.5 mmol) in 10 mL of THF was added and the mixture stirred at room temperature for 2 hours. The reaction mixture was poured into 40 mL of water and extracted with EtOAc (50 mL×2). The organic phase was concentrated in vacuo and the residue purified by reverse phase HPLC on a C18/40 g column (A: water 10 mM NH$_4$HCO$_3$, B: MeOH, 0~100%) to provide (E)-2-methoxy-5-(2-methoxyvinyl)-4-methylpyridine as a colorless oil (1.8 g). Yield 61% (ESI 180.1 (M+H)$^+$).

Step 2: 2-(6-methoxy-4-methylpyridin-3-yl)acetaldehyde

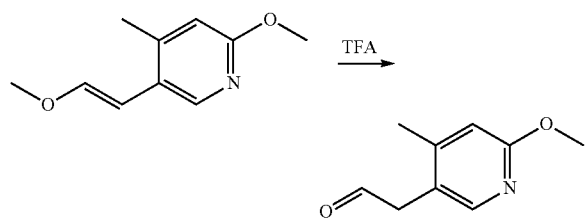

(E)-2-methoxy-5-(2-methoxyvinyl)-4-methylpyridine (1.8 g, 10 mmol) was treated with TFA (20 mL) at room temperature for 4 hours. The solvent was removed in vacuo to provide 2-(6-methoxy-4-methylpyridin-3-yl)acetaldehyde as a red oil (1.5 g, crude) used without further purification. (ESI 166.1 (M+H)$^+$).

Step 3: 2-(6-methoxy-4-methylpyridin-3-yl)-N,N-dimethylethanamine

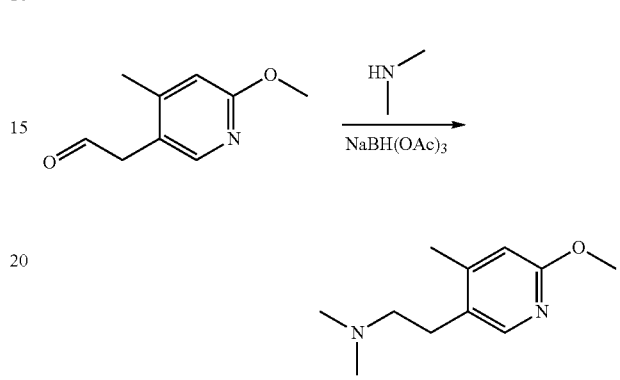

A mixture of 2-(6-methoxy-4-methylpyridin-3-yl)acetaldehyde (1.45 g, 8.78 mmol), dimethylamine (2M in THF, 17.5 mL, 35.72 mmol) and AcOH (0.8 g, 13.2 mmol) in DCE (30 mL) was stirred at room temperature for 15 mins. NaBH(OAc)$_3$ (3.71 g, 17.5 mmol) was added and stirred at room temperature for 3 hours. The solvent was removed in vacuo and the residue purified by silica gel column (DCM: MeOH 10:1) to provide 2-(6-methoxy-4-methylpyridin-3-yl)-N,N-dimethylethanamine as a yellow oil (850 mg). Yield 50% (ESI 195.1 (M+H)$^+$).

Step 4: 5-(2-(dimethylamino)ethyl)-4-methylpyridin-2-ol

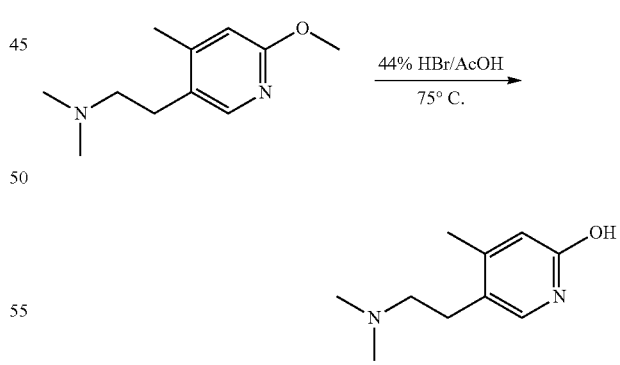

A mixture of 2-(6-methoxy-4-methylpyridin-3-yl)-N,N-dimethylethylamine (850 mg, 4.38 mmol) in HBr/AcOH (20 mL) was heated at 75° C. for 16 h. The solvent was removed in vacuo and the residue purified by reverse phase HPLC on a C18/40 g column (A: water 10 mM NH$_4$HCO$_3$, B: MeOH, 0~100%) to provide 5-(2-(dimethylamino)ethyl)-4-methylpyridin-2-ol as a red solid (650 mg). Yield 82% (ESI 181.1 (M+H)$^+$).

Step 5: Ethyl 2-(5-(2-(dimethylamino)ethyl)-4-methyl-2-oxopyridin-1(2H)-yl)-4-methylpentanoate

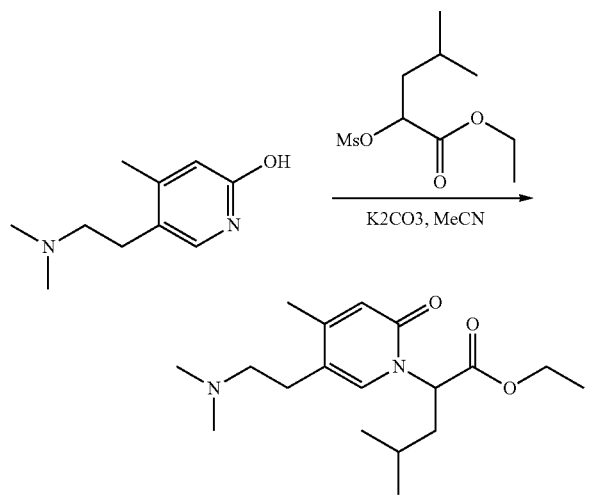

A mixture of 5-(2-(dimethylamino)ethyl)-4-methylpyridin-2-ol (650 g, 3.6 mmol), ethyl 4-methyl-2-(methylsulfonyloxy)pentanoate (1.71 g, 7.2 mmol) and K$_2$CO$_3$ (1.49 g, 10.8 mmol) in MeCN (20 mL) was stirred at 80° C. overnight. The solvent was removed in vacuo and the residue purified by reverse phase HPLC on a C18/40 g column (A: water 10 mM NH$_4$HCO$_3$, B: MeOH, 0~100%) to provide ethyl 2-(5-(2-(dimethylamino)ethyl)-4-methyl-2-oxopyridin-1(2H)-yl)-4-methylpentanoate (500 mg). Yield 43% (ESI 323.2 (M+H)$^+$).

Step 6: 2-(5-(2-(dimethylamino)ethyl)-4-methyl-2-oxopyridin-1(2H)-yl)-4-methylpentanoic acid

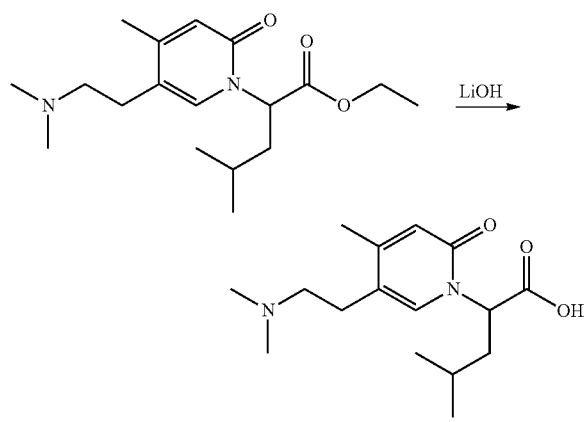

Ethyl 2-(5-(2-(dimethylamino)ethyl)-4-methyl-2-oxopyridin-1(2H)-yl)-4-methylpentanoate (500 mg, 1.55 mmol) was treated with LiOH—H$_2$O (260 mg, 6.2 mmol) in MeOH (10 mL) and H$_2$O (2 mL) at room temperature for 2 hours. The mixture was acidified to pH 4~5 with 1N HCl and purified by reverse phase HPLC on a C18/40 g column (A: water 10 mM NH$_4$HCO$_3$, B: MeOH, 0~100%) to provide 2-(5-(2-(dimethylamino)ethyl)-4-methyl-2-oxopyridin-1(2H)-yl)-4-methylpentanoic acid as a white solid (420 mg). Yield 92% (ESI 295.2 (M+H)$^+$).

Preparation of 2-(5-(2-(dimethylamino)ethyl)-4-methyl-2-oxopyridin-1(2H)-yl)-5-methylhexanoic Acid

Step 1: (R)-2-bromo-5-methylhexanoic Acid

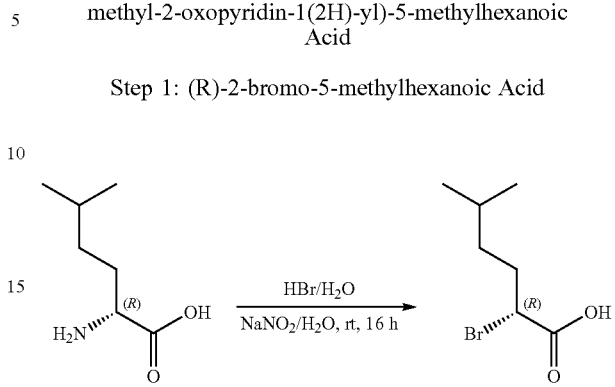

To a mixture of (R)-2-amino-5-methylhexanoic acid (30 g, 207 mmol) in 40% HBr (200 mL) and H$_2$O (200 mL) at 0° C. was added a solution of NaNO$_2$ (17 g, 248 mmol) in H$_2$O (15 mL) dropwise. The mixture was stirred at room temperature overnight. The mixture was extracted with DCM (200 mL). The organic phase was washed with brine (200 mL), dried over Na$_2$SO$_4$, concentrated in vacuo to provide (R)-2-bromo-5-methylhexanoic acid as a yellow oil (30 g). Yield 70% (ESI 211.1 (M+H)$^+$).

Step 2: Ethyl 2-bromo-5-methylhexanoate

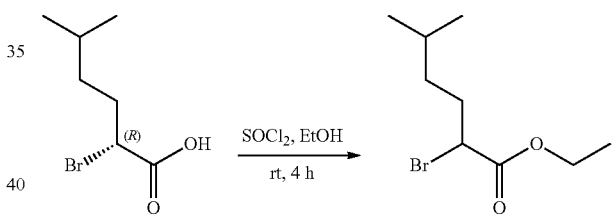

To a mixture of (R)-2-bromo-5-methylhexanoic acid (30 g, 144 mmol) in EtOH (200 mL) at 0° C. was added SOCl$_2$ (86 g, 720 mmol). The mixture was stirred for 4 h at room temperature. The solvent was removed in vacuo to provide ethyl 2-bromo-5-methylhexanoate as a colorless oil (35 g, crude). (ESI 239.1 (M+H)$^+$).

Step 3: Ethyl 2-(5-bromo-4-methyl-2-oxopyridin-1(2H)-yl)-5-methylhexanoate

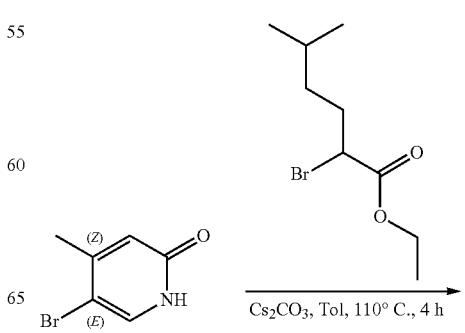

289
-continued

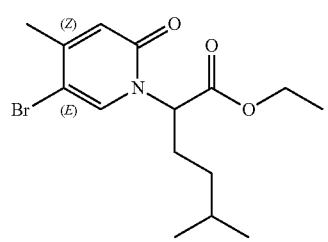

A mixture of 5-bromo-4-methylpyridin-2(1H)-one (8 g, 42.78 mmol), Cs$_2$CO$_3$ (27.9 g, 85.56 mmol) and ethyl 2-bromo-5-methylhexanoate (15 g, 64.17 mmol) in toluene (160 mL) was stirred at 110° C. for 4 hours. The solvent was concentrated in vacuo and the residue was purified by silica gel column (pet ether:EtOAc 4:1) to provide ethyl 2-(5-bromo-4-methyl-2-oxopyridin-1(2H)-yl)-5-methylhexanoate as a colorless oil (6.5 g). Yield 44% (ESI 346.1 (M+H)$^+$).

Step 4: (E)-ethyl 2-(5-(2-ethoxyvinyl)-4-methyl-2-oxopyridin-1(2H)-yl)-5-methylhexanoate

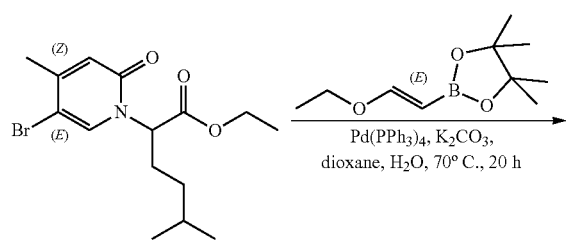

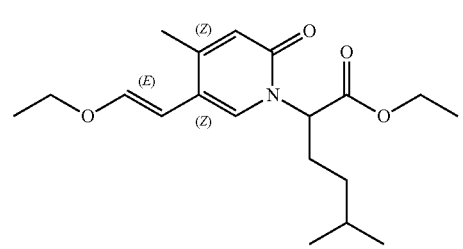

A mixture of ethyl 2-(5-bromo-4-methyl-2-oxopyridin-1(2H)-yl)-5-methylhexanoate (5.4 g, 15.7 mmol), (E)-2-(2-ethoxyvinyl)-4,4,5,5-tetramethyl-1,3,2-dioxaborolane (6.22 g, 31.4 mmol), Pd(PPh$_3$)$_4$ (912 mg, 0.79 mmol) and K$_2$CO$_3$ (4.33 g, 31.4 mmol) in 1,4-dioxane (70 mL) and water (7 mL) was stirred at 70° C. under N$_2$ for 20 h. The reaction mixture was diluted with 100 mL of water, extracted with EtOAc (100 mL×2). The combined organic phase was washed with brine (150 mL), dried over anhydrous Na$_2$SO$_4$, filtered and concentrated in vacuo. The residue was purified by silica gel column (pet ether:EtOAc 1:1) to provide (E)-ethyl 2-(5-(2-ethoxyvinyl)-4-methyl-2-oxopyridin-1(2H)-yl)-5-methylhexanoate (3.8 g) as a yellow oil. Yield 72% (ESI 336.2 (M+H)$^+$).

290

Step 5: Ethyl 5-methyl-2-(4-methyl-2-oxo-5-(2-oxoethyl)pyridin-1(2H)-yl)hexanoate

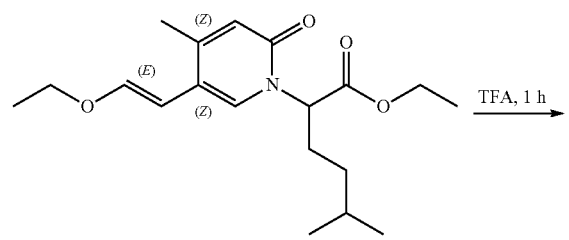

(E)-ethyl 2-(5-(2-ethoxyvinyl)-4-methyl-2-oxopyridin-1(2H)-yl)-5-methylhexanoate (3.8 g, 11.34 mmol) was treated with TFA (40 mL) at room temperature for 1 hour. The solvent was removed in vacuo and the residue was purified by silica gel column (EtOAc) to provide ethyl 5-methyl-2-(4-methyl-2-oxo-5-(2-oxoethyl)pyridin-1(2H)-yl)hexanoate as a colorless oil (2 g). Yield 57% (ESI 308.2 (M+H)$^+$).

Step 6: Ethyl 2-(5-(2-(dimethylamino)ethyl)-4-methyl-2-oxopyridin-1(2H)-yl)-5-methylhexanoate

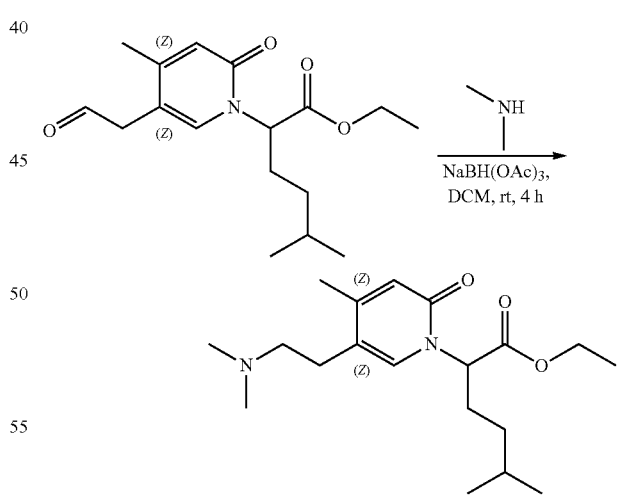

To a mixture of ethyl 5-methyl-2-(4-methyl-2-oxo-5-(2-oxoethyl)pyridin-1(2H)-yl)hexanoate (2 g, 6.51 mmol) in DCM (30 mL) was added dimethylamine (2 M) (6.5 mL, 13.02 mmol) and stirred at room temperature for 20 minutes. Then NaBH(OAc)$_3$ (2.76 g, 13.02 mmol) was added and stirred at room temperature for 4 h. The solvent was removed in vacuo and the residue was purified by silica gel column (DCM:MeOH 10:1) to provide ethyl 2-(5-(2-(dimethylamino)ethyl)-4-methyl-2-oxopyridin-1(2H)-yl)-5-methylhexanoate as a colorless oil (1.4 g). Yield 64% (ESI 337.3 (M+H)⁺).

Step 7: 2-(5-(2-(dimethylamino)ethyl)-4-methyl-2-oxopyridin-1(2H)-yl)-5-methylhexanoic acid

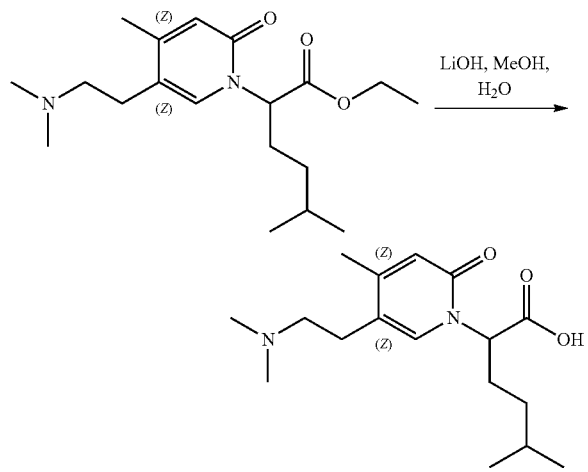

Ethyl 2-(5-(2-(dimethylamino)ethyl)-4-methyl-2-oxopyridin-1(2H)-yl)-5-methylhexanoate (1.4 g, 4.17 mmol) was treated with LiOH—H₂O (700 mg, 16.68 mmol) in MeOH (20 mL) and H₂O (4 mL) at room temperature for 2 hours. The reaction mixture was acidified to pH 4~5 with 1 N HCl. The solvent was removed in vacuo and the residue was purified by reverse phase HPLC on a C18/40 g column (A: water 10 mM NH₄HCO₃, B: MeOH, 0~100%) to provide 2-(5-(2-(dimethylamino)ethyl)-4-methyl-2-oxopyridin-1(2H)-yl)-5-methylhexanoic acid (900 mg) as a white solid. Yield 70% (ESI 309.2 (M+H)⁺).

Preparation of 2-(5-(2-(3-fluoroazetidine-1-yl)ethyl)-4-methyl-2-oxopyridin-1(2H)-yl)-4-methylpentanoic Acid Step 1: 5-(2-(3-fluoroazetidine-1-yl)ethyl)-4-methylpyridin-2-ol

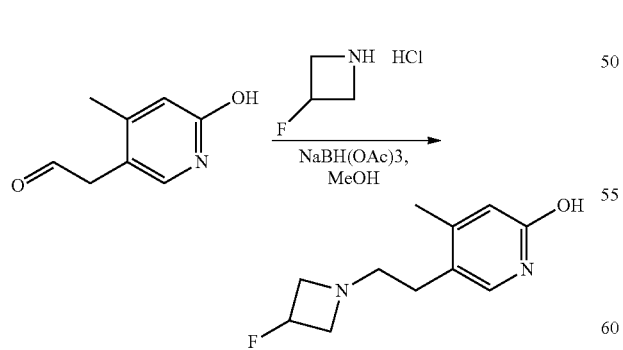

A mixture of 2-(6-hydroxy-4-methylpyridin-3-yl)acetaldehyde (2 g, 13.2 mmol), 3-fluoroazetidine hydrochloride (2.2 g, 19.8 mmol) in MeOH (20 mL) was stirred at room temperature for 30 mins. NaBH(OAc)₃ (5.6 g, 26.4 mmol) was added and stirred at room temperature for 2 hours. The solvent was removed in vacuo and the residue was purified by silica gel column (DCM:MeOH 2:1) to provide 5-(2-(3-fluoroazetidine-1-yl)ethyl)-4-methylpyridin-2-ol as a yellow oil (1 g). Yield 36% (ESI 211.1 (M+H)⁺).

Step 2: Ethyl 2-(5-(2-(3-fluoroazetidine-1-yl)ethyl)-4-methyl-2-oxopyridin-1(2H)-yl)-4-methylpentanoate

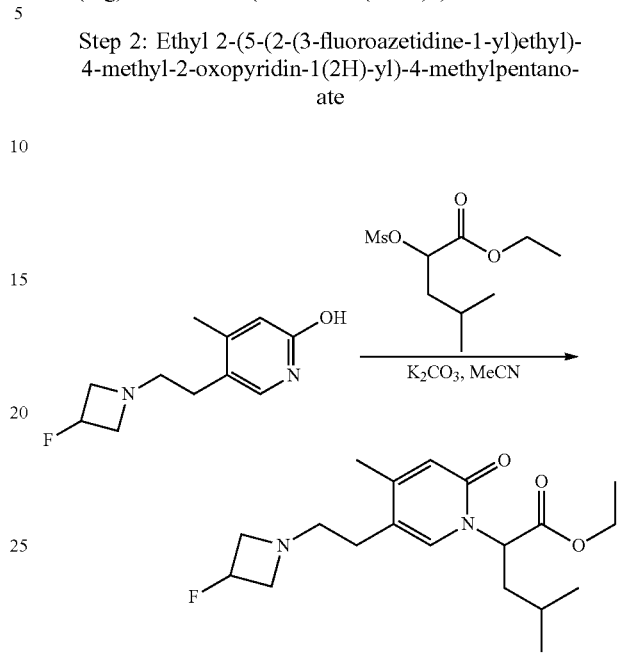

A mixture of methyl 5-(2-(dimethylamino)ethyl)pyridin-2(1H)-one (1 g, 4.76 mmol), ethyl 4-methyl-2-(methylsulfonyloxy)pentanoate (1.36 g, 5.71 mmol) and K₂CO₃ (1.97 g, 14.28 mmol) in MeCN (20 mL) was stirred at 85° C. overnight. The solvent was removed in vacuo and the residue purified by silica gel column (DCM:MeOH 1:2) to provide ethyl 2-(5-(2-(3-fluoroazetidine-1-yl)ethyl)-4-methyl-2-oxopyridin-1(2H)-yl)-4-methylpentanoate as a white solid (500 mg). Yield 30% (ESI 353.2 (M+H)⁺).

Step 3: 2-(5-(2-(3-fluoroazetidine-1-yl)ethyl)-4-methyl-2-oxopyridin-1(2H)-yl)-4-methylpentanoic Acid

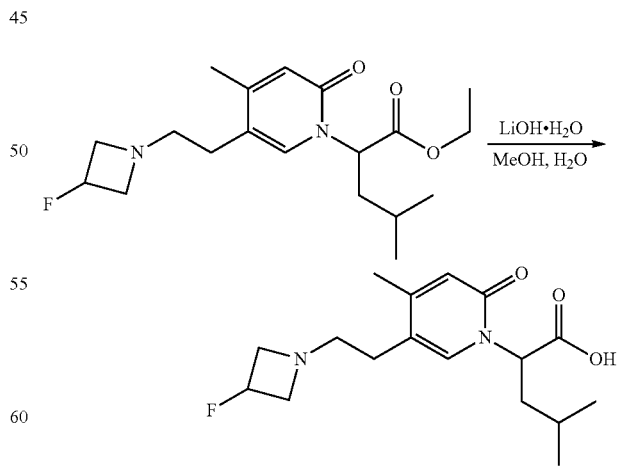

Ethyl 2-(5-(2-(3-fluoroazetidine-1-yl)ethyl)-4-methyl-2-oxopyridin-1(2H)-yl)-4-methylpentanoate (500 mg, 1.42 mmol) was treated with LiOH—H₂O (298 mg, 7.1 mmol) in MeOH (10 mL) and H₂O (2.5 mL) at room temperature for 2 hours. The mixture was acidified to pH 4~5 with 1N HCl, purified by reverse phase HPLC on a C18/40 g column (A: water 10 mM NH₄HCO₃, B: MeOH, 0~100%) to give 2-(5-(2-(3-fluoroazetidine-1-yl)ethyl)-4-methyl-2-oxopyridin-1(2H)-yl)-4-methylpentanoic acid as a white solid (360 mg). Yield 78% (ESI 325.1 (M+H)⁺).

Preparation of 2-(5-(2-((R)-3-fluoropyrrolidin-1-yl)ethyl)-4-methyl-2-oxopyridin-1(2H)-yl)-4-methylpentanoic Acid Step 1: Ethyl 2-(5-allyl-4-methyl-2-oxopyridin-1(2H)-yl)-4-methylpentanoate

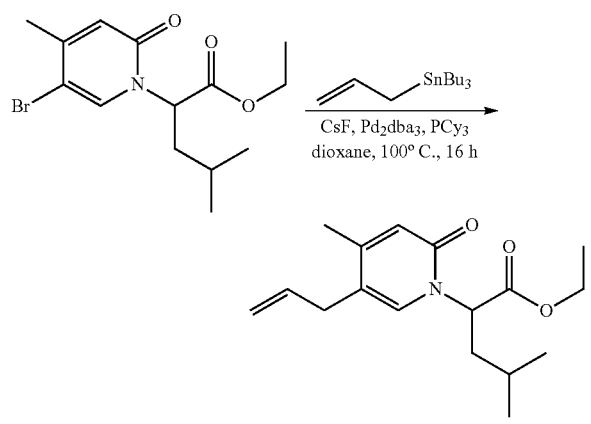

A mixture of ethyl 2-(5-bromo-4-methyl-2-oxopyridin-1(2H)-yl)-4-methylpentanoate (2.9 g, 8.78 mmol), allyltributylstannane (3.5 g, 10.54 mmol), Pd₂dba₃ (402 mg, 0.44 mmol), PCy₃ (247 mg, 0.88 mmol) and CsF (2.7 g, 17.56 mmol) in anhydrous dioxane (100 mL) was stirred at 100° C. for 16 h. The mixture was cooled to room temperature. The mixture was filtered and washed with dioxane (20 mL). The filtrate was concentrated in vacuo and the residue was purified by silica gel column (pet ether:EtOAc 3:1) to provide ethyl 2-(5-allyl-4-methyl-2-oxopyridin-1(2H)-yl)-4-methylpentanoate as a yellow oil (1.6 g). Yield 60% (ESI 292 (M+H)⁺).

Step 2: Ethyl 4-methyl-2-(4-methyl-2-oxo-5-(2-oxoethyl)pyridin-1(2H)-yl)pentanoate

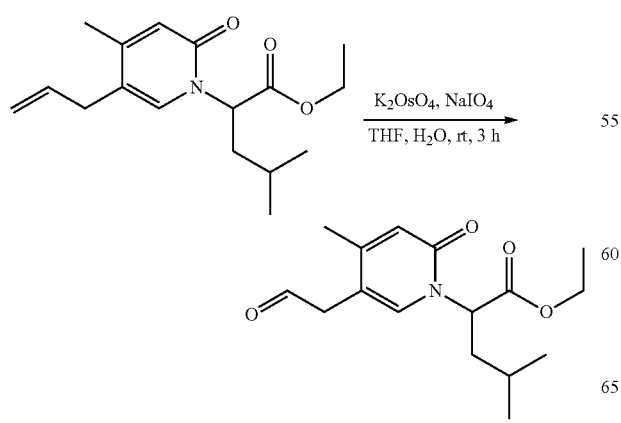

To a solution of ethyl 2-(5-allyl-4-methyl-2-oxopyridin-1(2H)-yl)-4-methylpentanoate (1.6 g, 5.49 mmol) in THF/H₂O (20 mL/10 mL) was added a solution of K₂OsO₄·2H₂O (20 mg, 0.055 mmol) in H₂O (1 mL) dropwise and stirred at room temperature for 1 h. A solution of NaIO₄ (2.3 g, 10.98 mmol) in H₂O (5 mL) was added dropwise and stirred at room temperature for 3 h. LCMS showed the reaction was completed. The reaction mixture was diluted with water (40 mL) and extracted with EtOAc (50 mL×3). The combined organic phase was dried over anhydrous Na₂SO₄, filtered and concentrated in vacuo to provide ethyl 4-methyl-2-(4-methyl-2-oxo-5-(2-oxoethyl)pyridin-1(2H)-yl)pentanoate as a brown oil which was used in next step without further purification. (ESI 294 (M+H)⁺).

Step 3: Ethyl 2-(5-(2-((R)-3-fluoropyrrolidin-1-yl)ethyl)-4-methyl-2-oxopyridin-1(2H)-yl)-4-methylpentanoate

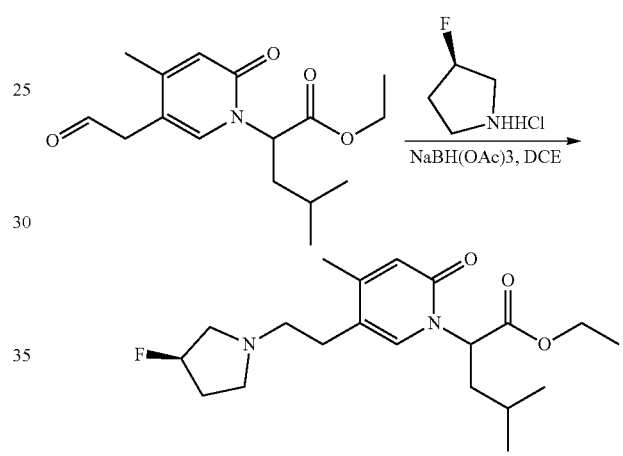

A mixture of ethyl 4-methyl-2-(4-methyl-2-oxo-5-(2-oxoethyl)pyridin-1(2H)-yl)pentanoate (950 mg, 3.24 mmol) and (R)-3-fluoropyrrolidine hydrochloride (814 mg, 6.48 mmol) in DCE (20 mL) was stirred at room temperature for 1 h. Then NaBH(OAc)₃ (2.1 g, 9.72 mmol) was added and stirred at room temperature for 2 h. The mixture was concentrated in vacuo and the residue was purified by reverse phase HPLC on a C18/40 g column (A: water/10 mM NH₄HCO₃, B: MeOH, 0~100%) to provide ethyl 2-(5-(2-((R)-3-fluoropyrrolidin-1-yl)ethyl)-4-methyl-2-oxopyridin-1(2H)-yl)-4-methylpentanoate as a yellow oil (550 mg). Yield 46% (ESI 367 (M+H)⁺).

Step 4: 2-(5-(2-((R)-3-fluoropyrrolidin-1-yl)ethyl)-4-methyl-2-oxopyridin-1(2H)-yl)-4-methylpentanoic Acid

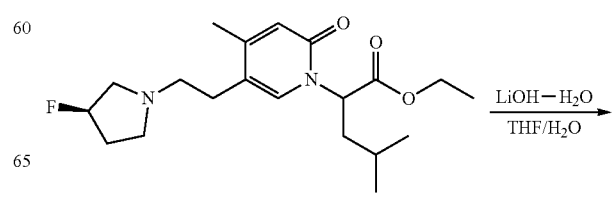

-continued

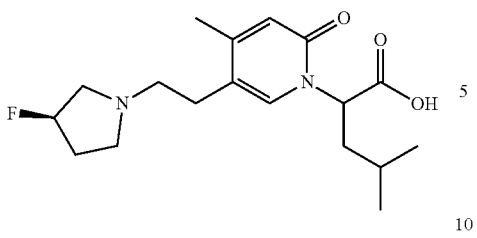

Ethyl 2-(5-(2-((R)-3-fluoropyrrolidin-1-yl)ethyl)-4-methyl-2-oxopyridin-1(2H)-yl)-4-methylpentanoate (550 mg, 1.50 mmol) was treated with LiOH—H₂O (120 mg, 4.50 mmol) in THF (6 mL) and water (2 mL) at room temperature for 2 hours. The reaction was acidified with 1N HCl to pH=8. The solvent was removed in vacuo and the residue was purified by reverse phase HPLC on a C18/40 g column (A: water/10 mM NH₄HCO₃, B: MeOH, 0~100%) to provide 2-(5-(2-((R)-3-fluoropyrrolidin-1-yl)ethyl)-4-methyl-2-oxopyridin-1(2H)-yl)-4-methylpentanoic acid as a white solid (270 mg). Yield 53% (ESI 339 (M+H)⁺).

Preparation of 2-(5-(2-(azetidin-1-yl)ethyl)-2-oxo-4-(trifluoromethyl)pyridin-1(2H)-yl)-4-methylpentanoic Acid Step 1: (E)-2-methoxy-5-(2-methoxyvinyl)-4-(trifluoromethyl)pyridine

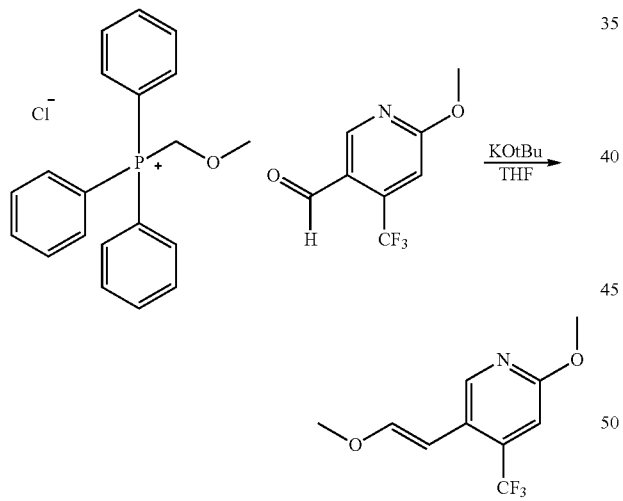

To a solution of (methoxymethyl)triphenylphosphonium chloride (1.0 g, 2.95 mmol) in THF (13.406 mL) at 0° C. was added potassium tert-butoxide (376 mg, 3.35 mmol). After stirring for 1 hour at 0° C., a solution of 6-methoxy-4-(trifluoromethyl)nicotinaldehyde (550 mg, 2.68 mmol) in THF (6.5 mL) was added. The reaction was allowed to stir overnight at room temperature and quenched with a NH₄Cl solution. The mixture was extracted (EtOAc×3), concentrated and purified by silica gel chromatography (0-100 Ethyl acetate:Hexanes) to provide (E)-2-methoxy-5-(2-methoxyvinyl)-4-(trifluoromethyl)pyridine (450 mgs). Yield 72% (ESI 234.2 (M+H)⁺).

Step 2: 2-(6-methoxy-4-(trifluoromethyl)pyridin-3-yl)acetaldehyde

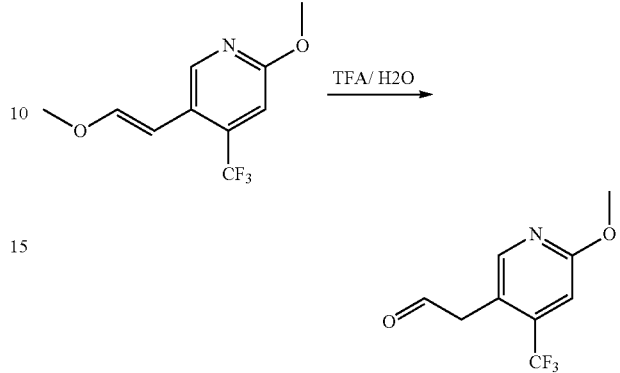

To a solution of (E)-2-methoxy-5-(2-methoxyvinyl)-4-(trifluoromethyl)pyridine (450 mg, 1.930 mmol) in DCM (29.689 mL) was added TFA (0.595 mL, 7.72 mmol) and water (0.591 mL, 32.8 mmol). The reaction was stirred for 18 hrs at 45° C. The reaction was diluted with DCM and quenched with NaHCO₃. The mixture was washed with water, dried with Na₂SO₄, filtered and concentrated to provide 2-(6-methoxy-4-(trifluoromethyl)pyridin-3-yl)acetaldehyde (343 mgs) used without further purification. Yield 81% (ESI 220.18 (M+H)⁺).

Step 3: 5-(2-(azetidin-1-yl)ethyl)-2-methoxy-4-(trifluoromethyl)pyridine

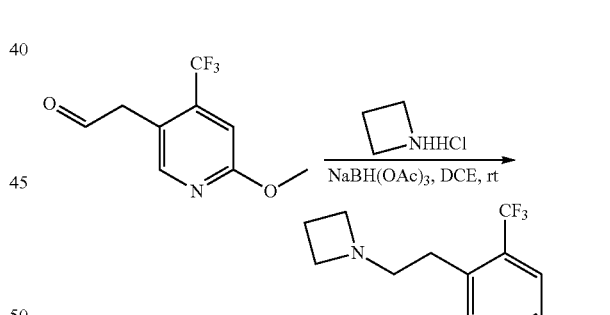

To a solution of 2-(6-methoxy-4-(trifluoromethyl)pyridin-3-yl)acetaldehyde (4 g, 18.1 mmol) in DCE (50 mL) was added azetidine hydrochloride (3.4 g, 36.2 mmol). The reaction mixture was stirred at room temperature for 20 mins. NaBH(OAc)₃ (7.7 g, 36.2 mmol) was added and stirred at room temperature for 16 hours. The reaction mixture was quenched by addition of MeOH (20 mL) and filtered. The filtrate was concentrated in vacuo and the residue was purified by reverse phase HPLC on a C18/80 g column (A: water 10 mM NH₄HCO₃, B: MeOH, 0~100%) to provide 5-(2-(azetidin-1-yl)ethyl)-2-methoxy-4-(trifluoromethyl)pyridine as a yellow oil (3 g). Yield 63% (ESI 261.2 (M+H)⁺).

Step 4: 5-(2-(azetidin-1-yl)ethyl)-4-(trifluoromethyl)pyridin-2(1H)-one

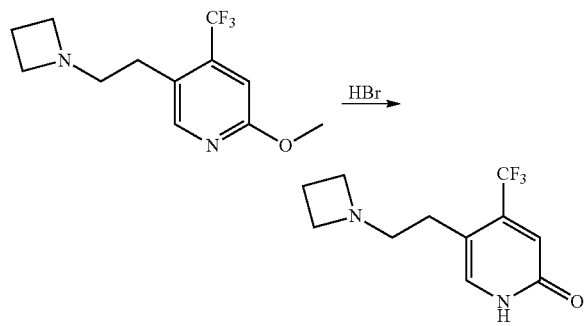

A mixture of 5-(2-(azetidin-1-yl)ethyl)-2-methoxy-4-(trifluoromethyl)pyridine (2.95 g, 11.3 mmol) in HBr/AcOH (20 mL) was stirred at 50° C. for 5 h. The reaction mixture was concentrated in vacuo and the residue was purified by reverse phase HPLC on a C18/80 g column (A: water 10 mM $NH_4HCO_3$, B: MeOH, 0~100%) to provide 5-(2-(azetidin-1-yl)ethyl)-4-(trifluoromethyl)pyridin-2(1H)-one as a yellow oil (710 mg). Yield 25% (ESI 247.1 $(M+H)^+$).

Step 5: Ethyl 2-(5-(2-(azetidin-1-yl)ethyl)-2-oxo-4-(trifluoromethyl)pyridin-1(2H)-yl)-4-methylpentanoate

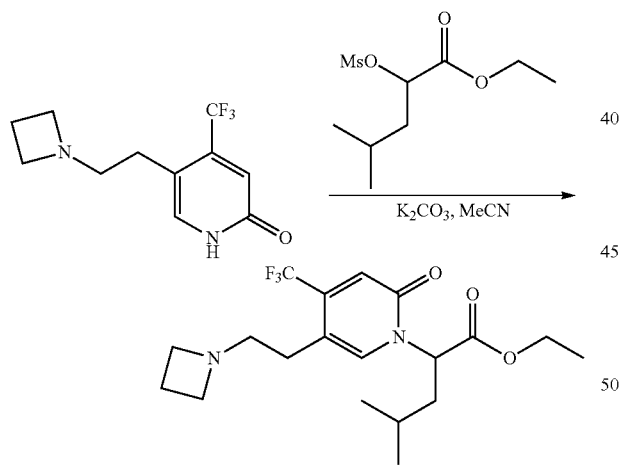

To a solution of 5-(2-(azetidin-1-yl)ethyl)-4-(trifluoromethyl)pyridin-2(1H)-one (710 mg, 2.9 mmol) in MeCN (10 mL) was added ethyl 4-methyl-2-(methylsulfonyloxy)pentanoate (1.1 g, 4.4 mmol) and $K_2CO_3$ (1.2 g, 8.7 mmol). The reaction mixture was stirred at 80° C. for 16 hours. The reaction mixture was concentrated in vacuo and the residue was purified by reverse phase HPLC on a C18/40 g column (A: water 10 mM $NH_4HCO_3$, B: MeOH, 0~100%) to provide ethyl 2-(5-(2-(azetidin-1-yl)ethyl)-2-oxo-4-(trifluoromethyl)pyridin-1(2H)-yl)-4-methylpentanoate as a yellow oil (500 mg). Yield 44% (ESI 389.2 $(M+H)^+$).

Step 6: 2-(5-(2-(azetidin-1-yl)ethyl)-2-oxo-4-(trifluoromethyl)pyridin-1(2H)-yl)-4-methylpentanoic Acid

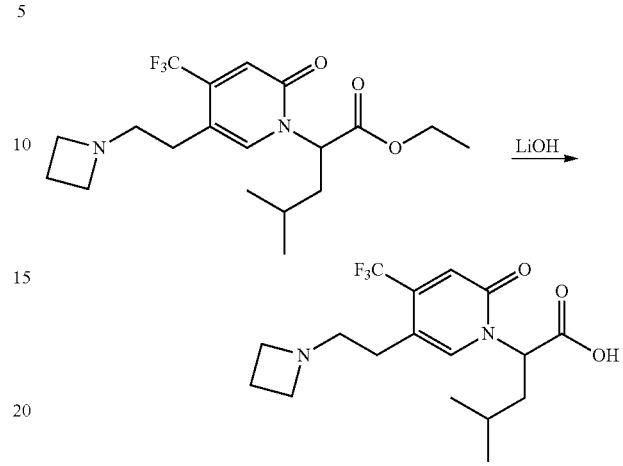

Ethyl 2-(5-(2-(azetidin-1-yl)ethyl)-2-oxo-4-(trifluoromethyl)pyridin-1(2H)-yl)-4-methylpentanoate (500 mg, 1.3 mmol) was treated with LiOH—$H_2O$ (270 mg, 6.5 mmol) in EtOH (5 mL) and water (1 mL) at room temperature for 2 hours. The reaction mixture was neutralized with 2 N HCl and concentrated in vacuo. The residue was purified by reverse phase HPLC on a C18/40 g column (A: water 10 mM $NH_4HCO_3$, B: MeOH, 0~100%) to provide 2-(5-(2-(azetidin-1-yl)ethyl)-2-oxo-4-(trifluoromethyl)pyridin-1(2H)-yl)-4-methylpentanoic acid as a yellow oil (410 mg). Yield 88% (ESI 361.2 $(M+H)^+$).

Preparation of 2-(5-(2-(dimethylamino)ethyl)-2-oxo-4-(trifluoromethyl)pyridin-1(2H)-yl)-4-methylpentanoic Acid

Step 1: 2-(6-methoxy-4-(trifluoromethyl)pyridin-3-yl)-N,N-dimethylethane-1-amine

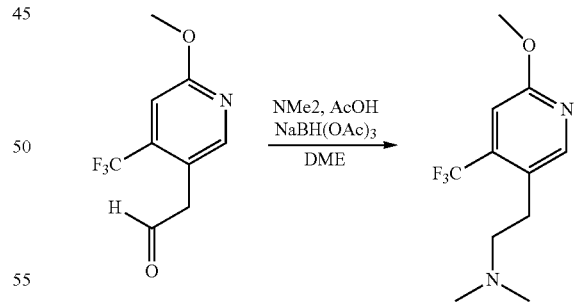

To a solution of 2-(6-methoxy-4-(trifluoromethyl)pyridin-3-yl)acetaldehyde (0.34 g, 1.6 mmol) in DCE (7.8 mL) was added dimethylamine (3.9 mL, 7.8 mmol) and acetic acid (0.05 mL, 0.78 mmol) and stirred for 1 hour. To the solution was added sodium triacetoxyborohydride (0.6 g, 3.1 mmol). The reaction was allowed to stir for 12 hours then concentrated and purified by silica gel chromatography (0-35% DCM (1% TEA):MeOH 0-30%) to provide 2-(6-methoxy-4-(trifluoromethyl)pyridin-3-yl)-N,N-dimethylethane-1-amine (305 mg). Yield 79% (ESI 249.27 $(M+H)^+$).

Step 2: 5-(2-(dimethylamino)ethyl)-4-(trifluoromethyl)pyridin-2(1H)-one

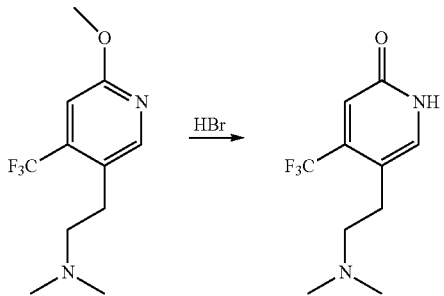 [SMILES: COc1cc(C(F)(F)F)c(CCN(C)C)cn1 ; Br ; CN(C)CCc1c[nH]c(=O)cc1C(F)(F)F]

HBr (33% in Acetic Acid) (4.04 mL, 24.57 mmol) was added to 2-(6-methoxy-4-(trifluoromethyl)pyridin-3-yl)-N,N-dimethylethane-1-amine (0.305 g, 1.229 mmol) and heated to 75° C. in a pressure vessel. After 4 hours, the solvent was removed and the residue purify by silica gel chromatography (0-25% DCM:MeOH with 1% TEA as a modifier) to provide 5-(2-(dimethylamino)ethyl)-4-(trifluoromethyl)pyridin-2(1H)-one (219 mg). Yield 76% (ESI 235.15 (M+H)$^+$). $^1$H NMR (400 MHz, MeOD) δ 7.56 (s, 1H), 6.85 (s, 1H), 2.76 (m, 2H), 2.61 (m, 1H), 2.37 (m, 6H)

Step 3: Ethyl 2-(5-(2-(dimethylamino)ethyl)-2-oxo-4-(trifluoromethyl)pyridin-1(2H)-yl)-4-methylpentanoate

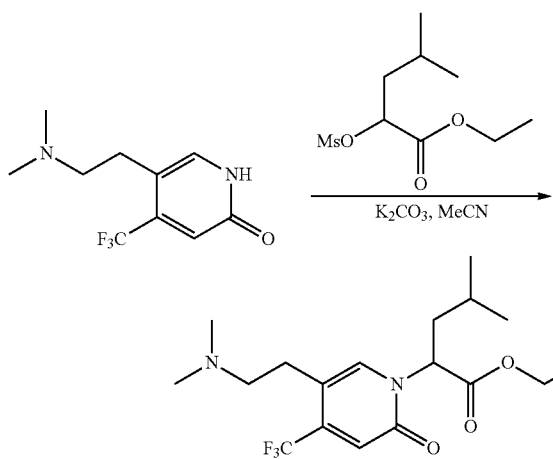

A mixture of 5-(2-(dimethylamino)ethyl)-4-(trifluoromethyl)pyridin-2(1H)-one (685 mg, 2.92 mmol), K$_2$CO$_3$ (1.60 g, 11.55 mmol) and ethyl 4-methyl-2-(methylsulfonyloxy)pentanoate (1.60 g, 6.70 mmol) in CH$_3$CN (60 mL) was stirred at 85° C. overnight. The solvent was concentrated in vacuo and the residue was purified by silica gel column (DCM:MeOH 2:1) to give ethyl 2-(5-(2-(dimethylamino)ethyl)-2-oxo-4-(trifluoromethyl)pyridin-1(2H)-yl)-4-methylpentanoate as brown oil (390 mg). Yield 35% (ESI 377.2 (M+H)$^+$). $^1$H NMR (500 MHz, MeOD) δ 7.84 (s, 1H), 6.68 (s, 1H), 5.51 (dd, J=11.0, 5.0 Hz, 1H), 4.23 (q, J=7.0 Hz, 2H), 2.77 (t, J=8.0 Hz, 2H), 2.53 (t, J=8.0 Hz, 2H), 2.33 (s, 6H), 2.18-2.12 (m, 1H), 2.08-2.02 (m, 1H), 1.46-1.38 (m, 1H), 1.27 (t, J=7.0 Hz, 3H), 0.97 (t, J=7.0 Hz, 6H).

Step 4: 2-(5-(2-(dimethylamino)ethyl)-2-oxo-4-(trifluoromethyl)pyridin-1(2H)-yl)-4-methylpentanoic Acid

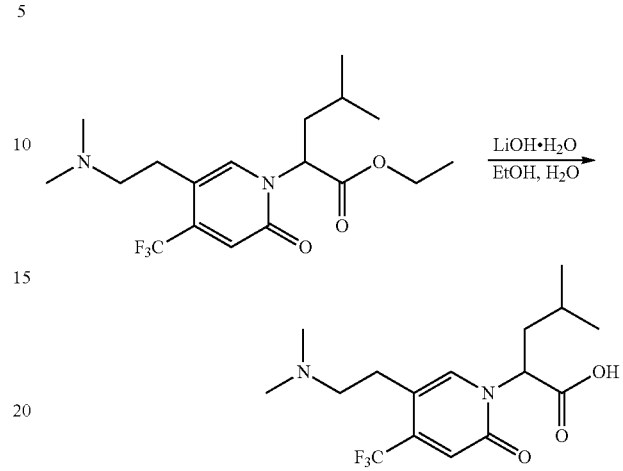

Ethyl 2-(5-(2-(dimethylamino)ethyl)-2-oxo-4-(trifluoromethyl)pyridin-1(2H)-yl)-4-methylpentanoate (390 mg, 1.0 mmol) was treated with LiOH monohydrate (435 mg, 10.36 mmol) in EtOH (10 mL) and H$_2$O (1 mL) at room temperature for 1 hour. The mixture was acidified to pH 4-5 with 1N HCl aqueous solution. The mixture was concentrated in vacuo and purified by silica gel column (MeOH:EtOAc 1:2) to give 2-(5-(2-(dimethylamino)ethyl)-2-oxo-4-(trifluoromethyl)pyridin-1(2H)-yl)-4-methylpentanoic acid as an oil (358 mg). Yield 99% (ESI 349.1 (M+H)$^+$).

Preparation of 2-(5-(2-(dimethylamino)ethyl)-2-oxo-4-(trifluoromethyl)pyridin-1(2H)-yl)-3-methylbutanoic Acid

Step 1: Ethyl 2-(5-(2-(dimethylamino)ethyl)-2-oxo-4-(trifluoromethyl)pyridin-1(2H)-yl)-3-methylbutanoate

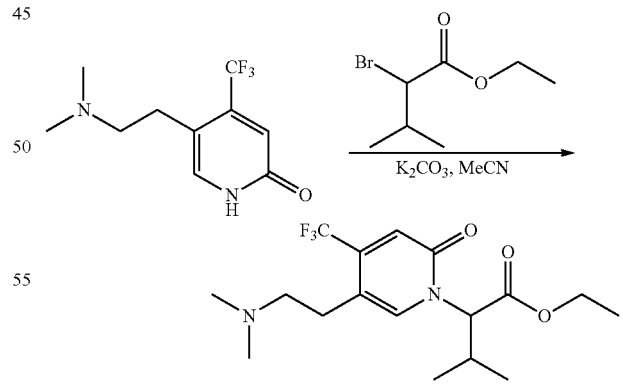

To a solution of 5-(2-(dimethylamino)ethyl)-4-(trifluoromethyl)pyridin-2(1H)-one (2.4 g, 10.2 mmol) in MeCN (40 mL) was added ethyl 2-bromo-3-methylbutanoate (4.3 g, 20.4 mmol) and K$_2$CO$_3$ (2.8 g, 20.4 mmol). The reaction mixture was stirred at 80° C. for 16 h. The reaction mixture was concentrated in vacuo and the residue was purified by reverse phase HPLC on a C18/40 g column (A: water 10 mM NH₄HCO₃, B: MeOH, 0~100%) to provide ethyl 2-(5-(2-(dimethylamino)ethyl)-2-oxo-4-(trifluoromethyl)pyridin-1(2H)-yl)-3-methylbutanoate as a yellow oil (2.6 g). Yield 69% (ESI 363.2 (M+H)⁺).

Step 2: 2-(5-(2-(dimethylamino)ethyl)-2-oxo-4-(trifluoromethyl)pyridin-1(2H)-yl)-3-methylbutanoic acid

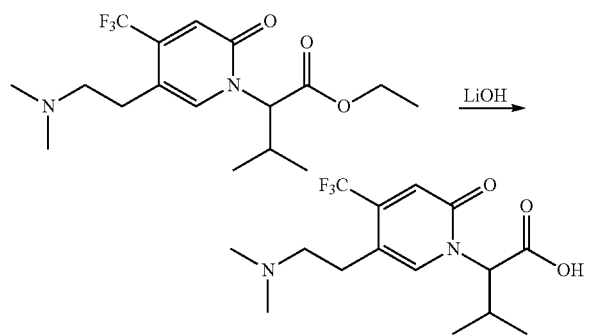

Ethyl 2-(5-(2-(dimethylamino)ethyl)-2-oxo-4-(trifluoromethyl)pyridin-1(2H)-yl)-3-methylbutanoate (2.6 g, 7.1 mmol) was treated with LiOH—H₂O (1.47 g, 35 mmol) in EtOH (15 mL) and water (3 mL) at room temperature for 2 h. The reaction mixture was neutralized with 2 N HCl, concentrated in vacuo and the residue was purified by reverse phase HPLC on a C18/40 g column (A: water 10 mM NH₄HCO₃, B: MeOH, 0~100%) to provide 2-(5-(2-(dimethylamino)ethyl)-2-oxo-4-(trifluoromethyl)pyridin-1 (2H)-yl)-3-methylbutanoic acid as a yellow oil (1.8 g). Yield 75% (ESI 335.2 (M+H)⁺).

Preparation of 3-cyclopropyl-2-(5-(2-(dimethylamino)ethyl)-2-oxo-4-(trifluoromethyl)pyridin-1 (2H)-yl)propanoic Acid Step 1: Ethyl 2-(5-bromo-2-oxo-4-(trifluoromethyl)pyridin-1(2H)-yl)-3-cyclopropylpropanoate

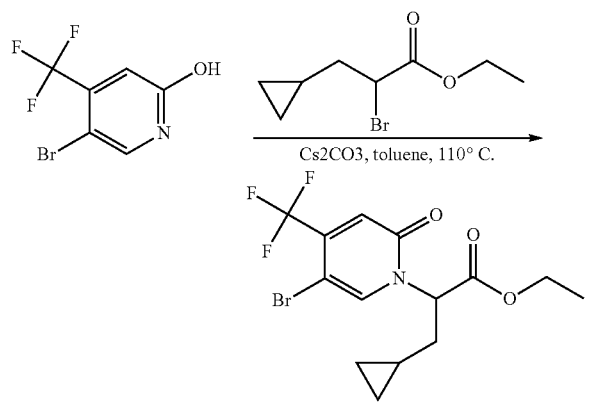

A mixture of 5-bromo-4-(trifluoromethyl)pyridin-2-ol (2.5 g, 10.33 mmol), Cs₂CO₃ (6.7 g, 20.66 mmol) and ethyl 2-bromo-3-cyclopropylpropanoate (3.4 g, 15.50 mmol) in toluene (100 mL) was stirred at 110° C. for 16 h. LCMS showed the reaction was completed. The mixture was filtered and washed with EtOAc (20 mL). The filtrate was concentrated in vacuo and the residue was purified by silica gel column (pet ether:EtOAc 10:1) to provide ethyl 2-(5-bromo-2-oxo-4-(trifluoromethyl)pyridin-1(2H)-yl)-3-cyclopropylpropanoate as a colorless oil (1.5 g). Yield 38% (ESI 384.0 (M+H)⁺).

Step 2: Ethyl 2-(5-allyl-2-oxo-4-(trifluoromethyl)pyridin-1(2H)-yl)-3-cyclopropylpropanoate

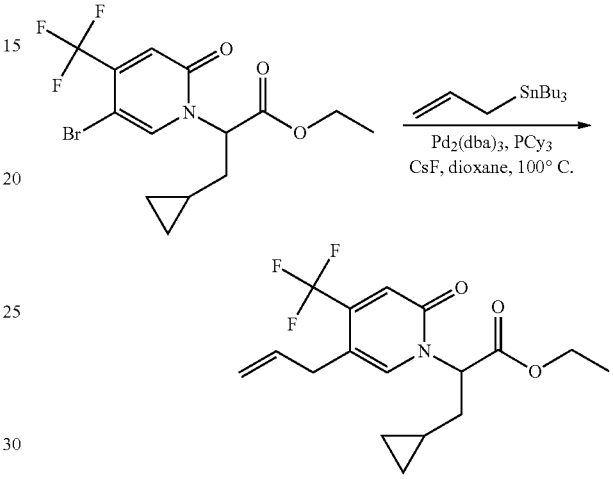

To a solution of ethyl 2-(5-bromo-2-oxo-4-(trifluoromethyl)pyridin-1(2H)-yl)-3-cyclopropylpropanoate (2.3 g, 6.02 mmol) and allyltributylstannane (2.4 g, 7.22 mmol) under nitrogen atmosphere in dioxane (50 mL) was added Pd₂dba₃ (348 mg, 0.30 mmol), PCy₃ (168 mg, 0.60 mmol), CsF (1.8 g, 12.04 mmol) and stirred at 100° C. for 16 h. The mixture was cooled to room temperature. A saturation NH₄Cl solution (100 mL) and EtOAc (100 mL) was added to the mixture and the aqueous layer was extracted with EtOAc (100 mL×2). The combined organic phase was washed with brine (100 mL), dried over anhydrous Na₂SO₄, filtered and concentrated in vacuo. The residue was purified by silica gel column (pet ether:EtOAc 10:1) to provide ethyl 2-(5-allyl-2-oxo-4-(trifluoromethyl)pyridin-1(2H)-yl)-3-cyclopropylpropanoate as a colorless oil (1.5 g). Yield 72% (ESI 344.0 (M+H)⁺).

Step 3: Ethyl 3-cyclopropyl-2-(2-oxo-5-(2-oxoethyl)-4-(trifluoromethyl)pyridin-1(2H)-yl)propanoate

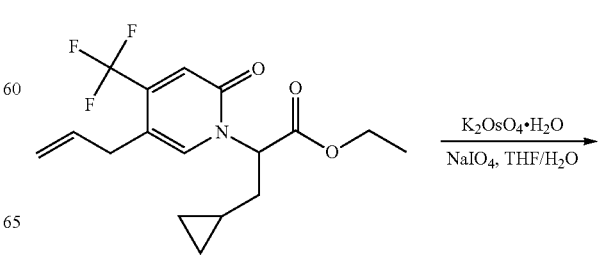

303
-continued

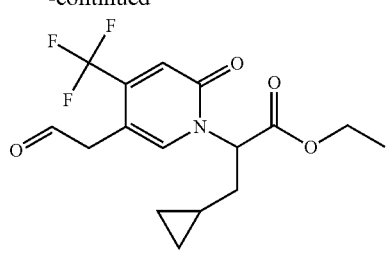

To a solution of ethyl 2-(5-allyl-2-oxo-4-(trifluoromethyl) pyridin-1(2H)-yl)-3-cyclopropylpropanoate (1.5 g, 4.37 mmol) in THF/H$_2$O (20 mL/20 mL) was added a solution of K$_2$OsO$_4$-2H$_2$O (16.0 mg, 0.0437 mmol) in H$_2$O (3 mL) and stirred at room temperature for 1 hour. A solution of NaIO$_4$ (1.8 g, 8.74 mmol) in H$_2$O (10 mL) was added dropwise and the mixture was stirred at room temperature for another hour. LCMS showed the reaction was completed. The reaction mixture was diluted with water (40 mL) and extracted with EtOAc (50 mL×3). The combined organic phase was dried over anhydrous Na$_2$SO$_4$, filtered and concentrated in vacuo to provide ethyl 3-cyclopropyl-2-(2-oxo-5-(2-oxoethyl)-4-(trifluoromethyl)pyridin-1(2H)-yl)propanoate as a brown oil used directly in the next reaction without further purification (1.5 g, crude). (ESI 346.1 (M+H)$^+$).

Step 4: Ethyl 3-cyclopropyl-2-(5-(2-(dimethylamino)ethyl)-2-oxo-4-(trifluoromethyl)pyridin-1(2H)-yl)propanoate

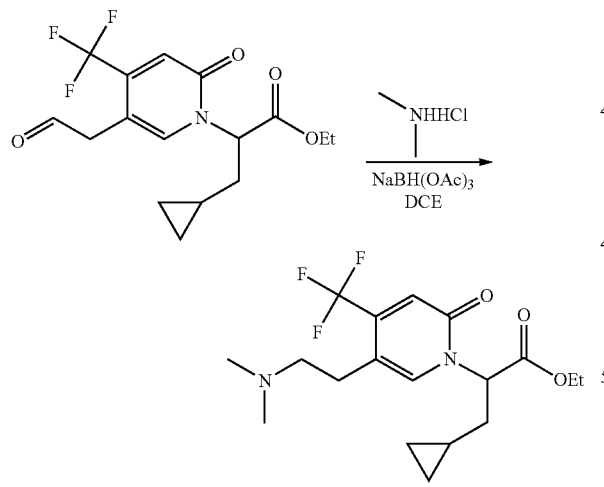

To a mixture of ethyl 3-cyclopropyl-2-(2-oxo-5-(2-oxoethyl)-4-(trifluoromethyl)pyridin-1(2H)-yl)propanoate (1.5 g, 4.34 mmol) in DCE (20 mL) at 25° C. was added dimethylamine hydrochloride (708 mg, 8.68 mmol) and stirred for 1 hour. NaBH(OAc)$_3$ (2.8 g, 13.02 mmol) was added at 5° C. and stirred at 25° C. for 16 hours. The mixture was concentrated in vacuo and the residue was purified by silica gel column (DCM:MeOH 10:1) to provide ethyl 3-cyclopropyl-2-(5-(2-(dimethylamino)ethyl)-2-oxo-4-(trifluoromethyl)pyridin-1(2H)-yl)propanoate as a colorless oil (400 mg) Yield 25% (ESI 375.1 [M+H]$^+$).

304

Step 5: 3-cyclopropyl-2-(5-(2-(dimethylamino) ethyl)-2-oxo-4-(trifluoromethyl)pyridin-1(2H)-yl) propanoic Acid

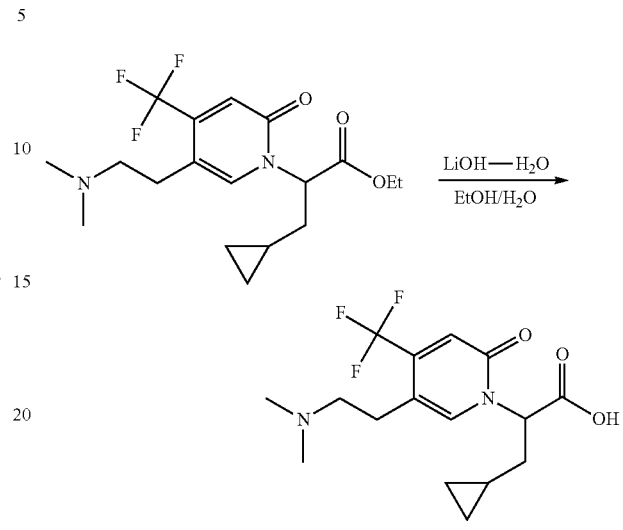

Ethyl 3-cyclopropyl-2-(5-(2-(dimethylamino)ethyl)-2-oxo-4-(trifluoromethyl)pyridin-1(2H)-yl)propanoate (400 mg, 1.07 mmol) was treated with LiOH—H$_2$O (224 mg, 5.35 mmol) in EtOH (5 mL) and water (2 mL) and the mixture was stirred at room temperature for 30 minutes. The mixture was acidified with 1N HCl to pH 5~6 and purified by reverse phase HPLC on a C18/120 g column (A: water/10 mM NH$_4$HCO$_3$, B: MeOH, 0~100%) to provide 3-cyclopropyl-2-(5-(2-(dimethylamino)ethyl)-2-oxo-4-(trifluoromethyl)pyridin-1(2H)-yl)propanoic acid as a white solid (150 mg). Yield 41% (ESI 347.0 (M+H)$^+$).

Preparation of 2-(5-(2-(dimethylamino)ethyl)-2-oxo-4-(trifluoromethyl)pyridin-1(2H)-yl)-5-methylhexanoic acid Step 1: Ethyl 2-(5-bromo-2-oxo-4-(trifluoromethyl) pyridin-1(2H)-yl)-5-methylhexanoate

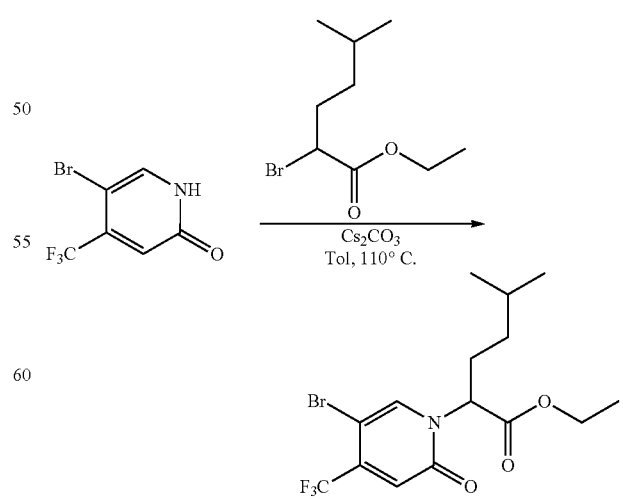

A mixture of 5-bromo-2-hydroxy-4-(trifluoromethyl) pyridine (6.00 g, 24.79 mmol), ethyl 2-bromo-5-methylhexanoate (8.82 g, 37.19 mmol) and Cs$_2$CO$_3$ (24.24 g, 74.38 mmol) in anhydrous toluene (120 mL) was heated at 110° C. under nitrogen atmosphere for 3 h. The solvent was removed in vacuo and the residue was purified by silica gel column (petroleum ether:EtOAc 23:1) to provide ethyl 2-(5-bromo-2-oxo-4-(trifluoromethyl)pyridin-1(2H)-yl)-5-methylhexanoate as brown oil (5.9 g). Yield 59%. (ESI 400.0 (M+H)$^+$, ESI 422.0 (M+Na)$^+$).

Step 2: (E)-ethyl 2-(5-(2-ethoxyvinyl)-2-oxo-4-(trifluoromethyl)pyridin-1(2H)-yl)-5-methylhexanoate

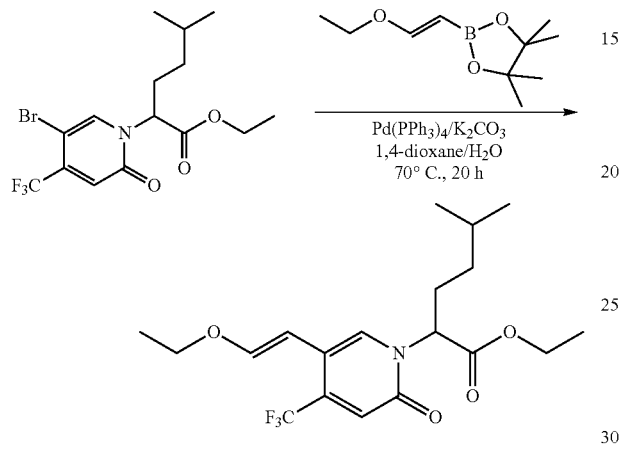

A mixture of ethyl 2-(5-bromo-2-oxo-4-(trifluoromethyl)pyridin-1(2H)-yl)-5-methylhexanoate (5.56 g, 13.97 mmol), (E)-1-ethoxyethene-2-boronic acid pinacol ester (4.15 g, 20.95 mmol), tetrakis(triphenylphosphine)palladium(0) (2.42 g, 2.10 mmol) and K$_2$CO$_3$ (5.79 g, 41.91 mmol) in co-solvent of anhydrous 1,4-dioxane (140 mL) and water (14 mL) was heated at 70° C. under nitrogen atmosphere for 20 h. The solvent was removed in vacuo and the residue was purified by silica gel column (petroleum ether:EtOAc 10:1) to provide (E)-ethyl 2-(5-(2-ethoxyvinyl)-2-oxo-4-(trifluoromethyl)pyridin-1(2H)-yl)-5-methylhexanoate as brown oil (3.4 g). Yield 63%. (ESI 390.1 (M+H)$^+$).

Step 3: Ethyl 5-methyl-2-(2-oxo-5-(2-oxoethyl)-4-(trifluoromethyl)pyridin-1(2H)-yl)hexanoate

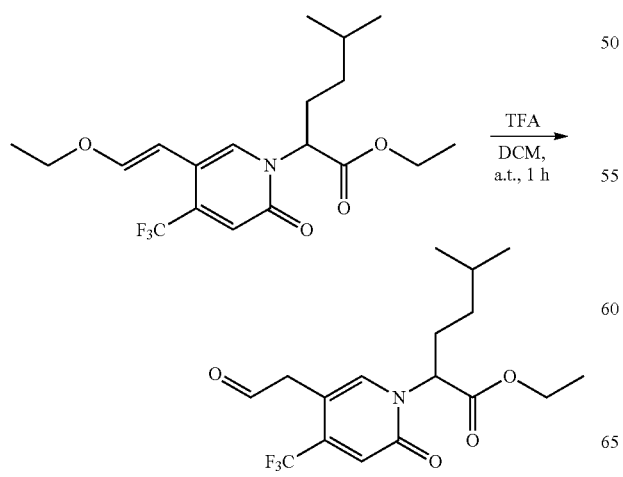

Trifluoroacetic acid (32 mL, 430.80 mmol) was added to a stirring solution of (E)-ethyl 2-(5-(2-ethoxyvinyl)-2-oxo-4-(trifluoromethyl)pyridin-1(2H)-yl)-5-methylhexanoate (5.2 g, 13.35 mmol) in DCM (64 mL) and the reaction mixture was stirred at room temperature for 1 h. The solvent was removed in vacuo to provide ethyl 5-methyl-2-(2-oxo-5-(2-oxoethyl)-4-(trifluoromethyl)pyridin-1(2H)-yl)hexanoate as brown oil (5.2 g, crude). (ESI 362.1 (M+H)$^+$).

Step 4: Ethyl 2-(5-(2-(dimethylamino)ethyl)-2-oxo-4-(trifluoromethyl)pyridin-1(2H)-yl)-5-methylhexanoate

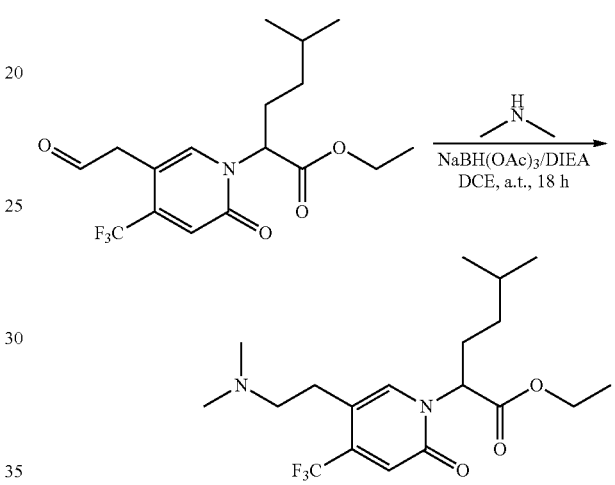

The mixture of ethyl 5-methyl-2-(2-oxo-5-(2-oxoethyl)-4-(trifluoromethyl)pyridin-1(2H)-yl)hexanoate (1.6 g, 4.45 mmol) and dimethylamine (60 mL, 2M in THF, 120 mmol) in 1,2-dichloroethane (43 mL) was stirred at ambient temperature for 1 h. Sodium triacetoxyborohydride (14.91 g, 70.34 mmol) was added in one portion and stirred at ambient temperature for 18 h. The solvent was removed in vacuo and the residue was purified by silica gel column (DCM:MeOH 3:1) to provide ethyl 2-(5-(2-(dimethylamino)ethyl)-2-oxo-4-(trifluoromethyl)pyridin-1(2H)-yl)-5-methylhexanoate as brown oil (1.2 g). Yield 72%. (ESI 391.1 (M+H)$^+$).

Step 5: 2-(5-(2-(dimethylamino)ethyl)-2-oxo-4-(trifluoromethyl)pyridin-1(2H)-yl)-5-methylhexanoic acid

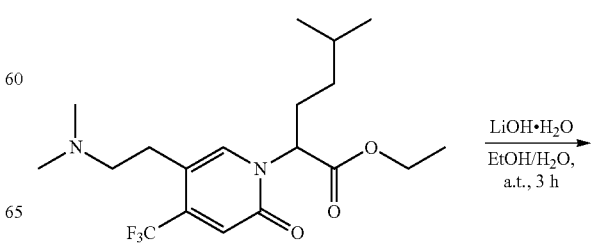

307

-continued

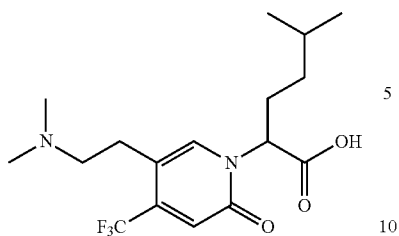

Ethyl 2-(5-(2-(dimethylamino)ethyl)-2-oxo-4-(trifluoromethyl)pyridin-1(2H)-yl)-5-methylhexanoate (925 mg, 2.37 mmol) was treated with LiOH monohydrate (298 mg, 7.11 mmol) in EtOH (10 mL) and H$_2$O (0.7 mL) at room temperature for 3 h. The reaction mixture was acidified to pH 4~5 with 1N HCl. The solvent was removed in vacuo and the residue was purified by reverse phase HPLC on a C18/40 g column (A: water 10 mM NH$_4$HCO$_3$, B: MeOH, 0~80%) to provide 2-(5-(2-(dimethylamino)ethyl)-2-oxo-4-(trifluoromethyl)pyridin-(2H)-yl)-5-methylhexanoic acid as a yellow solid (617 mg). Yield 72% (ESI 363.1 (M+H)$^+$).

Preparation of (3R)-2-(5-(2-(dimethylamino)ethyl)-2-oxo-4-(trifluoromethyl)pyridin-1(2H)-yl)-3-methylpentanoic Acid Step 1: Ethyl (3R)-2-bromo-3-methylpentanoate

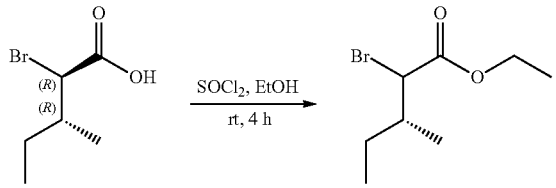

To a mixture of (2R,3R)-2-bromo-3-methylpentanoic acid (5 g, 25.6 mmol) in EtOH (50 mL) at 0° C. was added SOCl$_2$ (6.1 g, 51.2 mmol). The mixture was stirred for 4 h at room temperature. The solvent was removed in vacuo to provide ethyl (3R)-2-bromo-3-methylpentanoate as a yellow oil (5.3, crude). (ESI 223 (M+H)$^+$).

Step 2: Ethyl (3R)-2-(5-bromo-2-oxo-4-(trifluoromethyl)pyridin-1(2H)-yl)-3-methylpentanoate

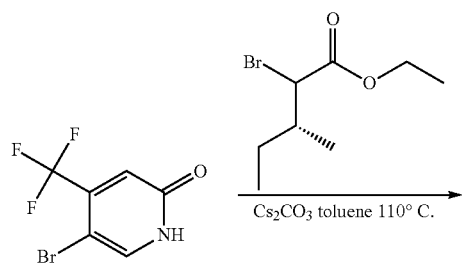

308

-continued

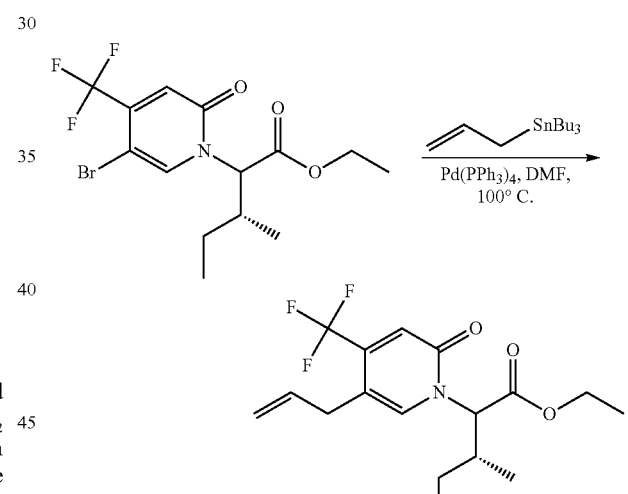

To a stirred solution of 5-bromo-4-(trifluoromethyl)pyridin-2(1H)-one (3.50 g, 14.52 mmol) and ethyl (3R)-2-bromo-3-methylpentanoate (3.54 g, 15.97 mmol) in toluene (50 mL) was added Cs$_2$CO$_3$ (5.38 g, 16.58 mmol) and stirred at 110° C. for 2 hours. The reaction was cooled to room temperature, filtered and washed with 20 mL of EtOAc. The filtrate was concentrated in vacuo and the residue was purified by silica gel column (pet ether:EtOAc 20:1) to provide ethyl (3R)-2-(5-bromo-2-oxo-4-(trifluoromethyl)pyridin-1(2H)-yl)-3-methylpentanoate as a white solid (2.2 g). Yield 40% (ESI 384.0 (M+H)$^+$).

Step 3: Ethyl (3R)-2-(5-allyl-2-oxo-4-(trifluoromethyl)pyridin-1(2H)-yl)-3-methylpentanoate To a solution of ethyl (3R)-2-(5-bromo-2-oxo-4-(trifluoromethyl)pyridin-1(2H)-yl)-3-methylpentanoate (2.2 g, 5.74 mmol) and allyltributylstannane (2.28 g, 6.89 mmol) under N$_2$ atmosphere in DMF (15 mL) was added Pd(PPh$_3$)$_4$ (0.67 g, 0.58 mmol) and stirred at 100° C. for 16 hours. The reaction mixture was concentrated in vacuo. The residue was diluted with 50 mL of EtOAc, poured into 20% aq. KF (100 mL), stirred at 20° C. for 1 hour and then filtered and washed with 100 mL of EtOAc. The filtrate was extracted with EA (100 mL×3). The combined organic phase was washed with brine (200 mL), dried over anhydrous Na$_2$SO$_4$, filtered and concentrated in vacuo and the residue was purified by silica gel column (pet ether:EtOAc 20:1) to provide ethyl (3R)-2-(5-allyl-2-oxo-4-(trifluoromethyl)pyridin-1(2H)-yl)-3-methylpentanoate as a colorless oil (1.51 g). Yield 76% (ESI 346 (M+H)$^+$).

Step 4: Ethyl (3R)-3-methyl-2-(2-oxo-5-(2-oxo-ethyl)-4-(trifluoromethyl)pyridin-1(2H)-yl)pentanoate

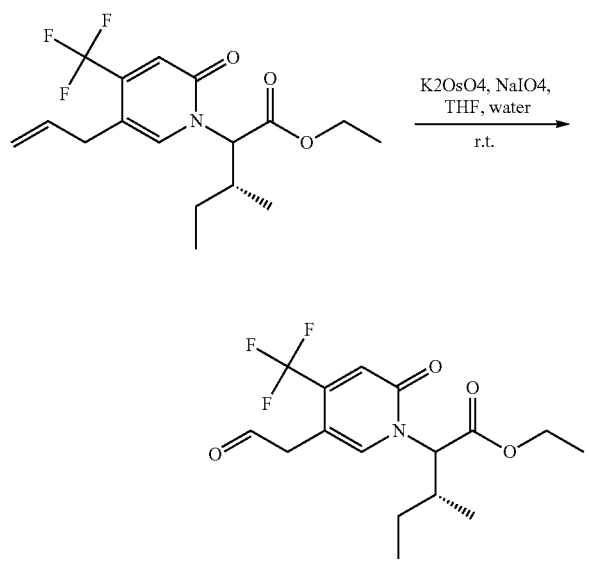

To a mixture of ethyl (3R)-2-(5-allyl-2-oxo-4-(trifluoromethyl)pyridin-1(2H)-yl)-3-methylpentanoate (1.51 g, 4.36 mmol) in THF (15 mL) and H$_2$O (10 mL) at 0° C. was added K$_2$OsO$_4$·2H$_2$O (130 mg, 0.345 mmol) and stirred at 0° C. for 5 mins. Then a solution of NaIO$_4$ (2.80 g, 13.08 mmol) in H$_2$O (5 mL) was added dropwise and stirred at 0° C. for 2 hours and then at 25° C. for 2 hours. The mixture was quenched with a saturated Na$_2$S$_2$O$_3$ solution (50 mL) and the mixture was extracted with EA (60 mL×3). The combined organics were washed with brine (30 mL×3), dried over anhydrous Na$_2$SO$_4$, filtered and concentrated in vacuo to provide crude product ethyl (3R)-3-methyl-2-(2-oxo-5-(2-oxoethyl)-4-(trifluoromethyl)pyridin-1(2H)-yl)pentanoate (1.5 g, crude) as yellow oil. (ESI 348 (M+H)$^+$).

Step 5: Ethyl (3R)-2-(5-(2-(dimethylamino)ethyl)-2-oxo-4-(trifluoromethyl)pyridin-1(2H)-yl)-3-methyl-pentanoate

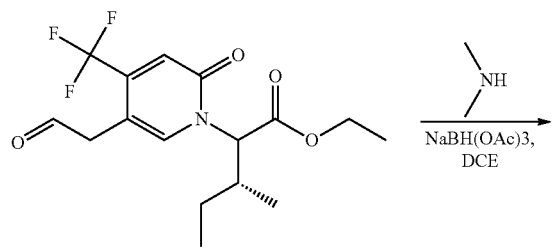

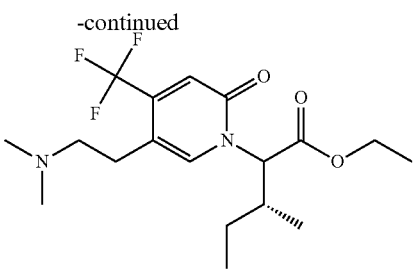

To a mixture of ethyl (3R)-3-methyl-2-(2-oxo-5-(2-oxo-ethyl)-4-(trifluoromethyl)pyridin-1(2H)-yl)pentanoate (1 g, 2.87 mmol) in DCE (10 mL) at 25° C. was added dimethylamine hydrochloride (700 mg, 8.62 mmol) and stirred at 25° C. for 10 min. Then NaBH(OAc)$_3$ (1.22 g, 5.74 mmol) was added and stirred at 25° C. for 2 hours. The mixture was concentrated in vacuo and the residue was purified by silica gel column (DCM:MeOH 10:1) to provide ethyl (3R)-2-(5-(2-(dimethylamino)ethyl)-2-oxo-4-(trifluoromethyl)pyridin-1(2H)-yl)-3-methylpentanoate as a yellow oil (550 mg). Yield 51% (ESI 377 (M+H)$^+$).

Step 6: (3R)-2-(5-(2-(dimethylamino)ethyl)-2-oxo-4-(trifluoromethyl)pyridin-1(2H)-yl)-3-methylpentanoic Acid

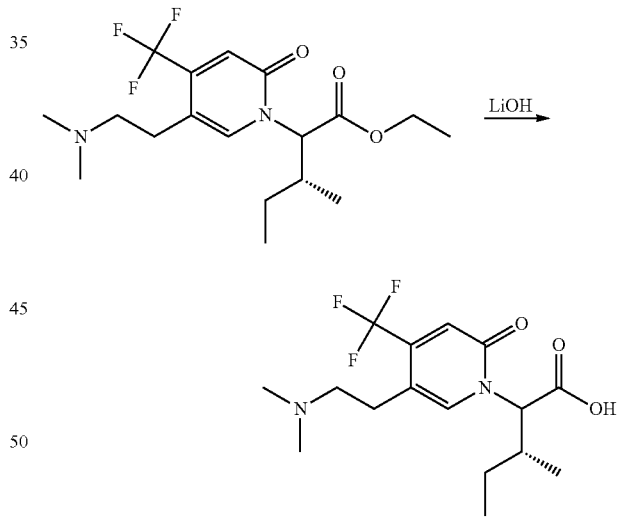

Ethyl (3R)-2-(5-(2-(dimethylamino)ethyl)-2-oxo-4-(trifluoromethyl)pyridin-1(2H)-yl)-3-methylpentanoate (550 mg, 1.46 mmol) was treated with LiOH—H$_2$O (240 mg, 5.84 mmol) in MeOH (5 mL) and water (1 mL) at room temperature for 1 hour. The MeOH was removed and the aqueous material acidified with 1N HCl to pH 4. The mixture was purified by reverse phase HPLC on a C18/40 g column (A: water 10 mM NH$_4$HCO$_3$, B: MeOH, 0~100%) to provide (3R)-2-(5-(2-(dimethylamino)ethyl)-2-oxo-4-(trifluoromethyl)pyridin-1(2H)-yl)-3-methylpentanoic acid as a yellow oil (400 mg). Yield 78.5% (ESI 349 (M+H)$^+$).

311

Preparation of 2-(5-(2-(dimethylamino)ethyl)-2-oxo-4-(trifluoromethyl)pyridin-1(2H)-yl)pentanoic acid Step 1: Ethyl 2-(5-bromo-2-oxo-4-(trifluoromethyl)pyridin-1(2H)-yl)pentanoate

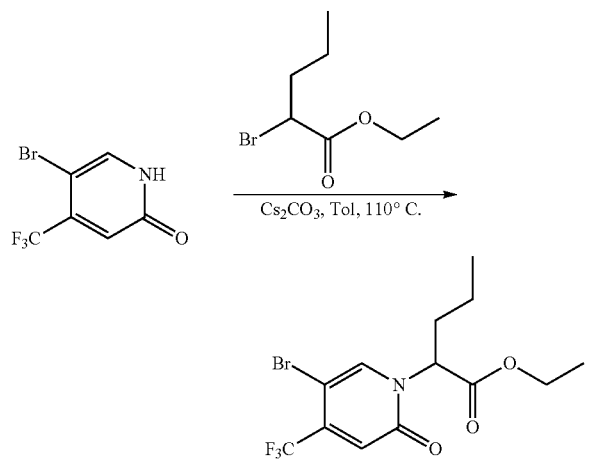

To a stirred solution of 5-bromo-4-(trifluoromethyl)pyridin-2(1H)-one (2 g, 8.29 mmol) and methyl 2-bromo-4-methylpentanoate (2.24 g, 10.78 mmol) in toluene (40 mL) was added Cs₂CO₃ (5.38 g, 16.58 mmol) portionwise and stirred at 110° C. for 2 hours. The reaction mixture was diluted with 50 mL of EtOAc, filtered and washed with 20 mL of EtOAc. The filtrate was concentrated in vacuo and the residue was purified by silica gel column (pet ether:EtOAc 20:1) to provide ethyl 2-(5-bromo-2-oxo-4-(trifluoromethyl)pyridin-1(2H)-yl)pentanoate as a white solid (2.3 g). Yield 65% (ESI 372.0 (M+H)⁺).

Step 2: Ethyl (E)-2-(5-(2-ethoxyvinyl)-2-oxo-4-(trifluoromethyl)pyridin-1(2H)-yl)pentanoate

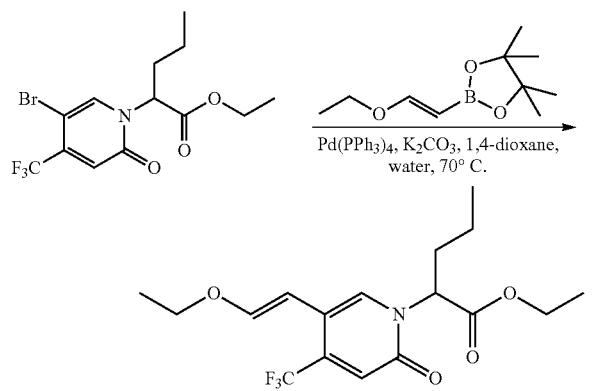

A mixture of ethyl 2-(5-bromo-2-oxo-4-(trifluoromethyl)pyridin-1(2H)-yl)pentanoate (2.2 g, 5.96 mmol), (E)-2-(2-ethoxyvinyl)-4,4,5,5-tetramethyl-1,3,2-dioxaborolane (1.35 g, 6.85 mmol), Pd(PPh₃)₄ (206 mg, 0.17 mmol) and K₂CO₃ (1.64 g, 11.92 mmol) in 1,4-dioxane (30 mL) and water (3 mL) was stirred at 70° C. under N₂ for 20 h. The reaction mixture was poured into 100 mL of water, extracted with EA (50 mL×3). The combined organic phase was washed with brine (150 mL), dried over anhydrous Na₂SO₄, filtered and concentrated in vacuo, purified by silica gel column (pet ether:EtOAc 10:1) to provide ethyl (E)-2-(5-(2-ethoxyvinyl)-2-oxo-4-(trifluoromethyl)pyridin-1(2H)-yl)pentanoate as a white solid (1 g). Yield 46% (ESI 362.1 (M+H)⁺).

Step 3: Ethyl 2-(2-oxo-5-(2-oxoethyl)-4-(trifluoromethyl)pyridin-1(2H)-yl)pentanoate

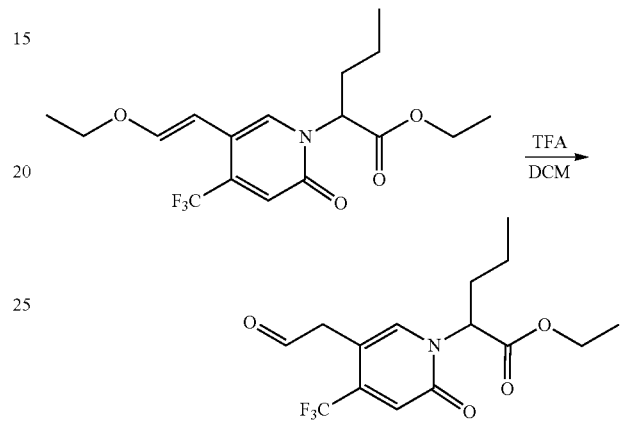

To a mixture of (E)-2-(5-(2-ethoxyvinyl)-2-oxo-4-(trifluoromethyl)pyridin-1(2H)-yl)pentanoate (920 mg, 2.55 mmol) in DCM (20 mL) was added TFA (10 mL). The mixture was stirred at room temperature for 4 hours. LCMS showed that the reaction was completed. The mixture was concentrated in vacuo to give crude product ethyl 2-(2-oxo-5-(2-oxoethyl)-4-(trifluoromethyl)pyridin-1(2H)-yl)pentanoate as a yellow oil (800 mg) used directly in the next reaction without further purification. Yield 94% (ESI 334.1 [M+H]⁺).

Step 4: Ethyl 2-(5-(2-(dimethylamino)ethyl)-2-oxo-4-(trifluoromethyl)pyridin-1(2H)-yl)pentanoate

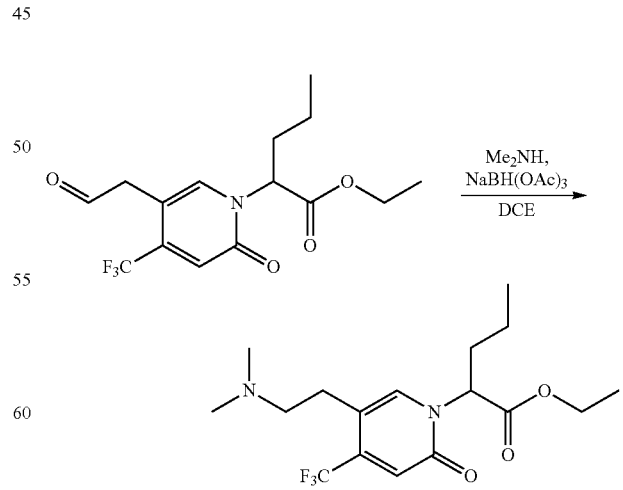

To a mixture of ethyl 2-(2-oxo-5-(2-oxoethyl)-4-(trifluoromethyl)pyridin-1(2H)-yl)pentanoate (750 mg, 2.25 mmol) in DCE (10 mL) at 25° C. was added dimethylamine (2M in THF, 1.7 mL, 3.4 mmol) and stirred at 25° C. for 10 min. NaBH(OAc)₃ (950 mg, 4.5 mmol) was added and stirred at 25° C. for 2 hours. The mixture was concentrated in vacuo and the residue was purified by silica gel column (DCM: MeOH 10:1) to provide ethyl 2-(5-(2-(dimethylamino) ethyl)-2-oxo-4-(trifluoromethyl)pyridin-1(2H)-yl)pentanoate as a yellow oil (630 mg). Yield 77% (ESI 363.1 (M+H)⁺).

Step 5: 2-(5-(2-(dimethylamino)ethyl)-2-oxo-4-(trifluoromethyl)pyridin-1(2H)-yl)pentanoic acid

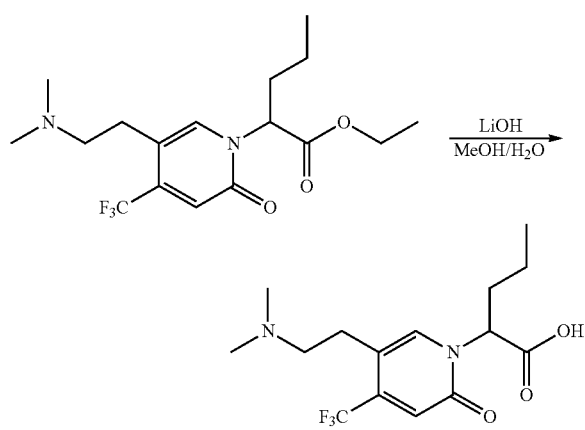

Ethyl 2-(5-(2-(dimethylamino)ethyl)-2-oxo-4-(trifluoromethyl)pyridin-1(2H)-yl)pentanoate (630 g, 1.74 mmol) was treated with LiOH—H₂O (142 mg, 3.48 mmol) in MeOH (6 mL) and water (3 mL) at 20° C. for 1 hour. The MeOH was removed and the remaining aqueous acidified with 1N HCl to pH=4. The mixture was purified by reverse phase HPLC on a C18/40 g column (A: water 10 mM NH₄HCO₃, B: MeOH, 0~100%) to provide 2-(5-(2-(dimethylamino)ethyl)-2-oxo-4-(trifluoromethyl)pyridin-1(2H)-yl)pentanoic acid as a yellow oil (430 mg). Yield 73% (ESI 335.1 (M+H)⁺).

Preparation of 2-(5-(2-(3-methoxyazetidin-1-yl) ethyl)-2-oxo-4-(trifluoromethyl)pyridin-1(2H)-yl)-4-methylpentanoic Acid Step 1: 2 (E)-ethyl 2-(5-(2-ethoxyvinyl)-2-oxo-4-(trifluoromethyl)pyridin-1(2H)-yl)-4-methylpentanoate

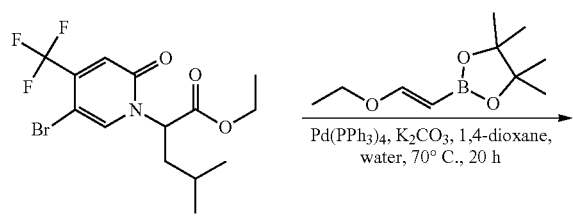

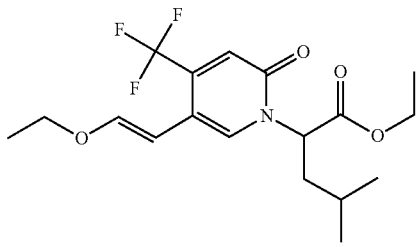

To a solution of ethyl 2-(5-bromo-2-oxo-4-(trifluoromethyl)pyridin-1(2H)-yl)-4-methylpentanoate (12 g, 31 mmol) in 1,4-dioxane (150 mL) and water (15 mL) was added (E)-2-(2-ethoxyvinyl)-4,4,5,5-tetramethyl-1,3,2-dioxaborolane (9.3 g, 45.5 mmol), K₂CO₃ (12.8 g, 93 mmol) and Pd(PPh₃)₄ (1.8 g, 1.55 mmol). The reaction mixture was stirred at 70° C. for 20 h. The reaction mixture was cooled to room temperature, diluted with EtOAc (300 mL) and washed with brine, dried over Na₂SO₄, concentrated in vacuo. The residue was purified by silica gel column (pet. Ether:EtOAc 1:2) to provide (E)-ethyl 2-(5-(2-ethoxyvinyl)-2-oxo-4-(trifluoromethyl)pyridin-1(2H)-yl)-4-methylpentanoate as a yellow oil (9 g). Yield 76% (ESI 376.1 (M+H)⁺).

Step 2: Ethyl 4-methyl-2-(2-oxo-5-(2-oxoethyl)-4-(trifluoromethyl)pyridin-1(2H)-yl)pentanoate

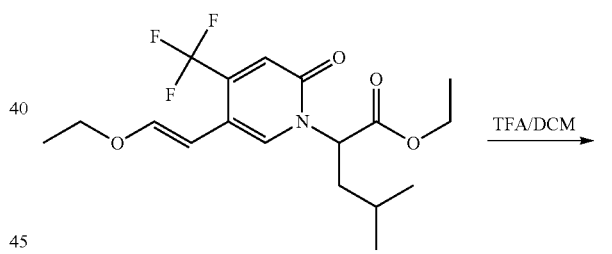

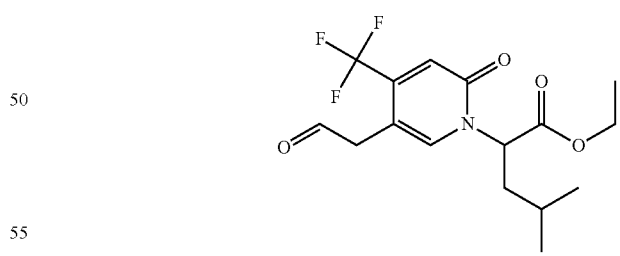

A mixture of (E)-ethyl 2-(5-(2-ethoxyvinyl)-2-oxo-4-(trifluoromethyl)pyridin-1(2H)-yl)-4-methylpentanoate (9 g, 24 mmol) in TFA (25 mL) and DCM (25 mL) was stirred at room temperature for 16 h. The reaction mixture was concentrated in vacuo to give crude ethyl 4-methyl-2-(2-oxo-5-(2-oxoethyl)-4-(trifluoromethyl)pyridin-1(2H)-yl) pentanoate as a yellow oil (9 g). Yield 100% (crude) (ESI 348.1 (M+H)⁺).

Step 3: Ethyl 2-(5-(2-(3-methoxyazetidin-1-yl)ethyl)-2-oxo-4-(trifluoromethyl)pyridin-1(2H)-yl)-4-methylpentanoate

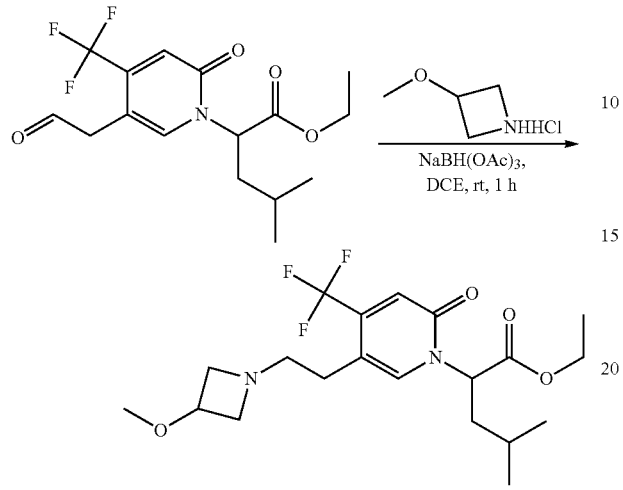

To a solution of ethyl 4-methyl-2-(2-oxo-5-(2-oxoethyl)-4-(trifluoromethyl)pyridin-1(2H)-yl)pentanoate (10 g crude, 24 mmol) in DCE (100 mL) was added 3-methoxyazetidine hydrochloride (5.9 g, 48 mmol) and stirred at room temperature for 20 min. NaBH(OAc)₃ (10.1 g, 48 mmol) was added and stirred at room temperature for 1 h. The reaction was quenched with MeOH (30 mL) and filtered. The filtrate was concentrated in vacuo and the residue was purified by reverse phase HPLC on a C18/120 g column (A: water 10 mM NH₄HCO₃, B: MeOH, 0~100%) to provide ethyl 2-(5-(2-(3-methoxyazetidin-1-yl)ethyl)-2-oxo-4-(trifluoromethyl)pyridin-1(2H)-yl)-4-methylpentanoate as a yellow oil (8 g). Yield 79% (ESI 419.2 (M+H)⁺).

Step 4: 2-(5-(2-(3-methoxyazetidin-1-yl)ethyl)-2-oxo-4-(trifluoromethyl)pyridin-1(2H)-yl)-4-methylpentanoic Acid

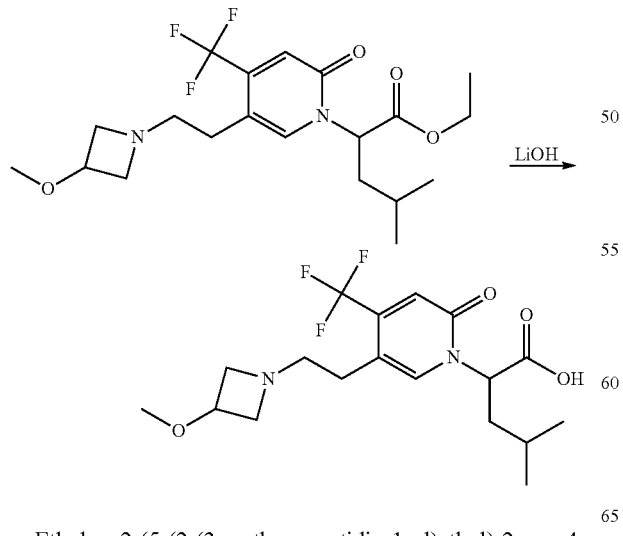

Ethyl 2-(5-(2-(3-methoxyazetidin-1-yl)ethyl)-2-oxo-4-(trifluoromethyl)pyridin-1(2H)-yl)-4-methylpentanoate (8 g, 19 mmol) was treated with LiOH—H₂O (2.4 g, 57 mmol) in EtOH (60 mL) and water (12 mL) at room temperature for 2 h. The reaction mixture was neutralized by 2 N HCl and concentrated in vacuo. The residue was purified by reverse phase HPLC on a C18/120 g column (A: water 10 mM NH₄HCO₃, B: MeOH, 0~100%) to provide 2-(5-(2-(3-methoxyazetidin-1-yl)ethyl)-2-oxo-4-(trifluoromethyl)pyridin-1(2H)-yl)-4-methylpentanoic acid as a yellow solid (6 g). Yield 80% (ESI 391.1 (M+H)⁺).

Preparation of 2-(5-(2-(dimethylamino)ethyl)-3-methyl-2-oxopyridin-1(2H)-yl)-4-methylpentanoic Acid

Step 1: Ethyl 2-(5-bromo-3-methyl-2-oxopyridin-1(2H)-yl)-4-methylpentanoate

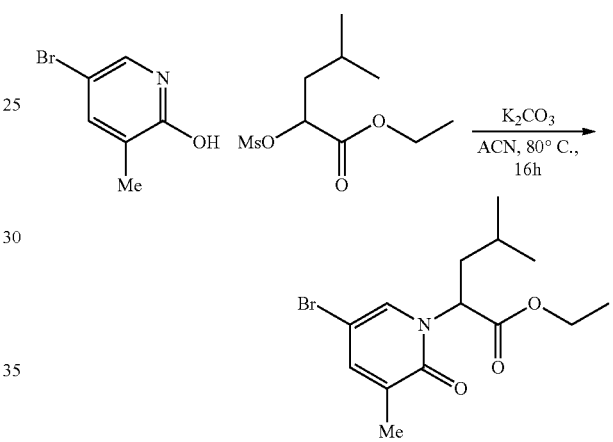

A mixture of 5-((dimethylamino)methyl)pyridin-2(1H)-one (500 mg, 3.28 mmol), K₂CO₃ (1.36 g, 9.86 mmol) and ethyl 4-methyl-2-(methylsulfonyloxy)pentanoate (1.17 g, 4.93 mmol) in CH₃CN (20 mL) was stirred at 80° C. overnight. The solvent was removed in vacuo and the residue was purified by silica gel column (pet ether:EtOAc 1:2) to provide ethyl 2-(5-((dimethylamino)methyl)-2-oxopyridin-1(2H)-yl)-4-methylpentanoate as a yellow oil (300 mg). Yield 31% (ESI 330 (M+H)⁺).

Step 2: Ethyl 2-(5-allyl-3-methyl-2-oxopyridin-1(2H)-yl)-4-methylpentanoate

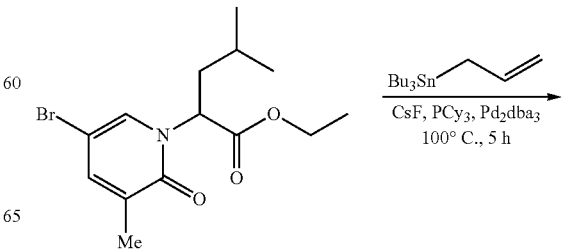

317
-continued

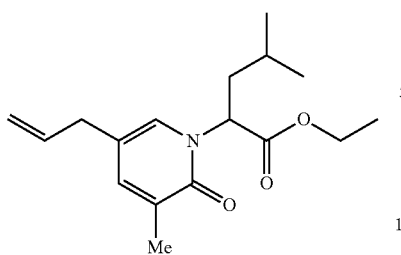

To a solution of ethyl 2-(5-bromo-3-methyl-2-oxopyridin-1(2H)-yl)-4-methylpentanoate (2.5 g, 7.57 mmol) and allyltributylstannane (2.5 g, 7.57 mmol) under $N_2$ atmosphere in dioxane (25 mL) was added $Pd_2(dba)_3$ (0.3 g, 0.38 mmol) and CsF (2.3 g, 15.1 mmol) and $PCy_3$ (212.0 mg, 0.76 mmol) and stirred at 100° C. for 5 hours. The mixture was cooled to room temperature, filtered and washed with EtOAc. The filtrate was concentrated in vacuo and the residue was purified by silica gel column (pet ether:EtOAc 20:1) to provide ethyl 2-(5-allyl-3-methyl-2-oxopyridin-1(2H)-yl)-4-methylpentanoate as a colorless oil (1.61 g). Yield 73% (ESI 292 (M+H)$^+$).

Step 3: Ethyl 4-methyl-2-(3-methyl-2-oxo-5-(2-oxoethyl)pyridin-1(2H)-yl)pentanoate

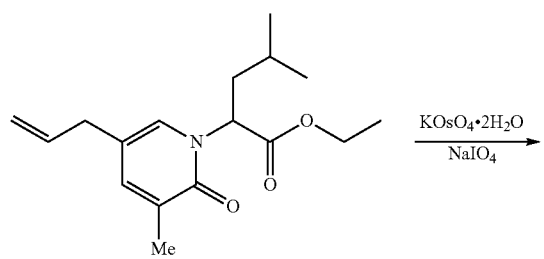

To a solution of ethyl 2-(5-allyl-3-methyl-2-oxopyridin-1(2H)-yl)-4-methylpentanoate (1.61 g, 5.53 mmol) in THF/$H_2O$ (24 mL/12 mL) was added a solution of $K_2OsO_4 \cdot 2H_2O$ (21 mg, 0.058 mmol) in $H_2O$ (4 mL) and stirred at room temperature for 1 h. A solution of $NaIO_4$ (2.37 g, 11.1 mmol) in $H_2O$ (20 mL) was added and stirred at room temperature for 2 h. LCMS showed the reaction was completed. The reaction mixture was diluted with 100 mL of water and extracted with EtOAc (100 mL×3). The combined organic phase was dried over anhydrous $Na_2SO_4$, filtered and concentrated in vacuo to give the crude product ethyl 4-methyl-2-(3-methyl-2-oxo-5-(2-oxoethyl)pyridin-1(2H)-yl)pentanoate as a yellow oil (1.6 g, crude) used directly in the next reaction. (ESI 294.1 (M+H)$^+$).

318
Step 4: Ethyl 2-(5-(2-(dimethylamino)ethyl)-3-methyl-2-oxopyridin-1(2H)-yl)-4-methylpentanoate

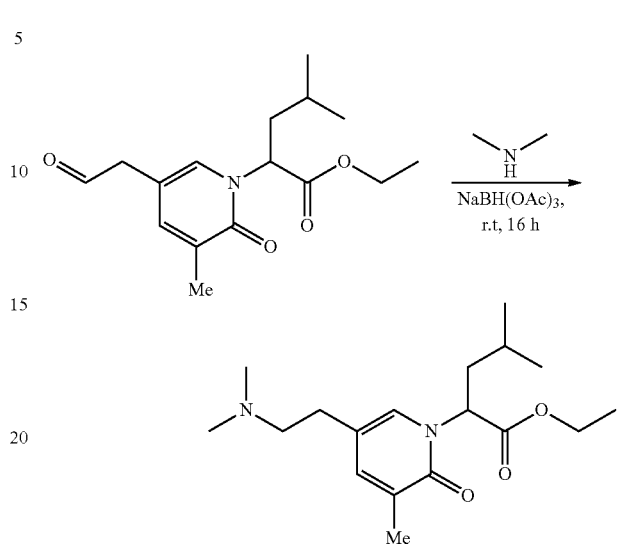

A mixture of ethyl 4-methyl-2-(3-methyl-2-oxo-5-(2-oxoethyl)pyridin-1(2H)-yl)pentanoate (2 g, 16.2 mmol), dimethylamine (2M in THF) (41 mL) in DCE (10 mL) was stirred at room temperature for 30 mins. Then $NaBH(OAc)_3$ (5.2 g, 24.39 mmol) was added and stirred at room temperature overnight. The reaction mixture was concentrated in vacuo and the residue was purified by reverse phase HPLC on a C18/40 g column (A: water 10 mM $NH_4HCO_3$, B: MeOH, 0~100%) to provide ethyl 2-(5-(2-(dimethylamino)ethyl)-3-methyl-2-oxopyridin-1(2H)-yl)-4-methylpentanoate as a yellow oil (1 g). Yield 46% (ESI 323.2 (M+H)$^+$).

Step 5: 2-(5-(2-(dimethylamino)ethyl)-3-methyl-2-oxopyridin-1(2H)-yl)-4-methylpentanoic

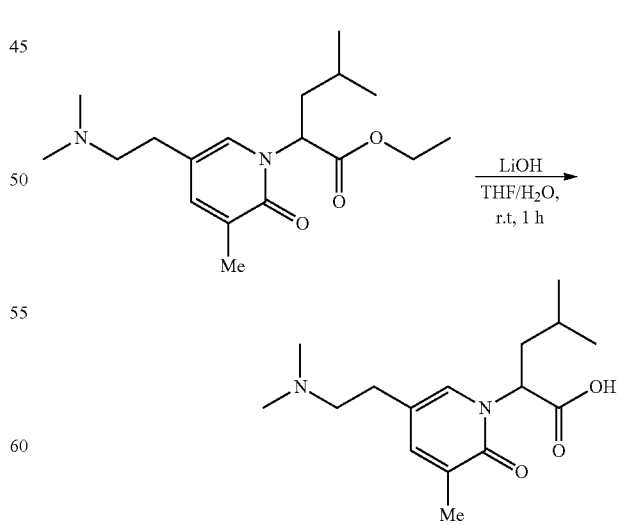

Ethyl 2-(5-((dimethylamino)methyl)-2-oxopyridin-1(2H)-yl)-4-methylpentanoate (606 mg, 1.88 mmol) was treated with LiOH—$H_2O$ (395 mg, 9.4 mmol) in THF (8 mL) and water (3 mL) at room temperature for 2 hours. The reaction was acidified with 1N HCl to pH=3~4. The solvent was removed in vacuo and the residue was purified by preparatory-HPLC A (30-80% MeCN) to provide 2-(5-(2-(dimethylamino)ethyl)-3-methyl-2-oxopyridin-1(2H)-yl)-4-methylpentanoic acid as a white solid (480 mg). Yield 87% (ESI 295 (M+H)$^+$).

Preparation of 2-(3-(difluoromethyl)-5-(2-(dimethylamino)ethyl)-2-oxopyridin-1(2H)-yl)-4-methylpentanoic Acid Step 1:
5-bromo-3-(difluoromethyl)-2-methoxypyridine

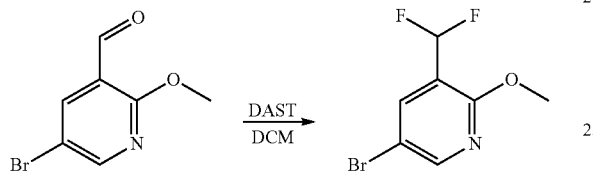

To a mixture of 5-bromo-2-methoxynicotinaldehyde (10.0 g, 46.3 mmol) in dry DCM (100 mL) under N$_2$ at 0° C. was added DAST (29.8 g, 185.2 mmol) and stirred at 0° C. for 2 days. The reaction was quenched with 100 mL of a saturated NaHCO3 solution. The aqueous layer was extracted with DCM (100 mL×3). The combined organic layers were washed with NaHCO$_3$ (sat, 100 mL) and brine (100 mL), dried over anhydrous Na$_2$SO$_4$, filtered and concentrated in vacuo to give 5-bromo-3-(difluoromethyl)-2-methoxypyridine as a yellow oil (11.0 g). Yield 100% (ESI 238.1 (M+H)$^+$).

Step 2: 5-bromo-3-(difluoromethyl)pyridin-2-ol

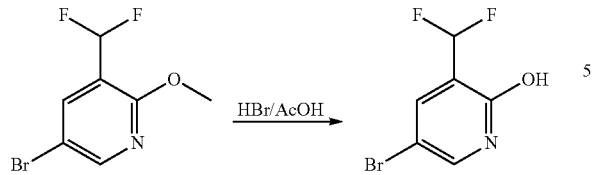

A mixture of 5-bromo-3-(difluoromethyl)-2-methoxypyridine (11.0 g, 46.2 mmol) in HBr (33% in acetic acid, 100 mL) was stirred at room temperature for 5 hours and then at 40° C. for 75 mins. The mixture was concentrated and poured into 100 mL of saturated NaHCO$_3$ solution and extracted with DCM. The combined organic layers dried over Na$_2$SO$_4$ and concentrated in vacuo to give 5-bromo-3-(difluoromethyl)pyridin-2-ol as a white solid (8.5 g) used without further purification. Yield 73.2% (ESI 226.0 (M+H)$^+$).

Step 3: Ethyl 2-(5-bromo-3-(difluoromethyl)-2-oxopyridin-1(2H)-yl)-4

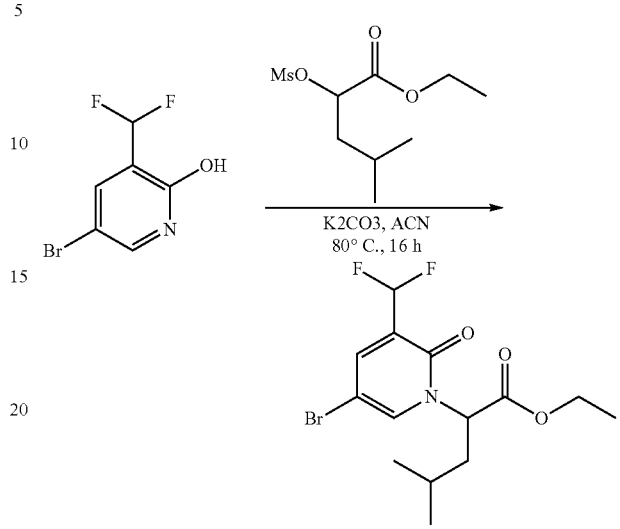

A mixture of 5-bromo-3-(difluoromethyl)pyridin-2-ol (7.0 g, 31.2 mmol), ethyl 4-methyl-2-((methylsulfonyl)oxy)pentanoate (14.0 g, 37.4 mmol) and K$_2$CO$_3$ (14.0 g, 62.5 mmol) in ACN (100 mL) was stirred at 80° C. overnight. The mixture was filtered and washed with ACN (20 mL). The filtrate was concentrated in vacuo and the residue purified by silica gel column (pet ether:EtOAc 4:1) to provide ethyl 2-(5-bromo-3-(difluoromethyl)-2-oxopyridin-1(2H)-yl)-4 as a white solid (10.0 g). Yield 80.3% (ESI 366.0 (M+H)$^+$).

Step 4: Ethyl 2-(5-allyl-3-(difluoromethyl)-2-oxopyridin-1(2H)-yl)-4-methylpentanoate

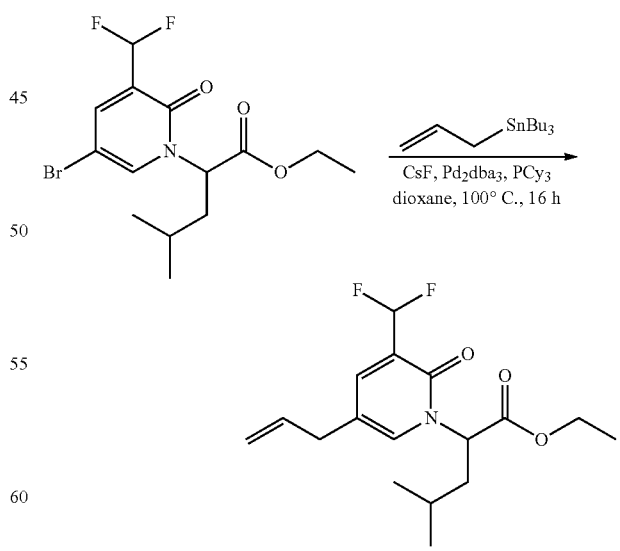

A mixture of ethyl 2-(5-bromo-3-(difluoromethyl)-2-oxopyridin-1(2H)-yl)-4 (6.0 g, 16.2 mmol), allyltributylstannane (7.0 g, 19.2 mmol), CsF (5.0 g, 32.4 mmol), Pd(dba)$_3$ (720 mg, 1.62 mmol) and PCy$_3$ (450 mg, 0.135 mmol) in dioxane (100 mL) was stirred at 100° C. overnight. The mixture was poured into water (200 mL), extracted with EtOAc (100 mL×3). The combined organic layers were washed with brine (200 mL), dried over Na₂SO₄, filtered and concentrated in vacuo. The residue was purified by silica gel column (pet ether:EtOAc 4:1) to give ethyl 2-(5-allyl-3-(difluoromethyl)-2-oxopyridin-1(2H)-yl)-4 as a white solid (3.0 g). Yield 71.6% (ESI 328.1 (M+H)⁺).

Step 5: Ethyl 2-(3-(difluoromethyl)-2-oxo-5-(2-oxoethyl)pyridin-1(2H)-yl)-4-methylpentanoate

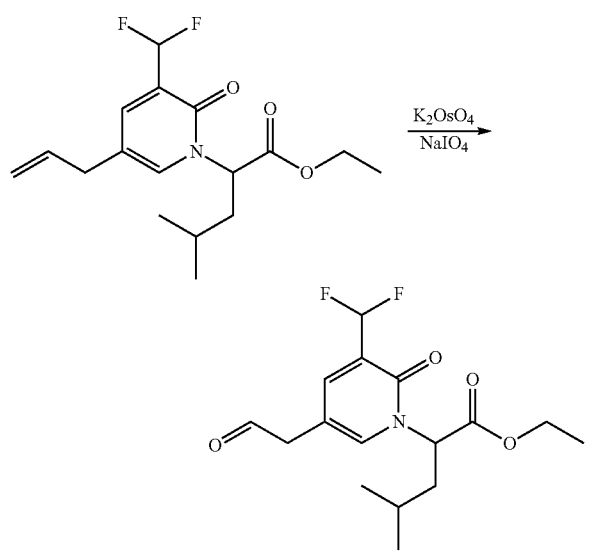

To a mixture of ethyl 2-(5-allyl-3-(difluoromethyl)-2-oxopyridin-1(2H)-yl)-4 (3.0 g, 9.1 mmol) in THF/H₂O (2/1, 100 mL) was added K₂OsO₄ (33.7 mg, 0.09 mmol) and stirred at room temperature for 1 hour. NaIO₄ (3.9, 18.3 mmol) was added and the mixture was stirred for 2 hours. The mixture was poured into water (200 mL) and extracted with EtOAc (100 mL×3). The combined organic layers were washed brine (200 mL) and dried over Na₂SO₄, filtered and concentrated in vacuo to give ethyl 2-(3-(difluoromethyl)-2-oxo-5-(2-oxoethyl)pyridin-1(2H)-yl)-4-methylpentanoate as a yellow oil (3.0 g, crude) used without further purification. (ESI 330.1 (M+H)⁺).

Step 6: Ethyl 2-(3-(difluoromethyl)-5-(2-(dimethylamino)ethyl)-2-oxopyridin-1(2H)-yl)-4-methylpentanoate

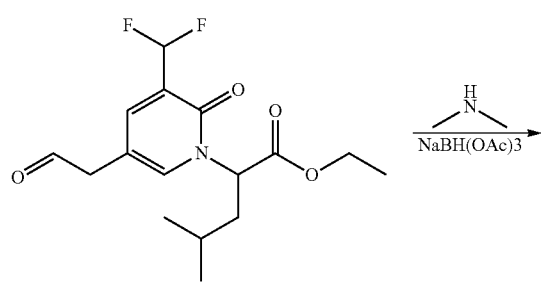

-continued

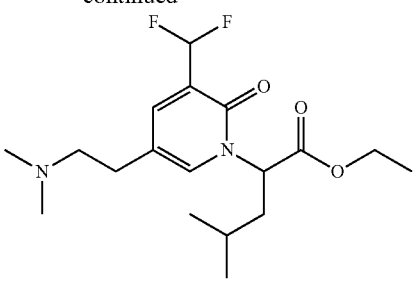

A mixture of ethyl 2-(3-(difluoromethyl)-2-oxo-5-(2-oxoethyl)pyridin-1(2H)-yl)-4-methylpentanoate (3.0 g, 9.1 mmol), dimethylamine (2M in THF, 14 mL, 28 mmol) in DCE (50 mL) was stirred at room temperature for 30 mins. NaBH(OAc)₃ (3.8 g, 18.2 mmol) was added portion-wise and the reaction was stirred at room temperature overnight. The solvent was concentrated in vacuo and the residue purified by reverse phase HPLC on a C18/120 g column (A: water 10 mM NH₄HCO₃, B: MeOH, 0~100%) to give ethyl 2-(3-(difluoromethyl)-5-(2-(dimethylamino)ethyl)-2-oxopyridin-1(2H)-yl)-4-methylpentanoate as a yellow oil (2.0 g). Yield 33.6% (ESI 359.2 (M+H)⁺).

Step 7: 2-(3-(difluoromethyl)-5-(2-(dimethylamino)ethyl)-2-oxopyridin-1(2H)-yl)-4-methylpentanoic Acid

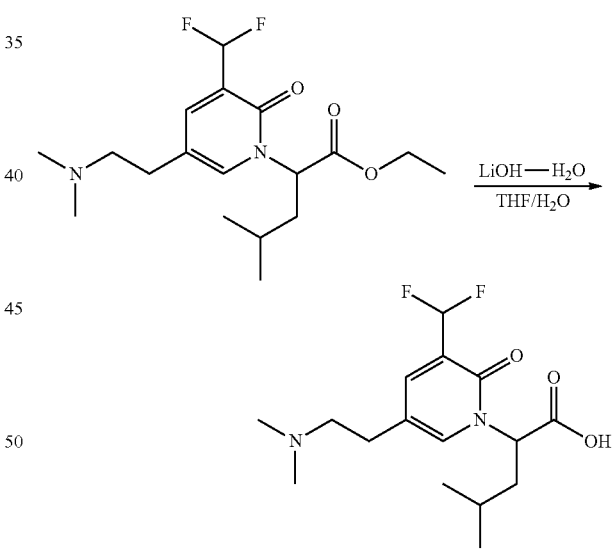

A mixture of ethyl 2-(3-(difluoromethyl)-5-(2-(dimethylamino)ethyl)-2-oxopyridin-1(2H)-yl)-4-methylpentanoate (2.0 g, 5.5 mmol) was treated with LiOH—H₂O (40 mg, 1.01 mmol) in THF (20 mL) and water (10 mL) at room temperature for 2 hours. The solvent was removed in vacuo and the residue purified by reverse phase HPLC on a C18/120 g column (A: water 10 mM NH₄HCO₃, B: MeOH, 0~100%) to give 2-(3-(difluoromethyl)-5-(2-(dimethylamino)ethyl)-2-oxopyridin-1(2H)-yl)-4-methylpentanoic acid as a white solid (1.2 g). Yield 85.6% (ESI 331.1 (M+H)⁺).

Preparation of 2-(5-(2-(dimethylamino)ethyl)-3-fluoro-2-oxopyridin-1(2H)-yl)-4-methylpentanoic Acid Step 1: Ethyl 2-(5-bromo-3-fluoro-2-oxopyridin-1(2H)-yl)-4-methylpentanoate

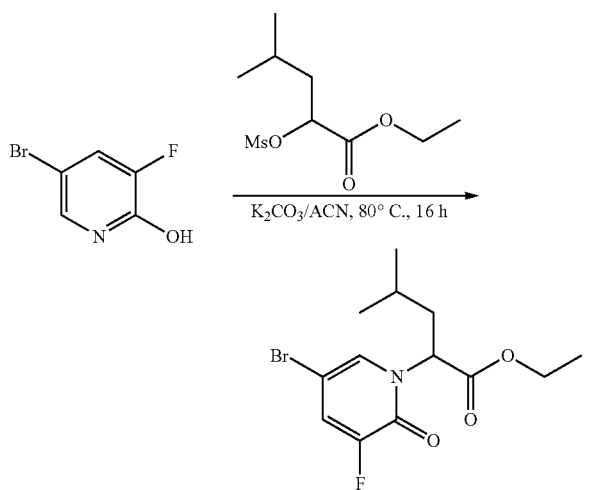

A mixture of 5-bromo-3-fluoropyridin-2-ol (5.0 g, 15.6 mmol), $K_2CO_3$ (7.36 g, 53.3 mmol) and ethyl 4-methyl-2-(methylsulfonyloxy)pentanoate (9.9 g, 23.4 mmol) in $CH_3CN$ (180 mL) was stirred at 80° C. overnight. The solvent was concentrated in vacuo and the residue was purified by silica gel column (pet ether:EtOAc 1:2) to give ethyl 2-(5-bromo-3-fluoro-2-oxopyridin-1(2H)-yl)-4-methylpentanoate as a yellow oil (6.5 g). Yield 81% (ESI 334.0 $(M+H)^+$).

Step 2: Ethyl 2-(5-allyl-3-fluoro-2-oxopyridin-1(2H)-yl)-4-methylpentanoate

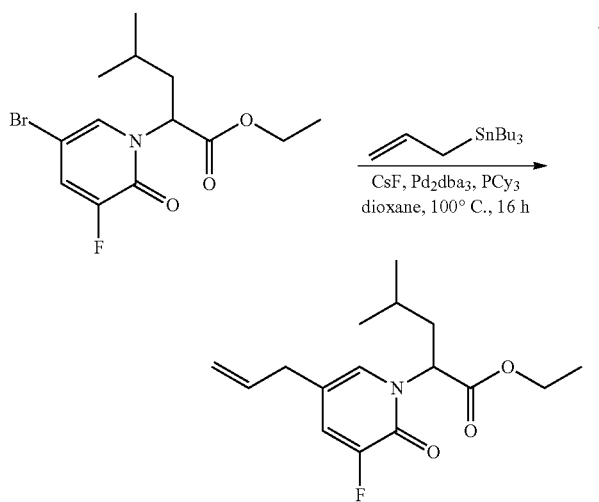

A mixture of ethyl 2-(5-bromo-3-fluoro-2-oxopyridin-1(2H)-yl)-4-methylpentanoate (5.0 g, 7.6 mmol), allyltributylstannane (6.0 g, 9.1 mmol), $Pd_2dba_3$ (240.0 mg, 0.76 mmol), $PCy_3$ (450 mg, 0.76 mmol), CsF (4.6 g, 15.1 mmol) in anhydrous dioxane (100 mL) was stirred under $N_2$ at 100° C. for 16 h. The mixture was cooled to room temperature and diluted with a saturated $NH_4Cl$ solution (100 mL) and EtOAc (100 mL). Separated the mixture and the aqueous layer was extracted with EtOAc (100 mL×2). The combined organic phase was washed with brine (100 mL), dried over anhydrous $Na_2SO_4$, filtered and concentrated in vacuo. The residue was purified by silica gel column (pet ether:EtOAc 4:1) to provide ethyl 2-(5-allyl-3-fluoro-4-methyl-2-oxopyridin-1(2H)-yl)-4-methylpentanoate as a yellow solid (3.0 g). Yield 69% (ESI 296.2 $(M+H)^+$).

Step 3: Ethyl 2-(3-fluoro-2-oxo-5-(2-oxoethyl)pyridin-1(2H)-yl)-4-methylpentanoate

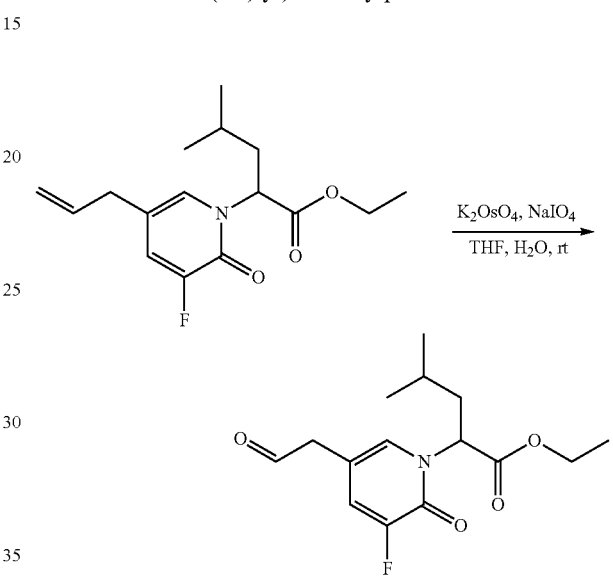

To a solution of ethyl 2-(5-allyl-3-fluoro-4-methyl-2-oxopyridin-1(2H)-yl)-4-methylpentanoate (5.5 g, 18.6 mmol) in $THF/H_2O$ (60 mL/20 mL) was added a solution of $K_2OsO_4 \cdot 2H_2O$ (60.0 mg, 0.16 mmol) in $H_2O$ (4 mL) and stirred at room temperature for 1 h. A solution of $NaIO_4$ (7.8 g, 37.2 mmol) in $H_2O$ (20 mL) was added and stirred at room temperature for 2 h. LCMS showed the reaction was completed. The reaction mixture was diluted with 100 mL of water and extracted with EtOAc (120 mL×3). The combined organic phase was dried over anhydrous $Na_2SO_4$, filtered and concentrated in vacuo to give the crude product ethyl 2-(3-fluoro-2-oxo-5-(2-oxoethyl)pyridin-1(2H)-yl)-4-methylpentanoate as a yellow oil (5.0 g, crude) used directly in the next reaction without further purification. (ESI 298.1 $(M+H)^+$).

Step 4: Ethyl 2-(5-(2-(dimethylamino)ethyl)-3-fluoro-2-oxopyridin-1(2H)-yl)-4-methylpentanoate

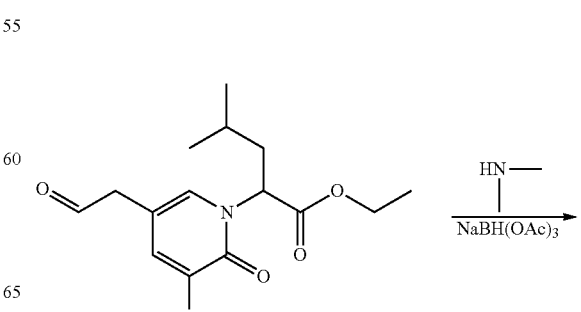

325
-continued

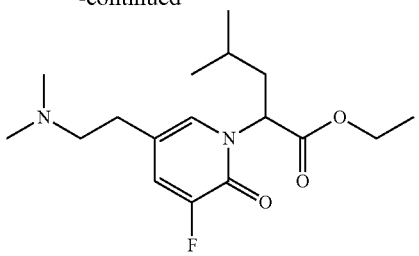

To a mixture of ethyl 2-(3-fluoro-2-oxo-5-(2-oxoethyl)pyridin-1(2H)-yl)-4-methylpentanoate (1.2 g, 4.0 mmol) in DCE (50 mL) at 25° C. was added dimethylamine (2.0 M in THF, 8.0 mL, 16.0 mmol) and stirred at 25° C. for 30 mins. NaBH(OAc)$_3$ (1.7 g, 8.0 mmol) was added at 5° C. and stirred at 25° C. for 16 hours. The mixture was concentrated in vacuo and the residue was purified by silica gel column (DCM:MeOH 10:1) to provide ethyl 2-(5-(2-(dimethylamino)ethyl)-3-fluoro-2-oxopyridin-1(2H)-yl)-4-methylpentanoate (800 mg) as a colorless oil. Yield 60% (ESI 327.1 (M+H)$^+$).

Step 5: 2-(5-(2-(dimethylamino)ethyl)-3-fluoro-2-oxopyridin-1(2H)-yl)-4-methylpentanoic acid

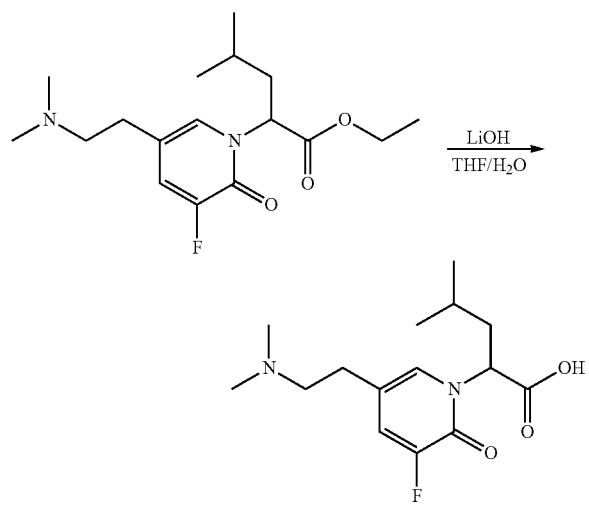

Ethyl 2-(5-(2-(dimethylamino)ethyl)-3-fluoro-2-oxopyridin-1(2H)-yl)-4-methylpentanoate (800 mg, 2.45 mmol) was treated with LiOH—H$_2$O (310.0 mg, 7.35 mmol) in THF (4 mL) and water (1 mL) at room temperature for 2 hours. The THF was removed and the aqueous acidified with 1N HCl to pH 5~6. The residue was purified by reverse phase HPLC on a C18/120 g column (A: water 10 mM NH$_4$HCO$_3$, B: MeOH, 0~100%) to provide 2-(5-(2-(dimethylamino)ethyl)-3-fluoro-2-oxopyridin-1(2H)-yl)-4-methylpentanoic acid as a white solid (700 mg). Yield 88% (ESI 299.2 (M+H)$^+$).

326
Preparation of 2-(3-fluoro-5-(2-(3-fluoroazetidine-1-yl)ethyl)-2-oxopyridin-1(2H)-yl)-4-methylpentanoic Acid Step 1: Ethyl 2-(3-fluoro-5-(2-(3-fluoroazetidine-1-yl)ethyl)-2-oxopyridin-1(2H)-yl)-4-methylpentanoate

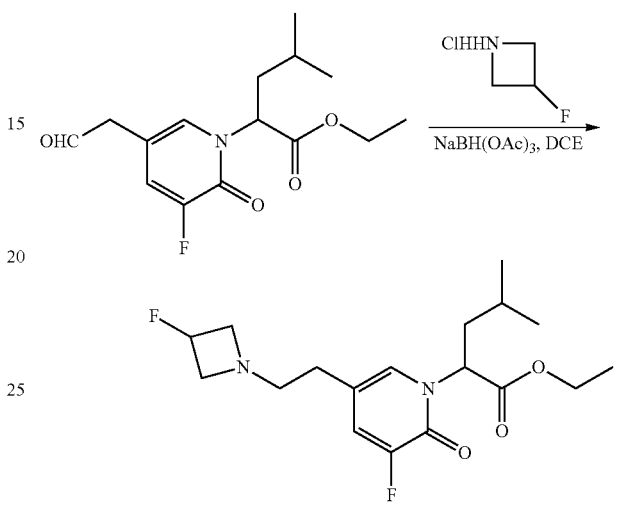

To a mixture of ethyl 2-(3-fluoro-2-oxo-5-(2-oxoethyl)pyridin-1(2H)-yl)-4-methylpentanoate (5 g, 15 mmol) in DCE (70 mL) at 25° C. was added 3-fluoroazetidine hydrochloride (1.8 g, 22.5 mmol) and stirred at 25° C. for 10 min. NaBH(OAc)$_3$ (6.4 g, 30 mmol) was added at 5° C. and stirred at 25° C. for 2 hours. The mixture was concentrated in vacuo and the residue was purified by silica gel column (DCM:MeOH 10:1) to provide ethyl 2-(3-fluoro-5-(2-(3-fluoroazetidine-1-yl)ethyl)-2-oxopyridin-1(2H)-yl)-4-methylpentanoate (3.8 g) as yellow oil. Yield: 63% (ESI 357.2 (M+H)$^+$).

Step 2: 2-(3-fluoro-5-(2-(3-fluoroazetidine-1-yl)ethyl)-2-oxopyridin-1(2H)-yl)-4-methylpentanoic Acid

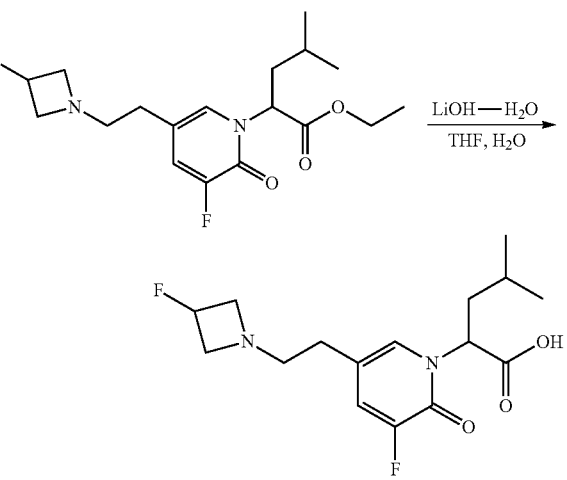

Methyl ethyl 2-(3-fluoro-5-(2-(3-fluoroazetidine-1-yl)ethyl)-2-oxopyridin-1(2H)-yl)-4-methylpentanoate (86 mg, 0.24 mmol) was treated with LiOH monohydrate (50 mg, 1.2 mmol) in THF (3 mL) and H$_2$O (0.5 mL) at room temperature for 1 hour. The reaction mixture was acidified to pH 4~5 with 1N HCl. The residue was purified by reverse phase HPLC on a C18/120 g column (A: water 10 mM NH$_4$HCO$_3$, B: MeOH, 0~100%) to provide 2-(3-fluoro-5-(2-(3-fluoroazetidine-1-yl)ethyl)-2-oxopyridin-1(2H)-yl)-4-methylpentanoic acid as a white solid (55 mg). Yield 70% (ESI 329.1 (M+H)$^+$).

Preparation of 2-(3-fluoro-5-(2-(3-fluoroazetidine-1-yl)ethyl)-2-oxopyridin-1(2H)-yl)pentanoic acid Step 1: Ethyl 2-(5-bromo-3-fluoro-2-oxopyridin-1(2H)-yl)pentanoate

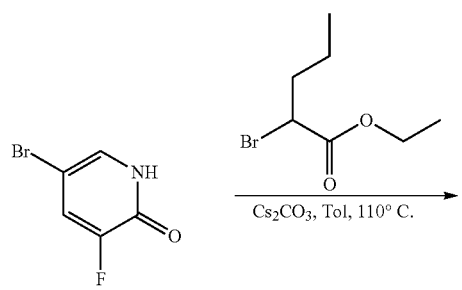

A mixture of 5-bromo-3-fluoropyridin-2(1H)-one (2.1 g, 11.0 mmol), ethyl 2-bromopentanoate (3.43 g, 16.5 mmol) and Cs$_2$CO$_3$ (7.17 g, 22.0 mmol) in Toluene (50 mL) was stirred at 110° C. overnight. The reaction mixture was filtered, washed with EtOAc, concentrated in vacuo. The residue was purified by silica gel column (pet ether:EtOAc 2:1) to provide ethyl 2-(5-bromo-3-fluoro-2-oxopyridin-1(2H)-yl)pentanoate as a white oil (2.9 g). Yield 82% (ESI 320.02 (M+H)$^+$).

Step 2: Ethyl 2-(5-allyl-3-fluoro-2-oxopyridin-1(2H)-yl)pentanoate

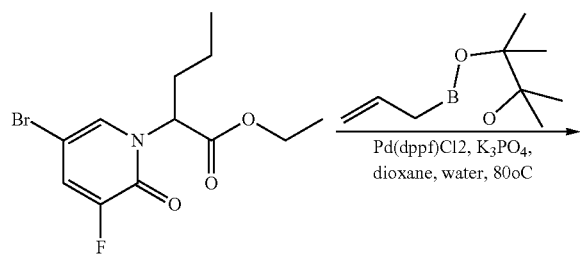

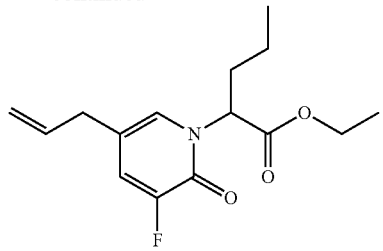

A mixture of ethyl 2-(5-bromo-3-fluoro-2-oxopyridin-1(2H)-yl)pentanoate (2.9 g, 13.2 mmol), 2-allyl-4,4,5,5-tetramethyl-1,3,2-dioxaborolane (2.66 g, 15.8 mmol), Pd(dppf)Cl$_2$ (482.5 mg, 0.66 mmol), and K$_3$PO$_4$ (5.60 g, 26.4 mmol) in 1,4-dioxane (30 mL) and H$_2$O (5 mL) was stirred at 80° C. for 2 hours. The reaction mixture was diluted with 50 mL of water, extracted with EA (60 mL×2). The combined organic phase was washed with brine (100 mL), dried over anhydrous Na$_2$SO$_4$, filtered and concentrated in vacuo and the residue purified by silica gel column (pet ether:EtOAc 1:2) to provide ethyl 2-(5-allyl-3-fluoro-2-oxopyridin-1(2H)-yl)pentanoate as a white oil (1.9 g). Yield 75% (ESI 282.24 (M+H)$^+$).

Step 3: Ethyl 2-(3-fluoro-2-oxo-5-(2-oxoethyl)pyridin-1(2H)-yl)pentanoate

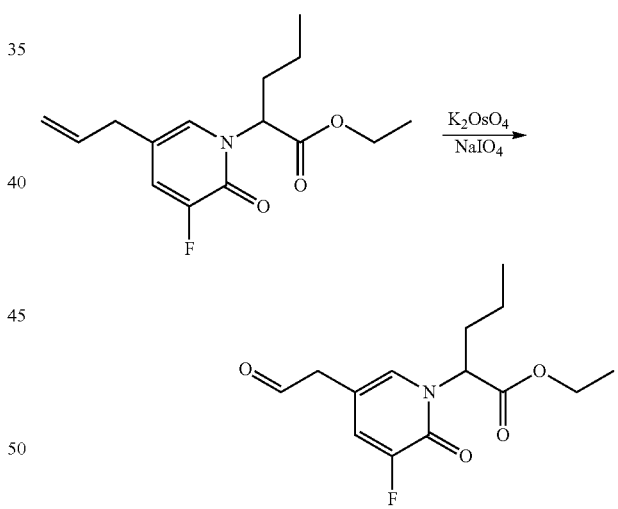

To a mixture of ethyl 2-(5-allyl-3-fluoro-2-oxopyridin-1(2H)-yl)pentanoate (1.9 g, 6.7 mmol) in THF (20 mL) and H$_2$O (30 mL) was added K$_2$OsO$_4$ (25.8 mg, 0.07 mmol) and stirred at room temperature for 1 hour. NaIO$_4$ (3.9, 13.4 mmol) was added and the mixture was stirred at room temperature for 2 hours. The mixture was poured into water (100 mL) and extracted with EtOAc (50 mL×3). The combined organic layers were washed brine (100 mL), dried over Na$_2$SO$_4$, filtered and concentrated in vacuo to provide ethyl 2-(3-fluoro-2-oxo-5-(2-oxoethyl)pyridin-1(2H)-yl)pentanoate as a yellow oil (1.7 g, crude) used directly in the next reaction. (ESI 284.12 (M+H)$^+$).

Step 4: Ethyl 2-(3-fluoro-5-(2-(3-fluoroazetidine-1-yl)ethyl)-2-oxopyridin-1(2H)-yl)pentanoate

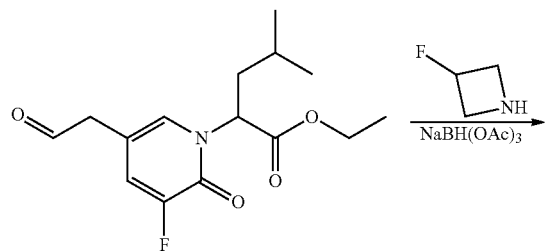

A mixture of ethyl 2-(3-fluoro-2-oxo-5-(2-oxoethyl)pyridin-1(2H)-yl)pentanoate (1.7 g, 6 mmol), AcOH (0.44 g, 7.2 mmol) and 3-fluoroazetidine hydrochloride (1.0 g, 9.0 mmol) in MeOH (30 mL) was stirred at room temperature for 30 mins. NaBH(OAc)$_3$ (2.54 g, 12 mmol) was added and stirred at room temperature for 2 hours. The solvent was concentrated in vacuo and the residue was purified by silica gel column (pet ether:EtOAc 4:1) to provide ethyl 2-(3-fluoro-5-(2-(3-fluoroazetidine-1-yl)ethyl)-2-oxopyridin-1 (2H)-yl)pentanoate as a yellow oil (700 mg). Yield 40% (ESI 343.18 (M+H)$^+$).

Step 5: 2-(3-fluoro-5-(2-(3-fluoroazetidine-1-yl)ethyl)-2-oxopyridin-1(2H)-yl)pentanoic Acid

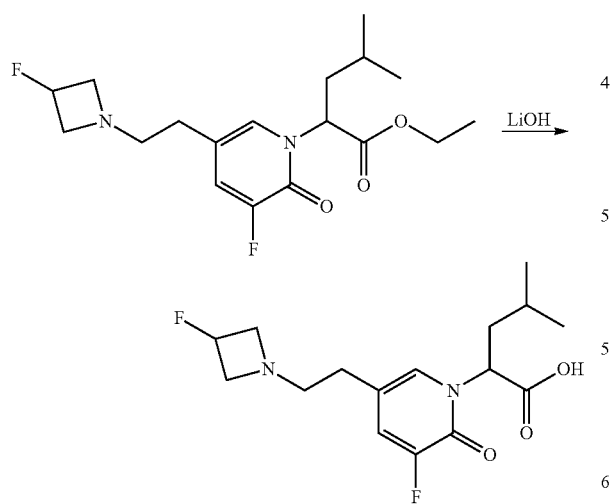

Ethyl 2-(3-fluoro-5-(2-(3-fluoroazetidine-1-yl)ethyl)-2-oxopyridin-1(2H)-yl)pentanoate (700 mg, 2.05 mmol) was treated with LiOH—H$_2$O (344 mg, 8.2 mmol) in EtOH (4 mL) and H$_2$O (1 mL) at room temperature for 2 hours. The reaction mixture was acidified to pH 4~5 with 1N HCl. The reaction mixture was concentrated in vacuo and the residue was purified by reverse phase HPLC on a C18/40 g column (A: water 10 mM NH$_4$HCO$_3$, B: MeOH, 20%) to provide 2-(3-fluoro-5-(2-(3-fluoroazetidine-1-yl)ethyl)-2-oxopyridin-1(2H)-yl)pentanoic acid as a yellow solid (500 mg). Yield 78% (ESI 315.14 (M+H)$^+$).

Preparation of (3R)-2-(3-fluoro-5-(2-(3-fluoroazetidine-1-yl)ethyl)-2-oxopyridin-1(2H)-yl)-3-methylpentanoic Acid

Step 1: (2R,3R)-2-bromo-3-methylpentanoic Acid

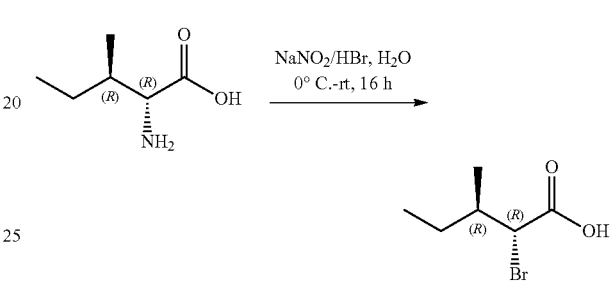

To a solution of D-isoleucine (10.0 g, 76.23 mmol) in H$_2$O (50 mL) was added 40% HBr in water (100 mL). The reaction mixture was cooled to 0° C. A solution of sodium nitrite (7.9 g, 114.35 mmol) in H$_2$O (10 mL) was added dropwise. Then the reaction mixture was stirred at room temperature for 3 hours. The reaction mixture was extracted with EtOAc (100 mL×3). The organic layer was washed with brine (50 mL) and dried over anhydrous Na$_2$SO$_4$, filtered and concentrated in vacuo to provide (2R,3R)-2-bromo-3-methylpentanoic acid as a brown oil used directly in the next reaction without further purification (14.0 g). Yield 95% (ESI 195.1 (M+H)$^+$).

Step 2: methyl (3R)-2-bromo-3-methylpentanoate

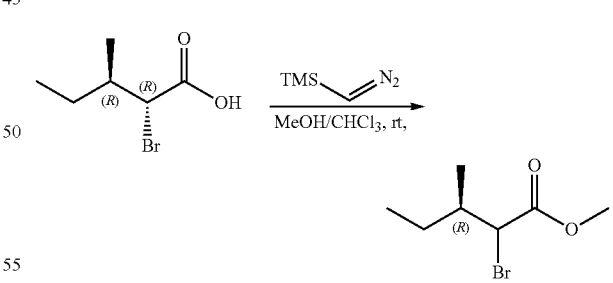

A mixture of (2R,3R)-2-bromo-3-methylpentanoic acid (12.6 g, 64.60 mmol) in MeOH/CHCl$_3$ (30 mL/90 mL) was cooled to 0° C. (Diazomethyl)trimethylsilane (2.0 M in hexane; 64.6 m L, 129.20 mmol) was added dropwise. The mixture was stirred at room temperature for 1 hour. LCMS showed that the reaction was completed. The mixture was concentrated in vacuo to provide methyl (3R)-2-bromo-3-methylpentanoate as a yellow oil used directly in the next reaction without further purification (12.0 g). Yield 89% (ESI 209.1 (M+H)$^+$).

Step 3: methyl (3R)-2-(5-bromo-3-fluoro-2-oxopyridin-1(2H)-yl)-3-methylpentanoate

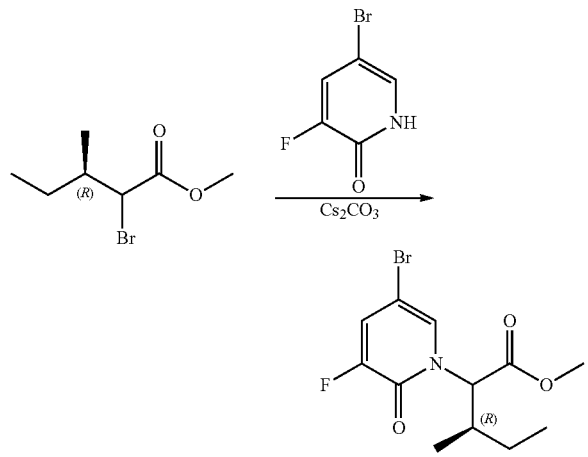

A mixture of 5-bromo-3-fluoropyridin-2(1H)-one (3.1 g, 16.15 mmol), Cs$_2$CO$_3$ (10.5 g, 32.3 mmol) and methyl (3R)-2-bromo-3-methylpentanoate (5.06 g, 24.23 mmol) in dioxane (100 mL) was stirred at 110° C. for 16 h. LCMS showed the reaction was completed. The mixture was filtered and washed with EtOAc (20 mL). The filtrate was concentrated in vacuo and the residue was purified by silica gel column (pet ether:EtOAc 10:1) to provide methyl (3R)-2-(5-bromo-3-fluoro-2-oxopyridin-1(2H)-yl)-3-methylpentanoate as a colorless oil (2.2 g). Yield 43% (ESI 322.0 (M+H)$^+$).

Step 4: methyl (3R)-2-(5-allyl-3-fluoro-2-oxopyridin-1(2H)-yl)-3-methylpentanoate

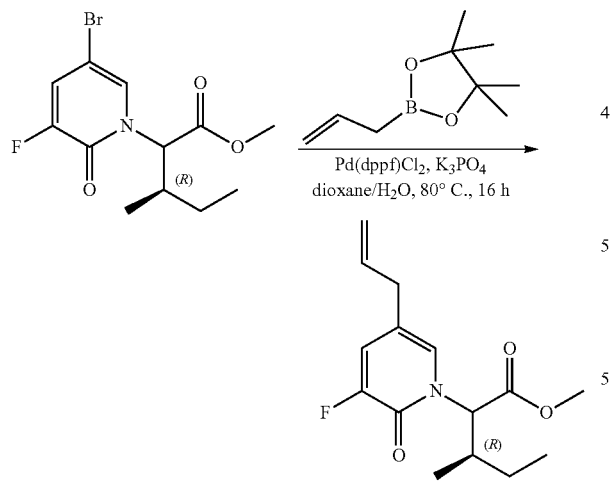

A mixture of methyl (3R)-2-(5-bromo-3-fluoro-2-oxopyridin-1(2H)-yl)-3-methylpentanoate (2.2 g, 6.87 mmol), 2-allyl-4,4,5,5-tetramethyl-1,3,2-dioxaborolane (3.5 g, 20.61 mmol), Pd(dppf)Cl$_2$ (251 mg, 0.34 mmol) and K$_3$PO$_4$ (2.9 g, 13.74 mmol, 2.0 eq) in dioxane (100 mL) and H$_2$O (10 mL) was stirred under nitrogen atmosphere at 80° C. for 16 hours. The mixture was concentrated in vacuo and the residue was purified by silica gel column (pet ether:EtOAc 10:1) to provide methyl (3R)-2-(5-allyl-3-fluoro-2-oxopyridin-1(2H)-yl)-3-methylpentanoate as a yellow oil (1.2 g). Yield 55% (ESI 282.1 (M+H)$^+$).

Step 5: methyl (3R)-2-(3-fluoro-2-oxo-5-(2-oxoethyl)pyridin-1(2H)-yl)-3-methylpentanoate

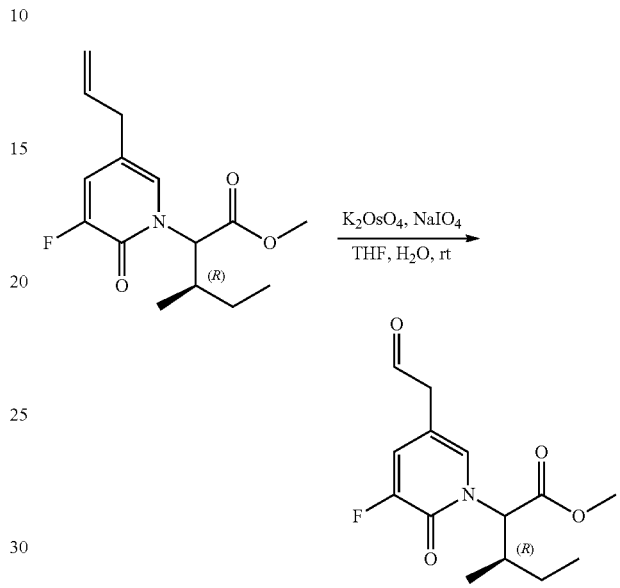

To a solution of methyl (3R)-2-(5-allyl-3-fluoro-2-oxopyridin-1(2H)-yl)-3-methylpentanoate (1.2 g, 4.27 mmol) in THF/H$_2$O (20 mL/20 mL) was added a solution of K$_2$OsO$_4$·2H$_2$O (15.7 mg, 0.043 mmol) in H$_2$O (3 mL) and stirred at room temperature for 1 hour. Then a solution of NaIO$_4$ (1.8 g, 8.54 mmol) in H$_2$O (10 mL) was added dropwise and the mixture was stirred at room temperature for 2 hours. LCMS showed the reaction was completed. The reaction mixture was diluted with H$_2$O (50 mL), extracted with EtOAc (50 mL×3). The combined organic phase was dried over anhydrous Na$_2$SO$_4$, filtered and concentrated in vacuo to provide methyl (3R)-2-(3-fluoro-2-oxo-5-(2-oxoethyl)pyridin-1(2H)-yl)-3-methylpentanoate as a colorless oil used directly in the next reaction without further purification (1.3 g, crude). (ESI 284.1 (M+H)$^+$).

Step 6: methyl (3R)-2-(3-fluoro-5-(2-(3-fluoroazetidine-1-yl)ethyl)-2-oxopyridin-1(2H)-yl)-3-methylpentanoate

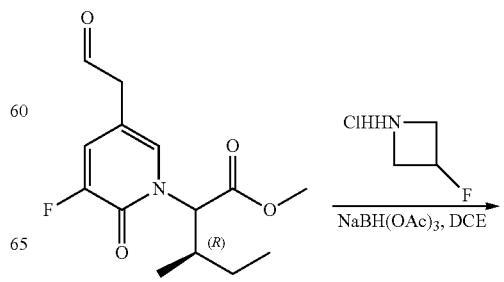

333
-continued

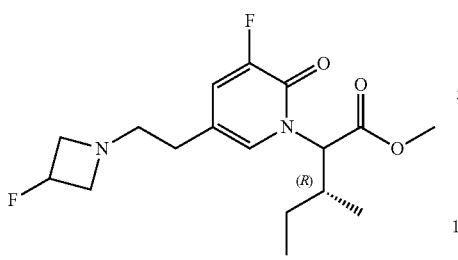

To a mixture of methyl (3R)-2-(3-fluoro-2-oxo-5-(2-oxoethyl)pyridin-1(2H)-yl)-3-methylpentanoate (1.3 g, 4.59 mmol) in DCE (20 mL) at 25° C. was added 3-fluoroazetidine hydrochloride (768 mg, 6.89 mmol) and stirred at 25° C. for 1 hour. NaBH(OAc)₃ (2.9 g, 13.77 mmol) was added at 5° C. and stirred at 25° C. for 16 hours. The mixture was concentrated in vacuo and the residue was purified by silica gel column (DCM:MeOH 20:1) to provide methyl (3R)-2-(3-fluoro-5-(2-(3-fluoroazetidine-1-yl)ethyl)-2-oxopyridin-1(2H)-yl)-3-methylpentanoate as a brown oil (800 mg). Yield 51% (ESI 343.1 [M+H]⁺).

Step 7: (3R)-2-(3-fluoro-5-(2-(3-fluoroazetidine-1-yl)ethyl)-2-oxopyridin-1(2H)-yl)-3-methylpentanoic Acid

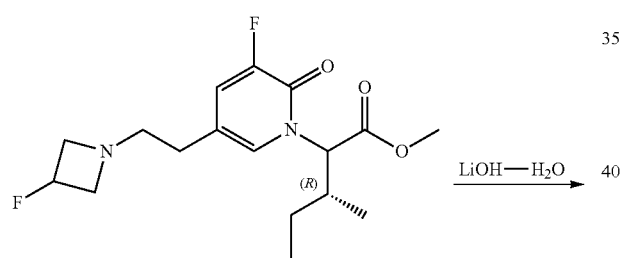

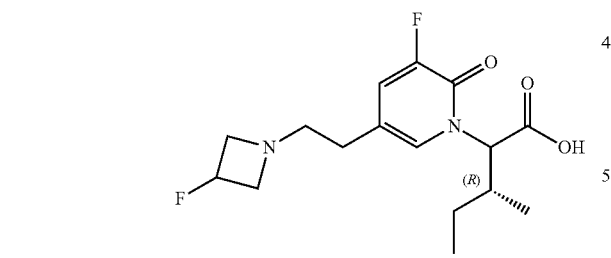

Methyl (3R)-2-(3-fluoro-5-(2-(3-fluoroazetidine-1-yl)ethyl)-2-oxopyridin-1(2H)-yl)-3-methylpentanoate (800 mg, 2.34 mmol) was treated with LiOH—H₂O (491 mg, 11.7 mmol) in EtOH (5 mL) and water (2 mL) and the mixture was stirred at room temperature for 30 minutes. The mixture was acidified with 1N HCl to pH 5~6, concentrated and purified by reverse phase HPLC on a C18/40 g column (A: water/0.01% TFA, B: MeOH, 0~100%) to provide (3R)-2-(3-fluoro-5-(2-(3-fluoroazetidine-1-yl)ethyl)-2-oxopyridin-1(2H)-yl)-3-methylpentanoic acid as a white solid (600 mg). Yield 78% (ESI 329.2 (M+H)⁺).

334
Preparation of 3-cyclopropyl-2-(3-fluoro-5-(2-(3-fluoroazetidine-1-yl)ethyl)-2-oxopyridin-1(2H)-yl) propanoic Acid Step 1: Ethyl 2-(5-bromo-3-fluoro-2-oxopyridin-1 (2H)-yl)-3-cyclopropylpropanoate

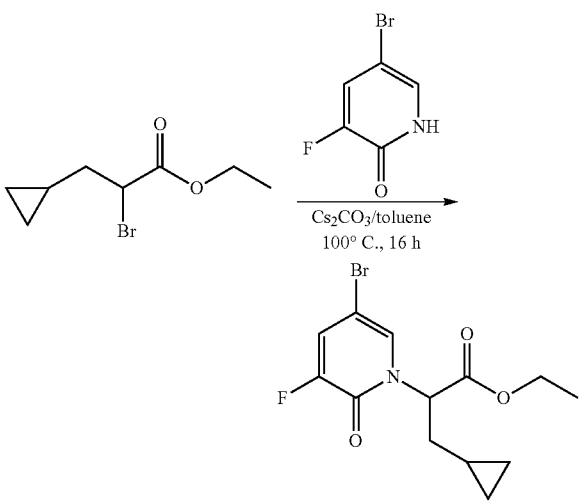

A mixture of 5-bromo-3-fluoropyridin-2(1H)-one (2.0 g, 10.4 mmol), Cs₂CO₃ (6.5 g, 20.8 mmol) and ethyl 2-bromo-3-cyclopropylpropanoate (2.7 g, 12.4 mmol) in toluene (50 mL) was stirred at 110° C. for 16 hours. LCMS showed the reaction was completed. The mixture was filtered and washed with EtOAc (20 mL). The filtrate was concentrated in vacuo and the residue was purified by silica gel column (pet ether:EtOAc 4:1) to provide ethyl 2-(5-bromo-3-fluoro-2-oxopyridin-1(2H)-yl)-3-cyclopropylpropanoate as a yellow oil (2.0 g). Yield 58% (ESI 333 (M+H)⁺).

Step 2: Ethyl 2-(5-allyl-3-fluoro-2-oxopyridin-1 (2H)-yl)-3-cyclopropylpropanoate

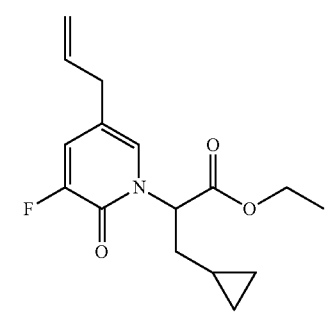

A mixture of ethyl 2-(5-bromo-3-fluoro-2-oxopyridin-1(2H)-yl)-3-cyclopropylpropanoate (1.5 g, 4.5 mmol), allyltributylstannane (1.5 g, 5.4 mmol), CsF (1.4 g, 9 mmol), Pd(dba)₃ (126 mg, 0.45 mmol) and PCy₃ (206 mg, 0.225 mmol) in dioxane (100 mL) was stirred at 100° C. overnight. The mixture was poured into water (200 mL) and extracted with EtOAc (100 mL×3). The combined organic layers were washed with brine (100 mL), dried over Na₂SO₄, filtered and concentrated in vacuo. The residue was purified by silica gel column (pet ether:EtOAc 4:1) to provide ethyl 2-(5-allyl-3-fluoro-2-oxopyridin-1(2H)-yl)-3-cyclopropylpropanoate as a yellow oil (1.0 g). Yield 83% (ESI 294 (M+H)+).

Step 3: Ethyl 3-cyclopropyl-2-(3-fluoro-2-oxo-5-(2-oxoethyl)pyridin-1(2H)-yl)propanoate

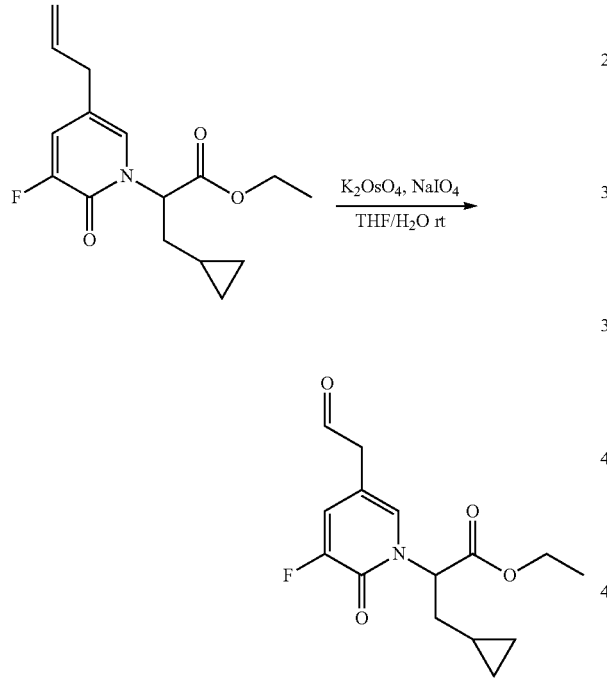

To a solution of ethyl 2-(5-allyl-3-fluoro-2-oxopyridin-1(2H)-yl)-3-cyclopropylpropanoate (800 mg, 2.7 mmol) in THF/H₂O (60 mL/20 mL) was added a solution of K₂OsO₄-2H₂O (10 mg, 0.027 mmol) in H₂O (4 mL) and stirred at room temperature for 1 h. Then a solution of NaIO₄ (1.1 g, 5.4 mmol) in H₂O (20 mL) was added and stirred at room temperature for 2 h. LCMS showed the reaction was completed. The reaction mixture was diluted with 100 mL of water and extracted with EtOAc (100 mL×3). The combined organic phase was dried over anhydrous Na₂SO₄, filtered and concentrated in vacuo to provide ethyl 3-cyclopropyl-2-(3-fluoro-2-oxo-5-(2-oxoethyl)pyridin-1(2H)-yl)propanoate as a yellow oil used directly in the next reaction without further purification (820 mg, crude). (ESI 296 (M+H)⁺).

Step 4: Ethyl 3-cyclopropyl-2-(3-fluoro-5-(2-(3-fluoroazetidine-1-yl)ethyl)-2-oxopyridin-1(2H)-yl)propanoate

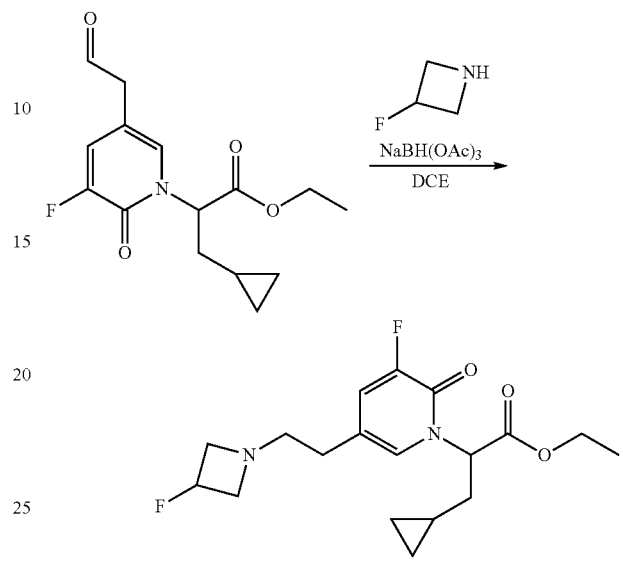

A mixture of ethyl 3-cyclopropyl-2-(3-fluoro-2-oxo-5-(2-oxoethyl)pyridin-1(2H)-yl)propanoate (500 mg, 1.7 mmol) and 3-fluoroazetidine hydrochloride (188 mg, 1.7 mmol) in DCE (20 mL) was stirred at room temperature for 10 minutes. NaBH(OAc)₃ (530 g, 1.5 mmol) was added and stirred at room temperature for 2 h. The mixture was diluted with water (50 mL) and extracted with DCM (50 mL×3). The combined organic phase was dried over anhydrous Na₂SO₄, filtered and concentrated in vacuo and the residue was purified by reverse phase HPLC on a C18/40 g column (A: water 10 mM NH₄HCO₃, B: MeOH, 0~100%) to provide ethyl 3-cyclopropyl-2-(3-fluoro-5-(2-(3-fluoroazetidine-1-yl)ethyl)-2-oxopyridin-1(2H)-yl)propanoate as a yellow oil (300 mg). Yield 31% (ESI 355 (M+H)⁺).

Step 5: 3-cyclopropyl-2-(3-fluoro-5-(2-(3-fluoroazetidine-1-yl)ethyl)-2-oxopyridin-1(2H)-yl)propanoic Acid

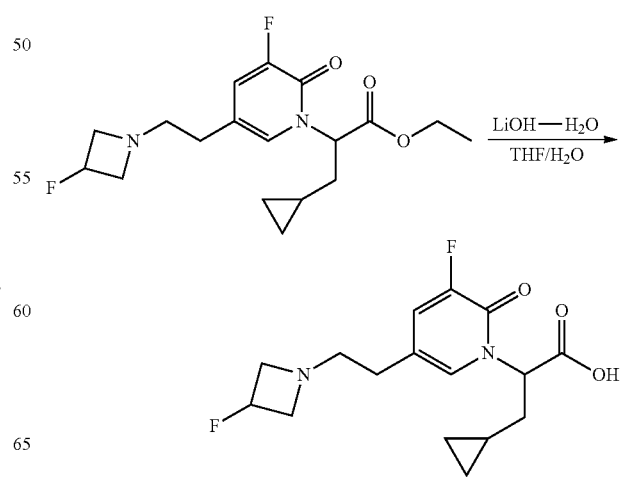

337

Ethyl 3-cyclopropyl-2-(3-fluoro-5-(2-(3-fluoroazetidine-1-yl)ethyl)-2-oxopyridin-1(2H)-yl)propanoate (300 mg, 0.84 mmol) was treated with LiOH—H₂O (178 mg, 4.20 mmol) in THF (10 mL) and water (5 mL) at room temperature for 2 hours. The reaction mixture was acidified to pH 5 with 1N HCl and concentrated. The mixture was purified by reverse phase HPLC on a C18/40 g column (A: water, B: MeOH, 0~100%) to provide 2-(3-fluoro-5-(2-(3-fluoroazetidine-1-yl)ethyl)-4-methyl-2-oxopyridin-1(2H)-yl)-4-methylpentanoic acid as a white solid (200 mg). Yield 86% (ESI 327 (M+H)⁺).

Preparation of 2-(3-fluoro-5-(2-(3-fluoroazetidine-1-yl)ethyl)-2-oxopyridin-1(2H)-yl)-3-methylbutanoic acid

Step 1: Ethyl 2-(5-bromo-3-fluoro-2-oxopyridin-1(2H)-yl)-3-methylbutanoate

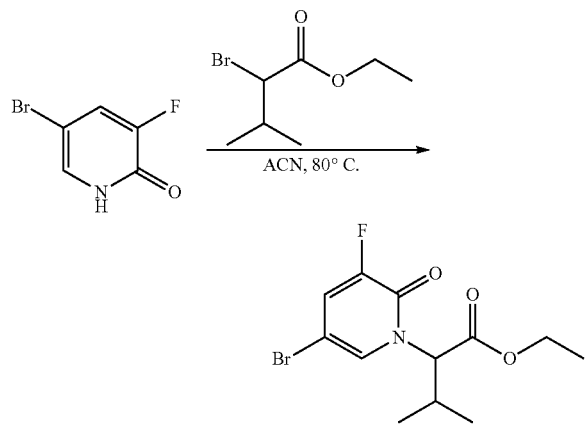

A mixture of 5-bromo-3-fluoropyridin-2(1H)-one (5.0 g, 26.2 mmol, 1.0 eq), K₂CO₃ (7.2 g, 52.4 mmol, 2.0 eq) and ethyl 2-bromo-3-methylbutanoate (6.5 g, 31.4 mmol, 1.2 eq) in ACN (100 mL) was stirred at 80° C. for 16 hours. LCMS showed the reaction was completed. The mixture was filtered and washed with EtOAc (20 mL). The filtrate was concentrated in vacuo and the residue was purified by silica gel column (pet ether:EtOAc 4:1) to provide ethyl 2-(5-bromo-3-fluoro-2-oxopyridin-1(2H)-yl)-3-methylbutanoate as a yellow oil (3.0 g). Yield 36% (ESI 320.1 (M+H)⁺).

Step 2: Ethyl 2-(5-allyl-3-fluoro-2-oxopyridin-1(2H)-yl)-3-methylbutanoate

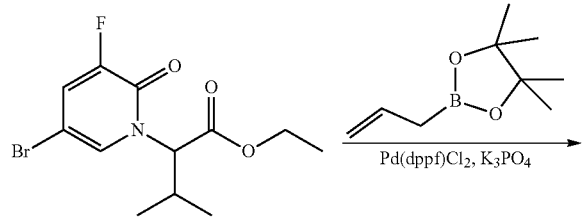

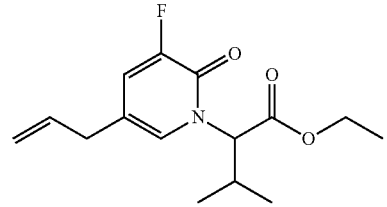

A mixture of ethyl 2-(5-bromo-3-fluoro-2-oxopyridin-1(2H)-yl)-3-methylbutanoate (3.0 g, 9.4 mmol, 1 eq), 2-allyl-4,4,5,5-tetramethyl-1,3,2-dioxaborolane (1.9 g, 11.3 mmol, 1.2 eq), Pd(dppf)Cl₂ (343.6 mg, 0.47 mmol, 0.05 eq) and K₃PO₄ (4.0 g, 18.8 mmol, 2.0 eq) in dioxane (100 mL) and H₂O (10 mL) was stirred at 100° C. overnight. Water (200 mL) was added and the solution was extracted with EtOAc (100 mL×3). The combined organic phases were washed with brine (100 mL), dried over anhydrous Na₂SO₄, filtered and concentrated in vacuo. The residue was purified by silica gel column (pet ether:EtOAc 4:1) to provide ethyl 2-(5-allyl-3-fluoro-2-oxopyridin-1(2H)-yl)-3-methylbutanoate as a yellow oil (2.4 g). Yield 92% (ESI 282.0 (M+H)+).

Step 3: Ethyl 2-(3-fluoro-2-oxo-5-(2-oxoethyl)pyridin-1(2H)-yl)-3-methylbutanoate

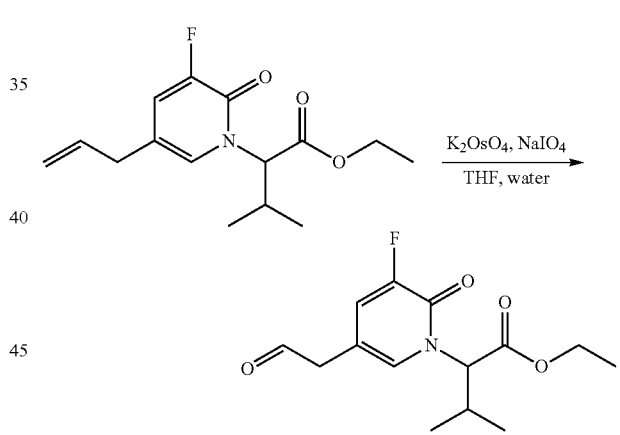

To a solution of ethyl 2-(5-allyl-3-fluoro-2-oxopyridin-1(2H)-yl)-3-methylbutanoate (2.4 g, 8.6 mmol, 1.0 eq) in THF (100 mL) and H₂O (30 mL) was added a solution of K₂OsO₄·2H₂O (32 mg, 0.086 mmol, 0.01 eq) in H₂O (4 mL). The mixture was stirred at room temperature for 1 hour. Then a solution of NaIO₄ (3.7 g, 17.2 mmol, 2.0 eq) in H₂O (20 mL) was added and stirred at room temperature for 2 hours. LCMS showed the reaction was completed. Water (100 mL) was added and the solution was extracted with EtOAc (100 mL×3). The combined organic phases were washed with brine (50 mL), dried over anhydrous Na₂SO₄, filtered and concentrated in vacuo to provide ethyl 2-(3-fluoro-2-oxo-5-(2-oxoethyl)pyridin-1(2H)-yl)-3-methylbutanoate as a yellow oil used directly in the next reaction without further purification (1.6 g, crude). (ESI 284.1 (M+H)⁺).

Step 4: Ethyl 2-(3-fluoro-5-(2-(3-fluoroazetidine-1-yl)ethyl)-2-oxopyridin-1(2H)-yl)-3-methylbutanoate

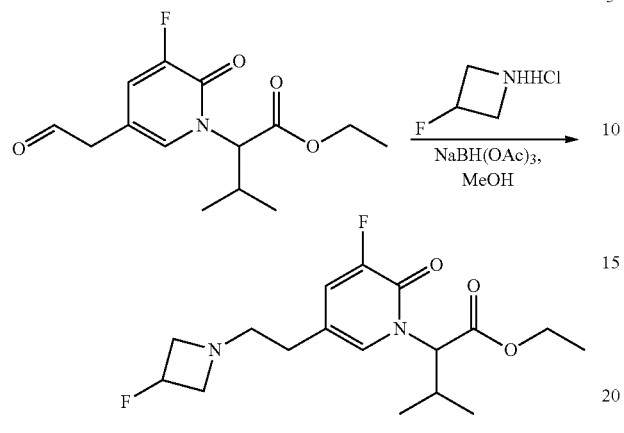

A mixture of ethyl 2-(3-fluoro-2-oxo-5-(2-oxoethyl)pyridin-1(2H)-yl)-3-methylbutanoate (1.6 g, 5.7 mmol, 1.0 eq) and 3-fluoroazetidine hydrochloride (427.5 mg, 5.7 mmol, 1.0 eq) in MeOH (20 mL) was stirred at room temperature for 10 minutes. NaBH(OAc)$_3$ (1.8 g, 8.6 mmol, 1.5 eq) was added and stirred at room temperature for 2 hours. LCMS showed the reaction was completed. The solvent was concentrated in vacuo and the residue was purified by silica gel column (pet ether:EtOAc 1:1) to provide ethyl 2-(3-fluoro-5-(2-(3-fluoroazetidine-1-yl)ethyl)-2-oxopyridin-1(2H)-yl)-3-methylbutanoate as a yellow oil (700 mg). Yield 24% for two steps (ESI 343.1 (M+H)$^+$).

Step 5: 2-(3-fluoro-5-(2-(3-fluoroazetidine-1-yl)ethyl)-2-oxopyridin-1(2H)-yl)-3-methylbutanoic acid

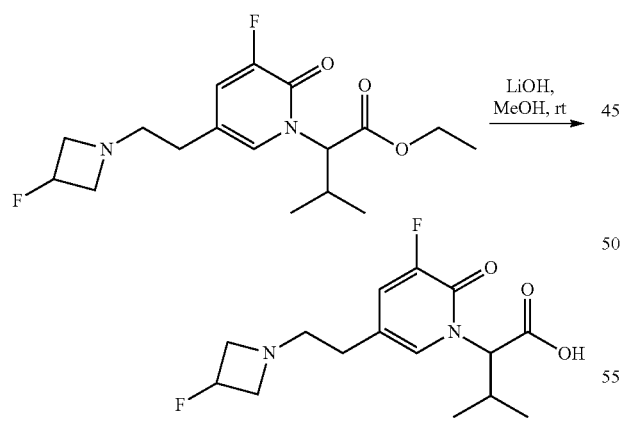

Ethyl 2-(3-fluoro-5-(2-(3-fluoroazetidine-1-yl)ethyl)-2-oxopyridin-1(2H)-yl)-3-methylbutanoate (700 mg, 2.0 mmol, 1.0 eq) was treated with LiOH—H$_2$O (336 mg, 8.0 mmol, 4.0 eq) in MeOH (10 mL) and water (5 mL) at room temperature for 2 hours. The reaction mixture was acidified to pH 5 with 1N HCl and concentrated. The mixture was purified by reverse phase HPLC on a C18/40 g column (A: water 10 mM NH$_4$HCO$_3$, B: MeOH, 0~100%) to provide 2-(3-fluoro-5-(2-(3-fluoroazetidine-1-yl)ethyl)-2-oxopyri-din-1(2H)-yl)-3-methylbutanoic acid as a white solid (500 mg). Yield 78% (ESI 315.1 (M+H)$^+$).

Preparation of 2-(3-fluoro-5-(2-((R)-3-fluoropyrrolidin-1-yl)ethyl)-2-oxopyridin-1(2H)-yl)-4-methylpentanoic Acid

Step 1: Ethyl 2-(3-fluoro-5-(2-((R)-3-fluoropyrrolidin-1-yl)ethyl)-2-oxopyridin-1(2H)-yl)-4-methylpentanoate

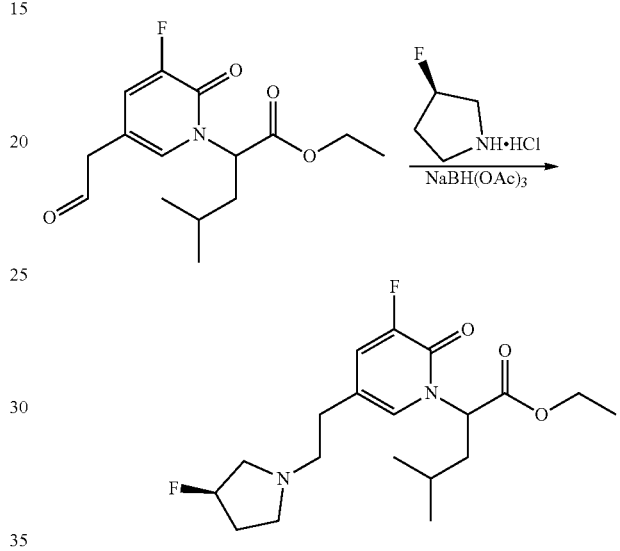

To a mixture of ethyl 2-(3-fluoro-2-oxo-5-(2-oxoethyl)pyridin-1(2H)-yl)-4-methylpentanoate (3.3 g, 11.2 mmol) in DCE (70 mL) at 25° C. was added (R)-3-fluoropyrrolidine hydrochloride (1.4 g, 11.2 mmol) and stirred at 25° C. for 30 mins. NaBH(OAc)$_3$ (4.6 g, 22.4 mmol) was added at 5° C. and stirred at 25° C. for 16 hours. The mixture was concentrated in vacuo and the residue was purified by silica gel column (DCM:MeOH 10:1) to give compound ethyl 2-(3-fluoro-5-(2-((R)-3-fluoropyrrolidin-1-yl)ethyl)-2-oxopyridin-1(2H)-yl)-4-methylpentanoate (1.7 g) as a yellow oil. Yield 41% (ESI 371.2 (M+H)$^+$).

Step 2: 2-(3-fluoro-5-(2-((R)-3-fluoropyrrolidin-1-yl)ethyl)-2-oxopyridin-1(2H)-yl)-4-methylpentanoic Acid

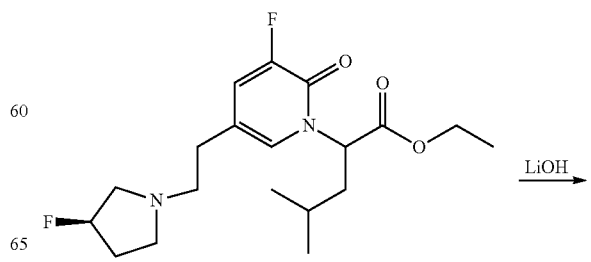

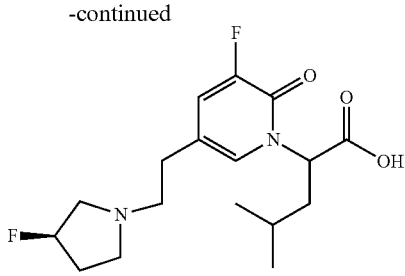

Ethyl 2-(3-fluoro-5-(2-((R)-3-fluoropyrrolidin-1-yl)ethyl)-2-oxopyridin-1(2H)-yl)-4-methylpentanoate (1.7 g, 4.59 mmol) was treated with LiOH—H$_2$O (960.0 mg, 23.0 mmol, 5.0 eq) in MeOH (12 mL) and water (5 mL) at room temperature for 2 hours. The MeOH was removed and the aqueous acidified with 1N HCl to pH=5. The residue was purified by reverse phase HPLC on a C18/40 g column (A: water 10 mM NH$_4$HCO$_3$, B: MeOH, 0~100%) to provide 2-(3-fluoro-5-(2-((R)-3-fluoropyrrolidin-1-yl)ethyl)-2-oxopyridin-1(2H)-yl)-4-methylpentanoic acid as a white solid (1.1 g). Yield 70% (ESI 343.1 (M+H)$^+$).

Preparation of 2-(5-(2-(dimethylamino)ethyl)-3-fluoro-4-methyl-2-oxopyridin-1(2H)-yl)-4-methylpentanoic Acid Step 1: 3-fluoro-4-methylpyridin-2(1H)-one

A mixture of 4-methylpyridin-2(1H)-one (10 g, 92 mmol, 1.0 eq) and selectfluor (16 g, 46 mmol, 0.5 eq) in CHCl$_3$ (100 mL) and water (100 mL) was stirred at 35° C. for 16 h. The reaction mixture was diluted with a saturated NaCl solution (100 mL) and extracted with DCM (100 mL×3). The combined organic phase was dried over anhydrous Na$_2$SO$_4$, filtered and concentrated in vacuo. The residue was purified by silica gel column (EtOAc:DCM:MeOH 100:10:6) to provide 3-fluoro-4-methylpyridin-2(1H)-one as a whittle solid (2.4 g). Yield 21% (ESI 128 (M+H)$^+$). $^1$H NMR (400 MHz, CDCl$_3$) δ 13.53 (s, 1H), 7.20 (dd, J=6.6, 0.6 Hz, 1H), 6.14 (t, J=6.1 Hz, 1H), 2.24 (d, J=2.5 Hz, 3H). $^{19}$F NMR (376 MHz, CDCl$_3$) δ −140.20.

Step 2: 5-bromo-3-fluoro-4-methylpyridin-2(1H)-one

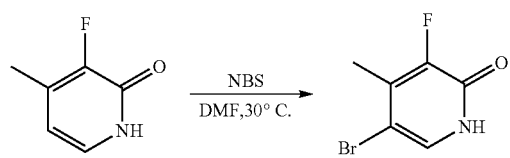

To a solution of 3-fluoro-4-methylpyridin-2(1H)-one (2.4 g, 18.9 mmol, 1.0 eq) in DMF (20 mL) was added NBS (3.7 g, 20.8 mmol, 1.1 eq) and stirred at 30° C. for 1 h. The reaction mixture was purified by reverse phase HPLC (A: water(0.01% TFA); B ACN, 45% of B) to provide 5-bromo-3-fluoro-4-methylpyridin-2(1H)-one as a whittle solid (3 g). Yield 77% (ESI 206 (M+H)$^+$). $^1$H NMR (500 MHz, CDCl$_3$) δ 7.42 (d, J=1.3 Hz, 1H), 2.31 (d, J=3.0 Hz, 3H).

Step 3: Ethyl 2-(5-bromo-3-fluoro-4-methyl-2-oxopyridin-1(2H)-yl)-4-methylpentanoate

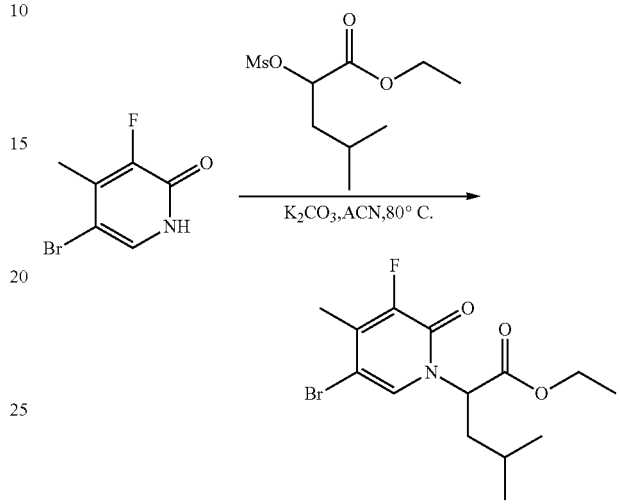

A mixture of 5-bromo-3-fluoro-4-methylpyridin-2(1H)-one (3.0 g, 14.6 mmol, 1.0 eq), K$_2$CO$_3$ (4 g, 29.3 mmol, 2.0 eq) and ethyl 4-methyl-2-((methylsulfonyl)oxy)pentanoate (7 g, 29.3 mmol, 2 eq) in CH$_3$CN (50 mL) was stirred at 80° C. for 16 h. LCMS showed the reaction was completed. The mixture was filtered and washed with CH$_3$CN (20 mL). The filtrate was concentrated in vacuo and the residue was purified by silica gel column (pet ether:EtOAc 4:1) to provide ethyl 2-(5-bromo-3-fluoro-4-methyl-2-oxopyridin-1(2H)-yl)-4-methylpentanoate as a yellow oil (4.5 g). Yield 89% (ESI 348 (M+H)$^+$).

Step 4: Ethyl 2-(5-allyl-3-fluoro-4-methyl-2-oxopyridin-1(2H)-yl)-4-methylpentanoate

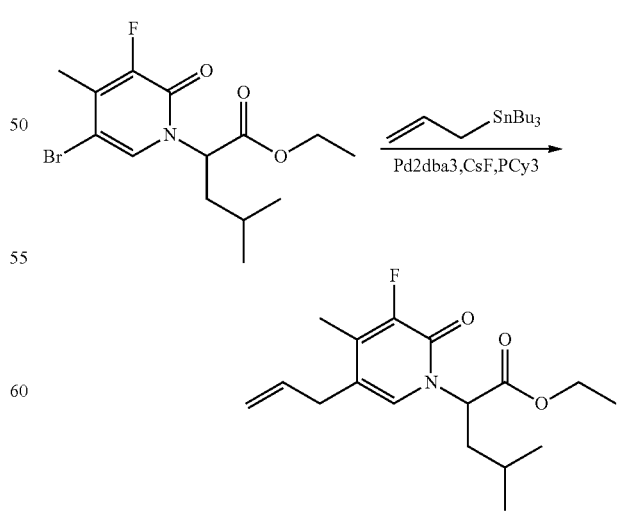

A mixture of ethyl 2-(5-bromo-3-fluoro-4-methyl-2-oxopyridin-1(2H)-yl)-4-methylpentanoate (4.5 g, 13 mmol, 1.0 eq), allyltributylstannane (35.6 g, 16.9 mmol, 1.3 eq), Pd₂dba₃ (595 mg, 0.65 mmol, 0.05 eq), PCy₃ (364 mg, 1.3 mmol, 0.1 eq) and CsF (4 g, 26 mmol, 2.0 eq) in anhydrous dioxane (100 mL) was stirred under N₂ at 100° C. for 16 hours. The mixture was cooled to room temperature. A saturated NH4Cl solution (100 mL) was added and the solution was extracted with EtOAc (100 mL×3). The combined organic layers were washed with brine (100 mL), dried over anhydrous Na₂SO₄, filtered and concentrated in vacuo. The residue was purified by silica gel column (pet ether:EtOAc 4:1) to provide ethyl 2-(5-allyl-3-fluoro-4-methyl-2-oxopyridin-1(2H)-yl)-4-methylpentanoate as a yellow solid (2 g). Yield 50% (ESI 310 (M+H)⁺). ¹H NMR (400 MHz, CDCl₃) δ 6.86 (s, 1H), 5.93-5.84 (m, 1H), 5.77-5.73 (m, 1H), 5.18-5.03 (m, 2H), 4.20 (q, J=8 Hz, 2H), 3.18-3.14 (m, 2H), 2.13 (d, J=2.8 Hz, 3H), 2.01-1.94 (m, 1H), 1.90-1.84 (m, 1H), 1.45-1.37 (m, 1H), 1.26 (t, J=8 Hz, 2H), 0.98-0.91 (m, 6H).

Step 5: Ethyl 2-(3-fluoro-4-methyl-2-oxo-5-(2-oxo-ethyl)pyridin-1(2H)-yl)-4-methylpentanoate

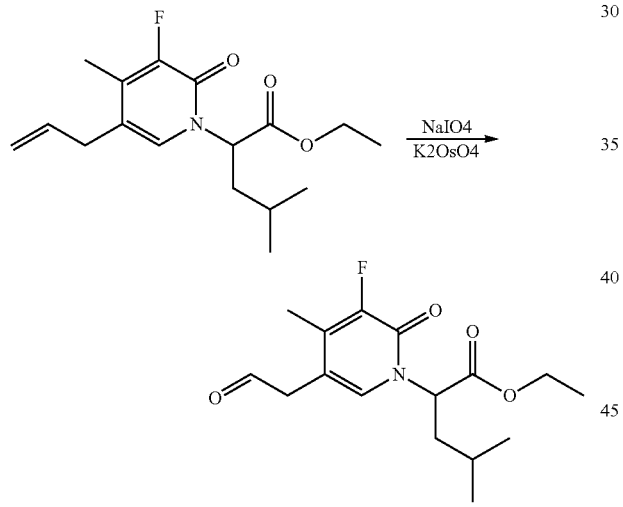

To a solution of ethyl 2-(5-allyl-3-fluoro-4-methyl-2-oxopyridin-1(2H)-yl)-4-methylpentanoate (1.8 g, 5.8 mmol, 1.0 eq) in THF/H₂O (60 mL/20 mL) was added a solution of K₂OsO₄·2H₂O (21 mg, 0.058 mmol, 0.01 eq) in H₂O (4 mL) and stirred at room temperature for 1 h. Then a solution of NaIO₄ (1.25 g, 11.7 mmol, 2.0 eq) in H₂O (20 mL) was added and stirred at room temperature for 2 h. LCMS showed the reaction was completed. The reaction mixture was diluted with 100 mL of water and extracted with EtOAc (100 mL×3). The combined organic phase was dried over anhydrous Na₂SO₄, filtered and concentrated in vacuo to provide ethyl 2-(3-fluoro-4-methyl-2-oxo-5-(2-oxoethyl)pyridin-1(2H)-yl)-4-methylpentanoate as a yellow oil used directly in the next reaction without further purification (2 g, crude). (ESI 312 (M+H)⁺).

Step 6: Ethyl 2-(5-(2-(dimethylamino)ethyl)-3-fluoro-4-methyl-2-oxopyridin-1(2H)-yl)-4-methyl-pentanoate

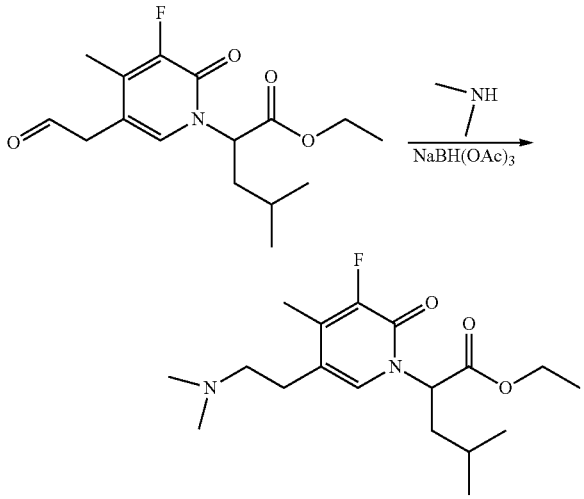

A mixture of ethyl 2-(3-fluoro-4-methyl-2-oxo-5-(2-oxoethyl)pyridin-1(2H)-yl)-4-methylpentanoate (2.0 g, 6.42 mmol) and dimethylamine (9.64 mL, 19.27 mmol) (2.0 M) in THF was added in DCE (32.1 mL) and stirred at room temperature for 10 mins. NaBH(OAc)₃ (4.08 g, 19.3 mmol, 3.0 eq) was added to the reaction mixture and stirred at room temperature for 2 h. The mixture was diluted with water (50 mL) and extracted with DCM (50 mL×3). The combined organic phase was dried over anhydrous Na₂SO₄. The solvent was removed in vacuo and the residue was purified by reverse phase HPLC in NH₄HCO₃ condition (A: water 10 mM NH₄HCO₃, B: MeOH, 0~100%) to provide ethyl 2-(5-(2-(dimethylamino)ethyl)-3-fluoro-4-methyl-2-oxopyridin-1(2H)-yl)-4-methylpentanoate (1.41 g, 4.14 mmol, 64.5% yield) as yellow oil. (ESI 341 (M+H)⁺).

Step 7: 2-(5-(2-(dimethylamino)ethyl)-3-fluoro-4-methyl-2-oxopyridin-1(2H)-yl)-4-methylpentanoic Acid

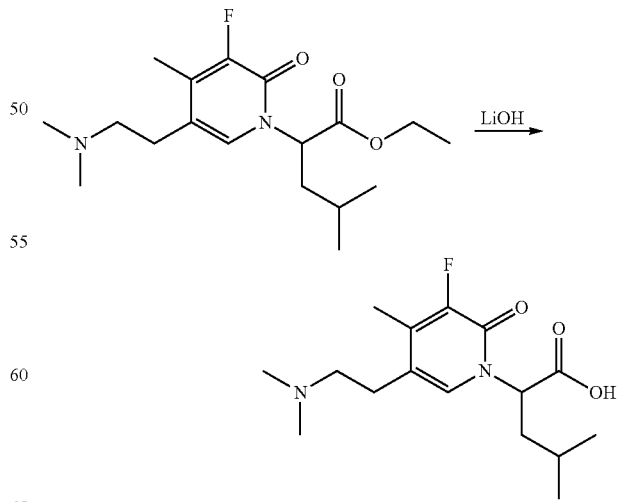

Ethyl 2-(5-(2-(dimethylamino)ethyl)-3-fluoro-4-methyl-2-oxopyridin-1(2H)-yl)-4-methylpentanoate (1.41 g, 4.14 mmol) was treated with lithium hydroxide (0.496 g, 20.71 mmol) in MeOH (10 mL) and water (5 mL) at room temperature for 2 hours. The MeOH was removed and the aqueous acidified with 1N HCl to pH=5. The residue was purified by reverse phase HPLC in neutral condition (A: water, B: MeOH, 0~100%) to provide 2-(5-(2-(dimethyl-amino)ethyl)-3-fluoro-4-methyl-2-oxopyridin-1(2H)-yl)-4-methylpentanoic acid (1.21 g, 3.87 mmol, 94% yield) (ESI 313 (M+H)$^+$).

Preparation of 2-(3-fluoro-5-(2-(3-fluoroazetidine-1-yl)ethyl)-4-methyl-2-oxopyridin-1(2H)-yl)-4-methylpentanoic Acid Step 1: Ethyl 2-(3-fluoro-5-(2-(3-fluoroazetidine-1-yl)ethyl)-4-methyl-2-oxopyridin-1(2H)-yl)-4-methylpentanoate

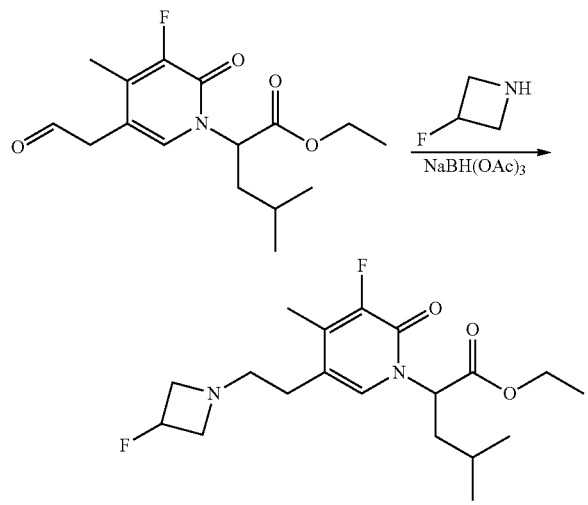

A mixture of ethyl 2-(3-fluoro-4-methyl-2-oxo-5-(2-oxoethyl)pyridin-1(2H)-yl)-4-methylpentanoate (2 g, 6.4 mmol) and 3-fluoroazetidine hydrochloride (2.1 g, 19.3 mmol, 3.0 eq) in DCE (20 mL) was stirred at room temperature for 10 minutes. NaBH(OAc)$_3$ (4.2 g, 19.3 mmol, 3.0 eq) was added to the reaction mixture and stirred at room temperature for 2 h. The mixture was diluted with water (50 mL) and extracted with DCM (50 mL×3). The combined organic phase was dried over anhydrous Na$_2$SO$_4$, filtered and concentrated in vacuo and the residue was purified by reverse phase HPLC (A: water 10 mM NH$_4$HCO$_3$, B: MeOH, 70% B) to provide ethyl 2-(3-fluoro-5-(2-(3-fluoroazetidine-1-yl)ethyl)-4-methyl-2-oxopyridin-1(2H)-yl)-4-methylpentanoate as a yellow oil (1 g). Yield 42% (ESI 371 (M+H)$^+$).

Step 2: 2-(3-fluoro-5-(2-(3-fluoroazetidine-1-yl)ethyl)-4-methyl-2-oxopyridin-1(2H)-yl)-4-methylpentanoic Acid

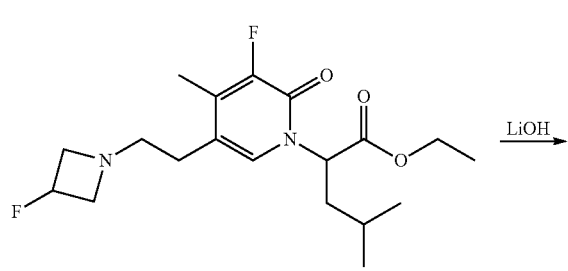

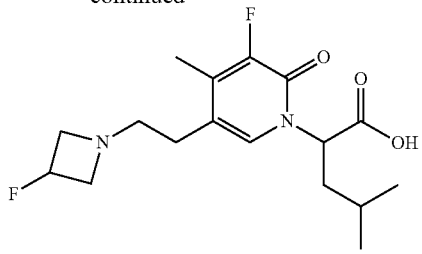

Ethyl 2-(3-fluoro-5-(2-(3-fluoroazetidine-1-yl)ethyl)-4-methyl-2-oxopyridin-1(2H)-yl)-4-methylpentanoate (1 g, 2.7 mmol, 1.0 eq) was treated with LiOH—H$_2$O (567 mg, 13.5 mmol, 5.0 eq) in MeOH (10 mL) and water (5 mL) at room temperature for 2 hours. The reaction mixture was acidified to pH 5 with 1N HCl and concentrated. The mixture was purified by reverse phase HPLC in neutral condition (A: water, B: MeOH, 60% B) to provide 2-(3-fluoro-5-(2-(3-fluoroazetidine-1-yl)ethyl)-4-methyl-2-oxopyridin-1(2H)-yl)-4-methylpentanoic acid as a white solid (800 mg). Yield 86% (ESI 343 (M+H)$^+$).

Preparation of 2-(3-fluoro-5-(2-(3-methoxyazetidin-1-yl)ethyl)-4-methyl-2-oxopyridin-1(2H)-yl)-4-methylpentanoic Acid Step 1: Ethyl 2-(3-fluoro-5-(2-(3-methoxyazetidin-1-yl)ethyl)-4-methyl-2-oxopyridin-1(2H)-yl)-4-methylpentanoate

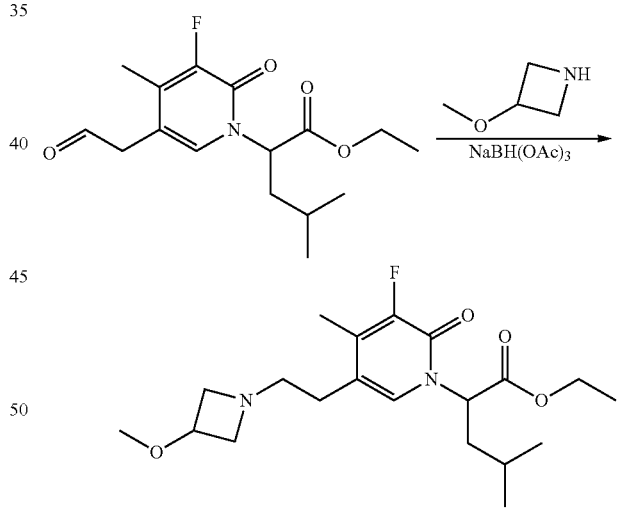

A mixture of ethyl 2-(3-fluoro-4-methyl-2-oxo-5-(2-oxoethyl)pyridin-1(2H)-yl)-4-methylpentanoate (4.5 g, 14.4 mmol) and 3-methoxyazetidine hydrochloride (2.7 g, 21.7 mmol) in DCE (20 mL) was stirred at room temperature for 1 h. NaBH(OAc)$_3$ (6.2 g, 29.2 mmol) was added and stirred at room temperature for 2 h. The mixture was diluted with water (50 mL) and extracted with DCM (50 mL×3). The combined organic phase was dried over anhydrous Na$_2$SO$_4$, filtered and concentrated in vacuo and the residue was purified by reverse phase HPLC on a C18/120 g column (A: water 10 mM NH$_4$HCO$_3$, B: MeOH, 0~100%) to provide ethyl 2-(3-fluoro-5-(2-(3-methoxyazetidin-1-yl)ethyl)-4- methyl-2-oxopyridin-1(2H)-yl)-4-methylpentanoate as a yellow oil (2.7 g). Yield 49% (ESI 383.1 (M+H)+).

Step 2: 2-(3-fluoro-5-(2-(3-methoxyazetidin-1-yl)ethyl)-4-methyl-2-oxopyridin-1(2H)-yl)-4-methylpentanoic Acid

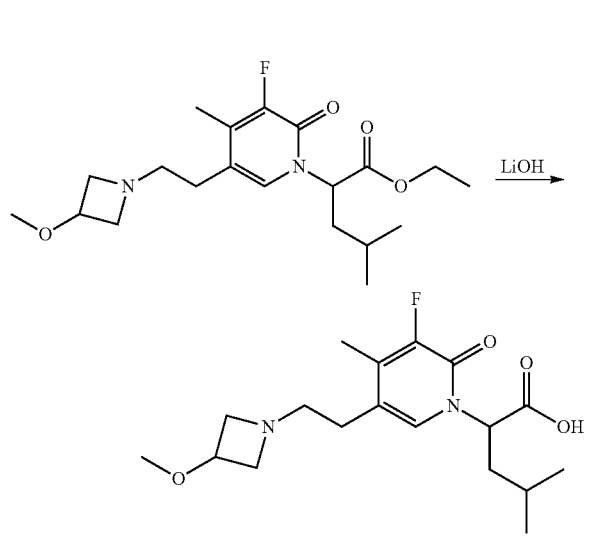

Ethyl 2-(3-fluoro-5-(2-(3-methoxyazetidin-1-yl)ethyl)-4-methyl-2-oxopyridin-1(2H)-yl)-4-methylpentanoate (3.0 g, 7.9 mmol) was treated with LiOH—H₂O (1.6 g, 39.3 mmol) in EtOH (20 mL) and water (5 mL) at room temperature for 2 hours. The EtOH was removed and the aqueous acidified with 1N HCl to pH 5 and concentrated. The mixture was purified by reverse phase HPLC on a C18/120 g column (A: water, B: MeOH, 0~100%) to provide 2-(3-fluoro-5-(2-(3-fluoroazetidine-1-yl)ethyl)-4-methyl-2-oxopyridin-1(2H)-yl)-4-methylpentanoic acid as a white solid (2.4 g). Yield 86% (ESI 355.3 (M+H)+).

Preparation of 2-(5-(2-(dimethylamino)ethyl)-3-fluoro-2-oxo-4-(trifluoromethyl)pyridin-1(2H)-yl)-4-methylpentanoic Acid Step 1: 5-bromo-3-fluoro-4-(trifluoromethyl)pyridin-2-ol

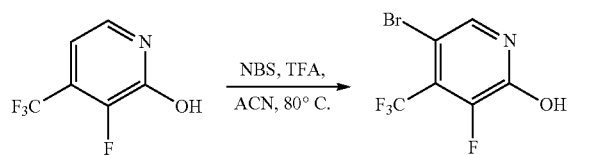 [SMILES: Oc1nccc(C(F)(F)F)c1F ; Oc1ncc(Br)c(C(F)(F)F)c1F]

A mixture of 3-fluoro-4-(trifluoromethyl)pyridin-2-ol (16.0 g, 88.35 mmol) and NBS (23.5 g, 132.53 mmol) in TFA (32 mL) and MeCN (320 mL) was stirred at 80° C. for 24 hours. LCMS showed the reaction was completed. The reaction was concentrated in vacuo and the residue was purified by silica gel column (petroleum ether:EtOAc 1:1) to provide 5-bromo-3-fluoro-4-(trifluoromethyl)pyridin-2-ol as a white solid (19.7 g). Yield 86% (ESI 259.9 (M+H)+).

Step 2: Ethyl 2-(5-bromo-3-fluoro-2-oxo-4-(trifluoromethyl)pyridin-1(2H)-yl)-4-methylpentanoate

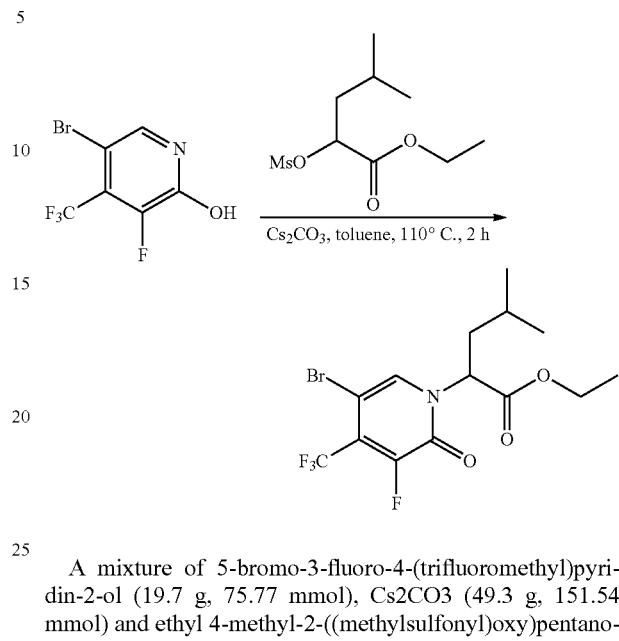

A mixture of 5-bromo-3-fluoro-4-(trifluoromethyl)pyridin-2-ol (19.7 g, 75.77 mmol), Cs2CO3 (49.3 g, 151.54 mmol) and ethyl 4-methyl-2-((methylsulfonyl)oxy)pentanoate (23.5 g, 98.5 mmol) in toluene (100 mL) was stirred at 110° C. for 2 h. LCMS showed the reaction was completed. The mixture was filtered and washed with EtOAc (20 mL). The filtrate was concentrated in vacuo and the residue was purified by silica gel column (pet ether:EtOAc 10:1) to provide ethyl 2-(5-bromo-3-fluoro-2-oxo-4-(trifluoromethyl)pyridin-1(2H)-yl)-4-methylpentanoate as a white solid (12.4 g). Yield 41% (ESI 402.0 (M+H)+).

Step 3: Ethyl (E)-2-(5-(2-ethoxyvinyl)-3-fluoro-2-oxo-4-(trifluoromethyl)pyridin-1(2H)-yl)-4-methylpentanoate

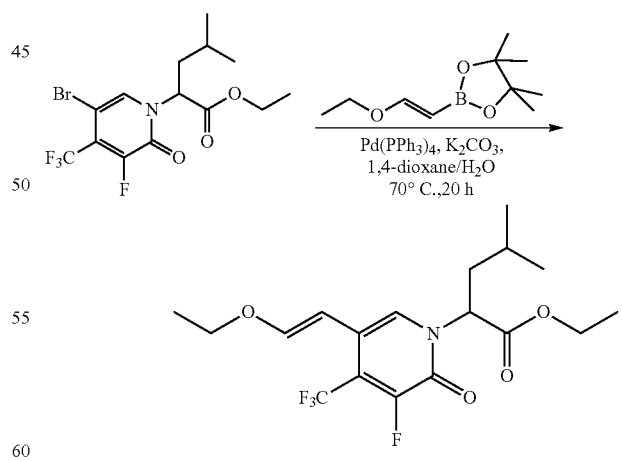

A mixture of ethyl 2-(5-bromo-3-fluoro-2-oxo-4-(trifluoromethyl)pyridin-1(2H)-yl)-4-methylpentanoate (9.7 g, 24.12 mmol), (E)-2-(2-ethoxyvinyl)-4,4,5,5-tetramethyl-1,3,2-dioxaborolane (5.7 g, 28.94 mmol), Pd(PPh₃)₄ (832 mg, 0.72 mmol) and K₂CO₃ (6.7 g, 48.24 mmol) in 1,4-dioxane (100 mL) and water (10 mL) was stirred at 70° C. under N₂ for 20 h. The reaction mixture was poured into 100 mL of water and extracted with EtOAc (100 mL×2). The combined organic phase was washed with brine (30 mL), dried over anhydrous Na₂SO₄, filtered and concentrated in vacuo. The residue was purified by silica gel column (pet ether:EtOAc 10:1) to provide ethyl (E)-2-(5-(2-ethoxyvinyl)-3-fluoro-2-oxo-4-(trifluoromethyl)pyridin-1(2H)-yl)-4-methylpentanoate (6.0 g). Yield 63% (ESI 394.1 (M+H)⁺).

Step 4: Ethyl 2-(3-fluoro-2-oxo-5-(2-oxoethyl)-4-(trifluoromethyl)pyridin-1(2H)-yl)-4-methylpentanoate

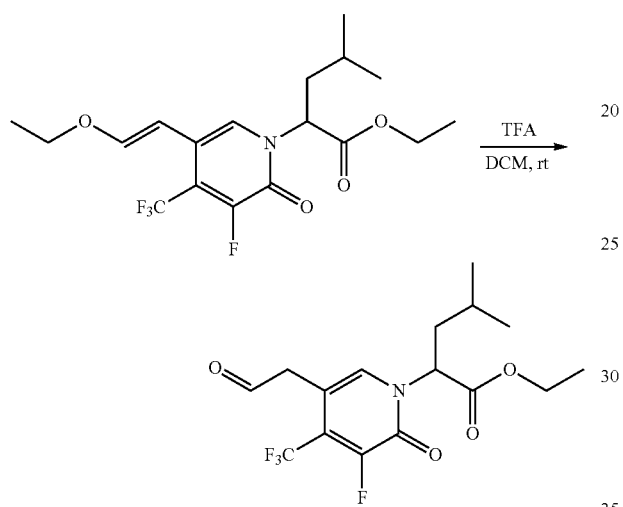

To a mixture of ethyl (E)-2-(5-(2-ethoxyvinyl)-3-fluoro-2-oxo-4-(trifluoromethyl)pyridin-1(2H)-yl)-4-methylpentanoate (6.0 g, 15.25 mmol) in DCM (50 mL) was added TFA (5 mL). The mixture was stirred at room temperature for 3 hours. LCMS showed that the reaction was completed. The mixture was concentrated in vacuo. The residue was dissolved in EtOAc (100 mL), washed with saturated NaHCO₃ (30 mL) and brine (30 mL), dried over anhydrous Na₂SO₄, filtered and concentrated in vacuo to give crude product ethyl 2-(3-fluoro-2-oxo-5-(2-oxoethyl)-4-(trifluoromethyl)pyridin-1(2H)-yl)-4-methylpentanoate as a colorless oil (5.5 g) used directly in the next reaction without further purification. Yield 99% (ESI 366.1 [M+H]⁺).

Step 5: Ethyl 2-(5-(2-(dimethylamino)ethyl)-3-fluoro-2-oxo-4-(trifluoromethyl)pyridin-1(2H)-yl)-4-methylpentanoate

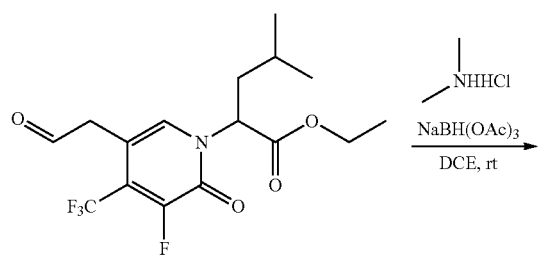

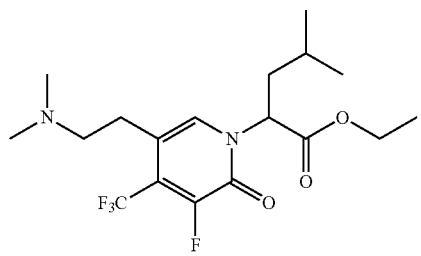

To a mixture of ethyl 2-(3-fluoro-2-oxo-5-(2-oxoethyl)-4-(trifluoromethyl)pyridin-1(2H)-yl)-4-methylpentanoate (5.5 g, 15.06 mmol) in DCE (100 mL) at 25° C. was added dimethylamine hydrochloride (2.5 g, 30.12 mmol) and stirred for 1 hour. NaBH(OAc)₃ (6.4 g, 30.12 mmol) was added at 5° C. and stirred at 25° C. for 16 hours. The mixture was concentrated in vacuo and the residue was purified by silica gel column (DCM:MeOH 10:1) to provide ethyl 2-(5-(2-(dimethylamino)ethyl)-3-fluoro-2-oxo-4-(trifluoromethyl)pyridin-1(2H)-yl)-4-methylpentanoate as a brown oil (4.5 g) Yield 76% (ESI 395.1 [M+H]⁺).

Step 6: 2-(5-(2-(dimethylamino)ethyl)-3-fluoro-2-oxo-4-(trifluoromethyl)pyridin-1(2H)-yl)-4-methylpentanoic Acid

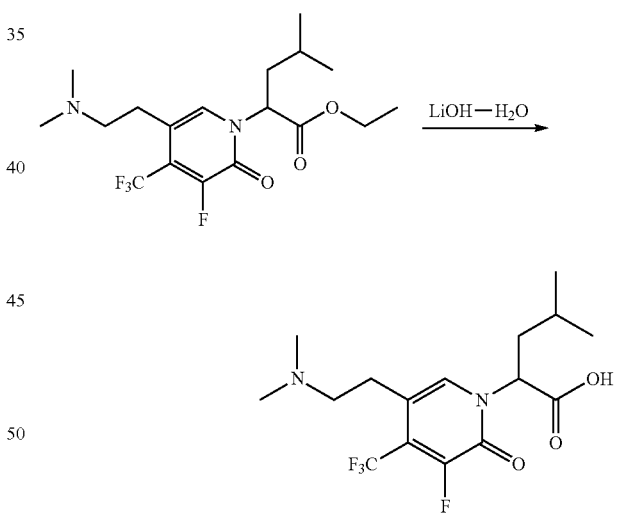

Ethyl 2-(5-(2-(dimethylamino)ethyl)-3-fluoro-2-oxo-4-(trifluoromethyl)pyridin-1(2H)-yl)-4-methylpentanoate (4.5 g, 11.41 mmol) was treated with LiOH—H₂O (2.4 g, 57.05 mmol) in EtOH (10 mL) and water (2 mL) and the mixture was stirred at room temperature for 1 hour. The mixture was acidified with 1N HCl to pH=5~6, concentrated and purified by reverse phase HPLC on a C18/40 g column (A: water 10 mM NH₄HCO₃, B: MeOH, 0~100%) to provide 2-(5-(2-(dimethylamino)ethyl)-3-fluoro-2-oxo-4-(trifluoromethyl)pyridin-1(2H)-yl)-4-methylpentanoic acid as a white solid (3.7 g). Yield 89% (ESI 367.1 (M+H)⁺).

351

Preparation of 4-methyl-2-(5-(2-(3-methylazetidin-1-yl)ethyl)-2-oxo-4-(trifluoromethyl)pyridin-1(2H)-yl)pentanoic Acid Step 1: Ethyl 4-methyl-2-(5-(2-(3-methylazetidin-1-yl)ethyl)-2-oxo-4-(trifluoromethyl)pyridin-1(2H)-yl)pentanoate

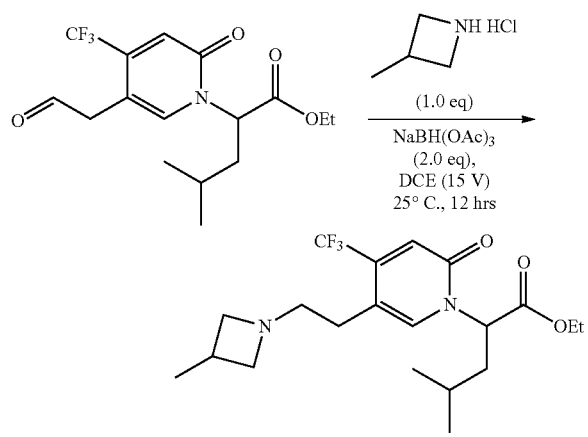

To a mixture of ethyl 4-methyl-2-(2-oxo-5-(2-oxoethyl)-4-(trifluoromethyl)pyridin-1(2H)-yl)pentanoate (16.0 g, 36.8 mmol, 1.00 eq) in DCE (100 mL) at 25° C. was added 3-methylazetidine (2.62 g, 36.8 mmol, 1.00 eq, HCl) and sodium triacetoxyborohydride (15.6 g, 73.7 mmol, 2.00 eq). The mixture was stirred at 0° C. for 10 mins, then 25° C. for 12 hrs. The mixture was diluted with H$_2$O (100 mL) and extracted with DCM (50.0 mL×2). The combined organic phase was washed with brine (100 mL), dried over Na$_2$SO$_4$, filtered and concentrated under reduced pressure. Purification by column chromatography (SiO$_2$, Petroleum ether:Ethyl acetate=100:1 to 0:1) provided ethyl 4-methyl-2-(5-(2-(3-methylazetidin-1-yl)ethyl)-2-oxo-4-(trifluoromethyl)pyridin-1(2H)-yl)pentanoate (9.00 g, 22.3 mmol, 61% yield) as a yellow oil. 1H NMR: (400 MHz, MeOD) δ 7.86 (s, 1H), 6.90 (s, 1H), 5.52-5.56 (m, 1H), 4.08-4.12 (m, 2H), 3.73-3.74 (m, 4H), 3.59-3.61 (m, 2H), 3.81-3.20 (m, 2H), 2.79-2.81 (m, 3H), 2.05-2.09 (m, 2H), 1.86-1.89 (m, 4H), 1.30-1.50 (m, 7H), 1.25-1.29 (m, 6H), 0.95-0.98 (m, 6H).

Step 2: 4-methyl-2-(5-(2-(3-methylazetidin-1-yl)ethyl)-2-oxo-4-(trifluoromethyl)pyridin-1(2H)-yl)pentanoic acid

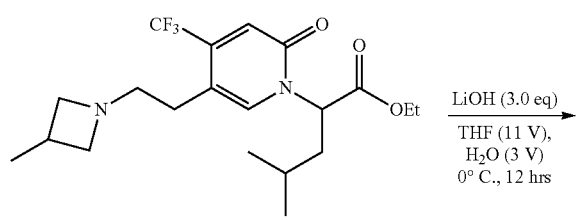

352

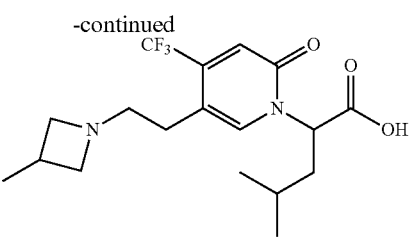

To a solution of ethyl 4-methyl-2-(5-(2-(3-methylazetidin-1-yl)ethyl)-2-oxo-4-(trifluoromethyl)pyridin-1(2H)-yl)pentanoate (9.00 g, 19.0 mmol, 1.00 eq) in THF (80.0 mL) and H$_2$O (8.00 mL) was added LiOH.H$_2$O (2.39 g, 57.0 mmol, 3.00 eq) at 0° C. The mixture was stirred at 20° C. for 12 hrs. The reaction mixture was adjusted to pH=7 with aq. 1M HCl and concentrated under reduced pressure. The resulting residue was purified by prep-HPLC (column: Phenomenex luna c18 250 mm*100 mm*10 um; mobile phase: [water (0.05% HCl)-ACN]; B %: 9%-39%, 20 min), concentrated under reduced pressure, then lyophilized to provide 4-methyl-2-(5-(2-(3-methylazetidin-1-yl)ethyl)-2-oxo-4-(trifluoromethyl)pyridin-1(2H)-yl)pentanoic acid (4.70 g, 12.0 mmol, 64% yield) as a white solid. 1H NMR: (400 MHz, MeOD) δ 7.79 (s, 1H), 6.87 (s, 1H), 5.60-5.64 (m, 1H), 4.20-4.30 (m, 2H), 3.75-3.85 (m, 2H), 3.35-3.40 (m, 2H), 2.85-2.89 (m, 3H), 2.02-2.09 (m, 2H), 1.26-1.35 (m, 4H), 0.92-0.96 (m, 6H).

Preparation of 2-(5-(2-(3-(fluoromethyl)azetidin-1-yl)ethyl)-2-oxo-4-(trifluoromethyl)pyridin-1(2H)-yl)-4-methylpentanoic Acid Step 1: Ethyl 2-(5-(2-(3-(fluoromethyl)azetidin-1-yl)ethyl)-2-oxo-4-(trifluoromethyl)pyridin-1(2H)-yl)-4-methylpentanoate

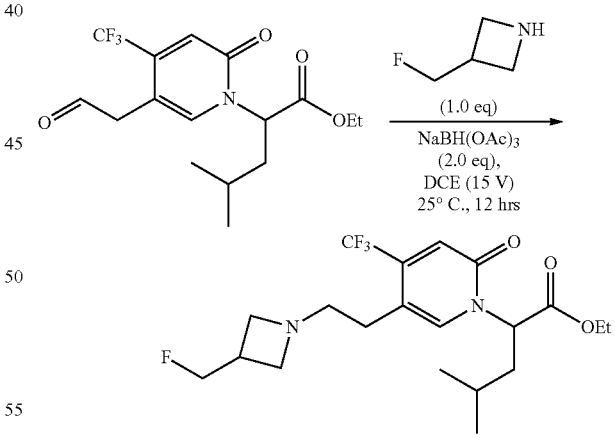

To a mixture of ethyl 4-methyl-2-(2-oxo-5-(2-oxoethyl)-4-(trifluoromethyl)pyridin-1(2H)-yl)pentanoate (12.0 g, 24.1 mmol, 1.00 eq) in DCE (100 mL) at 25° C. was added 3-(fluoromethyl)azetidine (3.04 g, 24.1 mmol, 1.00 eq, HCl) and DIPEA (6.25 g, 48.3 mmol, 8.42 mL, 2.00 eq) stirred at 0° C. for 10 mins. Sodium triacetoxyborohydride (10.2 g, 48.3 mmol, 2.00 eq) was added at 5° C. and then stirred at 25° C. for 12 hrs. The mixture was diluted with H2O (100 mL) and extracted with DCM (50.0 mL×2). The combined organic phase was washed with brine (100 mL), dried over Na₂SO₄, filtered and concentrated under reduced pressure to provide ethyl 2-(5-(2-(3-(fluoromethyl)azetidin-1-yl)ethyl)-2-oxo-4-(trifluoromethyl)pyridin-1 (2H)-yl)-4-methylpentanoate (10.1 g, 24.0 mmol, 99.3% yield) as a yellow oil used without further purification.

Step 2: 2-(5-(2-(3-(fluoromethyl)azetidin-1-yl)ethyl)-2-oxo-4-(trifluoromethyl)pyridin-1(2H)-yl)-4-methylpentanoic Acid

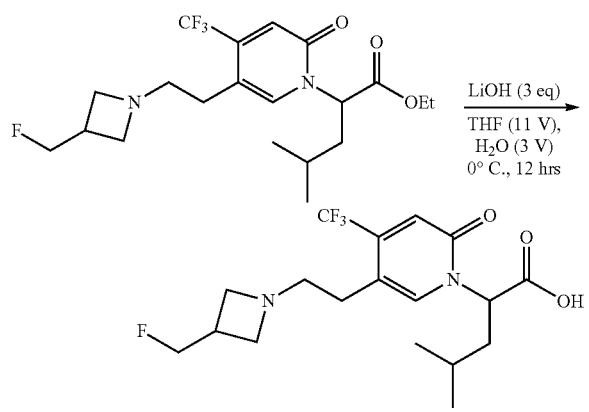

To a solution of ethyl 2-(5-(2-(3-(fluoromethyl)azetidin-1-yl)ethyl)-2-oxo-4-(trifluoromethyl)pyridin-1(2H)-yl)-4-methylpentanoate (10.1 g, 24.0 mmol, 1.00 eq) in THF (80.0 mL) and H₂O (10.0 mL) was added LiOH.H₂O (3.02 g, 72.0 mmol, 3.00 eq) at 0° C. The mixture was stirred at 20° C. for 12 hrs. The reaction mixture was adjusted to (pH=7) with aq. 1M HCl and concentrated under reduced pressure. The residue was purified by prep-HPLC (column: Phenomenex luna c18 250 mm*100 mm*10 um; mobile phase: [water (0.05% HCl)-ACN]; B %: 6%-36%, 20 min) and concentrated under reduced pressure, then lyophilized to give 2-(5-(2-(3-(fluoromethyl)azetidin-1-yl)ethyl)-2-oxo-4-(trifluoromethyl)pyridin-1(2H)-yl)-4-methylpentanoic acid (4.50 g, 11.4 mmol, 47.7% yield) as a white solid. 1H NMR: (400 MHz, MeOD) δ 7.82 (s, 1H), 6.89 (s, 1H), 5.59-5.63 (m, 1H), 4.50-4.62 (m, 2H), 4.3-4.32 (m, 2H), 4.11-4.14 (m, 2H), 3.37-3.41 (m, 6H), 2.86-2.90 (m, 2H), 2.06-2.10 (m, 2H), 1.53-1.55 (m, 1H), 0.93-0.97 (m, 6H).

Preparation of 2-(5-(2-(3-(methoxymethyl)azetidin-1-yl)ethyl)-2-oxo-4-(trifluoromethyl)pyridin-1(2H)-yl)-4-methylpentanoic Acid Step 1: Ethyl 2-(5-(2-(3-(methoxymethyl)azetidin-1-yl)ethyl)-2-oxo-4-(trifluoromethyl)pyridin-1(2H)-yl)-4-methylpentanoate

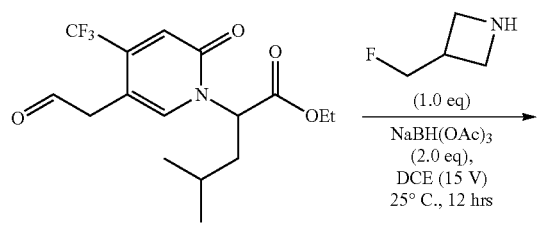

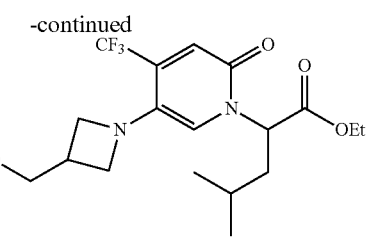

To a mixture of ethyl 4-methyl-2-(2-oxo-5-(2-oxoethyl)-4-(trifluoromethyl)pyridin-1(2H)-yl)pentanoate (11.0 g, 22.1 mmol, 1.00 eq) in DCE (100 mL) at 25° C. was added 3-(methoxymethyl)azetidine hydrochloride (3.05 g, 22.1 mmol, 1.00 eq) and DIPEA (5.73 g, 44.3 mmol, 7.72 mL, 2.00 eq) stirred at 0° C. for 10 mins. Sodium triacetoxyborohydride (9.40 g, 44.3 mmol, 2.00 eq) was added at 5° C. and stirred at 25° C. for 12 hrs. The mixture was diluted with H₂O (100 mL) and extracted with DCM (50.0 mL×2). The combined organic phase was washed with brine (100 mL), dried over Na₂SO₄, filtered and concentrated under reduced pressure to provide ethyl 2-(5-(2-(3-(methoxymethyl)azetidin-1-yl)ethyl)-2-oxo-4-(trifluoromethyl)pyridin-1(2H)-yl)-4-methylpentanoate (9.50 g, 21.9 mmol, 99.0% yield) as a yellow oil used without further purification.

Step 2: 2-(5-(2-(3-(methoxymethyl)azetidin-1-yl)ethyl)-2-oxo-4-(trifluoromethyl)pyridin-1(2H)-yl)-4-methylpentanoic Acid

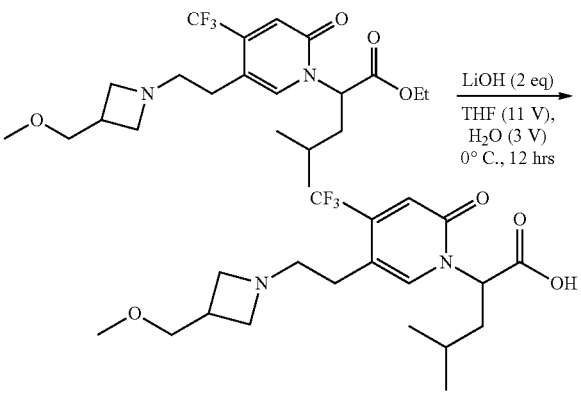

To a solution of ethyl 2-(5-(2-(3-(methoxymethyl)azetidin-1-yl)ethyl)-2-oxo-4-(trifluoromethyl)pyridin-1(2H)-yl)-4-methylpentanoate (9.50 g, 21.9 mmol, 1.00 eq) in THF (80.0 mL) and H₂O (10.0 mL) was added LiOH.H₂O (1.84 g, 43.9 mmol, 2.00 eq) at 0° C. The mixture was stirred at 20° C. for 12 hrs. The reaction mixture was adjusted to (pH=7) with aq. 1M HCl and concentrated under reduced pressure. The residue was purified by prep-HPLC (column: Phenomenex luna c18 250 mm*100 mm*10 um; mobile phase: [water(0.05% HCl)-ACN]; B %: 6%-36%, 20 min) and concentrated under reduced pressure, then lyophilized to give 2-(5-(2-(3-(methoxymethyl)azetidin-1-yl)ethyl)-2-oxo-4-(trifluoromethyl)pyridin-1(2H)-yl)-4-methylpentanoic acid (5.10 g, 12.6 mmol, 57.4% yield) as a yellow solid. 1H NMR: (400 MHz, MeOD) δ 7.86 (s, 1H), 6.89 (s, 1H), 5.58-5.62 (m, 1H), 4.07-4.26 (m, 4H), 3.36-3.49 (m, 7H), 3.07 (s, 1H), 2.84-2.88 (m, 2H), 2.07-2.11 (m, 2H), 1.37-1.41 (m, 1H), 0.94-0.97 (m, 6H).

Preparation of 2-(5-(2-(3,3-dimethylazetidin-1-yl)ethyl)-2-oxo-4-(trifluoromethyl)pyridin-1(2H)-yl)-4-methylpentanoic Acid Step 1: Ethyl 2-(5-(2-(3,3-dimethylazetidin-1-yl)ethyl)-2-oxo-4-(trifluoromethyl)pyridin-1(2H)-yl)-4-methylpentanoate

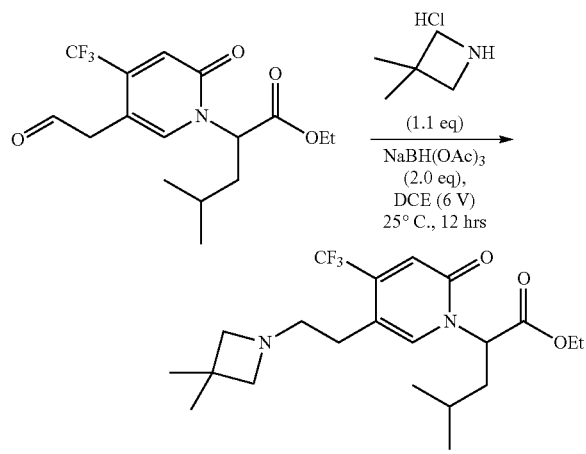

To a mixture of ethyl 4-methyl-2-(2-oxo-5-(2-oxoethyl)-4-(trifluoromethyl)pyridin-1(2H)-yl)pentanoate (20 g, 46.1 mmol) in DCE (140 mL) at 25° C. was added 3,3-dimethylazetidine hydrochloride (6.16 g, 50.7 mmol, HCl) and DIPEA (11.9 g, 92.1 mmol, 16.1 mL). After stirring at 10° C. for 10 mins, NaBH(OAc)₃ (19.5 g, 92.1 mmol) was added at 5° C. and stirred at 25° C. for 12 hrs. The mixture was diluted with H₂O (200 mL) and the mixture was extracted with DCM (200 mL×2). The combined organic phase was washed with brine (200 mL), dried over Na₂SO₄, filtered and concentrated under reduced pressure provide ethyl 2-(5-(2-(3,3-dimethylazetidin-1-yl)ethyl)-2-oxo-4-(trifluoromethyl)pyridin-1(2H)-yl)-4-methylpentanoate (20 g) as a yellow oil used without further purification.

Step 2: 2-(5-(2-(3,3-dimethylazetidin-1-yl)ethyl)-2-oxo-4-(trifluoromethyl)pyridin-1(2H)-yl)-4-methylpentanoic Acid

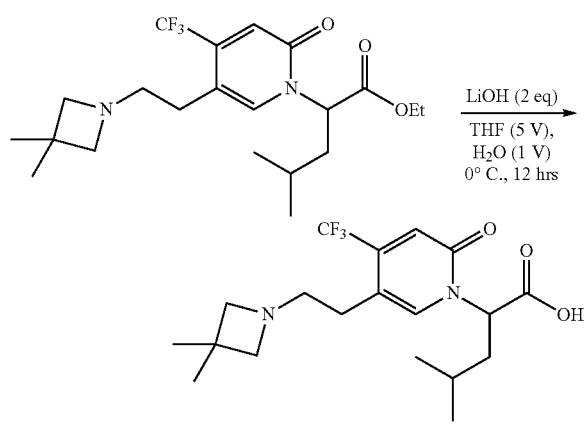

To a mixture of ethyl 2-(5-(2-(3,3-dimethylazetidin-1-yl)ethyl)-2-oxo-4-(trifluoromethyl)pyridin-1(2H)-yl)-4-methylpentanoate (20 g, 48.0 mmol) in THF (100 mL) and H₂O (20 mL) was added LiOH.H₂O (4.03 g, 96.0 mmol) in one portion at 15° C. under N₂. The mixture was stirred at 15° C. for 2 hrs. The reaction mixture was adjusted to (pH=6) with 1M HCl and then concentrated under reduced pressure. The residue was purified by prep-HPLC (HCl condition), concentrated under reduced pressure, then lyophilized to give 2-(5-(2-(3,3-dimethylazetidin-1-yl)ethyl)-2-oxo-4-(trifluoromethyl)pyridin-1(2H)-yl)-4-methylpentanoic acid (6.55 g, 16.7 mmol, 28% yield) as pink solid. 1H NMR: (400 MHz, MeOD) δ 7.94 (s, 1H), 6.91 (s, 1H), 5.59-5.63 (dd, J=4.0 Hz, 12 Hz, 1H), 4.02-4.04 (m, 2H), 3.85-3.92 (m, 2H), 3.34-3.49 (m, 2H), 2.83-2.96 (m, 2H), 2.04-2.20 (m, 2H), 1.39-1.48 (m, 4H), 1.32 (s, 3H), 0.95-0.97 (d, J=8.0 Hz, 6H)

Preparation of 2-(5-(2-(2-azaspiro[3.3]heptan-2-yl)ethyl)-2-oxo-4-(trifluoromethyl)pyridin-1(2H)-yl)-4-methylpentanoic Acid Step 1: Ethyl 2-(5-(2-(3-(methoxymethyl)azetidin-1-yl)ethyl)-2-oxo-4-(trifluoromethyl)pyridin-1(2H)-yl)-4-methylpentanoate

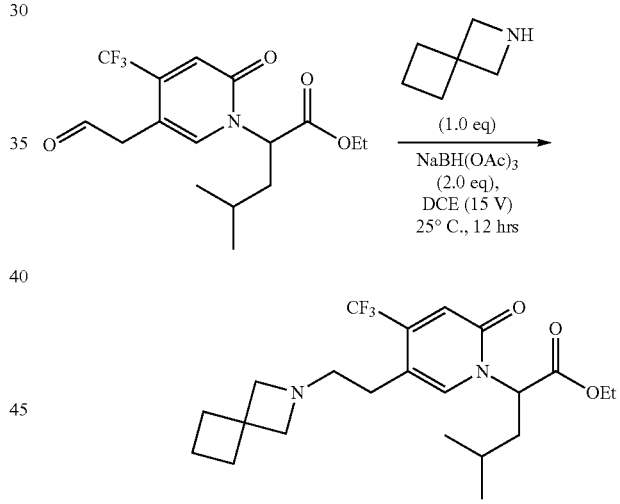

To a mixture of ethyl 4-methyl-2-(2-oxo-5-(2-oxoethyl)-4-(trifluoromethyl)pyridin-1(2H)-yl)pentanoate (11.0 g, 22.1 mmol, 70.0% purity, 1.00 eq) in DCE (100 mL) at 25° C. was added 2-azaspiro[3.3]heptane (2.96 g, 22.1 mmol, 1.00 eq, HCl) and DIPEA (5.73 g, 44.3 mmol, 7.72 mL, 2.00 eq). After stirring at 0° C. for 10 mins, sodium triacetoxyborohydride (9.40 g, 44.3 mmol, 2.00 eq) was added at 5° C. and stirred at 25° C. for 12 hrs. The mixture was diluted with H₂O (100 mL) and extracted with DCM (50.0 mL×2). The combined organic phase was washed with brine (100 mL), dried over Na₂SO₄, filtered and concentrated under reduced pressure to provide ethyl 2-(5-(2-(2-azaspiro[3.3]heptan-2-yl)ethyl)-2-oxo-4-(trifluoromethyl)pyridin-1(2H)-yl)-4-methylpentanoate (9.49 g, 22.1 mmol, 99.9% yield) as a yellow oil used without further purification.

Step 2: 2-(5-(2-(2-azaspiro[3.3]heptan-2-yl)ethyl)-2-oxo-4-(trifluoromethyl)pyridin-1(2H)-yl)-4-methylpentanoic Acid

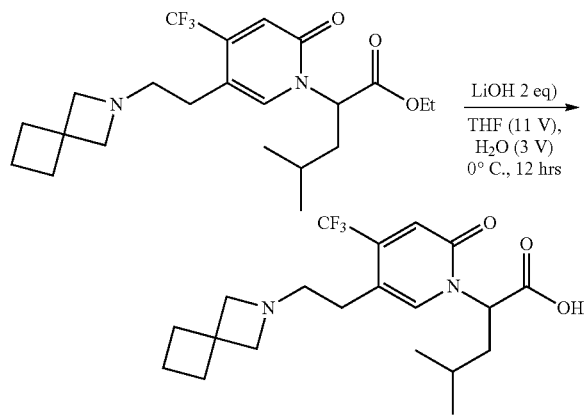

To a solution of ethyl 2-(5-(2-(2-azaspiro[3.3]heptan-2-yl)ethyl)-2-oxo-4-(trifluoromethyl)pyridin-1(2H)-yl)-4-methylpentanoate (9.50 g, 22.1 mmol, 1.00 eq) in THF (80.0 mL) and H₂O (10.0 mL) was added LiOH.H₂O (1.86 g, 44.3 mmol, 2.00 eq) at 0° C. The mixture was stirred at 20° C. for 12 hrs. The reaction mixture was adjusted to (pH=7) with aq. 1M HCl and concentrated under reduced pressure. The residue was purified by prep-HPLC (column: Phenomenex luna c18 250 mm*100 mm*10 um; mobile phase: [water (0.05% HCl)-ACN]; B %: 6%-36%, 20 min) and concentrated under reduced pressure, then lyophilized to give 2-(5-(2-(2-azaspiro[3.3]heptan-2-yl)ethyl)-2-oxo-4-(trifluoromethyl)pyridin-1(2H)-yl)-4-methylpentanoic acid (5.50 g, 13.3 mmol, 60.0% yield) as a white solid. 1H NMR: (400 MHz, MeOD) δ 7.86 (s, 1H), 6.90 (s, 1H), 5.60-5.64 (m, 1H), 4.11-4.25 (m, 4H), 3.32-3.36 (m, 2H), 2.83-2.87 (m, 2H), 2.07-2.11 (m, 6H), 1.86-1.90 (m, 1H), 1.37-1.39 (m, 1H), 0.94-0.97 (m, 6H).

Preparation of 2-(5-(2-(5-azaspiro[2.3]hexan-5-yl)ethyl)-2-oxo-4-(trifluoromethyl)pyridin-1(2H)-yl)-4-methylpentanoic Acid

Step 1: Ethyl 2-(5-(2-(5-azaspiro[2.3]hexan-5-yl)ethyl)-2-oxo-4-(trifluoromethyl)pyridin-1(2H)-yl)-4-methylpentanoate

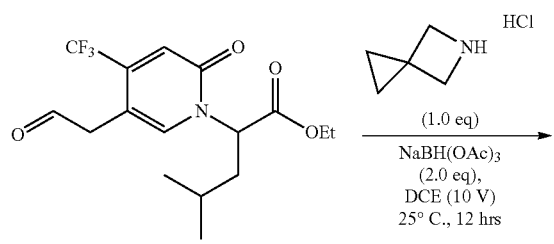

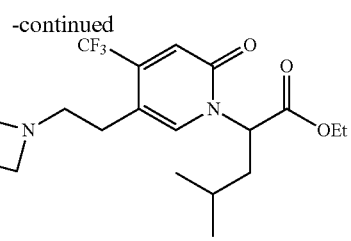

To a mixture of ethyl 4-methyl-2-(2-oxo-5-(2-oxoethyl)-4-(trifluoromethyl)pyridin-1(2H)-yl)pentanoate (10.0 g, 20.1 mmol, 70.0% purity, 1.00 eq) in DCE (100 mL) at 25° C. was added 5-azaspiro[2.3]hexane (2.05 g, 17.1 mmol, 0.85 eq, HCl). After stirring at 0° C. for 10 mins, sodium triacetoxyborohydride (8.54 g, 40.3 mmol, 2.00 eq) was added, the mixture was stirred at 25° C. for 12 hrs. The mixture was diluted with H₂O (100 mL) and extracted with DCM (50.0 mL×2). The combined organic phase was washed with brine (100 mL), dried over Na₂SO₄, filtered and concentrated under reduced pressure to give a residue. The residue was purified by column chromatography (SiO₂, Petroleum ether:Ethyl acetate=100:1 to 0:1) to provide ethyl 2-(5-(2-(5-azaspiro[2.3]hexan-5-yl)ethyl)-2-oxo-4-(trifluoromethyl)pyridin-1(2H)-yl)-4-methylpentanoate (5.10 g, 12.3 mmol, 61.0% yield) as a yellow oil.

Step 2: 2-(5-(2-(5-azaspiro[2.3]hexan-5-yl)ethyl)-2-oxo-4-(trifluoromethyl)pyridin-1(2H)-yl)-4-methylpentanoic Acid

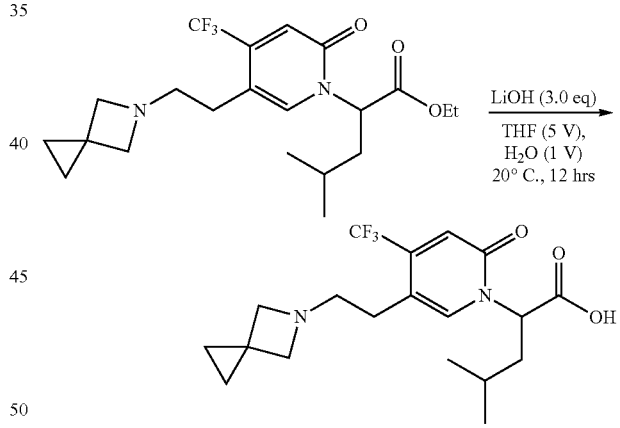

To a solution of ethyl 2-(5-(2-(5-azaspiro[2.3]hexan-5-yl)ethyl)-2-oxo-4-(trifluoromethyl)pyridin-1(2H)-yl)-4-methylpentanoate (5.10 g, 12.3 mmol, 1.00 eq) in THF (30.0 mL) and H₂O (3.00 mL) was added LiOH.H₂O (1.55 g, 36.9 mmol, 3.00 eq) at 0° C. The mixture was stirred at 20° C. for 12 hrs. The reaction mixture was adjusted to (pH=7) with aq. 1M HCl and concentrated under reduced pressure. The residue was purified by prep-HPLC (column: Phenomenex luna c18 250 mm*100 mm*10 um; mobile phase: [water (0.05% HCl)-ACN]; B %: 10%-40%, 25 min) and concentrated under reduced pressure, then lyophilized to give 2-(5-(2-(5-azaspiro[2.3]hexan-5-yl)ethyl)-2-oxo-4-(trifluoromethyl)pyridin-1(2H)-yl)-4-methylpentanoic acid (2.40 g, 5.53 mmol, 44.9% yield) as a white solid. 1H NMR: (400 MHz, MeOD) δ 7.86 (s, 1H), 6.89 (s, 1H), 5.62 (t, J=7.2 Hz, 1H), 4.27 (s, 4H), 3.47-3.55 (m, 2H), 2.90-2.94 (m, 2H), 2.06-2.12 (m, 2H), 1.34-1.39 (m, 1H), 0.94-0.97 (m, 6H), 0.81 (s, 4H).

Preparation of 2-(5-(3-(dimethylamino)propyl)-2-oxo-4-(trifluoromethyl)pyridin-1(2H)-yl)-4-methylpentanoic Acid Step 1: Ethyl 2-(5-(3-(dimethylamino)prop-1-yn-1-yl)-2-oxo-4-(trifluoromethyl)pyridin-1(2H)-yl)-4-methylpentanoate

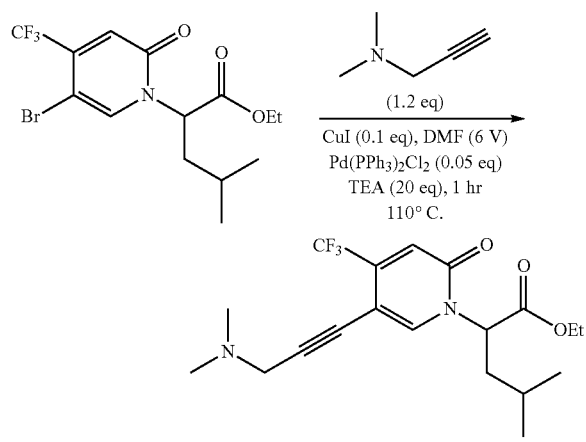

To a solution of ethyl 2-(5-bromo-2-oxo-4-(trifluoromethyl)pyridin-1(2H)-yl)-4-methylpentanoate (68.0 g, 177 mmol, 1.00 eq) in THF (408 mL) was added N,N-dimethylprop-2-yn-1-amine (19.1 g, 230 mmol, 24.4 mL, 1.3 eq), CuI (3.37 g, 17.7 mmol, 0.10 eq), Pd(PPh$_3$)$_2$Cl$_2$ (6.21 g, 8.85 mmol, 0.05 eq) and TEA (358 g, 3.54 mol, 493 mL, 20 eq). The reaction mixture was stirred at 25° C. for 12 hrs. The reaction was diluted with ethyl acetate, washed twice with saturated ammonium chloride solution and once with brine. The combined organic phases were dried over sodium sulfate, filtered and concentrated under reduced pressure. The crude was purified by silica gel chromatography (Petroleum ether:Ethyl acetate=3:1) to give ethyl 2-(5-(3-(dimethylamino)prop-1-yn-1-yl)-2-oxo-4-(trifluoromethyl)pyridin-1(2H)-yl)-4-methylpentanoate (20.0 g, 51.8 mmol, 29.2% yield) as a yellow oil.

Step 2: Ethyl 2-(5-(3-(dimethylamino)propyl)-2-oxo-4-(trifluoromethyl)pyridin-1(2H)-yl)-4-methylpentanoate

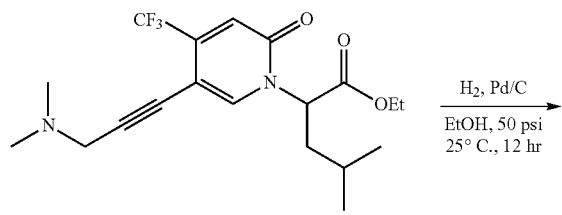

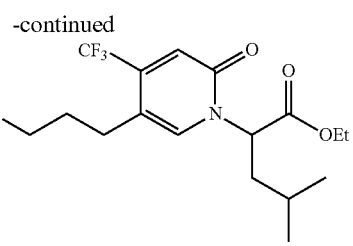

To a solution of ethyl 2-(5-(3-(dimethylamino)prop-1-yn-1-yl)-2-oxo-4-(trifluoromethyl)pyridin-1(2H)-yl)-4-methylpentanoate (20.0 g, 51.8 mmol, 1 eq) in EtOH (200 mL) was added Pd/C (6.00 g, 2.59 mmol, 5% purity, 0.05 eq). The mixture was stirred under H$_2$ (50 psi) at 15 C for 24 hr. The reaction mixture was filtered and the filtrate concentrated to give ethyl 2-(5-(3-(dimethylamino)propyl)-2-oxo-4-(trifluoromethyl)pyridin-1(2H)-yl)-4-methylpentanoate (19.7 g, 44.4 mmol, 85.7% yield) as a yellow oil.

Step 3: 2-(5-(3-(dimethylamino)propyl)-2-oxo-4-(trifluoromethyl)pyridin-1(2H)-yl)-4-methylpentanoic Acid

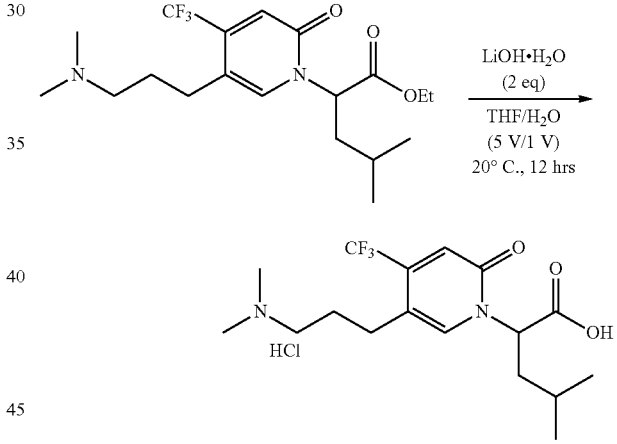

To a solution of ethyl 2-(5-(3-(dimethylamino)propyl)-2-oxo-4-(trifluoromethyl)pyridin-1(2H)-yl)-4-methylpentanoate (19.7 g, 50.4 mmol, 1 eq) in THF (98.0 mL) and H$_2$O (20.0 mL) was added LiOH·H$_2$O (4.23 g, 101 mmol, 2.00 eq) at 0° C. The reaction mixture was warmed to 20° C. and stirred at 20° C. for 12 hrs. The reaction mixture was adjusted to pH=7 with 1N aqueous HCl and concentrated under vacuum to give the crude product. The crude product was purified by prep-HPLC (column: Phenomenex luna C18 (250*70 mm, 10 um); mobile phase: [water (0.05% HCl)-ACN]; B %: 15%-45%, 20 min) to provide 2-(5-(3-(dimethylamino)propyl)-2-oxo-4-(trifluoromethyl)pyridin-1(2H)-yl)-4-methylpentanoic acid (5.40 g, 13.5 mmol, 26.8% yield, HCl) as a white solid. $^1$H NMR: 400 MHz D$_2$O δ: 7.71 (s, 1H), 7.00 (s, 1H), 5.40-5.45 (d, J=20 Hz, 1H), 3.13-3.17 (m, 2H), 2.84 (s, 6H), 2.65-2.67 (m, 2H), 1.95-1.99 (m, 4H), 1.25-1.30 (m, 1H), 0.86 (s, 9H)

361

Preparation of 2-(5-(2-(dimethylamino)ethyl)-2-oxo-4-(trifluoromethyl)pyridin-1(2H)-yl)-4-fluoro-4-methylpentanoic Acid

Step 1: 2-fluoro-2-methylpropyl trifluoromethanesulfonate

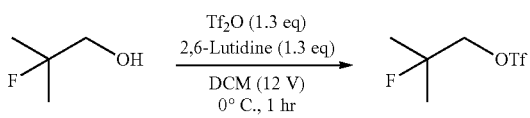

To a solution of alcohol (100 g, 1.09 mol, 1.00 eq) and 2,6-LUTIDINE (151 g, 1.41 mol, 164 mL, 1.30 eq) in DCM (1.20 L) was added Tf₂O (398 g, 1.41 mol, 233 mL, 1.30 eq) dropwise at 0° C. The solution was stirred at 0° C. for 1 hr. The reaction mixture was washed with 1 N HCl (2×1.00 L) and sat.NaHCO₃ (2×1.00 L). The combined organic layer was dried over Na₂SO₄, filtered and concentrated under vacuum (150 mbar, 25° C.) to give 2-fluoro-2-methylpropyl trifluoromethanesulfonate (214 g) as a light yellow oil used without further purification.

Step 2: Ethyl 2-((diphenylmethylene)amino)-4-fluoro-4-methylpentanoate

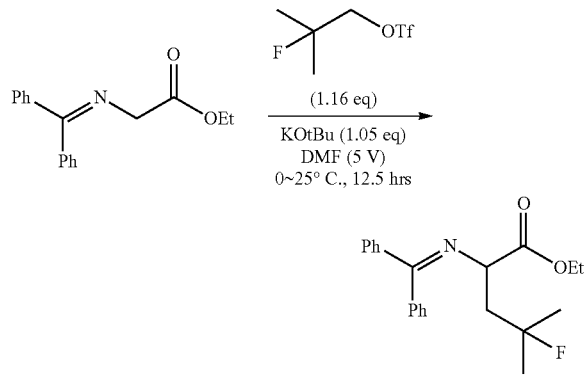

To a solution of KOtBu (97.0 g, 864 mmol, 1.05 eq) in DMF (1.10 L) was added ethyl 2-((diphenylmethylene)amino)acetate (220 g, 823 mmol, 1.00 eq) at 0° C. After stirring for 0.5 hr, 2-fluoro-2-methylpropyl trifluoromethanesulfonate (214 g, 955 mmol, 1.16 eq) was added. The reaction solution was warmed to 25° C. and stirred for 12 hrs. The reaction was poured into 5% aqueous NH₄Cl (0.80 L) and extracted with EtOAc (2.00 L and 1.00 L). The combined organic layers were washed with brine, dried over Na₂SO₄ and concentrated under vacuum to give the crude product. The crude product was purified by column chromatography (SiO₂, petroleum ether:ethyl acetate=100:1~0:1) to provide ethyl 2-((diphenylmethylene)amino)-4-fluoro-4-methylpentanoate (220 g) as a light yellow oil.

362

Step 3: 2-amino-4-fluoro-4-methylpentanoic Acid

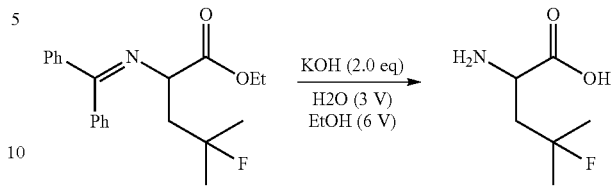

To a solution of ethyl 2-((diphenylmethylene)amino)-4-fluoro-4-methylpentanoate (220 g, 644 mmol, 1.00 eq) in EtOH (1.32 L) was added KOH (72.3 g, 1.29 mol, 2.00 eq) in H₂O (660 mL) at 25° C. The reaction solution was stirred for 1 hr at 25° C. The reaction was adjusted to pH=7 with HCl (1 M). The reaction solution was extracted with EtOAc (0.80 L×2), the combined aqueous phase was concentrated under reduced pressure to give 2-amino-4-fluoro-4-methylpentanoic acid (203 g, 48% purity, HCl) as a white solid used without further purification. 1H NMR 400 MHz CDCl₃ δ: 4.00-4.03 (m, 1H), 2.19-2.23 (m, 2H), 1.43-1.50 (m, 6H).

Step 4: 2-bromo-4-fluoro-4-methylpentanoic Acid

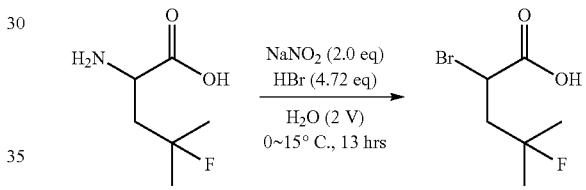

To a solution of 2-amino-4-fluoro-4-methylpentanoic acid (203 g, 1.09 mol, 1.00 eq, HCl) in HBr (4 M, 1.29 L, 40% purity, 4.72 eq) was added dropwise a solution of NaNO₂ (151 g, 2.19 mol, 2.00 eq) in H₂O (608 mL) at 0° C. The mixture was stirred at 0° C. for 1 hr, warmed to 15° C. and stirred at 15° C. for 12 hrs. The reaction mixture was extracted with MTBE (1.00 L and 500 mL). The organic layers were combined, washed with brine, dried over anhydrous Na₂SO₄, filtered and concentrated under vacuum. The residue was dissolved in MTBE (50.0 mL) and concentrated under vacuum to give 2-bromo-4-fluoro-4-methylpentanoic acid (127 g) as a yellow oil used without further purification. 1H NMR: 400 MHz CDCl₃ δ: 4.61-4.65 (m, 1H), 4.41-4.44 (m, 1H), 2.70-2.76 (m, 2H), 2.44-2.48 (m, 2H), 1.21-1.48 (m, 6H).

Step 5: Ethyl 2-bromo-4-fluoro-4-methylpentanoate

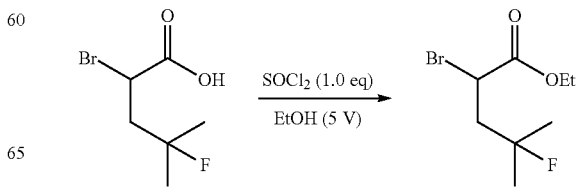

To a solution of 2-bromo-4-fluoro-4-methylpentanoic acid (127 g, 596 mmol, 1.00 eq) in EtOH (520 mL) was added SOCl$_2$ (70.9 g, 596 mmol, 43.2 mL, 1.00 eq) at 0° C. The reaction solution was stirred for 2 hrs at 60° C. The solution was poured into H$_2$O (400 mL) and extracted with MTBE (500 mL×2). The combined organic was washed with brine (500 mL), dried over anhydrous Na$_2$SO$_4$, filtered and concentrated under reduced pressure to give crude product. The crude product was purified by column chromatography (SiO$_2$, petroleum ether:ethyl acetate=100:1 to 10:1) to provide ethyl 2-bromo-4-fluoro-4-methylpentanoate (90.0 g) as a yellow oil. $^1$H NMR: 400 MHz CDCl$_3$ δ: 4.38-4.42 (m, 1H), 4.21-4.26 (m, 2H), 2.69-2.76 (m, 1H), 2.25-2.26 (m, 1H), 0.85-1.39 (m, 9H).

Step 6: Ethyl 2-(5-bromo-2-oxo-4-(trifluoromethyl) pyridin-1(2H)-yl)-4-fluoro-4-methylpentanoate

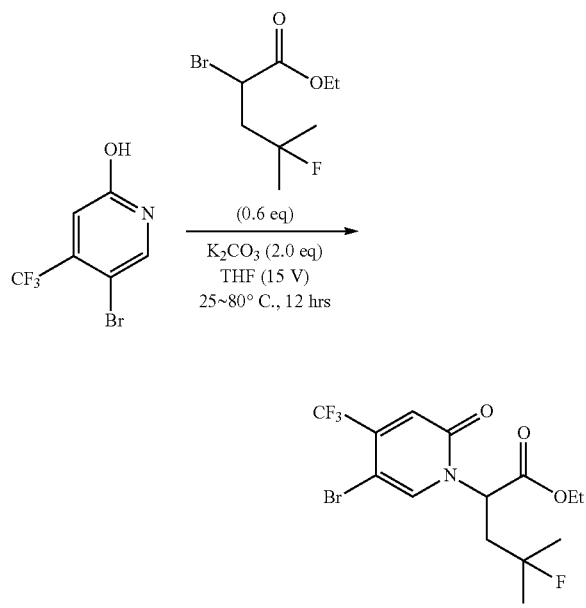

To a solution of 5-bromo-4-(trifluoromethyl)pyridin-2-ol (60.0 g, 249 mmol, 1.00 eq) and K$_2$CO$_3$ (103 g, 747 mmol, 2.00 eq) in THF (900 mL) was added ethyl 2-bromo-4-fluoro-4-methylpentanoate (151 g, 622 mmol, 2.50 eq) at 0° C. The mixture was heated to 70° C. and stirred at 70° C. for 12 hrs. The reaction was poured into aqueous NH$_4$Cl (1.00 L) at 0° C. and extracted with MBTE (1.00 L and 500 mL). The combined organic layer was washed with brine, dried over Na$_2$SO$_4$ and concentrated under vacuum to give the crude product. The crude product was purified by column chromatography (SiO$_2$, petroleum ether:ethyl acetate=100: 1~0:1) to give ethyl 2-(5-bromo-2-oxo-4-(trifluoromethyl) pyridin-1(2H)-yl)-4-fluoro-4-methylpentanoate (40.0 g, 99.5 mmol) as a white solid. $^1$H NMR: 400 MHz CDCl$_3$ δ: 7.66 (s, 1H), 6.94 (s, 1H), 5.48-5.51 (m, 1H), 4.22-4.27 (m, 2H), 2.56-2.65 (m, 1H), 2.30-2.32 (m, 1H), 1.26-1.59 (m, 9H).

Step 6: Ethyl 2-(5-allyl-2-oxo-4-(trifluoromethyl) pyridin-1(2H)-yl)-4-fluoro-4-methylpentanoate

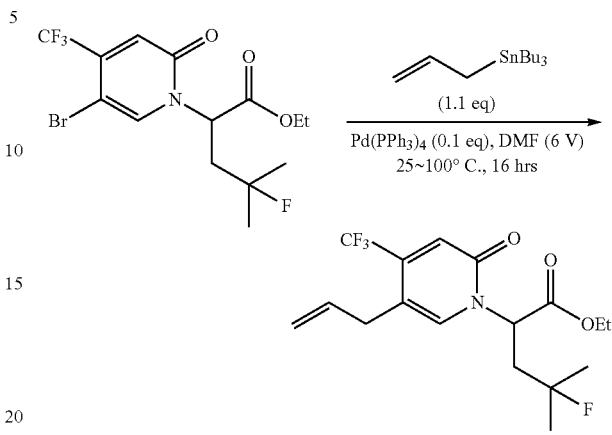

To a solution of ethyl 2-(5-bromo-2-oxo-4-(trifluoromethyl)pyridin-1(2H)-yl)-4-fluoro-4-methylpentanoate (25.0 g, 62.2 mmol, 1.00 eq) and allyltributylstannane (24.5 g, 74.0 mmol, 22.7 mL, 1.10 eq) in DMF (150 mL) was added Pd(PPh$_3$)$_4$ (7.18 g, 6.22 mmol, 0.10 eq) in one portion at 25° C. under N$_2$. The mixture was heated to 100° C. and stirred at 100° C. for 12 hrs. The reaction mixture was poured into a solution of KF (10.0 eq) in H$_2$O (200 mL) and ethyl acetate (200 mL). The resulting suspension was stirred at 15° C. for 0.5 hr, filtered and the filtrate was extracted with ethyl acetate (300 mL and 200 mL). The combined organic layer was washed with brine, dried over anhydrous Na$_2$SO$_4$, filtered and concentrated under vacuum to give the crude product. The crude product was purified by column chromatography (SiO$_2$, petroleum ether:ethyl acetate=100:1~0: 1) to afford ethyl 2-(5-allyl-2-oxo-4-(trifluoromethyl)pyridin-1(2H)-yl)-4-fluoro-4-methylpentanoate (19.8 g, 54.5 mmol, 87.7% yield) as a light yellow oil. $^1$H NMR: 400 MHz CDCl$_3$ δ: 7.23 (s, 1H), 6.89 (s, 1H), 5.88-5.93 (m, 1H), 5.45-5.47 (m, 1H), 5.10-5.21 (m, 2H), 4.19-4.26 (m, 2H), 3.29-3.30 (m, 2H), 2.57-2.68 (m, 1H), 2.30-2.37 (m, 1H), 0.93-1.40 (m, 9H).

Step 7: Ethyl 2-(5-(2,3-dihydroxypropyl)-2-oxo-4-(trifluoromethyl)pyridin-1(2H)-yl)-4-fluoro-4-methylpentanoate

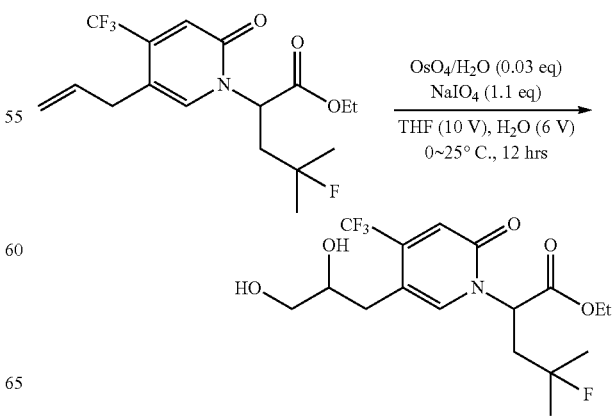

365

To a solution of ethyl 2-(5-allyl-2-oxo-4-(trifluoromethyl)pyridin-1(2H)-yl)-4-fluoro-4-methylpentanoate (19.8 g, 54.5 mmol, 1.00 eq) in THF (198 mL) and H$_2$O (20.0 mL) was added K$_2$OsO$_4$/2H$_2$O (602 mg, 1.64 mmol, 0.03 eq) at 0° C. Then a solution of NaIO$_4$ (11.7 g, 54.5 mmol, 3.02 mL, 1.00 eq) in H$_2$O (100 mL) was added dropwise at 0° C. and the solution stirred at 0° C. for 2 hrs. The solution was warmed to 25° C. and was stirred at 25° C. for 1 hr. The mixture was quenched with a sat.Na$_2$S$_2$O$_3$ solution (200 mL) and filtered. The filtrate was extracted with ethyl acetate (500 mL×2), dried over anhydrous Na$_2$SO$_4$, filtered and concentrated under vacuum to give ethyl 2-(5-(2,3-dihydroxypropyl)-2-oxo-4-(trifluoromethyl)pyridin-1(2H)-yl)-4-fluoro-4-methylpentanoate (21.0 g, crude) as a brown oil used without further purification.

Step 8: Ethyl 4-fluoro-4-methyl-2-(2-oxo-5-(2-oxoethyl)-4-(trifluoromethyl)pyridin-1(2H)-yl)pentanoate

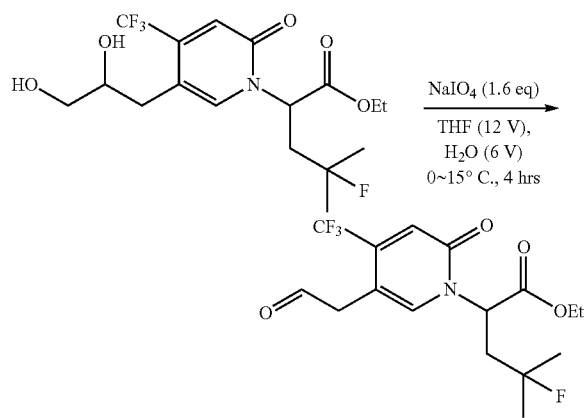

To a solution of ethyl 2-(5-(2,3-dihydroxypropyl)-2-oxo-4-(trifluoromethyl)pyridin-1(2H)-yl)-4-fluoro-4-methylpentanoate (21.0 g, 52.9 mmol, 1.00 eq) in THF (252 mL) was added a solution of NaIO$_4$ (17.0 g, 79.3 mmol, 4.39 mL, 1.50 eq) in H$_2$O (100 mL) at 0° C. The solution was stirred at 0° C. for 2 hrs, warmed to 25° C. and stirred at 25° C. for 2 hrs. The mixture was quenched with a sat. Na$_2$S$_2$O$_3$ solution (150 mL) and filtered. The filtrate was extracted with ethyl acetate (250 mL×2) and the combined organic layer washed with 1 N HCl (100 mL) and brine (100 mL), dried over anhydrous Na$_2$SO$_4$ and filtered. AcOH (21.0 mL) was added to the filtrate and the solution concentrated under vacuum to give ethyl 4-fluoro-4-methyl-2-(2-oxo-5-(2-oxoethyl)-4-(trifluoromethyl)pyridin-1(2H)-yl)pentanoate (21.0 g) as a brown oil used without further purification.

Step 9: Ethyl 2-(5-(2-(dimethylamino)ethyl)-2-oxo-4-(trifluoromethyl)pyridin-1(2H)-yl)-4-fluoro-4-methylpentanoate

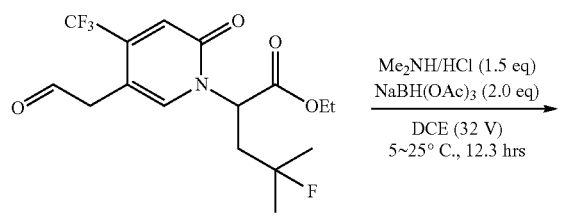

366

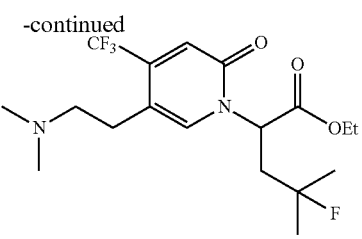

To a solution of ethyl 4-fluoro-4-methyl-2-(2-oxo-5-(2-oxoethyl)-4-(trifluoromethyl)pyridin-1(2H)-yl)pentanoate (13.3 g, 36.4 mmol, 1.00 eq) in DCE (80.0 mL) was added NaBH(OAc)$_3$ (15.4 g, 72.8 mmol, 2.00 eq) and DIEA (9.41 g, 72.8 mmol, 12.7 mL, 2.00 eq) at 25° C. The solution was stirred at 25° C. for 20 mins, cooled to 5° C. and Me$_2$NH/HCl (4.45 g, 54.6 mmol, 1.50 eq) was added. The reaction solution was warmed to 25° C. and stirred for 12 hrs. The reaction mixture was diluted with H$_2$O (50.0 mL) and was extracted with DCM (100 mL). The combined organic layer was washed with brine, dried over anhydrous Na$_2$SO$_4$, filtered and concentrated under vacuum to give 6-6 (14.9 g, crude) as a brown oil. Compound ethyl 2-(5-(2-(dimethylamino)ethyl)-2-oxo-4-(trifluoromethyl)pyridin-1(2H)-yl)-4-fluoro-4-methylpentanoate was used without further purification.

Step 10: 2-(5-(2-(dimethylamino)ethyl)-2-oxo-4-(trifluoromethyl)pyridin-1(2H)-yl)-4-fluoro-4-methylpentanoic Acid

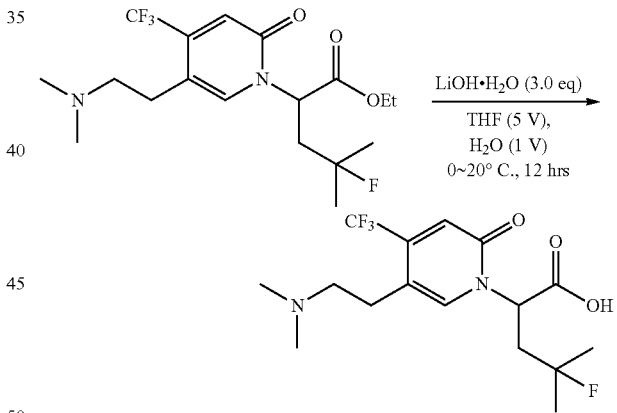

To a solution of ethyl 2-(5-(2-(dimethylamino)ethyl)-2-oxo-4-(trifluoromethyl)pyridin-1(2H)-yl)-4-fluoro-4-methylpentanoate (14.9 g, 37.8 mmol, 1.00 eq) in THF (75.0 mL) and H$_2$O (15.0 mL) was added LiOH.H$_2$O (4.76 g, 113 mmol, 3.00 eq) at 0° C. The reaction solution was warmed to 20° C. and stirred for 12 hrs. The reaction mixture was adjusted to pH=7 with 1 N HCl (50.0 mL) and concentrated under vacuum to give the crude product. The crude product was purified by pre-HPLC (column: Agela DuraShell C18 250*80 mm*10 um; mobile phase: [water (10 mM NH$_4$HCO$_3$)-ACN]; B %: 5%-30%, 20 min). Then the solution was concentrated under vacuum to give 2-(5-(2-(dimethylamino)ethyl)-2-oxo-4-(trifluoromethyl)pyridin-1(2H)-yl)-4-fluoro-4-methylpentanoic acid (2.00 g, 5.35 mmol, 14.2% yield, 98% purity) as a white solid. $^1$H NMR: 400 MHz D$_2$O δ: 7.79 (s, 1H), 6.97 (s, 1H), 5.51-5.53 (m, 1H), 3.27-3.31 (m, 2H), 3.00-3.04 (m, 2H), 2.91 (s, 6H), 2.49-2.58 (m, 2H), 1.34 (t, J=24.4 Hz, 6H).

Preparation of 2-(5-(2-(azetidin-1-yl)ethyl)-2-oxo-4-(trifluoromethyl)pyridin-1(2H)-yl)-4-fluoro-4-methylpentanoic Acid Step 1: Ethyl 2-(5-(2-(azetidin-1-yl)ethyl)-2-oxo-4-(trifluoromethyl)pyridin-1(2H)-yl)-4-fluoro-4-methylpentanoate

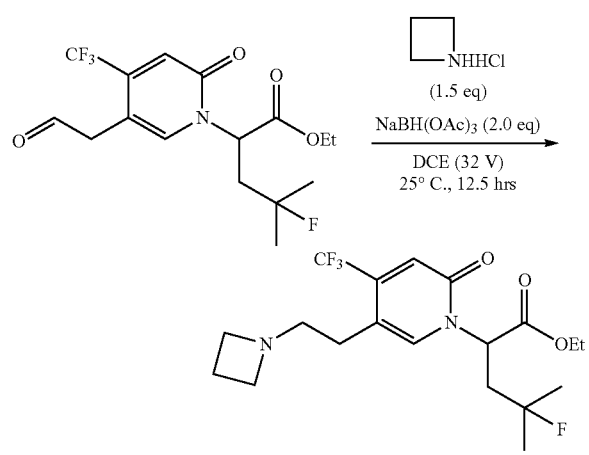

To a solution of ethyl 4-fluoro-4-methyl-2-(2-oxo-5-(2-oxoethyl)-4-(trifluoromethyl)pyridin-1(2H)-yl)pentanoate (21.0 g, 57.5 mmol, 1.00 eq) in DCE (126 mL) was added NaBH(OAc)₃ (24.4 g, 115 mmol, 2.00 eq) at 25° C. The solution was stirred at 25° C. for 20 mins, cooled to 5° C. and azetidine-HCl (5.38 g, 57.5 mmol, 1.00 eq) was added. The reaction solution was warmed to 25° C. and stirred for 12 hrs. The reaction mixture was diluted with H₂O (50.0 mL) and was extracted with DCM (100 mL). The combined organic layer was washed with brine, dried over anhydrous Na₂SO₄, filtered and concentrated under vacuum to give ethyl 2-(5-(2-(azetidin-1-yl)ethyl)-2-oxo-4-(trifluoromethyl)pyridin-1(2H)-yl)-4-fluoro-4-methylpentanoate (11.5 g, 25.2 mmol, 43.8% yield) as a brown oil. HNMR: 400 MHz CDCl₃ δ: 7.51 (s, 1H), 6.86 (s, 1H), 5.47-5.50 (m, 1H), 4.14-4.25 (m, 1H), 3.40-3.43 (m, 3H), 2.17-2.76 (m, 6H), 1.25-1.47 (m, 9H).

Step 2: 2-(5-(2-(azetidin-1-yl)ethyl)-2-oxo-4-(trifluoromethyl)pyridin-1(2H)-yl)-4-fluoro-4-methylpentanoic Acid

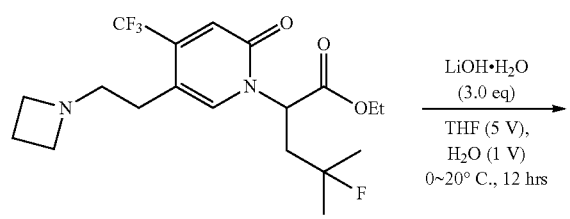

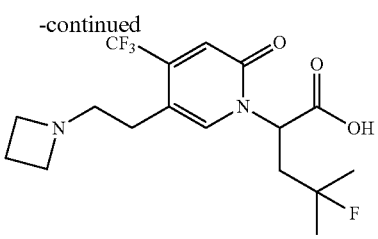

To a solution of ethyl 2-(5-(2-(azetidin-1-yl)ethyl)-2-oxo-4-(trifluoromethyl)pyridin-1(2H)-yl)-4-fluoro-4-methylpentanoate (11.5 g, 28.30 mmol, 1.00 eq) in THF (69.0 mL) and H₂O (36.0 mL) was added LiOH·H₂O (4.75 g, 113.19 mmol, 3.00 eq) at 0° C. The reaction solution was warmed to 20° C. and stirred for 12 hrs. The reaction mixture was adjusted to pH=7 with 1 N HCl (50.0 mL) and concentrated under vacuum to give the crude product. The crude product was purified by reversed-phase HPLC (0.10% NH₃·H₂O) to give 2-(5-(2-(azetidin-1-yl)ethyl)-2-oxo-4-(trifluoromethyl)pyridin-1(2H)-yl)-4-fluoro-4-methylpentanoic acid (5.00 g, 12.8 mmol, 45.1% yield) as an off-white solid. ¹H NMR: 400 MHz D₂O δ: 7.70 (s, 1H), 6.95 (s, 1H), 5.52 (s, 1H), 3.49-3.53 (m, 4H), 2.83-2.87 (m, 2H), 2.52-2.68 (m, 4H), 2.15-2.18 (m, 2H), 1.29-1.42 (m, 6H).

Preparation of Ethyl 2-(5-(2-(azetidin-1-yl)ethyl)-2-oxo-4-(trifluoromethyl)pyridin-1(2H)-yl)-4-fluoro-4-methylpentanoate Step 1: 2-bromo-4,4-dimethylpentanoic Acid

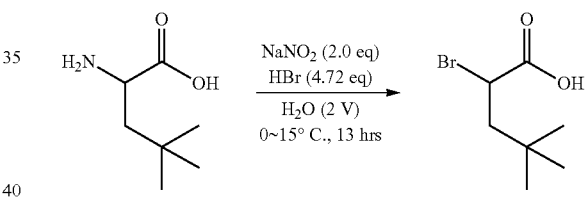

A solution of 2-amino-4,4-dimethylpentanoic acid (35.0 g, 241 mmol, 1.00 eq) in HBr (4 M, 284 mL, 40% purity, 4.72 eq) was added dropwise over NaNO₂ (16.6 g, 241 mmol, 1.00 eq) in H₂O (70.0 mL) at 0° C. The mixture was stirred at 0° C. for 1 hr, warmed to 15° C. and stirred at 15° C. for 12 hrs. The reaction mixture was extracted with MTBE (20.0 mL). The organic layer was washed with brine (20.0 mL), dried over sodium sulfate, and concentrated under reduced pressure. The residue was dissolved in MTBE (20.0 mL) and concentrated under reduced pressure to give to give 2-bromo-4,4-dimethylpentanoic acid (31.0 g) as a yellow oil used without further purification. 1H NMR: 400 MHz CDCl₃ δ: 4.28-4.32 (m, 1H), 2.32-2.38 (m, 1H), 1.92-1.97 (m, 1H), 0.95 (s, 9H).

Step 2: Ethyl 2-bromo-4,4-dimethylpentanoate

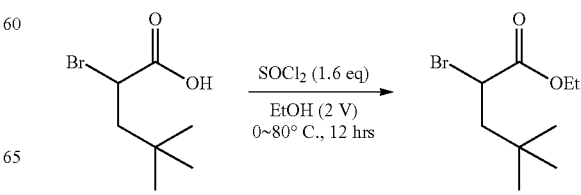

To a solution of 2-bromo-4,4-dimethylpentanoic acid (31.0 g, 148 mmol, 1.00 eq) in EtOH (62 mL) was added SOCl₂ (28.2 g, 237 mmol, 17.2 mL, 1.60 eq) at 0° C. The solution was warmed to 80° C. and stirred for 12 hrs. The mixture was concentrated under reduced pressure and the residue was dissolve in MTBE (60 mL) and washed with aqueous NaHCO₃ (60 mL). The organic layer was washed with brine (100 mL), dried over Na₂SO₄ and concentrated under vacuum to give ethyl 2-bromo-4,4-dimethylpentanoate (29.0 g, crude) as a yellow oil. 1H NMR: 400 MHz CDCl₃ δ: 4.20-4.30 (m, 3H), 2.33-2.40 (m, 1H), 1.89-1.94 (m, 1H), 1.29-1.32 (m, 3H), 0.93 (s, 9H).

Step 3: Ethyl 2-(5-bromo-2-oxo-4-(trifluoromethyl)pyridin-1(2H)-yl)-4,4-dimethylpentanoate

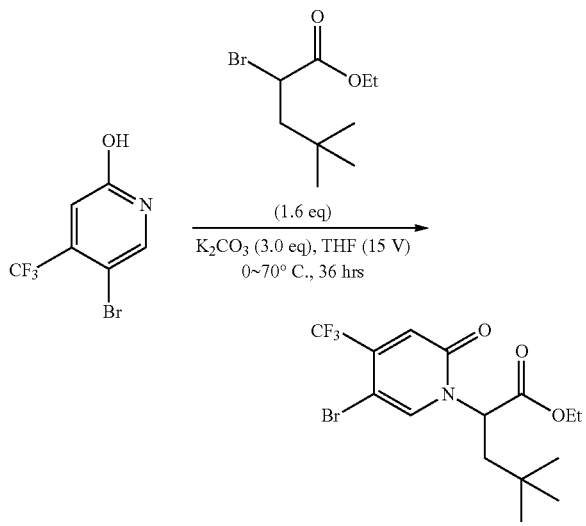

To a solution of 5-bromo-4-(trifluoromethyl)pyridin-2-ol (22.0 g, 90.9 mmol, 1.00 eq) and K₂CO₃ (37.7 g, 273 mmol, 3.00 eq) in THF (330 mL) was added ethyl 2-bromo-4,4-dimethylpentanoate (28.0 g, 118 mmol, 1.30 eq) at 0° C. The mixture was heated to 70° C. and stirred for 14 hrs. The reaction was poured into water (400 mL) and extracted with MTBE (400 mL×2). The combined organic phase was washed with brine (200 mL×2), dried with anhydrous Na₂SO₄, filtered and concentrated under vacuum. The residue was purified by silica gel chromatography (Petroleum ether:Ethyl acetate=3:1) to give ethyl 2-(5-bromo-2-oxo-4-(trifluoromethyl)pyridin-1(2H)-yl)-4,4-dimethylpentanoate (23.0 g, 57.8 mmol, 63.5% yield) as a yellow oil.

Step 4: Ethyl 2-(5-allyl-2-oxo-4-(trifluoromethyl)pyridin-1(2H)-yl)-4,4-dimethylpentanoate

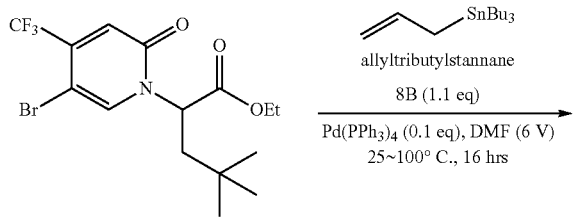

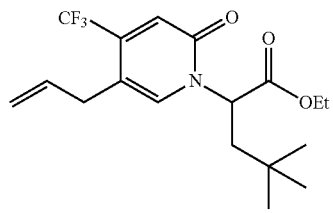

To a mixture of ethyl 2-(5-bromo-2-oxo-4-(trifluoromethyl)pyridin-1(2H)-yl)-4,4-dimethylpentanoate (23.0 g, 57.8 mmol, 1.00 eq) and allyltributylstannane (21.0 g, 63.5 mmol, 19.5 mL, 1.10 eq) in DMF (132 mL) was added Pd(PPh₃)₄ (3.34 g, 2.89 mmol, 0.05 eq) in one portion at 20° C. The reaction was purged with N₂ (3×) and stirred at 100° C. for 4 hrs under N₂. The reaction was dissolved in water (100 mL) and KF (23.0 g), extracted with MTBE (100 mL), dried with anhydrous Na₂SO₄, filtered and concentrated under vacuum. The residue was purified by silica gel chromatography (Petroleum ether:Ethyl acetate=3:1) to give ethyl 2-(5-allyl-2-oxo-4-(trifluoromethyl)pyridin-1(2H)-yl)-4,4-dimethylpentanoate (15.0 g, 41.74 mmol, 72.3% yield) as a yellow oil.

Step 5: Ethyl 2-(5-(2,3-dihydroxypropyl)-2-oxo-4-(trifluoromethyl)pyridin-1(2H)-yl)-4,4-dimethylpentanoate

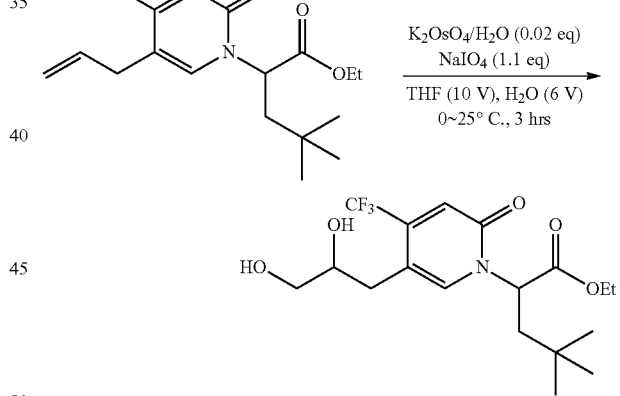

To a solution of ethyl 2-(5-allyl-2-oxo-4-(trifluoromethyl)pyridin-1(2H)-yl)-4,4-dimethylpentanoate (15.0 g, 49.1 mmol, 1.00 eq) in H₂O (15.0 mL) and THF (150 mL) was added K₂OsO₄·2H₂O (362 mg, 982. umol, 0.02 eq) at 0° C. The solution was stirred at 0° C. for 15 mins. Then a solution of NaIO₄ (11.6 g, 54.0 mmol, 2.99 mL, 1.10 eq) in H₂O (15.0 mL) was added dropwise at 0° C. and was stirred for 2 hrs at 0° C. The reaction was warmed to 25° C. and stirred for 12 hrs. The mixture was quenched with a saturated Na₂SO₃ solution, extracted with EtOAc (200 mL), dried over anhydrous Na₂SO₄, filtered and concentrated under vacuum to give ethyl 2-(5-(2,3-dihydroxypropyl)-2-oxo-4-(trifluoromethyl)pyridin-1(2H)-yl)-4,4-dimethylpentanoate (16.9 g, crude) as a yellow oil used without further purification.

Step 6: Ethyl 4,4-dimethyl-2-(2-oxo-5-(2-oxoethyl)-4-(trifluoromethyl)pyridin-1(2H)-yl)pentanoate

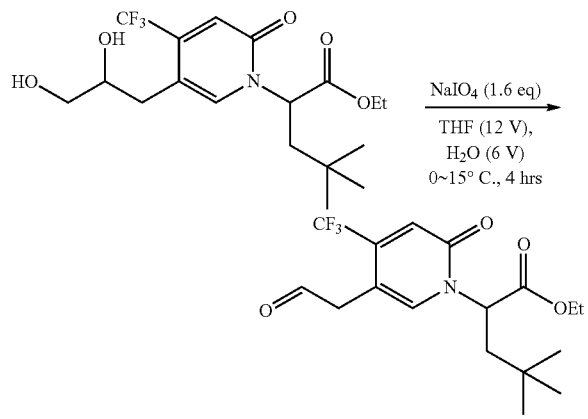

To a solution of ethyl 2-(5-(2,3-dihydroxypropyl)-2-oxo-4-(trifluoromethyl)pyridin-1(2H)-yl)-4,4-dimethylpentanoate (16.9 g, 43.0 mmol, 1.00 eq) in THF (200 mL) was added a solution of NaIO$_4$ (14.7 g, 68.7 mmol, 3.81 mL, 1.60 eq) in H$_2$O (100 mL) at 0° C. The solution was stirred at 0° C. for 2 hrs, then warmed to 25° C. and stirred for 2 hrs. The mixture was quenched with a saturated Na$_2$SO$_3$ solution and extracted with EtOAc (300 mL). The organic layer was washed with 1 N HCl solution and brine, then dried over anhydrous Na$_2$SO$_4$, filtered. AcOH was added to the filtrate and concentration under reduced pressure provided ethyl 4,4-dimethyl-2-(2-oxo-5-(2-oxoethyl)-4-(trifluoromethyl)pyridin-1(2H)-yl)pentanoate (16.8 g, crude) as a yellow oil used without further purification.

Step 7: Ethyl 2-(5-(2-(dimethylamino)ethyl)-2-oxo-4-(trifluoromethyl)pyridin-1(2H)-yl)-4,4-dimethylpentanoate

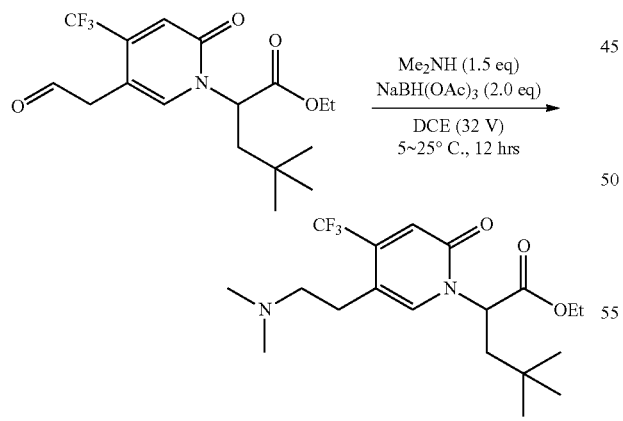

To a solution of ethyl 4,4-dimethyl-2-(2-oxo-5-(2-oxoethyl)-4-(trifluoromethyl)pyridin-1(2H)-yl)pentanoate (8.40 g, 23.3 mmol, 1.00 eq) in DCE (268 mL) was added Me$_2$NH (2.84 g, 34.9 mmol, 1.50 eq) at 25° C. The solution was stirred at 25° C. for 15 mins, then NaBH(OAc)$_3$ (9.85 g, 46.5 mmol, 2.00 eq) was added portion-wise at 5° C., and the solution stirred at 25° C. for 12 hrs. The reaction mixture was diluted with H$_2$O (200 mL) and extracted with DCM (100 mL). The organic layer was washed with brine, dried over anhydrous Na$_2$SO$_4$, filtered and concentrated under vacuum to give ethyl 2-(5-(2-(dimethylamino)ethyl)-2-oxo-4-(trifluoromethyl)pyridin-1(2H)-yl)-4,4-dimethylpentanoate (7.30 g, crude) as a brown oil used without further purification.

Step 8: 2-(5-(2-(dimethylamino)ethyl)-2-oxo-4-(trifluoromethyl)pyridin-1(2H)-yl)-4,4-dimethylpentanoic Acid

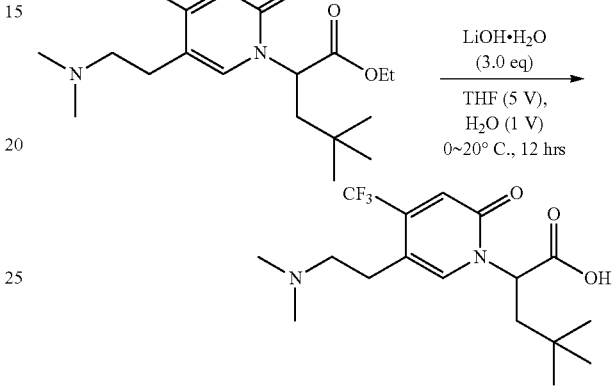

To a solution of ethyl 2-(5-(2-(dimethylamino)ethyl)-2-oxo-4-(trifluoromethyl)pyridin-1(2H)-yl)-4,4-dimethylpentanoate (7.30 g, 18.7 mmol, 1.00 eq) in THF (36.5 mL) and H$_2$O (7.30 mL) was added LiOH.H$_2$O (1.57 g, 37.4 mmol, 2.00 eq) at 0° C. The reaction mixture was warmed to 20° C. and stirred for 12 hrs. The reaction mixture was adjusted to pH=7 with 1N aqueous HCl and concentrated under vacuum to give the crude product. The crude product was purified by prep-HPLC (column: Phenomenex luna C18 250*50 mm*15 um; mobile phase: [water (0.1% TFA)-ACN]; B %: 10%-35%, 20 min). Lyophilization give 2-(5-(2-(dimethylamino)ethyl)-2-oxo-4-(trifluoromethyl)pyridin-1(2H)-yl)-4,4-dimethylpentanoic acid (0.51 g, 511 umol, 2.74% yield, HCl) as a yellow solid. $^1$H NMR: 400 MHz D$_2$O δ: 7.89 (s, 1H), 6.99 (s, 1H), 5.45-5.47 (d, J=12.0 Hz, 1H), 3.25-3.29 (m, 2H), 2.98-3.03 (m, 1H), 2.92 (s, 6H), 2.18-2.22 (m, 1H), 1.98-2.04 (m, 2H), 0.78 (s, 9H)

Preparation of Ethyl 2-(5-(2-(azetidin-1-yl)ethyl)-2-oxo-4-(trifluoromethyl)pyridin-1(2H)-yl)-4-fluoro-4-methylpentanoate Step 1: Ethyl 2-(5-(2-(azetidin-1-yl)ethyl)-2-oxo-4-(trifluoromethyl)pyridin-1(2H)-yl)-4,4-dimethylpentanoate

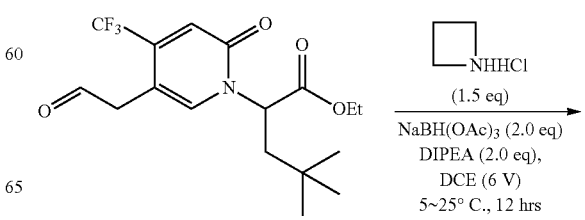

373

-continued

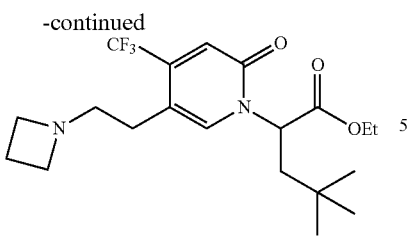

To a solution of ethyl 4,4-dimethyl-2-(2-oxo-5-(2-oxo-ethyl)-4-(trifluoromethyl)pyridin-1(2H)-yl)pentanoate (8.40 g, 23.3 mmol, 1.00 eq) in DCE (268 mL) was added azetidine hydrochloride (3.26 g, 34.9 mmol, 1.50 eq) and DIPEA (6.01 g, 46.5 mmol, 8.10 mL, 2.00 eq) at 25° C. The solution was stirred for 15 mins, then NaBH(OAc)$_3$ (9.85 g, 46.5 mmol, 2.00 eq) was added portion-wise at 5° C., and the solution was stirred at 25° C. for 12 hrs. The reaction mixture was diluted with H$_2$O (200 mL) and extracted with DCM (100 mL). The organic layer was washed with brine, dried over anhydrous Na$_2$SO$_4$, filtered and concentrated under vacuum to give ethyl 2-(5-(2-(azetidin-1-yl)ethyl)-2-oxo-4-(trifluoromethyl)pyridin-1(2H)-yl)-4,4-dimethylpentanoate (10.9 g, crude) as a yellow oil used without further purification.

Step 2: 2-(5-(2-(azetidin-1-yl)ethyl)-2-oxo-4-(trifluoromethyl)pyridin-1(2H)-yl)-4,4-dimethylpentanoic Acid

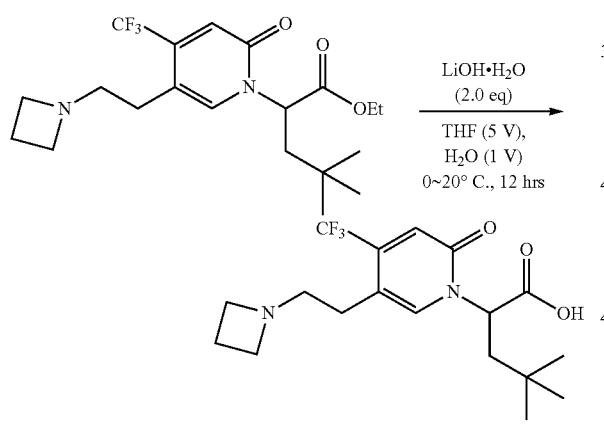

To a solution of ethyl 2-(5-(2-(azetidin-1-yl)ethyl)-2-oxo-4-(trifluoromethyl)pyridin-1(2H)-yl)-4,4-dimethylpentanoate (10.9 g, 27.0 mmol, 1.00 eq) in THF (54.5 mL) and H$_2$O (10.9 mL) was added LiOH.H$_2$O (2.27 g, 54.2 mmol, 2.00 eq) at 0° C. The reaction mixture was warmed to 20° C. and stirred for 12 hrs. The reaction mixture was adjusted to pH=7 with 1N aqueous HCl and concentrated under vacuum to give the crude product. The crude product was purified by prep-HPLC (column: Phenomenex luna C18 250*50 mm*15 um; mobile phase: [water (0.1% TFA)-ACN]; B %: 10%-35%, 23 min). Lyophilization provided 2-(5-(2-(azetidin-1-yl)ethyl)-2-oxo-4-(trifluoromethyl)pyridin-1(2H)-yl)-4,4-dimethylpentanoic acid (0.32 g, 857 umol, 3.16% yield) as a white solid 1H NMR: 400 MHz D$_2$O δ: 7.85 (s, 1H), 6.98 (s, 1H), 5.45 (s, 1H), 4.22 (m, 2H), 4.01-4.05 (m, 2H), 3.34-3.35 (m, 2H), 2.83 (m, 2H), 1.97-2.54 (m, 4H), 0.77 (s, 9H).

374

Preparation of 2-(5-(3-(dimethylamino)propyl)-2-oxo-4-(trifluoromethyl)pyridin-1(2H)-yl)-4,4-dimethylpentanoic Acid Step 1: Ethyl 2-(5-(3-(dimethylamino)prop-1-yn-1-yl)-2-oxo-4-(trifluoromethyl)pyridin-1(2H)-yl)-4,4-dimethylpentanoate

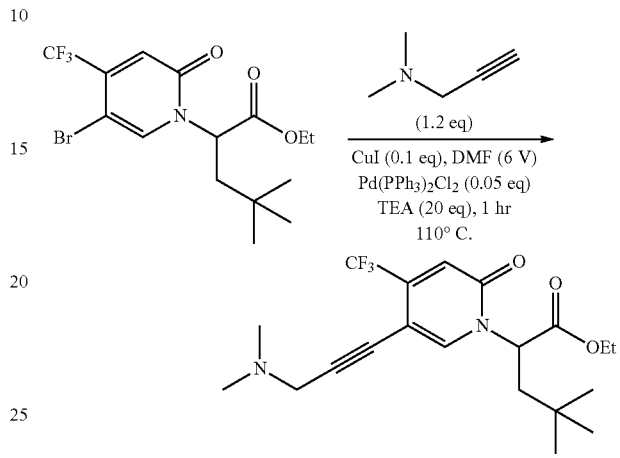

Ethyl 2-(5-bromo-2-oxo-4-(trifluoromethyl)pyridin-1(2H)-yl)-4,4-dimethylpentanoate (1.00 g, 2.51 mmol, 1.00 eq), N,N-dimethylprop-2-yn-1-amine (251 mg, 3.01 mmol, 320 uL, 1.20 eq), TEA (5.08 g, 50.2 mmol, 6.99 mL, 20.0 eq), Pd(PPh$_3$)$_2$Cl$_2$ (88.1 mg, 126 umol, 0.05 eq) and CuI (47.8 mg, 251 umol, 0.10 eq) were added to a microwave tube in DMF (6 mL). The sealed tube was heated under microwave conditions at 110° C. for 1 hr. The reaction was poured into water and extracted with MTBE (100 mL×2). The combined organic phase was washed with brine (50 mL×2), dried with anhydrous Na$_2$SO$_4$, filtered and concentrated under vacuum. The residue was purified by silica gel chromatography (Petroleum ether:Ethyl acetate=5:1) to give ethyl 2-(5-(3-(dimethylamino)prop-1-yn-1-yl)-2-oxo-4-(trifluoromethyl)pyridin-1(2H)-yl)-4,4-dimethylpentanoate (0.52 g, 1.3 mmol, 52.5% yield) as a yellow oil.

Step 2: Ethyl 2-(5-(3-(dimethylamino)propyl)-2-oxo-4-(trifluoromethyl)pyridin-1(2H)-yl)-4,4-dimethylpentanoate

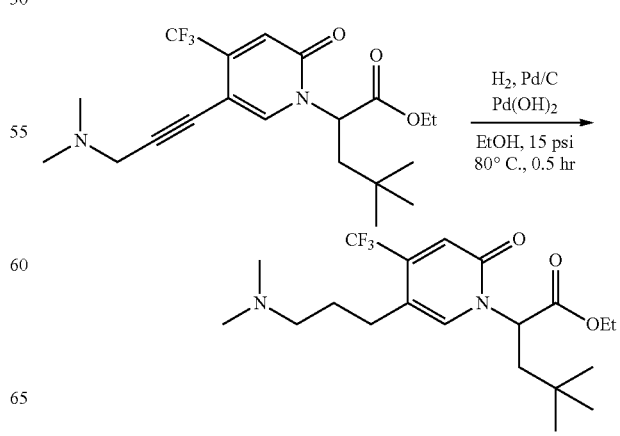

To a solution of ethyl 2-(5-(3-(dimethylamino)prop-1-yn-1-yl)-2-oxo-4-(trifluoromethyl)pyridin-1(2H)-yl)-4,4-dimethylpentanoate (3.70 g, 9.24 mmol, 1.00 eq) in EtOH (170 mL) was added Pd/C (1.10 g) and Pd(OH)₂ (1.10 g). The mixture was stirred under H₂ (50 psi) at 80° C. for 0.5 hr. The reaction mixture was filtered and concentrated to give ethyl 2-(5-(3-(dimethylamino)propyl)-2-oxo-4-(trifluoromethyl)pyridin-1(2H)-yl)-4,4-dimethylpentanoate used without further purification.

Step 3: 2-(5-(3-(dimethylamino)propyl)-2-oxo-4-(trifluoromethyl)pyridin-1(2H)-yl)-4,4-dimethylpentanoic Acid

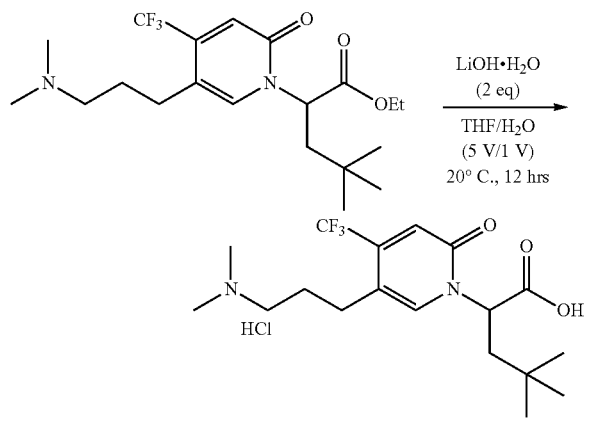

To a solution of ethyl 2-(5-(3-(dimethylamino)propyl)-2-oxo-4-(trifluoromethyl)pyridin-1(2H)-yl)-4,4-dimethylpentanoate (3.70 g, 9.15 mmol, 1.00 eq) in THF (18.5 mL) and H₂O (3.70 mL) was added LiOH·H₂O (768 mg, 18.3 mmol, 2.00 eq) at 0° C. The reaction mixture was warmed to 20° C. and stirred for 12 hrs. The reaction mixture was adjusted to pH=7 with 1N aqueous HCl and concentrated under vacuum to give the crude product. The crude product was purified by prep-HPLC (column: Phenomenex luna C18 (250*70 mm, 15 um); mobile phase: [water(0.05% HCl)-ACN]; B %: 5%-35%, 20 min) to give 2-(5-(3-(dimethylamino)propyl)-2-oxo-4-(trifluoromethyl)pyridin-1(2H)-yl)-4,4-dimethylpentanoic acid (2.2 g, 5.33 mmol, 58.25% yield) as a white solid. ¹H NMR: 400 MHz D₂O δ: 7.83 (s, 1H), 7.00 (s, 1H), 5.50-5.52 (m, 1H), 3.15-3.19 (m, 2H), 2.85 (s, 6H), 2.67-2.70 (m, 2H), 2.22-2.26 (m, 1H), 1.98-2.09 (m, 3H), 0.82 (s, 9H).

Example 3: Synthesis of Exemplary Compounds of the Invention

Prep-HPLC Methods

Crude samples were dissolved in MeOH and purified by prep HPLC using a Gilson 215 instrument, detection wavelength 214 nm:

Prep HPLC A: column: Xtimate C18, 21.2*250 mm, 10 μm; mobile phase: A water (10 mM ammonium hydrogen carbonate), B CH₃CN; gradient elution as in text; flow rate: 30 mL/min.

Prep HPLC B: column: Xtimate C18, 21.2*250 mm, 10 μm; mobile phase: A water (0.1% formic acid), B CH₃CN; gradient elution as in text; flow rate: 30 mL/min.

3-1. Preparation of (3S)-3-(4,5-difluoro-2',6'-dimethylbiphenyl-3-yl)-3-(2-(5-(2-(3-fluoroazetidine-1-yl)ethyl)-4-methyl-2-oxopyridin-1(2H)-yl)-4-methylpentanamido)propanoic Acid (Compounds D-P1 and D-P2)

Step 1: (3S)-ethyl 3-(4,5-difluoro-2',6'-dimethylbiphenyl-3-yl)-3-(2-(5-(2-(3-fluoroazetidine-1-yl)ethyl)-4-methyl-2-oxopyridin-1(2H)-yl)-4-methylpentanamido)propanoate

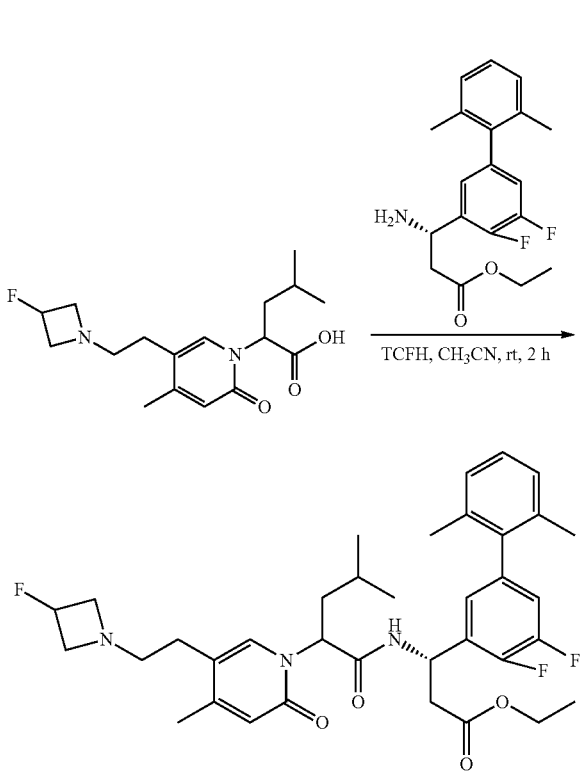

A mixture of 2-(5-(2-(3-fluoroazetidine-1-yl)ethyl)-4-methyl-2-oxopyridin-1(2H)-yl)-4-methylpentanoic acid (84 mg, 0.26 mmol), (S)-ethyl 3-amino-3-(4,5-difluoro-2',6'-dimethylbiphenyl-3-yl)propanoate (173 mg, 0.52 mmol), TCFH (94 mg, 0.34 mmol), and NMI (0.30 mL, 3.76 mmol) in acetonitrile (5 mL) was stirred at room temperature for 2 hours. The reaction mixture was poured into 100 mL of EtOAc, washed with water (30 mL), brine (30 mL), dried over Na₂SO₄, filtered and concentrated in vacuo. The reaction mixture was concentrated in vacuo and purified by reverse phase HPLC on a C18/40 g column (A: water/0.01% TFA, B: MeOH, 0~64%) to provide (3S)-ethyl 3-(4,5-difluoro-2',6'-dimethylbiphenyl-3-yl)-3-(2-(5-(2-(3-fluoroazetidine-1-yl)ethyl)-4-methyl-2-oxopyridin-1(2H)-yl)-4-methylpentanamido)propanoate as a white solid (131 mg). Yield 79% (ESI 640.2 (M+H)⁺).

Step 2: (3S)-3-(4,5-difluoro-2',6'-dimethylbiphenyl-3-yl)-3-(2-(5-(2-(3-fluoroazetidine-1-yl)ethyl)-4-methyl-2-oxopyridin-1(2H)-yl)-4-methylpentanamido)propanoic Acid

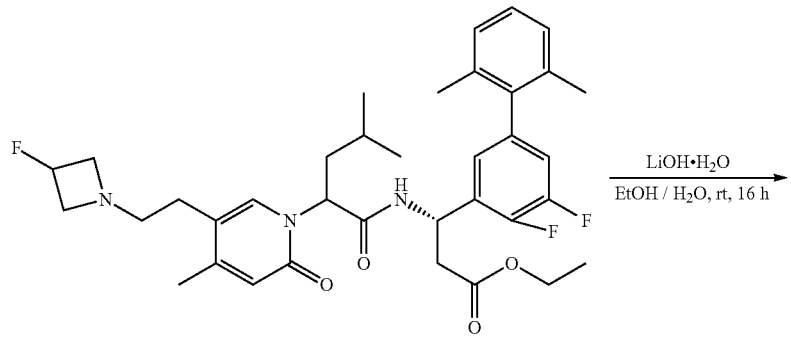

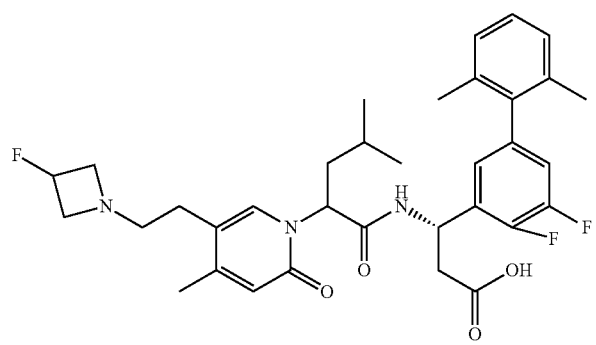

(3S)-ethyl 3-(4,5-difluoro-2',6'-dimethylbiphenyl-3-yl)-3-(2-(5-(2-(3-fluoroazetidine-1-yl)ethyl)-4-methyl-2-oxopyridin-1(2H)-yl)-4-methylpentanamido)propanoate (131 mg, 0.20 mmol) was treated with LiOH monohydrate (72 mg, 1.71 mmol) in EtOH (12.5 mL) and H$_2$O (0.25 mL) at room temperature for 16 hours. The reaction mixture was acidified to pH 4-5 with concentrated HCL. The reaction mixture was concentrated in vacuo and purified by prep-HPLC A (30-60% MeCN) to give the diastereomeric products D-P1 (23 mg) and D-P2 (23 mg) as white solids.

D-P1 ESI 612.2 (M+H)$^+$. $^1$H NMR (500 MHz, MeOD) δ 7.46 (s, 1H), 7.14 (t, J=8.0 Hz, 1H), 7.07 (t, J=6.0 Hz, 2H), 6.93-6.89 (m, 1H), 6.81 (d, J=5.5 Hz, 1H), 6.27 (s, 1H), 5.59-5.54 (m, 2H), 5.28-5.12 (m, 1H), 4.07-3.94 (m, 2H), 3.74-3.60 (m, 2H), 3.05-2.99 (m, 2H), 2.79-2.69 (m, 2H), 2.65-2.59 (m, 2H), 2.20 (s, 3H), 1.99 (s, 3H), 1.92 (t, J=7.0 Hz, 2H), 1.85 (s, 3H), 1.44-1.36 (m, 1H), 0.93 (d, J=6.5 Hz, 3H), 0.90 (d, J=6.5 Hz, 3H).

D-P2 ESI 612.2 (M+H)$^+$. $^1$H NMR (500 MHz, MeOD) δ 7.46 (s, 1H), 7.14 (t, J=8.0 Hz, 1H), 7.07 (t, J=6.0 Hz, 2H), 6.93-6.89 (m, 1H), 6.81 (d, J=5.5 Hz, 1H), 6.27 (s, 1H), 5.59-5.54 (m, 2H), 5.28-5.12 (m, 1H), 4.07-3.94 (m, 2H), 3.75-3.60 (m, 2H), 3.06-2.98 (m, 2H), 2.79-2.69 (m, 2H), 2.65-2.59 (m, 2H), 2.20 (s, 3H), 1.99 (s, 3H), 1.92 (t, J=7.0 Hz, 2H), 1.85 (s, 3H), 1.44-1.36 (m, 1H), 0.93 (d, J=6.5 Hz, 3H), 0.90 (d, J=6.5 Hz, 3H).

3-2. Preparation of (3S)-3-(3-cyclopropyl-2-(5-(2-(3-fluoroazetidine-1-yl)ethyl)-2-oxopyridin-1(2H)-yl)propanamido)-3-(4,5-difluoro-2',6'-dimethyl-[1,1'-biphenyl]-3-yl)propanoic Acid (Compounds E-P1 and E-P2)

Step 1: Ethyl (3S)-3-(3-cyclopropyl-2-(5-(2-(3-fluoroazetidine-1-yl)ethyl)-2-oxopyridin-1(2H)-yl)propanamido)-3-(4,5-difluoro-2',6'-dimethyl-[1,1'-biphenyl]-3-yl)propanoate

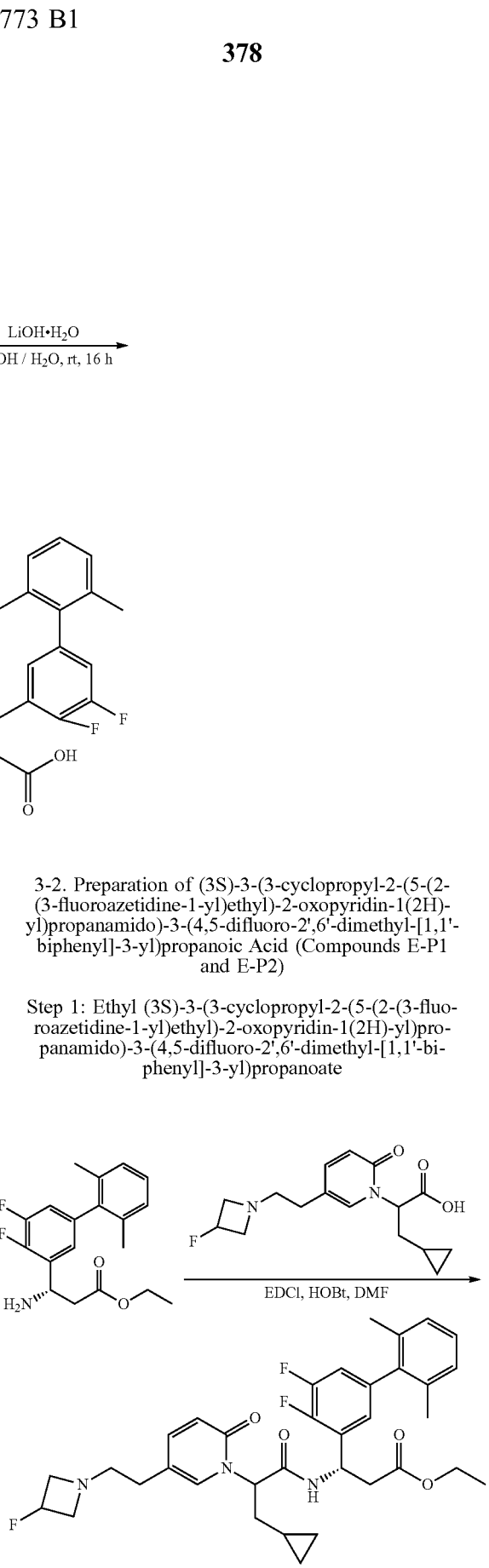

A mixture of ethyl (S)-3-amino-3-(4,5-difluoro-2',6'-dimethyl-[1,1'-biphenyl]-3-yl)propanoate (90 mg, 0.27 mmol), 3-cyclopropyl-2-(5-(2-(3-fluoroazetidine-1-yl)ethyl)-2-oxopyridin-1(2H)-yl)propanoic acid (125 mg, 0.40 mmol), HOBT (73 mg, 0.54 mmol), EDCI (104 mg, 0.54 mmol) and TEA (120 mg, 0.81 mmol) in DMF (2 mL) was stirred at 50° C. for 4 hours. The reaction mixture was concentrated in vacuo and purified by reverse phase HPLC on a C18/40 g column (A: water 10 mM $NH_4HCO_3$, B: MeOH, 0~100%) to provide ethyl (3S)-3-(3-cyclopropyl-2-(5-(2-(3-fluoroazetidine-1-yl)ethyl)-2-oxopyridin-1(2H)-yl)propanamido)-3-(4,5-difluoro-2',6'-dimethyl-[1,1'-biphenyl]-3-yl)propanoate as a yellow oil (60 mg). Yield 35% (ESI 624.2 $(M+H)^+$).

Step 2: (3S)-3-(3-cyclopropyl-2-(5-(2-(3-fluoroazetidine-1-yl)ethyl)-2-oxopyridin-1(2H)-yl)propanamido)-3-(4,5-difluoro-2',6'-dimethyl-[1,1'-biphenyl]-3-yl)propanoic Acid

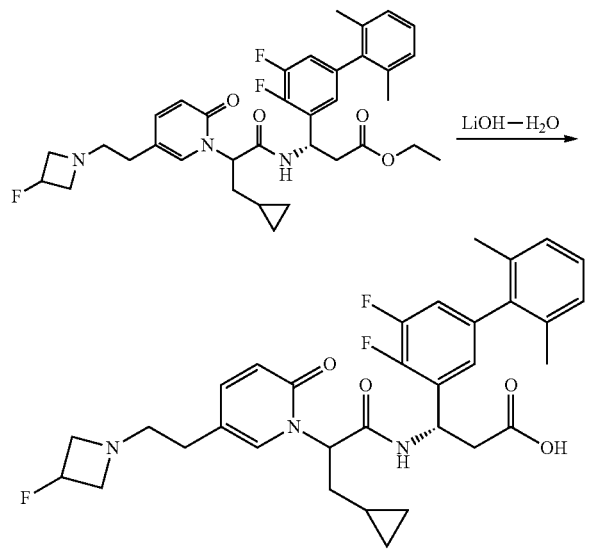

Ethyl (3S)-3-(3-cyclopropyl-2-(5-(2-(3-fluoroazetidine-1-yl)ethyl)-2-oxopyridin-1(2H)-yl)propanamido)-3-(4,5-difluoro-2',6'-dimethyl-[1,1'-biphenyl]-3-yl)propanoate (50 mg, 0.08 mmol) was treated with LiOH—$H_2O$ (13 mg, 0.32 mmol) in MeOH (2 mL) and $H_2O$ (0.5 mL) at room temperature for 1 hour. The reaction mixture was acidified to pH 4~5 with 1N HCl. The solvent was removed in vacuo and the residue was purified by prep-HPLC A (30-60% MeCN) to give the diastereomeric products E-P1 (1 mg) and E-P2 (1 mg) as white solids.

E-P1 ESI 596.2 $(M+H)^+$. $^1H$ NMR (500 MHz, MeOD) δ 7.47 (s, 1H), 7.33 (d, J=7.2 Hz, 1H), 7.07-6.99 (m, 3H), 6.88-6.80 (m, 1H), 6.71-6.70 (m, 1H), 6.34 (d, J=9.2 Hz, 1H), 5.45 (s, 2H), 5.19-5.03 (m, 1H), 3.96-3.84 (m, 2H), 3.57 (s, 2H), 2.97-2.96 (m, 2H), 2.67 (s, 2H), 2.50 (s, 2H), 1.91 (s, 5H), 1.79 (s, 3H), 0.55 (s, 1H), 0.35-0.34 (m, 2H), 0.07-0.00 (m, 2H).

E-P2 ESI 596.2 $(M+H)^+$. $^1H$ NMR (500 MHz, MeOD) δ 7.49 (s, 1H), 7.41 (d, J=9.0 Hz, 1H), 7.15-6.84 (m, 5H), 6.50 (d, J=9.3 Hz, 1H), 5.57-5.44 (m, 2H), 5.19-5.07 (m, 1H), 3.95-3.59 (m, 3H), 2.99 (s, 2H), 2.59-2.54 (m, 4H), 2.15-2.12 (m, 1H), 1.99-1.95 (m, 8H), 0.52-0.47 (m, 1H), 0.25-0.23 (m, 2H), 0.01-0.05 (m, 2H).

3-3. Preparation of (3S)-3-(2-(5-(2-(dimethylamino)ethyl)-2-oxo-4-(trifluoromethyl)pyridin-1(2H)-yl)-3-methylbutanamido)-3-(4-fluoro-2',4',5,6'-tetramethylbiphenyl-3-yl)propanoic Acid (Compounds F-P1 and F-P2)

Step 1: (3S)-ethyl 3-(2-(5-(2-(dimethylamino)ethyl)-2-oxo-4-(trifluoromethyl)pyridin-1(2H)-yl)-3-methylbutanamido)-3-(4-fluoro-2',4',5,6'-tetramethylbiphenyl-3-yl)propanoate

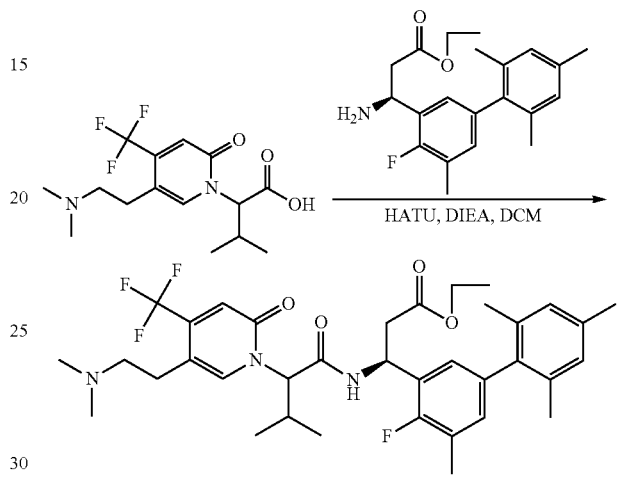

A mixture of 2-(5-(2-(dimethylamino)ethyl)-2-oxo-4-(trifluoromethyl)pyridin-1(2H)-yl)-3-methylbutanoic acid (150 mg, 0.45 mmol), (S)-ethyl 3-amino-3-(4-fluoro-2',4',5,6'-tetramethylbiphenyl-3-yl)propanoate (154 mg, 0.45 mmol), HATU (205 mg, 0.54 mmol) and DIEA (175 mg, 1.35 mmol) in DCM (5 mL) was stirred at room temperature for 1 hour. The solvent was removed in vacuo and the residue was purified by silica gel column (DCM:MeOH 4:1) to provide (3S)-ethyl 3-(2-(5-(2-(dimethylamino)ethyl)-2-oxo-4-(trifluoromethyl)pyridin-1(2H)-yl)-3-methylbutanamido)-3-(4-fluoro-2',4',5,6'-tetramethylbiphenyl-3-yl)propanoate as a brown oil (100 mg). Yield 33% (ESI 660.3 $(M+H)^+$).

Step 2: (3S)-3-(2-(5-(2-(dimethylamino)ethyl)-2-oxo-4-(trifluoromethyl)pyridin-1(2H)-yl)-3-methylbutanamido)-3-(4-fluoro-2',4',5,6'-tetramethylbiphenyl-3-yl)propanoic Acid

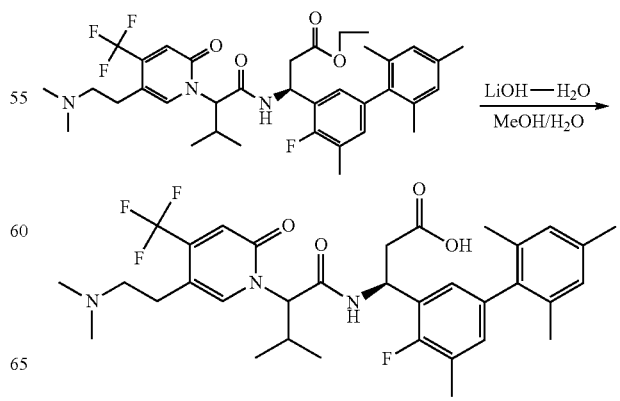

(3S)-ethyl 3-(2-(5-(2-(dimethylamino)ethyl)-2-oxo-4-(trifluoromethyl)pyridin-1(2H)-yl)-3-methylbutanamido)-3-(4-fluoro-2',4',5',6'-tetramethylbiphenyl-3-yl)propanoate (100 mg, 0.15 mmol) was treated with LiOH—H$_2$O (32 mg, 0.75 mmol) in MeOH (3 mL) and H$_2$O (1 mL) at room temperature for 3 hours. The reaction mixture was acidified to pH 4-5 with 1N HCl. The solvent was removed in vacuo and the residue was purified by prep-HPLC A (30-60% MeCN) to give the diastereomeric products F-P1 (30.0 mg) and F-P2 (32.0 mg) as white solids.

F-P1 ESI 632.2 (M+H)$^+$. $^1$H NMR (400 MHz, MeOD) δ 7.95 (s, 1H), 6.89 (s, 1H), 6.84-6.76 (m, 3H), 6.67 (s, 1H), 5.65-5.54 (m, 1H), 5.26 (d, J=11.3 Hz, 1H), 3.06-2.85 (m, 4H), 2.80-2.63 (m, 8H), 2.53-2.38 (m, 1H), 2.34-2.23 (m, 6H), 1.95 (s, 3H), 1.63 (s, 3H), 1.17 (d, J=6.5 Hz, 3H), 0.80 (d, J=6.5 Hz, 3H).

F-P2 ESI 632.2 (M+H)$^+$. $^1$H NMR (400 MHz, MeOD) δ 8.11-7.95 (m, 1H), 7.02-6.83 (m, 5H), 5.76 (s, 1H), 5.24 (d, J=10.9 Hz, 1H), 3.27-2.90 (m, 4H), 2.81 (d, J=3.7 Hz, 6H), 2.66-2.36 (m, 3H), 2.31 (d, J=5.7 Hz, 6H), 1.95 (t, J=5.8 Hz, 6H), 0.95 (s, 3H), 0.82-0.66 (m, 3H).

3-4. Preparation of (3S)-3-(2-(5-(2-(azetidin-1-yl)ethyl)-2-oxo-4-(trifluoromethyl)pyridin-1(2H)-yl)-4-methylpentanamido)-3-(4-fluoro-2',6'-dimethyl-5-(trifluoromethyl)biphenyl-3-yl)propanoic Acid (Compounds G-P1 and G-P2)

Step 1: (3S)-ethyl 3-(2-(5-(2-(azetidin-1-yl)ethyl)-2-oxo-4-(trifluoromethyl)pyridin-1(2H)-yl)-4-methylpentanamido)-3-(4-fluoro-2',6'-dimethyl-5-(trifluoromethyl)biphenyl-3-yl)propanoate

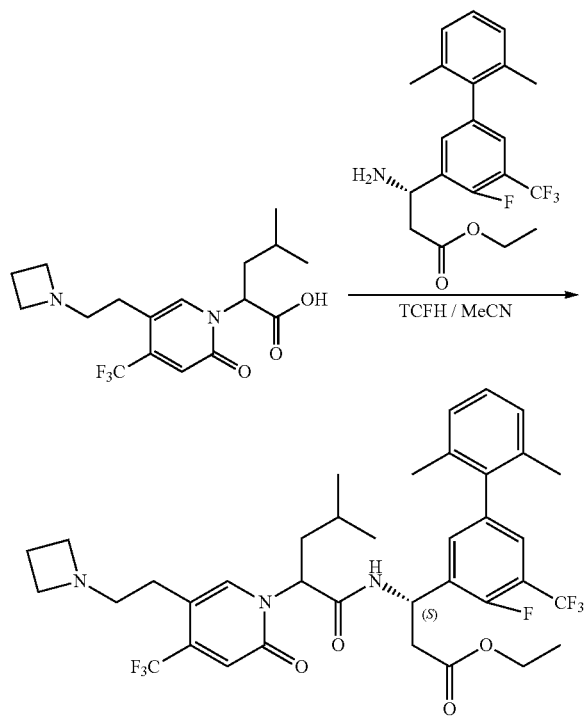

A mixture of 2-(5-(2-(azetidin-1-yl)ethyl)-2-oxo-4-(trifluoromethyl)pyridin-1(2H)-yl)-4-methylpentanoic acid (150 mg, 0.42 mmol), (S)-ethyl 3-amino-3-(4-fluoro-2',6'-dimethyl-5-(trifluoromethyl)biphenyl-3-yl)propanoate (161 mg, 0.42 mmol), TCFH (235 mg, 0.84 mmol), and NMI (138 mg, 1.68 mmol) in acetonitrile (4 mL) was stirred at room temperature for 2 hours. The reaction mixture was concentrated in vacuo and purified by reverse phase HPLC on a C18/40 g column (A: water 10 mM NH$_4$HCO$_3$, B: MeOH, 0~100%) to provide (3S)-ethyl 3-(2-(5-(2-(azetidin-1-yl)ethyl)-2-oxo-4-(trifluoromethyl)pyridin-1(2H)-yl)-4-methylpentanamido)-3-(4-fluoro-2',6'-dimethyl-5-(trifluoromethyl)biphenyl-3-yl)propanoate as colorless oil (155 mg). Yield 51% (ESI 726.1 (M+H)$^+$).

Step 2: (3S)-3-(2-(5-(2-(azetidin-1-yl)ethyl)-2-oxo-4-(trifluoromethyl)pyridin-1(2H)-yl)-4-methylpentanamido)-3-(4-fluoro-2',6'-dimethyl-5-(trifluoromethyl)biphenyl-3-yl)propanoic acid

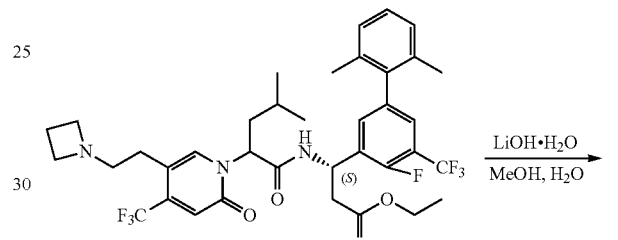

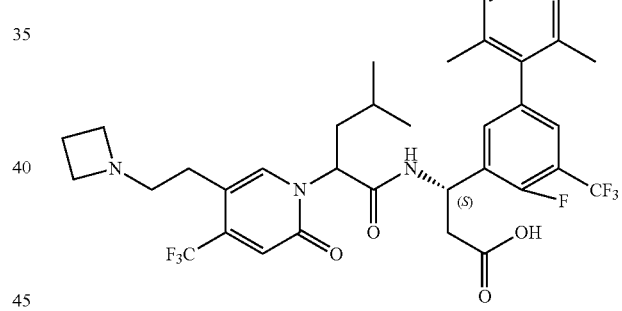

(3S)-ethyl 3-(2-(5-(2-(azetidin-1-yl)ethyl)-2-oxo-4-(trifluoromethyl)pyridin-1(2H)-yl)-4-methylpentanamido)-3-(4-fluoro-2',6'-dimethyl-5-(trifluoromethyl)biphenyl-3-yl)propanoate (155 mg, 0.21 mmol) was treated with LiOH monohydrate (35 mg, 0.84 mmol) in MeOH (4 mL) and H$_2$O (1 mL) at room temperature for 2 hours. The reaction mixture was acidified to pH 4-5 with 1N HCl. The mixture was concentrated in vacuo and the residue was purified by prep-HPLC A (30-65% MeCN) to give the diastereomeric products G-P1 (37.8 mg) and G-P2 (49.6 mg) as white solids.

G-P1 ESI 698.2 (M+H)$^+$. $^1$H NMR (400 MHz, MeOD) δ 7.85 (s, 1H), 7.41 (d, J=5.0 Hz, 1H), 7.36-7.27 (m, 1H), 7.21-7.09 (m, 3H), 6.74 (s, 1H), 5.71-5.54 (m, 2H), 4.04 (t, J=8.1 Hz, 4H), 3.29 (t, J=6.7 Hz, 2H), 2.86-2.82 (m, 2H), 2.78-2.68 (m, 2H), 2.50-2.36 (m, 2H), 2.08-1.93 (m, 5H), 1.86 (s, 3H), 1.44-1.41 (m, 1H), 1.13-0.79 (m, 6H).

G-P2 ESI 698.2 (M+H)⁺. ¹H NMR (400 MHz, MeOD) δ 7.76 (s, 1H), 7.50-7.44 (m, 1H), 7.41-7.33 (m, 1H), 7.22-7.18 (m, 1H), 7.14 (d, J=7.4 Hz, 2H), 6.90 (s, 1H), 5.813-5.80 (m, 1H), 5.64 (t, J=7.7 Hz, 1H), 4.13 (t, J=8.0 Hz, 4H), 3.55-3.34 (m, 2H), 2.99-2.88 (m, 1H), 2.85-2.81 (m, 1H), 2.71-2.66 (m, 1H), 2.60-2.54 (m, 1H), 2.53-2.43 (m, 2H), 2.07-1.93 (m, 7H), 1.76-1.61 (m, 1H), 1.42-1.37 (m, 1H), 0.95-0.83 (m, 6H).

3-5. Preparation of ((3S)-3-(2-(3-(difluoromethyl)-5-(2-(dimethylamino)ethyl)-2-oxopyridin-1(2H)-yl)-4-methylpentanamido)-3-(4-fluoro-2',4',5,6'-tetramethyl-[1,1'-biphenyl]-3-yl)propanoic Acid (Compounds H-P1 and H-P2)

Step 1: Ethyl (3S)-3-(2-(3-(difluoromethyl)-5-(2-(dimethylamino)ethyl)-2-oxopyridin-1(2H)-yl)-4-methylpentanamido)-3-(4-fluoro-2',4',5,6'-tetramethyl-[1,1'-biphenyl]-3-yl)propanoate

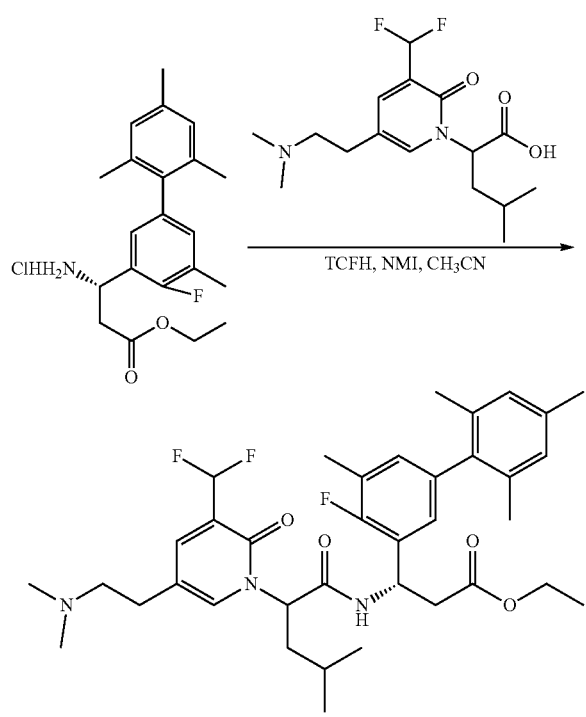

A mixture of ethyl (S)-3-amino-3-(4-fluoro-2',4',5,6'-tetramethyl-[1,1'-biphenyl]-3-yl)propanoate hydrochloride (120 mg, 0.35 mmol), 2-(3-(difluoromethyl)-5-(2-(dimethylamino)ethyl)-2-oxopyridin-1(2H)-yl)-4-methylpentanoic acid (138 mg, 0.42 mmol), TCFH (147 mg, 0.52 mmol) and NMI (86 mg, 1.05 mmol) in acetonitrile (5 mL) was stirred at room temperature for 1 hour. The solvent was removed in vacuo and the residue was purified by silica gel column (DCM:MeOH 4:1) to provide ethyl (3S)-3-(2-(3-(difluoromethyl)-5-(2-(dimethylamino)ethyl)-2-oxopyridin-1(2H)-yl)-4-methylpentanamido)-3-(4-fluoro-2',4',5,6'-tetramethyl-[1, 1'-biphenyl]-3-yl)propanoate as a brown solid (150 mg). Yield 65.2% (ESI 656.2 (M+H)⁺).

Step 2: (3S)-3-(2-(3-(difluoromethyl)-5-(2-(dimethylamino)ethyl)-2-oxopyridin-1(2H)-yl)-4-methylpentanamido)-3-(4-fluoro-2',4',5,6'-tetramethyl-[1,1'-biphenyl]-3-yl)propanoic Acid

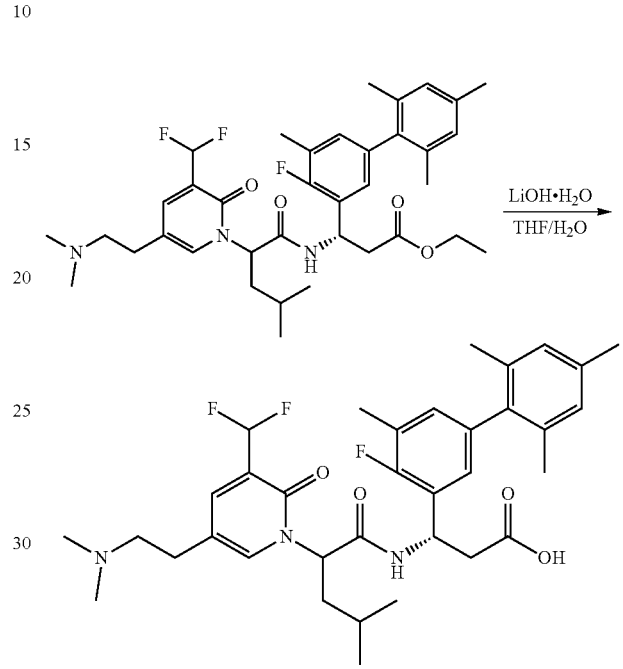

Ethyl (3S)-3-(2-(3-(difluoromethyl)-5-(2-(dimethylamino)ethyl)-2-oxopyridin-1(2H)-yl)-4-methylpentanamido)-3-(4-fluoro-2',4',5,6'-tetramethyl-[1,1'-biphenyl]-3-yl)propanoate (150 mg, 0.23 mmol) was treated with LiOH—H₂O (95.5 mg, 2.3 mmol) in THF (3 mL) and H₂O (1 mL) at room temperature for 3 hours. The reaction mixture was acidified to pH 4~5 with 1N HCl. The solvent was removed in vacuo and the residue was purified by prep-HPLC A (30-70% MeCN) to give the diastereomeric products H-P1 (24.0 mg) and H-P2 (33.0 mg) as white solids.

H-P1 ESI 628.3 (M+H)⁺. ¹H NMR (400 MHz, MeOD) δ 7.71 (s, 2H), 6.78 (s, 2H), 6.76-6.62 (m, 2H), 6.42 (t, J=55.1 Hz, 1H), 5.49-5.45 (m, 1H), 5.30 (t, J=5.7 Hz, 1H), 3.20-3.10 (m, 1H), 3.09-3.02 (m, 1H), 2.83-2.70 (m, 2H), 2.61 (s, 6H), 2.58-2.50 (m, 1H), 2.48-2.39 (m, 1H), 2.22-2.10 (m, 6H), 1.94-1.84 (m, 2H), 1.83 (s, 3H), 1.73 (s, 3H), 1.36-1.29 (m, 1H), 0.89-0.78 (m, 6H).

H-P2 ESI 628.3 (M+H)⁺. ¹H NMR (400 MHz, MeOD) δ 7.70 (s, 2H), 6.79-6.71 (m, 4H), 6.49 (t, J=55.1 Hz, 1H), 5.50-5.45 (m, 2H), 3.30-3.23 (m, 1H), 3.18-3.13 (m, 1H), 2.85-2.74 (m, 2H), 2.70 (s, 6H), 2.54-2.43 (m, 1H), 2.39-2.29 (m, 1H), 2.18 (s, 6H), 1.93-1.85 (m, 1H), 1.83 (d, J=5.9 Hz, 6H), 1.76-1.62 (m, 1H), 1.33-1.30 (m, 1H), 0.80-0.77 (m, 6H).

3-6. Preparation of (3S)-3-(4,4'-difluoro-2',5,6'-trimethyl-[1,1'-biphenyl]-3-yl)-3-(2-(3-(difluoromethyl)-5-(2-(dimethylamino)ethyl)-2-oxopyridin-1(2H)-yl)-4-methylpentanamido)propanoic Acid (Compounds I-P1 and I-P2)

Step 1: Ethyl (3S)-3-(4,4'-difluoro-2',5,6'-trimethyl-[1,1'-biphenyl]-3-yl)-3-(2-(3-(difluoromethyl)-5-(2-(dimethylamino)ethyl)-2-oxopyridin-1(2H)-yl)-4-methylpentanamido)propanoate

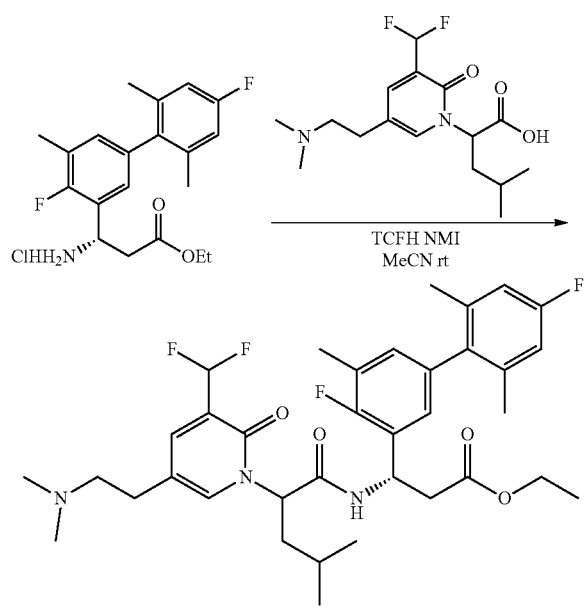

A mixture of 2-(3-(difluoromethyl)-5-(2-(dimethylamino)ethyl)-2-oxopyridin-1(2H)-yl)-4-methylpentanoic acid (120 mg, 0.39 mmol), ethyl (S)-3-amino-3-(4,4'-difluoro-2',5,6'-trimethyl-[1,1'-biphenyl]-3-yl)propanoate hydrochloride (120 mg, 0.36 mmol), TCFH (120 mg, 0.54 mmol), and NMI (75 mg, 1.08 mmol) in acetonitrile (5 mL) was stirred at room temperature for 20 hours. The reaction mixture was concentrated in vacuo and purified by reverse phase HPLC on a C18/40 g column (A: water 10 mM NH₄HCO₃, B: MeOH, 0~100%) to provide ethyl (3S)-3-(4,4'-difluoro-2',5,6'-trimethyl-[1,1'-biphenyl]-3-yl)-3-(2-(3-(difluoromethyl)-5-(2-(dimethylamino)ethyl)-2-oxopyridin-1(2H)-yl)-4-methylpentanamido)propanoate as brown solid (150 mg). Yield 63.2% (ESI 660.3 (M+H)⁺).

Step 2: (3S)-3-(4,4'-difluoro-2',5,6'-trimethyl-[1,1'-biphenyl]-3-yl)-3-(2-(3-(difluoromethyl)-5-(2-(dimethylamino)ethyl)-2-oxopyridin-1(2H)-yl)-4-methylpentanamido)propanoic Acid

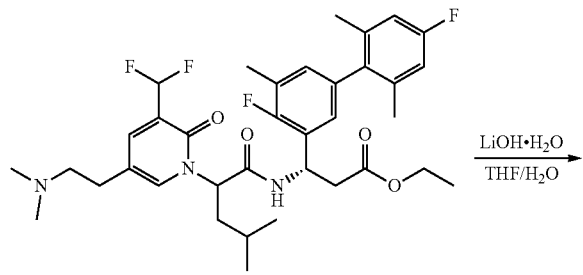

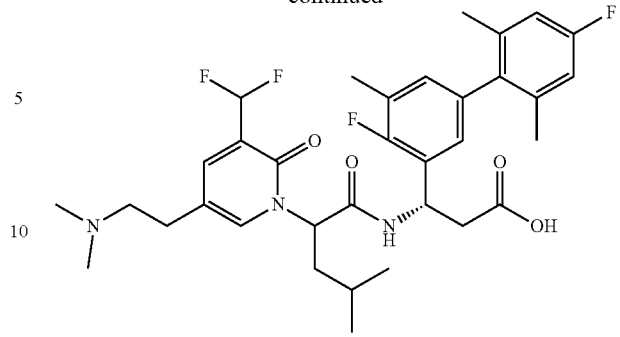

Ethyl (3S)-3-(4,4'-difluoro-2',5,6'-trimethyl-[1,1'-biphenyl]-3-yl)-3-(2-(3-(difluoromethyl)-5-(2-(dimethylamino)ethyl)-2-oxopyridin-1(2H)-yl)-4-methylpentanamido)propanoate (150 mg, 0.23 mmol) was treated with LiOH monohydrate (100 mg, 2.3 mmol) in EtOH (6 mL) and H₂O (0.8 mL) at 36° C. for 1 hour. The reaction mixture was acidified to pH 4~5 with 1N HCl. The solvent was removed in vacuo and the residue was purified by prep-HPLC A (30-60% MeCN) to provide the diastereomeric products I-P1 (20 mg) and I-P2 (22 mg) as white solids.

I-P1 ESI 632.2 (M+H)⁺. ¹H NMR (400 MHz, MeOD) δ 7.72 (s, 2H), 6.74-6.67 (m, 4H), 6.46 (t, J=55.2 Hz, 1H), 5.48-5.44 (m, 1H), 5.33-5.30 (m, 1H), 3.20-3.16 (m, 1H), 3.12-3.04 (m, 1H), 2.84-2.73 (m, 2H), 2.65 (s, 6H), 2.59-2.42 (m, 2H), 2.17 (s, 3H), 1.95-1.83 (m, 5H), 1.78 (s, 3H), 1.39-1.29 (m, 1H), 0.85-0.75 (m, 6H).

I-P2 ESI 632.2 (M+H)⁺. ¹H NMR (400 MHz, MeOD) δ 7.84 (s, 1H), 7.81 (s, 1H), 6.90-6.78 (m, 4H), 6.65 (t, J=55.2 Hz, 1H), 5.63-5.57 (m, 2H), 3.48-3.38 (m, 1H), 3.32-3.23 (m, 1H), 3.02-2.87 (m, 2H), 2.83 (s, 6H), 2.67-2.54 (m, 1H), 2.50-2.41 (m, 1H), 2.32 (d, J=1.6 Hz, 3H), 2.07-2.01 (m, 1H), 2.00 (d, J=6.2 Hz, 6H), 1.88-1.76 (m, 1H), 1.50-1.39 (m, 1H), 0.96-0.86 (m, 6H).

3-7. Preparation of (3S)-3-(2-(5-(2-(dimethylamino)ethyl)-4-methyl-2-oxopyridin-1(2H)-yl)-5-methylhexanamido)-3-(4-fluoro-2',5,6'-trimethylbiphenyl-3-yl)propanoic Acid (Compounds J-P1 and J-P2)

Step 1: (3S)-ethyl 3-(2-(5-(2-(dimethylamino)ethyl)-4-methyl-2-oxopyridin-1(2H)-yl)-5-methylhexanamido)-3-(4-fluoro-2',5,6'-trimethylbiphenyl-3-yl)propanoate

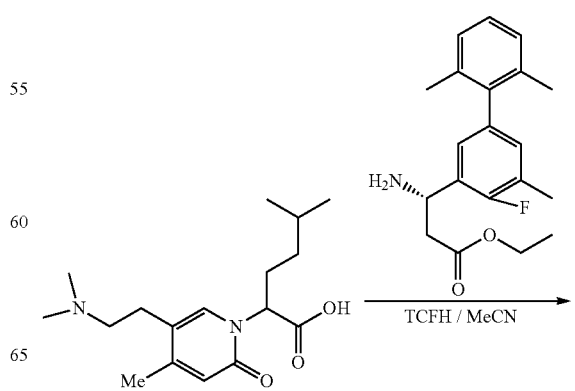

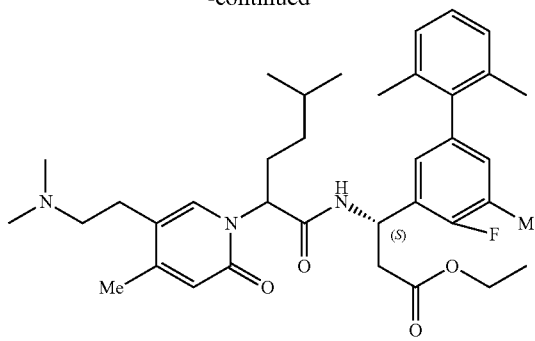

A mixture of 2-(5-(2-(dimethylamino)ethyl)-4-methyl-2-oxopyridin-1(2H)-yl)-5-methylhexanoic acid (150 mg, 0.49 mmol), (S)-ethyl 3-amino-3-(4-fluoro-2',5,6'-trimethylbiphenyl-3-yl)propanoate (161 mg, 0.49 mmol), TCFH (274 mg, 0.98 mmol), and NMI (201 mg, 2.45 mmol) in acetonitrile (5 mL) was stirred at room temperature for 2 hours. The reaction mixture was concentrated in vacuo and purified by reverse phase HPLC on a C18/40 g column (A: water 10 mM NH$_4$HCO$_3$, B: MeOH, 0~100%) to provide (3S)-ethyl 3-(2-(5-(2-(dimethylamino)ethyl)-4-methyl-2-oxopyridin-1(2H)-yl)-5-methylhexanamido)-3-(4-fluoro-2',5,6'-trimethylbiphenyl-3-yl)propanoate as colorless oil (170 mg). Yield 56% (ESI 620.2 (M+H)$^+$).

Step 2: (3S)-3-(2-(5-(2-(dimethylamino)ethyl)-4-methyl-2-oxopyridin-1(2H)-yl)-5-methylhexanamido)-3-(4-fluoro-2',5,6'-trimethylbiphenyl-3-yl)propanoic Acid

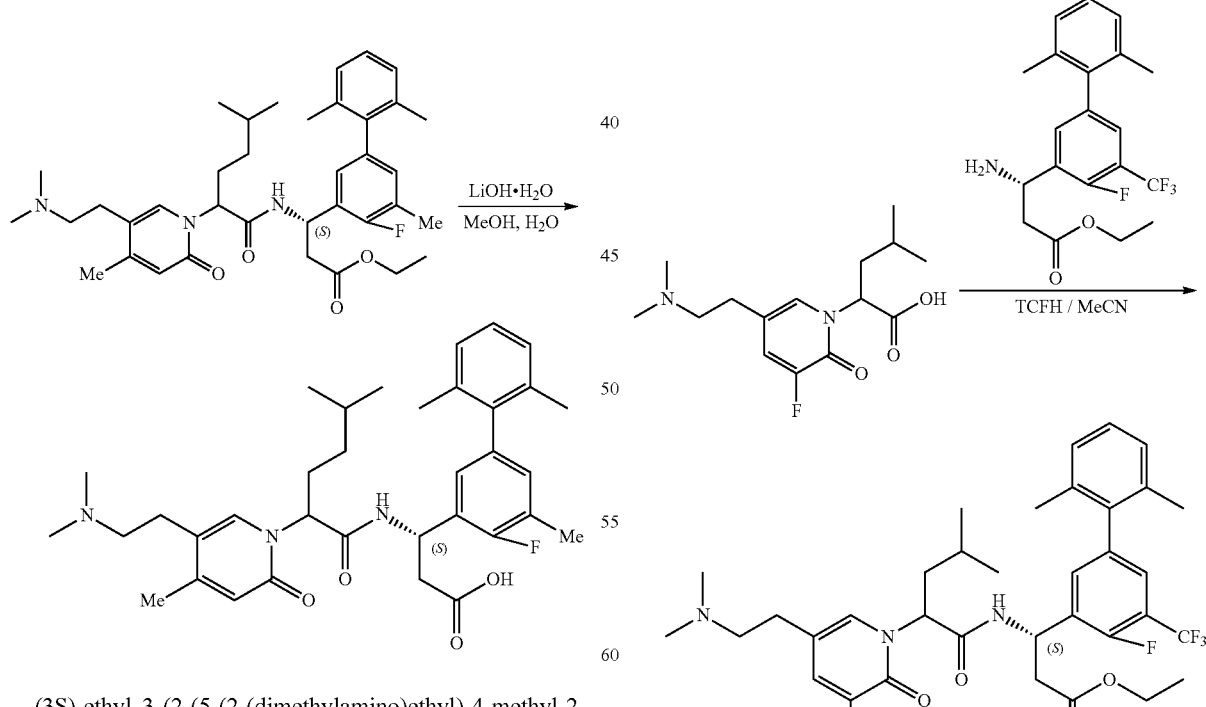

(3S)-ethyl 3-(2-(5-(2-(dimethylamino)ethyl)-4-methyl-2-oxopyridin-1(2H)-yl)-5-methylhexanamido)-3-(4-fluoro-2',5,6'-trimethylbiphenyl-3-yl)propanoate (170 mg, 0.27 mmol) was treated with LiOH monohydrate (57 mg, 1.35 mmol) in MeOH (4 mL) and H$_2$O (1 mL) at room temperature for 2 hours. The reaction mixture was acidified to pH 4-5 with 1N HCl. The reaction mixture was concentrated in vacuo and purified by prep-HPLC A (30-60% MeCN) to provide the diastereomeric products J-P1 (50 mg) and J-P2 (60.4 mg) as white solids.

J-P1 ESI 592.3 (M+H)$^+$. 1H NMR (400 MHz, MeOD) δ 7.57 (s, 1H), 7.17-7.10 (m, 1H), 7.07 (d, J=8.1 Hz, 2H), 6.87-6.82 (m, 2H), 6.33 (s, 1H), 5.49 (t, J=5.7 Hz, 1H), 5.39 (s, 1H), 3.26-3.05 (m, 2H), 2.88 (d, J=7.9 Hz, 2H), 2.82-2.69 (m, 6H), 2.69-2.58 (m, 2H), 2.26 (t, J=15.5 Hz, 6H), 2.22-2.10 (m, 1H), 1.97 (d, J=16.6 Hz, 4H), 1.91 (s, 3H), 1.60-1.53 (m, 1H), 1.29-1.14 (m, 1H), 1.09-1.04 (m, 1H), 0.89-0.87 (m, 6H).

J-P2 ESI 592.3 (M+H)+. $^1$H NMR (400 MHz, MeOD) δ 7.55 (s, 1H), 7.15-7.07 (m, 3H), 6.91 (d, J=6.9 Hz, 2H), 6.43 (s, 1H), 5.67-5.64 (m, 1H), 5.42 (t, J=7.7 Hz, 1H), 3.31-3.25 (m, 1H), 3.25-3.14 (m, 1H), 2.99-2.88 (m, 2H), 2.86 (d, J=17.8 Hz, 6H), 2.65-2.60 (m, 1H), 2.51-2.45 (m, 1H), 2.38-2.19 (m, 6H), 2.19-2.06 (m, 1H), 2.00 (s, 6H), 1.86-1.77 (m, 1H), 1.57-1.50 (m, 1H), 1.17-1.09 (m, 1H), 1.07-1.01 (m, 1H), 0.84 (t, J=6.4 Hz, 6H).

3-8. Preparation of (3S)-3-(2-(5-(2-(dimethylamino)ethyl)-3-fluoro-2-oxopyridin-1(2H)-yl)-4-methylpentanamido)-3-(4-fluoro-2',6'-dimethyl-5-(trifluoromethyl)biphenyl-3-yl)propanoic Acid (Compounds K-P1 and K-P2)

Step 1: (3S)-ethyl 3-(2-(5-(2-(dimethylamino)ethyl)-3-fluoro-2-oxopyridin-1(2H)-yl)-4-methylpentanamido)-3-(4-fluoro-2',6'-dimethyl-5-(trifluoromethyl)biphenyl-3-yl)propanoate

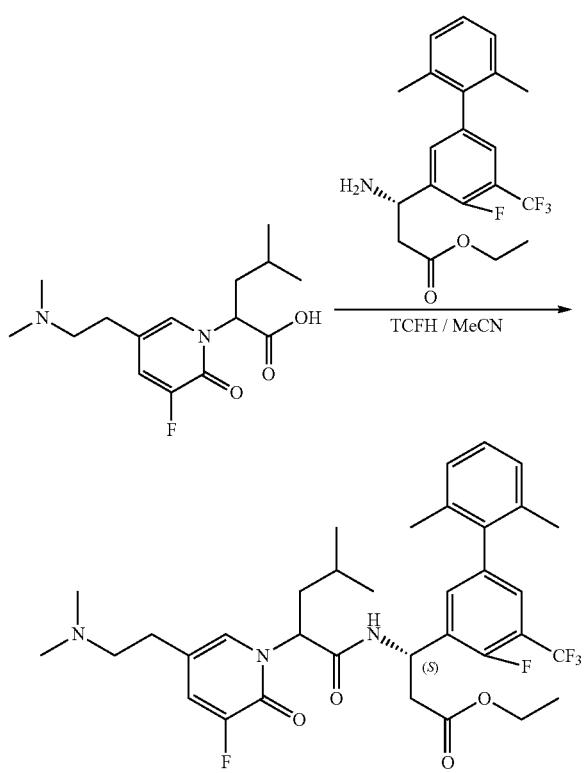

A mixture of 2-(5-(2-(dimethylamino)ethyl)-3-fluoro-2-oxopyridin-1(2H)-yl)-4-methylpentanoic acid (130 mg, 0.44 mmol), (S)-ethyl 3-amino-3-(4-fluoro-2',6'-dimethyl-5-(trifluoromethyl)biphenyl-3-yl)propanoate (169 mg, 0.44 mmol), TCFH (246 mg, 0.88 mmol), and NMI (144 mg, 1.76 mmol) in acetonitrile (4 mL) was stirred at room temperature for 2 hours. The reaction mixture was concentrated in vacuo and purified by reverse phase HPLC on a C18/40 g column (A: water 10 mM $NH_4HCO_3$, B: MeOH, 0~100%) to provide (3S)-ethyl 3-(2-(5-(2-(dimethylamino)ethyl)-3-fluoro-2-oxopyridin-1(2H)-yl)-4-methylpentanamido)-3-(4-fluoro-2',6'-dimethyl-5-(trifluoromethyl)biphenyl-3-yl)propanoate as yellow oil (150 mg). Yield 51% (ESI 664.2 $(M+H)^+$).

Step 2: (3S)-3-(2-(5-(2-(dimethylamino)ethyl)-3-fluoro-2-oxopyridin-1(2H)-yl)-4-methylpentanamido)-3-(4-fluoro-2',6'-dimethyl-5-(trifluoromethyl)biphenyl-3-yl)propanoic acid

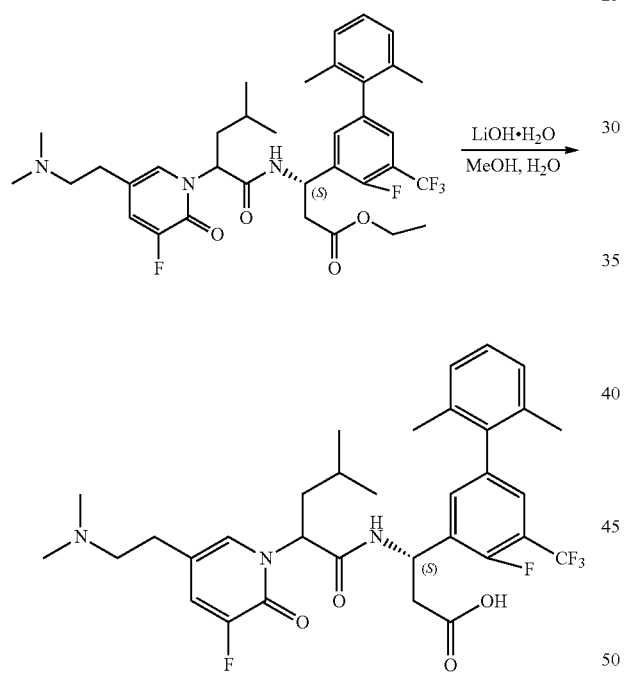

(3S)-ethyl 3-(2-(5-(2-(dimethylamino)ethyl)-3-fluoro-2-oxopyridin-1(2H)-yl)-4-methylpentanamido)-3-(4-fluoro-2',6'-dimethyl-5-(trifluoromethyl)biphenyl-3-yl)propanoate (150 mg, 0.23 mmol) was treated with LiOH monohydrate (39 mg, 0.92 mmol) in MeOH (4 mL) and $H_2O$ (1 mL) at 36° C. for 2 hours. The reaction mixture was acidified to pH 4-5 with 1N HCl. The reaction mixture was concentrated in vacuo and purified by prep-HPLC A (30-60% MeCN) to give the diastereomeric products K-P1 (41 mg) and K-P2 (46.8 mg) as white solids.

K-P1 ESI 636.2 $(M+H)^+$. $^1$H NMR (400 MHz, MeOD) δ 7.53 (s, 1H), 7.47-7.44 (m, 1H), 7.33-7.28 (m, 2H), 7.23-7.17 (m, 1H), 7.16-7.08 (m, 2H), 5.65-5.61 (m, 1H), 5.46 (t, J=5.7 Hz, 1H), 3.38 (d, J=7.8 Hz, 1H), 3.24-3.17 (m, 1H), 2.95-2.84 (m, 2H), 2.82-2.64 (m, 7H), 2.60-2.54 (m, 1H), 2.08-1.97 (m, 5H), 1.94 (s, 3H), 1.43 (s, 1H), 0.96-0.91 (m, 6H).

K-P2 ESI 636.2 $(M+H)^+$. $^1$H NMR (400 MHz, MeOD) δ 7.38 (s, 1H), 7.33-7.28 (m, 2H), 7.24 (d, J=6.3 Hz, 1H), 7.12-6.99 (m, 3H), 5.55-5.49 (m, 2H), 3.36-3.25 (m, 1H), 3.18-3.12 (m, 1H), 2.91-2.79 (m, 1H), 2.73 (d, J=11.7 Hz, 7H), 2.52-2.48 (m, 1H), 2.39-2.32 (m, 1H), 2.00-1.79 (m, 7H), 1.75-1.68 (m, 1H), 1.29-1.24 (m, 1H), 0.81-0.78 (m, 6H).

3-9. Preparation of (3S)-3-(4,5-difluoro-2',6'-dimethyl-[1,1'-biphenyl]-3-yl)-3-(2-(5-(2-(dimethylamino)ethyl)-2-oxo-4-(trifluoromethyl)pyridin-1(2H)-yl)-4-methylpentanamido)propanoic Acid (Compounds L-P1 and L-P2)

Step 1: Ethyl (3S)-3-(4,5-difluoro-2',6'-dimethyl-[1,1'-biphenyl]-3-yl)-3-(2-(5-(2-(dimethylamino)ethyl)-2-oxo-4-(trifluoromethyl)pyridin-1(2H)-yl)-4-methylpentanamido)propanoate

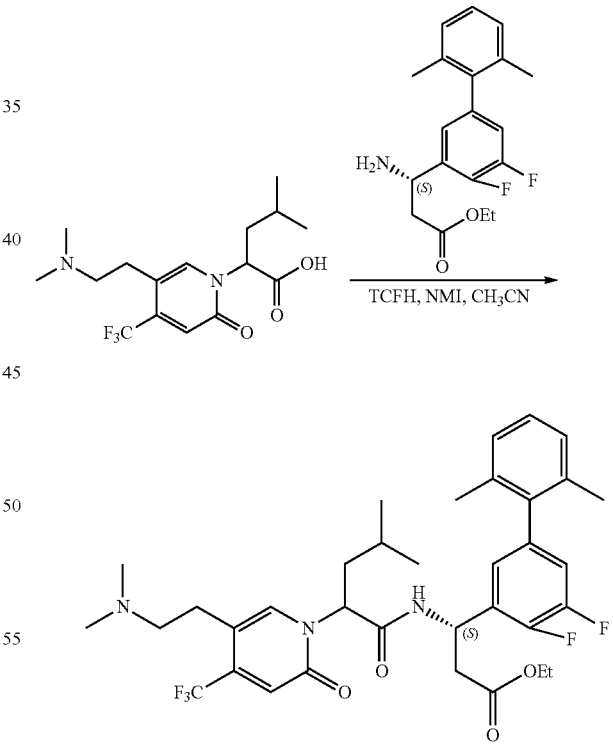

A mixture of 2-(5-(2-(dimethylamino)ethyl)-2-oxo-4-(trifluoromethyl)pyridin-1(2H)-yl)-4-methylpentanoic acid (100 mg, 0.29 mmol), ethyl (S)-3-amino-3-(4,5-difluoro-2',6'-dimethyl-[1,1'-biphenyl]-3-yl)propanoate (96 mg, 0.29 mmol), TCFH (100 mg, 0.34 mmol) and NMI (96.0 mg, 1.14 mmol) in $CH_3CN$ (3 mL) was stirred at room temperature for 1.5 hours. The reaction mixture was concentrated in vacuo and purified by reverse phase HPLC on a C18/40 g column (A: water 10 mM NH₄HCO₃, B: MeOH, 0~100%) to provide ethyl (3S)-3-(4,5-difluoro-2',6'-dimethyl-[1,1'-biphenyl]-3-yl)-3-(2-(5-(2-(dimethylamino)ethyl)-2-oxo-4-(trifluoromethyl)pyridin-1(2H)-yl)-4-methylpentanamido)propanoate as a yellow solid (131 mg). Yield 68.1% (ESI 664.2 [M+H]⁺).

Step 2: (3S)-3-(4,5-difluoro-2',6'-dimethyl-[1,1'-biphenyl]-3-yl)-3-(2-(5-(2-(dimethylamino)ethyl)-2-oxo-4-(trifluoromethyl)pyridin-1(2H)-yl)-4-methylpentanamido)propanoic Acid

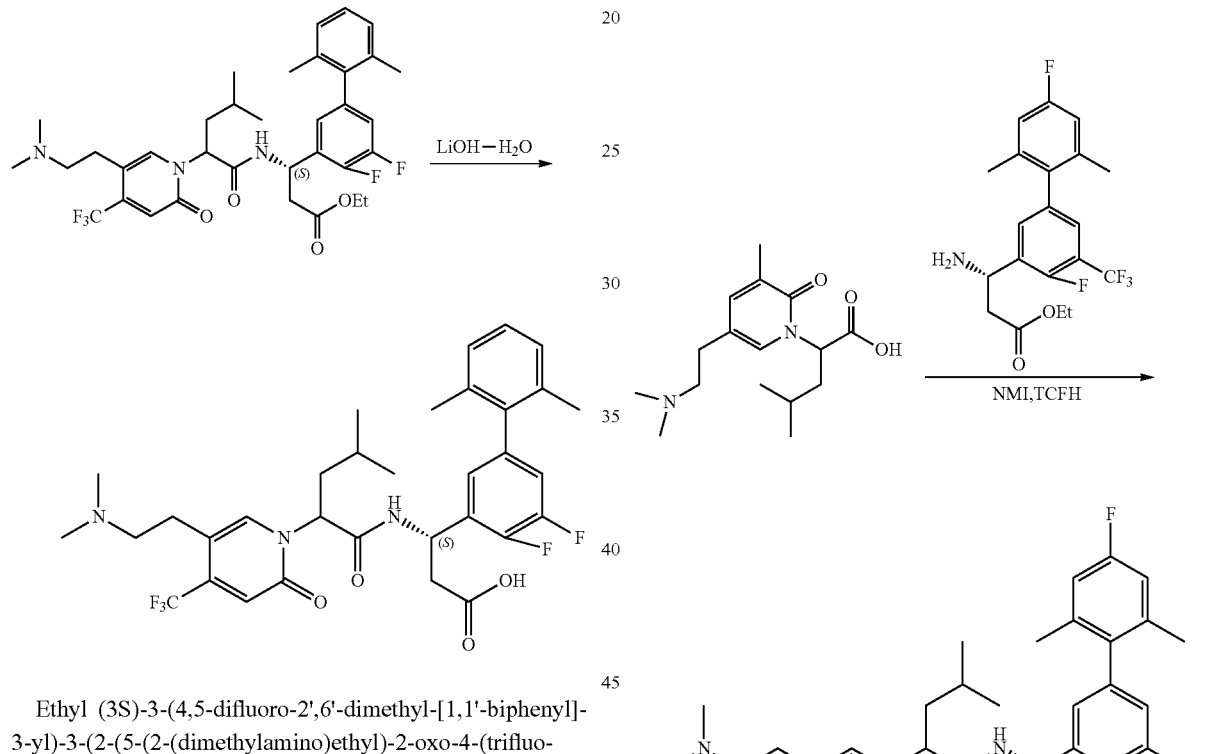

Ethyl (3S)-3-(4,5-difluoro-2',6'-dimethyl-[1,1'-biphenyl]-3-yl)-3-(2-(5-(2-(dimethylamino)ethyl)-2-oxo-4-(trifluoromethyl)pyridin-1(2H)-yl)-4-methylpentanamido)propanoate (131.0 mg, 0.19 mmol) was treated with LiOH—H₂O (100.0 mg, 2.38 mmol) in THF (2 mL) and water (0.5 mL) at 30° C. for 1 hour. The reaction mixture was acidified to pH 4~5 with 2N HCL. The solvent was removed in vacuo and the residue was purified by prep-HPLC A (30-60% MeCN) to give the diastereomeric product L-P1 (11.1 mg) and L-P2 (19.0 mg) as white solids.

L-P1 ESI 636.1 (M+H)⁺ ¹H NMR (400 MHz, MeOD) δ 7.77 (s, 1H), 7.05-6.92 (m, 3H), 6.83-6.76 (m, 2H), 6.63 (s, 1H), 5.58-5.45 (m, 2H), 3.03-2.96 (m, 2H), 2.84-2.81 (m, 2H), 2.65 (s, 6H), 2.62-2.60 (m, 2H), 1.92-1.79 (m, 5H), 1.72 (s, 3H), 1.33-1.30 (m, 1H), 0.86-0.81 (m, 6H).

L-P2 ESI 636.1 (M+H)⁺. ¹H NMR (400 MHz, MeOD) δ 7.72 (s, 1H), 7.07-6.97 (m, 3H), 6.90-6.80 (m, 3H), 6.77 (s, 1H), 5.63-5.59 (m, 1H), 5.49 (t, J=7.6 Hz, 1H), 3.22-3.08 (m, 2H), 2.88 (t, J=6.9 Hz, 2H), 2.72 (s, 6H), 2.58-2.38 (m, 2H), 1.92-1.83 (m, 7H), 1.64-1.56 (m, 1H), 1.33-1.24 (m, 1H), 0.77 (d, J=6.5 Hz, 6H).

3-10. Preparation of (3S)-3-(4,4'-difluoro-2',6'-dimethyl-5-(trifluoromethyl)-[1,1'-biphenyl]-3-yl)-3-(2-(5-(2-(dimethylamino)ethyl)-3-methyl-2-oxopyridin-1(2H)-yl)-4-methylpentanamido)propanoic Acid (Compounds M-P1 and M-P2)

Step 1: Ethyl (3S)-3-(4,4'-difluoro-2',6'-dimethyl-5-(trifluoromethyl)-[1,1'-biphenyl]-3-yl)-3-(2-(5-(2-(dimethylamino)ethyl)-3-methyl-2-oxopyridin-1(2H)-yl)-4-methylpentanamido)propanoate

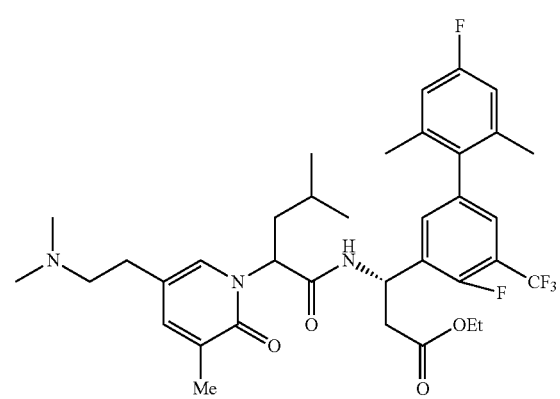

A mixture of 2-(5-(2-(dimethylamino)ethyl)-3-methyl-2-oxopyridin-1(2H)-yl)-4-methylpentanoic acid (160 mg, 0.54 mmol), ethyl (S)-3-amino-3-(4,4'-difluoro-2',6'-dimethyl-5-(trifluoromethyl)-[1,1'-biphenyl]-3-yl)propanoate (260 mg, 0.64 mmol), TCFH (226 mg, 0.81 mmol), NMI (221.4 mg, 2.7 mmol) and CH₃CN (5 mL) was stirred at room temperature for 1 hour. The reaction mixture was concentrated in vacuo and purified by reverse phase HPLC on a C18/40 g column (A: water 10 mM NH₄HCO₃, B: MeOH, 0~100%) to provide ethyl (3S)-3-(4,4'-difluoro-2',6'-dimethyl-5-(trifluoromethyl)-[1,1'-biphenyl]-3-yl)-3-(2-(5-(2-(dimethylamino)ethyl)-3-methyl-2-oxopyridin-1(2H)-yl)-4-methyl-pentanamido)propanoate as a colorless oil (180 mg). Yield 50% (ESI 678.3 (M+H)+).

Step 2: (3S)-3-(4,4'-difluoro-2',6'-dimethyl-5-(trifluoromethyl)-[1,1'-biphenyl]-3-yl)-3-(2-(5-(2-(dimethylamino)ethyl)-3-methyl-2-oxopyridin-1(2H)-yl)-4-methylpentanamido)propanoic Acid

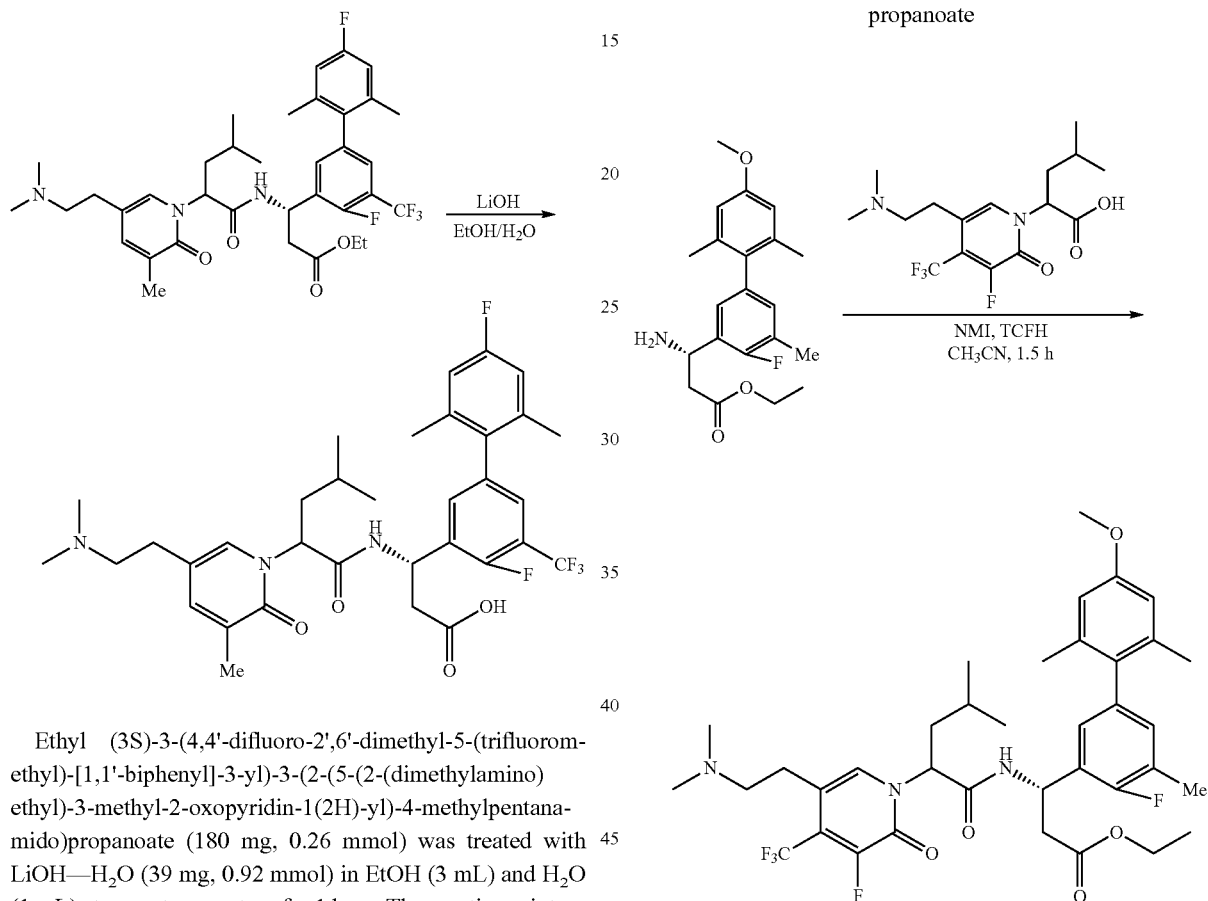

Ethyl (3S)-3-(4,4'-difluoro-2',6'-dimethyl-5-(trifluoromethyl)-[1,1'-biphenyl]-3-yl)-3-(2-(5-(2-(dimethylamino)ethyl)-3-methyl-2-oxopyridin-1(2H)-yl)-4-methylpentanamido)propanoate (180 mg, 0.26 mmol) was treated with LiOH—H$_2$O (39 mg, 0.92 mmol) in EtOH (3 mL) and H$_2$O (1 mL) at room temperature for 1 hour. The reaction mixture was acidified to pH 4~5 with 1N HCl. The solvent was removed in vacuo and the residue was purified by prep-HPLC A (30-60% MeCN) to give the diastereomeric products M-P1 (50 mg) and M-P2 (53.0 mg) as white solids.

M-P1 ESI 650.3 (M+H)+. $^1$H NMR (400 MHz, MeOD) δ 7.52 (s, 1H), 7.39 (s, 1H), 7.33-7.18 (m, 2H), 6.88 (d, J=9.6 Hz, 2H), 5.56-5.47 (m, 2H), 3.28-3.17 (m, 2H), 2.84-2.69 (m, 9H), 2.63-2.57 (m, 1H), 2.06-1.92 (m, 8H), 1.86 (s, 3H), 1.48-1.38 (m, 1H), 0.95-0.90 (m, 6H).

M-P2 ESI 650.3 (M+H)+. $^1$H NMR (400 MHz, MeOD) δ 7.56 (s, 1H), 7.43 (s, 1H), 7.38-7.22 (m, 2H), 6.92-6.87 (m, 2H), 5.65-5.54 (m, 2H), 3.46-3.39 (m, 1H), 3.29-3.24 (m, 1H), 2.97-2.75 (m, 8H), 2.67-2.61 (m, 1H), 2.51-2.45 (m, 1H), 2.05-1.90 (m, 1H), 1.45-1.38 (m, 1H), 0.94-0.88 (m, 6H).

3-11. Preparation of (3S)-3-(2-(5-(2-(dimethylamino)ethyl)-3-fluoro-2-oxo-4-(trifluoromethyl)pyridin-1(2H)-yl)-4-methylpentanamido)-3-(4-fluoro-4'-methoxy-2',5,6'-trimethyl-[1,1'-biphenyl]-3-yl)propanoic Acid (Compounds P-P1 and P-P2)

Step 1: Ethyl (3S)-3-(2-(5-(2-(dimethylamino)ethyl)-3-fluoro-2-oxo-4-(trifluoromethyl)pyridin-1(2H)-yl)-4-methylpentanamido)-3-(4-fluoro-4'-methoxy-2',5,6'-trimethyl-[1,1'-biphenyl]-3-yl)propanoate

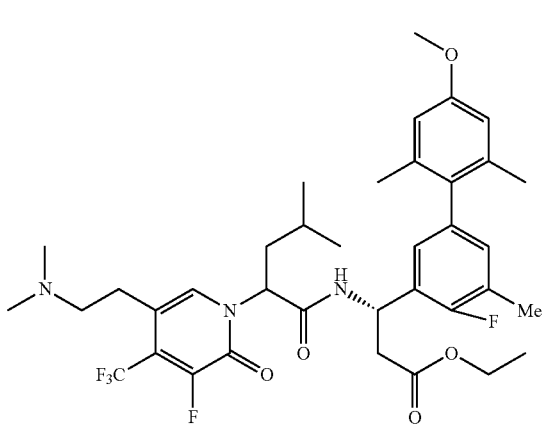

A mixture of ethyl (S)-3-amino-3-(4-fluoro-4'-methoxy-2',5,6'-trimethyl-[1,1'-biphenyl]-3-yl)propanoate (220 mg, 0.60 mmol), 2-(5-(2-(dimethylamino)ethyl)-3-fluoro-2-oxo-4-(trifluoromethyl)pyridin-1(2H)-yl)-4-methylpentanoic acid (100 mg, 0.55 mmol), TCFH (230 mg, 0.82 mmol), and NMI (177 mg, 2.18 mmol) in acetonitrile (10 mL) was stirred at room temperature for 20 hours. The reaction mixture was concentrated in vacuo and purified by reverse phase HPLC on a C18/40 g column (A: water 10 mM NH$_4$HCO$_3$, B: MeOH, 0~100%) to provide ethyl (3S)-3-(2-(5-(2-(dimethylamino)ethyl)-3-fluoro-2-oxo-4-(trifluoromethyl)pyridin-1(2H)-yl)-4-methylpentanamido)-3-(4-fluoro-4'-methoxy-2',5,6'-trimethyl-[1,1'-biphenyl]-3-yl)propanoate (214 mg) as a white solid. Yield 56% (ESI 708.3 (M+H)+).

Step 2: (3S)-3-(2-(5-(2-(dimethylamino)ethyl)-3-fluoro-2-oxo-4-(trifluoromethyl)pyridin-1(2H)-yl)-4-methylpentanamido)-3-(4-fluoro-4'-methoxy-2',5,6'-trimethyl-[1,1'-biphenyl]-3-yl)propanoic Acid

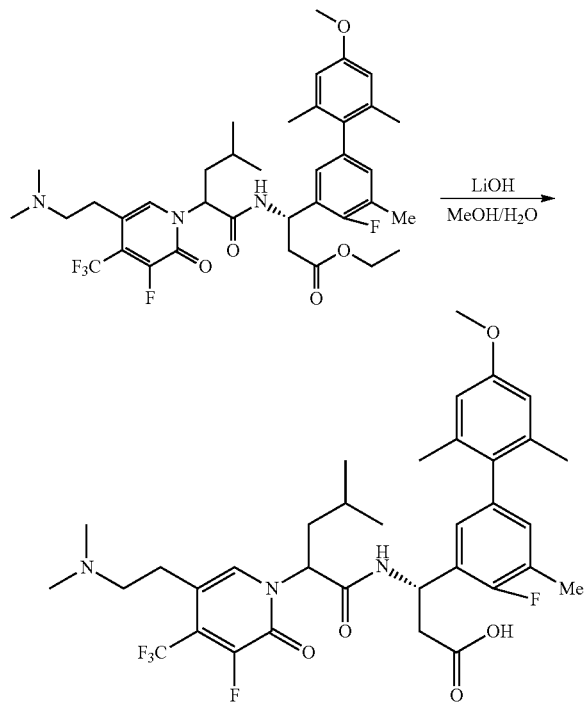

Ethyl (3S)-3-(2-(5-(2-(dimethylamino)ethyl)-3-fluoro-2-oxo-4-(trifluoromethyl)pyridin-1(2H)-yl)-4-methylpentanamido)-3-(4-fluoro-4'-methoxy-2',5,6'-trimethyl-[1,1'-biphenyl]-3-yl)propanoate (214 mg, 0.30 mmol) was treated with LiOH—H$_2$O (52 mg, 1.24 mmol) in MeOH (3 mL) and H$_2$O (1 mL) at room temperature for 2 hours. The reaction mixture was acidified to pH 4-5 with 1N HCl. The solvent was removed in vacuo and the residue was purified by prep-HPLC A (30-60% CH$_3$CN) to give the diastereomeric products P-P1 (39.8 mg) and P-P2 (48.6 mg) as white solids.

P-P1 ESI 680.4 (M+H)$^+$. $^1$H NMR (500 MHz, MeOD) δ 7.69 (s, 1H), 6.88-6.85 (m, 2H), 6.64 (d, J=10.6 Hz, 2H), 5.73-5.65 (m, 1H), 5.55 (t, J=6.8 Hz, 1H), 4.92 (s, 3H), 3.79 (s, 3H), 3.17-2.92 (m, 4H), 2.82-2.69 (m, 7H), 2.29 (s, 3H), 2.10-1.94 (m, 5H), 1.83 (s, 1H), 1.51-1.41 (m, 1H), 0.97-0.93 (m, 6H).

P-P2 ESI 680.3 (M+H)$^+$. $^1$H NMR (500 MHz, MeOD) δ 7.60 (s, 1H), 6.91 (t, J=7.1 Hz, 2H), 6.67 (s, 2H), 5.73-5.70 (m, 1H), 5.61 (t, J=7.5 Hz, 1H), 3.80 (s, 3H), 3.23-3.18 (m, 2H), 3.18-2.95 (m, 2H), 2.83 (s, 6H), 2.65-2.61 (m, 1H), 2.52-2.47 (m, 1H), 2.32 (s, 3H), 2.11-1.95 (m, 7H), 1.72-1.66 (m, 1H), 1.45-1.41 (m, 1H), 0.94-0.85 (m, 6H).

3-12. Preparation of (3S)-3-(2-(5-(2-(azetidin-1-yl)ethyl)-2-oxo-4-(trifluoromethyl)pyridin-1(2H)-yl)-4-methylpentanamido)-3-(4,4'-difluoro-2',6'-dimethyl-5-(trifluoromethyl)-[1,1'-biphenyl]-3-yl)propanoic Acid (Compounds R-P1 and R-P2)

Step 1: Ethyl (3S)-3-(2-(5-(2-(azetidin-1-yl)ethyl)-2-oxo-4-(trifluoromethyl)pyridin-1(2H)-yl)-4-methylpentanamido)-3-(4,4'-difluoro-2',6'-dimethyl-5-(trifluoromethyl)-[1,1'-biphenyl]-3-yl)propanoate

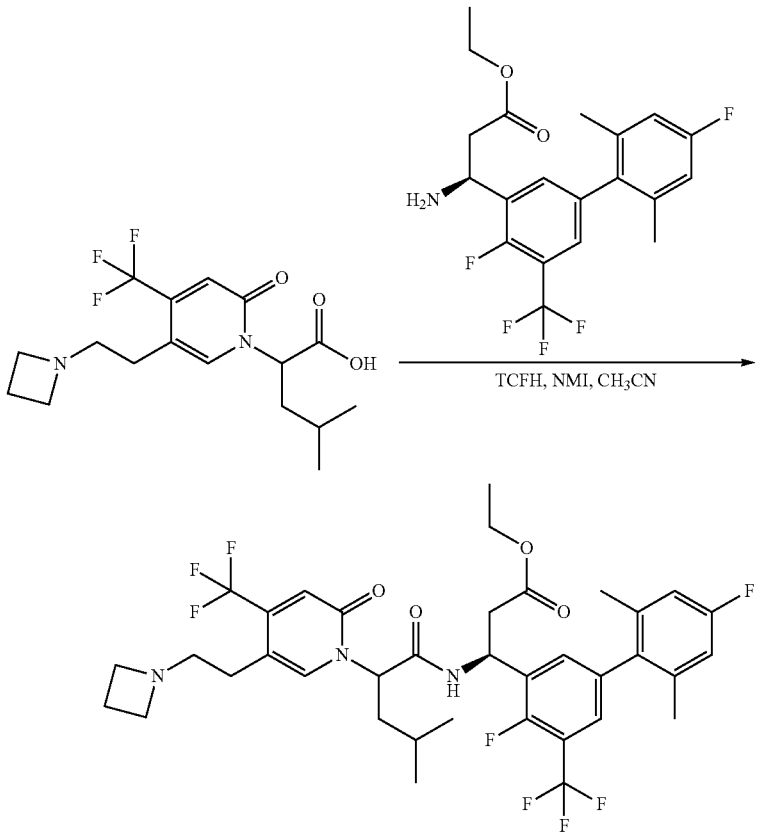

A mixture of 2-(5-(2-(azetidin-1-yl)ethyl)-2-oxo-4-(trifluoromethyl)pyridin-1(2H)-yl)-4-methylpentanoic acid (100 mg, 0.28 mmol), ethyl (S)-3-amino-3-(4,4'-difluoro-2',6'-dimethyl-5-(trifluoromethyl)-[1,1'-biphenyl]-3-yl)propanoate (112 mg, 0.28 mmol), NMI (69 mg, 0.84 mmol) and TCFH (95 mg, 0.34 mmol) in $CH_3CN$ (5 mL) was stirred at room temperature for 2 hours. The solvent was removed in vacuo and the residue was purified by silica gel column (MeOH/DCM 7%) to provide ethyl (3S)-3-(2-(5-(2-(azetidin-1-yl)ethyl)-2-oxo-4-(trifluoromethyl)pyridin-1(2H)-yl)-4-methylpentanamido)-3-(4,4'-difluoro-2',6'-dimethyl-5-(trifluoromethyl)-[1,1'-biphenyl]-3-yl)propanoate as a yellow oil (180 mg). Yield 87% (ESI 744.1 $[M+H]^+$).

Step 2: (3S)-3-(2-(5-(2-(azetidin-1-yl)ethyl)-2-oxo-4-(trifluoromethyl)pyridin-1(2H)-yl)-4-methylpentanamido)-3-(4,4'-difluoro-2',6'-dimethyl-5-(trifluoromethyl)-[1,1'-biphenyl]-3-yl)propanoic Acid

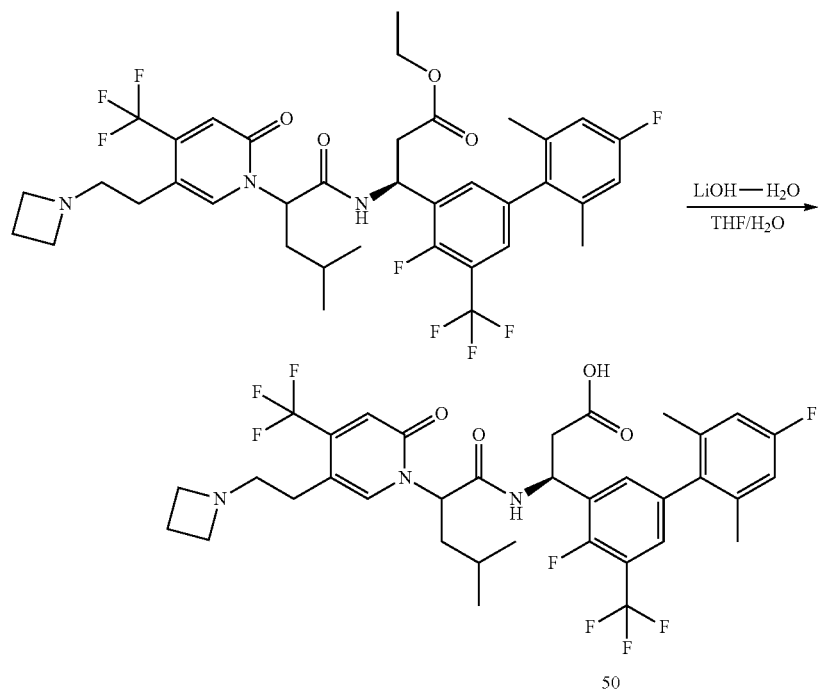

Ethyl (3S)-3-(2-(5-(2-(azetidin-1-yl)ethyl)-2-oxo-4-(trifluoromethyl)pyridin-1(2H)-yl)-4-methylpentanamido)-3-(4,4'-difluoro-2',6'-dimethyl-5-(trifluoromethyl)-[1,1'-biphenyl]-3-yl)propanoate (180 mg, 0.24 mmol) was treated with $LiOH$—$H_2O$ (50 mg, 1.20 mmol) in THF (3 mL), MeOH (2 mL) and $H_2O$ (1 mL) at room temperature for 16 hours. The reaction mixture was acidified to pH 4-5 with 1N HCl. The solvent was removed in vacuo and the residue was purified by prep-HPLC A (30-60% MeCN) to give the diastereomeric products R-P1 (65.0 mg) and R-P2 (35.0 mg) as white solids.

R-P1 ESI 716.2 $(M+H)^+$ $^1H$ NMR (400 MHz, MeOD) δ 7.85 (s, 1H), 7.40-7.32 (m, 2H), 6.90-6.86 (m, 2H), 6.75 (s, 1H), 5.64-5.60 (m, 2H), 4.07 (t, J=8.1 Hz, 4H), 3.36-3.33 (m, 1H), 3.31-3.27 (m, 1H), 2.91-2.69 (m, 4H), 2.49-2.44 (m, 2H), 2.06-1.97 (m, 5H), 1.89 (s, 3H), 1.48-1.36 (m, 1H), 0.99-0.91 (m, 6H).

R-P2 ESI 716.2 $(M+H)^+$ $^1H$ NMR (400 MHz, MeOD) δ 7.75 (s, 1H), 7.45-7.38 (m, 2H), 6.92 (s, 1H), 6.90 (s, 2H), 5.82-5.78 (m, 1H), 5.63 (t, J=7.7 Hz, 1H), 4.15 (t, J=7.9 Hz, 4H), 3.45-3.35 (m, 2H), 2.99-2.80 (m, 2H), 2.69-2.42 (m, 4H), 2.03-1.92 (m, 7H), 1.76-1.63 (m, 1H), 1.44-1.37 (m, 1H), 0.92-0.89 (m, 6H).

3-13. Preparation of (S)-3-(4,5-difluoro-2',6'-dimethyl-[1,1'-biphenyl]-3-yl)-3-((S)-2-(5-(2-(dimethylamino)ethyl)-4-methyl-2-oxopyridin-1(2H)-yl)-4-methylpentanamido)propanoic Acid (Compounds S-P1 and S-P2)

Step 1: Ethyl (S)-3-(4,5-difluoro-2',6'-dimethyl-[1,1'-biphenyl]-3-yl)-3-((S)-2-(5-(2-(dimethylamino)ethyl)-4-methyl-2-oxopyridin-1(2H)-yl)-4-methylpentanamido)propanoate

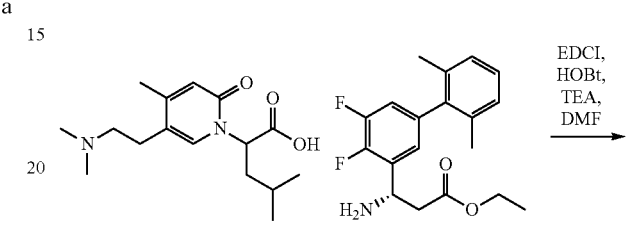

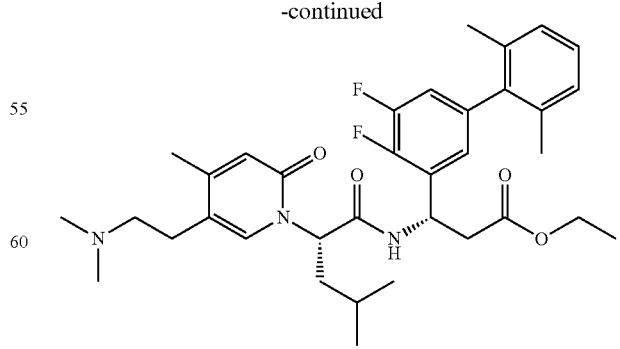

A mixture of 2-(5-(2-(dimethylamino)ethyl)-4-methyl-2-oxopyridin-1(2H)-yl)-4-methylpentanoic acid (80 mg, 0.27 mmol), ethyl (S)-3-amino-3-(4,5-difluoro-2',6'-dimethyl-[1,1'-biphenyl]-3-yl)propanoate (100 mg, 0.30 mmol), EDCI (77 mg, 0.41 mmol), TEA (0.2 mL) and HOBt (36 mg, 0.27 mmol) in acetonitrile (10 mL) was stirred at room temperature for 20 hours. The reaction mixture was concentrated in vacuo and purified by reverse phase HPLC on a C18/40 g column (A: water 10 mM NH₄HCO₃, B: MeOH, 0~100%) to provide ethyl (S)-3-(4,5-difluoro-2',6'-dimethyl-[1,1'-biphenyl]-3-yl)-3-((S)-2-(5-(2-(dimethylamino)ethyl)-4-methyl-2-oxopyridin-1(2H)-yl)-4-methylpentanamido)propanoate as yellow oil (75 mg). Yield 45% (ESI 610.3 (M+H)⁺).

Step 2: (S)-3-(4,5-difluoro-2',6'-dimethyl-[1,1'-biphenyl]-3-yl)-3-((S)-2-(5-(2-(dimethylamino)ethyl)-4-methyl-2-oxopyridin-1(2H)-yl)-4-methylpentanamido)propanoic acid

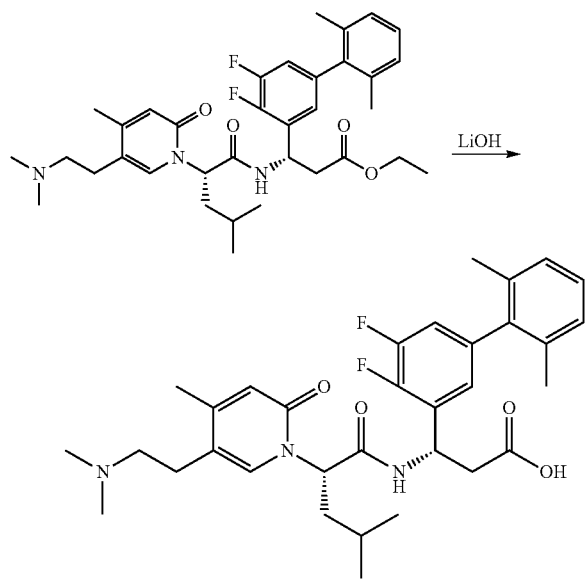

Ethyl (S)-3-(4,5-difluoro-2',6'-dimethyl-[1,1'-biphenyl]-3-yl)-3-((S)-2-(5-(2-(dimethylamino)ethyl)-4-methyl-2-oxopyridin-1(2H)-yl)-4-methylpentanamido)propanoate (75 mg, 0.12 mmol) was treated with LiOH monohydrate (26 mg, 0.62 mmol) in MeOH (2 mL) and H₂O (1 mL) at room temperature for 2 h. The reaction mixture was acidified to pH 4~5 with 1N HCL. The mixture was concentrated in vacuo and the residue was purified by prep-HPLC A (30-60% MeCN) to give the diastereomeric products S-P1 (28 mg) and S-P2 (38 mg) as white solids.

S-P1 ESI 582.2 (M+H)⁺. ¹H NMR (500 MHz, MeOD) δ 7.58 (s, 1H), 7.19-7.14 (m, 1H), 7.10 (d, J=8.6 Hz, 2H), 6.96-6.90 (m, 1H), 6.83 (d, J=5.8 Hz, 1H), 6.33 (s, 1H), 5.57 (s, 1H), 5.52-5.47 (m, 1H), 3.33-3.13 (m, 2H), 2.88 (t, J=7.3 Hz, 2H), 2.79 (s, 6H), 2.72-2.60 (m, 2H), 2.26 (s, 3H), 2.03-1.90 (m, 8H), 1.40 (d, J=7.3 Hz, 1H), 0.95-0.91 (m, 6H).

S-P2 ESI 582.2 (M+H)⁺. ¹H NMR (500 MHz, MeOD) δ 7.54 (s, 1H), 7.19-7.15 (m, 1H), 7.11 (d, J=7.8 Hz, 2H), 7.01-6.95 (m, 1H), 6.90 (d, J=5.9 Hz, 1H), 6.42 (s, 1H), 5.67-5.64 (m, 1H), 5.61-5.55 (m, 1H), 3.24-3.18 (m, 1H), 2.97-2.84 (m, 8H), 2.63 (dd, J=15.2, 4.2 Hz, 1H), 2.49 (dd, J=15.2, 9.9 Hz, 1H), 2.27 (s, 3H), 2.02 (s, 6H), 1.99-1.93 (m, 1H), 1.81-1.73 (m, 1H), 1.41-1.37 (m, 1H), 0.90-0.88 (m, 6H).

3-14. Preparation of (3S)-3-(2-(5-(2-(dimethylamino)ethyl)-4-methyl-2-oxopyridin-1(2H)-yl)-4-methylpentanamido)-3-(4-fluoro-2',4',5',6'-tetramethyl-[1,1'-biphenyl]-3-yl)propanoic Acid (Compounds T-P1 and T-P2)

Step 1: Ethyl (3S)-3-(2-(5-(2-(dimethylamino)ethyl)-4-methyl-2-oxopyridin-1(2H)-yl)-4-methylpentanamido)-3-(4-fluoro-2',4',5',6'-tetramethyl-[1,1'-biphenyl]-3-yl)propanoate

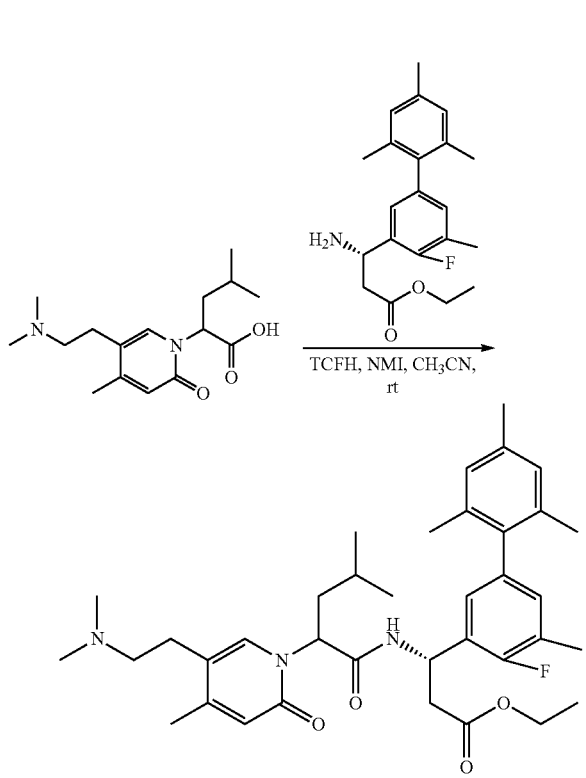

A mixture of 2-(5-(2-(dimethylamino)ethyl)-4-methyl-2-oxopyridin-1(2H)-yl)-4-methylpentanoic acid (100.0 mg, 0.34 mmol), ethyl (S)-3-amino-3-(4-fluoro-2',4',5',6'-tetramethyl-[1,1'-biphenyl]-3-yl)propanoate (117.0 mg, 0.34 mmol), TCFH (190.4 mg, 0.68 mmol), NMI (115.5 mg, 1.36 mmol) in CH₃CN (5 mL) was stirred at room temperature for 2 hours. The reaction mixture was concentrated in vacuo and purified by reverse phase HPLC on a C18/40 g column (A: water 10 mM NH₄HCO₃, B: MeOH, 0~100%) to provide ethyl (3S)-3-(2-(5-(2-(dimethylamino)ethyl)-4-methyl-2-oxopyridin-1(2H)-yl)-4-methylpentanamido)-3-(4-fluoro-2',4',5',6'-tetramethyl-[1,1'-biphenyl]-3-yl)propanoate as a white oil (95.0 mg). Yield 45% (ESI 620.3 (M+H)⁺).

Step 2: (3S)-3-(2-(5-(2-(dimethylamino)ethyl)-4-methyl-2-oxopyridin-1(2H)-yl)-4-methylpentanamido)-3-(4-fluoro-2',4',5,6'-tetramethyl-[1,1'-biphenyl]-3-yl)propanoic Acid 3-15. Preparation of (3S)-3-(4-fluoro-3'-methoxy-2',5,6'-trimethyl-[1,1'-biphenyl]-3-yl)-3-(2-(5-(2-(3-methoxyazetidin-1-yl)ethyl)-2-oxo-4-(trifluoromethyl)pyridin-1(2H)-yl)-4-methylpentanamido) propanoic Acid (Compounds N-P1 and N-P2)

Step 1: Ethyl (3S)-3-(4-fluoro-3'-methoxy-2',5,6'-trimethyl-[1,1'-biphenyl]-3-yl)-3-(2-(5-(2-(3-methoxyazetidin-1-yl)ethyl)-2-oxo-4-(trifluoromethyl)pyridin-1(2H)-yl)-4-methylpentanamido) propanoate

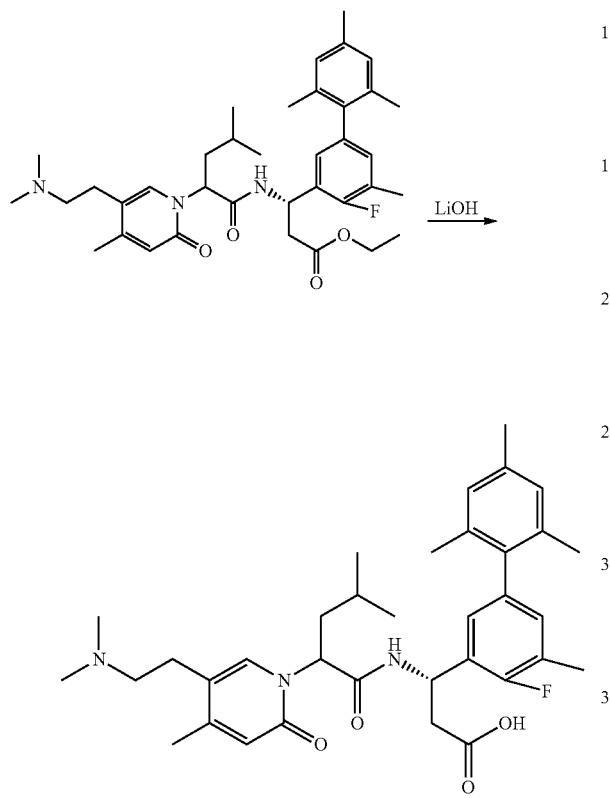

Ethyl (3S)-3-(2-(5-(2-(dimethylamino)ethyl)-4-methyl-2-oxopyridin-1(2H)-yl)-4-methylpentanamido)-3-(4-fluoro-2',4',5,6'-tetramethyl-[1,1'-biphenyl]-3-yl)propanoate (95.0 mg, 0.15 mmol) was treated with LiOH—H$_2$O (25.2 mg, 0.60 mmol) in MeOH (4 mL) and H$_2$O (1 mL) at room temperature for 2 hours. The reaction mixture was acidified to pH 4~5 with 1N HCl. The solvent was removed in vacuo and the residue was purified by prep-HPLC A (30-60% MeCN) to give the diastereomeric products T-P1 (26.2 mg) and T-P2 (58.3 mg) as white solids.

T-P1 ESI 592.3 (M+H)$^+$. $^1$H NMR (400 MHz, MeOD) δ 7.54 (s, 1H), 6.89 (d, J=3.6 Hz, 2H), 6.85-6.72 (m, 2H), 6.32 (s, 1H), 5.69-5.56 (m, 1H), 5.53-5.41 (m, 1H), 3.04-2.84 (m, 2H), 2.79 (t, J=7.3 Hz, 2H), 2.71-2.51 (m, 8H), 2.36-2.17 (m, 9H), 2.06-1.88 (m, 5H), 1.83 (s, 3H), 1.51-1.30 (m, 1H), 1.02-0.82 (m, 6H).

T-P2 ESI 592.3 (M+H)$^+$. $^1$H NMR (400 MHz, MeOD) δ 7.56 (s, 1H), 6.98-6.82 (m, 4H), 6.44 (s, 1H), 5.69-5.50 (m, 2H), 3.20 (d, J=38.2 Hz, 2H), 2.85 (d, J=33.5 Hz, 8H), 2.70-2.40 (m, 2H), 2.38-2.19 (m, 9H), 2.04-1.87 (m, 7H), 1.85-1.70 (m, 1H), 1.47-1.26 (m, 1H), 0.99-0.78 (m, 6H).

A mixture of 2-(5-(2-(3-methoxyazetidin-1-yl)ethyl)-2-oxo-4-(trifluoromethyl)pyridin-1(2H)-yl)-4-methylpentanoic acid (272 mg, 0.70 mmol, 1.25 eq), ethyl (S)-3-amino-3-(4-fluoro-3'-methoxy-2',5,6'-trimethyl-[1,1'-biphenyl]-3-yl)propanoate (200 mg, 0.56 mmol, 1.00 eq), NMI (0.5 mL) and TCFH (232 mg, 0.83 mmol, 1.50 eq) in CH$_3$CN (5 mL) was stirred at room temperature for 1 hour. The solvent was concentrated in vacuo and the residue was purified by prep-HPLC A (30-60% CH$_3$CN) to provide ethyl (3S)-3-(4-fluoro-3'-methoxy-2',5,6'-trimethyl-[1,1'-biphenyl]-3-yl)-3-(2-(5-(2-(3-methoxyazetidin-1-yl)ethyl)-2-oxo-4-(trifluoromethyl)pyridin-1(2H)-yl)-4-methylpentanamido)propanoate (201 mg). Yield 49% (ESI 732.2 [M+H]$^+$).

Step 2: (3S)-3-(4-fluoro-3'-methoxy-2',5,6'-trimethyl-[1,1'-biphenyl]-3-yl)-3-(2-(5-(2-(3-methoxyazetidin-1-yl)ethyl)-2-oxo-4-(trifluoromethyl)pyridin-1(2H)-yl)-4-methylpentanamido) propanoic Acid

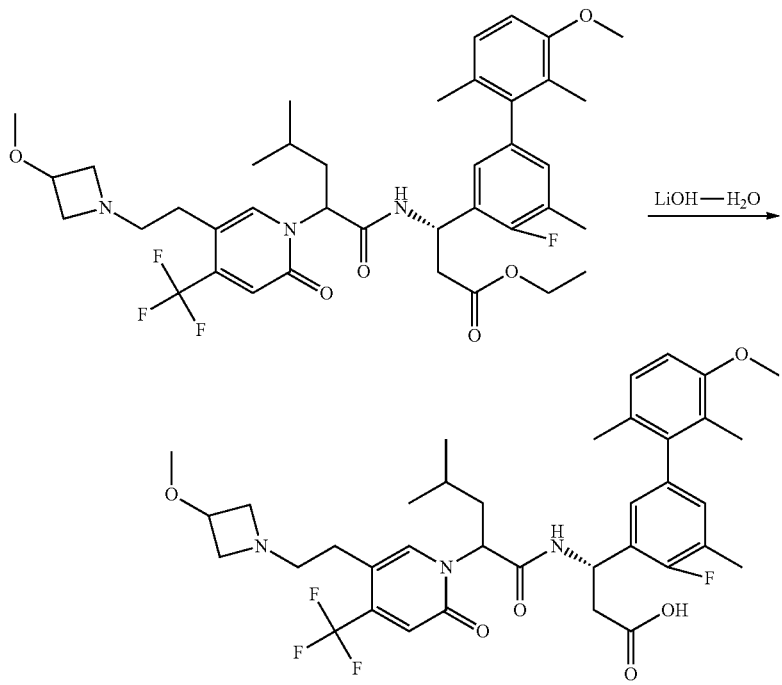

Ethyl (3S)-3-(4-fluoro-3'-methoxy-2',5,6'-trimethyl-[1,1'-biphenyl]-3-yl)-3-(2-(5-(2-(3-methoxyazetidin-1-yl)ethyl)-2-oxo-4-(trifluoromethyl)pyridin-1(2H)-yl)-4-methylpentanamido)propanoate (201 mg, 0.27 mmol, 1.00 eq) was treated with LiOH—H$_2$O (44 mg, 1.08 mmol, 4.00 eq) in MeOH (10 mL) and H$_2$O (5 mL) at room temperature for 2 hours. The reaction mixture was acidified to pH 4~5 with 1N HCl. The solvent was removed in vacuo and the residue was purified by prep-HPLC A (30-60% CH$_3$CN) to give the diastereomeric products N-P1 (31 mg) and N-P2 (41 mg) as white solids.

N-P1 ESI 704.4 (M+H)$^+$. $^1$H NMR (400 MHz, MeOD) δ 7.84 (s, 1H), 7.03-6.79 (m, 5H), 5.69-5.58 (m, 2H), 4.21-4.18 (m, 3H), 3.83 (s, 3H), 3.76-3.70 (m, 2H), 3.31 (s, 3H), 3.24-3.20 (m, 2H), 2.84-2.72 (m, 4H), 2.29 (s, 3H), 1.98 (t, J=7.6 Hz, 2H), 1.92-1.68 (m, 6H), 1.48-1.41 (m, 1H), 0.98-0.93 (m, 6H).

N-P2 ESI 704.4 (M+H)$^+$. $^1$H NMR (400 MHz, MeOD) δ 7.76 (s, 1H), 7.05 (d, J=8.4 Hz, 1H), 7.01-6.80 (m, 4H), 5.74-5.62 (m, 2H), 4.24 (s, 3H), 3.84 (s, 3H), 3.75-3.66 (m, 2H), 3.31 (s, 3H), 3.30-3.15 (m, 2H), 2.85-2.63 (m, 4H), 2.33 (s, 3H), 2.09-1.89 (m, 4H), 1.86 (d, J=3.1 Hz, 3H), 1.74-1.67 (m, 1H), 1.42-1.39 (m, 1H), 0.90 (d, J=6.3 Hz, 6H).

3-16. Preparation of (3S)-3-(2-(5-(2-(dimethylamino)ethyl)-2-oxo-4-(trifluoromethyl)pyridin-1(2H)-yl)-4-methylpentanamido)-3-(4-fluoro-3'-methoxy-2',5,6'-trimethyl-[1,1'-biphenyl]-3-yl) propanoic Acid (Compounds U-P1 and U-P2)

Step 1: Ethyl (3S)-3-(2-(5-(2-(dimethylamino)ethyl)-2-oxo-4-(trifluoromethyl)pyridin-1(2H)-yl)-4-methylpentanamido)-3-(4-fluoro-3'-methoxy-2',5,6'-trimethyl-[1,1'-biphenyl]-3-yl)propanoate

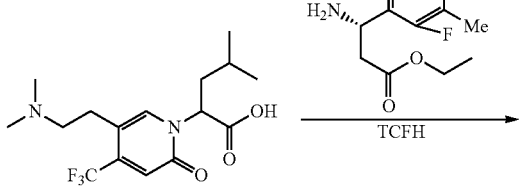

-continued

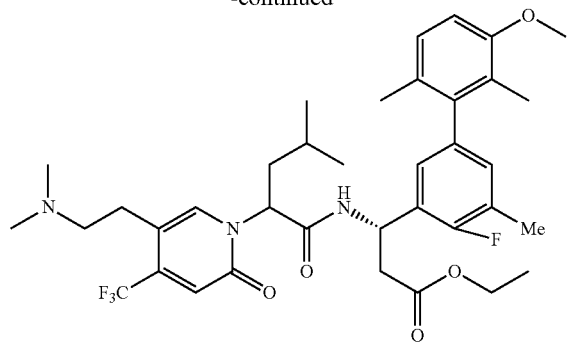

A mixture of 2-(5-(2-(dimethylamino)ethyl)-2-oxo-4-(trifluoromethyl)pyridin-1(2H)-yl)-4-methylpentanoic acid (232 mg, 0.67 mmol, 1.20 eq), ethyl (S)-3-amino-3-(4-fluoro-3'-methoxy-2',5,6'-trimethyl-[1,1'-biphenyl]-3-yl)propanoate (200 mg, 0.56 mmol, 1.00 eq), NMI (0.5 mL) and TCFH (233 mg, 0.83 mmol, 1.50 eq) in CH$_3$CN (5 mL) was stirred at room temperature for 1 hour. The solvent was concentrated in vacuo and the residue was purified by prep-HPLC A (30-60% CH3CN) to provide ethyl (3S)-3-(2-(5-(2-(dimethylamino)ethyl)-2-oxo-4-(trifluoromethyl)pyridin-1(2H)-yl)-4-methylpentanamido)-3-(4-fluoro-3'-methoxy-2',5,6'-trimethyl-[1,1'-biphenyl]-3-yl)propanoate as a white solid (250 mg). Yield 65% (ESI 690.2 [M+H]$^+$).

Step 2: (3S)-3-(2-(5-(2-(dimethylamino)ethyl)-2-oxo-4-(trifluoromethyl)pyridin-1(2H)-yl)-4-methylpentanamido)-3-(4-fluoro-3'-methoxy-2',5,6'-trimethyl-[1,1'-biphenyl]-3-yl)propanoic Acid

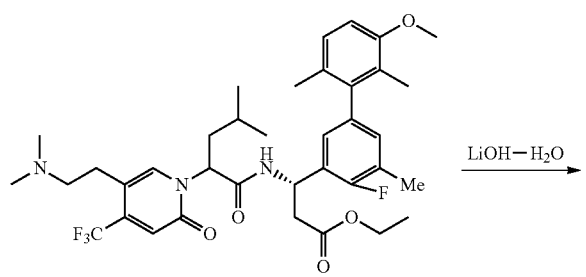

Ethyl (3S)-3-(2-(5-(2-(dimethylamino)ethyl)-2-oxo-4-(trifluoromethyl)pyridin-1(2H)-yl)-4-methylpentanamido)-3-(4-fluoro-3'-methoxy-2',5,6'-trimethyl-[1,1'-biphenyl]-3-yl)propanoate (250 mg, 0.32 mmol, 1.00 eq) was treated with LiOH—H$_2$O (19 mg, 0.81 mmol, 2.50 eq) in MeOH (5 mL) and H$_2$O (0.5 mL) at room temperature for 2 hours. The reaction mixture was acidified to pH 4~5 with 1N HCl. The solvent was removed in vacuo and the residue was purified by prep-HPLC A (30-60% CH$_3$CN) to give the diastereomeric products U-P1 (40.0 mg) and U-P2 (55.0 mg) as white solids.

U-P1 ESI 662.3 (M+H)$^+$. $^1$H NMR (400 MHz, MeOD) δ 7.90 (s, 1H), 7.04-6.99 (m, 1H), 6.86-6.76 (m, 4H), 5.70-5.66 (m, 1H), 5.58-5.55 (m, 1H), 3.83 (s, 3H), 3.15-3.03 (m, 2H), 2.97-2.93 (m, 2H), 2.74-2.69 (m, 8H), 2.29 (s, 3H), 2.00-1.96 (m, 2H), 1.92-1.67 (m, 6H), 1.48-1.41 (m, 1H), 0.97-0.93 (m, 6H).

U-P2 ESI 662.3 (M+H)$^+$. $^1$H NMR (400 MHz, MeOD) δ 7.84 (s, 1H), 7.05 (d, J=8.5 Hz, 1H), 7.03-6.79 (m, 4H), 5.73-5.69 (m, 1H), 5.61 (t, J=7.7 Hz, 1H), 3.84 (s, 3H), 3.33-3.22 (m, 2H), 3.01-2.98 (m, 2H), 2.82 (s, 6H), 2.67-2.62 (m, 1H), 2.55-2.49 (m, 1H), 2.32 (s, 3H), 2.24-1.88 (m, 4H), 1.86 (d, J=3.1 Hz, 3H), 1.81-1.60 (m, 1H), 1.45-1.37 (m, 1H), 0.90-0.88 (m, 6H).

3-17. Preparation of (3S)-3-(2-(5-(2-(dimethylamino)ethyl)-2-oxo-4-(trifluoromethyl)pyridin-1(2H)-yl)-4-methylpentanamido)-3-(4-fluoro-4'-methoxy-2',5,6'-trimethyl-[1,1'-biphenyl]-3-yl)propanoic Acid (Compounds V-P1 and V-P2)

Step 1: Ethyl (3S)-3-(2-(5-(2-(dimethylamino)ethyl)-2-oxo-4-(trifluoromethyl)pyridin-1(2H)-yl)-4-methylpentanamido)-3-(4-fluoro-4'-methoxy-2',5,6'-trimethyl-[1,1'-biphenyl]-3-yl)propanoate

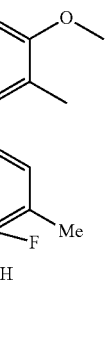 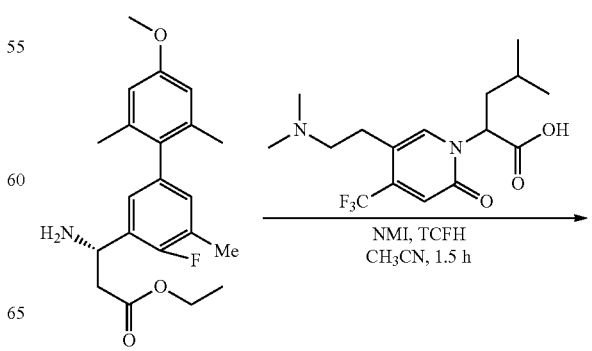

407

-continued

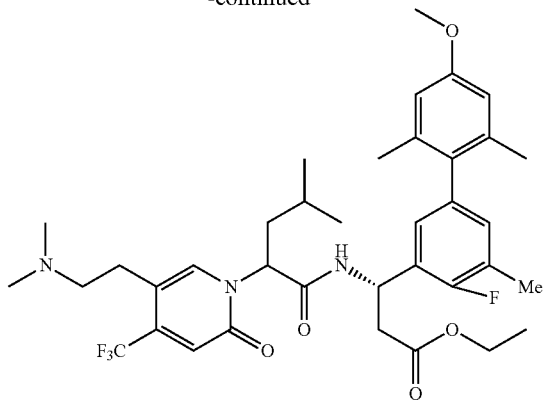

A mixture of 2-(5-(2-(dimethylamino)ethyl)-2-oxo-4-(trifluoromethyl)pyridin-1(2H)-yl)-4-methylpentanoic acid (170 mg, 0.49 mmol), ethyl (S)-3-amino-3-(4-fluoro-4'-methoxy-2',5,6'-trimethyl-[1,1'-biphenyl]-3-yl)propanoate (176 mg, 0.49 mmol), NMI (160 mg, 1.96 mmol) and TCFH (205.8 mg, 0.74 mmol) in CH₃CN (10 mL) was stirred at room temperature for 1.5 hours. The solvent was concentrated in vacuo and the residue was purified by silica gel column (DCM:MeOH 9:1) to provide ethyl (3S)-3-(2-(5-(2-(dimethylamino)ethyl)-2-oxo-4-(trifluoromethyl)pyridin-1(2H)-yl)-4-methylpentanamido)-3-(4-fluoro-4'-methoxy-2',5,6'-trimethyl-[1,1'-biphenyl]-3-yl)propanoate as a yellow solid (131 mg). Yield 39% (ESI 690.3 [M+H]⁺).

Step 2: (3S)-3-(2-(5-(2-(dimethylamino)ethyl)-2-oxo-4-(trifluoromethyl)pyridin-1(2H)-yl)-4-methylpentanamido)-3-(4-fluoro-4'-methoxy-2',5,6'-trimethyl-[1,1'-biphenyl]-3-yl)propanoic Acid

408

Ethyl (3S)-3-(2-(5-(2-(dimethylamino)ethyl)-2-oxo-4-(trifluoromethyl)pyridin-1(2H)-yl)-4-methylpentanamido)-3-(4-fluoro-4'-methoxy-2',5,6'-trimethyl-[1,1'-biphenyl]-3-yl)propanoate (131 mg, 0.19 mmol) was treated with LiOH—H₂O (32 mg, 0.76 mmol) in MeOH (10 mL) and H₂O (5 mL) at room temperature for 2 hours. The reaction mixture was acidified to pH 4~5 with 1N HCl. The solvent was removed in vacuo and the residue was purified by prep-HPLC A (30-60% CH₃CN) to give the diastereomeric products V-P1 (24 mg) and V-P2 (15 mg) as white solids.

V-P1 ESI 662.3 (M+H)⁺. ¹H NMR (500 MHz, MeOD) δ 7.90 (s, 1H), 6.85 (t, J=7.6 Hz, 2H), 6.76 (s, 1H), 6.63 (d, J=18.7 Hz, 2H), 5.68 (t, J=7.9 Hz, 1H), 5.57-5.54 (m, 1H), 3.80 (s, 3H), 3.12-3.02 (m, 2H), 2.98-2.90 (m, 2H), 2.90-2.46 (m, 8H), 2.28 (s, 3H), 2.06-1.94 (m, 5H), 1.80 (s, 3H), 1.48-1.41 (m, 1H), 0.97-0.93 (m, 6H).

V-P2 ESI 662.3 (M+H)⁺. ¹H NMR (500 MHz, MeOD) δ 7.87 (s, 1H), 6.92-6.90 (m, 3H), 6.67 (s, 2H), 5.73-5.70 (m, 1H), 5.62 (t, J=7.6 Hz, 1H), 3.80 (s, 3H), 3.30-3.20 (m, 2H), 3.01-2.97 (m, 2H), 2.83 (s, 6H), 2.70-2.59 (m, 1H), 2.55-2.50 (m, 1H), 2.32 (s, 3H), 1.98 (d, J=4.0 Hz, 7H), 1.73-1.68 (m, 1H), 1.43-1.36 (m, 1H), 0.90-0.88 (m, 6H).

3-18. Preparation of (3S)-3-(5-chloro-4-fluoro-2',6'-dimethyl-[1,1'-biphenyl]-3-yl)-3-(2-(5-(2-(3-methoxyazetidin-1-yl)ethyl)-2-oxo-4-(trifluoromethyl)pyridin-1(2H)-yl)-4-methylpentanamido)propanoic Acid (Compounds W-P1 and W-P2)

Step 1: Ethyl (3S)-3-(5-chloro-4-fluoro-2',6'-dimethyl-[1,1'-biphenyl]-3-yl)-3-(2-(5-(2-(3-methoxyazetidin-1-yl)ethyl)-2-oxo-4-(trifluoromethyl)pyridin-1(2H)-yl)-4-methylpentanamido)propanoate

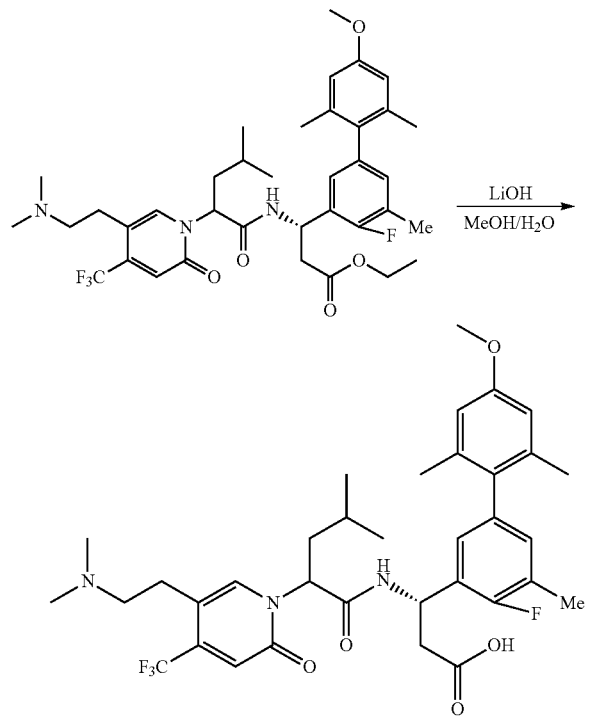

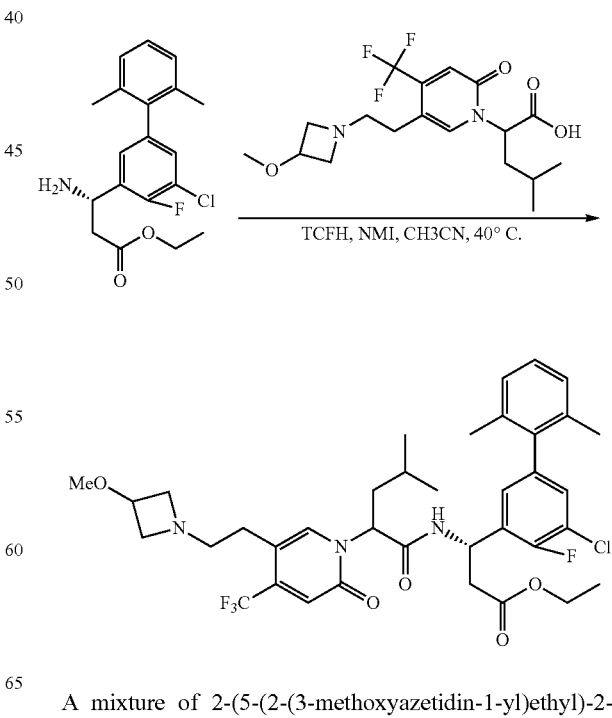

A mixture of 2-(5-(2-(3-methoxyazetidin-1-yl)ethyl)-2-oxo-4-(trifluoromethyl)pyridin-1(2H)-yl)-4-methylpentanoic acid (167 mg, 0.43 mmol), ethyl (S)-3-amino-3-(5-chloro-4-fluoro-2',6'-dimethyl-[1,1'-biphenyl]-3-yl) propanoate (150 mg, 0.43 mmol), TCFH (182 mg, 0.65 mmol) and NMI (176 mg, 2.15 mmol) in CH₃CN (4 mL) was stirred at 40° C. for 2 hours. The reaction mixture was concentrated in vacuo and purified by reverse phase HPLC on a C18/40 g column (A: water 10 mM NH₄HCO₃, B: MeOH, 0~100%) to provide ethyl (3S)-3-(5-chloro-4-fluoro-2',6'-dimethyl-[1,1'-biphenyl]-3-yl)-3-(2-(5-(2-(3-methoxyazetidin-1-yl)ethyl)-2-oxo-4-(trifluoromethyl)pyridin-1(2H)-yl)-4-methylpentanamido)propanoate as a yellow oil (150 mg). Yield 48% (ESI 722.2 (M+H)⁺).

Step 2: (3S)-3-(5-chloro-4-fluoro-2',6'-dimethyl-[1,1'-biphenyl]-3-yl)-3-(2-(5-(2-(3-methoxyazetidin-1-yl)ethyl)-2-oxo-4-(trifluoromethyl)pyridin-1(2H)-yl)-4-methylpentanamido)propanoic Acid

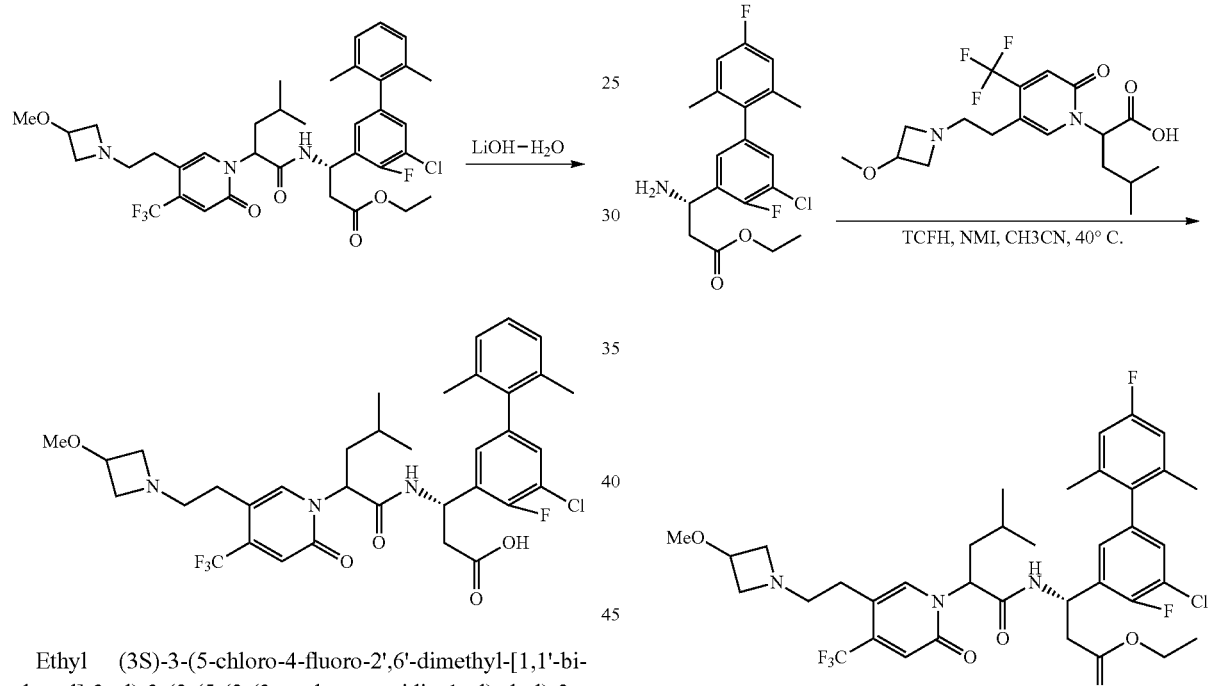

Ethyl (3S)-3-(5-chloro-4-fluoro-2',6'-dimethyl-[1,1'-biphenyl]-3-yl)-3-(2-(5-(2-(3-methoxyazetidin-1-yl)ethyl)-2-oxo-4-(trifluoromethyl)pyridin-1(2H)-yl)-4-methylpentanamido)propanoate (150 mg, 0.21 mmol) was treated with LiOH—H₂O (42 mg, 1 mmol) in MeOH (3 mL) and H₂O (1 mL) at room temperature for 2 hours. The reaction mixture was acidified to pH 4-5 with 1N HCl. The solvent was removed in vacuo and the residue was purified by prep-HPLC A (30-60% CH₃CN) to give the diastereomeric products W-P1 (46 mg) and W-P2 (57 mg) as white solids.

W-P1 ESI 694.2 (M+H)⁺. ¹H NMR (400 MHz, MeOD) δ 7.85 (s, 1H), 7.21-7.00 (m, 5H), 6.74 (s, 1H), 5.72-5.50 (m, 2H), 4.27-4.08 (m, 3H), 3.80-3.61 (m, 2H), 3.31 (s, 3H), 3.26-3.09 (m, 2H), 2.86-2.70 (m, 4H), 2.09-1.93 (m, 5H), 1.84 (s, 3H), 1.50-1.37 (m, 1H), 1.04-0.83 (m, 6H).

W-P2 ESI 694.2 (M+H)⁺. ¹H NMR (400 MHz, MeOD) δ 7.75 (s, 1H), 7.26-7.06 (m, 5H), 6.90 (s, 1H), 5.79-5.70 (m, 1H), 5.63 (t, J=7.7 Hz, 1H), 4.44-4.22 (m, 3H), 3.98-3.76 (m, 2H), 3.41-3.34 (m, 5H), 2.99-2.74 (m, 2H), 2.70-2.49 (m, 2H), 2.08-1.89 (m, 7H), 1.77-1.62 (m, 1H), 1.48-1.32 (m, 1H), 0.90 (d, J=6.4 Hz, 6H).

3-19. Preparation of (3S)-3-(5-chloro-4,4'-difluoro-2',6'-dimethyl-[1,1'-biphenyl]-3-yl)-3-(2-(5-(2-(3-methoxyazetidin-1-yl)ethyl)-2-oxo-4-(trifluoromethyl)pyridin-1(2H)-yl)-4-methylpentanamido) propanoic Acid (Compounds X-P1 and X-P2)

Step 1: (3S)-3-(5-chloro-4,4'-difluoro-2',6'-dimethyl-[1,1'-biphenyl]-3-yl)-3-(2-(5-(2-(3-methoxyazetidin-1-yl)ethyl)-2-oxo-4-(trifluoromethyl)pyridin-1(2H)-yl)-4-methylpentanamido)propanoate ethyl

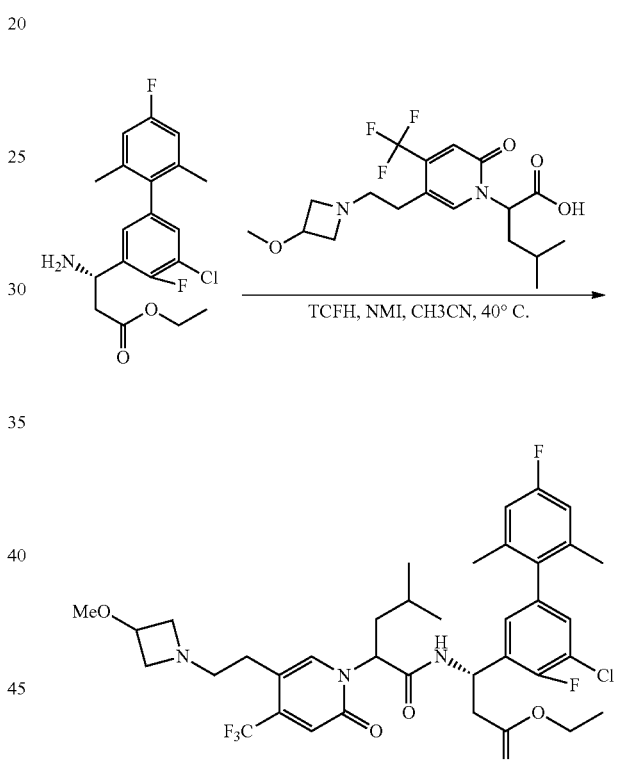

A mixture of 2-(5-(2-(3-methoxyazetidin-1-yl)ethyl)-2-oxo-4-(trifluoromethyl)pyridin-1(2H)-yl)-4-methylpentanoic acid (160 mg, 0.41 mmol), ethyl (S)-3-amino-3-(5-chloro-4,4'-difluoro-2',6'-dimethyl-[1,1'-biphenyl]-3-yl) propanoate (150 mg, 0.41 mmol), TCFH (174 mg, 0.62 mmol) and NMI (168 mg, 2.05 mmol) in CH₃CN (4 mL) was stirred at 40° C. for 2 hours. The reaction mixture was concentrated in vacuo and purified by reverse phase HPLC on a C18/40 g column (A: water 10 mM NH₄HCO₃, B: MeOH, 0~100%) to provide ethyl (3S)-3-(5-chloro-4,4'-difluoro-2',6'-dimethyl-[1,1'-biphenyl]-3-yl)-3-(2-(5-(2-(3-methoxyazetidin-1-yl)ethyl)-2-oxo-4-(trifluoromethyl)pyridin-1(2H)-yl)-4-methylpentanamido)propanoate as a yellow oil (150 mg). Yield 49% (ESI 740.2 (M+H)⁺).

Step 2: (3S)-3-(5-chloro-4,4'-difluoro-2',6'-dimethyl-[1,1'-biphenyl]-3-yl)-3-(2-(5-(2-(3-methoxyazetidin-1-yl)ethyl)-2-oxo-4-(trifluoromethyl)pyridin-1(2H)-yl)-4-methylpentanamido)propanoic Acid

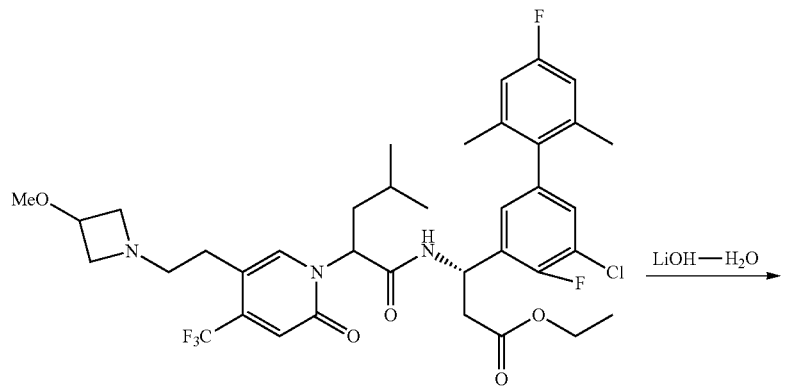

Ethyl (3S)-3-(5-chloro-4,4'-difluoro-2',6'-dimethyl-[1,1'-biphenyl]-3-yl)-3-(2-(5-(2-(3-methoxyazetidin-1-yl)ethyl)-2-oxo-4-(trifluoromethyl)pyridin-1(2H)-yl)-4-methylpentanamido)propanoate (150 mg, 0.20 mmol) was treated with LiOH—H$_2$O (42 mg, 1 mmol) in MeOH (3 mL) and H$_2$O (1 mL) at room temperature for 2 hours. The reaction mixture was acidified to pH 4~5 with 1N HCl. The solvent was removed in vacuo and the residue was purified by prep-HPLC A (30-60% CH$_3$CN) to give the diastereomeric products X-P1 (35 mg) and X-P2 (49 mg) as white solids.

X-P1 ESI 712.2 (M+H)$^+$. $^1$H NMR (400 MHz, MeOD) δ 7.85 (s, 1H), 7.13 (d, J=6.6 Hz, 1H), 7.07-7.00 (m, 1H), 6.90-6.79 (m, 2H), 6.74 (s, 1H), 5.72-5.48 (m, 2H), 4.26-4.07 (m, 3H), 3.80-3.64 (m, 2H), 3.32 (s, 3H), 3.19 (t, J=6.2 Hz, 2H), 2.86-2.71 (m, 4H), 2.08-1.95 (m, 5H), 1.86 (d, J=4.4 Hz, 3H), 1.51-1.36 (m, 1H), 1.01-0.88 (m, 6H).

X-P2 ESI 712.2 (M+H)$^+$. $^1$H NMR (400 MHz, MeOD) δ 7.74 (s, 1H), 7.25-7.16 (m, 1H), 7.15-7.05 (m, 1H), 6.93-6.83 (m, 3H), 5.81-5.68 (m, 1H), 5.63 (t, J=7.7 Hz, 1H), 4.44-4.23 (m, 3H), 3.95-3.78 (m, 2H), 3.40-3.34 (m, 5H), 3.00-2.75 (m, 2H), 2.70-2.47 (m, 2H), 2.08-1.93 (m, 7H), 1.76-1.64 (m, 1H), 1.47-1.33 (m, 1H), 0.96-0.84 (m, 6H).

3-20. Preparation of (3S)-3-(4,4'-difluoro-2',5,6'-trimethylbiphenyl-3-yl)-3-(2-(5-(2-(dimethylamino)ethyl)-2-oxo-4-(trifluoromethyl)pyridin-1(2H)-yl)-5-methylhexanamido)propanoic Acid (Compounds Y-P1 and Y-P2)

Step 1: (3S)-ethyl 3-(4,4'-difluoro-2',5,6'-trimethylbiphenyl-3-yl)-3-(2-(5-(2-(dimethylamino)ethyl)-2-oxo-4-(trifluoromethyl)pyridin-1(2H)-yl)-5-methylhexanamido)propanoate

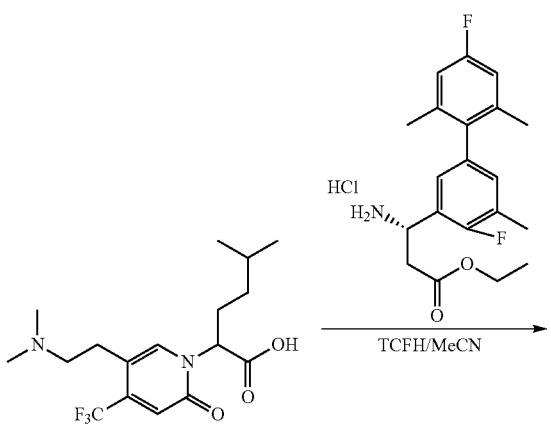

-continued

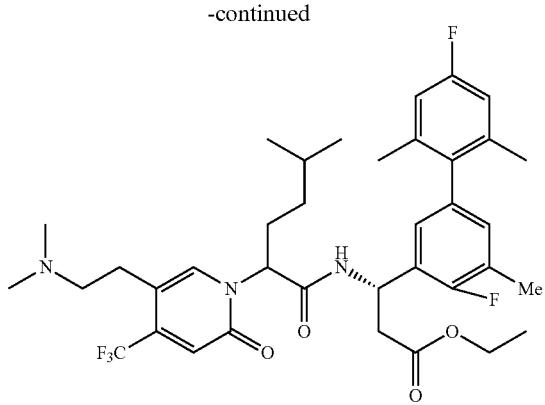

A mixture of 2-(5-(2-(dimethylamino)ethyl)-2-oxo-4-(trifluoromethyl)pyridin-1(2H)-yl)-5-methylhexanoic acid (273 mg, 0.75 mmol), (S)-ethyl 3-amino-3-(4,4'-difluoro-2',5,6'-trimethylbiphenyl-3-yl)propanoate hydrochloride (164 mg, 0.39 mmol), TCFH (211 mg, 0.75 mmol), and NMI (0.45 mL, 5.70 mmol) in acetonitrile (9 mL) was stirred at room temperature for 16 hours. The reaction mixture was concentrated in vacuo and purified by reverse phase HPLC on a C18/40 g column (A: water 10 mM $NH_4HCO_3$, B: MeOH, 0~80%) to provide (3S)-ethyl 3-(4,4'-difluoro-2',5,6'-trimethylbiphenyl-3-yl)-3-(2-(5-(2-(dimethylamino)ethyl)-2-oxo-4-(trifluoromethyl)pyridin-1(2H)-yl)-5-methylhexanamido)propanoate as a brown solid (262 mg). Yield 97% (ESI 692.3 $(M+H)^+$).

Step 2: (3S)-3-(4,4'-difluoro-2',5,6'-trimethylbiphenyl-3-yl)-3-(2-(5-(2 (dimethylamino)ethyl)-2-oxo-4-(trifluoromethyl)pyridin-1(2H)-yl)-5-methylhexanamido)propanoic Acid ethyl)pyridin-1(2H)-yl)-5-methylhexanamido)propanoate (262 mg, 0.38 mmol) was treated with LiOH monohydrate (80 mg, 1.90 mmol) in EtOH (6 mL) and $H_2O$ (0.10 mL) at 36° C. for 1 hour. The reaction mixture was acidified to pH 4~5 with 1N HCl. The reaction mixture was concentrated in vacuo and purified by prep-HPLC A (30-60% MeCN) to give the diastereomeric products Y-P1 (68 mg) and Y-P2 (66 mg) as white solids.

Y-P1 ESI 664.2 $(M+H)^+$. 1H NMR (400 MHz, MeOD) δ 7.89 (s, 1H), 6.87-6.85 (m, 1H), 6.83-6.78 (m, 2H), 6.76-6.73 (m, 1H), 6.70 (s, 1H), 5.56-5.52 (m, 1H), 5.50-5.46 (m, 1H), 3.10-3.03 (m, 2H), 2.95-2.91 (m, 2H), 2.75-2.66 (m, 8H), 2.26 (d, J=1.2 Hz, 3H), 2.22-2.14 (m, 1H), 2.00-1.92 (m, 4H), 1.78 (s, 3H), 1.60-1.53 (m, 1H), 1.29-1.18 (m, 1H), 1.13-1.04 (m, 1H), 0.88 (d, J=2.8 Hz, 3H), 0.86 (d, J=2.8 Hz, 3H).

Y-P2 ESI 664.2 (M+H)+. $^1$H NMR (400 MHz, MeOD) δ 7.92 (s, 1H), 6.95-6.93 (m, 1H), 6.91-6.88 (m, 1H), 6.87 (s, 1H), 6.82 (s, 1H), 6.80 (s, 1H), 5.72-5.68 (m, 1H), 5.47 (t, J=7.6 Hz, 1H), 3.24-3.12 (m, 2H), 3.02-2.93 (m, 2H), 2.78 (t, J=5.8 Hz, 6H), 2.67-2.62 (m, 1H), 2.58-2.52 (m, 1H), 2.30 (d, J=1.6 Hz, 3H), 2.13-2.04 (m, 1H), 2.00 (s, 3H), 1.99 (s, 3H), 1.84-1.75 (m, 1H), 1.52-1.44 (m, 1H), 1.15-0.99 (m, 2H), 0.80 (d, J=4.0 Hz, 3H), 0.77 (d, J=4.5 Hz, 3H).

3-21. Preparation of (3S)-3-(2-(5-(2-(dimethylamino)ethyl)-2-oxo-4-(trifluoromethyl)pyridin-1 (2H)-yl)-5-methylhexanamido)-3-(4-fluoro-2',5,6'-trimethyl-[1,1'-biphenyl]-3-yl)propanoic Acid (Compounds Z-P1 and Z-P2)

Step 1: (3S)-ethyl 3-(2-(5-(2-(dimethylamino)ethyl)-2-oxo-4-(trifluoromethyl)pyridin-1(2H)-yl)-5-methylhexanamido)-3-(4-fluoro-2',5,6'-trimethylbiphenyl-3-yl)propanoate

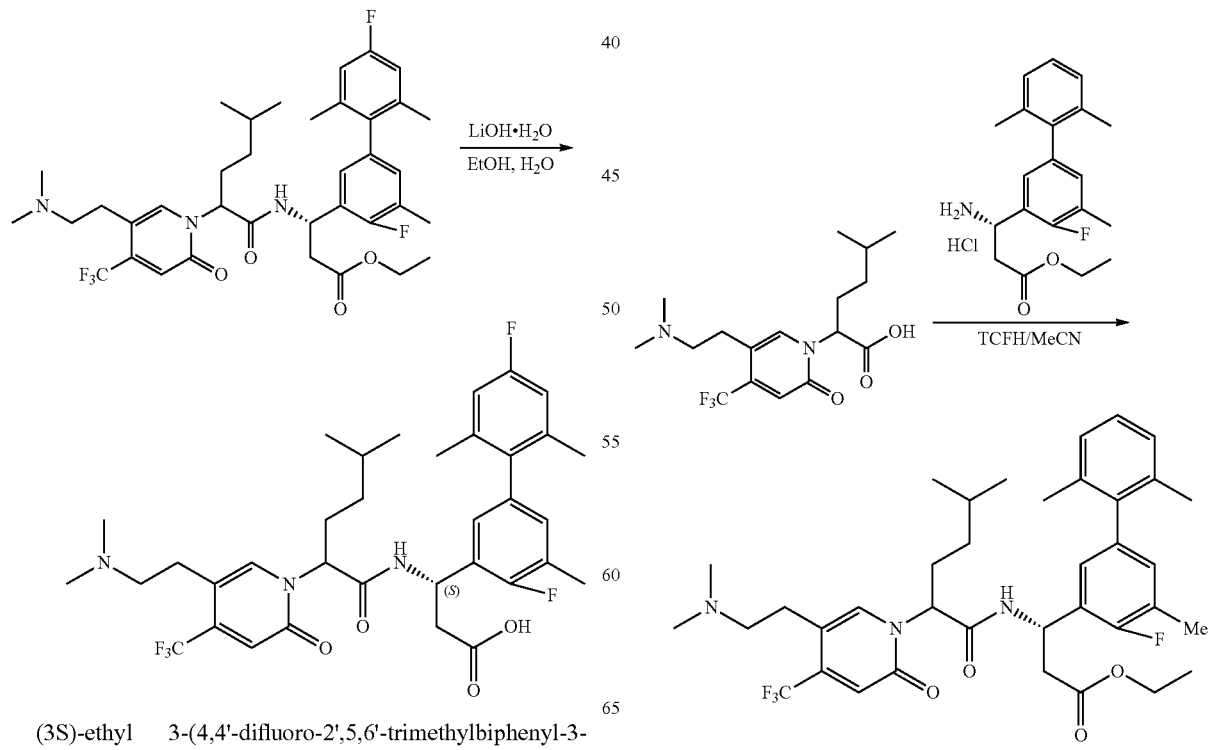

(3S)-ethyl 3-(4,4'-difluoro-2',5,6'-trimethylbiphenyl-3-yl)-3-(2-(5-(2-(dimethylamino)ethyl)-2-oxo-4-(trifluorom- A mixture of 2-(5-(2-(dimethylamino)ethyl)-2-oxo-4-(trifluoromethyl)pyridin-1(2H)-yl)-5-methylhexanoic acid (283 mg, 0.78 mmol), (S)-ethyl 3-amino-3-(4-fluoro-2',5,6'-trimethylbiphenyl-3-yl)propanoate hydrochloride (170 mg, 0.46 mmol), TCFH (248 mg, 0.88 mmol), and NMI (0.21 mL, 2.63 mmol) in acetonitrile (10 mL) was stirred at room temperature for 20 hours. The reaction mixture was concentrated in vacuo and purified by reverse phase HPLC on a C18/40 g column (A: water 10 mM NH$_4$HCO$_3$, B: MeOH, 0~100%) to provide (3S)-ethyl 3-(2-(5-(2-(dimethylamino)ethyl)-2-oxo-4-(trifluoromethyl)pyridin-1(2H)-yl)-5-methylhexanamido)-3-(4-fluoro-2',5,6'-trimethylbiphenyl-3-yl)propanoate as a brown solid (223 mg). Yield 71% (ESI 674.3 (M+H)$^+$).

Step 2: (3S)-3-(2-(5-(2-(dimethylamino)ethyl)-2-oxo-4-(trifluoromethyl)pyridin-1(2H)-yl)-5-methylhexanamido)-3-(4-fluoro-2',5,6'-trimethyl-[1,1'-biphenyl]-3-yl)propanoic Acid

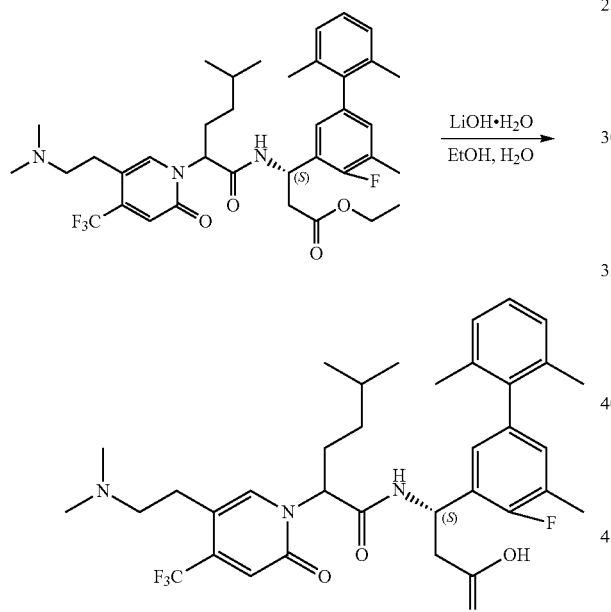

(3S)-ethyl 3-(2-(5-(2-(dimethylamino)ethyl)-2-oxo-4-(trifluoromethyl)pyridin-1(2H)-yl)-5-methylhexanamido)-3-(4-fluoro-2',5,6'-trimethylbiphenyl-3-yl)propanoate (223 mg, 0.33 mmol) was treated with LiOH monohydrate (35 mg, 0.82 mmol) in EtOH (6 mL) and H$_2$O (0.08 mL) at 36° C. for 1 h. The reaction mixture was acidified to pH 4-5 with 1N HCl. The reaction mixture was concentrated in vacuo and purified by prep-HPLC A (30-60% MeCN) to give the diastereomeric products Z-P1 (60 mg) and Z-P2 (59 mg) as white solids.

Z-P1 ESI 646.3 (M+H)$^+$. $^1$H NMR (400 MHz, MeOD) δ 7.89 (s, 1H), 7.09 (t, J=7.4 Hz, 1H), 7.04 (d, J=6.8 Hz, 1H), 7.00 (d, J=7.2 Hz, 1H), 6.89-6.87 (m, 1H), 6.84 (d, J=7.0 Hz, 1H), 6.71 (s, 1H), 5.57-5.54 (m, 1H), 5.51-5.47 (m, 1H), 3.12-3.02 (m, 2H), 2.93 (t, J=7.9 Hz, 2H), 2.74 (s, 6H), 2.73-2.69 (m, 2H), 2.27 (d, J=1.4 Hz, 3H), 2.24-2.14 (m, 1H), 2.02-1.90 (m, 4H), 1.79 (s, 3H), 1.61-1.51 (m, 1H), 1.27-1.18 (m, 1H), 1.13-1.03 (m, 1H), 0.88 (d, J=2.4 Hz, 3H), 0.86 (d, J=2.4 Hz, 3H).

Z-P2 ESI 646.3 (M+H)+. $^1$H NMR (400 MHz, MeOD) δ 7.87 (s, 1H), 7.13-7.05 (m, 3H), 6.94-6.88 (m, 3H), 5.73-5.69 (m, 1H), 5.45 (t, J=7.6 Hz, 1H), 3.27-3.15 (m, 2H), 2.98 (t, J=6.8 Hz, 2H), 2.80 (s, 6H), 2.66-2.61 (m, 1H), 2.55-2.49 (m, 1H), 2.31 (d, J=1.2 Hz, 3H), 2.14-2.05 (m, 1H), 1.99 (d, J=2.6 Hz, 6H), 1.82-1.73 (m, 1H), 1.56-1.46 (m, 1H), 1.16-0.99 (m, 2H), 0.81 (t, J=6.5 Hz, 6H).

3-22. Preparation of (3S)-3-(4-fluoro-2',4',5,6'-tetramethyl-[1,1'-biphenyl]-3-yl)-3-(2-(5-(2-(3-methoxyazetidin-1-yl)ethyl)-2-oxo-4-(trifluoromethyl)pyridin-1(2H)-yl)-4-methylpentanamido) propanoic Acid (Compounds AA-P1 and AA-P2)

Step 1: Ethyl (3S)-3-(4-fluoro-2',4',5,6'-tetramethyl-[1,1'-biphenyl]-3-yl)-3-(2-(5-(2-(3-methoxyazetidin-1-yl)ethyl)-2-oxo-4-(trifluoromethyl)pyridin-1(2H)-yl)-4-methylpentanamido)propanoate

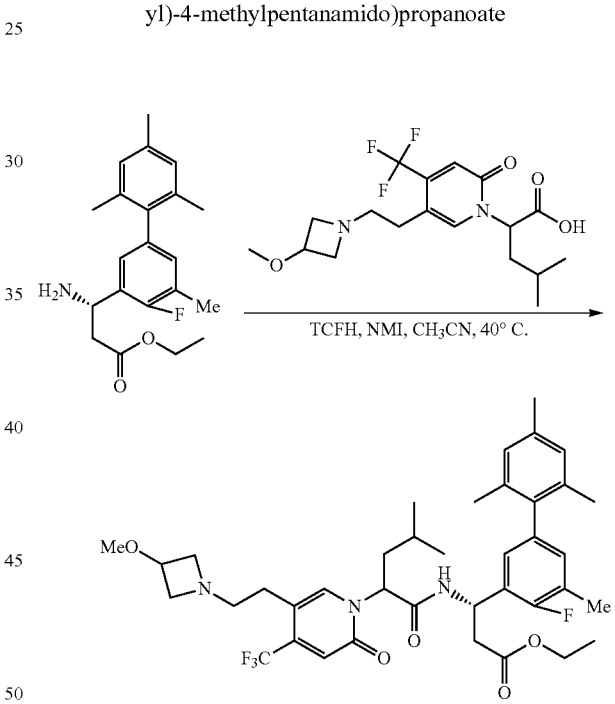

A mixture of 2-(5-(2-(3-methoxyazetidin-1-yl)ethyl)-2-oxo-4-(trifluoromethyl)pyridin-1(2H)-yl)-4-methylpentanoic acid (168 mg, 0.43 mmol), ethyl (S)-3-amino-3-(4-fluoro-2',4',5,6'-tetramethyl-[1,1'-biphenyl]-3-yl)propanoate (150 mg, 0.43 mmol), TCFH (182 mg, 0.65 mmol) and NMI (177 mg, 2.2 mmol) in CH$_3$CN (4 mL) was stirred at 40° C. for 2 hours. The reaction mixture was concentrated in vacuo and purified by reverse phase HPLC on a C18/40 g column (A: water 10 mM NH$_4$HCO$_3$, B: MeOH, 0~100%) to provide ethyl (3S)-3-(4-fluoro-2',4',5,6'-tetramethyl-[1,1'-biphenyl]-3-yl)-3-(2-(5-(2-(3-methoxyazetidin-1-yl)ethyl)-2-oxo-4-(trifluoromethyl)pyridin-1(2H)-yl)-4-methylpentanamido)propanoate as a yellow oil (160 mg). Yield 51% (ESI 716.2 (M+H)$^+$).

Step 2: (3S)-3-(4-fluoro-2',4',5,6'-tetramethyl-[1,1'-biphenyl]-3-yl)-3-(2-(5-(2-(3-methoxyazetidin-1-yl)ethyl)-2-oxo-4-(trifluoromethyl)pyridin-1(2H)-yl)-4-methylpentanamido)propanoic Acid

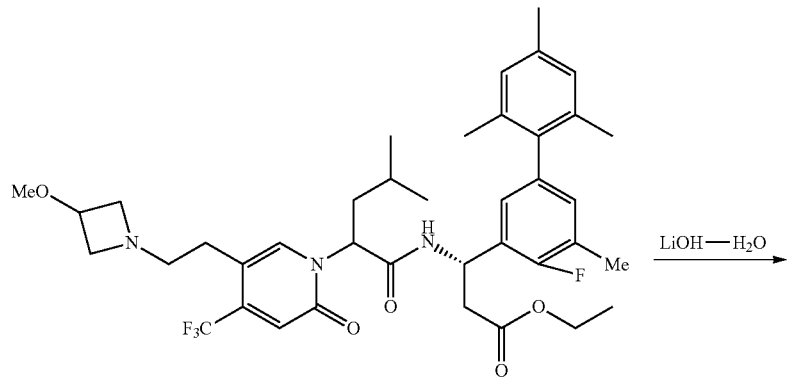

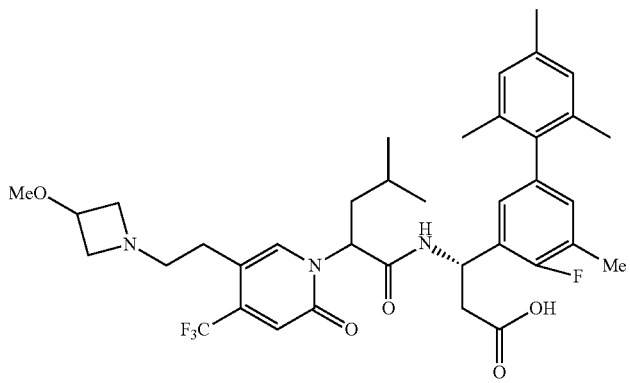

Ethyl (3S)-3-(4-fluoro-2',4',5,6'-tetramethyl-[1,1'-biphenyl]-3-yl)-3-(2-(5-(2-(3-methoxyazetidin-1-yl)ethyl)-2-oxo-4-(trifluoromethyl)pyridin-1(2H)-yl)-4-methylpentanamido)propanoate (160 mg, 0.22 mmol) was treated with LiOH—H$_2$O (42 mg, 1 mmol) in MeOH (3 mL) and H$_2$O (1 mL) at room temperature for 2 hours. The reaction mixture was acidified to pH 4~5 with 1N HCl. The solvent was removed in vacuo and the residue was purified by prep-HPLC A (30-60% CH$_3$CN) to give the diastereomeric products AA-P1 (46 mg) and AA-P2 (61 mg) as white solids.

AA-P1 ESI 688.3 (M+H)$^+$. $^1$H NMR (400 MHz, MeOD) δ 7.83 (s, 1H), 6.97-6.81 (m, 4H), 6.75 (s, 1H), 5.75-5.52 (m, 2H), 4.20-4.00 (m, 3H), 3.61 (d, J=11.2 Hz, 2H), 3.30 (s, 3H), 3.14 (t, J=6.9 Hz, 2H), 2.87-2.66 (m, 4H), 2.29 (s, 6H), 2.04-1.90 (m, 5H), 1.80 (s, 3H), 1.50-1.38 (m, 1H), 1.05-0.88 (m, 6H).

AA-P2 ESI 688.3 (M+H)$^+$. $^1$H NMR (400 MHz, MeOD) δ 7.74 (s, 1H), 6.97-6.84 (m, 5H), 5.80-5.69 (m, 1H), 5.62 (t, J=7.7 Hz, 1H), 4.46-4.21 (m, 3H), 3.93-3.76 (m, 2H), 3.40-3.34 (m, 5H), 3.04-2.76 (m, 2H), 2.70-2.45 (m, 2H), 2.38-2.21 (m, 6H), 2.07-1.88 (m, 7H), 1.75-1.61 (m, 1H), 1.49-1.33 (m, 1H), 1.03-0.83 (m, 6H).

3-23. Preparation of (3S)-3-(4-fluoro-2',5,6'-trimethyl-[1,1'-biphenyl]-3-yl)-3-(2-(5-(2-(3-methoxyazetidin-1-yl)ethyl)-2-oxo-4-(trifluoromethyl)pyridin-1(2H)-yl)-4-methylpentanamido) propanoic Acid (Compounds AB-P1 and AB-P2)

Step 1: Ethyl (3S)-3-(4-fluoro-2',5,6'-trimethyl-[1,1'-biphenyl]-3-yl)-3-(2-(5-(2-(3-methoxyazetidin-1-yl)ethyl)-2-oxo-4-(trifluoromethyl)pyridin-1(2H)-yl)-4-methylpentanamido)propanoate

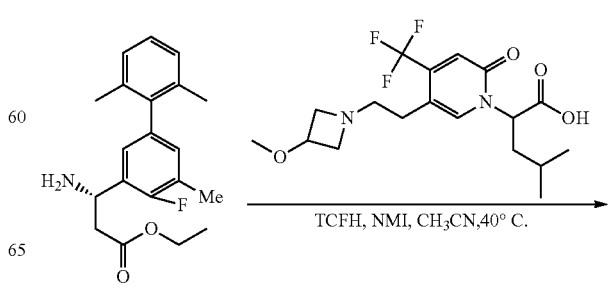

419

-continued

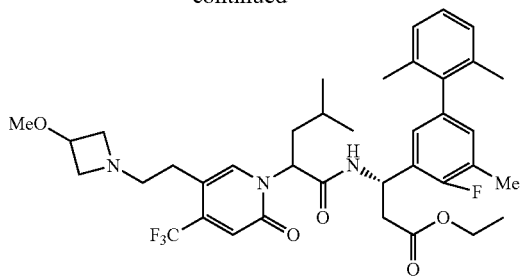

A mixture of 2-(5-(2-(3-methoxyazetidin-1-yl)ethyl)-2-oxo-4-(trifluoromethyl)pyridin-1(2H)-yl)-4-methylpentanoic acid (180 mg, 0.46 mmol), ethyl (S)-3-amino-3-(4-fluoro-2',5,6'-trimethyl-[1,1'-biphenyl]-3-yl)propanoate (150 mg, 0.46 mmol), TCFH (193 mg, 0.69 mmol) and NMI (188 mg, 2.3 mmol) in $CH_3CN$ (4 mL) was stirred at 40° C. for 2 hours. The reaction mixture was concentrated in vacuo and purified by reverse phase HPLC on a C18/40 g column (A: water 10 mM $NH_4HCO_3$, B: MeOH, 0~100%) to provide ethyl (3S)-3-(4-fluoro-2',5,6'-trimethyl-[1,1'-biphenyl]-3-yl)-3-(2-(5-(2-(3-methoxyazetidin-1-yl)ethyl)-2-oxo-4-(trifluoromethyl)pyridin-1(2H)-yl)-4-methylpentanamido)propanoate as a yellow oil (140 mg). Yield 43% (ESI 702.1 (M+H)$^+$).

Step 2: (3S)-3-(4-fluoro-2',5,6'-trimethyl-[1,1'-biphenyl]-3-yl)-3-(2-(5-(2-(3-methoxyazetidin-1-yl)ethyl)-2-oxo-4-(trifluoromethyl)pyridin-1(2H)-yl)-4-methylpentanamido)propanoic Acid

420

Ethyl (3S)-3-(4-fluoro-2',5,6'-trimethyl-[1,1'-biphenyl]-3-yl)-3-(2-(5-(2-(3-methoxyazetidin-1-yl)ethyl)-2-oxo-4-(trifluoromethyl)pyridin-1(21)-yl)-4-methylpentanamido)propanoate (140 mg, 0.20 mmol) was treated with LiOH—$H_2O$ (42 mg, 1 mmol) in MeOH (3 mL) and $H_2O$ (1 mL) at room temperature for 2 hours. The reaction mixture was acidified to pH 4~5 with 1N HCl. The solvent was removed in vacuo and the residue was purified by prep-HPLC A (30-60% $CH_3CN$) to give the diastereomeric products AB-P1 (34 mg) and AB-P2 (46 mg) as white solids.

AB-P1 ESI 674.3 (M+H)$^+$. $^1$H NMR (400 MHz, MeOD) δ 7.84 (s, 1H), 7.16-6.98 (m, 3H), 6.88 (t, J=7.5 Hz, 2H), 6.76 (s, 1H), 5.74-5.53 (m, 2H), 4.24-4.04 (m, 3H), 3.70-3.53 (m, 2H), 3.30 (s, 3H), 3.14 (t, J=7.1 Hz, 2H), 2.84-2.66 (m, 4H), 2.30 (s, 3H), 2.03-1.91 (m, 5H), 1.84 (s, 3H), 1.52-1.34 (m, 1H), 1.14-0.86 (m, 6H).

AB-P2 ESI 674.3 (M+H)$^+$. $^1$H NMR (400 MHz, MeOD) δ 7.75 (s, 1H), 7.20-7.06 (m, 3H), 7.00-6.86 (m, 3H), 5.84-5.71 (m, 1H), 5.62 (t, J=7.7 Hz, 1H), 4.46-4.22 (m, 3H), 3.97-3.75 (m, 2H), 3.42-3.34 (m, 5H), 3.00-2.76 (m, 2H), 2.69-2.45 (m, 2H), 2.34 (d, J=1.7 Hz, 3H), 2.09-1.92 (m, 7H), 1.71-1.59 (m, 1H), 1.49-1.35 (m, 1H), 1.04-0.83 (m, 6H).

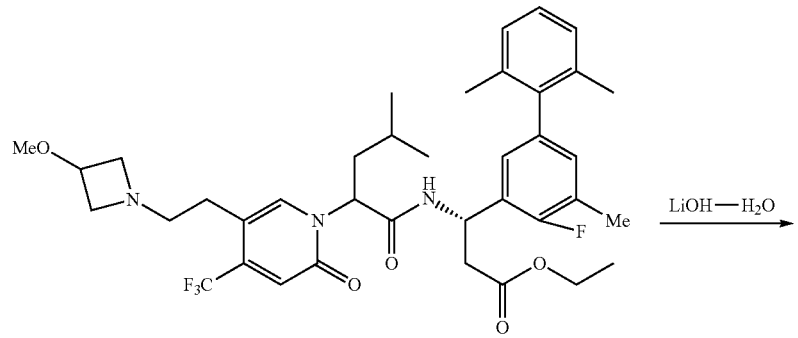

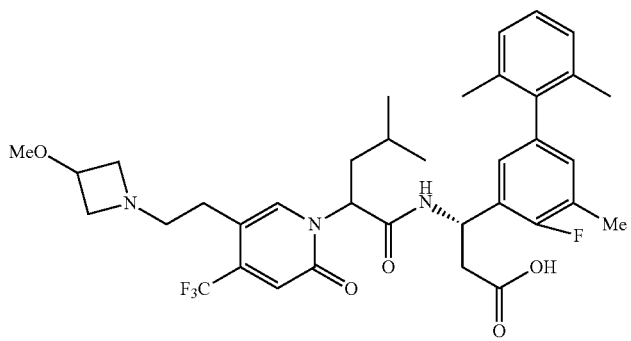

3-24. Preparation of (3S)-3-(2-(5-(2-(dimethylamino)ethyl)-2-oxo-4-(trifluoromethyl)pyridin-1(2H)-yl)-4-methylpentanamido)-3-(4-fluoro-2',4',5,6'-tetramethylbiphenyl-3-yl)propanoic Acid (Compounds AC-P1 and AC-P2)

Step 1: (3S)-ethyl 3-(2-(5-(2-(dimethylamino)ethyl)-2-oxo-4-(trifluoromethyl)pyridin-1(2H)-yl)-4-methylpentanamido)-3-(4-fluoro-2',4',5,6'-tetramethylbiphenyl-3-yl)propanoate

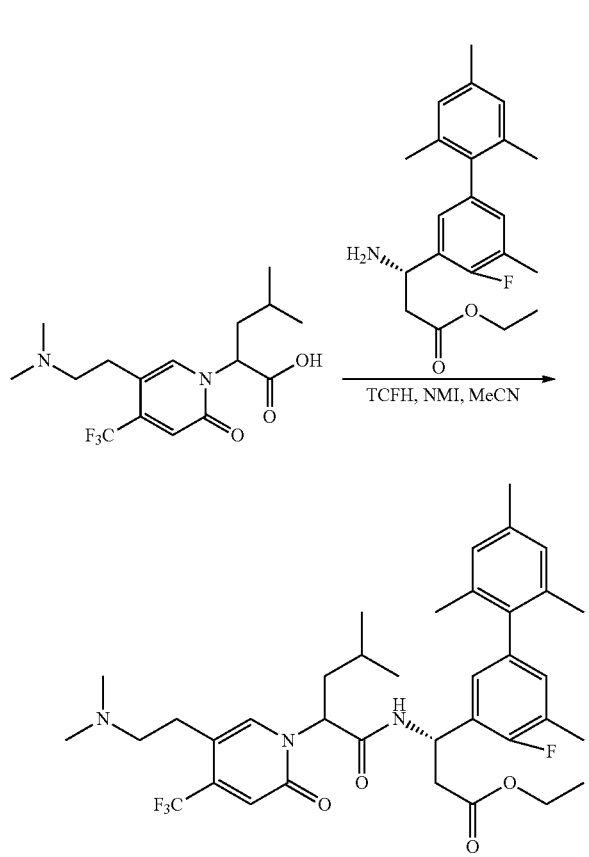

A mixture of 2-(5-(2-(dimethylamino)ethyl)-2-oxo-4-(trifluoromethyl)pyridin-1(2H)-yl)-4-methylpentanoic acid (150 mg, 0.43 mmol, 1.0 eq), (S)-ethyl 3-amino-3-(4-fluoro-2',4',5,6'-tetramethylbiphenyl-3-yl)propanoate (148 mg, 0.361 mg, 1.29 mmol, 3 eq), TCHF (361 mg, 1.29 mmol, 3 eq) and NMI (176 mg, 2.15 mmol, 5.0 eq) in CH$_3$CN (5 mL) was stirred at room temperature for 16 hours. LCMS showed that the reaction was completed. The solvent was concentrated in vacuo and the residue was purified by reverse phase HPLC on a C18/40 g column (A: water 10 mM NH$_4$HCO$_3$, B: MeOH, 0~100%) to provide (3S)-ethyl 3-(2-(5-(2-(dimethylamino)ethyl)-2-oxo-4-(trifluoromethyl)pyridin-1(2H)-yl)-4-methylpentanamido)-3-(4-fluoro-2',4',5,6'-tetramethylbiphenyl-3-yl)propanoate as a yellow solid (130 mg). Yield 45% (ESI 674.2 [M+H]$^+$).

Step 2: (3S)-3-(2-(5-(2-(dimethylamino)ethyl)-2-oxo-4-(trifluoromethyl)pyridin-1(2H)-yl)-4-methylpentanamido)-3-(4-fluoro-2',4',5,6'-tetramethylbiphenyl-3-yl)propanoic Acid

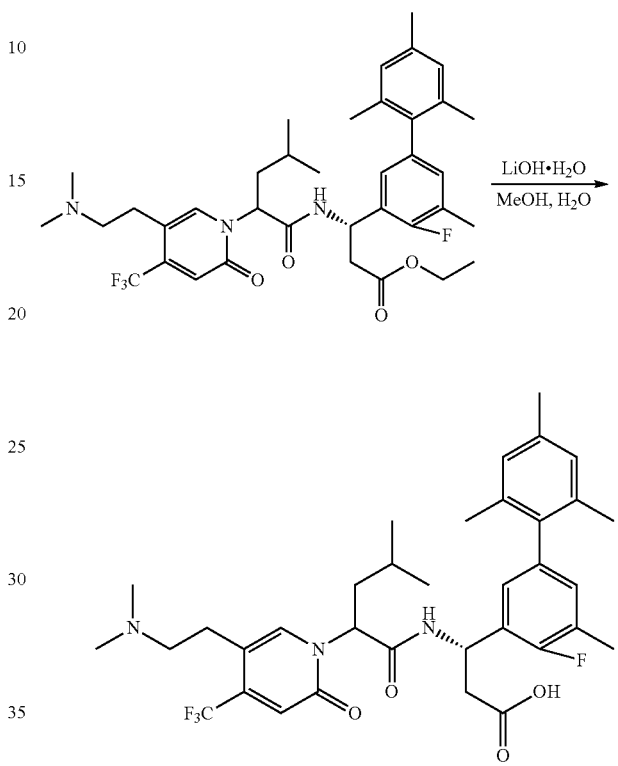

(3S)-ethyl 3-(2-(5-(2-(dimethylamino)ethyl)-2-oxo-4-(trifluoromethyl)pyridin-1(2H)-yl)-4-methylpentanamido)-3-(4-fluoro-2',4',5,6'-tetramethylbiphenyl-3-yl)propanoate (130 mg, 0.19 mmol, 1.0 eq) was treated with LiOH—H$_2$O (40 mg, 0.95 mmol, 5.0 eq) in MeOH (4 mL) and water (1 mL) at 28° C. for 1 hour. LCMS showed that the reaction was completed. The reaction mixture was acidified to pH 5~6 with 1N HCl. The solvent was removed in vacuo and the residue was purified by prep-HPLC A (30-60% MeCN) to give the diastereomeric products AC-P1 (42 mg) and AC-P2 (34 mg) as white solids.

AC-P1 ESI 646.3 (M+H)+. $^1$H NMR (400 MHz, MeOD) δ 7.90 (s, 1H), 6.89 (s, 1H), 6.84 (d, J=8.0 Hz, 3H), 6.74 (s, 1H), 5.68 (t, J=8.0 Hz, 1H), 5.57-5.54 (m, 1H), 3.12-3.06 (m, 2H), 2.95 (d, J=7.4 Hz, 2H), 2.78-2.67 (m, 8H), 2.29 (d, J=4.2 Hz, 6H), 2.02-1.93 (m, 5H), 1.77 (s, 3H), 1.47-1.41 (m, 1H), 0.97-0.93 (m, 6H).

AC-P2 ESI 646.3 (M+H)+. $^1$H NMR (400 MHz, MeOD) δ 7.87 (s, 1H), 6.90 (d, J=5.8 Hz, 5H), 5.73-5.70 (m, 1H), 5.62 (t, J=7.6 Hz, 1H), 3.30-3.17 (m, 2H), 3.00 (t, J=6.5 Hz, 2H), 2.82 (s, 6H), 2.66-2.60 (m, 1H), 2.55-2.49 (m, 1H), 2.31 (d, J=7.7 Hz, 6H), 2.01-1.96 (m, 7H), 1.76-1.66 (m, 1H), 1.43-1.36 (m, 1H), 0.93-0.84 (m, 6H).

3-25. Preparation of (3S)-3-(4,4'-difluoro-2',5,6'-trimethyl-[1,1'-biphenyl]-3-yl)-3-(2-(5-(2-(dimethylamino)ethyl)-2-oxo-4-(trifluoromethyl)pyridin-1(2H)-yl)pentanamido)propanoic Acid (Compounds AD-P1 and AD-P2)

Step 1: Ethyl (3S)-3-(4,4'-difluoro-2',5,6'-trimethyl-[1,1'-biphenyl]-3-yl)-3-(2-(5-(2-(dimethylamino)ethyl)-2-oxo-4-(trifluoromethyl)pyridin-1(2H)-yl)pentanamido)propanoate

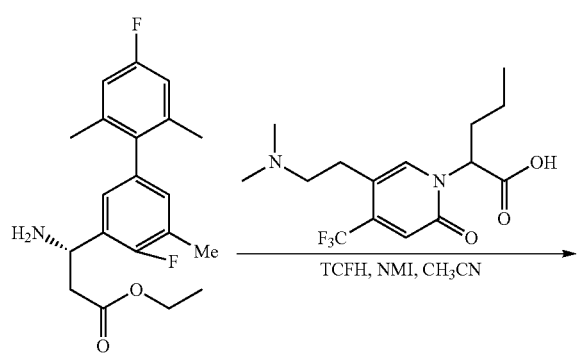

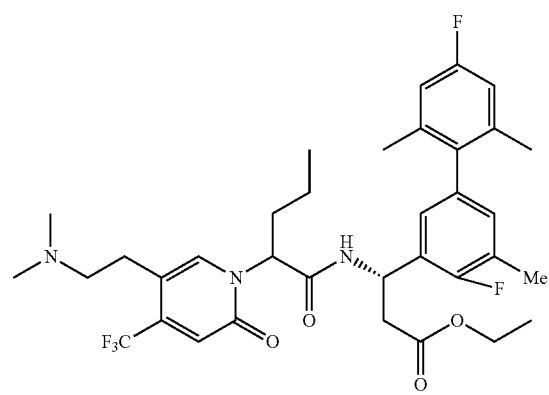

A mixture of ethyl (S)-3-amino-3-(4,4'-difluoro-2',5,6'-trimethyl-[1,1'-biphenyl]-3-yl)propanoate (150 mg, 0.43 mmol), 2-(5-(2-(dimethylamino)ethyl)-2-oxo-4-(trifluoromethyl)pyridin-1(2H)-yl)-4-methylpentanoic acid (174 mg, 0.52 mmol), TCFH (180 mg, 0.64 mmol) and NMI (70 mg, 0.86 mmol) in CH$_3$CN (5 mL) was stirred at 20° C. for 2 hours. The reaction mixture was concentrated in vacuo and purified by reverse phase HPLC on a C18/40 g column (A: water 10 mM NH$_4$HCO$_3$, B: MeOH, 0~100%) to provide ethyl (3S)-3-(4,4'-difluoro-2',5,6'-trimethyl-[1,1'-biphenyl]-3-yl)-3-(2-(5-(2-(dimethylamino)ethyl)-2-oxo-4-(trifluoromethyl)pyridin-1(2H)-yl)pentanamido)propanoate as a yellow oil (200 mg). Yield 70% (ESI 664.3 (M+H)$^+$).

Step 2: (3S)-3-(4,4'-difluoro-2',5,6'-trimethyl-[1,1'-biphenyl]-3-yl)-3-(2-(5-(2-(dimethylamino)ethyl)-2-oxo-4-(trifluoromethyl)pyridin-1(2H)-yl)pentanamido)propanoic acid

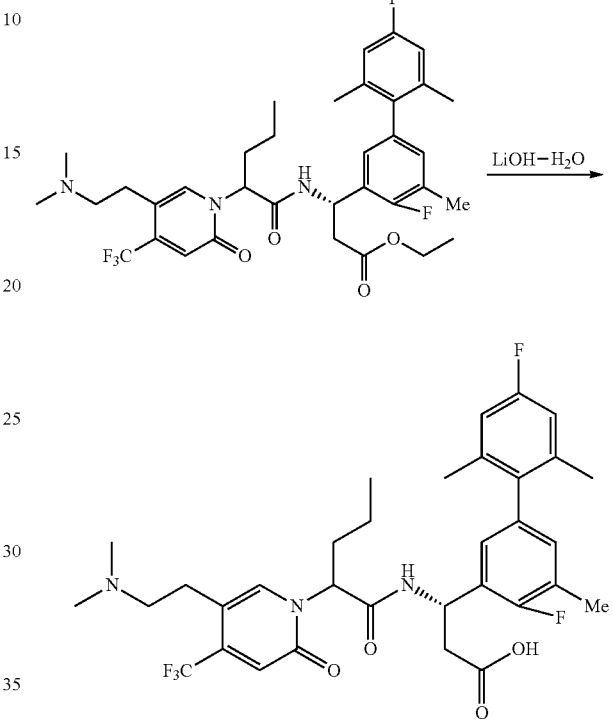

Ethyl (3S)-3-(4,4'-difluoro-2',5,6'-trimethyl-[1,1'-biphenyl]-3-yl)-3-(2-(5-(2-(dimethylamino)ethyl)-2-oxo-4-(trifluoromethyl)pyridin-1(2H)-yl)pentanamido)propanoate (200 mg, 0.3 mmol) was treated with LiOH—H$_2$O (37 mg, 0.9 mmol) in MeOH (2 mL) and H$_2$O (1 mL) at room temperature for 2 hours. The reaction mixture was acidified to pH 4~5 with 1N HCl. The solvent was removed in vacuo and the residue was purified by prep-HPLC A (30-60% MeCN) to give the diastereomeric products AD-P1 (57 mg) and AD-P2 (51 mg) as white solids.

AD-P1 ESI 636.2 (M+H)$^+$. $^1$H NMR (500 MHz, MeOD) δ 7.90 (s, 1H), 6.89-6.77 (m, 4H), 6.74 (s, 1H), 5.58-5.55 (m, 2H), 3.16-3.13 (m, 2H), 2.98-2.95 (m, 2H), 2.81 (s, 6H), 2.75-2.72 (m, 2H), 2.29 (s, 3H), 2.18-2.12 (m, 1H), 2.01-2.00 (m, 4H), 1.82 (m, 3H), 1.36-1.31 (m, 2H), 0.97 (t, J=7.4 Hz, 3H).

AD-P2 ESI 636.2 (M+H)$^+$. $^1$H NMR (500 MHz, MeOD) δ 7.84 (s, 1H), 6.93-6.89 (m, 3H), 6.84 (d, J=9.6 Hz, 2H), 5.72-5.69 (m, 1H), 5.52 (t, J=7.6 Hz, 1H), 3.28-3.22 (m, 2H), 3.02-2.99 (m, 2H), 2.83 (s, 6H), 2.65-2.61 (m, 1H), 2.55-2.50 (m, 1H), 2.32 (t, J=6.4 Hz, 3H), 2.10-2.05 (m, 1H), 2.01 (s, 6H), 1.84-1.79 (m, 1H), 1.25-1.23 (m, 2H), 0.90 (t, J=7.4 Hz, 3H).

3-26. Preparation of (3S)-3-(2',6'-dichloro-4,4'-difluoro-5-methyl-[1,1'-biphenyl]-3-yl)-3-(2-(5-(2-(dimethylamino)ethyl)-2-oxo-4-(trifluoromethyl)pyridin-1(2H)-yl)-4-methylpentanamido)propanoic Acid (Compounds AE-P1 and AE-P2)

Step 1: Ethyl (3S)-3-(2',6'-dichloro-4,4'-difluoro-5-methyl-[1,1'-biphenyl]-3-yl)-3-(2-(5-(2-(dimethylamino)ethyl)-2-oxo-4-(trifluoromethyl)pyridin-1(2H)-yl)-4-methylpentanamido)propanoate

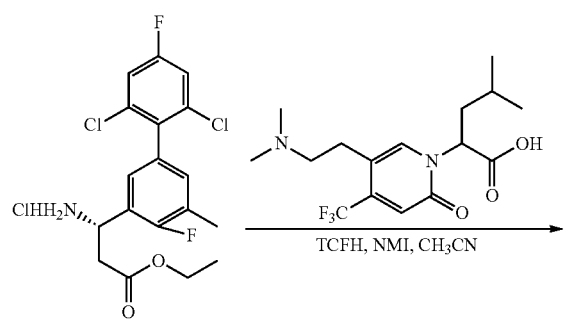

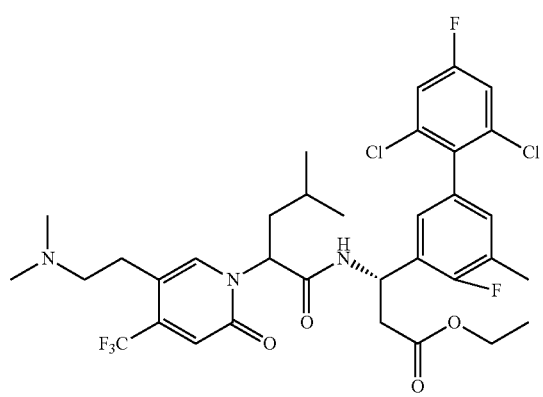

A mixture of ethyl (S)-3-amino-3-(2',6'-dichloro-4,4'-difluoro-5-methyl-[1,1'-biphenyl]-3-yl)propanoate hydrochloride (450 mg, 1.06 mmol), 2-(5-(2-(dimethylamino)ethyl)-2-oxo-4-(trifluoromethyl)pyridin-1(2H)-yl)-4-methylpentanoic acid (370 mg, 1.06 mmol), TCFH (356 mg, 1.27 mmol) and NMI (261 mg, 3.18 mmol) in CH$_3$CN (10 mL) was stirred at room temperature for 1 hour. The solvent was removed in vacuo and the residue was purified by silica gel column (DCM:MeOH 4:1) to provide ethyl (3S)-3-(2',6'-dichloro-4,4'-difluoro-5-methyl-[1,1'-biphenyl]-3-yl)-3-(2-(5-(2-(dimethylamino)ethyl)-2-oxo-4-(trifluoromethyl)pyridin-1(2H)-yl)-4-methylpentanamido)propanoate as a brown solid (610 mg). Yield 80% (ESI 718.0 (M+H)$^+$).

Step 2: (3S)-3-(2',6'-dichloro-4,4'-difluoro-5-methyl-[1,1'-biphenyl]-3-yl)-3-(2-(5-(2-(dimethylamino)ethyl)-2-oxo-4-(trifluoromethyl)pyridin-1(2H)-yl)-4-methylpentanamido)propanoic Acid

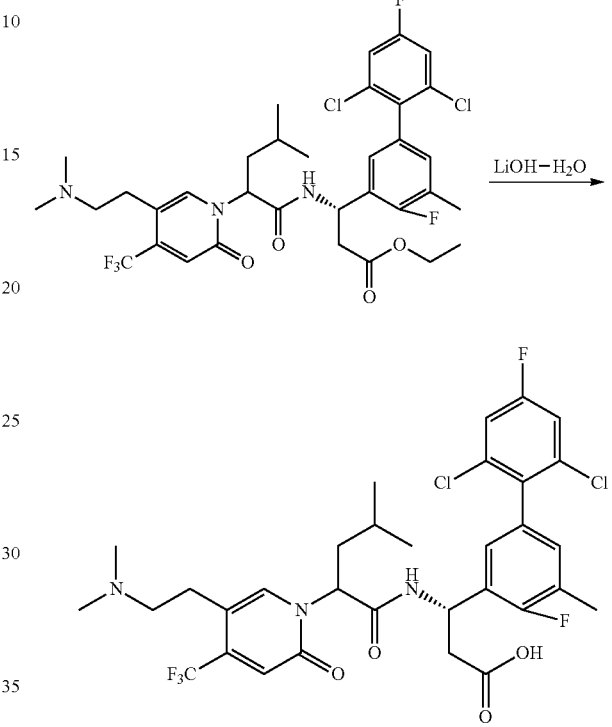

Ethyl (3S)-3-(2',6'-dichloro-4,4'-difluoro-5-methyl-[1,1'-biphenyl]-3-yl)-3-(2-(5-(2-(dimethylamino)ethyl)-2-oxo-4-(trifluoromethyl)pyridin-1(2H)-yl)-4-methylpentanamido)propanoate (110 mg, 0.15 mmol) was treated with LiOH—H$_2$O (32 mg, 0.75 mmol) in THF (3 mL) and H$_2$O (1 mL) at room temperature for 3 hours. The reaction mixture was acidified to pH 4~5 with 1N HCl. The solvent was removed in vacuo and the residue was purified by prep-HPLC A (30-60% MeCN) to provide the diastereomeric products AE-P1 (29.0 mg) and AE-P2 (31.0 mg) as white solids.

AE-P1 ESI 690.0 (M+H)$^+$. $^1$H NMR (400 MHz, MeOD) δ 7.89 (s, 1H), 7.38-7.5 (m, 1H), 7.29-7.25 (m, 1H), 6.99 (t, J=7.5 Hz, 2H), 6.77 (s, 1H), 5.71 (t, J=8.0 Hz, 1H), 5.60-5.56 (m, 1H), 3.05-2.91 (m, 4H), 2.80-2.60 (m, 8H), 2.29 (t, J=0.8 Hz, 3H), 1.99 (t, J=7.5 Hz, 2H), 1.49-1.42 (m, 1H), 0.98-0.93 (m, 6H).

AE-P2 ESI 690.0 (M+H)$^+$. $^1$H NMR (400 MHz, MeOD) δ 7.88 (s, 1H), 7.37 (t, J=9.0 Hz, 2H), 7.09-7.03 (m, 2H), 6.92 (s, 1H), 5.76-5.72 (m, 1H), 5.65 (t, J=7.7 Hz, 1H), 3.29-3.10 (m, 2H), 3.00 (t, J=6.6 Hz, 2H), 2.80 (s, 6H), 2.66-2.61 (m, 1H), 2.56-2.50 (m, 1H), 2.34 (d, J=1.4 Hz, 3H), 2.01-1.94 (m, 1H), 1.77-1.61 (m, 1H), 1.43-1.37 (m, 1H), 0.90-0.87 (m, 6H).

3-27. Preparation of (3S)-3-(2-(5-(2-(azetidin-1-yl)ethyl)-2-oxo-4-(trifluoromethyl)pyridin-1(2H)-yl)-4-methylpentanamido)-3-(3',4-difluoro-2',5,6'-trimethyl-[1,1'-biphenyl]-3-yl)propanoic Acid (Compounds AF-P1 and AF-P2)

Step 1: Ethyl (3S)-3-(2-(5-(2-(azetidin-1-yl)ethyl)-2-oxo-4-(trifluoromethyl)pyridin-1(2H)-yl)-4-methylpentanamido)-3-(3',4-difluoro-2',5,6'-trimethyl-[1,1'-biphenyl]-3-yl)propanoate

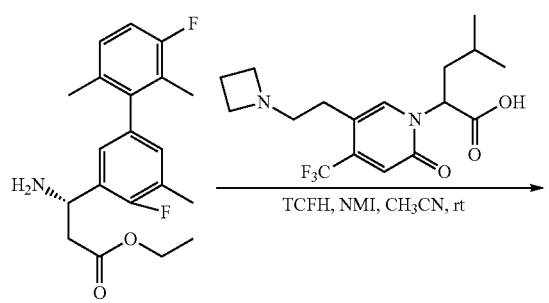

A mixture of ethyl (S)-3-amino-3-(3',4-difluoro-2',5,6'-trimethyl-[1,1'-biphenyl]-3-yl)propanoate (120.0 mg, 0.34 mmol), 2-(5-(2-(azetidin-1-yl)ethyl)-2-oxo-4-(trifluoromethyl)pyridin-1(2H)-yl)-4-methylpentanoic acid (122.4 mg, 0.34 mmol), TCFH (190.4 mg, 0.68 mmol), NMI (115.5 mg, 1.36 mmol) in CH$_3$CN (5 mL) was stirred at room temperature for 2 hours. The solvent was concentrated in vacuo and the residue was purified by reverse phase HPLC on a C18/40 g column (A: water 10 mM NH$_4$HCO$_3$, B: MeOH, 0~100%) to provide ethyl (3S)-3-(2-(5-(2-(azetidin-1-yl)ethyl)-2-oxo-4-(trifluoromethyl)pyridin-1(2H)-yl)-4-methylpentanamido)-3-(3',4-difluoro-2',5,6'-trimethyl-[1,1'-biphenyl]-3-yl)propanoate as a white oil (90.0 mg). Yield 38% (ESI 690.3 (M+H)$^+$).

Step 2: (3S)-3-(2-(5-(2-(azetidin-1-yl)ethyl)-2-oxo-4-(trifluoromethyl)pyridin-1(2H)-yl)-4-methylpentanamido)-3-(3',4-difluoro-2',5,6'-trimethyl-[1,1'-biphenyl]-3-yl)propanoic Acid

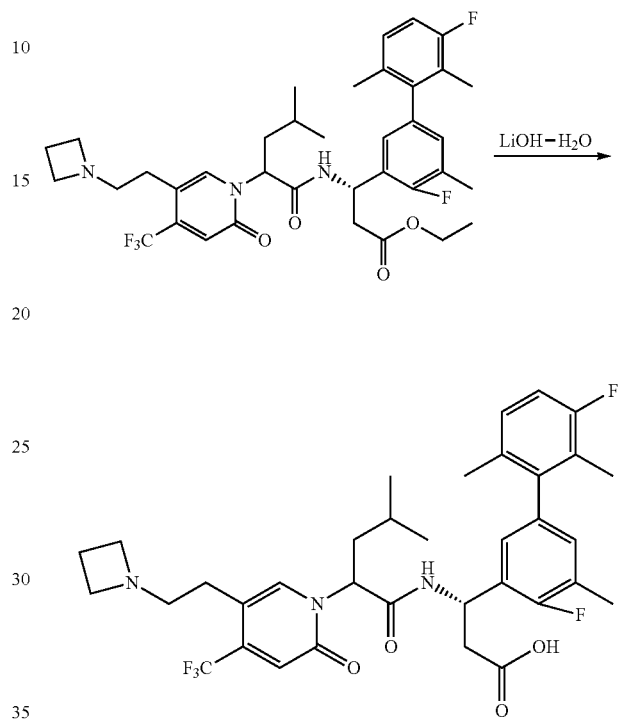

Ethyl (3S)-3-(2-(5-(2-(azetidin-1-yl)ethyl)-2-oxo-4-(trifluoromethyl)pyridin-1(2H)-yl)-4-methylpentanamido)-3-(3',4-difluoro-2',5,6'-trimethyl-[1,1'-biphenyl]-3-yl)propanoate (90 mg, 0.13 mmol) was treated with LiOH—H$_2$O (22 mg, 0.52 mmol) in MeOH (4 mL) and H$_2$O (1 mL) at room temperature for 2 hours. The reaction mixture was acidified to pH 4~5 with 1N HCl. The solvent was removed in vacuo and the residue was purified by prep-HPLC A (30-60% MeCN) to provide the diastereomeric products AF-P1 (15 mg) and AF-P2 (15 mg) as white solids.

AF-P1 ESI 662.2 (M+H)$^+$. $^1$H NMR (400 MHz, MeOD) δ 7.84 (s, 1H), 7.14-7.01 (m, 1H), 7.00-6.84 (m, 3H), 6.79 (d, J=7.3 Hz, 1H), 5.70-5.51 (m, 2H), 4.13-3.94 (m, 4H), 3.28-3.18 (m, 2H), 2.86 (t, J=6.9 Hz, 2H), 2.72 (d, J=6.5 Hz, 2H), 2.54-2.37 (m, 2H), 2.31 (s, 3H), 2.06-1.95 (m, 3H), 1.96-1.70 (m, 5H), 1.50-1.32 (m, 1H), 1.01-0.83 (m, 6H).

AF-P2 ESI 662.2 (M+H)$^+$. $^1$H NMR (400 MHz, MeOD) δ 7.74 (s, 1H), 7.19-7.04 (m, 1H), 7.03-6.82 (m, 4H), 5.85-5.70 (m, 1H), 5.61 (t, J=7.6 Hz, 1H), 4.13 (t, J=7.5 Hz, 4H), 3.41 (s, 2H), 2.94 (d, J=15.8 Hz, 1H), 2.87-2.73 (m, 1H), 2.70-2.58 (m, 1H), 2.56-2.40 (m, 3H), 2.35 (d, J=1.5 Hz, 3H), 2.00 (t, J=7.6 Hz, 4H), 1.94-1.85 (m, 3H), 1.73-1.57 (m, 1H), 1.48-1.36 (m, 1H), 0.91 (d, J=6.6 Hz, 6H).

3-28. Preparation of (3S)-3-(2-(5-(2-(azetidin-1-yl)ethyl)-2-oxo-4-(trifluoromethyl)pyridin-1(2H)-yl)-4-methylpentanamido)-3-(4-fluoro-3'-methoxy-2',5,6'-trimethyl-[1,1'-biphenyl]-3-yl)propanoic Acid (Compounds AG-P1 and AG-P2)

Step 1: Ethyl (3S)-3-(2-(5-(2-(azetidin-1-yl)ethyl)-2-oxo-4-(trifluoromethyl)pyridin-1(2H)-yl)-4-methylpentanamido)-3-(4-fluoro-3'-methoxy-2',5,6'-trimethyl-[1,1'-biphenyl]-3-yl)propanoate

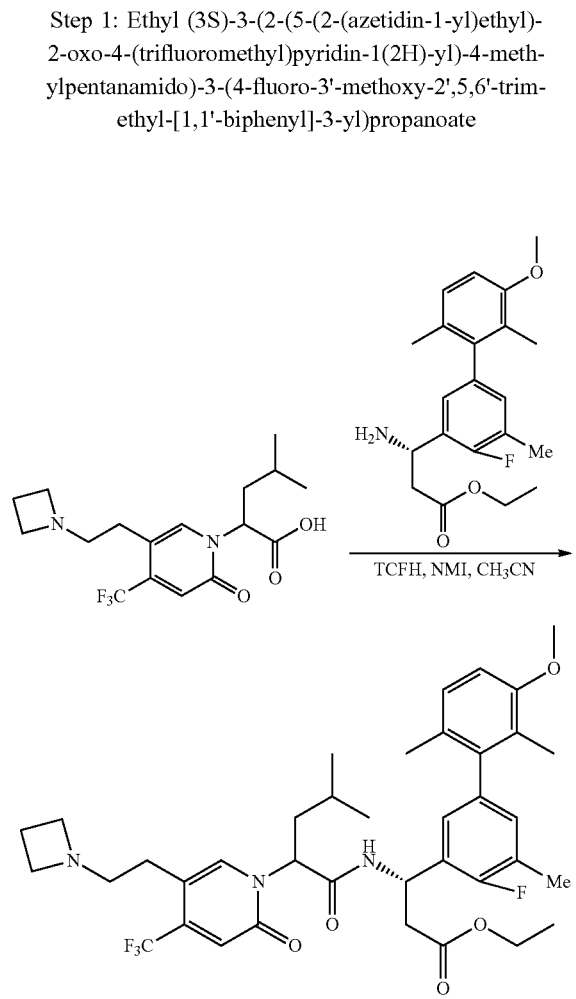

A mixture of 2-(5-(2-(azetidin-1-yl)ethyl)-2-oxo-4-(trifluoromethyl)pyridin-1(2H)-yl)-4-methylpentanoic acid (160 mg, 0.44 mmol, 1.0 eq), ethyl (S)-3-amino-3-(4-fluoro-3'-methoxy-2',5,6'-trimethyl-[1,1'-biphenyl]-3-yl)propanoate (158 mg, 0.44 mmol, 1.0 eq), N,N,N,N-Tetramethylchloroformamidinium hexafluorophosphate (246 mg, 0.88 mmol, 2 eq) and NMI (144 mg, 1.76 mmol, 4.0 eq) in $CH_3CN$ (5 mL) was stirred at room temperature for 2 hours. LCMS showed that the reaction was completed. The solvent was concentrated in vacuo and the residue was purified by reverse phase HPLC on a C18/40 g column (A: water 10 mM $NH_4HCO_3$, B: MeOH, 0~100%) to provide ethyl (3S)-3-(2-(5-(2-(azetidin-1-yl)ethyl)-2-oxo-4-(trifluoromethyl)pyridin-1(2H)-yl)-4-methylpentanamido)-3-(4-fluoro-3'-methoxy-2',5,6'-trimethyl-[1,1'-biphenyl]-3-yl)propanoate as a yellow solid (170 mg). Yield 55% (ESI 702.1 $[M+H]^+$).

Step 2: (3S)-3-(2-(5-(2-(azetidin-1-yl)ethyl)-2-oxo-4-(trifluoromethyl)pyridin-1(2H)-yl)-4-methylpentanamido)-3-(4-fluoro-3'-methoxy-2',5,6'-trimethyl-[1,1'-biphenyl]-3-yl)propanoic Acid

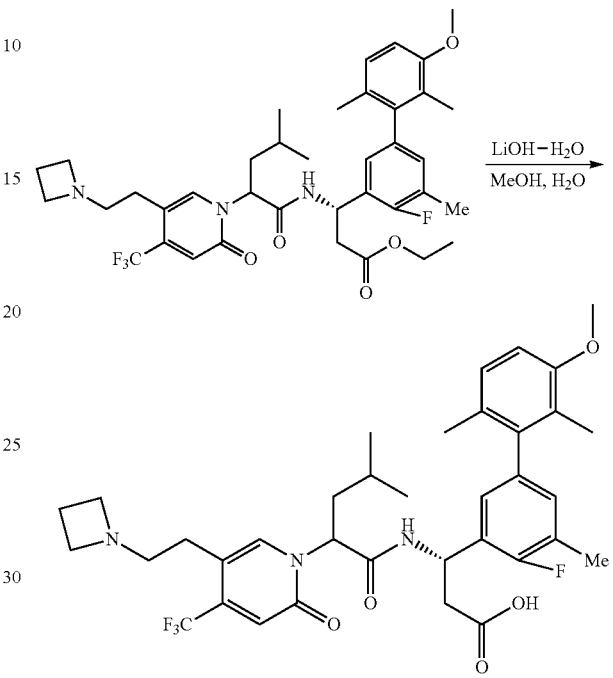

Ethyl (3S)-3-(2-(5-(2-(azetidin-1-yl)ethyl)-2-oxo-4-(trifluoromethyl)pyridin-1(2H)-yl)-4-methylpentanamido)-3-(4-fluoro-3'-methoxy-2',5,6'-trimethyl-[1,1'-biphenyl]-3-yl)propanoate (170 mg, 0.24 mmol, 1.0 eq) was treated with LiOH—$H_2O$ (40 mg, 0.96 mmol, 4.0 eq) in MeOH (4 mL) and water (1 mL) at 30° C. for 1 hour. LCMS showed that the reaction was completed. The reaction mixture was acidified to pH 5~6 with 1N HCl. The solvent was removed in vacuo and the residue was purified by prep-HPLC A (30-60% MeCN) to provide the diastereomeric products AG-P1 (50.8 mg) and AG-P2 (60 mg) as white solids.

AG-P1 ESI 674.3 (M+H)+. $^1$H NMR (500 MHz, MeOD) δ 7.83 (s, 1H), 7.03 (t, J=7.8 Hz, 1H), 6.92-6.76 (m, 4H), 5.63-5.59 (m, 2H), 4.03-3.97 (m, 4H), 3.83 (s, 3H), 3.32-3.24 (m, 2H), 2.86 (t, J=6.7 Hz, 2H), 2.72-2.70 (m, 2H), 2.49-2.37 (m, 2H), 2.30 (s, 3H), 1.99 (t, J=7.6 Hz, 2H), 1.89 (d, J=37.2 Hz, 3H), 1.78 (d, J=34.9 Hz, 3H), 1.49-1.34 (m, 1H), 0.96-0.92 (m, 6H).

AG-P2 ESI 674.2 (M+H)+. $^1$H NMR (500 MHz, MeOD) δ 7.74 (s, 1H), 7.06 (d, J=8.3 Hz, 1H), 6.94-6.89 (m, 3H), 6.84 (d, J=8.4 Hz, 1H), 5.79-5.76 (m, 1H), 5.60 (t, J=7.6 Hz, 1H), 4.14 (t, J=8.0 Hz, 4H), 3.84 (d, J=1.1 Hz, 3H), 3.50-3.40 (m, 1H), 3.36 (d, J=9.5 Hz, 1H), 2.94 (d, J=16.2 Hz, 1H), 2.86-2.76 (m, 1H), 2.69-2.61 (m, 1H), 2.57-2.44 (m, 3H), 2.34 (d, J=1.3 Hz, 3H), 2.05-1.96 (m, 1H), 1.93 (d, J=6.2 Hz, 3H), 1.86 (d, J=4.9 Hz, 3H), 1.68-1.63 (m, 1H), 1.45-1.40 (m, 1H), 0.90 (d, J=6.3 Hz, 6H).

3-29. Preparation of (3S)-3-(2-(5-(2-(dimethylamino)ethyl)-2-oxo-4-(trifluoromethyl)pyridin-1(2H)-yl)-4-methylpentanamido)-3-(2'-ethyl-4-fluoro-5,6'-dimethyl-[1,1'-biphenyl]-3-yl)propanoic Acid (Compounds AH-P1 and AH-P2)

Step 1: Ethyl (3S)-3-(2-(5-(2-(dimethylamino)ethyl)-2-oxo-4-(trifluoromethyl)pyridin-1(2H)-yl)-4-methylpentanamido)-3-(2'-ethyl-4-fluoro-5,6'-dimethyl-[1,1'-biphenyl]-3-yl)propanoate

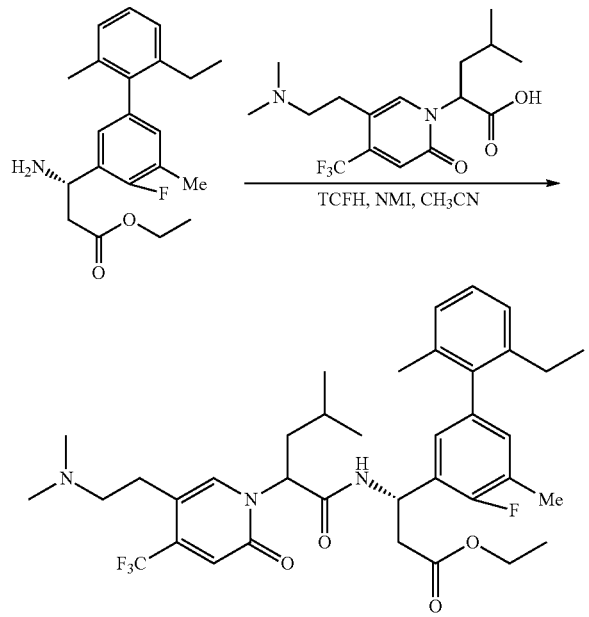

A mixture of ethyl (S)-3-amino-3-(2'-ethyl-4-fluoro-5,6'-dimethyl-[1,1'-biphenyl]-3-yl)propanoate (150 mg, 0.43 mmol), 2-(5-(2-(dimethylamino)ethyl)-2-oxo-4-(trifluoromethyl)pyridin-1(2H)-yl)-4-methylpentanoic acid (101 mg, 0.52 mmol), TCFH (180 mg, 0.64 mmol) and NMI (70 mg, 0.86 mmol) in CH$_3$CN (5 mL) was stirred at 20° C. for 2 hours. The solvent was concentrated in vacuo and the residue was purified by reverse phase HPLC on a C18/40 g column (A: water 10 mM NH$_4$HCO$_3$, B: MeOH, 0~100%) to provide ethyl (3S)-3-(2-(5-(2-(dimethylamino)ethyl)-2-oxo-4-(trifluoromethyl)pyridin-1(2H)-yl)-4-methylpentanamido)-3-(2'-ethyl-4-fluoro-5,6'-dimethyl-[1,1'-biphenyl]-3-yl)propanoate as a yellow oil (180 mg). Yield 62% (ESI 674.2 (M+H)$^+$).

Step 2: (3S)-3-(2-(5-(2-(dimethylamino)ethyl)-2-oxo-4-(trifluoromethyl)pyridin-1(2H)-yl)-4-methylpentanamido)-3-(2'-ethyl-4-fluoro-5,6'-dimethyl-[1,1'-biphenyl]-3-yl)propanoic Acid

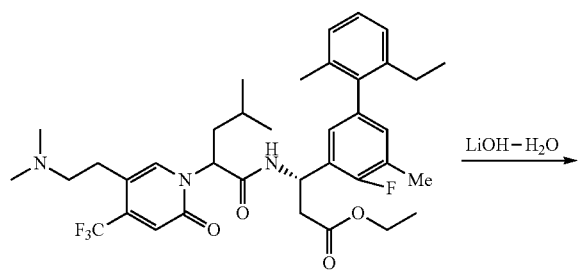

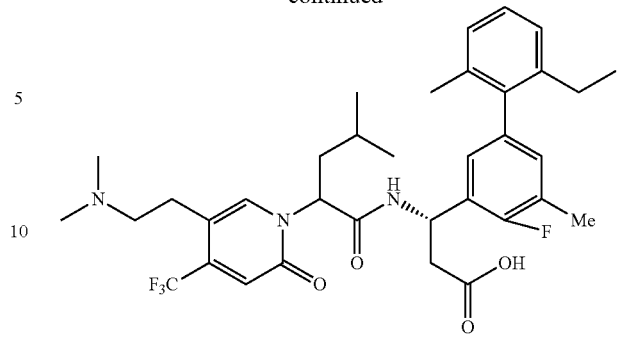

Ethyl (3S)-3-(2-(5-(2-(dimethylamino)ethyl)-2-oxo-4-(trifluoromethyl)pyridin-1(2H)-yl)-4-methylpentanamido)-3-(2'-ethyl-4-fluoro-5,6'-dimethyl-[1,1'-biphenyl]-3-yl)propanoate (150 mg, 0.22 mmol) was treated with LiOH—H$_2$O (28 mg, 0.66 mmol) in MeOH (2 mL) and H$_2$O (1 mL) at room temperature for 2 hours. The reaction mixture was acidified to pH 4-5 with 1N HCl. The solvent was removed in vacuo and the residue was purified by prep-HPLC A (30-60% MeCN) to give the diastereomeric products AH-P1 (66 mg) and AH-P2 (46 mg) as white solids.

AH-P1 ESI 646.3 (M+H)$^+$. $^1$H NMR (400 MHz, MeOD) δ 7.90 (s, 1H), 7.16-7.05 (m, 3H), 6.90-6.86 (m, 2H), 6.76 (d, J=7.9 Hz, 1H), 5.70-5.57 (m, 2H), 3.09 (d, J=7.1 Hz, 2H), 2.95 (d, J=7.2 Hz, 2H), 2.75-2.70 (m, 8H), 2.34-2.29 (m, 4H), 2.20-2.18 (m, 1H), 2.00-1.96 (m, 3H), 1.79 (s, 1H), 1.47-1.39 (m, 1H), 1.02-0.92 (m, 8H), 0.83 (t, J=7.5 Hz, 2H).

AH-P2 ESI 646.3 (M+H)$^+$. $^1$H NMR (400 MHz, MeOD) δ 7.84 (d, J=6.6 Hz, 1H), 7.18 (t, J=7.5 Hz, 1H), 7.12-7.07 (m, 2H), 6.96-6.89 (m, 3H), 5.74-5.70 (m, 1H), 5.61 (t, J=7.6 Hz, 1H), 3.31-3.14 (m, 2H), 3.00 (t, J=6.7 Hz, 2H), 2.81 (d, J=1.2 Hz, 6H), 2.62-2.61 (m, 1H), 2.57-2.44 (m, 1H), 2.36-2.31 (m, 5H), 2.00-1.97 (m, 4H), 1.71-1.65 (m, 1H), 1.42-1.37 (m, 1H), 1.02-0.98 (m, 3H), 0.88 (d, J=6.5 Hz, 6H).

3-30. Preparation of (3S)-3-(5-chloro-4-fluoro-2',4',6'-trimethyl-[1,1'-biphenyl]-3-yl)-3-(2-(5-(2-(dimethylamino)ethyl)-2-oxo-4-(trifluoromethyl)pyridin-1(2H)-yl)-4-methylpentanamido)propanoic Acid (Compounds AI-P1 and AI-P2)

Step 1: Ethyl (3S)-3-(5-chloro-4-fluoro-2',4',6'-trimethyl-[1,1'-biphenyl]-3-y)-3-(2-(5-(2-(dimethylamino)ethyl)-2-oxo-4-(trifluoromethyl)pyridin-1(2H)-yl)-4-methylpentanamido)propanoate

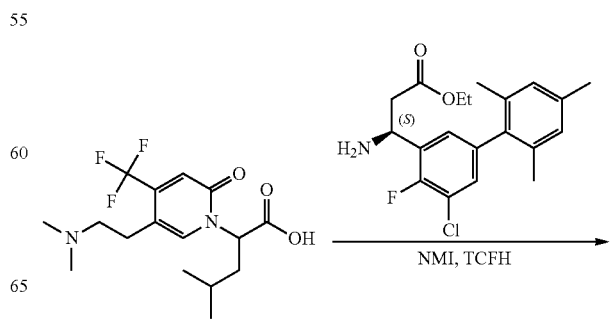

-continued

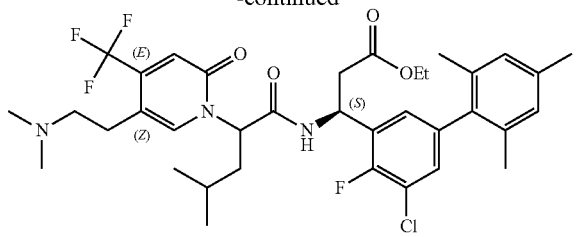

A mixture of 2-(5-(2-(dimethylamino)ethyl)-2-oxo-4-(trifluoromethyl)pyridin-1(2H)-yl)-4-methylpentanoic acid (120 mg, 0.34 mmol), ethyl (S)-3-amino-3-(5-chloro-4-fluoro-2',4',6'-trimethyl-[1,1'-biphenyl]-3-yl)propanoate (145 mg, 0.40 mmol), TCFH (142 mg, 0.51 mmol), NMI (139.4 mg, 1.7 mmol) in CH₃CN (4 mL) was stirred at room temperature for 1 hour. The solvent was concentrated in vacuo and the residue was by reverse phase HPLC on a C18/40 g column (A: water 10 mM NH₄HCO₃, B: MeOH, 0~100%) to provide ethyl (3S)-3-(5-chloro-4-fluoro-2',4',6'-trimethyl-[1,1'-biphenyl]-3-yl)-3-(2-(5-(2-(dimethylamino)ethyl)-2-oxo-4-(trifluoromethyl)pyridin-1(2H)-yl)-4-methylpentanamido)propanoate as a red oil (175 mg). Yield 74% (ESI 694.2 (M+H)⁺).

Step 2: (3S)-3-(5-chloro-4-fluoro-2',4',6'-trimethyl-[1,1'-biphenyl]-3-yl)-3-(2-(5-(2-(dimethylamino)ethyl)-2-oxo-4-(trifluoromethyl)pyridin-1(2H)-yl)-4-methylpentanamido)propanoic Acid

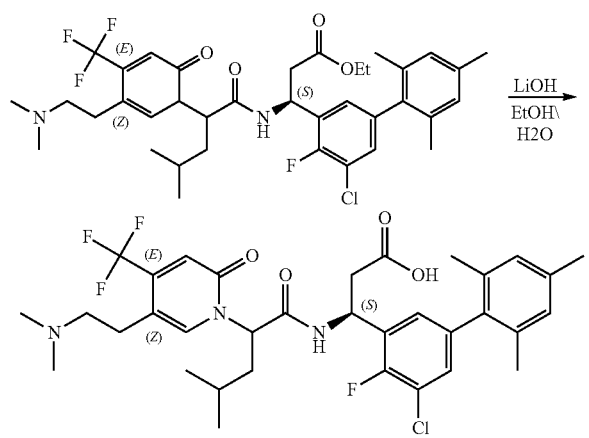

Ethyl (3S)-3-(5-chloro-4-fluoro-2',4',6'-trimethyl-[1,1'-biphenyl]-3-yl)-3-(2-(5-(2-(dimethylamino)ethyl)-2-oxo-4-(trifluoromethyl)pyridin-1(2H)-yl)-4-methylpentanamido)propanoate (175 mg, 0.25 mmol) was treated with LiOH—H₂O (52.5 mg, 1.25 mmol) in EtOH (3 mL) and H₂O (1 mL) at room temperature for 2 hours. The reaction mixture was acidified to pH 4~5 with 1N HCl. The solvent was removed in vacuo and the residue was purified by prep-HPLC A (30-60% MeCN) to give the diastereomeric products AI-P1 (29 mg) and AI-P2 (23 mg) as white solids.

AI-P1 ESI 666.2 (M+H)⁺. ¹H NMR (400 MHz, MeOD) δ 7.90 (s, 1H), 7.08-7.06 (m, 1H), 7.01-6.98 (m, 1H), 6.92 (s, 1H), 6.87 (s, 1H), 6.71 (s, 1H), 5.70-5.65 (m, 1H), 5.56-5.62 (m, 1H), 3.17-2.89 (m, 4H), 2.82-2.63 (m, 8H), 2.30 (s, 3H), 2.08-1.91 (m, 5H), 1.76 (s, 3H), 1.52-1.38 (m, 1H), 1.03-0.83 (m, 6H).

AI-P2 ESI 666.2 (M+H)⁺. ¹H NMR (400 MHz, MeOD) δ 7.89 (s, 1H), 7.16-7.13 (m, 1H), 7.08-67.05 (m, 1H), 6.93 (s, 2H), 6.89 (s, 1H), 5.77-5.54 (m, 2H), 3.28-3.17 (m, 2H), 3.02-2.98 (m, 2H), 2.83 (s, 6H), 2.71-2.47 (m, 2H), 2.31 (s, 3H), 2.11-1.87 (m, 7H), 1.83-1.64 (m, 1H), 1.46-1.23 (m, 1H), 1.06-0.62 (m, 6H).

3-31. Preparation of (3S)-3-(2-(5-(2-(azetidin-1-yl)ethyl)-2-oxo-4-(trifluoromethyl)pyridin-1(2H)-yl)-4-methylpentanamido)-3-(2',4-difluoro-4',5,6'-trimethylbiphenyl-3-yl)propanoic Acid (Compounds AJ-P1 and AJ-P2)

Step 1: Ethyl (3S)-3-(2-(5-(2-(azetidin-1-yl)ethyl)-2-oxo-4-(trifluoromethyl)pyridin-1(2H)-yl)-4-methylpentanamido)-3-(2',4-difluoro-4',5,6'-trimethyl-[1,1'-biphenyl]-3-y)propanoate

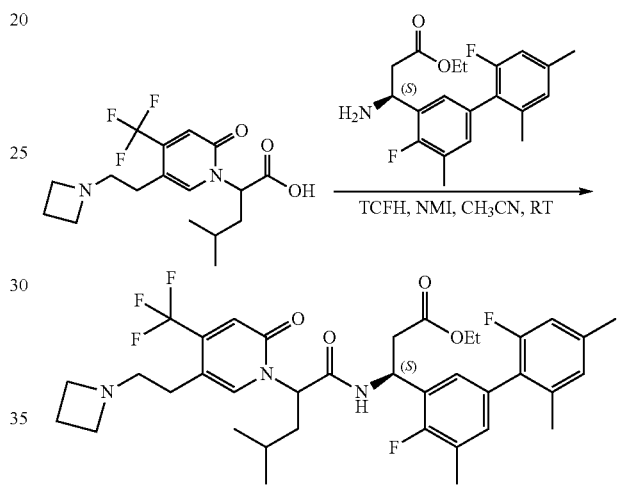

A mixture of 2-(5-(2-(azetidin-1-yl)ethyl)-2-oxo-4-(trifluoromethyl)pyridin-1(2H)-yl)-4-methylpentanoic acid (150 mg, 0.42 mmol), ethyl (S)-3-amino-3-(2',4-difluoro-4',5,6'-trimethyl-[1,1'-biphenyl]-3-yl)propanoate (145 mg, 0.42 mmol), TCFH (141 mg, 0.50 mmol) and NMI (104 mg, 1.26 mmol) in CH₃CN (5 mL) was stirred at room temperature for 1 hour. The solvent was removed in vacuo and the residue was purified by silica gel column (DCM:MeOH 4:1) to provide ethyl (3S)-3-(2-(5-(2-(azetidin-1-yl)ethyl)-2-oxo-4-(trifluoromethyl)pyridin-1(2H)-yl)-4-methylpentanamido)-3-(2',4-difluoro-4',5,6'-trimethyl-[1,1'-biphenyl]-3-yl)propanoate as a white solid (130 mg). Yield 45% (ESI 690.3 (M+H)⁺).

Step 2: (3S)-3-(2-(5-(2-(azetidin-1-yl)ethyl)-2-oxo-4-(trifluoromethyl)pyridin-1(2H)-yl)-4-methylpentanamido)-3-(2',4-difluoro-4',5,6'-trimethylbiphenyl-3-yl)propanoic Acid

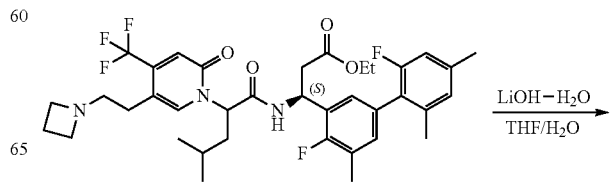

435

-continued

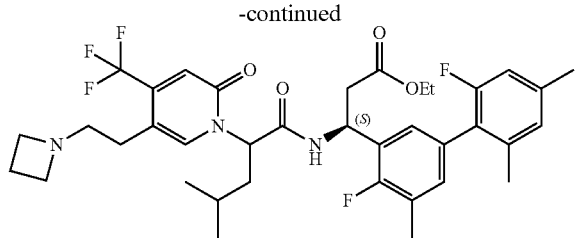

Ethyl (3S)-3-(2-(5-(2-(azetidin-1-yl)ethyl)-2-oxo-4-(trifluoromethyl)pyridin-1(2H)-yl)-4-methylpentanamido)-3-(2',4-difluoro-4',5,6'-trimethyl-[1,1'-biphenyl]-3-yl)propanoate (130 mg, 0.19 mmol) was treated with LiOH—H$_2$O (40 mg, 0.95 mmol) in THF (3 mL) and H$_2$O (1 mL) at room temperature for 3 hours. The reaction mixture was acidified to pH 4-5 with 1N HCl. The solvent was removed in vacuo and the residue was purified by prep-HPLC A (30-60% MeCN) to give the diastereomeric products AJ-P1 (30.0 mg) and AJ-P2 (29.7 mg) as white solids.

AJ-P1 ESI 662.2 (M+H)+. $^1$H NMR (400 MHz, MeOD) δ 7.83 (s, 1H), 6.99 (t, J=6.3 Hz, 2H), 6.92 (s, 1H), 6.79 (t, J=4.9 Hz, 2H), 5.68 (t, J=8.0 Hz, 1H), 5.59 (t, J=6.6 Hz, 1H), 4.00-3.96 (m, 4H), 3.30-3.25 (m, 2H), 2.85 (t, J=6.9 Hz, 2H), 2.72-2.70 (m, 2H), 2.44-2.37 (m, 2H), 2.35 (s, 3H), 2.29 (d, J=1.2 Hz, 3H), 2.05 (s, 3H), 2.00 (t, J=7.6 Hz, 2H), 1.45-1.40 (m, 1H), 0.95 (t, J=7.1 Hz, 6H).

AJ-P2 ESI 662.2 (M+H)+. $^1$H NMR (400 MHz, MeOD) δ 7.76 (s, 1H), 7.08 (d, J=6.5 Hz, 1H), 7.04 (d, J=6.9 Hz, 1H), 6.93 (d, J=8.1 Hz, 2H), 6.82 (d, J=10.4 Hz, 1H), 5.78-5.74 (m, 1H), 5.64 (t, J=7.7 Hz, 1H), 4.11 (t, J=8.0 Hz, 4H), 3.44-3.38 (m, 1H), 2.96-2.89 (m, 1H), 2.84-2.76 (m, 1H), 2.67-2.62 (m, 1H), 2.57-2.43 (i, 3H), 2.35-2.33 (m, 6H), 2.11 (s, 3H), 2.02-1.94 (m, 1H), 1.71-1.64 (m, 1H), 1.44-1.30 (m, 2H), 0.91-0.88 (m, 6H).

3-32. Preparation of (3S)-3-(4,4'-difluoro-2',5,6'-trimethyl-[1,1'-biphenyl]-3-yl)-3-(2-(5-(2-(dimethylamino)ethyl)-2-oxo-4-(trifluoromethyl)pyridin-1(2H)-yl)-4-methylpentanamido)propanoic Acid (Compounds AK-P1 and AK-P2)

Step 1: Ethyl (3S)-3-(4,4'-difluoro-2',5,6'-trimethyl-[1,1'-biphenyl]-3-yl)-3-(2-(5-(2-(dimethylamino)ethyl)-2-oxo-4-(trifluoromethyl)pyridin-1(2H)-yl)-4-methylpentanamido)propanoate

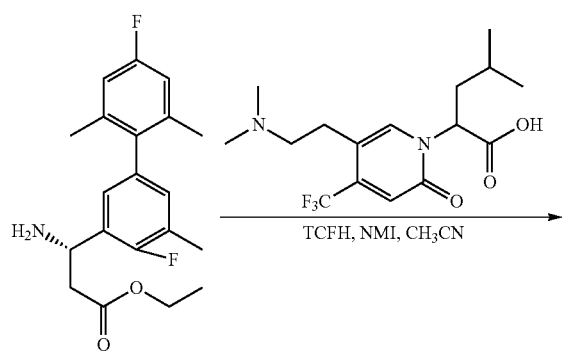

436

-continued

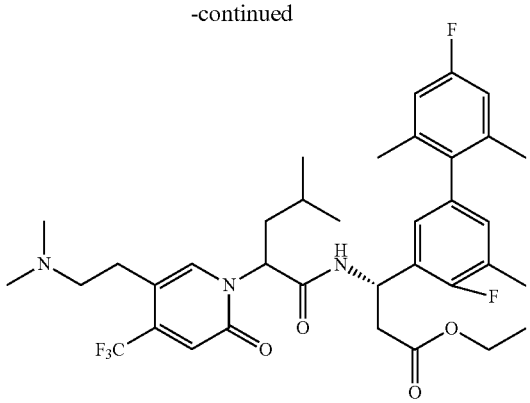

A mixture of ethyl (S)-3-amino-3-(4,4'-difluoro-2',5,6'-trimethyl-[1,1'-biphenyl]-3-yl)propanoate (150 mg, 0.43 mmol), 2-(5-(2-(dimethylamino)ethyl)-2-oxo-4-(trifluoromethyl)pyridin-1(2H)-yl)-4-methylpentanoic acid (180 mg, 0.51 mmol), TCFH (240 mg, 0.86 mmol) and NMI (106 mg, 1.29 mmol) in CH$_3$CN (5 mL) was stirred at 20° C. for 2 hours. The solvent was concentrated in vacuo and the residue was purified by reverse phase HPLC on a C18/40 g column (A: water 10 mM NH$_4$HCO$_3$, B: MeOH, 0~100%) to provide ethyl (3S)-3-(4,4'-difluoro-2',5,6'-trimethyl-[1,1'-biphenyl]-3-yl)-3-(2-(5-(2-(dimethylamino)ethyl)-2-oxo-4-(trifluoromethyl)pyridin-1(2H)-yl)-4-methylpentanamido)propanoate as a yellow oil (120 mg). Yield 41% (ESI 678.1 (M+H)$^+$).

Step 2: (3S)-3-(4,4'-difluoro-2',5,6'-trimethyl-[1,1'-biphenyl]-3-yl)-3-(2-(5-(2-(dimethylamino)ethyl)-2-oxo-4-(trifluoromethyl)pyridin-1(2H)-yl)-4-methylpentanamido)propanoic Acid

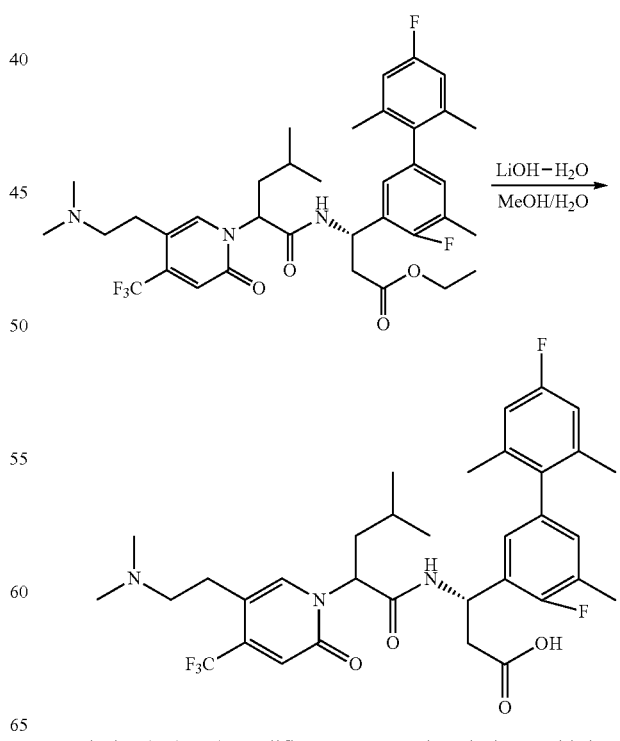

Ethyl (3S)-3-(4,4'-difluoro-2',5,6'-trimethyl-[1,1'-biphenyl]-3-yl)-3-(2-(5-(2-(dimethylamino)ethyl)-2-oxo-4-(trifluoromethyl)pyridin-1(2H)-yl)-4-methylpentanamido)propanoate (100 mg, 0.14 mmol) was treated with LiOH—H₂O (18 mg, 0.44 mmol) in MeOH (2 mL) and H₂O (1 mL) at room temperature for 2 hours. The reaction mixture was acidified to pH 4~5 with 1N HCl. The solvent was removed in vacuo and the residue was purified by prep-HPLC A (30-60% MeCN) to provide the diastereomeric products AK-P1 (36 mg) and AK-P2 (32 mg) as white solids.

AK-P1 ESI 650.3 (M+H)⁺. ¹H NMR (400 MHz, MeOD) δ 7.91 (s, 1H), 6.88-6.74 (m, 5H), 5.69 (t, J=8.1 Hz, 1H), 5.58-5.54 (m, 1H), 3.19-3.07 (m, 2H), 3.02-2.95 (m, 2H), 2.84-2.67 (m, 8H), 2.30 (t, J=8.2 Hz, 3H), 2.03-1.94 (m, 5H), 1.80 (d, J=9.4 Hz, 3H), 1.48-1.39 (m, 1H), 0.97-0.88 (m, 6H).

AK-P2 ESI 650.2 (M+H)⁺. ¹H NMR (400 MHz, MeOD) δ 7.88 (s, 1H), 6.93-6.83 (m, 5H), 5.71-5.62 (m, 2H), 3.19 (s, 2H), 3.00-2.97 (m, 2H), 2.80 (s, 6H), 2.67-2.57 (m, 2H), 2.32 (d, J=1.5 Hz, 3H), 2.01-1.93 (m, 7H), 1.79-1.74 (m, 1H), 1.42-1.35 (m, 1H), 0.90-0.87 (m, 6H).

3-33. Preparation of (3S)-3-(4,4'-difluoro-2',5,6'-trimethyl-[1,1'-biphenyl]-3-yl)-3-(2-(5-(2-(dimethylamino)ethyl)-3-fluoro-4-methyl-2-oxopyridin-1(2H)-yl)-4-methylpentanamido)propanoic Acid (Compounds AL-P1 and AL-P2)

Step 1: Ethyl (S)-3-(4,4'-difluoro-2',5,6'-trimethyl-[1,1'-biphenyl]-3-yl)-3-((S)-2-(5-(2-(dimethylamino)ethyl)-3-fluoro-4-methyl-2-oxopyridin-1(2H)-yl)-4-methylpentanamido)propanoate

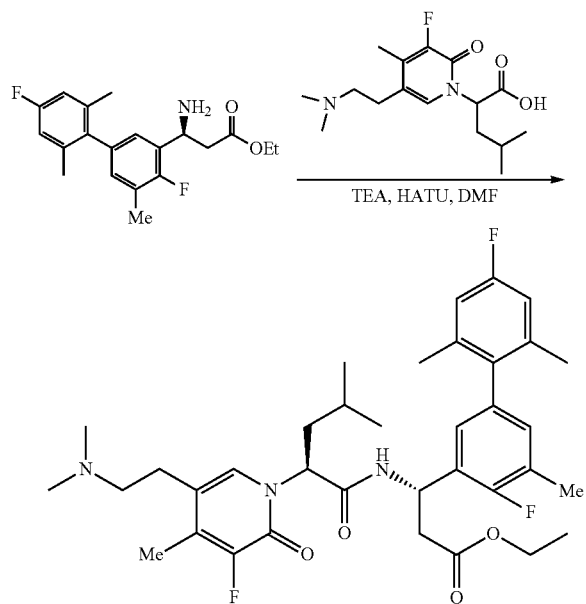

To a solution of 2-(5-(2-(dimethylamino)ethyl)-3-fluoro-4-methyl-2-oxopyridin-1(2H)-yl)-4-methylpentanoic acid (1 g, 3.20 mmol) and HATU (2.434 g, 6.40 mmol) in DMF (16.01 mL) was added TEA (0.892 mL, 6.40 mmol) at room temperature. After stirring for 5 minutes, ethyl (S)-3-amino-3-(4,4'-difluoro-2',5,6'-trimethyl-[1,1'-biphenyl]-3-yl)propanoate (1.668 g, 4.80 mmol) in 5.0 mL DMF was added to the solution. The reaction mixture was diluted with 200 mL of water and 10 mL of brine. The mixture was washed (EtOAc; 200 mL×3). The combined organic phase was dried over Na₂SO₄, concentrated and purified by silica gel column (DCM:MeOH 10:1) to provide ethyl (S)-3-(4,4'-difluoro-2',5,6'-trimethyl-[1,1'-biphenyl]-3-yl)-3-((S)-2-(5-(2-(dimethylamino)ethyl)-3-fluoro-4-methyl-2-oxopyridin-1(2H)-yl)-4-methylpentanamido)propanoate (1.76 g, 86% yield) as pinkish oil. (ESI 642 (M+H)⁺)

Step 2: (3S)-3-(4,4'-difluoro-2',5,6'-trimethyl-[1,1'-biphenyl]-3-yl)-3-(2-(5-(2-(dimethylamino)ethyl)-3-fluoro-4-methyl-2-oxopyridin-1(2H)-yl)-4-methylpentanamido)propanoic Acid

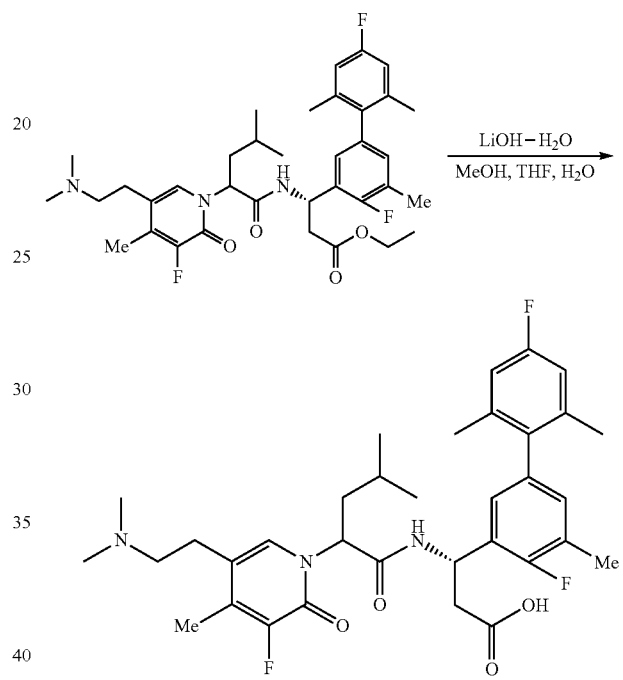

Ethyl (3S)-3-(4,4'-difluoro-2',5,6'-trimethyl-[1,1'-biphenyl]-3-yl)-3-(2-(5-(2-(dimethylamino)ethyl)-3-fluoro-4-methyl-2-oxopyridin-1(2H)-yl)-4-methylpentanamido)propanoate (1.65 g, 2.6 mmol, 1.0 eq) was treated with LiOH monohydrate (391 mg, 9.3 mmol, 4.0 eq) in methanol (5 mL), THF (5 mL) and H₂O (5 mL) at room temperature for 2 hours. The reaction mixture was acidified to pH 4~5 with 1N HCl aqueous solution, concentrated in vacuo and the residue was purified by prep HPLC A to provide the diastereomeric products AL-P1 (383 mg) and AL-P2 (239 mg) as white solids.

AL-P1 ESI 614.2 (M+H)⁺. ¹H NMR (400 MHz, MeOD) δ 7.48 (s, 1H), 6.86-6.81 (m, 4H), 5.66-5.60 (m, 1H), 5.50-5.47 (m, 1H), 3.22-3.12 (m, 2H), 2.93-2.89 (m, 2H), 2.77 (s, 6H), 2.72-2.61 (m, 2H), 2.29 (d, J=1.6 Hz, 3H), 2.25 (d, J=2.8 Hz, 3H), 2.00-1.93 (m, 5H), 1.88 (s, 3H), 1.46-1.36 (m, 1H), 0.95-0.90 (m, 6H).

AL-P2 ESI 614.2 (M+H)⁺. ¹H NMR (400 MHz, MeOD) δ 7.43 (s, 1H), 6.88 (dd, J=24.6, 8.2 Hz, 4H), 5.66-5.57 (m, 2H), 3.27-3.13 (m, 2H), 2.97-2.93 (m, 2H), 2.86 (s, 6H), 2.62-2.57 (m, 1H), 2.51-2.39 (m, 1H), 2.33 (d, J=1.7 Hz, 3H), 2.25 (d, J=2.7 Hz, 3H), 2.05-1.93 (m, 7H), 1.80-1.73 (m, 1H), 1.41-1.34 (m, 1H), 0.91-0.89 (m, 6H).

3-34. Preparation of (3S)-3-(2-(5-(2-(dimethyl-amino)ethyl)-3-fluoro-4-methyl-2-oxopyridin-1(2H)-yl)-4-methylpentanamido)-3-(4-fluoro-2',5,6'-trimethyl-[1,1'-biphenyl]-3-yl)propanoic Acid (Compounds AM-P1 and AM-P2)

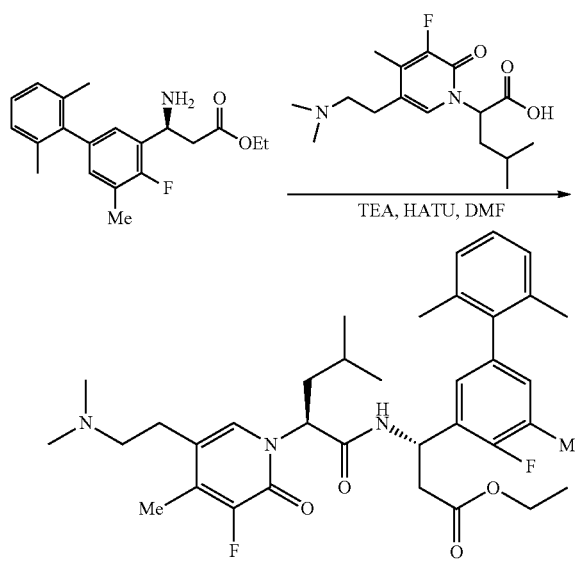

To a solution of 2-(5-(2-(dimethylamino)ethyl)-3-fluoro-4-methyl-2-oxopyridin-1(2H)-yl)-4-methylpentanoic acid (1 g, 3.20 mmol) and HATU (2.434 g, 6.40 mmol) in DMF (16.01 mL) was added TEA (0.892 mL, 6.40 mmol) at room temperature. After stirring for 5 minutes, ethyl (S)-3-amino-3-(4,4'-difluoro-2',5,6'-trimethyl-[1,1'-biphenyl]-3-yl)propanoate (1.668 g, 4.80 mmol) in 5.0 mL DMF was added to the solution. The reaction mixture was diluted with 200 mL of water and 10 mL of brine. The mixture was washed (EtOAc; 200 mL×3). The combined organic phase was dried over Na$_2$SO$_4$, concentrated and purified by silica gel column (DCM:MeOH 10:1) to provide ethyl (S)-3-(4,4'-difluoro-2',5,6'-trimethyl-[1,1'-biphenyl]-3-yl)-3-((S)-2-(5-(2-(dimethylamino)ethyl)-3-fluoro-4-methyl-2-oxopyridin-1(2H)-yl)-4-methylpentanamido)propanoate (1.76 g, 86% yield) as pinkish oil. (ESI 642 (M+H)$^+$)

Step 2: (3S)-3-(4,4'-difluoro-2',5,6'-trimethyl-[1,1'-biphenyl]-3-yl)-3-(2-(5-(2-(dimethylamino)ethyl)-3-fluoro-4-methyl-2-oxopyridin-1(2H)-yl)-4-methyl-pentanamido)propanoic Acid

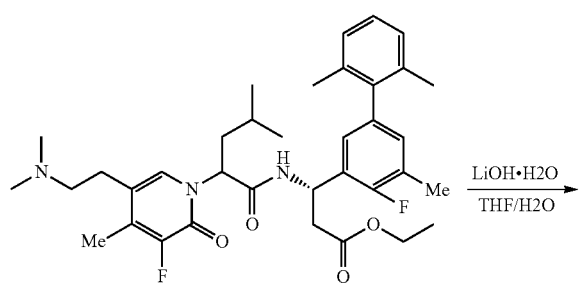

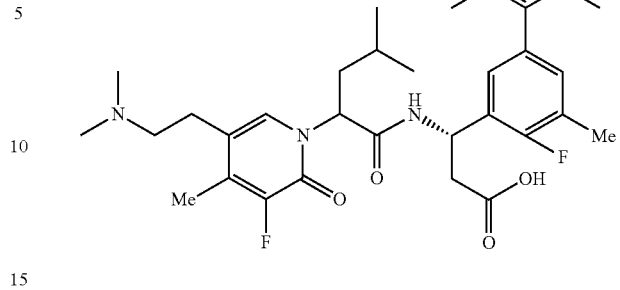

Ethyl (3S)-3-(2-(5-(2-(dimethylamino)ethyl)-3-fluoro-4-methyl-2-oxopyridin-1(2H)-yl)-4-methylpentanamido)-3-(4-fluoro-2',5,6'-trimethyl-[1,1'-biphenyl]-3-yl)propanoate (1.2 g, 1.93 mmol) was treated with LiOH—H$_2$O (162 mg, 3.85 mmol) in THF (12 mL) and H$_2$O (2 mL) at room temperature for 30 mins. The reaction mixture was acidified to pH 4~5 with 2N HCl. The solvent was removed in vacuo and the residue was purified by purified by prep-HPLC A (30-60% MeCN) to give the diastereomeric products AM-P1 (482 mg) and AM-P2 (237 mg) as white solids.

AM-P1 ESI 596.3 (M+H)$^+$. $^1$H NMR (400 MHz, MeOD) δ 7.47 (s, 1H), 7.16-7.01 (m, 3H), 6.90-6.79 (m, 2H), 5.68-5.64 (m, 1H), 5.51-5.48 (m, 1H), 3.17-3.08 (m, 2H), 2.92-2.88 (m, 2H), 2.76 (s, 6H), 2.72-2.44 (m, 2H), 2.29 (s, 3H), 2.23 (d, J=2.6 Hz, 3H), 1.99-1.94 (m, 5H), 1.87 (s, 3H), 1.42-1.38 (m, 1H), 0.94-0.90 (m, 6H).

AM-P2 ESI 596.2 (M+H)$^+$. $^1$H NMR (400 MHz, MeOD) δ 7.39 (s, 1H), 7.15-7.08 (m, 3H), 6.93-6.90 (m, 2H), 5.67-5.60 (m, 2H), 3.32-3.28 (m, 1H), 3.22-3.16 (m, 1H), 2.96-2.92 (m, 2H), 2.84 (s, 6H), 2.63-2.58 (m, 1H), 2.50-2.43 (m, 1H), 2.32 (d, J=1.6 Hz, 3H), 2.24 (d, J=2.8 Hz, 3H), 2.01-1.93 (m, 7H), 1.78-1.71 (m, 1H), 1.41-1.34 (m, 1H), 0.90 (d, J=6.8 Hz, 6H).

3-35. Preparation of (3S)-3-(2-(5-(2-(azetidin-1-yl)ethyl)-2-oxo-4-(trifluoromethyl)pyridin-1(2H)-yl)-4-methylpentanamido)-3-(4-fluoro-2',4',5,6'-tetramethyl-[1,1'-biphenyl]-3-yl)propanoic Acid (Compounds AN-P1 and AN-P2)

Step 1: Ethyl (3S)-3-(2-(5-(2-(azetidin-1-yl)ethyl)-2-oxo-4-(trifluoromethyl)pyridin-1(2H)-yl)-4-methylpentanamido)-3-(4-fluoro-2',4',5,6'-tetramethyl-[1,1'-biphenyl]-3-yl)propanoate

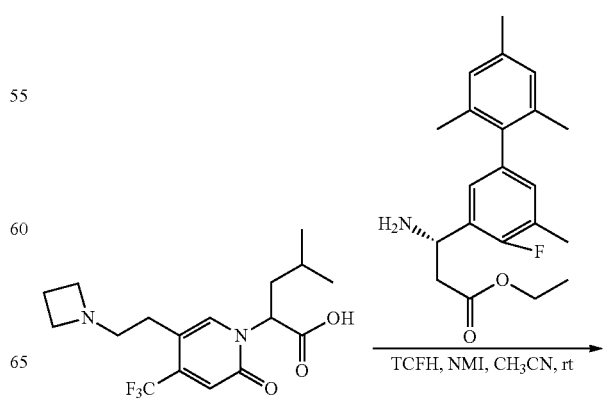

-continued

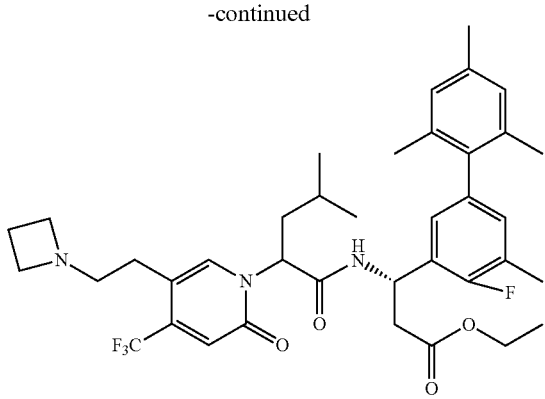

A mixture of 2-(5-(2-(azetidin-1-yl)ethyl)-2-oxo-4-(trifluoromethyl)pyridin-1(2H)-yl)-4-methylpentanoic acid (150 mg, 0.41 mmol), ethyl (S)-3-amino-3-(4-fluoro-2',4',5,6'-tetramethyl-[1,1'-biphenyl]-3-yl)propanoate (141 mg, 0.41 mmol), TCFH (230 mg, 0.82 mmol), NMI (135 mg, 1.64 mmol) in CH$_3$CN (5 mL) was stirred at room temperature for 2 hours. The solvent was concentrated in vacuo and the residue was purified by reverse phase HPLC on a C18/40 g column (A: water 10 mM NH$_4$HCO$_3$, B: MeOH, 0~100%) to provide ethyl (3S)-3-(2-(5-(2-(azetidin-1-yl)ethyl)-2-oxo-4-(trifluoromethyl)pyridin-1(2H)-yl)-4-methylpentanamido)-3-(4-fluoro-2',4',5,6'-tetramethyl-[1,1'-biphenyl]-3-yl)propanoate as a white oil (90 mg). Yield 32% (ESI 686.3 (M+H)$^+$).

Step 2: (3S)-3-(2-(5-(2-(azetidin-1-yl)ethyl)-2-oxo-4-(trifluoromethyl)pyridin-1(2H)-yl)-4-methylpentanamido)-3-(4-fluoro-2',4',5,6'-tetramethyl-[1,1'-biphenyl]-3-yl)propanoic Acid Ethyl (3S)-3-(2-(5-(2-(azetidin-1-yl)ethyl)-2-oxo-4-(trifluoromethyl)pyridin-1(2H)-yl)-4-methylpentanamido)-3-(4-fluoro-2',4',5,6'-tetramethyl-[1,1'-biphenyl]-3-yl)propanoate (90 mg, 0.14 mmol) was treated with LiOH—H$_2$O (24 mg, 0.56 mmol) in MeOH (4 mL) and H$_2$O (1 mL) at room temperature for 2 hours. The reaction mixture was acidified to pH 4~5 with 1N HCl. The solvent was removed in vacuo and the residue was purified by prep-HPLC A (30-60% MeCN) to give the diastereomeric products AN-P1 (22 mg) and AN-P2 (22 mg) as white solids.

AN-P1 ESI 658.3 (M+H)$^+$. $^1$H NMR (400 MHz, MeOD) δ 7.84 (s, 1H), 6.96-6.83 (m, 4H), 6.80 (s, 1H), 5.73-5.50 (m, 2H), 4.03 (s, 4H), 3.15 (s, 2H), 2.86 (t, J=6.7 Hz, 2H), 2.77-2.62 (m, 2H), 2.51-2.38 (m, 2H), 2.30 (s, 6H), 2.09-1.91 (m, 5H), 1.85 (s, 3H), 1.49-1.30 (m, 1H), 1.04-0.83 (m, 6H).

AN-P2 ESI 658.3 (M+H)$^+$. $^1$H NMR (400 MHz, MeOD) δ 7.75 (s, 1H), 6.92 (t, J=7.5 Hz, 5H), 5.84-5.72 (m, 1H), 5.61 (t, J=7.6 Hz, 1H), 4.14 (s, 4H), 3.42 (s, 2H), 2.94 (d, J=16.0 Hz, 2H), 2.87-2.59 (m, 2H), 2.56-2.41 (m, 2H), 2.37-2.25 (m, 6H), 2.05-1.88 (m, 7H), 1.72-1.59 (m, 1H), 1.47-1.34 (m, 1H), 0.96-0.82 (m, 6H).

3-36. Preparation of (3S)-3-(2-(5-(2-(azetidin-1-yl)ethyl)-2-oxo-4-(trifluoromethyl)pyridin-1(2H)-yl)-4-methylpentanamido)-3-(5-chloro-4-fluoro-2',6'-dimethyl-[1,1'-biphenyl]-3-yl)propanoic Acid (Compounds AG-P1 and AO-P2)

Step 1: Ethyl (3S)-3-(2-(5-(2-(azetidin-1-yl)ethyl)-2-oxo-4-(trifluoromethyl)pyridin-1(2H)-yl)-4-methylpentanamido)-3-(5-chloro-4-fluoro-2',6'-dimethyl-[1,1'-biphenyl]-3-yl)propanoate

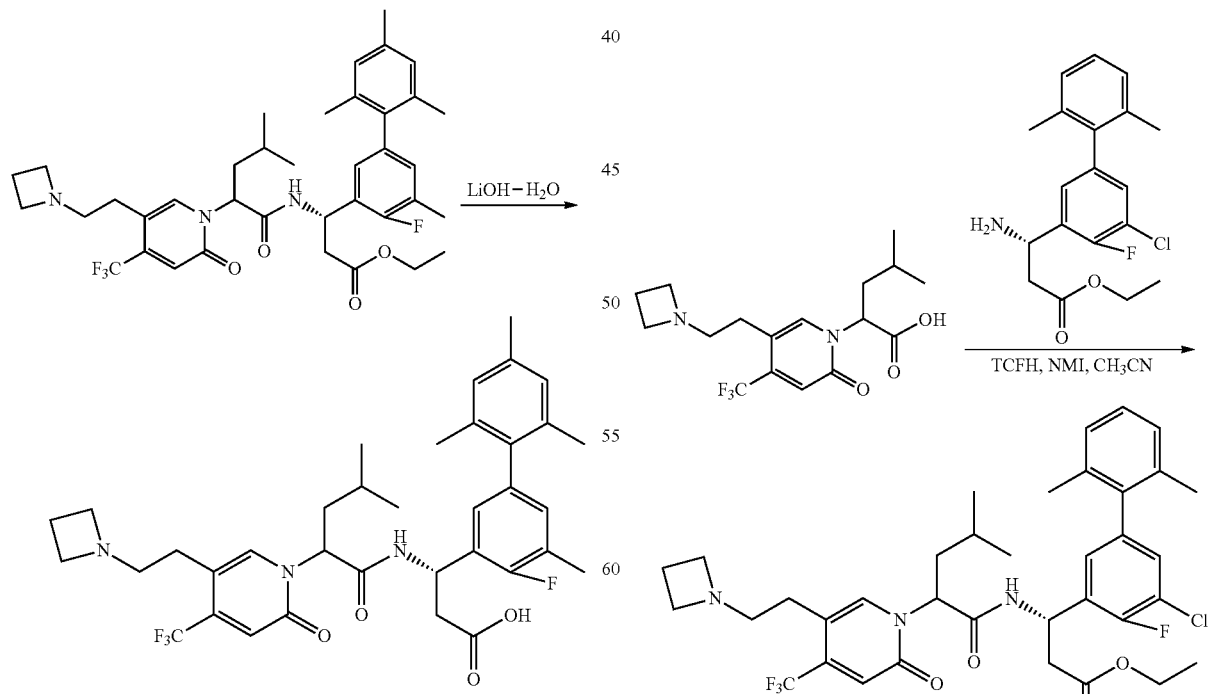

A mixture of 2-(5-(2-(azetidin-1-yl)ethyl)-2-oxo-4-(trifluoromethyl)pyridin-1(2H)-yl)-4-methylpentanoic acid (150 mg, 0.42 mmol), ethyl (S)-3-amino-3-(5-chloro-4-fluoro-2',6'-dimethyl-[1,1'-biphenyl]-3-yl)propanoate (154 mg, 0.42 mmol), TCFH (180 mg, 0.63 mmol) and NMI (100 mg, 1.26 mmol) in CH$_3$CN (5 mL) was stirred at 40° C. for 2 hours. The solvent was concentrated in vacuo and the residue was purified by reverse phase HPLC on a C18/40 g column (A: water 10 mM NH$_4$HCO$_3$, B: MeOH, 0~100%) to provide ethyl (3S)-3-(2-(5-(2-(azetidin-1-yl)ethyl)-2-oxo-4-(trifluoromethyl)pyridin-1(2H)-yl)-4-methylpentanamido)-3-(5-chloro-4-fluoro-2',6'-dimethyl-[1,1'-biphenyl]-3-yl)propanoate as a yellow oil (150 mg). Yield 52.8% (ESI 692.0 (M+H)$^+$).

Step 2: Ethyl (3S)-3-(2-(5-(2-(azetidin-1-yl)ethyl)-2-oxo-4-(trifluoromethyl)pyridin-1(2H)-yl)-4-methylpentanamido)-3-(5-chloro-4-fluoro-2',6'-dimethyl-[1,1'-biphenyl]-3-yl)propanoate Ethyl (3S)-3-(2-(5-(2-(azetidin-1-yl)ethyl)-2-oxo-4-(trifluoromethyl)pyridin-1(2H)-yl)-4-methylpentanamido)-3-(5-chloro-4-fluoro-2',6'-dimethyl-[1,1'-biphenyl]-3-yl)propanoate (150 mg, 0.22 mmol) was treated with LiOH—H$_2$O (95.5 mg, 2.3 mmol) in MeOH (4 mL) and H$_2$O (4 mL) at room temperature for 2 hours. The reaction mixture was acidified to pH 4~5 with 1N HCl. The solvent was removed in vacuo and the residue was purified by prep-HPLC A (30-60% CH$_3$CN) to give the diastereomeric products AO-P1 (29 mg) and AO-P2 (34 mg) as white solids.

AO-P1 ESI 664.2 (M+H)$^+$. $^1$H NMR (400 MHz, MeOD) δ 7.72 (s, 1H), 7.11-6.90 (m, 5H), 6.65 (s, 1H), 5.60-5.40 (m, 2H), 3.91 (t, J=8.2 Hz, 4H), 3.21-3.11 (m, 2H), 2.73 (t, J=7.0 Hz, 2H), 2.67-2.55 (m, 2H), 2.41-2.25 (m, 2H), 1.96-1.83 (m, 5H), 1.77 (s, 3H), 1.36-1.24 (m, 1H), 0.88-0.77 (m, 6H).

AO-P2 ESI 664.2 (M+H)$^+$. $^1$H NMR (400 MHz, MeOD) δ 7.75 (s, 1H), 7.26-7.07 (m, 5H), 6.90 (s, 1H), 5.86-5.74 (m, 1H), 5.62 (t, J=7.6 Hz, 1H), 4.14 (t, J=7.9 Hz, 4H), 3.49-3.36 (m, 2H), 3.01-2.74 (m, 2H), 2.71-2.62 (m, 1H), 2.59-2.43 (m, 3H), 2.12-1.91 (m, 7H), 1.77-1.58 (m, 1H), 1.49-1.32 (m, 1H), 0.90 (d, J=6.6 Hz, 6H).

3-37. Preparation of (3S)-3-(2-(5-(2-(azetidin-1-yl)ethyl)-2-oxo-4-(trifluoromethyl)pyridin-1(2H)-yl)-4-methylpentanamido)-3-(4-fluoro-2',5,6'-trimethyl-[1,1'-biphenyl]-3-yl)propanoic Acid (Compounds AP-P1 and AP-P2)

Step 1: Ethyl (3S)-3-(2-(5-(2-(azetidin-1-yl)ethyl)-2-oxo-4-(trifluoromethyl)pyridin-1(2H)-yl)-4-methylpentanamido)-3-(4-fluoro-2',5,6'-trimethyl-[1,1'-biphenyl]-3-yl)propanoate

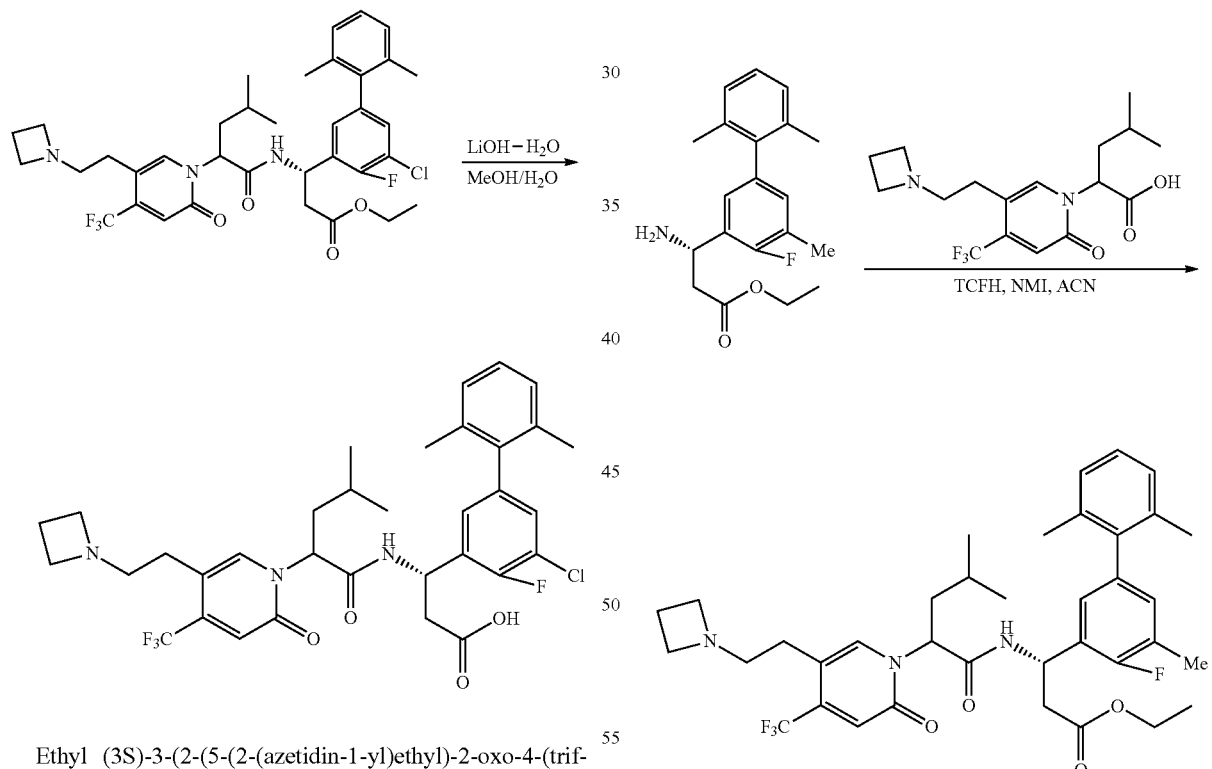

A mixture of 2-(5-(2-(azetidin-1-yl)ethyl)-2-oxo-4-(trifluoromethyl)pyridin-1(2H)-yl)-4-methylpentanoic acid (262 mg, 0.73 mmol, 1.20 eq), ethyl (S)-3-amino-3-(4-fluoro-2',5,6'-trimethyl-[1,1'-biphenyl]-3-yl)propanoate (200 mg, 0.61 mmol, 1.00 eq), NMI (0.5 mL) and TCFH (255 mg, 0.91 mmol, 1.50 eq) in CH$_3$CN (5 mL) was stirred at room temperature for 1 hour. The solvent was concentrated in vacuo and the residue was purified reverse phase HPLC on a C18/40 g column (A: water 10 mM NH₄HCO₃, B: MeOH, 0~100%) to provide ethyl (3S)-3-(2-(5-(2-(azetidin-1-yl)ethyl)-2-oxo-4-(trifluoromethyl)pyridin-1(2H)-yl)-4-methylpentanamido)-3-(4-fluoro-2',5,6'-trimethyl-[1,1'-biphenyl]-3-yl)propanoate as a white solid (300 mg). Yield 73.5% (ESI 672.3 [M+H]⁺).

Step 2: (3S)-3-(2-(5-(2-(azetidin-1-yl)ethyl)-2-oxo-4-(trifluoromethyl)pyridin-1(2H)-yl)-4-methylpentanamido)-3-(4-fluoro-2',5,6'-trimethyl-[1,1'-biphenyl]-3-y)propanoic Acid

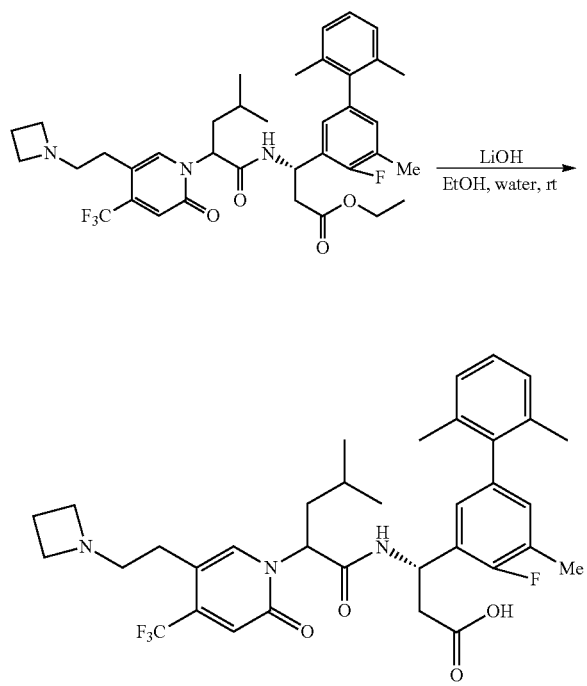

Ethyl (3S)-3-(2-(5-(2-(azetidin-1-yl)ethyl)-2-oxo-4-(trifluoromethyl)pyridin-1(2H)-yl)-4-methylpentanamido)-3-(4-fluoro-2',5,6'-trimethyl-[1,1'-biphenyl]-3-yl)propanoate (300 mg, 0.45 mmol, 1.00 eq) was treated with LiOH—H₂O (100 mg, 2.38 mmol, 5.00 eq) in MeOH (5 mL) and H₂O (1 mL) at room temperature for 1 hour. The reaction mixture was acidified to pH 4~5 with 1N HCl. The solvent was removed in vacuo and the residue was purified by prep-HPLC A (30-60% MeCN) to give AP-P1 (30 mg) and AP-P2 (50 mg) as white solids.

AP-P1 ESI 644.2 (M+H)⁺. ¹H NMR (400 MHz, MeOD) δ 7.84 (s, 1H), 7.17-7.02 (m, 3H), 6.96-6.85 (m, 2H), 6.80 (s, 1H), 5.71-5.56 (m, 2H), 4.13-3.94 (m, 4H), 3.33-3.29 (m, 2H), 2.86 (t, J=6.7 Hz, 2H), 2.71 (d, J=6.1 Hz, 2H), 2.48-2.40 (m, 2H), 2.31 (d, J=1.7 Hz, 3H), 2.07-1.92 (m, 5H), 1.89 (s, 3H), 1.45-1.39 (m, 1H), 0.99-0.84 (m, 6H).

AP-P2 ESI 644.2 (M+H)⁺. ¹H NMR (400 MHz, MeOD) δ 7.75 (s, 1H), 7.12-7.08 (m, 3H), 6.97-6.91 (m, 3H), 5.79-5.76 (m, 1H), 5.61 (t, J=7.6 Hz, 1H), 4.14 (t, J=7.5 Hz, 4H), 3.53-3.34 (m, 2H), 2.94 (d, J=15.6 Hz, 1H), 2.88-2.71 (m, 1H), 2.68-2.63 (m, 1H), 2.54-2.44 (m, 3H), 2.34 (s, 3H), 2.02-1.96 (m, 7H), 1.75-1.54 (m, 1H), 1.45-1.39 (m, 1H), 0.90 (d, J=6.4 Hz, 6H).

3-38. Preparation of (3S)-3-(2-(5-(2-(azetidin-1-yl)ethyl)-2-oxo-4-(trifluoromethyl)pyridin-1(2H)-yl)-4-methylpentanamido)-3-(4,4'-difluoro-2',5,6'-trimethyl-[1,1'-biphenyl]-3-yl)propanoic Acid (Compounds AQ-P1 and AQ-P2)

Step 1: Ethyl (3S)-3-(2-(5-(2-(azetidin-1-yl)ethyl)-2-oxo-4-(trifluoromethyl)pyridin-1(2H)-yl)-4-methylpentanamido)-3-(4,4'-difluoro-2',5,6'-trimethyl-[1,1'-biphenyl]-3-yl)propanoate

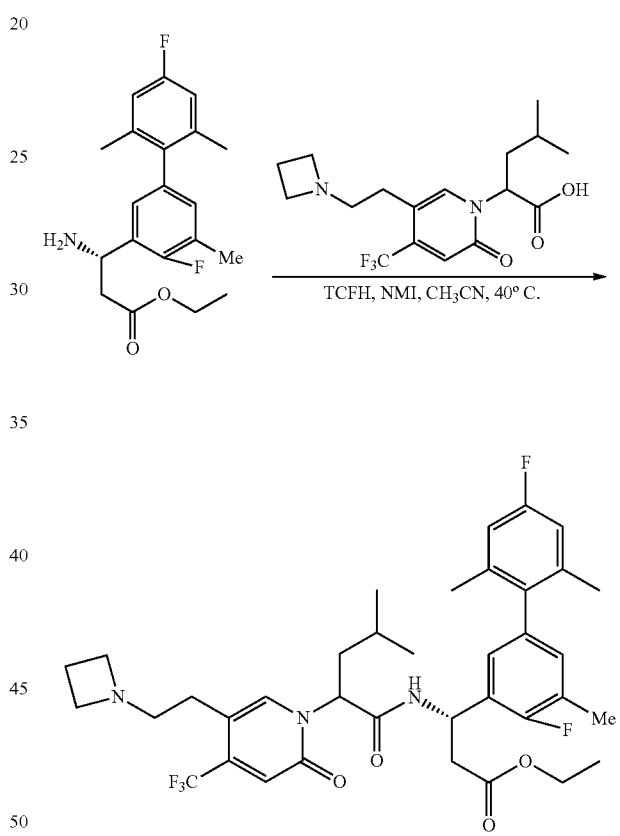

A mixture of 2-(5-(2-(azetidin-1-yl)ethyl)-2-oxo-4-(trifluoromethyl)pyridin-1(2H)-yl)-4-methylpentanoic acid (165 mg, 0.46 mmol), ethyl (S)-3-amino-3-(4,4'-difluoro-2',5,6'-trimethyl-[1,1'-biphenyl]-3-yl)propanoate (160 mg, 0.46 mmol), TCFH (193 mg, 0.69 mmol) and NMI (188 mg, 2.3 mmol) in CH₃CN (4 mL) was stirred at 40° C. for 2 hours. The solvent was concentrated in vacuo and the residue was purified by reverse phase HPLC on a C18/40 g column (A: water 10 mM NH₄HCO₃, B: MeOH, 0~100%) to provide ethyl (3S)-3-(2-(5-(2-(azetidin-1-yl)ethyl)-2-oxo-4-(trifluoromethyl)pyridin-1(2H)-yl)-4-methylpentanamido)-3-(4,4'-difluoro-2',5,6'-trimethyl-[1,1'-biphenyl]-3-yl)propanoate as a yellow oil (200 mg). Yield 62% (ESI 690.2 (M+H)⁺).

Step 2: (3S)-3-(2-(5-(2-(azetidin-1-yl)ethyl)-2-oxo-4-(trifluoromethyl)pyridin-1(2H)-yl)-4-methylpentanamido)-3-(4,4'-difluoro-2',5,6'-trimethyl-[1,1'-biphenyl]-3-yl)propanoic Acid

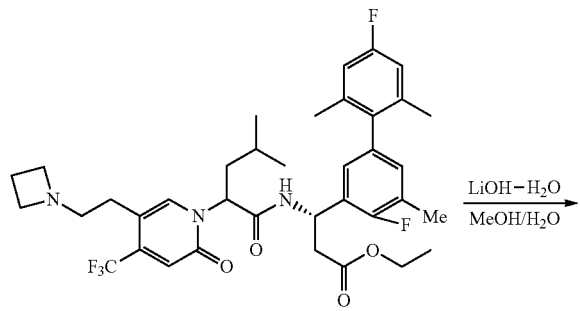

Ethyl (3S)-3-(2-(5-(2-(azetidin-1-yl)ethyl)-2-oxo-4-(trifluoromethyl)pyridin-1(2H)-yl)-4-methylpentanamido)-3-(4,4'-difluoro-2',5,6'-trimethyl-[1,1'-biphenyl]-3-yl)propanoate (200 mg, 0.29 mmol) was treated with LiOH—H₂O (42 mg, 1 mmol) in MeOH (3 mL) and H₂O (1 mL) at room temperature for 2 hours. The reaction mixture was acidified to pH 4~5 with 1N HCl. The solvent was removed in vacuo and the residue was purified by prep-HPLC A (30-60% CH₃CN) to give the diastereomeric products AQ-P1 (54 mg) and AQ-1-P2 (53 mg) as white solids.

AQ-P1 ESI 662.2 (M+H)⁺. ¹H NMR (400 MHz, MeOD) δ 7.86 (s, 1H), 6.94-6.74 (m, 5H), 5.72-5.55 (m, 2H), 4.05 (t, J=8.0 Hz, 4H), 3.33-3.25 (m, 2H), 2.86 (t, J=7.1 Hz, 2H), 2.77-2.64 (m, 2H), 2.55-2.38 (m, 2H), 2.30 (s, 3H), 2.06-1.94 (m, 5H), 1.87 (s, 3H), 1.53-1.34 (m, 1H), 1.01-0.86 (m, 6H).

AQ-P2 ESI 662.2 (M+H)⁺. ¹H NMR (400 MHz, MeOD) δ 7.78 (s, 1H), 6.98-6.89 (m, 3H), 6.85 (d, J=9.6 Hz, 2H), 5.80-5.70 (m, 1H), 5.63 (t, J=7.6 Hz, 1H), 4.14 (s, 4H), 3.52-3.36 (m, 2H), 2.97-2.43 (m, 6H), 2.33 (s, 3H), 2.06-1.93 (m, 7H), 1.77-1.63 (m, 1H), 1.49-1.29 (m, 1H), 0.96-0.84 (m, 6H).

3-39. Preparation of (3S)-3-(4,4'-difluoro-2',5,6'-trimethyl-[1,1'-biphenyl]-3-yl)-3-(2-(5-(2-(3-fluoroazetidine-1-yl)ethyl)-4-methyl-2-oxopyridin-1(2H)-yl)-4-methylpentanamido)propanoic Acid (Compounds AR-P1 and AR-P2)

Step 1: Ethyl (3S)-3-(4,4'-difluoro-2',5,6'-trimethyl-[1,1'-biphenyl]-3-yl)-3-(2-(5-(2-(3-fluoroazetidine-1-yl)ethyl)-4-methyl-2-oxopyridin-1(2H)-yl)-4-methylpentanamido)propanoate

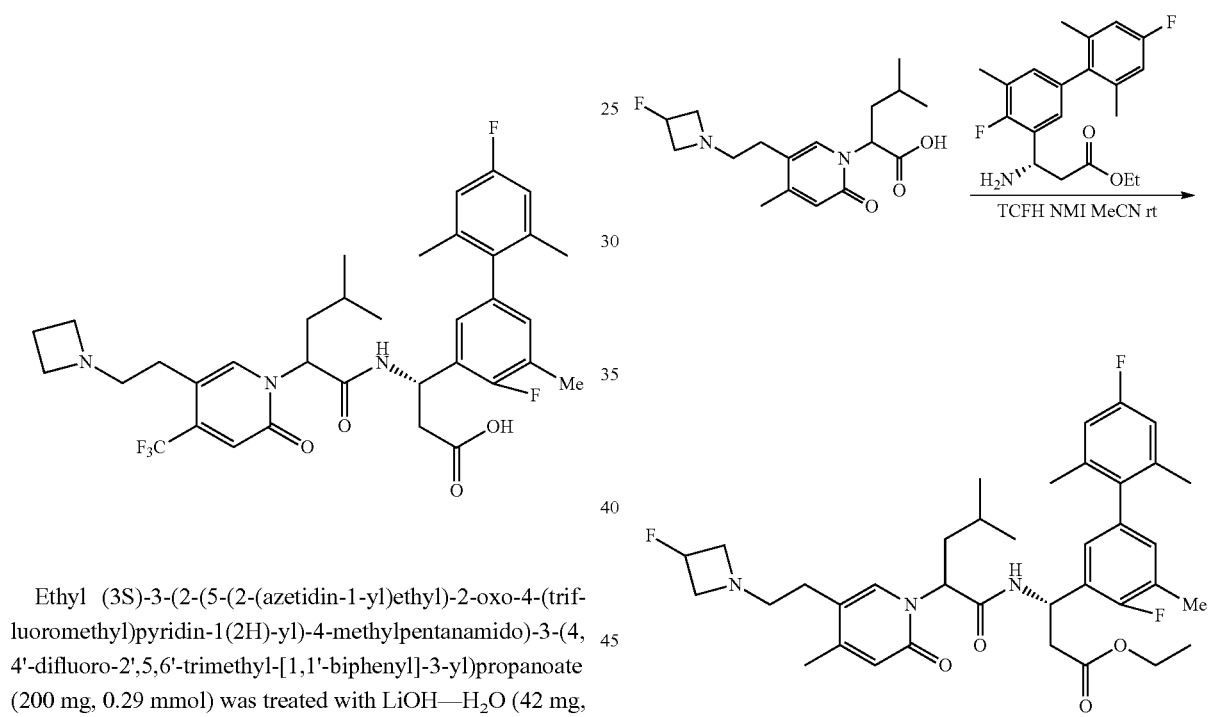

A mixture of 2-(5-(2-(3-fluoroazetidine-1-yl)ethyl)-4-methyl-2-oxopyridin-1(2H)-yl)-4-methylpentanoic acid (112 mg, 0.34 mmol), ethyl (S)-3-amino-3-(4,4'-difluoro-2',5,6'-trimethyl-[1,1'-biphenyl]-3-yl)propanoate (100 mg, 0.29 mmol), TCFH (120 mg, 0.43 mmol) and NMI (71 mg, 0.87 mmol) in CH₃CN (5 mL) was stirred at room temperature for 2 hours. The solvent was concentrated in vacuo and the residue was purified by reverse phase HPLC on a C18/40 g column (A: water 10 mM NH₄HCO₃, B: MeOH, 0~100%) to provide ethyl (3S)-3-(4,4'-difluoro-2',5,6'-trimethyl-[1,1'-biphenyl]-3-yl)-3-(2-(5-(2-(3-fluoroazetidine-1-yl)ethyl)-4-methyl-2-oxopyridin-1(2H)-yl)-4-methylpentanamido)propanoate as a yellow oil (150 mg). Yield 79.7% (ESI 654.3 (M+H)⁺).

Step 2: (3S)-3-(4,4'-difluoro-2',5,6'-trimethyl-[1,1'-biphenyl]-3-yl)-3-(2-(5-(2-(3-fluoroazetidine-1-yl)ethyl)-4-methyl-2-oxopyridin-1(2H)-yl)-4-methylpentanamido)propanoic Acid

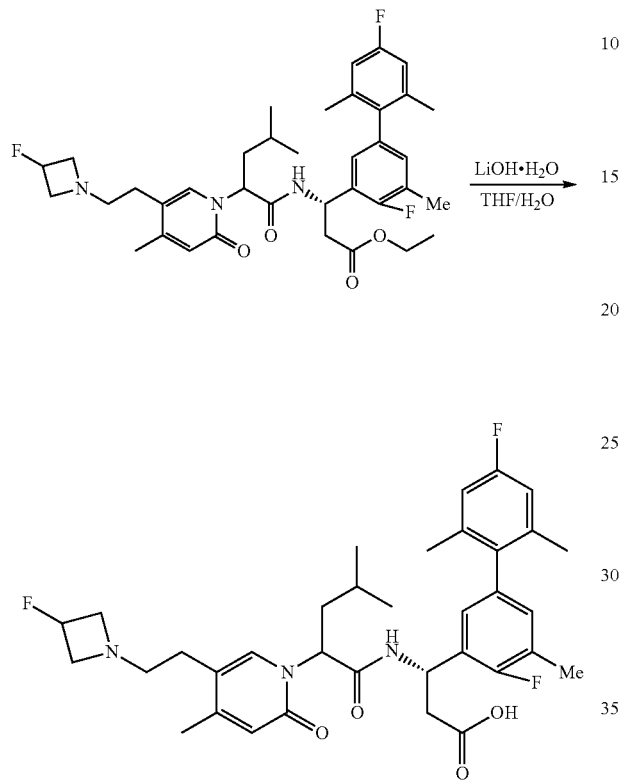

Ethyl (3S)-3-(4,4'-difluoro-2',5,6'-trimethyl-[1,1'-biphenyl]-3-yl)-3-(2-(5-(2-(3-fluoroazetidine-1-yl)ethyl)-4-methyl-2-oxopyridin-1(2H)-yl)-4-methylpentanamido)propanoate (150 mg, 0.23 mmol) was treated with LiOH—H$_2$O (100 mg, 2.3 mmol) in THF (3 mL) and H$_2$O (3 mL) at room temperature for 2 hours. The reaction mixture was acidified to pH 4~5 with 1N HCl. The solvent was removed in vacuo and the residue was purified by prep-HPLC A (30-60% CH$_3$CN) to give the diastereomeric products AR-P1 (43 mg) and AR-P2 (36 mg) as white solids.

AR-P1 ESI 626.3 (M+H)$^+$. $^1$H NMR (400 MHz, MeOD) δ 7.49 (s, 1H), 6.92-6.68 (m, 4H), 6.30 (s, 1H), 5.74-5.52 (m, 2H), 5.30-5.12 (m, 1H), 4.15-3.90 (m, 2H), 3.75-3.57 (m, 2H), 3.05-3.00 (m, 2H), 2.85-2.62 (m, 3H), 2.32-2.27 (m, 4H), 2.22 (d, J=1.2 Hz, 3H), 1.99 (s, 3H), 1.96-1.92 (m, 2H), 1.85 (s, 3H), 1.45-1.35 (m, 1H), 0.96-0.91 (m, 6H).

AR-P2 ESI 626.2 (M+H)$^+$. $^1$H NMR (400 MHz, MeOD) δ 7.33 (s, 1H), 6.87-6.81 (m, 4H), 6.30 (s, 1H), 5.62-5.43 (m, 2H), 5.34-5.08 (m, 1H), 4.37-4.12 (m, 2H), 4.00-3.76 (m, 2H), 3.19-3.11 (m, 2H), 2.79-2.67 (m, 1H), 2.62-2.36 (m, 3H), 2.20 (d, J=1.6 Hz, 3H), 2.12 (s, 3H), 1.89 (s, 6H), 1.85-1.75 (m, 1H), 1.69-1.58 (m, 1H), 1.32-1.21 (m, 1H), 0.82-0.72 (m, 6H).

3-40. Preparation of (3S)-3-(4,4'-difluoro-2',5,6'-trimethylbiphenyl-3-yl)-3-(2-(5-(2-((R)-3-fluoropyrrolidin-1-yl)ethyl)-4-methyl-2-oxopyridin-1(2H)-yl)-4-methylpentanamido)propanoic Acid (Compounds AS-P1 and AS-P2)

Step 1: (3S)-ethyl 3-(4,4'-difluoro-2',5,6'-trimethyl-biphenyl-3-yl)-3-(2-(5-(2-((R)-3-fluoropyrrolidin-1-yl)ethyl)-4-methyl-2-oxopyridin-1(2H)-yl)-4-methylpentanamido)propanoate

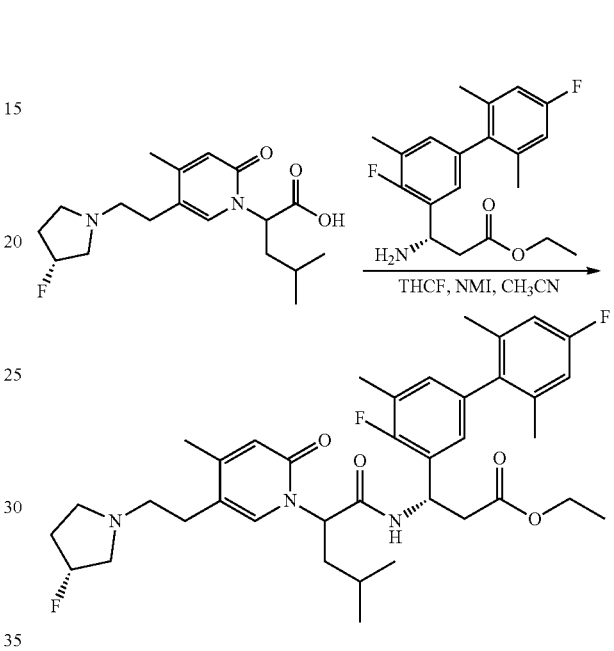

A mixture of 2-(5-(2-((R)-3-fluoropyrrolidin-1-yl)ethyl)-4-methyl-2-oxopyridin-1(2H)-yl)-4-methylpentanoic acid (120 mg, 0.36 mmol), (S)-ethyl 3-amino-3-(4,4'-difluoro-2',5,6'-trimethylbiphenyl-3-yl)propanoate (123 mg, 0.36 mmol), TCFH (114 mg, 0.41 mmol) and NMI (84 mg, 1.02 mmol) in CH$_3$CN (5 mL) was stirred at room temperature for 1 hour. The solvent was removed in vacuo and the residue was purified by silica gel column (DCM:MeOH 4:1) to provide (3S)-ethyl 3-(4,4'-difluoro-2',5,6'-trimethylbiphenyl-3-yl)-3-(2-(5-(2-((R)-3-fluoropyrrolidin-1-yl)ethyl)-4-methyl-2-oxopyridin-1(2H)-yl)-4-methylpentanamido)propanoate as a white solid (120 mg). Yield 51% (ESI 668.2 (M+H)$^+$).

Step 2: (3S)-3-(4,4'-difluoro-2',5,6'-trimethylbiphenyl-3-yl)-3-(2-(5-(2-((R)-3-fluoropyrrolidin-1-yl)ethyl)-4-methyl-2-oxopyridin-1(2H)-yl)-4-methylpentanamido)propanoic Acid

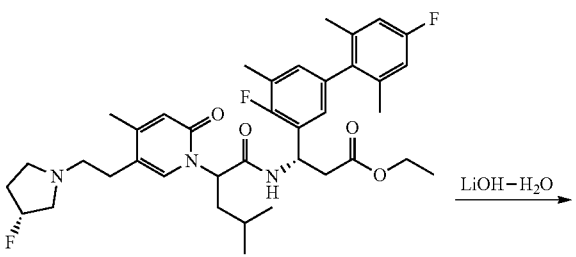

451
-continued

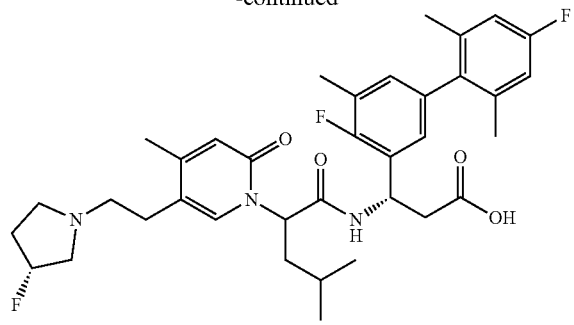

(3S)-ethyl 3-(4,4'-difluoro-2',5,6'-trimethylbiphenyl-3-yl)-3-(2-(5-(2-((R)-3-fluoropyrrolidin-1-yl)ethyl)-4-methyl-2-oxopyridin-1(2H)-yl)-4-methylpentanamido)propanoate (120 mg, 0.18 mmol)) was treated with LiOH—H$_2$O (32 mg, 0.75 mmol) in THF (3 mL) and H$_2$O (1 mL) at room temperature for 3 hours. The reaction mixture was acidified to pH 4~5 with 1N HCl. The solvent was removed in vacuo and the residue was purified by prep-HPLC A (30-60% CH$_3$CN) to give the diastereomeric products AS-P1 (28.0 mg) and AS-P2 (43.0 mg) as white solids.

AS-P1 ESI 640.3 (M+H)$^+$. $^1$H NMR (400 MHz, MeOD) δ 7.56 (s, 1H), 6.84-6.79 (m, 4H), 6.26 (s, 1H), 5.65-5.60 (m, 1H), 5.55-5.50 (m, 1H), 5.35-5.52 (m, 1H), 3.38-3.33 (m, 1H), 3.32-2.66 (m, 9H), 2.39-2.11 (m, 8H), 1.98-1.92 (m, 5H), 1.81 (s, 3H), 1.46-1.39 (m, 1H), 0.96-0.91 (m, 6H).

AS-P2 ESI 640.3 (M+H)+. $^1$H NMR (400 MHz, MeOD) δ 7.57 (s, 1H), 6.90-6.82 (m, 4H), 6.42 (s, 1H), 5.64-5.58 (m, 2H), 5.40-5.24 (m, 1H), 3.51-3.37 (m, 3H), 3.32-3.10 (m, 3H), 2.92-2.76 (m, 2H), 2.68-2.55 (m, 2H), 2.40-2.21 (m, 8H), 2.05-1.88 (m, 7H), 1.80-1.73 (m, 1H), 1.41-1.34 (m, 1H), 0.96-0.87 (m, 6H).

3-41. Preparation of (3S)-3-(4,4'-difluoro-2',5,6'-trimethyl-[1,1'-biphenyl]-3-yl)-3-(2-(3-fluoro-5-(2-((R)-3-fluoropyrrolidin-1-yl)ethyl)-2-oxopyridin-1(2H)-yl)-4-methylpentanamido)propanoic Acid (Compounds AT-P1 and AT-P2)

Step 1: Ethyl (3S)-3-(4,4'-difluoro-2',5,6'-trimethyl-[1,1'-biphenyl]-3-yl)-3-(2-(3-fluoro-5-(2-((R)-3-fluoropyrrolidin-1-yl)ethyl)-2-oxopyridin-1(2H)-yl)-4-methylpentanamido)propanoate

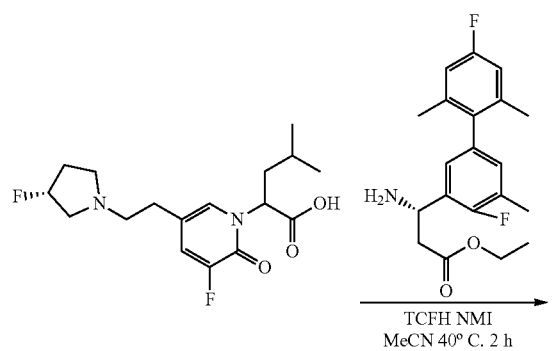

452
-continued

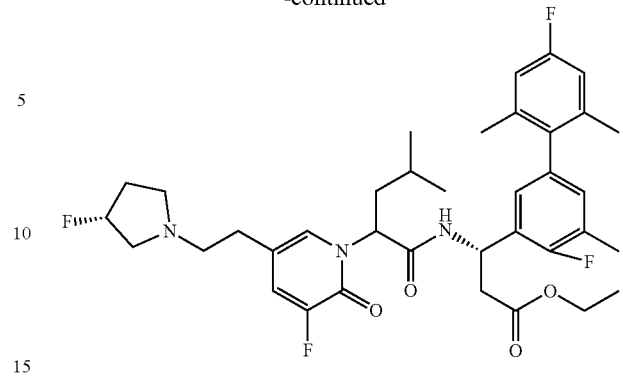

A mixture of 2-(3-fluoro-5-(2-((R)-3-fluoropyrrolidin-1-yl)ethyl)-2-oxopyridin-1(2H)-yl)-4-methylpentanoic acid (120 mg, 0.35 mmol), ethyl (S)-3-amino-3-(4,4'-difluoro-2',5,6'-trimethyl-[1,1'-biphenyl]-3-yl)propanoate (140 mg, 0.42 mmol), TCFH (117 mg, 0.42 mmol) and NMI (86 mg, 1.05 mmol) in CH$_3$CN (5 mL) was stirred at 40° C. for 2 hours. The solvent was concentrated in vacuo and the residue was purified by reverse phase HPLC on a C18/40 g column (A: water 10 mM NH$_4$HCO$_3$, B: MeOH, 0~100%) to provide ethyl (3S)-3-(4,4'-difluoro-2',5,6'-trimethyl-[1,1'-biphenyl]-3-yl)-3-(2-(3-fluoro-5-(2-((R)-3-fluoropyrrolidin-1-yl)ethyl)-2-oxopyridin-1(2H)-yl)-4-methylpentanamido)propanoate as a yellow oil (150 mg). Yield 63.8% (ESI 672.3 (M+H)$^+$).

Step 2: Ethyl (3S)-3-(4,4'-difluoro-2',5,6'-trimethyl-[1,1'-biphenyl]-3-yl)-3-(2-(3-fluoro-5-(2-((R)-3-fluoropyrrolidin-1-yl)ethyl)-2-oxopyridin-1(2H)-yl)-4-methylpentanamido)propanoate

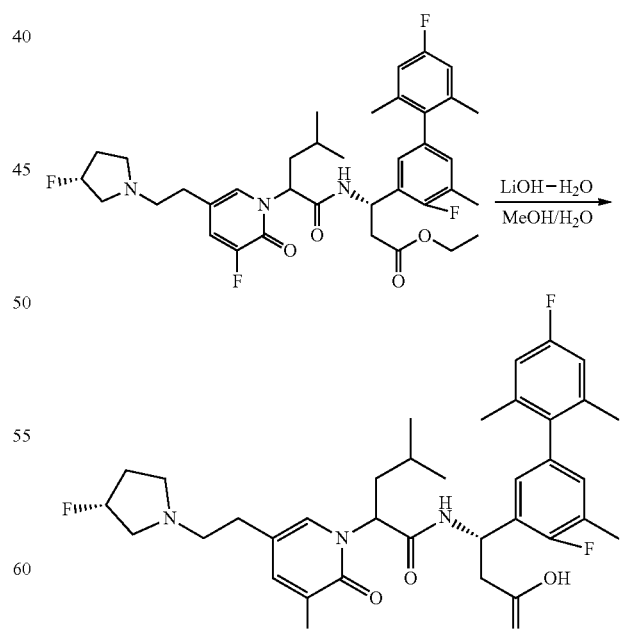

Ethyl (3S)-3-(4,4'-difluoro-2',5,6'-trimethyl-[1,1'-biphenyl]-3-yl)-3-(2-(3-fluoro-5-(2-((R)-3-fluoropyrrolidin-1-yl)ethyl)-2-oxopyridin-1(2H)-yl)-4-methylpentanamido)propanoate (150 mg, 0.22 mmol) was treated with LiOH—H₂O (94 mg, 2.2 mmol) in MeOH (5 mL) and H₂O (5 mL) at room temperature for 2 hours. The reaction mixture was acidified to pH 4~5 with 1N HCl. The solvent was removed in vacuo and the residue was purified by prep-HPLC A (30-60% CH₃CN) to give the diastereomeric products AT-P1 (28 mg) and AT-P2 (37 mg) as white solids.

AT-P1 ESI 644.2 (M+H)⁺. ¹H NMR (400 MHz, MeOD) δ 7.50 (s, 1H), 7.37 (d, J=10.1 Hz, 1H), 6.92-6.77 (m, 4H), 5.74-5.62 (m, 1H), 5.57-5.46 (m, 1H), 5.27 (d, J=53.4 Hz, 1H), 3.29-2.96 (m, 6H), 2.84-2.56 (m, 4H), 2.40-2.10 (m, 5H), 2.07-1.90 (m, 5H), 1.87 (s, 3H), 1.49-1.38 (m, 1H), 1.03-0.89 (m, 6H).

AT-P2 ESI 644.2 (M+H)⁺. ¹H NMR (400 MHz, MeOD) δ 7.49 (s, 1H), 7.41 (d, J=10.3 Hz, 1H), 6.97-6.76 (m, 4H), 5.67 (t, J=7.7 Hz, 1H), 5.62-5.52 (m, 1H), 5.33 (d, J=55.0 Hz, 1H), 3.69-3.34 (m, 6H), 2.92-2.77 (m, 2H), 2.65-2.43 (m, 2H), 2.30 (d, J=17.3 Hz, 5H), 2.10-1.89 (m, 7H), 1.86-1.74 (m, 1H), 1.48-1.34 (m, 1H), 0.95-0.86 (m, 6H).

3-42. Preparation of (3S)-3-(4-fluoro-2',5,6'-trimethyl-[1,1'-biphenyl]-3-yl)-3-(2-(3-fluoro-5-(2-((R)-3-fluoropyrrolidin-1-yl)ethyl)-2-oxopyridin-1(2H)-yl)-4-methylpentanamido)propanoic Acid (Compounds AU-P1 and AU-P2)

Step 1: Ethyl (3S)-3-(4-fluoro-2',5,6'-trimethyl-[1,1'-biphenyl]-3-yl)-3-(2-(3-fluoro-5-(2-((R)-3-fluoropyrrolidin-1-yl)ethyl)-2-oxopyridin-1(2H)-yl)-4-methylpentanamido)propanoate

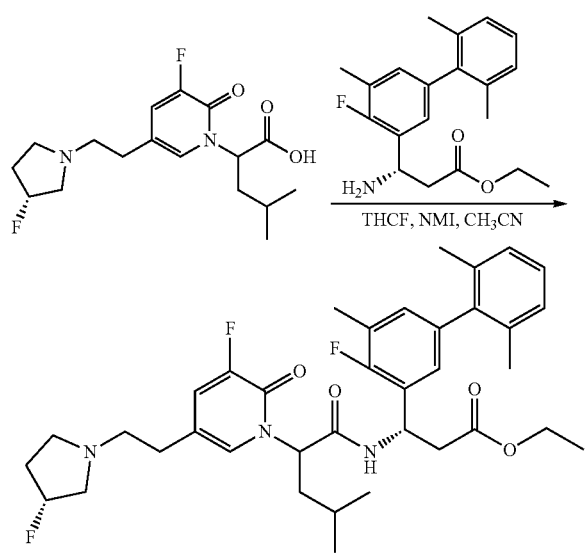

A mixture of 2-(3-fluoro-5-(2-((R)-3-fluoropyrrolidin-1-yl)ethyl)-2-oxopyridin-1(2H)-yl)-4-methylpentanoic acid (150 mg, 0.44 mmol), ethyl (S)-3-amino-3-(4-fluoro-2',5,6'-trimethyl-[1,1'-biphenyl]-3-yl)propanoate (144 mg, 0.44 mmol), TCFH (148 mg, 0.53 mmol), NMI (108 mg, 1.32 mmol) in CH₃CN (4 mL) was stirred at room temperature for 1 hour. LCMS showed that the reaction was completed. The solvent was concentrated in vacuo and the residue was purified by reverse phase HPLC on a C18/120 g column (A: water 10 mM NH₄HCO₃, B: CH3CN, 0~100%) to provide ethyl (3S)-3-(4-fluoro-2',5,6'-trimethyl-[1,1'-biphenyl]-3-yl)-3-(2-(3-fluoro-5-(2-((R)-3-fluoropyrrolidin-1-yl)ethyl)-2-oxopyridin-1(2H)-yl)-4-methylpentanamido)propanoate as a colorless oil (130 mg). Yield 45% (ESI 654.2 (M+H)⁺).

Step 2: (3S)-3-(4-fluoro-2',5,6'-trimethyl-[1,1'-biphenyl]-3-yl)-3-(2-(3-fluoro-5-(2-((R)-3-fluoropyrrolidin-1-yl)ethyl)-2-oxopyridin-1(2H)-yl)-4-methylpentanamido)propanoic Acid

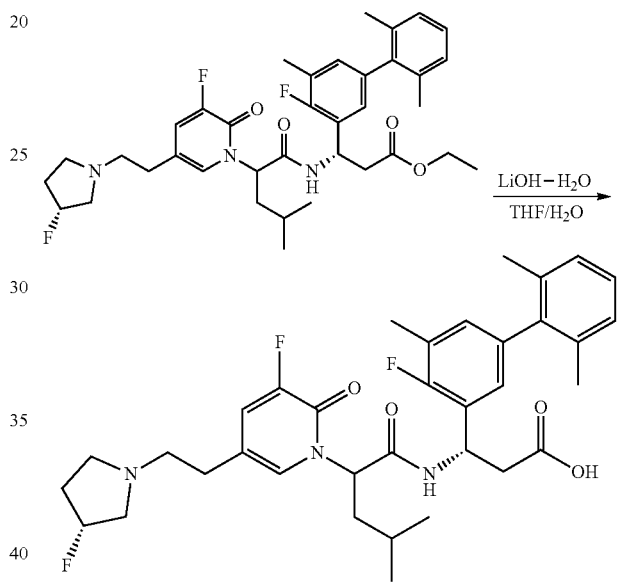

Ethyl (3S)-3-(4-fluoro-2',5,6'-trimethyl-[1,1'-biphenyl]-3-yl)-3-(2-(3-fluoro-5-(2-((R)-3-fluoropyrrolidin-1-yl)ethyl)-2-oxopyridin-1(2H)-yl)-4-methylpentanamido)propanoate (130 mg, 0.20 mmol) was treated with LiOH—H₂O (83 mg, 2.0 mmol) in THF (2 mL) and H₂O (1 mL) at 35° C. for 1 hour. The reaction mixture was acidified to pH 4~5 with 1N HCl. The solvent was removed in vacuo and the residue was purified by prep-HPLC A (30-60% MeCN) to give the diastereomeric products AU-P1 (33 mg) and AU-P2 (53 mg) as white solids.

AU-P1 ESI 626.2 (M+H)+. ¹H NMR (400 MHz, MeOD) δ 7.51 (s, 1H), 7.38-7.35 (m, 1H), 7.15-7.06 (m, 3H), 6.88-6.81 (m, 2H), 5.73-5.68 (m, 1H), 5.53-5.50 (m, 1H), 5.35-5.19 (m, 1H), 3.44-3.35 (m, 1H), 3.30-3.08 (m, 5H), 2.80-2.65 (m, 4H), 2.37-2.18 (m, 5H), 1.98-1.95 (m, 5H), 1.88 (s, 3H), 1.47-1.40 (m, 1H), 097-0.93 (m, 6H).

AU-P2 ESI 626.2 (M+H)+. ¹H NMR (400 MHz, MeOD) δ 7.50 (s, 1H), 7.41-7.38 (m, 1H), 7.14-7.07 (m, 3H), 6.93-6.90 (m, 2H), 5.70-5.66 (m, 1H), 5.61-5.58 (m, 1H), 5.40-5.25 (m, 1H), 3.65-3.37 (m, 5H), 3.30-3.25 (m, 1H), 2.91-2.79 (m, 2H), 2.64-2.48 (m, 2H), 2.39-2.25 (m, 5H), 2.00-1.94 (m, 7H), 1.84-1.75 (m, 1H), 1.43-1.35 (m, 1H), 0.92-0.89 (m, 6H).

3-43. Preparation of (3S)-3-(4-fluoro-2',5,6'-trimethyl-[1,1'-biphenyl]-3-yl)-3-(2-(3-fluoro-5-(2-(3-fluoroazetidine-1-yl)ethyl)-2-oxopyridin-1(2H)-yl)-4-methylpentanamido)propanoic Acid (Compounds AV-P1 and AV-P2)

Step 1: Ethyl (3S)-3-(4-fluoro-2',5,6'-trimethyl-[1,1'-biphenyl]-3-yl)-3-(2-(3-fluoro-5-(2-(3-fluoroazetidine-1-yl)ethyl)-2-oxopyridin-1(2H)-yl)-4-methylpentanamido)propanoate

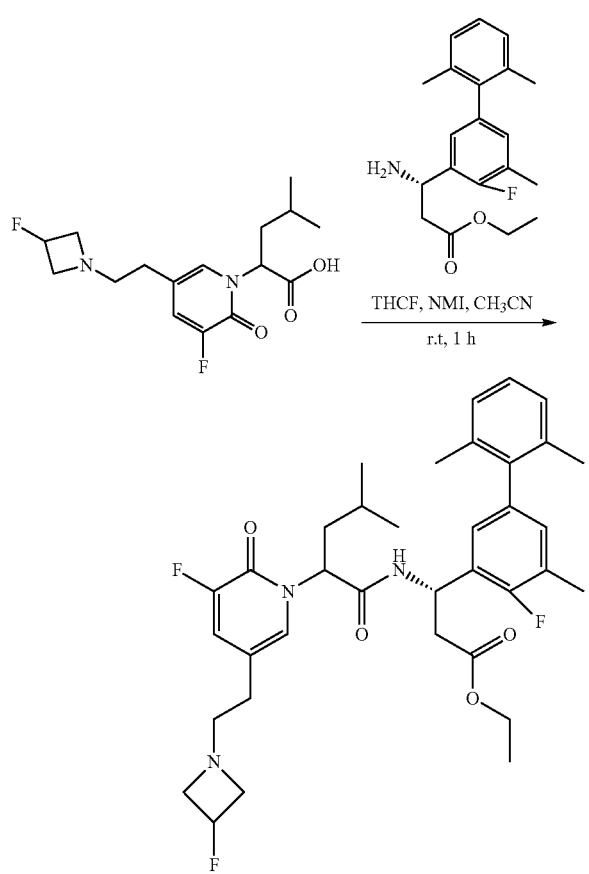

A mixture of ethyl (S)-3-amino-3-(4-fluoro-2',5,6'-trimethyl-[1,1'-biphenyl]-3-yl)propanoate (142 mg, 0.43 mmol), 2-(3-fluoro-5-(2-(3-fluoroazetidine-1-yl)ethyl)-2-oxopyridin-1(2H)-yl)-4-methylpentanoic acid (120 mg, 0.36 mmol), TCHF (151 mg, 0.54 mmol) and NMI (147.6 mg, 1.8 mmol) in CH₃CN (4 mL) was stirred at room temperature for 1 hour. The solvent was removed in vacuo and the residue was purified by reverse phase HPLC on a C18/40 g column (A: water 10 mM NH₄HCO₃, B: MeOH, 0~100%) to provide ethyl (3S)-3-(4-fluoro-2',5,6'-trimethyl-[1,1'-biphenyl]-3-yl)-3-(2-(3-fluoro-5-(2-(3-fluoroazetidine-1-yl)ethyl)-2-oxopyridin-1(2H)-yl)-4-methylpentanamido)propanoate as a yellow solid(110 mg). Yield 48% (ESI 640.2 [M+H]⁺).

Step 2: (3S)-3-(4-fluoro-2',5,6'-trimethyl-[1,1'-biphenyl]-3-yl)-3-(2-(3-fluoro-5-(2-(3-fluoroazetidine-1-yl)ethyl)-2-oxopyridin-1(2H)-yl)-4-methylpentanamido)propanoic Acid

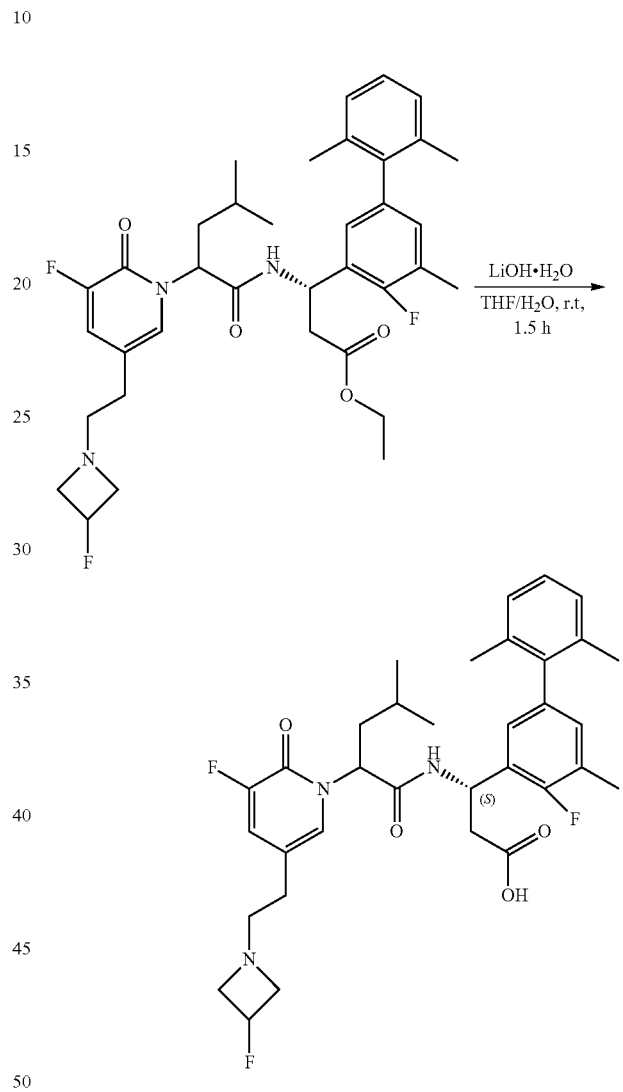

Ethyl (3S)-3-(4-fluoro-2',5,6'-trimethyl-[1,1'-biphenyl]-3-yl)-3-(2-(3-fluoro-5-(2-(3-fluoroazetidine-1-yl)ethyl)-2-oxopyridin-1(2H)-yl)-4-methylpentanamido)propanoate (110 mg, 0.17 mmol) was treated with LiOH—H₂O (36 mg, 0.86 mmol) in THF (20 mL) and water (8 mL) at 30° C. for 1 hour. The reaction mixture was acidified to pH 4~5 with 2N HCL. The solvent was removed in vacuo and the residue was purified by preparatory HPLC B to give the diastereomeric product AV-P1 (40 mg) and AV-P2 (39 mg) as white solids.

AV-P1 ESI 612.3 (M+H)⁺. ¹H NMR (400 MHz, MeOD) δ 7.76 (s, 0.18H, FA), 7.50-7.27 (m, 2H), 7.23-7.02 (m, 3H), 6.96-6.75 (m, 2H), 5.69 (t, J=8.0 Hz, 1H), 5.50 (t, J=6.1 Hz, 1H), 5.20 (d, J=57.4 Hz, 1H), 4.11 (s, 1H), 3.95 (s, 1H), 3.75-3.53 (m, 2H), 3.21-3.05 (m, 2H), 2.85-2.52 (m, 4H), 2.30 (s, 3H), 2.05-1.82 (m, 8H), 1.56-1.32 (m, 1H), 1.06-0.83 (m, 6H). AV-P2 ESI 612.3 (M+H)$^+$. $^1$H NMR (400 MHz, MeOD) δ 8.36 (s, 0.27H, FA), 7.51-7.29 (m, 2H), 7.09 (t, J=7.6 Hz, 3H), 6.94 (t, J=7.0 Hz, 2H), 5.80-5.58 (m, 2H), 5.57-5.18 (m, 1H), 4.54-4.21 (m, 2H), 4.16-3.93 (m, 2H), 3.39 (d, J=5.5 Hz, 2H), 2.83-2.48 (m, 4H), 2.33 (d, J=1.6 Hz, 3H), 2.00 (s, 7H), 1.88-1.66 (m, 1H), 1.54-1.26 (m, 1H), 1.23-0.69 (m, 6H).

3-44. Preparation of (3S)-3-(2-(5-(2-(dimethylamino)ethyl)-3-methyl-2-oxopyridin-1(2H)-yl)-4-methylpentanamido)-3-(4-fluoro-2',5,6'-trimethyl-[1,1'-biphenyl]-3-yl)propanoic Acid (Compounds AW-P1 and AW-P2)

Step 1: Ethyl (3S)-3-(2-(5-(2-(dimethylamino)ethyl)-3-methyl-2-oxopyridin-1(2H)-yl)-4-methylpentanamido)-3-(4-fluoro-2',5,6'-trimethyl-[1,1'-biphenyl]-3-yl)propanoate

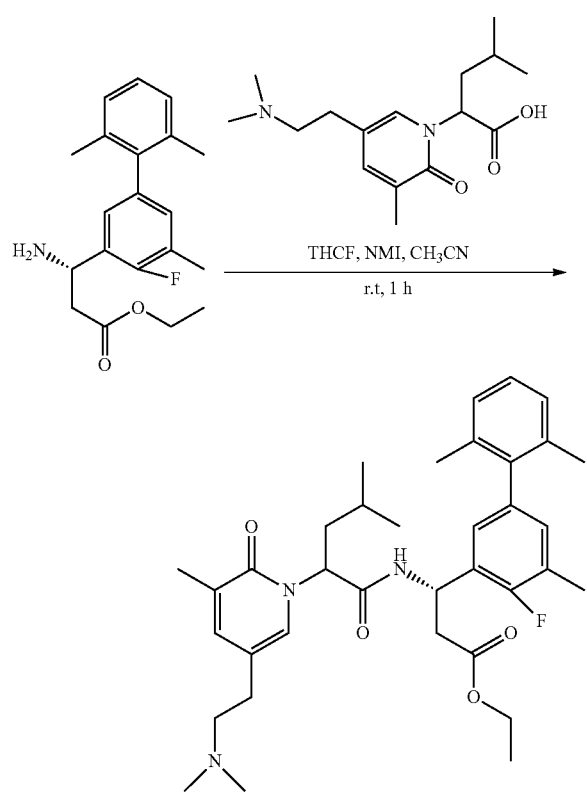

A mixture of ethyl (S)-3-amino-3-(4-fluoro-2',5,6'-trimethyl-[1,1'-biphenyl]-3-yl)propanoate (130.0 mg, 0.44 mmol), 2-(5-(2-(dimethylamino)ethyl)-3-methyl-2-oxopyridin-1(2H)-yl)-4-methylpentanoic acid (145.0 mg, 0.44 mmol), TCHF (131 mg, 0.47 mmol) and NMI (96.0 mg, 1.17 mmol) in CH$_3$CN (4 mL) was stirred at room temperature for 1 hour. The solvent was removed in vacuo and the residue was purified by reverse phase HPLC on a C18/40 g column (A: water 10 mM NH$_4$HCO$_3$, B: MeOH, 0~100%) to provide ethyl (3S)-3-(2-(5-(2-(dimethylamino)ethyl)-3-methyl-2-oxopyridin-1(2H)-yl)-4-methylpentanamido)-3-(4-fluoro-2',5,6'-trimethyl-[1,1'-biphenyl]-3-yl)propanoate as a yellow solid (130 mg). Yield 48.6% (ESI 606.2 [M+H]$^+$).

Step 2: (3S)-3-(2-(5-(2-(dimethylamino)ethyl)-3-methyl-2-oxopyridin-1(2H)-yl)-4-methylpentanamido)-3-(4-fluoro-2',5,6'-trimethyl-[1,1'-biphenyl]-3-yl)propanoic Acid

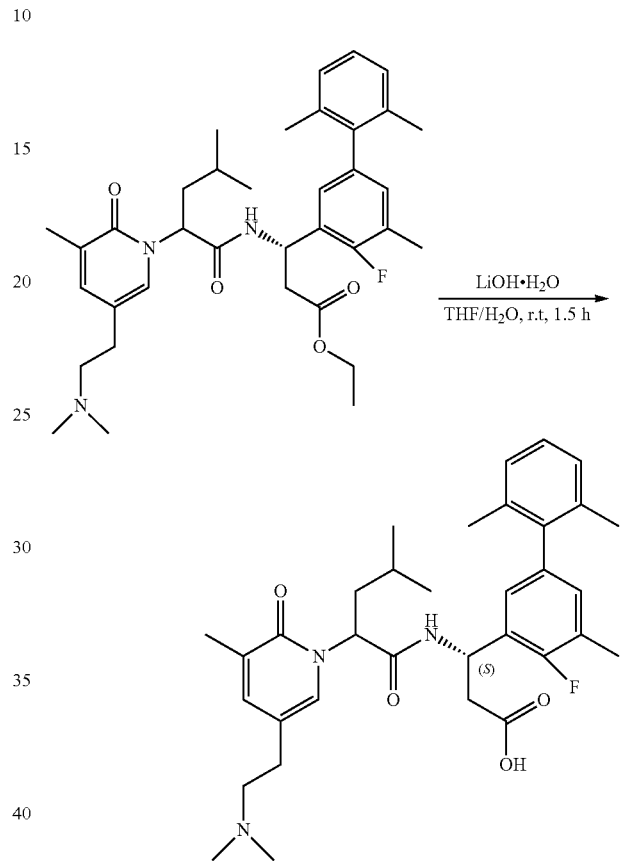

Ethyl (3S)-3-(2-(5-(2-(dimethylamino)ethyl)-3-methyl-2-oxopyridin-1(2H)-yl)-4-methylpentanamido)-3-(4-fluoro-2',5,6'-trimethyl-[1,1'-biphenyl]-3-yl)propanoate (130.0 mg, 0.21 mmol) was treated with LiOH—H$_2$O (46.0 mg, 1.0 mmol) in THF (6 mL) and water (3 mL) at 30° C. for 1 hour. The reaction mixture was acidified to pH 4~5 with 1 N HCl. The solvent was removed in vacuo and the residue was purified by Prep HPLC A (30-60% MeCN) to give the diastereomeric products AW-P1 (30.3 mg) and AW-P2 (46.0 mg) as white solids.

AW-P1 ESI 578.3 (M+H)$^+$. $^1$H NMR (400 MHz, MeOD) δ 7.46 (s, 1H), 7.43 (s, 1H), 7.17-7.07 (m, 3H), 6.88-6.86 (m, 1H), 6.74-6.71 (m, 1H), 5.57-5.54 (m, 1H), 5.36 (t, J=5.0 Hz, 1H), 3.38-3.5 (m, 1H), 3.19-3.06 (m, 1H), 2.83-2.77 (m, 2H), 2.67 (s, 6H), 2.64-2.59 (m, 1H), 2.53-2.47 (m, 1H), 2.30 (d, J=1.7 Hz, 3H), 2.05 (s, 3H), 1.98-1.93 (m, 8H), 1.48-1.39 (m, 1H), 0.95-0.89 (m, 6H).

AW-P2 ESI 578.3 (M+H)$^+$. $^1$H NMR (400 MHz, MeOD) δ 7.51 (s, 1H), 7.41 (s, 1H), 7.17-7.02 (m, 3H), 6.89-6.87 (m, 1H), 6.81-6.79 (m, 1H), 5.64-5.60 (m, 1H), 5.55-5.51 (m, 1H), 3.45-3.38 (m, 1H), 3.30-3.23 (m, 1H), 2.97-2.72 (m, 8H), 2.61-2.56 (m, 1H), 2.45-2.39 (m, 1H), 2.31 (d, J=1.8 Hz, 3H), 2.06-1.80 (m, 1H), 1.46-1.39 (m, 1H), 0.94-0.88 (m, 6H).

3-45. Preparation of (3S)-3-(2-(5-(2-(dimethyl-amino)ethyl)-3-fluoro-2-oxopyridin-1(2H)-yl)-4-methylpentanamido)-3-(4-fluoro-2',5,6'-trimethylbiphenyl-3-yl)propanoic Acid (Compounds AX-P1 and AX-P2)

Step 1: (3S)-ethyl 3-(2-(5-(2-(dimethylamino)ethyl)-3-fluoro-2-oxopyridin-1(2H)-yl)-4-methylpentanamido)-3-(4-fluoro-2',5,6'-trimethylbiphenyl-3-yl)propanoate

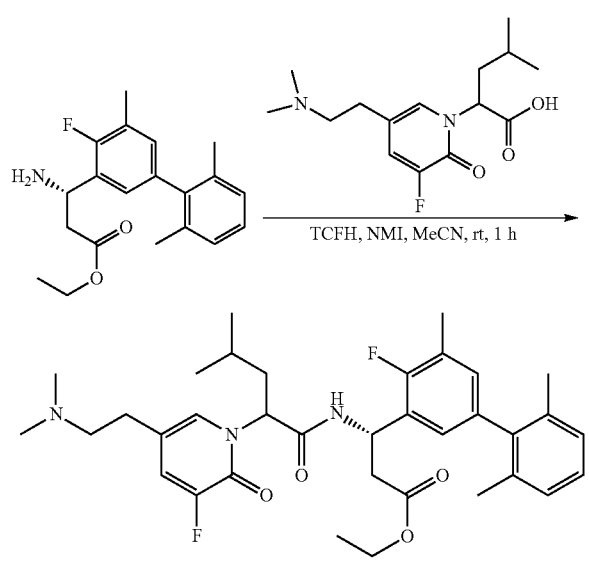

A mixture of 2-(5-(2-(dimethylamino)ethyl)-3-fluoro-2-oxopyridin-1(2H)-yl)-4-methylpentanoic acid (109 mg, 0.36 mmol), (S)-ethyl 3-amino-3-(4-fluoro-2',5,6'-trimethylbiphenyl-3-yl)propanoate (120 mg, 0.36 mmol), TCFH (114 mg, 0.41 mmol) and NMI (84 mg, 1.02 mmol) in CH$_3$CN (5 mL) was stirred at room temperature for 1 hour. The solvent was removed in vacuo and the residue was purified by silica gel column (DCM:MeOH 4:1) to provide (3S)-ethyl 3-(2-(5-(2-(dimethylamino)ethyl)-3-fluoro-2-oxopyridin-1(2H)-yl)-4-methylpentanamido)-3-(4-fluoro-2',5,6'-trimethylbiphenyl-3-yl)propanoate as a white solid (130 mg). Yield 59% (ESI 610.2 (M+H)$^+$).

Step 2: (3S)-3-(2-(5-(2-(dimethylamino)ethyl)-3-fluoro-2-oxopyridin-1(2H)-yl)-4-methylpentanamido)-3-(4-fluoro-2',5,6'-trimethylbiphenyl-3-yl)propanoic Acid

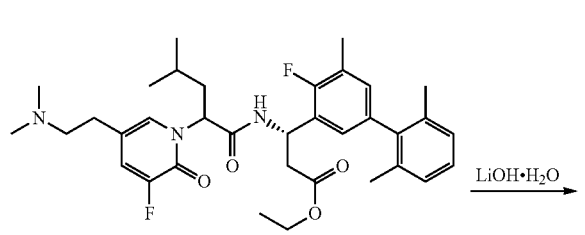

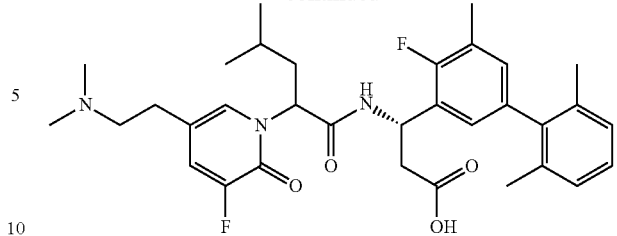

(3S)-ethyl 3-(2-(5-(2-(dimethylamino)ethyl)-3-fluoro-2-oxopyridin-1(2H)-yl)-4-methylpentanamido)-3-(4-fluoro-2',5,6'-trimethylbiphenyl-3-yl)propanoate (130 mg, 0.21 mmol)) was treated with LiOH—H$_2$O (32 mg, 0.75 mmol) in THF (3 mL) and H$_2$O (1 mL) at room temperature for 3 hours. The reaction mixture was acidified to pH 4~5 with 1N HCl. The solvent was removed in vacuo and the residue was purified by pre-HPLC A (30-60% MeCN) to give the diastereomeric products AX-P1 (32.0 mg) and AX-P2 (35.0 mg) as white solids.

AX-P1 ESI 582.1 (M+H)$^+$. $^1$H NMR (400 MHz, MeOD) δ 7.48 (s, 1H), 7.40 (d, J=10.2 Hz, 1H), 7.15-7.08 (m, 3H), 6.86 (d, J=6.8 Hz, 1H), 6.78 (d, J=6.4 Hz, 1H), 5.67 (t, J=8.1 Hz, 1H), 5.43 (t, J=5.5 Hz, 1H), 3.18-3.13 (m, 1H), 3.03-2.99 (m, 1H), 2.81-2.77 (m, 2H), 2.68-2.53 (m, 8H), 2.29 (s, 3H), 2.00-1.94 (m, 5H), 1.92 (s, 3H), 1.45-1.39 (m, 1H), 0.96-0.90 (m, 6H).

AX-P2 ESI 582.1 (M+H)$^+$. $^1$H NMR (400 MHz, MeOD) δ 7.50 (s, 1H), 7.43-7.40 (m, 1H), 7.15-7.07 (m, 3H), 6.91 (d, J=6.9 Hz, 2H), 5.66-5.58 (m, 2H), 3.41-3.34 (m, 1H), 3.28-3.22 (m, 1H), 2.99-2.91 (m, 1H), 2.85-2.81 (m, 7H), 2.61-2.55 (m, 1H), 2.47-2.41 (m, 1H), 2.32 (d, J=1.8 Hz, 3H), 2.04-1.97 (m, 7H), 1.85-1.77 (m, 1H), 1.44-1.36 (m, 1H), 0.92-0.89 (m, 6H).

3-46. Preparation of (3S)-3-(2-(5-(2-(dimethyl-amino)ethyl)-4-methyl-2-oxopyridin-1(2H)-yl)-4-methylpentanamido)-3-(4-fluoro-2',5,6'-trimethylbiphenyl-3-yl)propanoic Acid (Compounds AZ-P1 and AZ-P2)

Step 1: Ethyl (3S)-3-(2-(5-(2-(dimethylamino)ethyl)-4-methyl-2-oxopyridin-1(2H)-yl)-4-methylpentanamido)-3-(4-fluoro-2',5,6'-trimethyl-[1,1'-biphenyl]-3-yl)propanoate

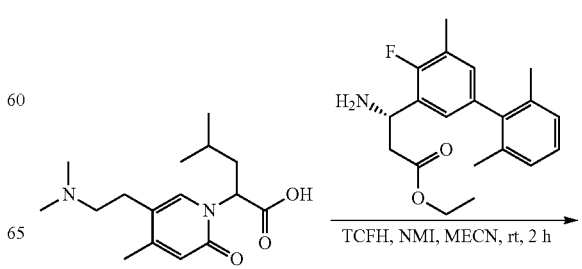

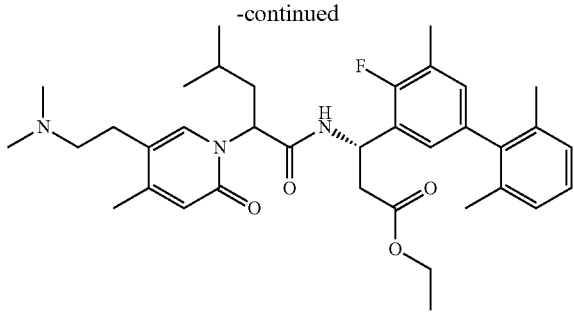

A mixture of 2-(5-(2-(dimethylamino)ethyl)-4-methyl-2-oxopyridin-1(2H)-yl)-4-methylpentanoic acid (100 mg, 0.34 mmol), ethyl (S)-3-amino-3-(4-fluoro-2',5,6'-trimethyl-[1,1'-biphenyl]-3-yl)propanoate (112 mg, 0.34 mmol), TCFH (115 mg, 0.41 mmol), NMI (84 mg, 1.02 mmol) in CH₃CN (5 mL) was stirred at room temperature for 1 hour. The solvent was removed in vacuo and the residue was purified by silica gel column (DCM:MeOH 4:1) to provide ethyl (3S)-3-(2-(5-(2-(dimethylamino)ethyl)-4-methyl-2-oxopyridin-1(2H)-yl)-4-methylpentanamido)-3-(4-fluoro-2',5,6'-trimethyl-[1,1'-biphenyl]-3-yl)propanoate as a white solid (90 mg). Yield 44% (ESI 606.2 (M+H)⁺).

Step 2: (3S)-3-(2-(5-(2-(dimethylamino)ethyl)-4-methyl-2-oxopyridin-1(2H)-yl)-4-methylpentanamido)-3-(4-fluoro-2',5,6'-trimethylbiphenyl-3-yl)propanoic Acid

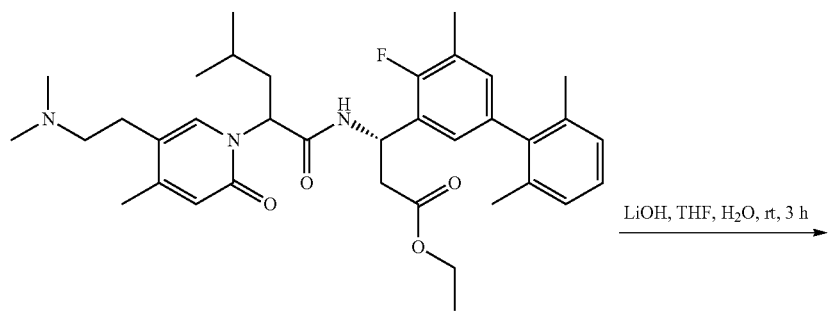

Ethyl (3S)-3-(2-(5-(2-(dimethylamino)ethyl)-4-methyl-2-oxopyridin-1(2H)-yl)-4-methylpentanamido)-3-(4-fluoro-2',5,6'-trimethyl-[1,1'-biphenyl]-3-yl)propanoate (90 mg, 0.15 mmol)) was treated with LiOH—H₂O (32 mg, 0.75 mmol) in THF (3 mL) and H₂O (1 mL) at room temperature for 3 hours. The reaction mixture was acidified to pH 4~5 with 1N HCl. The solvent was removed in vacuo and the residue was purified by prep-HPLC A (30-60% MeCN) to give the diastereomeric products AZ-P1 (30.0 mg) and AZ-P2 (26.0 mg) as white solids.

AZ-P1 ESI 578.2 (M+H)⁺. ¹H NMR (500 MHz, MeOD) δ 7.57 (s, 1H), 7.18-7.03 (m, 3H), 6.86-6.81 (m, 2H), 6.35 (s, 1H), 5.59-5.55 (m, 1H), 5.49-5.46 (m, 1H), 3.25-3.16 (m, 1H), 3.13-3.108 (m, 1H), 2.87 (t, J=7.2 Hz, 2H), 2.75 (s, 6H), 2.70-2.59 (m, 2H), 2.29 (d, J=1.5 Hz, 3H), 2.26 (s, 3H), 1.99-1.94 (m, 5H), 1.90 (s, 3H), 1.46-1.37 (m, 1H), 0.94-0.89 (m, 6H).

AZ-P2 ESI 578.2 (M+H)⁺. ¹H NMR (500 MHz, MeOD) δ 7.55 (s, 1H), 7.15-7.07 (m, 3H), 6.90 (d, J=6.9 Hz, 2H), 6.43 (s, 1H), 5.65-5.56 (m, 2H), 3.31-3.28 (m, 1H), 3.22-3.15 (m, 1H), 2.98-2.88 (m, 2H), 2.84 (s, 6H), 2.63-2.59 (m, 1H), 2.50-2.44 (m, 1H), 2.32 (d, J=1.5 Hz, 3H), 2.26 (s, 3H), 2.03-1.91 (m, 7H), 1.80-1.72 (m, 1H), 1.42-1.32 (m, 1H), 0.90-0.88 (m, 6H).

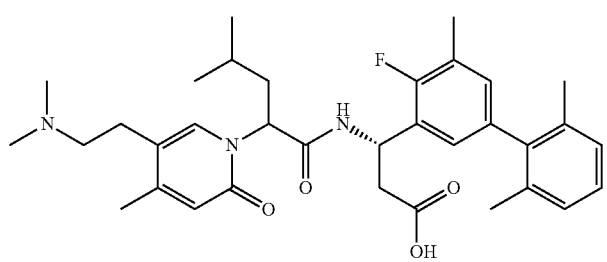

3-47. Preparation of (3S)-3-(2-(5-(2-(dimethyl-amino)ethyl)-2-oxo-4-(trifluoromethyl)pyridin-1(2H)-yl)-4-methylpentanamido)-3-(4-fluoro-2',5,6'-trimethyl-[1,1'-biphenyl]-3-yl)propanoic Acid
(Compounds BA-P1 and BA-P2)

Step 1: Ethyl (3S)-3-(2-(5-(2-(dimethylamino)ethyl)-2-oxo-4-(trifluoromethyl)pyridin-1(2H)-yl)-4-methylpentanamido)-3-(4-fluoro-2',5,6'-trimethyl-[1,1'-biphenyl]-3-yl)propanoate

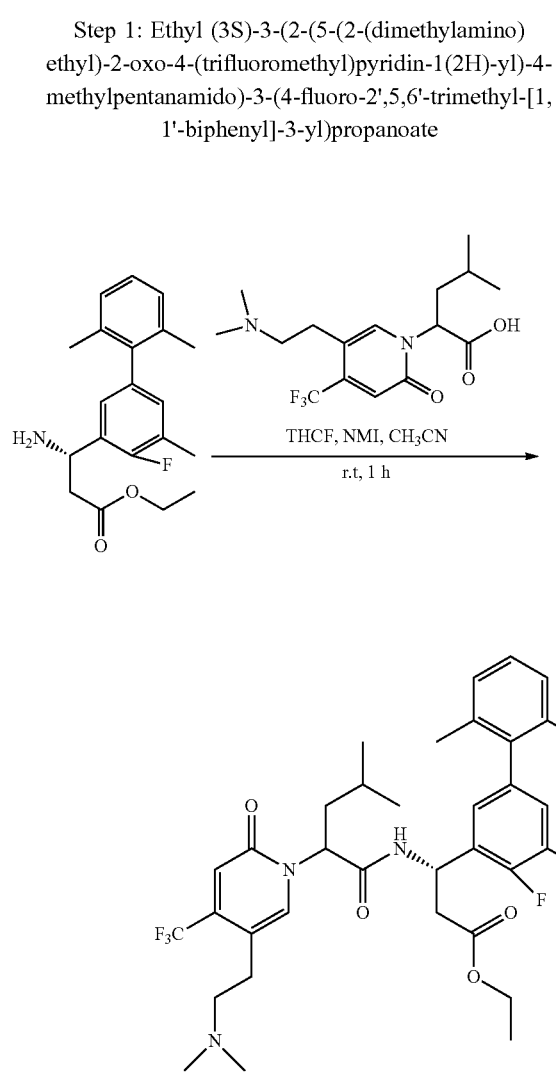

A mixture of ethyl (S)-3-amino-3-(4-fluoro-2',5,6'-trimethyl-[1,1'-biphenyl]-3-yl)propanoate (95.0 mg, 0.29 mmol), 2-(5-(2-(dimethylamino)ethyl)-2-oxo-4-(trifluoromethyl)pyridin-1(2H)-yl)-4-methylpentanoic acid (100.0 mg, 0.29 mmol), TCHF (97.0 mg, 0.35 mmol) and NMI (71.0 mg, 0.87 mmol) in CH$_3$CN (4 mL) was stirred at room temperature for 1 hour. The solvent was removed in vacuo and the residue was purified by reverse phase HPLC on a C18/40 g column (A: water 10 mM NH$_4$HCO$_3$, B: MeOH, 0~100%) to provide ethyl (3S)-3-(2-(5-(2-(dimethylamino)ethyl)-2-oxo-4-(trifluoromethyl)pyridin-1(2H)-yl)-4-methylpentanamido)-3-(4-fluoro-2',5,6'-trimethyl-[1,1'-biphenyl]-3-yl)propanoate as a yellow solid (100.0 mg). Yield 52.3% (ESI 660.2 [M+H]$^+$).

Step 2: (3S)-3-(2-(5-(2-(dimethylamino)ethyl)-2-oxo-4-(trifluoromethyl)pyridin-1(2H)-yl)-4-methylpentanamido)-3-(4-fluoro-2',5,6'-trimethyl-[1,1'-biphenyl]-3-yl)propanoic Acid Ethyl (3S)-3-(2-(5-(2-(dimethylamino)ethyl)-2-oxo-4-(trifluoromethyl)pyridin-1(2H)-yl)-4-methylpentanamido)-3-(4-fluoro-2',5,6'-trimethyl-[1,1'-biphenyl]-3-yl)propanoate (100.0 mg, 0.15 mmol) was treated with LiOH—H$_2$O (32.0 mg, 0.75 mmol) in THF (3 mL) and water (1 mL) at 30° C. for 1 hour. The reaction mixture was acidified to pH 4~5 with 2N HCl. The solvent was removed in vacuo and the residue was purified by prep-HPLC A (30-60% MeCN) to give the diastereomeric products BA-P1 (16.4 mg) and BA-P2 (12.5 mg) as white solids.

BA-P1 ESI 632.2 (M+H)$^+$. $^1$H NMR (500 MHz, MeOD) δ 7.77 (s, 1H), 7.03-6.86 (m, 3H), 6.79-6.70 (m, 2H), 6.64 (s, 1H), 5.56 (t, J=8.0 Hz, 1H), 5.48-5.38 (m, 1H), 2.98-2.92 (m, 2H), 2.83-2.78 (m, 2H), 2.62-2.59 (m, 8H), 2.17 (s, 3H), 1.87 (d, J=11.3 Hz, 5H), 1.71 (s, 3H), 1.34-1.30 (m, 1H), 0.85-0.81 (m, 6H).

BA-P2 ESI 632.2 (M+H)$^+$. $^1$H NMR (500 MHz, MeOD) δ 7.71 (s, 1H), 7.03-6.95 (m, 3H), 6.82-6.77 (m, 3H), 5.60-5.57 (m, 1H), 5.49 (t, J=7.7 Hz, 1H), 3.15-3.06 (m, 2H), 2.88 (t, J=6.6 Hz, 2H), 2.70 (s, 6H), 2.54-2.50 (m, 1H), 2.42-2.37 (m, 1H), 2.21 (s, 3H), 1.90-1.85 (m, 7H), 1.62-1.52 (m, 1H), 1.33-1.22 (m, 1H), 0.79-0.77 (m, 6H).

3-48. Preparation of (3S)-3-(2-(5-(3-(azetidin-1-yl)propyl)-2-oxo-4-(trifluoromethyl)pyridin-1(2H)-yl)-4-methylpentanamido)-3-(2,2',4-trifluoro-4',6'-dimethyl-5-(trifluoromethyl)biphenyl-3-yl)propanoic Acid (Compounds HD-P1 and HD-P2)

Step 1: (3S)-ethyl 3-(2-(5-(3-(azetidin-1-yl)propyl)-2-oxo-4-(trifluoromethyl)pyridin-1(2H)-yl)-4-methylpentanamido)-3-(2,2',4-trifluoro-4',6'-dimethyl-5-(trifluoromethyl)biphenyl-3-yl)propanoate

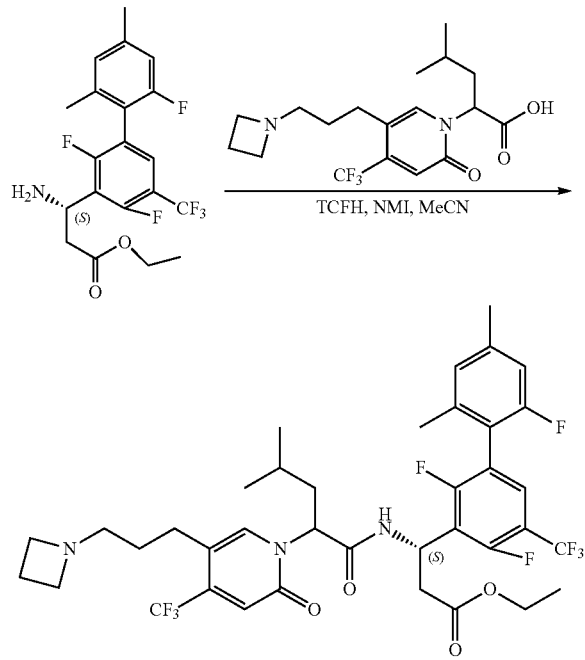

A mixture of 2-(5-(3-(azetidin-1-yl)propyl)-2-oxo-4-(trifluoromethyl)pyridin-1(2H)-yl)-4-methylpentanoic acid (100 mg, 0.28 mmol), (3S)-ethyl 3-amino-3-(2,2',4-trifluoro-4',6'-dimethyl-5-(trifluoromethyl)biphenyl-3-yl)propanoate (120 mg, 0.29 mmol), NMI (71 mg, 0.87 mmol) and TCFH (98 mg, 0.35 mmol) in CH₃CN (4 mL) was stirred at room temperature for 2 hours. The solvent was concentrated in vacuo and the residue was purified by reverse phase HPLC on a C18/40 g column (A: water 10 mM NH4HCO3, B: CH3CN, 0~100%) to provide (3S)-ethyl 3-(2-(5-(3-(azetidin-1-yl)propyl)-2-oxo-4-(trifluoromethyl)pyridin-1(2H)-yl)-4-methylpentanamido)-3-(2,2',4-trifluoro-4',6'-dimethyl-5-(trifluoromethyl)biphenyl-3-yl)propanoate as a yellow oil (110 mg). Yield 52% (ESI 776.3 [M+H]⁺).

Step 2: (3S)-3-(2-(5-(3-(azetidin-1-yl)propyl)-2-oxo-4-(trifluoromethyl)pyridin-1(2H)-yl)-4-methylpentanamido)-3-(2,2',4-trifluoro-4',6'-dimethyl-5-(trifluoromethyl)biphenyl-3-yl)propanoic acid

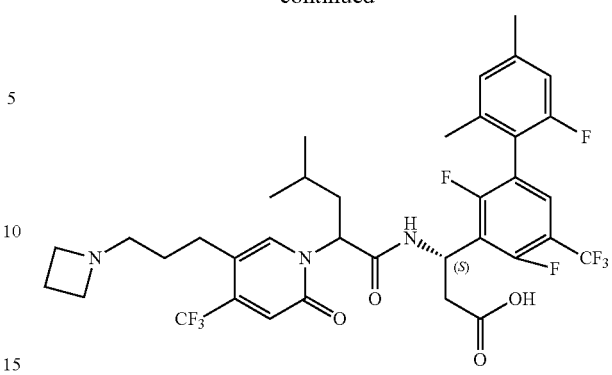

(3S)-ethyl 3-(2-(5-(3-(azetidin-1-yl)propyl)-2-oxo-4-(trifluoromethyl)pyridin-1(2H)-yl)-4-methylpentanamido)-3-(2,2',4-trifluoro-4',6'-dimethyl-5-(trifluoromethyl)biphenyl-3-yl)propanoate (110 mg, 0.14 mmol) was treated with LiOH—H₂O (24 mg, 0.56 mmol) in EtOH (3 mL) and H₂O (1 mL) at room temperature for 1 hour. The reaction mixture was acidified to pH 5~6 with 1N HCl. The reaction was concentrated in vacuo and the residue purified by prep-HPLC A (30-60% CH₃CN) to give the diastereomeric products HD-P1 (27 mg) and HD-P2 (28 mg) as white solids.

HD-P1 ESI 748.2 (M+H)⁺. ¹H NMR (400 MHz, MeOD) δ 7.77 (s, 1H), 7.53-7.43 (m, 1H), 6.98 (s, 1H), 6.90-6.73 (m, 2H), 5.81-5.71 (m, 2H), 4.05 (t, J=8.1 Hz, 4H), 3.14 (t, J=7.7 Hz, 2H), 3.01-2.89 (m, 1H), 2.84-2.53 (m, 3H), 2.51-2.30 (m, 5H), 2.18-1.90 (m, 5H), 1.90-1.66 (m, 2H), 1.46-1.23 (m, 1H), 1.06-0.86 (m, 6H).

HD-P2 ESI 748.2 (M+H)⁺. ¹H NMR (400 MHz, MeOD) δ 7.79 (s, 1H), 7.52 (t, J=7.4 Hz, 1H), 7.00 (s, 1H), 6.93-6.75 (m, 2H), 5.89-5.73 (m, 1H), 5.69-5.62 (m, 1H), 4.17-3.93 (m, 4H), 3.21-3.00 (m, 2H), 2.94-2.84 (m, 1H), 2.75-2.56 (m, 3H), 2.51-2.30 (m, 5H), 2.10 (d, J=11.8 Hz, 3H), 1.98-1.55 (m, 4H), 1.42-1.22 (m, 1H), 0.92-0.80 (m, 6H).

3-49. Preparation of (3S)-3-(2-(5-(3-(azetidin-1-yl)propyl)-2-oxo-4-(trifluoromethyl)pyridin-1(2H)-yl)-4-methylpentanamido)-3-(2,4-difluoro-2',6'-dimethyl-5-(trifluoromethyl)-[1,1'-biphenyl]-3-yl)propanoic Acid (Compounds HE-P1 and HE-P2)

Step 1: Ethyl (3S)-3-(2-(5-(3-(azetidin-1-yl)propyl)-2-oxo-4-(trifluoromethyl)pyridin-1(2H)-yl)-4-methylpentanamido)-3-(2,4-difluoro-2',6'-dimethyl-5-(trifluoromethyl)-[1,1'-biphenyl]-3-yl)propanoate

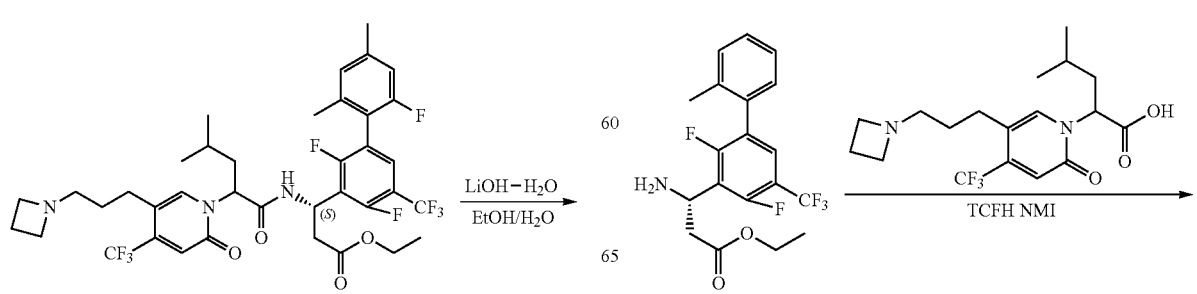

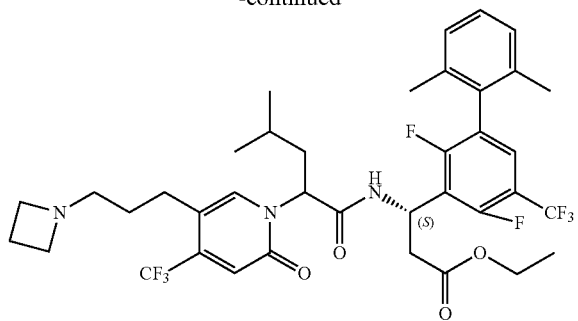

A mixture of ethyl (S)-3-amino-3-(2,4-difluoro-2',6'-dimethyl-5-(trifluoromethyl)-[1,1'-biphenyl]-3-yl)propanoate (116 mg, 0.29 mmol), 2-(5-(3-(azetidin-1-yl)propyl)-2-oxo-4-(trifluoromethyl)pyridin-1(2H)-yl)-4-methylpentanoic acid (100 mg, 0.27 mmol), TCFH (151 mg, 0.54 mmol) and NMI (110 mg, 1.35 mmol) in CH$_3$CN (2 mL) was stirred at 25° C. for 2 hr. The solvent was concentrated in vacuo and the residue was purified The reaction was concentrated and purified by reverse phase HPLC on a C18/40 g column (A: water 10 mM NH$_4$HCO$_3$, B: MeOH, 0~90%) to provide ethyl (3S)-3-(2-(5-(3-(azetidin-1-yl)propyl)-2-oxo-4-(trifluoromethyl)pyridin-1(2H)-yl)-4-methylpentanamido)-3-(2,4-difluoro-2',6'-dimethyl-5-(trifluoromethyl)-[1,1'-biphenyl]-3-yl)propanoate as a yellow solid (120 mg). Yield 58.6% (ESI 758.3 [M+H]$^+$).

Step 2: (3S)-3-(2-(5-(3-(azetidin-1-yl)propyl)-2-oxo-4-(trifluoromethyl)pyridin-1(2H)-yl)-4-methylpentanamido)-3-(2,4-difluoro-2',6'-dimethyl-5-(trifluoromethyl)-[1,1'-biphenyl]-3-yl)propanoic Acid

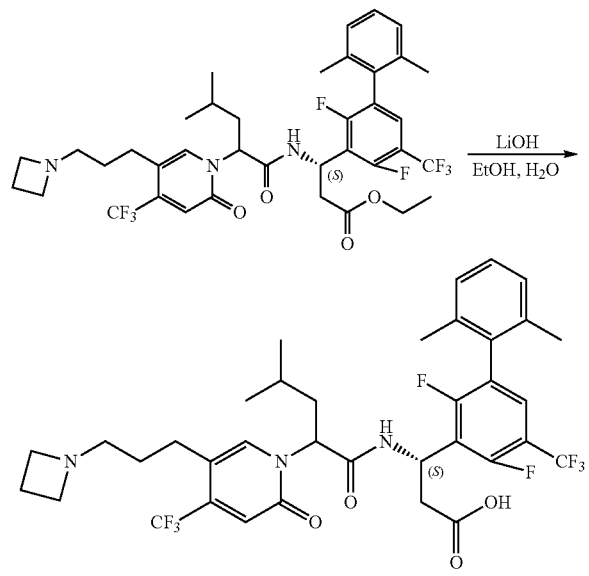

Ethyl (3S)-3-(2-(5-(3-(azetidin-1-yl)propyl)-2-oxo-4-(trifluoromethyl)pyridin-1(2H)-yl)-4-methylpentanamido)-3-(2,4-difluoro-2',6'-dimethyl-5-(trifluoromethyl)-[1,1'-biphenyl]-3-yl)propanoate (120 mg, 0.16 mmol) was treated with LiOH—H$_2$O (13 mg, 0.32 mmol) in EtOH (2 mL) and H$_2$O (0.5 mL) at room temperature for 30 mins. The reaction mixture was acidified to pH 5~6 with 1N HCl. The reaction was concentrated in vacuo and the residue purified by prep-HPLC A (40-65% CH$_3$CN) to give the diastereomeric products HE-P1 (40 mg) and HE-P2 (42 mg) as yellow solids.

HE-P1 ESI 730.3 (M+H)$^+$. $^1$H NMR (400 MHz, MeOD) δ 7.75 (s, 1H), 7.37 (t, J=7.6 Hz, 1H), 7.23-7.16 (m, 1H), 7.14-7.08 (m, 2H), 6.78 (s, 1H), 5.78-5.70 (m, 2H), 3.88 (s, 4H), 3.05-2.91 (m, 3H), 2.76-2.70 (m, 1H), 2.66-2.57 (m, 2H), 2.41-2.32 (m, 2H), 2.09-1.91 (m, 6H), 1.90 (s, 3H), 1.77-1.69 (m, 1H), 1.36-1.30 (m, 1H), 0.99-0.85 (m, 6H).

HE-P2 ESI 730.3 (M+H)$^+$. $^1$H NMR (400 MHz, MeOD) δ 7.79 (s, 1H), 7.44 (t, J=7.5 Hz, 1H), 7.25-7.19 (m, 1H), 7.15 (d, J=7.4 Hz, 2H), 6.84 (s, 1H), 5.85-5.79 (m, 1H), 5.63 (t, J=7.6 Hz, 1H), 4.08 (s, 4H), 3.18-3.05 (m, 2H), 2.95-2.87 (m, 1H), 2.71-2.59 (m, 3H), 2.48-2.39 (m, 2H), 2.02 (d, J=5.7 Hz, 6H), 1.95-1.78 (m, 3H), 1.70-1.60 (m, 1H), 1.34-1.27 (m, 1H), 0.90-0.82 (m, 6H).

3-50. Preparation of (3S)-3-(2-(5-(2-(diethylamino)ethyl)-2-oxo-4-(trifluoromethyl)pyridin-1(2H)-yl)-4-methylpentanamido)-3-(2,4-difluoro-2',4',6'-trimethyl-5-(trifluoromethyl)-[1,1'-biphenyl]-3-yl) propanoic Acid (Compounds HF-P1 and HF-P2)

Step 1: Ethyl (3S)-3-(2-(5-(2-(diethylamino)ethyl)-2-oxo-4-(trifluoromethyl)pyridin-1(2H)-yl)-4-methylpentanamido)-3-(2,4-difluoro-2',4',6'-trimethyl-5-(trifluoromethyl)-[1,1'-biphenyl]-3-yl)propanoate

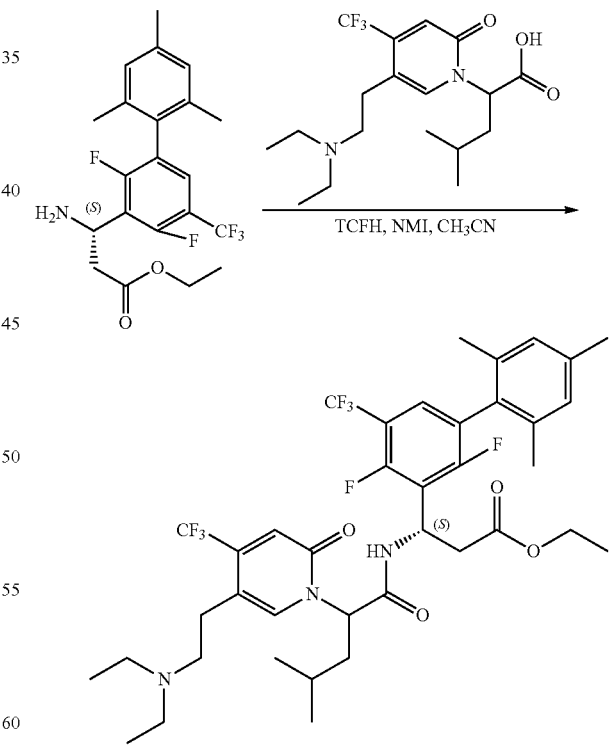

A mixture of ethyl (S)-3-amino-3-(2,4-difluoro-2',4',6'-trimethyl-5-(trifluoromethyl)-[1,1'-biphenyl]-3-yl)propanoate (125 mg, 0.3 mmol), 2-(5-(2-(diethylamino)ethyl)-2-oxo-4-(trifluoromethyl)pyridin-1(2H)-yl)-4-methylpentanoic acid (120 mg, 0.32 mmol), TCFH (150 mg, 0.54 mmol) and NMI (110 mg, 1.35 mmol) in CH₃CN (2.5 mL) was stirred at 50° C. for 30 mins. The reaction was concentrated in vacuo and the residue purified The reaction was concentrated and purified by reverse phase HPLC on a C18/40 g column (A: water 10 mM NH₄HCO₃, B: MeOH, 0~90%) to provide ethyl (3S)-3-(2-(5-(2-(diethylamino)ethyl)-2-oxo-4-(trifluoromethyl)pyridin-1(2H)-yl)-4-methylpentanamido)-3-(2,4-difluoro-2',4',6'-trimethyl-5-(trifluoromethyl)-[1,1'-biphenyl]-3-yl)propanoate as a yellow solid (140 mg). Yield 60.3% (ESI 774.3 [M+H]⁺).

Step 2: (3S)-3-(2-(5-(2-(diethylamino)ethyl)-2-oxo-4-(trifluoromethyl)pyridin-1(2H)-yl)-4-methylpentanamido)-3-(2,4-difluoro-2',4',6'-trimethyl-5-(trifluoromethyl)-[1,1'-biphenyl]-3-yl)propanoic Acid

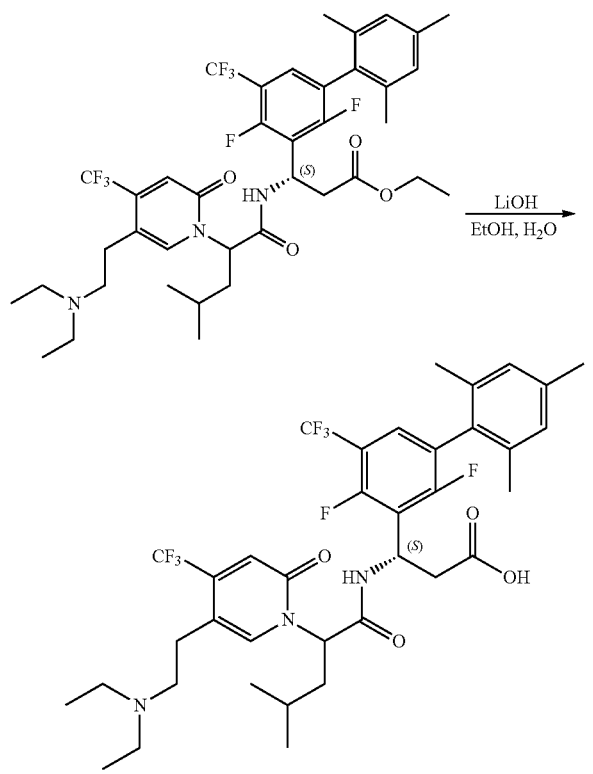

Ethyl (3S)-3-(2-(5-(2-(diethylamino)ethyl)-2-oxo-4-(trifluoromethyl)pyridin-1(2H)-yl)-4-methylpentanamido)-3-(2,4-difluoro-2',4',6'-trimethyl-5-(trifluoromethyl)-[1,1'-biphenyl]-3-yl)propanoate (140 mg, 0.18 mmol) was treated with LiOH—H₂O (23 mg, 0.54 mmol) in EtOH (3 mL) and H₂O (1 mL) at room temperature for 30 mins. The reaction mixture was acidified to pH 5~6 with 1N HCl. The reaction was concentrated in vacuo and the residue purified by prep-HPLC A (35-60% CH₃CN) to give the diastereomeric products HF-P1 (46 mg) and HF-P2 (50 mg) as white solids.

HF-P1 ESI 746.3 (M+H)⁺. ¹H NMR (400 MHz, MeOD) δ 7.89 (s, 1H), 7.33 (t, J=7.6 Hz, 1H), 6.94 (d, J=4.0 Hz, 2H), 6.82 (s, 1H), 5.79-5.67 (m, 2H), 3.25-3.11 (m, 6H), 3.04-2.88 (m, 3H), 2.78-2.69 (m, 1H), 2.29 (s, 3H), 2.06-1.91 (m, 5H), 1.86 (s, 3H), 1.42-1.35 (m, 1H), 1.28 (t, J=7.3 Hz, 6H), 0.94 (t, J=6.5 Hz, 6H).

HF-P2 ESI 746.3 (M+H)⁺. 1H NMR (400 MHz, MeOD) δ 7.88 (s, 1H), 7.39 (t, J=7.6 Hz, 1H), 6.96 (s, 2H), 6.88 (s, 1H), 5.82-5.64 (m, 2H), 3.29-3.15 (m, 6H), 2.96 (t, J=7.7 Hz, 2H), 2.91-2.82 (m, 1H), 2.70 (d, J=15.0 Hz, 1H), 2.31 (s, 3H), 1.98 (d, J=4.2 Hz, 6H), 1.92-1.79 (m, 1H), 1.77-1.67 (m, 1H), 1.36-1.23 (m, 7H), 0.93-0.82 (m, 6H).

3-51. Preparation of (3S)-3-(2-(5-(2-(azetidin-1-yl)ethyl)-2-oxo-4-(trifluoromethyl)pyridin-1(2H)-yl)-4-methylpentanamido)-3-(3'-cyclopropoxy-2,4-difluoro-2',6'-dimethyl-5-(trifluoromethyl)biphenyl-3-yl)propanoic Acid (Compounds HG-P1 and HG-P2)

Step 1: (3S)-ethyl 3-(2-(5-(2-(azetidin-1-yl)ethyl)-2-oxo-4-(trifluoromethyl)pyridin-1(2H)-yl)-4-methylpentanamido)-3-(3'-cyclopropoxy-2,4-difluoro-2',6'-dimethyl-5-(trifluoromethyl)biphenyl-3-yl)propanoate

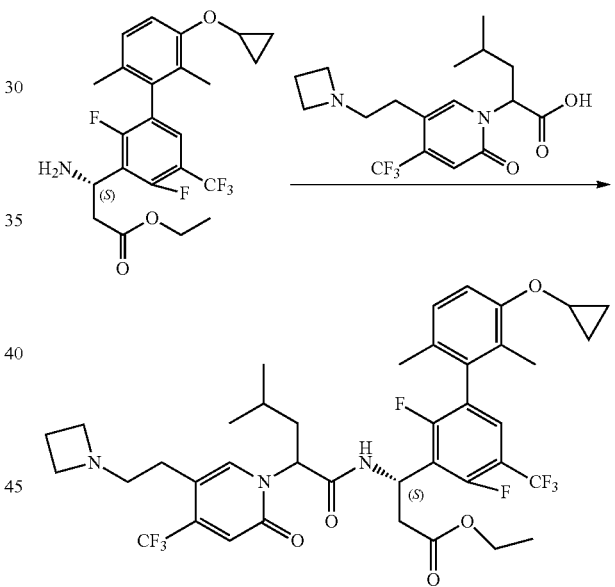

A mixture of (3S)-ethyl 3-amino-3-(3'-cyclopropoxy-2,4-difluoro-2',6'-dimethyl-5-(trifluoromethyl)biphenyl-3-yl)propanoate (150 mg, 0.33 mmol), 2-(5-(2-(azetidin-1-yl)ethyl)-2-oxo-4-(trifluoromethyl)pyridin-1(2H)-yl)-4-methylpentanoic acid (119 mg, 0.33 mmol), TCFH (174 mg, 0.62 mmol) and NMI (82 mg, 1.0 mmol) in MeCN (5 mL) was stirred at room temperature for 1 hour. The solvent was removed in vacuo and the residue was purified by silica gel column (DCM:MeOH 97:3) to provide (3S)-ethyl 3-(2-(5-(2-(azetidin-1-yl)ethyl)-2-oxo-4-(trifluoromethyl)pyridin-1(2H)-yl)-4-methylpentanamido)-3-(3'-cyclopropoxy-2,4-difluoro-2',6'-dimethyl-5-(trifluoromethyl)biphenyl-3-yl)propanoate as a colorless oil (130 mg). Yield 53% (ESI 800.3 (M+H)⁺).

Step 2: (3S)-3-(2-(5-(2-(azetidin-1-yl)ethyl)-2-oxo-4-(trifluoromethyl)pyridin-1(2H)-yl)-4-methylpentanamido)-3-(3'-cyclopropoxy-2,4-difluoro-2',6'-dimethyl-5-(trifluoromethyl)biphenyl-3-yl)propanoic Acid

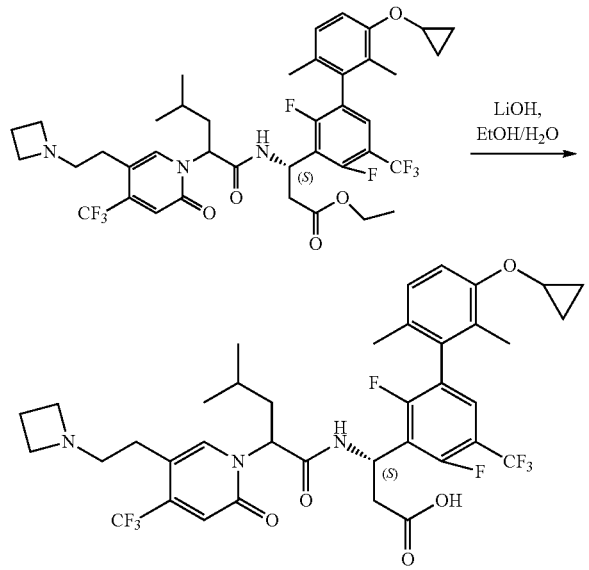

(3S)-ethyl 3-(2-(5-(2-(azetidin-1-yl)ethyl)-2-oxo-4-(trifluoromethyl)pyridin-1(2H)-yl)-4-methylpentanamido)-3-(3'-cyclopropoxy-2,4-difluoro-2',6'-dimethyl-5-(trifluoromethyl)biphenyl-3-yl)propanoate (120 mg, 0.16 mmol) was treated with LiOH—H$_2$O (35 mg, 0.9 mmol) in EtOH (3 mL) and H$_2$O (1 mL) at room temperature for 2 hours. The reaction mixture was acidified to pH 4~5 with 1N HCl. The reaction was concentrated in vacuo and the residue purified The reaction was concentrated in vacuo and the residue purified by prep-HPLC A (30-60% CH$_3$CN) to give the diastereomeric products HG-P1 (30.1 mg) and HG-P2 (42.0 mg) as white solids.

HG-P1 ESI 772.3 (M+H)$^+$. 1H NMR (400 MHz, MeOD) δ 7.79 (s, 1H), 7.35 (t, J=7.5 Hz, 1H), 7.22 (d, J=8.4 Hz, 1H), 7.09 (d, J=8.0 Hz, 1H), 6.85 (s, 1H), 5.71-5.68 (m, 2H), 4.04 (t, J=8.0 Hz, 4H), 3.82-3.73 (m, 1H), 3.29-3.18 (m, 2H), 2.92 (dd, J=15.0, 8.7 Hz, 1H), 2.84 (t, J=6.8 Hz, 2H), 2.77-2.69 (m, 1H), 2.48-2.37 (m, 2H), 2.04-1.85 (m, 5H), 1.81-1.69 (m, 3H), 1.38 (dd, J=13.7, 7.2 Hz, 1H), 0.93 (t, J=6.2 Hz, 6H), 0.78 (dd, J=11.2, 5.2 Hz, 2H), 0.70 (t, J=6.8 Hz, 2H).

HG-P2 ESI 772.3 (M+H)$^+$. 1H NMR (400 MHz, MeOD) δ 7.73 (s, 1H), 7.41 (t, J=7.6 Hz, 1H), 7.25 (d, J=8.4 Hz, 1H), 7.12 (d, J=8.4 Hz, 1H), 6.90 (d, J=13.3 Hz, 1H), 5.90 (dd, J=10.8, 4.2 Hz, 1H), 5.63 (t, J=7.7 Hz, 1H), 4.12 (t, J=8.0 Hz, 4H), 3.79-3.75 (m, 1H), 3.48-3.33 (m, 2H), 3.01-2.76 (m, 3H), 2.60 (dd, J=15.5, 4.1 Hz, 1H), 2.53-2.35 (m, 2H), 2.02-1.85 (m, 4H), 1.81 (d, J=3.2 Hz, 3H), 1.76-1.67 (m, 1H), 1.34-1.30 (m, 1H), 1.02-0.81 (m, 6H), 0.81-0.75 (m, 2H), 0.70 (d, J=3.1 Hz, 2H).

3-52. Preparation of (3S)-3-(2-(5-(2-(azetidin-1-yl)ethyl)-2-oxo-4-(trifluoromethyl)pyridin-1(2H)-yl)-4-methylpentanamido)-3-(5-cyclopropyl-2,3',4-trifluoro-2',6'-dimethyl-[1,1'-biphenyl]-3-yl)propanoic Acid (Compounds HH-P1 and HH-P2)

Step 1: Ethyl (3S)-3-(2-(5-(2-(azetidin-1-yl)ethyl)-2-oxo-4-(trifluoromethyl)pyridin-1(21)-yl)-4-methylpentanamido)-3-(5-cyclopropyl-2,3',4-trifluoro-2',6'-dimethyl-[1,1'-biphenyl]-3-yl)propanoate

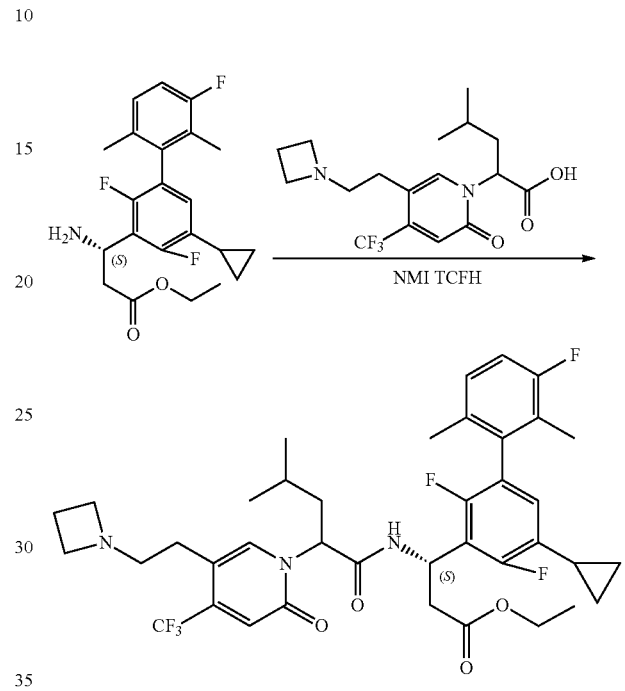

A mixture of ethyl (3S)-3-amino-3-(5-cyclopropyl-2,3',4-trifluoro-2',6'-dimethyl-[1,1'-biphenyl]-3-yl)propanoate (120 mg, 0.3 mmol), 2-(5-(2-(azetidin-1-yl)ethyl)-2-oxo-4-(trifluoromethyl)pyridin-1(2H)-yl)-4-methylpentanoic acid (108 mg, 0.3 mmol), TCFH (126 mg, 0.45 mmol) and NMI (123 mg, 1.5 mmol) in CH$_3$CN (3 mL) was stirred at room temperature overnight. The reaction was concentrated in vacuo and the residue purified by reverse phase HPLC on a C18/40 g column (A: water 10 mM NH$_4$HCO$_3$, B: MeOH, 20~95%) to provide ethyl (3S)-3-(2-(5-(2-(azetidin-1-yl)ethyl)-2-oxo-4-(trifluoromethyl)pyridin-1(2H)-yl)-4-methylpentanamido)-3-(5-cyclopropyl-2,3',4-trifluoro-2',6'-dimethyl-[1,1'-biphenyl]-3-yl)propanoate as a light yellow solid (140 mg). Yield 62% (ESI 734.2 [M+H]$^+$).

Step 2: (3S)-3-(2-(5-(2-(azetidin-1-yl)ethyl)-2-oxo-4-(trifluoromethyl)pyridin-1(2H)-yl)-4-methylpentanamido)-3-(5-cyclopropyl-2,3',4-trifluoro-2',6'-dimethyl-[1,1'-biphenyl]-3-yl)propanoic Acid

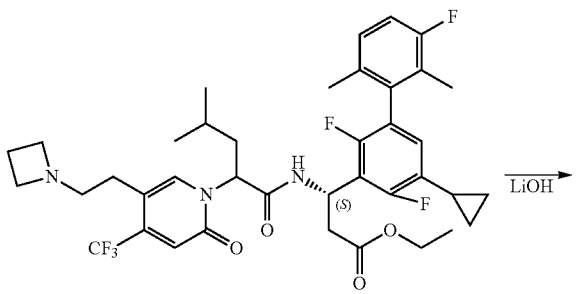

473

-continued

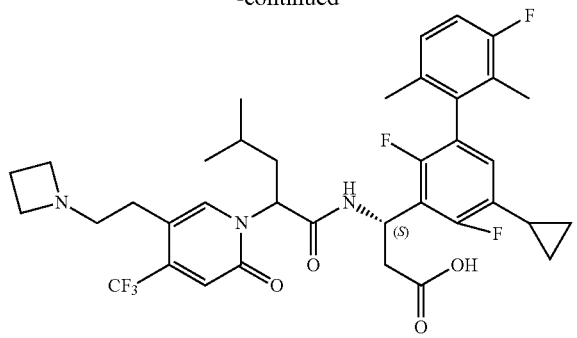

Ethyl (3S)-3-(2-(5-(2-(azetidin-1-yl)ethyl)-2-oxo-4-(trifluoromethyl)pyridin-1(2H)-yl)-4-methylpentanamido)-3-(5-cyclopropyl-2,3',4-trifluoro-2',6'-dimethyl-[1,1'-biphenyl]-3-yl)propanoate (140 mg, 0.19 mmol) was treated with LiOH—H$_2$O (24 mg, 0.57 mmol) in EtOH (2 mL) and water (0.5 mL) at room temperature for 1 hour. The reaction mixture was acidified to pH 4~5 with 2N HCl. The reaction was concentrated in vacuo and the residue purified by prep-HPLC A (20-85% MeCN) to give the diastereomeric products HH-P1 (35 mg) and HH-P2 (58 mg) as white solids.

HH-P1 ESI 706.2 (M+H)$^+$ $^1$H NMR (400 MHz, MeOD) δ 7.80 (s, 1H), 7.12-7.03 (m, 1H), 7.00-6.91 (m, 1H), 6.87 (s, 1H), 6.62 (t, J=8.0 Hz, 1H), 5.80-5.58 (m, 2H), 4.00 (t, J=7.7 Hz, 4H), 3.30-3.19 (m, 2H), 2.97-2.78 (m, 3H), 2.71-2.62 (m, 1H), 2.49-2.34 (m, 2H), 2.13-1.76 (m, 9H), 1.46-1.33 (m, 1H), 1.00-0.86 (m, 8H), 0.66 (d, J=4.8 Hz, 2H).

HH-P2 ESI 706.2 (M+H)$^+$ $^1$H NMR (400 MHz, MeOD) δ 7.70 (s, 1H), 7.14-7.04 (m, 1H), 7.02-6.87 (m, 2H), 6.67 (t, J=8.1 Hz, 1H), 5.98-5.86 (m, 1H), 5.62 (t, J=7.7 Hz, 1H), 4.11 (t, J=8.1 Hz, 4H), 3.45-3.33 (m, 2H), 2.99-2.71 (m, 3H), 2.60-2.36 (m, 3H), 2.17-2.03 (m, 1H), 2.00-1.86 (m, 7H), 1.80-1.67 (m, 1H), 1.41-1.29 (m, 1H), 1.06-0.94 (m, 2H), 0.93-0.82 (m, 6H), 0.72-0.62 (m, 2H).

3-53. Preparation of (3S)-3-(2-(5-(2-(azetidin-1-yl)ethyl)-2-oxo-4-(trifluoromethyl)pyridin-1(2H)-yl)-4-methylpentanamido)-3-(5-cyclopropyl-2,4,4'-trifluoro-2',6'-dimethyl-[1,1'-biphenyl]-3-yl)propanoic Acid (Compounds HI-P1 and HI-P2)

Step 1: Ethyl (3S)-3-(2-(5-(2-(azetidin-1-yl)ethyl)-2-oxo-4-(trifluoromethyl)pyridin-1(2H)-yl)-4-methylpentanamido)-3-(5-cyclopropyl-2,4,4'-trifluoro-2',6'-dimethyl-[1,1'-biphenyl]-3-yl)propanoate

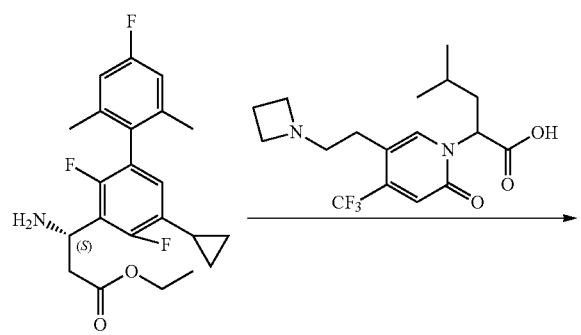

474

-continued

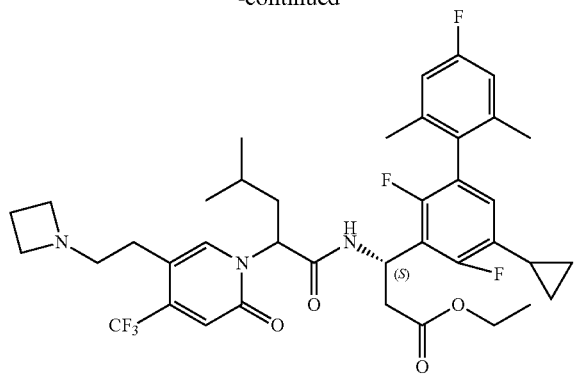

A mixture of 2-(5-(2-(azetidin-1-yl)ethyl)-2-oxo-4-(trifluoromethyl)pyridin-1(2H)-yl)-4-methylpentanoic acid (150 mg, 0.42 mmol), ethyl (S)-3-amino-3-(5-cyclopropyl-2,4,4'-trifluoro-2',6'-dimethyl-[1,1'-biphenyl]-3-yl)propanoate (162 mg, 0.42 mmol), NMI (0.14 mL) and TCFH (141 mg, 0.504 mmol) in CH$_3$CN (5 mL) was stirred at room temperature for 1 hour. The solvent was concentrated in vacuo and the residue was purified by prep-HPLC A (30-90% CH$_3$CN) to provide ethyl (3S)-3-(2-(5-(2-(azetidin-1-yl)ethyl)-2-oxo-4-(trifluoromethyl)pyridin-1(2H)-yl)-4-methylpentanamido)-3-(5-cyclopropyl-2,4,4'-trifluoro-2',6'-dimethyl-[1,1'-biphenyl]-3-yl)propanoate as a white solid (160 mg). Yield 52% (ESI 734.3 [M+H]$^+$).

Step 2: (3S)-3-(2-(5-(2-(azetidin-1-yl)ethyl)-2-oxo-4-(trifluoromethyl)pyridin-1(2H)-yl)-4-methylpentanamido)-3-(5-cyclopropyl-2,4,4'-trifluoro-2',6'-dimethyl-[1,1'-biphenyl]-3-yl)propanoic Acid

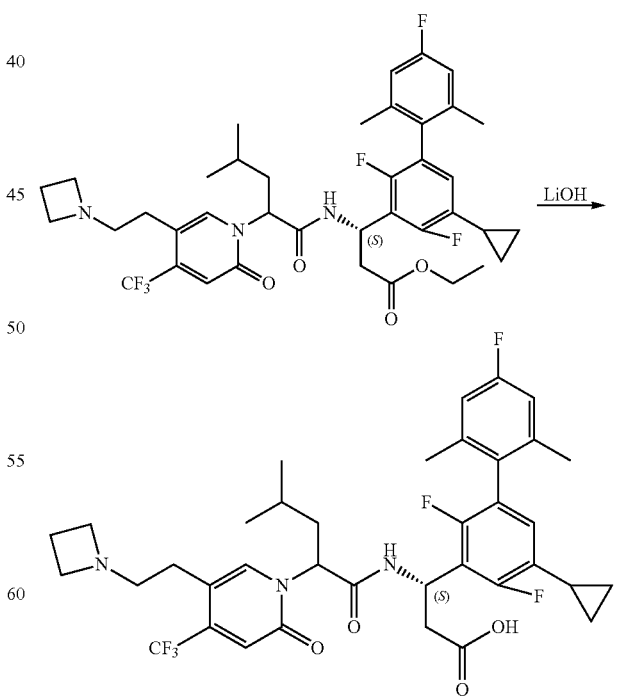

Ethyl (3S)-3-(2-(5-(2-(azetidin-1-yl)ethyl)-2-oxo-4-(trifluoromethyl)pyridin-1(2H)-yl)-4-methylpentanamido)-3-

(5-cyclopropyl-2,4,4'-trifluoro-2',6'-dimethyl-[1,1'-biphenyl]-3-yl)propanoate (160 mg, 0.22 mmol) was treated with LiOH—H$_2$O (46 mg, 1.1 mmol) in MeOH (4 mL) and H$_2$O (0.4 mL) at room temperature for 2 hours. The reaction mixture was acidified to pH 4~5 with 1N HCl. The reaction was concentrated in vacuo and the residue purified by prep-HPLC A (30-70% CH$_3$CN) to give the diastereomeric products HI-P1 (44.0 mg) and HI-P2 (36.0 mg) as white solids.

HI-P1 ESI 706.3 (M+H)$^+$. $^1$H NMR (400 MHz, MeOD) δ 7.79 (s, 1H), 6.91-6.79 (m, 3H), 6.61 (t, J=8.2 Hz, 1H), 5.82-5.71 (m, 1H), 5.67 (t, J=8.1 Hz, 1H), 4.01 (t, J=8.1 Hz, 4H), 3.28-3.22 (m, 2H), 2.94-2.79 (m, 3H), 2.72-2.60 (m, 1H), 2.49-2.34 (m, 2H), 2.11-1.87 (m, 9H), 1.45-1.33 (m, 1H), 1.04-0.85 (m, 8H), 0.70-0.60 (m, 2H).

HI-P2 ESI 706.3 (M+H)$^+$. $^1$H NMR (400 MHz, MeOD) δ 7.69 (s, 1H), 6.93 (s, 1H), 6.86 (d, J=9.6 Hz, 2H), 6.66 (t, J=8.1 Hz, 1H), 5.98-5.85 (m, 1H), 5.62 (t, J=7.7 Hz, 1H), 4.12 (t, J=8.1 Hz, 4H), 3.44-3.34 (m, 2H), 2.97-2.72 (m, 3H), 2.58-2.36 (m, 3H), 2.14-2.04 (m, 1H), 2.02-1.88 (m, 7H), 1.80-1.66 (m, 1H), 1.46-1.26 (m, 1H), 1.07-0.96 (m, 2H), 0.94-0.81 (m, 6H), 0.72-0.63 (m, 2H).

3-54. Preparation of (3S)-3-(2,4-difluoro-3'-methoxy-2',6'-dimethyl-5-(trifluoromethyl)-[1,1'-biphenyl]-3-yl)-3-(2-(5-(3-(dimethylamino)propyl)-2-oxo-4-(trifluoromethyl)pyridin-1(2H)-yl)-4-methylpentanamido)propanoic Acid (Compounds HJ-P1 and HJ-P2)

Step 1: Ethyl (3S)-3-(2,4-difluoro-3'-methoxy-2',6'-dimethyl-5-(trifluoromethyl)-[1,1'-biphenyl]-3-yl)-3-(2-(5-(3-(dimethylamino)propyl)-2-oxo-4-(trifluoromethyl)pyridin-1(2H)-yl)-4-methylpentanamido)propanoate

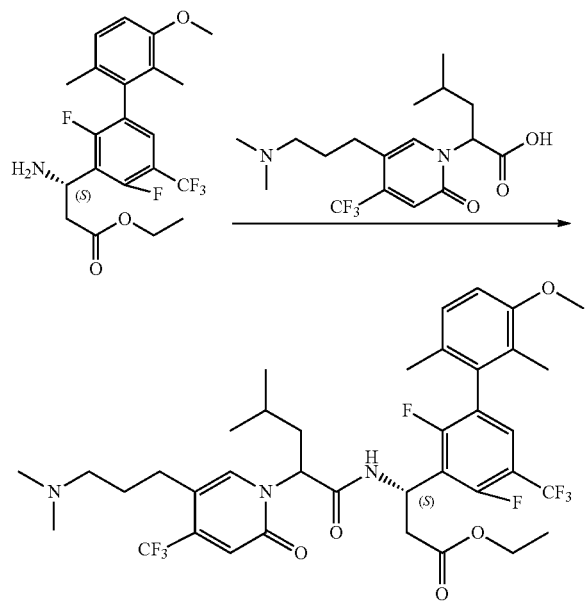

A mixture of 2-(5-(3-(dimethylamino)propyl)-2-oxo-4-(trifluoromethyl)pyridin-1(2H)-yl)-4-methylpentanoic acid (150 mg, 0.41 mmol), ethyl (3S)-3-amino-3-(2,4-difluoro-3'-methoxy-2',6'-dimethyl-5-(trifluoromethyl)-[1,1'-biphenyl]-3-yl)propanoate (176 mg, 0.41 mmol), NMI (0.15 mL) and TCFH (141 mg, 0.507 mmol) in CH$_3$CN (5 mL) was stirred at room temperature for 1 hour. The solvent was concentrated in vacuo and the residue was purified by prep-HPLC A (30-90% CH$_3$CN) to provide ethyl (3S)-3-(2,4-difluoro-3'-methoxy-2',6'-dimethyl-5-(trifluoromethyl)-[1,1'-biphenyl]-3-yl)-3-(2-(5-(3-(dimethylamino)propyl)-2-oxo-4-(trifluoromethyl)pyridin-1(2H)-yl)-4-methylpentanamido)propanoate (160 mg). Yield 52% (ESI 776.3 [M+H]$^+$).

Step 2: (3S)-3-(2,4-difluoro-3'-methoxy-2',6'-dimethyl-5-(trifluoromethyl)-[1,1'-biphenyl]-3-yl)-3-(2-(5-(3-(dimethylamino)propyl)-2-oxo-4-(trifluoromethyl)pyridin-1(2H)-yl)-4-methylpentanamido) propanoic Acid

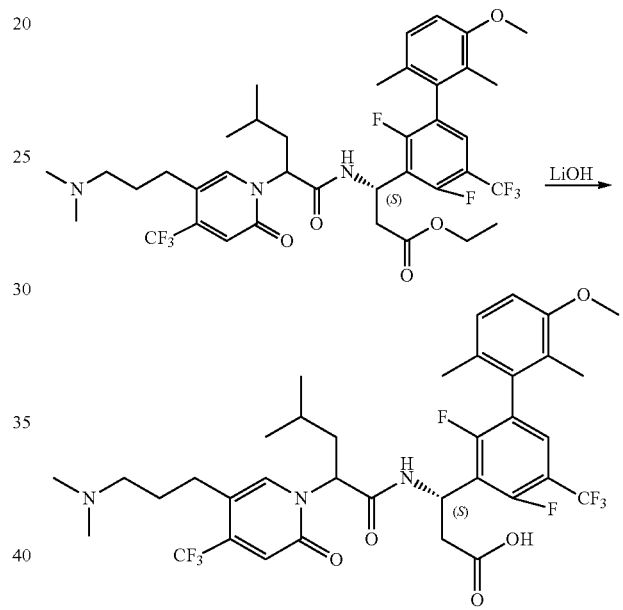

Ethyl (3S)-3-(2,4-difluoro-3'-methoxy-2',6'-dimethyl-5-(trifluoromethyl)-[1,1'-biphenyl]-3-yl)-3-(2-(5-(3-(dimethylamino)propyl)-2-oxo-4-(trifluoromethyl)pyridin-1(2H)-yl)-4-methylpentanamido)propanoate (160 mg, 0.21 mmol) was treated with LiOH—H$_2$O (46 mg, 1.1 mmol) in MeOH (4 mL) and H$_2$O (0.4 mL) at room temperature for 2 hours. The reaction mixture was acidified to pH 4~5 with 1N HCl. The reaction was concentrated in vacuo and the residue purified by prep-HPLC A (30-70% CH$_3$CN) to give the diastereomeric products HJ-P1 (36.0 mg) and HJ-P2 (41.0 mg) as white solids.

HJ-P1 ESI 748.3 (M+H)$^+$. $^1$H NMR (400 MHz, MeOD) δ 7.76 (s, 1H), 7.34 (t, J=7.5 Hz, 1H), 7.12-7.03 (m, 1H), 6.89 (d, J=8.3 Hz, 1H), 6.80 (s, 1H), 5.82-5.67 (m, 2H), 3.82 (s, 3H), 3.08 (t, J=8.1 Hz, 2H), 2.98-2.91 (m, 1H), 2.80 (s, 6H), 2.75-2.58 (m, 3H), 2.10-1.69 (m, 10H), 1.35 (s, 1H), 0.93 (d, J=6.6 Hz, 6H).

HJ-P2 ESI 748.3 (M+H)$^+$. $^1$H NMR (400 MHz, MeOD) δ 7.79 (s, 1H), 7.39 (t, J=7.6 Hz, 1H), 7.11 (d, J=8.5 Hz, 1H), 6.91 (d, J=8.4 Hz, 1H), 6.85 (s, 1H), 5.88-5.77 (m, 1H), 5.62 (t, J=7.6 Hz, 1H), 3.84 (s, 3H), 3.15-2.95 (m, 2H), 2.96-2.84 (m, 1H), 2.79 (s, 6H), 2.70-2.58 (m, 3H), 2.11-1.83 (m, 9H), 1.72-1.57 (m, 1H), 1.42-1.17 (m, 1H), 0.97-0.70 (m, 6H).

3-55. Preparation of (3S)-3-(2-(5-(2-(azetidin-1-yl)ethyl)-2-oxo-4-(trifluoromethyl)pyridin-1(2H)-yl)-4-methylpentanamido)-3-(3'-cyclopropyl-2,4-difluoro-2',6'-dimethyl-5-(trifluoromethyl)-[1,1'-biphenyl]-3-yl)propanoic Acid (Compounds HK-P1 and HK-P2)

Step 1: Ethyl (3S)-3-(2-(5-(2-(azetidin-1-yl)ethyl)-2-oxo-4-(trifluoromethyl)pyridin-1(2H)-yl)-4-methylpentanamido)-3-(3'-cyclopropyl-2,4-difluoro-2',6'-dimethyl-5-(trifluoromethyl)-[1,1'-biphenyl]-3-yl)propanoate

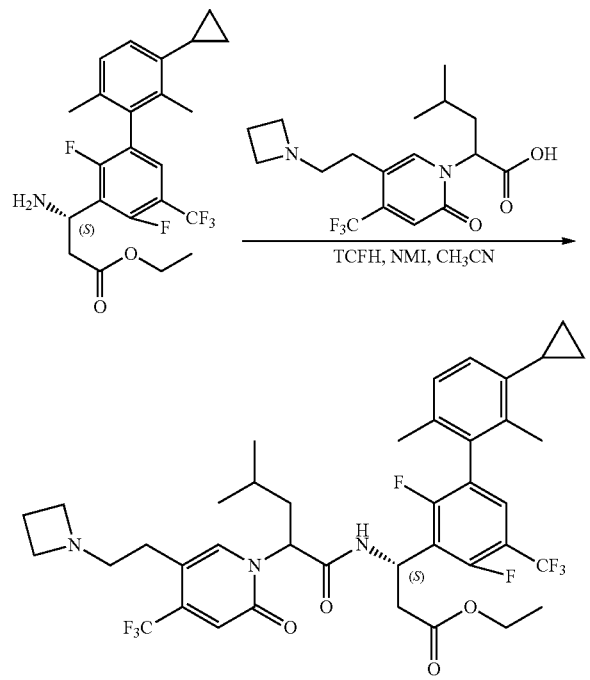

A mixture of ethyl (3S)-3-amino-3-(3'-cyclopropyl-2,4-difluoro-2',6'-dimethyl-5-(trifluoromethyl)-[1,1'-biphenyl]-3-yl)propanoate (210.0 mg, 0.48 mmol), 2-(5-(2-(azetidin-1-yl)ethyl)-2-oxo-4-(trifluoromethyl)pyridin-1(2H)-yl)-4-methylpentanoic acid (136.9 mg, 0.38 mmol), TCFH (134.7 mg, 0.48 mmol) and NMI (118.2 mg, 1.44 mmol) in CH$_3$CN (5 mL) was stirred at room temperature for 16 hours. The reaction was concentrated in vacuo and the residue purified by reverse phase HPLC on a C18/40 g column (A: water 10 mM NH$_4$HCO$_3$, B: MeOH, 0~100%) to provide ethyl (3S)-3-(2-(5-(2-(azetidin-1-yl)ethyl)-2-oxo-4-(trifluoromethyl)pyridin-1(2H)-yl)-4-methylpentanamido)-3-(3'-cyclopropyl-2,4-difluoro-2',6'-dimethyl-5-(trifluoromethyl)-[1,1'-biphenyl]-3-yl)propanoate as a light yellow solid (100.0 mg). Yield 34% (ESI 784.3 [M+H]$^+$).

Step 2: (3S)-3-(2-(5-(2-(azetidin-1-yl)ethyl)-2-oxo-4-(trifluoromethyl)pyridin-1(2H)-yl)-4-methylpentanamido)-3-(3'-cyclopropyl-2,4-difluoro-2',6'-dimethyl-5-(trifluoromethyl)-[1,1'-biphenyl]-3-yl)propanoic Acid

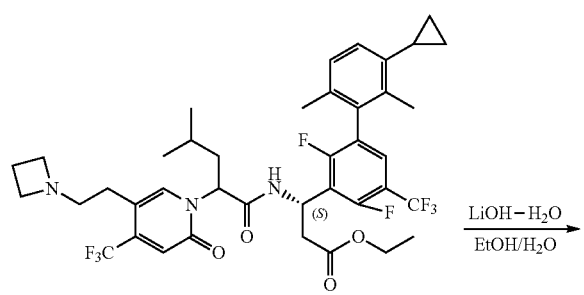

-continued

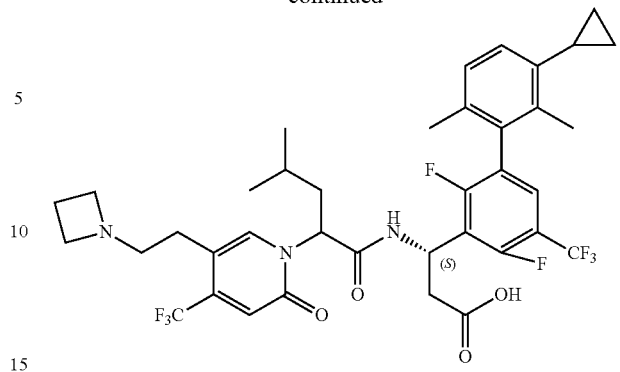

Ethyl (3S)-3-(2-(5-(2-(azetidin-1-yl)ethyl)-2-oxo-4-(trifluoromethyl)pyridin-1(2H)-yl)-4-methylpentanamido)-3-(3'-cyclopropyl-2,4-difluoro-2',6'-dimethyl-5-(trifluoromethyl)-[1,1'-biphenyl]-3-yl)propanoate (100.0 mg, 0.13 mmol) was treated with LiOH—H$_2$O (16.4 mg, 0.39 mmol) in EtOH (2 mL) and water (0.5 mL) at room temperature for 1 hour. The reaction mixture was acidified to pH 4~5 with 2N HCl. The reaction was concentrated in vacuo and the residue purified by prep-HPLC A (30-80% MeCN) to give the diastereomeric products HK-P1 (5.6 mg) and HK-P2 (48.8 mg) as white solids.

HK-P1 ESI 756.2 (M+H)$^+$ $^1$H NMR (400 MHz, MeOD) δ 7.79 (d, J=3.7 Hz, 1H), 7.36 (t, J=7.6 Hz, 1H), 7.07-6.97 (m, 2H), 6.86 (d, J=3.2 Hz, 1H), 5.78-5.65 (m, 2H), 4.04 (t, J=8.1 Hz, 4H), 3.29-3.21 (m, 2H), 2.96-2.88 (m, 1H), 2.84 (t, J=6.8 Hz, 2H), 2.77-2.70 (m, 1H), 2.51-2.35 (m, 2H), 2.11-1.96 (m, 4H), 1.97-1.82 (m, 5H), 1.44-1.31 (m, 1H), 0.96-0.89 (m, 8H), 0.65-0.54 (m, 2H).

HK-P2 ESI 756.2 (M+H)$^+$ $^1$H NMR (400 MHz, MeOD) δ 7.73 (s, 1H), 7.43 (t, J=7.6 Hz, 1H), 7.08-7.00 (m, 2H), 6.91 (s, 1H), 5.91 (d, J=8.6 Hz, 1H), 5.67-5.61 (m, 1H), 4.12 (t, J=8.1 Hz, 4H), 3.344-3.32 (m, 2H), 2.97-2.74 (m, 3H), 2.64-2.57 (m, 1H), 2.51-2.39 (m, 2H), 2.10 (d, J=2.5 Hz, 3H), 1.99-1.86 (m, 5H), 1.76-1.67 (m, 1H), 1.40-1.28 (m, 1H), 0.96-0.83 (m, 8H), 0.65-0.57 (m, 2H).

3-56. Preparation of (3S)-3-(5-cyclopropyl-2,4-difluoro-2',4',6'-trimethylbiphenyl-3-yl)-3-(2-(5-(2-(dimethylamino)ethyl)-2-oxo-4-(trifluoromethyl)pyridin-1(2H)-yl)-4-methylpentanamido)propanoic Acid (Compounds HL-P1 and HL-P2)

Step 1: (3S)-ethyl 3-(5-cyclopropyl-2,4-difluoro-2',4',6'-trimethylbiphenyl-3-yl)-3-(2-(5-(2-(dimethylamino)ethyl)-2-oxo-4-(trifluoromethyl)pyridin-1(2H)-yl)-4-methylpentanamido)propanoate

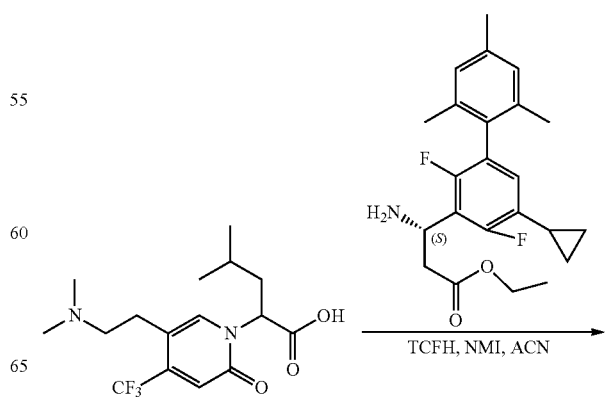

479

-continued

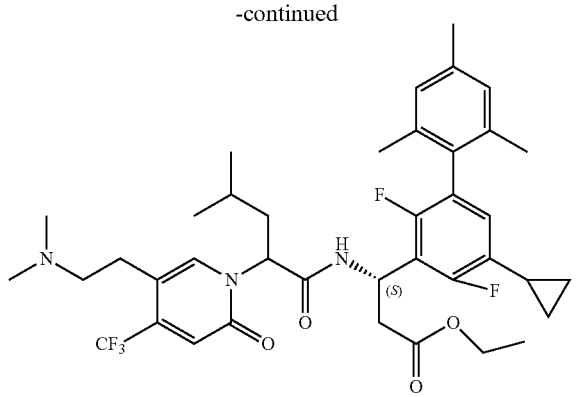

A mixture of (S)-ethyl 3-amino-3-(5-cyclopropyl-2,4-difluoro-2',4',6'-trimethylbiphenyl-3-yl)propanoate (120 mg, 0.31 mmol), 2-(5-(2-(dimethylamino)ethyl)-2-oxo-4-(trifluoromethyl)pyridin-1(2H)-yl)-4-methylpentanoic acid (108 mg, 0.31 mmol), TCFH (174 mg, 0.62 mmol) and NMI (82 mg, 1.0 mmol) in MeCN (5 mL) was stirred at room temperature for 1 hour. The solvent was removed in vacuo and the residue was purified by silica gel column (DCM: MeOH 97:3) to provide (3S)-ethyl 3-(5-cyclopropyl-2,4-difluoro-2',4',6'-trimethylbiphenyl-3-yl)-3-(2-(5-(2-(dimethylamino)ethyl)-2-oxo-4-(trifluoromethyl)pyridin-1(2H)-yl)-4-methylpentanamido)propanoate as a colorless oil (130 mg). Yield 59% (ESI 718.3 (M+H)$^+$).

Step 2: (3S)-3-(5-cyclopropyl-2,4-difluoro-2',4',6'-trimethylbiphenyl-3-yl)-3-(2-(5-(2-(dimethylamino)ethyl)-2-oxo-4-(trifluoromethyl)pyridin-1(2H)-yl)-4-methylpentanamido)propanoic acid

480

4-(trifluoromethyl)pyridin-1(2H)-yl)-4-methylpentanamido)propanoate (130 mg, 0.18 mmol) was treated with LiOH—H$_2$O (38 mg, 0.9 mmol) in EtOH (3 mL) and H$_2$O (1 mL) at room temperature for 2 hours. The reaction mixture was acidified to pH 4~5 with 1N HCl. The reaction was concentrated in vacuo and the residue purified by prep-HPLC A (30-60% CH$_3$CN) to give the diastereomeric products HL-P1 (50.2 mg) and HL-P2 (41.8 mg) as white solids.

HL-P1 ESI 690.3 (M+H)$^+$. 1H NMR (400 MHz, MeOD) δ 7.87 (s, 1H), 6.88 (t, J=18.3 Hz, 3H), 6.56 (t, J=7.8 Hz, 1H), 5.71 (dd, J=15.9, 7.0 Hz, 2H), 3.08 (d, J=7.9 Hz, 2H), 3.00-2.81 (m, 3H), 2.84-2.55-2.50 (m, 7H), 2.27 (s, 3H), 2.09-2.00 (m, 1H), 1.96 (dd, J=14.8, 7.0 Hz, 2H), 1.92 (s, 3H), 1.84 (s, 3H), 1.40-1.38 (m, 1H), 0.93 (t, J=6.5 Hz, 8H), 0.63 (d, J=5.1 Hz, 2H).

HL-P2 ESI 690.3 (M+H)$^+$. 1H NMR (400 MHz, MeOD) δ 7.87 (s, 1H), 6.88 (t, J=18.3 Hz, 3H), 6.56 (t, J=7.8 Hz, 1H), 5.71 (dd, J=15.9, 7.0 Hz, 2H), 3.08 (d, J=7.9 Hz, 2H), 3.00-2.81 (m, 3H), 2.84-2.55-2.50 (m, 7H), 2.27 (s, 3H), 2.09-2.00 (m, 1H), 1.96 (dd, J=14.8, 7.0 Hz, 2H), 1.92 (s, 3H), 1.84 (s, 3H), 1.40-1.37 (m, 1H), 0.93 (t, J=6.5 Hz, 8H), 0.63 (d, J=5.1 Hz, 2H).

3-57. Preparation of (3S)-3-(2-(5-(2-(azetidin-1-yl)ethyl)-2-oxo-4-(trifluoromethyl)pyridin-1(2H)-yl)-4-methylpentanamido)-3-(5-cyclopropyl-2,4-difluoro-2',4',6'-trimethylbiphenyl-3-yl)propanoic Acid (Compounds HM-P1 and HM-P2)

Step 1: (3S)-ethyl 3-(2-(5-(2-(azetidin-1-yl)ethyl)-2-oxo-4-(trifluoromethyl)pyridin-1(2H)-yl)-4-methylpentanamido)-3-(5-cyclopropyl-2,4-difluoro-2',4',6'-trimethylbiphenyl-3-yl)propanoate

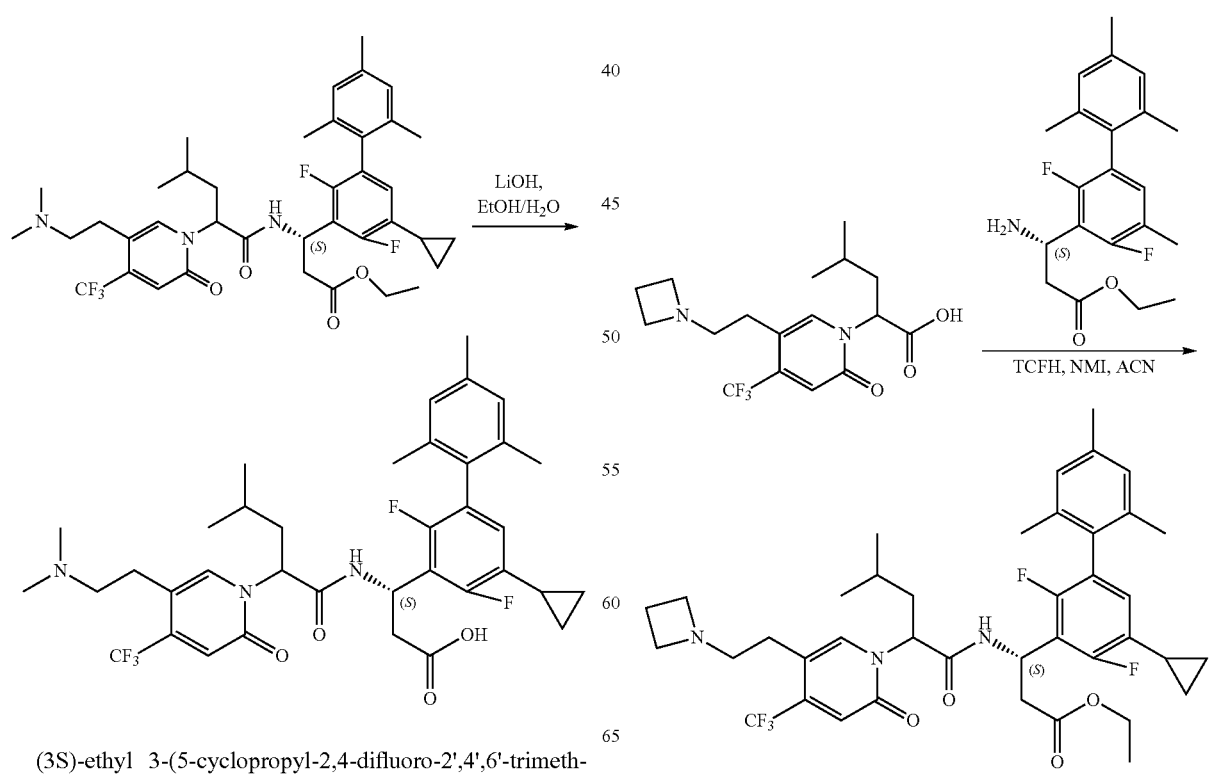

(3S)-ethyl 3-(5-cyclopropyl-2,4-difluoro-2',4',6'-trimethylbiphenyl-3-yl)-3-(2-(5-(2-(dimethylamino)ethyl)-2-oxo- A mixture of (S)-ethyl 3-amino-3-(5-cyclopropyl-2,4-difluoro-2',4',6'-trimethylbiphenyl-3-yl)propanoate (120 mg, 0.31 mmol), 2-(5-(2-(azetidin-1-yl)ethyl)-2-oxo-4-(trifluoromethyl)pyridin-1(2H)-yl)-4-methylpentanoic acid (112 mg, 0.31 mmol), TCFH (174 mg, 0.62 mmol) and NMI (82 mg, 1.0 mmol) in MeCN (5 mL) was stirred at room temperature for 1 hour. The solvent was removed in vacuo and the residue was purified by silica gel column (DCM:MeOH 97:3) to provide (3S)-ethyl 3-(2-(5-(2-(azetidin-1-yl)ethyl)-2-oxo-4-(trifluoromethyl)pyridin-1(2H)-yl)-4-methylpentanamido)-3-(5-cyclopropyl-2,4-difluoro-2',4',6'-trimethylbiphenyl-3-yl)propanoate as a colorless oil (120 mg). Yield 53% (ESI 730.3 (M+H)⁺).

Step 2: (3S)-3-(2-(5-(2-(azetidin-1-yl)ethyl)-2-oxo-4-(trifluoromethyl)pyridin-1(2H)-yl)-4-methylpentanamido)-3-(5-cyclopropyl-2,4-difluoro-2',4',6'-trimethylbiphenyl-3-yl)propanoic Acid

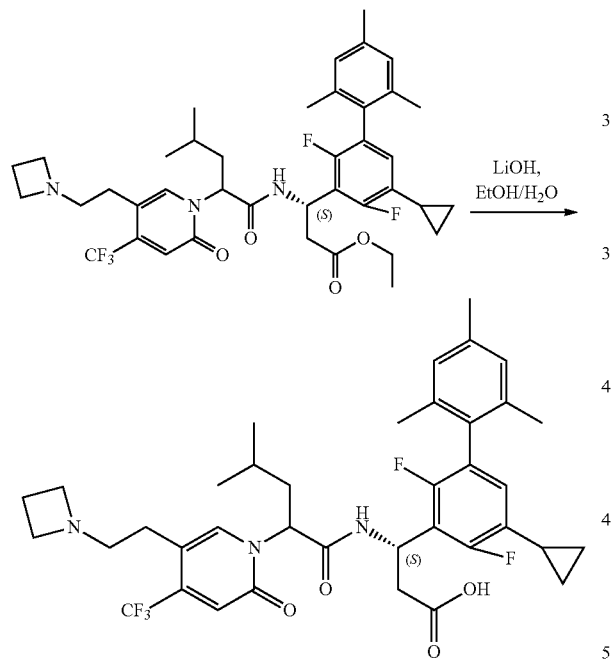

(3S)-ethyl 3-(2-(5-(2-(azetidin-1-yl)ethyl)-2-oxo-4-(trifluoromethyl)pyridin-1(2H)-yl)-4-methylpentanamido)-3-(5-cyclopropyl-2,4-difluoro-2',4',6'-trimethylbiphenyl-3-yl)propanoate (120 mg, 0.16 mmol) was treated with LiOH—H₂O (35 mg, 0.9 mmol) in EtOH (3 mL) and H₂O (1 mL) at room temperature for 2 hours. The reaction mixture was acidified to pH 4~5 with 1N HCl. The reaction was concentrated in vacuo and the residue purified by prep-HPLC A (30-60% CH₃CN) to give the diastereomeric products HM-P1 (30.2 mg) and HM-P2 (31.8 mg) as white solids.

HM-P1 ESI 702.3 (M+H)⁺. 1H NMR (400 MHz, MeOD) δ 7.80 (s, 1H), 6.97-6.79 (m, 3H), 6.58 (t, J=8.1 Hz, 1H), 5.84-5.61 (m, 2H), 4.00 (t, J=8.1 Hz, 4H), 3.30-3.21 (m, 2H), 2.88-2.85 (m, 3H), 2.67 (dd, J=14.8, 4.8 Hz, 1H), 2.48-2.37 (m, 2H), 2.28 (d, J=6.4 Hz, 3H), 2.13-1.96 (m, 3H), 1.90 (d, J=21.3 Hz, 6H), 1.46-1.31 (m, 1H), 0.94-0.90 (m, 8H), 0.64-0.62 (m, 2H).

HM-P2 ESI 702.3 (M+H)⁺. 1H NMR (400 MHz, MeOD) δ 7.70 (s, 1H), 7.00-6.86 (m, 3H), 6.63 (t, J=8.2 Hz, 1H), 5.93 (dd, J=11.4, 3.5 Hz, 1H), 5.62 (t, J=7.7 Hz, 1H), 4.11 (t, J=8.0 Hz, 4H), 3.50-3.33-3.30 (m, 2H), 2.97-2.76 (m, 3H), 2.47-2.45 (m, 3H), 2.29 (s, 3H), 2.08-2.05 (m, 1H), 2.00-1.89 (m, 7H), 1.74-1.70 (m, 1H), 1.37-1.35 (m, 1H), 1.04-0.95 (m, 2H), 0.88 (dd, J=11.4, 6.6 Hz, 6H), 0.67-0.65 (m, 2H).

3-58. Preparation of (3S)-3-(2-(5-(2-(azetidin-1-yl)ethyl)-2-oxo-4-(trifluoromethyl)pyridin-1(2H)-yl)-4-methylpentanamido)-3-(2,4-difluoro-2',3',6'-trimethyl-5-(trifluoromethyl)-[1,1'-biphenyl]-3-yl)propanoic Acid (Compounds HN-P1 and HN-P2)

Step 1: Ethyl (3S)-3-(2-(5-(2-(azetidin-1-yl)ethyl)-2-oxo-4-(trifluoromethyl)pyridin-1(2H)-yl)-4-methylpentanamido)-3-(2,4-difluoro-2',3',6'-trimethyl-5-(trifluoromethyl)-[1,1'-biphenyl]-3-yl)propanoate

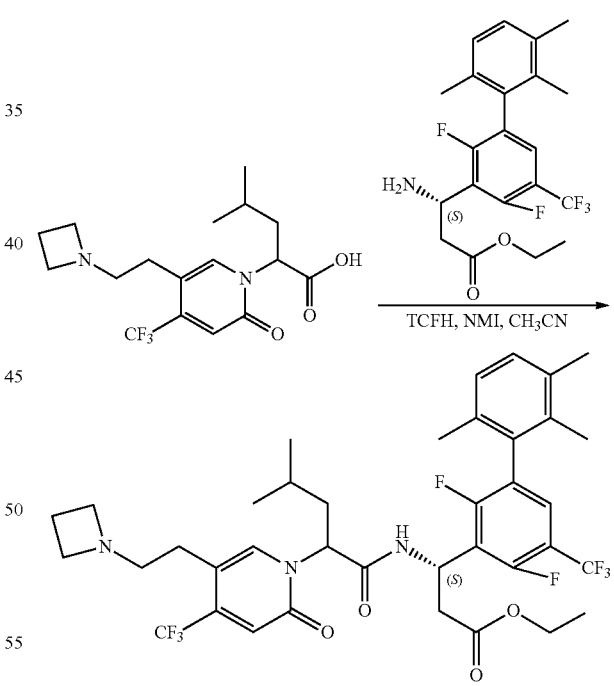

A mixture of 2-(5-(2-(azetidin-1-yl)ethyl)-2-oxo-4-(trifluoromethyl)pyridin-1(2H)-yl)-4-methylpentanoic acid (120.0 mg, 0.33 mmol), ethyl (3S)-3-amino-3-(2,4-difluoro-2',3',6'-trimethyl-5-(trifluoromethyl)-[1,1'-biphenyl]-3-yl)propanoate (138.3 mg, 0.33 mmol), TCFH (184.8 mg, 0.66 mmol) and NMI (108.2 mg, 1.32 mmol) in CH₃CN (10 mL) was stirred at room temperature for 1 hour. The reaction was concentrated in vacuo and the residue purified by silica gel column (DCM:MeOH 4:1) to provide ethyl (3S)-3-(2-(5-(2-(azetidin-1-yl)ethyl)-2-oxo-4-(trifluoromethyl)pyridin-1(2H)-yl)-4-methylpentanamido)-3-(2,4-difluoro-2',3',6'-trimethyl-5-(trifluoromethyl)-[1,1'-biphenyl]-3-yl) propanoate as a brown solid (125.0 mg). Yield 50% (ESI 758.7 (M+H)+).

Step 2: (3S)-3-(2-(5-(2-(azetidin-1-yl)ethyl)-2-oxo-4-(trifluoromethyl)pyridin-1(2H)-yl)-4-methylpentanamido)-3-(2,4-difluoro-2',3',6'-trimethyl-5-(trifluoromethyl)-[1,1'-biphenyl]-3-yl)propanoic Acid

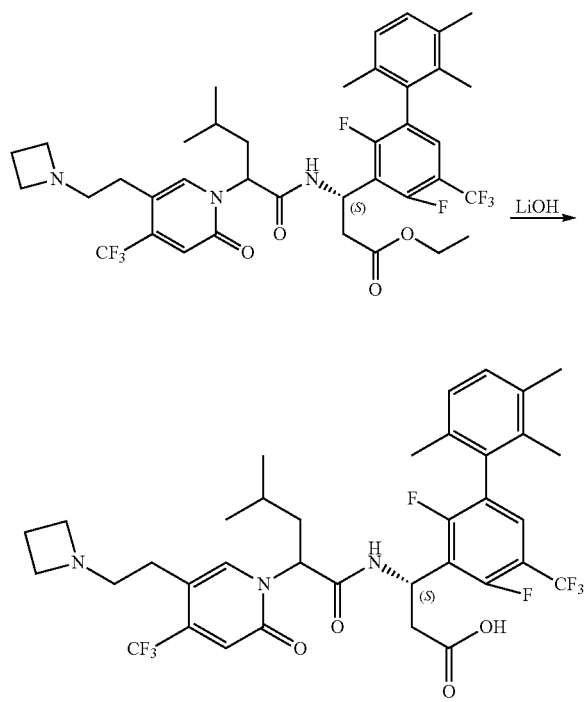

Ethyl (3S)-3-(2-(5-(2-(azetidin-1-yl)ethyl)-2-oxo-4-(trifluoromethyl)pyridin-1(2H)-yl)-4-methylpentanamido)-3-(2,4-difluoro-2',3',6'-trimethyl-5-(trifluoromethyl)-[1,1'-biphenyl]-3-yl)propanoate (122 mg, 0.16 mmol)) was treated with LiOH—H₂O (26.9 mg, 0.64 mmol) in MeOH (4 mL) and H₂O (1 mL) at room temperature for 2 hours. The reaction mixture was acidified to pH 4~5 with 1N HCl. The reaction was concentrated in vacuo and the residue purified by prep-HPLC A (30-60% MeCN) to give the diastereomeric products HN-P1 (36.1 mg) and HN-P2 (37.6 mg) as white solids.

HN-P1 ESI 730.7 (M+H)+. 1H NMR (400 MHz, DMSO) δ 9.29 (d, J=6.4 Hz, 1H), 7.72 (s, 1H), 7.50 (t, J=7.3 Hz, 1H), 7.14 (d, J=7.8 Hz, 1H), 7.04 (t, J=7.6 Hz, 1H), 6.71 (d, J=5.1 Hz, 1H), 5.58-5.50 (m, 1H), 5.44 (s, 1H), 3.18-3.03 (m, 5H), 2.98-2.79 (m, 3H), 2.39-2.30 (m, 2H), 2.23 (d, J=6.6 Hz, 3H), 1.99-1.63 (m, 10H), 1.28 (d, J=35.1 Hz, 1H), 0.90-0.70 (m, 6H).

HN-P2 ESI 730.7 (M+H)+. 1H NMR (400 MHz, MeOD) δ 7.73 (s, 1H), 7.42 (t, J=7.6 Hz, 1H), 7.13 (d, J=7.7 Hz, 1H), 7.04 (d, J=7.7 Hz, 1H), 6.91 (s, 1H), 5.98-5.84 (m, 1H), 5.63 (d, J=7.7 Hz, 1H), 4.12 (t, J=8.1 Hz, 4H), 3.43-3.34 (m, 2H), 2.92-2.77 (m, 3H), 2.63-2.53 (m, 1H), 2.53-2.42 (m, 2H), 2.29 (s, 3H), 1.98-1.85 (m, 7H), 1.77-1.66 (m, 1H), 1.39-1.27 (m, 1H), 0.92-0.76 (m, 6H).

3-59. Preparation of (3S)-3-(2-(5-(2-(azetidin-1-yl) ethyl)-2-oxo-4-(trifluoromethyl)pyridin-1(2H)-yl)-4-methylpentanamido)-3-(2,3',4-trifluoro-2',6'-dimethyl-5-(trifluoromethyl)biphenyl-3-yl)propanoic Acid (Compounds HO-P1 and HO-P2)

Step 1: (3S)-ethyl 3-(2-(5-(2-(azetidin-1-yl)ethyl)-2-oxo-4-(trifluoromethyl)pyridin-1(2H)-yl)-4-methylpentanamido)-3-(2,3',4-trifluoro-2',6'-dimethyl-5-(trifluoromethyl)biphenyl-3-yl)propanoate

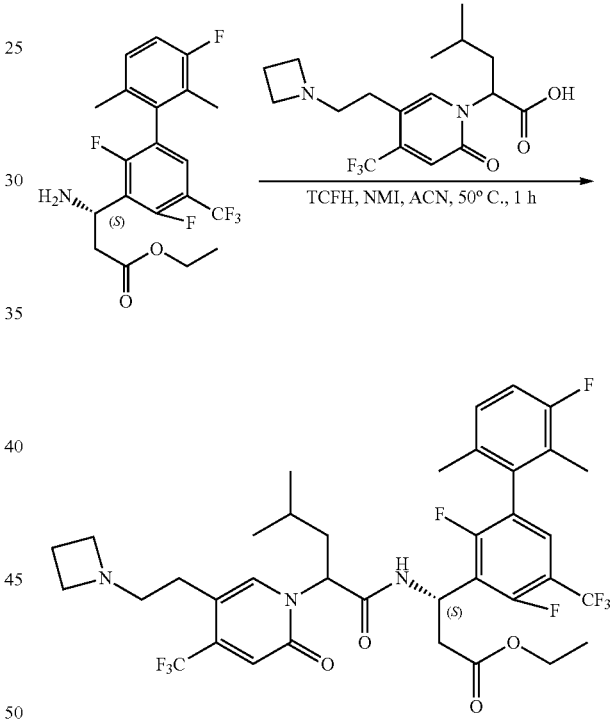

A mixture of (3S)-ethyl 3-amino-3-(2,3',4-trifluoro-2',6'-dimethyl-5-(trifluoromethyl)biphenyl-3-yl)propanoate (100 mg, 0.24 mmol), 2-(5-(2-(azetidin-1-yl)ethyl)-2-oxo-4-(trifluoromethyl)pyridin-1(2H)-yl)-4-methylpentanoic acid (86 mg, 0.24 mmol), NMI (59 mg, 0.72 mmol) and TCFH (101 mg, 0.36 mmol) in CH₃CN (5 mL) was stirred at 50° C. for 1 hour. The solvent was concentrated in vacuo and the residue was purified by silica gel column (DCM:MeOH 12:1) to provide (3S)-ethyl 3-(2-(5-(2-(azetidin-1-yl)ethyl)-2-oxo-4-(trifluoromethyl)pyridin-1(2H)-yl)-4-methylpentanamido)-3-(2,3',4-trifluoro-2',6'-dimethyl-5-(trifluoromethyl)biphenyl-3-yl)propanoate as a yellow oil (116 mg). Yield 63.8% (ESI 762.3 [M+H]+).

485

Step 2: (3S)-3-(2-(5-(2-(azetidin-1-yl)ethyl)-2-oxo-4-(trifluoromethyl)pyridin-1(2H)-yl)-4-methylpentanamido)-3-(2,3',4-trifluoro-2',6'-dimethyl-5-(trifluoromethyl)biphenyl-3-yl)propanoic acid

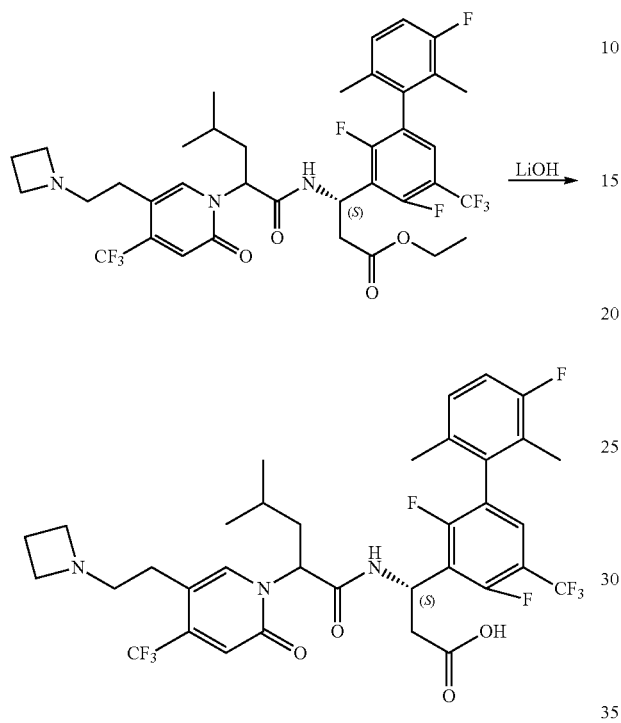

(3S)-ethyl 3-(2-(5-(2-(azetidin-1-yl)ethyl)-2-oxo-4-(trifluoromethyl)pyridin-1(2H)-yl)-4-methylpentanamido)-3-(2,3',4-trifluoro-2',6'-dimethyl-5-(trifluoromethyl)biphenyl-3-yl)propanoate (116 mg, 0.15 mmol) was treated with LiOH—H$_2$O (18.9 mg, 0.45 mmol) in EtOH (2 mL) and water (0.5 mL) at room temperature for 1 hour. The reaction mixture was acidified to pH 4-5 with 1N HCl. The reaction was concentrated in vacuo and the residue purified by prep-HPLC A (30-80% MeCN) to give the diastereomeric products HO-P1 (34 mg) and HO-P2 (26 mg) as white solids.

HO-P1 ESI 734.1 (M+H)$^+$. $^1$H NMR (400 MHz, MeOD) δ 7.80 (s, 1H), 7.43 (t, J=7.5 Hz, 1H), 7.13 (d, J=6.3 Hz, 1H), 7.02 (t, J=8.9 Hz, 1H), 6.84 (s, 1H), 5.76-5.65 (m, 2H), 4.05 (t, J=8.1 Hz, 4H), 3.29-3.18 (m, 2H), 2.96-2.87 (m, 1H), 2.84 (t, J=6.9 Hz, 2H), 2.79-2.72 (m, 1H), 2.49-2.41 (m, 2H), 1.99-1.89 (m, 8H), 1.39-1.33 (m, 1H), 0.96-0.91 (m, 6H).

HO-P2 ESI 734.1 (M+H)+. $^1$H NMR (400 MHz, MeOD) δ 7.74 (s, 1H), 7.49 (t, J=7.6 Hz, 1H), 7.21-7.12 (m, 1H), 7.05 (t, J=9.0 Hz, 1H), 6.91 (s, 1H), 5.92-5.86 (m, 1H), 5.64 (t, J=7.7 Hz, 1H), 4.11 (t, J=8.1 Hz, 4H), 3.39-3.31 (m, 2H), 2.93-2.75 (m, 3H), 2.66-2.59 (m, 1H), 2.49-2.41 (m, 2H), 2.00 (s, 3H), 1.96-1.86 (m, 4H), 1.76-1.71 (m, 1H), 1.36-1.29 (m, 1H), 0.91-0.86 (m, 6H).

486

3-60. Preparation of (3S)-3-(2-(5-(2-(azetidin-1-yl)ethyl)-2-oxo-4-(trifluoromethyl)pyridin-1(2H)-yl)-4-methylpentanamido)-3-(4'-chloro-2,4-difluoro-2',6'-dimethyl-5-(trifluoromethyl)-[1,1'-biphenyl]-3-yl)propanoic Acid (Compounds HP-P1 and HP-P2)

Step 1: Ethyl (3S)-3-(2-(5-(2-(azetidin-1-yl)ethyl)-2-oxo-4-(trifluoromethyl)pyridin-1(2H)-yl)-4-methylpentanamido)-3-(4'-chloro-2,4-difluoro-2',6'-dimethyl-5-(trifluoromethyl)-[1,1'-biphenyl]-3-yl)propanoate

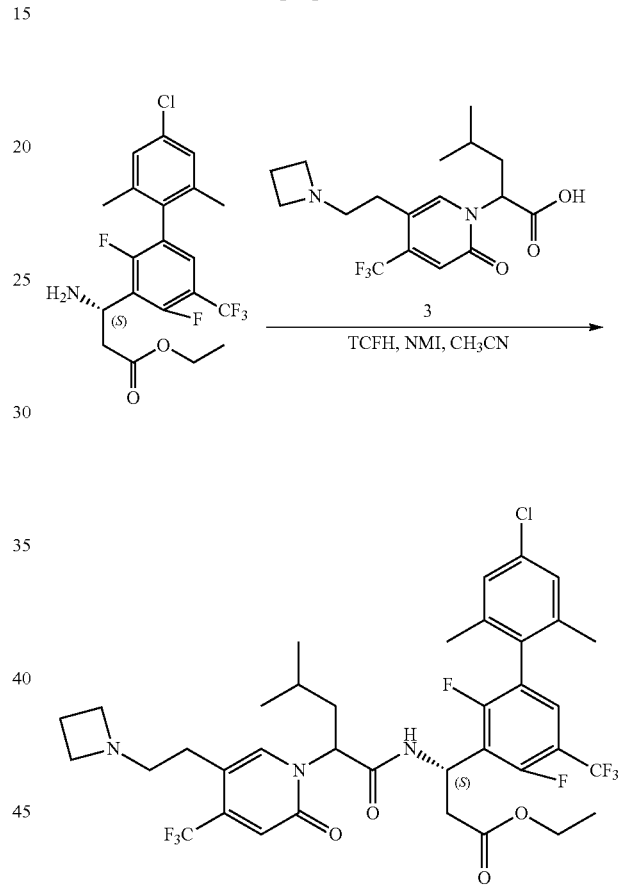

A mixture of ethyl (S)-3-amino-3-(4'-chloro-2,4-difluoro-2',6'-dimethyl-5-(trifluoromethyl)-[1,1'-biphenyl]-3-yl)propanoate (120.0 mg, 0.28 mmol), 2-(5-(2-(azetidin-1-yl)ethyl)-2-oxo-4-(trifluoromethyl)pyridin-1(2H)-yl)-4-methylpentanoic acid (100.9 mg, 0.28 mmol), TCFH (95.4 mg, 0.34 mmol) and NMI (115.0 mg, 1.40 mmol) in CH$_3$CN (5 mL) was stirred at room temperature overnight. The reaction was concentrated in vacuo and the residue purified by reverse phase HPLC on a C18/40 g column (A: water 10 mM NH$_4$HCO$_3$, B: MeOH, 0~100%) to provide ethyl (3S)-3-(2-(5-(2-(azetidin-1-yl)ethyl)-2-oxo-4-(trifluoromethyl)pyridin-1(2H)-yl)-4-methylpentanamido)-3-(4'-chloro-2,4-difluoro-2',6'-dimethyl-5-(trifluoromethyl)-[1,1'-biphenyl]-3-yl)propanoate as a light yellow solid (80.0 mg). Yield 37% (ESI 778.2 [M+H]$^+$).

Step 2: (3S)-3-(2-(5-(2-(azetidin-1-yl)ethyl)-2-oxo-4-(trifluoromethyl)pyridin-1(2H)-yl)-4-methylpentanamido)-3-(4'-chloro-2,4-difluoro-2',6'-dimethyl-5-(trifluoromethyl)-[1,1'-biphenyl]-3-yl)propanoic Acid

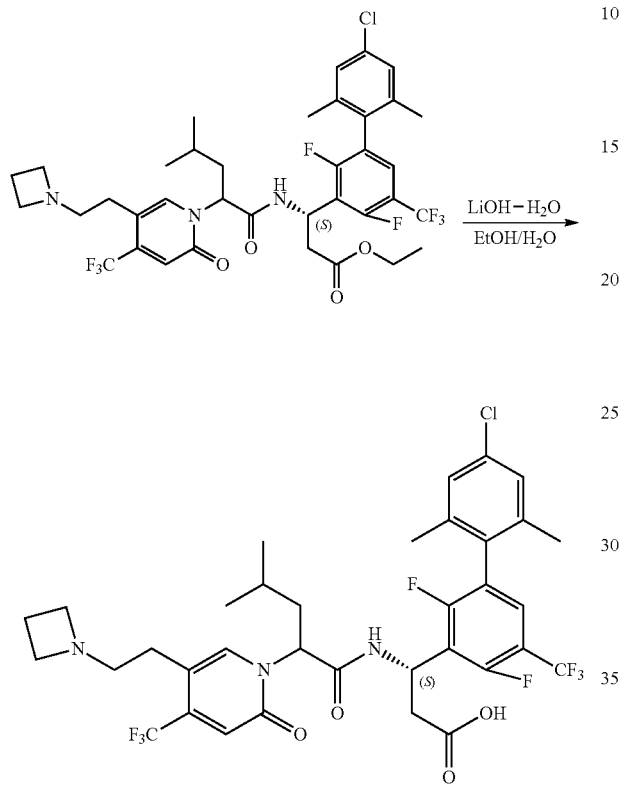

Ethyl (3S)-3-(2-(5-(2-(azetidin-1-yl)ethyl)-2-oxo-4-(trifluoromethyl)pyridin-1(2H)-yl)-4-methylpentanamido)-3-(4'-chloro-2,4-difluoro-2',6'-dimethyl-5-(trifluoromethyl)-[1,1'-biphenyl]-3-yl)propanoate (80.0 mg, 0.10 mmol) was treated with LiOH—H$_2$O (12.6 mg, 0.30 mmol) in EtOH (2 mL) and water (0.5 mL) at room temperature for 30 mins. The reaction mixture was acidified to pH 4~5 with 2N HCL. The reaction was concentrated in vacuo and the residue purified by prep-HPLC A (30-80% MeCN) to give the diastereomeric products HP-P1 (12.5 mg) and HP-P2 (24.5 mg) as white solids.

HP-P1 ESI 750.2 (M+H)$^+$ $^1$H NMR (400 MHz, MeOD) δ 7.79 (s, 1H), 7.43 (t, J=7.5 Hz, 1H), 7.17 (s, 2H), 6.85 (s, 1H), 5.80-5.62 (m, 2H), 4.06 (t, J=8.1 Hz, 4H), 3.39-3.32 (m, 1H), 3.28-3.21 (m, 1H), 2.98-2.65 (m, 4H), 2.55-2.36 (m, 2H), 2.07-1.95 (m, 5H), 1.93 (s, 3H), 1.48-1.30 (m, 1H), 0.93 (t, J=6.5 Hz, 6H).

HP-P2 ESI 750.2 (M+H)$^+$ $^1$H NMR (400 MHz, MeOD) δ 7.72 (s, 1H), 7.49 (t, J=7.6 Hz, 1H), 7.20 (s, 2H), 6.92 (s, 1H), 5.92-5.86 (m, 1H), 5.63 (t, J=7.7 Hz, 1H), 4.12 (t, J=8.1 Hz, 4H), 3.47-3.32 (m, 2H), 2.99-2.72 (m, 3H), 2.64-2.57 (m, 1H), 2.50-2.40 (m, 2H), 2.02 (d, J=1.8 Hz, 6H), 1.97-1.85 (m, 1H), 1.79-1.65 (m, 1H), 1.40-1.28 (m, 1H), 0.91-0.85 (m, 6H).

3-61. Preparation of (3S)-3-(2,4-difluoro-2',6'-dimethyl-5-(trifluoromethyl)-[1,1'-biphenyl]-3-yl)-3-(2-(5-(2-(dimethylamino)ethyl)-2-oxo-4-(trifluoromethyl)pyridin-1(2H)-yl)-4-methylpentanamido) propanoic Acid (Compounds HQ-P1 and HQ-P2)

Step 1: Ethyl (3S)-3-(2,4-difluoro-2',6'-dimethyl-5-(trifluoromethyl)-[1,1'-biphenyl]-3-yl)-3-(2-(5-(2-(dimethylamino)ethyl)-2-oxo-4-(trifluoromethyl)pyridin-1(2H)-yl)-4-methylpentanamido)propanoate

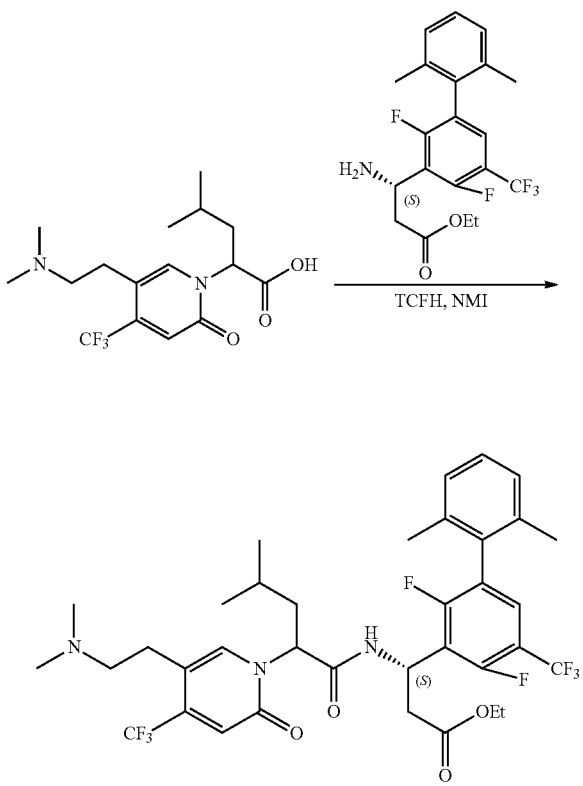

A mixture of 2-(5-(2-(dimethylamino)ethyl)-2-oxo-4-(trifluoromethyl)pyridin-1(2H)-yl)-4-methylpentanoic acid (86 mg, 0.23 mmol), ethyl (S)-3-amino-3-(2,4-difluoro-2',6'-dimethyl-5-(trifluoromethyl)-[1,1'-biphenyl]-3-yl)propanoate hydrochloride (92.0 mg, 0.23 mmol), TCFH (78.0 mg, 0.28 mmol) and NMI (38.0 mg, 0.46 mmol) in CH$_3$CN (4 mL) was stirred at room temperature for 2 hrs. The reaction mixture was concentrated in vacuo and the residue was purified by reverse phase HPLC on a C18/40 g column (A: water 10 mM NH$_4$HCO$_3$, B: MeOH, 0~100%) to provide ethyl (3S)-3-(2,4-difluoro-2',6'-dimethyl-5-(trifluoromethyl)-[1,1'-biphenyl]-3-yl)-3-(2-(5-(2-(dimethylamino)ethyl)-2-oxo-4-(trifluoromethyl)pyridin-1(2H)-yl)-4-methylpentanamido)propanoate as a yellow solid (90.0 mg). Yield 53.4% (ESI 732.2 [M+H]⁺).

Step 2: (3S)-3-(2,4-difluoro-2',6'-dimethyl-5-(trifluoromethyl)-[1,1'-biphenyl]-3-yl)-3-(2-(5-(2-(dimethylamino)ethyl)-2-oxo-4-(trifluoromethyl)pyridin-1(2H)-yl)-4-methylpentanamido)propanoic acid

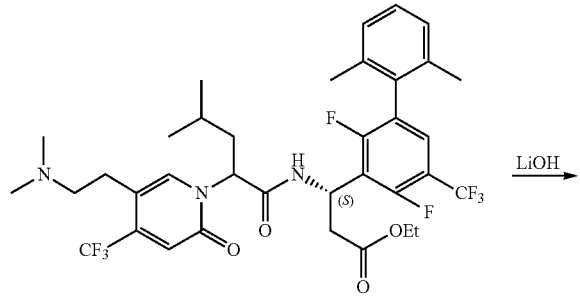

Ethyl (3S)-3-(2,4-difluoro-2',6'-dimethyl-5-(trifluoromethyl)-[1,1'-biphenyl]-3-yl)-3-(2-(5-(2-(dimethylamino)ethyl)-2-oxo-4-(trifluoromethyl)pyridin-1(2H)-yl)-4-methylpentanamido)propanoate (90.0 mg, 0.12 mmol) was treated with LiOH—H₂O (29.0 mg, 0.68 mmol) in EtOH (3 mL) and water (1 mL) at 30° C. for 1 hour. The reaction mixture was acidified to pH 4-5 with 2N HCl. The reaction was concentrated in vacuo and the residue purified by Prep HPLC A (30-80% MeCN) to give the diastereomeric products HQ-P1 (15.1 mg) and HQ-P2 (35.4 mg) as white solids.

HQ-P1 ESI 704.2 (M+H)⁺ ¹H NMR (400 MHz, MeOD) δ 7.86 (s, 1H), 7.37 (t, J=7.5 Hz, 1H), 7.20 (t, J=7.5 Hz, 1H), 7.15-7.03 (m, 2H), 6.82 (s, 1H), 5.76-5.60 (m, 2H), 3.12-3.09 (m, 2H), 2.98-2.92 (m, 3H), 2.78-2.72 (m, 7H), 2.09-1.92 (m, 5H), 1.90 (s, 3H), 1.49-1.31 (m, 1H), 0.99-0.89 (m, 6H).

HQ-P2 ESI 704.2 (M+H)⁺ ¹H NMR (400 MHz, MeOD) δ 7.83 (s, 1H), 7.44 (t, J=7.7 Hz, 1H), 7.26-7.17 (m, J=16.0 Hz, 1H), 7.14 (d, J=7.6 Hz, 2H), 6.90 (s, 1H), 5.84-5.80 (m, 1H), 5.66 (t, J=7.6 Hz, 1H), 3.26-3.18 (m, 2H), 2.97 (t, J=7.3 Hz, 2H), 2.90-2.75 (m, 7H), 2.68-2.65 (m, 1H), 2.02 (d, J=3.1 Hz, 6H), 1.96-1.82 (m, 1H), 1.77-1.72 (m, 1H), 1.34-1.29 (m, 1H), 0.90-0.85 (m, 6H).

3-62. Preparation of (3S)-3-(2-(5-(2-(azetidin-1-yl)ethyl)-2-oxo-4-(trifluoromethyl)pyridin-1(2H)-yl)-4-methylpentanamido)-3-(2,3',4-trifluoro-2',4',6'-trimethyl-5-(trifluoromethyl)-[1,1'-biphenyl]-3-yl) propanoic Acid (Compounds HR-P1 and HR-P2)

Step 1: Ethyl (3S)-3-(2-(5-(2-(azetidin-1-yl)ethyl)-2-oxo-4-(trifluoromethyl)pyridin-1(2H)-yl)-4-methylpentanamido)-3-(2,3',4-trifluoro-2',4',6'-trimethyl-5-(trifluoromethyl)-[1,1'-biphenyl]-3-yl)propanoate

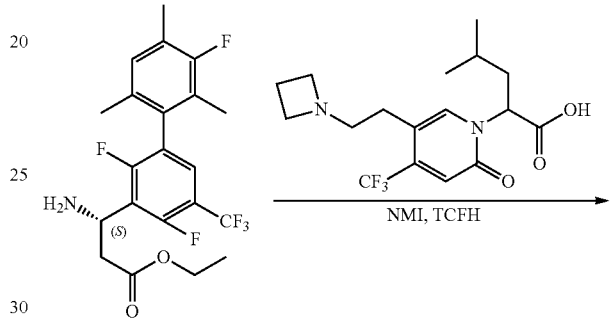

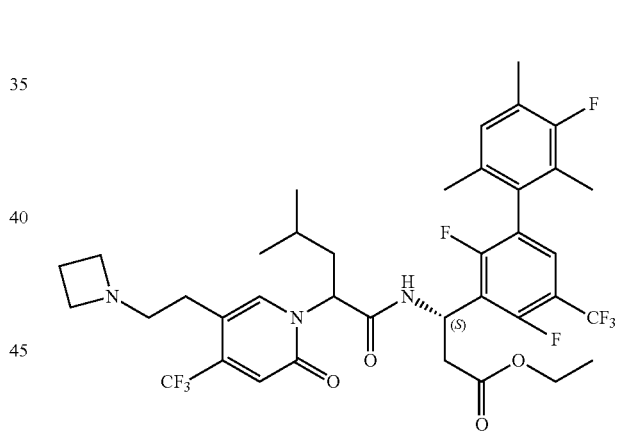

A mixture of ethyl (3S)-3-amino-3-(2,3',4-trifluoro-2',4',6'-trimethyl-5-(trifluoromethyl)-[1,1'-biphenyl]-3-yl)propanoate (90 mg, 0.21 mmol), 2-(5-(2-(azetidin-1-yl)ethyl)-2-oxo-4-(trifluoromethyl)pyridin-1(2H)-yl)-4-methylpentanoic acid (81 mg, 0.21 mmol), NMI (0.2 mL) and TCFH (88 mg, 0.32 mmol) in CH₃CN (3 mL) was stirred at room temperature for 2 hours. The solvent was concentrated in vacuo and the residue purified by reverse phase HPLC on a C18/40 g column (A: water 10 mM NH4HCO3, B: CH3CN, 0~100%) to provide ethyl (3S)-3-(2-(5-(2-(azetidin-1-yl)ethyl)-2-oxo-4-(trifluoromethyl)pyridin-1(2H)-yl)-4-methylpentanamido)-3-(2,3',4-trifluoro-2',4',6'-trimethyl-5-(trifluoromethyl)-[1,1'-biphenyl]-3-yl)propanoate as a white solid (80 mg). Yield 50% (ESI 776.2 [M+H]⁺).

Step 2: (3S)-3-(2-(5-(2-(azetidin-1-yl)ethyl)-2-oxo-4-(trifluoromethyl)pyridin-1(2H)-yl)-4-methylpentanamido)-3-(2,3',4-trifluoro-2',4',6'-trimethyl-5-(trifluoromethyl)-[1,1'-biphenyl]-3-yl)propanoic Acid

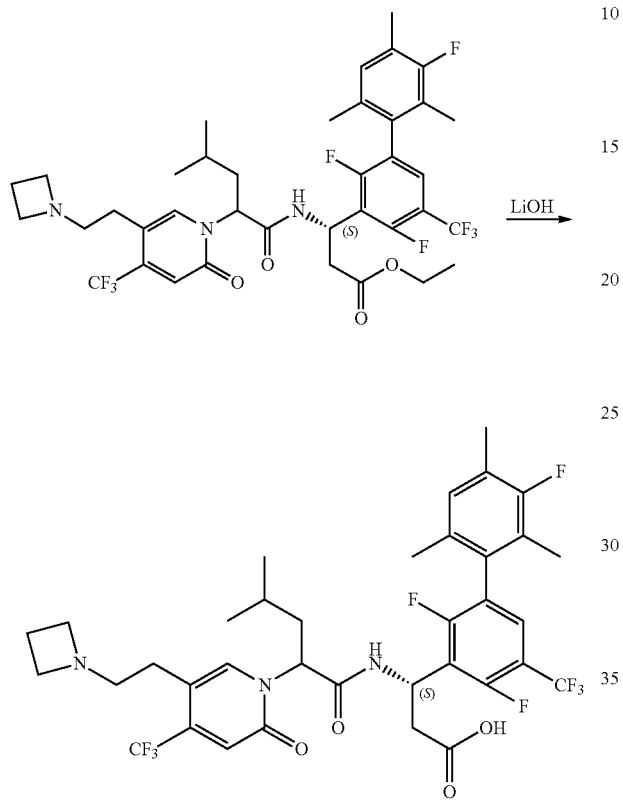

Ethyl (3S)-3-(2-(5-(2-(azetidin-1-yl)ethyl)-2-oxo-4-(trifluoromethyl)pyridin-1(2H)-yl)-4-methylpentanamido)-3-(2,3',4-trifluoro-2',4',6'-trimethyl-5-(trifluoromethyl)-[1,1'-biphenyl]-3-yl)propanoate (80 mg, 0.1 mmol) was treated with LiOH—H$_2$O (13 mg, 0.3 mmol) in MeOH (2.0 mL) and H$_2$O (0.5 mL) at room temperature for 2 hours. The reaction mixture was acidified to pH 5~6 with 1N HCl. The reaction was concentrated in vacuo and the residue purified by prep-HPLC A (50-80% CH$_3$CN) to give the diastereomeric products HR-P1 (22.0 mg) and HR-P2 (25.0 mg) as white solids.

HR-P1 ESI 748.2 (M+H)$^+$. $^1$H NMR (400 MHz, MeOD) δ 7.79 (s, 1H), 7.40 (t, J=7.5 Hz, 1H), 6.99 (d, J=7.9 Hz, 1H), 6.85 (d, J=3.0 Hz, 1H), 5.78-5.60 (m, 2H), 4.04 (t, J=8.0 Hz, 4H), 3.29-3.20 (m, 2H), 2.95-2.80 (m, 3H), 2.77-2.68 (m, 1H), 2.51-2.37 (m, 2H), 2.25 (d, J=1.6 Hz, 3H), 2.09-1.75 (m, 8H), 1.37 (s, 1H), 0.93 (t, J=6.4 Hz, 6H).

HR-P2 ESI 748.2 (M+H)$^+$. $^1$H NMR (400 MHz, MeOD) δ 7.72 (s, 1H), 7.46 (t, J=7.5 Hz, 1H), 7.03 (d, J=7.6 Hz, 1H), 6.91 (s, 1H), 5.87-5.82 (m, 1H), 5.63 (t, J=7.7 Hz, 1H), 4.12 (t, J=7.8 Hz, 4H), 3.45-3.34 (m, 2H), 2.95-2.74 (m, 3H), 2.64-2.56 (m, 1H), 2.50-2.36 (m, 2H), 2.27 (d, J=1.5 Hz, 3H), 2.02-1.83 (m, 7H), 1.78-1.65 (m, 1H), 1.40-1.26 (m, 1H), 0.93-0.84 (m, 6H).

3-63. Preparation of (3S)-3-(2-(5-(3-(dimethylamino)propyl)-2-oxo-4-(trifluoromethyl)pyridin-1(2H)-yl)-4-methylpentanamido)-3-(2,3',4-trifluoro-2',6'-dimethyl-5-(trifluoromethyl)biphenyl-3-yl)propanoic Acid (Compounds HS-P1 and HS-P2)

Step 1: (3S)-ethyl 3-(2-(5-(3-(dimethylamino)propyl)-2-oxo-4-(trifluoromethyl)pyridin-1(2H)-yl)-4-methylpentanamido)-3-(2,3',4-trifluoro-2',6'-dimethyl-5-(trifluoromethyl)biphenyl-3-yl)propanoate

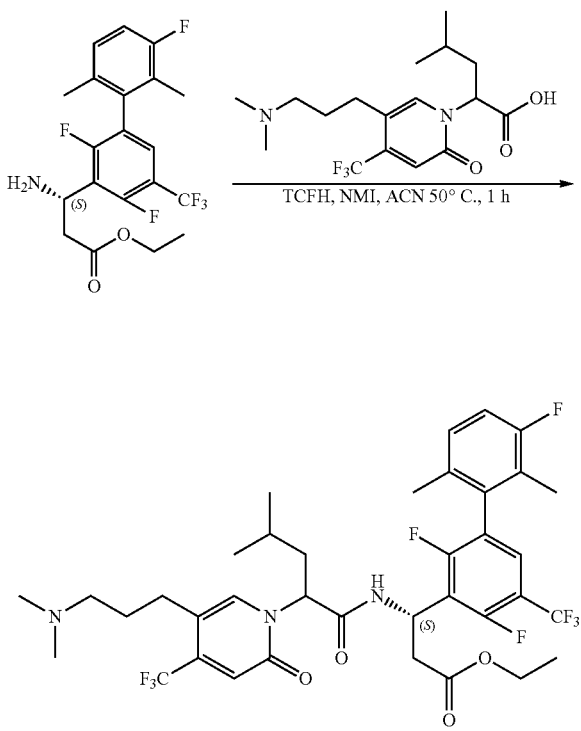

A mixture of (3S)-ethyl 3-amino-3-(2,3',4-trifluoro-2',6'-dimethyl-5-(trifluoromethyl)biphenyl-3-yl)propanoate (100 mg, 0.24 mmol), 2-(5-(3-(dimethylamino)propyl)-2-oxo-4-(trifluoromethyl)pyridin-1(2H)-yl)-4-methylpentanoic acid (86 mg, 0.24 mmol), NMI (59 mg, 0.72 mmol) and TCFH (101 mg, 0.36 mmol) in CH$_3$CN (5 mL) was stirred at 50° C. for 1 hour. The solvent was concentrated in vacuo and the residue was purified by silica gel column (DCM:MeOH 15:1) to provide (3S)-ethyl 3-(2-(5-(3-(dimethylamino)propyl)-2-oxo-4-(trifluoromethyl)pyridin-1(2H)-yl)-4-methylpentanamido)-3-(2,3',4-trifluoro-2',6'-dimethyl-5-(trifluoromethyl)biphenyl-3-yl)propanoate as a yellow oil (110 mg). Yield 60.4% (ESI 764.3 [M+H]$^+$).

Step 2: (3S)-3-(2-(5-(3-(dimethylamino)propyl)-2-oxo-4-(trifluoromethyl)pyridin-1(2H)-yl)-4-methylpentanamido)-3-(2,3',4-trifluoro-2',6'-dimethyl-5-(trifluoromethyl)biphenyl-3-yl)propanoic acid

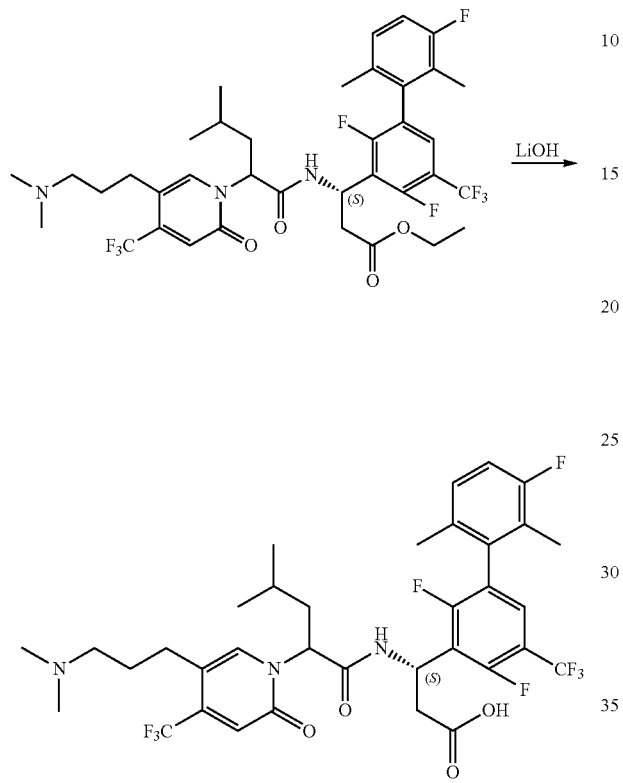

(3S)-ethyl 3-(2-(5-(3-(dimethylamino)propyl)-2-oxo-4-(trifluoromethyl)pyridin-1(2H)-yl)-4-methylpentanamido)-3-(2,3',4-trifluoro-2',6'-dimethyl-5-(trifluoromethyl)biphenyl-3-yl)propanoate (110 mg, 0.14 mmol) was treated with LiOH—H$_2$O (18.1 mg, 0.43 mmol) in EtOH (2 mL) and water (0.5 mL) at room temperature for 1 hour. The reaction mixture was acidified to pH 4~5 with 1N HCl. The reaction was concentrated in vacuo and the residue purified by prep-HPLC A (30-80% MeCN) to give the diastereomeric products HS-P1 (29 mg) and HS-P2 (30 mg) as white solids.

HS-P1 ESI 736.2 (M+H)$^+$. $^1$H NMR (400 MHz, DMSO) δ 9.23 (d, J=6.5 Hz, 1H), 7.73 (s, 1H), 7.61 (t, J=6.9 Hz, 1H), 7.21-7.11 (m, 2H), 6.71 (s, 1H), 5.64-5.53 (m, 1H), 5.45-5.41 (m, 1H), 2.98-2.81 (m, 3H), 2.47-2.35 (m, 2H), 2.31-2.26 (m, 2H), 2.16 (s, 6H), 1.93-1.73 (m, 8H), 1.61-1.55 (m, 2H), 1.32-1.29 (m, 1H), 0.92-0.83 (m, 6H).

HS-P2 ESI 736.2 (M+H)$^+$. $^1$H NMR (400 MHz, MeOD) δ 7.80 (s, 1H), 7.46 (t, J=7.5 Hz, 1H), 7.20-7.12 (m, 1H), 7.04 (t, J=9.0 Hz, 1H), 6.85 (s, 1H), 5.85-5.69 (m, 1H), 5.64 (t, J=7.7 Hz, 1H), 3.11-2.96 (m, 2H), 2.96-2.89 (m, 1H), 2.79 (s, 6H), 2.70-2.60 (m, 3H), 2.05-1.84 (m, 9H), 1.70-1.60 (m, 1H), 1.36-1.26 (m, 1H), 0.89-0.82 (m, 6H).

3-64. Preparation of (3S)-3-(2,4-difluoro-2',3',6'-trimethyl-5-(trifluoromethyl)-[1,1'-biphenyl]-3-yl)-3-(2-(5-(3-(dimethylamino)propyl)-2-oxo-4-(trifluoromethyl)pyridin-1(2H)-yl)-4-methylpentanamido) propanoic Acid (HT-P1 and HT-P2)

Step 1: Ethyl (3S)-3-(2,4-difluoro-2',3',6'-trimethyl-5-(trifluoromethyl)-[1,1'-biphenyl]-3-yl)-3-(2-(5-(3-(dimethylamino)propyl)-2-oxo-4-(trifluoromethyl)pyridin-1(2H)-yl)-4-methylpentanamido)propanoate

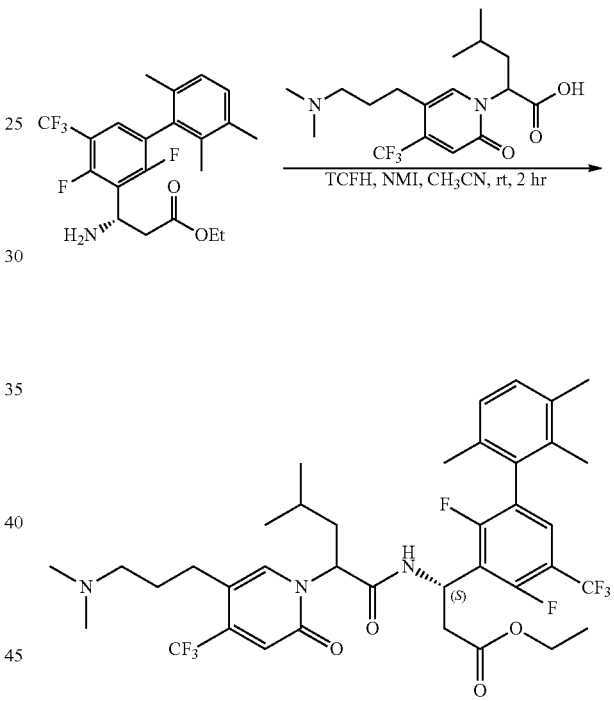

A mixture of ethyl (3S)-3-amino-3-(2,4-difluoro-2',3',6'-trimethyl-5-(trifluoromethyl)-[1,1'-biphenyl]-3-yl)propanoate (160 mg, 0.39 mmol), 2-(5-(3-(dimethylamino)propyl)-2-oxo-4-(trifluoromethyl)pyridin-1(2H)-yl)-4-methylpentanoic acid (153 mg, 0.42 mmol), TCFH (218 mg, 0.78 mmol) and NMI (160 mg, 1.95 mmol) in CH$_3$CN (5 mL) was stirred at room temperature for 2 hours. The reaction was concentrated and purified by reverse phase HPLC on a C18/40 g column (A: water 10 mM NH$_4$HCO3, B: CH$_3$OH, 0~85%) to provide ethyl (3S)-3-(2,4-difluoro-2',3',6'-trimethyl-5-(trifluoromethyl)-[1,1'-biphenyl]-3-yl)-3-(2-(5-(3-(dimethylamino)propyl)-2-oxo-4-(trifluoromethyl)pyridin-1(2H)-yl)-4-methylpentanamido)propanoate as a yellow solid (120 mg). Yield 43.9% (ESI 760.3 [M+H]$^+$).

Step 2: (3S)-3-(2,4-difluoro-2',3',6'-trimethyl-5-(trifluoromethyl)-[1,1'-biphenyl]-3-yl)-3-(2-(5-(3-(dimethylamino)propyl)-2-oxo-4-(trifluoromethyl)pyridin-1(2H)-yl)-4-methylpentanamido)propanoic Acid 3-65. Preparation of (3S)-3-(4'-cyclopropyl-2,4-difluoro-2',6'-dimethyl-5-(trifluoromethyl)-[1,1'-biphenyl]-3-yl)-3-(2-(5-(3-(dimethylamino)propyl)-2-oxo-4-(trifluoromethyl)pyridin-1(2H)-yl)-4-methylpentanamido)propanoic Acid (Compounds HU-P1 and HU-P2)

Step 1: Ethyl (3S)-3-(4'-cyclopropyl-2,4-difluoro-2',6'-dimethyl-5-(trifluoromethyl)-[1,1'-biphenyl]-3-yl)-3-(2-(5-(3-(dimethylamino)propyl)-2-oxo-4-(trifluoromethyl)pyridin-1(2H)-yl)-4-methylpentanamido)propanoate

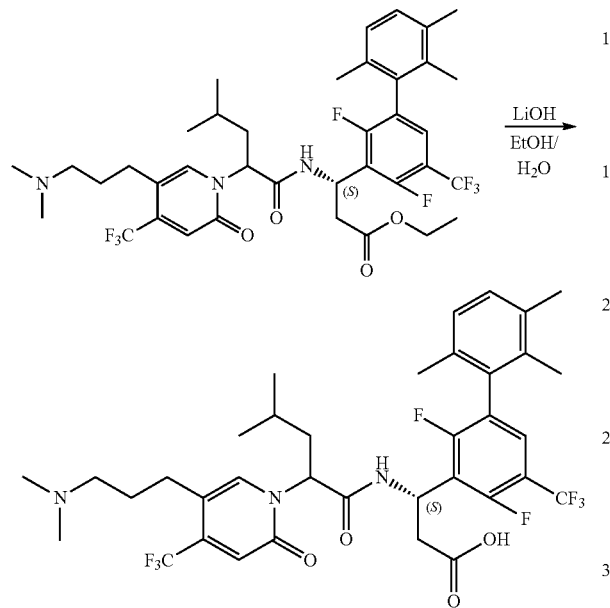

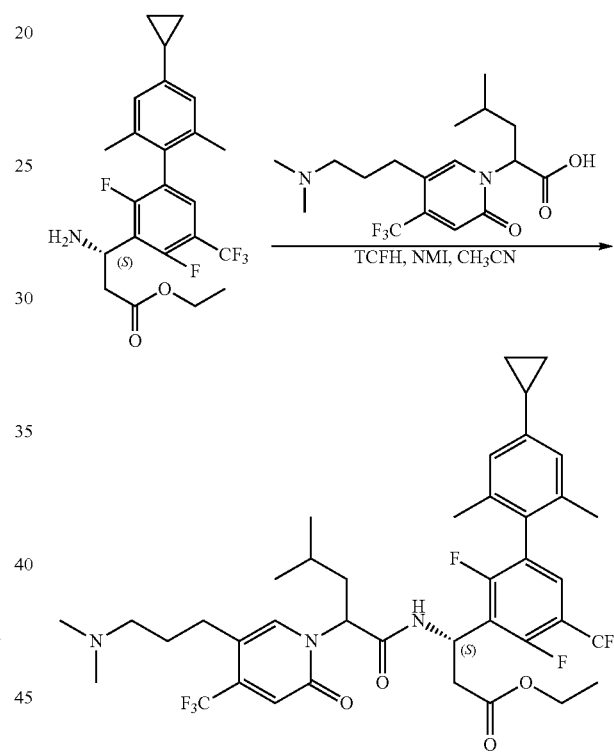

(3S)-3-(2,4-difluoro-2',3',6'-trimethyl-5-(trifluoromethyl)-[1,1'-biphenyl]-3-yl)-3-(2-(5-(3-(dimethylamino)propyl)-2-oxo-4-(trifluoromethyl)pyridin-1(2H)-yl)-4-methylpentanamido)propanoic acid (120 mg, 0.17 mmol) was treated with LiOH—H$_2$O (22 mg, 0.52 mmol) in EtOH (4 mL) and H$_2$O (1 mL) at room temperature for 2 hr. The reaction mixture was acidified to pH 5~6 with 1N HCl. The reaction was concentrated in vacuo and the residue purified by prep-HPLC A (30-65% CH$_3$CN) to give the diastereomeric products HT-P1 (20 mg) and HT-P2 (23 mg) as white solids.

HT-P1 ESI 732.2 (M+H)$^+$. $^1$H NMR (400 MHz, DMSO) δ 9.22 (d, J=6.3 Hz, 1H), 7.73 (s, 1H), 7.49 (t, J=7.4 Hz, 1H), 7.14 (m, J=7.7 Hz, 1H), 7.04 (t, J=8.0 Hz, 1H), 6.72 (d, J=5.5 Hz, 1H), 5.68-5.54 (m, 1H), 5.46 (d, J=6.1 Hz, 1H), 3.44 (m, 1H), 2.97 (m, J=16.3, 8.5 Hz, 1H), 2.90-2.75 (m, 1H), 2.46-2.34 (m, 2H), 2.31-2.22 (m, 5H), 2.16 (s, 6H), 1.84 (m, J=18.7, 9.9 Hz, 5H), 1.73 (d, J=29.3 Hz, 3H), 1.63-1.49 (m, 2H), 1.27 (m, J=13.6, 6.8 Hz, 1H), 0.85 (m, J=10.1, 6.6 Hz, 6H).

HT-P2 ESI 732.2 (M+H)$^+$. $^1$H NMR (400 MHz, MeOD) δ 7.81 (s, 1H), 7.40 (t, J=7.6 Hz, 1H), 7.14 (d, J=7.7 Hz, 1H), 7.05 (d, J=7.7 Hz, 1H), 6.87 (s, 1H), 5.84 (m, J=9.8, 4.5 Hz, 1H), 5.64 (t, J=7.6 Hz, 1H), 3.15-2.97 (m, 2H), 2.94-2.83 (m, 1H), 2.80 (s, 6H), 2.72-2.57 (m, 3H), 2.30 (d, J=2.3 Hz, 3H), 2.09-1.85 (m, 9H), 1.66 (m, J=14.1, 7.2 Hz, 1H), 1.33 (m, J=13.1, 6.6 Hz, 1H), 0.95-0.71 (m, 6H).

A mixture of ethyl (S)-3-amino-3-(4'-cyclopropyl-2,4-difluoro-2',6'-dimethyl-5-(trifluoromethyl)-[1,1'-biphenyl]-3-yl)propanoate (140.0 mg, 0.32 mmol), 2-(5-(3-(dimethylamino)propyl)-2-oxo-4-(trifluoromethyl)pyridin-1(2H)-yl)-4-methylpentanoic acid (116.0 mg, 0.32 mmol), TCFH (106.6 mg, 0.38 mmol) and NMI (131.4 mg, 1.60 mmol) in CH$_3$CN (5 mL) was stirred at room temperature overnight. The reaction was concentrated in vacuo and the residue purified by reverse phase HPLC on a C18/40 g column (A: water 10 mM NH$_4$HCO$_3$, B: MeOH, 0~100%) to provide ethyl (3S)-3-(4'-cyclopropyl-2,4-difluoro-2',6'-dimethyl-5-(trifluoromethyl)-[1,1'-biphenyl]-3-yl)-3-(2-(5-(3-(dimethylamino)propyl)-2-oxo-4-(trifluoromethyl)pyridin-1(2H)-yl)-4-methylpentanamido)propanoate as a light yellow solid (150.0 mg). Yield 60% (ESI 786.3 [M+H]$^+$).

497

Step 2: (3S)-3-(4'-cyclopropyl-2,4-difluoro-2',6'-dimethyl-5-(trifluoromethyl)-[1,1'-biphenyl]-3-yl)-3-(2-(5-(3-(dimethylamino)propyl)-2-oxo-4-(trifluoromethyl)pyridin-1(2H)-yl)-4-methylpentanamido) propanoic Acid

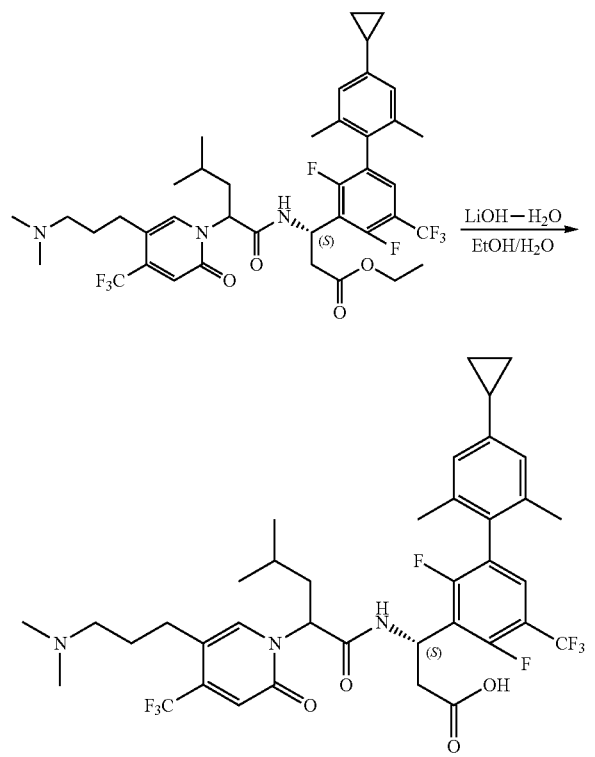

Ethyl (3S)-3-(4'-cyclopropyl-2,4-difluoro-2',6'-dimethyl-5-(trifluoromethyl)-[1,1'-biphenyl]-3-yl)-3-(2-(5-(3-(dimethylamino)propyl)-2-oxo-4-(trifluoromethyl)pyridin-1 (2H)-yl)-4-methylpentanamido)propanoate (150.0 mg, 0.19 mmol) was treated with LiOH—H$_2$O (23.9 mg, 0.57 mmol) in EtOH (2 mL) and water (0.5 mL) at room temperature for 1 hour. The reaction mixture was acidified to pH 4~5 with 2N HCl. The reaction was concentrated in vacuo and the residue purified by prep-HPLC A (30-80% MeCN) to give the diastereomeric products HU-P1 (54.5 mg) and HU-P2 (50.5 mg) as white solids.

HU-P1 ESI 758.3 (M+H)$^+$ $^1$H NMR (400 MHz, MeOD) δ 7.76 (s, 1H), 7.34 (t, J=7.6 Hz, 1H), 6.87-6.76 (m, 3H), 5.81-5.67 (m, 2H), 3.12-3.04 (m, 2H), 2.98-2.90 (m, 1H), 2.79 (s, 6H), 2.76-2.57 (m, 3H), 2.11-1.79 (m, 1H), 1.41-1.27 (m, 1H), 0.99-0.89 (m, 8H), 0.71-0.65 (m, 2H).

HU-P2 ESI 758.3 (M+H)$^+$ $^1$H NMR (400 MHz, MeOD) δ 7.79 (s, 1H), 7.39 (t, J=7.6 Hz, 1H), 6.85 (s, 3H), 5.85-5.79 (m, 1H), 5.62 (t, J=7.6 Hz, 1H), 3.13-2.94 (m, 2H), 2.93-2.84 (m, 1H), 2.79 (s, 6H), 2.70-2.57 (m, 3H), 2.09-1.81 (m, 10H), 1.70-1.58 (m, 1H), 1.36-1.26 (m, 1H), 0.99-0.92 (m, 2H), 0.89-0.83 (m, 6H), 0.72-0.65 (m, 2H).

498

3-66. Preparation of (3S)-3-(2-(5-(2-(dimethylamino)ethyl)-2-oxo-4-(trifluoromethyl)pyridin-1 (2H)-yl)-4-methylpentanamido)-3-(2,2',4-trifluoro-4',5,6'-trimethyl-[1,1'-biphenyl]-3-yl)propanoic Acid (Compounds HV-P1 and HV-P2)

Step 1: Ethyl (3S)-3-(2-(5-(2-(dimethylamino) ethyl)-2-oxo-4-(trifluoromethyl)pyridin-1(2H)-yl)-4-methylpentanamido)-3-(2,2',4-trifluoro-4',5,6'-trimethyl-[1,1'-biphenyl]-3-yl)propanoate

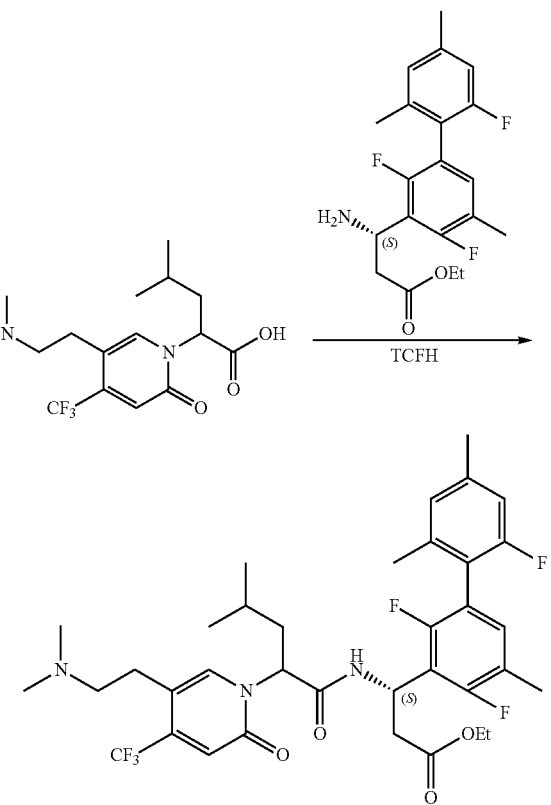

A mixture of 2-(5-(2-(dimethylamino)ethyl)-2-oxo-4-(trifluoromethyl)pyridin-1(2H)-yl)-4-methylpentanoic acid (142 mg, 0.41 mmol), ethyl (3S)-3-amino-3-(2,2',4-trifluoro-4',5,6'-trimethyl-[1,1'-biphenyl]-3-yl)propanoate hydrochloride (150.0 mg, 0.41 mmol), TCFH (137.0 mg, 0.48 mmol) and NMI (67.0 mg, 0.81 mmol) in CH$_3$CN (4 mL) was stirred at room temperature for 2 hrs. The reaction mixture was concentrated in vacuo and the residue was purified by reverse phase HPLC on a C18/40 g column (A: water 10 mM NH$_4$HCO$_3$, B: MeOH, 0~100%) to provide ethyl (3S)-3-(2-(5-(2-(dimethylamino)ethyl)-2-oxo-4-(trifluoromethyl)pyridin-1(2H)-yl)-4-methylpentanamido)-3-(2,2',4-trifluoro-4',5,6'-trimethyl-[1,1'-biphenyl]-3-yl)propanoate as a yellow solid (160.0 mg). Yield 56.1% (ESI 696.2 [M+H]$^+$).

Step 2: (3S)-3-(2-(5-(2-(dimethylamino)ethyl)-2-oxo-4-(trifluoromethyl)pyridin-1(2H)-yl)-4-methylpentanamido)-3-(2,2',4-trifluoro-4',5,6'-trimethyl-[1,1'-biphenyl]-3-yl)propanoic Acid 3-67. Preparation of (3S)-3-(2-(5-(3-(dimethylamino)propyl)-2-oxo-4-(trifluoromethyl)pyridin-1(2H)-yl)-4-methylpentanamido)-3-(2,4,4'-trifluoro-2',6'-dimethyl-5-(trifluoromethyl)-[1,1'-biphenyl]-3-yl)propanoic Acid (Compounds HW-P1 and HW-P2)

Step 1: Ethyl (3S)-3-(2-(5-(3-(dimethylamino)propyl)-2-oxo-4-(trifluoromethyl)pyridin-1(2H)-yl)-4-methylpentanamido)-3-(2,4,4'-trifluoro-2',6'-dimethyl-5-(trifluoromethyl)-[1,1'-biphenyl]-3-yl)propanoate

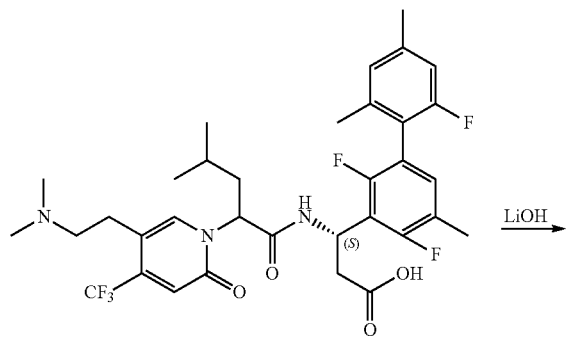

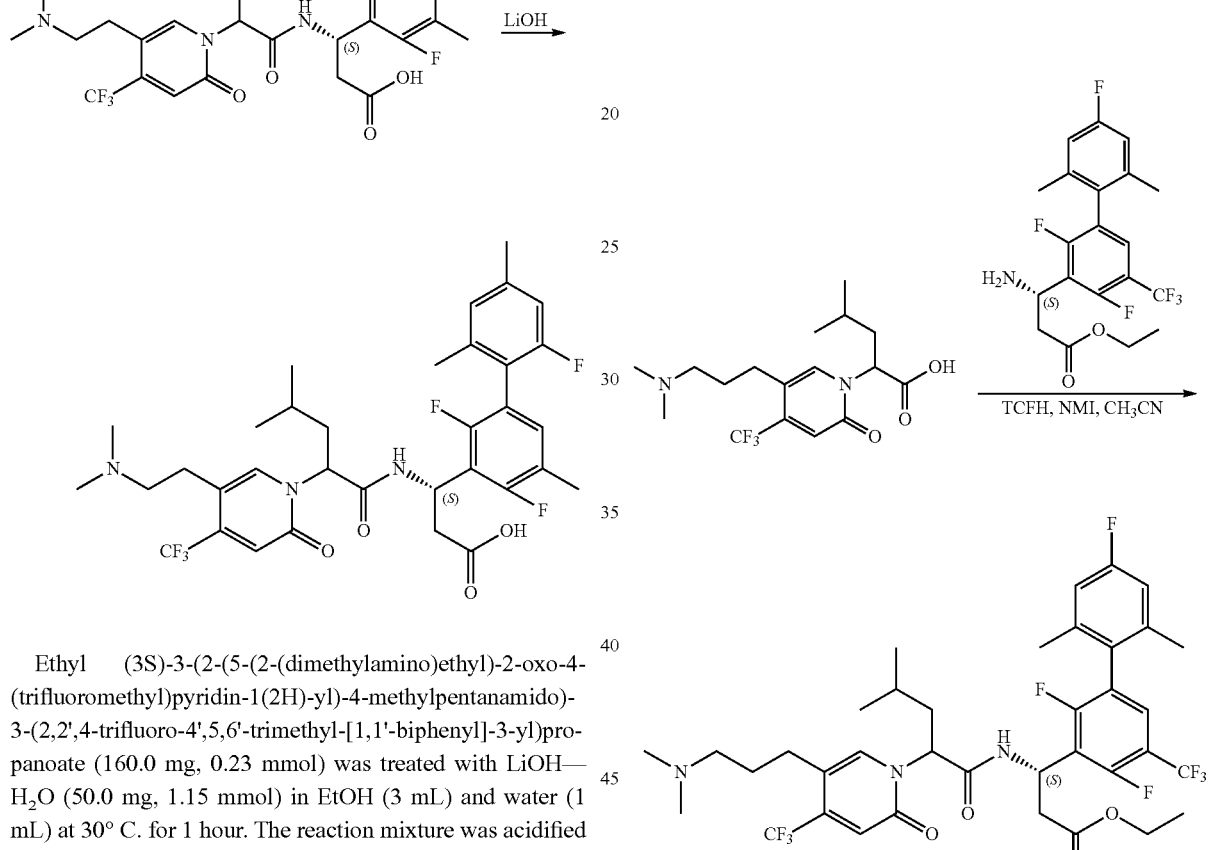

Ethyl (3S)-3-(2-(5-(2-(dimethylamino)ethyl)-2-oxo-4-(trifluoromethyl)pyridin-1(2H)-yl)-4-methylpentanamido)-3-(2,2',4-trifluoro-4',5,6'-trimethyl-[1,1'-biphenyl]-3-yl)propanoate (160.0 mg, 0.23 mmol) was treated with LiOH—H$_2$O (50.0 mg, 1.15 mmol) in EtOH (3 mL) and water (1 mL) at 30° C. for 1 hour. The reaction mixture was acidified to pH 4~5 with 2N HCl. The reaction was concentrated in vacuo and the residue purified by Prep HPLC A (30-80% MeCN) to give the diastereomeric products HV-P1 (41.3 mg) and HV-P2 (45.5 mg) as white solids.

HV-P1 ESI 668.2 (M+H)$^+$ $^1$H NMR (400 MHz, MeOD) δ 7.86 (s, 1H), 7.02-6.89 (m, 2H), 6.83-6.77 (m, 2H), 5.77-5.64 (m, 2H), 3.11-3.07 (m, 2H), 2.97-2.91 (m, 3H), 2.74-2.66 (m, 7H), 2.33 (s, 3H), 2.23 (s, 3H), 2.06-1.96 (m, 5H), 1.42-1.39 (m, 1H), 0.95-0.92 (m, 6H).

HV-P2 ESI 668.2 (M+H)$^+$ $^1$H NMR (400 MHz, MeOD) δ 7.82 (s, 1H), 7.03 (t, J=8.2 Hz, 1H), 6.93 (d, J=16.0 Hz, 2H), 6.82 (d, J=10.3 Hz, 1H), 5.87-5.82 (m, 1H), 5.67-5.63 (m, 1H), 3.23-3.13 (m, 2H), 2.98-2.95 (m, 2H), 2.82-2.79 (m, 7H), 2.57-2.51 (m, 1H), 2.34 (s, 3H), 2.27 (s, 3H), 2.08 (d, J=6.1 Hz, 3H), 1.95-1.88 (m, 1H), 1.79-1.70 (m, 1H), 1.40-1.25 (m, 1H), 0.93-0.80 (m, 6H).

A mixture of 2-(5-(3-(dimethylamino)propyl)-2-oxo-4-(trifluoromethyl)pyridin-1(2H)-yl)-4-methylpentanoic acid (100.0 mg, 0.28 mmol), ethyl (S)-3-amino-3-(2,4,4'-trifluoro-2',6'-dimethyl-5-(trifluoromethyl)-[1,1'-biphenyl]-3-yl)propanoate (117.3 mg, 0.28 mmol), TCFH (156.8 mg, 0.56 mmol) and NMI (91.8 mg, 1.12 mmol) in CH$_3$CN (10 mL) was stirred at room temperature for 1 hour. The reaction was concentrated in vacuo and the residue purified by silica gel column (DCM:MeOH 4:1) to provide ethyl (3S)-3-(2-(5-(3-(dimethylamino)propyl)-2-oxo-4-(trifluoromethyl)pyridin-1(2H)-yl)-4-methylpentanamido)-3-(2,4,4'-trifluoro-2',6'-dimethyl-5-(trifluoromethyl)-[1,1'-biphenyl]-3-yl)propanoate as a brown solid (150.0 mg). Yield 71% (ESI 764.7 (M+H)$^+$).

501

Step 2: (3S)-3-(2-(5-(3-(dimethylamino)propyl)-2-oxo-4-(trifluoromethyl)pyridin-1(2H)-yl)-4-methylpentanamido)-3-(2,4,4'-trifluoro-2',6'-dimethyl-5-(trifluoromethyl)-[1,1'-biphenyl]-3-yl)propanoic Acid

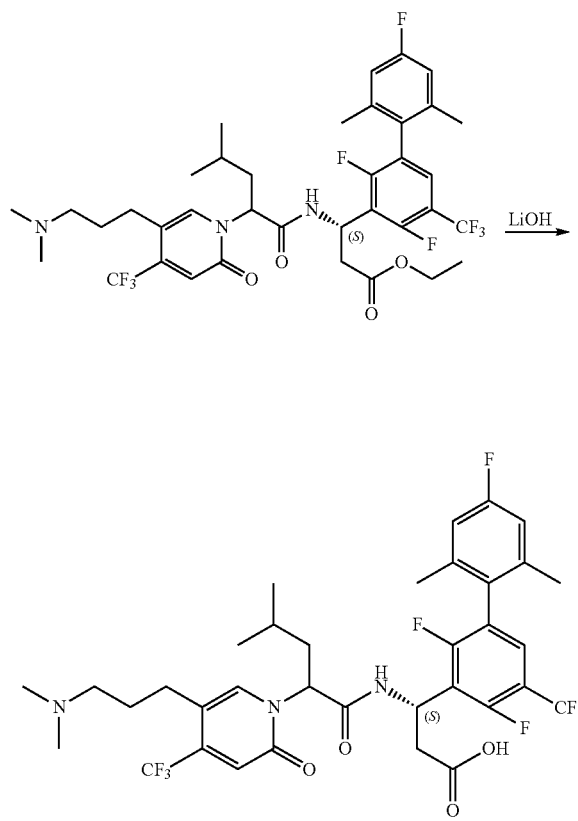

Ethyl (3S)-3-(2-(5-(3-(dimethylamino)propyl)-2-oxo-4-(trifluoromethyl)pyridin-1(2H)-yl)-4-methylpentanamido)-3-(2,4,4'-trifluoro-2',6'-dimethyl-5-(trifluoromethyl)-[1,1'-biphenyl]-3-yl)propanoate (150 mg, 0.20 mmol)) was treated with LiOH—H₂O (33.6 mg, 0.80 mmol) in MeOH (4 mL) and H₂O (1 mL) at room temperature for 2 hours. The reaction mixture was acidified to pH 4~5 with 1N HCl. The reaction was concentrated in vacuo and the residue purified by prep-HPLC A (30-60% MeCN) to give the diastereomeric products HW-P1 (60.1 mg) and HW-P2 (50.0 mg) as white solids.

HW-P1 ESI 736.6 (M+H)⁺. 1H NMR (400 MHz, MeOD) δ 7.76 (s, 1H), 7.39 (t, J=7.5 Hz, 1H), 6.88 (d, J=9.3 Hz, 2H), 6.80 (s, 1H), 5.78-5.67 (m, 2H), 3.14-3.02 (m, 2H), 3.01-2.88 (m, 1H), 2.80 (s, 6H), 2.75-2.55 (m, 3H), 2.12-1.84 (m, 10H), 1.34 (s, 1H), 0.94 (d, J=6.6 Hz, 6H).

HW-P2 ESI 736.6 (M+H)⁺. 1H NMR (400 MHz, MeOD) δ 7.79 (s, 1H), 7.45 (t, J=7.6 Hz, 1H), 6.96-6.80 (m, 3H), 5.86-5.75 (m, 1H), 5.62 (t, J=7.6 Hz, 1H), 3.14-2.97 (m,

502

2H), 2.97-2.85 (m, 1H), 2.79 (s, 6H), 2.71-2.50 (m, 3H), 2.07-1.87 (m, 8H), 1.67-1.52 (m, 1H), 1.35-1.25 (m, 1H), 0.93-0.77 (m, 6H).

3-68. Preparation of (3S)-3-(2-(5-(3-(azetidin-1-yl)propyl)-2-oxo-4-(trifluoromethyl)pyridin-1(2H)-yl)-4-methylpentanamido)-3-(2,4-difluoro-2',4',5,6'-tetramethylbiphenyl-3-yl)propanoic Acid (Compounds HX-P1 and HX-P2)

Step 1: (3S)-ethyl 3-(2-(5-(3-(azetidin-1-yl)propyl)-2-oxo-4-(trifluoromethyl)pyridin-1(2H)-yl)-4-methylpentanamido)-3-(2,4-difluoro-2',4',5,6'-tetramethylbiphenyl-3-yl)propanoate

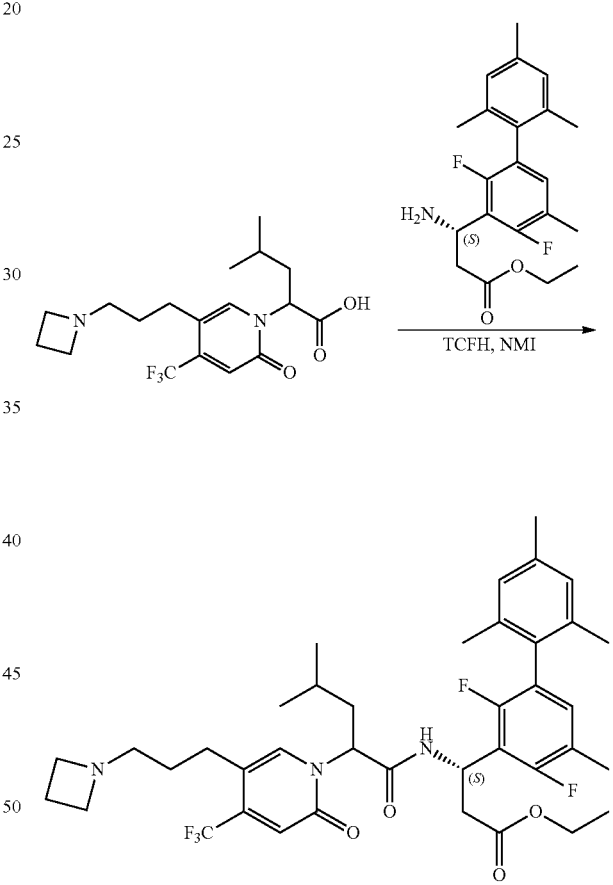

A mixture of 2-(5-(3-(azetidin-1-yl)propyl)-2-oxo-4-(trifluoromethyl)pyridin-1(2H)-yl)-4-methylpentanoic acid (100 mg, 0.27 mmol), (S)-ethyl 3-amino-3-(2,4-difluoro-2',4',5,6'-tetramethylbiphenyl-3-yl)propanoate (97 mg, 0.27 mmol), NMI (0.5 mL) and TCFH (378 mg, 1.35 mmol) in CH₃CN (5 mL) was stirred at room temperature for 1 hour. The reaction was concentrated in vacuo and the residue purified by prep-HPLC A (30-90% CH₃CN) to provide (3S)-ethyl 3-(2-(5-(3-(azetidin-1-yl)propyl)-2-oxo-4-(trifluoromethyl)pyridin-1(2H)-yl)-4-methylpentanamido)-3-(2,4-difluoro-2',4',5,6'-tetramethylbiphenyl-3-yl)propanoate as a white solid (140 mg). Yield 73% (ESI 718.3 [M+H]+).

Step 2: (3S)-3-(2-(5-(3-(azetidin-1-yl)propyl)-2-oxo-4-(trifluoromethyl)pyridin-1(2H)-yl)-4-methylpentanamido)-3-(2,4-difluoro-2',4',5,6'-tetramethylbiphenyl-3-yl)propanoic Acid

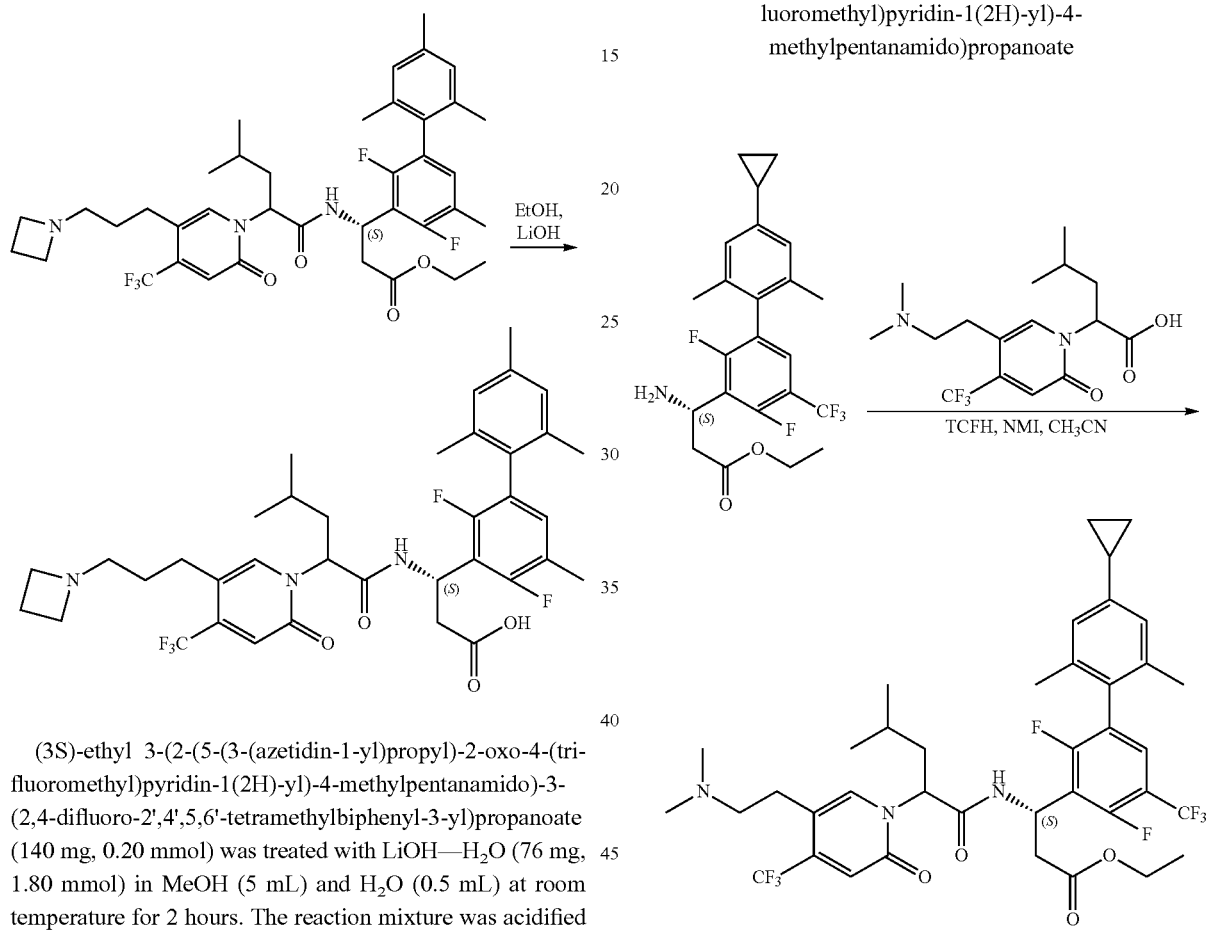

(3S)-ethyl 3-(2-(5-(3-(azetidin-1-yl)propyl)-2-oxo-4-(trifluoromethyl)pyridin-1(2H)-yl)-4-methylpentanamido)-3-(2,4-difluoro-2',4',5,6'-tetramethylbiphenyl-3-yl)propanoate (140 mg, 0.20 mmol) was treated with LiOH—H$_2$O (76 mg, 1.80 mmol) in MeOH (5 mL) and H$_2$O (0.5 mL) at room temperature for 2 hours. The reaction mixture was acidified to pH 4~5 with 1N HCl. The reaction was concentrated in vacuo and the residue purified by prep-HPLC A (30-70% CH$_3$CN) to give the diastereomeric products HX-P1 (41.0 mg) and HX-P2 (40.0 mg) as white solids.

HX-P1 ESI 690.3 (M+H)+. $^1$H NMR (400 MHz, MeOD) δ 7.77 (s, 1H), 6.91-6.83 (m, 3H), 6.79 (s, 1H), 5.84-5.66 (m, 2H), 4.05 (t, J=8.2 Hz, 4H), 3.14 (t, J=7.5 Hz, 2H), 3.04-2.89 (m, 1H), 2.73-2.56 (m, 3H), 2.49-2.35 (m, 2H), 2.28 (s, 3H), 2.23 (s, 3H), 2.00 (t, J=7.6 Hz, 2H), 1.91 (d, J=21.2 Hz, 6H), 1.86-1.69 (m, 2H), 1.40-1.27 (m, 1H), 0.98-0.87 (m, 6H).

HX-P2 ESI 690.3 (M+H)+. $^1$H NMR (400 MHz, MeOD) δ 7.78 (s, 1H), 6.97-6.79 (m, 4H), 5.91-5.81 (m, 1H), 5.56 (t, J=7.5 Hz, 1H), 4.16-3.95 (m, 4H), 3.17-2.97 (m, 2H), 2.93-2.81 (m, 1H), 2.70-2.51 (m, 3H), 2.48-2.37 (m, 2H), 2.29 (s, 3H), 2.27 (s, 3H), 2.04-1.69 (m, 9H), 1.65-1.52 (m, 1H), 1.41-1.22 (m, 1H), 0.94-0.78 (m, 6H).

3-69. Preparation of (3S)-3-(4'-cyclopropyl-2,4-difluoro-2',6'-dimethyl-5-(trifluoromethyl)-[1,1'-biphenyl]-3-yl)-3-(2-(5-(2-(dimethylamino)ethyl)-2-oxo-4-(trifluoromethyl)pyridin-1(2H)-yl)-4-methylpentanamido)propanoic Acid (Compounds HY-P1 and HY-P2)

Step 1: Ethyl (3S)-3-(4'-cyclopropyl-2,4-difluoro-2',6'-dimethyl-5-(trifluoromethyl)-[1,1'-biphenyl]-3-yl)-3-(2-(5-(2-(dimethylamino)ethyl)-2-oxo-4-(trifluoromethyl)pyridin-1(2H)-yl)-4-methylpentanamido)propanoate

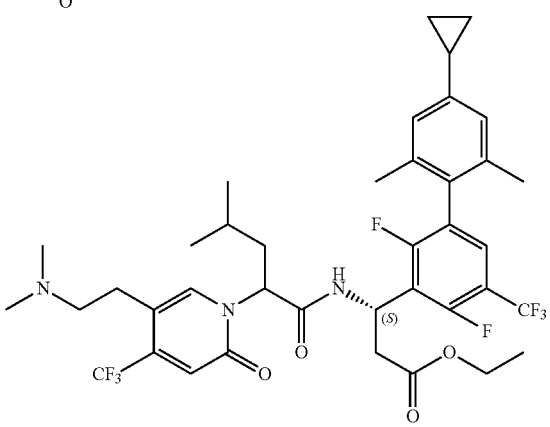

A mixture of ethyl (S)-3-amino-3-(4'-cyclopropyl-2,4-difluoro-2',6'-dimethyl-5-(trifluoromethyl)-[1,1'-biphenyl]-3-yl)propanoate (140.0 mg, 0.29 mmol), 2-(5-(2-(dimethylamino)ethyl)-2-oxo-4-(trifluoromethyl)pyridin-1(2H)-yl)-4-methylpentanoic acid (101.0 mg, 0.29 mmol), TCFH (97.6 mg, 0.35 mmol) and NMI (71.4 mg, 0.87 mmol) in CH$_3$CN (5 mL) was stirred at room temperature overnight. The reaction was concentrated in vacuo and the residue purified by reverse phase HPLC on a C18/40 g column (A: water 10 mM NH$_4$HCO$_3$, B: MeOH, 0~100%) to provide ethyl (3S)-3-(4'-cyclopropyl-2,4-difluoro-2',6'-dimethyl-5-(trifluoromethyl)-[1,1'-biphenyl]-3-yl)-3-(2-(5-(2-(dimethylamino)ethyl)-2-oxo-4-(trifluoromethyl)pyridin-1(2H)-yl)-4-methylpentanamido)propanoate as a light yellow solid (130.0 mg). Yield 57% (ESI 772.3 [M+H]+).

Step 2: (3S)-3-(4'-cyclopropyl-2,4-difluoro-2',6'-dimethyl-5-(trifluoromethyl)-[1,1'-biphenyl]-3-yl)-3-(2-(5-(2-(dimethylamino)ethyl)-2-oxo-4-(trifluoromethyl)pyridin-1(2H)-yl)-4-methylpentanamido) propanoic Acid

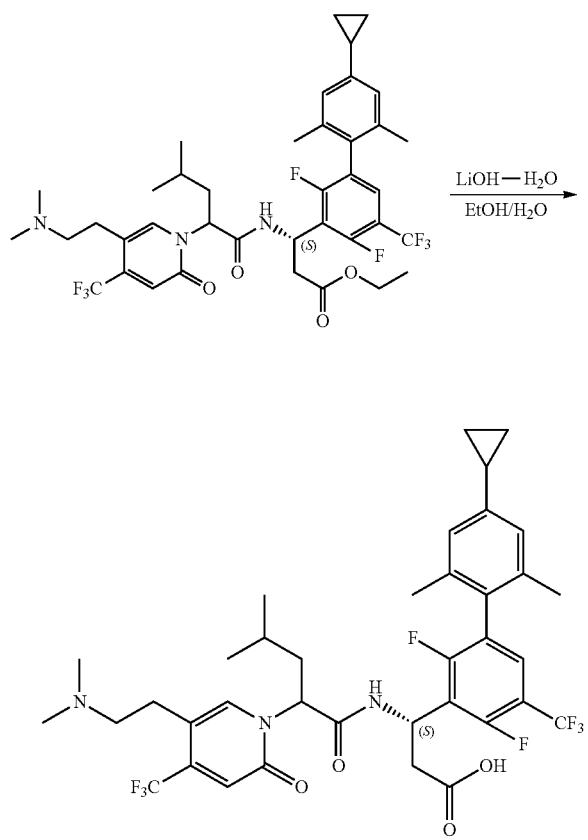

Ethyl (3S)-3-(4'-cyclopropyl-2,4-difluoro-2',6'-dimethyl-5-(trifluoromethyl)-[1,1'-biphenyl]-3-yl)-3-(2-(5-(2-(dimethylamino)ethyl)-2-oxo-4-(trifluoromethyl)pyridin-1(2H)-yl)-4-methylpentanamido)propanoate (130.0 mg, 0.17 mmol) was treated with LiOH—H₂O (21.4 mg, 0.51 mmol) in EtOH (2 mL) and water (0.5 mL) at room temperature for 30 mins. The reaction mixture was acidified to pH 5~6 with 2N HCl. The reaction was concentrated in vacuo and the residue purified by prep-HPLC A (30-80% MeCN) to give the diastereomeric products HY-P1 (40 mg) and HY-P2 (50.3 mg) as white solids.

HY-P1 ESI 744.2 (M+H)⁺ ¹H NMR (400 MHz, MeOD) δ 7.85 (s, 1H), 7.34 (t, J=7.6 Hz, 1H), 6.82 (d, J=4.5 Hz, 3H), 5.73-5.67 (m, 2H), 3.17-3.01 (m, 2H), 2.99-2.89 (m, 3H), 2.79-2.68 (m, 7H), 2.05-1.91 (m, 5H), 1.91-1.79 (m, 4H), 1.44-1.33 (m, 1H), 0.98-0.91 (m, 8H), 0.72-0.64 (m, 2H).

HY-P2 ESI 744.3 (M+H)⁺ ¹H NMR (400 MHz, MeOD) δ 7.83 (s, 1H), 7.41 (t, J=7.6 Hz, 1H), 6.90 (s, 1H), 6.85 (s, 2H), 5.85-5.78 (m, 1H), 5.65 (t, J=7.8 Hz, 1H), 3.27-3.12 (m, 2H), 2.96 (t, J=7.1 Hz, 2H), 2.89-2.75 (m, 7H), 2.70-2.62 (m, 1H), 1.97 (d, J=3.3 Hz, 6H), 1.94-1.83 (m, 2H), 1.79-1.65 (m, 1H), 1.38-1.24 (m, 1H), 1.01-0.92 (m, 2H), 0.91-0.84 (m, 6H), 0.75-0.63 (m, 2H).

3-70. Preparation of (3S)-3-(2,4-difluoro-2',4',6'-trimethyl-5-(trifluoromethyl)biphenyl-3-yl)-3-(2-(5-(3-(dimethylamino)propyl)-2-oxo-4-(trifluoromethyl)pyridin-1(2H)-yl)-4-methylpentanamido) propanoic Acid (Compounds HZ-P1 and HZ-P2)

Step 1: (3S)-ethyl 3-(2,4-difluoro-2',4',6'-trimethyl-5-(trifluoromethyl)biphenyl-3-yl)-3-(2-(5-(3-(dimethylamino)propyl)-2-oxo-4-(trifluoromethyl)pyridin-1(2H)-yl)-4-methylpentanamido)propanoate

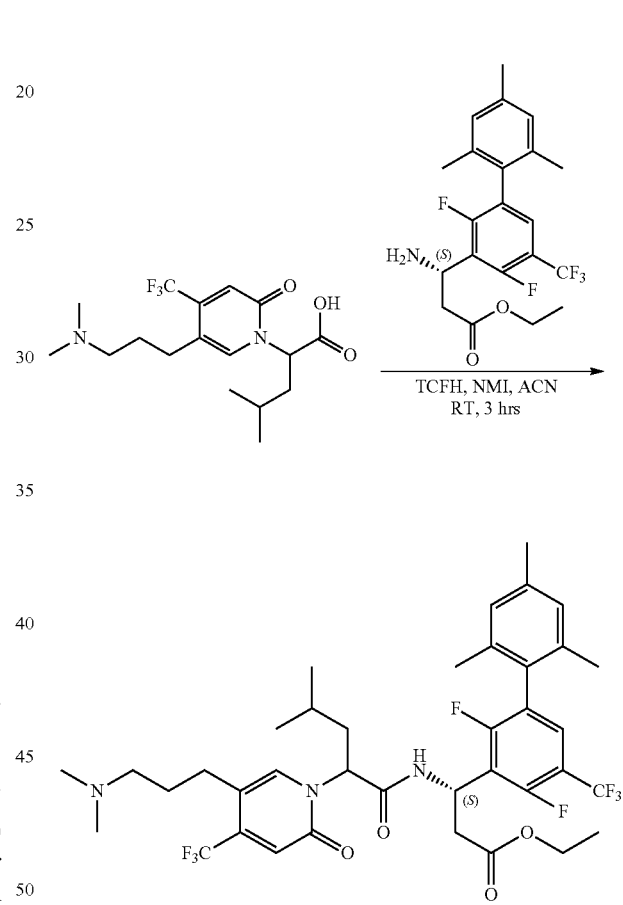

A mixture of (S)-ethyl 3-amino-3-(2,4-difluoro-2',4',6'-trimethyl-5-(trifluoromethyl)biphenyl-3-yl)propanoate (208 mg, 0.50 mmol), 2-(5-(3-(dimethylamino)propyl)-2-oxo-4-(trifluoromethyl)pyridin-1(2H)-yl)-4-methylpentanoic acid (180 mg, 0.50 mmol), TCFH (280 mg, 1.0 mmol) and NMI (123 mg, 1.5 mmol) in MeCN (5 mL) was stirred at room temperature for 3 hrs. The solvent was removed in vacuo and the residue was purified by silica gel column (DCM:MeOH 97:3) to provide (3S)-ethyl 3-(2,4-difluoro-2',4',6'-trimethyl-5-(trifluoromethyl)biphenyl-3-yl)-3-(2-(5-(3-(dimethylamino)propyl)-2-oxo-4-(trifluoromethyl)pyridin-1(2H)-yl)-4-methylpentanamido)propanoate as a colorless oil (200 mg). Yield 53% (ESI 760.3 (M+H)⁺).

Step 2: (3S)-3-(2,4-difluoro-2',4',6'-trimethyl-5-(trifluoromethyl)biphenyl-3-yl)-3-(2-(5-(3-(dimethylamino)propyl)-2-oxo-4-(trifluoromethyl)pyridin-1(2H)-yl)-4-methylpentanamido)propanoic Acid

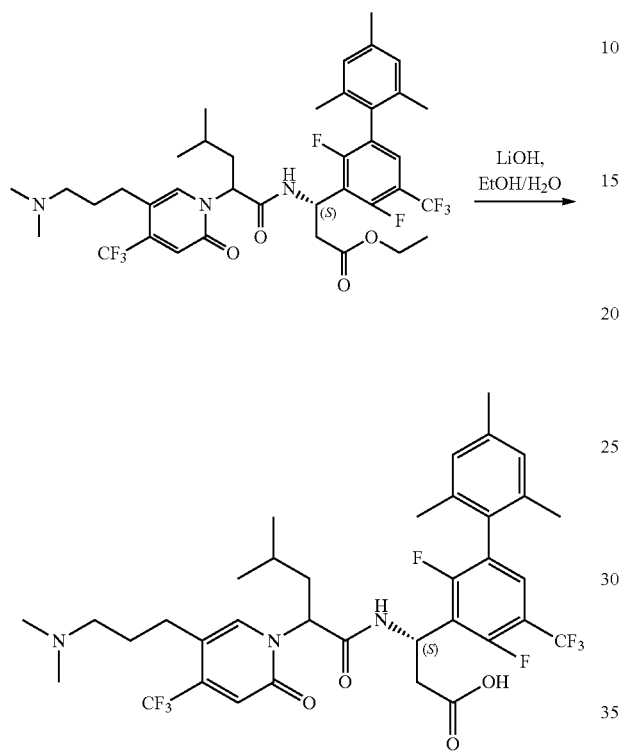

3-71. Preparation of (3S)-3-(4'-cyclopropyl-2,4-difluoro-2',5,6'-trimethylbiphenyl-3-yl)-3-(2-(5-(3-(dimethylamino)propyl)-2-oxo-4-(trifluoromethyl)pyridin-1(2H)-yl)-4-methylpentanamido)propanoic Acid (Compounds IA-P1 and IA-P2)

Step 1: (3S)-ethyl 3-(4'-cyclopropyl-2,4-difluoro-2',5,6'-trimethylbiphenyl-3-yl)-3-(2-(5-(3-(dimethylamino)propyl)-2-oxo-4-(trifluoromethyl)pyridin-1(2H)-yl)-4-methylpentanamido)propanoate

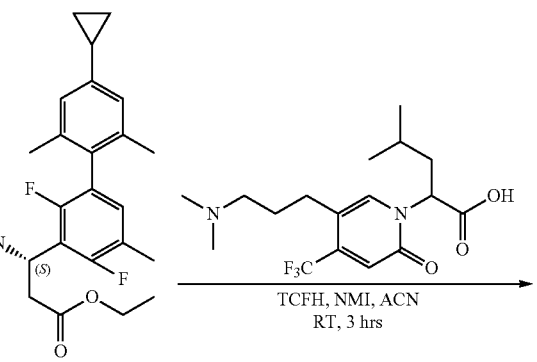

(3S)-ethyl 3-(2,4-difluoro-2',4',6'-trimethyl-5-(trifluoromethyl)biphenyl-3-yl)-3-(2-(5-(3-(dimethylamino)propyl)-2-oxo-4-(trifluoromethyl)pyridin-1(2H)-yl)-4-methylpentanamido)propanoate (200 mg, 0.26 mmol) was treated with LiOH—H$_2$O (55 mg, 1.3 mmol) in EtOH (3 mL) and H$_2$O (1 mL) at room temperature for 2 hours. The reaction mixture was acidified to pH 4-5 with 1N HCl. The reaction was concentrated in vacuo and the residue purified by prep-HPLC A (30-60% CH$_3$CN) to give the diastereomeric products HZ-P1 (7.0 mg) and HZ-P2 (62.0 mg) as white solids.

HZ-P1 ESI 732.3 (M+H)$^+$. 1H NMR (400 MHz, MeOD) δ 7.76 (s, 1H), 7.35 (t, J=7.6 Hz, 1H), 6.94 (s, 2H), 6.80 (s, 1H), 5.79-5.70 (m, 2H), 3.14-3.07 (m, 2H), 2.95-2.90 (m, 1H), 2.81 (s, 6H), 2.72-2.58 (m, 3H), 2.30 (s, 3H), 2.11-1.92 (m, 7H), 1.87 (s, 3H), 1.34 (s, 1H), 0.94 (d, J=6.5 Hz, 6H).

HZ-P2 ESI 732.3 (M+H)$^+$. 1H NMR (400 MHz, MeOD) δ 7.79 (s, 1H), 7.40 (t, J=7.6 Hz, 1H), 6.97 (s, 2H), 6.85 (s, 1H), 5.82-5.80 (m, 1H), 5.62 (t, J=7.6 Hz, 1H), 3.15-2.95 (m, 2H), 2.89-2.85 (m, 1H), 2.79 (s, 6H), 2.63-2.60 (m, 3H), 2.31 (s, 3H), 2.08-1.83 (m, 9H), 1.72-1.58 (m, 1H), 1.31-1.25 (m, 1H), 0.86-0.82 (m, 6H).

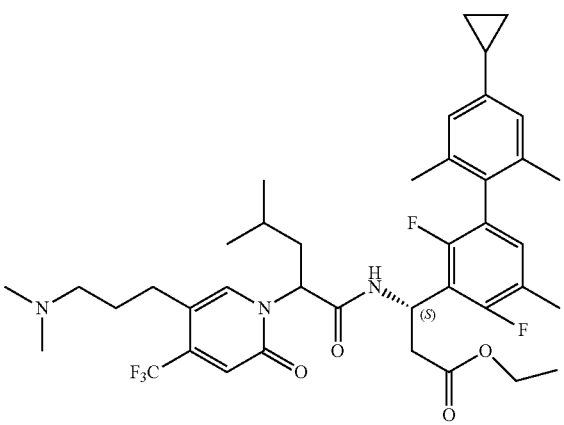

A mixture of (S)-ethyl 3-amino-3-(4'-cyclopropyl-2,4-difluoro-2',5,6'-trimethylbiphenyl-3-yl)propanoate (107 mg, 0.28 mmol), 2-(5-(3-(dimethylamino)propyl)-2-oxo-4-(trifluoromethyl)pyridin-1(2H)-yl)-4-methylpentanoic acid (100 mg, 0.28 mmol), TCFH (157 mg, 0.56 mmol) and NMI (69 mg, 0.84 mmol) in MeCN (5 mL) was stirred at room temperature for 3 hrs. The solvent was removed in vacuo and the residue was purified by silica gel column (DCM:MeOH 97:3) to provide (3S)-ethyl 3-(4'-cyclopropyl-2,4-difluoro-2',5,6'-trimethylbiphenyl-3-yl)-3-(2-(5-(3-(dimethylamino)propyl)-2-oxo-4-(trifluoromethyl)pyridin-1(2H)-yl)-4-methylpentanamido)propanoate as a colorless oil (100 mg). Yield 49% (ESI 732.3 (M+H)$^+$).

Step 2: (3S)-3-(4'-cyclopropyl-2,4-difluoro-2',5,6'-trimethylbiphenyl-3-yl)-3-(2-(5-(3-(dimethylamino)propyl)-2-oxo-4-(trifluoromethyl)pyridin-1(2H)-yl)-4-methylpentanamido)propanoic Acid

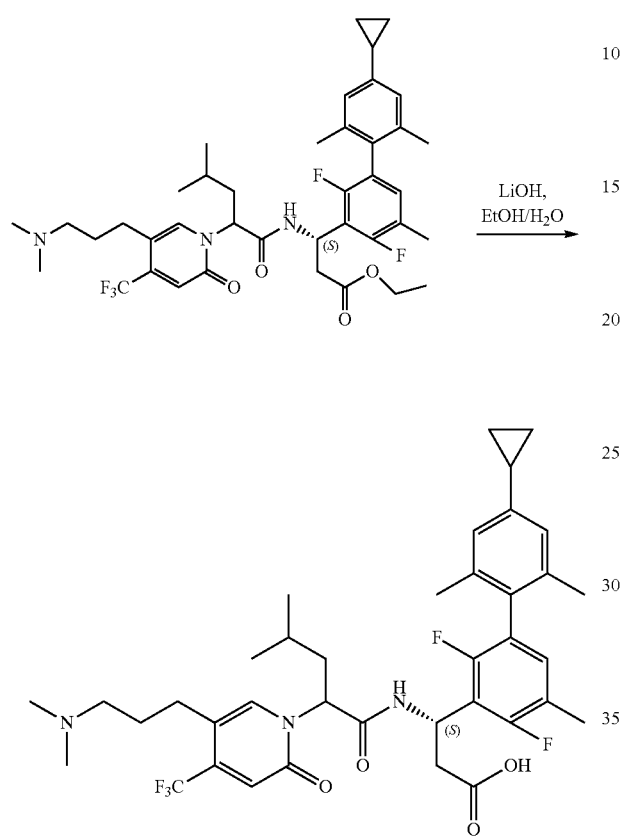

(3S)-ethyl 3-(4'-cyclopropyl-2,4-difluoro-2',5,6'-trimethylbiphenyl-3-yl)-3-(2-(5-(3-(dimethylamino)propyl)-2-oxo-4-(trifluoromethyl)pyridin-1(2H)-yl)-4-methylpentanamido)propanoate (100 mg, 0.14 mmol) was treated with LiOH—H$_2$O (27 mg, 0.65 mmol) in EtOH (3 mL) and H$_2$O (1 mL) at room temperature for 2 hours. The reaction mixture was acidified to pH 4~5 with 1N HCl. The reaction was concentrated in vacuo and the residue purified by prep-HPLC A (30-60% CH$_3$CN) to give the diastereomeric products IA-P1 (37.3 mg) and IA-P2 (38.5 mg) as white solids.

IA-P1 ESI 704.3 (M+H)$^+$. 1H NMR (400 MHz, MeOD) δ 7.78 (d, J=13.1 Hz, 1H), 6.84 (t, J=8.0 Hz, 1H), 6.79-6.75 (m, 3H), 5.78-5.67 (m, 2H), 3.10-3.00 (m, 2H), 2.93-2.90 (m, 1H), 2.77 (s, 6H), 2.69-2.59 (m, 3H), 2.24 (d, J=18.1 Hz, 3H), 2.08-1.97 (m, 3H), 1.97-1.74 (m, 8H), 1.34-1.30 (m, 1H), 1.02-0.82 (m, 8H), 0.72-0.56 (m, 2H).

IA-P2 ESI 704.3 (M+H)$^+$. 1H NMR (400 MHz, MeOD) δ 7.79 (s, 1H), 6.89 (t, J=8.2 Hz, 1H), 6.82 (d, J=16.3 Hz, 3H), 5.84-5.80 (m, 1H), 5.57 (t, J=7.5 Hz, 1H), 3.01-3.00 (m, 2H), 2.85-2.83 (m, 1H), 2.77 (s, 6H), 2.68-2.59 (m, 2H), 2.53-2.51 (m, 1H), 2.26 (s, 3H), 2.05-1.83 (m, 10H), 1.62- 1.60 (m, 1H), 1.34-1.30 (m, 1H), 1.03-0.91 (m, 2H), 0.86-0.83 (m, 6H), 0.71-0.64 (m, 2H).

3-72. Preparation of (3S)-3-(2-(5-(2-(2-azaspiro[3.4]octan-2-yl)ethyl)-2-oxo-4-(trifluoromethyl)pyridin-1(2H)-yl)-4-methylpentanamido)-3-(2,4-difluoro-2',5,6'-trimethyl-[1,1'-biphenyl]-3-yl)propanoic Acid (IB-P1 and IB-P2)

Step 1: Ethyl (3S)-3-(2-(5-(2-(2-azaspiro[3.4]octan-2-yl)ethyl)-2-oxo-4-(trifluoromethyl)pyridin-1(2H)-yl)-4-methylpentanamido)-3-(2,4-difluoro-2',5,6'-trimethyl-[1,1'-biphenyl]-3-yl)propanoate

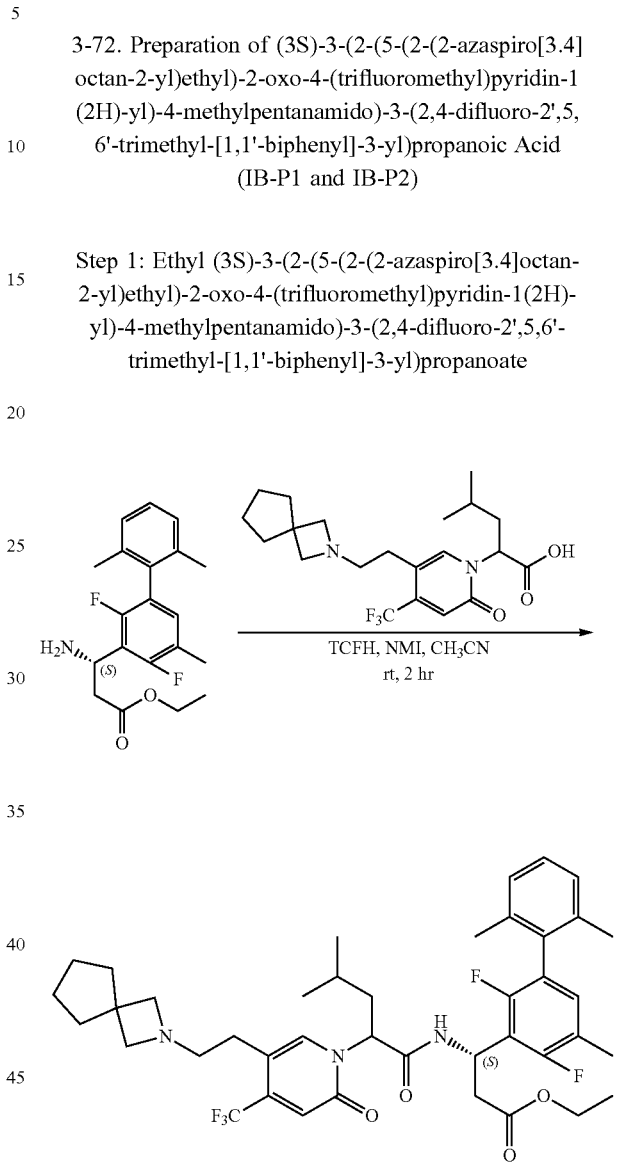

A mixture of ethyl (S)-3-amino-3-(2,4-difluoro-2',5,6'-trimethyl-[1,1'-biphenyl]-3-yl)propanoate (140 mg, 0.40 mmol), 2-(5-(2-(2-azaspiro[3.4]octan-2-yl)ethyl)-2-oxo-4-(trifluoromethyl)pyridin-1(2H)-yl)-4-methylpentanoic acid (182 mg, 0.54 mmol), TCFH (224 mg, 0.80 mmol) and NMI (164 mg, 2.0 mmol) in CH$_3$CN (5 mL) was stirred at room temperature for 2 hours. The reaction was concentrated and purified by reverse phase HPLC on a C18/40 g column (A: water 10 mM NH$_4$HCO3, B: CH$_3$OH, 0~85%) to provide ethyl (3S)-3-(2-(5-(2-(2-azaspiro[3.4]octan-2-yl)ethyl)-2-oxo-4-(trifluoromethyl)pyridin-1(2H)-yl)-4-methylpentanamido)-3-(2,4-difluoro-2',5,6'-trimethyl-[1,1'-biphenyl]-3-yl)propanoate as a yellow solid (130 mg). Yield 43.3% (ESI 744.3 [M+H]$^+$).

511

Step 2: (3S)-3-(2-(5-(2-(2-azaspiro[3.4]octan-2-yl)ethyl)-2-oxo-4-(trifluoromethyl)pyridin-1(2H)-yl)-4-methylpentanamido)-3-(2,4-difluoro-2',5,6'-trimethyl-[1,1'-biphenyl]-3-yl)propanoic Acid

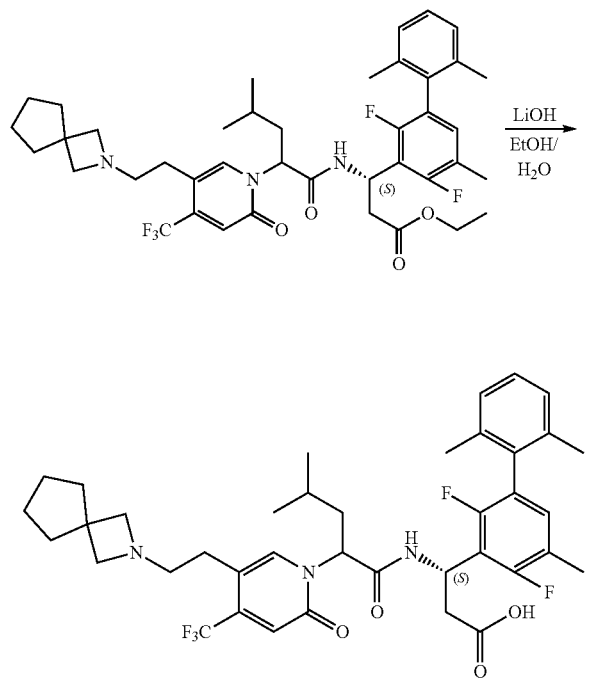

Ethyl (3S)-3-(2-(5-(2-(2-azaspiro[3.4]octan-2-yl)ethyl)-2-oxo-4-(trifluoromethyl)pyridin-1(2H)-yl)-4-methylpentanamido)-3-(2,4-difluoro-2',5,6'-trimethyl-[1,1'-biphenyl]-3-yl)propanoate (130 mg, 0.17 mmol) was treated with LiOH—H$_2$O (22 mg, 0.52 mmol) in EtOH (4 mL) and H$_2$O (1 mL) at room temperature for 2 hr. The reaction mixture was acidified to pH 5~6 with 1N HCl. The reaction was concentrated in vacuo and the residue purified by prep-HPLC A (30-65% CH$_3$CN) to give the diastereomeric products IB-P1 (48 mg) and IB-P2 (65 mg) as white solids.

IB-P1 ESI 716.2 (M+H)$^+$. $^1$H NMR (400 MHz, MeOD) δ 7.90 (s, 1H), 7.18 (m, J=24.2, 7.1 Hz, 3H), 6.94 (m, J=14.9, 6.5 Hz, 2H), 5.87 (m, J=9.8, 4.8 Hz, 1H), 5.75 (m, J=9.4, 6.8 Hz, 1H), 3.95 (d, J=9.1 Hz, 4H), 3.38 (m, 1H), 3.32 (m, J=7.3 Hz, 1H), 3.03 (m, J=15.2, 9.9 Hz, 1H), 2.93 (t, J=6.7 Hz, 2H), 2.70 (m, J=15.3, 4.9 Hz, 1H), 2.31 (s, 3H), 2.11-1.98 (m, 8H), 1.92 (d, J=6.3 Hz, 4H), 1.75-1.56 (m, 4H), 1.51-1.38 (m, 1H), 0.99 (m, J=6.6, 1.2 Hz, 6H).

IB-P2 ESI 716.2 (M+H)$^+$. $^1$H NMR (400 MHz, MeOD) δ 7.71 (s, 1H), 7.22-7.05 (m, 3H), 6.99-6.73 (m, 2H), 5.92 (m, J=11.5, 3.4 Hz, 1H), 5.62 (t, J=7.7 Hz, 1H), 3.99 (s, 4H), 3.43-3.31 (m, 2H), 2.95-2.75 (m, 3H), 2.47 (m, J=16.1, 3.6 Hz, 1H), 2.28 (s, 3H), 2.01 (d, J=5.5 Hz, 6H), 1.91 (m, J=26.9, 12.0, 7.3 Hz, 5H), 1.74-1.56 (m, 5H), 1.44-1.26 (m, 1H), 0.89 (m, J=9.1, 6.6 Hz, 6H).

512

3-73. Preparation of (3S)-3-(2,4-difluoro-2',5,6'-trimethyl-3'-(trifluoromethyl)-[1,1'-biphenyl]-3-yl)-3-(2-(5-(2-(dimethylamino)ethyl)-2-oxo-4-(trifluoromethyl)pyridin-1(2H)-yl)-4-methylpentanamido)propanoic Acid (Compounds IC-P1 and IC-P2)

Step 1: Ethyl (3S)-3-(2,4-difluoro-2',5,6'-trimethyl-3'-(trifluoromethyl)-[1,1'-biphenyl]-3-yl)-3-(2-(5-(2-(dimethylamino)ethyl)-2-oxo-4-(trifluoromethyl)pyridin-1(2H)-yl)-4-methylpentanamido)propanoate

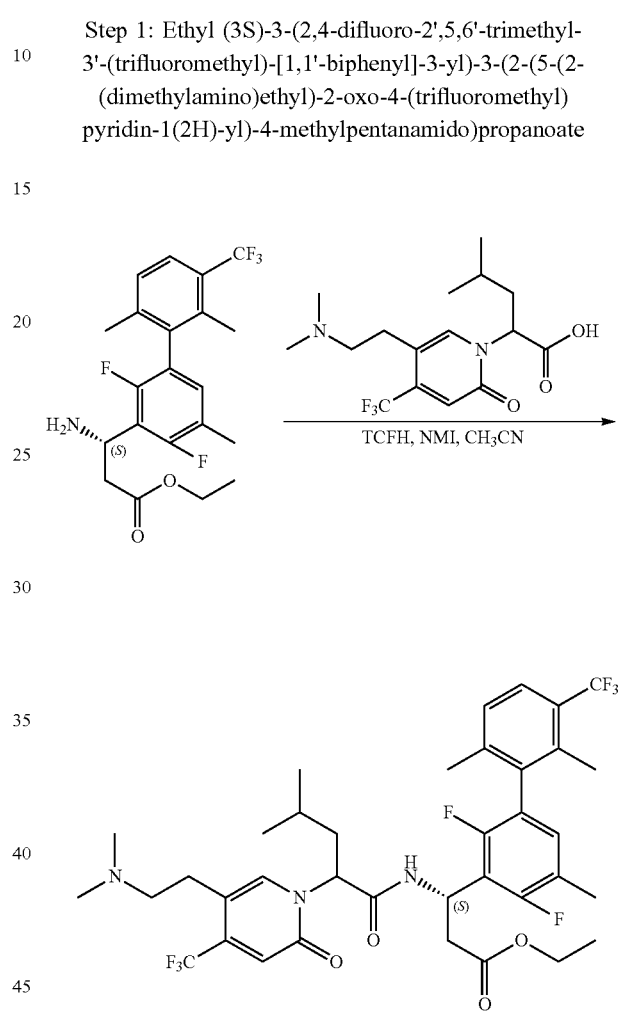

A mixture of ethyl (3S)-3-amino-3-(2,4-difluoro-2',5,6'-trimethyl-3'-(trifluoromethyl)-[1,1'-biphenyl]-3-yl)propanoate (170.0 mg, 0.41 mmol), 2-(5-(2-(dimethylamino)ethyl)-2-oxo-4-(trifluoromethyl)pyridin-1(2H)-yl)-4-methylpentanoic acid (142.8 mg, 0.49 mmol), TCFH (137.5 mg, 0.76 mmol) and NMI (68.8 mg, 1.64 mmol) in CH$_3$CN (5 mL) was stirred at room temperature overnight. The reaction was concentrated in vacuo and the residue purified by reverse phase HPLC on a C18/40 g column (A: water 10 mM NH$_4$HCO$_3$, B: MeOH, 0~100%) to provide ethyl (3S)-3-(2,4-difluoro-2',5,6'-trimethyl-3'-(trifluoromethyl)-[1,1'-biphenyl]-3-yl)-3-(2-(5-(2-(dimethylamino)ethyl)-2-oxo-4-(trifluoromethyl)pyridin-1(2H)-yl)-4-methylpentanamido)propanoate as a light yellow solid (210.0 mg). Yield 69% (ESI 746.3 [M+H]$^+$).

Step 2: (3S)-3-(2,4-difluoro-2',5,6'-trimethyl-3'-(trifluoromethyl)-[1,1'-biphenyl]-3-yl)-3-(2-(5-(2-(dimethylamino)ethyl)-2-oxo-4-(trifluoromethyl)pyridin-1(2H)-yl)-4-methylpentanamido)propanoic acid

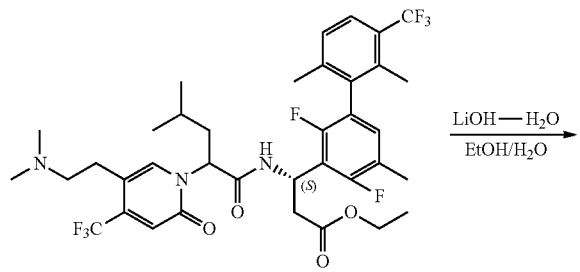

Ethyl (3S)-3-(2,4-difluoro-2',5,6'-trimethyl-3'-(trifluoromethyl)-[1,1'-biphenyl]-3-yl)-3-(2-(5-(2-(dimethylamino)ethyl)-2-oxo-4-(trifluoromethyl)pyridin-1(2H)-yl)-4-methylpentanamido)propanoate (210.0 mg, 0.28 mmol) was treated with LiOH—H$_2$O (35.2 mg, 0.84 mmol) in EtOH (2 mL) and water (0.5 mL) at room temperature for 1 hour. The reaction mixture was acidified to pH 4~5 with 2N HCL. The reaction was concentrated in vacuo and the residue purified by prep-HPLC A (30-80% MeCN) to give the diastereomeric products IC-P1 (53.3 mg) and IC-P2 (78.3 mg) as white solids.

IC-P1 ESI 718.3 (M+H)$^+$ $^1$H NMR (400 MHz, MeOD) δ 7.87 (d, J=3.6 Hz, 1H), 7.56 (d, J=8.1 Hz, 1H), 7.26 (d, J=8.2 Hz, 1H), 6.90 (t, J=8.1 Hz, 1H), 6.83 (s, 1H), 5.75-5.64 (m, 2H), 3.18-3.01 (m, 2H), 3.00-2.85 (m, 3H), 2.79-2.64 (m, 7H), 2.25 (s, 3H), 2.10-1.94 (m, 8H), 1.46-1.33 (m, 1H), 0.96-0.90 (m, 6H).

IC-P2 ESI 718.3 (M+H)$^+$ $^1$H NMR (400 MHz, MeOD) δ 7.81 (s, 1H), 7.58 (d, J=8.1 Hz, 1H), 7.29 (d, J=8.1 Hz, 1H), 6.96 (t, J=8.2 Hz, 1H), 6.90 (s, 1H), 5.86-5.80 (m, 1H), 5.66-5.60 (m, 1H), 3.28-3.10 (m, 2H), 3.01-2.94 (m, 2H), 2.86-2.74 (m, 7H), 2.62-2.55 (m, 1H), 2.29 (s, 3H), 2.12 (s, 3H), 2.07 (d, J=3.9 Hz, 3H), 1.97-1.82 (m, 1H), 1.80-1.66 (m, 1H), 1.39-1.28 (m, 1H), 0.90-0.82 (m, 6H).

3-74. Preparation of (3S)-3-(2-(5-(2-(2-azaspiro[3.3]heptan-2-yl)ethyl)-2-oxo-4-(trifluoromethyl)pyridin-1(2H)-yl)-4-methylpentanamido)-3-(2,4-difluoro-2',5,6'-trimethyl-[1,1'-biphenyl]-3-yl)propanoic Acid (Compounds ID-P1 and ID-P2)

Step 1: Ethyl (3S)-3-(2-(5-(2-(2-azaspiro[3.3]heptan-2-yl)ethyl)-2-oxo-4-(trifluoromethyl)pyridin-1(2H)-yl)-4-methylpentanamido)-3-(2,4-difluoro-2',5,6'-trimethyl-[1,1'-biphenyl]-3-yl)propanoate

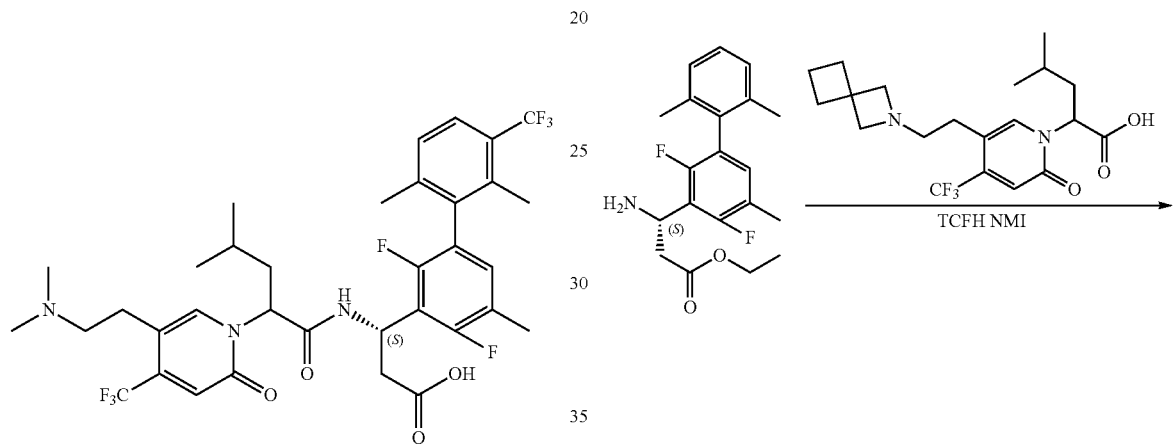

A mixture of ethyl (S)-3-amino-3-(2,4-difluoro-2',5,6'-trimethyl-[1,1'-biphenyl]-3-yl)propanoate (220 mg, 0.63 mmol), 2-(5-(2-(2-azaspiro[3.3]heptan-2-yl)ethyl)-2-oxo-4-(trifluoromethyl)pyridin-1(2H)-yl)-4-methylpentanoic acid (240 mg, 0.6 mmol), TCFH (336 mg, 1.2 mmol) and NMI (246 mg, 3.0 mmol) in CH$_3$CN (4 mL) was stirred at 25° C. for 16 hr. The reaction was concentrated and purified by reverse phase HPLC on a C18/40 g column (A: water 10 mM NH$_4$HCO$_3$, B: MeOH, 0~90%) to provide ethyl (3S)-3-(2-(5-(2-(2-azaspiro[3.3]heptan-2-yl)ethyl)-2-oxo-4-(trifluoromethyl)pyridin-1(2H)-yl)-4-methylpentanamido)-3-(2,4-difluoro-2',5,6'-trimethyl-[1,1'-biphenyl]-3-yl)propanoate as a yellow solid (310 mg). Yield 70.8% (ESI 730.4 [M+H]$^+$).

515

Step 2: (3S)-3-(2-(5-(2-(2-azaspiro[3.3]heptan-2-yl)ethyl)-2-oxo-4-(trifluoromethyl)pyridin-1(2H)-yl)-4-methylpentanamido)-3-(2,4-difluoro-2',5,6'-trimethyl-[1,1'-biphenyl]-3-yl)propanoic Acid

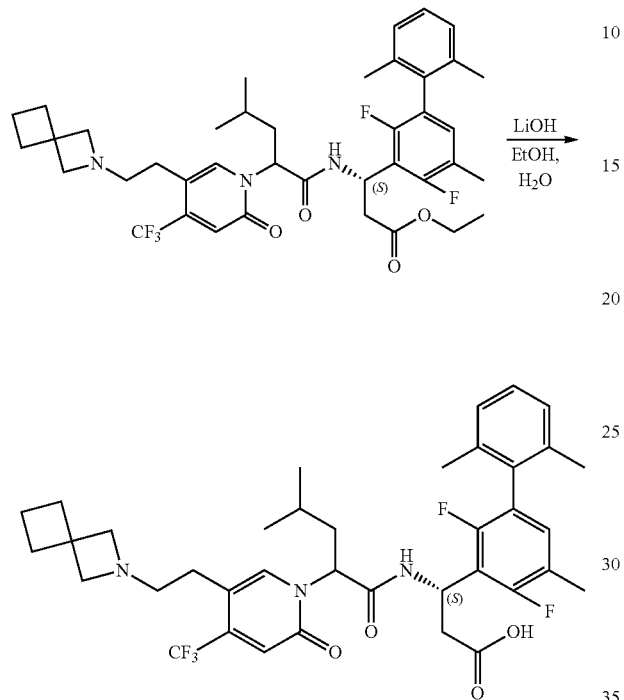

Ethyl (3S)-3-(2-(5-(2-(2-azaspiro[3.3]heptan-2-yl)ethyl)-2-oxo-4-(trifluoromethyl)pyridin-1(2H)-yl)-4-methylpentanamido)-3-(2,4-difluoro-2',5,6'-trimethyl-[1,1'-biphenyl]-3-yl)propanoate (310 mg, 0.42 mmol) was treated with LiOH—H$_2$O (54 mg, 1.28 mmol) in EtOH (4 mL) and H$_2$O (1 mL) at room temperature for 30 min. The reaction mixture was acidified to pH 5~6 with 1N HCl. The reaction was concentrated in vacuo and the residue purified by prep-HPLC A (40-60% CH$_3$CN) to give the diastereomeric products ID-P1 (72 mg) and ID-P2 (96 mg) as white solids.

ID-P1 ESI 702.3 (M+H)$^+$. $^1$H NMR (400 MHz, MeOD) δ 7.81 (s, 1H), 7.18-7.03 (m, 3H), 6.94-6.83 (m, 2H), 5.83-5.75 (m, 1H), 5.69 (t, J=7.9 Hz, 1H), 3.96 (s, 4H), 3.28-3.13 (m, 2H), 3.02-2.91 (m, 1H), 2.85 (s, 2H), 2.64 (d, J=15.1 Hz, 1H), 2.24 (t, J=7.4 Hz, 7H), 2.04-1.89 (m, 8H), 1.88-1.76 (m, 211), 1.43-1.33 (m, 1H), 0.98-0.88 (m, 6H).

ID-P2 ESI 702.3 (M+H)$^+$. $^1$H NMR (400 MHz, MeOD) δ 7.71 (s, 1H), 7.19-7.07 (m, 3H), 6.97-6.88 (m, 2H), 5.95-5.86 (m, 1H), 5.61 (t, J=7.7 Hz, 1H), 4.10 (s, 4H), 3.41-3.31 (m, 2H), 2.95-2.74 (m, 3H), 2.52-2.39 (m, 1H), 2.36-2.17 (m, 7H), 2.01 (d, J=6.7 Hz, 6H), 1.98-1.89 (m, 1H), 1.90-1.79 (m, 2H), 1.75-1.64 (m, 1H), 1.42-1.33 (m, 1H), 0.93-0.83 (m, 6H).

516

3-75. Preparation of (3S)-3-(2-(5-(2-(azetidin-1-yl)ethyl)-2-oxo-4-(trifluoromethyl)pyridin-1(2H)-yl)-4-methylpentanamido)-3-(2,4-difluoro-3'-methoxy-2',6'-dimethyl-5-(trifluoromethyl)-[1,1'-biphenyl]-3-yl)propanoic Acid (Compounds IE-P1 and IE-P2)

Step 1: Ethyl (3S)-3-(2-(5-(2-(azetidin-1-yl)ethyl)-2-oxo-4-(trifluoromethyl)pyridin-1(2H)-yl)-4-methylpentanamido)-3-(2,4-difluoro-3'-methoxy-2',6'-dimethyl-5-(trifluoromethyl)-[1,1'-biphenyl]-3-yl)propanoate

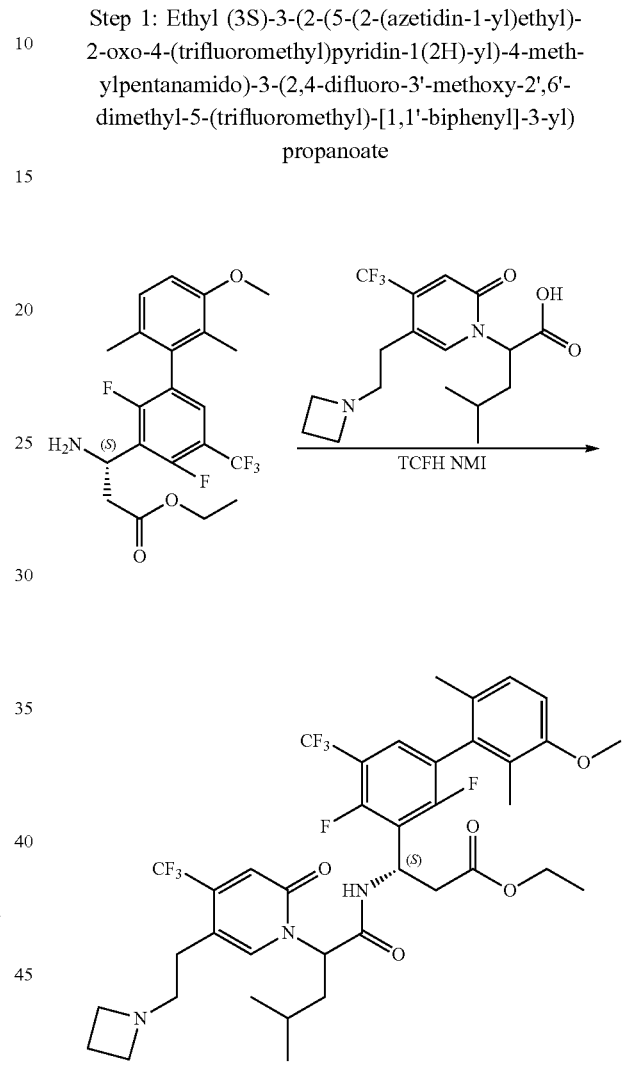

A mixture of ethyl (3S)-3-amino-3-(2,4-difluoro-3'-methoxy-2',6'-dimethyl-5-(trifluoromethyl)-[1,1'-biphenyl]-3-yl)propanoate (150 mg, 0.35 mmol), 2-(5-(2-(azetidin-1-yl)ethyl)-2-oxo-4-(trifluoromethyl)pyridin-1(2H)-yl)-4-methylpentanoic acid (150 mg, 0.41 mmol), TCFH (213 mg, 0.76 mmol) and NMI (156 mg, 1.9 mmol) in CH$_3$CN (3 mL) was stirred at 50° C. for 30 min. The reaction was concentrated and purified by reverse phase HPLC on a C18/40 g column (A: water 10 mM NH$_4$HCO$_3$, B: MeOH, 0~90%) to provide ethyl (3S)-3-(2-(5-(2-(azetidin-1-yl)ethyl)-2-oxo-4-(trifluoromethyl)pyridin-1(2H)-yl)-4-methylpentanamido)-3-(2,4-difluoro-3'-methoxy-2',6'-dimethyl-5-(trifluoromethyl)-[1,1'-biphenyl]-3-yl)propanoate as a yellow solid (180 mg). Yield 66.4% (ESI 774.3 [M+H]$^+$).

Step 2: (3S)-3-(2-(5-(2-(azetidin-1-yl)ethyl)-2-oxo-4-(trifluoromethyl)pyridin-1(2H)-yl)-4-methylpentanamido)-3-(2,4-difluoro-3'-methoxy-2',6'-dimethyl-5-(trifluoromethyl)-[1,1'-biphenyl]-3-yl)propanoic Acid

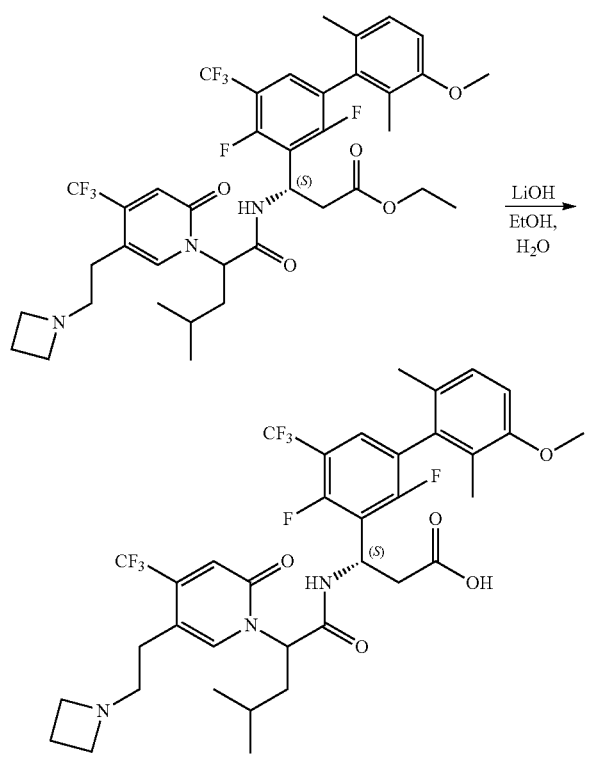

Ethyl (3S)-3-(2-(5-(2-(azetidin-1-yl)ethyl)-2-oxo-4-(trifluoromethyl)pyridin-1(2H)-yl)-4-methylpentanamido)-3-(2,4-difluoro-3'-methoxy-2',6'-dimethyl-5-(trifluoromethyl)-[1,1'-biphenyl]-3-yl)propanoate (180 mg, 0.23 mmol) was treated with LiOH—H₂O (30 mg, 0.7 mmol) in EtOH (2 mL) and H₂O (0.5 mL) at room temperature for 30 min. The reaction mixture was acidified to pH 5~6 with 1N HCl. The reaction was concentrated in vacuo and the residue purified by prep-HPLC A (35-60% CH₃CN) to give the diastereomeric products IE-P1 (46 mg) and IE-P2 (53 mg) as white solids.

IE-P1 ESI 746.3 (M+H)⁺. ¹H NMR (400 MHz, MeOD) δ 7.79 (s, 1H), 7.36 (t, J=7.3 Hz, 1H), 7.09 (d, J=8.2 Hz, 1H), 6.93-6.83 (m, 2H), 5.76-5.65 (m, 2H), 4.04 (t, J=7.9 Hz, 4H), 3.83 (s, 3H), 3.29-3.19 (m, 2H), 2.95-2.88 (m, 1H), 2.84 (t, J=6.7 Hz, 2H), 2.76-2.69 (m, 1H), 2.48-2.39 (m, 2H), 2.04-1.95 (m, 2H), 1.85 (t, J=30.1 Hz, 6H), 1.41-1.32 (m, 1H), 0.93 (t, J=6.5 Hz, 6H).

IE-P2 ESI 746.3 (M+H)⁺. 1H NMR (400 MHz, MeOD) δ 7.74 (s, 1H), 7.42 (t, J=7.6 Hz, 1H), 7.12 (d, J=8.4 Hz, 1H), 6.92 (d, J=6.3 Hz, 2H), 5.96-5.84 (m, 1H), 5.64 (t, J=7.7 Hz, 1H), 4.12 (t, J=8.1 Hz, 4H), 3.84 (s, 3H), 3.43-3.31 (m, 2H), 2.96-2.74 (m, 3H), 2.69-2.57 (m, 1H), 2.53-2.39 (m, 2H), 1.98-1.82 (m, 7H), 1.76-1.65 (m, 1H), 1.39-1.27 (m, 1H), 0.92-0.83 (m, 6H).

3-76. Preparation of (3S)-3-(2,4-difluoro-2',4',6'-trimethyl-5-(trifluoromethyl)-[1,1'-biphenyl]-3-yl)-3-(2-(5-(2-(dimethylamino)ethyl)-2-oxo-4-(trifluoromethyl)pyridin-1(2H)-yl)-4-methylpentanamido)propanoic Acid (Compounds IF-P1 and IF-P2)

Step 1: Ethyl (3S)-3-(2,4-difluoro-2',4',6'-trimethyl-5-(trifluoromethyl)-[1,1'-biphenyl]-3-yl)-3-(2-(5-(2-(dimethylamino)ethyl)-2-oxo-4-(trifluoromethyl)pyridin-1(2H)-yl)-4-methylpentanamido)propanoate

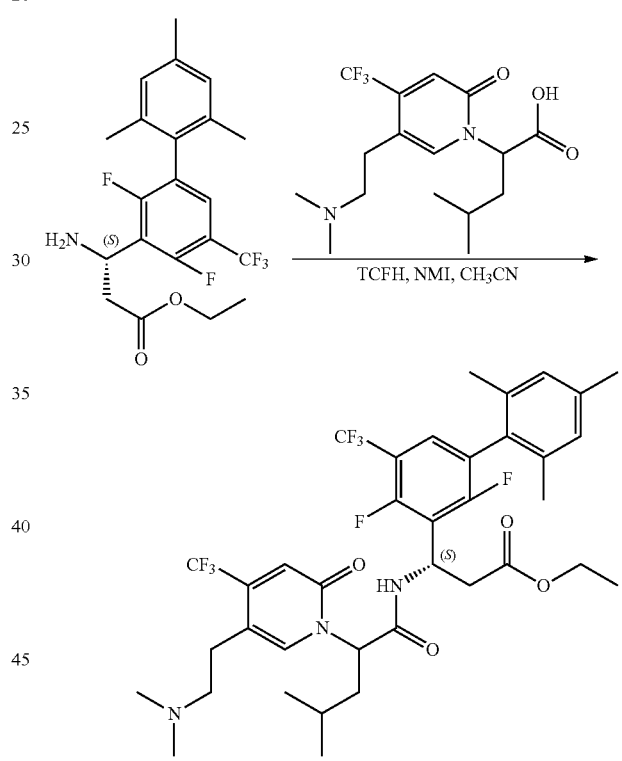

A mixture of ethyl (S)-3-amino-3-(2,4-difluoro-2',4',6'-trimethyl-5-(trifluoromethyl)-[1,1'-biphenyl]-3-yl)propanoate (210 mg, 0.5 mmol), 2-(5-(2-(dimethylamino)ethyl)-2-oxo-4-(trifluoromethyl)pyridin-1(2H)-yl)-4-methylpentanoic acid (200 mg, 0.57 mmol), TCFH (364 mg, 1.3 mmol) and NMI (246 mg, 3.0 mmol) in CH₃CN (4 mL) was stirred at 50° C. for 1 hr. The reaction was concentrated and purified by reverse phase HPLC on a C18/40 g column (A: water 10 mM NH₄HCO₃, B: MeOH, 0~90%) to provide ethyl (3S)-3-(2,4-difluoro-2',4',6'-trimethyl-5-(trifluoromethyl)-[1,1'-biphenyl]-3-yl)-3-(2-(5-(2-(dimethylamino)ethyl)-2-oxo-4-(trifluoromethyl)pyridin-1(2H)-yl)-4-methylpentanamido)propanoate as a yellow solid (330 mg). Yield 88.5% (ESI 746.3 [M+H]⁺).

Step 2: (3S)-3-(2,4-difluoro-2',4',5,6'-tetramethyl-[1,1'-biphenyl]-3-yl)-3-(2-(5-(2-(dimethylamino)ethyl)-2-oxo-4-(trifluoromethyl)pyridin-1(2H)-yl)-4-methylpentanamido)propanoic acid

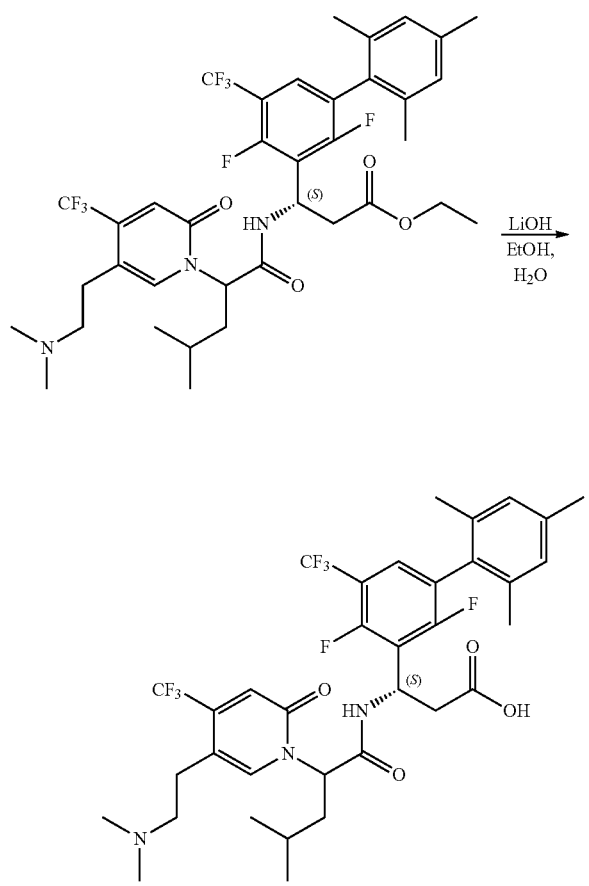

Ethyl (3S)-3-(2,4-difluoro-2',4',6'-trimethyl-5-(trifluoromethyl)-[1,1'-biphenyl]-3-yl)-3-(2-(5-(2-(dimethylamino)ethyl)-2-oxo-4-(trifluoromethyl)pyridin-1(2H)-yl)-4-methylpentanamido)propanoate (330 mg, 0.44 mmol) was treated with LiOH—H$_2$O (56 mg, 1.34 mmol) in MeOH (4 mL) and H$_2$O (1 mL) at room temperature for 30 min. The reaction mixture was acidified to pH 5~6 with 1N HCl. The reaction was concentrated in vacuo and the residue purified by prep-HPLC A (30-58% CH$_3$CN) to give the diastereomeric products IF-P1 (96 mg) and IF-P2 (94 mg) as white solids.

IF-P1 ESI 718.3 (M+H)$^+$. $^1$H NMR (400 MHz, MeOD) δ 7.86 (s, 1H), 7.34 (t, J=7.6 Hz, 1H), 6.94 (d, J=3.7 Hz, 2H), 6.82 (s, 1H), 5.76-5.65 (m, 2H), 3.12-3.04 (m, 2H), 2.99-2.88 (m, 3H), 2.80-2.70 (m, 7H), 2.29 (s, 3H), 2.06-1.92 (m, 5H), 1.86 (s, 3H), 1.44-1.33 (m, 1H), 0.93 (t, J=7.0 Hz, 6H).

IF-P2 ESI 718.3 (M+H)$^+$. 1H NMR (400 MHz, MeOD) δ 7.84 (s, 1H), 7.41 (t, J=7.6 Hz, 1H), 6.97 (s, 2H), 6.89 (s, 1H), 5.85-5.76 (m, 1H), 5.66 (t, J=7.8 Hz, 1H), 3.25-3.09 (m, 2H), 2.96 (t, J=7.2 Hz, 2H), 2.90-2.81 (m, 1H), 2.79 (s, 6H), 2.71-2.62 (m, 1H), 2.31 (s, 3H), 1.98 (d, J=3.1 Hz, 6H), 1.93-1.81 (m, 1H), 1.76-1.67 (m, 1H), 1.36-1.27 (m, 1H), 0.92-0.82 (m, 6H).

3-77. Preparation of (3S)-3-(2-(5-(2-(azetidin-1-yl)ethyl)-2-oxo-4-(trifluoromethyl)pyridin-1(2H)-yl)-4-methylpentanamido)-3-(2,4-difluoro-2',4',6'-trimethyl-5-(trifluoromethyl)biphenyl-3-yl)propanoic Acid (Compounds IG-P1 and IG-P2)

Step 1: (3S)-ethyl 3-(2-(5-(2-(azetidin-1-yl)ethyl)-2-oxo-4-(trifluoromethyl)pyridin-1(2H)-yl)-4-methylpentanamido)-3-(2,4-difluoro-2',4',6'-trimethyl-5-(trifluoromethyl)biphenyl-3-yl)propanoate

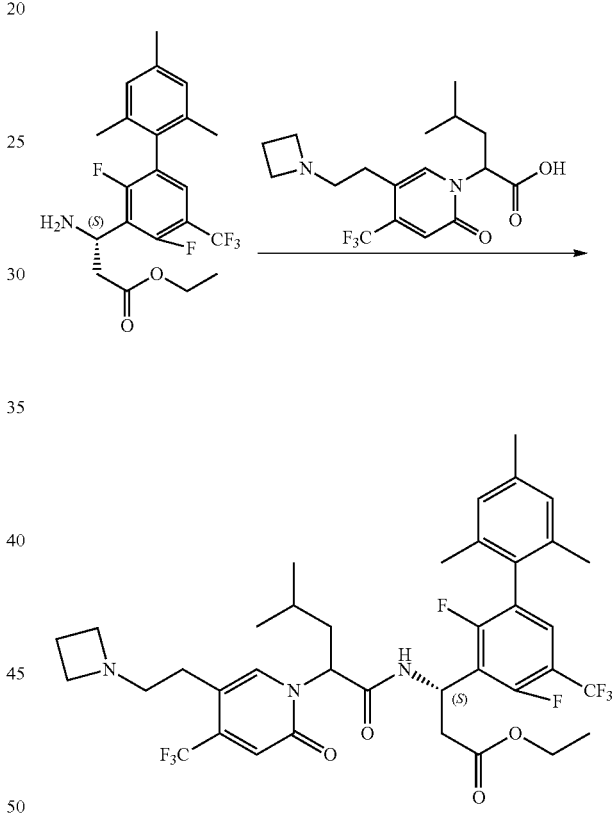

A mixture of 2-(5-(2-(azetidin-1-yl)ethyl)-2-oxo-4-(trifluoromethyl)pyridin-1(2H)-yl)-4-methylpentanoic acid (150 mg, 0.41 mmol), (S)-ethyl 3-amino-3-(2,4-difluoro-2',4',6'-trimethyl-5-(trifluoromethyl)biphenyl-3-yl)propanoate (173 mg, 0.41 mmol), NMI (0.5 mL) and TCFH (364 mg, 1.30 mmol) in CH$_3$CN (5 mL) was stirred at room temperature for 1 hour. The solvent was concentrated in vacuo and the residue was purified by prep-HPLC A (30-90% CH$_3$CN) to provide (3S)-ethyl 3-(2-(5-(2-(azetidin-1-yl)ethyl)-2-oxo-4-(trifluoromethyl)pyridin-1(2H)-yl)-4-methylpentanamido)-3-(2,4-difluoro-2',4',6'-trimethyl-5-(trifluoromethyl)biphenyl-3-yl)propanoate as a white solid (150 mg). Yield 54% (ESI 758.2 [M+H]$^+$).

521

Step 2: (3S)-3-(2-(5-(2-(azetidin-1-yl)ethyl)-2-oxo-4-(trifluoromethyl)pyridin-1(2H)-yl)-4-methylpentanamido)-3-(2,4-difluoro-2',4',6'-trimethyl-5-(trifluoromethyl)biphenyl-3-yl)propanoic acid

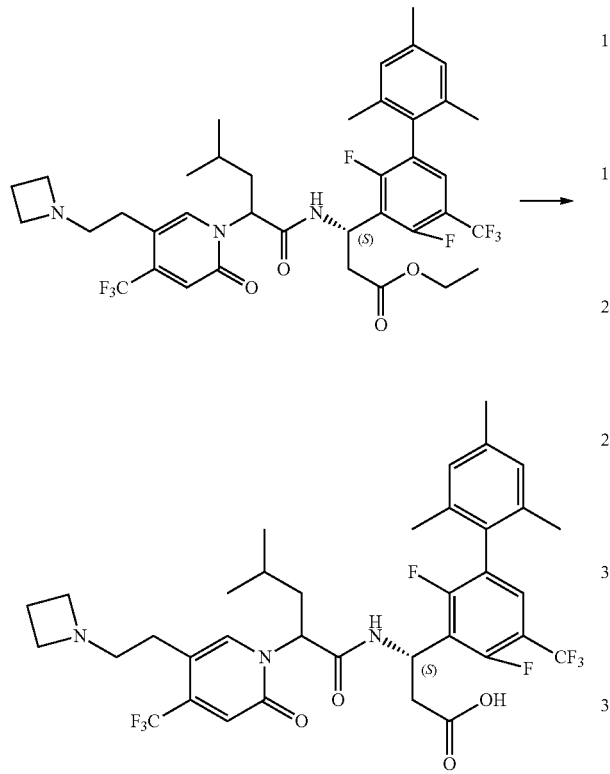

(3S)-ethyl 3-(2-(5-(2-(azetidin-1-yl)ethyl)-2-oxo-4-(trifluoromethyl)pyridin-1(2H)-yl)-4-methylpentanamido)-3-(2,4-difluoro-2',4',6'-trimethyl-5-(trifluoromethyl)biphenyl-3-yl)propanoate (150 mg, 0.19 mmol) was treated with LiOH—H$_2$O (42 mg, 1.00 mmol) in MeOH (4 mL) and H$_2$O (0.4 mL) at room temperature for 2 hours. The reaction mixture was acidified to pH 4~5 with 1N HCL. The reaction was concentrated in vacuo and the residue purified by prep-HPLC A (30-70% CH$_3$CN) to give the diastereomeric products IG-P1 (33.0 mg) and IG-P2 (51.0 mg) as white solids.

IG-P1 ESI 730.2 (M+H)$^+$. $^1$H NMR (400 MHz, MeOD) δ 7.79 (s, 1H), 7.37 (t, J=7.5 Hz, 1H), 6.95 (s, 2H), 6.85 (s, 1H), 5.79-5.65 (m, 2H), 4.03 (t, J=8.1 Hz, 4H), 3.27-3.20 (m, 2H), 3.00-2.69 (m, 4H), 2.50-2.38 (m, 2H), 2.30 (s, 3H), 2.05-1.83 (m, 8H), 1.52-1.28 (m, 1H), 0.93 (t, J=6.4 Hz, 6H).

IG-P2 ESI 730.2 (M+H)$^+$. $^1$H NMR (400 MHz, MeOD) δ 7.73 (s, 1H), 7.43 (t, J=7.6 Hz, 1H), 6.97 (s, 2H), 6.91 (s, 1H), 6.00-5.83 (m, 1H), 5.63 (t, J=7.7 Hz, 1H), 4.11 (t, J=8.0 Hz, 4H), 3.50-3.33 (m, 2H), 2.99-2.75 (m, 3H), 2.69-2.57 (m, 1H), 2.49-2.37 (m, 2H), 2.31 (s, 3H), 2.02-1.84 (m, 7H), 1.77-1.64 (m, 1H), 1.46-1.19 (m, 1H), 1.03-0.80 (m, 6H).

522

3-78. Preparation of (3S)-3-(2-(5-(2-(azetidin-1-yl)ethyl)-2-oxo-4-(trifluoromethyl)pyridin-1(2H)-yl)-4-methylpentanamido)-3-(4'-cyclopropyl-2,3',4-trifluoro-2',6'-dimethyl-5-(trifluoromethyl)-[1,1'-biphenyl]-3-yl)propanoic Acid (Compounds IH-P1 and IH-P2)

Step 1: Ethyl (3S)-3-(2-(5-(2-(azetidin-1-yl)ethyl)-2-oxo-4-(trifluoromethyl)pyridin-1(2H)-yl)-4-methylpentanamido)-3-(4'-cyclopropyl-2,3',4-trifluoro-2',6'-dimethyl-5-(trifluoromethyl)-[1,1'-biphenyl]-3-yl)propanoate

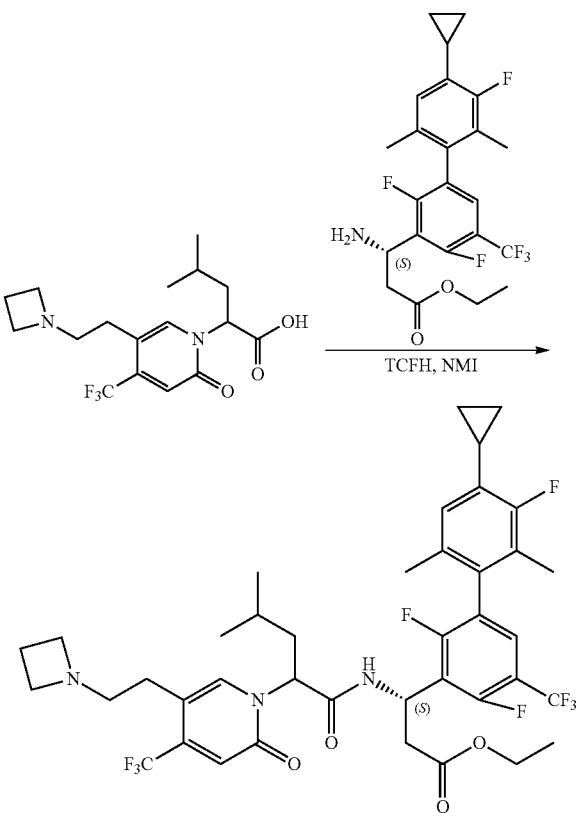

A mixture of ethyl (3S)-3-amino-3-(4'-cyclopropyl-2,3',4-trifluoro-2',6'-dimethyl-5-(trifluoromethyl)-[1,1'-biphenyl]-3-yl)propanoate (80 mg, 0.17 mmol), 2-(5-(2-(azetidin-1-yl)ethyl)-2-oxo-4-(trifluoromethyl)pyridin-1(2H)-yl)-4-methylpentanoic acid (120 mg, 0.33 mmol), TCFH (74 mg, 0.26 mmol), and 1-methylimidazole (57 mg, 0.70 mmol) in acetonitrile (5 mL) was stirred at room temperature for 2 hours. The mixture was purified by reverse phase HPLC on a C18/40 g column (A: water 10 mM NH$_4$HCO$_3$, B: MeOH, 0~100%) to provide ethyl (3S)-3-(2-(5-(2-(azetidin-1-yl)ethyl)-2-oxo-4-(trifluoromethyl)pyridin-1(2H)-yl)-4-methylpentanamido)-3-(4'-cyclopropyl-2,3',4-trifluoro-2',6'-dimethyl-5-(trifluoromethyl)-[1,1'-biphenyl]-3-yl)propanoate (100 mg) as a brown solid. Yield 71.4% (ESI 802.3 (M+H)$^+$).

Step 2: (3S)-3-(2-(5-(2-(azetidin-1-yl)ethyl)-2-oxo-4-(trifluoromethyl)pyridin-1(2H)-yl)-4-methylpentanamido)-3-(4'-cyclopropyl-2,3',4-trifluoro-2',6'-dimethyl-5-(trifluoromethyl)-[1,1'-biphenyl]-3-yl) propanoic Acid

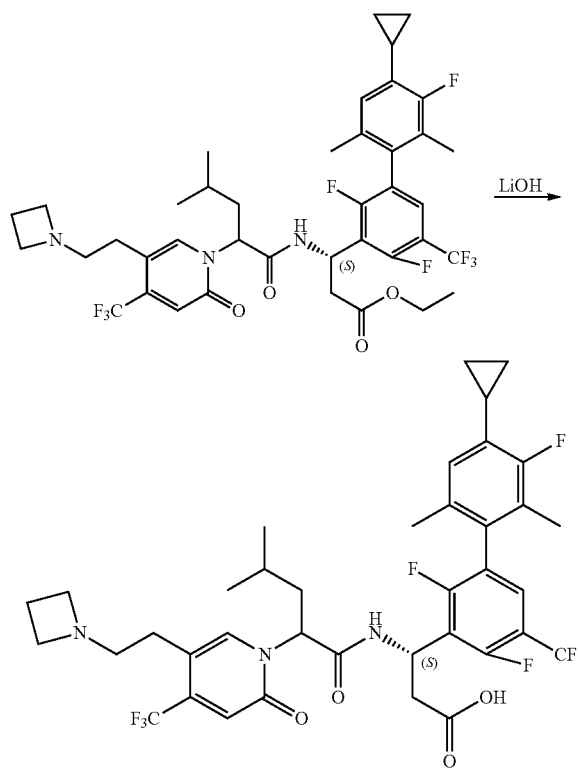

Ethyl (3S)-3-(2-(5-(2-(azetidin-1-yl)ethyl)-2-oxo-4-(trifluoromethyl)pyridin-1(2H)-yl)-4-methylpentanamido)-3-(4'-cyclopropyl-2,3',4-trifluoro-2',6'-dimethyl-5-(trifluoromethyl)-[1,1'-biphenyl]-3-yl)propanoate (100 mg, 0.13 mmol) was treated with LiOH—H$_2$O (27 mg, 0.65 mmol) in MeOH (5 mL) and H$_2$O (1 mL) at room temperature for 2 hours. The reaction mixture was acidified to pH 6~7 with 1N HCl. The reaction was concentrated in vacuo and the residue purified by prep-HPLC A (30-60% CH$_3$CN) to give the diastereomeric products IH-P1 (13.8 mg) and IH-P2 (16.7 mg) as white solids.

IH-P1 ESI 774.2 (M+H)$^+$. $^1$H NMR (400 MHz, MeOD) δ 7.79 (s, 1H), 7.39 (t, J=7.5 Hz, 1H), 6.85 (d, J=4.6 Hz, 1H), 6.71-6.68 (m, 1H), 5.74-5.67 (m, 2H), 4.02 (t, J=7.8 Hz, 4H), 3.30-3.26 (m, 2H), 2.93-2.70 (m, 4H), 2.48-2.38 (m, 2H), 2.12-1.96 (m, 3H), 1.93-1.91 (m, 3H), 1.86-1.82 (m, 3H), 1.41-1.36 (m, 1H), 1.01-0.92 (m, 8H), 0.75-0.69 (m, 2H).

IH-P2 ESI 774.2 (M+H)$^+$. $^1$H NMR (400 MHz, MeOD) δ 7.72 (s, 1H), 7.46 (t, J=7.6 Hz, 1H), 6.92 (s, 1H), 6.72 (d, J=7.2 Hz, 1H), 5.87-5.91 (m, 1H), 5.63 (t, J=7.6 Hz, 1H), 4.12 (t, J=8.0 Hz, 4H), 3.44-3.33 (m, 2H), 2.93-2.77 (m, 3H), 2.63-2.58 (m, 1H), 2.49-2.41 (m, 2H), 2.13-2.06 (m, 1H), 1.95-1.88 (m, 7H), 1.75-1.68 (m, 1H), 1.37-1.29 (m, 1H), 1.02-0.97 (m, 2H), 0.91-0.86 (m, 6H), 0.77-0.74 (m, 2H).

3-79. Preparation of (3S)-3-(2,4-difluoro-2',4',6'-trimethyl-5-(trifluoromethyl)-[1,1'-biphenyl]-3-yl)-3-(4-methyl-2-(5-(2-(3-methylazetidin-1-yl)ethyl)-2-oxo-4-(trifluoromethyl)pyridin-1(2H)-yl) pentanamido)propanoic Acid (Compounds II-P1 and II-P2)

Step 1: Ethyl (3S)-3-(2,4-difluoro-2',4',6'-trimethyl-5-(trifluoromethyl)-[1,1'-biphenyl]-3-yl)-3-(4-methyl-2-(5-(2-(3-methylazetidin-1-yl)ethyl)-2-oxo-4-(trifluoromethyl)pyridin-1(2H)-yl)pentanamido) propanoate

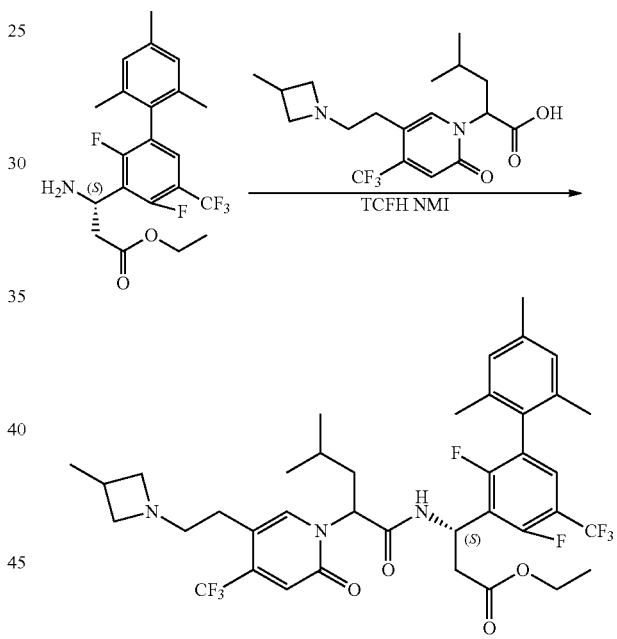

A mixture of ethyl (S)-3-amino-3-(2,4-difluoro-2',4',6'-trimethyl-5-(trifluoromethyl)-[1,1'-biphenyl]-3-yl)propanoate (120 mg, 0.29 mmol), 4-methyl-2-(5-(2-(3-methylazetidin-1-yl)ethyl)-2-oxo-4-(trifluoromethyl)pyridin-1(2H)-yl) pentanoic acid (108 mg, 0.29 mmol), TCFH (120 mg, 0.43 mmol) and NMI (119 mg, 1.45 mmol) in CH$_3$CN (3 mL) was stirred at room temperature overnight. The reaction was concentrated in vacuo and the residue purified by reverse phase HPLC on a C18/40 g column (A: water 10 mM NH$_4$HCO$_3$, B: MeOH, 20~95%) to provide ethyl (3S)-3-(2,4-difluoro-2',4',6'-trimethyl-5-(trifluoromethyl)-[1,1'-biphenyl]-3-yl)-3-(4-methyl-2-(5-(2-(3-methylazetidin-1-yl)ethyl)-2-oxo-4-(trifluoromethyl)pyridin-1(2H)-yl) pentanamido)propanoate as a light yellow solid (150 mg). Yield 67% (ESI 772.2 [M+H]$^+$).

525

Step 2: (3S)-3-(2,4-difluoro-2',4',6'-trimethyl-5-(trifluoromethyl)-[1,1'-biphenyl]-3-yl)-3-(4-methyl-2-(5-(2-(3-methylazetidin-1-yl)ethyl)-2-oxo-4-(trifluoromethyl)pyridin-1(2H)-yl)pentanamido)propanoic acid

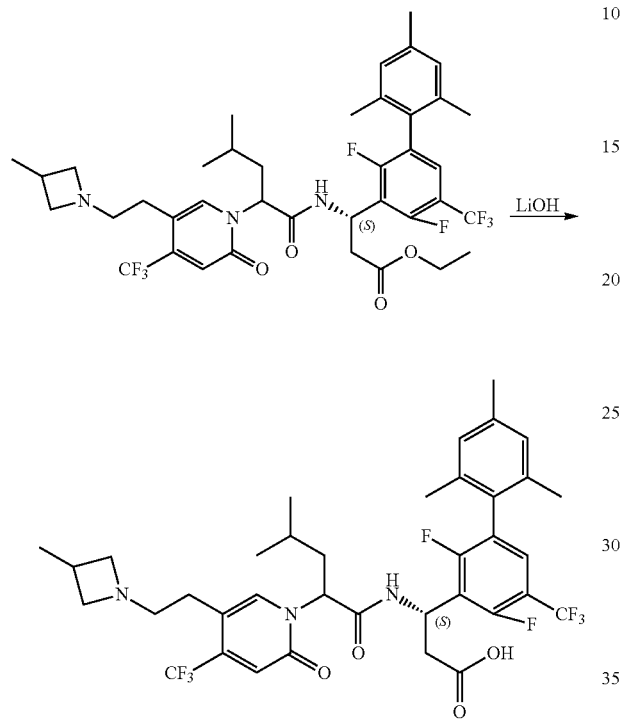

Ethyl (3S)-3-(2,4-difluoro-2',4',6'-trimethyl-5-(trifluoromethyl)-[1,1'-biphenyl]-3-yl)-3-(4-methyl-2-(5-(2-(3-methylazetidin-1-yl)ethyl)-2-oxo-4-(trifluoromethyl)pyridin-1(2H)-yl)pentanamido)propanoate (150 mg, 0.19 mmol) was treated with LiOH—H₂O (24 mg, 0.57 mmol) in EtOH (2 mL) and water (0.5 mL) at room temperature for 1 hour. The reaction mixture was acidified to pH 4~5 with 2N HCl. The reaction was concentrated in vacuo and the residue purified by prep-HPLC A (20-85% MeCN) to give the diastereomeric products II-P1 (33 mg) and II-P2 (49 mg) as white solids.

II-P1 ESI 744.3 (M+H)⁺ ¹H NMR (400 MHz, MeOD) δ 7.79 (s, 1H), 7.37 (t, J=7.5 Hz, 1H), 6.95 (s, 2H), 6.84 (s, 1H), 5.77-5.61 (m, 2H), 4.12 (t, J=9.2 Hz, 2H), 3.67 (t, J=8.8 Hz, 2H), 3.28-3.20 (m, 2H), 3.00-2.78 (m, 4H), 2.76-2.67 (m, 1H), 2.30 (s, 3H), 2.05-1.95 (m, 5H), 1.89 (s, 3H), 1.45-1.30 (m, 1H), 1.24 (d, J=6.9 Hz, 3H), 0.96-0.84 (m, 6H).

II-P2 ESI 744.3 (M+H)⁺ ¹H NMR (400 MHz, MeOD) δ 7.73 (s, 1H), 7.42 (t, J=7.6 Hz, 1H), 6.98 (s, 2H), 6.91 (s, 1H), 5.89-5.82 (m, 1H), 5.63 (t, J=7.7 Hz, 1H), 4.20 (d, J=9.9 Hz, 2H), 3.75 (s, 2H), 3.45-3.34 (m, 2H), 3.02-2.85 (m, 4H), 2.65-2.53 (m, 1H), 2.31 (s, 3H), 2.03-1.84 (m, 7H), 1.75-1.65 (m, 1H), 1.42-1.18 (m, 4H), 0.95-0.85 (m, 6H).

526

3-80. Preparation of (3S)-3-(2,4-difluoro-2',4',5,6'-tetramethyl-[1,1'-biphenyl]-3-yl)-3-(2-(5-(3-(dimethylamino)propyl)-2-oxo-4-(trifluoromethyl)pyridin-1(2H)-yl)-4-methylpentanamido)propanoic Acid (Compounds IJ-P1 and IJ-P2)

Step 1: Ethyl (3S)-3-(2,4-difluoro-2',4',5,6'-tetramethyl-[1,1'-biphenyl]-3-yl)-3-(2-(5-(3-(dimethylamino)propyl)-2-oxo-4-(trifluoromethyl)pyridin-1(2H)-yl)-4-methylpentanamido)propanoate

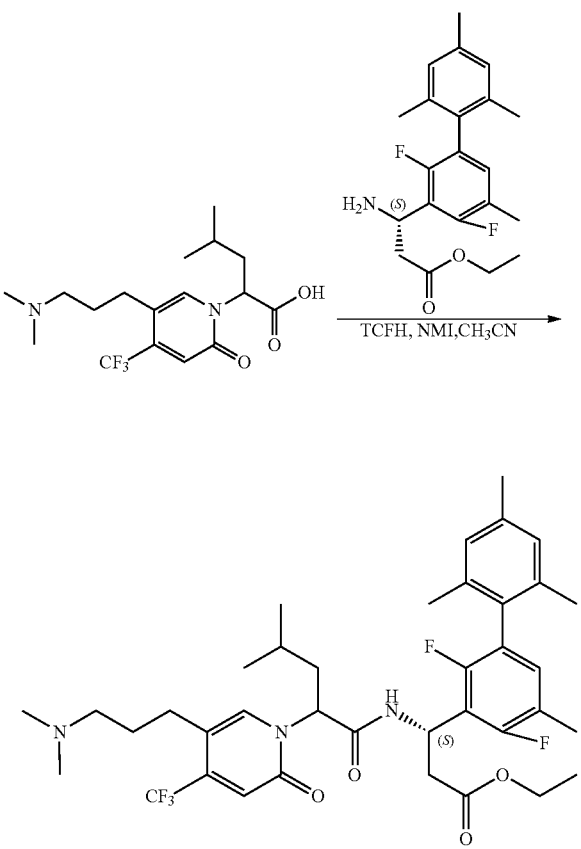

A mixture of ethyl (S)-3-amino-3-(2,4-difluoro-2',4',5,6'-tetramethyl-[1,1'-biphenyl]-3-yl)propanoate (120.0 mg, 0.33 mmol), 2-(5-(3-(dimethylamino)propyl)-2-oxo-4-(trifluoromethyl)pyridin-1(2H)-yl)-4-methylpentanoic acid (119.6 mg, 0.33 mmol), TCFH (138.9 mg, 0.50 mmol) and NMI (81.3 mg, 0.99 mmol) in CH₃CN (3 mL) was stirred at 50° C. for 0.5 hour. The reaction was concentrated in vacuo and the residue purified by reverse phase HPLC on a C18/40 g column (A: water 10 mM NH₄HCO₃, B: MeOH, 0~100%) to provide ethyl (3S)-3-(2,4-difluoro-2',4',5,6'-tetramethyl-[1,1'-biphenyl]-3-yl)-3-(2-(5-(3-(dimethylamino)propyl)-2-oxo-4-(trifluoromethyl)pyridin-1(2H)-yl)-4-methylpentanamido)propanoate as a light yellow solid (160.0 mg). Yield 68% (ESI 706.2 [M+H]⁺).

Step 2: (3S)-3-(2,4-difluoro-2',4',5,6'-tetramethyl-[1,1'-biphenyl]-3-yl)-3-(2-(5-(3-(dimethylamino)propyl)-2-oxo-4-(trifluoromethyl)pyridin-1(2H)-yl)-4-methylpentanamido)propanoic Acid 3-81. Preparation of (3S)-3-(2,4-difluoro-2',3',6'-trimethyl-5-(trifluoromethyl)-[1,1'-biphenyl]-3-yl)-3-(2-(5-(2-(ethyl(methyl)amino)ethyl)-2-oxo-4-(trifluoromethyl)pyridin-1(2H)-yl)-4-methylpentanamido)propanoic Acid (Compounds IK-P1 and IK-P2)

Step 1: Ethyl (3S)-3-(2,4-difluoro-2',3',6'-trimethyl-5-(trifluoromethyl)-[1,1'-biphenyl]-3-yl)-3-(2-(5-(2-(ethyl(methyl)amino)ethyl)-2-oxo-4-(trifluoromethyl)pyridin-1(2H)-yl)-4-methylpentanamido)propanoate

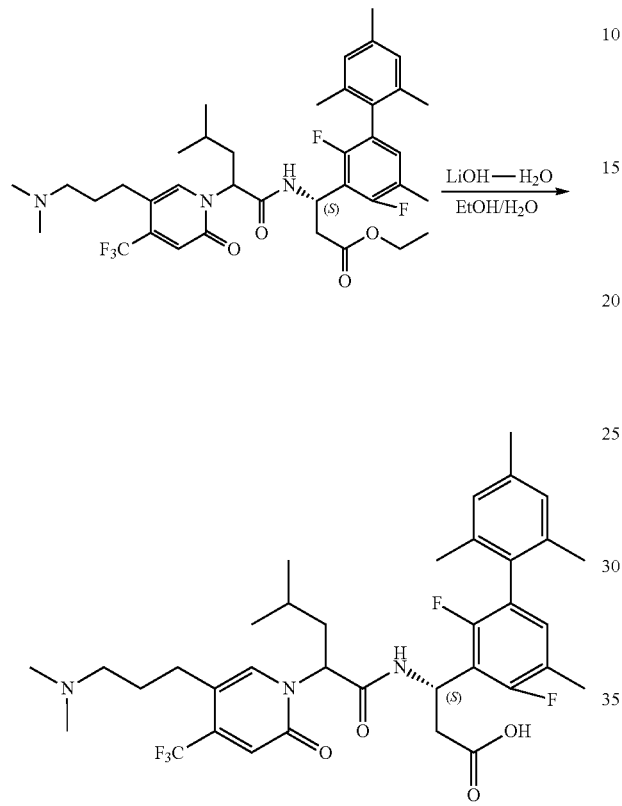

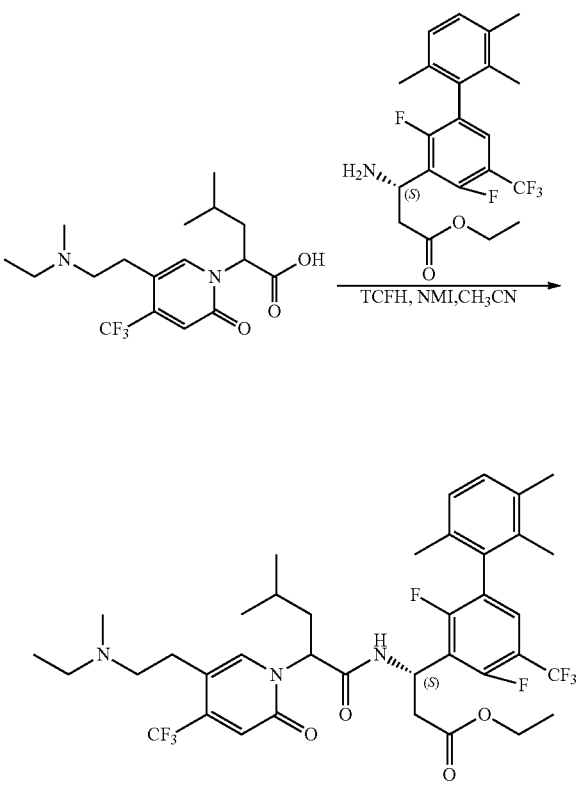

Ethyl (3S)-3-(2,4-difluoro-2',4',5,6'-tetramethyl-[1,1'-biphenyl]-3-yl)-3-(2-(5-(3-(dimethylamino)propyl)-2-oxo-4-(trifluoromethyl)pyridin-1(2H)-yl)-4-methylpentanamido)propanoate (160.0 mg, 0.23 mmol) was treated with LiOH—H$_2$O (29.0 mg, 0.69 mmol) in EtOH (2 mL) and water (0.5 mL) at room temperature for 30 mins. The reaction mixture was acidified to pH 4~5 with 2N HCl. The reaction was concentrated in vacuo and the residue purified by prep-HPLC A (30-80% MeCN) to give the diastereomeric products IJ-P1 (52.0 mg) and IJ-P2 (44.0 mg) as white solids.

IJ-P1 ESI 678.3 (M+H)$^+$ $^1$H NMR (400 MHz, MeOD) δ 7.77 (s, 1H), 6.94-6.75 (m, 4H), 5.78-5.72 (m, 2H), 3.09-3.02 (m, 2H), 2.98-2.90 (m, 1H), 2.78 (s, 6H), 2.73-2.59 (m, 3H), 2.28 (s, 3H), 2.23 (s, 3H), 2.11-1.96 (m, 3H), 1.97-1.81 (m, 7H), 1.41-1.26 (m, 1H), 0.95-0.91 (m, 6H).

IJ-P2 ESI 678.3 (M+H)$^+$ $^1$H NMR (400 MHz, MeOD) δ 7.79 (s, 1H), 6.98-6.80 (m, 4H), 5.88-5.82 (m, 1H), 5.57 (t, J=7.5 Hz, 1H), 3.08-2.92 (m, 2H), 2.91-2.73 (m, 7H), 2.72-2.45 (m, 3H), 2.28 (d, J=10.7 Hz, 6H), 2.03-1.88 (m, 9H), 1.66-1.58 (m, 1H), 1.39-1.27 (m, 1H), 0.90-0.83 (m, 6H).

A mixture of 2-(5-(2-(ethyl(methyl)amino)ethyl)-2-oxo-4-(trifluoromethyl)pyridin-1(2H)-yl)-4-methylpentanoic acid (100.0 mg, 0.28 mmol), ethyl (3S)-3-amino-3-(2,4-difluoro-2',3',6'-trimethyl-5-(trifluoromethyl)-[1,1'-biphenyl]-3-yl)propanoate (116.2 mg, 0.28 mmol), TCFH (156.8 mg, 0.56 mmol) and NMI (91.8 mg, 1.12 mmol) in CH$_3$CN (10 mL) was stirred at room temperature for 1 hour. The reaction was concentrated in vacuo and the residue purified by silica gel column (DCM:MeOH 4:1) to provide ethyl (3S)-3-(2,4-difluoro-2',3',6'-trimethyl-5-(trifluoromethyl)-[1,1'-biphenyl]-3-yl)-3-(2-(5-(2-(ethyl(methyl)amino)ethyl)-2-oxo-4-(trifluoromethyl)pyridin-1(2H)-yl)-4-methylpentanamido)propanoate as a brown solid (110.0 mg). Yield 52% (ESI 760.7 (M+H)$^+$).

Step 2: (3S)-3-(2,4-difluoro-2',3',6'-trimethyl-5-(trifluoromethyl)-[1,1'-biphenyl]-3-yl)-3-(2-(5-(2-(ethyl(methyl)amino)ethyl)-2-oxo-4-(trifluoromethyl)pyridin-1(2H)-yl)-4-methylpentanamido)propanoic Acid

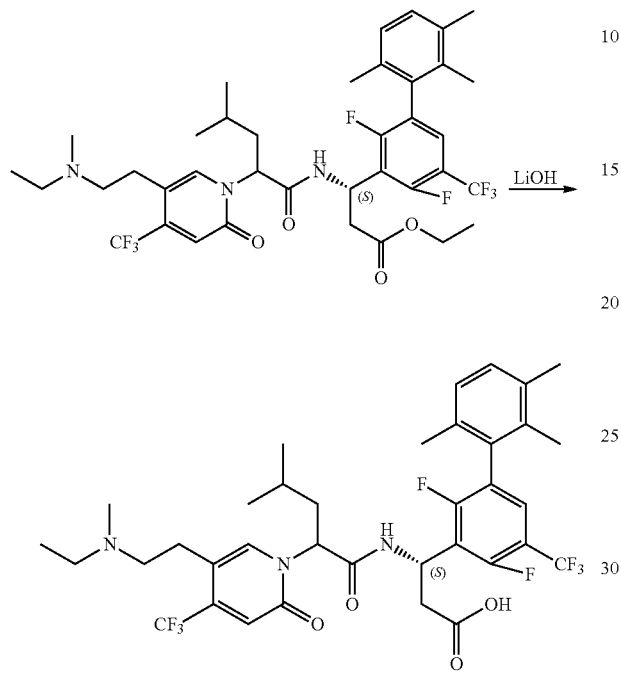

Ethyl (3S)-3-(2,4-difluoro-2',3',6'-trimethyl-5-(trifluoromethyl)-[1,1'-biphenyl]-3-yl)-3-(2-(5-(2-(ethyl(methyl)amino)ethyl)-2-oxo-4-(trifluoromethyl)pyridin-1(2H)-yl)-4-methylpentanamido)propanoate (110 mg, 0.14 mmol) was treated with LiOH—H$_2$O (23.5 mg, 0.56 mmol) in MeOH (4 mL) and H$_2$O (1 mL) at room temperature for 2 hours. The reaction mixture was acidified to pH 4~5 with 1N HCL. The reaction was concentrated in vacuo and the residue purified by prep-HPLC A (30-60% MeCN) to give the diastereomeric products IK-P1 (34.1 mg) and IK-P2 (29.4 mg) as white solids.

IK-P1 ESI 732.7 (M+H)$^+$. 1H NMR (400 MHz, MeOD) δ 7.88 (s, 1H), 7.32 (t, J=7.6 Hz, 1H), 7.10 (d, J=7.7 Hz, 1H), 7.04-6.96 (m, 1H), 6.82 (d, J=4.5 Hz, 1H), 5.78-5.66 (m, 2H), 3.19-3.05 (m, 4H), 3.00-2.85 (m, 3H), 2.80-2.70 (m, 4H), 2.26 (d, J=2.0 Hz, 3H), 2.03-1.87 (m, 5H), 1.81 (d, J=15.0 Hz, 3H), 1.43-1.32 (m, 1H), 1.26 (d, J=7.3 Hz, 3H), 0.93 (d, J=6.9 Hz, 6H).

IK-P2 ESI 732.7 (M+H)$^+$. 1H NMR (400 MHz, MeOD) δ 7.87 (s, 1H), 7.39 (t, J=7.6 Hz, 1H), 7.12 (d, J=7.8 Hz, 1H), 7.03 (d, J=7.9 Hz, 1H), 6.88 (s, 1H), 5.85-5.75 (m, 1H), 5.71-5.61 (m, 1H), 3.27-3.09 (m, 4H), 3.00-2.84 (m, 3H), 2.79 (s, 3H), 2.72-2.62 (m, 1H), 2.28 (d, J=2.1 Hz, 3H), 1.98-1.79 (m, 7H), 1.82-1.68 (m, 1H), 1.41-1.22 (m, 4H), 0.92-0.78 (m, 6H).

3-82. Preparation of (3S)-3-(2,4-difluoro-3'-methoxy-2',6'-dimethyl-5-(trifluoromethyl)biphenyl-3-yl)-3-(2-(5-(2-(dimethylamino)ethyl)-2-oxo-4-(trifluoromethyl)pyridin-1(2H)-yl)-4-methylpentanamido)propanoic Acid (Compounds IL-P1 and IL-P2)

Step 1: (3S)-ethyl 3-(2,4-difluoro-3'-methoxy-2',6'-dimethyl-5-(trifluoromethyl)biphenyl-3-yl)-3-(2-(5-(2-(dimethylamino)ethyl)-2-oxo-4-(trifluoromethyl)pyridin-1(2H)-yl)-4-methylpentanamido)propanoate

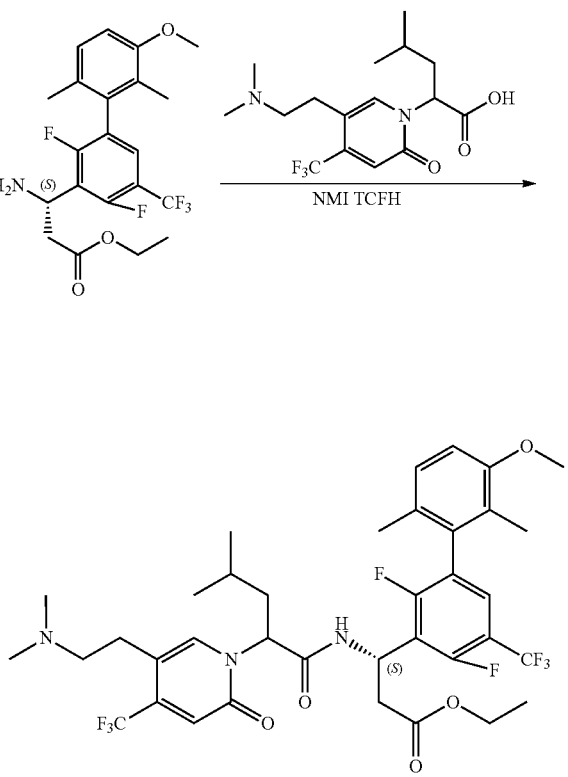

A mixture of 2-(5-(2-(dimethylamino)ethyl)-2-oxo-4-(trifluoromethyl)pyridin-1(2H)-yl)-4-methylpentanoic acid (122 mg, 0.35 mmol), (3S)-ethyl 3-amino-3-(2,4-difluoro-3'-methoxy-2',6'-dimethyl-5-(trifluoromethyl)biphenyl-3-yl)propanoate (150 mg, 0.35 mmol), NMI (86 mg, 1.05 mmol) and TCFH (147 mg, 0.53 mmol) in CH$_3$CN (4 mL) was stirred at room temperature for 2 hours. The solvent was concentrated in vacuo and the residue was purified by reverse phase HPLC on a C18/40 g column (A: water 10 mM NH$_4$HCO$_3$, B: CH$_3$CN, 0~100%) to provide (3S)-ethyl 3-(2,4-difluoro-3'-methoxy-2',6'-dimethyl-5-(trifluoromethyl)biphenyl-3-yl)-3-(2-(5-(2-(dimethylamino)ethyl)-2-oxo-4-(trifluoromethyl)pyridin-1(2H)-yl)-4-methylpentanamido)propanoate as a yellow oil (180 mg). Yield 68% (ESI 762.3 [M+H]$^+$).

531

Step 2: (3S)-3-(2,4-difluoro-3'-methoxy-2',6'-dimethyl-5-(trifluoromethyl)biphenyl-3-yl)-3-(2-(5-(2-(dimethylamino)ethyl)-2-oxo-4-(trifluoromethyl)pyridin-1(2H)-yl)-4-methylpentanamido)propanoic acid

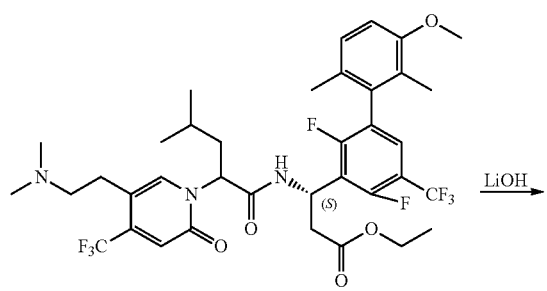

(3S)-ethyl 3-(2,4-difluoro-3'-methoxy-2',6'-dimethyl-5-(trifluoromethyl)biphenyl-3-yl)-3-(2-(5-(2-(dimethylamino)ethyl)-2-oxo-4-(trifluoromethyl)pyridin-1(2H)-yl)-4-methylpentanamido)propanoate (180 mg, 0.24 mmol) was treated with LiOH—H$_2$O (40 mg, 0.96 mmol) in EtOH (3 mL) and H$_2$O (1 mL) at room temperature for 1 hour. The reaction mixture was acidified to pH 5~6 with 1N HCl. The reaction was concentrated in vacuo and the residue purified by prep-HPLC A (30-60% CH$_3$CN) to give the diastereomeric products IL-P1 (47 mg) and IL-P2 (57 mg) as white solids.

IL-P1 ESI 734.2 (M+H)$^+$. $^1$H NMR (400 MHz, MeOD) δ 7.86 (s, 1H), 7.34 (t, J=7.6 Hz, 1H), 7.12-7.05 (m, 1H), 6.92-6.81 (m, 2H), 5.78-5.63 (m, 2H), 3.82 (s, 3H), 3.19-3.04 (m, 2H), 3.02-2.87 (m, 3H), 2.83-2.69 (m, 7H), 2.09-1.93 (m, 2H), 1.93-1.73 (m, 6H), 1.45-1.33 (m, 1H), 0.93 (t, J=7.1 Hz, 6H).

IL-P2 ESI 734.2 (M+H)$^+$. $^1$H NMR (400 MHz, MeOD) δ 7.83 (s, 1H), 7.40 (t, J=7.7 Hz, 1H), 7.11 (d, J=8.2 Hz, 1H), 7.00-6.84 (m, 2H), 5.86-5.77 (m, 1H), 5.66 (t, J=7.7 Hz, 1H), 3.84 (s, 3H), 3.26-3.06 (m, 2H), 3.01-2.71 (m, 9H), 2.78-2.50 (m, 1H), 2.02-1.80 (m, 7H), 1.80-1.55 (m, 1H), 1.53-1.22 (m, 1H), 0.97-0.77 (m, 6H).

532

3-83. Preparation of (3S)-3-(2,4-difluoro-2',3',6'-trimethyl-5-(trifluoromethyl)biphenyl-3-yl)-3-(2-(5-(2-(dimethylamino)ethyl)-2-oxo-4-(trifluoromethyl)pyridin-1(2H)-yl)-4-methylpentanamido)propanoic Acid (Compounds IM-P1 and IM-P2)

Step 1: (3S)-ethyl 3-(2,4-difluoro-2',3',6'-trimethyl-5-(trifluoromethyl)biphenyl-3-yl)-3-(2-(5-(2-(dimethylamino)ethyl)-2-oxo-4-(trifluoromethyl)pyridin-1(2H)-yl)-4-methylpentanamido)propanoate

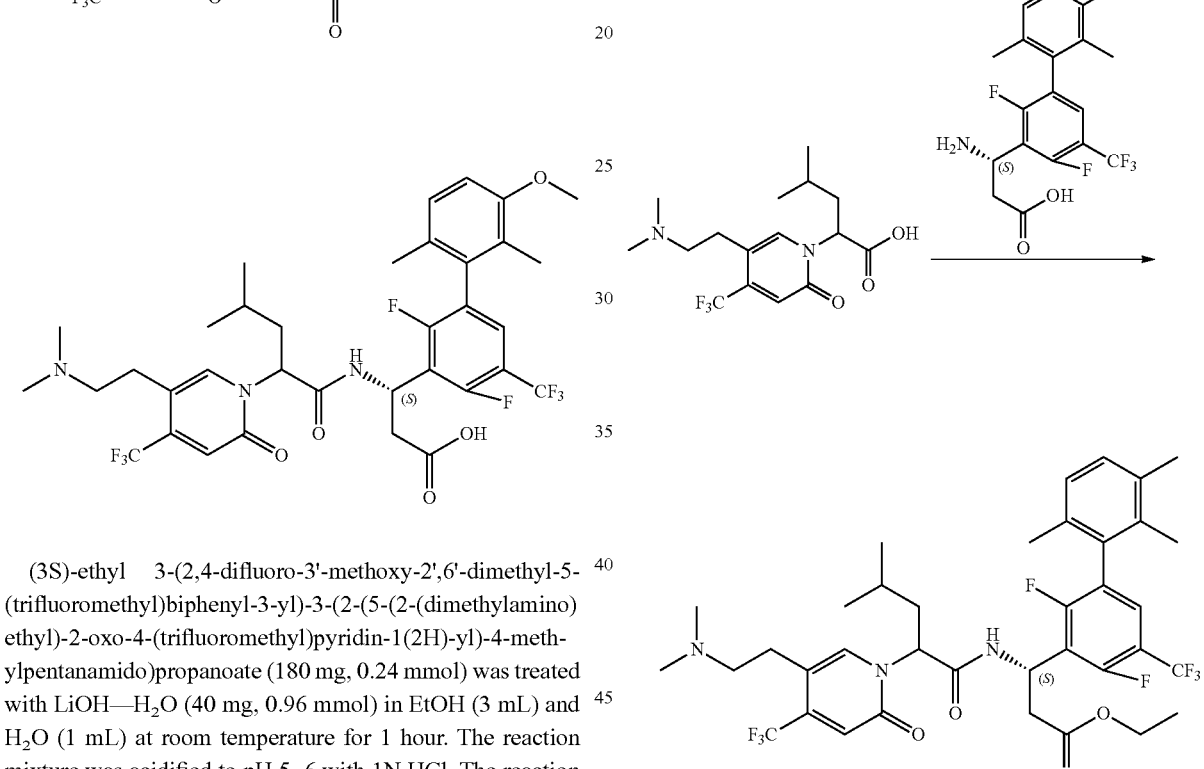

A mixture of 2-(5-(2-(dimethylamino)ethyl)-2-oxo-4-(trifluoromethyl)pyridin-1(2H)-yl)-4-methylpentanoic acid (100 mg, 0.29 mmol), (3S)-ethyl 3-amino-3-(2,4-difluoro-2',3',6'-trimethyl-5-(trifluoromethyl)biphenyl-3-yl)propanoate (120 mg, 0.29 mmol), NMI (0.5 mL) and TCFH (378 mg, 1.35 mmol) in CH$_3$CN (5 mL) was stirred at room temperature for 1 hour. The reaction was concentrated in vacuo and the residue purified by prep-HPLC A (30-90% CH$_3$CN) to provide (3S)-ethyl 3-(2,4-difluoro-2',3',6'-trimethyl-5-(trifluoromethyl)biphenyl-3-yl)-3-(2-(5-(2-(dimethylamino)ethyl)-2-oxo-4-(trifluoromethyl)pyridin-1(2H)-yl)-4-methylpentanamido)propanoate as a white solid (130 mg). Yield 60% (ESI 746.3 [M+H]$^+$).

Step 2: (3S)-3-(2,4-difluoro-2',3',6'-trimethyl-5-(trifluoromethyl)biphenyl-3-yl)-3-(2-(5-(2-(dimethylamino)ethyl)-2-oxo-4-(trifluoromethyl)pyridin-1(2H)-yl)-4-methylpentanamido)propanoic acid

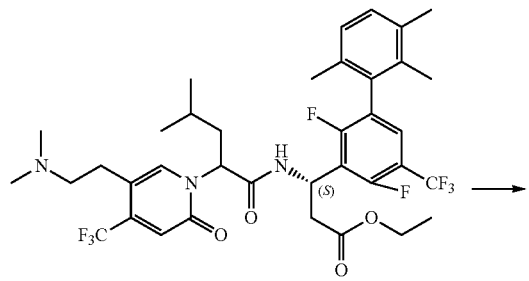

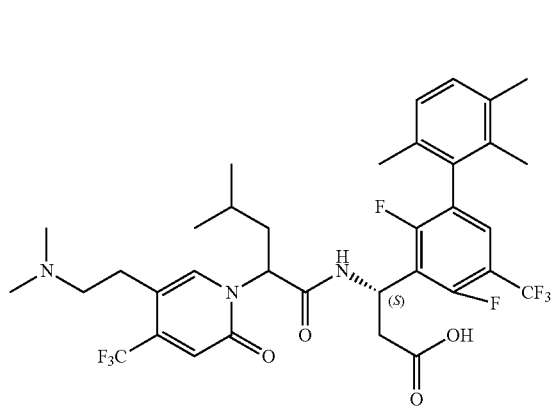

(3S)-ethyl 3-(2,4-difluoro-2',3',6'-trimethyl-5-(trifluoromethyl)biphenyl-3-yl)-3-(2-(5-(2-(dimethylamino)ethyl)-2-oxo-4-(trifluoromethyl)pyridin-1(2H)-yl)-4-methylpentanamido)propanoate (130 mg, 0.17 mmol) was treated with LiOH—H$_2$O (42 mg, 1.00 mmol) in MeOH (4 mL) and H$_2$O (0.5 mL) at room temperature for 2 hours. The reaction mixture was acidified to pH 4~5 with 1N HCl. The reaction was concentrated in vacuo and the residue purified by prep-HPLC A (30-70% CH$_3$CN) to give the diastereomeric products IM-P1 (35.0 mg) and IM-P2 (30.0 mg) as white solids.

IM-P1 ESI 718.2 (M+H)$^+$. $^1$H NMR (400 MHz, MeOD) δ 7.86 (s, 1H), 7.33 (s, 1H), 7.10 (d, J=7.6 Hz, 1H), 7.05-6.95 (m, 1H), 6.83 (d, J=4.1 Hz, 1H), 5.76-5.62 (m, 2H), 3.17-3.02 (m, 2H), 2.98-2.86 (m, 3H), 2.75 (d, J=14.0 Hz, 7H), 2.27 (d, J=2.8 Hz, 3H), 2.04-1.88 (m, 5H), 1.82 (d, J=15.0 Hz, 3H), 1.43-1.23 (m, 1H), 1.00-0.86 (m, 6H).

IM-P2 ESI 718.2 (M+H)$^+$. $^1$H NMR (400 MHz, MeOD) δ 7.83 (s, 1H), 7.40 (t, J=7.7 Hz, 1H), 7.12 (d, J=7.8 Hz, 1H), 7.04 (d, J=7.8 Hz, 1H), 6.90 (s, 1H), 5.89-5.76 (m, 1H), 5.65 (t, J=7.8 Hz, 1H), 3.26-3.11 (m, 2H), 2.97 (t, J=7.0 Hz, 2H), 2.90-2.75 (m, 7H), 2.73-2.60 (m, 1H), 2.29 (s, 3H), 2.00-1.84 (m, 7H), 1.80-1.66 (m, 1H), 1.39-1.23 (m, 1H), 0.95-0.82 (m, 6H).

3-84. Preparation of (3S)-3-(2,4-difluoro-2',6'-dimethyl-5-(trifluoromethyl)-[1,1'-biphenyl]-3-yl)-3-(2-(5-(3-(dimethylamino)propyl)-2-oxo-4-(trifluoromethyl)pyridin-1(2H)-yl)-4-methylpentanamido) propanoic Acid (IN-P1 and IN-P2)

Step 1: Ethyl (3S)-3-(2,4-difluoro-2',6'-dimethyl-5-(trifluoromethyl)-[1,1'-biphenyl]-3-y)-3-(2-(5-(3-(dimethylamino)propyl)-2-oxo-4-(trifluoromethyl)pyridin-1(2H)-yl)-4-methylpentanamido)propanoate

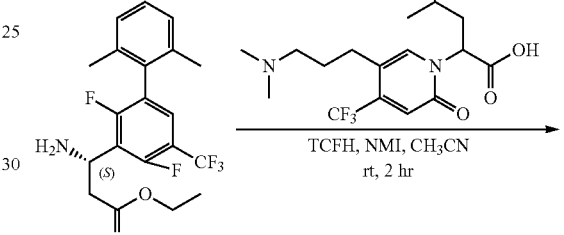

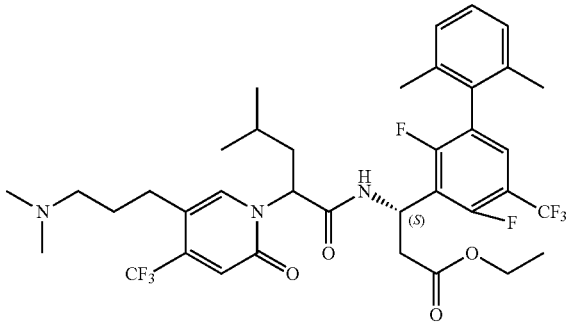

A mixture of ethyl (S)-3-amino-3-(2,4-difluoro-2',6'-dimethyl-5-(trifluoromethyl)-[1,1'-biphenyl]-3-yl)propanoate (136 mg, 0.34 mmol), 2-(5-(3-(dimethylamino)propyl)-2-oxo-4-(trifluoromethyl)pyridin-1(2H)-yl)-4-methylpentanoic acid (120 mg, 0.30 mmol), TCFH (168 mg, 0.60 mmol) and NMI (123 mg, 1.5 mmol) in CH$_3$CN (2 mL) was stirred at room temperature for 2 hours. The reaction was concentrated and purified by reverse phase HPLC on a C18/40 g column (A: water 10 mM NH$_4$HCO$_3$, B: CH$_3$OH, 0~85%) to provide ethyl (3S)-3-(2,4-difluoro-2',6'-dimethyl-5-(trifluoromethyl)-[1,1'-biphenyl]-3-yl)-3-(2-(5-(3-(dimethylamino)propyl)-2-oxo-4-(trifluoromethyl)pyridin-1

(2H)-yl)-4-methylpentanamido)propanoate as a yellow oil (120 mg). Yield 43.3% (ESI 746.3 [M+H]+).

Step 2: (3S)-3-(2,4-difluoro-2',6'-dimethyl-5-(trifluoromethyl)-[1,1'-biphenyl]-3-yl)-3-(2-(5-(3-(dimethylamino)propyl)-2-oxo-4-(trifluoromethyl)pyridin-1(2H)-yl)-4-methylpentanamido)propanoic Acid

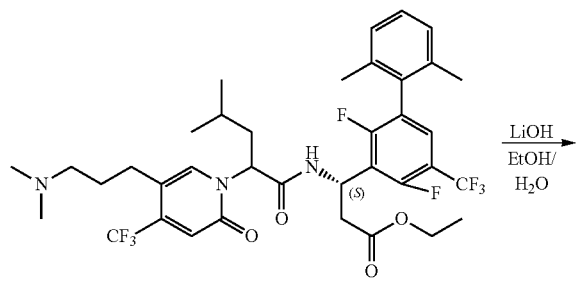

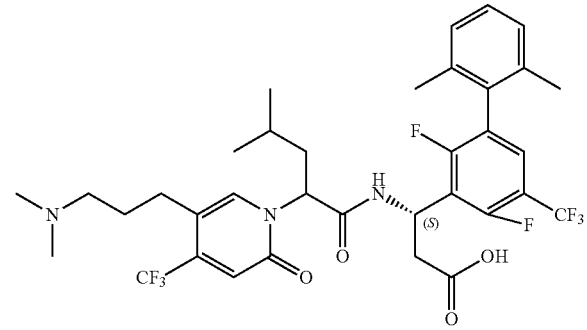

Ethyl (3S)-3-(2,4-difluoro-2',6'-dimethyl-5-(trifluoromethyl)-[1,1'-biphenyl]-3-yl)-3-(2-(5-(3-(dimethylamino)propyl)-2-oxo-4-(trifluoromethyl)pyridin-1(2H)-yl)-4-methylpentanamido)propanoate (120 mg, 0.16 mmol) was treated with LiOH—H$_2$O (17 mg, 0.40 mmol) in EtOH (4 mL) and H$_2$O (1 mL) at room temperature for 2 hrs. The reaction mixture was acidified to pH 5~6 with 1N HCl. The reaction was concentrated in vacuo and the residue purified by prep-HPLC A (30-65% CH$_3$CN) to give the diastereomeric products IN-P1 (33 mg) and IN-P2 (36 mg) as white solids.

IN-P1 ESI 718.2 (M+H)+. $^1$H NMR (400 MHz, MeOD) δ 7.77 (s, 1H), 7.38 (m, J=7.6 Hz, 1H), 7.16 (m, J=7.7, 6.3 Hz, 3H), 6.80 (s, 1H), 5.75 (m, J=16.2, 8.0 Hz, 2H), 3.10 (s, 2H), 2.95 (m, J=15.7, 9.3 Hz, 1H), 2.81 (s, 6H), 2.77-2.59 (m, 3H), 2.08-1.89 (m, 10H), 1.34 (s, 1H), 0.94 (d, J=6.6 Hz, 6H).

IN-P2 ESI 718.2 (M+H)+. $^1$H NMR (400 MHz, MeOD) δ 7.79 (s, 1H), 7.43 (m, J=7.6 Hz, 1H), 7.27-7.09 (m, 3H), 6.85 (s, 1H), 5.82 (m, J=10.0, 4.8 Hz, 1H), 5.62 (m, J=7.6 Hz, 1H), 3.17-2.97 (m, 2H), 2.91-2.80 (m, 3H), 2.80 (s, 4H), 2.69-2.54 (m, 3H), 2.20-1.81 (m, 9H), 1.73-1.53 (m, 1H), 1.31 (m, J=13.3, 6.6 Hz, 1H), 0.86 (m, J=9.8, 6.7 Hz, 6H).

3-85. Preparation of (3S)-3-(4'-cyclopropyl-2,3',4-trifluoro-2',5,6'-trimethyl-[1,1'-biphenyl]-3-y)-3-(2-(5-(3-(dimethylamino)propyl)-2-oxo-4-(trifluoromethyl)pyridin-1(2H)-yl)-4-methylpentanamido) propanoic Acid Step 1: Ethyl (3S)-3-(4'-cyclopropyl-2,3',4-trifluoro-2',5,6'-trimethyl-[1,1'-biphenyl]-3-y)-3-(2-(5-(3-(dimethylamino)propyl)-2-oxo-4-(trifluoromethyl)pyridin-1(2H)-yl)-4-methylpentanamido)propanoate

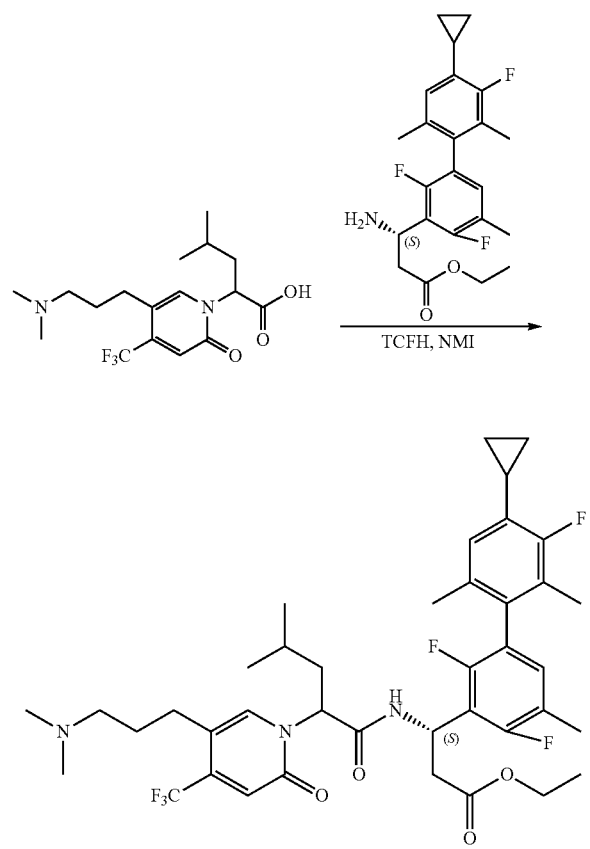

A mixture of ethyl (3S)-3-amino-3-(4'-cyclopropyl-2,3',4-trifluoro-2',5,6'-trimethyl-[1,1'-biphenyl]-3-yl)propanoate (197 mg, 0.48 mmol), 2-(5-(3-(dimethylamino)propyl)-2-oxo-4-(trifluoromethyl)pyridin-1(2H)-yl)-4-methylpentanoic acid (160 mg, 0.44 mmol), TCFH (185 mg, 0.66 mmol), and 1-methylimidazole (144 mg, 1.76 mmol) in acetonitrile (8 mL) was stirred at room temperature for 2 hours. The mixture was purified by reverse phase HPLC on a C18/40 g column (A: water 10 mM NH$_4$HCO$_3$, B: MeOH, 0~100%) to provide ethyl (3S)-3-(4'-cyclopropyl-2,3',4-trifluoro-2',5,6'-trimethyl-[1,1'-biphenyl]-3-yl)-3-(2-(5-(3-(dimethylamino)propyl)-2-oxo-4-(trifluoromethyl)pyridin-1(2H)-yl)-4-methylpentanamido)propanoate (230 mg) as a yellow solid. Yield 70.0% (ESI 750.3 (M+H)+).

Step 2: (3S)-3-(4'-cyclopropyl-2,3',4-trifluoro-2',5,
6'-trimethyl-[1,1'-biphenyl]-3-y)-3-(2-(5-(3-(dimeth-
ylamino)propyl)-2-oxo-4-(trifluoromethyl)pyridin-1
(2H)-yl)-4-methylpentanamido)propanoic Acid

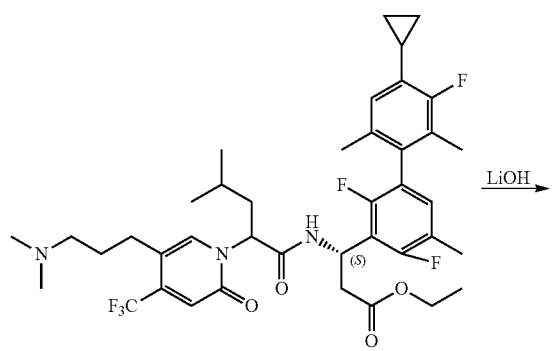

Ethyl (3S)-3-(4'-cyclopropyl-2,3',4-trifluoro-2',5,6'-trim-ethyl-[1,1'-biphenyl]-3-yl)-3-(2-(5-(3-(dimethylamino)pro-pyl)-2-oxo-4-(trifluoromethyl)pyridin-1(2H)-yl)-4-methyl-pentanamido)propanoate (230 mg, 0.31 mmol) was treated with LiOH—H$_2$O (51.6 mg, 1.23 mmol) in MeOH (5 mL) and H$_2$O (1 ml) at room temperature for 2 hours. The reaction mixture was acidified to pH 6~7 with 2N HCl. The reaction was concentrated in vacuo and the residue purified by prep-HPLC A (30-60% CH$_3$CN) to give the diastereo-meric products IO-P1 (79.7 mg) and IO-P2 (60.6 mg) as white solids.

IO-P1 ESI 722.2 (M+H)$^+$. $^1$H NMR (400 MHz, MeOD) δ 7.77 (s, 1H), 6.86 (t, J=8.2 Hz, 1H), 6.80 (d, J=3.5 Hz, 1H), 6.65-6.63 (m, 1H), 5.77-5.71 (m, 2H), 3.07 (t, J=7.8 Hz, 2H), 2.96-2.90 (m, 1H), 2.79 (s, 6H), 2.73-2.59 (m, 3H), 2.23 (s, 3H), 2.12-1.82 (m, 1H), 1.38-1.32 (m, 1H), 1.01-0.92 (m, 8H), 0.77-0.70 (m, 2H).

IO-P2 ESI 722.2 (M+H)$^+$. $^1$H NMR (400 MHz, MeOD) δ 7.79 (s, 1H), 6.90 (t, J=8.2 Hz, 1H), 6.85 (s, 1H), 6.67 (d, J=7.3 Hz, 1H), 5.85-5.85 (m, 1H), 5.57 (t, J=6.9 Hz, 1H), 3.14-3.11 (m, 2H), 2.89-2.78 (m, 7H), 2.68-2.52 (m, 3H), 2.27 (s, 3H), 2.14-1.89 (m, 10H), 1.66-1.57 (m, 1H), 1.36-1.29 (m, 1H), 1.03-0.92 (m, 2H), 0.86 (t, J=7.8 Hz, 6H), 0.76-0.70 (m, 2H).

3-86. Preparation of (3S)-3-(2-(5-(3-(azetidin-1-yl)
propyl)-2-oxo-4-(trifluoromethyl)pyridin-1(2H)-yl)-
4-methylpentanamido)-3-(2,4-difluoro-2',4',6'-trim-
ethyl-5-(trifluoromethyl)-[1,1'-biphenyl]-3-yl)
propanoic Acid (Compounds IP-P1 and IP-P2)

Step 1: Ethyl (3S)-3-(2-(5-(3-(azetidin-1-yl)propyl)-
2-oxo-4-(trifluoromethyl)pyridin-1(2H)-yl)-4-meth-
ylpentanamido)-3-(2,4-difluoro-2',4',6'-trimethyl-5-
(trifluoromethyl)-[1,1'-biphenyl]-3-yl)propanoate

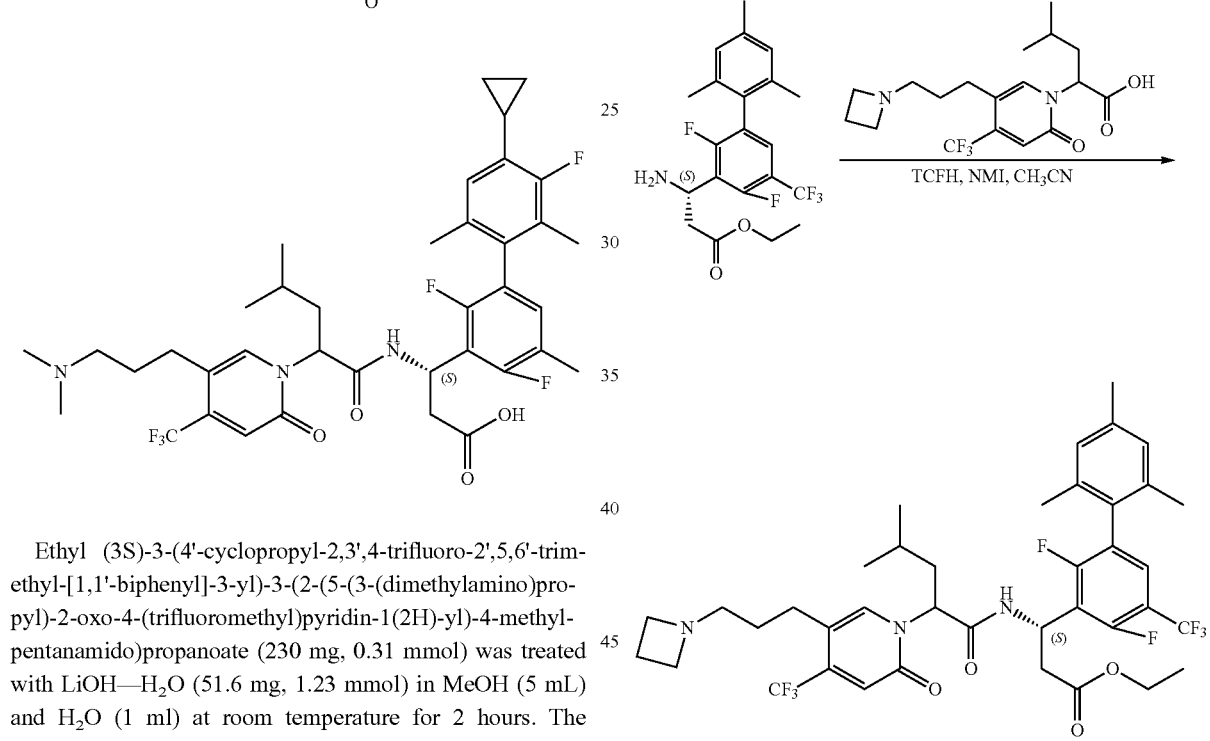

A mixture of ethyl (S)-3-amino-3-(2,4-difluoro-2',4',6'-trimethyl-5-(trifluoromethyl)-[1,1'-biphenyl]-3-yl)propano-ate (112.0 mg, 0.27 mmol), 2-(5-(3-(azetidin-1-yl)propyl)-2-oxo-4-(trifluoromethyl)pyridin-1(2H)-yl)-4-methylpentanoic acid (100.0 mg, 0.27 mmol), TCFH (151.2 mg, 0.54 mmol) and NMI (88.6 mg, 1.08 mmol) in CH$_3$CN (8 mL) was stirred at room temperature for 1 hour. The reaction was concentrated in vacuo and the residue purified by silica gel column (DCM:MeOH 4:1) to provide ethyl (3S)-3-(2-(5-(3-(azetidin-1-yl)propyl)-2-oxo-4-(trifluorom-ethyl)pyridin-1(2H)-yl)-4-methylpentanamido)-3-(2,4-dif-luoro-2',4',6'-trimethyl-5-(trifluoromethyl)-[1,1'-biphenyl]-3-yl)propanoate as a brown solid (130.0 mg). Yield 63% (ESI 772.6 (M+H)$^+$).

Step 2: (3S)-3-(2-(5-(3-(azetidin-1-yl)propyl)-2-oxo-4-(trifluoromethyl)pyridin-1(2H)-yl)-4-methylpentanamido)-3-(2,4-difluoro-2',4',6'-trimethyl-5-(trifluoromethyl)-[1,1'-biphenyl]-3-yl)propanoic Acid

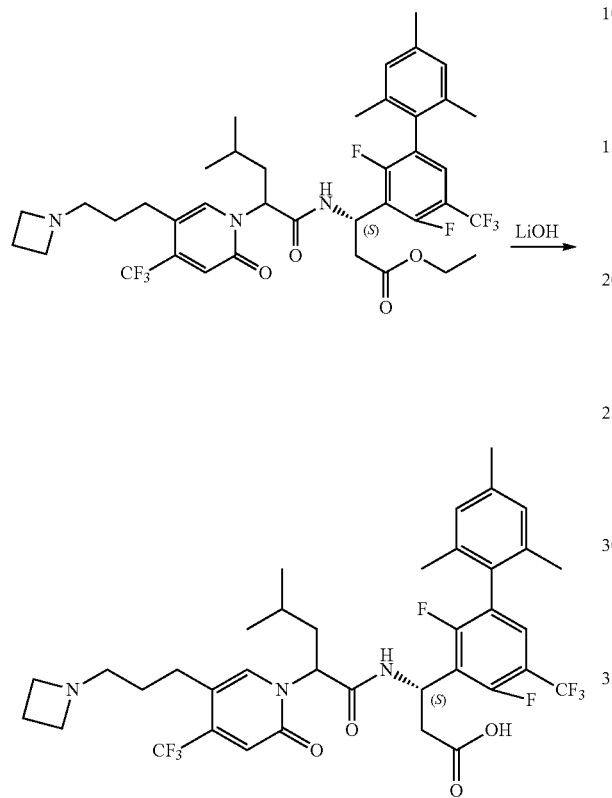

Ethyl (3S)-3-(2-(5-(3-(azetidin-1-yl)propyl)-2-oxo-4-(trifluoromethyl)pyridin-1(2H)-yl)-4-methylpentanamido)-3-(2,4-difluoro-2',4',6'-trimethyl-5-(trifluoromethyl)-[1,1'-biphenyl]-3-yl)propanoate (130 mg, 0.17 mmol)) was treated with LiOH—H$_2$O (28.6 mg, 0.68 mmol) in MeOH (4 mL) and H$_2$O (1 mL) at room temperature for 2 hours. The reaction mixture was acidified to pH 4~5 with 1N HCl. The reaction was concentrated in vacuo and the residue purified by prep-HPLC A (30-60% MeCN) to give the diastereomeric products IP-P1 (38.0 mg) and IP-P2 (42.0 mg) as white solids.

IP-P1 ESI 744.7 (M+H)$^+$. 1H NMR (400 MHz, MeOD) δ 7.76 (s, 1H), 7.34 (d, J=7.4 Hz, 1H), 6.94 (s, 1H), 6.79 (s, 2H), 5.74 (d, J=4.1 Hz, 2H), 4.08 (t, J=7.7 Hz, 4H), 3.21-3.11 (m, 2H), 2.97-2.89 (m, 1H), 2.71-2.58 (m, 3H), 2.45 (s, 2H), 2.30 (s, 3H), 2.06-1.91 (m, 5H), 1.83 (d, J=43.4 Hz, 5H), 1.34 (s, 1H), 0.93 (d, J=6.5 Hz, 6H).

IP-P2 ESI 744.7 (M+H)$^+$. 1H NMR (400 MHz, MeOD) δ 7.78 (s, 1H), 7.40 (t, J=7.7 Hz, 1H), 6.90 (d, J=55.2 Hz, 3H), 5.87-5.78 (m, 1H), 5.61 (t, J=7.6 Hz, 1H), 4.15-3.99 (m, 4H), 3.19-2.97 (m, 2H), 2.94-2.82 (m, 1H), 2.69-2.54 (m, 3H), 2.50-2.37 (m, 2H), 2.31 (s, 3H), 2.03-1.71 (m, 9H), 1.73-1.53 (m, 1H), 1.39-1.20 (m, 1H), 0.89-0.72 (m, 6H).

3-87. Preparation of (3S)-3-(2-(5-(2-(ethyl(methyl)amino)ethyl)-2-oxo-4-(trifluoromethyl)pyridin-1(2H)-yl)-4-methylpentanamido)-3-(2,3',4-trifluoro-2',6'-dimethyl-5-(trifluoromethyl)biphenyl-3-yl)propanoic Acid (Compounds IQ-P1 and IQ-P2)

Step 1: (3S)-ethyl 3-(2-(5-(2-(ethyl(methyl)amino)ethyl)-2-oxo-4-(trifluoromethyl)pyridin-1(2H)-yl)-4-methylpentanamido)-3-(2,3',4-trifluoro-2',6'-dimethyl-5-(trifluoromethyl)biphenyl-3-yl)propanoate

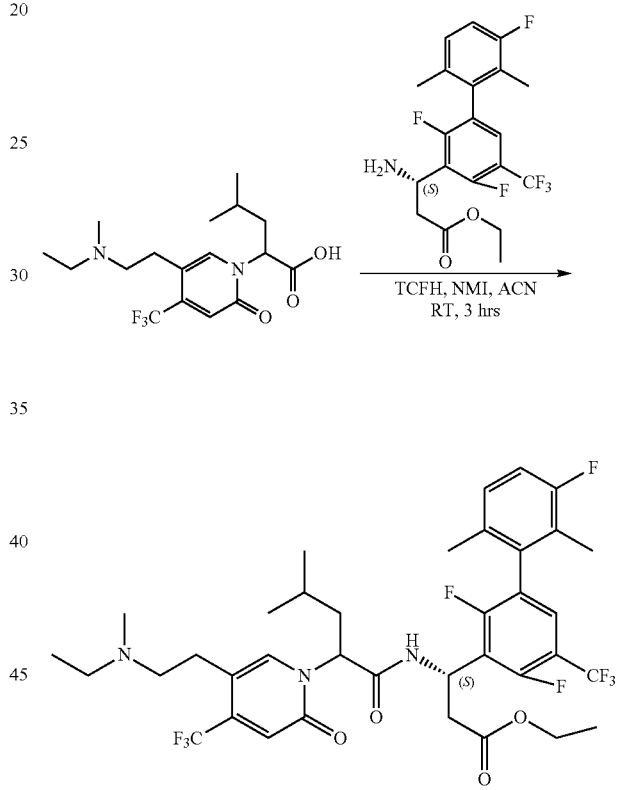

A mixture of (3S)-ethyl 3-amino-3-(2,3',4-trifluoro-2',6'-dimethyl-5-(trifluoromethyl)biphenyl-3-yl)propanoate (118 mg, 0.28 mmol), 2-(5-(2-(ethyl(methyl)amino)ethyl)-2-oxo-4-(trifluoromethyl)pyridin-1(2H)-yl)-4-methylpentanoic acid (100 mg, 0.28 mmol), TCFH (157 mg, 0.56 mmol) and NMI (69 mg, 0.84 mmol) in MeCN (5 mL) was stirred at room temperature for 1 hour. The solvent was removed in vacuo and the residue was purified by silica gel column (DCM:MeOH 97:3) to provide (3S)-ethyl 3-(2-(5-(2-(ethyl(methyl)amino)ethyl)-2-oxo-4-(trifluoromethyl)pyridin-1(2H)-yl)-4-methylpentanamido)-3-(2,3',4-trifluoro-2',6'-dimethyl-5-(trifluoromethyl)biphenyl-3-yl)propanoate as a colorless oil (120 mg). Yield 55% (ESI 764.3 (M+H)$^+$).

541

Step 2: (3S)-3-(2-(5-(2-(ethyl(methyl)amino)ethyl)-2-oxo-4-(trifluoromethyl)pyridin-1(2H)-yl)-4-methylpentanamido)-3-(2,3',4-trifluoro-2',6'-dimethyl-5-(trifluoromethyl)biphenyl-3-yl)propanoic acid

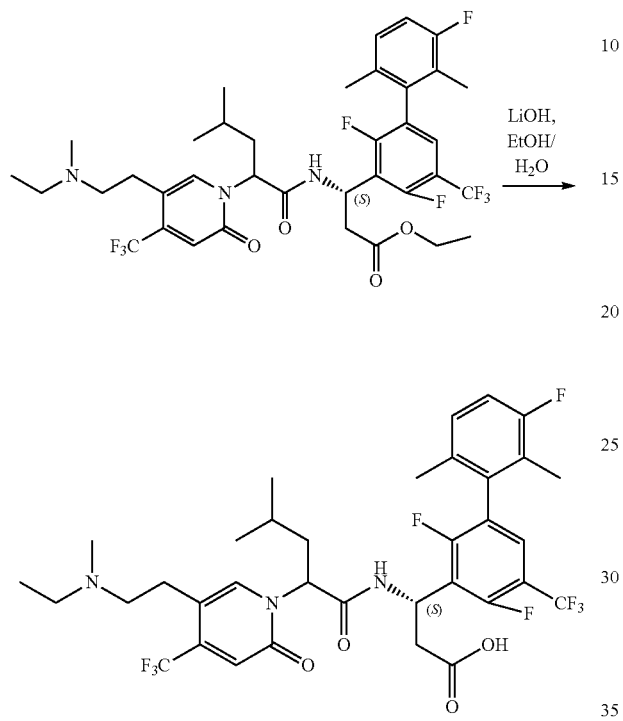

(3S)-ethyl 3-(2-(5-(2-(ethyl(methyl)amino)ethyl)-2-oxo-4-(trifluoromethyl)pyridin-1(2H)-yl)-4-methylpentanamido)-3-(2,3',4-trifluoro-2',6'-dimethyl-5-(trifluoromethyl)biphenyl-3-yl)propanoate (100 mg, 0.13 mmol) was treated with LiOH—H$_2$O (27 mg, 0.65 mmol) in EtOH (3 mL) and H$_2$O (1 mL) at room temperature for 3 hours. The reaction mixture was acidified to pH 4~5 with 1N HCl. The reaction was concentrated in vacuo and the residue purified by prep-HPLC A (30-60% CH$_3$CN) to give the diastereomeric products IQ-P1 (30.3 mg) and IQ-P2 (23.1 mg) as white solids.

IQ-P1 ESI 736.3 (M+H)$^+$. 1H NMR (400 MHz, MeOD) δ 7.88 (s, 1H), 7.39 (t, J=7.2 Hz 1H), 7.13-7.10 (m, 1H), 7.01 (t, J=8.8 Hz 1H), 6.81 (d, J=2.0 Hz, 1H), 5.72-5.68 (m, 2H), 3.15-3.08 (m, 4H), 2.97-2.92 (m, 3H), 2.79-2.74 (m, 4H), 2.02-1.87 (m, 8H), 1.38-1.35 (m, 1H), 1.28 (t, J=7.2 Hz, 3H), 0.93-0.90 (m, 6H).

IQ-P2 ESI 736.3 (M+H)$^+$. 1H NMR (400 MHz, MeOD) δ 7.87 (s, 1H), 7.46 (t, J=7.5 Hz, 1H), 7.23-7.11 (m, 1H), 7.04 (t, J=8.9 Hz, 1H), 6.88 (s, 1H), 5.78-5.75 (m, 1H), 5.68 (t, J=7.8 Hz, 1H), 3.28-3.08 (m, 4H), 2.97 (t, J=7.5 Hz, 2H), 2.90-2.84 (m, 1H), 2.80 (s, 3H), 2.72-2.70 (m, 1H), 2.00 (d, J=3.2 Hz, 3H), 1.93-1.90 (m, 3H), 1.86-1.83 (m, 1H), 1.80-1.68 (m, 1H), 1.37-1.22 (m, 4H), 0.87-0.85 (m, 6H).

542

3-88. Preparation of (3S)-3-(2-(5-(2-(dimethylamino)ethyl)-2-oxo-4-(trifluoromethyl)pyridin-1(2H)-yl)-4-methylpentanamido)-3-(2,4,4'-trifluoro-2',6'-dimethyl-5-(trifluoromethyl)-[1,1'-biphenyl]-3-yl)propanoic Acid (Compounds IR-P1 and IR-P2)

Step 1: Ethyl (3S)-3-(2-(5-(2-(dimethylamino)ethyl)-2-oxo-4-(trifluoromethyl)pyridin-1(2H)-yl)-4-methylpentanamido)-3-(2,4,4'-trifluoro-2',6'-dimethyl-5-(trifluoromethyl)-[1,1'-biphenyl]-3-yl)propanoate

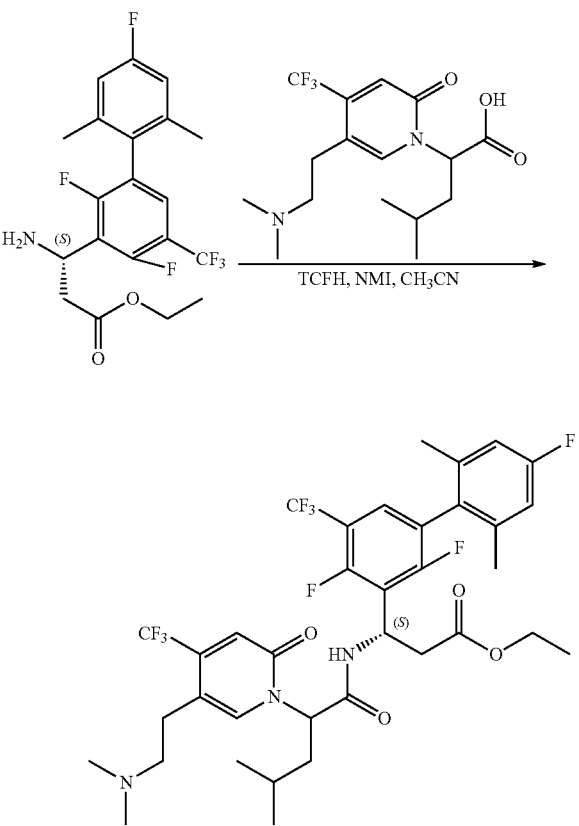

A mixture of ethyl (S)-3-amino-3-(2,4,4'-trifluoro-2',6'-dimethyl-5-(trifluoromethyl)-[1,1'-biphenyl]-3-yl)propanoate (100 mg, 0.24 mmol), 2-(5-(2-(dimethylamino)ethyl)-2-oxo-4-(trifluoromethyl)pyridin-1(2H)-yl)-4-methylpentanoic acid (100 mg, 0.29 mmol), TCFH (150 mg, 0.52 mmol) and NMI (106 mg, 1.3 mmol) in CH$_3$CN (3 mL) was stirred at 50° C. for 1 hr. The reaction was concentrated and purified by reverse phase HPLC on a C18/40 g column (A: water 10 mM NH$_4$HCO$_3$, B: MeOH, 0~90%) to provide ethyl (3S)-3-(2-(5-(2-(dimethylamino)ethyl)-2-oxo-4-(trifluoromethyl)pyridin-1(2H)-yl)-4-methylpentanamido)-3-(2,4,4'-trifluoro-2',6'-dimethyl-5-(trifluoromethyl)-[1,1'-biphenyl]-3-yl)propanoate as a yellow solid (110 mg). Yield 61.1% (ESI 750.3 [M+H]$^+$).

Step 2: (3S)-3-(2-(5-(2-(dimethylamino)ethyl)-2-oxo-4-(trifluoromethyl)pyridin-1(2H)-yl)-4-methylpentanamido)-3-(2,4,4'-trifluoro-2',6'-dimethyl-5-(trifluoromethyl)-[1,1'-biphenyl]-3-yl)propanoic Acid

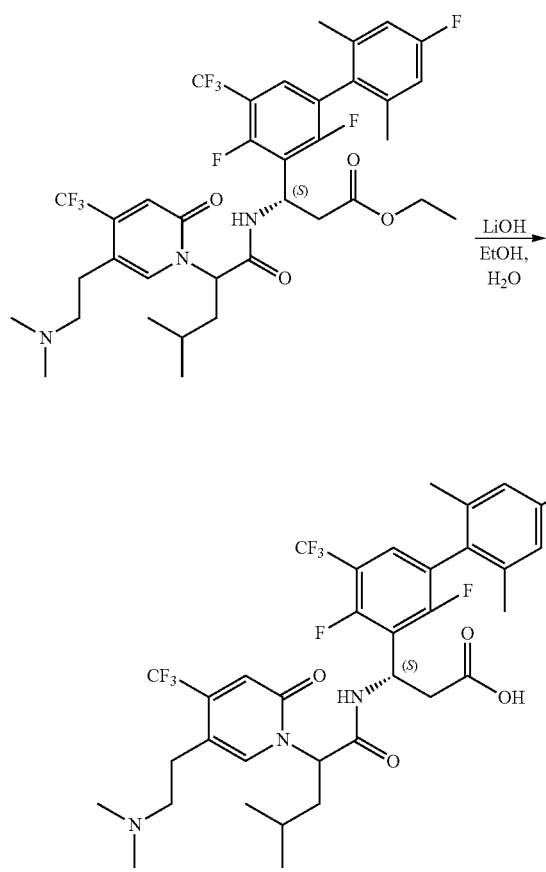

Ethyl (3S)-3-(2,4-difluoro-2',4',6'-trimethyl-5-(trifluoromethyl)-[1,1'-biphenyl]-3-yl)-3-(2-(5-(2-(dimethylamino)ethyl)-2-oxo-4-(trifluoromethyl)pyridin-1(2H)-yl)-4-methylpentanamido)propanoate (110 mg, 0.15 mmol) was treated with LiOH—H$_2$O (13 mg, 0.3 mmol) in EtOH (2 mL) and H$_2$O (0.5 mL) at room temperature for 30 mins. The reaction mixture was acidified to pH 5~6 with 1N HCl. The reaction was concentrated in vacuo and the residue purified by prep-HPLC A (35-60% CH$_3$CN) to give the diastereomeric products IR-P1 (32 mg) and IR-P2 (39 mg) as white solids.

IR-P1 ESI 722.3 (M+H)$^+$. $^1$H NMR (400 MHz, MeOD) δ 7.87 (s, 1H), 7.41 (t, J=7.5 Hz, 1H), 6.95-6.86 (m, 2H), 6.84 (s, 1H), 5.79-5.62 (m, 2H), 3.12 (s, 2H), 3.02-2.88 (m, 3H), 2.85-2.68 (m, 7H), 2.11-1.84 (m, 8H), 1.45-1.36 (m, 1H), 1.02-0.88 (m, 6H).

IR-P2 ESI 722.3 (M+H)$^+$. 1H NMR (400 MHz, MeOD) δ 7.83 (s, 1H), 7.46 (t, J=7.6 Hz, 1H), 6.92 (d, J=9.9 Hz, 3H), 5.80 (dd, J=9.9, 5.6 Hz, 1H), 5.65 (t, J=7.7 Hz, 1H), 3.25-3.14 (m, 2H), 2.96 (t, J=7.0 Hz, 2H), 2.91-2.73 (m, 7H), 2.67 (d, J=13.7 Hz, 1H), 2.03 (d, J=2.6 Hz, 6H), 1.93-1.84 (m, 1H), 1.78-1.69 (m, 1H), 1.36-1.27 (m, 1H), 0.95-0.79 (m, 6H).

3-89. Preparation of (3S)-3-(2-(5-(2-(azetidin-1-yl)ethyl)-2-oxo-4-(trifluoromethyl)pyridin-1(2H)-yl)-4-methylpentanamido)-3-(2,4-difluoro-2',4',5,6'-tetramethylbiphenyl-3-yl)propanoic Acid (Compounds IS-P1 and IS-P2)

Step 1: (3S)-ethyl 3-(2-(5-(2-(azetidin-1-yl)ethyl)-2-oxo-4-(trifluoromethyl)pyridin-1(2H)-yl)-4-methylpentanamido)-3-(2,4-difluoro-2',4',5,6'-tetramethylbiphenyl-3-yl)propanoate

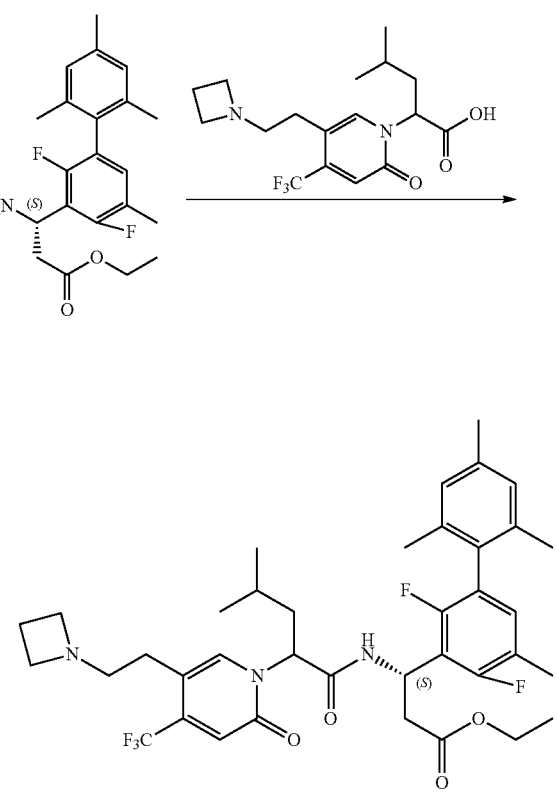

A mixture of 2-(5-(2-(azetidin-1-yl)ethyl)-2-oxo-4-(trifluoromethyl)pyridin-1(2H)-yl)-4-methylpentanoic acid (240 mg, 0.66 mmol), (S)-ethyl 3-amino-3-(2,4-difluoro-2',4',5,6'-tetramethylbiphenyl-3-yl)propanoate (240 mg, 0.66 mmol), NMI (0.5 mL) and TCFH (378 mg, 1.35 mmol) in CH$_3$CN (5 mL) was stirred at room temperature for 1 hour. The solvent was concentrated in vacuo and the residue was purified by prep-HPLC A (30-90% CH$_3$CN) to provide (3S)-ethyl 3-(2-(5-(2-(azetidin-1-yl)ethyl)-2-oxo-4-(trifluoromethyl)pyridin-1(2H)-yl)-4-methylpentanamido)-3-(2,4-difluoro-2',4',5,6'-tetramethylbiphenyl-3-yl)propanoate as a white solid (290 mg). Yield 62% (ESI 704.3 [M+H]$^+$).

545

Step 2: (3S)-3-(2-(5-(2-(azetidin-1-yl)ethyl)-2-oxo-4-(trifluoromethyl)pyridin-1(2H)-yl)-4-methylpentanamido)-3-(2,4-difluoro-2',4',5',6'-tetramethylbiphenyl-3-yl)propanoic Acid

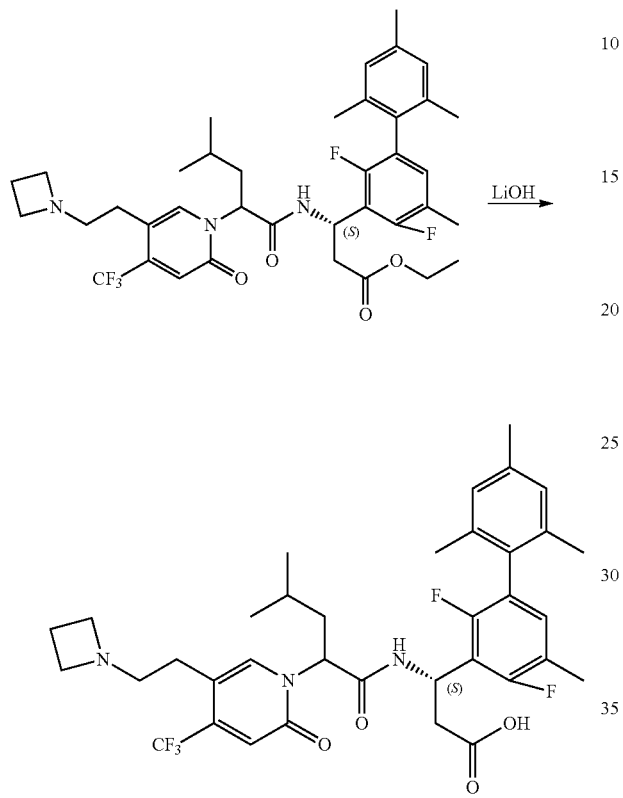

(3S)-ethyl 3-(2-(5-(2-(azetidin-1-yl)ethyl)-2-oxo-4-(trifluoromethyl)pyridin-1(2H)-yl)-4-methylpentanamido)-3-(2,4-difluoro-2',4',5',6'-tetramethylbiphenyl-3-yl)propanoate (290 mg, 0.41 mmol) was treated with LiOH—H$_2$O (86 mg, 2.05 mmol) in MeOH (5 mL) and H$_2$O (0.5 mL) at room temperature for 2 hours. The reaction mixture was acidified to pH 4-5 with 1N HCl. The reaction was concentrated in vacuo and the residue purified by prep-HPLC A (30-70% CH$_3$CN) to give the diastereomeric products IS-P1 (66.0 mg) and IS-P2 (93.0 mg) as white solids.

IS-P1 ESI 675.9 (M+H)$^+$. $^1$H NMR (400 MHz, MeOD) δ 7.79 (s, 1H), 6.90 (s, 2H), 6.86 (s, 2H), 5.83-5.71 (m, 1H), 5.67 (t, J=6.1 Hz, 1H), 3.99 (t, J=8.1 Hz, 4H), 3.27-3.18 (m, 2H), 2.94-2.78 (m, 3H), 2.72-2.60 (m, 1H), 2.47-2.34 (m, 2H), 2.26 (d, J=15.9 Hz, 6H), 2.06-1.93 (m, 5H), 1.90 (s, 3H), 1.50-1.29 (m, 1H), 0.92 (t, J=6.1 Hz, 6H).

IS-P2 ESI 676.0 (M+H)$^+$. $^1$H NMR (400 MHz, MeOD) δ 7.68 (s, 1H), 7.02-6.85 (m, 4H), 5.97-5.87 (m, 1H), 5.61 (t, J=7.7 Hz, 1H), 4.11 (t, J=8.1 Hz, 4H), 3.47-3.32 (m, 2H), 2.97-2.72 (m, 3H), 2.54-2.39 (m, 3H), 2.28 (d, J=6.5 Hz, 6H), 2.00-1.87 (m, 7H), 1.79-1.66 (m, 1H), 1.46-1.26 (m, 1H), 0.94-0.80 (m, 6H).

546

3-90. Preparation of Preparation of (3S)-3-(2-(5-(3-(dimethylamino)propyl)-2-oxo-4-(trifluoromethyl)pyridin-1(2H)-yl)-4-methylpentanamido)-3-(2,2',4-trifluoro-4',6'-dimethyl-5-(trifluoromethyl)-[1,1'-biphenyl]-3-yl)propanoic Acid (Compounds IT-P1 and IT-P2)

Step 1: Ethyl (3S)-3-(2-(5-(3-(dimethylamino)propyl)-2-oxo-4-(trifluoromethyl)pyridin-1(2H)-yl)-4-methylpentanamido)-3-(2,2',4-trifluoro-4',6'-dimethyl-5-(trifluoromethyl)-[1,1'-biphenyl]-3-yl)propanoate

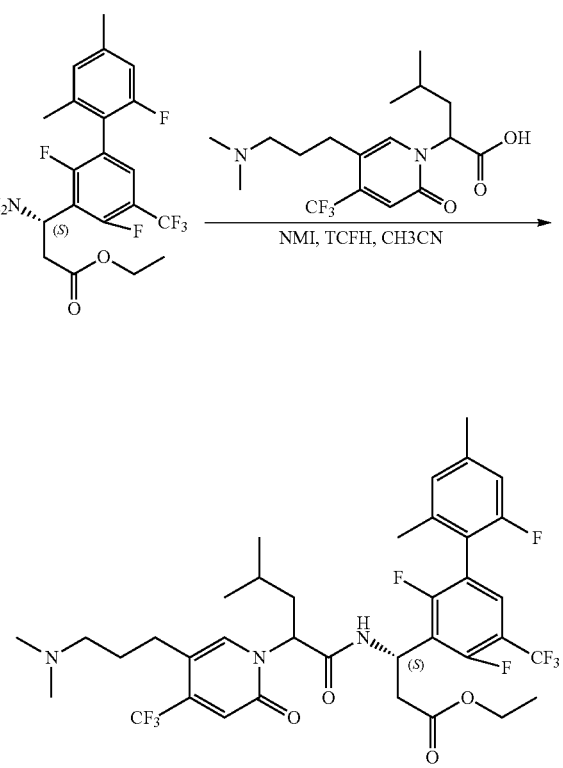

A mixture of ethyl (3S)-3-amino-3-(2,2',4-trifluoro-4',6'-dimethyl-5-(trifluoromethyl)-[1,1'-biphenyl]-3-yl)propanoate (120.0 mg, 0.29 mmol), 2-(5-(3-(dimethylamino)propyl)-2-oxo-4-(trifluoromethyl)pyridin-1(2H)-yl)-4-methylpentanoic acid (105.0 mg, 0.29 mmol), TCFH (123.2 mg, 0.44 mmol) and NMI (118.9 mg, 1.45 mmol) in CH$_3$CN (3 mL) was stirred at room temperature overnight. The reaction was concentrated in vacuo and the residue purified by reverse phase HPLC on a C18/40 g column (A: water 10 mM NH$_4$HCO$_3$, B: MeOH, 0~100%) to provide ethyl (3S)-3-(2-(5-(3-(dimethylamino)propyl)-2-oxo-4-(trifluoromethyl)pyridin-1(2H)-yl)-4-methylpentanamido)-3-(2,2',4-trifluoro-4',6'-dimethyl-5-(trifluoromethyl)-[1,1'-biphenyl]-3-yl)propanoate as a light yellow solid (160.0 mg). Yield 73% (ESI 764.3 [M+H]$^+$).

547

Step 2: (3S)-3-(2-(5-(3-(dimethylamino)propyl)-2-oxo-4-(trifluoromethyl)pyridin-1(2H)-yl)-4-methylpentanamido)-3-(2,2',4-trifluoro-4',6'-dimethyl-5-(trifluoromethyl)-[1,1'-biphenyl]-3-yl)propanoic Acid

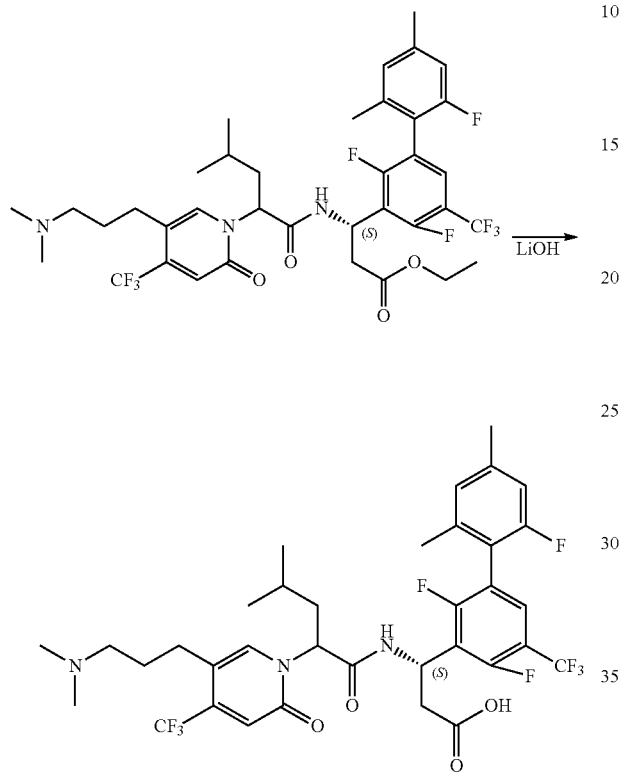

Ethyl (3S)-3-(2-(5-(3-(dimethylamino)propyl)-2-oxo-4-(trifluoromethyl)pyridin-1(2H)-yl)-4-methylpentanamido)-3-(2,2',4-trifluoro-4',6'-dimethyl-5-(trifluoromethyl)-[1,1'-biphenyl]-3-yl)propanoate (160.0 mg, 0.21 mmol) was treated with LiOH—H₂O (26.5 mg, 0.63 mmol) in EtOH (2 mL) and water (0.5 mL) at room temperature for 1 hour. The reaction mixture was acidified to pH 4~5 with 2N HCl. The reaction was concentrated in vacuo and the residue purified by prep-HPLC A (30-80% MeCN) to give the diastereomeric products IT-P1 (30.0 mg) and IT-P2 (49.0 mg) as white solids.

IT-P1 ESI 736.2 (M+H)⁺ ¹H NMR (400 MHz, MeOD) δ 7.77 (s, 1H), 7.52-7.43 (m, 1H), 6.98 (s, 1H), 6.90-6.75 (m, 2H), 5.84-5.67 (m, 2H), 3.08 (t, J=8.1 Hz, 2H), 2.97-2.87 (m, 1H), 2.83-2.55 (m, 9H), 2.35 (s, 3H), 2.13-1.82 (m, 7H), 1.40-1.27 (m, 1H), 0.97-0.90 (m, 6H).

IT-P2 ESI 736.2 (M+H)⁺ ¹H NMR (400 MHz, MeOD) δ 7.80 (s, 1H), 7.52 (t, J=7.5 Hz, 1H), 7.00 (s, 1H), 6.93-6.80 (m, 2H), 5.84-5.75 (m, 1H), 5.70-5.60 (m, 1H), 3.15-2.96 (m, 2H), 2.93-2.72 (m, 7H), 2.70-2.59 (m, 3H), 2.37 (s, 3H), 2.15-1.84 (m, 6H), 1.75-1.55 (m, 1H), 1.37-1.15 (m, 1H), 0.92-0.80 (m, 6H).

548

3-91. Preparation of Preparation of (3S)-3-(2-(5-(2-(ethyl(methyl)amino)ethyl)-2-oxo-4-(trifluoromethyl)pyridin-1(2H)-yl)-4-methylpentanamido)-3-(2,4,4'-trifluoro-2',6'-dimethyl-5-(trifluoromethyl)-[1,1'-biphenyl]-3-yl)propanoic Acid (Compounds IU-P1 and IU-P2)

Step 1: Ethyl (3S)-3-(2-(5-(2-(ethyl(methyl)amino)ethyl)-2-oxo-4-(trifluoromethyl)pyridin-1(2H)-yl)-4-methylpentanamido)-3-(2,4,4'-trifluoro-2',6'-dimethyl-5-(trifluoromethyl)-[1,1'-biphenyl]-3-yl)propanoate

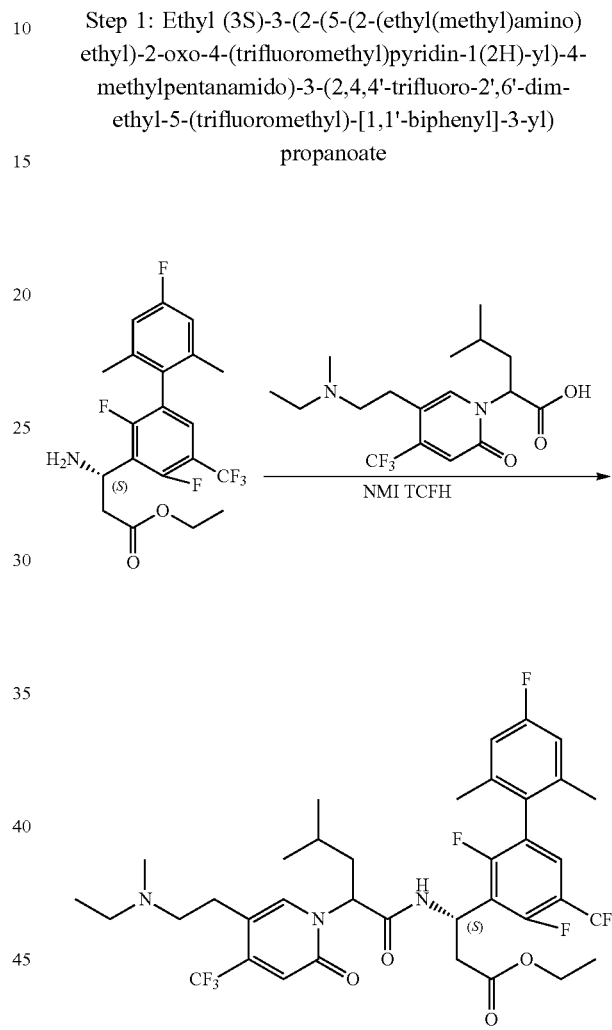

A mixture of ethyl (S)-3-amino-3-(2,4,4'-trifluoro-2',6'-dimethyl-5-(trifluoromethyl)-[1,1'-biphenyl]-3-yl)propanoate (120 mg, 0.29 mmol), 2-(5-(2-(ethyl(methyl)amino)ethyl)-2-oxo-4-(trifluoromethyl)pyridin-1(2H)-yl)-4-methylpentanoic acid (100 mg, 0.29 mmol), TCFH (162.4 mg, 0.58 mmol) and NMI (119.0 mg, 1.45 mmol) in CH₃CN (3 mL) was stirred at room temperature overnight. The reaction was concentrated in vacuo and the residue purified by reverse phase HPLC on a C18/40 g column (A: water 10 mM NH₄HCO₃, B: MeOH, 20~90%) to provide ethyl (3S)-3-(2-(5-(2-(ethyl(methyl)amino)ethyl)-2-oxo-4-(trifluoromethyl)pyridin-1(2H)-yl)-4-methylpentanamido)-3-(2,4,4'-trifluoro-2',6'-dimethyl-5-(trifluoromethyl)-[1,1'-biphenyl]-3-yl)propanoate as a light yellow solid (160.0 mg). Yield 73% (ESI 764.3 [M+H]⁺).

549

Step 2: (3S)-3-(2-(5-(2-(ethyl(methyl)amino)ethyl)-2-oxo-4-(trifluoromethyl)pyridin-1(2H)-yl)-4-methylpentanamido)-3-(2,4,4'-trifluoro-2',6'-dimethyl-5-(trifluoromethyl)-[1,1'-biphenyl]-3-yl)propanoic Acid

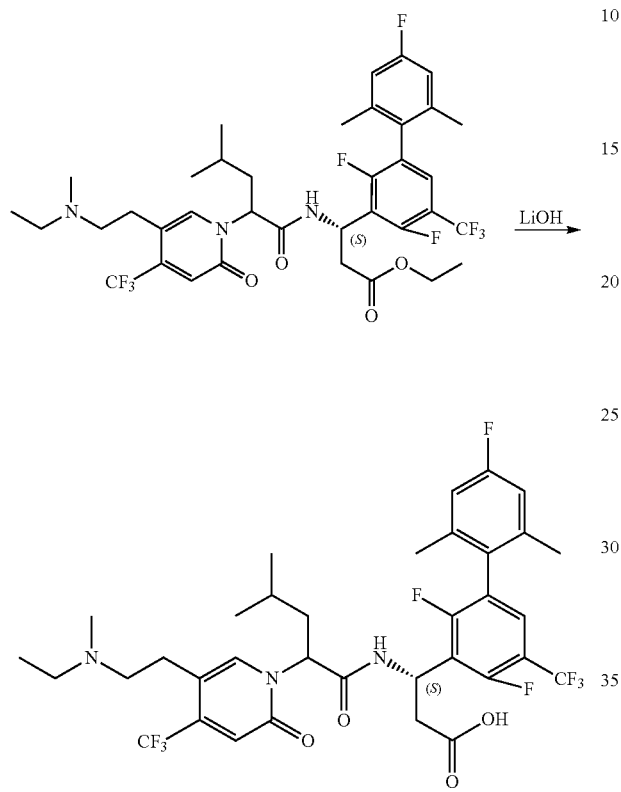

Ethyl (3S)-3-(2-(5-(2-(ethyl(methyl)amino)ethyl)-2-oxo-4-(trifluoromethyl)pyridin-1(2H)-yl)-4-methylpentanamido)-3-(2,4,4'-trifluoro-2',6'-dimethyl-5-(trifluoromethyl)-[1,1'-biphenyl]-3-yl)propanoate (160.0 mg, 0.21 mmol) was treated with LiOH—H$_2$O (26.5 mg, 0.63 mmol) in EtOH (3 mL) and water (1 mL) at room temperature for 1 hour. The reaction mixture was acidified to pH 4~5 with 2N HCl. The reaction was concentrated in vacuo and the residue purified by prep-HPLC A (30-90% MeCN) to give the diastereomeric products IU-P1 (34.0 mg) and IU-P2 (32.0 mg) as white solids.

IU-P1 ESI 736.2 (M+H)$^+$ $^1$H NMR (400 MHz, MeOD) δ 7.87 (s, 1H), 7.39 (t, J=7.5 Hz, 1H), 6.93-6.75 (m, 3H), 5.78-5.65 (m, 2H), 3.22-3.04 (m, 4H), 3.02-2.88 (m, 3H), 2.83-2.70 (m, 4H), 2.07-1.86 (m, 8H), 1.43-1.23 (m, 4H), 0.94 (t, J=6.8 Hz, 6H).

IU-P2 ESI 736.2 (M+H)$^+$ $^1$H NMR (400 MHz, MeOD) δ 7.85 (s, 1H), 7.45 (t, J=7.5 Hz, 1H), 6.96-6.81 (m, 3H), 5.83-5.74 (m, 1H), 5.66 (t, J=7.8 Hz, 1H), 3.27-3.09 (m, 4H), 2.97 (t, J=7.4 Hz, 2H), 2.92-2.63 (m, 5H), 2.03 (d, J=3.5 Hz, 6H), 1.92-1.82 (m, 1H), 1.79-1.65 (m, 1H), 1.37-1.25 (m, 4H), 0.94-0.81 (m, 6H)

3-92. Preparation of Preparation of (3S)-3-(2-(5-(2-(azetidin-1-yl)ethyl)-2-oxo-4-(trifluoromethyl)pyridin-1(2H)-yl)-4-methylpentanamido)-3-(2,4,4'-trifluoro-2',6'-dimethyl-5-(trifluoromethyl)-[1,1'-biphenyl]-3-yl)propanoic Acid (Compounds IV-P1 and IV-P2)

Step 1: Ethyl (3S)-3-(2-(5-(2-(azetidin-1-yl)ethyl)-2-oxo-4-(trifluoromethyl)pyridin-1(2H)-yl)-4-methylpentanamido)-3-(2,4,4'-trifluoro-2',6'-dimethyl-5-(trifluoromethyl)-[1,1'-biphenyl]-3-yl)propanoate

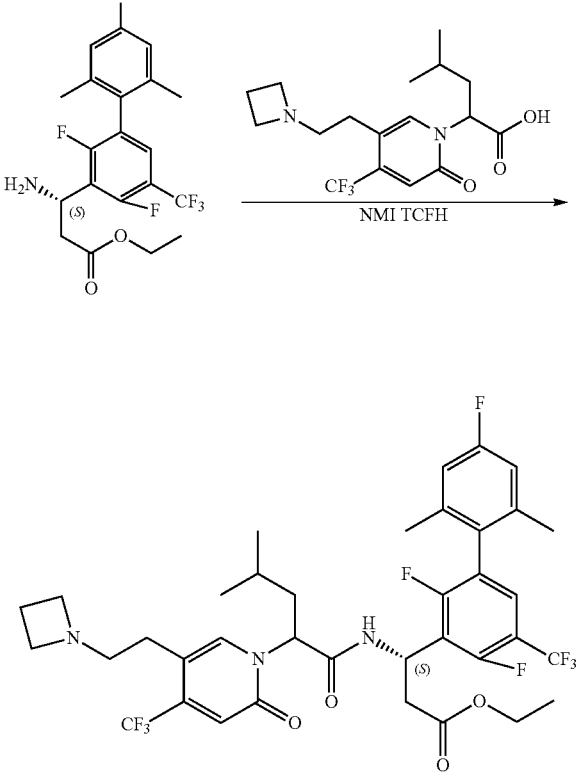

A mixture of ethyl (S)-3-amino-3-(2,4,4'-trifluoro-2',6'-dimethyl-5-(trifluoromethyl)-[1,1'-biphenyl]-3-yl)propanoate (120.0 mg, 0.29 mmol), 2-(5-(2-(azetidin-1-yl)ethyl)-2-oxo-4-(trifluoromethyl)pyridin-1(2H)-yl)-4-methylpentanoic acid (103.0 mg, 0.29 mmol), TCFH (162.4 mg, 0.58 mmol) and NMI (118.9 mg, 1.45 mmol) in CH$_3$CN (3 mL) was stirred at room temperature overnight. The reaction was concentrated in vacuo and the residue purified by reverse phase HPLC on a C18/40 g column (A: water 10 mM NH$_4$HCO$_3$, B: MeOH, 20~80%) to provide ethyl (3S)-3-(2-(5-(2-(azetidin-1-yl)ethyl)-2-oxo-4-(trifluoromethyl)pyridin-1(2H)-yl)-4-methylpentanamido)-3-(2,4,4'-trifluoro-2',6'-dimethyl-5-(trifluoromethyl)-[1,1'-biphenyl]-3-yl)propanoate as a light yellow solid (180.0 mg). Yield 82.6% (ESI 762.3 [M+H]$^+$).

Step 2: (3S)-3-(2-(5-(2-(azetidin-1-yl)ethyl)-2-oxo-4-(trifluoromethyl)pyridin-1(2H)-yl)-4-methylpentanamido)-3-(2,4,4'-trifluoro-2',6'-dimethyl-5-(trifluoromethyl)-[1,1'-biphenyl]-3-yl)propanoic Acid

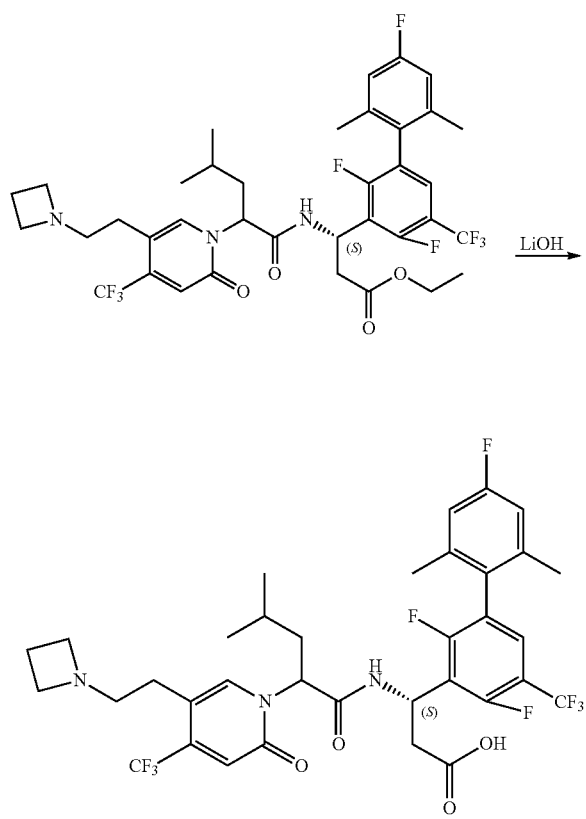

Ethyl (3S)-3-(2-(5-(2-(azetidin-1-yl)ethyl)-2-oxo-4-(trifluoromethyl)pyridin-1(2H)-yl)-4-methylpentanamido)-3-(2,4,4'-trifluoro-2',6'-dimethyl-5-(trifluoromethyl)-[1,1'-biphenyl]-3-yl)propanoate (180.0 mg, 0.24 mmol) was treated with LiOH—H$_2$O (30.2 mg, 0.72 mmol) in EtOH (3 mL) and water (1 mL) at room temperature for 1 hour. The reaction mixture was acidified to pH 4~5 with 2N HCl. The reaction was concentrated in vacuo and the residue purified by prep-HPLC A (30-90% MeCN) to give the diastereomeric products IV-P1 (34.0 mg) and IV-P2 (27.0 mg) as white solids.

IV-P1 ESI 734.2 (M+H)$^+$ $^1$H NMR (400 MHz, MeOD) δ 7.79 (s, 1H), 7.41 (t, J=7.5 Hz, 1H), 6.97-6.78 (m, 3H), 5.78-5.60 (m, 2H), 4.05 (t, J=7.8 Hz, 4H), 3.29-3.20 (m, 2H), 2.97-2.80 (m, 3H), 2.78-2.69 (m, 1H), 2.53-2.38 (m, 2H), 2.08-1.90 (m, 8H), 1.45-1.31 (m, 1H), 0.93 (t, J=6.4 Hz, 6H).

IV-P2 ESI 734.2 (M+H)$^+$ $^1$H NMR (400 MHz, MeOD) δ 7.73 (s, 1H), 7.48 (t, J=7.6 Hz, 1H), 7.00-6.86 (m, 3H), 5.95-5.85 (m, 1H), 5.63 (t, J=7.7 Hz, 1H), 4.12 (t, J=7.9 Hz, 4H), 3.50-3.34 (m, 2H), 2.96-2.73 (m, 3H), 2.65-2.55 (m, 1H), 2.52-2.40 (m, 2H), 2.03 (d, J=1.7 Hz, 6H), 1.96-1.85 (m, 1H), 1.78-1.65 (m, 1H), 1.40-1.25 (m, 1H), 0.95-0.82 (m, 6H).

3-93. Preparation of Preparation of (3S)-3-(2-(5-(3-(dimethylamino)propyl)-2-oxo-4-(trifluoromethyl)pyridin-1(2H)-yl)-4-methylpentanamido)-3-(2,3',4-trifluoro-2',4',5,6'-tetramethyl-[1,1'-biphenyl]-3-yl)propanoic Acid (Compounds IW-P1 and IW-P2)

Step 1: Ethyl (3S)-3-(2-(5-(3-(dimethylamino)propyl)-2-oxo-4-(trifluoromethyl)pyridin-1(2H)-yl)-4-methylpentanamido)-3-(2,3',4-trifluoro-2',4',5,6'-tetramethyl-[1,1'-biphenyl]-3-yl)propanoate

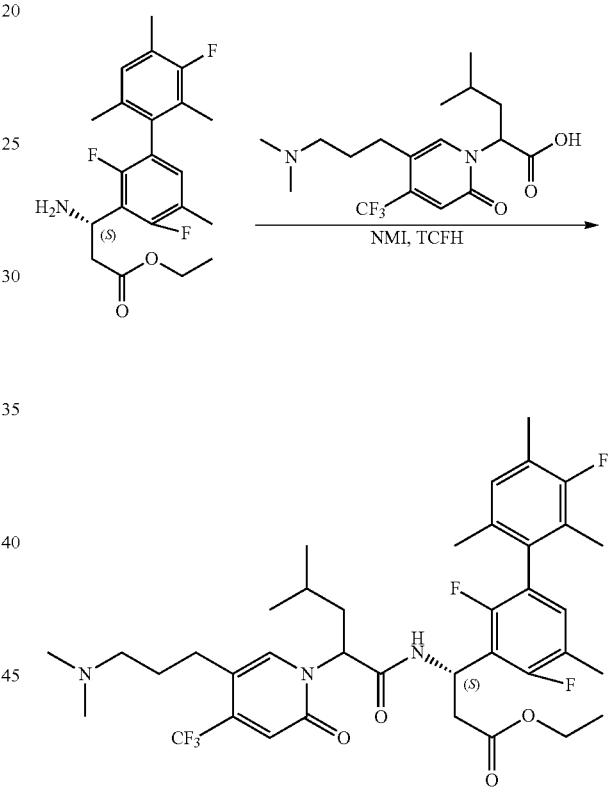

A mixture of ethyl (3S)-3-amino-3-(2,3',4-trifluoro-2',4',5,6'-tetramethyl-[1,1'-biphenyl]-3-yl)propanoate (170 mg, 0.45 mmol), 2-(5-(3-(dimethylamino)propyl)-2-oxo-4-(trifluoromethyl)pyridin-1(2H)-yl)-4-methylpentanoic acid (151 mg, 0.54 mmol), TCFH (213.2 mg, 0.76 mmol) and NMI (177 mg, 2.16 mmol) in CH$_3$CN (3 mL) was stirred at room temperature overnight. The reaction was concentrated in vacuo and the residue purified by reverse phase HPLC on a C18/40 g column (A: water 10 mM NH$_4$HCO$_3$, B: MeOH, 20~95%) to provide ethyl (3S)-3-(2-(5-(3-(dimethylamino)propyl)-2-oxo-4-(trifluoromethyl)pyridin-1(2H)-yl)-4-methylpentanamido)-3-(2,3',4-trifluoro-2',4',5,6'-tetramethyl-[1,1'-biphenyl]-3-yl)propanoate as a light yellow solid (210.0 mg). Yield 65% (ESI 724.2 [M+H]$^+$).

Step 2: (3S)-3-(2-(5-(3-(dimethylamino)propyl)-2-oxo-4-(trifluoromethyl)pyridin-1(2H)-yl)-4-methylpentanamido)-3-(2,3',4-trifluoro-2',4',5,6'-tetramethyl-[1,1'-biphenyl]-3-yl)propanoic Acid

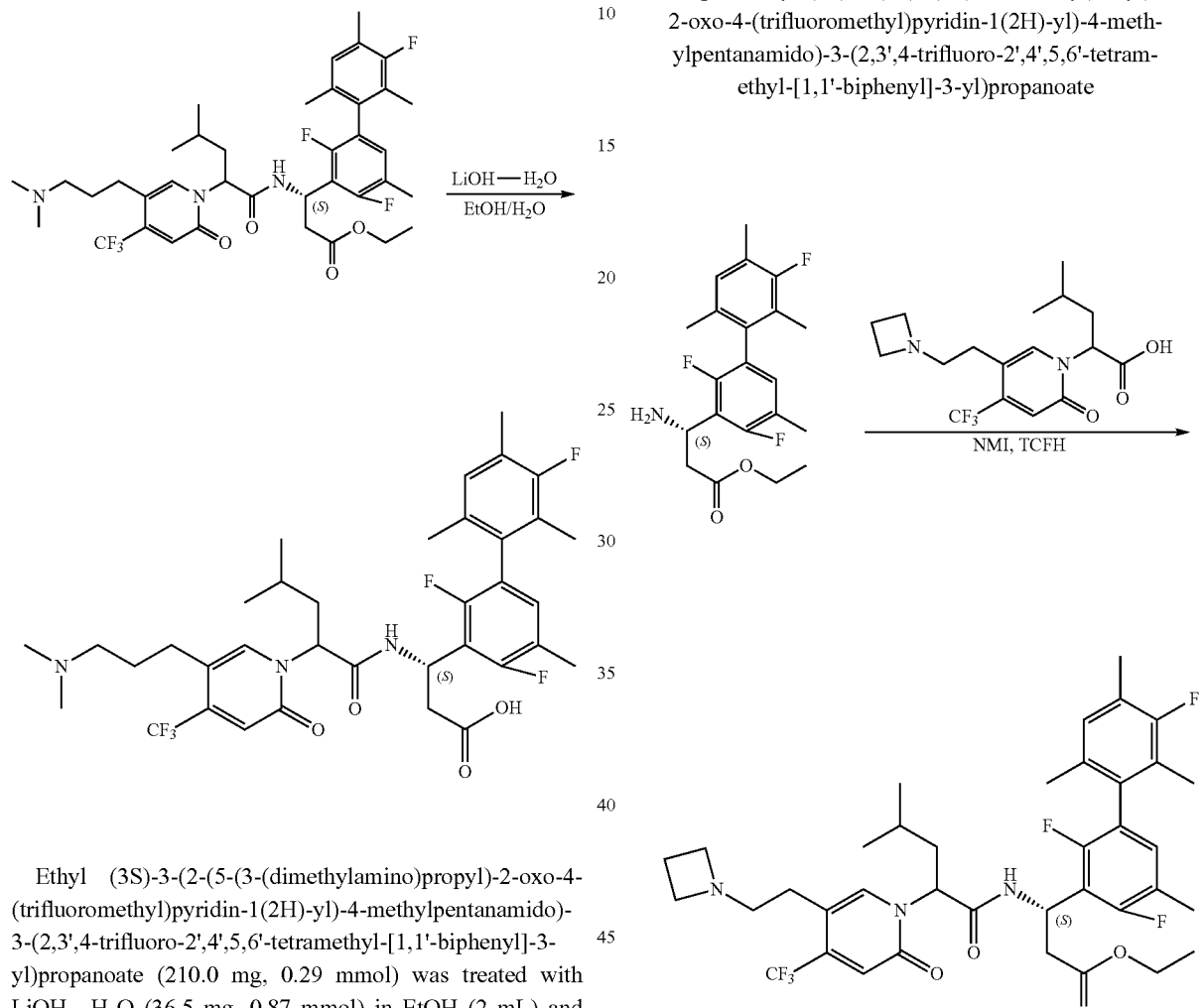

Ethyl (3S)-3-(2-(5-(3-(dimethylamino)propyl)-2-oxo-4-(trifluoromethyl)pyridin-1(2H)-yl)-4-methylpentanamido)-3-(2,3',4-trifluoro-2',4',5,6'-tetramethyl-[1,1'-biphenyl]-3-yl)propanoate (210.0 mg, 0.29 mmol) was treated with LiOH—H$_2$O (36.5 mg, 0.87 mmol) in EtOH (2 mL) and water (0.5 mL) at room temperature for 1 hour. The reaction mixture was acidified to pH 4~5 with 2N HCl. The reaction was concentrated in vacuo and the residue purified by prep-HPLC A (20-85% MeCN) to give the diastereomeric products IW-P1 (68 mg) and IW-P2 (52 mg) as white solids.

IW-P1 ESI 696.2 (M+H)$^+$ $^1$H NMR (400 MHz, MeOD) δ 7.79 (s, 1H), 6.98-6.80 (m, 3H), 5.83-5.69 (m, 2H), 3.09 (t, J=7.9 Hz, 2H), 3.00-2.90 (m, 1H), 2.81 (d, J=0.8 Hz, 6H), 2.73-2.58 (m, 3H), 2.26 (d, J=1.3 Hz, 6H), 2.15-1.78 (m, 10H), 1.43-1.30 (m, 1H), 1.00-0.90 (m, 6H).

IW-P2 ESI 696.2 (M+H)$^+$ $^1$H NMR (400 MHz, MeOD) δ 7.79 (s, 1H), 7.02-6.79 (m, 3H), 5.89-5.79 (m, 1H), 5.57 (t, J=7.6 Hz, 1H), 3.09-2.95 (m, 2H), 2.91-2.71 (m, 7H), 2.70-2.47 (m, 3H), 2.32-2.19 (m, 6H), 2.07-1.83 (m, 9H), 1.67-1.55 (m, 1H), 1.37-1.27 (m, 1H), 0.90-0.80 (m, 6H).

3-94. Preparation of Preparation of (3S)-3-(2-(5-(2-(azetidin-1-yl)ethyl)-2-oxo-4-(trifluoromethyl)pyridin-1(2H)-yl)-4-methylpentanamido)-3-(2,3',4-trifluoro-2',4',5,6'-tetramethyl-[1,1'-biphenyl]-3-yl)propanoic Acid (Compounds IX-P1 and IX-P2)

Step 1: Ethyl (3S)-3-(2-(5-(2-(azetidin-1-yl)ethyl)-2-oxo-4-(trifluoromethyl)pyridin-1(2H)-yl)-4-methylpentanamido)-3-(2,3',4-trifluoro-2',4',5,6'-tetramethyl-[1,1'-biphenyl]-3-yl)propanoate

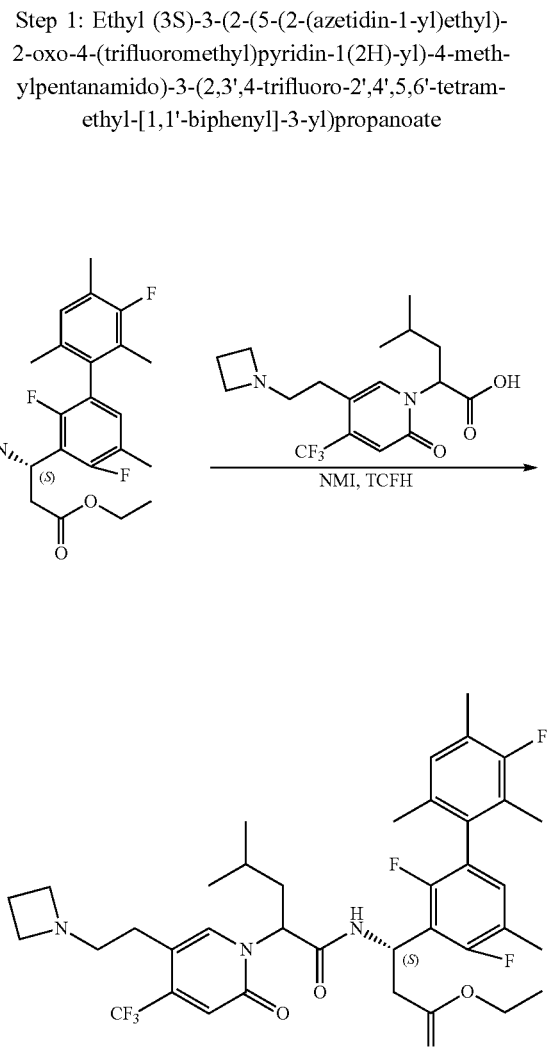

A mixture of ethyl (3S)-3-amino-3-(2,3',4-trifluoro-2',4',5,6'-tetramethyl-[1,1'-biphenyl]-3-yl)propanoate (170 mg, 0.45 mmol), 2-(5-(2-(azetidin-1-yl)ethyl)-2-oxo-4-(trifluoromethyl)pyridin-1(2H)-yl)-4-methylpentanoic acid (162 mg, 0.45 mmol), NMI (0.5 mL) and TCFH (241 mg, 0.86 mmol) in CH$_3$CN (3 mL) was stirred at room temperature for 2 hours. The solvent was concentrated in vacuo and the residue was purified by prep-HPLC A (50-80% CH3CN) to provide ethyl (3S)-3-(2-(5-(2-(azetidin-1-yl)ethyl)-2-oxo-4-(trifluoromethyl)pyridin-1(2H)-yl)-4-methylpentanamido)-3-(2,3',4-trifluoro-2',4',5,6'-tetramethyl-[1,1'-biphenyl]-3-yl)propanoate as a white solid (200 mg). Yield 62% (ESI 722.1 [M+H]$^+$).

555

Step 2: (3S)-3-(2-(5-(2-(azetidin-1-yl)ethyl)-2-oxo-4-(trifluoromethyl)pyridin-1(2H)-yl)-4-methylpentanamido)-3-(2,3',4-trifluoro-2',4',5,6'-tetramethyl-[1,1'-biphenyl]-3-yl)propanoic Acid

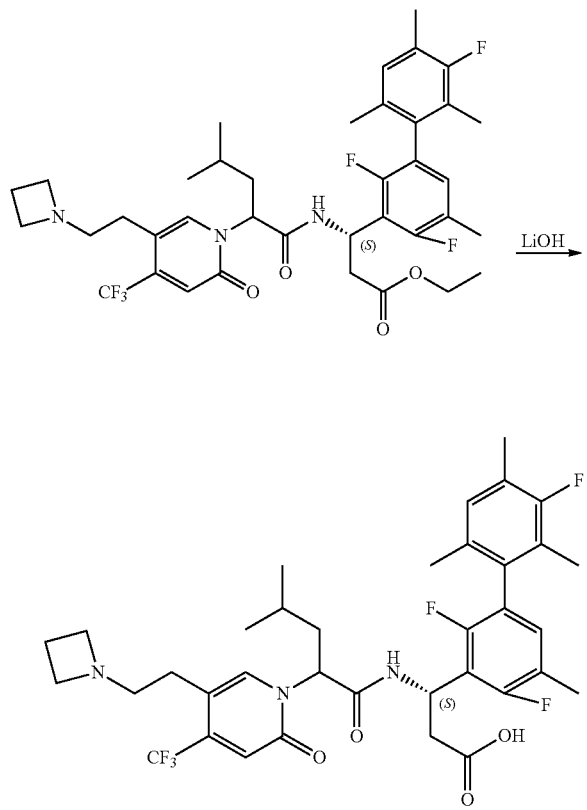

Ethyl (3S)-3-(2-(5-(2-(azetidin-1-yl)ethyl)-2-oxo-4-(trifluoromethyl)pyridin-1(2H)-yl)-4-methylpentanamido)-3-(2,3',4-trifluoro-2',4',5,6'-tetramethyl-[1,1'-biphenyl]-3-yl)propanoate (200 mg, 0.28 mmol) was treated with LiOH—H$_2$O (35 mg, 0.84 mmol) in MeOH (3.0 mL) and H$_2$O (1.0 mL) at room temperature for 2 hours. The reaction mixture was acidified to pH 5~6 with 1N HCl. The reaction was concentrated in vacuo and the residue purified by prep-HPLC A (50-80% CH$_3$CN) to give the diastereomeric products IX-P1 (42.0 mg) and IX-P2 (53.0 mg) as white solids.

IX-P1 ESI 694.2 (M+H)$^+$. $^1$H NMR (400 MHz, MeOD) δ 7.79 (s, 1H), 7.01-6.77 (m, 3H), 5.84-5.58 (m, 2H), 4.00 (t, J=8.0 Hz, 4H), 3.29-3.20 (m, 2H), 2.95-2.80 (m, 3H), 2.70-2.60 (m, 1H), 2.50-2.35 (m, 2H), 2.24 (d, J=3.4 Hz, 6H), 2.04-1.80 (m, 8H), 1.45-1.33 (m, 1H), 0.93 (t, J=6.1 Hz, 6H).

IX-P2 ESI 694.2 (M+H)$^+$. $^1$H NMR (400 MHz, MeOD) δ 7.69 (s, 1H), 7.00-6.90 (m, 3H), 5.97-5.85 (m, 1H), 5.61 (t, J=7.7 Hz, 1H), 4.10 (t, J=8.0 Hz, 4H), 3.47-3.34 (m, 2H), 2.96-2.73 (m, 3H), 2.57-2.37 (m, 3H), 2.31-2.17 (m, 6H), 1.99-1.84 (m, 7H), 1.78-1.65 (m, 1H), 1.42-1.30 (m, 1H), 0.93-0.82 (m, 6H).

556

3-95. Preparation of ((3S)-3-(2-(5-(2-(azetidin-1-yl)ethyl)-2-oxo-4-(trifluoromethyl)pyridin-1(2H)-yl)-4-methylpentanamido)-3-(2,2',4-trifluoro-4',6'-dimethyl-5-(trifluoromethyl)biphenyl-3-yl)propanoic Acid (Compounds IY-P1 and IY-P2)

Step 1: (3S)-ethyl 3-(2-(5-(2-(azetidin-1-yl)ethyl)-2-oxo-4-(trifluoromethyl)pyridin-1(2H)-yl)-4-methylpentanamido)-3-(2,2',4-trifluoro-4',6'-dimethyl-5-(trifluoromethyl)biphenyl-3-yl)propanoate

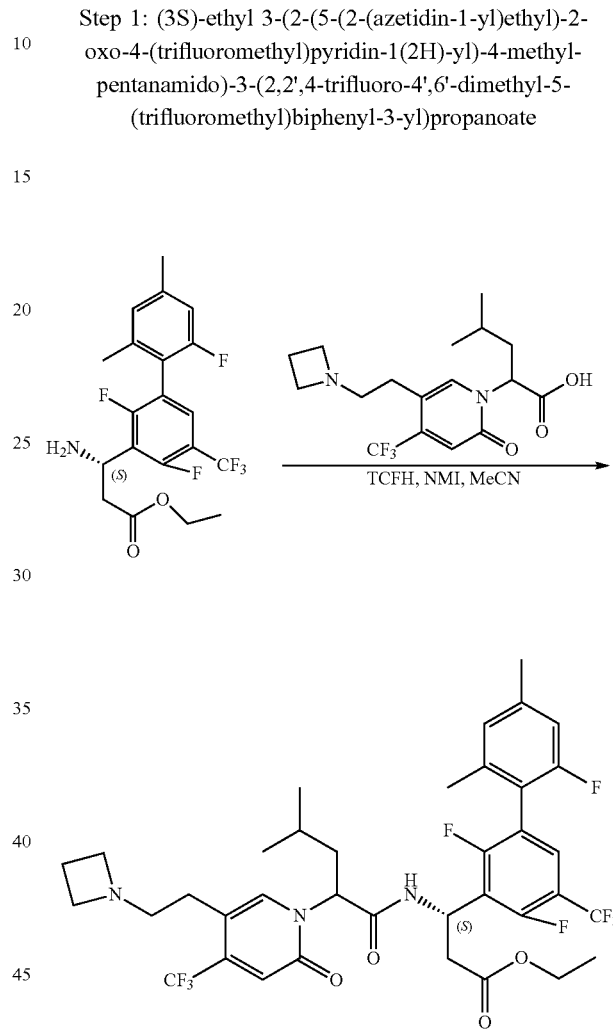

A mixture of 2-(5-(2-(azetidin-1-yl)ethyl)-2-oxo-4-(trifluoromethyl)pyridin-1(2H)-yl)-4-methylpentanoic acid (115 mg, 0.32 mmol), (3S)-ethyl 3-amino-3-(2,2',4-trifluoro-4',6'-dimethyl-5-(trifluoromethyl)biphenyl-3-yl)propanoate (120 mg, 0.29 mmol), NMI (71 mg, 0.87 mmol) and TCFH (98 mg, 0.35 mmol) in CH$_3$CN (4 mL) was stirred at room temperature for 2 hours. The solvent was concentrated in vacuo and the residue purified by reverse phase HPLC on a C18/40 g column (A: water 10 mM NH$_4$HCO$_3$, B: CH$_3$CN, 0~100%) to provide (3S)-ethyl 3-(2-(5-(2-(azetidin-1-yl)ethyl)-2-oxo-4-(trifluoromethyl)pyridin-1(2H)-yl)-4-methylpentanamido)-3-(2,2',4-trifluoro-4',6'-dimethyl-5-(trifluoromethyl)biphenyl-3-yl)propanoate as a yellow oil (140 mg). Yield 64% (ESI 762.3 [M+H]$^+$).

Step 2: ((3S)-3-(2-(5-(2-(azetidin-1-yl)ethyl)-2-oxo-4-(trifluoromethyl)pyridin-1(2H)-yl)-4-methylpentanamido)-3-(2,2',4-trifluoro-4',6'-dimethyl-5-(trifluoromethyl)biphenyl-3-yl)propanoic acid 3-96. Preparation of (3S)-3-(2-(5-(2-(dimethylamino)ethyl)-2-oxo-4-(trifluoromethyl)pyridin-1(2H)-yl)-4-methylpentanamido)-3-(2,2',4-trifluoro-4',6'-dimethyl-5-(trifluoromethyl)biphenyl-3-yl)propanoic Acid (Compounds IZ-P1 and IZ-P2)

Step 1: (3S)-ethyl 3-(2-(5-(2-(dimethylamino)ethyl)-2-oxo-4-(trifluoromethyl)pyridin-1(2H)-yl)-4-methylpentanamido)-3-(2,2',4-trifluoro-4',6'-dimethyl-5-(trifluoromethyl)biphenyl-3-yl)propanoate

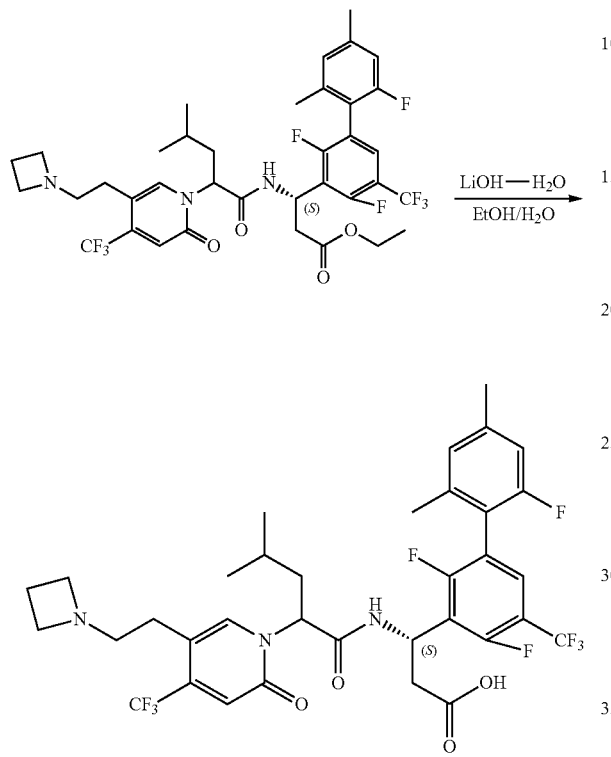

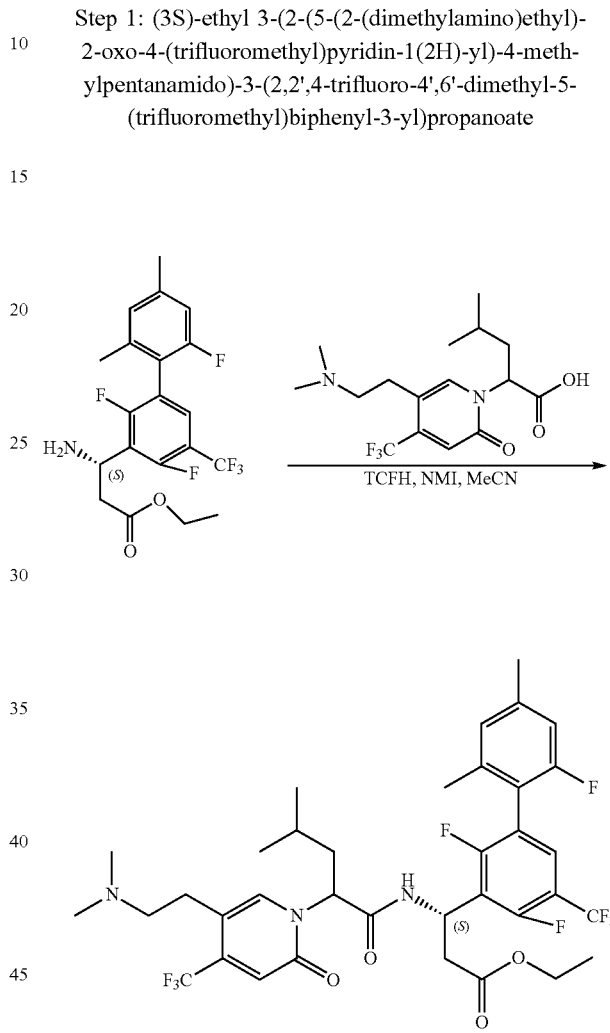

(3S)-ethyl 3-(2-(5-(2-(azetidin-1-yl)ethyl)-2-oxo-4-(trifluoromethyl)pyridin-1(2H)-yl)-4-methylpentanamido)-3-(2,2',4-trifluoro-4',6'-dimethyl-5-(trifluoromethyl)biphenyl-3-yl)propanoate (140 mg, 0.19 mmol) was treated with LiOH—H$_2$O (32 mg, 0.76 mmol) in EtOH (3 mL) and H$_2$O (1 mL) at room temperature for 1 hour. The reaction mixture was acidified to pH 5~6 with 1N HCl. The reaction was concentrated in vacuo and the residue purified by prep-HPLC A (30-60% CH$_3$CN) to give the diastereomeric products IY-P1 (36 mg) and IY-P2 (51 mg) as white solids.

IY-P1 ESI 734.2 (M+H)$^+$. $^1$HNMR (400 MHz, MeOD) δ 7.81 (s, 1H), 7.55-7.45 (m, 1H), 6.98 (s, 1H), 6.89-6.80 (m, 2H), 5.79-5.67 (m, 2H), 4.12-3.97 (m, 4H), 3.35-3.12 (m, 2H), 3.00-2.66 (m, 4H), 2.52-2.27 (m, 5H), 2.16-1.88 (m, 5H), 1.44-1.30 (m, 1H), 0.98-0.90 (m, 6H).

IY-P2 ESI 734.2 (M+H)$^+$. $^1$H NMR (400 MHz, MeOD) δ 7.73 (s, 1H), 7.55 (t, J=7.5 Hz, 1H), 7.01 (s, 1H), 6.99-6.85 (m, 2H), 5.97-5.82 (m, 1H), 5.66 (t, J=7.7 Hz, 1H), 4.12 (t, J=8.0 Hz, 4H), 3.45-3.31 (m, 2H), 2.97-2.76 (m, 3H), 2.66-2.57 (m, 1H), 2.53-2.39 (m, 2H), 2.37 (s, 3H), 2.11 (d, J=5.0 Hz, 3H), 1.97-1.86 (m, 1H), 1.78-1.67 (m, 1H), 1.40-1.27 (m, 1H), 0.95-0.81 (m, 6H).

A mixture of 2-(5-(2-(dimethylamino)ethyl)-2-oxo-4-(trifluoromethyl)pyridin-1(2H)-yl)-4-methylpentanoic acid (110 mg, 0.32 mmol), (3S)-ethyl 3-amino-3-(2,2',4-trifluoro-4',6'-dimethyl-5-(trifluoromethyl)biphenyl-3-yl)propanoate (120 mg, 0.29 mmol), NMI (71 mg, 0.87 mmol) and TCFH (98 mg, 0.35 mmol) in CH$_3$CN (4 mL) was stirred at room temperature for 2 hours. The solvent was concentrated in vacuo and the residue purified by reverse phase HPLC on a C18/40 g column (A: water 10 mM NH4HCO3, B: CH3CN, 0~100%) to provide (3S)-ethyl 3-(2-(5-(2-(dimethylamino)ethyl)-2-oxo-4-(trifluoromethyl)pyridin-1(2H)-yl)-4-methylpentanamido)-3-(2,2',4-trifluoro-4',6'-dimethyl-5-(trifluoromethyl)biphenyl-3-yl)propanoate as a yellow oil (140 mg). Yield 65% (ESI 750.3 [M+H]$^+$).

Step 2: (3S)-3-(2-(5-(2-(dimethylamino)ethyl)-2-oxo-4-(trifluoromethyl)pyridin-1(2H)-yl)-4-methylpentanamido)-3-(2,2',4-trifluoro-4',6'-dimethyl-5-(trifluoromethyl)biphenyl-3-yl)propanoic acid 3-97. Preparation of (3S)-3-(2,4-difluoro-2',5,6'-trimethyl-4'-(trifluoromethyl)biphenyl-3-yl)-3-(2-(5-(2-(dimethylamino)ethyl)-2-oxo-4-(trifluoromethyl)pyridin-(2H)-yl)-4-methylpentanamido) Propanoic Acid (Compounds JA-P1 and JA-P2)

Step 1: (3S)-ethyl 3-(2,4-difluoro-2',5,6'-trimethyl-4'-(trifluoromethyl)biphenyl-3-yl)-3-(2-(5-(2-(dimethylamino)ethyl)-2-oxo-4-(trifluoromethyl)pyridin-1(2H)-yl)-4-methylpentanamido)propanoate

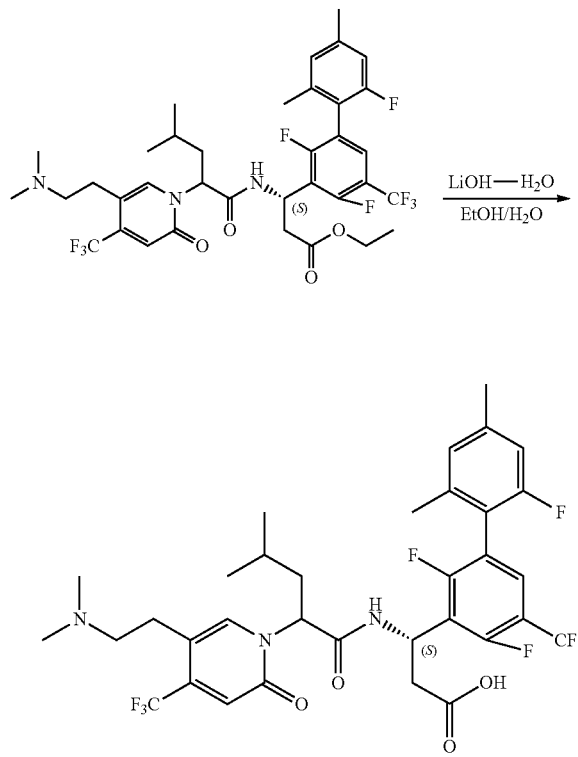

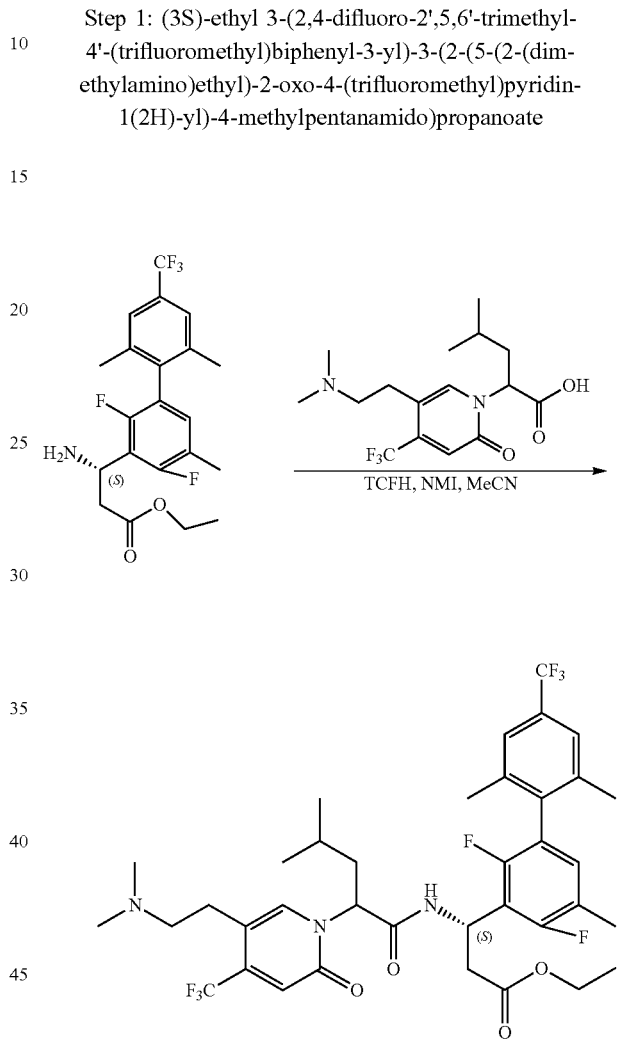

(3S)-ethyl 3-(2-(5-(2-(dimethylamino)ethyl)-2-oxo-4-(trifluoromethyl)pyridin-1(2H)-yl)-4-methylpentanamido)-3-(2,2',4-trifluoro-4',6'-dimethyl-5-(trifluoromethyl)biphenyl-3-yl)propanoate (140 mg, 0.19 mmol) was treated with LiOH—H$_2$O (32 mg, 0.76 mmol) in EtOH (3 mL) and H$_2$O (1 mL) at room temperature for 1 hour. The reaction mixture was acidified to pH 5~6 with 1N HCL. The reaction was concentrated in vacuo and the residue purified by prep-HPLC A (30-60% CH$_3$CN) to give the diastereomeric products IZ-P1 (38 mg) and IZ-P2 (52 mg) as white solids.

IZ-P1 ESI 722.2 (M+H)$^+$. $^1$H NMR (400 MHz, MeOD) δ 7.86 (s, 1H), 7.56-7.36 (m, 1H), 6.97 (s, 1H), 6.89-6.80 (m, 2H), 5.79-5.64 (m, 2H), 3.18-3.03 (m, 2H), 3.02-2.87 (m, 3H), 2.81-2.69 (m, 7H), 2.35 (s, 3H), 2.12-1.90 (m, 5H), 1.48-1.31 (m, 1H), 0.99-0.87 (m, 6H).

IZ-P2 ESI 722.2 (M+H)$^+$. $^1$H NMR (400 MHz, MeOD) δ 7.84 (s, 1H), 7.53 (t, J=7.5 Hz, 1H), 7.00 (s, 1H), 6.94-6.83 (m, 2H), 5.87-5.77 (m, 1H), 5.73-5.63 (m, 1H), 3.27-3.06 (m, 2H), 3.01-2.92 (m, 2H), 2.91-2.73 (m, 7H), 2.73-2.60 (m, 1H), 2.36 (s, 3H), 2.11 (d, J=6.6 Hz, 3H), 1.97-1.63 (m, 2H), 1.43-1.20 (m, 1H), 0.98-0.82 (m, 6H).

A mixture of (S)-ethyl 3-amino-3-(2,4-difluoro-2',5,6'-trimethyl-4'-(trifluoromethyl)biphenyl-3-yl)propanoate (170 mg, 0.41 mmol), 2-(5-(2-(dimethylamino)ethyl)-2-oxo-4-(trifluoromethyl)pyridin-1(2H)-yl)-4-methylpentanoic acid (140 mg, 0.41 mmol), NMI (100 mg, 1.23 mmol) and TCFH (140 mg, 0.49 mmol) in CH$_3$CN (6 mL) was stirred at room temperature for 2 hours. The solvent was concentrated in vacuo and the residue purified by reverse phase HPLC on a C18/40 g column (A: water 10 mM NH4HCO3, B: CH3CN, 0~100%) to provide (3S)-ethyl 3-(2,4-difluoro-2',5,6'-trimethyl-4'-(trifluoromethyl)biphenyl-3-yl)-3-(2-(5-(2-(dimethylamino)ethyl)-2-oxo-4-(trifluoromethyl)pyridin-1(2H)-yl)-4-methylpentanamido)propanoate as a yellow oil (200 mg). Yield 66% (ESI 746.1 [M+H]$^+$).

Step 2: (3S)-3-(2,4-difluoro-2',5,6'-trimethyl-4'-(trifluoromethyl)biphenyl-3-yl)-3-(2-(5-(2-(dimethylamino)ethyl)-2-oxo-4-(trifluoromethyl)pyridin-1(2H)-yl)-4-methylpentanamido)propanoic acid 3-98. Preparation of (3S)-3-(2-(5-(2-(5-azaspiro[2.3]hexan-5-yl)ethyl)-2-oxo-4-(trifluoromethyl)pyridin-1(2H)-yl)-4-methylpentanamido)-3-(2,4-difluoro-2',4',5,6'-tetramethylbiphenyl-3-yl)propanoic Acid (Compounds JB-P1 and JB-P2)

Step 1: (3S)-ethyl 3-(2-(5-(2-(5-azaspiro[2.3]hexan-5-yl)ethyl)-2-oxo-4-(trifluoromethyl)pyridin-1(2H)-yl)-4-methylpentanamido)-3-(2,4-difluoro-2',4',5,6'-tetramethylbiphenyl-3-yl)propanoate

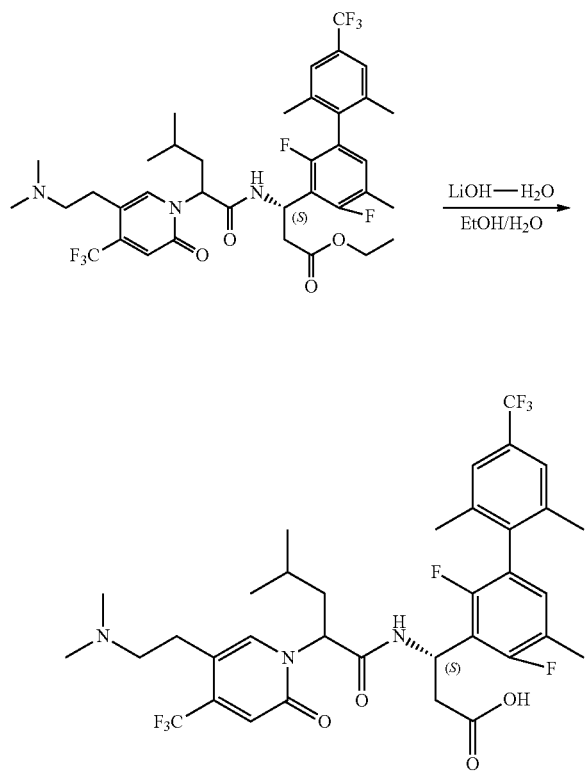

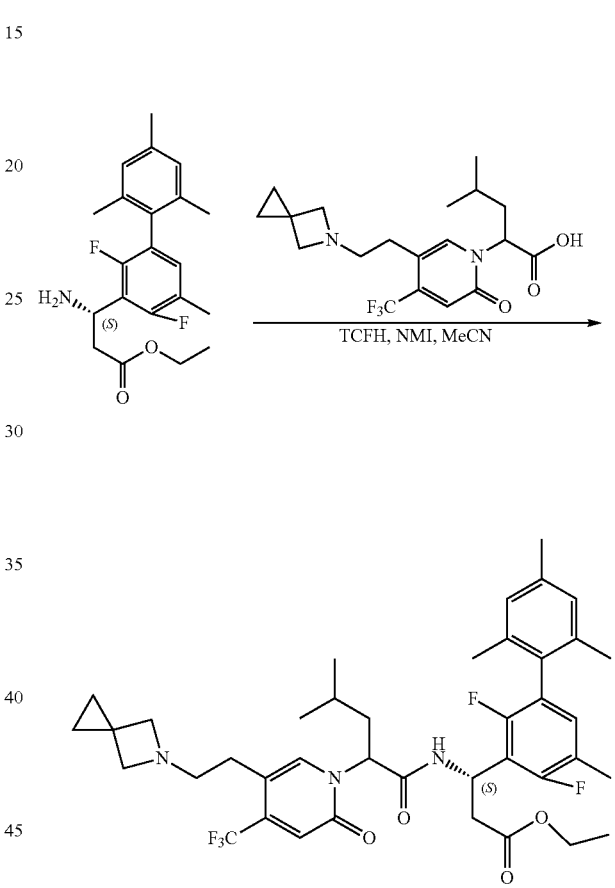

(3S)-ethyl 3-(2,4-difluoro-2',5,6'-trimethyl-4'-(trifluoromethyl)biphenyl-3-yl)-3-(2-(5-(2-(dimethylamino)ethyl)-2-oxo-4-(trifluoromethyl)pyridin-1(2H)-yl)-4-methylpentanamido)propanoate (200 mg, 0.27 mmol) was treated with LiOH—H$_2$O (45 mg, 1.08 mmol) in EtOH (3 mL) and H$_2$O (1 mL) at room temperature for 1 hour. The reaction mixture was acidified to pH 5~6 with 1N HCl. The reaction was concentrated in vacuo and the residue purified by prep-HPLC A (30-60% CH$_3$CN) to give the diastereomeric products JA-P1 (56 mg) and JA-P2 (65 mg) as white solids.

JA-P1 ESI 718.3 (M+H)$^+$. 1H NMR (400 MHz, MeOD) δ 7.87 (s, 1H), 7.39 (d, J=2.4 Hz, 2H), 6.92 (t, J=8.1 Hz, 1H), 6.82 (s, 1H), 5.75-5.65 (m, 2H), 3.17-2.83 (m, 5H), 2.82-2.65 (m, 7H), 2.25 (s, 3H), 2.07 (s, 3H), 2.02-1.91 (m, 5H), 1.54-1.27 (m, 1H), 0.93 (t, J=6.8 Hz, 6H).

JA-P2 ESI 718.3 (M+H)$^+$. 1H NMR (400 MHz, MeOD) δ 7.83 (s, 1H), 7.42 (s, 2H), 6.98 (t, J=8.1 Hz, 1H), 6.90 (s, 1H), 5.88-5.84 (m, 1H), 5.63 (t, J=7.7 Hz, 1H), 3.29-3.09 (m, 2H), 3.04-2.92 (m, 2H), 2.88-2.76 (m, 7H), 2.62-2.52 (m, 1H), 2.29 (s, 3H), 2.09 (d, J=3.4 Hz, 6H), 1.95-1.68 (m, 2H), 1.40-1.25 (m, 1H), 0.92-0.82 (m, 6H).

A mixture of (S)-ethyl 3-amino-3-(2,4-difluoro-2',4',5,6'-tetramethylbiphenyl-3-yl)propanoate (160 mg, 0.43 mmol), 2-(5-(2-(5-azaspiro[2.3]hexan-5-yl)ethyl)-2-oxo-4-(trifluoromethyl)pyridin-1(2H)-yl)-4-methylpentanoic acid (150 mg, 0.39 mmol), NMI (100 mg, 1.17 mmol) and TCFH (130 mg, 0.47 mmol) in CH$_3$CN (6 mL) was stirred at room temperature for 2 hours. The solvent was concentrated in vacuo and the residue purified by reverse phase HPLC on a C18/40 g column (A: water 10 mM NH4HCO3, B: CH3CN, 0~100%) to provide (3S)-ethyl 3-(2-(5-(2-(5-azaspiro[2.3]hexan-5-yl)ethyl)-2-oxo-4-(trifluoromethyl)pyridin-1(2H)-yl)-4-methylpentanamido)-3-(2,4-difluoro-2',4',5,6'-tetramethylbiphenyl-3-yl)propanoate as a yellow oil (210 mg). Yield 75% (ESI 730.3 [M+H]$^+$).

Step 2: (3S)-3-(2-(5-(2-(5-azaspiro[2.3]hexan-5-yl)ethyl)-2-oxo-4-(trifluoromethyl)pyridin-1(2H)-yl)-4-methylpentanamido)-3-(2,4-difluoro-2',4',5,6'-tetramethylbiphenyl-3-yl)propanoic Acid

3-99. Preparation of (3S)-3-(2,4-difluoro-2',3',5,5',6'-pentamethylbiphenyl-3-yl)-3-(2-(5-(2-(dimethylamino)ethyl)-2-oxo-4-(trifluoromethyl)pyridin-1(2H)-yl)-4-methylpentanamido)propanoic Acid (Compounds JC-P1 and JC-P2)

Step 1: (3S)-ethyl 3-(2,4-difluoro-2',3',5,5',6'-pentamethylbiphenyl-3-yl)-3-(2-(5-(2-(dimethylamino)ethyl)-2-oxo-4-(trifluoromethyl)pyridin-1(2H)-yl)-4-methylpentanamido)propanoate

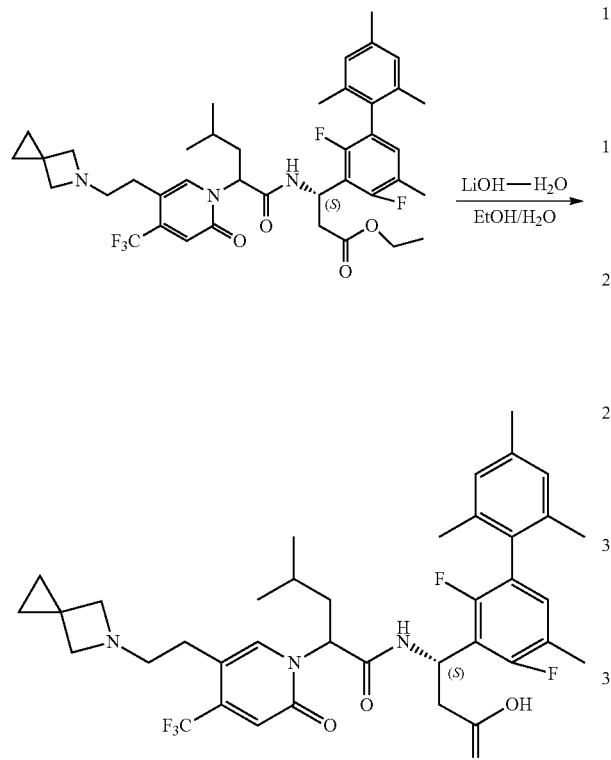

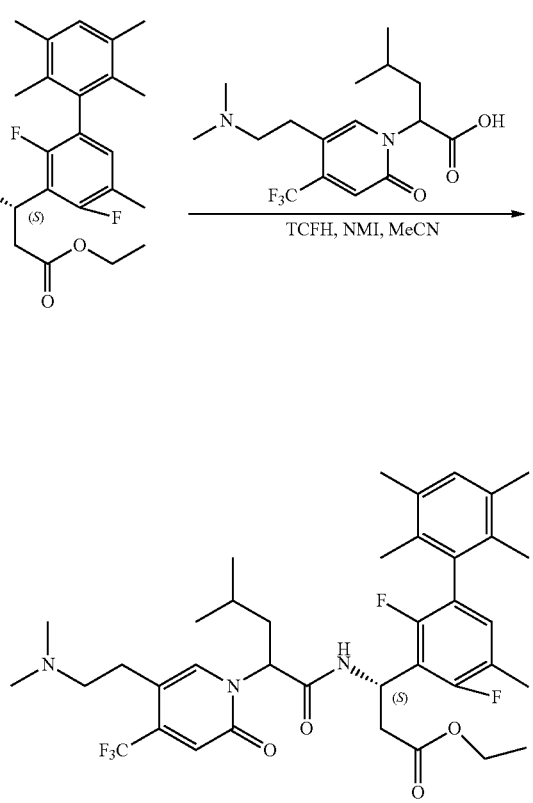

(3S)-ethyl 3-(2-(5-(2-(5-azaspiro[2.3]hexan-5-yl)ethyl)-2-oxo-4-(trifluoromethyl)pyridin-1(2H)-yl)-4-methylpentanamido)-3-(2,4-difluoro-2',4',5,6'-tetramethylbiphenyl-3-yl)propanoate (210 mg, 0.29 mmol) was treated with LiOH—H$_2$O (37 mg, 0.87 mmol) in EtOH (3 mL) and H$_2$O (1 mL) at room temperature for 1 hour. The reaction mixture was acidified to pH 5~6 with 1N HCl. The reaction was concentrated in vacuo and the residue purified by prep-HPLC A (30-60% CH$_3$CN) to give the diastereomeric products JB-P1 (50 mg) and JB-P2 (55 mg) as white solids.

JB-P1 ESI 702.3 (M+H)$^+$. $^1$H NMR (400 MHz, MeOD) δ 7.83 (s, 1H), 6.97-6.76 (m, 4H), 5.80-5.61 (m, 2H), 4.04 (s, 4H), 3.45-3.32 (m, 2H), 3.12-2.81 (m, 3H), 2.70-2.61 (m, 1H), 2.28 (s, 3H), 2.24 (s, 3H), 2.01-1.93 (m, 5H), 1.89 (s, 3H), 1.58-1.26 (m, 1H), 0.98-0.89 (m, 6H), 0.72 (s, 4H).

JB-P2 ESI 702.3 (M+H)$^+$. $^1$H NMR (400 MHz, MeOD) δ 7.75 (s, 1H), 7.07-6.86 (m, 4H), 5.96-5.89 (m, 1H), 5.64 (t, J=7.7 Hz, 1H), 4.34-4.02 (m, 4H), 3.66-3.37 (m, 2H), 3.11-2.71 (m, 3H), 2.56-2.48 (m, 1H), 2.37-2.19 (m, 6H), 2.10-1.87 (m, 7H), 1.77-1.60 (m, 1H), 1.46-1.30 (m, 1H), 1.00-0.64 (m, 10H).

A mixture of (S)-ethyl 3-amino-3-(2,4-difluoro-2',3',5,5',6'-pentamethylbiphenyl-3-yl)propanoate (160 mg, 0.43 mmol), 2-(5-(2-(dimethylamino)ethyl)-2-oxo-4-(trifluoromethyl)pyridin-1(2H)-yl)-4-methylpentanoic acid (150 mg, 0.43 mmol), NMI (110 mg, 1.29 mmol) and TCFH (150 mg, 0.52 mmol) in CH$_3$CN (6 mL) was stirred at room temperature for 2 hours. The solvent was concentrated in vacuo and the residue purified by reverse phase HPLC on a C18/40 g column (A: water 10 mM NH4HCO3, B: CH3CN, 0~100%) to provide (3S)-ethyl 3-(2,4-difluoro-2',3',5,5',6'-pentamethylbiphenyl-3-yl)-3-(2-(5-(2-(dimethylamino)ethyl)-2-oxo-4-(trifluoromethyl)pyridin-1(2H)-yl)-4-methylpentanamido)propanoate as a yellow oil (200 mg). Yield 69% (ESI 706.2 [M+H]$^+$).

Step 2: (3S)-3-(2,4-difluoro-2',3',5,5',6'-pentamethylbiphenyl-3-yl)-3-(2-(5-(2-(dimethylamino)ethyl)-2-oxo-4-(trifluoromethyl)pyridin-1(2H)-yl)-4-methylpentanamido)propanoic acid 3-100. Preparation of (3S)-3-(2-(5-(2-(azetidin-1-yl)ethyl)-2-oxo-4-(trifluoromethyl)pyridin-1(2H)-yl)-4-fluoro-4-methylpentanamido)-3-(2,4-difluoro-2',5,6'-trimethyl-4'-(trifluoromethyl)biphenyl-3-yl) propanoic Acid (Compounds JD-P1 and JD-P2)

Step 1: (3S)-ethyl 3-(2-(5-(2-(azetidin-1-yl)ethyl)-2-oxo-4-(trifluoromethyl)pyridin-1(2H)-yl)-4-fluoro-4-methylpentanamido)-3-(2,4-difluoro-2',5,6'-trimethyl-4'-(trifluoromethyl)biphenyl-3-yl)propanoate

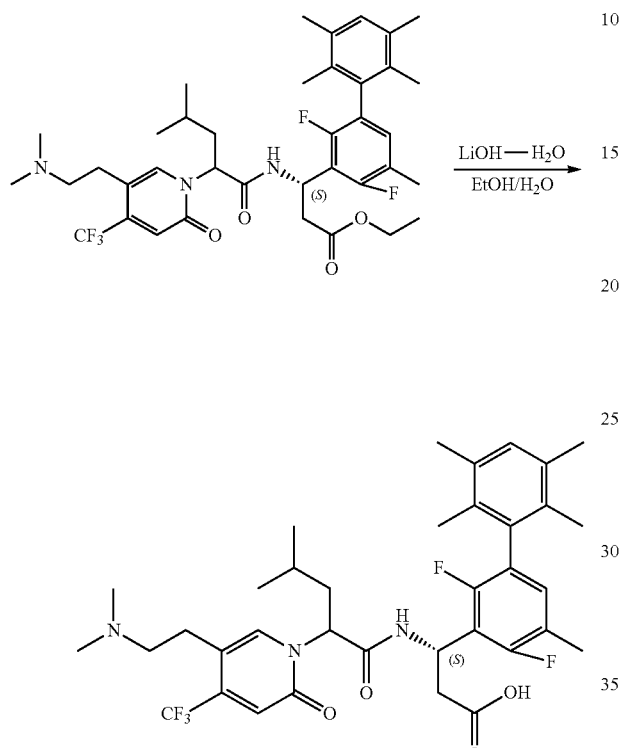

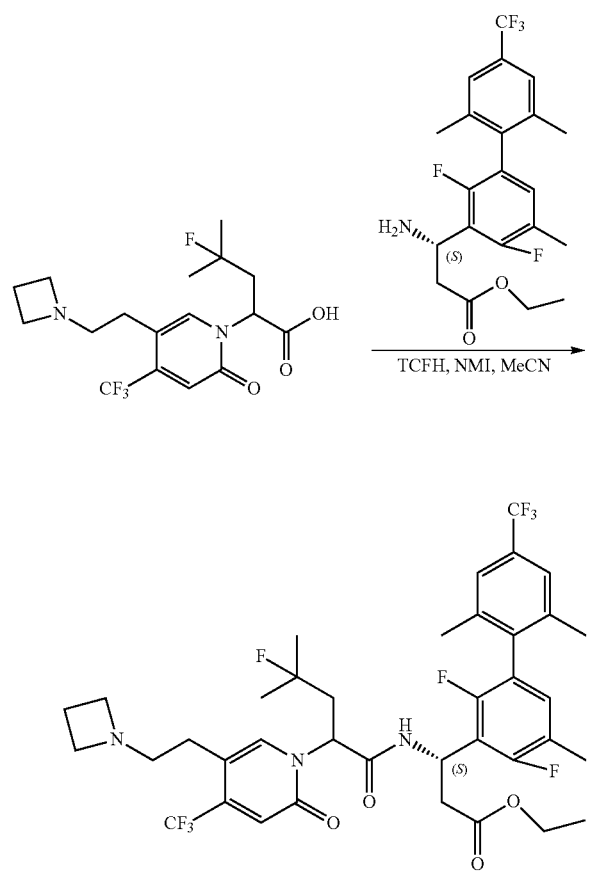

(3S)-ethyl 3-(2,4-difluoro-2',3',5,5',6'-pentamethylbiphenyl-3-yl)-3-(2-(5-(2-(dimethylamino)ethyl)-2-oxo-4-(trifluoromethyl)pyridin-1(2H)-yl)-4-methylpentanamido)propanoate (200 mg, 0.28 mmol) was treated with LiOH—H$_2$O (47 mg, 1.12 mmol) in EtOH (3 mL) and H$_2$O (1 mL) at room temperature for 1 hour. The reaction mixture was acidified to pH 5~6 with 1N HCl. The reaction was concentrated in vacuo and the residue purified by prep-HPLC A (30-60% CH$_3$CN) to give the diastereomeric products JC-P1 (56 mg) and JC-P2 (64 mg) as white solids.

JC-P1 ESI 678.3 (M+H)$^+$, $^1$H NMR (400 MHz, MeOD) δ 7.89 (s, 1H), 6.97 (s, 1H), 6.88-6.79 (m, 2H), 5.84-5.63 (m, 2H), 3.18-2.89 (m, 5H), 2.79-2.65 (m, 7H), 2.32-2.17 (m, 9H), 1.98 (t, J=7.6 Hz, 2H), 1.86 (s, 3H), 1.76 (s, 3H), 1.47-1.34 (m, 1H), 0.95 (t, J=6.9 Hz, 6H).

JC-P2 ESI 678.3 (M+H)$^+$. $^1$H NMR (400 MHz, MeOD) δ 7.86 (s, 1H), 6.99 (s, 1H), 6.94-6.84 (m, 2H), 5.91-5.84 (m, 1H), 5.66 (t, J=7.7 Hz, 1H), 3.28-3.10 (m, 2H), 3.09-2.92 (m, 2H), 2.89-2.73 (m, 7H), 2.70-2.52 (m, 1H), 2.28 (s, 3H), 2.25 (s, 6H), 1.99-1.82 (m, 7H), 1.83-1.61 (m, 1H), 1.49-1.25 (m, 1H), 0.94-0.84 (m, 6H).

A mixture of 2-(5-(2-(azetidin-1-yl)ethyl)-2-oxo-4-(trifluoromethyl)pyridin-1(2H)-yl)-4-fluoro-4-methylpentanoic acid (100 mg, 0.26 mmol), (S)-ethyl 3-amino-3-(2,4-difluoro-2',5,6'-trimethyl-4'-(trifluoromethyl)biphenyl-3-yl) propanoate (120 mg, 0.29 mmol), NMI (64 mg, 0.78 mmol) and TCFH (90 mg, 0.32 mmol) in CH$_3$CN (4 mL) was stirred at room temperature for 2 hours. The solvent was concentrated in vacuo and the residue purified by reverse phase HPLC on a C18/40 g column (A: water 10 mM NH4HCO3, B: CH3CN, 0~100%) to provide (3S)-ethyl 3-(2-(5-(2-(azetidin-1-yl)ethyl)-2-oxo-4-(trifluoromethyl)pyridin-1(2H)-yl)-4-fluoro-4-methylpentanamido)-3-(2,4-difluoro-2',5,6'-trimethyl-4'-(trifluoromethyl)biphenyl-3-yl) propanoate as a yellow oil (80 mg). Yield 39% (ESI 776.1 [M+H]$^+$).

Step 2: (3S)-3-(2-(5-(2-(azetidin-1-yl)ethyl)-2-oxo-4-(trifluoromethyl)pyridin-1(2H)-yl)-4-fluoro-4-methylpentanamido)-3-(2,4-difluoro-2',5,6'-trimethyl-4'-(trifluoromethyl)biphenyl-3-yl)propanoic acid 3-101. Preparation of (3S)-3-(2-(5-(2-(azetidin-1-yl)ethyl)-2-oxo-4-(trifluoromethyl)pyridin-1(2H)-yl)-4-methylpentanamido)-3-(2,4-difluoro-2',5,6'-trimethyl-4'-(trifluoromethyl)biphenyl-3-yl)propanoic Acid (Compounds JE-P1 and JE-P2)

Step 1: (3S)-ethyl 3-(2-(5-(2-(azetidin-1-yl)ethyl)-2-oxo-4-(trifluoromethyl)pyridin-1(2H)-yl)-4-methylpentanamido)-3-(2,4-difluoro-2',5,6'-trimethyl-4'-(trifluoromethyl)biphenyl-3-yl)propanoate

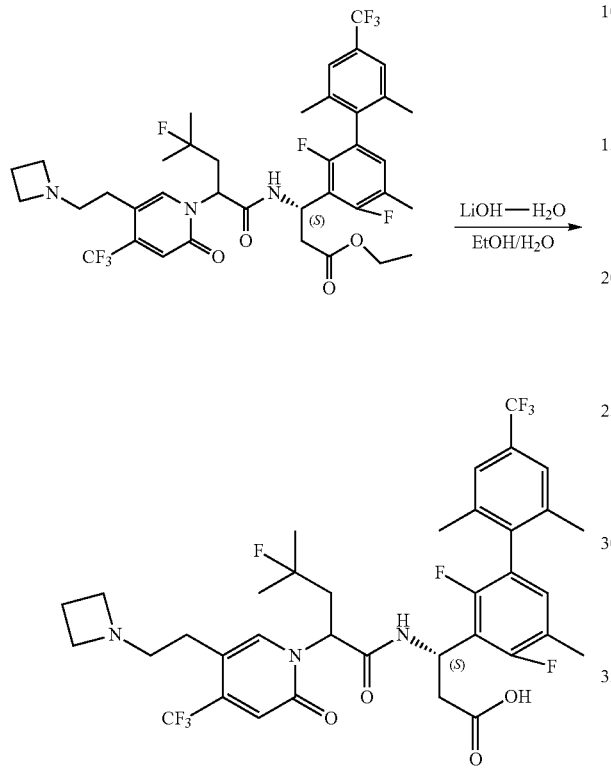

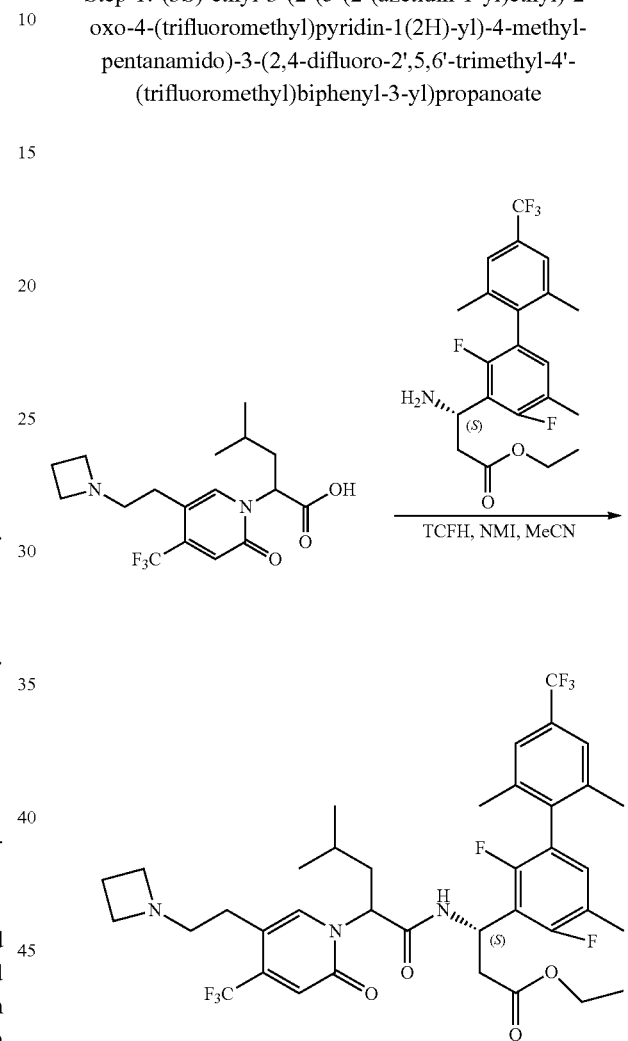

(3S)-ethyl 3-(2-(5-(2-(azetidin-1-yl)ethyl)-2-oxo-4-(trifluoromethyl)pyridin-1(2H)-yl)-4-fluoro-4-methylpentanamido)-3-(2,4-difluoro-2',5,6'-trimethyl-4'-(trifluoromethyl)biphenyl-3-yl)propanoate (80 mg, 0.10 mmol) was treated with LiOH—H$_2$O (17 mg, 0.40 mmol) in EtOH (3 mL) and H$_2$O (1 mL) at room temperature for 1 hour. The reaction mixture was acidified to pH 5~6 with 1N HCl. The reaction was concentrated in vacuo and the residue purified by prep-HPLC A (30-60% CH$_3$CN) to give the diastereomeric products JD-P1 (17 mg) and JD-P2 (15 mg) as white solids.

JD-P1 ESI 748.2 (M+H)$^+$. $^1$H NMR (400 MHz, MeOD) δ 7.86 (s, 1H), 7.39 (s, 2H), 6.93 (t, J=8.1 Hz, 1H), 6.81 (s, 1H), 6.08-5.62 (m, 2H), 4.03 (t, J=8.0 Hz, 4H), 3.30-3.18 (m, 3H), 2.98-2.75 (m, 3H), 2.72-2.62 (m, 1H), 2.58-2.36 (m, 4H), 2.25 (s, 3H), 2.07 (s, 3H), 2.02 (s, 3H), 1.45-1.28 (m, 6H).

JD-P2 ESI 748.3 (M+H)$^+$. $^1$H NMR (400 MHz, MeOD) δ 7.69 (s, 1H), 7.42 (s, 2H), 6.99 (t, J=8.2 Hz, 1H), 6.92 (s, 1H), 5.95-5.88 (m, 1H), 5.78 (t, J=6.7 Hz, 1H), 4.11 (t, J=7.9 Hz, 4H), 3.46-3.31 (m, 2H), 3.00-2.69 (m, 3H), 2.64-2.38 (m, 4H), 2.30 (s, 3H), 2.26-2.15 (m, 1H), 2.09 (s, 6H), 1.36-1.24 (m, 6H).

A mixture of 2-(5-(2-(azetidin-1-yl)ethyl)-2-oxo-4-(trifluoromethyl)pyridin-1(2H)-yl)-4-methylpentanoic acid (160 mg, 0.44 mmol), (S)-ethyl 3-amino-3-(2,4-difluoro-2',5,6'-trimethyl-4'-(trifluoromethyl)biphenyl-3-yl)propanoate (180 mg, 0.44 mmol), NMI (110 mg, 1.32 mmol) and TCFH (150 mg, 0.53 mmol) in CH$_3$CN (6 mL) was stirred at room temperature for 2 hours. The solvent was concentrated in vacuo and the residue purified by reverse phase HPLC on a C18/40 g column (A: water 10 mM NH4HCO3, B: CH3CN, 0~100%) to provide (3S)-ethyl 3-(2-(5-(2-(azetidin-1-yl)ethyl)-2-oxo-4-(trifluoromethyl)pyridin-1(2H)-yl)-4-methylpentanamido)-3-(2,4-difluoro-2',5,6'-trimethyl-4'-(trifluoromethyl)biphenyl-3-yl)propanoate as a yellow oil (180 mg). Yield 54% (ESI758.2 [M+H]$^+$).

Step 2: of (3S)-3-(2-(5-(2-(azetidin-1-yl)ethyl)-2-oxo-4-(trifluoromethyl)pyridin-1(2)-yl)-4-methyl-pentanamido)-3-(2,4-difluoro-2',5,6'-trimethyl-4'-(trifluoromethyl)biphenyl-3-yl)propanoic acid 3-102. Preparation of (3S)-3-(2-(5-(2-(azetidin-1-yl)ethyl)-2-oxo-4-(trifluoromethyl)pyridin-1(2H)-yl)-4-methylpentanamido)-3-(2,4-difluoro-2',5,6'-trimethyl-[1,1'-biphenyl]-3-yl)propanoic Acid (Compounds JF-P1 and JF-P2)

Step 1: Ethyl (3S)-3-(2-(5-(2-(azetidin-1-yl)ethyl)-2-oxo-4-(trifluoromethyl)pyridin-1(2H)-yl)-4-methylpentanamido)-3-(2,4-difluoro-2',5,6'-trimethyl-[1,1'-biphenyl]-3-yl)propanoate

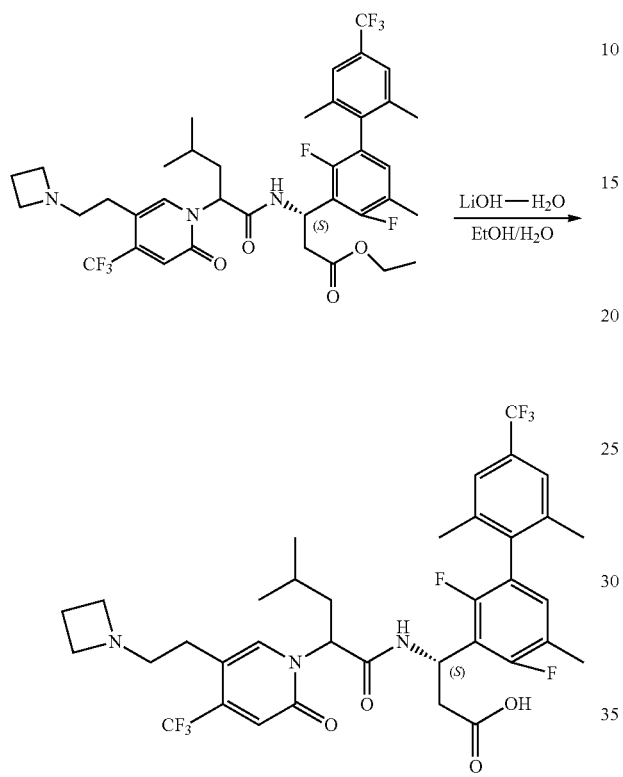

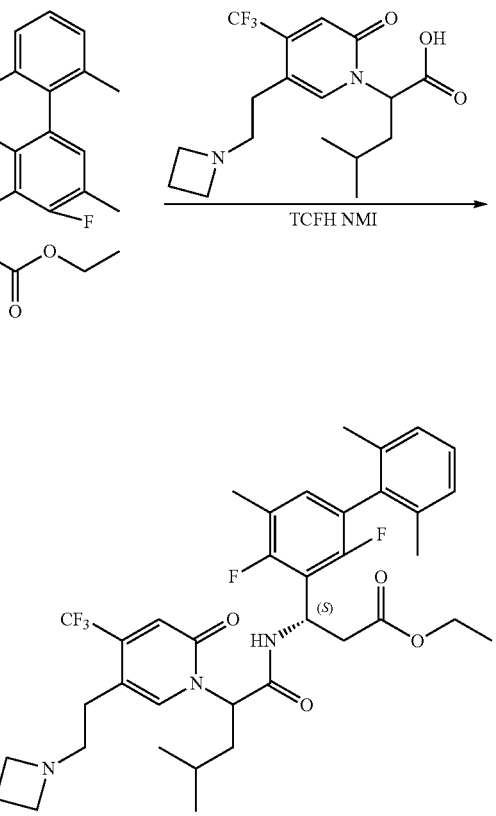

(3S)-ethyl 3-(2-(5-(2-(azetidin-1-yl)ethyl)-2-oxo-4-(trifluoromethyl)pyridin-1(2H)-yl)-4-methylpentanamido)-3-(2,4-difluoro-2',5,6'-trimethyl-4'-(trifluoromethyl)biphenyl-3-yl)propanoate (180 mg, 0.24 mmol) was treated with LiOH—$H_2O$ (30 mg, 0.72 mmol) in EtOH (3 mL) and $H_2O$ (1 mL) at room temperature for 1 hour. The reaction mixture was acidified to pH 5~6 with 1N HCl. The reaction was concentrated in vacuo and the residue purified by prep-HPLC A (30-60% $CH_3CN$) to give the diastereomeric products JE-P1 (48 mg) and JE-P2 (55 mg) as white solids.

JE-P1 ESI 730.3 (M+H)$^+$. $^1$H NMR (400 MHz, MeOD) δ 7.80 (s, 1H), 7.39 (s, 2H), 6.94 (t, J=8.1 Hz, 1H), 6.86 (s, 1H), 5.79-5.63 (m, 2H), 4.02 (t, J=8.1 Hz, 4H), 3.35-3.20 (m, 2H), 2.98-2.80 (m, 3H), 2.72-2.63 (m, 1H), 2.49-2.37 (m, 2H), 2.26 (s, 3H), 2.08 (s, 3H), 2.05-1.93 (m, 5H), 1.50-1.28 (m, 1H), 0.93 (t, J=6.1 Hz, 6H).

JE-P2 ESI 730.3 (M+H)$^+$. $^1$H NMR (400 MHz, MeOD) δ 7.69 (s, 1H), 7.42 (s, 2H), 6.99 (t, J=8.2 Hz, 1H), 6.92 (s, 1H), 5.96-5.88 (m, 1H), 5.61 (t, J=7.7 Hz, 1H), 4.11 (t, J=8.1 Hz, 4H), 3.46-3.31 (m, 2H), 2.97-2.73 (m, 3H), 2.60-2.38 (m, 3H), 2.30 (s, 3H), 2.10 (d, J=2.6 Hz, 6H), 1.99-1.89 (m, 1H), 1.80-1.66 (m, 1H), 1.51-1.22 (m, 1H), 0.92-0.83 (m, 6H).

A mixture of ethyl (S)-3-amino-3-(2,4-difluoro-2',5,6'-trimethyl-[1,1'-biphenyl]-3-yl)propanoate (240 mg, 0.6 mmol), 2-(5-(2-(azetidin-1-yl)ethyl)-2-oxo-4-(trifluoromethyl)pyridin-1(2H)-yl)-4-methylpentanoic acid (253 mg, 0.66 mmol), TCFH (336 mg, 1.2 mmol) and NMI (246 mg, 3.0 mmol) in $CH_3CN$ (4 mL) was stirred at 60° C. for 30 min. The reaction was concentrated and purified by reverse phase HPLC on a C18/40 g column (A: water 10 mM $NH_4HCO_3$, B: MeOH, 0~90%) to provide ethyl (3S)-3-(2-(5-(2-(azetidin-1-yl)ethyl)-2-oxo-4-(trifluoromethyl)pyridin-1(2H)-yl)-4-methylpentanamido)-3-(2,4-difluoro-2',5,6'-trimethyl-[1,1'-biphenyl]-3-yl)propanoate as a yellow solid (280 mg). Yield 67.7% (ESI 690.3 [M+H]$^+$).

Step 2: (3S)-3-(2-(5-(2-(azetidin-1-yl)ethyl)-2-oxo-4-(trifluoromethyl)pyridin-1(2H)-yl)-4-methylpentanamido)-3-(2,4-difluoro-2',5,6'-trimethyl-[1,1'-biphenyl]-3-yl)propanoic Acid

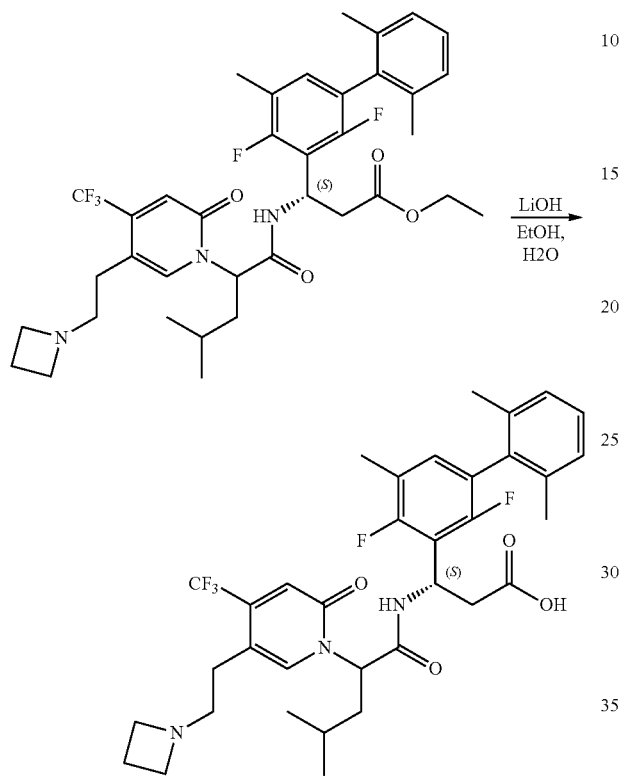

Ethyl (3S)-3-(2-(5-(2-(azetidin-1-yl)ethyl)-2-oxo-4-(trifluoromethyl)pyridin-1(2H)-yl)-4-methylpentanamido)-3-(2,4-difluoro-2',5,6'-trimethyl-[1,1'-biphenyl]-3-yl)propanoate (280 mg, 0.41 mmol) was treated with LiOH—$H_2O$ (50 mg, 1.2 mmol) in MeOH (4 mL) and $H_2O$ (1 mL) at room temperature for 30 min. The reaction mixture was acidified to pH 5~6 with 1N HCl. The reaction was concentrated in vacuo and the residue purified by prep-HPLC A (35-58% $CH_3CN$) to give the diastereomeric products JF-P1 (74 mg) and JF-P2 (81 mg) as white solids.

JF-P1 ESI 662.3 (M+H)$^+$. $^1$H NMR (400 MHz, MeOD) δ 7.79 (s, 1H), 7.17-7.03 (m, 3H), 6.94-6.85 (m, 2H), 5.78-5.71 (m, 1H), 5.67 (t, J=8.1 Hz, 1H), 4.01 (t, J=8.1 Hz, 4H), 2.94-2.79 (m, 3H), 2.71-2.59 (m, 1H), 2.48-2.36 (m, 2H), 2.25 (s, 3H), 2.06-1.88 (m, 8H), 1.42-1.33 (m, 1H), 0.93 (t, J=6.5 Hz, 6H).

JF-P2 ESI 662.3 (M+H)$^+$. $^1$H NMR (400 MHz, MeOD) δ 7.69 (s, 1H), 7.20-7.04 (m, 3H), 6.98-6.90 (m, 2H), 5.97-5.88 (m, 1H), 5.61 (t, J=7.7 Hz, 1H), 4.12 (s, 4H), 3.47-3.33 (m, 2H), 2.93-2.74 (m, 3H), 2.59-2.40 (m, 3H), 2.29 (s, 3H), 2.01 (d, J=2.4 Hz, 6H), 1.96-1.87 (m, 1H), 1.80-1.68 (m, 1H), 1.42-1.30 (m, 1H), 0.92-0.83 (m, 6H).

3-103. Preparation of (3S)-3-(2-(5-(2-(azetidin-1-yl)ethyl)-2-oxo-4-(trifluoromethyl)pyridin-1(2H)-yl)-4-methylpentanamido)-3-(2,4-difluoro-2',6'-dimethyl-5-(trifluoromethyl)-[1,1'-biphenyl]-3-yl)propanoic Acid (Compounds JG-P1 and JG-P2)

Step 1: Ethyl (3S)-3-(2-(5-(2-(azetidin-1-yl)ethyl)-2-oxo-4-(trifluoromethyl)pyridin-1(2H)-yl)-4-methylpentanamido)-3-(2,4-difluoro-2',6'-dimethyl-5-(trifluoromethyl)-[1,1'-biphenyl]-3-yl)propanoate

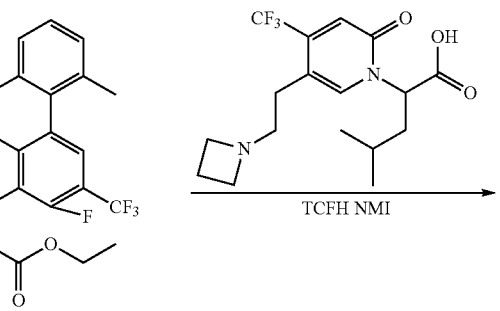

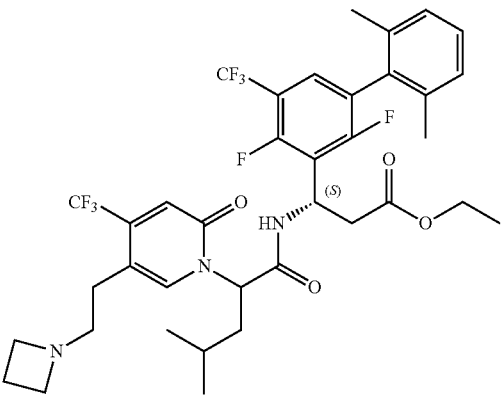

A mixture of ethyl (S)-3-amino-3-(2,4-difluoro-2',6'-dimethyl-5-(trifluoromethyl)-[1,1'-biphenyl]-3-yl)propanoate (240 mg, 0.6 mmol), 2-(5-(2-(azetidin-1-yl)ethyl)-2-oxo-4-(trifluoromethyl)pyridin-1(2H)-yl)-4-methylpentanoic acid (230 mg, 0.58 mmol), TCFH (325 mg, 1.16 mmol) and NMI (238 mg, 2.9 mmol) in $CH_3CN$ (4 mL) was stirred at 50° C. for 30 mins. The reaction was purified by reverse phase HPLC on a C18/40 g column (A: water 10 mM $NH_4HCO_3$, B: MeOH, 0~90%) to provide ethyl (3S)-3-(2-(5-(2-(azetidin-1-yl)ethyl)-2-oxo-4-(trifluoromethyl)pyridin-1(2H)-yl)-4-methylpentanamido)-3-(2,4-difluoro-2',6'-dimethyl-5-(trifluoromethyl)-[1,1'-biphenyl]-3-yl)propanoate as a yellow solid (250 mg). Yield 58.0% (ESI 744.3 [M+H]$^+$).

573

Step 2: (3S)-3-(2-(5-(2-(azetidin-1-yl)ethyl)-2-oxo-4-(trifluoromethyl)pyridin-1(2H)-yl)-4-methylpentanamido)-3-(2,4-difluoro-2',6'-dimethyl-5-(trifluoromethyl)-[1,1'-biphenyl]-3-yl)propanoic Acid

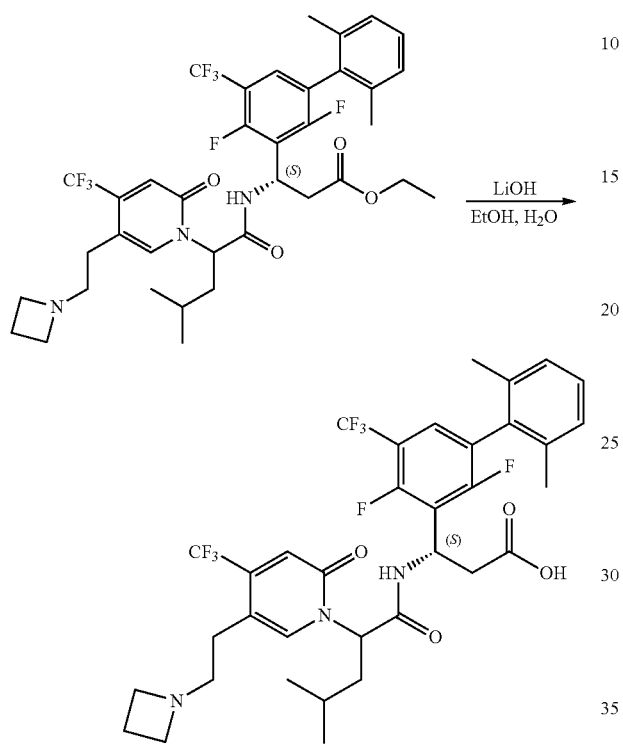

Ethyl (3S)-3-(2-(5-(2-(azetidin-1-yl)ethyl)-2-oxo-4-(trifluoromethyl)pyridin-1(2H)-yl)-4-methylpentanamido)-3-(2,4-difluoro-2',6'-dimethyl-5-(trifluoromethyl)-[1,1'-biphenyl]-3-yl)propanoate (250 mg, 0.34 mmol) was treated with LiOH—H$_2$O (58 mg, 1.37 mmol) in MeOH (4 mL) and H$_2$O (1 mL) at room temperature for 30 mins. The reaction mixture was acidified to pH 5~6 with 1N HCl. The reaction was concentrated in vacuo and the residue purified by prep-HPLC A (40-61% CH$_3$CN) to give the diastereomeric products JG-P1 (72 mg) and JG-P2 (78 mg) as white solids.

JG-P1 ESI 716.3 (M+H)$^+$. $^1$H NMR (400 MHz, MeOD) δ 7.80 (s, 1H), 7.40 (t, J=7.5 Hz, 1H), 7.25-7.15 (m, 1H), 7.12 (d, J=7.7 Hz, 2H), 6.85 (s, 1H), 5.77-5.66 (m, 2H), 4.04 (t, J=8.0 Hz, 4H), 3.28 (s, 2H), 2.92 (M, 1H), 2.84 (t, J=6.8 Hz, 2H), 2.76 (s, 1H), 2.46-2.38 (m, 2H), 2.05-1.95 (m, 5H), 1.95 (d, J=13.7 Hz, 3H), 1.38 (s, 1H), 0.93 (t, J=6.4 Hz, 6H).

JG-P2 ESI 716.3 (M+H)$^+$. $^1$H NMR (400 MHz, MeOD) δ 7.73 (s, 1H), 7.46 (t, J=7.7 Hz, 1H), 7.25-7.19 (m, 1H), 7.15 (d, J=7.6 Hz, 2H), 6.91 (s, 1H), 5.91 (M, 1H), 5.64 (t, J=7.6 Hz, 1H), 4.12 (t, J=7.8 Hz, 4H), 3.47-3.32 (m, 2H), 2.95-2.77 (m, 3H), 2.65-2.55 (m, 1H), 2.50-2.40 (m, 2H), 2.02 (d, J=2.2 Hz, 6H), 1.96-1.88 (m, 1H), 1.75-1.67 (m, 1H), 1.39-1.28 (m, 1H), 0.92-0.84 (m, 6H).

574

3-104. Preparation of (3S)-3-(2,4-difluoro-2',4',5,6'-tetramethyl-[1,1'-biphenyl]-3-y)-3-(2-(5-(2-(dimethylamino)ethyl)-2-oxo-4-(trifluoromethyl)pyridin-1(2H)-yl)-4-methylpentanamido)propanoic Acid (Compounds JH-P1 and JH-P2)

Step 1: Ethyl (3S)-3-(2,4-difluoro-2',4',5,6'-tetramethyl-[1,1'-biphenyl]-3-yl)-3-(2-(5-(2-(dimethylamino)ethyl)-2-oxo-4-(trifluoromethyl)pyridin-1(2H)-yl)-4-methylpentanamido)propanoate

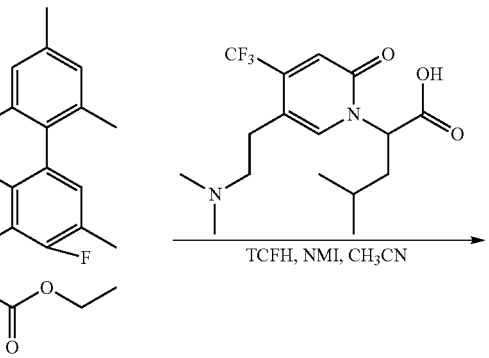

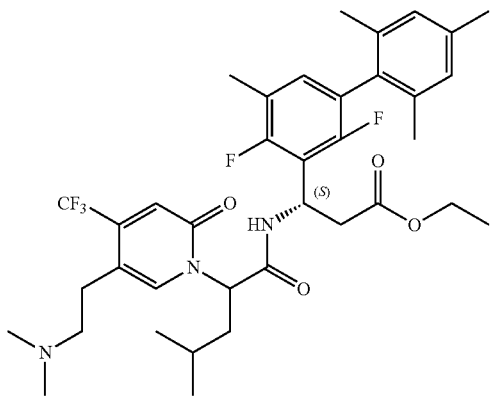

A mixture of ethyl (S)-3-amino-3-(2,4-difluoro-2',4',5,6'-tetramethyl-[1,1'-biphenyl]-3-yl)propanoate (220 mg, 0.61 mmol), 2-(5-(2-(dimethylamino)ethyl)-2-oxo-4-(trifluoromethyl)pyridin-1(2H)-yl)-4-methylpentanoic acid (250 mg, 0.65 mmol), TCFH (364 mg, 1.3 mmol) and NMI (266 mg, 3.25 mmol) in CH$_3$CN (4.5 mL) was stirred at 60° C. for 30 mins. The reaction was concentrated and purified by reverse phase HPLC on a C18/40 g column (A: water 10 mM NH$_4$HCO$_3$, B: MeOH, 0~80%) to provide ethyl (3S)-3-(2,4-difluoro-2',4',5,6'-tetramethyl-[1,1'-biphenyl]-3-yl)-3-(2-(5-(2-(dimethylamino)ethyl)-2-oxo-4-(trifluoromethyl)pyridin-1(2H)-yl)-4-methylpentanamido)propanoate as a yellow solid (300 mg). Yield 71.1% (ESI 692.3 [M+H]$^+$).

Step 2: (3S)-3-(2,4-difluoro-2',4',5,6'-tetramethyl-[1,1'-biphenyl]-3-y)-3-(2-(5-(2-(dimethylamino)ethyl)-2-oxo-4-(trifluoromethyl)pyridin-1(2H)-yl)-4-methylpentanamido)propanoic acid 3-105. Preparation of (3S)-3-(2-(5-(2-(azetidin-1-yl)ethyl)-2-oxo-4-(trifluoromethyl)pyridin-1(2H)-yl)-4-methylpentanamido)-3-(2,4-difluoro-2',5,6'-trimethyl-3'-(trifluoromethyl)-[1,1'-biphenyl]-3-yl) propanoic Acid (Compounds JI-P1 and JI-P2)

Step 1: Ethyl (3S)-3-(2-(5-(2-(azetidin-1-yl)ethyl)-2-oxo-4-(trifluoromethyl)pyridin-1(2H)-yl)-4-methylpentanamido)-3-(2,4-difluoro-2',5,6'-trimethyl-3'-(trifluoromethyl)-[1,1'-biphenyl]-3-yl)propanoate

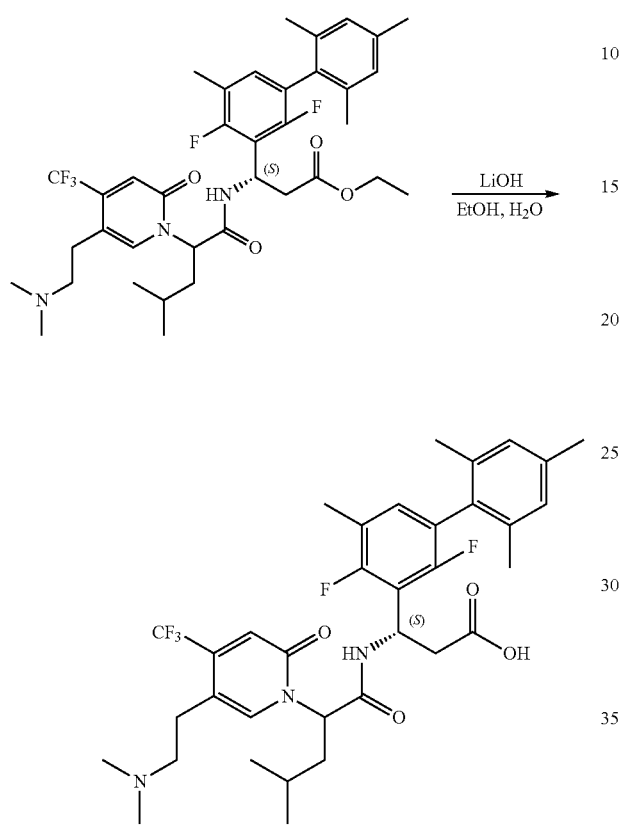

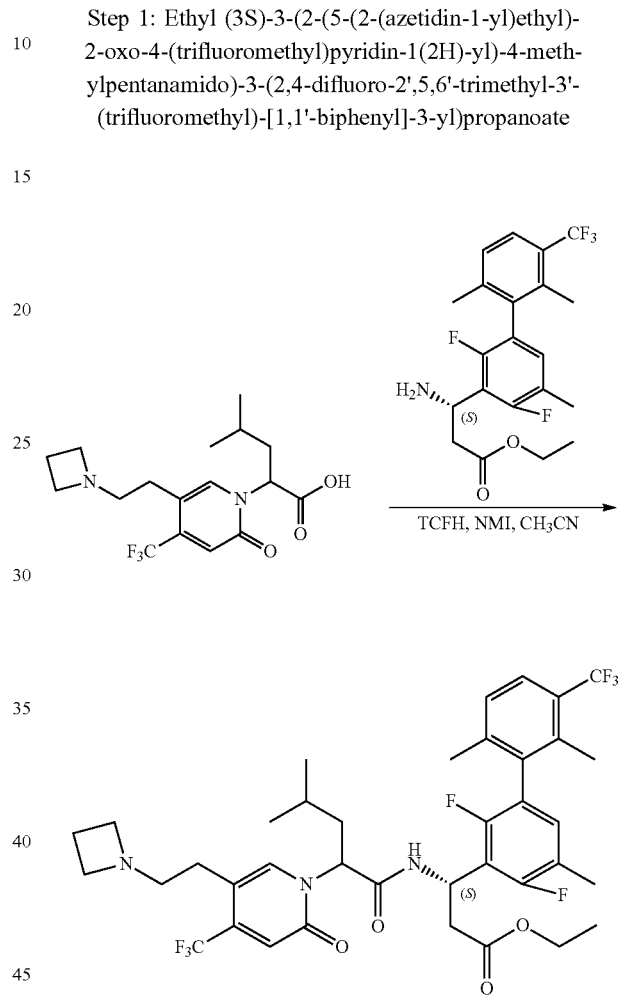

Ethyl (3S)-3-(2,4-difluoro-2',4',5,6'-tetramethyl-[1,1'-biphenyl]-3-yl)-3-(2-(5-(2-(dimethylamino)ethyl)-2-oxo-4-(trifluoromethyl)pyridin-1(2H)-yl)-4-methylpentanamido) propanoate (300 mg, 0.43 mmol) was treated with LiOH—H$_2$O (56 mg, 1.34 mmol) in MeOH (4 mL) and H$_2$O (0 mL) at room temperature for 1 hr. The reaction mixture was acidified to pH 5~6 with 1N HCl. The reaction was concentrated in vacuo and the residue purified by prep-HPLC A (35-62% CH$_3$CN) to give the diastereomeric products JH-P1 (113 mg) and JH-P2 (87 mg) as white solids.

JH-P1 ESI 664.3 (M+H)$^+$. $^1$H NMR (400 MHz, MeOD) δ 7.86 (s, 1H), 6.96-6.77 (m, 4H), 5.81-5.63 (m, 2H), 3.10 (d, J=21.9 Hz, 2H), 2.98-2.86 (m, 3H), 2.76-2.63 (m, 7H), 2.25 (d, J=19.9 Hz, 6H), 2.01-1.92 (m, 5H), 1.87 (s, 3H), 1.44-1.35 (m, 1H), 0.93 (t, J=6.8 Hz, 6H).

JH-P2 ESI 664.3 (M+H)$^+$. 1H NMR (400 MHz, MeOD) δ 7.83 (d, J=11.6 Hz, 1H), 7.01-6.84 (m, 4H), 5.85 (d, J=8.7 Hz, 1H), 5.63 (s, 1H), 3.25-3.09 (m, 2H), 3.05-2.91 (m, 2H), 2.77 (s, 7H), 2.55 (d, J=14.8 Hz, 1H), 2.28 (d, J=10.3 Hz, 6H), 1.96 (d, J=3.6 Hz, 6H), 1.93-1.85 (m, 1H), 1.80-1.67 (m, 1H), 1.39-1.27 (m, 1H), 0.93-0.81 (m, 6H).

A mixture of ethyl (3S)-3-amino-3-(2,4-difluoro-2',5,6'-trimethyl-3'-(trifluoromethyl)-[1,1'-biphenyl]-3-yl)propanoate (174.5 mg, 0.42 mmol), 2-(5-(2-(azetidin-1-yl)ethyl)-2-oxo-4-(trifluoromethyl)pyridin-1(2H)-yl)-4-methylpentanoic acid (150.0 mg, 0.42 mmol), TCFH (140.3 mg, 0.50 mmol) and NMI (137.9 mg, 1.68 mmol) in CH$_3$CN (5 mL) was stirred at room temperature overnight. The reaction was concentrated in vacuo and the residue purified by reverse phase HPLC on a C18/40 g column (A: water 10 mM NH$_4$HCO$_3$, B: MeOH, 0~100%) to provide ethyl (3S)-3-(2-(5-(2-(azetidin-1-yl)ethyl)-2-oxo-4-(trifluoromethyl) pyridin-1(2H)-yl)-4-methylpentanamido)-3-(2,4-difluoro-2',5,6'-trimethyl-3'-(trifluoromethyl)-[1,1'-biphenyl]-3-yl) propanoate as a light yellow solid (160.0 mg). Yield 51% (ESI 758.3 [M+H]$^+$).

577

Step 2: (3S)-3-(2-(5-(2-(azetidin-1-yl)ethyl)-2-oxo-4-(trifluoromethyl)pyridin-1(2H)-yl)-4-methylpentanamido)-3-(2,4-difluoro-2',5,6'-trimethyl-3'-(trifluoromethyl)-[1,1'-biphenyl]-3-yl)propanoic Acid

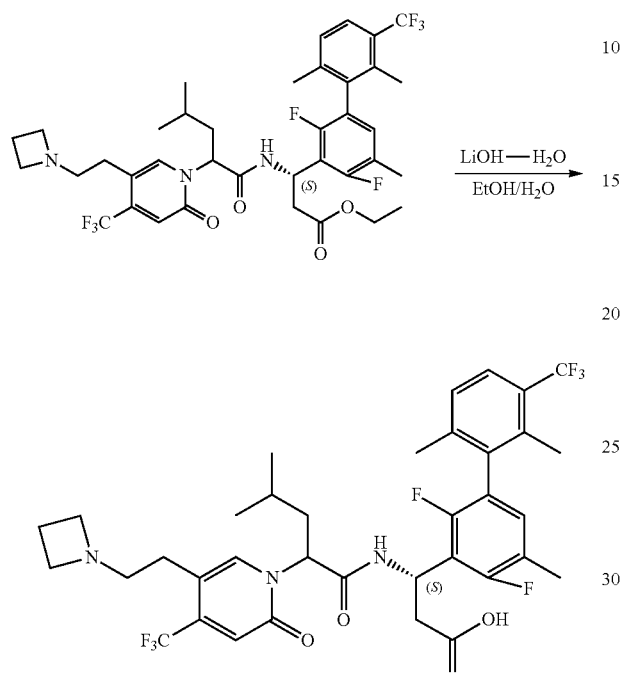

Ethyl (3S)-3-(2-(5-(2-(azetidin-1-yl)ethyl)-2-oxo-4-(trifluoromethyl)pyridin-1(2H)-yl)-4-methylpentanamido)-3-(2,4-difluoro-2',5,6'-trimethyl-3'-(trifluoromethyl)-[1,1'-biphenyl]-3-yl)propanoate (160.0 mg, 0.21 mmol) was treated with LiOH—H$_2$O (26.4 mg, 0.63 mmol) in EtOH (2 mL) and water (0.5 mL) at room temperature for 1 hour. The reaction mixture was acidified to PH 4~5 with 2N HCL. The reaction was concentrated in vacuo and the residue purified by prep-HPLC A (30-80% MeCN) to give the diastereomeric products JI-P1 (39.5 mg) and JI-P2 (53.3 mg) as white solids.

JI-P1 ESI 730.2 (M+H)$^+$ $^1$H NMR (400 MHz, MeOD) δ 7.80 (d, J=4.4 Hz, 1H), 7.57 (d, J=8.1 Hz, 1H), 7.27 (d, J=8.0 Hz, 1H), 6.92 (t, J=8.2 Hz, 1H), 6.86 (s, 1H), 5.79-5.61 (m, 2H), 4.01 (t, J=8.1 Hz, 4H), 3.37-3.31 (m, 1H), 3.29-3.20 (m, 1H), 2.95-2.80 (m, 3H), 2.71-2.64 (m, 1H), 2.49-2.35 (m, 2H), 2.26 (s, 3H), 2.14-1.92 (m, 8H), 1.46-1.30 (m, 1H), 0.93 (t, J=6.7 Hz, 6H).

JI-P2 ESI 730.1 (M+H)$^+$ $^1$H NMR (400 MHz, MeOD) δ 7.70 (s, 1H), 7.59 (d, J=8.1 Hz, 1H), 7.30 (d, J=8.1 Hz, 1H), 6.98 (t, J=8.2 Hz, 1H), 6.92 (s, 1H), 5.94-5.88 (m, 1H), 5.64-5.58 (m, 1H), 4.10 (t, J=8.0 Hz, 4H), 3.44-3.32 (m, 2H), 2.96-2.74 (m, 3H), 2.58-2.37 (m, 3H), 2.30 (s, 3H), 2.12 (s, 3H), 2.07 (d, J=2.6 Hz, 3H), 2.00-1.86 (m, 1H), 1.80-1.66 (m, 1H), 1.41-1.31 (m, 1H), 0.92-0.85 (m, 6H).

578

3-106. Preparation of (3S)-3-(2,4-difluoro-2',5,6'-trimethyl-3'-(trifluoromethyl)-[1,1'-biphenyl]-3-yl)-3-(2-(5-(3-(dimethylamino)propyl)-2-oxo-4-(trifluoromethyl)pyridin-1(2H)-yl)-4-methylpentanamido)propanoic Acid (Compounds JJ-P1 and JJ-P2)

Step 1: Ethyl (3S)-3-(2,4-difluoro-2',5,6'-trimethyl-3'-(trifluoromethyl)-[1,1'-biphenyl]-3-yl)-3-(2-(5-(3-(dimethylamino)propyl)-2-oxo-4-(trifluoromethyl)pyridin-1(2H)-yl)-4-methylpentanamido)propanoate

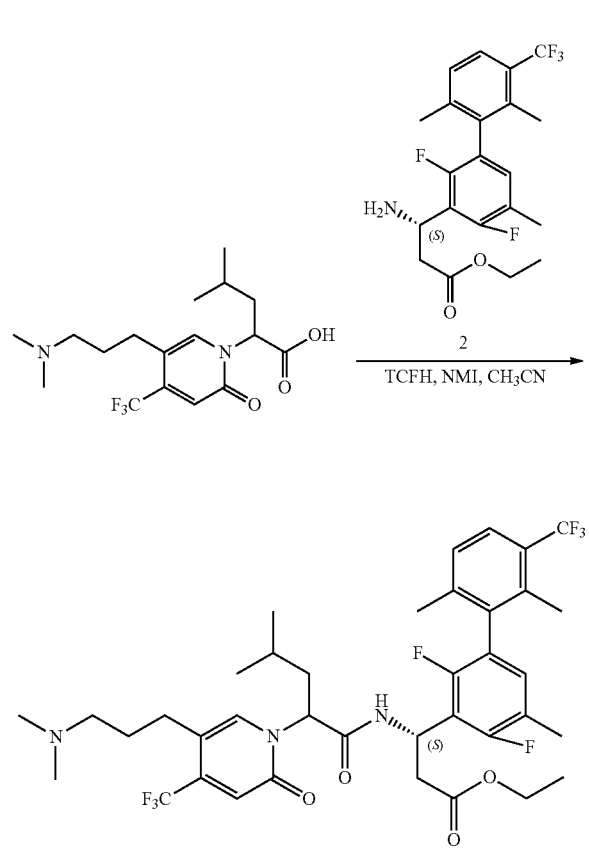

A mixture of ethyl (3S)-3-amino-3-(2,4-difluoro-2',5,6'-trimethyl-3'-(trifluoromethyl)-[1,1'-biphenyl]-3-yl)propanoate (114.6 mg, 0.28 mmol), 2-(5-(3-(dimethylamino)propyl)-2-oxo-4-(trifluoromethyl)pyridin-1(2H)-yl)-4-methylpentanoic acid (100.0 mg, 0.28 mmol), TCFH (95.4 mg, 0.34 mmol) and NMI (92.0 mg, 1.12 mmol) in CH$_3$CN (5 mL) was stirred at room temperature overnight. The reaction was concentrated in vacuo and the residue purified by reverse phase HPLC on a C18/40 g column (A: water 10 mM NH$_4$HCO$_3$, B: MeOH, 0~100%) to provide ethyl (3S)-3-(2,4-difluoro-2',5,6'-trimethyl-3'-(trifluoromethyl)-[1,1'-biphenyl]-3-yl)-3-(2-(5-(3-(dimethylamino)propyl)-2-oxo-4-(trifluoromethyl)pyridin-1(2H)-yl)-4-methylpentanamido)propanoate as a light yellow solid (100.0 mg). Yield 48% (ESI 760.3 [M+H]$^+$).

Step 2: (3S)-3-(2,4-difluoro-2',5,6'-trimethyl-3'-(trifluoromethyl)-[1,1'-biphenyl]-3-yl)-3-(2-(5-(3-(dimethylamino)propyl)-2-oxo-4-(trifluoromethyl)pyridin-1(2H)-yl)-4-methylpentanamido)propanoic Acid 3-107. Preparation of (3S)-3-(2-(5-(2-(dimethylamino)ethyl)-2-oxo-4-(trifluoromethyl)pyridin-1(2H)-yl)-4-methylpentanamido)-3-(2,3',4-trifluoro-2',6'-dimethyl-5-(trifluoromethyl)biphenyl-3-yl)propanoic Acid (Compounds JK-P1 and JK-P2)

Step 1: (3S)-ethyl 3-(2-(5-(2-(dimethylamino)ethyl)-2-oxo-4-(trifluoromethyl)pyridin-1(2H)-yl)-4-methylpentanamido)-3-(2,3',4-trifluoro-2',6'-dimethyl-5-(trifluoromethyl)biphenyl-3-yl)propanoate

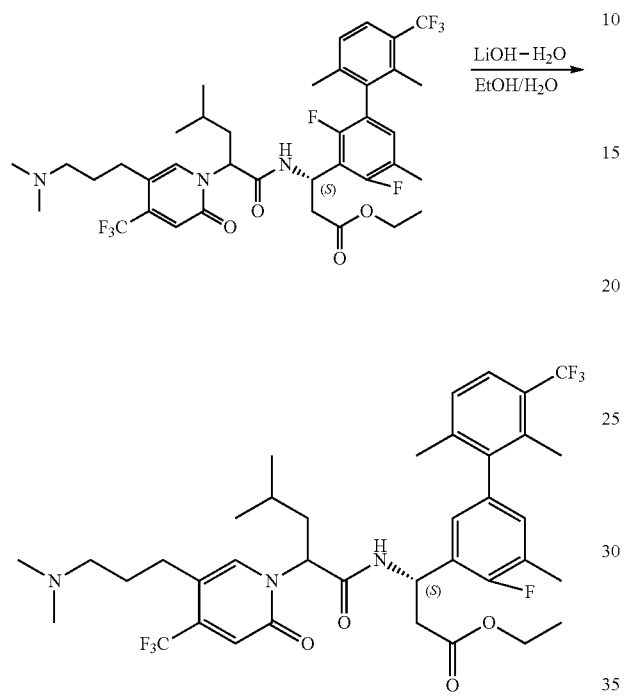

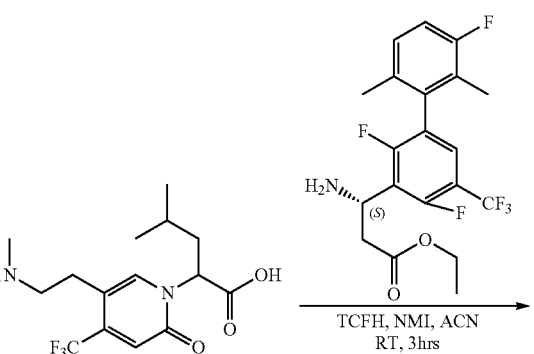

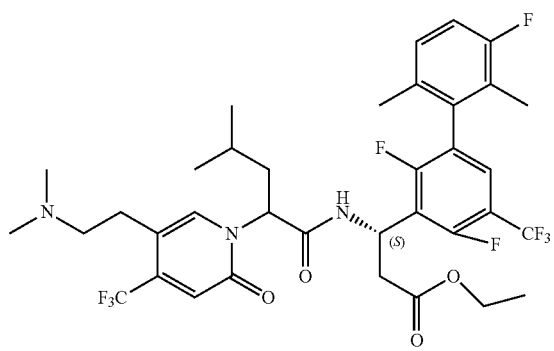

Ethyl (3S)-3-(2,4-difluoro-2',5,6'-trimethyl-3'-(trifluoromethyl)-[1,1'-biphenyl]-3-yl)-3-(2-(5-(3-(dimethylamino)propyl)-2-oxo-4-(trifluoromethyl)pyridin-1(2H)-yl)-4-methylpentanamido)propanoate (100.0 mg, 0.13 mmol) was treated with LiOH—H$_2$O (16.4 mg, 0.39 mmol) in EtOH (2 mL) and water (0.5 mL) at room temperature for 1 hour. The reaction mixture was acidified to pH 4~5 with 2N HCl. The reaction was concentrated in vacuo and the residue purified by prep-HPLC A (30-80% MeCN) to give the diastereomeric products JJ-P1 (6.0 mg) and JJ-P2 (36.5 mg) as white solids.

JJ-P1 ESI 732.2 (M+H)$^+$ $^1$H NMR (400 MHz, MeOD) δ 7.77 (d, J=3.4 Hz, 1H), 7.56 (d, J=8.1 Hz, 1H), 7.26 (d, J=8.0 Hz, 1H), 6.90 (t, J=8.1 Hz, 1H), 6.79 (s, 1H), 5.81-5.67 (m, 2H), 3.14-3.00 (m, 2H), 2.97-2.89 (m, 1H), 2.78 (s, 6H), 2.72-2.58 (m, 3H), 2.25 (s, 3H), 2.11-1.81 (m, 10H), 1.41-1.29 (m, 1H), 0.93 (d, J=6.6 Hz, 6H).

JJ-P2 ESI 732.2 (M+H)$^+$ $^1$H NMR (400 MHz, MeOD) δ 7.79 (s, 1H), 7.58 (d, J=8.1 Hz, 1H), 7.29 (d, J=8.0 Hz, 1H), 6.95 (t, J=8.1 Hz, 1H), 6.84 (s, 1H), 5.86-5.80 (m, 1H), 5.61-5.55 (m, 1H), 3.11-2.91 (m, 2H), 2.91-2.82 (m, 1H), 2.77 (s, 6H), 2.70-2.51 (m, 3H), 2.29 (s, 3H), 2.14-2.04 (m, 6H), 2.03-1.88 (m, 3H), 1.67-1.58 (m, 1H), 1.38-1.28 (m, 1H), 0.92-0.81 (m, 6H).

A mixture of (3S)-ethyl 3-amino-3-(2,3',4-trifluoro-2',6'-dimethyl-5-(trifluoromethyl)biphenyl-3-yl)propanoate (120 mg, 0.29 mmol), 2-(5-(2-(dimethylamino)ethyl)-2-oxo-4-(trifluoromethyl)pyridin-1(2H)-yl)-4-methylpentanoic acid (100 mg, 0.29 mmol), TCFH (157 mg, 0.56 mmol) and NMI (69 mg, 0.84 mmol) in MeCN (5 mL) was stirred at room temperature for 1 hour. The solvent was removed in vacuo and the residue was purified by silica gel column (DCM:MeOH 97:3) to provide (3S)-ethyl 3-(2-(5-(2-(dimethylamino)ethyl)-2-oxo-4-(trifluoromethyl)pyridin-1(2H)-yl)-4-methylpentanamido)-3-(2,3',4-trifluoro-2',6'-dimethyl-5-(trifluoromethyl)biphenyl-3-yl)propanoate as a colorless oil (120 mg). Yield 55% (ESI 750.3 (M+H)$^+$).

Step 2: (3S)-3-(2-(5-(2-(dimethylamino)ethyl)-2-oxo-4-(trifluoromethyl)pyridin-1(2H)-yl)-4-methylpentanamido)-3-(2,3',4-trifluoro-2',6'-dimethyl-5-(trifluoromethyl)biphenyl-3-yl)propanoic acid

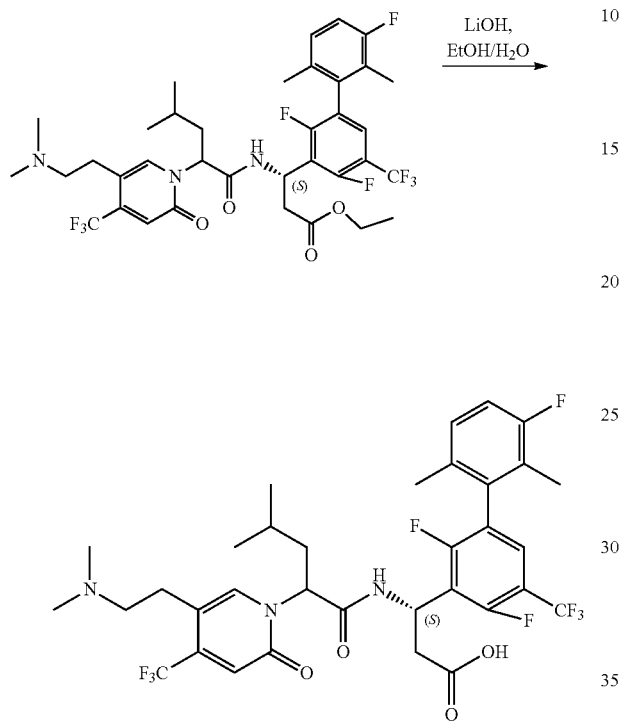

(3S)-ethyl 3-(2-(5-(2-(dimethylamino)ethyl)-2-oxo-4-(trifluoromethyl)pyridin-1(2H)-yl)-4-methylpentanamido)-3-(2,3',4-trifluoro-2',6'-dimethyl-5-(trifluoromethyl)biphenyl-3-yl)propanoate (100 mg, 0.13 mmol) was treated with LiOH—H$_2$O (27 mg, 0.65 mmol) in EtOH (3 mL) and H$_2$O (1 mL) at room temperature for 3 hours. The reaction mixture was acidified to pH 4~5 with 1N HCl. The reaction was concentrated in vacuo and the residue purified by prep-HPLC A (30-60% CH$_3$CN) to give the diastereomeric products JK-P1 (30.3 mg) and JK-P2 (23.1 mg) as white solids.

JK-P1 ESI 722.3 (M+H)$^+$. 1H NMR (400 MHz, DMSO) δ 9.26 (d, J=6.4 Hz, 1H), 7.78 (s, 1H), 7.62 (t, J=7.5 Hz, 1H), 7.25-7.12 (m, 2H), 6.70 (s, 1H), 5.58-5.55 (m, 1H), 5.46 (d, J=6.2 Hz, 1H), 3.04-2.87 (m, 2H), 2.67-2.52 (m, 2H), 2.36 (t, J=7.3 Hz, 2H), 2.18 (s, 6H), 1.96-1.73 (m, 8H), 1.35-1.27 (m, 1H), 0.85-0.83 (m, 6H).

JK-P2 ESI 722.3 (M+H)$^+$. 1H NMR (400 MHz, MeOD) δ 7.84 (s, 1H), 7.48 (t, J=7.6 Hz, 1H), 7.24-7.10 (m, 1H), 7.04 (t, J=9.0 Hz, 1H), 6.90 (s, 1H), 5.80-5.78 (m, 1H), 5.66 (t, J=7.8 Hz, 1H), 3.19-3.15 (m, 2H), 2.96 (t, J=7.2 Hz, 2H), 2.92-2.76 (m, 7H), 2.69-2.66 (m, 1H), 2.00 (d, J=2.4 Hz, 3H), 1.97-1.92 (m, 3H), 1.93-1.86 (m, 1H), 1.79-1.70 (m, 1H), 1.33-1.30 (m, 1H), 0.88-0.85 (m, 6H).

3-108. Preparation of (3S)-3-(4-methyl-2-(5-(2-(3-methylazetidin-1-yl)ethyl)-2-oxo-4-(trifluoromethyl)pyridin-1(2H)-yl)pentanamido)-3-(2,3',4-trifluoro-2',6'-dimethyl-5-(trifluoromethyl)biphenyl-3-yl)propanoic Acid (Compounds JL-P1 and JL-P2)

Step 1: (3S)-ethyl 3-(4-methyl-2-(5-(2-(3-methylazetidin-1-yl)ethyl)-2-oxo-4-(trifluoromethyl)pyridin-1(2H)-yl)pentanamido)-3-(2,3',4-trifluoro-2',6'-dimethyl-5-(trifluoromethyl)biphenyl-3-yl)propanoate

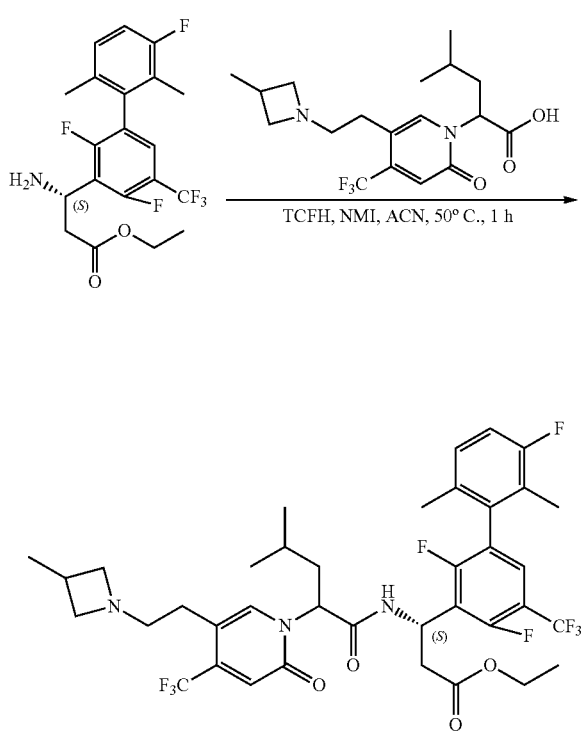

A mixture of (3S)-ethyl 3-amino-3-(2,3',4-trifluoro-2',6'-dimethyl-5-(trifluoromethyl)biphenyl-3-yl)propanoate (120 mg, 0.28 mmol), 4-methyl-2-(5-(2-(3-methylazetidin-1-yl)ethyl)-2-oxo-4-(trifluoromethyl)pyridin-1(2H)-yl)pentanoic acid (105 mg, 0.28 mmol), NMI (69 mg, 0.84 mmol) and TCFH (117 mg, 0.42 mmol) in CH$_3$CN (10 mL) was stirred at 50° C. for 1 hour. The solvent was concentrated in vacuo and the residue was purified by silica gel column (DCM: MeOH 10:1) to provide (3S)-ethyl 3-(4-methyl-2-(5-(2-(3-methylazetidin-1-yl)ethyl)-2-oxo-4-(trifluoromethyl)pyridin-1(2H)-yl)pentanamido)-3-(2,3',4-trifluoro-2',6'-dimethyl-5-(trifluoromethyl)biphenyl-3-yl)propanoate as a yellow oil (151 mg). Yield 68.0% (ESI 776.3 [M+H]$^+$).

583

Step 2: (3S)-3-(4-methyl-2-(5-(2-(3-methylazetidin-1-yl)ethyl)-2-oxo-4-(trifluoromethyl)pyridin-1(2H)-yl)pentanamido)-3-(2,3',4-trifluoro-2',6'-dimethyl-5-(trifluoromethyl)biphenyl-3-yl)propanoic Acid

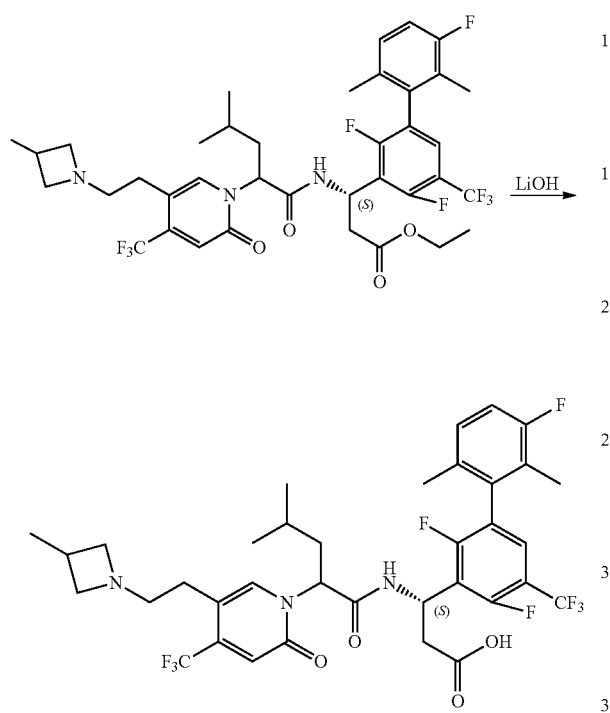

(3S)-ethyl 3-(4-methyl-2-(5-(2-(3-methylazetidin-1-yl)ethyl)-2-oxo-4-(trifluoromethyl)pyridin-1(2H)-yl)pentanamido)-3-(2,3',4-trifluoro-2',6'-dimethyl-5-(trifluoromethyl)biphenyl-3-yl)propanoate (151 mg, 0.19 mmol) was treated with LiOH—H$_2$O (24.5 mg, 0.58 mmol) in EtOH (3 mL) and water (1 mL) at room temperature for 1 hour. The reaction mixture was acidified to pH 4~5 with 1N HCl. The reaction was concentrated in vacuo and the residue purified by prep-HPLC A (20-70% MeCN) to give the diastereomeric products JL-P1 (49 mg) and JL-P2 (51 mg) as white solids.

JL-P1 ESI 748.2 (M+H)$^+$. $^1$H NMR (400 MHz, MeOD) δ 7.81 (s, 1H), 7.42 (t, J=7.5 Hz, 1H), 7.13 (t, J=5.9 Hz, 1H), 7.02 (t, J=8.9 Hz, 1H), 6.84 (s, 1H), 5.77-5.65 (m, 2H), 4.13 (t, J=9.2 Hz, 2H), 3.67 (t, J=8.8 Hz, 2H), 3.30-3.20 (m, 2H), 2.89-2.81 (m, 5H), 2.04-1.83 (m, 8H), 1.41-1.35 (m, 1H), 1.24 (d, J=6.9 Hz, 3H), 0.93 (t, J=6.0 Hz, 6H).

JL-P2 ESI 748.2 (M+H)$^+$. 1H NMR (400 MHz, MeOD) δ 7.77 (s, 1H), 7.49 (t, J=7.5 Hz, 1H), 7.20-7.13 (m, 1H), 7.04 (t, J=8.9 Hz, 1H), 6.90 (s, 1H), 5.89-5.81 (m, 1H), 5.66 (t, J=7.8 Hz, 1H), 4.13 (t, J=9.2 Hz, 2H), 3.66 (s, 2H), 3.30 (s, 2H), 2.96-2.74 (m, 4H), 2.68-2.62 (m, 1H), 2.00 (d, J=2.2 Hz, 3H), 1.97-1.83 (m, 4H), 1.77-1.71 (m, 1H), 1.36-1.29 (m, 1H), 1.25 (d, J=6.9 Hz, 3H), 0.90-0.85 (m, 6H).

584

3-109. Preparation of (3S)-3-(2-(5-(2-(azetidin-1-yl)ethyl)-2-oxo-4-(trifluoromethyl)pyridin-1(2H)-yl)-4-methylpentanamido)-3-(2,4-difluoro-3'-methoxy-2',5,6'-trimethyl-[1,1'-biphenyl]-3-yl)propanoic Acid (Compounds JM-P1 and JM-P2)

Step 1: Ethyl (3S)-3-(2-(5-(2-(azetidin-1-yl)ethyl)-2-oxo-4-(trifluoromethyl)pyridin-1(2H)-yl)-4-methylpentanamido)-3-(2,4-difluoro-3'-methoxy-2',5,6'-trimethyl-[1,1'-biphenyl]-3-yl)propanoate

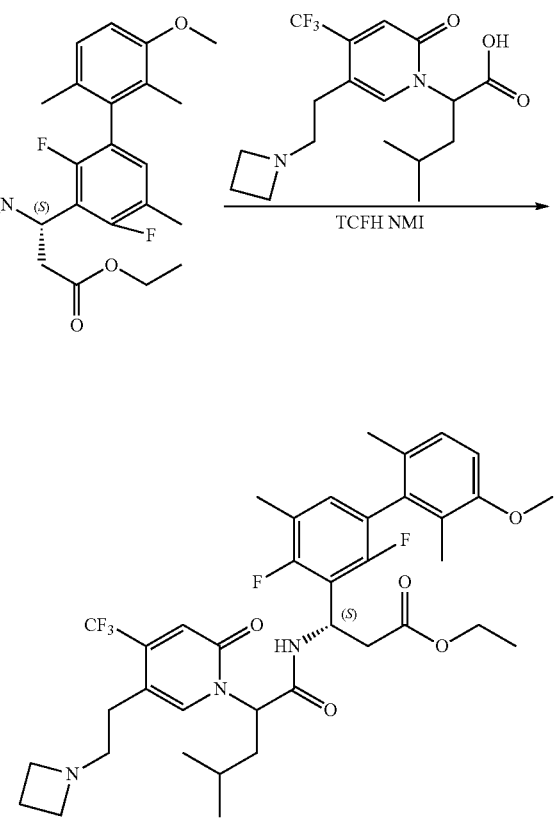

A mixture of ethyl (3S)-3-amino-3-(2,4-difluoro-3'-methoxy-2',5,6'-trimethyl-[1,1'-biphenyl]-3-yl)propanoate (190 mg, 0.5 mmol), 2-(5-(2-(azetidin-1-yl)ethyl)-2-oxo-4-(trifluoromethyl)pyridin-1(2H)-yl)-4-methylpentanoic acid (198 mg, 0.55 mmol), TCFH (302 mg, 1.08 mmol) and NMI (220 mg, 2.7 mmol) in CH$_3$CN (4 mL) was stirred at 25° C. for 1 hr. The reaction was concentrated and purified by reverse phase HPLC on a C18/40 g column (A: water 10 mM NH$_4$HCO$_3$, B: MeOH, 0~90%) to provide ethyl (3S)-3-(2-(5-(2-(azetidin-1-yl)ethyl)-2-oxo-4-(trifluoromethyl)pyridin-1(2H)-yl)-4-methylpentanamido)-3-(2,4-difluoro-3'-methoxy-2',5,6'-trimethyl-[1,1'-biphenyl]-3-yl)propanoate as a yellow solid (250 mg). Yield 69.4% (ESI 720.3 [M+H]$^+$).

Step 2: (3S)-3-(2-(5-(2-(azetidin-1-yl)ethyl)-2-oxo-4-(trifluoromethyl)pyridin-1(2H)-yl)-4-methylpentanamido)-3-(2,4-difluoro-3'-methoxy-2',5',6'-trimethyl-[1,1'-biphenyl]-3-yl)propanoic acid 3-110. Preparation of (3S)-3-(4,4'-difluoro-2',5,6'-trimethyl-[1,1'-biphenyl]-3-yl)-3-(2-(3-fluoro-5-(2-(3-fluoroazetidine-1-yl)ethyl)-2-oxopyridin-1(2H)-yl)-4-methylpentanamido)propanoic Acid (JN-P1 and JN-P2)

Step 1: Ethyl (3S)-3-(4,4'-difluoro-2',5,6'-trimethyl-[1,1'-biphenyl]-3-yl)-3-(2-(3-fluoro-5-(2-(3-fluoroazetidine-1-yl)ethyl)-2-oxopyridin-1(2H)-yl)-4-methylpentanamido)propanoate

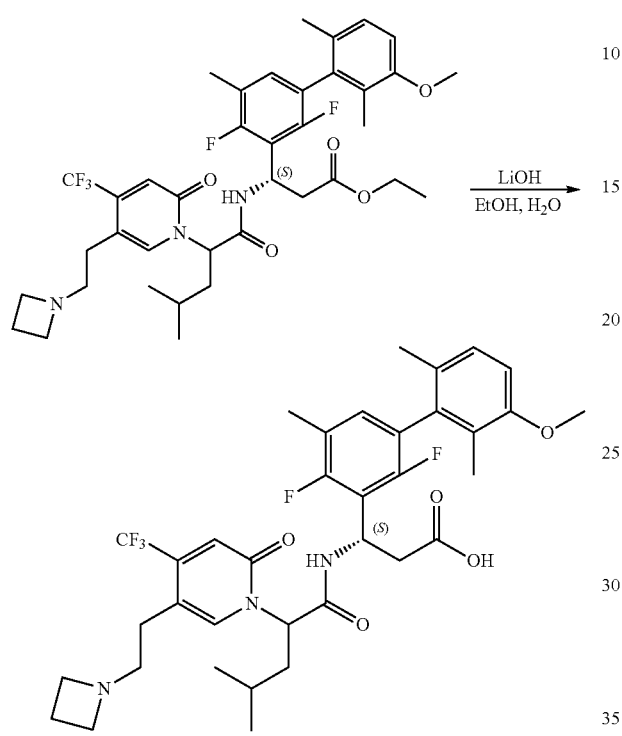

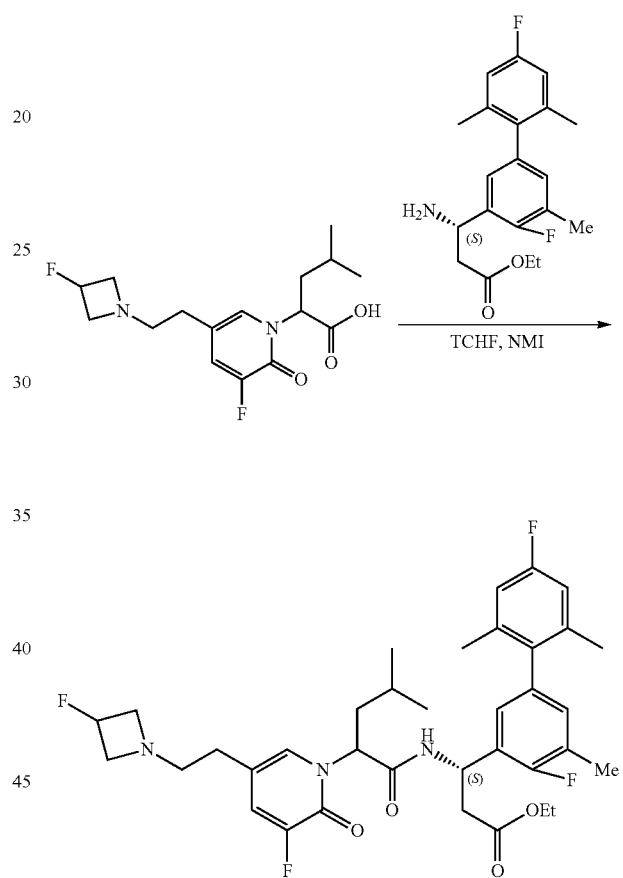

Ethyl (3S)-3-(2-(5-(2-(azetidin-1-yl)ethyl)-2-oxo-4-(trifluoromethyl)pyridin-1(2H)-yl)-4-methylpentanamido)-3-(2,4-difluoro-3'-methoxy-2',5',6'-trimethyl-[1,1'-biphenyl]-3-yl)propanoate (250 mg, 0.35 mmol) was treated with LiOH—H$_2$O (42 mg, 1 mmol) in EtOH (4 mL) and H$_2$O (1 mL) at room temperature for 30 min. The reaction mixture was acidified to pH 5-6 with 1N HCl. The reaction was concentrated in vacuo and the residue purified by prep-HPLC A (35-65% CH$_3$CN) to give the diastereomeric products JM-P1 (68 mg) and JM-P2 (86 mg) as white solids.

JM-P1 ESI 692.3 (M+H)$^+$. $^1$H NMR (400 MHz, MeOD) δ 7.79 (s, 1H), 7.04 (d, J=8.4 Hz, 1H), 6.90-6.79 (m, 3H), 5.77-5.63 (m, 2H), 3.99 (t, J=8.0 Hz, 4H), 3.81 (s, 3H), 3.30-3.23 (m, 2H), 2.94-2.81 (m, 3H), 2.70-2.61 (m, 1H), 2.46-2.35 (m, 2H), 2.24 (s, 3H), 1.97 (t, J=7.6 Hz, 2H), 1.93-1.77 (m, 6H), 1.44-1.34 (m, 1H), 0.92 (t, J=6.2 Hz, 6H).

JM-P2 ESI 692.3 (M+H)$^+$. $^1$H NMR (400 MHz, MeOD) δ 7.69 (s, 1H), 7.06 (d, J=8.4 Hz, 1H), 6.96-6.82 (m, 3H), 5.95-5.87 (m, 1H), 5.61 (t, J=7.7 Hz, 1H), 4.12 (t, J=8.1 Hz, 4H), 3.82 (s, 3H), 3.47-3.33 (m, 2H), 2.98-2.73 (m, 3H), 2.56-2.40 (m, 3H), 2.28 (s, 3H), 1.97-1.88 (m, 4H), 1.86 (d, J=3.0 Hz, 3H), 1.78-1.68 (m, 1H), 1.41-1.30 (m, 1H), 0.88 (dd, J=10.5, 6.6 Hz, 6H).

A mixture of 2-(3-fluoro-5-(2-(3-fluoroazetidine-1-yl)ethyl)-2-oxopyridin-1(2H)-yl)-4-methylpentanoic acid (200.0 mg, 0.61 mmol), ethyl (S)-3-amino-3-(4,4'-difluoro-2',5,6'-trimethyl-[1,1'-biphenyl]-3-yl)propanoate (260.0 mg, 0.61 mmol), TCHF (205.0 mg, 0.73 mmol) and NMI (150.0 mg, 1.83 mmol) in CH$_3$CN (4 mL) was stirred at room temperature for 1.5 hours. The solvent was removed in vacuo and the residue was purified by reverse phase HPLC on a C18/40 g column (A: water 10 mM NH$_4$HCO$_3$, B: MeOH, 0~100%) to provide ethyl (3S)-3-(4,4'-difluoro-2',5,6'-trimethyl-[1,1'-biphenyl]-3-yl)-3-(2-(3-fluoro-5-(2-(3-fluoroazetidine-1-yl)ethyl)-2-oxopyridin-1(2H)-yl)-4-methylpentanamido)propanoate as a yellow solid (210.0 mg). Yield 52.5% (ESI 658.3 [M+H]$^+$).

Step 2: (3S)-3-(4,4'-difluoro-2',5,6'-trimethyl-[1,1'-biphenyl]-3-yl)-3-(2-(3-fluoro-5-(2-(3-fluoroazetidin-1-yl)ethyl)-2-oxopyridin-1(2H)-yl)-4-methylpentanamido)propanoic Acid

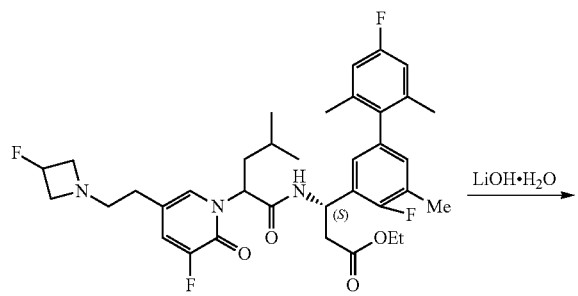

Ethyl (3S)-3-(4,4'-difluoro-2',5,6'-trimethyl-[1,1'-biphenyl]-3-yl)-3-(2-(3-fluoro-5-(2-(3-fluoroazetidine-1-yl)ethyl)-2-oxopyridin-1(2H)-yl)-4-methylpentanamido)propanoate (210.0 mg, 0.32 mmol) was treated with LiOH—H$_2$O (150.0 mg, 3.2 mmol) in THF (4 mL) and water (2 mL) at 30° C. for 1 hour. The reaction mixture was acidified to pH 4~5 with 2N HCl. The solvent was removed in vacuo and the residue purified by prep-HPLC A (30-60% MeCN) to provide the diastereomeric products JN-P1 (81 mg) and JN-P2 (83 mg) as white solids.

JN-P1 ESI 630.2 (M+H)$^+$. $^1$H NMR (400 MHz, MeOD) δ 7.30 (s, 1H), 7.25-7.22 (m, 1H), 6.77-6.75 (m, 1H), 6.72-6.69 (m, 3H), 5.55 (t, J=8.0 Hz, 1H), 5.40-5.37 (m, 1H), 5.18-5.01 (m, 1H), 3.99-3.82 (m, 2H), 3.66-3.48 (m, 2H), 3.06-2.99 (m, 2H), 2.66-2.50 (m, 4H), 2.18 (d, J=1.5 Hz, 3H), 1.89-1.81 (m, 5H), 1.78 (s, 3H), 1.34-1.27 (m, 1H), 0.85-0.78 (m, 6H).

JN-P2 ESI 630.2 (M+H)$^+$. $^1$H NMR (400 MHz, MeOD) δ 7.27-7.23 (m, 2H), 6.80 (d, J=6.9 Hz, 2H), 6.73 (d, J=9.6 Hz, 2H), 5.56-5.49 (m, 2H), 5.28-5.11 (m, 1H), 4.33-4.18 (m, 2H), 3.97-3.83 (m, 2H), 3.27-3.22 (m, 2H), 2.64-2.35 (m, 4H), 2.21 (d, J=1.9 Hz, 3H), 1.89-1.82 (m, 7H), 1.69-1.62 (m, 1H), 1.31-1.21 (m, 1H), 0.83-0.78 (m, 6H).

3-111. Preparation of (3S)-3-(2-(5-(2-(azetidin-1-yl)ethyl)-2-oxo-4-(trifluoromethyl)pyridin-1(2H)-yl)-4-methylpentanamido)-3-(3',4-difluoro-2',6'-dimethyl-5-(trifluoromethyl)-[1,1'-biphenyl]-3-yl)propanoic Acid Step 1: Ethyl (3S)-3-(2-(5-(2-(azetidin-1-yl)ethyl)-2-oxo-4-(trifluoromethyl)pyridin-1(2H)-yl)-4-methylpentanamido)-3-(3',4-difluoro-2',6'-dimethyl-5-(trifluoromethyl)-[1,1'-biphenyl]-3-yl)propanoate

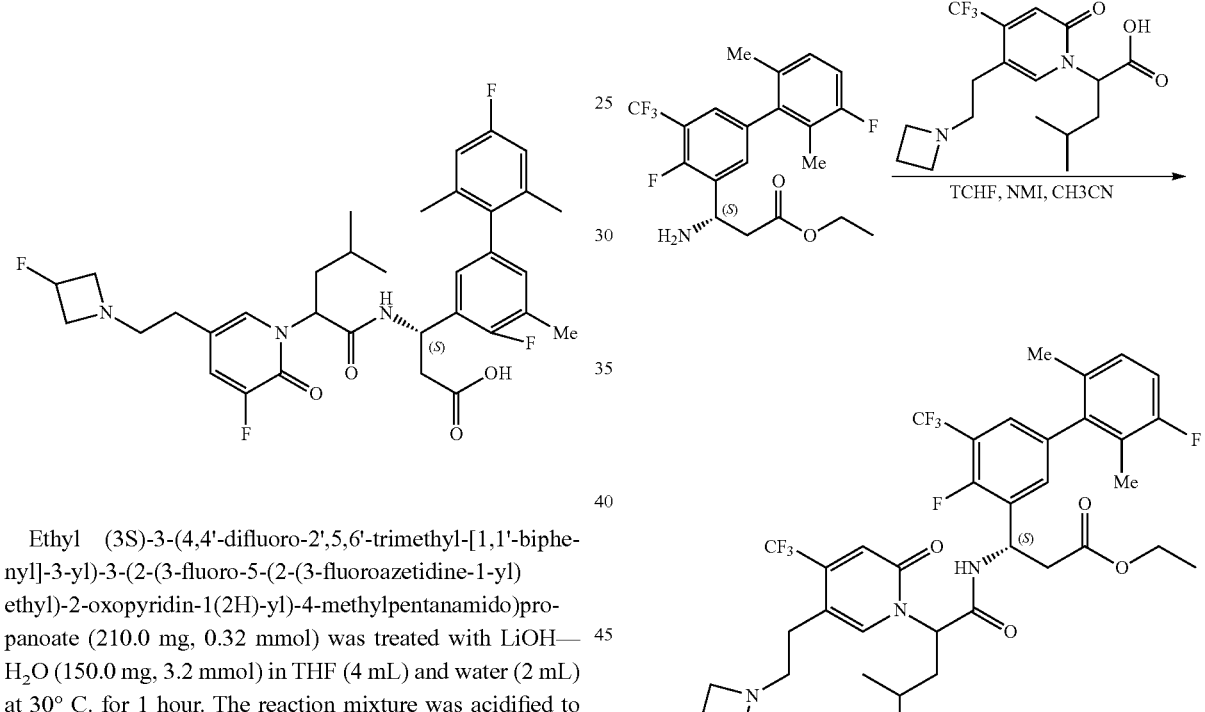

A mixture of ethyl (S)-3-amino-3-(3',4-difluoro-2',6'-dimethyl-5-(trifluoromethyl)-[1,1'-biphenyl]-3-yl)propanoate (230 mg, 0.57 mmol), 2-(5-(2-(azetidin-1-yl)ethyl)-2-oxo-4-(trifluoromethyl)pyridin-1(2H)-yl)-4-methylpentanoic acid (205 mg, 0.57 mmol), NMI (0.6 ML) and TCFH (241 mg, 0.86 mmol) in CH$_3$CN (3 mL) was stirred at room temperature for 2.0 hour. The solvent was concentrated in vacuo and the residue was purified by prep-HPLC A (50-80% CH3CN) to provide ethyl (3S)-3-(2-(5-(2-(azetidin-1-yl)ethyl)-2-oxo-4-(trifluoromethyl)pyridin-1(2H)-yl)-4-methylpentanamido)-3-(3',4-difluoro-2',6'-dimethyl-5-(trifluoromethyl)-[1,1'-biphenyl]-3-yl)propanoate as a white solid (320 mg). Yield 76% (ESI 744.2 [M+H]$^+$).

589

Step 2: (3S)-3-(2-(5-(2-(azetidin-1-yl)ethyl)-2-oxo-4-(trifluoromethyl)pyridin-1(2H)-yl)-4-methylpentanamido)-3-(3',4-difluoro-2',6'-dimethyl-5-(trifluoromethyl)-[1,1'-biphenyl]-3-yl) propanoic Acid

590

3-112. Preparation of (3S)-3-(2-(5-(2-(azetidin-1-yl)ethyl)-2-oxo-4-(trifluoromethyl)pyridin-1(2H)-yl)-4-methylpentanamido)-3-(4-fluoro-3'-methoxy-2',6'-dimethyl-5-(trifluoromethyl)biphenyl-3-yl)propanoic Acid (Compounds JP-P1 and JP-P2)

Step 1: (3S)-ethyl 3-(2-(5-(2-(azetidin-1-yl)ethyl)-2-oxo-4-(trifluoromethyl)pyridin-1(2H)-yl)-4-methylpentanamido)-3-(4-fluoro-3'-methoxy-2',6'-dimethyl-5-(trifluoromethyl)biphenyl-3-yl)propanoate

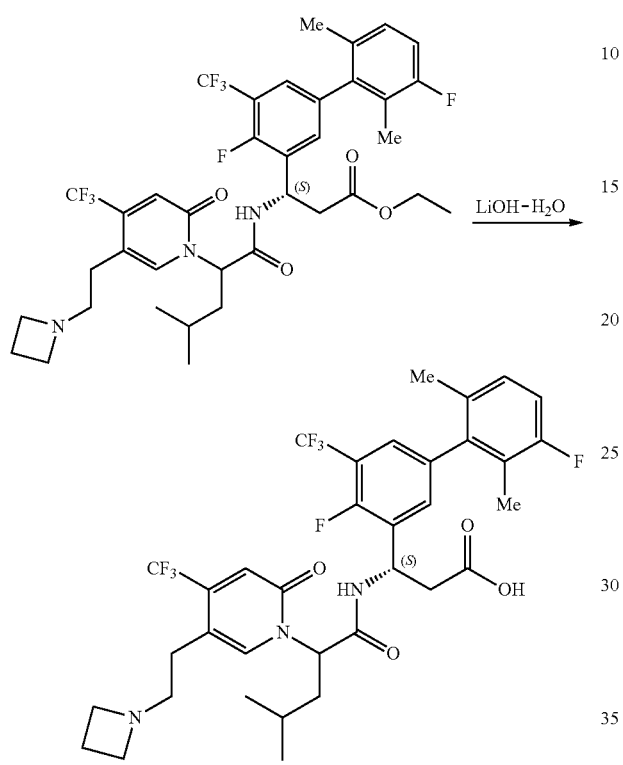

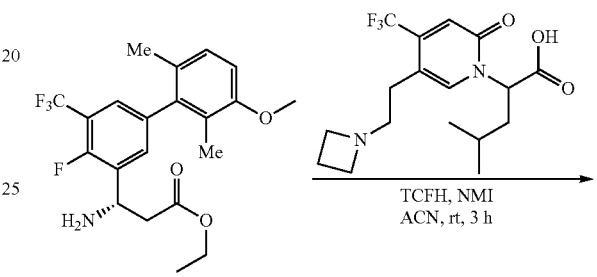

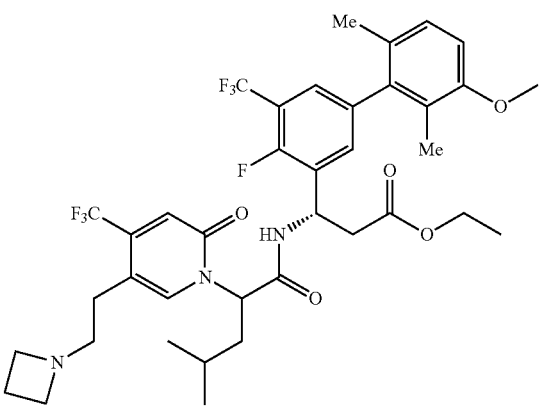

Ethyl (3S)-3-(2-(5-(2-(azetidin-1-yl)ethyl)-2-oxo-4-(trifluoromethyl)pyridin-1(2H)-yl)-4-methylpentanamido)-3-(3',4-difluoro-2',6'-dimethyl-5-(trifluoromethyl)-[1,1'-biphenyl]-3-yl)propanoate (320 mg, 0.43 mmol) was treated with LiOH—$H_2O$ (35 mg, 0.84 mmol) in MeOH (3.0 mL) and $H_2O$ (1.0 mL) at room temperature for 2 hours. The reaction mixture was acidified to pH 5~6 with 1N HCl. The solvent was removed in vacuo and the residue was purified by prep-HPLC A (50-80% $CH_3CN$) to provide the diastereomeric products JO-P1 (100 mg) and JO-P2 (102 mg) as white solids.

JO-P1 ESI 716.2 $(M+H)^+$. $^1$H NMR (400 MHz, MeOD) δ 7.84 (s, 1H), 7.42-7.29 (m, 2H), 7.18-7.03 (m, 1H), 6.98 (t, J=9.0 Hz, 1H), 6.71 (d, J=10.0 Hz, 1H), 5.70-5.50 (m, 2H), 4.05 (t, J=8.1 Hz, 4H), 3.30-3.25 (m, 1H), 2.87-2.65 (m, 4H), 2.50-2.38 (m, 2H), 2.08-1.86 (m, 5H), 1.83-1.68 (m, 3H), 1.47-1.33 (m, 1H), 0.93-0.85 (m, 6H).

JO-P2 ESI 716.2 $(M+H)^+$. $^1$H NMR (400 MHz, MeOD) δ 7.73 (s, 1H), 7.48-7.38 (m, 2H), 7.19-7.09 (m, 1H), 7.00 (t, J=9.0 Hz, 1H), 6.88 (s, 1H), 5.88-5.78 (m, 1H), 5.61 (t, J=7.5 Hz, 1H), 4.13 (t, J=8.1 Hz, 4H), 3.49-3.32 (m, 2H), 2.97-2.73 (m, 2H), 2.70-2.40 (m, 4H), 2.05-1.85 (m, 7H), 1.73-1.60 (m, 1H), 1.44-1.26 (m, 1H), 0.87 (d, J=6.6 Hz, 6H).

A mixture of (S)-ethyl 3-amino-3-(4-fluoro-3'-methoxy-2',6'-dimethyl-5-(trifluoromethyl)biphenyl-3-yl)propanoate (200 mg, 0.48 mmol), 2-(5-(2-(azetidin-1-yl)ethyl)-2-oxo-4-(trifluoromethyl)pyridin-1(2H)-yl)-4-methylpentanoic acid (173 mg, 0.48 mmol), NMI (120 mg, 1.44 mmol) and TCFH (160 mg, 0.58 mmol) in $CH_3CN$ (8 mL) was stirred at room temperature for 2 hours. The solvent was concentrated in vacuo and the residue was purified by reverse phase HPLC on a C18/40 g column (A: water 10 mM NH4HCO3, B: CH3CN, 0~100%) to provide (3S)-ethyl 3-(2-(5-(2-(azetidin-1-yl)ethyl)-2-oxo-4-(trifluoromethyl)pyridin-1(2H)-yl)-4-methylpentanamido)-3-(4-fluoro-3'-methoxy-2',6'-dimethyl-5-(trifluoromethyl)biphenyl-3-yl)propanoate as a yellow oil (270 mg). Yield 72% (ESI 756.2 $[M+H]^+$).

Step 2: (3S)-3-(2-(5-(2-(azetidin-1-yl)ethyl)-2-oxo-4-(trifluoromethyl)pyridin-1(2H)-yl)-4-methylpentanamido)-3-(4-fluoro-3'-methoxy-2',6'-dimethyl-5-(trifluoromethyl)biphenyl-3-yl)propanoic Acid

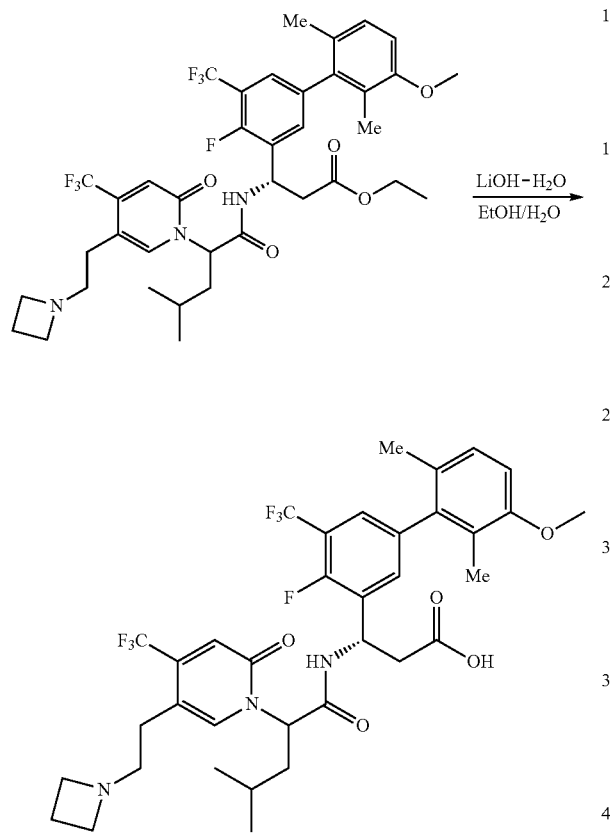

(3S)-ethyl 3-(2-(5-(2-(azetidin-1-yl)ethyl)-2-oxo-4-(trifluoromethyl)pyridin-1(2H)-yl)-4-methylpentanamido)-3-(4-fluoro-3'-methoxy-2',6'-dimethyl-5-(trifluoromethyl)biphenyl-3-yl)propanoate (270 mg, 0.36 mmol) was treated with LiOH—H$_2$O (60 mg, 1.44 mmol) in EtOH (3 mL) and H$_2$O (1 mL) at room temperature for 2 hours. The reaction mixture was acidified to pH 5~6 with 1N HCl. The solvent was removed in vacuo and the residue purified by prep-HPLC A (30-60% CH$_3$CN) to give the diastereomeric products JP-P1 (75 mg) and JP-P2 (85 mg) as white solids.

JP-P1 ESI 727.8 (M+H)$^+$. 1H NMR (400 MHz, MeOD) δ 7.83 (s, 1H), 7.36-7.25 (m, 2H), 7.05 (t, J=8.7 Hz, 1H), 6.87-6.73 (m, 2H), 5.64-5.59 (m, 2H), 4.04 (t, J=8.1 Hz, 4H), 3.82 (s, 3H), 3.29-3.25 (m, 2H), 2.85-2.69 (m, 4H), 2.47-2.39 (m, 2H), 2.05-1.94 (m, 2H), 1.91-1.68 (m, 6H), 1.43-1.37 (m, 1H), 0.94-0.90 (m, 6H).

JP-P2 ESI 727.8 (M+H)$^+$. 1H NMR (400 MHz, MeOD) δ 7.73 (s, 1H), 7.42-7.31 (m, 2H), 7.09 (d, J=8.3 Hz, 1H), 6.89-6.87 (m, 2H), 5.81-5.78 (m, 1H), 5.61 (t, J=7.6 Hz, 1H), 4.13 (t, J=8.0 Hz, 4H), 3.83 (s, 3H), 3.44-3.32 (m, 2H), 2.94-2.42 (m, 6H), 2.00-1.84 (m, 7H), 1.68-1.61 (m, 1H), 1.41-1.34 (m, 1H), 0.87-0.85 (m, 6H).

3-113. Preparation of (S)-3-((S)-2-(5-(2-(azetidin-1-yl)ethyl)-2-oxo-4-(trifluoromethyl)pyridin-1(2H)-yl)-4-methylpentanamido)-3-(4-fluoro-2',3',6'-trimethyl-5-(trifluoromethyl)biphenyl-3-yl)propanoic Acid (Compounds JQ-P1 and JQ-P2)

Step 1: (S)-ethyl 3-((S)-2-(5-(2-(azetidin-1-yl)ethyl)-2-oxo-4-(trifluoromethyl)pyridin-1(2H)-yl)-4-methylpentanamido)-3-(4-fluoro-2',3',6'-trimethyl-5-(trifluoromethyl)biphenyl-3-yl)propanoate

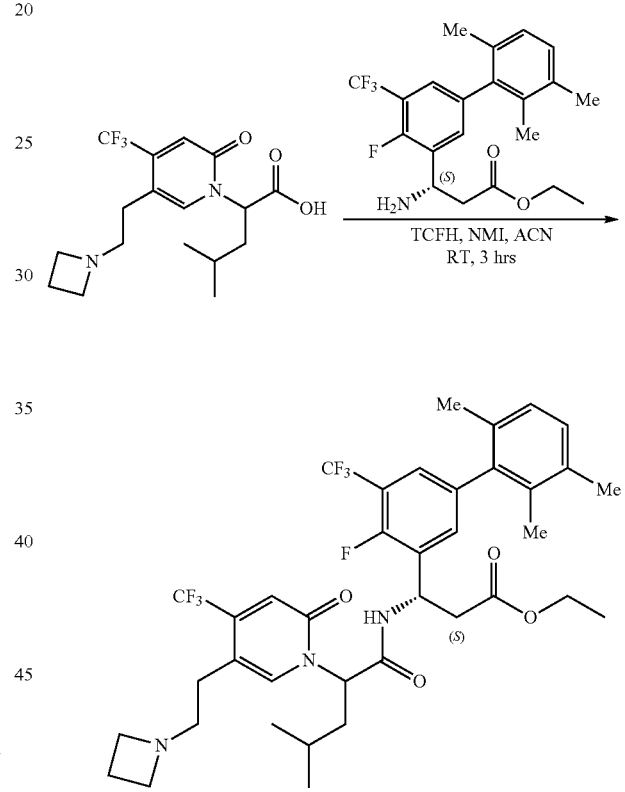

A mixture of (S)-ethyl 3-amino-3-(4-fluoro-2',3',6'-trimethyl-5-(trifluoromethyl)biphenyl-3-yl)propanoate (170 mg, 0.43 mmol), 2-(5-(2-(azetidin-1-yl)ethyl)-2-oxo-4-(trifluoromethyl)pyridin-1(2H)-yl)-4-methylpentanoic acid (155 mg, 0.43 mmol), TCFH (241 mg, 0.86 mmol) and NMI (106 mg, 1.3 mmol) in MeCN (5 mL) was stirred at room temperature for 1 hour. The solvent was removed in vacuo and the residue was purified by silica gel column (DCM:MeOH 10:1) to provide (S)-ethyl 3-((S)-2-(5-(2-(azetidin-1-yl)ethyl)-2-oxo-4-(trifluoromethyl)pyridin-1(2H)-yl)-4-methylpentanamido)-3-(4-fluoro-2',3',6'-trimethyl-5-(trifluoromethyl)biphenyl-3-yl)propanoate as a colorless oil (200 mg). Yield 63% (ESI 740.3 (M+H)$^+$).

593

Step 2: (S)-3-((S)-2-(5-(2-(azetidin-1-yl)ethyl)-2-oxo-4-(trifluoromethyl)pyridin-1(2H)-yl)-4-methyl-pentanamido)-3-(4-fluoro-2',3',6'-trimethyl-5-(trifluoromethyl)biphenyl-3-yl)propanoic Acid

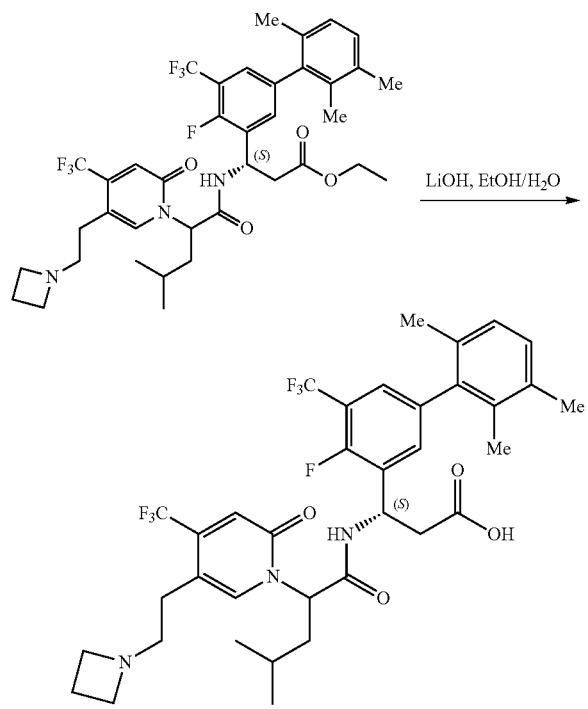

(S)-ethyl 3-((S)-2-(5-(2-(azetidin-1-yl)ethyl)-2-oxo-4-(trifluoromethyl)pyridin-1(2H)-yl)-4-methylpentanamido)-3-(4-fluoro-2',3',6'-trimethyl-5-(trifluoromethyl)biphenyl-3-yl)propanoate (200 mg, 0.27 mmol) was treated with LiOH—H$_2$O (53 mg, 1.27 mmol) in EtOH (3 mL) and H$_2$O (1 mL) at room temperature for 2 hours. The reaction mixture was acidified to pH 4~5 with 1N HCl. The solvent was removed in vacuo and the residue purified by prep-HPLC A (30-60% CH$_3$CN) to give the diastereomeric products JQ-P1 (62 mg) and JQ-P2 (87 mg) as white solids.

JQ-P1 ESI 712.3 (M+H)$^+$. 1H NMR (400 MHz, MeOD) δ 7.82 (d, J=5.2 Hz, 1H), 7.36 (s, 1H), 7.29-7.22 (m, 1H), 7.07 (d, J=7.7 Hz, 1H), 7.03-6.92 (m, 1H), 6.75 (d, J=16.4 Hz, 1H), 5.62-5.60 (m, 2H), 4.05 (t, J=7.9 Hz, 4H), 3.30 (s, 2H), 2.83 (d, J=3.3 Hz, 2H), 2.76-2.64 (m, 2H), 2.54-2.37 (m, 2H), 2.26 (s, 3H), 2.06-1.95 (m, 2H), 1.99-1.92 (m, 3H), 1.78 (s, 3H), 1.39 (d, J=6.4 Hz, 1H), 0.94-0.90 (m, 6H).

JQ-P2 ESI 712.3 (M+H)$^+$. 1H NMR (400 MHz, MeOD) δ 7.73 (s, 1H), 7.41 (d, J=6.4 Hz, 1H), 7.32 (d, J=6.3 Hz, 1H), 7.08 (d, J=7.7 Hz, 1H), 7.01 (d, J=7.7 Hz, 1H), 6.88 (s, 1H), 5.80 (d, J=10.3 Hz, 1H), 5.61 (t, J=7.7 Hz, 1H), 4.13 (t, J=7.9 Hz, 4H), 3.34-3.29 (m, 2H), 2.91 (d, J=16.4 Hz, 1H), 2.85-2.74 (m, 1H), 2.68-2.64 (m, 1H), 2.58-2.38 (m, 3H), 2.28 (s, 3H), 1.98-1.93 (m, 7H), 1.67-1.64 (m, 1H), 1.39-1.37 (m, 1H), 0.87 (s, 6H).

594

3-114. Preparation of (3S)-3-(2-(5-(2-(azetidin-1-yl)ethyl)-2-oxo-4-(trifluoromethyl)pyridin-1(2H)-yl)-4-fluoro-4-methylpentanamido)-3-(4-fluoro-2',4',6'-trimethyl-5-(trifluoromethyl)biphenyl-3-yl)propanoic Acid (Compounds JR-P1 and JR-P2)

Step 1: (3S)-ethyl 3-(2-(5-(2-(azetidin-1-yl)ethyl)-2-oxo-4-(trifluoromethyl)pyridin-1(2H)-yl)-4-fluoro-4-methylpentanamido)-3-(4-fluoro-2',4',6'-trimethyl-5-(trifluoromethyl)biphenyl-3-yl)propanoate

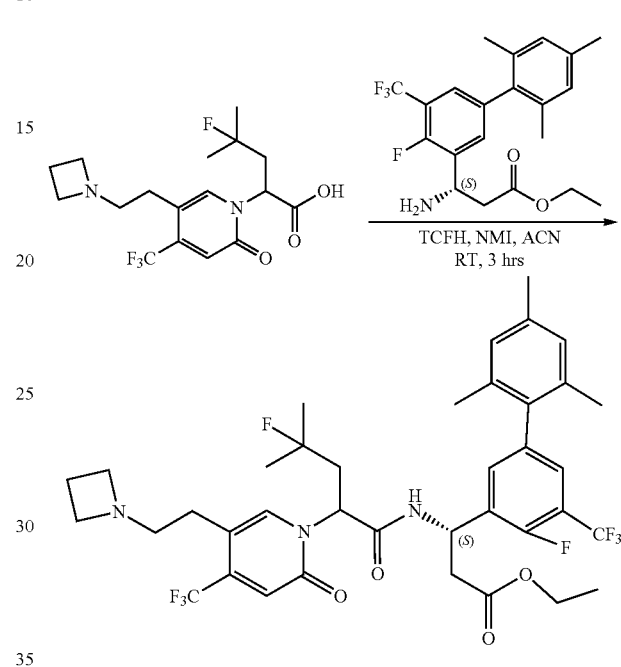

A mixture of (S)-ethyl 3-amino-3-(4-fluoro-2',4',6'-trimethyl-5-(trifluoromethyl)biphenyl-3-yl)propanoate (170 mg, 0.43 mmol), 2-(5-(2-(azetidin-1-yl)ethyl)-2-oxo-4-(trifluoromethyl)pyridin-1(2H)-yl)-4-fluoro-4-methylpentanoic acid (163 mg, 0.43 mmol), TCFH (241 mg, 0.86 mmol) and NMI (106 mg, 1.3 mmol) in MeCN (5 mL) was stirred at room temperature for 1 hour. The solvent was removed in vacuo and the residue purified by silica gel column (DCM:MeOH 97:3) to provide (3S)-ethyl 3-(2-(5-(2-(azetidin-1-yl)ethyl)-2-oxo-4-(trifluoromethyl)pyridin-1(2H)-yl)-4-fluoro-4-methylpentanamido)-3-(4-fluoro-2',4',6'-trimethyl-5-(trifluoromethyl)biphenyl-3-yl)propanoate as a colorless oil (100 mg). Yield 31% (ESI 758.3 (M+H)$^+$).

Step 2: (3S)-3-(2-(5-(2-(azetidin-1-yl)ethyl)-2-oxo-4-(trifluoromethyl)pyridin-1(2H)-yl)-4-fluoro-4-methylpentanamido)-3-(4-fluoro-2',4',6'-trimethyl-5-(trifluoromethyl)biphenyl-3-yl)propanoic Acid

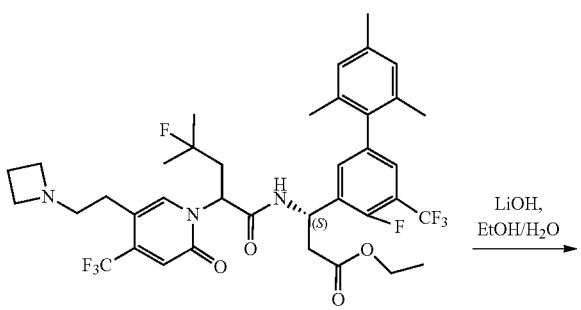

595

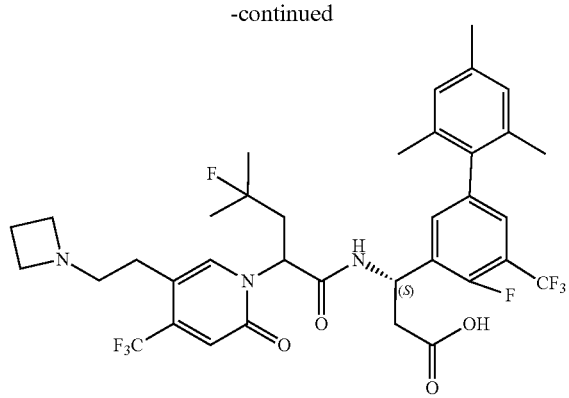

(3S)-ethyl 3-(2-(5-(2-(azetidin-1-yl)ethyl)-2-oxo-4-(trifluoromethyl)pyridin-1(2H)-yl)-4-fluoro-4-methylpentanamido)-3-(4-fluoro-2',4',6'-trimethyl-5-(trifluoromethyl)biphenyl-3-yl)propanoate (100 mg, 0.13 mmol) was treated with LiOH—H$_2$O (27 mg, 0.65 mmol) in EtOH (3 mL) and H$_2$O (1 mL) at room temperature for 2 hours. The reaction mixture was acidified to pH 4~5 with 1N HCl. The solvent was removed in vacuo and the residue was purified by prep-HPLC A (30-60% CH$_3$CN) to give the diastereomeric products JR-P1 (36 mg) and JR-P2 (22 mg) as white solids.

JR-P1 ESI 730.3 (M+H)$^+$. 1H NMR (400 MHz, MeOD) δ 7.90 (s, 1H), 7.26 (d, J=6.4 Hz, 2H), 6.92 (s, 2H), 6.58 (s, 1H), 5.65 (s, 1H), 5.59-5.50 (m, 1H), 4.09 (t, J=8.1 Hz, 4H), 3.33 (d, J=11.0 Hz, 2H), 2.90-2.40 (m, 8H), 2.30 (s, 3H), 1.99-1.90 (m, 3H), 1.84 (d, J=15.3 Hz, 3H), 1.46-1.25 (m, 6H).

JR-P2 ESI 730.3 (M+H)$^+$. 1H NMR (400 MHz, MeOD) δ 7.73 (s, 1H), 7.43 (d, J=4.9 Hz, 1H), 7.32 (d, J=6.5 Hz, 1H), 6.94 (s, 2H), 6.88 (s, 1H), 5.78 (t, J=6.6 Hz, 2H), 4.14 (s, 4H), 3.51-3.36 (m, 2H), 2.92 (d, J=15.8 Hz, 1H), 2.82-2.79 (m, 1H), 2.68-2.42 (m, 5H), 2.30 (s, 3H), 2.16-2.13 (m, 1H), 1.95 (d, J=3.6 Hz, 6H), 1.34-1.31 (m, 6H).

3-115. Preparation of (3S)-3-(2-(5-(3-(dimethylamino)propyl)-2-oxo-4-(trifluoromethyl)pyridin-1 (2H)-yl)-4-methylpentanamido)-3-(4-fluoro-2',4',6'-trimethyl-5-(trifluoromethyl)-[1,1'-biphenyl]-3-yl) propanoic Acid (Compounds JS-P1 and JS-P2)

Step 1: Ethyl (3S)-3-(2-(5-(3-(dimethylamino)propyl)-2-oxo-4-(trifluoromethyl)pyridin-1(2H)-yl)-4-methylpentanamido)-3-(4-fluoro-2',4',6'-trimethyl-5-(trifluoromethyl)-[1,1'-biphenyl]-3-yl)propanoate

596

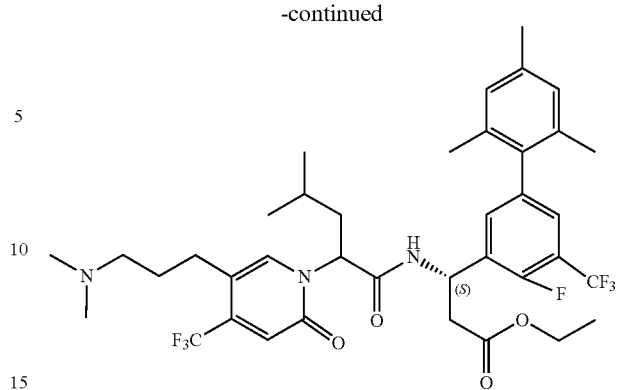

A mixture of ethyl (S)-3-amino-3-(4-fluoro-2',4',6'-trimethyl-5-(trifluoromethyl)-[1,1'-biphenyl]-3-yl)propanoate (290 mg, 0.73 mmol), 2-(5-(3-(dimethylamino)propyl)-2-oxo-4-(trifluoromethyl)pyridin-1(2H)-yl)-4-methylpentanoic acid (240 mg, 0.662 mmol), N,N,N',N'-tetramethylchloroformamidinium hexafluorophosphate (278 mg, 0.993 mmol) and 1-methylimidazole (217 mg, 2.65 mmol) in acetonitrile (10 mL) was stirred at room temperature for 2 hours. The mixture was purified by reverse phase HPLC on a C18/40 g column (A: water 10 mM NH$_4$HCO$_3$, B: MeOH, 0~100%) to provide ethyl (3S)-3-(2-(5-(3-(dimethylamino)propyl)-2-oxo-4-(trifluoromethyl)pyridin-1(2H)-yl)-4-methylpentanamido)-3-(4-fluoro-2',4',6'-trimethyl-5-(trifluoromethyl)-[1,1'-biphenyl]-3-yl)propanoate (370 mg) as a white solid. Yield 75% (ESI 742.2 (M+H)$^+$).

Step 2: (3S)-3-(2-(5-(3-(dimethylamino)propyl)-2-oxo-4-(trifluoromethyl)pyridin-1(2H)-yl)-4-methylpentanamido)-3-(4-fluoro-2',4',6'-trimethyl-5-(trifluoromethyl)-[1,1'-biphenyl]-3-yl)propanoic Acid

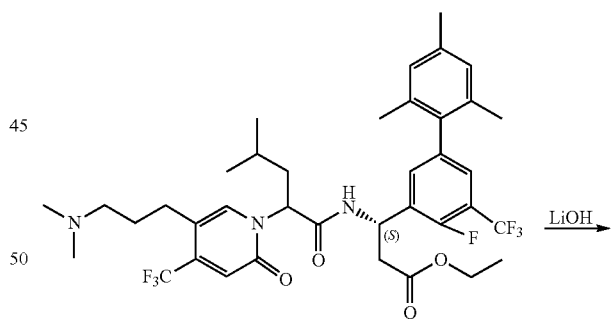

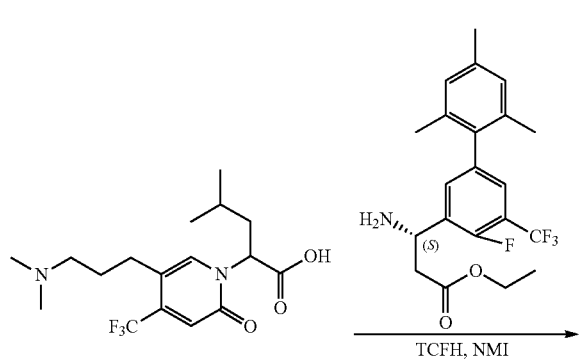

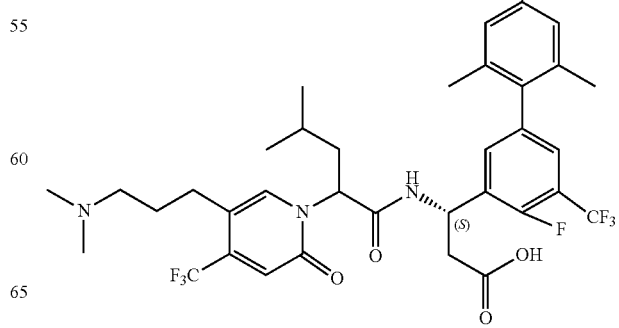

Ethyl (3S)-3-(2-(5-(3-(dimethylamino)propyl)-2-oxo-4-(trifluoromethyl)pyridin-1(2H)-yl)-4-methylpentanamido)-3-(4-fluoro-2',4',6'-trimethyl-5-(trifluoromethyl)-[1,1'-biphenyl]-3-yl)propanoate (370 mg, 0.50 mmol) was treated with LiOH—H$_2$O (84 mg, 2.0 mmol) in MeOH (5 mL) and H$_2$O (1 mL) at room temperature for 2 hours. The reaction mixture was acidified to pH 4~5 with 1N HCl. The solvent was removed in vacuo and the residue was purified by prep-HPLC A (30-60% CH$_3$CN) to give the diastereomeric products JS-P1 (123 mg) and JS-P2 (91 mg) as white solids.

JS-P1 ESI 713.9 (M+H)$^+$. 1H NMR (400 MHz, MeOD) δ 7.78 (s, 1H), 7.35 (d, J=5.0 Hz, 1H), 7.30-7.21 (m, 1H), 6.91 (d, J=13.8 Hz, 2H), 6.68 (s, 1H), 5.70-5.66 (m, 1H), 5.59 (t, J=6.8 Hz, 1H), 3.09-3.04 (m, 2H), 2.79 (s, 6H), 2.74-2.63 (m, 4H), 2.29 (s, 3H), 2.03-1.95 (m, 7H), 1.78 (s, 3H), 1.42-1.33 (m, 1H), 0.94-0.91 (m, 6H).

JS-P2 ESI 713.9 (M+H)$^+$. 1H NMR (400 MHz, MeOD) δ 7.80 (s, 1H), 7.37-7.30 (m, 2H), 6.94 (s, 2H), 6.83 (s, 1H), 5.76-5.72 (m, 1H), 5.58 (t, J=7.6 Hz, 1H), 3.05-3.00 (m, 2H), 2.79 (s, 6H), 2.74-2.49 (m, 4H), 2.30 (s, 3H), 2.03-1.91 (m, 9H), 1.67-1.60 (m, 1H), 1.37-1.29 (m, 1H), 0.86-0.83 (m, 6H).

3-116. Preparation of (3S)-3-(2-(5-(2-(5-azaspiro[2.3]hexan-5-yl)ethyl)-2-oxo-4-(trifluoromethyl)pyridin-1(2H)-yl)-4-methylpentanamido)-3-(4-fluoro-2',6'-dimethyl-5-(trifluoromethyl)-[1,1'-biphenyl]-3-yl)propanoic Acid (Compounds JT-P1 and JT-P2)

Step 1: Ethyl (3S)-3-(2-(5-(2-(5-azaspiro[2.3]hexan-5-yl)ethyl)-2-oxo-4-(trifluoromethyl)pyridin-1(2H)-yl)-4-methylpentanamido)-3-(4-fluoro-2',6'-dimethyl-5-(trifluoromethyl)-[1,1'-biphenyl]-3-yl)propanoate

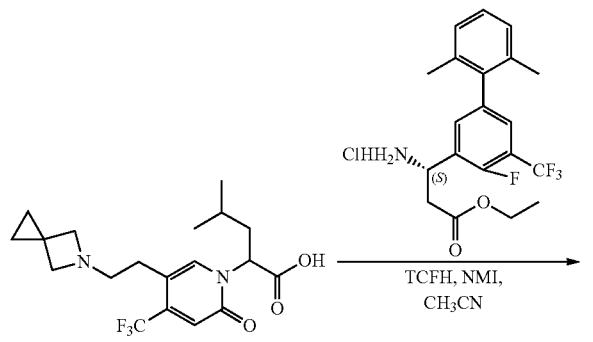

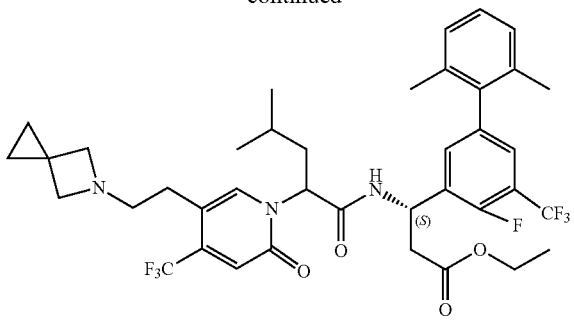

A mixture of ethyl (S)-3-amino-3-(4-fluoro-2',6'-dimethyl-5-(trifluoromethyl)-[1,1'-biphenyl]-3-yl)propanoate hydrochloride (150 mg, 0.36 mmol), 2-(5-(2-(5-azaspiro[2.3]hexan-5-yl)ethyl)-2-oxo-4-(trifluoromethyl)pyridin-1(2H)-yl)-4-methylpentanoic acid (139.0 mg, 0.36 mmol), TCHF (120.6 mg, 0.43 mmol) and NMI (88.7 mg, 1.08 mmol) in CH$_3$CN (5 mL) was stirred at room temperature overnight. The solvent was removed in vacuo and the residue was purified by reverse phase HPLC on a C18/40 g column (A: water 10 mM NH$_4$HCO$_3$, B: MeOH, 0~100%) to provide ethyl (3S)-3-(2-(5-(2-(5-azaspiro[2.3]hexan-5-yl)ethyl)-2-oxo-4-(trifluoromethyl)pyridin-1(2H)-yl)-4-methylpentanamido)-3-(4-fluoro-2',6'-dimethyl-5-(trifluoromethyl)-[1,1'-biphenyl]-3-yl)propanoate as a light yellow solid (100 mg). Yield 37% (ESI 752.3 [M+H]$^+$).

Step 2: (3S)-3-(2-(5-(2-(5-azaspiro[2.3]hexan-5-yl)ethyl)-2-oxo-4-(trifluoromethyl)pyridin-1(2H)-yl)-4-methylpentanamido)-3-(4-fluoro-2',6'-dimethyl-5-(trifluoromethyl)-[1,1'-biphenyl]-3-yl)propanoic Acid

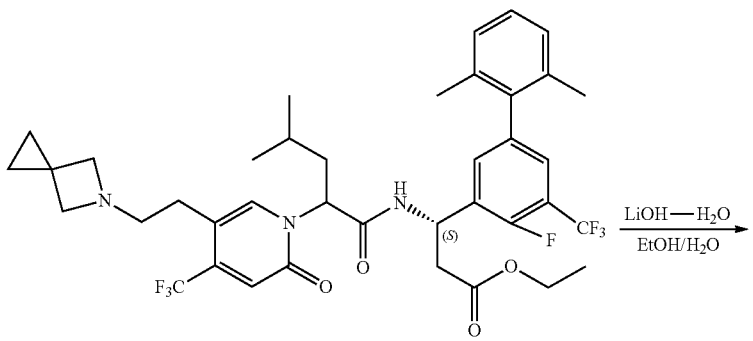

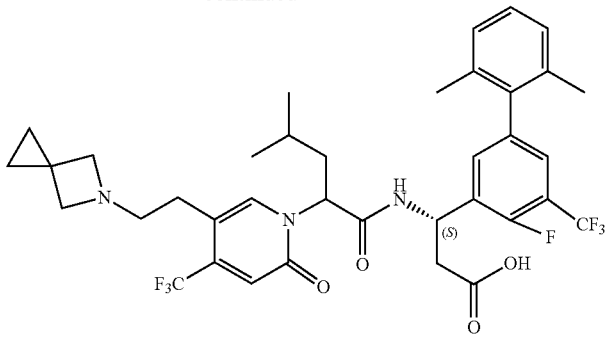

Ethyl (3S)-3-(2-(5-(2-(5-azaspiro[2.3]hexan-5-yl)ethyl)-2-oxo-4-(trifluoromethyl)pyridin-1(2H)-yl)-4-methylpentanamido)-3-(4-fluoro-2',6'-dimethyl-5-(trifluoromethyl)-[1,1'-biphenyl]-3-yl)propanoate (100.0 mg, 0.13 mmol) was treated with LiOH—H$_2$O (16.4 mg, 0.39 mmol) in EtOH (2 mL) and water (0.5 mL) at room temperature for 1 hour. The reaction mixture was acidified to pH 5~6 with 2N HCl. The solvent was removed in vacuo and the residue purified by prep-HPLC A (30-80% MeCN) to give the diastereomeric products JT-P1 (29 mg) and JT-P2 (38 mg) as white solids.

JT-P1 ESI 724.2 (M+H)$^+$ $^1$H NMR (400 MHz, MeOD) δ 7.84 (s, 1H), 7.40 (d, J=5.2 Hz, 1H), 7.29 (d, J=6.3 Hz, 1H), 7.19-7.06 (m, 3H), 6.73 (s, 1H), 5.67-5.60 (m, 2H), 4.10 (s, 4H), 3.42-3.33 (m, 2H), 2.87 (t, J=7.1 Hz, 2H), 2.72 (d, J=6.9 Hz, 2H), 2.07-1.90 (m, 5H), 1.84 (s, 3H), 1.46-1.34 (m, 1H), 1.00-0.88 (m, 6H), 0.75 (s, 4H).

JT-P2 ESI 724.2 (M+H)$^+$ $^1$H NMR (400 MHz, MeOD) δ 7.75 (s, 1H), 7.46-7.43 (m, 1H), 7.37-7.34 (m, 1H), 7.21-7.10 (m, 3H), 6.88 (s, 1H), 5.81-5.76 (m, 1H), 5.63 (t, J=7.7 Hz, 1H), 4.26-4.09 (m, 4H), 3.53-3.39 (m, 2H), 3.03-2.75 (m, 2H), 2.70-2.50 (m, 2H), 2.04-1.91 (m, 7H), 1.69-1.60 (m, 1H), 1.45-1.35 (m, 1H), 0.90-0.86 (m, 6H), 0.83-0.72 (m, 4H).

3-117. Preparation of (3S)-3-(2-(5-(2-(5-azaspiro[2.3]hexan-5-yl)ethyl)-2-oxo-4-(trifluoromethyl)pyridin-1(2H)-yl)-4-methylpentanamido)-3-(4-fluoro-2',4',5,6'-tetramethylbiphenyl-3-yl)propanoic Acid (Compounds JU-P1 and JU-P2)

Step 1: (3S)-ethyl 3-(2-(5-(2-(5-azaspiro[2.3]hexan-5-yl)ethyl)-2-oxo-4-(trifluoromethyl)pyridin-1(2H)-yl)-4-methylpentanamido)-3-(4-fluoro-2',4',5,6'-tetramethylbiphenyl-3-yl)propanoate

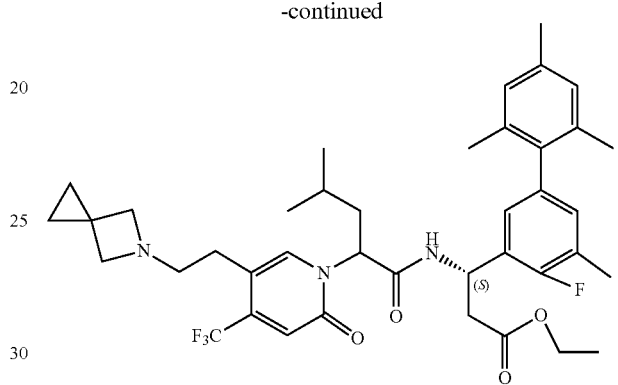

A mixture of 2-(5-(2-(5-azaspiro[2.3]hexan-5-yl)ethyl)-2-oxo-4-(trifluoromethyl)pyridin-1(2H)-yl)-4-methylpentanoic acid (150 mg, 0.39 mmol), (S)-ethyl 3-amino-3-(4-fluoro-2',4',5,6'-tetramethylbiphenyl-3-yl)propanoate (133 mg, 0.39 mmol), NMI (160 mg, 1.96 mmol) and TCHF (218 mg, 0.78 mmol) in CH$_3$CN (5 mL) was stirred at room temperature for 1.5 hours. The solvent was concentrated in vacuo and the residue purified by silica gel column (DCM:MeOH 9:1) to provide (3S)-ethyl 3-(2-(5-(2-(5-azaspiro[2.3]hexan-5-yl)ethyl)-2-oxo-4-(trifluoromethyl)pyridin-1(2H)-yl)-4-methylpentanamido)-3-(4-fluoro-2',4',5,6'-tetramethylbiphenyl-3-yl)propanoate as a colorless oil (180 mg). Yield 65% (ESI 712.3 [M+H]$^+$).

Step 2: (3S)-3-(2-(5-(2-(5-azaspiro[2.3]hexan-5-yl)ethyl)-2-oxo-4-(trifluoromethyl)pyridin-1(2H)-yl)-4-methylpentanamido)-3-(4-fluoro-2',4',5,6'-tetramethylbiphenyl-3-yl)propanoic Acid

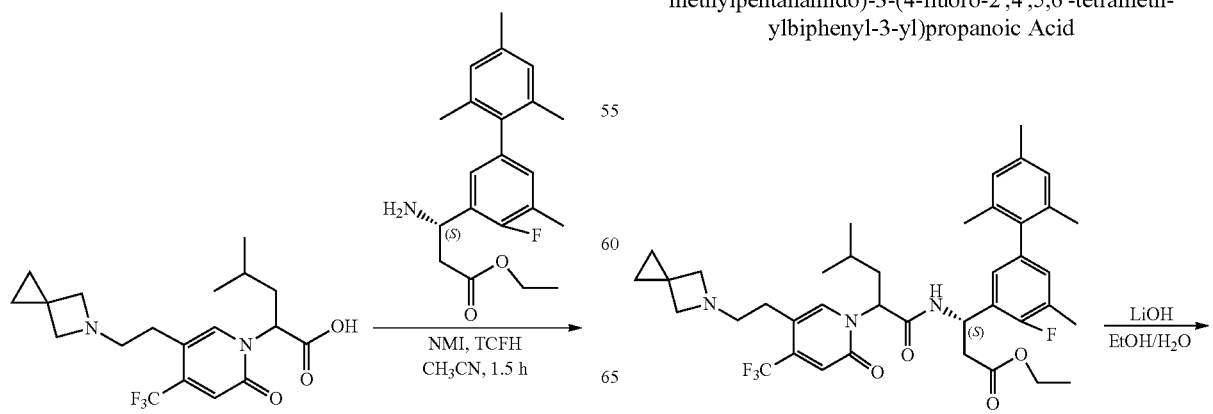

601

-continued

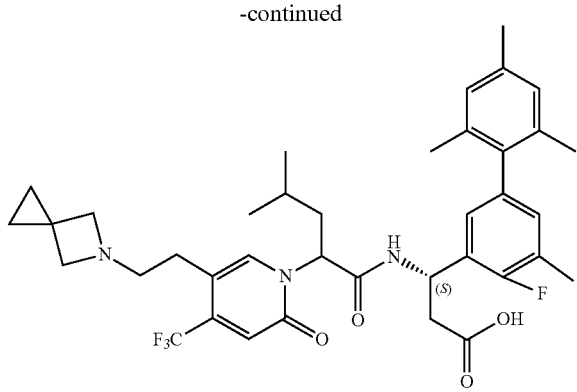

(3S)-ethyl 3-(2-(5-(2-(5-azaspiro[2.3]hexan-5-yl)ethyl)-2-oxo-4-(trifluoromethyl)pyridin-1(2H)-yl)-4-methylpentanamido)-3-(4-fluoro-2',4',5,6'-tetramethylbiphenyl-3-yl)propanoate (180 mg, 0.25 mmol) was treated with LiOH—H$_2$O (53 mg, 1.27 mmol) in EtOH (3 mL) and H$_2$O (1 mL) at room temperature for 2 hours. The reaction mixture was acidified to pH 4~5 with 1N HCl. The solvent was removed in vacuo and the residue purified by prep-HPLC A (30-60% CH$_3$CN) to give the diastereomeric products JU-P1 (51 mg) and JU-P2 (60 mg) as white solids.

602

JU-P1 ESI 684.3 (M+H)$^+$. 1H NMR (400 MHz, MeOD) δ 7.75 (s, 1H), 6.92-6.89 (m, 5H), 5.60 (t, J=7.2 Hz, 1H), 5.75-5.72 (m, 1H), 4.27 (d, J=8.1 Hz, 4H), 3.55-3.40 (m, 2H), 2.98-2.53 (m, 4H), 2.28 (s, 3H), 2.30 (s, 3H), 2.08-1.93 (m, 7H), 1.99-1.95 (m, 1H), 1.42-1.40 (m, 1H), 1.09-0.69 (m, 10H).

JU-P2 ESI 684.3 (M+H)$^+$. 1H NMR (400 MHz, MeOD) δ 7.75 (s, 1H), 7.00-6.80 (m, 5H), 5.74-5.70 (m, 1H), 5.60 (t, J=7.6 Hz, 1H), 4.18 (s, 4H), 3.58-3.42 (m, 2H), 2.97 (d, J=16.0 Hz, 1H), 2.89-2.74 (m, 1H), 2.67-2.63 (m, 1H), 2.53-2.50 (m, 1H), 2.29 (d, J=11.2 Hz, 6H), 2.03-1.97 (m, 7H), 1.65-1.61 (m, 1H), 1.43-1.41 (m, 1H), 0.88 (d, J=5.6 Hz, 6H), 0.77 (t, J=10.3 Hz, 4H).

3-118. Preparation of (3S)-3-(4-fluoro-2',3',6'-trimethyl-5-(trifluoromethyl)biphenyl-3-yl)-3-(2-(5-(2-(3-(methoxymethyl)azetidin-1-yl)ethyl)-2-oxo-4-(trifluoromethyl)pyridin-1(2H)-yl)-4-methylpentanamido)propanoic Acid (Compounds JV-P1 and JV-P2)

Step 1: (3S)-ethyl 3-(4-fluoro-2',3',6'-trimethyl-5-(trifluoromethyl)biphenyl-3-yl)-3-(2-(5-(2-(3-(methoxymethyl)azetidin-1-yl)ethyl)-2-oxo-4-(trifluoromethyl)pyridin-1(2H)-yl)-4-methylpentanamido)propanoate

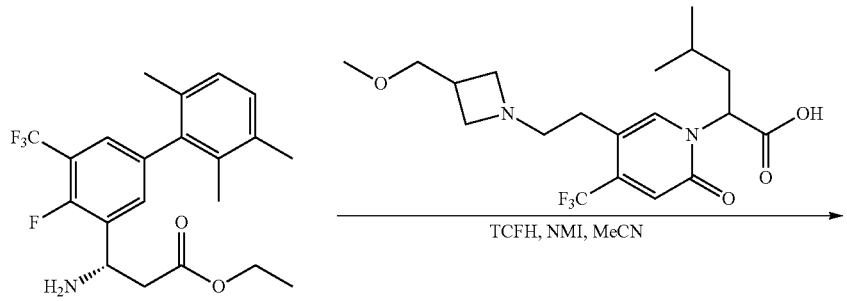

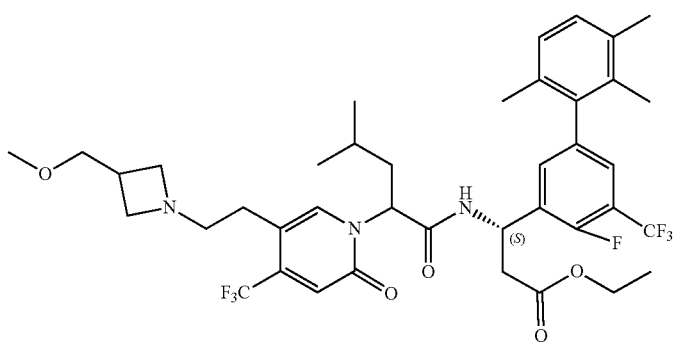

A mixture of (S)-ethyl 3-amino-3-(4-fluoro-2',3',6'-trimethyl-5-(trifluoromethyl)biphenyl-3-yl)propanoate (240 mg, 0.60 mmol), 2-(5-(2-(3-(methoxymethyl)azetidin-1-yl)ethyl)-2-oxo-4-(trifluoromethyl)pyridin-1(2H)-yl)-4-methylpentanoic acid (242 mg, 0.60 mmol), NMI (197 mg, 1.8 mmol) and TCFH (252 mg, 0.9 mmol) in CH$_3$CN (8 mL) was stirred at room temperature for 2 hours. The solvent was concentrated in vacuo and the residue was purified by reverse phase HPLC on a C18/40 g column (A: water 10 mM NH$_4$HCO$_3$, B: CH$_3$CN, 0~100%) to provide (3S)-ethyl 3-(4-fluoro-2',3',6'-trimethyl-5-(trifluoromethyl)biphenyl-3-yl)-3-(2-(5-(2-(3-(methoxymethyl)azetidin-1-yl)ethyl)-2-oxo-4-(trifluoromethyl)pyridin-1(2H)-yl)-4-methylpentanamido)propanoate as a yellow oil (270 mg). Yield 57% (ESI 784.0 [M+H]$^+$).

Step 2: (3S)-3-(4-fluoro-2',3',6'-trimethyl-5-(trifluoromethyl)biphenyl-3-yl)-3-(2-(5-(2-(3-(methoxymethyl)azetidin-1-yl)ethyl)-2-oxo-4-(trifluoromethyl)pyridin-1(2H)-yl)-4-methylpentanamido)propanoic (3S)-ethyl 3-(4-fluoro-2',3',6'-trimethyl-5-(trifluoromethyl)biphenyl-3-yl)-3-(2-(5-(2-(3-(methoxymethyl)azetidin-1-yl)ethyl)-2-oxo-4-(trifluoromethyl)pyridin-1(2H)-yl)-4-methylpentanamido)propanoate (270 mg, 0.34 mmol) was treated with LiOH—H$_2$O (57 mg, 1.36 mmol) in EtOH (3 mL) and H$_2$O (1 mL) at room temperature for 2 hours. The reaction mixture was acidified to pH 5~6 with 1N HCl. The solvent was removed in vacuo and the residue was purified by prep-HPLC A (30-60% CH$_3$CN) to give the diastereomeric products JV-P1 (67 mg) and JV-P2 (90 mg) as white solids.

JV-P1 ESI 755.9 (M+H)$^+$. 1H NMR (400 MHz, MeOD) δ 7.83 (d, J=5.9 Hz, 1H), 7.38-7.24 (m, 2H), 7.08-6.95 (m, 2H), 6.74 (d, J=19.4 Hz, 1H), 5.64-5.60 (m, 2H), 4.13-4.09 (m, 2H), 3.89-3.81 (m, 2H), 3.47-3.38 (m, 5H), 3.28-3.24 (m, 2H), 3.05-2.95 (s, 1H), 2.89-2.66 (m, 4H), 2.26 (d, J=2.9 Hz, 3H), 2.06-1.89 (m, 5H), 1.76-1.75 (m, 3H), 1.44-1.36 (m, 1H), 0.94-0.91 (m, 6H).

JV-P2 ESI 755.9 (M+H)$^+$. 1H NMR (400 MHz, MeOD) δ 7.73 (s, 1H), 7.42-7.31 (m, 2H), 7.09-7.00 (m, 2H), 6.88 (s, 1H), 5.81-5.78 (m, 1H), 5.61 (t, J=7.6 Hz, 1H), 4.25-4.17 (m, 2H), 3.98-3.88 (m, 2H), 3.50 (d, J=4.4 Hz, 2H), 3.45-

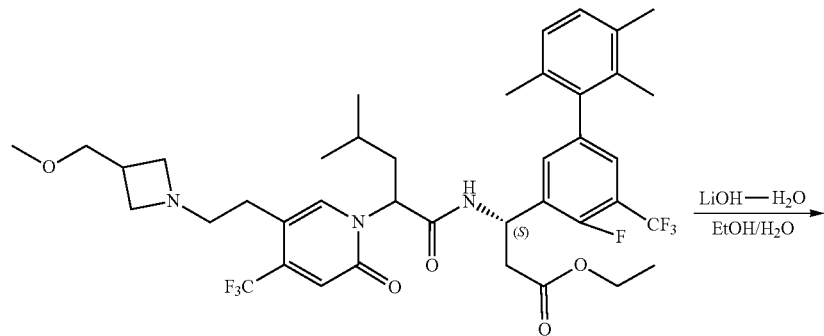

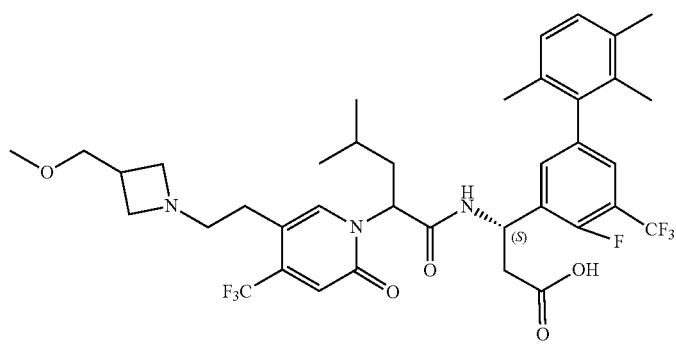

3.32 (m, 5H), 3.11-3.02 (m, 1H), 2.94-2.74 (m, 2H), 2.68-2.51 (m, 2H), 2.28 (s, 3H), 2.00-1.89 (m, 7H), 1.69-1.61 (m, 1H), 1.42-1.33 (m, 1H), 0.88-0.86 (m, 6H).

3-119. Preparation of (S)-3-((R)-2-(5-(2-(2-azaspiro[3.3]heptan-2-yl)ethyl)-2-oxo-4-(trifluoromethyl)pyridin-1(2H)-yl)-4-methylpentanamido)-3-(3',4-difluoro-2',5,6'-trimethyl-[1,1'-biphenyl]-3-yl) propanoic Acid (Compounds JW-P1 and JW-P2)

Step 1: Ethyl (3S)-3-(2-(5-(2-(2-azaspiro[3.3]heptan-2-yl)ethyl)-2-oxo-4-(trifluoromethyl)pyridin-1(2H)-yl)-4-methylpentanamido)-3-(3',4-difluoro-2',5,6'-trimethyl-[1,1'-biphenyl]-3-yl)propanoate

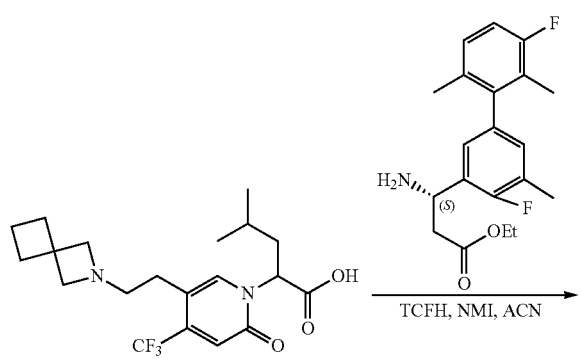

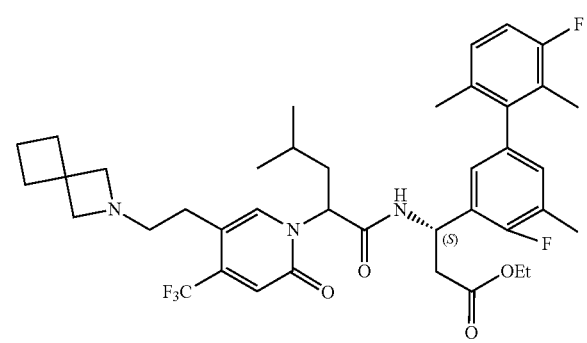

A mixture of 2-(5-(2-(2-azaspiro[3.3]heptan-2-yl)ethyl)-2-oxo-4-(trifluoromethyl)pyridin-1(2H)-yl)-4-methylpentanoic acid (250.0 mg, 0.63 mmol), ethyl (S)-3-amino-3-(3',4-difluoro-2',5,6'-trimethyl-[1,1-biphenyl]-3-yl)propanoate hydrochloride (218.0 mg, 0.63 mmol), TCHF (210.0 mg, 0.75 mmol) and NMI (155.0 mg, 1.89 mmol) in CH$_3$CN (5 mL) was stirred at room temperature for 2 hrs. The mixture was concentrated in vacuo and the residue was purified by reverse phase HPLC on a C18/40 g column (A: water 10 mM NH$_4$HCO$_3$, B: CH3CN, 0~100%) to provide ethyl (3S)-3-(2-(5-(2-(2-azaspiro[3.3]heptan-2-yl)ethyl)-2-oxo-4-(trifluoromethyl)pyridin-1(2H)-yl)-4-methylpentanamido)-3-(3',4-difluoro-2',5,6'-trimethyl-[1,1'-biphenyl]-3-yl)propanoate as a yellow solid (300.0 mg). Yield 66.1% (ESI 730.0 [M+H]$^+$).

Step 2: (S)-3-((R)-2-(5-(2-(2-azaspiro[3.3]heptan-2-yl)ethyl)-2-oxo-4-(trifluoromethyl)pyridin-1(2H)-yl)-4-methylpentanamido)-3-(3',4-difluoro-2',5,6'-trimethyl-[1,1'-biphenyl]-3-yl)propanoic acid

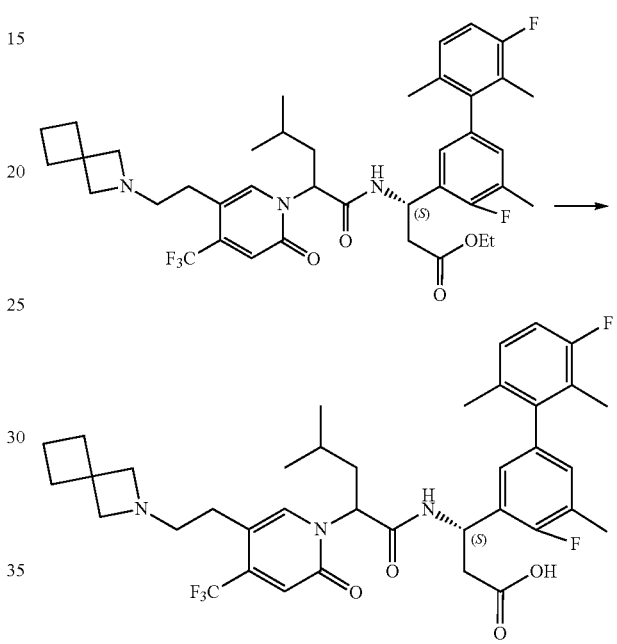

Ethyl (3S)-3-(2-(5-(2-(2-azaspiro[3.3]heptan-2-yl)ethyl)-2-oxo-4-(trifluoromethyl)pyridine-1(2H)-yl)-4-methylpentanamido)-3-(3',4-difluoro-2',5,6'-trimethyl-[1,1'-biphenyl]-3-yl)propanoate (300.0 mg, 0.41 mmol) was treated with LiOH—H$_2$O (86.0 mg, 2.05 mmol) in EtOH (4 mL) and water (2 mL) at 30° C. for 1 hour. The reaction mixture was acidified to pH 4~5 with 2N HCl. The solvent was removed in vacuo and the residue was purified by Prep HPLC A (30-60% MeCN) to give the diastereomeric products JW-P1 (64 mg) and JW-P2 (85 mg) as white solids.

JW-P1 ESI 702.2 (M+H)$^+$ $^1$H NMR (400 MHz, MeOD) δ 7.82 (s, 1H), 7.10-6.99 (m, 1H), 6.96-6.81 (m, 3H), 6.76 (d, J=6.0 Hz, 1H), 5.65-5.59 (m, 2H), 4.05-3.88 (m, 4H), 3.26-3.12 (m, 2H), 2.83 (t, J=7.0 Hz, 2H), 2.68 (d, J=6.6 Hz, 2H), 2.33-2.15 (m, 7H), 2.00-1.73 (m, 10H), 1.46-1.32 (m, 1H), 0.94-0.91 (m, 6H).

JW-P2 ESI 702.2 (M+H)$^+$ $^1$H NMR (400 MHz, MeOD) δ 7.72 (s, 1H), 7.11-7.02 (m, 1H), 6.98-6.81 (m, 4H), 5.73 (dd, J=11.0, 3.4 Hz, 1H), 5.60 (t, J=7.2 Hz, 1H), 4.12-4.09 (m, 4H), 3.32-3.3 (m, 2H), 2.88-2.85 (m, 2H), 2.60-2.45 (m, 2H), 2.39-2.19 (m, 7H), 2.03-1.78 (m, 9H), 1.66-1.54 (m, 1H), 1.43-1.38 (m, 1H), 0.90-0.88 (m, 6H).

3-120. Preparation of (3S)-3-(2-(5-(2-(2-azaspiro [3.3]heptan-2-yl)ethyl)-2-oxo-4-(trifluoromethyl) pyridin-1(2H)-yl)-4-methylpentanamido)-3-(4-fluoro-2',4',5,6'-tetramethyl-[1,1'-biphenyl]-3-yl) propanoic Acid (Compounds JX-P1 and JX-P2)

Step 1: Ethyl (3S)-3-(2-(5-(2-(2-azaspiro[3.3]heptan-2-yl)ethyl)-2-oxo-4-(trifluoromethyl)pyridin-1 (2H)-yl)-4-methylpentanamido)-3-(4-fluoro-2',4',5, 6'-tetramethyl-[1,1'-biphenyl]-3-yl)propanoate

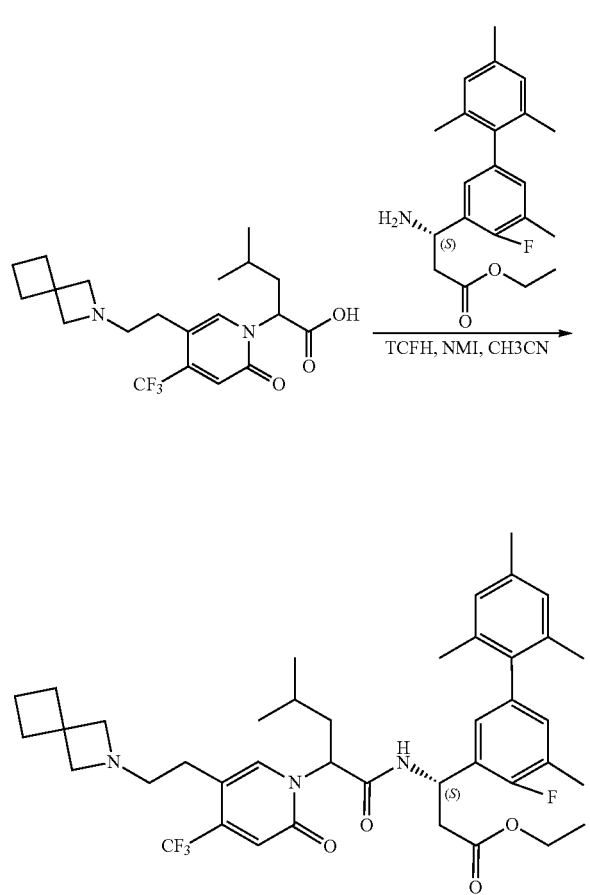

A mixture of 2-(5-(2-(2-azaspiro[3.3]heptan-2-yl)ethyl)-2-oxo-4-(trifluoromethyl)pyridin-1(2H)-yl)-4-methylpentanoic acid (250 mg, 0.63 mmol), ethyl (S)-3-amino-3-(4-fluoro-2',4',5,6'-tetramethyl-[1,1'-biphenyl]-3-yl)propanoate (216 mg, 0.63 mmol), NMI (0.6 mL) and TCFH (213 mg, 0.76 mmol) in CH₃CN (3 mL) was stirred at room temperature for 2 hours. The solvent was concentrated in vacuo and the residue was purified by prep-HPLC A (50-70% CH3CN) to provide ethyl (3S)-3-(2-(5-(2-(2-azaspiro[3.3]heptan-2-yl)ethyl)-2-oxo-4-(trifluoromethyl)pyridin-1(2H)-yl)-4-methylpentanamido)-3-(4-fluoro-2',4',5,6'-tetramethyl-[1,1'-biphenyl]-3-yl)propanoate as a white solid (280 mg). Yield 62% (ESI 726.2 [M+H]⁺).

Step 2: (3S)-3-(2-(5-(2-(2-azaspiro[3.3]heptan-2-yl) ethyl)-2-oxo-4-(trifluoromethyl)pyridin-1(2H)-yl)-4-methylpentanamido)-3-(4-fluoro-2',4',5,6'-tetramethyl-[1,1'-biphenyl]-3-yl)propanoic Acid

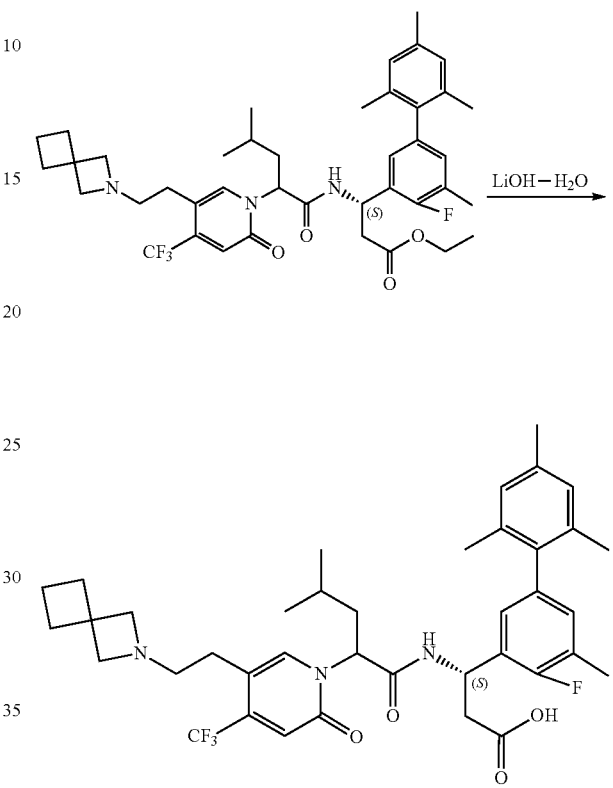

Ethyl (3S)-3-(2-(5-(2-(2-azaspiro[3.3]heptan-2-yl)ethyl)-2-oxo-4-(trifluoromethyl)pyridin-1(2H)-yl)-4-methylpentanamido)-3-(4-fluoro-2',4',5,6'-tetramethyl-[1,1'-biphenyl]-3-yl)propanoate (280 mg, 0.39 mmol) was treated with LiOH—H₂O (33 mg, 0.78 mmol) in MeOH (3.0 mL) and H₂O (1.0 mL) at room temperature for 2 hours. The reaction mixture was acidified to pH 5~6 with 1N HCl. The solvent was removed in vacuo and the residue was purified by prep-HPLC A (50-80% CH₃CN) to give the diastereomeric products JX-P1 (57 mg) and JX-P2 (127 mg) as white solids.

JX-P1 ESI 698.3 (M+H)⁺. ¹H NMR (400 MHz, MeOD) δ 7.83 (s, 1H), 6.92-6.78 (m, 4H), 6.74 (s, 1H), 5.67 (t, J=8.0 Hz, 1H), 5.59 (t, J=6.8 Hz, 1H), 4.02-3.87 (m, 4H), 3.27-3.15 (m, 2H), 2.82 (t, J=7.0 Hz, 2H), 2.68 (d, J=6.8 Hz, 2H), 2.33-2.15 (m, 10H), 2.03-1.90 (m, 5H), 1.87-1.73 (m, 5H), 1.45-1.34 (m, 1H), 0.92 (t, J=6.2 Hz, 6H).

JX-P2 ESI 698.3 (M+H)⁺. ¹H NMR (400 MHz, MeOD) δ 7.72 (s, 1H), 6.93-6.85 (m, 5H), 5.75-5.70 (m, 1H), 5.62-5.58 (m, 1H), 4.11 (s, 4H), 3.40-3.32 (m, 2H), 2.91 (d, J=16.0 Hz, 1H), 2.83-2.75 (m, 1H), 2.62-2.53 (m, 1H), 2.51-2.43 (m, 1H), 2.38-2.20 (m, 10H), 2.03-1.79 (m, 9H), 1.63-1.57 (m, 1H), 1.45-1.38 (m, 1H), 0.88 (d, J=6.6 Hz, 6H).

3-121. Preparation of (3S)-3-(2-(5-(2-(dimethylamino)ethyl)-2-oxo-4-(trifluoromethyl)pyridin-1(2H)-yl)-4-fluoro-4-methylpentanamido)-3-(4-fluoro-2',4',6'-trimethyl-5-(trifluoromethyl)-[1,1'-biphenyl]-3-yl)propanoic Acid (Compounds JY-P1 and JY-P2)

Step 1: Ethyl (3S)-3-(2-(5-(2-(dimethylamino)ethyl)-2-oxo-4-(trifluoromethyl)pyridin-1(2H)-yl)-4-fluoro-4-methylpentanamido)-3-(4-fluoro-2',4',6'-trimethyl-5-(trifluoromethyl)-[1,1'-biphenyl]-3-yl)propanoate

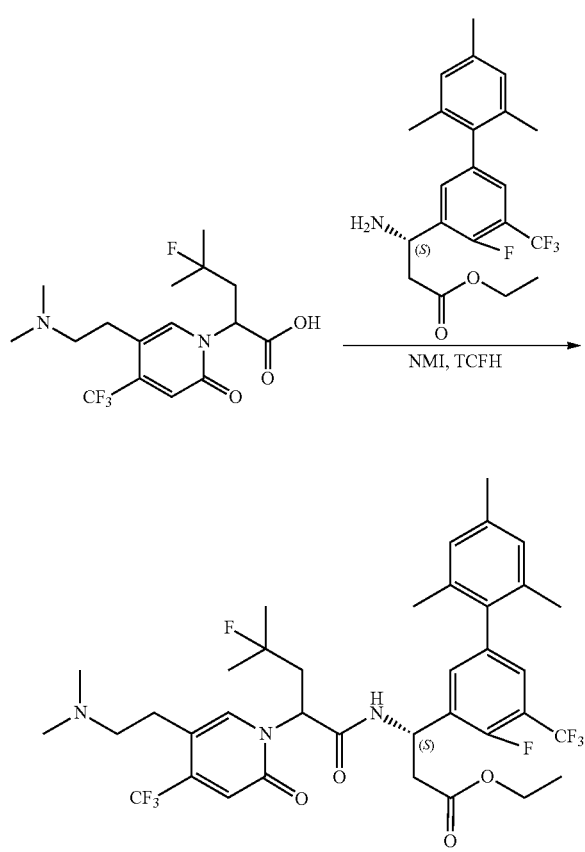

A mixture of 2-(5-(2-(dimethylamino)ethyl)-2-oxo-4-(trifluoromethyl)pyridin-1(2H)-yl)-4-fluoro-4-methylpentanoic acid (270 mg, 0.74 mmol), ethyl (S)-3-amino-3-(4-fluoro-2',4',6'-trimethyl-5-(trifluoromethyl)-[1,1'-biphenyl]-3-yl)propanoate (200 mg, 0.74 mmol), NMI (0.5 mL) and TCFH (294 mg, 1.11 mmol) in CH₃CN (3 mL) was stirred at room temperature for 2 hours. The solvent was concentrated in vacuo and the residue purified by prep-HPLC A (50-80% CH₃CN) to provide ethyl (3S)-3-(2-(5-(2-(dimethylamino)ethyl)-2-oxo-4-(trifluoromethyl)pyridin-1(2H)-yl)-4-fluoro-4-methylpentanamido)-3-(4-fluoro-2',4',6'-trimethyl-5-(trifluoromethyl)-[1,1'-biphenyl]-3-yl)propanoate as a white solid (300 mg). Yield 55% (ESI 746.2 [M+H]⁺).

Step 2: (3S)-3-(2-(5-(2-(dimethylamino)ethyl)-2-oxo-4-(trifluoromethyl)pyridin-1(2H)-yl)-4-fluoro-4-methylpentanamido)-3-(4-fluoro-2',4',6'-trimethyl-5-(trifluoromethyl)-[1,1'-biphenyl]-3-yl)propanoic Acid

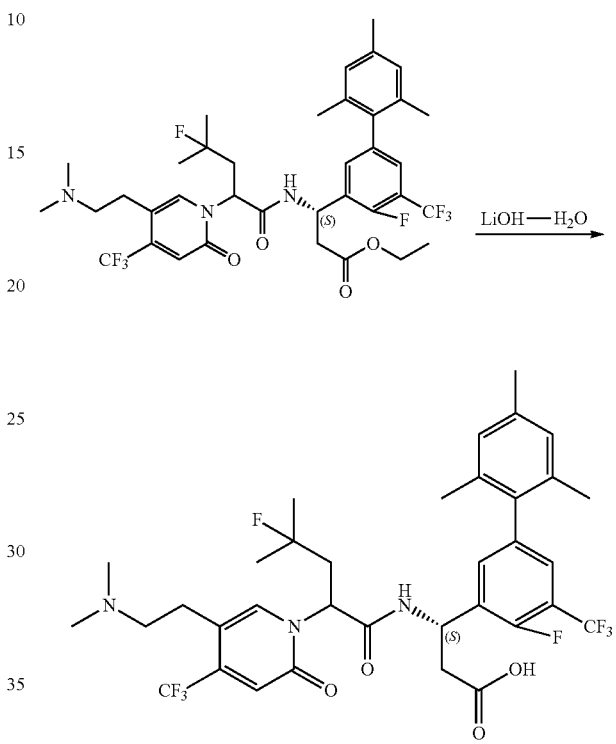

Ethyl (3S)-3-(2-(5-(2-(dimethylamino)ethyl)-2-oxo-4-(trifluoromethyl)pyridin-1(2H)-yl)-4-fluoro-4-methylpentanamido)-3-(4-fluoro-2',4',6'-trimethyl-5-(trifluoromethyl)-[1,1'-biphenyl]-3-yl)propanoate (300 mg, 0.40 mmol) was treated with LiOH—H₂O (34 mg, 0.80 mmol) in MeOH (3 mL) and H₂O (1.0 mL) at room temperature for 2 hours. The reaction mixture was acidified to pH 4~5 with 1N HC. The solvent was removed in vacuo and the residue purified by prep-HPLC A (50-80% CH₃CN) to give the diastereomeric products JY-P1 (111 mg) and JY-P2 (102 mg) as white solids.

JY-P1 ESI 717.9 (M+H)⁺. ¹H NMR (400 MHz, MeOD) δ 7.95 (s, 1H), 7.35-7.20 (m, 2H), 6.90 (d, J=13.6 Hz, 2H), 6.59 (s, 1H), 5.79 (s, 1H), 5.59-5.50 (m, 1H), 3.19-3.06 (m, 2H), 3.00-2.88 (m, 2H), 2.82-2.57 (m, 8H), 2.55-2.42 (m, 2H), 2.29 (s, 3H), 1.93 (s, 3H), 1.75 (s, 3H), 1.43-1.25 (m, 6H).

JY-P2 ESI 717.9 (M+H)⁺. ¹H NMR (400 MHz, MeOD) δ 7.83 (s, 1H), 7.40 (d, J=6.3 Hz, 1H), 7.31 (d, J=6.4 Hz, 1H), 6.94 (s, 2H), 6.87 (s, 1H), 5.80-5.68 (m, 2H), 3.27-3.14 (m, 2H), 2.98 (t, J=6.4 Hz, 2H), 2.84 (s, 6H), 2.65-2.48 (m, 3H), 2.30 (s, 3H), 2.25-2.12 (m, 1H), 1.95 (s, 6H), 1.37-1.25 (m, 6H).

3-122. Preparation of (3S)-3-(2-(5-(2-(dimethyl-amino)ethyl)-2-oxo-4-(trifluoromethyl)pyridin-1(2H)-yl)-4-methylpentanamido)-3-(4-fluoro-2',4',6'-trimethyl-5-(trifluoromethyl)-[1,1'-biphenyl]-3-yl)propanoic Acid (Compounds JZ-P1 and JZ-P2)

Step 1: Ethyl (3S)-3-(2-(5-(2-(dimethylamino)ethyl)-2-oxo-4-(trifluoromethyl)pyridin-1(2H)-yl)-4-methylpentanamido)-3-(4-fluoro-2',4',6'-trimethyl-5-(trifluoromethyl)-[1,1'-biphenyl]-3-yl)propanoate Step 2: (3S)-3-(2-(5-(2-(dimethylamino)ethyl)-2-oxo-4-(trifluoromethyl)pyridin-1(2)-yl)-4-methylpentanamido)-3-(4-fluoro-2',4',6'-trimethyl-5-(trifluoromethyl)-[1,1'-biphenyl]-3-yl)propanoic Acid

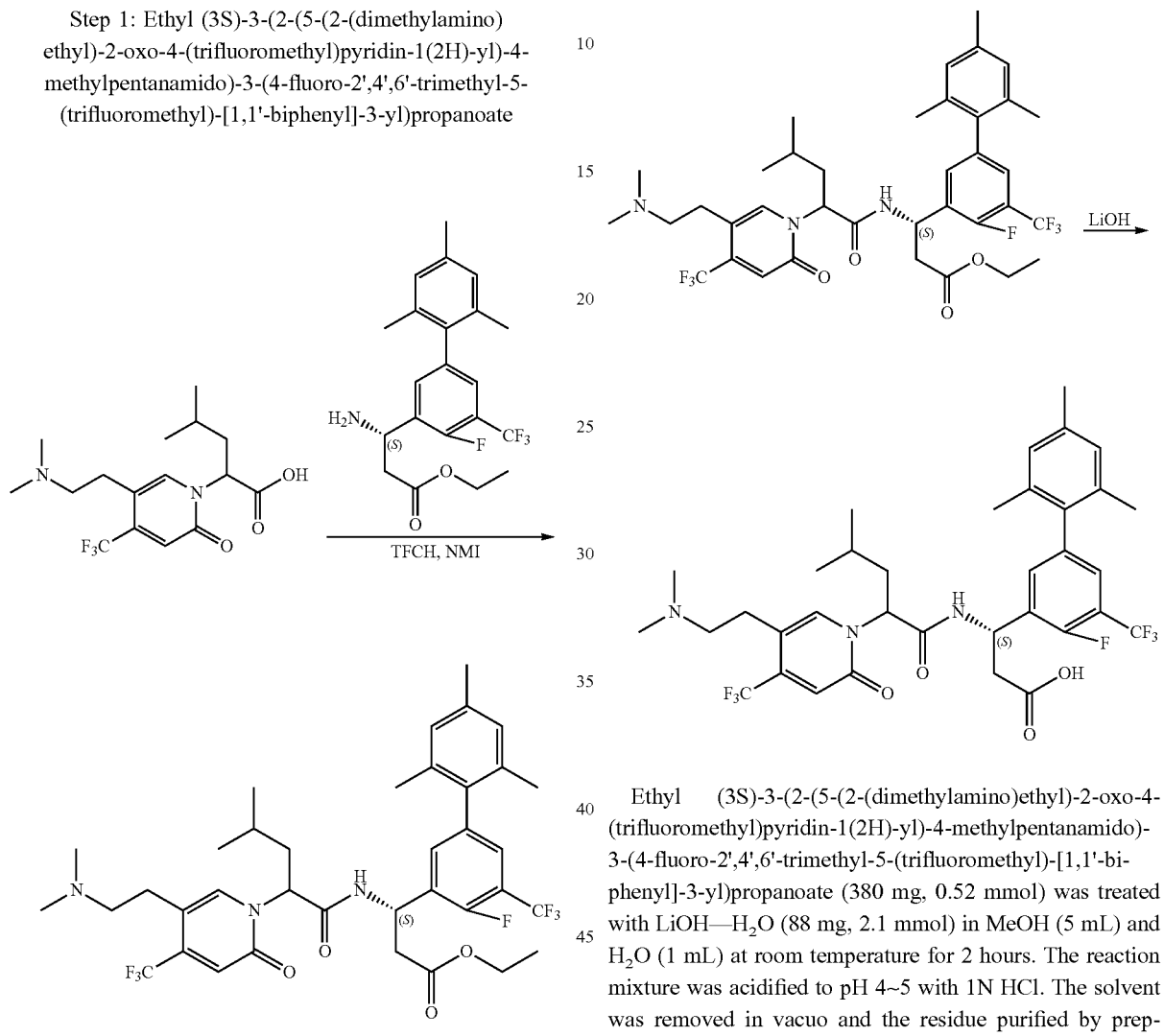

A mixture of ethyl (S)-3-amino-3-(4-fluoro-2',4',6'-trimethyl-5-(trifluoromethyl)-[1,1'-biphenyl]-3-yl)propanoate (301 mg, 0.76 mmol), 2-(5-(2-(dimethylamino)ethyl)-2-oxo-4-(trifluoromethyl)pyridin-1(2H)-yl)-4-methylpentanoic acid (240 mg, 0.69 mmol), TCHF (290 mg, 1.04 mmol) and NMI (226 mg, 2.76 mmol) in acetonitrile (10 mL) was stirred at room temperature for 2 hours. The mixture was purified by reverse phase HPLC on a C18/40 g column (A: water 10 mM NH$_4$HCO$_3$, B: MeOH, 0~100%) to provide ethyl (3S)-3-(2-(5-(2-(dimethylamino)ethyl)-2-oxo-4-(trifluoromethyl)pyridin-1(2H)-yl)-4-methylpentanamido)-3-(4-fluoro-2',4',6'-trimethyl-5-(trifluoromethyl)-[1,1'-biphenyl]-3-yl)propanoate (380 mg) as a white solid. Yield 75.6% (ESI 728.1 (M+H)$^+$).

Ethyl (3S)-3-(2-(5-(2-(dimethylamino)ethyl)-2-oxo-4-(trifluoromethyl)pyridin-1(2H)-yl)-4-methylpentanamido)-3-(4-fluoro-2',4',6'-trimethyl-5-(trifluoromethyl)-[1,1'-biphenyl]-3-yl)propanoate (380 mg, 0.52 mmol) was treated with LiOH—H$_2$O (88 mg, 2.1 mmol) in MeOH (5 mL) and H$_2$O (1 mL) at room temperature for 2 hours. The reaction mixture was acidified to pH 4~5 with 1N HCl. The solvent was removed in vacuo and the residue purified by prep-HPLC A (30-60% CH$_3$CN) to provide the diastereomeric products JZ-P1 (116 mg) and JZ-P2 (88 mg) as white solids.

JZ-P1 ESI 699.9 (M+H)$^+$. 1H NMR (400 MHz, MeOD) δ 7.87 (s, 1H), 7.33 (d, J=5.0 Hz, 1H), 7.25 (d, J=8.0 Hz, 1H), 6.92 (s, 1H), 6.88 (s, 1H), 6.68 (s, 1H), 5.66-5.54 (m, 2H), 3.13-3.05 (m, 2H), 2.95-2.91 (m, 2H), 2.77 (s, 6H), 2.73-2.70 (m, 2H), 2.29 (s, 3H), 1.99-1.94 (m, 5H), 1.74 (s, 3H), 1.46-1.38 (m, 1H), 0.95-0.91 (m, 6H).

JZ-P2 ESI 699.9 (M+H)$^+$. 1H NMR (400 MHz, MeOD) δ 7.83 (s, 1H), 7.38 (d, J=4.9 Hz, 1H), 7.32 (d, J=6.4 Hz, 1H), 6.94 (s, 2H), 6.87 (s, 1H), 5.73-5.69 (m, 1H), 5.60 (t, J=7.7 Hz, 1H), 3.18-3.28 (m, 2H), 2.98 (t, J=7.0 Hz, 2H), 2.83 (s, 6H), 2.68-2.52 (m, 2H), 2.30 (s, 3H), 2.00-1.93 (m, 7H), 1.74-1.67 (m, 1H), 1.40-1.33 (m, 1H), 0.88-0.86 (m, 6H).

3-123. Preparation of (3S)-3-(4-fluoro-2',4',6'-trimethyl-5-(trifluoromethyl)-[1,1'-biphenyl]-3-yl)-3-(4-methyl-2-(5-(2-(3-methylazetidin-1-yl)ethyl)-2-oxo-4-(trifluoromethyl)pyridin-1(2H)-yl)pentanamido)propanoic Acid (Compounds KA-P1 and KA-P2)

Step 1: Ethyl (3S)-3-(4-fluoro-2',4',6'-trimethyl-5-(trifluoromethyl)-[1,1'-biphenyl]-3-yl)-3-(4-methyl-2-(5-(2-(3-methylazetidin-1-yl)ethyl)-2-oxo-4-(trifluoromethyl)pyridin-1(2H)-yl)pentanamido)propanoate

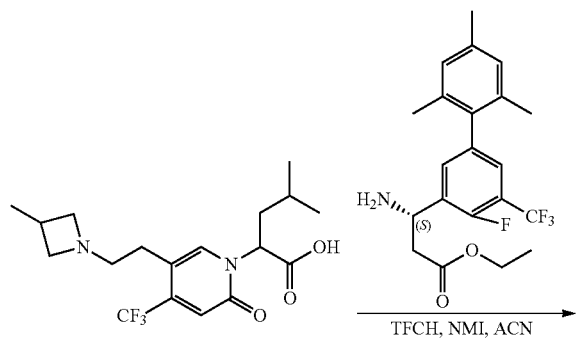

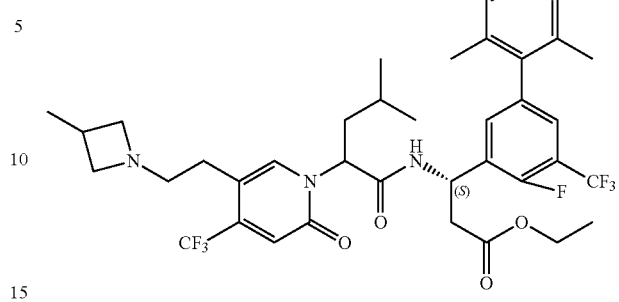

A mixture of ethyl 4-methyl-2-(5-(2-(3-methylazetidin-1-yl)ethyl)-2-oxo-4-(trifluoromethyl)pyridin-1(2H)-yl)pentanoic acid (190.7 mg, 0.51 mmol), ethyl (S)-3-amino-3-(4-fluoro-2',4',6'-trimethyl-5-(trifluoromethyl)-[1,1'-biphenyl]-3-yl)propanoate (202.5 mg, 0.51 mmol), TCFH (285.6 mg, 1.02 mmol) and NMI (167.3 mg, 2.04 mmol) in $CH_3CN$ (10 mL) was stirred at room temperature for 1 hour. The solvent was removed in vacuo and the residue purified by silica gel column (DCM:MeOH 4:1) to provide ethyl (3S)-3-(4-fluoro-2',4',6'-trimethyl-5-(trifluoromethyl)-[1,1'-biphenyl]-3-yl)-3-(4-methyl-2-(5-(2-(3-methylazetidin-1-yl)ethyl)-2-oxo-4-(trifluoromethyl)pyridin-1(2H)-yl)pentanamido)propanoate as a brown solid (250 mg). Yield 65% (ESI 754.3 $(M+H)^+$).

Step 2: (3S)-3-(4-fluoro-2',4',6'-trimethyl-5-(trifluoromethyl)-[1,1'-biphenyl]-3-yl)-3-(4-methyl-2-(5-(2-(3-methylazetidin-1-yl)ethyl)-2-oxo-4-(trifluoromethyl)pyridin-1(2H)-yl)pentanamido)propanoic acid

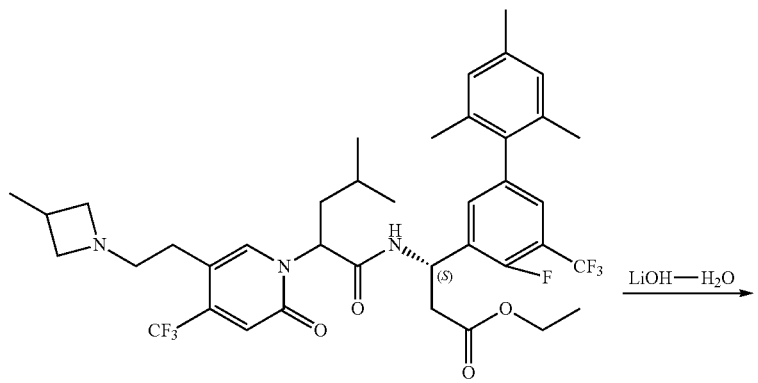

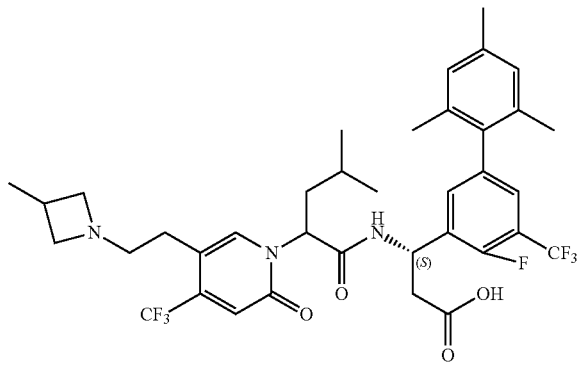

Ethyl (3S)-3-(4-fluoro-2',4',6'-trimethyl-5-(trifluoromethyl)-[1,1'-biphenyl]-3-yl)-3-(4-methyl-2-(5-(2-(3-methylazetidin-1-yl)ethyl)-2-oxo-4-(trifluoromethyl)pyridin-1(2H)-yl)pentanamido)propanoate (250.0 mg, 0.33 mmol)) was treated with LiOH—H$_2$O (54.6 mg, 1.3 mmol) in MeOH (4 mL) and H$_2$O (1 mL) at room temperature for 2 hours. The reaction mixture was acidified to pH 4~5 with 1N HCl. The solvent was removed in vacuo and the residue purified by prep-HPLC A (30-60% MeCN) to give the diastereomeric products KA-P1 (96 mg) and KA-P2 (87 mg) as white solids.

KA-P1 ESI 726.3 (M+H)$^+$. 1H NMR (400 MHz, MeOD) δ 7.83 (s, 1H), 7.41-7.31 (m, 1H), 7.32-7.17 (m, 1H), 6.91 (d, J=11.7 Hz, 2H), 6.70 (s, 1H), 5.69-5.53 (m, 2H), 4.21-4.04 (m, 2H), 3.66 (t, J=8.7 Hz, 2H), 2.98-2.79 (m, 3H), 2.77-2.63 (m, 2H), 2.29 (s, 3H), 2.06-1.89 (m, 5H), 1.78 (d, J=11.5 Hz, 3H), 1.49-1.31 (m, 1H), 1.23 (d, J=6.9 Hz, 3H), 0.98-0.81 (m, 6H).

KA-P2 ESI 726.3 (M+H)$^+$. 1H NMR (400 MHz, MeOD) δ 7.73 (s, 1H), 7.46-7.36 (m, 1H), 7.36-7.23 (m, 1H), 6.91 (d, J=27.6 Hz, 3H), 5.83-5.73 (m, 1H), 5.61 (t, J=7.6 Hz, 1H), 4.28-4.10 (m, 2H), 3.83-3.64 (m, 2H), 3.45-3.33 (m, 2H), 3.02-2.86 (m, 2H), 2.86-2.73 (m, 1H), 2.69-2.45 (m, 2H), 2.30 (s, 3H), 2.04-1.87 (m, 7H), 1.68-1.56 (m, 1H), 1.44-1.19 (m, 4H), 0.86 (d, J=6.6 Hz, 6H).

3-124. Preparation of (S)-3-(4-fluoro-2',5,6'-trimethylbiphenyl-3-yl)-3-((S)-2-(5-(2-(3-(fluoromethyl)azetidin-1-yl)ethyl)-2-oxo-4-(trifluoromethyl)pyridin-1(2H)-yl)-4-methylpentanamido)propanoic Acid (Compounds KB-P1 and KB-P2)

Step 1: (3S)-ethyl 3-(4-fluoro-2',5,6'-trimethylbiphenyl-3-yl)-3-(2-(5-(2-(3-(fluoromethyl)azetidin-1-yl)ethyl)-2-oxo-4-(trifluoromethyl)pyridin-1(2H)-yl)-4-methylpentanamido)propanoate

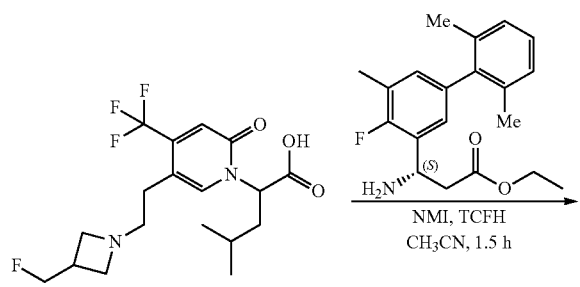

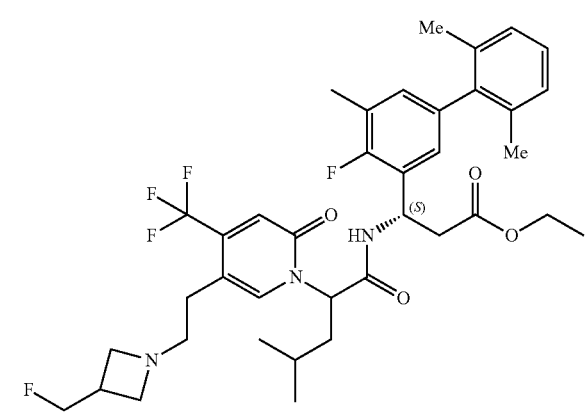

A mixture of 2-(5-(2-(3-(fluoromethyl)azetidin-1-yl)ethyl)-2-oxo-4-(trifluoromethyl)pyridin-1(2H)-yl)-4-methylpentanoic acid (180 mg, 0.46 mmol), (S)-ethyl 3-amino-3-(4-fluoro-2',5,6'-trimethylbiphenyl-3-yl)propanoate (151 mg, 0.46 mmol), NMI (160 mg, 1.96 mmol) and TCFH (252 mg, 0.9 mmol) in CH$_3$CN (5 mL) was stirred at room temperature for 1.5 hours. The solvent was removed in vacuo and the residue purified by silica gel column (DCM: MeOH 9:1) to provide (3S)-ethyl 3-(4-fluoro-2',5,6'-trimethylbiphenyl-3-yl)-3-(2-(5-(2-(3-(fluoromethyl)azetidin-1-yl)ethyl)-2-oxo-4-(trifluoromethyl)pyridin-1(2H)-yl)-4-methylpentanamido)propanoate as a colorless oil (230 mg). Yield 71% (ESI 704.3 [M+H]$^+$).

Step 2: 3-(4-fluoro-2',5,6'-trimethylbiphenyl-3-yl)-3-((S)-2-(5-(2-(3-(fluoromethyl)azetidin-1-yl)ethyl)-2-oxo-4-(trifluoromethyl)pyridin-1(2H)-yl)-4-methylpentanamido)propanoic Acid

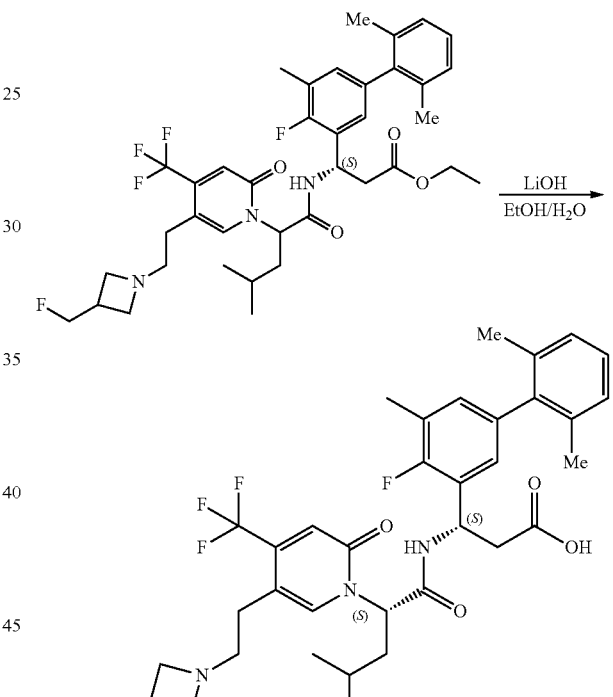

Ethyl 3-(4-fluoro-2',5,6'-trimethylbiphenyl-3-yl)-3-(2-(5-(2-(3-(fluoromethyl)azetidin-1-yl)ethyl)-2-oxo-4-(trifluoromethyl)pyridin-1(2H)-yl)-4-methylpentanamido)propanoate (230 mg, 0.33 mmol) was treated with LiOH—H$_2$O (69 mg, 1.64 mmol) in EtOH (3 mL) and H$_2$O (1 mL) at room temperature for 2 hours. The reaction mixture was acidified to pH 4~5 with 1N HCl. The solvent was removed in vacuo and the residue purified by prep-HPLC A (30-60% CH$_3$CN) to provide diastereomeric products KB-P1 (50 mg) and KB-P2 (101 mg) as white solids.

KB-P1 ESI 676.3 (M+H)$^+$. 1H NMR (400 MHz, MeOD) δ 7.82 (s, 1H), 7.07-7.03 (m, 3H), 6.93-6.82 (m, 2H), 6.75 (s, 1H), 5.70-5.55 (m, 2H), 4.57 (d, J=4.4 Hz, 1H), 4.45 (d, J=4.1 Hz, 1H), 4.03 (t, J=9.4 Hz, 2H), 3.82-3.67 (m, 2H), 3.13-3.10 (m, 3H), 2.80 (t, J=7.0 Hz, 2H), 2.71 (d, J=6.3 Hz, 2H), 2.28 (d, J=1.6 Hz, 3H), 2.02-1.90 (m, 5H), 1.84 (s, 3H), 1.41-1.39 (m, 1H), 0.93-0.90 (m, 6H).

KB-P2 ESI 676.3 (M+H)⁺. 1H NMR (400 MHz, MeOD) δ 7.73 (s, 1H), 7.15-7.00 (m, 3H), 7.00-6.82 (m, 3H), 5.75 (m, 1H), 5.60 (t, J=7.6 Hz, 1H), 4.60 (t, J=7.3 Hz, 1H), 4.49 (t, J=7.5 Hz, 1H), 4.25-4.22 (m, 2H), 4.04-3.84 (m, 2H), 3.45-3.32 (m, 2H), 3.25-3.11 (m, 1H), 2.92-2.90 (m, 1H), 2.84-2.74 (m, 1H), 2.63-2.60 (m, 1H), 2.50-2.48 (m, 1H), 2.31 (d, J=1.8 Hz, 3H), 2.04-1.84 (m, 7H), 1.64-1.60 (m, 1H), 1.41-1.39 (m, 1H), 0.87 (d, J=6.6 Hz, 6H).

3-125. Preparation of (3S)-3-(4'-cyclopropyl-4-fluoro-2',5,6'-trimethylbiphenyl-3-yl)-3-(2-(5-(2-(dimethylamino)ethyl)-2-oxo-4-(trifluoromethyl)pyridin-1(2H)-yl)-4-methylpentanamido)propanoic Acid (Compounds KC-P1 and KC-P2)

Step 1: (S)-ethyl 3-(5-bromo-2-fluoro-3-methylphenyl)-3-((S)-2-(5-(2-(dimethylamino)ethyl)-2-oxo-4-(trifluoromethyl)pyridin-1(2H)-yl)-4-methylpentanamido)propanoate

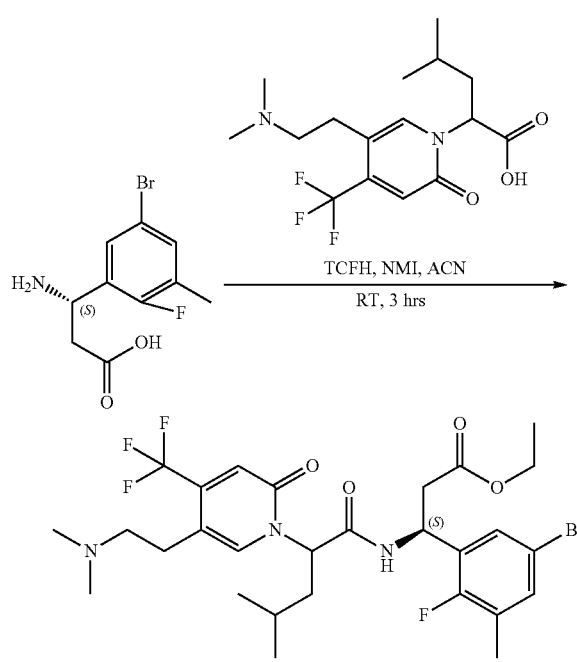

A mixture of (S)-ethyl 3-amino-3-(5-bromo-2-fluoro-3-methylphenyl)propanoate (8.6 g, 28.0 mmol), 2-(5-(2-(dimethylamino)ethyl)-2-oxo-4-(trifluoromethyl)pyridin-1(2H)-yl)-4-methylpentanoic acid (9.8 g, 28.0 mmol), TCFH (9.4 g, 34.0 mmol) and NMI (6.9 g, 84.0 mmol) in MeCN (5 mL) was stirred at room temperature for 3 hrs. The solvent was removed in vacuo and the residue was purified by silica gel column (DCM:MeOH 97:3) to provide (S)-ethyl 3-(5-bromo-2-fluoro-3-methylphenyl)-3-(5-(2-(dimethylamino)ethyl)-2-oxo-4-(trifluoromethyl)pyridin-1(2H)-yl)-4-methylpentanamido)propanoate as a white solid (12.2 g). Yield 68% (ESI 634.3 (M+H)⁺).

Step 2: (S)-ethyl 3-(2-(5-(2-(dimethylamino)ethyl)-2-oxo-4-(trifluoromethyl)pyridin-1(2H)-yl)-4-methylpentanamido)-3-(2-fluoro-3-methyl-5-(4,4,5,5-tetramethyl-1,3,2-dioxaborolan-2-yl)phenyl)propanoate

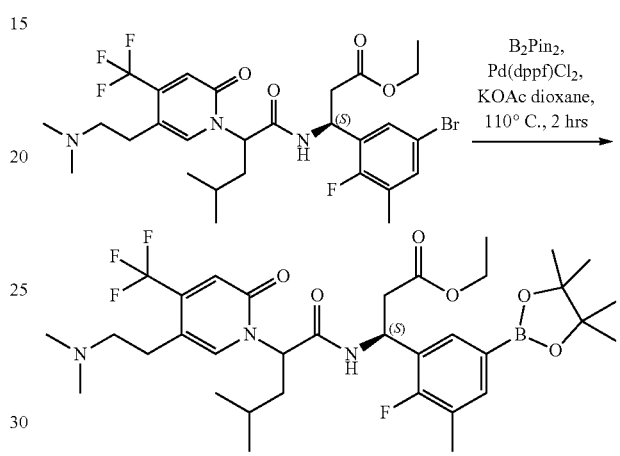

A mixture of (S)-ethyl 3-(5-bromo-2-fluoro-3-methylphenyl)-3-(2-(5-(2-(dimethylamino)ethyl)-2-oxo-4-(trifluoromethyl)pyridin-1(2H)-yl)-4-methylpentanamido)propanoate (633 mg, 1.0 mmol) in dioxane (5 mL) was added B₂Pin₂ (508 mg, 2.0 mmol), Pd(dppf)Cl₂ (73 mg, 0.1 mmol) and KOAc (294 mg, 3.0 mmol). The mixture was heated to 110° C. for 2 hrs under nitrogen atmosphere. Water (20 mL) was added and the solution was extracted with EtOAc (20 mL·3). The combined organic phases were concentrated in vacuo and the residue was purified by silica gel column (pet ether:EtOAc 2:1) to provide (S)-ethyl 3-(2-(5-(2-(dimethylamino)ethyl)-2-oxo-4-(trifluoromethyl)pyridin-1(2H)-yl)-4-methylpentanamido)-3-(2-fluoro-3-methyl-5-(4,4,5,5-tetramethyl-1,3,2-dioxaborolan-2-yl)phenyl)propanoate (600 mg) as a dark solid. Yield 88% (ESI 682.1 [M+H]⁺).

Step 3: (3S)-ethyl 3-(4'-cyclopropyl-4-fluoro-2',5,6'-trimethylbiphenyl-3-yl)-3-(2-(5-(2-(dimethylamino)ethyl)-2-oxo-4-(trifluoromethyl)pyridin-1(2H)-yl)-4-methylpentanamido)propanoate

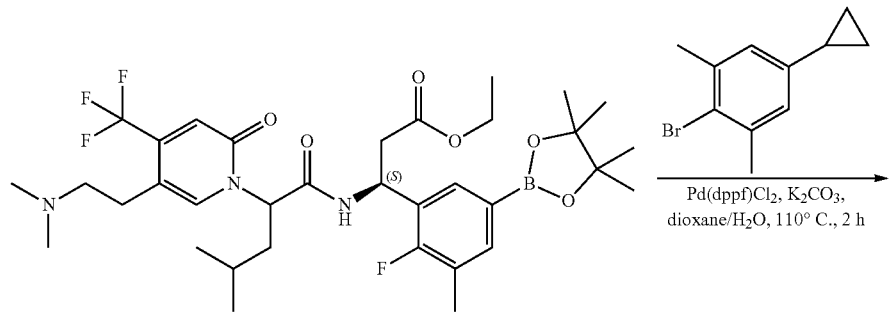

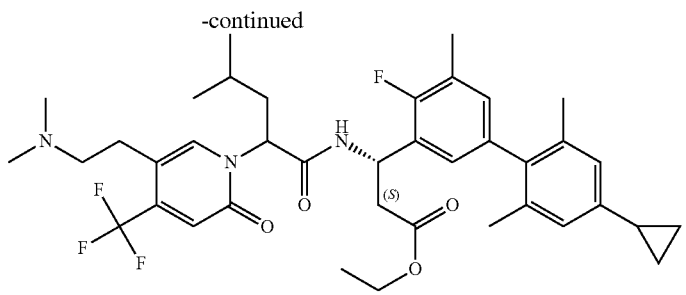

To a mixture of 2-bromo-5-cyclopropyl-1,3-dimethylbenzene (100 mg, 0.45 mmol), (3S)-ethyl 3-(2-(5-(2-(dimethylamino)ethyl)-2-oxo-4-(trifluoromethyl)pyridin-1(2H)-yl)-4-methylpentanamido)-3-(2-fluoro-3-methyl-5-(4,4,5,5-tetramethyl-1,3,2-dioxaborolan-2-yl)phenyl)propanoate (300 mg, 0.45 mmol) in dioxane (10 mL) and H$_2$O (1 mL) was added Pd(dppf)Cl$_2$ (37 mg, 0.05 mmol) and K$_2$CO$_3$ (207 mg, 1.5 mmol). The mixture was heated to 110° C. for 2 hrs under nitrogen atmosphere. Water (20 mL) was added and the solution was extracted with EtOAc (20 mL×3). The combined organic phases were concentrated in vacuo and the residue purified by silica gel column (pet ether:EtOAc 2:1) to provide (3S)-ethyl 3-(4'-cyclopropyl-4-fluoro-2',5,6'-trimethylbiphenyl-3-yl)-3-(2-(5-(2-(dimethylamino)ethyl)-2-oxo-4-(trifluoromethyl)pyridin-1(2H)-yl)-4-methylpentanamido)propanoate (150 mg). Yield 48% (ESI 700.1 [M+H]+).

Step 4: (3S)-3-(4'-cyclopropyl-4-fluoro-2',5,6'-trimethylbiphenyl-3-yl)-3-(2-(5-(2-(dimethylamino)ethyl)-2-oxo-4-(trifluoromethyl)pyridin-1(2H)-yl)-4-methylpentanamido)propanoic Acid

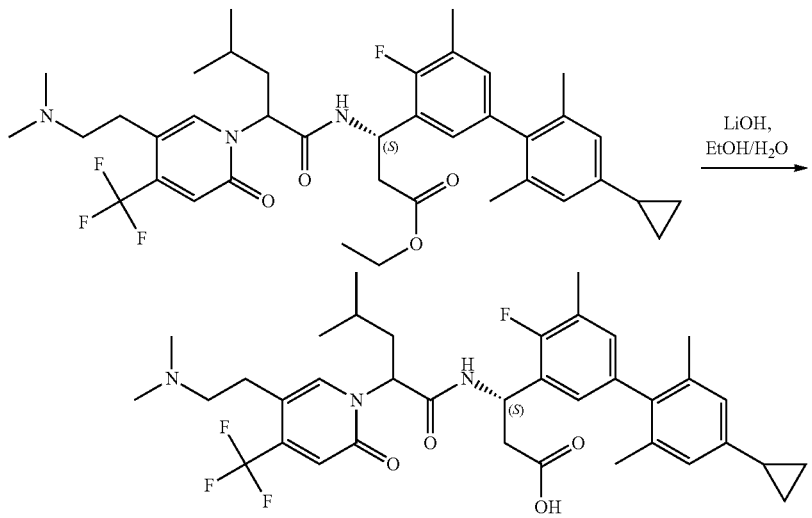

A mixture of (3S)-ethyl 3-(4'-cyclopropyl-4-fluoro-2',5,6'-trimethylbiphenyl-3-yl)-3-(2-(5-(2-(dimethylamino)ethyl)-2-oxo-4-(trifluoromethyl)pyridin-1(2H)-yl)-4-methylpentanamido)propanoate in EtOH (3 mL) and H$_2$O (1 mL) was treated with LiOH—H$_2$O (42 mg, 1.0 mmol) at room temperature for 30 mins. The reaction mixture was acidified to pH 4~5 with 1N HCl. The solvent was removed in vacuo and the residue purified by prep-HPLC A (30-60% MeCN) to give the diastereomeric products KC-P1 (39 mg) and KC-P2 (35 mg) as white solids.

KC-P1 ESI 672.1 (M+H)+. 1H NMR (400 MHz, MeOD) δ 7.90 (s, 1H), 6.84 (t, J=5.9 Hz, 2H), 6.78 (s, 1H), 6.74 (d, J=4.4 Hz, 2H), 5.68 (t, J=8.1 Hz, 1H), 5.61-5.48 (m, 1H), 3.07 (d, J=7.3 Hz, 2H), 2.94 (d, J=7.0 Hz, 2H), 2.72 (d, J=9.8 Hz, 8H), 2.27 (d, J=1.3 Hz, 3H), 2.02-1.92 (m, 5H), 1.85-1.83 (m, 1H), 1.76 (s, 3H), 1.43-1.40 (m, 1H), 1.00-0.87 (m, 8H), 0.70-0.63 (m, 2H).

KC-P2 ESI 672.1 (M+H)⁺. 1H NMR (400 MHz, MeOD) δ 7.75 (d, J=12.3 Hz, 1H), 6.79 (t, J=6.1 Hz, 3H), 6.69 (s, 2H), 5.60 (d, J=6.9 Hz, 1H), 5.51 (t, J=7.6 Hz, 1H), 3.18-3.04 (m, 2H), 2.89 (t, J=6.6 Hz, 2H), 2.71 (s, 6H), 2.48-2.45 (m, 2H), 2.21 (s, 3H), 1.87-1.85 (m, 7H), 1.76-1.73 (m, 1H), 1.58-1.55 (m, 1H), 1.32-1.25 (m, 1H), 0.88-0.81 (m, 2H), 0.81-0.69 (m, 6H), 0.63-0.52 (m, 2H).

3-126. Preparation of (3S)-3-(2-(5-(2-(2-azaspiro[3.3]heptan-2-yl)ethyl)-2-oxo-4-(trifluoromethyl)pyridin-1(2H)-yl)-4-methylpentanamido)-3-(4-fluoro-2',6'-dimethyl-5-(trifluoromethyl)-[1,1'-biphenyl]-3-yl)propanoic Acid (KD-P1 and KD-P2)

Step 1: Ethyl (3S)-3-(2-(5-(2-(2-azaspiro[3.3]heptan-2-yl)ethyl)-2-oxo-4-(trifluoromethyl)pyridin-1(2H)-yl)-4-methylpentanamido)-3-(4-fluoro-2',6'-dimethyl-5-(trifluoromethyl)-[1,1'-biphenyl]-3-yl)propanoate

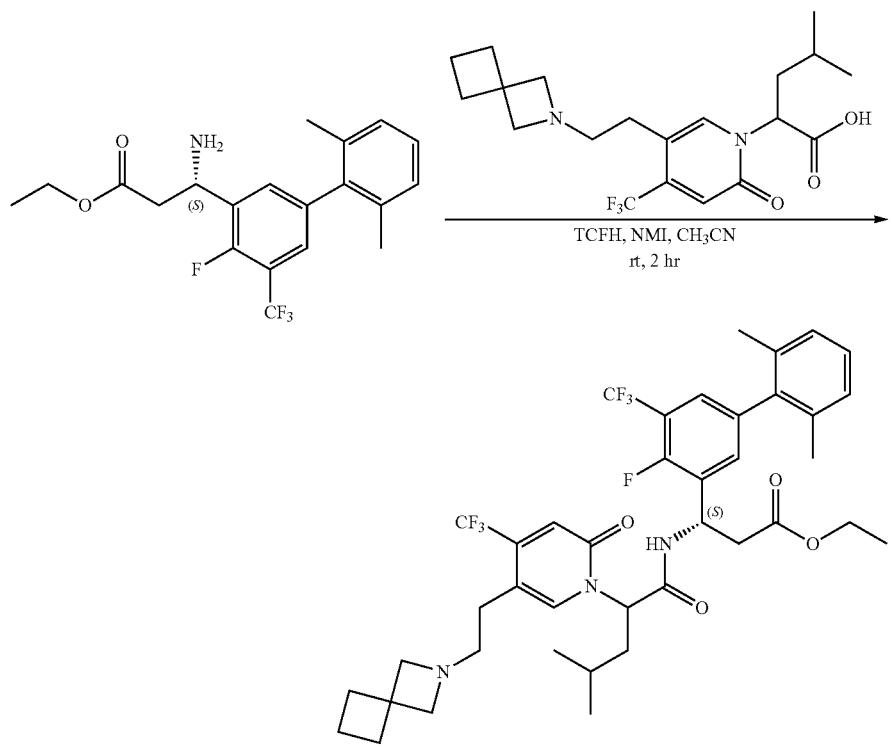

A mixture of ethyl (S)-3-amino-3-(4-fluoro-2',6'-dimethyl-5-(trifluoromethyl)-[1,1'-biphenyl]-3-yl)propanoate (220 mg, 0.57 mmol), 2-(5-(2-(2-azaspiro[3.3]heptan-2-yl)ethyl)-2-oxo-4-(trifluoromethyl)pyridin-1(2H)-yl)-4-methylpentanoic acid (228 mg, 0.57 mmol), TCFH (319 mg, 1.14 mmol) and NMI (234 mg, 2.85 mmol) in CH₃CN (5 mL) was stirred at room temperature for 2 hours. The reaction was concentrated and purified by reverse phase HPLC on a C18/40 g column (A: water 10 mM NH₄HCO3, B: CH₃OH, 0~80%) to provide ethyl (3S)-3-(2-(5-(2-(2-azaspiro[3.3]heptan-2-yl)ethyl)-2-oxo-4-(trifluoromethyl)pyridin-1(2H)-yl)-4-methylpentanamido)-3-(4-fluoro-2',6'-dimethyl-5-(trifluoromethyl)-[1,1'-biphenyl]-3-yl)propanoate (290 mg). Yield 66.4% (ESI 766.3 [M+H]⁺).

623

Step 2: (3S)-3-(2-(5-(2-(2-azaspiro[3.3]heptan-2-yl)ethyl)-2-oxo-4-(trifluoromethyl)pyridin-1(2H)-yl)-4-methylpentanamido)-3-(4-fluoro-2',6'-dimethyl-5-(trifluoromethyl)-[1,1'-biphenyl]-3-yl)propanoic Acid

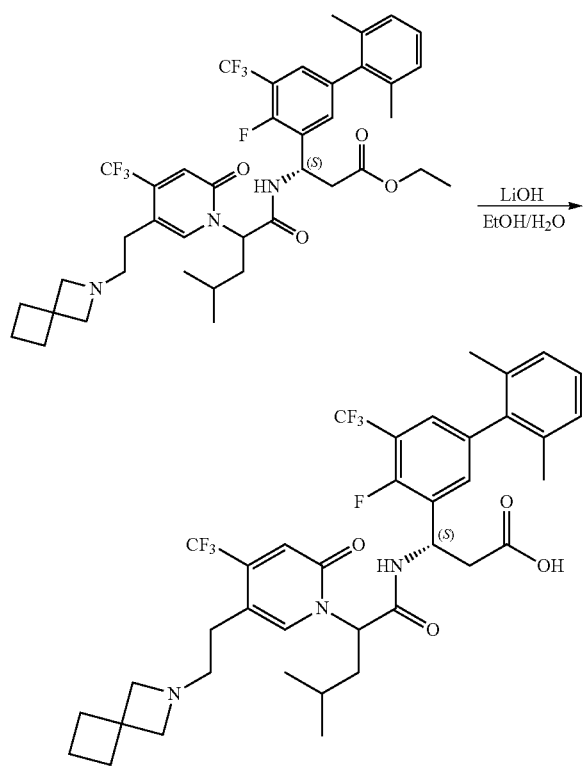

624

Ethyl (3S)-3-(2-(5-(2-(2-azaspiro[3.3]heptan-2-yl)ethyl)-2-oxo-4-(trifluoromethyl)pyridin-1(2H)-yl)-4-methylpentanamido)-3-(4-fluoro-2',6'-dimethyl-5-(trifluoromethyl)-[1,1'-biphenyl]-3-yl)propanoate (290 mg, 0.38 mmol) was treated with LiOH—H$_2$O (48 mg, 1.14 mmol) in EtOH (4 mL) and H$_2$O (1 mL) at room temperature for 30 min. LCMS showed that the reaction was completed. The reaction mixture was acidified to pH 5~6 with 1N HCl. The solvent was removed in vacuo and the residue purified by prep-HPLC A (35-63% CH$_3$CN) to give the diastereomeric products KD-P1 (97 mg) and KD-P2 (114 mg) as white solids.

KD-P1 ESI 738.3 (M+H)$^+$. $^1$H NMR (400 MHz, MeOD) δ 7.82 (s, 1H), 7.39 (d, J=5.1 Hz, 1H), 7.29 (d, J=4.8 Hz, 1H), 7.20-7.04 (m, 3H), 6.73 (s, 1H), 5.68-5.59 (m, 2H), 4.01 (s, 4H), 3.29-3.16 (m, 2H), 2.83 (t, J=7.0 Hz, 2H), 2.71 (d, J=6.9 Hz, 2H), 2.25 (t, J=7.7 Hz, 4H), 2.03-1.93 (m, 5H), 1.88-1.78 (m, 5H), 1.43-1.34 (m, 1H), 0.93 (t, J=6.4 Hz, 6H).

KD-P2 ESI 738.3 (M+H)$^+$. $^1$H NMR (400 MHz, MeOD) δ 7.73 (s, 1H), 7.44 (d, J=5.5 Hz, 1H), 7.35 (d, J=6.2 Hz, 1H), 7.23-7.08 (m, 3H), 6.87 (s, 1H), 5.82-5.73 (m, 1H), 5.62 (t, J=7.6 Hz, 1H), 4.11 (s, 4H), 3.41-3.315 (m, 2H), 2.90 (d, J=16.4 Hz, 1H), 2.84-2.72 (m, 1H), 2.66-2.48 (m, 2H), 2.38-2.23 (m, 4H), 2.06-1.92 (m, 7H), 1.92-1.81 (m, 2H), 1.68-1.57 (m, 1H), 1.46-1.34 (m, 1H), 0.93-0.84 (m, 6H)

3-127. Preparation of (3S)-3-(4-fluoro-2',6'-dimethyl-5-(trifluoromethyl)-[1,1'-biphenyl]-3-yl)-3-(2-(5-(2-(3-(methoxymethyl)azetidin-1-yl)ethyl)-2-oxo-4-(trifluoromethyl)pyridin-1(2H)-yl)-4-methylpentanamido)propanoic Acid (KE-P1 and KE-P2)

Step 1: Ethyl (3S)-3-(4-fluoro-2',6'-dimethyl-5-(trifluoromethyl)-[1,1'-biphenyl]-3-yl)-3-(2-(5-(2-(3-(methoxymethyl)azetidin-1-yl)ethyl)-2-oxo-4-(trifluoromethyl)pyridin-1(2H)-yl)-4-methylpentanamido)propanoate

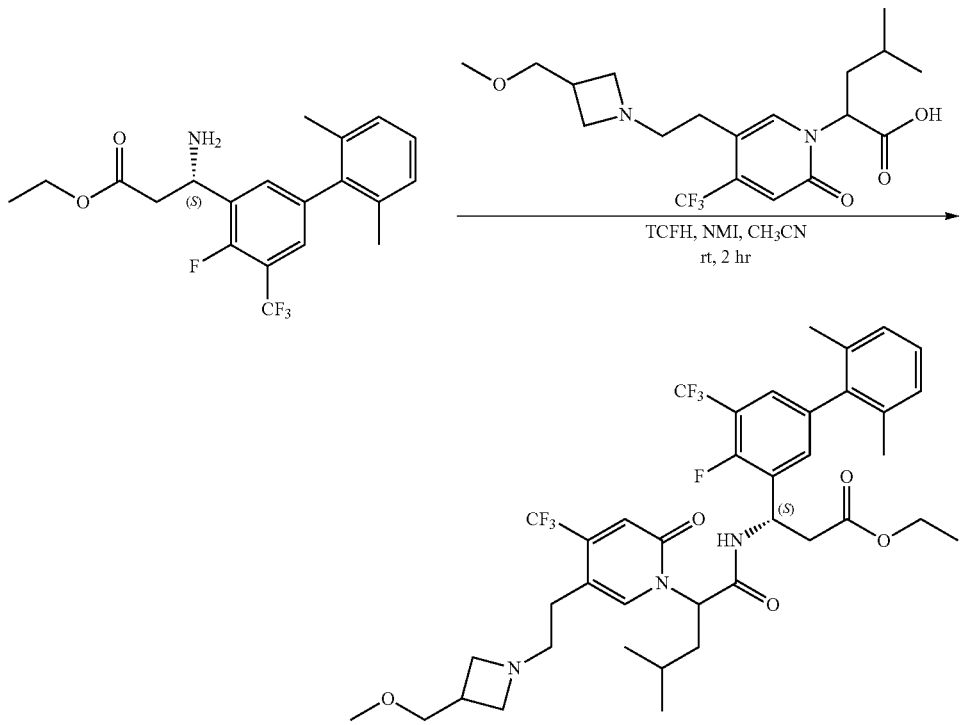

A mixture of ethyl (S)-3-amino-3-(4-fluoro-2',6-dimethyl-5-(trifluoromethyl)-[1,1'-biphenyl]-3-yl)propanoate (200 mg, 0.52 mmol), 2-(5-(2-(3-(methoxymethyl)azetidin-1-yl)ethyl)-2-oxo-4-(trifluoromethyl)pyridin-1(2H)-yl)-4-methylpentanoic acid (210 mg, 0.52 mmol), TCFH (291 mg, 1.04 mmol) and NMI (213 mg, 2.6 mmol) in CH$_3$CN (5 mL) was stirred at room temperature for 2 hours. The reaction was concentrated and purified by reverse phase HPLC on a C18/40 g column (A: water 10 mM NH$_4$HCO3, B: CH$_3$OH, 0~85%) to provide ethyl (3S)-3-(4-fluoro-2',6'-dimethyl-5-(trifluoromethyl)-[1,1'-biphenyl]-3-yl)-3-(2-(5-(2-(3-(methoxymethyl)azetidin-1-yl)ethyl)-2-oxo-4-(trifluoromethyl)pyridin-1(2H)-yl)-4-methylpentanamido)propanoate as a yellow solid (250 mg). Yield 62.4% (ESI 770.3 [M+H]$^+$).

Step 2: (3S)-3-(4-fluoro-2',6'-dimethyl-5-(trifluoromethyl)-[1,1'-biphenyl]-3-yl)-3-(2-(5-(2-(3-(methoxymethyl)azetidin-1-yl)ethyl)-2-oxo-4-(trifluoromethyl)pyridin-1(2H)-yl)-4-methylpentanamido)propanoic Acid

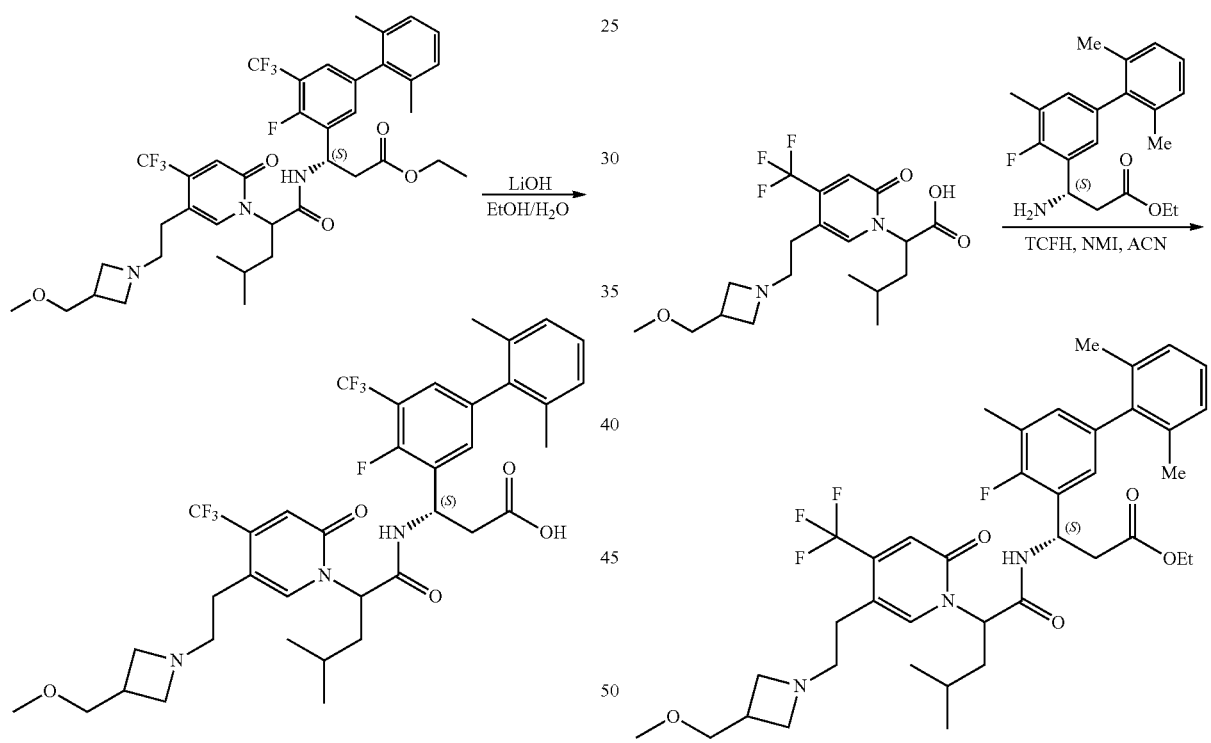

Ethyl (3S)-3-(4-fluoro-2',6'-dimethyl-5-(trifluoromethyl)-[1,1'-biphenyl]-3-yl)-3-(2-(5-(2-(3-(methoxymethyl)azetidin-1-yl)ethyl)-2-oxo-4-(trifluoromethyl)pyridin-1(2H)-yl)-4-methylpentanamido)propanoate (250 mg, 0.32 mmol) was treated with LiOH—H$_2$O (40 mg, 0.96 mmol) in EtOH (4 mL) and H$_2$O (1 mL) at room temperature for 2 hr. The reaction mixture was acidified to pH 5~6 with 1N HCl. The solvent was removed in vacuo and the residue purified by prep-HPLC A (30-65% CH$_3$CN) to give the diastereomeric products KE-P1 (91 mg) and KE-P2 (104 mg) as white solids.

KE-P1 ESI 742.3 (M+H)$^+$. $^1$H NMR (400 MHz, MeOD) δ 7.82 (s, 1H), 7.39 (d, J=5.0 Hz, 1H), 7.33-7.26 (m, 1H), 7.17 (t, J=7.5 Hz, 1H), 7.14-7.05 (m, 2H), 6.73 (s, 1H), 5.62 (t, J=6.8 Hz, 2H), 4.19-4.04 (m, 2H), 3.95-3.81 (m, 2H), 3.46 (d, J=4.1 Hz, 2H), 3.41 (s, 3H), 3.29-3.24 (m, 2H), 3.01 (s, 1H), 2.83 (t, J=7.0 Hz, 2H), 2.75-2.66 (m, 2H), 2.03-1.94 (m, 5H), 1.84 (s, 3H), 1.43-1.35 (m, 1H), 0.98-0.85 (m, 6H).

KE-P2 ESI 742.3 (M+H)$^+$. $^1$H NMR (400 MHz, MeOD) δ 7.73 (s, 1H), 7.51-7.28 (m, 2H), 7.3-7.01 (m, 3H), 6.88 (s, 1H), 5.90-5.71 (m, 1H), 5.61 (t, J=7.6 Hz, 1H), 4.31-4.11 (m, 2H), 4.07-3.80 (m, 2H), 3.53-3.47 (m, 2H), 3.43 (s, 3H), 3.40-3.31 (m, 2H), 3.12-3.00 (m, 1H), 2.96-2.86 (m, 1H), 2.84-2.73 (m, 1H), 2.70-2.61 (m, 1H), 2.59-2.48 (m, 1H), 2.04-1.91 (m, 7H), 1.71-1.60 (m, 1H), 1.43-1.32 (m, 1H), 0.87 (d, J=6.5 Hz, 6H).

3-128. Preparation of (3S)-3-(4-fluoro-2',5,6'-trimethyl-[1,1'-biphenyl]-3-y)-3-(2-(5-(2-(3-(methoxymethyl)azetidin-1-yl)ethyl)-2-oxo-4-(trifluoromethyl)pyridin-1(2H)-yl)-4-methylpentanamido)propanoic Acid (Compounds KF-P1 and KF-P2)

Step 1: Ethyl (S)-3-(4-fluoro-2',5,6'-trimethyl-[1,1'-biphenyl]-3-yl)-3-((S)-2-(5-(2-(3-(methoxymethyl)azetidin-1-yl)ethyl)-2-oxo-4-(trifluoromethyl)pyridin-1(2H)-yl)-4-methylpentanamido)propanoate

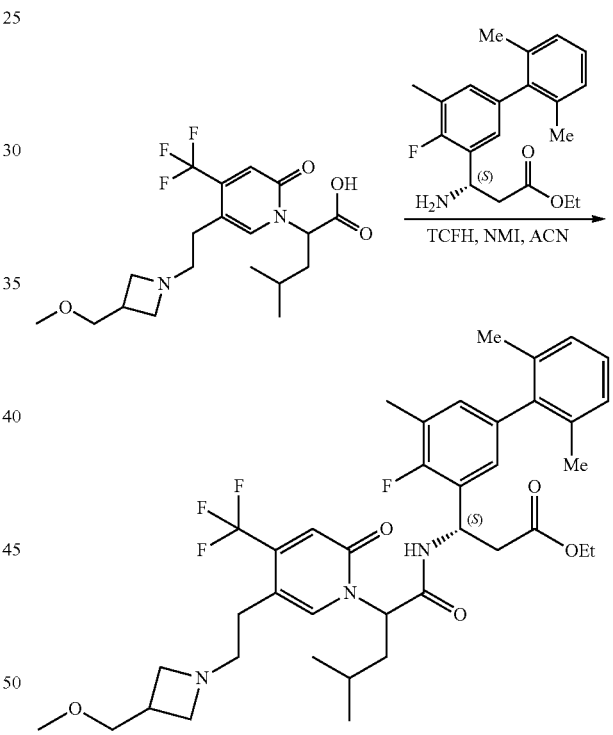

A mixture of (S)-2-(5-(2-(3-(methoxymethyl)azetidin-1-yl)ethyl)-2-oxo-4-(trifluoromethyl)pyridin-1(2H)-yl)-4-methylpentanoic acid (277.0 mg, 0.68 mmol), ethyl (S)-3-amino-3-(4-fluoro-2',5,6'-trimethyl-[1,1'-biphenyl]-3-yl)propanoate (230.0 mg, 0.70 mmol), TCHF (211.0 mg, 0.84 mmol) and NMI (115.0 mg, 1.4 mmol) in CH$_3$CN (5 mL) was stirred at room temperature for 1.5 h. The mixture was concentrated in vacuo and the residue was purified by reverse phase HPLC on a C18/40 g column (A: water 10 mM NH$_4$HCO$_3$, B: MeOH, 0~100%) to provide ethyl (S)-3-(4-fluoro-2',5,6'-trimethyl-[1,1'-biphenyl]-3-yl)-3-((S)-2-(5-(2-(3-(methoxymethyl)azetidin-1-yl)ethyl)-2-oxo-4-(trifluoromethyl)pyridin-1(2H)-yl)-4-methylpentanamido)propanoate (300 mg). Yield 61.2% (ESI 715.9 [M+H]$^+$).

Step 2: (3S)-3-(4-fluoro-2',5,6'-trimethyl-[1,1'-biphenyl]-3-y)-3-(2-(5-(2-(3-(methoxymethyl)azetidin-1-yl)ethyl)-2-oxo-4-(trifluoromethyl)pyridin-1(2H)-yl)-4-methylpentanamido)propanoic Acid Ethyl (S)-3-(4-fluoro-2',5,6'-trimethyl-[1,1'-biphenyl]-3-yl)-3-((S)-2-(5-(2-(3-(methoxymethyl)azetidin-1-yl)ethyl)-2-oxo-4-(trifluoromethyl)pyridin-1(2H)-yl)-4-methylpentanamido)propanoate (300.0 mg, 0.42 mmol) was treated with LiOH—H$_2$O (88.0 mg, 2.1 mmol) in EtOH (4 mL) and water (2 mL) at 30° C. for 1 hour. The reaction mixture was acidified to pH 4~5 with 2N HCl. The solvent was removed in vacuo and the residue purified by purified by Prep HPLC A (30-80% MeCN) to give the diastereomeric product KF-P1 (66 mg) and KF-P2 (113 mg) as white solids.

KF-P1 ESI 688.3 (M+H)$^+$ $^1$H NMR (400 MHz, MeOD) δ 7.81 (s, 1H), 7.13-6.98 (m, 3H), 6.87 (dd, J=13.1, 6.8 Hz, 2H), 6.77 (s, 1H), 5.68-5.52 (m, 2H), 4.08 (t, J=9.6 Hz, 2H), 3.84-3.77 (m, 2H), 3.49-3.37 (m, 5H), 3.26 (t, J=7.2 Hz, 2H), 2.98 (m, 1H), 2.83 (t, J=6.8 Hz, 2H), 2.69 (d, J=6.8 Hz, 2H), 2.28 (s, 3H), 2.03-1.90 (m, 5H), 1.85 (s, 3H), 1.45-1.33 (m, 1H), 0.94-0.89 (m, 6H).

KF-P2 ESI 688.3 (M+H)$^+$ $^1$H NMR (400 MHz, MeOD) δ 7.72 (s, 1H), 7.13-7.05 (m, 3H), 6.98-6.83 (m, 3H), 5.75 (dd, J=10.9, 3.4 Hz, 1H), 5.59 (t, J=7.6 Hz, 1H), 4.21 (dd, J=17.0, 7.5 Hz, 2H), 3.94 (dd, J=23.0, 13.3 Hz, 2H), 3.50 (d, J=4.7 Hz, 2H), 3.47-3.35 (m, 5H), 3.07-3.05 (m, 1H), 2.91-2.89 (m, 1H), 2.82-2.80 (m, 1H), 2.65-2.60 (dd, J=15.5, 3.5 Hz, 1H), 2.49 (dd, J=15.5, 11.0 Hz, 1H), 2.31 (s, 3H), 2.00-1.93 (m, 7H), 1.67-1.60 (m, 1H), 1.43-1.33 (m, 1H), 0.88-0.86 (m, 6H).

3-129. Preparation of (3S)-3-(4-fluoro-2',6'-dimethyl-5-(trifluoromethyl)-[1,1'-biphenyl]-3-yl)-3-(4-methyl-2-(5-(2-(3-methylazetidin-1-yl)ethyl)-2-oxo-4-(trifluoromethyl)pyridin-1(2H)-yl)pentanamido)propanoic Acid (Compounds KG-P1 and KG-P2)

Step 1: Ethyl (3S)-3-(4-fluoro-2',6'-dimethyl-5-(trifluoromethyl)-[1,1'-biphenyl]-3-yl)-3-(4-methyl-2-(5-(2-(3-methylazetidin-1-yl)ethyl)-2-oxo-4-(trifluoromethyl)pyridin-1(2H)-yl)pentanamido)propanoate

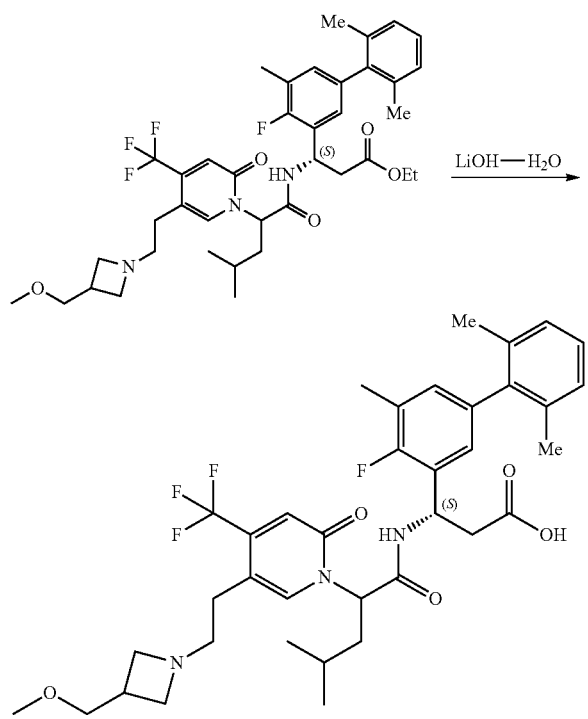

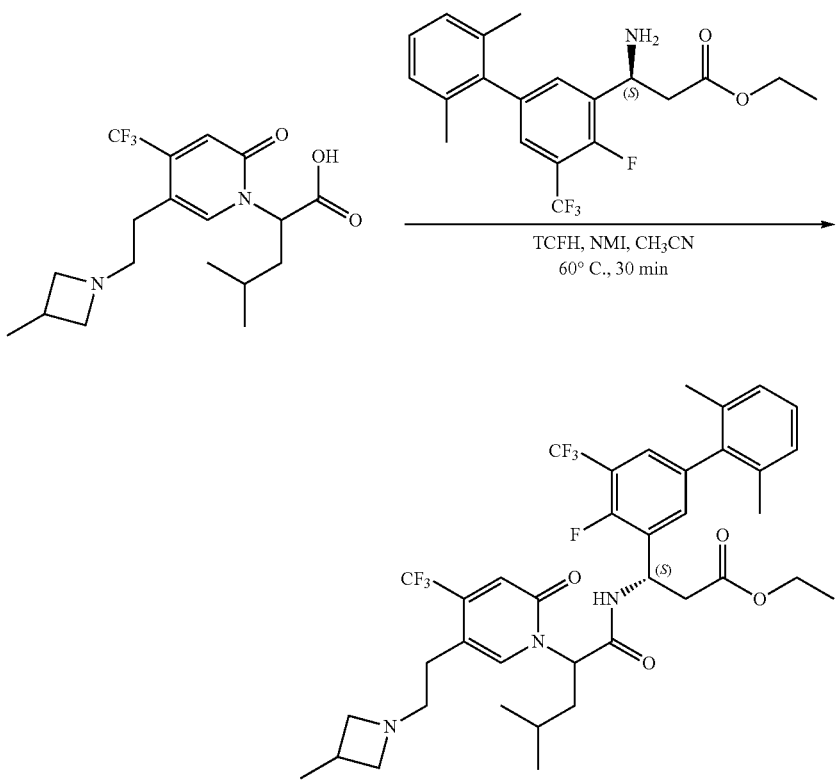

A mixture of ethyl (S)-3-amino-3-(4-fluoro-2',6'-dimethyl-5-(trifluoromethyl)-[1,1'-biphenyl]-3-yl)propanoate (250 mg, 0.65 mmol), 4-methyl-2-(5-(2-(3-methylazetidin-1-yl)ethyl)-2-oxo-4-(trifluoromethyl)pyridin-1(2H)-yl)pentanoic acid (243 mg, 0.65 mmol), TCFH (364 mg, 1.3 mmol) and NMI (267 mg, 3.25 mmol) in CH$_3$CN (5 mL) was stirred at 60° C. for 1.5 hours. The reaction mixture was purified by reverse phase HPLC on a C18/40 g column (A: water 10 mM NH4HCO3, B: CH3CN, 0~100%) to provide ethyl (3S)-3-(4-fluoro-2',6'-dimethyl-5-(trifluoromethyl)-[1,1'-biphenyl]-3-yl)-3-(4-methyl-2-(5-(2-(3-methylazetidin-1-yl)ethyl)-2-oxo-4-(trifluoromethyl)pyridin-1(2H)-yl)pentanamido)propanoate as a yellow solid (300 mg). Yield 62.4% (ESI 739.3 [M+H]$^+$).

Step 2: (3S)-3-(4-fluoro-2',6'-dimethyl-5-(trifluoromethyl)-[1,1'-biphenyl]-3-yl)-3-(4-methyl-2-(5-(2-(3-methylazetidin-1-yl)ethyl)-2-oxo-4-(trifluoromethyl)pyridin-1(2H)-yl)pentanamido)propanoic Acid

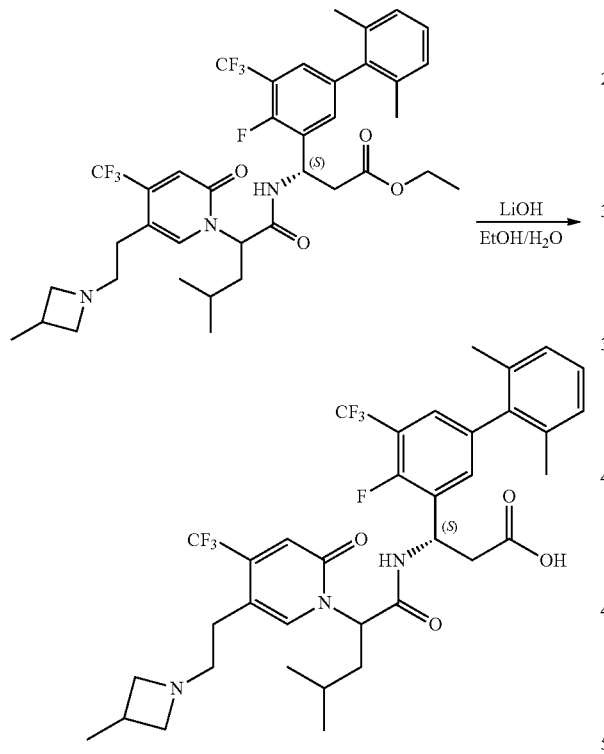

Ethyl (3S)-3-(4-fluoro-2',6'-dimethyl-5-(trifluoromethyl)-[1,1'-biphenyl]-3-yl)-3-(4-methyl-2-(5-(2-(3-methylazetidin-1-yl)ethyl)-2-oxo-4-(trifluoromethyl)pyridin-1(2H)-yl)pentanamido)propanoate(300 mg, 0.41 mmol) was treated with LiOH—H$_2$O (52 mg, 1.23 mmol) in EtOH (4 mL) and H$_2$O (1 mL) at room temperature for 30 min. LCMS showed that the reaction was completed. The reaction mixture was acidified to pH 5~6 with 1N HCl. The solvent was removed in vacuo and the residue purified by prep-HPLC A (30-60% CH$_3$CN) to give the diastereomeric products KG-P1 (88 mg) and KG-P2 (106 mg) as white solids.

KG-P1 ESI 711.3 (M+H)$^+$. $^1$H NMR (400 MHz, MeOD) δ 7.82 (s, 1H), 7.39 (d, J=4.8 Hz, 1H), 7.29 (d, J=4.9 Hz, 1H), 7.20-7.04 (m, 3H), 6.73 (s, 1H), 5.62 (t, J=6.7 Hz, 2H), 4.14 (t, J=9.1 Hz, 2H), 3.68 (t, J=8.4 Hz, 2H), 3.295-3.25 (m, 2H), 2.96-2.87 (m, 1H), 2.83 (t, J=6.9 Hz, 2H), 2.75-2.66 (m, 2H), 2.03-1.92 (m, 5H), 1.85 (s, 3H), 1.43-1.35 (m, 1H), 1.24 (d, J=6.8 Hz, 3H), 0.9-0.88 (m, 6H).

KG-P2 ESI 711.3 (M+H)$^+$. $^1$H NMR (400 MHz, MeOD) δ 7.73 (s, 1H), 7.44 (d, J=6.4 Hz, 1H), 7.38-7.33 (m, 1H), 7.33-7.21 (m, 3H), 6.88 (s, 1H), 5.82-5.76 (m, 1H), 5.61 (t, J=7.6 Hz, 1H), 4.21 (t, J=9.4 Hz, 2H), 3.76 (t, J=8.5 Hz, 2H), 3.45-3.33 (m, 2H), 3.00-2.86 (m, 2H), 2.83-2.74 (m, 1H), 2.69-2.47 (m, 2H), 2.04-1.90 (m, 7H), 1.69-1.59 (m, 1H), 1.43-1.33 (m, 1H), 1.28 (d, J=6.9 Hz, 3H), 0.87 (d, J=6.6 Hz, 6H).

3-130. Preparation of (3S)-3-(2-(5-(2-(azetidin-1-yl)ethyl)-2-oxo-4-(trifluoromethyl)pyridin-1(2H)-yl)-4,4-dimethylpentanamido)-3-(4-fluoro-2',5,6'-trimethylbiphenyl-3-yl)propanoic Acid (Compounds KH-P1 and KH-P2)

Step 1: (3S)-ethyl 3-(2-(5-(2-(azetidin-1-yl)ethyl)-2-oxo-4-(trifluoromethyl)pyridin-1(2H)-yl)-4,4-dimethylpentanamido)-3-(4-fluoro-2',5,6'-trimethylbiphenyl-3-yl)propanoate

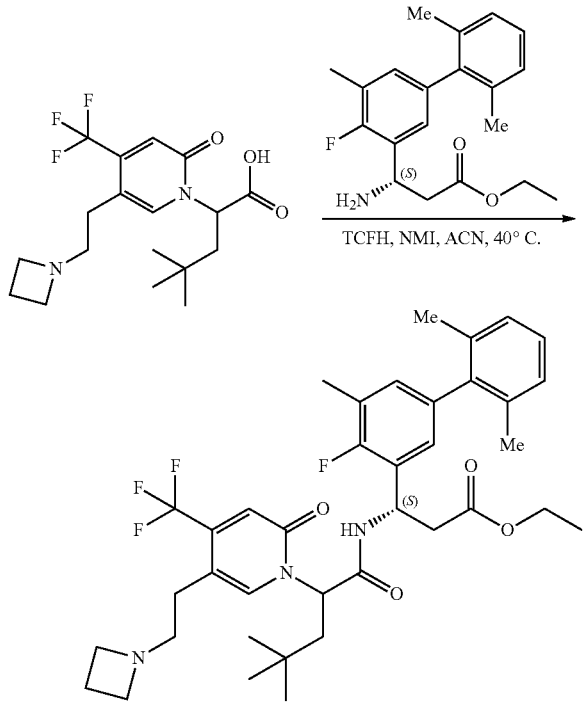

A mixture of 2-(5-(2-(azetidin-1-yl)ethyl)-2-oxo-4-(trifluoromethyl)pyridin-1(2H)-yl)-4,4-dimethylpentanoic acid (300 mg, 0.80 mmol), (S)-ethyl 3-amino-3-(4-fluoro-2',5,6'-trimethylbiphenyl-3-yl)propanoate (264 mg, 0.80 mmol), NMI (0.5 mL) and TCFH (336 mg, 1.20 mmol) in CH$_3$CN (5 mL) was stirred at room temperature for 1 hour. The solvent was concentrated in vacuo and the residue purified by prep-HPLC A (30-90% CH$_3$CN) to provide (3S)-ethyl 3-(2-(5-(2-(azetidin-1-yl)ethyl)-2-oxo-4-(trifluoromethyl) pyridin-1(2H)-yl)-4,4-dimethylpentanamido)-3-(4-fluoro-2',5,6'-trimethylbiphenyl-3-yl)propanoate as a white solid (250 mg). Yield 45% (ESI 686.3 [M+H]$^+$).

631

Step 2: (3S)-3-(2-(5-(2-(azetidin-1-yl)ethyl)-2-oxo-4-(trifluoromethyl)pyridin-1(2H)-yl)-4,4-dimethylpentanamido)-3-(4-fluoro-2',5,6'-trimethylbiphenyl-3-yl)propanoic Acid

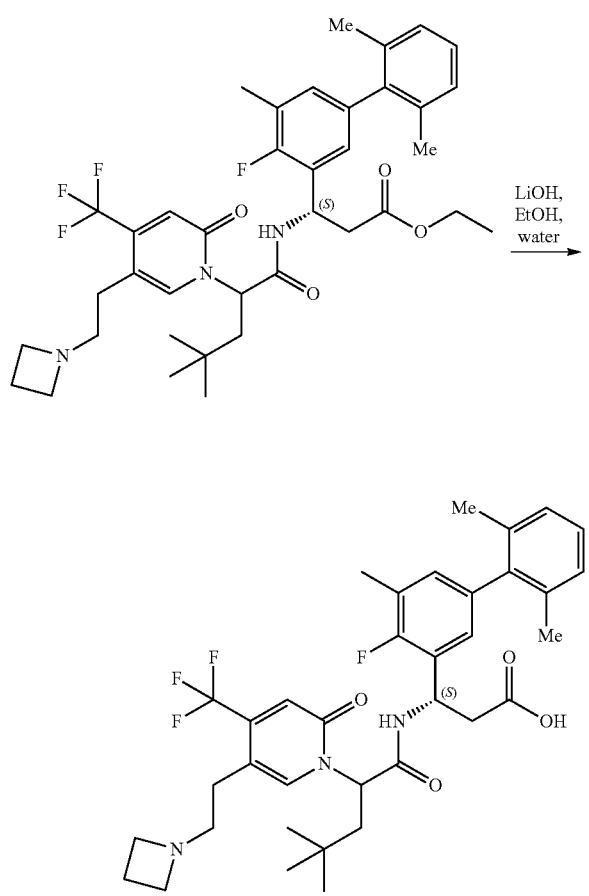

(3S)-ethyl 3-(2-(5-(2-(azetidin-1-yl)ethyl)-2-oxo-4-(trifluoromethyl)pyridin-1(2H)-yl)-4,4-dimethylpentanamido)-3-(4-fluoro-2',5,6'-trimethylbiphenyl-3-yl)propanoate (250 mg, 0.36 mmol) was treated with LiOH—H$_2$O (76 mg, 1.80 mmol) in MeOH (5 mL) and H$_2$O (0.5 mL) at room temperature for 2 hours. The reaction mixture was acidified to pH 4~5 with 1N HCl. The solvent was removed in vacuo and the residue purified by prep-HPLC A (30-60% CH$_3$CN) to give the diastereomeric products KH-P1 (72 mg) and KH-P2 (75 mg) as white solids.

KH-P1 ESI 658.3 (M+H)$^+$. $^1$H NMR (400 MHz, MeOD) δ 7.92 (s, 1H), 7.17-7.00 (m, 3H), 6.86 (d, J=6.9 Hz, 2H), 6.73 (s, 1H), 5.68 (s, 1H), 5.54 (t, J=6.5 Hz, 1H), 4.02 (t, J=8.1 Hz, 4H), 3.27 (t, J=7.1 Hz, 2H), 2.83 (t, J=7.0 Hz, 2H), 2.70 (d, J=6.5 Hz, 2H), 2.49-2.36 (m, 2H), 2.29 (d, J=1.7 Hz, 3H), 2.23-2.10 (m, 1H), 2.03-1.95 (m, 4H), 1.86 (s, 3H), 0.90 (s, 9H).

KH-P2 ESI 658.3 (M+H)$^+$. $^1$H NMR (400 MHz, MeOD) δ 7.75 (s, 1H), 7.19-7.07 (m, 3H), 7.02-6.85 (m, 3H), 5.87-5.72 (m, 1H), 5.69-5.55 (m, 1H), 4.15 (s, 4H), 3.47-

632

3.35 (m, 2H), 3.01-2.75 (m, 2H), 2.71-2.41 (m, 4H), 2.41-2.27 (m, 4H), 2.00 (d, J=6.9 Hz, 6H), 1.49 (d, J=13.2 Hz, 1H), 0.88 (s, 9H).

3-131. Preparation of (3S)-3-(2-(5-(2-(dimethylamino)ethyl)-2-oxo-4-(trifluoromethyl)pyridin-1(2H)-yl)-4,4-dimethylpentanamido)-3-(4-fluoro-2',5,6'-trimethylbiphenyl-3-yl)propanoic Acid (Compounds KI-P1 and KI-P2)

Step 1: (3S)-ethyl 3-(2-(5-(2-(dimethylamino)ethyl)-2-oxo-4-(trifluoromethyl)pyridin-1(2H)-yl)-4,4-dimethylpentanamido)-3-(4-fluoro-2',5,6'-trimethylbiphenyl-3-yl)propanoate

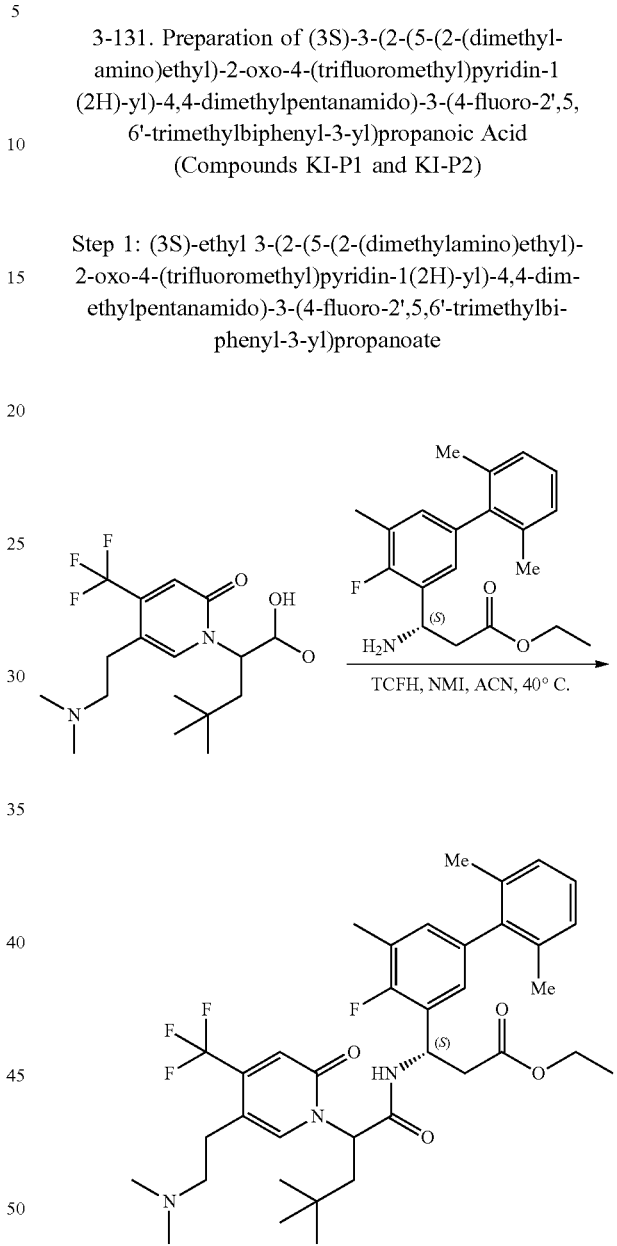

A mixture of 2-(5-(2-(dimethylamino)ethyl)-2-oxo-4-(trifluoromethyl)pyridin-1(2H)-yl)-4,4-dimethylpentanoic acid (250 mg, 0.69 mmol), (S)-ethyl 3-amino-3-(4-fluoro-2',5,6'-trimethylbiphenyl-3-yl)propanoate (227 mg, 0.69 mmol), NMI (0.5 mL) and TCFH (291 mg, 1.04 mmol) in CH$_3$CN (5 mL) was stirred at room temperature for 1 hour. The solvent was concentrated in vacuo and the residue purified by prep-HPLC A (30-90% CH$_3$CN) to provide (3S)-ethyl 3-(2-(5-(2-(dimethylamino)ethyl)-2-oxo-4-(trifluoromethyl)pyridin-1(2H)-yl)-4,4-dimethylpentanamido)-3-(4-fluoro-2',5,6'-trimethylbiphenyl-3-yl)propanoate as a white solid (200 mg). Yield 43% (ESI 674.2 [M+H]$^+$).

Step 2: (3S)-3-(2-(5-(2-(dimethylamino)ethyl)-2-oxo-4-(trifluoromethyl)pyridin-1(2H)-yl)-4,4-dimethylpentanamido)-3-(4-fluoro-2',5,6'-trimethylbiphenyl-3-yl)propanoic Acid

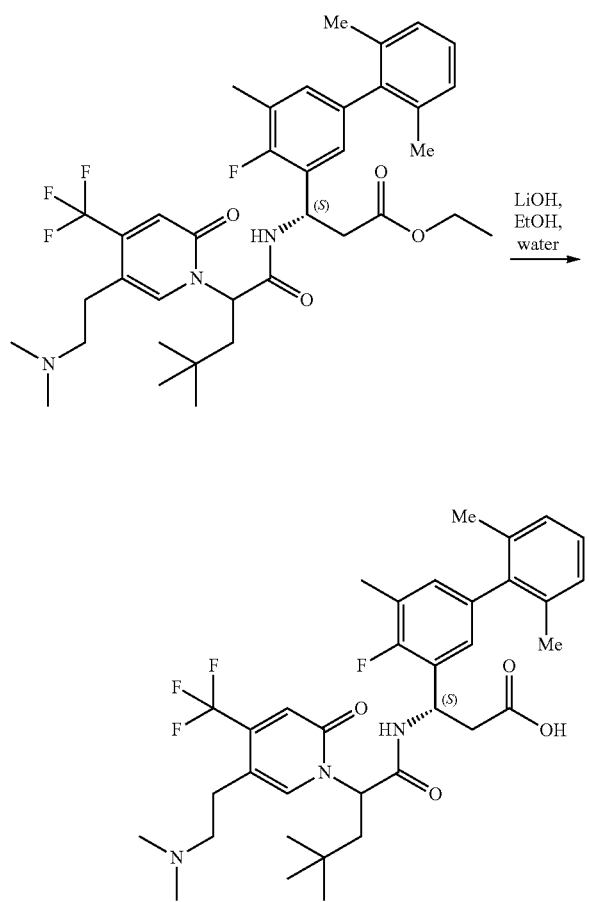

(3S)-ethyl 3-(2-(5-(2-(dimethylamino)ethyl)-2-oxo-4-(trifluoromethyl)pyridin-1(2H)-yl)-4,4-dimethylpentanamido)-3-(4-fluoro-2',5,6'-trimethylbiphenyl-3-yl)propanoate (200 mg, 0.30 mmol) was treated with LiOH—H₂O (63 mg, 1.50 mmol) in MeOH (5 mL) and H₂O (0.5 mL) at room temperature for 2 hours. The reaction mixture was acidified to pH 4~5 with 1N HCl. The solvent was removed in vacuo and the residue purified by prep-HPLC A (30-60% CH$_3$CN) to give the diastereomeric products KI-P1 (67 mg) and KI-P2 (62 mg) as white solids.

KI-P1 ESI 646.3 (M+H)⁺. ¹H NMR (400 MHz, MeOD) δ 7.97 (s, 1H), 7.15-6.98 (m, 3H), 6.84 (d, J=7.1 Hz, 2H), 6.70 (s, 1H), 5.74 (s, 1H), 5.58-5.44 (m, 1H), 3.12-2.84 (m, 4H), 2.77-2.64 (m, 8H), 2.28 (d, J=1.6 Hz, 3H), 2.20-2.11 (m, 1H), 2.02-1.90 (m, 4H), 1.79 (s, 3H), 0.91 (s, 9H).

KI-P2 ESI 646.3 (M+H)⁺. ¹H NMR (400 MHz, MeOD) δ 7.87 (s, 1H), 7.19-7.04 (m, 3H), 7.00-6.85 (m, 3H), 5.73 (d, J=10.3 Hz, 1H), 5.66-5.56 (m, 1H), 3.32-3.15 (m, 2H), 3.07-2.95 (m, 2H), 2.83 (s, 6H), 2.66-2.44 (m, 2H), 2.32 (d, J=1.6 Hz, 3H), 2.30-2.23 (m, 1H), 1.99 (d, J=4.0 Hz, 6H), 1.65-1.51 (m, 1H), 0.86 (d, J=1.7 Hz, 9H).

3-132. Preparation of (3S)-3-(2-(5-(3-(dimethylamino)propyl)-2-oxo-4-(trifluoromethyl)pyridin-1(2H)-yl)-4-methylpentanamido)-3-(4-fluoro-2',4',5,6'-tetramethyl-[1,1'-biphenyl]-3-yl)propanoic Acid (Compounds KJ-P1 and KJ-P2)

Step 1: Ethyl (3S)-3-(2-(5-(3-(dimethylamino)propyl)-2-oxo-4-(trifluoromethyl)pyridin-1(2H)-yl)-4-methylpentanamido)-3-(4-fluoro-2',4',5,6'-tetramethyl-[1,1'-biphenyl]-3-yl)propanoate

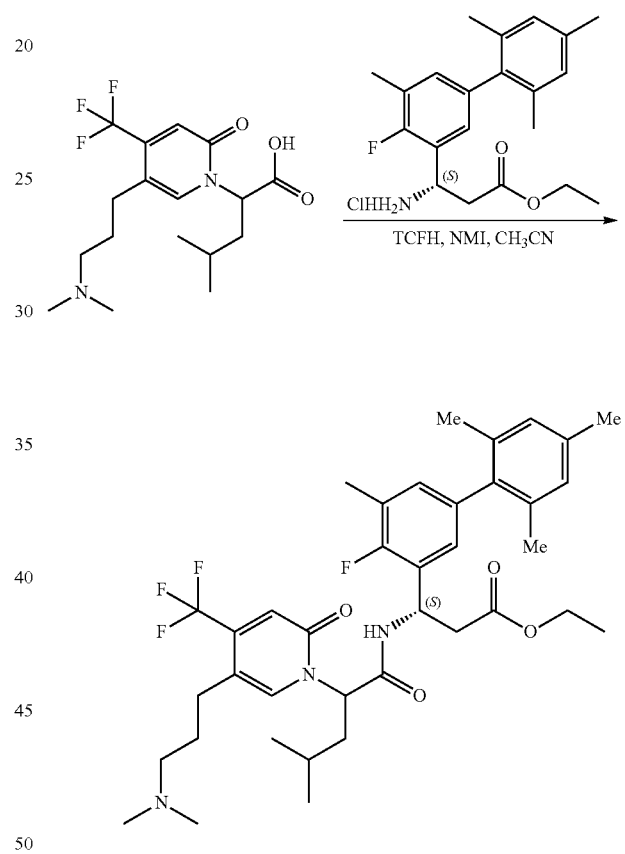

A mixture of ethyl (S)-3-amino-3-(4-fluoro-2',4',5,6'-tetramethyl-[1,1'-biphenyl]-3-yl)propanoate hydrochloride (239.3 mg, 0.63 mmol), 2-(5-(3-(dimethylamino)propyl)-2-oxo-4-(trifluoromethyl)pyridin-1(2H)-yl)-4-methylpentanoic acid (230.0 mg, 0.63 mmol), TCHF (213.2 mg, 0.76 mmol) and NMI (206.9 mg, 2.52 mmol) in CH$_3$CN (5 mL) was stirred at room temperature overnight. The solvent was removed in vacuo and the residue purified by reverse phase HPLC on a C18/40 g column (A: water 10 mM NH$_4$HCO$_3$, B: MeOH, 0~100%) to provide ethyl (3S)-3-(2-(5-(3-(dimethylamino)propyl)-2-oxo-4-(trifluoromethyl)pyridin-1(2H)-yl)-4-methylpentanamido)-3-(4-fluoro-2',4',5,6'-tetramethyl-[1,1'-biphenyl]-3-yl)propanoate as a light yellow solid (270.0 mg). Yield 62% (ESI 688.3 [M+H]⁺).

635

Step 2: (3S)-3-(2-(5-(3-(dimethylamino)propyl)-2-oxo-4-(trifluoromethyl)pyridin-1(2H)-yl)-4-methylpentanamido)-3-(4-fluoro-2',4',5,6'-tetramethyl-[1,1'-biphenyl]-3-yl)propanoic Acid

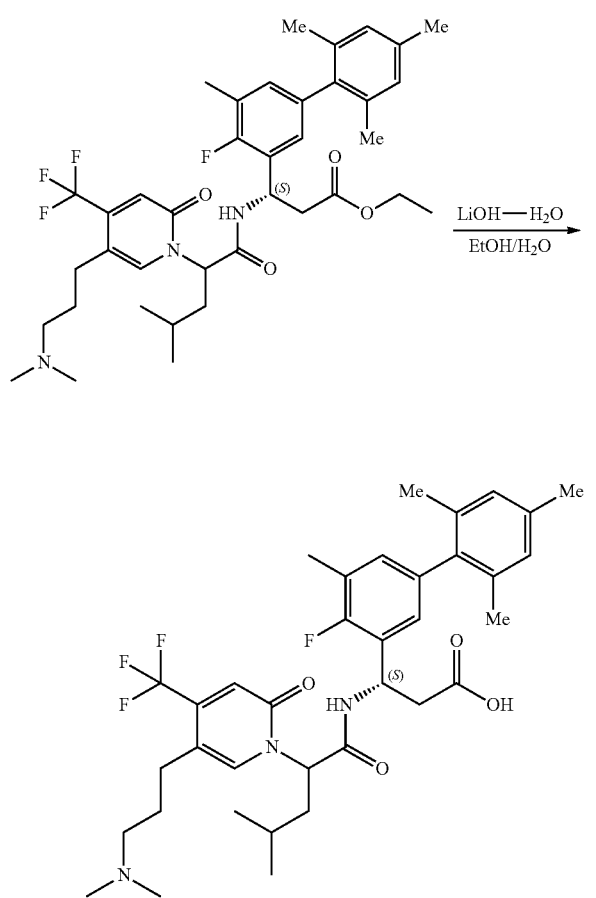

Ethyl (3S)-3-(2-(5-(3-(dimethylamino)propyl)-2-oxo-4-(trifluoromethyl)pyridin-1(2H)-yl)-4-methylpentanamido)-3-(4-fluoro-2',4',5,6'-tetramethyl-[1,1'-biphenyl]-3-yl)propanoate (270.0 mg, 0.39 mmol) was treated with LiOH—H$_2$O (49.1 mg, 1.17 mmol) in EtOH (2 mL) and water (0.5 mL) at room temperature for 1 hour. The reaction mixture was acidified to PH 4-5 with 2N HCl. The solvent was removed in vacuo and the residue purified by prep-HPLC A (30-80% MeCN) to give the diastereomeric products KJ-P1 (84 mg) and KJ-P2 (74 mg) as white solids.

KJ-P1 ESI 660.0 (M+H)$^+$ $^1$H NMR (400 MHz, MeOD) δ 7.80 (s, 1H), 6.95-6.78 (m, 4H), 6.72 (s, 1H), 5.75-5.69 (m, 1H), 5.58 (t, J=6.8 Hz, 1H), 3.12-2.97 (m, 2H), 2.78 (s, 6H), 2.72-2.62 (m, 4H), 2.33-2.23 (m, 6H), 2.05-1.88 (m, 7H), 1.80 (s, 3H), 1.43-1.34 (m, 1H), 0.96-0.92 (m, 6H).

KJ-P2 ESI 660.0 (M+H)$^+$ $^1$H NMR (400 MHz, MeOD) δ 7.83 (s, 1H), 6.93-6.86 (m, 4H), 6.84 (s, 1H), 5.77-5.72 (m, 1H), 5.60-5.53 (m, 1H), 3.09-2.94 (m, 2H), 2.79 (s, 6H), 2.73-2.45 (m, 4H), 2.36-2.26 (m, 6H), 2.10-1.85 (m, 9H), 1.65-1.54 (m, 1H), 1.42-1.30 (m, 1H), 0.87-0.81 (m, 6H).

636

3-133. Preparation of (3S)-3-(2-(5-(2-(azetidin-1-yl)ethyl)-2-oxo-4-(trifluoromethyl)pyridin-1(2H)-yl)-4-methylpentanamido)-3-(3',4-difluoro-2',4',5,6'-tetramethyl-[1,1'-biphenyl]-3-yl)propanoic Acid (Compounds KK-P1 and KK-P2)

Step 1: Ethyl (3S)-3-(2-(5-(2-(azetidin-1-yl)ethyl)-2-oxo-4-(trifluoromethyl)pyridin-1(2H)-yl)-4-methylpentanamido)-3-(3',4-difluoro-2',4',5,6'-tetramethyl-[1,1'-biphenyl]-3-yl)propanoate

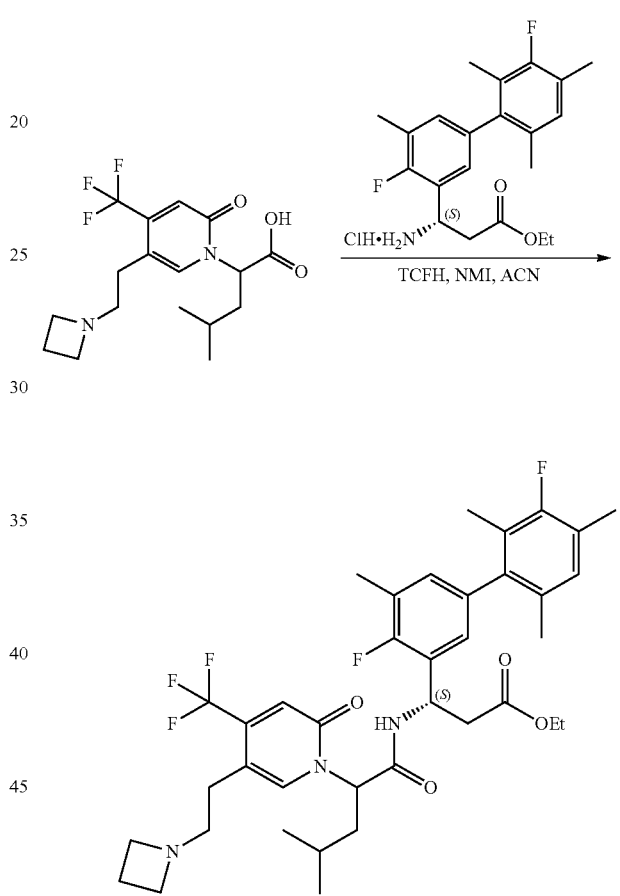

A mixture of 2-(5-(2-(azetidin-1-yl)ethyl)-2-oxo-4-(trifluoromethyl)pyridin-1(2H)-yl)-4-methylpentanoic acid (230.0 mg, 0.64 mmol), ethyl (S)-3-amino-3-(3',4-difluoro-2',4',5,6'-tetramethyl-[1,1'-biphenyl]-3-yl)propanoate hydrochloride (230.0 mg, 0.64 mmol), TCHF (214.0 mg, 0.76 mmol) and NMI (105.0 mg, 1.28 mmol) in CH$_3$CN (5 mL) was stirred at room temperature for 2 hours. The solvent was concentrated in vacuo and the residue purified by reverse phase HPLC on a C18/40 g column (A: water 10 mM NH$_4$HCO$_3$, B: MeOH, 0~100%) to provide ethyl (3S)-3-(2-(5-(2-(azetidin-1-yl)ethyl)-2-oxo-4-(trifluoromethyl)pyridin-1(2H)-yl)-4-methylpentanamido)-3-(3',4-difluoro-2',4',5,6'-tetramethyl-[1,1'-biphenyl]-3-yl)propanoate as a yellow solid (220 mg). Yield 50.1% (ESI 704.3 [M+H]$^+$).

Step 2: (3S)-3-(2-(5-(2-(azetidin-1-yl)ethyl)-2-oxo-4-(trifluoromethyl)pyridin-1(2H)-yl)-4-methylpentanamido)-3-(3',4-difluoro-2',4',5',6'-tetramethyl-[1,1'-biphenyl]-3-yl)propanoic Acid

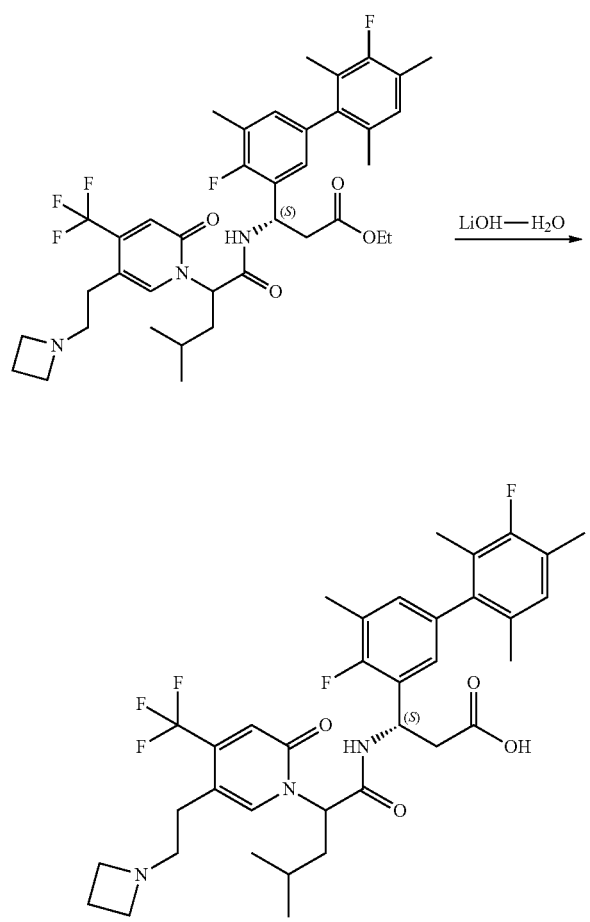

Ethyl (3S)-3-(2-(5-(2-(azetidin-1-yl)ethyl)-2-oxo-4-(trifluoromethyl)pyridin-1(2H)-yl)-4-methylpentanamido)-3-(3',4-difluoro-2',4',5',6'-tetramethyl-[1,1'-biphenyl]-3-yl) propanoate (220.0 mg, 0.31 mmol) was treated with LiOH—$H_2O$ (66.0 mg, 1.55 mmol) in EtOH (4 mL) and water (2 mL) at 30° C. for 1 hour. The reaction mixture was acidified to pH 4~5 with 2N HCl. The solvent was removed in vacuo and the residue purified by Prep HPLC A (30-80% MeCN) to give the diastereomeric products KK-P1 (85 mg) and KK-P2 (84 mg) as white solids.

KK-P1 ESI 676.1 $(M+H)^+$ $^1$H NMR (400 MHz, MeOD) δ 7.84 (s, 1H), 6.94-6.76 (m, 3H), 6.77 (d, J=9.2 Hz, 1H), 5.68-5.54 (m, 2H), 4.07-4.02 (s, 4H), 3.28 (d, J=6.7 Hz, 2H), 2.85 (t, J=6.9 Hz, 2H), 2.71-2.68 (m, 2H), 2.43 (m, 2H), 2.30 (s, 3H), 2.25 (s, 3H), 2.00 (t, J=7.5 Hz, 2H), 1.95-1.88 (m, 3H), 1.80 (d, J=16.8 Hz, 3H), 1.42-4.41 (m, 1H), 0.96-0.92 (m, 6H).

KK-P2 ESI 676.1 $(M+H)^+$ $^1$H NMR (400 MHz, MeOD) δ 7.62 (s, 1H), 6.84-6.78 (m, 4H), 5.64 (dd, J=10.8, 3.3 Hz, 1H), 5.49 (t, J=7.6 Hz, 1H), 4.04-3.99 (m, 4H), 3.31-3.21 (m, 2H), 2.84-2.69 (m, 2H), 2.55-2.50 (m, 1H), 2.44-2.29 (m, 3H), 2.22 (d, J=1.7 Hz, 3H), 2.14 (d, J=1.6 Hz, 3H), 1.91-1.78 (m, 7H), 1.60-1.49 (m, 1H), 1.37-1.22 (m, 1H), 0.80-0.73 (m, 6H).

3-134. Preparation of (3S)-3-(4-fluoro-3'-methoxy-2',5',6'-trimethylbiphenyl-3-yl)-3-(4-methyl-2-(5-(2-(3-methylazetidin-1-yl)ethyl)-2-oxo-4-(trifluoromethyl)pyridin-1(2H)-yl)pentanamido)propanoic Acid (Compounds KL-P1 and KL-P2)

Step 1: (3S)-ethyl 3-(4-fluoro-3'-methoxy-2',5',6'-trimethylbiphenyl-3-yl)-3-(4-methyl-2-(5-(2-(3-methylazetidin-1-yl)ethyl)-2-oxo-4-(trifluoromethyl)pyridin-1(2H)-yl)pentanamido)propanoate

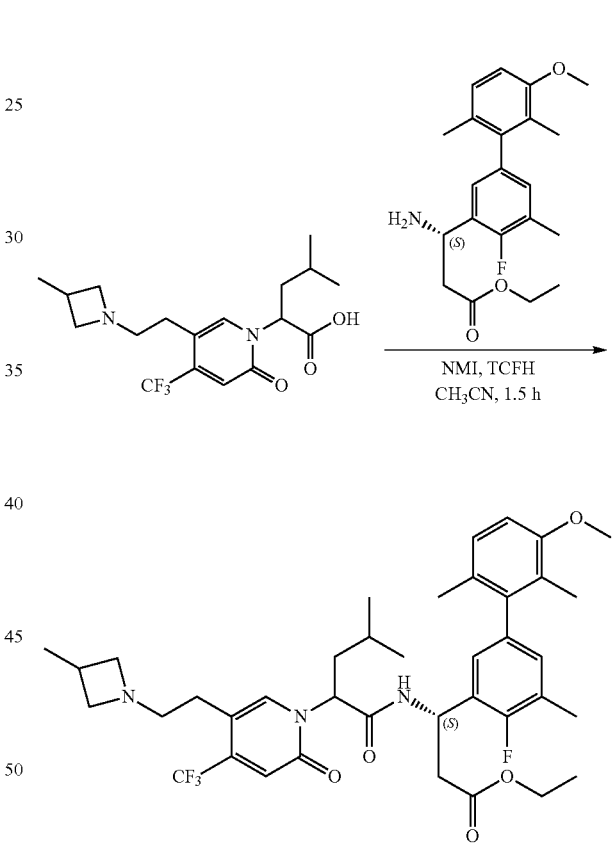

A mixture of 4-methyl-2-(5-(2-(3-methylazetidin-1-yl)ethyl)-2-oxo-4-(trifluoromethyl)pyridin-1(2H)-yl)pentanoic acid (170 mg, 0.45 mmol), (S)-ethyl 3-amino-3-(4-fluoro-3'-methoxy-2',5',6'-trimethylbiphenyl-3-yl)propanoate (163 mg, 0.45 mmol), NMI (160 mg, 1.96 mmol) and TCFH (252 mg, 0.9 mmol) in $CH_3CN$ (5 mL) was stirred at room temperature for 1.5 hours. The solvent was concentrated in vacuo and the residue purified by silica gel column (DCM: MeOH 9:1) to provide (3S)-ethyl 3-(4-fluoro-3'-methoxy-2',5',6'-trimethylbiphenyl-3-yl)-3-(4-methyl-2-(5-(2-(3-methylazetidin-1-yl)ethyl)-2-oxo-4-(trifluoromethyl)

pyridin-1(2H)-yl)pentanamido)propanoate as a yellow solid (220 mg). Yield 68% (ESI 716.3 [M+H]⁺).

Step 2: (3S)-3-(4-fluoro-3'-methoxy-2',5,6'-trimethylbiphenyl-3-yl)-3-(4-methyl-2-(5-(2-(3-methylazetidin-1-yl)ethyl)-2-oxo-4-(trifluoromethyl)pyridin-1(2H)-yl)pentanamido)propanoic Acid

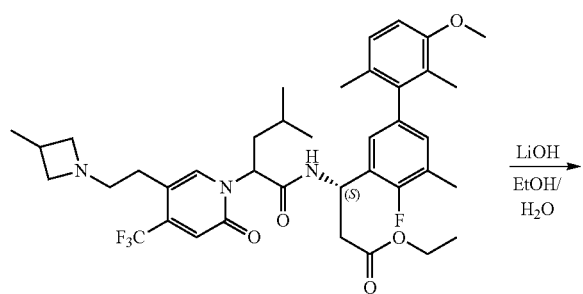

(3S)-ethyl 3-(4-fluoro-3'-methoxy-2',5,6'-trimethylbiphenyl-3-yl)-3-(4-methyl-2-(5-(2-(3-methylazetidin-1-yl)ethyl)-2-oxo-4-(trifluoromethyl)pyridin-1(2H)-yl)pentanamido)propanoate (220 mg, 0.31 mmol) was treated with LiOH—H₂O (64 mg, 1.53 mmol) in EtOH (3 mL) and H₂O (1 mL) at room temperature for 2 hours. The reaction mixture was acidified to pH 4~5 with 1N HCl. The solvent was removed in vacuo and the residue purified by prep-HPLC A (30-80% CH₃CN) to give the diastereomeric products KL-P1 (73 mg) and KL-P2 (100 mg) as white solids.

KL-P1 ESI 688.3 (M+H)⁺. 1H NMR (400 MHz, MeOD) δ 7.84 (s, 1H), 7.02 (t, J=7.7 Hz, 1H), 6.92-6.67 (m, 4H), 5.73-5.51 (m, 2H), 4.18-4.00 (m, 2H), 3.82 (s, 3H), 3.70-3.55 (m, 2H), 3.31-3.22 (m, 2H), 3.01-2.79 (m, 3H), 2.70 (d, J=6.0 Hz, 2H), 2.32 (d, J=25.7 Hz, 3H), 1.98 (t, J=7.5 Hz, 2H), 1.82-1.80 (m, 6H), 1.49-1.37 (m, 1H), 1.24 (d, J=6.9 Hz, 3H), 0.94-0.90 (m, 6H).

KL-P2 ESI 688.3 (M+H)⁺. 1H NMR (400 MHz, MeOD) δ 7.74 (s, 1H), 7.05 (d, J=8.3 Hz, 1H), 7.00-6.84 (m, 3H), 6.83 (d, J=8.4 Hz, 1H), 5.76-5.75 (m, 1H), 5.60 (t. J=7.5 Hz, 1H), 4.21 (t, J=9.3 Hz, 2H), 3.83 (d, J=1.0 Hz, 3H), 3.80-3.67 (m, 2H), 3.46-3.35 (m, 2H), 3.04-2.86 (m, 2H), 2.85-2.74 (m, 1H), 2.71-2.59 (m, 1H), 2.50-2.48 (m, 1H), 2.33 (d, J=1.7 Hz, 3H), 2.06-1.95 (m, 1H), 1.93 (d, J=6.5 Hz, 3H), 1.85 (d, J=5.3 Hz, 3H), 1.68-1.56 (m, 1H), 1.42-1.40 (m, 1H), 1.29 (d, J=6.9 Hz, 3H), 0.89 (d, J=6.6 Hz, 6H).

3-135. Preparation of (3S)-3-(2-(5-(2-(3,3-dimethylazetidin-1-yl)ethyl)-2-oxo-4-(trifluoromethyl)pyridin-1(2H)-yl)-4-methylpentanamido)-3-(4-fluoro-2',5,6'-trimethyl-[1,1'-biphenyl]-3-yl)propanoic Acid (Compounds KM-P1 and KM-P2)

Step 1: Ethyl (3S)-3-(2-(5-(2-(3,3-dimethylazetidin-1-yl)ethyl)-2-oxo-4-(trifluoromethyl)pyridin-1(2H)-yl)-4-methylpentanamido)-3-(4-fluoro-2',5,6'-trimethyl-[1,1'-biphenyl]-3-yl)propanoate

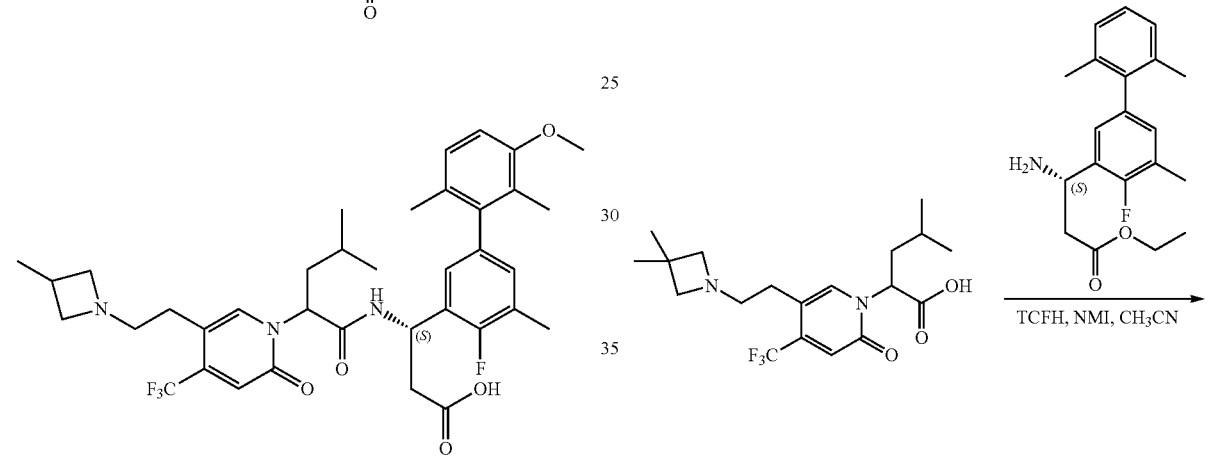

A mixture of ethyl (S)-3-amino-3-(4-fluoro-2',5,6'-trimethyl-[1,1'-biphenyl]-3-yl)propanoate (216.6 mg, 0.59 mmol), 2-(5-(2-(3,3-dimethylazetidin-1-yl)ethyl)-2-oxo-4-(trifluoromethyl)pyridin-1(2H)-yl)-4-methylpentanoic acid (230.0 mg, 0.59 mmol), TCHF (199.2 mg, 0.71 mmol) and NMI (145.3 mg, 1.77 mmol) in CH₃CN (5 mL) was stirred at 40° C. for 1 hour. The solvent was removed in vacuo and the residue purified by reverse phase HPLC on a C18/40 g column (A: water 10 mM NH₄HCO₃, B: MeOH, 0~100%) to provide ethyl (3S)-3-(2-(5-(2-(3,3-dimethylazetidin-1-yl)ethyl)-2-oxo-4-(trifluoromethyl)pyridin-1(2H)-yl)-4-methylpentanamido)-3-(4-fluoro-2',5,6'-trimethyl-[1,1'-biphenyl]-3-yl)propanoate as a light yellow solid (270.0 mg). Yield 65% (ESI 700.3 [M+H]⁺).

Step 2: (3S)-3-(2-(5-(2-(3,3-dimethylazetidin-1-yl)ethyl)-2-oxo-4-(trifluoromethyl)pyridin-1(2H)-yl)-4-methylpentanamido)-3-(4-fluoro-2',5,6'-trimethyl-[1,1'-biphenyl]-3-yl)propanoic Acid

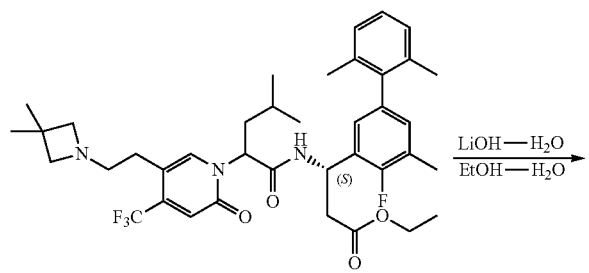

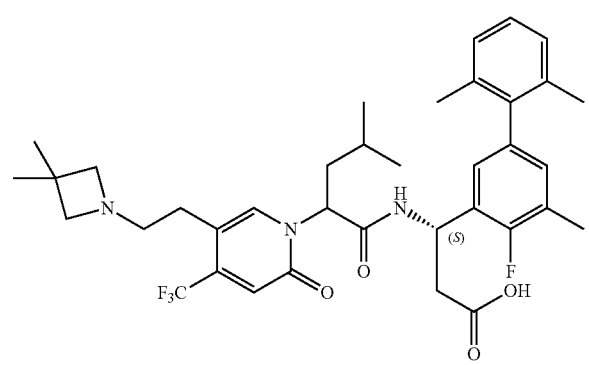

Ethyl (3S)-3-(2-(5-(2-(3,3-dimethylazetidin-1-yl)ethyl)-2-oxo-4-(trifluoromethyl)pyridin-1(2H)-yl)-4-methylpentanamido)-3-(4-fluoro-2',5,6'-trimethyl-[1,1'-biphenyl]-3-yl)propanoate (270.0 mg, 0.39 mmol) was treated with LiOH—H$_2$O (49.1 mg, 1.17 mmol) in EtOH (2 mL) and H$_2$O (0.5 mL) at room temperature for 1 hour. The reaction mixture was acidified to pH 4~5 with 2N HCl. The solvent was removed in vacuo and the residue purified by prep-HPLC A (30-80% MeCN) to give the diastereomeric products KM-P1 (83 mg) and KM-P2 (96 mg) as white solids.

KM-P1 ESI 672.3 (M+H)⁺ ¹H NMR (400 MHz, MeOD) δ 7.87 (s, 1H), 7.15-7.02 (m, 3H), 6.94-6.84 (m, 2H), 6.78 (s, 1H), 5.72-5.61 (m, 2H), 3.84-3.71 (m, 4H), 3.32-3.20 (m, 2H), 2.85 (t, J=7.1 Hz, 2H), 2.78-2.66 (m, 2H), 2.29 (d, J=1.4 Hz, 3H), 2.04-1.94 (m, 5H), 1.85 (s, 3H), 1.45-1.38 (m, 1H), 1.34 (s, 6H), 0.94 (t, J=6.6 Hz, 6H).

KM-P2 ESI 672.3 (M+H)⁺ ¹H NMR (400 MHz, MeOD) δ 7.73 (s, 1H), 7.17-7.05 (m, 3H), 6.98-6.87 (m, 3H), 5.80-5.75 (m, 1H), 5.62 (t, J=7.6 Hz, 1H), 3.91 (s, 4H), 3.42 (t, J=5.9 Hz, 2H), 3.00-2.74 (m, 2H), 2.66-2.46 (m, 2H), 2.33 (d, J=1.7 Hz, 3H), 2.05-1.94 (m, 7H), 1.66-1.58 (m, 1H), 1.47-1.35 (m, 7H), 0.89 (d, J=6.6 Hz, 6H).

3-136. Preparation of (3S)-3-(2-(5-(2-(dimethylamino)ethyl)-2-oxo-4-(trifluoromethyl)pyridin-1(2H)-yl)-4-methylpentanamido)-3-(4-fluoro-2',3',5,6'-tetramethyl-[1,1'-biphenyl]-3-yl)propanoic Acid (Compounds KN-P1 and KN-P2)

Step 1: 2,3,6-trimethylphenyl trifluoromethanesulfonate

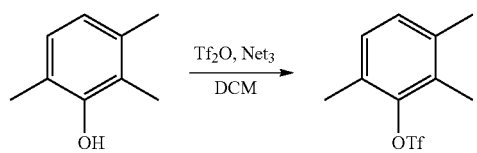

A mixture of 2,3,6-trimethylphenol (5.0 g, 36.7 mmol) and triethylamine (11.1 g, 110.1 mmol) in DCM (100 mL) was cooled at 0° C. Trifluoromethanesulfonic anhydride (15.5 g, 55.1 mmol) was added dropwise to the reaction mixture and the mixture was stirred at 0° C. for 3 hours. The mixture was quenched with a NH$_4$Cl aqueous solution (50 mL). The organic layer was washed with brine (50 mL), dried over anhydrous Na$_2$SO$_4$, filtered and the filtrate was concentrated in vacuo. The residue was purified by silica gel column (pet ether) to provide 2,3,6-trimethylphenyl trifluoromethanesulfonate as a colourless oil (8.0 g). Yield 81% (no Mass) ¹H NMR (400 MHz, CDCl$_3$) δ 7.03 (dd, J=19.3, 7.8 Hz, 2H), 2.35 (s, 3H), 2.27 (d, J=5.2 Hz, 6H).

Step 2: Ethyl (3S)-3-(2-(5-(2-(dimethylamino)ethyl)-2-oxo-4-(trifluoromethyl)pyridin-1(2H)-yl)-4-methylpentanamido)-3-(4-fluoro-2',3',5,6'-tetramethyl-[1,1'-biphenyl]-3-yl)propanoate

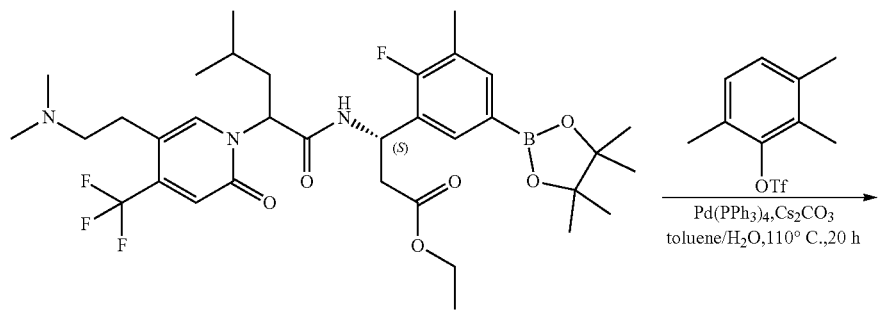

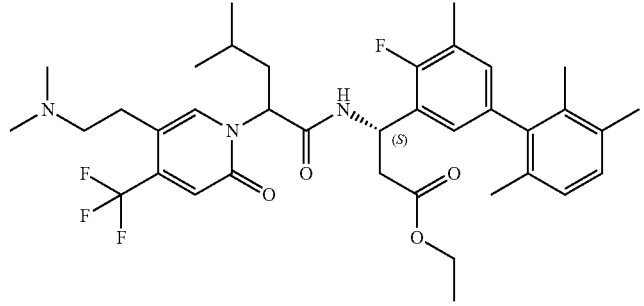

A mixture of ethyl (3S)-3-(2-(5-(2-(dimethylamino)ethyl)-2-oxo-4-(trifluoromethyl)pyridin-1(2H)-yl)-4-methylpentanamido)-3-(2-fluoro-3-methyl-5-(4,4,5,5-tetramethyl-1,3,2-dioxaborolan-2-yl)phenyl)propanoate (250.0 mg, 0.37 mmol), 2,3,6-trimethylphenyl trifluoromethanesulfonate (119.1 mg, 0.44 mmol), Cs₂CO₃ (361.6 mg, 1.11 mmol) and Pd(PPh₃)₄ (42.7 mg, 0.037 mmol) in toluene (6 mL) and H₂O (0.6 mL) was stirred at 110° C. under a nitrogen atmosphere for 20 hours. LCMS showed that the reaction was completed. The reaction mixture was filtered and the filtrate was concentrated in vacuo. The residue was purified by silica gel column (EtOAc) to provide ethyl (3S)-3-(2-(5-(2-(dimethylamino)ethyl)-2-oxo-4-(trifluoromethyl)pyridin-1(2H)-yl)-4-methylpentanamido)-3-(4-fluoro-2',3',5,6'-tetramethyl-[1,1'-biphenyl]-3-yl)propanoate a light yellow oil (110 mg). Yield 45% (ESI 674.3 (M+H)⁺)

Step 3: (3S)-3-(2-(5-(2-(dimethylamino)ethyl)-2-oxo-4-(trifluoromethyl)pyridin-1(2H)-yl)-4-methylpentanamido)-3-(4-fluoro-2',3',5,6'-tetramethyl-[1,1'-biphenyl]-3-yl)propanoic Acid Ethyl (3S)-3-(2-(5-(2-(dimethylamino)ethyl)-2-oxo-4-(trifluoromethyl)pyridin-1(2H)-yl)-4-methylpentanamido)-3-(4-fluoro-2',3',5,6'-tetramethyl-[1,1'-biphenyl]-3-yl)propanoate (110.0 mg, 0.16 mmol) was treated with LiOH—H₂O (35.6 mg, 0.80 mmol) in EtOH (2 mL) and water (0.5 mL) at room temperature for 1 hour. The reaction mixture was acidified to pH 4~5 with 2N HCl. The solvent was removed in vacuo and the residue purified by prep-HPLC A (30-80% MeCN) to provide the diastereomeric products KN-P1 (47 mg) and KN-P2 (39 mg) as white solids.

KN-P1 ESI 646.3 (M+H)⁺ ¹H NMR (400 MHz, MeOD) δ 7.91 (d, J=8.6 Hz, 1H), 7.02 (d, J=7.7 Hz, 1H), 6.97-6.72 (m, 4H), 5.71-5.66 (m, 1H), 5.58-5.54 (m, 1H), 3.16-3.00 (m, 2H), 2.96-2.91 (m, 2H), 2.79-2.64 (m, 8H), 2.32-2.21 (m, 6H), 1.99-1.88 (m, 2H), 1.92 (d, J=12.7 Hz, 3H), 1.74 (d, J=9.6 Hz, 3H), 1.47-1.39 (m, 1H), 0.96-0.91 (m, 6H).

KN-P2 ESI 646.2 (M+H)⁺ ¹H NMR (400 MHz, MeOD) δ 7.88 (s, 1H), 7.03 (d, J=7.7 Hz, 1H), 6.97 (d, J=7.7 Hz, 1H), 6.94-6.85 (m, 3H), 5.74-5.70 (m, 1H), 5.62 (t, J=7.7 Hz, 1H), 3.28-3.16 (m, 2H), 3.03-2.95 (m, 2H), 2.82 (d, J=4.2 Hz, 6H), 2.67-2.61 (m, 1H), 2.56-2.49 (m, 1H), 2.32

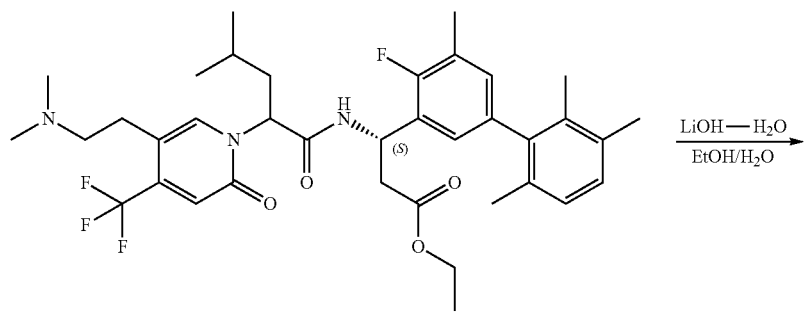

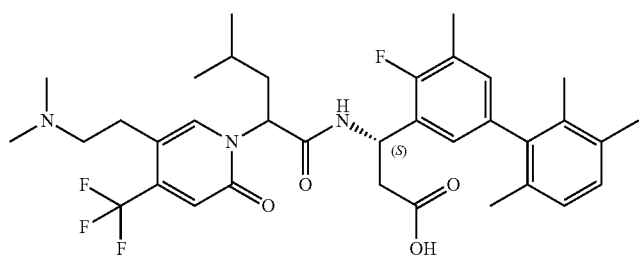

(d, J=1.5 Hz, 3H), 2.27 (s, 3H), 2.03-1.84 (m, 7H), 1.74-1.65 (m, 1H), 1.42-1.35 (m, 1H), 0.92-0.82 (m, 6H).

3-137. Preparation of (3S)-3-(4,4'-difluoro-2',5,6'-trimethylbiphenyl-3-yl)-3-(2-(5-(2-(dimethylamino)ethyl)-3-fluoro-2-oxo-4-(trifluoromethyl)pyridin-1(2H)-yl)-4-methylpentanamido)propanoic Acid (Compounds KO-P1 and KO-P2)

Step 1: (3S)-ethyl 3-(4,4'-difluoro-2',5,6'-trimethylbiphenyl-3-yl)-3-(2-(5-(2-(dimethylamino)ethyl)-3-fluoro-2-oxo-4-(trifluoromethyl)pyridin-1(2H)-yl)-4-methylpentanamido)propanoate

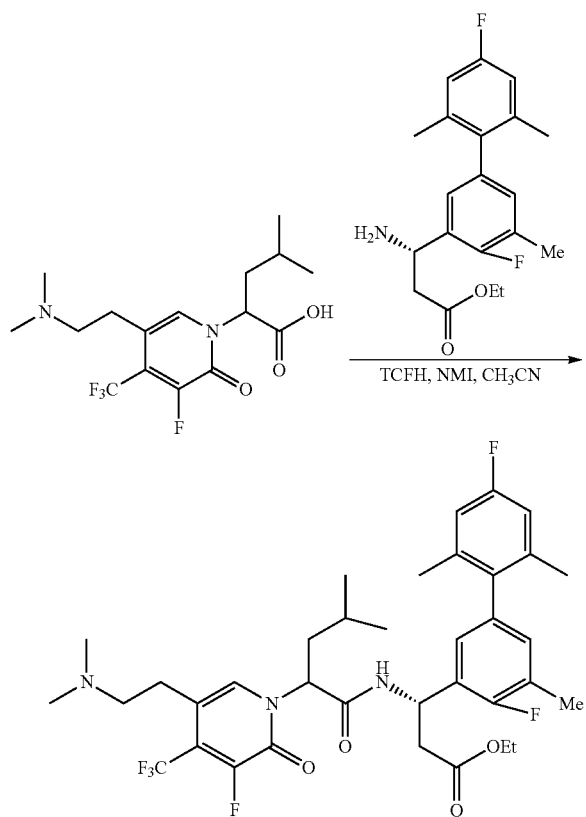

A mixture of 2-(5-(2-(dimethylamino)ethyl)-3-fluoro-2-oxo-4-(trifluoromethyl)pyridin-1(2H)-yl)-4-methylpentanoic acid (150 mg, 0.41 mmol), (S)-ethyl 3-amino-3-(4,4'-difluoro-2',5,6'-trimethylbiphenyl-3-yl)propanoate (142 mg, 0.41 mmol), TCFH (230 mg, 0.82 mmol) and NMI (67 mg, 0.82 mmol) in CH$_3$CN (6 mL) was stirred at room temperature for 1 hour. The solvent was removed in vacuo and the residue purified by silica gel column (DCM:MeOH 10:1) to provide (3S)-ethyl 3-(4,4'-difluoro-2',5,6'-trimethylbiphenyl-3-yl)-3-(2-(5-(2-(dimethylamino)ethyl)-3-fluoro-2-oxo-4-(trifluoromethyl)pyridin-1(2H)-yl)-4-methylpentanamido)propanoate as a yellow oil (120 mg). Yield 42% (ESI 696.1 (M+H)$^+$).

Step 2: (3S)-3-(4,4'-difluoro-2',5,6'-trimethylbiphenyl-3-yl)-3-(2-(5-(2-(dimethylamino)ethyl)-3-fluoro-2-oxo-4-(trifluoromethyl)pyridin-1(2H)-yl)-4-methylpentanamido)propanoic Acid

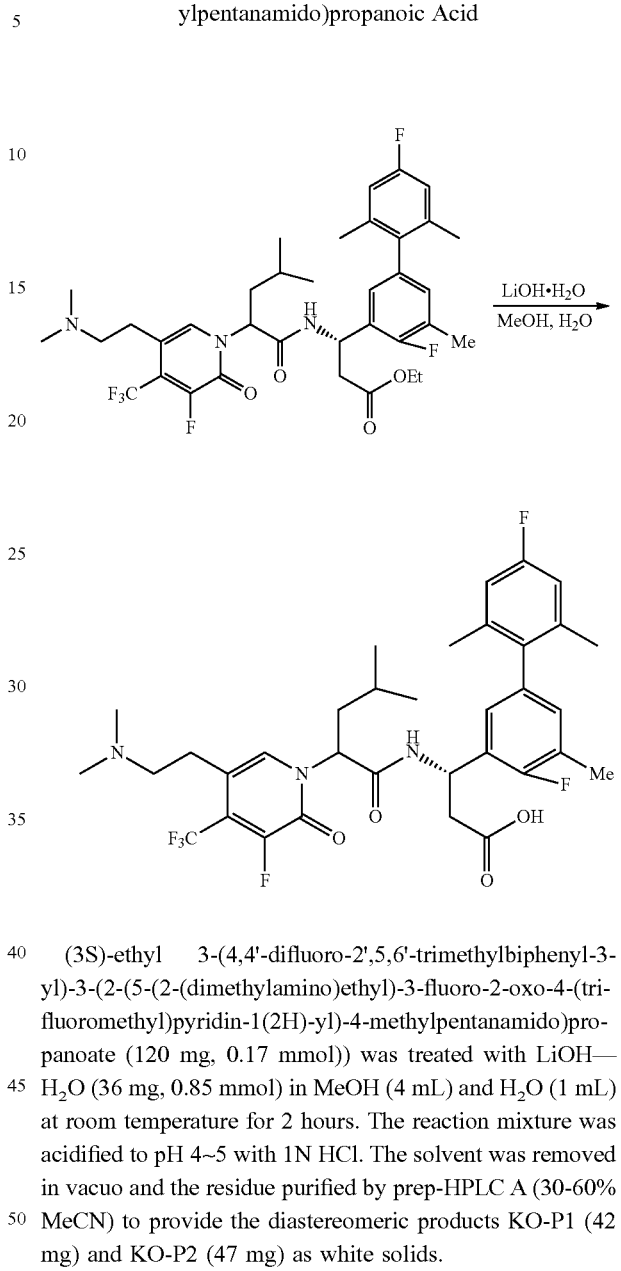

(3S)-ethyl 3-(4,4'-difluoro-2',5,6'-trimethylbiphenyl-3-yl)-3-(2-(5-(2-(dimethylamino)ethyl)-3-fluoro-2-oxo-4-(trifluoromethyl)pyridin-1(2H)-yl)-4-methylpentanamido)propanoate (120 mg, 0.17 mmol)) was treated with LiOH—H$_2$O (36 mg, 0.85 mmol) in MeOH (4 mL) and H$_2$O (1 mL) at room temperature for 2 hours. The reaction mixture was acidified to pH 4~5 with 1N HCl. The solvent was removed in vacuo and the residue purified by prep-HPLC A (30-60% MeCN) to provide the diastereomeric products KO-P1 (42 mg) and KO-P2 (47 mg) as white solids.

KO-P1 ESI 668.2 (M+H)$^+$ $^1$H NMR (400 MHz, MeOD) δ 7.71 (s, 1H), 6.88-6.79 (m, 4H), 5.68 (t, J=8.0 Hz, 1H), 5.55 (t, J=6.8 Hz, 1H), 3.09 (d, J=7.2 Hz, 2H), 3.00 (d, J=7.9 Hz, 2H), 2.81-2.68 (m, 8H), 2.29 (s, 3H), 1.98 (d, J=10.1 Hz, 5H), 1.83 (s, 3H), 1.48-1.41 (m, 1H), 0.96-0.92 (m, 6H).

KO-P2 ESI 668.2 (M+H)$^+$ $^1$H NMR (400 MHz, MeOD) δ 7.66 (s, 1H), 6.93 (t, J=7.5 Hz, 2H), 6.84 (d, J=9.6 Hz, 2H), 5.74-5.70 (m, 1H), 5.63 (t, J=7.6 Hz, 1H), 3.29-3.15 (m, 2H), 3.06-3.00 (m, 2H), 2.83 (d, J=7.9 Hz, 6H), 2.67-2.59 (m, 1H), 2.55-2.49 (m, 1H), 2.32 (d, J=1.2 Hz, 3H), 2.08-1.96 (m, 7H), 1.76-1.66 (m, 1H), 1.42-1.37 (m, 1H), 0.90-0.85 (m, 6H).

3-138. Preparation of (3S)-3-(2-(5-(2-(azetidin-1-yl)ethyl)-2-oxo-4-(trifluoromethyl)pyridin-1(2H)-yl)-4-methylpentanamido)-3-(4-fluoro-4'-methoxy-2',5,6'-trimethylbiphenyl-3-yl)propanoic Acid (Compounds KP-P1 and KP-P2)

Step 1: (3S)-ethyl 3-(2-(5-(2-(azetidin-1-yl)ethyl)-2-oxo-4-(trifluoromethyl)pyridin-1(2H)-yl)-4-methylpentanamido)-3-(4-fluoro-4'-methoxy-2',5,6'-trimethylbiphenyl-3-yl)propanoate

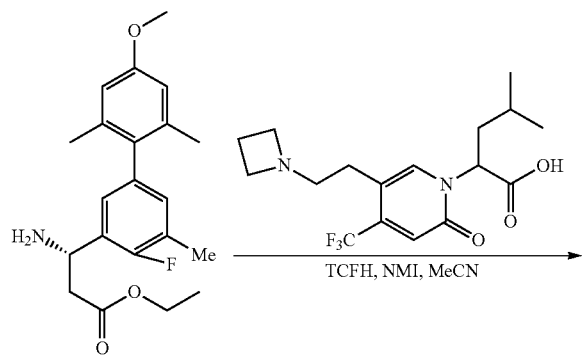

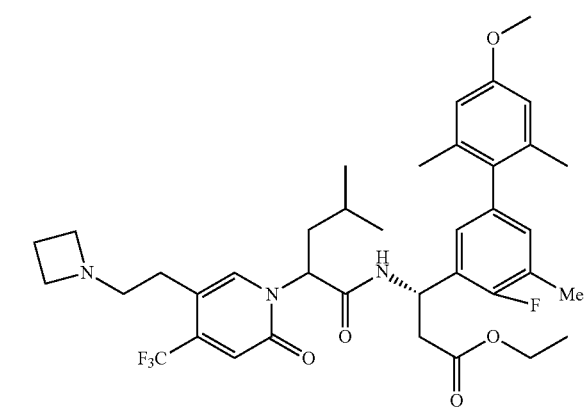

A mixture of (S)-ethyl 3-amino-3-(4-fluoro-4'-methoxy-2',5,6'-trimethylbiphenyl-3-yl)propanoate (170 mg, 0.47 mmol), 2-(5-(2-(azetidin-1-yl)ethyl)-2-oxo-4-(trifluoromethyl)pyridin-1(2H)-yl)-4-methylpentanoic acid (169 mg, 0.47 mmol), TCFH (263 mg, 0.94 mmol) and NMI (241 mg, 2.94 mmol) in CH$_3$CN (6 mL) was stirred at room temperature for 1 hour. The solvent was removed in vacuo and the residue purified by silica gel column (DCM:MeOH 10:1) to provide (3S)-ethyl 3-(2-(5-(2-(azetidin-1-yl)ethyl)-2-oxo-4-(trifluoromethyl)pyridin-1(2H)-yl)-4-methylpentanamido)-3-(4-fluoro-4'-methoxy-2',5,6'-trimethylbiphenyl-3-yl)propanoate as a yellow oil (140 mg). Yield 42% (ESI 702.2 (M+H)$^+$).

Step 2: (3S)-3-(2-(5-(2-(azetidin-1-yl)ethyl)-2-oxo-4-(trifluoromethyl)pyridin-1(2H)-yl)-4-methylpentanamido)-3-(4-fluoro-4'-methoxy-2',5,6'-trimethylbiphenyl-3-yl)propanoic Acid

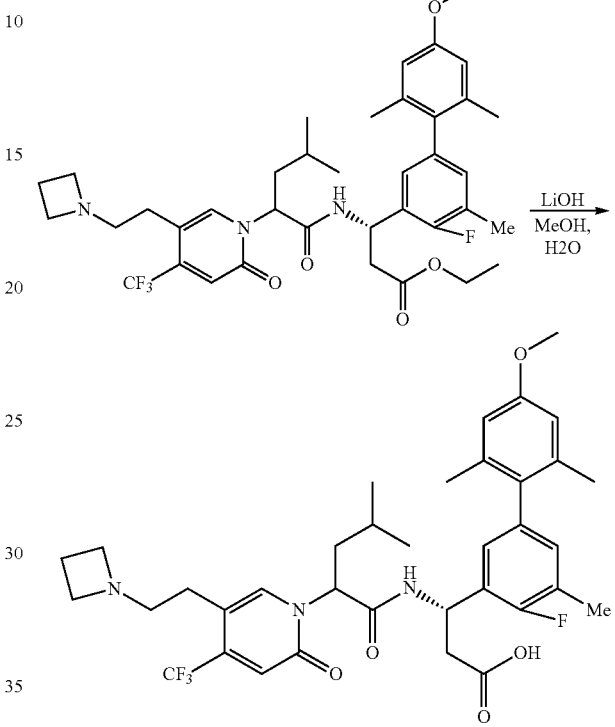

(3S)-ethyl 3-(2-(5-(2-(azetidin-1-yl)ethyl)-2-oxo-4-(trifluoromethyl)pyridin-1(2H)-yl)-4-methylpentanamido)-3-(4-fluoro-4'-methoxy-2',5,6'-trimethylbiphenyl-3-yl)propanoate (140 mg, 0.2 mmol)) was treated with LiOH—H$_2$O (42 mg, 1 mmol) in MeOH (4 mL) and H$_2$O (1 mL) at room temperature for 2 hours. The reaction mixture was acidified to pH 4~5 with 1N HCl. The solvent was removed in vacuo and the residue purified by prep-HPLC A (30-60% MeCN) to provide the diastereomeric products KP-P1 (48 mg) and KP-P2 (47 mg) as white solids.

KP-P1 ESI 674.2 (M+H)$^+$. $^1$H NMR (400 MHz, MeOD) δ 7.85 (s, 1H), 6.89-6.85 (m, 2H), 6.80 (s, 1H), 6.64 (d, J=6.8 Hz, 2H), 5.67-5.57 (m, 2H), 4.05-4.00 (m, 4H), 3.79 (s, 3H), 3.29 (d, J=6.6 Hz, 2H), 2.86 (t, J=6.9 Hz, 2H), 2.77-2.65 (m, 2H), 2.53-2.38 (m, 2H), 2.29 (d, J=1.3 Hz, 3H), 2.06-1.92 (m, 5H), 1.86 (s, 3H), 1.51-1.29 (m, 1H), 0.96-0.92 (m, 6H).

KP-P2 ESI 674.2 (M+H)$^+$. $^1$H NMR (400 MHz, MeOD) δ 7.75 (s, 1H), 6.95-6.90 (m, 3H), 6.67 (s, 2H), 5.79-5.75 (m, 1H), 5.61 (t, J=7.6 Hz, 1H), 4.14 (t, J=8.0 Hz, 4H), 3.80 (s, 3H), 3.46-3.41 (m, 1H), 3.39-3.34 (m, 1H), 2.96-2.92 (m, 1H), 2.84-2.81 (m, 1H), 2.67-2.63 (m, 1H), 2.55-2.44 (m, 3H), 2.32 (d, J=1.4 Hz, 3H), 2.05-1.93 (m, 7H), 1.71-1.61 (m, 1H), 1.45-1.38 (m, 1H), 0.90-0.88 (m, 6H).

3-139. Preparation of (3S)-3-(3-cyclopropyl-2-(5-(2-(dimethylamino)ethyl)-2-oxo-4-(trifluoromethyl)pyridin-1(2H)-yl)propanamido)-3-(4-fluoro-2',4',5,6'-tetramethyl-[1,1'-biphenyl]-3-yl)propanoic Acid (Compounds KQ-P1 and KQ-P2)

Step 1: Ethyl (3S)-3-(3-cyclopropyl-2-(5-(2-(dimethylamino)ethyl)-2-oxo-4-(trifluoromethyl)pyridin-1(2H)-yl)propanamido)-3-(4-fluoro-2',4',5,6'-tetramethyl-[1,1'-biphenyl]-3-yl)propanoate A mixture of ethyl (S)-3-amino-3-(4-fluoro-2',4',5,6'-tetramethyl-[1,1'-biphenyl]-3-yl)propanoate (162.4 mg, 0.47 mmol), 3-cyclopropyl-2-(5-(2-(dimethylamino)ethyl)-2-oxo-4-(trifluoromethyl)pyridin-1(2H)-yl)propanoic acid (150.0 mg, 0.43 mmol), TCHF (144.8 mg, 0.52 mmol) and NMI (105.9 mg, 1.29 mmol) in CH₃CN (5 mL) was stirred at room temperature for 1 hour. The solvent was removed in vacuo and the residue purified by reverse phase HPLC on a C18/40 g column (A: water 10 mM NH₄HCO₃, B: MeOH, 0~100%) to provide ethyl (3S)-3-(3-cyclopropyl-2-(5-(2-(dimethylamino)ethyl)-2-oxo-4-(trifluoromethyl)pyridin-1(2H)-yl)propanamido)-3-(4-fluoro-2',4',5,6'-tetramethyl-[1,1'-biphenyl]-3-yl)propanoate as a yellow solid (120.0 mg). Yield 41.2% (ESI 672.3 [M+H]$^+$).

Step 2: (3S)-3-(3-cyclopropyl-2-(5-(2-(dimethylamino)ethyl)-2-oxo-4-(trifluoromethyl)pyridin-1(2H)-yl)propanamido)-3-(4-fluoro-2',4',5,6'-tetramethyl-[1,1'-biphenyl]-3-yl)propanoic Acid Ethyl (3S)-3-(3-cyclopropyl-2-(5-(2-(dimethylamino)ethyl)-2-oxo-4-(trifluoromethyl)pyridin-1(2H)-yl)propanamido)-3-(4-fluoro-2',4',5,6'-tetramethyl-[1,1'-biphenyl]-3-yl)propanoate (100.0 mg, 0.15 mmol) was treated with LiOH—H₂O (18.9 mg, 0.45 mmol) in EtOH (2 mL) and water (0.5 mL) at room temperature for 0.5 hour. The reaction mixture was acidified to pH 6~7 with 2N HCl. The solvent was removed in vacuo and the residue purified by prep-HPLC A (30-80% MeCN) to provide the diastereomeric products KQ-P1 (22 mg) and KQ-P2 (20 mg) as white solids.

KQ-P1 ESI 644.2 (M+H)$^+$ $^1$H NMR (400 MHz, MeOD) δ 7.74 (s, 1H), 6.78-6.61 (m, 4H), 6.55 (s, 1H), 5.49-5.37 (m, 2H), 2.94-2.88 (m, 2H), 2.82-2.69 (m, 2H), 2.66-2.44 (m, 8H), 2.19-2.03 (m, 6H), 1.92-1.85 (m, 1H), 1.82-1.71 (m, 4H), 1.60 (s, 3H), 0.56-0.38 (m, 1H), 0.34-0.19 (m, 2H), 0.07-0.17 (m, 2H).

KQ-P2 ESI 644.2 (M+H)$^+$ $^1$H NMR (400 MHz, MeOD) δ 7.82 (s, 1H), 6.98-6.79 (m, 5H), 5.70 (dd, J=10.3, 4.1 Hz, 1H), 5.57 (t, J=7.4 Hz, 1H), 3.27-3.15 (m, 2H), 2.96 (t, J=6.9 Hz, 2H), 2.79 (s, 6H), 2.69-2.42 (m, 2H), 2.34-2.20 (m, 6H), 2.14-1.99 (m, 1H), 1.92 (d, J=10.7 Hz, 6H), 1.67-1.49 (m, 1H), 0.55 (dd, J=13.0, 6.4 Hz, 1H), 0.57-0.53 (m, 2H), 0.08–0.16 (m, 2H).

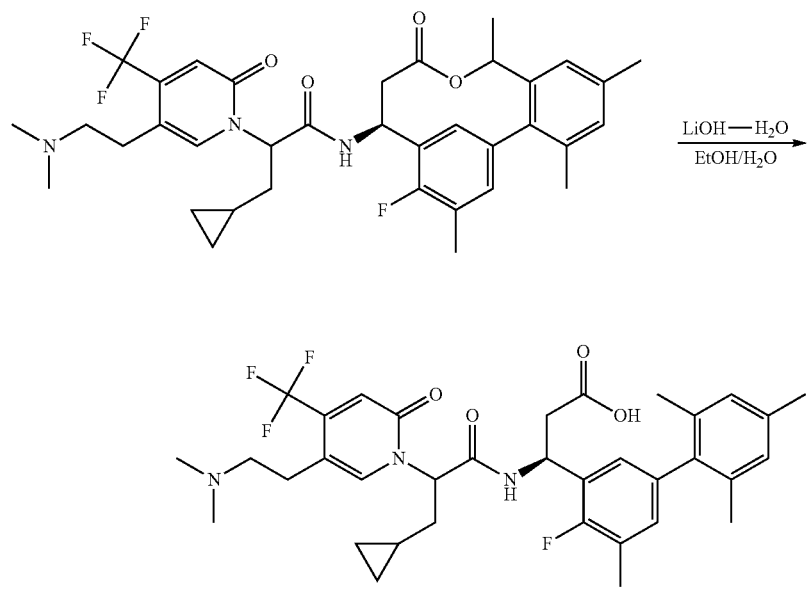

3-140. Preparation of (3S)-3-(4-fluoro-2',4',5,6'-tetramethylbiphenyl-3-yl)-3-(4-methyl-2-(5-(2-(3-methylazetidin-1-yl)ethyl)-2-oxo-4-(trifluoromethyl)pyridin-1(2H)-yl)pentanamido)propanoic Acid (Compounds KR-P1 and KR-P2)

Step 1: (3S)-ethyl 3-(4-fluoro-2',4',5,6'-tetramethylbiphenyl-3-yl)-3-(4-methyl-2-(5-(2-(3-methylazetidin-1-yl)ethyl)-2-oxo-4-(trifluoromethyl)pyridin-1(2H)-yl) pentanamido)propanoate

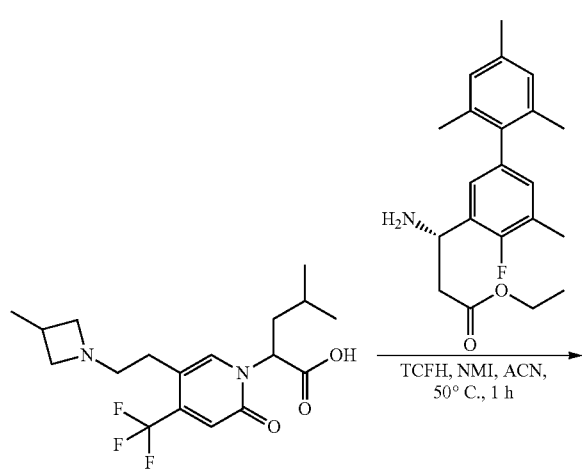

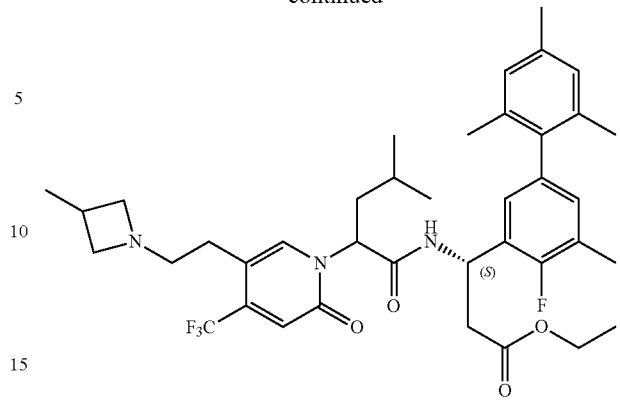

A mixture of 4-methyl-2-(5-(2-(3-methylazetidin-1-yl)ethyl)-2-oxo-4-(trifluoromethyl)pyridin-1(2H)-yl)pentanoic acid (240 mg, 0.58 mmol), (S)-ethyl 3-amino-3-(4-fluoro-2',4',5,6'-tetramethylbiphenyl-3-yl)propanoate (200 mg, 0.58 mmol), NMI (142 mg, 1.74 mmol) and TCFH (243 mg, 0.87 mmol) in $CH_3CN$ (10 mL) was stirred at 50° C. for 1 hour. The solvent was concentrated in vacuo and the residue purified by silica gel column (DCM:MeOH 15:1) to provide (3S)-ethyl 3-(4-fluoro-2',4',5,6'-tetramethylbiphenyl-3-yl)-3-(4-methyl-2-(5-(2-(3-methylazetidin-1-yl)ethyl)-2-oxo-4-(trifluoromethyl)pyridin-1(2H)-yl)pentanamido)propanoate as a yellow oil (310 mg). Yield 75.7% (ESI 700.3 [M+H]$^+$).

Step 2: (3S)-3-(4-fluoro-2',4',5,6'-tetramethylbiphenyl-3-yl)-3-(4-methyl-2-(5-(2-(3-methylazetidin-1-yl)ethyl)-2-oxo-4-(trifluoromethyl)pyridin-1(2H)-yl) pentanamido)propanoic Acid

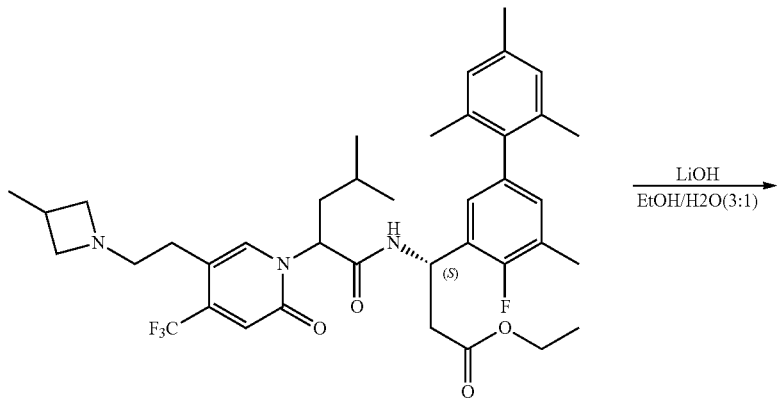

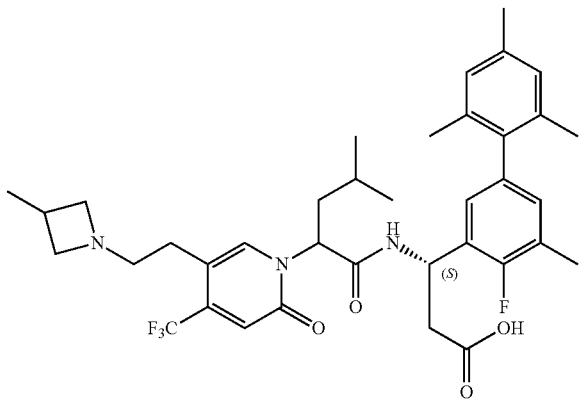

653

(3S)-ethyl 3-(4-fluoro-2',4',5,6'-tetramethylbiphenyl-3-yl)-3-(4-methyl-2-(5-(2-(3-methylazetidin-1-yl)ethyl)-2-oxo-4-(trifluoromethyl)pyridin-1(2H)-yl) pentanamido)propanoate (310 mg, 0.44 mmol) was treated with LiOH—H₂O (56 mg, 1.33 mmol) in EtOH (2 mL) and H₂O (1 mL) at room temperature for 30 mins. The reaction mixture was acidified to pH 4~5 with 1N HCl. The solvent was removed in vacuo and the residue purified by prep-HPLC A (30-70% CH₃CN) to provide the diastereomeric products KR-P1 (60 mg) and KR-P2 (118 mg) as white solids.

KR-P1 ESI 672.3 (M+H)⁺. ¹H NMR (400 MHz, MeOD) δ 7.85 (s, 1H), 6.86-6.82 (m, 4H), 6.75 (s, 1H), 5.66-5.64 (m, 1H), 5.61-5.53 (m, 1H), 4.14-4.01 (m, 2H), 3.63-3.59 (m, 2H), 3.30-3.20 (m, 2H), 2.89-2.82 (m, 3H), 2.73-2.64 (m, 2H), 2.29 (s, 6H), 2.01-1.90 (m, 5H), 1.81 (s, 3H), 1.49-1.36 (m, 1H), 1.24 (d, J=6.9 Hz, 3H), 0.94 (t, J=7.2 Hz, 6H).

KR-P2 ESI 672.3 (M+H)⁺. ¹H NMR (400 MHz, MeOD) δ 7.76 (s, 1H), 6.98-6.83 (m, 5H), 5.78-5.76 (m, 1H), 5.61-5.59 (m, 1H), 4.24-4.21 (m, 2H), 3.75-3.70 (m, 2H), 3.47-3.33 (m, 2H), 3.01-2.85 (m, 2H), 2.88-2.73 (m, 1H), 2.65-2.61 (m, 1H), 2.58-2.44 (m, 1H), 2.33-2.22 (m, 6H), 2.01-1.86 (m, 7H), 1.60-1.55 (m, 1H), 1.45-1.34 (m, 1H), 1.29 (d, J=6.9 Hz, 3H), 0.85-0.80 (m, 6H).

3-141. Preparation of (3S)-3-(4-fluoro-2',5,6'-trimethylbiphenyl-3-yl)-3-(4-methyl-2-(5-(2-(3-methylazetidin-1-yl)ethyl)-2-oxo-4-(trifluoromethyl)pyridin-1(2H)-yl)pentanamido)propanoic Acid (Compounds KS-P1 and KS-P2)

Step 1: (3S)-ethyl 3-(4-fluoro-2',5,6'-trimethylbiphenyl-3-yl)-3-(4-methyl-2-(5-(2-(3-methylazetidin-1-yl)ethyl)-2-oxo-4-(trifluoromethyl)pyridin-1(2H)-yl)pentanamido)propanoate

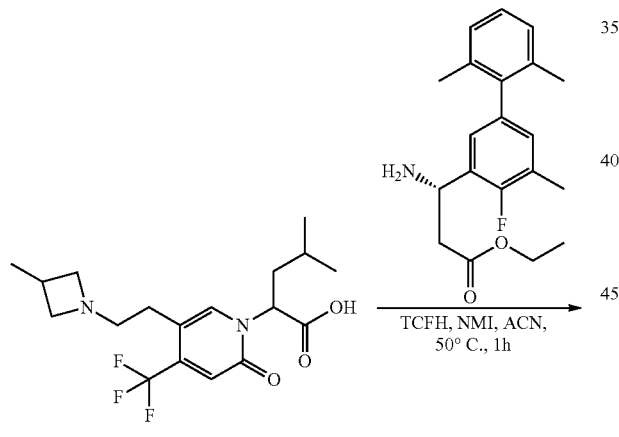

TCFH, NMI, ACN, 50° C., 1h

654

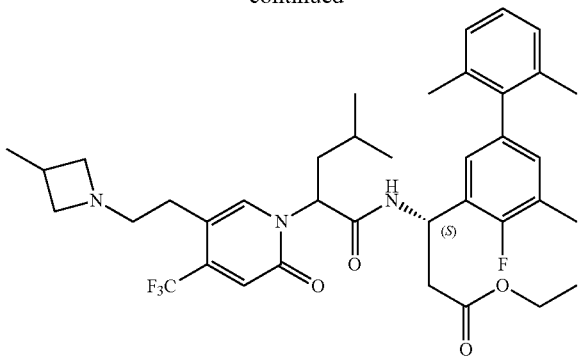

A mixture of 4-methyl-2-(5-(2-(3-methylazetidin-1-yl)ethyl)-2-oxo-4-(trifluoromethyl)pyridin-1(2H)-yl)pentanoic acid (250 mg, 0.61 mmol), ethyl (S)-3-amino-3-(4-fluoro-4'-methoxy-2',5,6'-trimethyl-[1,1'-biphenyl]-3-yl)propanoate (201 mg, 0.61 mmol), NMI (150 mg, 1.83 mmol) and TCFH (256 mg, 0.91 mmol) in CH₃CN (10 mL) was stirred at 50° C. for 1 hour. The solvent was concentrated in vacuo and the residue purified by silica gel column (DCM:MeOH 10:1) to provide (3S)-ethyl 3-(4-fluoro-2',5,6'-trimethylbiphenyl-3-yl)-3-(4-methyl-2-(5-(2-(3-methylazetidin-1-yl)ethyl)-2-oxo-4-(trifluoromethyl)pyridin-1(2H)-yl)pentanamido)propanoate as a yellow oil (320 mg). Yield 76.6% (ESI 686.2 [M+H]⁺).

Step 2: (3S)-3-(4-fluoro-2',5,6'-trimethylbiphenyl-3-yl)-3-(4-methyl-2-(5-(2-(3-methylazetidin-1-yl)ethyl)-2-oxo-4-(trifluoromethyl)pyridin-1(2H)-yl)pentanamido)propanoic Acid

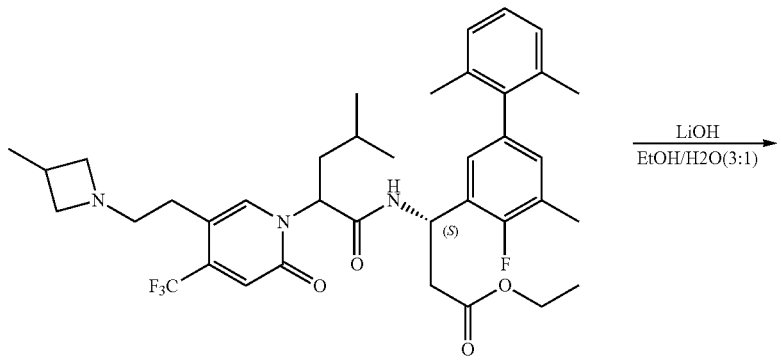

LiOH
EtOH/H2O(3:1)

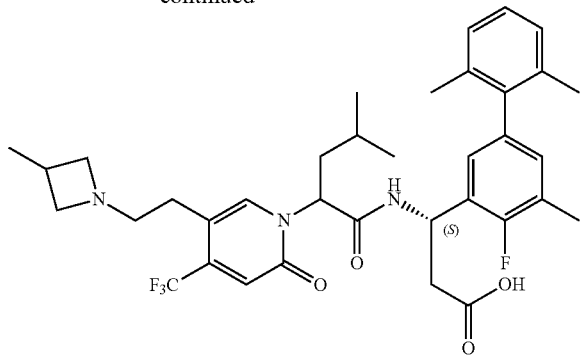

(3S)-ethyl 3-(4-fluoro-2',5,6'-trimethylbiphenyl-3-yl)-3-(4-methyl-2-(5-(2-(3-methylazetidin-1-yl)ethyl)-2-oxo-4-(trifluoromethyl)pyridin-1(2H)-yl)pentanamido)propanoate (320 mg, 0.47 mmol) was treated with LiOH—H$_2$O (59 mg, 1.41 mmol) in EtOH (2 mL) and H$_2$O (1 mL) at room temperature for 30 mins. The reaction mixture was acidified to pH 4~5 with 1N HCl. The solvent was removed in vacuo and the residue purified by prep-HPLC A (30-60% CH$_3$CN) to provide the diastereomeric products KS-P1 (75 mg) and KS-P2 (132 mg) as white solids.

KS-P1 ESI 658.2 (M+H)$^+$. $^1$H NMR (400 MHz, MeOD) δ 7.86 (s, 1H), 7.15-6.99 (m, 3H), 6.94-6.81 (m, 3H), 6.76 (s, 1H), 5.61-5.63 (m, 2H), 4.07-4.09 (m, 2H), 3.60-3.62 (m, 2H), 3.22-3.24 (m, 2H), 2.94-2.76 (m, 3H), 2.72-2.62 (m, 2H), 2.28-2.29 (m, 2H), 2.03-1.93 (m, 5H), 1.85 (s, 3H), 1.41-1.42 (m, 1H), 1.24 (d, J=6.9 Hz, 3H), 0.97-0.88 (m, 6H).

KS-P2 ESI 658.2 (M+H)$^+$. $^1$H NMR (400 MHz, MeOD) δ 7.76 (s, 1H), 7.11-7.09 (m, 3H), 6.98-6.81 (m, 3H), 5.77-5.75 (m, 1H), 5.61 (t, J=7.6 Hz, 1H), 4.21-4.18 (m, 2H), 3.75-3.72 (m, 2H), 3.44-3.34 (m, 2H), 3.05-2.85 (m, 2H), 2.85-2.71 (m, 1H), 2.65-2.63 (m, 1H), 2.52-2.50 (m, 1H), 2.33 (d, J=1.4 Hz, 3H), 2.03-1.90 (m, 7H), 1.65-1.59 (m, 1H), 1.43-1.38 (m, 1H), 1.29 (d, J=6.9 Hz, 3H), 0.89-0.82 (m, 6H).

3-142. Preparation of (3S)-3-(2-(5-(2-(azetidin-1-yl)ethyl)-2-oxo-4-(trifluoromethyl)pyridin-1(2H)-yl)-4-methylpentanamido)-3-(2,4,4'-trifluoro-2',3',6'-trimethyl-5-(trifluoromethyl)-[1,1'-biphenyl]-3-yl)propanoic Acid (Compounds KT-P1 and KT-P2)

Step 1: Ethyl (3S)-3-(2-(5-(2-(azetidin-1-yl)ethyl)-2-oxo-4-(trifluoromethyl)pyridin-1(2H)-yl)-4-methylpentanamido)-3-(2,4,4'-trifluoro-2',3',6'-trimethyl-5-(trifluoromethyl)-[1,1'-biphenyl]-3-yl)propanoate

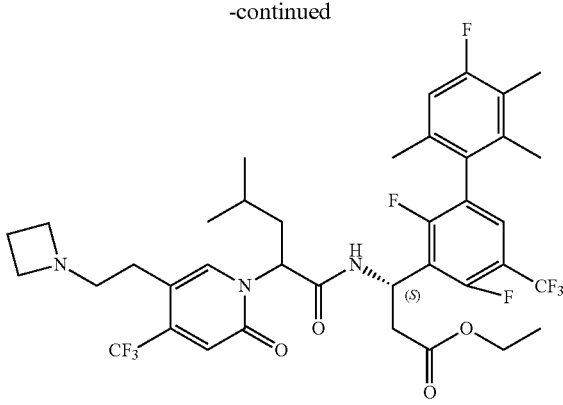

A mixture of ethyl (3S)-3-amino-3-(2,4,4'-trifluoro-2',3',6'-trimethyl-5-(trifluoromethyl)-[1,1'-biphenyl]-3-yl)propanoate (140 mg, 0.32 mmol), 2-(5-(2-(azetidin-1-yl)ethyl)-2-oxo-4-(trifluoromethyl)pyridin-1(2H)-yl)-4-methylpentanoic acid (116 mg, 0.32 mmol), TCFH (179 mg, 0.64 mmol) and NMI (131 mg, 1.6 mmol) in CH$_3$CN (5 mL) was stirred at room temperature for 2 hours. The solvent was removed in vacuo and the residue purified by reverse phase HPLC on a C18/40 g column (A: water 10 mM NH$_4$HCO3, B: CH$_3$OH, 0~85%) to provide ethyl (3S)-3-(2-(5-(2-(azetidin-1-yl)ethyl)-2-oxo-4-(trifluoromethyl)pyridin-1(2H)-yl)-4-methylpentanamido)-3-(2,4,4'-trifluoro-2',3',6'-trimethyl-5-(trifluoromethyl)-[1,1'-biphenyl]-3-yl)propanoate as a yellow solid (140 mg). Yield 56.4% (ESI 776.3 [M+H]$^+$).

Step 2: (3S)-3-(2-(5-(2-(azetidin-1-yl)ethyl)-2-oxo-4-(trifluoromethyl)pyridin-1(2H)-yl)-4-methylpentanamido)-3-(2,4,4'-trifluoro-2',3',6'-trimethyl-5-(trifluoromethyl)-[1,1'-biphenyl]-3-yl)propanoic Acid

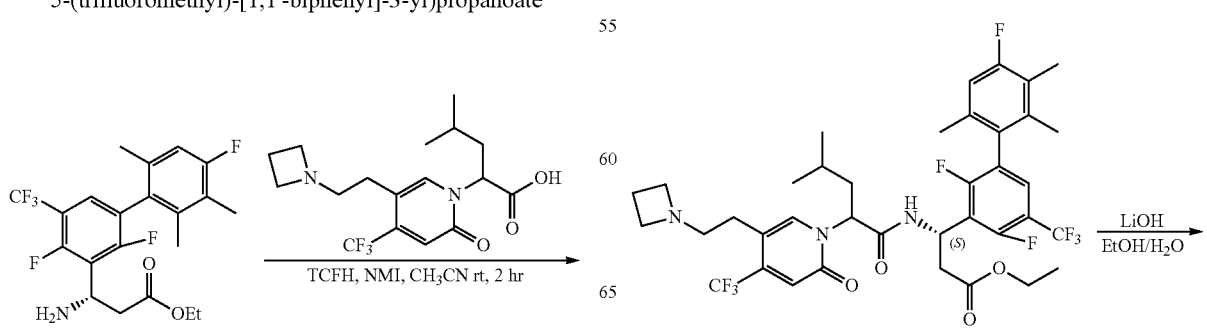

-continued

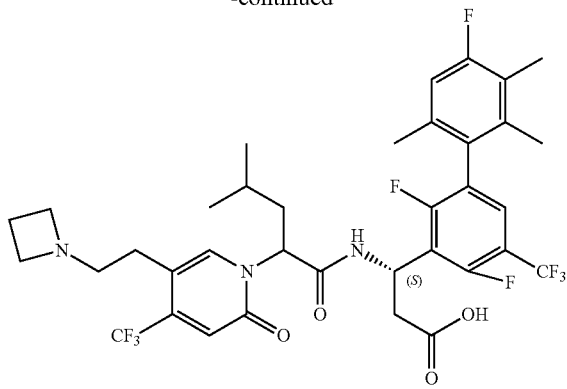

Ethyl (3S)-3-(2-(5-(2-(azetidin-1-yl)ethyl)-2-oxo-4-(trifluoromethyl)pyridin-1(2H)-yl)-4-methylpentanamido)-3-(2,4,4'-trifluoro-2',3',6'-trimethyl-5-(trifluoromethyl)-[1,1'-biphenyl]-3-yl)propanoate (140 mg, 0.18 mmol) was treated with LiOH—H$_2$O (22 mg, 0.54 mmol) in EtOH (4 mL) and H$_2$O (1 mL) at room temperature for 2 hrs. The reaction mixture was acidified to pH 5~6 with 1N HCl. The solvent was removed in vacuo and the residue purified by prep-HPLC A (30-65% CH$_3$CN) to provide the diastereomeric products KT-P1 (24 mg) and KT-P2 (30 mg) as white solids.

KT-P1 ESI 748.2 (M+H)$^+$. $^1$H NMR (400 MHz, MeOD) δ 7.81 (s, 1H), 7.39 (m, J=7.5 Hz, 1H), 6.99-6.80 (m, 2H), 5.71 (m, J=9.2, 5.9 Hz, 2H), 4.12 (m, J=8.1 Hz, 4H), 3.42-3.30 (m, 2H), 2.99-2.71 (m, 4H), 2.52-2.35 (m, 2H), 2.18 (s, 3H), 2.09-1.93 (m, 5H), 1.86 (s, 3H), 1.45-1.32 (m, 1H), 0.94 (m, J=6.9 Hz, 6H).

KT-P2 ESI 748.2 (M+H)$^+$. $^1$H NMR (400 MHz, MeOD) δ 7.72 (s, 1H), 7.44 (m, J=7.6 Hz, 1H), 7.00-6.77 (m, 2H), 5.90 (d, J=8.1 Hz, 1H), 5.63 (m, J=7.7 Hz, 1H), 4.12 (m, J=8.1 Hz, 4H), 3.39 (m, J=19.1, 13.7 Hz, 2H), 2.86 (m, J=14.4, 13.3 Hz, 3H), 2.60 (m, J=15.6, 4.2 Hz, 1H), 2.45 (m, J=8.1 Hz, 2H), 2.20 (s, 3H), 1.94 (m, J=21.4, 9.3, 4.8 Hz, 7H), 1.72 (m, J=14.4, 7.3 Hz, 1H), 1.33 (m, J=13.4, 6.7 Hz, 1H), 0.88 (m, J=10.6, 6.6 Hz, 6H).

Example 4: Characterization of Exemplary Compounds of the Invention

The following compounds were synthesized using procedures similar to the ones used in example 3.

4-1. (3S)-3-(4,5-difluoro-2',6'-dimethylbiphenyl-3-yl)-3-(2-(5-(((R)-3-fluoropyrrolidin-1-yl)methyl)-2-oxopyridin-1(2H)-yl)-4-methylpentanamido)propanoic Acid (Diastereomeric Compounds BB-P1 and BB-P2)

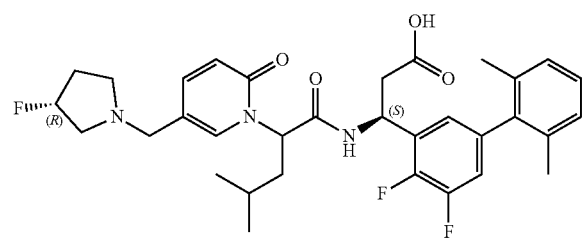

BB-P1 ESI 598.2 (M+H)$^+$. $^1$H NMR (500 MHz, MeOD) δ 7.74 (d, J=2.1 Hz, 1H), 7.53-7.42 (m, 1H), 7.16-7.00 (m, 3H), 6.93-6.80 (m, 2H), 6.42 (d, J=9.3 Hz, 1H), 5.71 (t, J=8.1 Hz, 1H), 5.55 (t, J=7.1 Hz, 1H), 5.34-5.13 (m, 1H), 3.80-3.61 (m, 2H), 3.17-2.93 (m, 3H), 2.83-2.63 (m, 3H), 2.33-2.16 (m, 1H), 2.16-2.02 (m, 1H), 1.98 (s, 3H), 1.92 (t, J=7.6 Hz, 2H), 1.83 (s, 3H), 1.47-1.33 (m, 1H), 0.99-0.87 (m, 6H).

BB-P2 ESI 598.2 (M+H)+. $^1$H NMR (500 MHz, MeOD) δ 7.69 (d, J=2.2 Hz, 1H), 7.62-7.51 (m, 1H), 7.16-7.01 (m, 3H), 6.99-6.84 (m, 2H), 6.54 (d, J=9.3 Hz, 1H), 5.80-5.69 (m, 1H), 5.51-5.45 (m, 1H), 5.33 (d, J=54.4 Hz, 1H), 4.18 (d, J=13.2 Hz, 1H), 3.83 (d, J=13.2 Hz, 1H), 3.55-3.31 (m, 4H), 2.73-2.64 (m, 1H), 2.58-2.46 (m, 1H), 2.42-2.18 (m, 2H), 2.03-1.86 (m, 7H), 1.58-1.36 (m, 2H), 0.84 (s, 6H).

4-2. (3S)-3-(4,5-difluoro-2',6'-dimethylbiphenyl-3-yl)-3-(2-(5-(2-((R)-3-fluoropyrrolidin-1-yl)ethyl)-2-oxopyridin-1(2H)-yl)-4-methylpentanamido)propanoic Acid (Diastereomeric Compounds BC-P1 and BC-P2)

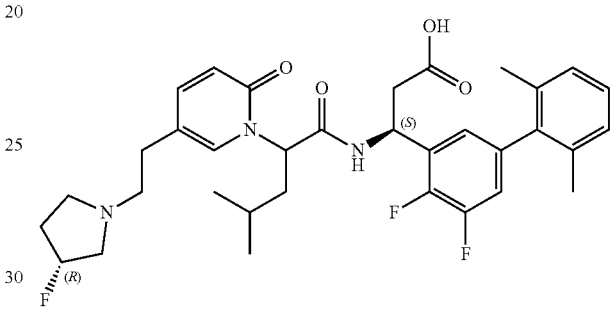

BC-P1 ESI 612.2 (M+H)$^+$. $^1$H NMR (500 MHz, MeOD) δ 7.63 (s, 1H), 7.45 (d, J=9.3 Hz, 1H), 7.22-7.04 (m, 3H), 6.98-6.87 (m, 1H), 6.80 (d, J=5.1 Hz, 1H), 6.43 (d, J=9.3 Hz, 1H), 5.68-5.57 (m, 1H), 5.50 (d, J=5.7 Hz, 1H), 5.29 (d, J=53.5 Hz, 1H), 3.48-3.33 (m, 1H), 3.31-3.02 (m, 5H), 2.83-2.57 (m, 4H), 2.42-2.10 (m, 2H), 2.05-1.81 (m, 8H), 1.51-1.35 (m, 1H), 0.98-0.79 (m, 6H).

BC-P2 ESI 612.2 (M+H)$^+$. $^1$H NMR (500 MHz, MeOD) δ 7.61 (s, 1H), 7.47 (d, J=9.3 Hz, 1H), 7.19-7.00 (m, 3H), 6.97-6.90 (m, 1H), 6.86 (d, J=4.7 Hz, 1H), 6.51 (d, J=9.2 Hz, 1H), 5.66-5.52 (m, 2H), 5.36 (s, 1H), 3.66-3.32 (m, 5H), 3.16 (s, 1H), 2.83 (s, 2H), 2.63-2.42 (m, 2H), 2.30 (d, J=29.3 Hz, 2H), 2.05-1.85 (m, 8H), 1.45-1.30 (m, 1H), 0.88 (t, J=6.1 Hz, 6H).

4-3. (3S)-3-(4,5-difluoro-2'-methyl-6'-(trifluoromethyl)-[1,1'-biphenyl]-3-yl)-3-(2-(5-(2-(dimethylamino)ethyl)-4-methyl-2-oxopyridin-1(2H)-yl)-4-methylpentanamido)propanoic Acid (Diastereomeric Compounds BD-P1 and BD-P2)

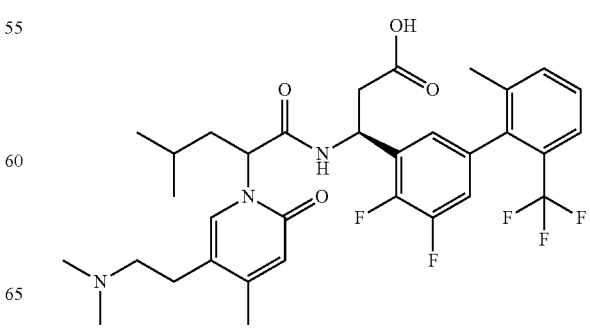

BD-P1 ESI 636.2 (M+H)+. $^1$H NMR (500 MHz, MeOD) δ 7.65-7.46 (m, 4H), 7.03-6.87 (m, 2H), 6.30 (d, J=21.6 Hz, 1H), 5.55-5.52 (m, 2H), 3.18-3.02 (m, 2H), 2.88-2.84 (m, 2H), 2.78 (s, 3H)), 2.75 (S, 3H), 2.67-2.64 (m, 2H), 2.25 (s, 3H), 2.06 (s, 2H), 1.97-1.85 (m, 3H), 1.45-1.35 (m, 1H), 0.94-0.90 (m, 6H).

BD-P2 ESI 636.2 (M+H)+. $^1$H NMR (500 MHz, MeOD) δ 7.67-7.44 (m, 4H), 7.08-6.91 (m, 2H), 6.42 (d, J=20.9 Hz, 1H), 5.70-5.51 (m, 2H), 3.32-3.23 (m, 1H), 3.20-3.18 (m, 1H), 2.99-2.74 (m, 8H), 2.64-2.59 (m, 1H), 2.52-2.47 (m, 1H), 2.28-2.26 (d, J=10.0 Hz, 3H), 2.07-2.06 (d, J=6.6 Hz, 3H), 2.00-1.88 (m, 1H), 1.81-1.65 (m, 1H), 1.43-1.32 (m, 1H), 0.90-0.87 (m, 6H).

4-4. (3S)-3-(4-fluoro-2',5,6'-trimethylbiphenyl-3-yl)-3-(2-(5-(2-(3-fluoroazetidine-1-yl)ethyl)-2-oxopyridin-1(2H)-yl)-4-methylpentanamido)propanoic Acid (Diastereomeric Compounds BE-P1 and BE-P2)

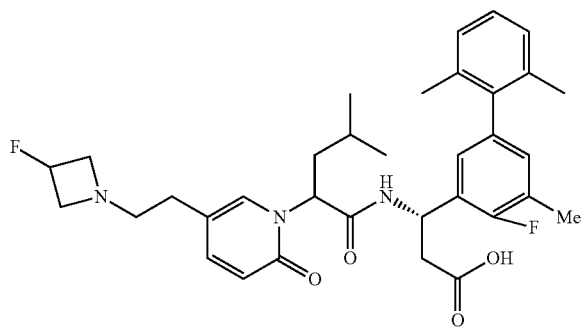 [SMILES: Cc1cc(-c2c(C)cccc2C)cc([C@H](CC(=O)O)NC(=O)C(CC(C)C)n2cc(CCN3CC(F)C3)ccc2=O)c1F]

BE-P1 ESI 594.2 (M+H)+. $^1$H NMR (500 MHz, MeOD) δ 7.52 (d, J=2.1 Hz, 1H), 7.47-7.39 (m, 1H), 7.19-7.02 (m, 3H), 6.89 (d, J=5.6 Hz, 1H), 6.83-6.73 (m, 1H), 6.48 (d, J=9.3 Hz, 1H), 5.69-5.57 (m, 1H), 5.54-5.43 (m, 1H), 5.33-5.09 (m, 1H), 4.20-4.06 (m, 1H), 4.03-3.87 (m, 1H), 3.78-3.63 (m, 2H), 3.27-3.06 (m, 2H), 2.77-2.53 (m, 4H), 2.31 (d, J=1.3 Hz, 3H), 2.03-1.85 (m, 8H), 1.58-1.34 (m, 1H), 1.03-0.84 (m, 6H).

BE-P2 ESI 594.2 (M+H)+. $^1$H NMR (500 MHz, MeOD) δ 7.57-7.41 (m, 2H), 7.23-7.05 (m, 3H), 6.92 (d, J=6.9 Hz, 2H), 6.56 (d, J=9.3 Hz, 1H), 5.67-5.57 (m, 2H), 5.46-5.17 (m, 1H), 4.50-4.24 (m, 2H), 4.08-3.89 (m, 2H), 3.42-3.35 (m, 2H), 2.86-2.60 (m, 3H), 2.57-2.45 (m, 1H), 2.33 (s, 3H), 2.05-1.91 (m, 7H), 1.86-1.71 (m, 1H), 1.48-1.32 (m, 1H), 0.91 (t, J=6.3 Hz, 6H).

4-5. (3S)-3-(5-chloro-4-fluoro-2',6'-dimethyl-[1,1'-biphenyl]-3-yl)-3-(2-(3-fluoro-5-(2-(3-fluoroazetidine-1-yl)ethyl)-2-oxopyridin-1(2H)-yl)-4-methylpentanamido)propanoic Acid (Diastereomeric Compounds BD2-P1 and BD2-P2)

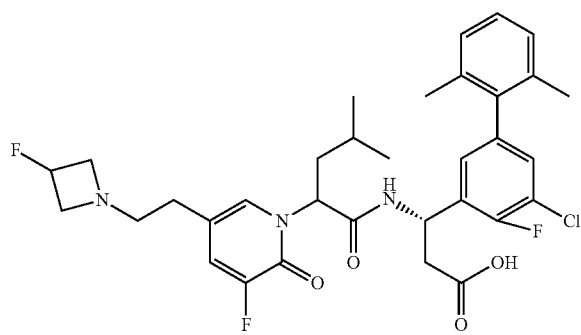 [SMILES: Cc1cccc(C)c1-c1cc(Cl)c(F)c([C@H](CC(=O)O)NC(=O)C(CC(C)C)n2cc(CCN3CC(F)C3)cc(F)c2=O)c1]

BD2-P1 ESI 632.1 (M+H)+. $^1$H NMR (400 MHz, MeOD) δ 7.69-7.28 (m, 2H), 7.23-7.05 (m, 4H), 6.97 (dd, J=6.3, 1.9 Hz, 1H), 5.69 (dd, J=9.4, 6.8 Hz, 1H), 5.52 (t, J=6.4 Hz, 1H), 5.25 (dt, J=57.2, 4.2 Hz, 1H), 4.15 (dt, J=44.5, 9.1 Hz, 2H), 3.96-3.70 (m, 2H), 3.23 (dt, J=11.3, 5.6 Hz, 2H), 2.94-2.45 (m, 4H), 2.13-1.80 (m, 8H), 1.59-1.25 (m, 1H), 1.15-0.78 (m, 6H).

BD2-P2 ESI 632.1 (M+H)+. $^1$H NMR (400 MHz, MeOD) δ 7.54-7.27 (m, 2H), 7.14 (dt, J=12.8, 6.1 Hz, 5H), 5.87-5.52 (m, 2H), 5.30 (dt, J=57.3, 4.4 Hz, 1H), 4.43-4.14 (m, 2H), 4.06-3.75 (m, 2H), 3.33-3.25 (m, 2H), 2.87-2.40 (m, 4H), 2.17-1.85 (m, 7H), 1.88-1.67 (m, 1H), 1.50-1.22 (m, 1H), 0.91 (d, J=6.6 Hz, 6H).

4-6. (3S)-3-(5-chloro-4-fluoro-2',6'-dimethyl-[1,1'-biphenyl]-3-yl)-3-(2-(3-fluoro-5-(2-((R)-3-fluoropyrrolidin-1-yl)ethyl)-2-oxopyridin-1(2H)-yl)-4-methylpentanamido)propanoic Acid (Diastereomeric Compounds BE2-P1 and BE2-P2)

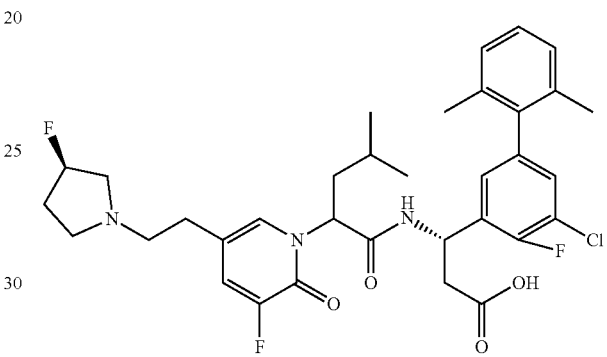

BE2-P1 ESI 646.2 (M+H)+. $^1$H NMR (400 MHz, MeOD) δ 7.51 (s, 1H), 7.37 (d, J=10.2 Hz, 1H), 7.16-7.08 (m, 4H), 6.98-6.97 (m, 1H), 5.71-5.67 (m, 1H), 5.52-5.49 (m, 1H), 5.35-5.21 (m, 1H), 3.41-3.12 (m, 6H), 2.81-2.69 (m, 4H), 2.37-2.20 (m, 2H), 2.05-1.88 (m, 8H), 1.44-1.40 (m, 1H), 0.96-0.92 (m, 6H).

BE2-P2 ESI 646.2 (M+H)+. $^1$H NMR (400 MHz, MeOD) δ 7.51 (s, 1H), 7.40 (d, J=10.2 Hz, 1H), 7.18-7.06 (m, 5H), 5.70-5.58 (m, 2H), 5.41-5.27 (m, 1H), 3.67-3.21 (m, 6H), 2.88-2.83 (m, 2H), 2.60-2.53 (m, 2H), 2.39-2.27 (m, 2H), 1.97-1.83 (m, 7H), 1.83-1.76 (m, 1H), 1.40-1.35 (m, 1H), 0.91-0.89 (m, 6H).

4-7. (3S)-3-(5-chloro-4-fluoro-2',6'-dimethyl-[1,1'-biphenyl]-3-yl)-3-(2-(5-(2-(dimethylamino)ethyl)-2-oxo-4-(trifluoromethyl)pyridin-1(2H)-yl)-4-methylpentanamido)propanoic Acid (Diastereomeric Compounds BF-P1 and BF-P2)

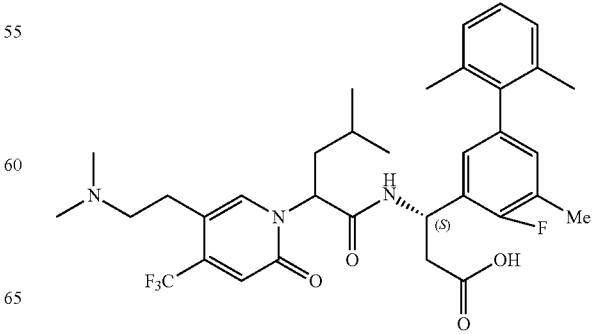

BF-P1 ESI 652.2 (M+H)+. $^1$H NMR (400 MHz, MeOD) δ 7.91 (s, 1H), 7.11-7.03 (m, 5H), 6.75 (s, 1H), 5.82-5.62 (m, 1H), 5.62-5.46 (m, 1H), 3.21-2.89 (m, 4H), 2.83 (s, 6H), 2.77-2.72 (m, 2H), 2.05-1.89 (m, 5H), 1.83 (s, 3H), 1.46-1.40 (m, 1H), 0.98-0.93 (m, 6H).

BF-P2 ESI 652.2 (M+H)+. $^1$H NMR (400 MHz, MeOD) δ 7.91 (s, 1H), 7.24-7.04 (m, 5H), 6.89 (s, 1H), 5.75-5.70 (m, 1H), 5.66-5.62 (m, 1H), 3.29-3.21 (m, 2H), 3.09-2.98 (m, 2H), 2.84 (d, J=5.9 Hz, 6H), 2.68-2.53 (m, 2H), 2.03-1.86 (m, 7H), 1.76-1.69 (m, 1H), 1.42-1.33 (m, 1H), 0.88-0.86 (m, 6H).

4-8. (3S)-3-(2-(5-(2-(dimethylamino)ethyl)-2-oxo-4-(trifluoromethyl)pyridin-1(2H)-yl)-4-methylpentanamido)-3-(4-fluoro-2',6'-dimethyl-5-(trifluoromethyl)biphenyl-3-yl)propanoic Acid (Diastereomeric Compounds BG-P1 and BG-P2)

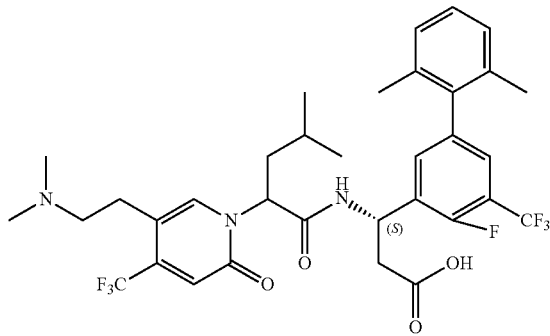

BG-P1 ESI 686.2 (M+H)+. $^1$H NMR (400 MHz, MeOD) δ 7.90 (s, 1H), 7.39 (d, J=4.8 Hz, 1H), 7.31 (d, J=6.3 Hz, 1H), 7.19 (t, J=7.5 Hz, 1H), 7.13 (d, J=7.1 Hz, 1H), 7.09 (d, J=7.4 Hz, 1H), 6.73 (s, 1H), 5.73-5.64 (m, 1H), 5.62-5.59 (m, 1H), 3.17-3.12 (m, 2H), 2.97 (d, J=8.4 Hz, 2H), 2.80 (d, J=11.1 Hz, 6H), 2.76-2.73 (m, 2H), 2.11-1.89 (m, 5H), 1.82 (s, 3H), 1.47-1.41 (m, 1H), 0.98-0.93 (m, 6H).

BG-P2 ESI 686.2 (M+H)+. $^1$H NMR (400 MHz, MeOD) δ 7.85 (s, 1H), 7.44 (d, J=5.4 Hz, 1H), 7.38 (d, J=6.6 Hz, 1H), 7.22-7.18 (m, 1H), 7.14 (d, J=7.3 Hz, 2H), 6.90 (s, 1H), 5.76-5.72 (m, 1H), 5.64 (t, J=7.7 Hz, 1H), 3.25 (d, J=8.1 Hz, 2H), 3.00 (t, J=7.0 Hz, 2H), 2.85 (s, 6H), 2.71-2.66 (m, 1H), 2.61-2.54 (m, 1H), 2.02 (d, J=2.4 Hz, 6H), 1.99-1.94 (m, 1H), 1.78-1.68 (m, 1H), 1.46-1.30 (m, 1H), 0.91-0.89 (m, 6H).

4-9. (3S)-3-(2-(5-(2-(dimethylamino)ethyl)-3-methyl-2-oxopyridin-1(2H)-yl)-4-methylpentanamido)-3-(4-fluoro-2',6'-dimethyl-5-(trifluoromethyl)biphenyl-3-yl)propanoic Acid (Diastereomeric Compounds BH-P1 and BH-P2)

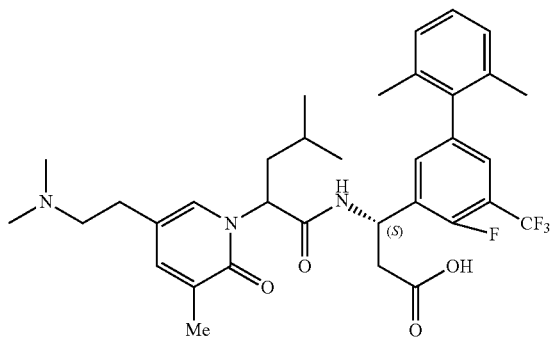

BH-P1 ESI 632.2 (M+H)+. $^1$H NMR (400 MHz, MeOD) δ 7.52 (s, 1H), 7.42 (s, 1H), 7.32 (d, J=4.9 Hz, 1H), 7.24-7.18 (m, 2H), 7.17-7.10 (m, 2H), 5.52 (s, 1H), 5.45 (t, J=5.3 Hz, 1H), 3.37 (d, J=7.6 Hz, 1H), 3.32-3.29 (m, 1H), 3.27-3.17 (m, 1H), 2.82 (t, J=6.5 Hz, 2H), 2.74 (s, 6H), 2.71-2.66 (m, 1H), 2.56-2.51 (m, 1H), 2.03 (d, J=14.9 Hz, 1H), 1.97 (d, J=7.2 Hz, 6H), 1.94 (s, 3H), 1.44-1.39 (m, 1H), 0.95-0.90 (m, 6H).

BH-P2 ESI 632.2 (M+H)+. $^1$H NMR (400 MHz, MeOD) δ 7.86 (s, 1H), 7.44 (d, J=4.8 Hz, 1H), 7.38 (d, J=6.5 Hz, 1H), 7.22-7.18 (m, 1H), 7.14 (d, J=7.2 Hz, 2H), 6.90 (s, 1H), 5.76-5.72 (m, 1H), 5.64 (t, J=7.6 Hz, 1H), 3.35 (s, 3H), 3.25 (s, 2H), 3.00 (t, J=7.1 Hz, 2H), 2.86 (s, 6H), 2.70-2.54 (m, 2H), 2.02 (d, J=2.4 Hz, 6H), 1.99-1.92 (m, 1H), 1.77-1.72 (m, 1H), 1.46-1.30 (m, 1H), 0.91-0.89 (m, 6H).

4-10. (3S)-3-(2',6'-dichloro-4,4'-difluoro-5-methylbiphenyl-3-yl)-3-(2-(3-fluoro-5-(2-(3-fluoroazetidine-1-yl)ethyl)-2-oxopyridin-1(2H)-yl)-4-methylpentanamido)propanoic Acid (Diastereomeric Compounds BI-P1 and BI-P2)

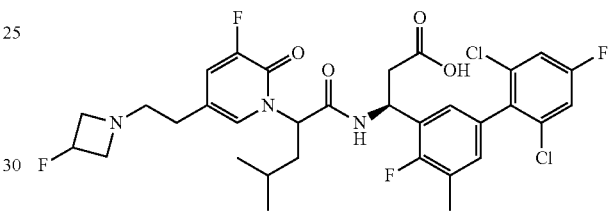

GI-P1 ESI 670.1 (M+H)+. $^1$H NMR (400 MHz, MeOD) δ 7.42 (s, 1H), 7.40-7.32 (m, 3H), 7.01 (d, J=6.7 Hz, 1H), 6.96 (d, J=6.6 Hz, 1H), 5.70 (t, J=8.1 Hz, 1H), 5.59-5.46 (m, 1H), 5.32-5.08 (m, 1H), 4.18-3.92 (m, 2H), 3.82-3.57 (m, 2H), 3.22-3.03 (m, 2H), 2.79-2.53 (m, 4H), 2.31 (d, J=1.3 Hz, 3H), 1.97 (t, J=7.6 Hz, 2H), 1.51-1.33 (m, 1H), 1.01-0.86 (m, 6H).

GI-P2 ESI 670.1 (M+H)+. $^1$H NMR (400 MHz, MeOD) δ 7.45-7.31 (m, 4H), 7.14-6.99 (m, 2H), 5.75-5.61 (m, 2H), 5.42-5.18 (m, 1H), 4.44-4.21 (m, 2H), 4.11-3.85 (m, 2H), 3.36-3.34 (m, 2H), 2.80-2.44 (m, 4H), 2.34 (d, J=1.3 Hz, 3H), 2.03-1.90 (m, 1H), 1.83-1.70 (m, 1H), 1.47-1.30 (m, 1H), 0.99-0.86 (m, 6H).

4-11. (3S)-3-(3-cyclopropyl-2-(3-fluoro-5-(2-(3-fluoroazetidine-1-yl)ethyl)-2-oxopyridin-1(2H)-yl)propanamido)-3-(4,4'-difluoro-2',5,6'-trimethyl-[1,1'-biphenyl]-3-yl)propanoic Acid (Diastereomeric Compounds BJ-P1 and BJ-P2)

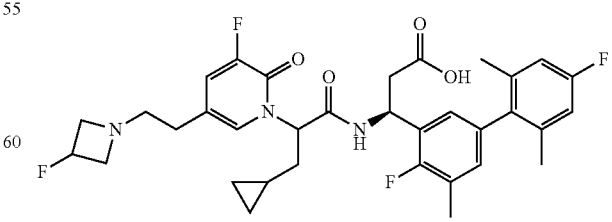

BJ-P1 ESI 628.2 (M+H)+. $^1$H NMR (400 MHz, MeOD) δ 7.37 (s, 1H), 7.26 (d, J=10.2 Hz, 1H), 6.91-6.64 (m, 4H), 5.55 (t, J=7.6 Hz, 1H), 5.48-5.40 (m, 1H), 5.13 (d, J=57.3

Hz, 1H), 3.98 (d, J=16.3 Hz, 2H), 3.63 (s, 2H), 3.03 (d, J=6.5 Hz, 2H), 2.74-2.59 (m, 2H), 2.59-2.50 (m, 3H), 1.99-1.85 (m, 5H), 1.81 (d, J=9.0 Hz, 3H), 0.56 (d, J=7.3 Hz, 1H), 0.36 (d, J=8.0 Hz, 2H), 0.13--0.07 (m, 2H).

BJ-P2 ESI 628.2 (M+H)$^+$. $^1$H NMR (400 MHz, MeOD) δ 7.50-7.28 (m, 2H), 7.03-6.71 (m, 4H), 5.75-5.55 (m, 2H), 5.30 (d, J=57.3 Hz, 1H), 4.47-4.17 (m, 2H), 4.12-3.75 (m, 2H), 3.44-3.32 (m, 2H), 2.82-2.46 (m, 4H), 2.32 (s, 3H), 2.18-1.91 (m, 7H), 1.77-1.60 (m, 1H), 0.58 (s, 1H), 0.42-0.23 (m, 2H), 0.15--0.07 (m, 2H).

4-12. (3S)-3-(4,4'-difluoro-2',5,6'-trimethyl-[1,1'-biphenyl]-3-yl)-3-((3R)-2-(3-fluoro-5-(2-(3-fluoro-azetidine-1-yl)ethyl)-2-oxopyridin-1(2H)-yl)-3-methylpentanamido)propanoic Acid (Diastereomeric Compounds BK-P1 and BK-P2)

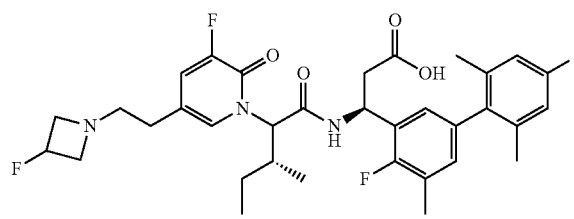

BK-P1 ESI 630.2 (M+H)$^+$. $^1$H NMR (400 MHz, MeOD) δ 7.52 (s, 1H), 7.31-7.28 (m, 1H), 6.86-6.76 (m, 4H), 5.66-5.55 (m, 1H), 5.35-5.33 (d, J=11.2 Hz, 1H), 5.23.5.09 (m, 1H), 3.85-3.80 (m, 2H), 3.52-3.49 (m, 2H), 2.91-2.88 (t, J=6.7 Hz, 2H), 2.80-2.78 (m, 2H), 2.55-2.52 (t, J=7.1 Hz, 2H), 2.28 (d, J=1.5 Hz, 4H), 1.98 (s, 3H), 1.75 (s, 3H), 1.69-1.68 (m, 1H), 1.30-1.26 (m, 1H), 1.03-0.99 (t, J=7.4 Hz, 3H), 0.75-0.74 (d, J=6.6 Hz, 3H).

BK-P2 ESI 630.2 (M+H)$^+$. $^1$H NMR (400 MHz, MeOD) δ 7.46 (s, 1H), 7.36-7.34 (d, J=10.3 Hz, 1H), 7.00-6.93 (dd, J=20.7, 6.6 Hz, 2H), 6.86-6.84 (d, J=9.6 Hz, 2H), 5.75-5.72 (dd, J=10.3, 4.1 Hz, 1H), 5.39-5.23 (m, 2H), 4.47-4.22 (m, 2H), 4.09-3.85 (m, 2H), 3.30-3.28 (m, 2H), 2.75-2.72 (m, 2H), 2.67-2.47 (m, 2H), 2.41-2.20 (m, 4H), 2.02 (s, 6H), 1.17-1.10 (m, 1H), 1.08-0.88 (m, 4H), 0.85-0.81 (t, J=7.2 Hz, 3H).

4-13. (3S)-3-(4,4'-difluoro-2',5,6'-trimethyl-[1,1'-biphenyl]-3-yl)-3-(2-(3-fluoro-5-(2-(3-fluoroazeti-dine-1-yl)ethyl)-2-oxopyridin-1(2H)-yl)-3-methylbutanamido)propanoic Acid (Diastereomeric Compounds BL-P1 and BL-P2)

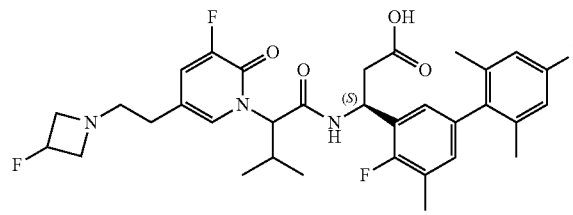

BL-P1 ESI 616.2 (M+H)$^+$. 1H NMR (400 MHz, MeOD) δ 7.52 (s, 1H), 7.29 (d, J=10.9 Hz, 1H), 6.94-6.65 (m, 4H), 5.62 (s, 1H), 5.26 (d, J=11.1 Hz, 1H), 5.07 (s, 1H), 3.75 (s, 2H), 3.15 (s, 1H), 2.78 (s, 5H), 2.48 (d, J=31.1 Hz, 3H), 2.28 (s, 3H), 1.98 (s, 3H), 1.74 (s, 3H), 1.14 (d, J=6.4 Hz, 3H), 0.78 (d, J=6.6 Hz, 3H).

BL-P2 ESI 616.2 (M+H)$^+$. $^1$H NMR (400 MHz, MeOD) δ 7.44 (s, 1H), 7.40-7.28 (m, 1H), 7.02-6.72 (m, 4H), 5.88-5.62 (m, 1H), 5.38 (s, 2H), 5.24 (d, J=11.0 Hz, 2H), 4.32 (s, 2H), 3.97 (s, 2H), 2.74 (d, J=5.1 Hz, 2H), 2.66-2.39 (m, 3H), 2.33 (d, J=1.6 Hz, 3H), 2.01 (d, J=3.3 Hz, 6H), 1.00 (d, J=6.4 Hz, 3H), 0.75 (d, J=6.7 Hz, 3H).

4-14. (3S)-3-(2'-cyclopropyl-4-fluoro-5,6'-dimethyl-[1,1'-biphenyl]-3-yl)-3-(2-(5-(2-(dimethylamino)ethyl)-2-oxo-4-(trifluoromethyl)pyridin-1(2H)-yl)-4-methylpentanamido)propanoic Acid (Diastereomeric Compounds BM-P1 and BM-P2)

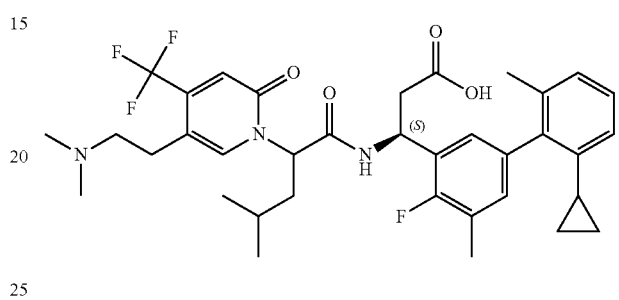

BM-P1 ESI 658.3 (M+H)$^+$. $^1$H NMR (400 MHz, MeOD) δ 7.91 (d, J=5.9 Hz, 1H), 7.13 (t, J=7.7 Hz, 1H), 7.07-6.87 (m, 3H), 6.76 (d, J=11.4 Hz, 2H), 5.83-5.64 (m, 1H), 5.57 (t, J=5.9 Hz, 1H), 3.18-2.98 (m, 2H), 2.94 (d, J=7.1 Hz, 2H), 2.82 (d, J=4.7 Hz, 1H), 2.80-2.48 (m, 8H), 2.32 (d, J=17.2 Hz, 3H), 2.12-1.89 (m, 3H), 1.81 (s, 1H), 1.57-1.26 (m, 2H), 1.02-0.83 (m, 6H), 0.75-0.61 (m, 1H), 0.60-0.22 (m, 3H).

BM-P2 ESI 658.3 (M+H)$^+$. $^1$H NMR (400 MHz, MeOD) δ 7.83 (d, J=11.7 Hz, 1H), 7.28-6.65 (m, 6H), 5.82-5.43 (m, 2H), 3.30-3.09 (m, 2H), 2.99 (t, J=6.9 Hz, 2H), 2.80 (d, J=2.6 Hz, 6H), 2.70-2.42 (m, 2H), 2.33 (d, J=1.6 Hz, 3H), 2.10-1.90 (m, 4H), 1.80-1.60 (m, 1H), 1.55-1.28 (m, 2H), 1.00-0.80 (m, 6H), 0.79-0.45 (m, 4H).

4-15. (3S)-3-(5-chloro-4,4'-difluoro-2',6'-dimethyl-[1,1'-biphenyl]-3-yl)-3-(2-(3-fluoro-5-(2-(3-fluoroazetidine-1-yl)ethyl)-2-oxopyridin-1(2H)-yl)-4-methylpentanamido)propanoic Acid (Diastereomeric Compounds BN-P1 and BN-P2)

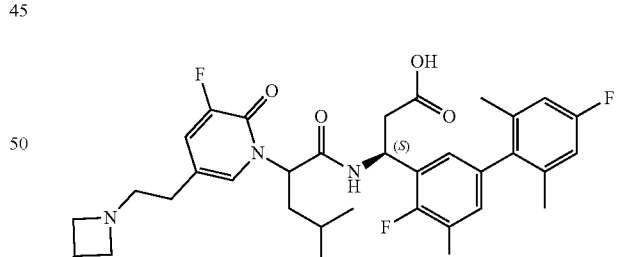

BN-P1 ESI 650.2 (M+H)$^+$. $^1$H NMR (400 MHz, MeOD) δ 7.38 (s, 1H), 7.34-7.27 (m, 1H), 7.12-7.06 (m, 1H), 6.96-6.88 (m, 1H), 6.81 (d, J=9.6 Hz, 2H), 5.65-5.52 (m, 1H), 5.45 (t, J=6.3 Hz, 1H), 5.18 (d, J=57.7 Hz, 1H), 4.14-3.88 (m, 2H), 3.72 (s, 2H), 3.10 (s, 2H), 2.78-2.52 (m, 4H), 2.02-1.75 (m, 8H), 1.46-1.28 (m, 1H), 0.98-0.76 (m, 6H).

BN-P2 ESI 650.2 (M+H)$^+$. $^1$H NMR (400 MHz, MeOD) δ 7.33 (d, J=8.4 Hz, 2H), 7.19-7.09 (m, 1H), 7.06-6.94 (m, 1H), 6.83 (d, J=9.6 Hz, 2H), 5.70-5.51 (m, 2H), 5.27 (d, J=57.4 Hz, 1H), 4.32 (s, 2H), 4.00 (s, 2H), 2.76-2.35 (m,

4H), 1.96 (d, J=13.7 Hz, 6H), 1.94-1.85 (m, 1H), 1.80-1.67 (m, 1H), 1.39-1.24 (m, 1H), 0.96-0.63 (m, 6H).

4-16. (3S)-3-(2-(5-(2-(azetidin-1-yl)ethyl)-2-oxo-4-(trifluoromethyl)pyridin-1(2H)-yl)-4-methylpentanamido)-3-(4-fluoro-2'-methoxy-5-methyl-6'-(trifluoromethyl)biphenyl-3-yl)propanoic Acid (Diastereomeric Compounds BO-P1 and BO-P2)

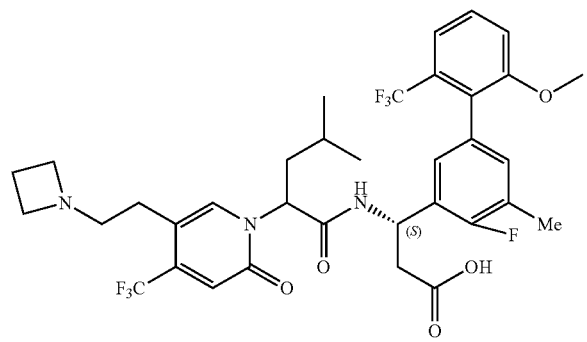

BO-P1 ESI 714.2 (M+H)+. 1H NMR (500 MHz, MeOD) δ 7.83 (d, J=6.8 Hz, 1H), 7.57-7.48 (m, 1H), 7.41-7.25 (m, 2H), 7.04-6.96 (m, 1H), 6.93 (t, J=7.0 Hz, 1H), 6.82 (d, J=10.1 Hz, 1H), 5.74-5.60 (m, 2H), 4.09-3.89 (m, 4H), 3.72 (d, J=21.5 Hz, 3H), 3.32-3.19 (m, 2H), 2.94-2.81 (m, 2H), 2.77-2.62 (m, 2H), 2.50-2.34 (m, 2H), 2.29 (s, 3H), 2.06-1.89 (m, 2H), 1.53-1.32 (m, 1H), 0.96-0.92 (m, 6H).
BO-P2 ESI 714.1 (M+H)+. 1H NMR (500 MHz, MeOD) δ 7.71 (d, J=4.3 Hz, 1H), 7.54 (t, J=8.2 Hz, 1H), 7.37 (d, J=8.0 Hz, 1H), 7.33 (d, J=8.3 Hz, 1H), 7.07-7.00 (m, 1H), 6.97 (d, J=6.6 Hz, 1H), 6.91 (d, J=4.9 Hz, 1H), 5.85-5.72 (m, 1H), 5.63-5.59 (m, 1H), 4.14 (s, 4H), 3.75 (d, J=2.7 Hz, 3H), 3.40 (d, J=25.2 Hz, 2H), 2.94 (d, J=16.0 Hz, 1H), 2.82 (d, J=9.4 Hz, 1H), 2.70-2.57 (m, 1H), 2.54-2.42 (m, 3H), 2.32 (s, 3H), 2.08-1.91 (m, 1H), 1.70-1.57 (m, 1H), 1.46-1.41 (m, 1H), 0.91 (t, J=4.9 Hz, 6H).

4-17. (3S)-3-(3',4-difluoro-2',5,6'-trimethyl-[1,1'-biphenyl]-3-yl)-3-(2-(3-fluoro-5-(2-(3-fluoroazetidine-1-yl)ethyl)-2-oxopyridin-1(2H)-yl)-4-methylpentanamido)propanoic Acid (Diastereomeric Compounds BP-P1 and BP-P2)

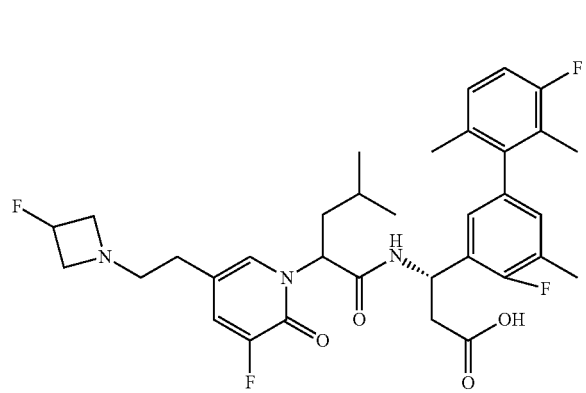 [SMILES: Cc1cc(-c2c(C)ccc(F)c2C)cc([C@H](CC(=O)O)NC(=O)C(CC(C)C)n2cc(CCN3CC(F)C3)cc(F)c2=O)c1F]

BP-P1 ESI 630.3 (M+H)+. 1H NMR (400 MHz, MeOD) δ 7.42 (s, 1H), 7.34 (d, J=10.6 Hz, 1H), 7.15-7.02 (m, 1H), 7.01-6.76 (m, 3H), 5.67 (t, J=7.6 Hz, 1H), 5.51 (s, 1H), 5.20 (d, J=57.8 Hz, 1H), 4.00 (d, J=43.3 Hz, 2H), 3.76-3.45 (m, 2H), 3.09 (d, J=5.7 Hz, 2H), 2.84-2.50 (m, 4H), 2.31 (s, 3H), 2.02-1.64 (m, 8H), 1.48-1.18 (m, 1H), 1.06-0.77 (m, 6H).
BP-P2 ESI 630.3 (M+H)+. 1H NMR (400 MHz, MeOD) δ 7.37 (d, J=10.7 Hz, 2H), 7.16-7.03 (m, 1H), 6.95 (t, J=8.9 Hz, 3H), 5.75-5.52 (m, 2H), 5.30 (d, J=57.4 Hz, 1H), 4.30 (d, J=18.4 Hz, 2H), 3.97 (s, 2H), 3.31-3.14 (m, 2H), 2.84-2.42 (m, 4H), 2.34 (d, J=1.3 Hz, 3H), 2.03-1.84 (m, 7H), 1.83-1.66 (m, 1H), 1.50-1.21 (m, 1H), 0.99-0.75 (m, 6H).

4-18. (3S)-3-(4-fluoro-2',5,6'-trimethyl-[1,1'-biphenyl]-3-yl)-3-(2-(3-fluoro-5-(2-(3-methoxyazetidin-1-yl)ethyl)-4-methyl-2-oxopyridin-1(2H)-yl)-4-methylpentanamido)propanoic Acid (Compounds BQ-P1 and BQ-P2)

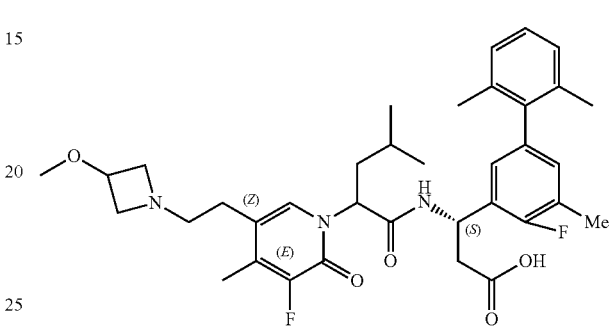

BQ-P1 ESI 638.3 (M+H)+. 1H NMR (400 MHz, MeOD) δ 7.39 (s, 1H), 7.16-7.04 (m, 3H), 6.88 (t, J=7.3 Hz, 2H), 5.64-5.53 (m, 2H), 4.24-4.08 (m, 3H), 3.73-3.61 (m, 2H), 3.30-3.26 (m, 5H), 2.83-2.67 (m, 4H), 2.31 (s, 3H), 2.24 (t, J=6.7 Hz, 3H), 2.02-1.92 (m, 8H), 1.40-1.35 (m, 1H), 0.96-0.90 (m, 6H).
BQ-P2 ESI 638.3 (M+H)+. 1H NMR (400 MHz, MeOD) δ 7.20 (s, 1H), 7.04-6.94 (m, 3H), 6.84-6.80 (t, J=7.6 Hz, 2H), 5.61-5.42 (m, 2H), 4.37-4.09 (m, 3H), 3.83-3.70 (m, 2H), 3.38-3.22 (m, 5H), 2.83-2.32 (m, 4H), 2.22 (d, J=1.6 Hz, 3H), 2.10 (d, J=2.8 Hz, 3H), 1.96-1.80 (m, 7H), 1.63-1.52 (m, 1H), 1.32-1.19 (m, 1H), 0.79-0.78 (m, 6H).

4-19. (3S)-3-(4-fluoro-2',5,6'-trimethyl-[1,1'-biphenyl]-3-yl)-3-(2-(3-fluoro-5-(2-(3-fluoroazetidine-1-yl)ethyl)-2-oxopyridin-1(2H)-yl)pentanamido)propanoic Acid (Diastereomeric Compounds BR-Pt and BR-P2)

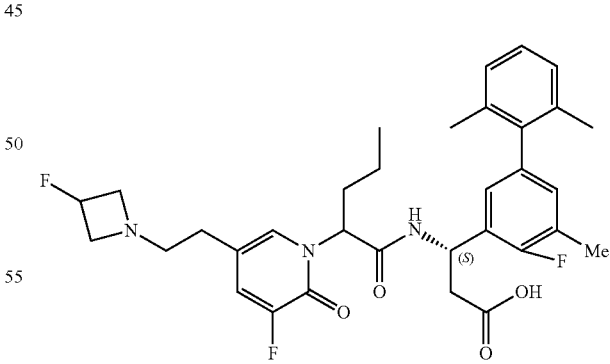

BR-P1 ESI 598.3 (M+H)+. 1H NMR (400 MHz, MeOD) δ 7.49-7.23 (m, 2H), 7.19-7.00 (m, 3H), 6.96-6.66 (m, 2H), 5.74-5.44 (m, 2H), 5.19 (d, J=57.3 Hz, 1H), 3.94 (s, 2H), 3.77-3.41 (m, 2H), 3.18-3.00 (m, 2H), 2.87-2.47 (m, 4H), 2.38-2.22 (m, 3H), 2.22-2.06 (m, 1H), 2.06-1.73 (m, 7H), 1.44-1.20 (m, 2H), 1.06-0.78 (m, 3H).
BR-P2 ESI 598.3 (M+H)+. 1H NMR (400 MHz, MeOD) δ 7.44-7.29 (m, 2H), 7.18-7.01 (m, 3H), 6.99-6.79 (m, 2H), 5.73-5.49 (m, 2H), 5.24 (d, J=57.6 Hz, 1H), 4.11 (s, 2H), 3.73 (d, J=9.2 Hz, 2H), 3.14 (d, J=6.1 Hz, 2H), 2.75-2.48 (m, 4H), 2.33 (d, J=1.7 Hz, 3H), 2.16-2.04 (m, 1H), 2.02 (t, J=8.9 Hz, 6H), 1.91-1.76 (m, 1H), 1.35-1.12 (m, 2H), 0.91 (t, J=7.4 Hz, 3H).

4-20. (3S)-3-(2-(5-(2-(azetidin-1-yl)ethyl)-2-oxo-4-(trifluoromethyl)pyridin-1(2H)-yl)-4-methylpentanamido)-3-(5'-cyano-4-fluoro-2',5-dimethyl-[1,1'-biphenyl]-3-yl)propanoic Acid (Diastereomeric Compounds BS-P1 and BS-P2)

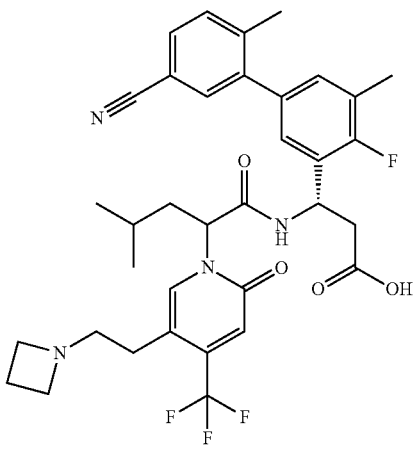 [SMILES: Cc1ccc(C#N)cc1-c1cc(C)c(F)c([C@H](CC(=O)O)NC(=O)C(CC(C)C)n2cc(CCN3CCC3)c(C(F)(F)F)cc2=O)c1]

BS-P1 ESI 655.3 (M+H)⁺. 1H NMR (400 MHz, MeOD) δ 7.84 (s, 1H), 7.69-7.57 (m, 1H), 7.54 (s, 1H), 7.47 (d, J=8.0 Hz, 1H), 7.17-7.01 (m, 2H), 6.82 (s, 1H), 5.75-5.43 (m, 2H), 4.04 (t, J=8.1 Hz, 4H), 3.15 (s, 2H), 2.85 (t, J=6.9 Hz, 2H), 2.78-2.61 (m, 2H), 2.52-2.37 (m, 2H), 2.31 (d, J=7.7 Hz, 6H), 2.11-1.90 (m, 2H), 1.42 (d, J=7.2 Hz, 1H), 0.96 (t, J=6.4 Hz, 6H).

BS-P2 ESI 655.3 (M+H)+. ¹H NMR (400 MHz, MeOD) δ 7.74 (s, 1H), 7.68-7.60 (m, 1H), 7.56 (d, J=1.6 Hz, 1H), 7.49 (d, J=7.9 Hz, 1H), 7.16 (d, J=6.7 Hz, 2H), 6.93 (s, 1H), 5.83-5.71 (m, 1H), 5.64 (t, J=7.7 Hz, 1H), 4.15 (t, J=8.0 Hz, 4H), 3.42 (d, J=15.1 Hz, 2H), 3.01-2.75 (m, 2H), 2.70-2.42 (m, 4H), 2.41-2.26 (m, 6H), 2.10-1.93 (m, 1H), 1.79-1.63 (m, 1H), 1.55-1.29 (m, 1H), 0.93 (t, J=6.4 Hz, 6H).

4-21. (3S)-3-(2-(5-(2-(azetidin-1-yl)ethyl)-2-oxo-4-(trifluoromethyl)pyridin-1(2H)-yl)-4-methylpentanamido)-3-(2'-cyano-4-fluoro-4',5-dimethyl-[1,1'-biphenyl]-3-yl)propanoic Acid (Diastereomeric Compounds BT-P1 and BT-P2)

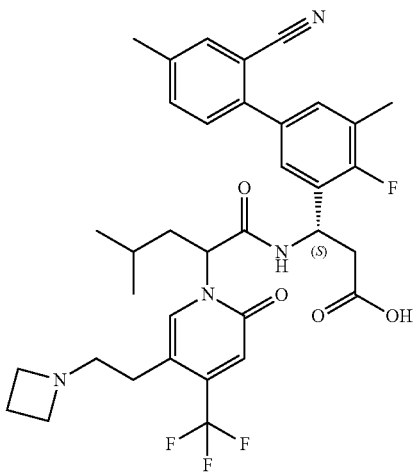

BT-P1 ESI 655.3 (M+H)⁺. ¹H NMR (400 MHz, MeOD) δ 7.85 (s, 1H), 7.60 (s, 1H), 7.47 (s, 1H), 7.36-7.30 (s, 3H), 6.74 (s, 1H), 5.78-5.59 (m, 2H), 3.84-3.80 (m, 4H), 3.15-3.10 (m, 2H), 2.75-2.72 (m, 4H), 2.43 (s, 3H), 2.34-2.30 (m, 5H), 2.06-2.01 (m, 2H), 1.40-1.37 (m, 1H), 0.99-0.96 (m, 6H).

BT-P2 ESI 655.3 (M+H)⁺. ¹H NMR (400 MHz, MeOD) δ 7.72 (s, 1H), 7.66 (s, 1H), 7.57 (d, J=8.1 Hz, 1H), 7.51-7.34 (m, 3H), 6.92 (s, 1H), 5.75-5.69 (m, 2H), 4.05-4.01 (m, 4H), 2.95-2.55 (m, 5H), 2.46-2.37 (m, 9H), 2.06-1.96 (m, 1H), 1.85-1.75 (m, 1H), 1.49-1.37 (m, 1H), 0.94-0.92 (m, 6H).

4-22. (3S)-3-(2-(5-(2-(azetidin-1-yl)ethyl)-2-oxo-4-(trifluoromethyl)pyridin-1(2H)-yl)-4-methylpentanamido)-3-(6'-cyano-3',4-difluoro-2',5-dimethyl-[1,1'-biphenyl]-3-yl)propanoic Acid (Diastereomeric Compounds BU-P1 and BU-P2)

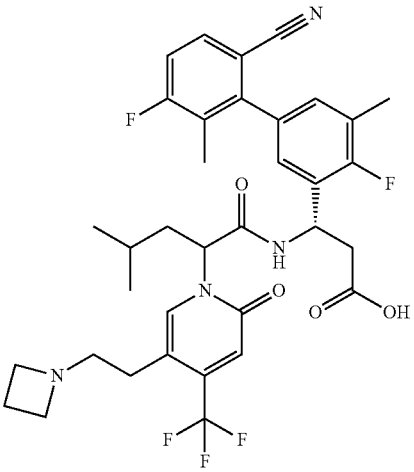 [SMILES: Cc1cc(-c2c(C#N)ccc(F)c2C)cc([C@H](CC(=O)O)NC(=O)C(CC(C)C)n2cc(CCN3CCC3)c(C(F)(F)F)cc2=O)c1F]

BU-P1 ESI 673.3 (M+H)⁺. ¹H NMR (400 MHz, MeOD) δ 7.83 (s, 1H), 7.71-7.62 (m, 1H), 7.31-7.27 (t, J=8.8 Hz, 1H), 7.14-7.10 (m, 2H), 6.80-6.75 (d, J=22.1 Hz, 1H), 5.76-5.62 (m, 2H), 4.02-3.97 (m, 4H), 3.32-3.15 (m, 2H), 2.95-2.60 (m, 4H), 2.51-2.25 (m, 5H), 2.11-1.93 (m, 5H), 1.45-1.44 (m, 1H), 0.97-0.96 (m, 6H).

BU-P2 ESI 673.3 (M+H)⁺. ¹H NMR (400 MHz, MeOD) δ 7.81-7.66 (m, 2H), 7.37-7.08 (m, 3H), 6.92 (s, 1H), 5.85-5.56 (m, 2H), 4.16-4.10 (m, 4H), 3.43-3.42 (m, 2H), 3.02-2.75 (m, 2H), 2.66 (d, J=12.1 Hz, 1H), 2.62-2.30 (m, 6H), 2.18-1.95 (m, 4H), 1.80-1.64 (m, 1H), 1.45-1.38 (m, 1H), 0.92-0.91 (m, 6H).

4-23. (3S)-3-(2-(5-(2-(azetidin-1-yl)ethyl)-2-oxo-4-(trifluoromethyl)pyridin-1(2H)-yl)-4-methylpentanamido)-3-(2'-cyano-4,5'-difluoro-4',5-dimethylbiphenyl-3-yl)propanoic Acid (Diastereomeric Compounds BV-P1 and BV-P2)

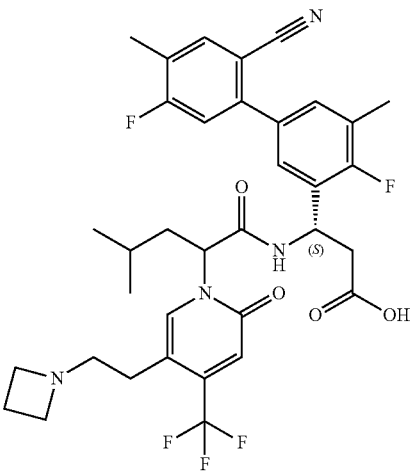

BV-P1 ESI 673.2 (M+H)⁺. ¹H NMR (400 MHz, MeOD) δ 7.96 (s, 1H), 7.73-7.46 (m, 2H), 7.31 (d, J=4.5 Hz, 1H), 7.07-6.69 (m, 1H), 5.75 (s, 1H), 5.62 (t, J=6.8 Hz, 1H), 3.96 (s, 4H), 3.27-3.11 (m, 2H), 2.92-2.58 (m, 4H), 2.45-2.21 (m, 8H), 2.12-1.91 (m, 2H), 1.41 (s, 1H), 1.04-0.88 (m, 6H).

BV-P2 ESI 673.2 (M+H)⁺. ¹H NMR (400 MHz, MeOD) δ 7.78 (d, J=7.6 Hz, 1H), 7.72 (s, 1H), 7.47-7.38 (m, 2H), 7.32 (d, J=10.2 Hz, 1H), 6.93 (s, 1H), 5.78-5.65 (m, 2H), 4.13 (t, J=8.0 Hz, 4H), 3.48-3.35 (m, 2H), 2.99-2.75 (m, 2H), 2.70-2.42 (m, 4H), 2.37 (s, 6H), 2.11-1.93 (m, 1H), 1.85-1.71 (m, 1H), 1.51-1.30 (m, 1H), 1.05-0.85 (m, 6H).

4-24. (3S)-3-(2-(5-(2-(azetidin-1-yl)ethyl)-2-oxo-4-(trifluoromethyl)pyridin-1(2H)-yl)-4-methylpentanamido)-3-(2'-cyano-4-fluoro-4'-methoxy-5-methyl-[1,1'-biphenyl]-3-yl)propanoic Acid (Diastereomeric Compounds BW-P1 and BW-P2)

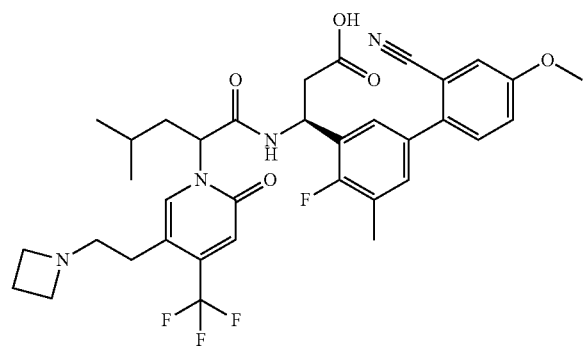 [SMILES: COc1ccc(-c2cc(C)c(F)c([C@H](CC(=O)O)NC(=O)C(CC(C)C)n3cc(CCN4CCC4)c(C(F)(F)F)cc3=O)c2)c(C#N)c1]

BW-P1 ESI 671.2 (M+H)⁺. ¹H NMR (500 MHz, MeOD) δ 7.93 (s, 1H), 7.44 (s, 1H), 7.26 (s, 2H), 7.15 (d, J=52.3 Hz, 2H), 6.75 (s, 1H), 5.80-5.70 (m, 1H), 5.68-5.60 (m, 1H), 3.95 (d, J=7.9 Hz, 4H), 3.90 (d, J=10.4 Hz, 3H), 3.24 (m, 2H), 2.81 (m, 1H), 2.75 (m, 3H), 2.46-2.35 (m, 2H), 2.31 (s, 3H), 2.04 (m, 2H), 1.48-1.38 (m, 2H), 0.98 (m, 6H).

BW-P2 ESI 671.2 (M+H)⁺. ¹H NMR (500 MHz, MeOD) δ 7.72 (s, 1H), 7.50 (d, J=8.7 Hz, 1H), 7.38 (ddm, 2H), 7.35-7.29 (m, 2H), 6.93 (s, 1H), 5.75 (m, 1H), 5.70 (t, J=7.7 Hz, 1H), 4.11 (m, 4H), 3.91 (s, 3H), 3.39 (m, 2H), 2.94 (d, J=16.7 Hz, 1H), 2.86-2.77 (m, 1H), 2.66 (m, 1H), 2.55 (m, 1H), 2.50-2.41 (m, 2H), 2.37 (s, 3H), 2.02 (m, 1H), 1.83-1.74 (m, 1H), 1.41 (m, 2H), 0.93 (m, 6H).

4-25. (3S)-3-(2-(5-(2-(azetidin-1-yl)ethyl)-2-oxo-4-(trifluoromethyl)pyridin-1(2H)-yl)-4-methylpentanamido)-3-(2'-cyano-5'-ethyl-4-fluoro-5-methyl-[1,1'-biphenyl]-3-yl)propanoic Acid (Diastereomeric Compounds BX-P1 and BX-P2)

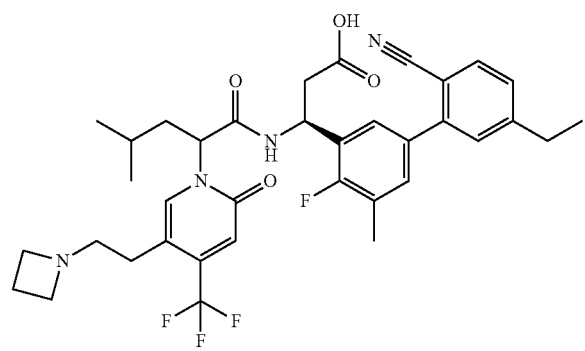 [SMILES: CCc1ccc(C#N)c(-c2cc(C)c(F)c([C@H](CC(=O)O)NC(=O)C(CC(C)C)n3cc(CCN4CCC4)c(C(F)(F)F)cc3=O)c2)c1]

BX-P1 ESI 669.2 (M+H)⁺. ¹H NMR (400 MHz, MeOD) δ 7.96-7.83 (m, 1H), 7.70 (d, J=7.9 Hz, 1H), 7.46-7.16 (m, 4H), 6.76 (s, 1H), 5.82-5.48 (m, 2H), 4.07-3.90 (m, 4H), 3.31-3.14 (m, 2H), 2.88-2.66 (m, 6H), 2.49-2.30 (m, 5H), 2.13-1.99 (m, 2H), 1.52-1.21 (m, 4H), 0.97 (d, J=6.6 Hz, 6H).

BX-P2 ESI 669.3 (M+H)⁺. ¹H NMR (400 MHz, MeOD) δ 7.84-7.66 (m, 2H), 7.47-7.28 (m, 4H), 6.93 (s, 1H), 5.73 (t, J=7.7 Hz, 2H), 4.16 (t, J=8.0 Hz, 4H), 3.53-3.34 (m, 2H), 3.04-2.30 (m, 1H), 2.10-1.93 (m, 1H), 1.89-1.77 (m, 1H), 1.46-1.23 (m, 4H), 1.01-0.83 (m, 6H).

4-26. (3S)-3-(4,4'-difluoro-2',5,6'-trimethyl-[1,1'-biphenyl]-3-yl)-3-(2-(3-fluoro-5-(2-(3-fluoroazetidin-1-yl)ethyl)-2-oxopyridin-1(2H)-yl)pentanamido)propanoic Acid (Diastereomeric Compounds BY-P1 and BY-P2)

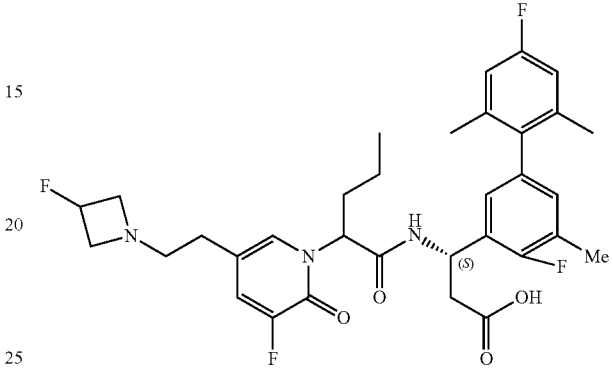

BY-P1 ESI 616.3 (M+H)⁺. 1H NMR (400 MHz, MeOD) δ 7.43 (s, 1H), 7.38-7.27 (m, 1H), 6.91-6.68 (m, 4H), 5.67-5.44 (m, 2H), 5.21 (d, J=57.3 Hz, 1H), 4.02 (d, J=35.4 Hz, 2H), 3.83-3.54 (m, 2H), 3.20-2.99 (m, 2H), 2.82-2.53 (m, 4H), 2.29 (d, J=1.6 Hz, 3H), 2.24-2.08 (m, 1H), 2.05-1.92 (m, 4H), 1.88 (s, 3H), 1.42-1.21 (m, 2H), 0.96 (t, J=7.4 Hz, 3H).

BY-P2 ESI 616.3 (M+H)⁺. ¹H NMR (400 MHz, MeOD) δ 7.44-7.28 (m, 2H), 7.01-6.76 (m, 4H), 5.69-5.49 (m, 2H), 5.29 (d, J=57.4 Hz, 1H), 4.38-4.13 (m, 2H), 4.02-3.74 (m, 2H), 3.37-3.20 (m, 2H), 2.81-2.43 (m, 4H), 2.33 (d, J=1.7 Hz, 3H), 2.16-2.04 (m, 1H), 2.01 (s, 6H), 1.90-1.77 (m, 1H), 1.35-1.09 (m, 2H), 0.92 (t, J=7.4 Hz, 3H).

4-27. (3S)-3-(2-(5-(2-(dimethylamino)ethyl)-2-oxo-4-(trifluoromethyl)pyridin-1(2H)-yl)pentanamido)-3-(4-fluoro-2',5,6'-trimethyl-[1,1'-biphenyl]-3-yl)propanoic Acid (Diastereomeric Compounds BZ-P1 and BZ-P2)

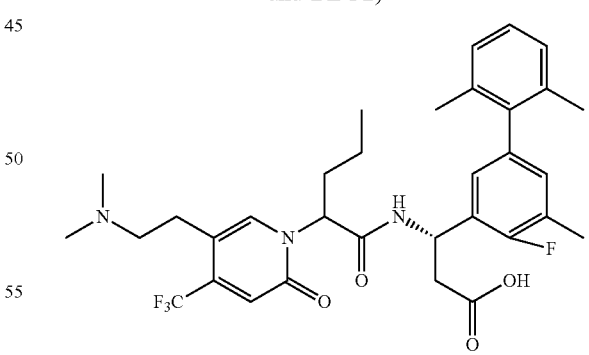

BZ-P1 ESI 618.3 (M+H)⁺. ¹H NMR (500 MHz, MeOD) δ 7.90 (s, 1H), 7.11-7.02 (m, 3H), 6.90-6.86 (m, 2H), 6.74 (s, 1H), 5.59-5.56 (m, 2H), 3.18-3.14 (m, 2H), 2.99 (d, J=22.6 Hz, 2H), 2.81 (s, 6H), 2.76-2.73 (m, 2H), 2.29 (s, 3H), 2.19-2.12 (m, 1H), 2.02-1.95 (m, 4H), 1.80 (s, 3H), 1.37-1.30 (m, 2H), 0.96 (t, J=7.3 Hz, 3H).

BZ-P2 ESI 618.3 (M+H)⁺. ¹H NMR (500 MHz, MeOD) δ 7.86 (s, 1H), 7.14-7.65 (m, 3H), 6.95-6.89 (m, 3H), 5.73 (d, J=7.3 Hz, 1H), 5.53 (t, J=7.6 Hz, 1H), 3.33-3.20 (m, 2H), 3.01 (t, J=6.8 Hz, 2H), 2.82 (s, 6H), 2.68-2.62 (m, 1H), 2.56-2.51 (m, 1H), 2.32 (s, 3H), 2.07-2.00 (m, 7H), 1.82-1.72 (m, 1H), 1.23 (s, 2H), 0.89 (d, J=3.5 Hz, 3H).

4-28. (3S)-3-(5-chloro-4-fluoro-2',6'-dimethyl-[1,1'-biphenyl]-3-yl)-3-(2-(5-(2-(dimethylamino)ethyl)-2-oxo-4-(trifluoromethyl)pyridin-1(2H)-yl)-5-methyl-hexanamido)propanoic Acid (Diastereomeric Compounds CA-P1 and CA-P2)

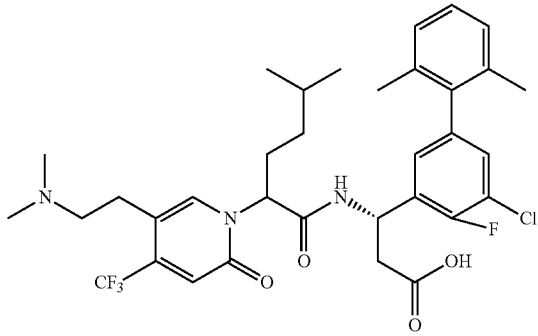

CA-P1 ESI 666.3 (M+H)$^+$. $^1$H NMR (400 MHz, MeOD) δ 7.88 (s, 1H), 7.13 (t, J=7.6 Hz, 1H), 7.09-7.06 (m, 2H), 7.04 (s, 1H), 7.02 (s, 1H), 6.69 (s, 1H), 5.53 (t, J=7.2 Hz, 1H), 5.49-5.45 (m, 1H), 3.16-3.04 (m, 2H), 2.94 (t, J=8.0 Hz, 2H), 2.76 (s, 6H), 2.73-2.71 (m, 2H), 2.23-2.14 (m, 1H), 1.99 (s, 3H), 1.97-1.91 (m, 1H), 1.79 (s, 3H), 1.63-1.51 (m, 1H), 1.27-1.18 (m, 1H), 1.13-1.04 (m, 1H), 0.88 (d, J=3.2 Hz, 3H), 0.86 (d, J=3.6 Hz, 3H).

CA-P2 ESI 666.2 (M+H)$^+$. $^1$H NMR (400 MHz, MeOD) δ 7.86 (s, 1H), 7.17-7.13 (m, 2H), 7.10-7.08 (m, 3H), 6.88 (s, 1H), 5.71-5.68 (m, 1H), 5.46 (t, J=7.4 Hz, 1H), 3.28-3.15 (m, 2H), 2.98 (t, J=7.0 Hz, 2H), 2.81 (s, 6H), 2.68-2.63 (m, 1H), 2.58-2.52 (m, 1H), 2.16-2.05 (m, 1H), 2.01 (s, 3H), 2.00 (s, 3H), 1.83-1.74 (m, 1H), 1.56-1.46 (m, 1H), 1.16-0.99 (m, 2H), 0.82 (d, J=5.2 Hz, 3H), 0.80 (d, J=4.8 Hz, 3H).

4-29. (3S)-3-(2-(5-(2-(dimethylamino)ethyl)-2-oxo-4-(trifluoromethyl)pyridin-1(2H)-yl)-4-methylpentanamido)-3-(2-fluoro-3-methyl-5-((S)-2-methylpiperidin-1-yl)phenyl)propanoic Acid (Diastereomeric Compounds CB-P1 and CB-P2)

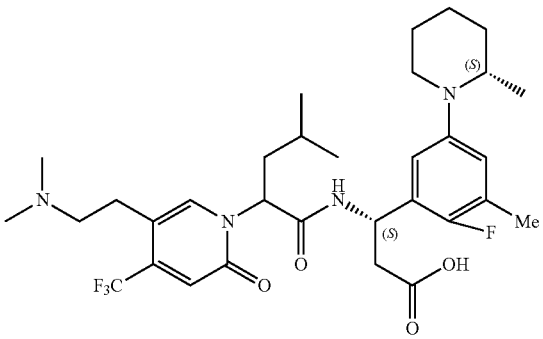

CB-P1 ESI 625.4 (M+H)$^+$. $^1$H NMR (400 MHz, MeOD) δ 7.92 (s, 1H), 6.91-6.74 (m, 3H), 5.74 (t, J=8.0 Hz, 1H), 5.49 (t, J=7.0 Hz, 1H), 3.49-3.38 (m, 1H), 3.13-2.82 (m, 6H), 2.77-2.62 (m, 8H), 2.21 (s, 3H), 2.01 (t, J=7.6 Hz, 2H), 1.91-1.36 (m, 7H), 0.98 (d, J=6.5 Hz, 6H), 0.79 (d, J=6.4 Hz, 3H).

CB-P2 ESI 625.4 (M+H)$^+$. $^1$H NMR (400 MHz, MeOD) δ 7.89 (s, 1H), 7.01-6.78 (m, 3H), 5.74-5.55 (m, 2H), 3.59-3.44 (m, 1H), 3.30-3.14 (m, 2H), 3.08-2.90 (m, 4H), 2.82 (s, 6H), 2.62-2.42 (m, 2H), 2.25 (d, J=1.7 Hz, 3H), 2.04-1.35 (m, 9H), 0.99-0.86 (m, 9H).

4-30. (3S)-3-(2-(5-(2-(azetidin-1-yl)ethyl)-2-oxo-4-(trifluoromethyl)pyridin-1(2H)-yl)-4-methylpentanamido)-3-(2'-cyclopropyl-4,5'-difluoro-5-methyl-[1,1'-biphenyl]-3-yl)propanoic Acid (Diastereomeric Compounds CC-P1 and CC-P2)

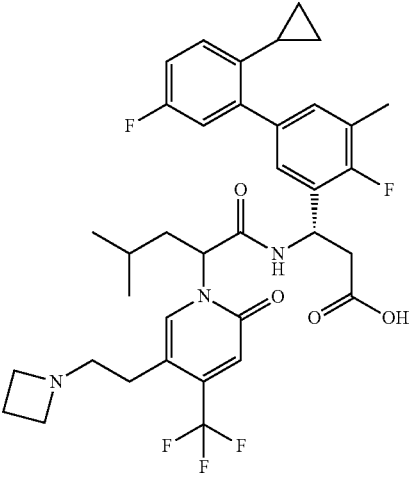 [SMILES: Cc1cc(-c2cc(F)ccc2C2CC2)cc([C@H](CC(=O)O)NC(=O)C(CC(C)C)n2cc(CCN3CCC3)c(C(F)(F)F)cc2=O)c1F]

CC-P1 ESI 674.4 (M+H)$^+$. $^1$H NMR (400 MHz, MeOD) δ 7.87 (s, 1H), 7.23-7.17 (m, 2H), 7.03-6.98 (m, 2H), 6.89-6.82 (m, 2H), 5.73-5.56 (m, 2H), 4.09 (t, J=8.1 Hz, 4H), 3.35-3.32 (m, 2H), 2.87-2.84 (m, 2H), 2.76-2.75 (m, 2H), 2.48-2.43 (m, 2H), 2.31 (d, J=1.6 Hz, 3H), 2.05-1.97 (m, 2H), 1.81-1.74 (m, 1H), 1.16-1.39 (m, 1H), 0.97-0.91 (m, 6H), 0.79-0.74 (m, 2H), 0.57-0.53 (m, 2H).

CC-P2 ESI 674.3 (M+H)$^+$. $^1$H NMR (400 MHz, MeOD) δ 7.74 (s, 1H), 7.27-7.21 (m, 2H), 7.05-6.91 (m, 4H), 5.77-5.74 (m, 1H), 5.64 (t, J=7.6 Hz, 1H), 4.14 (t, J=8.1 Hz, 4H), 3.42-3.32 (m, 2H), 2.96-2.81 (m, 2H), 2.67-2.45 (m, 4H), 2.35 (t, J=8.8 Hz, 3H), 2.03-1.96 (m, 1H), 1.83-1.66 (m, 2H), 1.42-1.38 (m, 1H), 0.92-0.89 (m, 6H), 0.84-0.79 (m, 2H), 0.63-0.59 (m, 2H).

4-31. (3S)-3-(2-(5-(2-(azetidin-1-yl)ethyl)-2-oxo-4-(trifluoromethyl)pyridin-1(2H)-yl)-4-methylpentanamido)-3-(6'-cyano-4-fluoro-2',3',5-trimethyl-[1,1'-biphenyl]-3-yl)propanoic Acid (Diastereomeric Compounds CD-P1 and CD-P2)

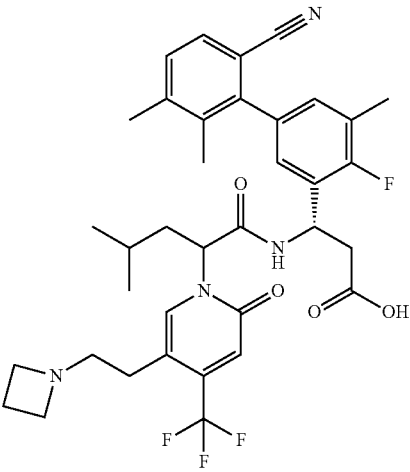 [SMILES: Cc1ccc(C#N)c(-c2cc(C)c(F)c([C@H](CC(=O)O)NC(=O)C(CC(C)C)n3cc(CCN4CCC4)c(C(F)(F)F)cc3=O)c2)c1C]

CD-P1 ESI 669.4 (M+H)$^+$. $^1$H NMR (400 MHz, MeOD) δ 7.85 (d, J=8.9 Hz, 1H), 7.61-7.27 (m, 2H), 7.16-6.95 (m, 2H), 6.77 (d, J=35.8 Hz, 1H), 5.80-5.43 (m, 2H), 4.11-3.86 (m, 4H), 3.31-3.15 (m, 2H), 2.94-2.60 (m, 4H), 2.51-2.24 (m, 8H), 2.15-1.89 (m, 5H), 1.56-1.38 (m, 1H), 1.09-0.83 (m, 6H).

CD-P2 ESI 669.4 (M+H)+. 1H NMR (400 MHz, MeOD) δ 7.72 (d, J=6.8 Hz, 1H), 7.54 (d, J=7.9 Hz, 1H), 7.36 (d, J=7.9 Hz, 1H), 7.22-7.05 (m, 2H), 6.91 (s, 1H), 5.90-5.53 (m, 2H), 4.32-3.89 (m, 4H), 3.54-3.33 (m, 2H), 3.11-2.29 (m, 12H), 2.07-1.92 (m, 4H), 1.83-1.64 (m, 1H), 1.52-1.30 (m, 1H), 0.97-0.81 (m, 6H).

4-32. (3S)-3-(2-(5-(2-(azetidin-1-yl)ethyl)-2-oxo-4-(trifluoromethyl)pyridin-1(2H)-yl)-4-methylpentanamido)-3-(5'-cyano-4-fluoro-2',4',5-trimethyl-[1,1'-biphenyl]-3-yl)propanoic Acid (Diastereomeric Compounds CE-P1 and CE-P2)

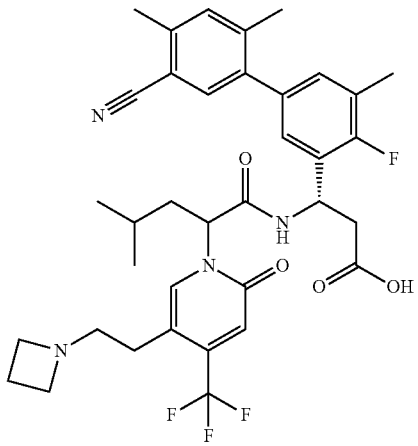

CE-P1 ESI 669.2 (M+H)+. 1H NMR (400 MHz, MeOD) δ 7.74 (s, 1H), 7.26 (d, J=40.1 Hz, 2H), 6.96 (t, J=7.5 Hz, 2H), 6.65 (s, 1H), 5.74-5.22 (m, 2H), 3.92 (t, J=8.1 Hz, 4H), 3.21-3.09 (m, 2H), 2.66 (dt, J=11.9, 7.1 Hz, 4H), 2.49-2.19 (m, 5H), 2.15 (d, J=20.6 Hz, 6H), 1.90 (m, J=13.4, 6.1 Hz, 2H), 1.47-1.10 (m, 1H), 0.83 (t, J=6.2 Hz, 6H).

CE-P2 ESI 669.2 (M+H)+. 1H NMR (400 MHz, MeOD) δ 7.75 (s, 1H), 7.42 (d, J=42.0 Hz, 2H), 7.13 (d, J=6.4 Hz, 2H), 6.92 (s, 1H), 5.92-5.45 (m, 2H), 4.14 (t, J=8.0 Hz, 4H), 3.40 (d, J=16.8 Hz, 2H), 2.92 (s, 2H), 2.75-2.55 (m, 1H), 2.52-2.41 (m, 6H), 2.40-2.18 (m, 6H), 2.12-1.88 (m, 1H), 1.82-1.53 (m, 1H), 1.53-1.20 (m, 1H), 0.92 (t, J=6.6 Hz, 6H).

4-33. (3S)-3-(4,5-difluoro-2',6'-dimethyl-[1,1'-biphenyl]-3-yl)-3-(2-(5-(2-(dimethylamino)ethyl)-2-oxopyridin-1(2H)-yl)-4-methylpentanamido)propanoic Acid (Diastereomeric Compounds CF-P1 and CF-P2)

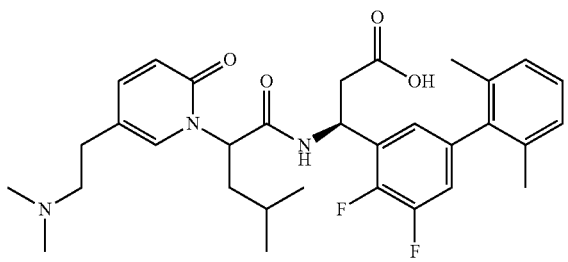 [SMILES: Cc1cccc(C)c1-c1cc(F)c(F)c([C@H](CC(=O)O)NC(=O)C(CC(C)C)n2cc(CCN(C)C)ccc2=O)c1]

CF-P1 ESI 568.2 (M+H)+. 1H NMR (500 MHz, MeOD) δ 7.64 (d, J=2.0 Hz, 1H), 7.54-7.51 (m, 1H), 7.18 (t, J=7.5 Hz, 1H), 7.11 (t, J=6.8 Hz, 2H), 6.99-6.90 (m, 1H), 6.78 (d, J=5.9 Hz, 1H), 6.52 (d, J=9.3 Hz, 1H), 5.61-5.56 (m, 1H), 5.42 (t, J=5.6 Hz, 1H), 3.32-3.19 (s, 1H), 3.24-3.10 (m, 1H), 2.88-2.80 (m, 2H), 2.73 (s, 6H), 2.70-2.64 (m, 1H), 2.59-2.53 (m, 1H), 2.06-1.89 (m, 8H), 1.50-1.36 (m, 1H), 0.97-0.90 (m, 6H).

CF-P2 ESI 568.2 (M+H)+. 1H NMR (500 MHz, MeOD) δ 1H NMR (500 MHz, MeOD) δ 7.65 (d, J=2.1 Hz, 1H), 7.54-7.50 (m, 1H), 7.22-7.13 (m, 1H), 7.14-7.07 (m, 2H), 7.01-6.90 (m, 1H), 6.88 (d, J=5.8 Hz, 1H), 6.54 (d, J=9.3 Hz, 1H), 5.66-5.52 (m, 2H), 3.38-3.34 (m, 1H), 3.28-3.21 (m, 1H), 2.98-2.86 (m, 1H), 2.86-2.73 (m, 7H), 2.64-2.59 (m, 1H), 2.51-2.44 (m, 1H), 2.08-1.91 (m, 7H), 1.92-1.81 (m, 1H), 1.49-1.35 (m, 1H), 0.93-0.88 (m, 6H).

4-34. (3S)-3-(2-(5-(2-(dimethylamino)ethyl)-2-oxopyridin-1(2H)-yl)-4-methylpentanamido)-3-(4,4',5-trifluoro-2',6'-dimethyl-[1,1'-biphenyl]-3-yl)propanoic Acid (Diastereomeric Compounds CG-P1 and CG-P2)

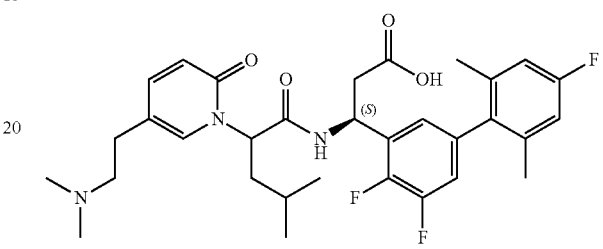

CG-P1 ESI 586.2 (M+H)+. 1H NMR (500 MHz, MeOD) δ 7.65 (s, 1H), 7.57-7.48 (m, 1H), 6.99-6.90 (m, 1H), 6.87 (d, J=8.8 Hz, 2H), 6.79 (d, J=5.8 Hz, 1H), 6.52 (d, J=9.4 Hz, 1H), 5.56 (s, 1H), 5.42 (t, J=5.6 Hz, 1H), 3.32-3.27 (m, 1H), 3.23-3.16 (m, 1H), 2.93-2.80 (m, 2H), 2.75 (s, 6H), 2.70-2.62 (m, 1H), 2.59-2.52 (m, 1H), 2.10-1.91 (m, 8H), 1.44 (s, 1H), 0.98-0.87 (m, 6H).

CG-P2 ESI 586.2 (M+H)+. 1H NMR (500 MHz, MeOD) δ 7.65 (d, J=2.1 Hz, 1H), 7.56-7.50 (m, 1H), 7.01-6.94 (m, 1H), 6.90-6.81 (m, 3H), 6.55 (d, J=9.3 Hz, 1H), 5.64-5.54 (m, 2H), 3.45-3.36 (m, 1H), 3.31-3.24 (m, 1H), 2.99-2.90 (m, 1H), 2.90-2.78 (m, 7H), 2.64-2.55 (m, 1H), 2.51-2.41 (m, 1H), 2.07-1.95 (m, 7H), 1.92-1.83 (m, 1H), 1.46-1.36 (m, 1H), 0.96-0.86 (m, 6H).

4-35. (3S)-3-(4,5-difluoro-2',6'-dimethyl-[1,1'-biphenyl]-3-yl)-3-(2-(5-(2-(3-fluoroazetidine-1-yl)ethyl)-2-oxopyridin-1(2H)-yl)-4-methylpentanamido)propanoic Acid (Diastereomeric Compounds CH-P1 and CH-P2)

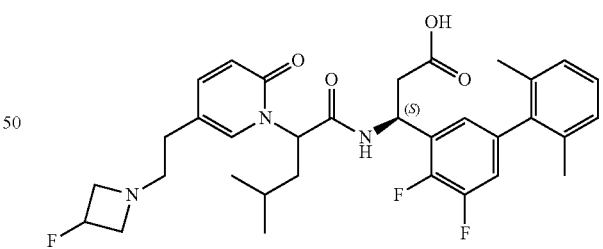

CH-P1 ESI 598.2 (M+H)+. 1H NMR (500 MHz, MeOD) δ 7.54 (d, J=1.9 Hz, 1H), 7.46-7.40 (m, 1H), 7.21-7.14 (m, 1H), 7.11 (d, J=7.3 Hz, 2H), 6.99-6.90 (m, 1H), 6.81 (d, J=5.9 Hz, 1H), 6.47 (d, J=9.3 Hz, 1H), 5.62 (t, J=8.1 Hz, 1H), 5.51 (t, J=6.1 Hz, 1H), 5.31-5.14 (m, 1H), 4.17-3.96 (m, 2H), 3.82-3.67 (m, 2H), 3.21-3.11 (m, 2H), 2.78-2.58 (m, 4H), 2.03-1.89 (m, 8H), 1.47-1.40 (m, 1H), 0.97-0.88 (m, 6H).

CH-P2 ESI 598.2 (M+H)+. 1H NMR (500 MHz, MeOD) δ 7.53 (d, J=2.0 Hz, 1H), 7.49-7.42 (m, 1H), 7.16 (d, J=7.4 Hz, 1H), 7.11 (d, J=7.7 Hz, 2H), 7.03-6.94 (m, 1H), 6.92 (d, J=5.9 Hz, 1H), 6.55 (d, J=9.3 Hz, 1H), 5.68-5.60 (m, 2H), 5.41-5.22 (m, 1H), 4.47-4.27 (m, 2H), 4.09-3.94 (m, 2H), 3.37 (s, 2H), 2.79-2.62 (m, 3H), 2.60-2.50 (m, 1H), 2.03 (d, J=2.2 Hz, 6H), 1.98-1.91 (m, 1H), 1.84-1.76 (m, 1H), 1.47-1.37 (m, 1H), 0.91 (t, J=6.1 Hz, 6H).

4-36. (3S)-3-(4-fluoro-2',5,6'-trimethyl-[1,1'-biphenyl]-3-yl)-3-(2-(5-(2-(3-fluoroazetidine-1-yl)ethyl)-4-methyl-2-oxopyridin-1(2H)-yl)-4-methylpentanamido)propanoic Acid (Diastereomeric Compounds CI-P1 and CI-P2)

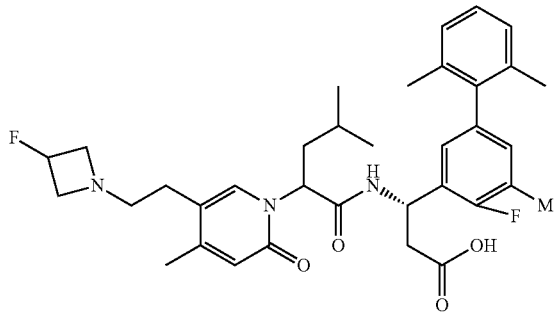

CI-P1 ESI 608.2 (M+H)+. 1H NMR (500 MHz, MeOD) δ 8.45 (s, 0.47HCOOH), 7.54 (s, 1H), 7.15-7.05 (m, 3H), 6.89-6.81 (m, 2H), 6.30 (s, 1H), 5.68-5.48 (m, 2H), 5.40-5.14 (m, 1H), 4.35-4.13 (m, 2H), 4.06-3.86 (m, 2H), 3.26-3.20 (m, 2H), 2.88-2.65 (m, 4H), 2.29 (s, 3H), 2.23 (s, 3H), 2.01-1.89 (m, 5H), 1.85 (s, 3H), 1.48-1.38 (m, 1H), 0.98-0.91 (m, 6H).

CI-P2 ESI 608.2 (M+H)+. 1H NMR (500 MHz, MeOD) δ 8.45 (s, 0.23HCOOH), 7.46 (s, 1H), 7.20-7.02 (m, 3H), 6.93 (d, J=5.0 Hz, 2H), 6.44 (s, 1H), 5.75-5.54 (m, 2H), 5.34 (d, J=57.3 Hz, 1H), 4.48-4.35 (m, 2H), 4.16-3.96 (m, 2H), 3.42-3.34 (m, 2H), 2.90-2.82 (m, 1H), 2.74-2.63 (m, 2H), 2.60-2.52 (m, 1H), 2.33 (s, 3H), 2.25 (s, 3H), 2.07-1.85 (m, 7H), 1.82-1.70 (m, 1H), 1.44-1.34 (m, 1H), 0.91-0.87 (m, 6H).

4-37. (3S)-3-(2-(5-((dimethylamino)methyl)-2-oxo-4-(trifluoromethyl)pyridin-1(2H)-yl)-4-methylpentanamido)-3-(4-fluoro-2',5,6'-trimethyl-[1,1'-biphenyl]-3-yl)propanoic Acid (Diastereomeric Compounds CJ-P1 and CJ-P2)

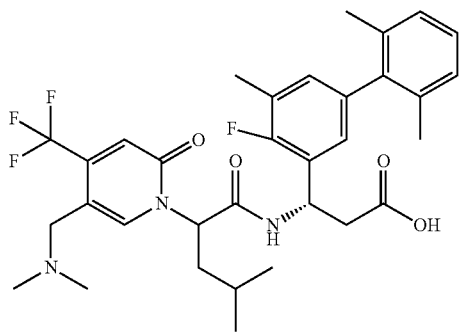 [SMILES: Cc1cc(-c2c(C)cccc2C)cc([C@H](CC(=O)O)NC(=O)C(CC(C)C)n2cc(CN(C)C)c(C(F)(F)F)cc2=O)c1F]

CJ-P1 ESI 618.2 (M+H)+. 1H NMR (400 MHz, MeOD) δ 8.07 (s, 1H), 7.15-7.00 (m, 3H), 6.94-6.83 (m, 2H), 6.77 (s, 1H), 5.75 (t, J=8.1 Hz, 1H), 5.63-5.52 (m, 1H), 3.83-3.59 (m, 2H), 2.82-2.72 (m, 2H), 2.52 (s, 6H), 2.29 (d, J=1.3 Hz, 3H), 2.05-1.95 (m, 5H), 1.80 (s, 3H), 1.49-1.37 (m, 1H), 1.01-0.91 (m, 6H).

CJ-P2 ESI 618.2 (M+H)+. 1H NMR (400 MHz, MeOD) δ 8.09 (s, 1H), 7.18-7.00 (m, 3H), 7.00-6.84 (m, 3H), 5.81-5.70 (m, 1H), 5.63-5.46 (m, 1H), 4.10 (d, J=14.4 Hz, 1H), 3.87 (d, J=14.4 Hz, 1H), 2.79-2.55 (m, 8H), 2.34 (d, J=1.5 Hz, 3H), 2.05-1.93 (m, 7H), 1.71-1.61 (m, 1H), 1.48-1.39 (m, 1H), 0.93-0.82 (m, 6H).

4-38. (3S)-3-(4,4'-difluoro-2',5,6'-trimethyl-[1,1'-biphenyl]-3-yl)-3-(2-(5-((dimethylamino)methyl)-2-oxo-4-(trifluoromethyl)pyridin-1(2H)-yl)-4-methylpentanamido)propanoic Acid (Diastereomeric Compounds CK-P1 and CK-P2)

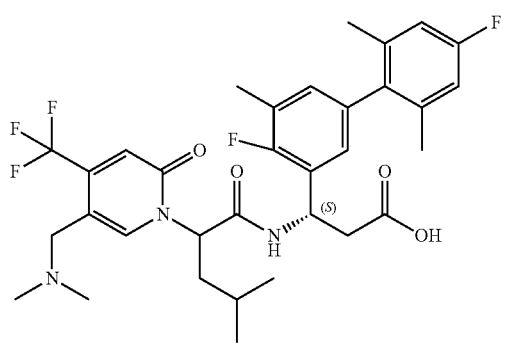

CK-P1 ESI 636.1 (M+H)+. 1H NMR (400 MHz, MeOD) δ 8.06 (s, 1H), 6.95-6.72 (m, 5H), 5.75 (t, J=8.1 Hz, 1H), 5.62-5.56 (m, 1H), 3.79-3.65 (m, 2H), 2.86-2.65 (m, 2H), 2.52 (s, 6H), 2.29 (s, 3H), 2.04-1.93 (m, 5H), 1.81 (s, 3H), 1.50-1.38 (m, 1H), 0.96 (t, J=7.4 Hz, 6H).

CK-P2 ESI 636.1 (M+H)+. 1H NMR (400 MHz, MeOD) δ 8.08 (s, 1H), 6.95-6.88 (m, 3H), 6.85 (d, J=9.6 Hz, 2H), 5.76-5.70 (m, 1H), 5.55 (t, J=7.5 Hz, 1H), 4.08 (d, J=14.4 Hz, 1H), 3.85 (d, J=14.4 Hz, 1H), 2.79-2.52 (m, 8H), 2.34 (s, 3H), 2.03-1.93 (m, 7H), 1.70-1.61 (m, 1H), 1.50-1.38 (m, 1H), 0.95-0.80 (m, 6H).

4-39. (3S)-3-(2-(5-((dimethylamino)methyl)-2-oxo-4-(trifluoromethyl)pyridin-1(2H)-yl)-4-methylpentanamido)-3-(4-fluoro-2',4',5,6'-tetramethyl-[1,1'-biphenyl]-3-yl)propanoic Acid (Diastereomeric Compounds CL-P1 and CL-P2)

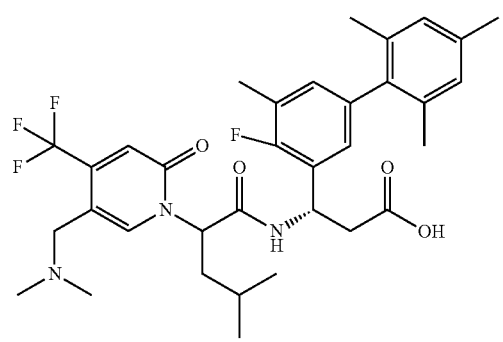

CL-P1 ESI 632.2 (M+H)+. 1H NMR (400 MHz, MeOD) δ 8.05 (s, 1H), 6.92-6.82 (m, 4H), 6.76 (s, 1H), 5.75 (t, J=8.1 Hz, 1H), 5.63-5.50 (m, 1H), 3.78-3.62 (m, 2H), 2.88-2.65 (m, 2H), 2.50 (s, 6H), 2.29 (d, J=3.7 Hz, 6H), 2.03-1.89 (m, 5H), 1.76 (s, 3H), 1.52-1.36 (m, 1H), 0.96 (t, J=7.2 Hz, 6H).

CL-P2 ESI 632.2 (M+H)⁺. ¹H NMR (400 MHz, MeOD) δ 8.09 (s, 1H), 6.95-6.83 (m, 5H), 5.81-5.68 (m, 1H), 5.54 (t, J=7.4 Hz, 1H), 4.09 (d, J=14.4 Hz, 1H), 3.85 (d, J=14.3 Hz, 1H), 2.81-2.52 (m, 8H), 2.32 (d, J=9.8 Hz, 6H), 1.97 (t, J=9.1 Hz, 7H), 1.71-1.58 (m, 1H), 1.50-1.34 (m, 1H), 0.88 (d, J=6.4 Hz, 6H).

4-40. (3S)-3-(4,5-difluoro-2',4',6'-trimethyl-[1,1'-biphenyl]-3-yl)-3-(2-(5-((dimethylamino)methyl)-2-oxo-4-(trifluoromethyl)pyridin-1(2H)-yl)-4-methyl-pentanamido)propanoic Acid (Diastereomeric Compounds CM-P1 and CM-P2)

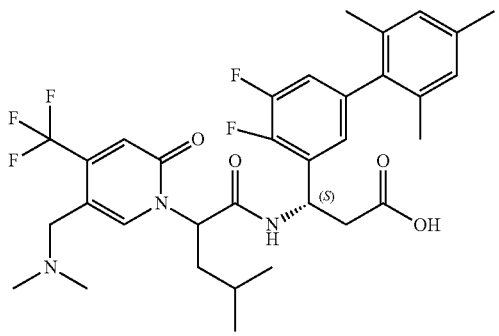

CM-P1 ESI 636.2 (M+H)⁺. ¹H NMR (400 MHz, MeOD) δ 7.99 (s, 1H), 6.92-6.84 (m, 4H), 6.72 (s, 1H), 5.82-5.68 (m, 1H), 5.61-5.55 (m, 1H), 3.61-3.48 (m, 2H), 2.83-2.65 (m, 2H), 2.38 (s, 6H), 2.30 (s, 3H), 2.03-1.92 (m, 5H), 1.73 (s, 3H), 1.49-1.37 (m, 1H), 0.99-0.93 (m, 6H).

CM-P2 ESI 636.2 (M+H)⁺. ¹H NMR (400 MHz, MeOD) δ 8.08 (s, 1H), 7.02-6.84 (m, 5H), 5.77-5.72 (m, 1H), 5.59-5.52 (m, 1H), 4.08 (d, J=14.4 Hz, 1H), 3.85 (d, J=14.4 Hz, 1H), 2.79-2.75 (m, 1H), 2.70-2.54 (m, 7H), 2.31 (s, 3H), 2.02-1.87 (m, 7H), 1.74-1.57 (m, 1H), 1.49-1.37 (m, 1H), 0.91-0.86 (m, 6H).

4-41. (3S)-3-(2-(5-(2-(dimethylamino)ethyl)-3-fluoro-2-oxopyridin-1(2H)-yl)-4-methylpentanamido)-3-(4,4',5-trifluoro-2',6'-dimethyl-[1,1'-biphenyl]-3-yl)propanoic Acid (Diastereomeric Compounds CN-P1 and CN-P2)

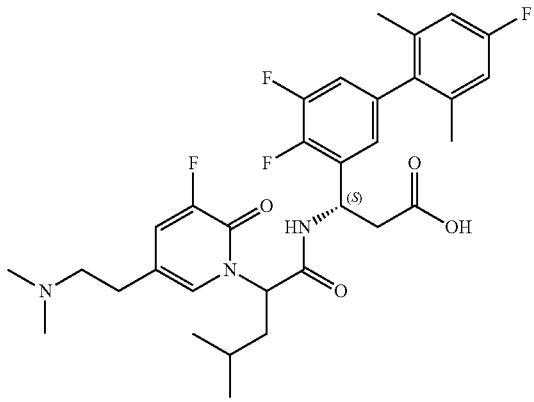

CN-P1 ESI 604.2 (M+H)⁺. ¹H NMR (400 MHz, MeOD) δ 7.44 (s, 1H), 7.34-7.30 (m, 1H), 6.96-6.75 (m, 4H), 5.76-5.71 (m, 1H), 5.60-5.48 (m, 1H), 2.76-2.55 (m, 6H), 2.39 (s, 6H), 2.07-1.90 (m, 5H), 1.84 (s, 3H), 1.49-1.33 (m, 1H), 0.98-0.92 (m, 6H).

CN-P2 ESI 604.2 (M+H)⁺. ¹H NMR (400 MHz, MeOD) δ 7.50 (s, 1H), 7.46-7.10 (m, 1H), 7.04-6.93 (m, 1H), 6.91-6.84 (m, 3H), 5.67-5.57 (m, 2H), 3.47-3.37 (m, 1H), 3.31-3.21 (m, 1H), 3.02-2.91 (m, 1H), 2.90-2.79 (m, 7H), 2.64-2.57 (m, 1H), 2.50-2.42 (m, 1H), 2.07-1.92 (m, 7H), 1.90-1.78 (m, 1H), 1.47-1.31 (m, 1H), 0.94-0.89 (m, 6H).

4-42. (3S)-3-(4,5-difluoro-2',4',6'-trimethyl-[1,1'-biphenyl]-3-yl)-3-(2-(5-(2-(dimethylamino)ethyl)-3-fluoro-2-oxopyridin-1(2H)-yl)-4-methylpentanamido)propanoic Acid (Diastereomeric Compounds CO-P1 and CO-P2)

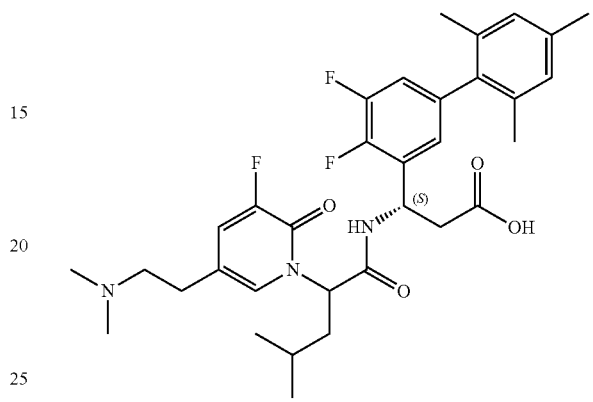

CO-P1 ESI 600.2 (M+H)⁺. ¹H NMR (400 MHz, MeOD) δ 7.49-7.44 (m, 2H), 6.92 (t, J=8.2 Hz, 3H), 6.76 (d, J=6.0 Hz, 1H), 5.65-5.61 (m, 1H), 5.40 (t, J=5.6 Hz, 1H), 3.19-3.15 (m, 2H), 2.90-2.84 (m, 3H), 2.75-2.63 (m, 7H), 2.57-2.52 (m, 1H), 2.31 (s, 3H), 2.03-1.87 (m, 9H), 1.46-1.40 (m, 1H), 0.98-0.91 (m, 6H).

CO-P2 ESI 600.2 (M+H)⁺. ¹H NMR (400 MHz, MeOD) δ 7.37-7.29 (m, 2H), 6.87-6.71 (m, 4H), 5.57-5.42 (m, 2H), 3.34-3.24 (m, 1H), 3.18-3.07 (m, 1H), 2.87-2.81 (m, 1H), 2.73-2.70 (m, 7H), 2.50-2.45 (m, 1H), 2.36-2.30 (m, 1H), 2.19 (s, 3H), 1.96-1.80 (m, 7H), 1.74-1.63 (m, 1H), 1.30-1.25 (m, 1H), 0.81-0.79 (m, 6H).

4-43. (3S)-3-(2-(5-(2-(3-fluoroazetidine-1-yl)ethyl)-4-methyl-2-oxopyridin-1(2H)-yl)-4-methylpentanamido)-3-(4,4',5-trifluoro-2',6'-dimethylbiphenyl-3-yl)propanoic Acid (Diastereomeric Compounds CP-P1 and CP-P2)

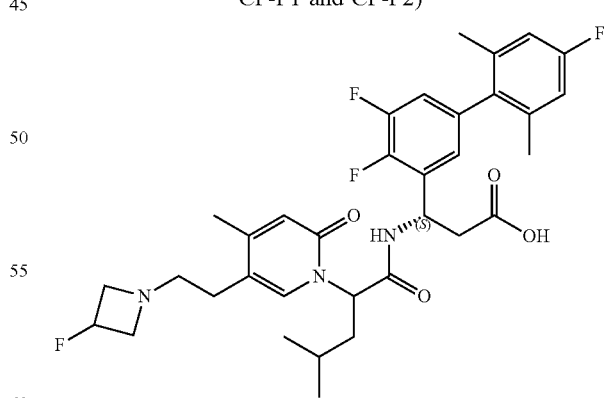

CP-P1 ESI 630.2 (M+H)⁺. 1H NMR (400 MHz, MeOD) δ 7.49 (s, 1H), 6.99-6.89 (m, 1H), 6.89-6.76 (m, 3H), 6.29 (s, 1H), 5.66-5.50 (m, 2H), 5.40-5.10 (m, 1H), 4.14-3.90 (m, 2H), 3.86-3.55 (m, 2H), 3.03 (s, 2H), 2.86-2.53 (m, 4H), 2.23 (s, 3H), 2.06-1.90 (m, 5H), 1.86 (s, 3H), 1.49-1.32 (m, 1H), 1.02-0.84 (m, 6H).

CP-P2 ESI 630.2 (M+H)⁺. 1H NMR (400 MHz, MeOD) δ 7.49 (s, 1H), 7.09-6.86 (m, 4H), 6.44 (s, 1H), 5.72-5.55 (m, 2H), 5.30 (d, J=57.8 Hz, 1H), 4.28 (s, 2H), 3.93 (s, 2H), 3.19 (s, 2H), 2.87-2.50 (m, 4H), 2.25 (s, 3H), 2.04 (s, 6H), 1.93-1.73 (m, 2H), 1.47-1.28 (m, 1H), 0.91-0.85 (m, 6H).

4-44. (3S)-3-(5-chloro-4,4'-difluoro-2',6'-dimethylbiphenyl-3-yl)-3-(2-(5-(2-(dimethylamino)ethyl)-2-oxo-4-(trifluoromethyl)pyridin-1(2H)-yl)-4-methylpentanamido)propanoic Acid (Diastereomeric Compounds CQ-P1 and CQ-P2)

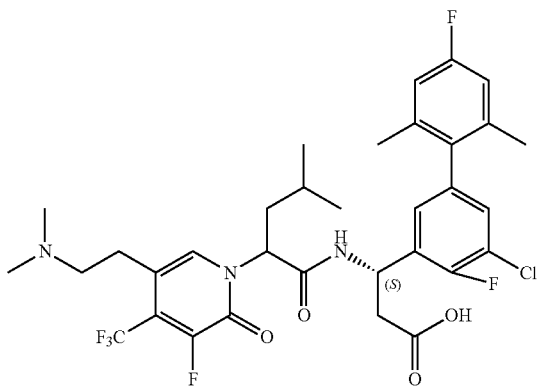

CQ-P1 ESI 670.2 (M+H)⁺. 1H NMR (400 MHz, MeOD) δ 7.90 (s, 1H), 7.13-7.11 (m, 1H), 7.04-7.02 (m, 1H), 6.88-6.81 (m, 2H), 6.74 (s, 1H), 5.69-5.65 (m, 1H), 5.57-5.53 (m, 1H), 3.16-3.10 (m, 2H), 2.97-2.94 (m, 2H), 2.80 (s, 6H), 2.74-2.71 (m, 2H), 2.02-1.98 (m, 5H), 1.84 (s, 3H), 1.47-1.40 (m, 1H), 0.98-0.93 (m, 6H).

CQ-P2 ESI 670.2 (M+H)⁺. 1H NMR (400 MHz, MeOD) δ 7.86 (s, 1H), 7.20-7.18 (m, 1H), 7.07 (d, J=6.1 Hz, 1H), 6.88 (d, J=11.2 Hz, 3H), 5.73-5.67 (m, 1H), 5.63 (t, J=7.6 Hz, 1H), 3.30-3.18 (m, 2H), 3.01 (t, J=6.9 Hz, 2H), 2.85 (s, 6H), 2.69-2.60 (m, 1H), 2.58-2.52 (m, 1H), 2.03-1.95 (m, 7H), 1.77-1.70 (m, 1H), 1.41-1.36 (m, 1H), 0.91-0.89 (m, 6H).

4-45. (3S)-3-(5-chloro-4,4'-difluoro-2',6'-dimethylbiphenyl-3-yl)-3-(2-(5-(2-(3-fluoroazetidine-1-yl)ethyl)-4-methyl-2-oxopyridin-1(2H)-yl)-4-methylpentanamido)propanoic Acid (Diastereomeric Compounds CR-P1 and CR-P2)

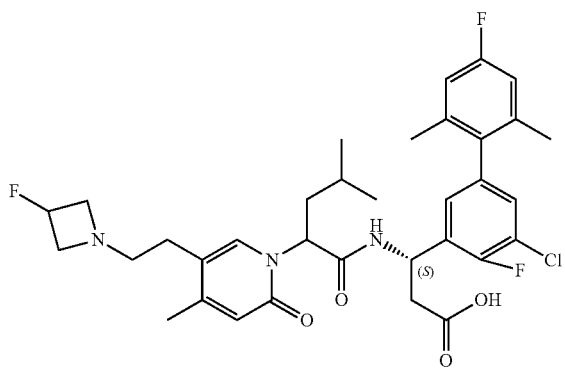

CR-P1 ESI 646.2 (M+H)⁺. 1H NMR (400 MHz, MeOD) δ 7.50 (s, 1H), 7.15-7.13 (m, 1H), 6.99-6.97 (m, 1H), 6.88-6.85 (m, 2H), 6.29 (s, 1H), 5.64-5.49 (m, 2H), 5.32-5.18 (m, 1H), 4.11-4.07 (m, 2H), 3.85-3.72 (m, 2H), 3.10 (t, J=6.9 Hz, 2H), 2.82-2.62 (m, 4H), 2.24 (s, 3H), 2.09-1.90 (m, 5H), 1.89 (d, J=8.2 Hz, 3H), 1.43-1.38 (m, 1H), 0.96-0.92 (m, 6H).

CR-P2 ESI 646.2 (M+H)⁺. 1H NMR (400 MHz, MeOD) δ 7.45 (s, 1H), 7.21-7.18 (m, 1H), 7.08-7.06 (m, 1H), 6.89 (d, J=9.6 Hz, 2H), 6.43 (s, 1H), 5.73-5.53 (m, 2H), 5.43-5.25 (m, 1H), 4.44-4.41 (m, 2H), 4.16-4.01 (m, 2H), 3.39-3.36 (m, 2H), 2.91-2.87 (m, 1H), 2.73-2.62 (m, 2H), 2.52-2.49 (m, 1H), 2.25 (s, 3H), 2.03 (s, 6H), 1.98-1.88 (m, 1H), 1.81-1.72 (m, 1H), 1.44-1.33 (m, 1H), 0.91-0.89 (m, 6H).

4-46. (3S)-3-(2-(5-(2-(dimethylamino)ethyl)-2-oxo-4-(trifluoromethyl)pyridin-1(2H)-yl)-4-methylpentanamido)-3-(4,4',5-trifluoro-2',6'-dimethylbiphenyl-3-yl)propanoic Acid (Diastereomeric Compounds CS-P1 and CS-P2)

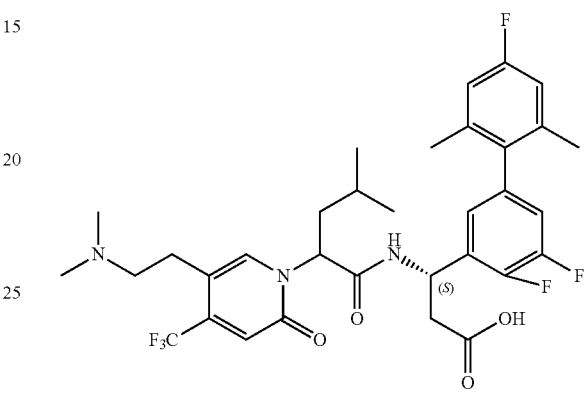

CS-P1 ESI 654.2 (M+H)⁺. 1H NMR (400 MHz, MeOD) δ 7.89 (s, 1H), 6.98-6.78 (m, 4H), 6.75 (s, 1H), 5.69-5.65 (m, 1H), 5.59-5.56 (m, 1H), 3.15-3.06 (m, 2H), 2.95 (d, J=6.2 Hz, 2H), 2.77 (s, 6H), 2.74-2.71 (m, 2H), 2.13-1.91 (m, 5H), 1.85 (s, 3H), 1.50-1.40 (m, 1H), 0.98-0.94 (m, 6H).

CS-P2 ESI 654.2 (M+H)⁺. 1H NMR (400 MHz, MeOD) δ 7.86 (s, 1H), 7.05-6.96 (m, 1H), 6.95-6.83 (m, 4H), 5.73-5.69 (m, 1H), 5.63 (t, J=7.7 Hz, 1H), 3.28-3.14 (m, 2H), 2.99 (t, J=7.0 Hz, 2H), 2.82 (s, 6H), 2.69-2.64 (m, 1H), 2.62-2.52 (m, 1H), 2.03 (d, J=2.1 Hz, 6H), 1.99-1.94 (m, 1H), 1.77-1.72 (m, 1H), 1.45-1.31 (m, 1H), 0.91-0.89 (m, 6H).

4-47. (3S)-3-(5-chloro-4,4'-difluoro-2',6'-dimethylbiphenyl-3-yl)-3-(2-(5-(2-(3-fluoroazetidine-1-yl)ethyl)-2-oxopyridin-1(2H)-yl)-4-methylpentanamido)propanoic Acid (Diastereomeric Compounds CT-P1 and CT-P2)

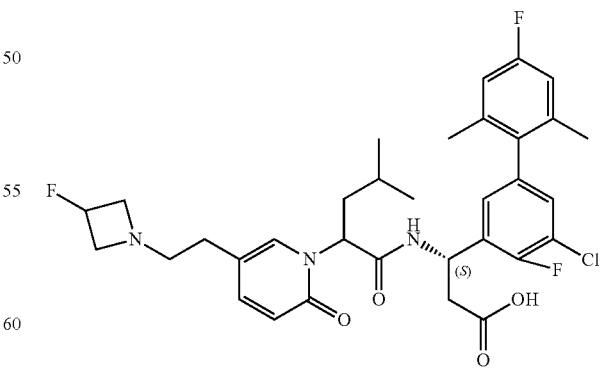

CT-P1 ESI 632.2 (M+H)⁺. 1H NMR (400 MHz, MeOD) δ 7.59 (s, 1H), 7.46-7.43 (m, 1H), 7.15-7.13 (m, 1H), 7.00-6.92 (m, 1H), 6.87 (d, J=9.6 Hz, 2H), 6.45 (d, J=9.3 Hz, 1H), 5.68-5.57 (m, 1H), 5.51 (t, J=6.2 Hz, 1H), 5.38-5.16 (m, 1H), 4.25-4.04 (m, 2H), 3.96-3.76 (m, 2H), 3.25-3.13

(m, 2H), 2.83-2.58 (m, 4H), 2.08-1.92 (m, 5H), 1.88 (s, 3H), 1.47-1.40 (m, 1H), 0.97-0.92 (m, 6H).

CT-P2 ESI 632.2 (M+H)⁺. 1H NMR (400 MHz, MeOD) δ 7.54 (s, 1H), 7.49 (d, J=8.8 Hz, 1H), 7.20-7.18 (m, 1H), 7.04 (d, J=4.5 Hz, 1H), 6.88 (d, J=9.6 Hz, 2H), 6.56 (d, J=9.1 Hz, 1H), 5.71-5.57 (m, 2H), 5.34 (d, J=59.0 Hz, 1H), 4.40 (s, 2H), 4.08 (s, 2H), 3.42 (s, 1H), 2.70 (d, J=52.7 Hz, 3H), 2.52 (s, 1H), 2.03 (d, J=3.5 Hz, 6H), 1.99-1.93 (m, 2H), 1.88-1.76 (m, 1H), 1.49-1.31 (m, 1H), 0.91 (t, J=6.7 Hz, 6H).

4-48. (3S)-3-(4,4'-difluoro-2',5,6'-trimethylbiphenyl-3-yl)-3-(2-(5-(2-(dimethylamino)ethyl)-3-fluoro-2-oxopyridin-1(2H)-yl)-4-methylpentanamido)propanoic Acid (Diastereomeric Compounds CU-P1 and CU-P2)

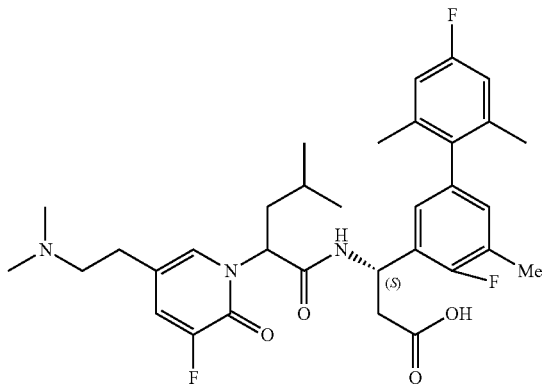

CU-P1 ESI 600.3 (M+H)⁺. 1H NMR (400 MHz, MeOD) δ 7.52 (s, 1H), 7.47-7.44 (m, 1H), 6.91-6.81 (m, 3H), 6.78 (d, J=6.8 Hz, 1H), 5.64-5.60 (m, 1H), 5.40 (t, J=5.6 Hz, 1H), 3.36 (d, J=6.1 Hz, 1H), 3.24-3.12 (m, 1H), 2.97-2.77 (m, 2H), 2.73 (s, 6H), 2.70-2.61 (m, 1H), 2.57-2.52 (m, 1H), 2.30 (d, J=1.6 Hz, 3H), 2.12-1.96 (m, 5H), 1.95 (s, 3H), 1.52-1.37 (m, 1H), 0.97-0.91 (m, 6H).

CU-P2 ESI 600.2 (M+H)⁺. 1H NMR (400 MHz, MeOD) δ 7.50 (s, 1H), 7.45-7.42 (m, 1H), 6.89 (t, J=6.1 Hz, 2H), 6.84 (d, J=9.6 Hz, 2H), 5.66-5.62 (m, 1H), 5.59-5.56 (m, 1H), 3.47-3.36 (m, 1H), 3.30-3.25 (m, 1H), 3.00-2.94 (m, 1H), 2.90-2.77 (m, 7H), 2.61-2.56 (m, 1H), 2.46-2.40 (m, 1H), 2.32 (d, J=1.8 Hz, 3H), 2.09-1.94 (m, 7H), 1.87-1.79 (m, 1H), 1.48-1.37 (m, 1H), 0.93-0.90 (m, 6H).

4-49. (3S)-3-(5-chloro-4,4'-difluoro-2',6'-dimethylbiphenyl-3-yl)-3-(2-(5-(2-(dimethylamino)ethyl)-3-fluoro-2-oxopyridin-1(2H)-yl)-4-methylpentanamido)propanoic Acid (Diastereomeric Compounds CV-P1 and CV-P2)

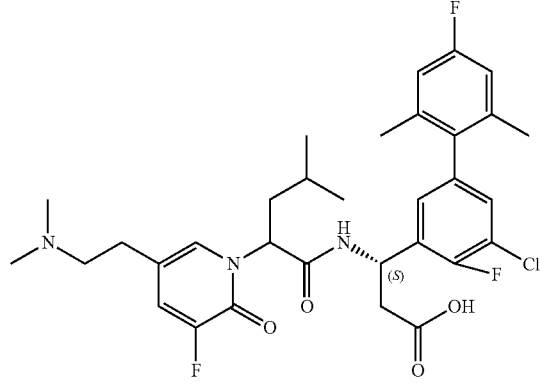

CV-P1 ESI 620.2 (M+H)⁺. 1H NMR (400 MHz, MeOD) δ 7.53 (s, 1H), 7.46-7.43 (m, 1H), 7.15-7.12 (m, 1H), 6.95-6.93 (m, 1H), 6.87 (d, J=9.6 Hz, 2H), 5.65-5.61 (m, 1H), 5.42 (t, J=5.8 Hz, 1H), 3.31-3.26 (m, 1H), 3.20-3.15 (m, 1H), 2.96-2.81 (m, 2H), 2.75 (s, 6H), 2.70-2.65 (m, 1H), 2.59-2.54 (m, 1H), 2.19-1.78 (m, 8H), 1.46-1.40 (m, 1H), 0.97-0.91 (m, 6H).

CV-P2 ESI 620.2 (M+H)⁺. 1H NMR (400 MHz, MeOD) δ 7.50 (s, 1H), 7.45-7.42 (m, 1H), 7.18-7.16 (m, 1H), 7.04-7.02 (m, 1H), 6.88 (d, J=9.6 Hz, 2H), 5.67-5.63 (m, 1H), 5.59-5.56 (m, 1H), 3.46-3.36 (m, 1H), 3.29-3.22 (m, 1H), 2.98-2.92 (m, 1H), 2.86-2.84 (m, 1H), 2.82 (s, 6H), 2.62-2.58 (m, 1H), 2.51-2.41 (m, 1H), 2.03 (d, J=1.5 Hz, 6H), 1.97 (t, J=7.1 Hz, 1H), 1.90-1.78 (m, 1H), 1.41-1.36 (m, 1H), 0.97-0.74 (m, 6H).

4-50. (3S)-3-(4,4'-difluoro-2',5,6'-trimethylbiphenyl-3-yl)-3-(2-(5-(2-(dimethylamino)ethyl)-4-methyl-2-oxopyridin-1(2H)-yl)-4-methylpentanamido)propanoic Acid (Diastereomeric Compounds CW-P1 and CW-P2)

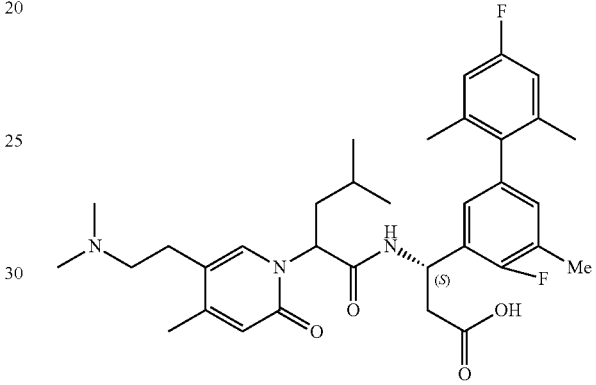

CW-P1 ESI 596.3 (M+H)⁺. 1H NMR (400 MHz, MeOD) δ 7.59 (s, 1H), 6.83 (t, J=7.2 Hz, 4H), 6.32 (s, 1H), 5.70-5.56 (m, 1H), 5.54-5.47 (m, 1H), 3.21-3.06 (m, 2H), 2.95-2.83 (m, 2H), 2.79 (s, 6H), 2.73-2.55 (m, 2H), 2.35-2.20 (m, 6H), 2.07-1.91 (m, 5H), 1.85 (s, 3H), 1.50-1.29 (m, 1H), 1.02-0.83 (m, 6H).

CW-P2 ESI 596.3 (M+H)⁺. 1H NMR (400 MHz, MeOD) δ 7.57 (s, 1H), 6.99-6.78 (m, 4H), 6.43 (s, 1H), 5.71-5.53 (m, 2H), 3.28-3.06 (m, 2H), 2.97-2.85 (m, 2H), 2.81 (s, 6H), 2.66-2.56 (m, 1H), 2.56-2.40 (m, 1H), 2.36-2.24 (m, 6H), 2.05-1.89 (m, 7H), 1.86-1.72 (m, 1H), 1.43-1.28 (m, 1H), 0.89 (t, J=5.2 Hz, 6H).

4-51. (3S)-3-(4'-chloro-4-fluoro-2',5,6'-trimethylbiphenyl-3-yl)-3-(2-(5-(2-(dimethylamino)ethyl)-4-methyl-2-oxopyridin-1(2H)-yl)-4-methylpentanamido)propanoic Acid (Diastereomeric Compounds CX-P1 and CX-P2)

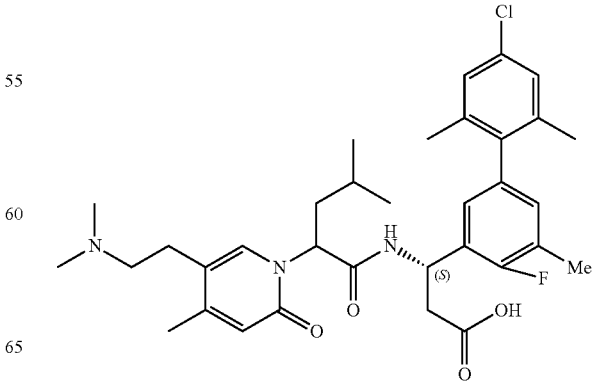

CX-P1 ESI 612.2 (M+H)⁺. 1H NMR (400 MHz, MeOD) δ 7.58 (s, 1H), 7.11 (d, J=2.5 Hz, 2H), 6.92-6.76 (m, 2H), 6.32 (s, 1H), 5.61-5.41 (m, 2H), 3.25-3.05 (m, 2H), 2.88 (t, J=7.3 Hz, 2H), 2.78 (s, 6H), 2.71-2.54 (m, 2H), 2.28 (d, J=13.0 Hz, 6H), 2.05-1.92 (m, 5H), 1.88 (s, 3H), 1.48-1.32 (m, 1H), 1.04-0.85 (m, 6H).

CX-P2 ESI 612.2 (M+H)⁺. 1H NMR (400 MHz, MeOD) δ 7.55 (s, 1H), 7.13 (s, 2H), 6.93-6.84 (m, 2H), 6.42 (s, 1H), 5.70-5.54 (m, 2H), 3.24-3.11 (m, 2H), 2.99-2.76 (m, 8H), 2.64-2.42 (m, 2H), 2.36-2.20 (m, 6H), 2.03-1.90 (m, 7H), 1.83-1.72 (m, 1H), 1.47-1.28 (m, 1H), 0.90 (t, J=6.2 Hz, 6H).

4-52. (3S)-3-(2-(5-(2-(dimethylamino)ethyl)-3-fluoro-2-oxopyridin-1(2H)-yl)-4-methylpentanamido)-3-(4-fluoro-2',4',5,6'-tetramethyl-[1,1'-biphenyl]-3-yl)propanoic Acid (Diastereomeric Compounds CY-P1 and CY-P2)

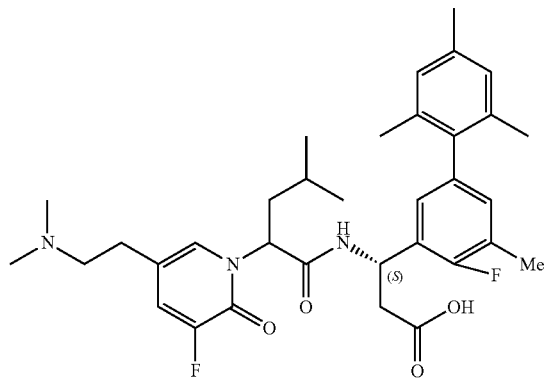

CY-P1 ESI 596.3 (M+H)⁺. ¹H NMR (400 MHz, MeOD) δ 7.59-7.37 (m, 2H), 6.96-6.64 (m, 4H), 5.76-5.58 (m, 1H), 5.39 (t, J=5.5 Hz, 1H), 3.42-3.25 (m, 1H), 3.23-3.06 (m, 1H), 2.96-2.76 (m, 2H), 2.73-2.46 (m, 8H), 2.41-2.22 (m, 6H), 2.05-1.88 (m, 8H), 1.44 (m, J=13.7, 6.7 Hz, 1H), 0.93 (m, J=17.3, 6.6 Hz, 6H).

CY-P2 ESI 596.3 (M+H)⁺. 1H NMR (400 MHz, MeOD) δ 7.51 (s, 1H), 7.42 (m, J=10.3, 2.1 Hz, 1H), 6.89 (m, J=7.0, 4.6 Hz, 4H), 5.62 (m, J=14.0, 9.4, 5.4 Hz, 2H), 3.43-3.30 (m, 1H), 3.23 (s, 1H), 2.93 (m, J=9.6, 4.9 Hz, 1H), 2.87-2.75 (m, 7H), 2.59 (m, J=14.9, 4.0 Hz, 1H), 2.44 (m, J=14.8, 10.1 Hz, 1H), 2.34-2.22 (m, 6H), 2.05-1.91 (m, 7H), 1.84-1.72 (m, 1H), 1.46-1.22 (m, 1H), 0.91 (m, J=6.6, 3.1 Hz, 6H).

4-53. (3S)-3-(4-fluoro-2',4',5,6'-tetramethyl-[1,1'-biphenyl]-3-yl)-3-(2-(3-fluoro-5-(2-((R)-3-fluoropyrrolidin-1-yl)ethyl)-2-oxopyridin-1(2H)-yl)-4-methylpentanamido)propanoic Acid (Diastereomeric Compounds CZ-P1 and CZ-P2)

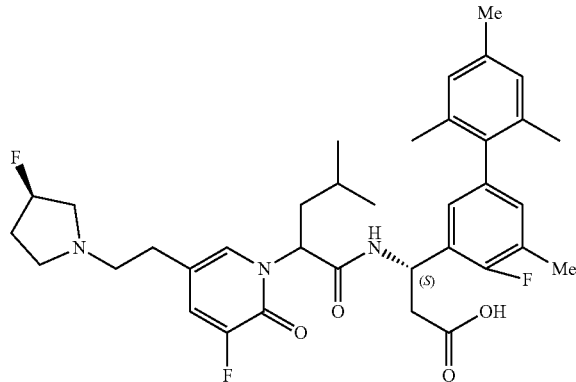

CZ-P1 ESI 640.2 (M+H)⁺. 1H NMR (400 MHz, MeOD) δ 7.50 (s, 1H), 7.41-7.31 (m, 1H), 6.91 (s, 2H), 6.85 (d, J=7.0 Hz, 1H), 6.79 (d, J=6.7 Hz, 1H), 5.70 (s, 1H), 5.49 (s, 1H), 5.24 (d, J=53.7 Hz, 1H), 3.26-3.00 (m, 5H), 2.88-2.56 (m, 4H), 2.41-2.13 (m, 9H), 2.07-1.90 (m, 5H), 1.85 (s, 3H), 1.53-1.26 (m, 1H), 1.05-0.80 (m, 6H).

CZ-P2 ESI 640.2 (M+H)⁺. 1H NMR (500 MHz, MeOD) δ 7.49 (s, 1H), 7.47-7.36 (m, 1H), 6.90 (d, J=8.8 Hz, 4H), 5.67 (t, J=7.7 Hz, 1H), 5.61-5.52 (m, 1H), 5.33 (d, J=54.6 Hz, 1H), 3.73-3.38 (m, 5H), 3.28 (s, 1H), 2.97-2.76 (m, 2H), 2.65-2.43 (m, 2H), 2.41-2.19 (m, 6H), 2.07-1.88 (m, 7H), 1.84-1.73 (m, 1H), 1.51-1.20 (m, 1H), 0.91 (d, J=6.5 Hz, 6H).

4-54. (3S)-3-(2-(5-(2-(dimethylamino)ethyl)-3-methyl-2-oxopyridin-1(2H)-yl)-4-methylpentanamido)-3-(4-fluoro-2',4',5,6'-tetramethyl-[1,1'-biphenyl]-3-yl)propanoic Acid (Diastereomeric Compounds DA-P1 and DA-P2)

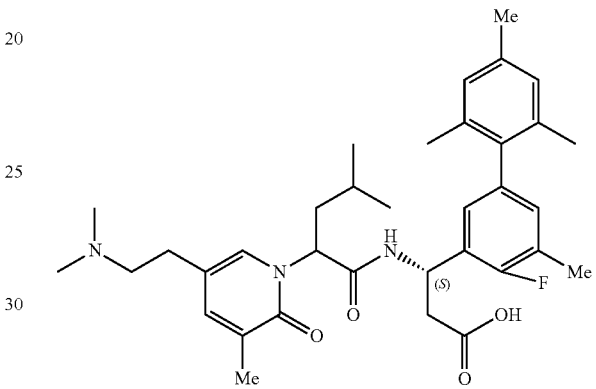

DA-P1 ESI 592.3 (M+H)⁺. 1H NMR (400 MHz, MeOD) δ 7.35 (S, 1H), 7.32 (S, 1H), 6.80 (d, J=8.4 Hz, 2H), 6.73 (d, J=5.5 Hz, 1H), 6.59 (d, J=6.7 Hz, 1H), 5.48-5.46 (m, 1H), 5.23 (t, J=5.1 Hz, 1H), 3.08-2.98 (m, 1H), 2.68-2.67 (m, 2H), 2.56 (s, 6H), 2.51-2.35 (m, 3H), 2.25-2.11 (m, 6H), 1.97-1.74 (m, 1H), 1.36-1.24 (m, 1H), 0.88-0.76 (m, 6H).

DA-P2 ESI 592.3 (M+H)⁺. ¹H NMR (400 MHz, MeOD) δ 7.40 (s, 1H), 7.29 (s, 1H), 6.78-6.74 (m, 3H), 6.67 (d, J=7.0 Hz, 1H), 5.52-5.48 (m, 1H), 5.42-5.39 (m, 1H), 3.33-3.27 (m, 1H), 3.20-3.14 (m, 1H), 2.85-2.61 (m, 8H), 2.49-2.44 (m, 1H), 2.33-2.27 (m, 1H), 2.18 (s, 6H), 1.97-1.67 (m, 1H), 1.38-1.24 (m, 1H), 0.82-0.77 (m, 6H).

4-55. (3S)-3-(4,4'-difluoro-2',6'-dimethyl-5-(trifluoromethyl)-[1,1'-biphenyl]-3-y)-3-(2-(5-(2-(dimethylamino)ethyl)-3-fluoro-2-oxopyridin-1(2H)-yl)-4-methylpentanamido)propanoic Acid (Diastereomeric Compounds DB-P1 and DB-P2)

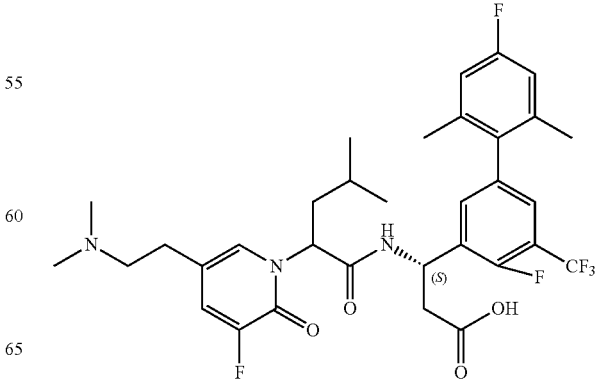

DB-P1 ESI 654.3 (M+H)⁺. 1H NMR (400 MHz, MeOD) δ 7.55 (s, 1H), 7.50-7.37 (m, 1H), 7.40-7.25 (m, 2H), 6.89 (d, J=9.6 Hz, 2H), 5.73-5.55 (m, 1H), 5.47 (t, J=5.9 Hz, 1H), 3.27-3.13 (m, 1H), 2.98-2.82 (m, 3H), 2.78 (s, 6H), 2.73-2.64 (m, 1H), 2.63-2.50 (m, 1H), 2.13-1.97 (m, 5H), 1.93 (s, 3H), 1.42 (s, 1H), 1.11-0.79 (m, 6H).

DB-P2 ESI 654.3 (M+H)⁺. 1H NMR (400 MHz, MeOD) δ 7.51 (s, 1H), 7.48-7.41 (m, 1H), 7.38 (t, J=6.0 Hz, 2H), 6.90 (d, J=9.6 Hz, 2H), 5.76-5.43 (m, 2H), 3.42 (d, J=10.1 Hz, 1H), 3.28 (d, J=12.8 Hz, 1H), 2.96 (d, J=9.5 Hz, 1H), 2.85 (d, J=7.2 Hz, 6H), 2.74-2.54 (m, 1H), 2.55-2.34 (m, 1H), 2.15-1.93 (m, 6H), 1.93-1.72 (m, 1H), 1.52-1.27 (m, 1H), 0.92 (t, J=6.5 Hz, 6H).

4-56. (3S)-3-(4-fluoro-2',4',5,6'-tetramethylbiphenyl-3-yl)-3-(2-(3-fluoro-5-(2-(3-fluoroazetidine-1-yl)ethyl)-2-oxopyridin-1(2H)-yl)-4-methylpentanamido)propanoic Acid (Diastereomeric Compounds DC-P1 and DC-P2)

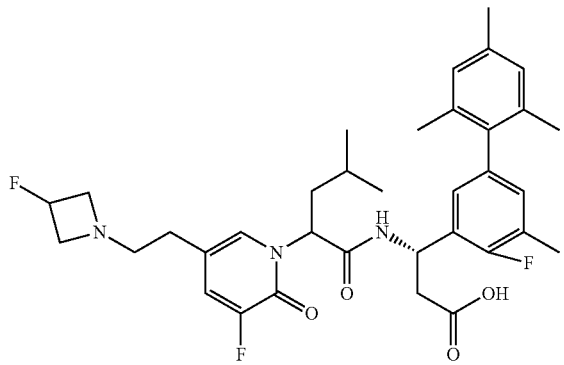 [SMILES: Cc1cc(C)c(-c2cc(C)c(F)c([C@H](CC(=O)O)NC(=O)C(CC(C)C)n3cc(CCN4CC(F)C4)cc(F)c3=O)c2)c(C)c1]

DC-P1 ESI 626.3 (M+H)⁺. ¹H NMR (400 MHz, MeOD) δ 7.45-7.33 (m, 2H), 6.96-6.85 (m, 3H), 6.83-6.75 (m, 1H), 5.69 (t, J=8.1 Hz, 1H), 5.52-5.45 (m, 1H), 5.30-5.10 (m, 1H), 4.23-4.09 (m, 1H), 4.02-3.89 (m, 1H), 3.78-3.62 (m, 2H), 3.26-3.16 (m, 2H), 2.78-2.56 (m, 4H), 2.36-2.25 (m, 6H), 2.00-1.92 (m, 5H), 1.88 (s, 3H), 1.48-1.39 (m, 1H), 0.98-0.86 (m, 6H).

DC-P2 ESI 626.3 (M+H)⁺. 1H NMR (400 MHz, MeOD) δ 7.45-7.35 (m, 2H), 6.97-6.86 (m, 4H), 5.76-5.62 (m, 2H), 5.42-5.20 (m, 1H), 4.49-4.28 (m, 2H), 4.12-3.95 (m, 2H), 3.44-3.36 (m, 2H), 2.78-2.63 (m, 2H), 2.67-2.52 (m, 1H), 2.61-2.52 (m, 1H), 2.37-2.25 (m, 6H), 2.01-1.91 (m, 7H), 1.85-1.69 (m, 1H), 1.43-1.36 (m, 1H), 0.96-0.85 (m, 6H).

4-57. (3S)-3-(2'-chloro-4,4'-difluoro-5,6'-dimethyl-[1,1'-biphenyl]-3-yl)-3-(2-(3-fluoro-5-(2-(3-fluoroazetidine-1-yl)ethyl)-2-oxopyridin-1(2H)-yl)-4-methylpentanamido)propanoic Acid (Diastereomeric Compounds DD-P1 and DD-P2)

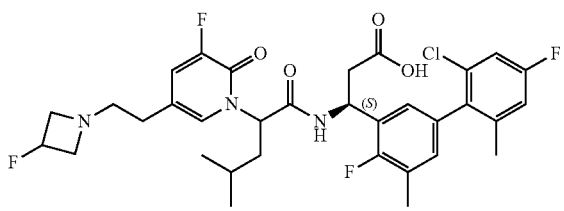

DD-P1 ESI 650.2 (M+H)⁺. ¹H NMR (400 MHz, MeOD) δ 7.43-7.34 (m, 2H), 7.17-7.13 (m, 1H), 7.06-7.01 (m, 1H), 6.89-6.85 (m, 1H), 5.72-5.67 (m, 1H), 5.54-5.49 (m, 1H), 5.32-5.09 (m, 1H), 4.15-3.65 (m, 4H), 3.19-3.10 (m, 2H), 2.78-2.60 (m, 4H), 2.31 (s, 3H), 2.08-1.92 (m, 5H), 1.49-1.39 (m, 1H), 0.97-0.93 (m, 6H).

DD-P2 ESI 650.2 (M+H)⁺. ¹H NMR (400 MHz, MeOD) δ 7.39-7.36 (m, 2H), 7.15 (d, J=8.5 Hz, 1H), 7.08-6.96 (m, 3H), 5.73-5.61 (m, 2H), 5.41-5.22 (m, 1H), 4.48-4.28 (m, 2H), 4.11-3.94 (m, 2H), 3.42-3.33 (m, 2H), 2.80-2.47 (m, 4H), 2.34 (d, J=1.8 Hz, 3H), 2.09 (d, J=2.7 Hz, 3H), 2.03-1.90 (m, 1H), 1.83-1.72 (m, 1H), 1.44-1.30 (m, 1H), 0.94-0.89 (m, 6H).

4-58. (3S)-3-(2-(3-fluoro-5-(2-(3-fluoroazetidine-1-yl)ethyl)-2-oxopyridin-1(2H)-yl)-4-methylpentanamido)-3-(2',4,4'-trifluoro-5,6'-dimethylbiphenyl-3-yl)propanoic Acid (Diastereomeric Compounds DE-P1 and DE-P2)

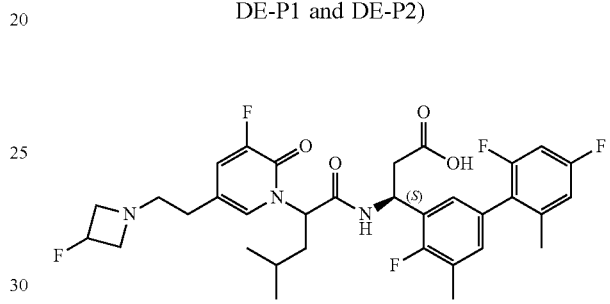

DE-P1 ESI 634.2 (M+H)⁺. 1H NMR (400 MHz, MeOD) δ 7.43 (s, 1H), 7.36 (d, J=10.3 Hz, 1H), 7.02 (d, J=6.8 Hz, 1H), 6.98-6.89 (m, 2H), 6.85 (t, J=9.2 Hz, 1H), 5.69 (t, J=8.1 Hz, 1H), 5.53-5.50 (m, 1H), 5.30-5.08 (m, 1H), 4.09-3.99 (m, 2H), 3.77-3.63 (m, 2H), 3.15-3.12 (m, 2H), 2.79-2.69 (m, 2H), 2.66-2.62 (m, 2H), 2.31 (s, 3H), 2.09 (s, 3H), 1.97 (t, J=7.6 Hz, 2H), 1.51-1.37 (m, 1H), 0.98-0.93 (m, 6H).

DE-P2 ESI 634.2 (M+H)⁺. 1H NMR (400 MHz, MeOD) δ 7.43-7.32 (m, 2H), 7.06 (d, J=6.7 Hz, 2H), 6.93 (d, J=9.3 Hz, 1H), 6.88-6.83 (m, 1H), 5.74-5.59 (m, 2H), 5.39-5.24 (m, 1H), 4.42-4.32 (m, 2H), 4.10-3.88 (m, 2H), 3.40-3.37 (m, 2H), 2.81-2.71 (m, 2H), 2.65-2.60 (m, 1H), 2.55-2.48 (m, 1H), 2.34 (d, J=1.6 Hz, 3H), 2.16 (s, 3H), 2.03-1.93 (m, 1H), 1.86-1.75 (m, 1H), 1.45-1.33 (m, 1H), 0.93-0.91 (m, 6H).

4-59. (3S)-3-(2-(5-(2-(azetidin-1-yl)ethyl)-2-oxo-4-(trifluoromethyl)pyridin-1(2H)-yl)-4-methylpentanamido)-3-(2'-cyclopropyl-4,4'-difluoro-5,6'-dimethyl-[1,1'-biphenyl]-3-yl)propanoic Acid (Diastereomeric Compounds DF-P1 and DF-P2)

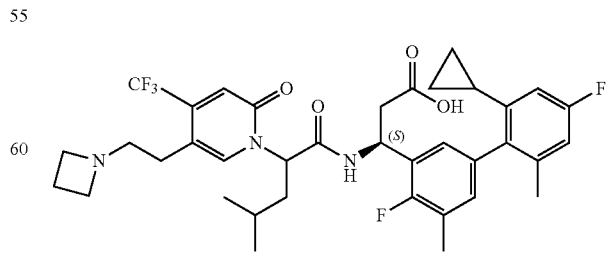

DF-P1 ESI 688.2 (M+H)⁺. ¹H NMR (400 MHz, MeOD) δ 7.84 (s, 1H), 6.95 (dd, J=19.9, 7.2 Hz, 2H), 6.86-6.64 (m,

2H), 6.55-6.23 (m, 1H), 5.75-5.49 (m, 2H), 3.85 (t, J=7.7 Hz, 4H), 3.33 (m, J=3.2, 1.6 Hz, 2H), 3.13 (m, J=6.8 Hz, 2H), 2.90-2.58 (m, 2H), 2.51-2.21 (m, 5H), 2.01 (d, J=5.3 Hz, 4H), 1.87 (s, 1H), 1.40 (s, 2H), 1.07-0.85 (m, 6H), 0.75 (m, J=8.6, 3.5 Hz, 1H), 0.66-0.43 (m, 3H).

DF-P2 ESI 688.2 (M+H)$^+$. $^1$H NMR (400 MHz, MeOD) δ 7.74 (d, J=11.5 Hz, 1H), 6.94 (m, J=46.9, 28.6, 8.1 Hz, 4H), 6.50 (d, J=10.4 Hz, 1H), 5.78 (m, J=11.0, 3.1 Hz, 1H), 5.62 (m, J=7.3 Hz, 1H), 4.13 (m, J=8.0 Hz, 4H), 3.50-3.32 (m, 2H), 2.94 (d, J=16.3 Hz, 1H), 2.81 (d, J=7.7 Hz, 2H), 2.68-2.61 (m, 1H), 2.57-2.42 (m, 3H), 2.34 (d, J=1.1 Hz, 3H), 2.05-1.79 (m, 4H), 1.65 (m, J=13.9, 7.1 Hz, 1H), 1.50-1.30 (m, 2H), 0.88 (d, J=6.6 Hz, 6H), 0.74 (m, J=14.0, 7.3 Hz, 2H), 0.60 (m, J=6.4, 5.0 Hz, 2H).

4-60. (3S)-3-((3R)-2-(5-(2-(dimethylamino)ethyl)-2-oxo-4-(trifluoromethyl)pyridin-1(2H)-yl)-3-methyl-pentanamido)-3-(4-fluoro-2',4',5,6'-tetramethylbi-phenyl-3-yl)propanoic Acid (Diastereomeric Compounds DG-P1 and DG-P2)

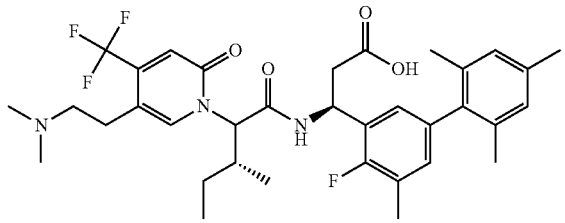

DG-P1 ESI 646.2 (M+H)$^+$. 1H NMR (400 MHz, MeOD) δ 7.94 (s, 1H), 6.89 (s, 1H), 6.82-6.75 (m, 3H), 6.66 (s, 1H), 5.65-5.53 (m, 1H), 5.33 (d, J=11.3 Hz, 1H), 3.05-2.83 (m, 5H), 2.82-2.62 (m, 6H), 2.40-2.18 (m, 8H), 2.03-1.88 (m, 3H), 1.78-1.67 (m, 1H), 1.63 (s, 3H), 1.38-1.21 (m, 1H), 1.07-0.96 (m, 3H), 0.75 (d, J=6.5 Hz, 3H).

DG-P2 ESI 646.2 (M+H)+. 1H NMR (400 MHz, MeOD) δ 7.92 (s, 1H), 6.91-6.72 (m, 5H), 5.69-5.52 (m, 1H), 5.21 (d, J=10.9 Hz, 1H), 3.14-2.79 (m, 3H), 2.68 (s, 6H), 2.55-2.36 (m, 2H), 2.22-2.06 (m, H), 1.84 (d, J=3.6 Hz, 4H), 1.32-0.99 (m, 3H), 0.93-0.61 (m, 7H).

4-61. (3S)-3-(2',6'-dichloro-4-fluoro-4',5-dimethylbi-phenyl-3-yl)-3-(2-(5-(2-(dimethylamino)ethyl)-2-oxo-4-(trifluoromethyl)pyridin-1(2H)-yl)-3-methylbutanamido)propanoic Acid (Diastereomeric Compounds DH-P1 and DH-P2)

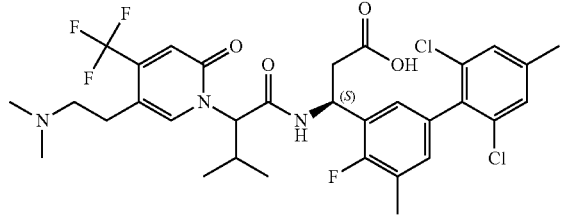

DH-P1 ESI 672.1 (M+H)$^+$. 1H NMR (400 MHz, MeOD) δ: 7.91 (s, 1H), 7.27 (d, J=6.0 Hz, 1H), 7.14 (d, J=5.2 Hz, 1H), 6.90 (t, J=6.0 Hz, 2H), 6.67 (d, J=5.6 Hz, 1H), 5.64-5.60 (m, 1H), 5.29 (d, J=11.2 Hz, 1H), 2.97-2.85 (m, 4H), 2.78-2.61 (m, 8H), 2.46-2.40 (m, 1H), 2.36 (s, 3H), 2.27 (s, 3H), 1.16 (d, J=6.4 Hz, 3H), 0.78 (d, J=6.4 Hz, 3H).

DH-P2 ESI 672.2 (M+H)$^+$. 1H NMR (400 MHz, MeOD) δ: 8.01 (s, 1H), 7.30 (s, 2H), 7.09-7.07 (m, 1H), 7.00 (d, J=7.2 Hz, 1H), 6.90 (s, 1H), 5.78-5.74 (m, 1H), 5.23 (d, J=11.2 Hz, 1H), 3.27-3.20 (m, 1H), 3.17-3.11 (m, 1H), 3.09-3.01 (m, 1H), 2.99-2.93 (m, 1H), 2.78 (s, 6H), 2.61-2.50 (m, 2H), 2.47-2.37 (m, 4H), 2.31 (d, J=1.2 Hz, 3H), 0.94 (d, J=6.4 Hz, 3H), 0.71 (d, J=6.8 Hz, 3H).

4-62. (3S)-3-(2-(5-(2-(azetidin-1-yl)ethyl)-2-oxo-4-(trifluoromethyl)pyridin-1(2H)-yl)-4-methylpentana-mido)-3-(2'-cyclopropyl-4-fluoro-4',5,6'-trimethyl-[1,1'-biphenyl]-3-yl)propanoic Acid (Diastereomeric Compounds DI-P1 and DI-P2)

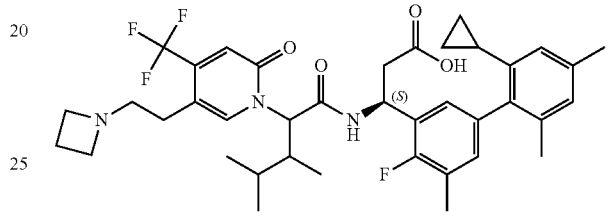

DI-P1 ESI 684.3 (M+H)$^+$. $^1$H NMR (400 MHz, MeOD) δ 7.84 (s, 1H), 6.97-6.78 (m, 4H), 6.58 (s, 1H), 5.69-5.59 (m, 2H), 3.97-3.94 (m, 4H), 3.26-3.21 (m, 2H), 2.86-2.81 (m, 2H), 2.72-2.68 (m, 2H), 2.46-2.38 (m, 2H), 2.29 (d, J=4.9 Hz, 6H), 2.03-1.97 (m, 3H), 1.85 (s, 2H), 1.48-1.31 (m, 2H), 0.98-0.91 (m, 6H), 0.67 (d, J=8.4 Hz, 1H), 0.59-0.44 (m, 3H).

DI-P2 ESI 684.3 (M+H)$^+$. $^1$H NMR (400 MHz, MeOD) δ 7.73 (d, J=10.5 Hz, 1H), 7.02-6.96 (m, 2H), 6.91 (s, 1H), 6.90 (s, 1H), 6.59 (s, 1H), 5.78-5.75 (m, 1H), 5.64-5.59 (m, 1H), 4.14-4.10 (m, 4H), 3.47-3.38 (m, 2H), 2.97-2.92 (m, 1H), 2.85-2.75 (m, 1H), 2.69-2.60 (m, 1H), 2.55-2.45 (m, 3H), 2.34 (s, 3H), 2.29 (s, 3H), 2.05-1.96 (m, 4H), 1.71-1.61 (m, 1H), 1.49-1.39 (m, 2H), 0.90 (d, J=6.6 Hz, 6H), 0.70-0.66 (m, 2H), 0.58-0.55 (m, 2H).

4-63. (3S)-3-(2',6'-dichloro-4-fluoro-5-methylbiphe-nyl-3-yl)-3-(2-(5-(2-(dimethylamino)ethyl)-2-oxo-4-(trifluoromethyl)pyridin-1(2H)-yl)-4-methylpentana-mido)propanoic Acid (Diastereomeric Compounds DJ-P1 and DJ-P2)

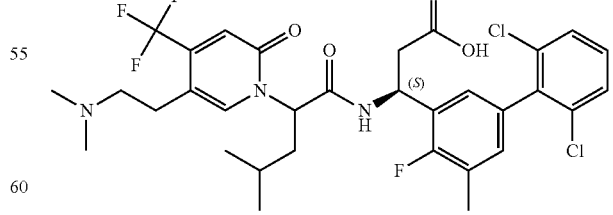

DJ-P1 ESI 672.2 (M+H)$^+$. 1H NMR (400 MHz, MeOD) δ: 7.89 (s, 1H), 7.46 (d, J=8.0 Hz, 1H), 7.39 (d, J=7.2 Hz, 1H), 7.32 (t, J=8.0 Hz, 1H), 7.00-6.96 (m, 2H), 6.75 (s, 1H), 5.72-5.68 (m, 1H), 5.60-5.56 (m, 1H), 3.10-3.01 (m, 2H), 2.94-2.92 (m, 2H), 2.74-2.65 (m, 8H), 2.27 (d, J=1.2 Hz,

3H), 2.01-1.93 (m, 2H), 1.47-1.41 (m, 1H), 0.95 (d, J=6.4 Hz, 3H), 0.93 (d, J=6.4 Hz, 3H).

DJ-P2 ESI 672.2 (M+H)⁺. 1H NMR (400 MHz, MeOD) δ: 7.91-5.88 (m, 1H), 7.47 (d, J=8.0 Hz, 2H), 7.35-7.31 (m, 1H), 7.08-7.02 (m, 2H), 6.89 (s, 1H), 5.78-5.74 (m, 1H), 5.64 (t, J=7.6 Hz, 1H), 3.27-3.15 (m, 2H), 3.06-2.95 (m, 2H), 2.80 (s, 6H), 2.65-2.60 (m, 1H), 2.55-2.49 (m, 1H), 2.32 (s, 3H), 1.99-1.92 (m, 1H), 1.71-1.64 (m, 1H), 1.41-1.34 (m, 1H), 0.86-0.84 (m, 6H).

4-64. (3S)-3-(2-(5-(2-(azetidin-1-yl)ethyl)-2-oxo-4-(trifluoromethyl)pyridin-1(2H)-yl)-4-methylpentanamido)-3-(4-fluoro-2',5,6'-trimethyl-4'-(trifluoromethyl)biphenyl-3-yl)propanoic Acid (Diastereomeric Compounds DK-P1 and DK-P2)

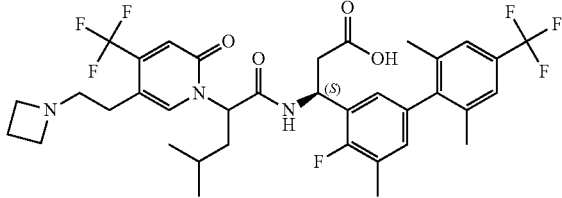

DK-P1 ESI 712.2 (M+H)⁺. 1H NMR (400 MHz, MeOD) δ: 7.88 (s, 1H), 7.39 (s, 1H), 7.35 (s, 1H), 6.91 (t, J=6.2 Hz, 2H), 6.70 (s, 1H), 5.66-5.57 (m, 2H), 4.04 (t, J=8.2 Hz, 4H), 3.29 (t, J=7.4 Hz, 2H), 2.84 (t, J=7.2 Hz, 2H), 2.78-2.67 (m, 2H), 2.48-2.40 (m, 2H), 2.30 (d, J=1.2 Hz, 3H), 2.08 (s, 3H), 2.03-1.99 (m, 2H), 1.91 (s, 3H), 1.47-1.40 (m, 1H), 0.95 (d, J=6.8 Hz, 3H), 0.93 (d, J=6.4 Hz, 3H).

DK-P2 ESI 712.2 (M+H)⁺. 1H NMR (400 MHz, MeOD) δ: 7.74 (s, 1H), 7.41 (s, 2H), 6.98 (s, 1H), 6.96 (s, 1H), 6.90 (s, 1H), 5.79-5.76 (m, 1H), 5.60 (t, J=8.0 Hz, 1H), 4.15 (t, J=8.0 Hz, 4H), 3.48-3.42 (m, 1H), 3.38-3.33 (m, 1H), 2.98-2.91 (m, 1H), 2.84-2.77 (m, 1H), 2.69-2.64 (m, 1H), 2.55-2.45 (m, 3H), 2.35 (d, J=1.6 Hz, 3H), 2.09 (s, 3H), 2.08 (s, 3H), 2.03-1.96 (m, 1H), 1.69-1.62 (m, 1H), 1.46-1.36 (m, 1H), 0.89 (d, J=1.6 Hz, 3H), 0.87 (d, J=2.0 Hz, 3H).

4-65. (3S)-3-(2'-chloro-4-fluoro-5,6'-dimethyl-[1,1'-biphenyl]-3-yl)-3-(2-(5-(2-(dimethylamino)ethyl)-2-oxo-4-(trifluoromethyl)pyridin-1(2H)-yl)-4-methylpentanamido)propanoic Acid (Diastereomeric Compounds DL-P1 and DL-P2)

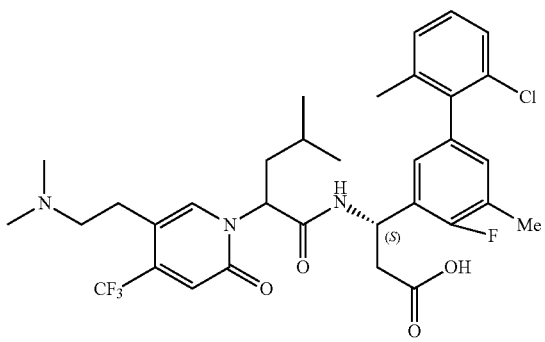

DL-P1 ESI 652.2 (M+H)⁺. 1H NMR (400 MHz, MeOD) δ 7.90 (d, J=4.5 Hz, 1H), 7.37-7.09 (m, 3H), 6.93 (m, J=10.9, 4.9 Hz, 2H), 6.75 (d, J=6.5 Hz, 1H), 5.68 (m, J=30.2, 23.4 Hz, 2H), 3.00 (d, J=50.0 Hz, 4H), 2.73 (m, J=14.3 Hz, 8H), 2.30 (s, 3H), 2.13-1.83 (m, 5H), 1.45 (d, J=6.4 Hz, 1H), 0.96 (m, J=12.9, 6.6, 2.5 Hz, 6H).

DL-P2 ESI 652.2 (M+H)⁺. 1H NMR (400 MHz, MeOD) δ 7.88 (s, 1H), 7.34-7.09 (m, 3H), 7.11-6.51 (m, 3H), 5.69 (m, J=21.6, 10.6, 4.3 Hz, 2H), 3.15 (s, 2H), 2.98 (s, 2H), 2.88-2.53 (m, 8H), 2.34 (s, 3H), 2.08 (d, J=5.6 Hz, 3H), 1.98-1.81 (m, 1H), 1.78 (s, 1H), 1.40 (s, 1H), 0.89 (m, J=6.4, 4.6 Hz, 6H).

4-66. (3S)-3-(2-(5-(2-(azetidin-1-yl)ethyl)-2-oxo-4-(trifluoromethyl)pyridin-1(2H)-yl)-4-methylpentanamido)-3-(2',4-difluoro-5,6'-dimethylbiphenyl-3-yl)propanoic Acid (Diastereomeric Compounds DM-P1 and DM-P2)

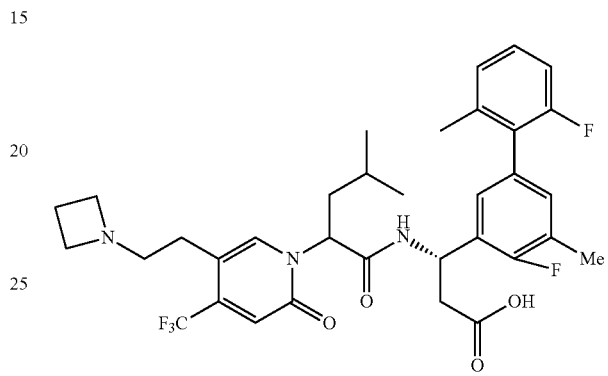

DM-P1 ESI 648.2 (M+H)⁺. 1H NMR (400 MHz, MeOD) δ 7.84 (s, 1H), 7.30-7.23 (m, 1H), 7.16-7.09 (m, 1H), 7.06-6.92 (m, 3H), 6.81 (s, 1H), 5.71-5.60 (m, 2H), 4.01 (t, J=8.1 Hz, 4H), 3.29 (s, 2H), 2.86 (t, J=6.8 Hz, 2H), 2.72 (d, J=6.6 Hz, 2H), 2.46-2.36 (m, 2H), 2.36-2.31 (m, 3H), 2.10 (s, 3H), 2.00 (t, J=7.6 Hz, 2H), 1.51-1.42 (m, 1H), 0.98-0.93 (m, 6H).

DM-P2 ESI 648.2 (M+H)⁺. 1H NMR (400 MHz, MeOD) δ 7.75 (s, 1H), 7.31-7.19 (m, 1H), 7.15-7.04 (m, 3H), 6.99 (t, J=8.8 Hz, 1H), 6.92 (s, 1H), 5.81-5.75 (m, 1H), 5.64 (t, J=7.6 Hz, 1H), 4.14 (t, J=8.0 Hz, 4H), 3.49-3.35 (m, 2H), 2.94 (d, J=15.7 Hz, 1H), 2.87-2.75 (m, 1H), 2.69-2.56 (m, 1H), 2.57-2.43 (m, 3H), 2.35 (d, J=1.5 Hz, 3H), 2.17 (d, J=8.1 Hz, 3H), 2.04-1.95 (m, 1H), 1.72-1.62 (m, 1H), 1.46-1.32 (m, 1H), 0.97-0.91 (m, 6H).

4-67. (3S)-3-(3',4-difluoro-2',4',5,6'-tetramethylbiphenyl-3-yl)-3-(2-(5-(2-(dimethylamino)ethyl)-2-oxo-4-(trifluoromethyl)pyridin-1(2H)-yl)-4-methylpentanamido)propanoic Acid (Diastereomeric Compounds DN-P1 and DN-P2)

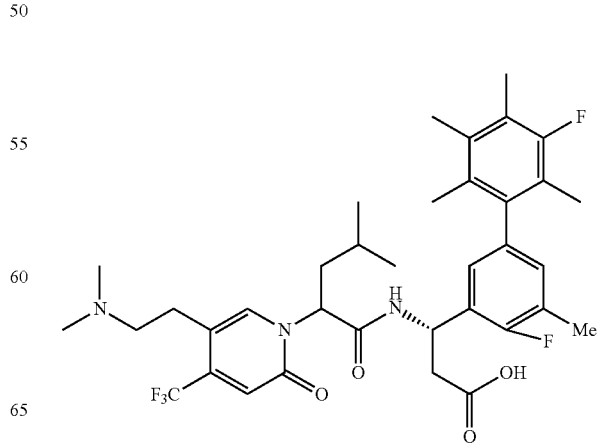

DN-P1 ESI 664.2 (M+H)⁺. ¹H NMR (400 MHz, MeOD) δ 7.85 (s, 1H), 7.01-6.79 (m, 4H), 5.78-5.58 (m, 2H), 3.29-3.07 (m, 2H), 3.04-2.89 (m, 2H), 2.81 (s, 6H), 2.70-2.42 (m, 2H), 2.33 (s, 3H), 2.26 (s, 3H), 2.13-1.83 (m, 7H), 1.81-1.60 (m, 1H), 1.52-1.30 (m, 1H), 1.02-0.81 (m, 6H).

DN-P2 ESI 664.2 (M+H)⁺. ¹H NMR (400 MHz, MeOD) δ 7.91 (s, 1H), 6.99-6.68 (m, 4H), 5.82-5.50 (m, 2H), 3.19-2.89 (m, 4H), 2.83-2.54 (m, 8H), 2.38-2.22 (m, 6H), 2.13-1.80 (m, 5H), 1.72 (d, J=14.7 Hz, 3H), 1.51-1.36 (m, 1H), 1.06-0.84 (m, 6H).

4-68. (3S)-3-(2-(5-(2-(azetidin-1-yl)ethyl)-2-oxo-4-(trifluoromethyl)pyridin-1(2H)-yl)-4-methylpentanamido)-3-(4'-cyano-4-fluoro-2',5,6'-trimethylbiphenyl-3-yl)propanoic Acid (Diastereomeric Compounds DO-P1 and DO-P2)

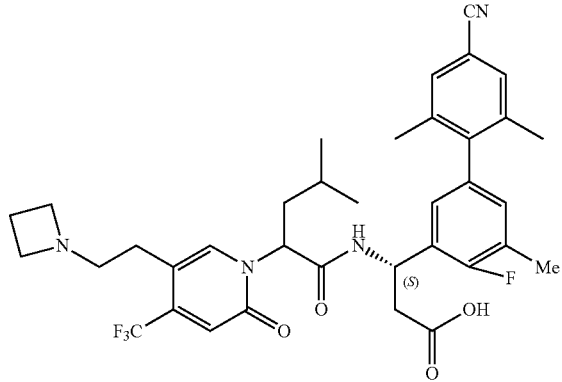

DO-P1 ESI 669.2 (M+H)⁺. 1H NMR (400 MHz, MeOD) δ 7.84 (s, 1H), 7.47 (d, J=10.3 Hz, 2H), 6.91 (d, J=6.7 Hz, 2H), 6.75 (s, 1H), 5.59 (d, J=7.7 Hz, 2H), 4.06 (t, J=8.1 Hz, 4H), 3.31-3.27 (m, 2H), 2.98-2.85 (m, 2H), 2.79-2.64 (m, 2H), 2.58-2.39 (m, 2H), 2.31 (s, 3H), 2.14-1.88 (m, 8H), 1.54-1.27 (m, 1H), 1.10-0.80 (m, 6H).

DO-P2 ESI 669.2 (M+H)⁺. 1H NMR (400 MHz, MeOD) δ 7.74 (s, 1H), 7.50 (s, 2H), 7.06-6.84 (m, 3H), 5.90-5.71 (m, 1H), 5.61 (t, J=7.6 Hz, 1H), 4.10 (s, 4H), 3.36 (s, 2H), 3.09-2.74 (m, 2H), 2.74-2.60 (m, 1H), 2.55-2.39 (m, 3H), 2.35 (s, 3H), 2.13-1.89 (m, 7H), 1.75-1.62 (m, 1H), 1.50-1.35 (m, 1H), 0.98-0.81 (m, 6H).

4-69. (3S)-3-(2'-cyano-4-fluoro-5,6'-dimethylbiphenyl-3-yl)-3-(2-(5-(2-(dimethylamino)ethyl)-2-oxo-4-(trifluoromethyl)pyridin-1(2H)-yl)-4-methylpentanamido)propanoic Acid (Diastereomeric Compounds DP-P1 and DP-P2)

DP-P1 ESI 643.2 (M+H)⁺. ¹H NMR (400 MHz, MeOD) δ 7.89 (s, 1H), 7.59 (s, 2H), 7.43 (t, J=7.7 Hz, 1H), 7.06 (s, 2H), 6.71 (d, J=26.7 Hz, 1H), 5.73 (s, 1H), 5.60 (d, J=7.3 Hz, 1H), 3.10 (s, 2H), 2.93 (d, J=8.3 Hz, 2H), 2.80-2.69 (m, 8H), 2.32 (s, 3H), 2.19 (s, 2H), 2.00 (s, 3H), 1.49-1.42 (m, 1H), 1.00-0.92 (m, 6H).

DP-P1 ESI 643.2 (M+H)⁺. ¹H NMR (400 MHz, MeOD) δ 7.81 (s, 1H), 7.66-7.52 (m, 2H), 7.45 (t, J=7.7 Hz, 1H), 7.13 (d, J=6.4 Hz, 2H), 6.90 (s, 1H), 5.77-5.59 (m, 2H), 3.23 (s, 2H), 3.01 (s, 2H), 2.83 (s, 6H), 2.69-2.53 (m, 1H), 2.58-2.49 (m, 1H), 2.37 (d, J=1.6 Hz, 3H), 2.19 (s, 3H), 2.05-1.96 (m, 1H), 1.81 (s, 1H), 1.42-1.36 (m, 1H), 0.99-0.91 (m, 6H).

4-70. (3S)-3-(2-(5-(2-(azetidin-1-yl)ethyl)-2-oxo-4-(trifluoromethyl)pyridin-1(2H)-yl)-4-methylpentanamido)-3-(4-fluoro-2'-methoxy-5,6'-dimethylbiphenyl-3-yl)propanoic Acid (Diastereomeric Compounds DQ-P1 and DQ-P2)

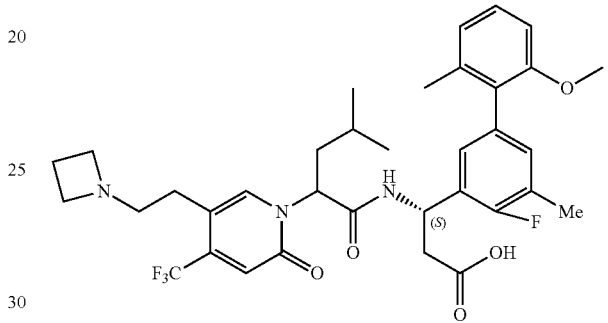

DQ-P1 ESI 660.2 (M+H)⁺. 1H NMR (400 MHz, MeOD) δ 7.82 (s, 1H), 7.21 (t, J=8.0 Hz, 1H), 6.99-6.82 (m, 5H), 5.70-5.62 (m, 2H), 4.01-3.96 (m, 4H), 3.66 (s, 3H), 3.30-3.27 (m, 2H), 2.88-2.85 (m, 2H), 2.71 (d, J=7.4 Hz, 2H), 2.45-2.39 (m, 2H), 2.29 (s, 3H), 2.02-1.93 (m, 5H), 1.45-1.38 (m, 1H), 0.97-0.93 (m, 6H).

DQ-P2 ESI 660.2 (M+H)⁺. 1H NMR (400 MHz, MeOD) δ 7.73 (s, 1H), 7.22 (t, J=8.0 Hz, 1H), 7.00-6.87 (m, 5H), 5.79-5.75 (m, 1H), 5.62 (t, J=7.6 Hz, 1H), 4.13 (t, J=7.9 Hz, 4H), 3.68 (s, 3H), 3.49-3.35 (m, 2H), 2.97-2.91 (d, J=16.1 Hz, 1H), 2.85-2.77 (m, 1H), 2.66-2.62 (m, 1H), 2.56-2.42 (m, 3H), 2.32 (d, J=1.7 Hz, 3H), 2.04 (s, 3H), 2.02-1.97 (m, 1H), 1.72-1.60 (m, 1H), 1.49-1.36 (m, 1H), 0.91 (d, J=6.5 Hz, 6H).

4-71. (3S)-3-(2'-cyclopropyl-4-fluoro-4',5,6'-trimethyl-[1,1'-biphenyl]-3-yl)-3-(2-(5-(2-(dimethylamino)ethyl)-4-methyl-2-oxopyridin-1(2H)-yl)-4-methylpentanamido)propanoic Acid (Diastereomeric Compounds DR-P1 and DR-P2)

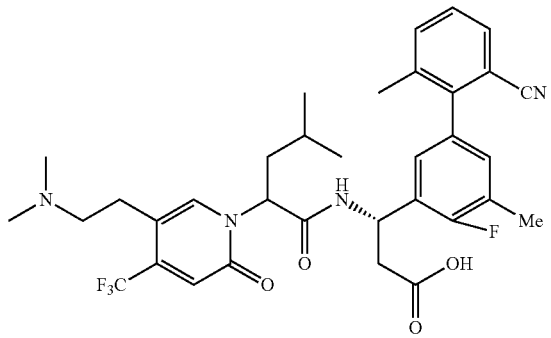 [SMILES: Cc1cc(-c2c(C)cccc2C#N)cc([C@H](CC(=O)O)NC(=O)C(CC(C)C)n2cc(CCN(C)C)c(C(F)(F)F)cc2=O)c1F]

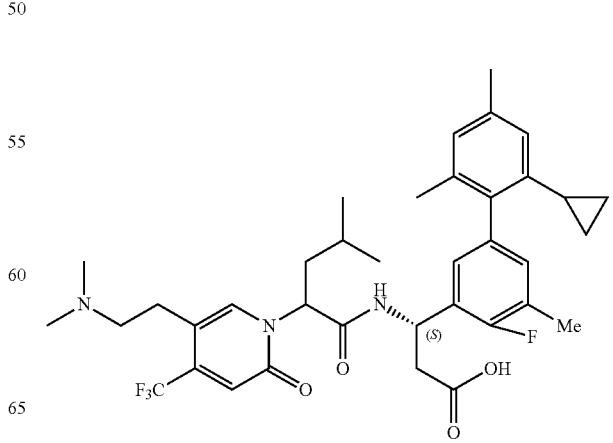

DR-P1 ESI 618.3 (M+H)+. 1H NMR (400 MHz, MeOD) δ 7.57 (d, J=1.8 Hz, 1), 6.91-6.84 (m, 3H), 6.57 (d, J=11.0 Hz, 1H), 6.38 (d, J=8.9 Hz, 1H), 5.59 (d, J=5.8 Hz, 1H), 5.46 (t, J=5.9 Hz, 1H), 3.22-3.06 (m, 2H), 2.87 (t, J=7.1 Hz, 2H), 2.74 (s, 6H), 2.71-2.56 (m, 2H), 2.27 (d, J=13.3 Hz, 9H), 2.04-1.87 (m, 5H), 1.48-1.38 (m, 2H), 0.95-0.89 (m, 6H), 0.72-0.67 (m, 1H), 0.63-0.55 (m, 1H), 0.53-0.48 (m, 2H).

DR-P2 ESI 618.3 (M+H)+. 1H NMR (400 MHz, MeOD) δ 7.54 (d, J=10.5 Hz, 1H), 6.98-6.89 (m, 2H), 6.89 (s, 1H), 6.59 (s, 1H), 6.44 (d, J=5.1 Hz, 1H), 5.65-5.56 (m, 2H), 3.34-3.26 (m, 2H), 3.20-3.13 (m, 2H), 2.94-2.88 (m, 2H), 2.81 (d, J=2.0 Hz, 6H), 2.64-2.57 (m, 1H), 2.48-2.41 (m, 1H), 2.32-2.246 (m, 9H), 1.99-1.92 (m, 4H), 1.81-1.74 (m, 1H), 1.49-1.33 (m, 1H), 0.92-0.85 (m, 6H), 0.68-0.63 (m, 2H), 0.58-0.51 (m, 2H).

4-72. (3S)-3-(4'-cyclopropyl-4-fluoro-2',5,6'-trimethyl-[1,1'-biphenyl]-3-yl)-3-(2-(5-(2-(dimethylamino)ethyl)-4-methyl-2-oxopyridin-1(2H)-yl)-4-methylpentanamido)propanoic Acid (Diastereomeric Compounds DS-P1 and DS-P2)

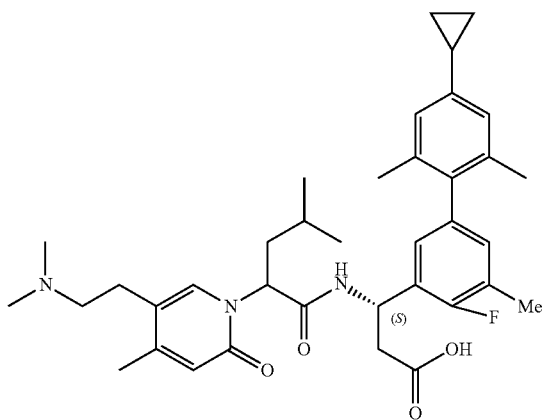

DS-P1 ESI 618.3 (M+H)+. 1H NMR (400 MHz, MeOD) δ 7.46 (s, 1H), 6.84-6.65 (m, 3H), 6.45 (d, J=11.2 Hz, 1H), 6.27 (d, J=8.7 Hz, 1H), 5.48-5.46 (m, 1H), 5.33 (d, J=5.6 Hz, 1H), 3.15-2.95 (m, 2H), 2.78-2.74 (m, 3H), 2.60 (d, J=25.4 Hz, 6H), 2.58-2.40 (m, 2H), 2.17 (s, 6H), 2.13 (s, 3H), 1.95-1.73 (m, 5H), 1.34-1.28 (m, 2H), 0.86-0.73 (m, 6H), 0.62-0.32 (m, 4H).

DS-P2 ESI 618.3 (M+H)+. 1H NMR (400 MHz, MeOD) δ 7.43 (s, 1H), 7.40 (s, 1H), 6.84 (t, J=6.2 Hz, 2H), 6.77 (s, 1H), 6.47 (s, 1H), 6.32 (d, J=5.5 Hz, 1H), 5.52-5.44 (m, 2H), 3.09-3.06 (m, 1H), 2.88-2.67 (m, 8H), 2.51-2.45 (m, 1H), 2.37-2.29 (m, 1H), 2.24-2.09 (m, 9H), 1.85-1.81 (m, 4H), 1.70-1.59 (m, 1H), 1.39-1.16 (m, 2H), 0.78-0.76 (m, 6H), 0.54 (t, J=7.6 Hz, 2H), 0.45 (d, J=4.5 Hz, 2H).

4-73. (3S)-3-(2'-chloro-4,4'-difluoro-5,6'-dimethyl-[1,1'-biphenyl]-3-yl)-3-(2-(5-(2-(dimethylamino)ethyl)-2-oxo-4-(trifluoromethyl)pyridin-1(2H)-yl)-4-methylpentanamido)propanoic Acid (Diastereomeric Compounds DT-P1 and DT-P2)

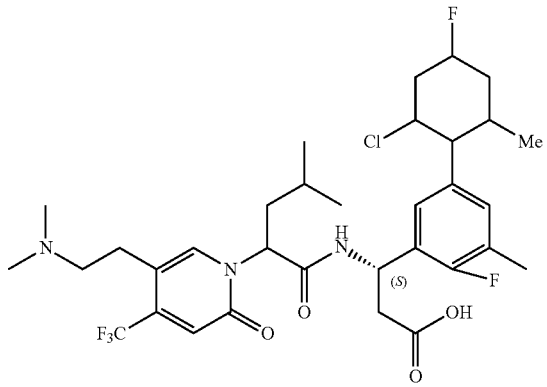

DT-P1 ESI 670.2 (M+H)+. 1H NMR (400 MHz, MeOD) δ 7.90 (d, J=3.1 Hz, 1H), 7.14-6.92 (m, 4H), 6.76 (d, J=5.6 Hz, 1H), 5.72-5.65 (m, 1H), 5.60-5.56 (m, 1H), 3.10-2.87 (m, 4H), 2.76-2.66 (m, 8H), 2.30 (s, 3H), 2.09-1.91 (m, 5H), 1.47-1.41 (m, 1H), 1.00-0.92 (m, 6H).

DT-P2 ESI 670.2 (M+H)+. 1H NMR (400 MHz, MeOD) δ 7.84 (s, 1H), 7.16-7.12 (m, 1H), 7.07-6.95 (m, 3H), 6.91 (d, J=2.7 Hz, 1H), 5.74-5.59 (m, 2H), 3.32-3.21 (m, 2H), 3.03-2.99 (m, 2H), 2.84 (d, J=2.9 Hz, 6H), 2.67-2.49 (m, 2H), 2.34 (d, J=1.6 Hz, 3H), 2.03-1.90 (m, 1H), 1.76-1.67 (m, 1H), 1.46-1.37 (m, 1H), 0.92-0.89 (m, 6H).

4-74. (3S)-3-(2',6'-dichloro-4-fluoro-4',5-dimethyl-[1,1'-biphenyl]-3-yl)-3-(2-(5-(2-(dimethylamino)ethyl)-2-oxo-4-(trifluoromethyl)pyridin-1(2H)-yl)-4-methylpentanamido)propanoic Acid (Diastereomeric Compounds DU-P1 and DU-P2)

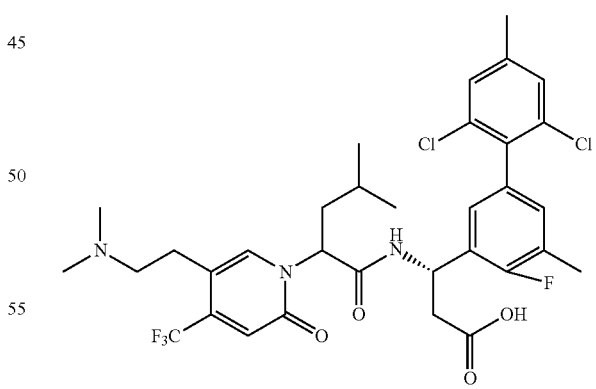

DU-P1 ESI 686.1 (M+H)+. 1H NMR (400 MHz, MeOD) δ 7.90 (s, 1H), 7.31 (s, 1H), 7.23 (s, 1H), 7.02-6.91 (m, 2H), 6.76 (s, 1H), 5.76-5.66 (m, 1H), 5.63-5.53 (m, 1H), 3.15-3.04 (m, 2H), 2.94 (t, J=11.0 Hz, 2H), 2.80-2.66 (m, 8H), 2.38 (s, 3H), 2.29 (d, J=1.3 Hz, 3H), 2.04-1.92 (m, 2H), 1.51-1.42 (m, 1H), 1.01-0.90 (m, 6H).

DU-P2 ESI 686.1 (M+H)+. 1H NMR (400 MHz, MeOD) δ 7.88 (s, 1H), 7.32 (s, 2H), 7.09-6.99 (m, 2H), 6.91 (s, 1H), 5.79-5.71 (m, 1H), 5.65 (t, J=7.7 Hz, 1H), 3.30-3.15 (m, 2H), 3.00 (t, J=6.8 Hz, 2H), 2.81 (s, 6H), 2.67-2.50 (m, 2H), 2.39 (s, 3H), 2.33 (d, J=1.5 Hz, 3H), 2.02-1.92 (m, 1H), 1.73-1.65 (m, 1H), 1.44-1.36 (m, 1H), 0.91-0.85 (m, 6H).

4-75. (3S)-3-(2-(5-(2-(dimethylamino)ethyl)-4-methyl-2-oxopyridin-1(2H)-yl)-4-methylpentanamido)-3-(4-fluoro-2',5,6'-trimethyl-4'-(trifluoromethyl)biphenyl-3-yl)propanoic Acid (Diastereomeric Compounds DV-P1 and DV-P2)

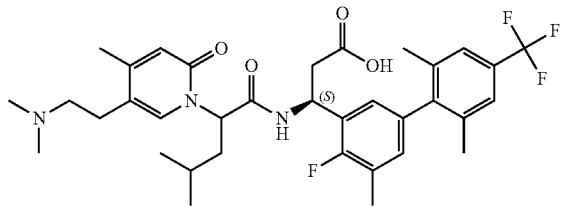

DV-P1 ESI 646.3 (M+H)+. 1H NMR (400 MHz, MeOD) δ: 7.59 (s, 1H), 7.40 (s, 1H), 7.38 (s, 1H), 6.89 (d, J=6.8 Hz, 1H), 6.84 (d, J=6.4 Hz, 1H), 6.28 (s, 1H), 5.55 (t, J=5.6 Hz, 1H), 5.49 (t, J=6.0 Hz, 1H), 3.16-3.08 (m, 2H), 2.87 (t, J=7.2 Hz, 2H), 2.78 (s, 6H), 2.73-2.68 (m, 1H), 2.65-2.60 (m, 1H), 2.31 (s, 3H), 2.25 (s, 3H), 2.08 (s, 3H), 2.01-1.90 (m, 5H), 1.45-1.38 (m, 1H), 0.94 (d, J=6.4 Hz, 3H), 0.91 (d, J=6.8 Hz, 3H).

DV-P2 ESI 646.3 (M+H)+. 1H NMR (400 MHz, MeOD) δ: 7.55 (s, 1H), 7.41 (s, 2H), 6.95-6.93 (m, 1H), 6.90 (d, J=6.4 Hz, 1H), 6.41 (s, 1H), 5.63-5.60 (m, 1H), 5.58-5.56 (m, 1H), 3.38-3.36 (m, 1H), 3.25-3.19 (m, 1H), 2.95-2.90 (m, 2H), 2.85 (s, 6H), 2.64-2.59 (m, 1H), 2.50-2.44 (m, 1H), 2.34 (d, J=1.6 Hz, 3H), 2.26 (s, 3H), 2.08 (s, 6H), 2.00-1.93 (m, 1H), 1.83-1.76 (m, 1H), 1.42-1.35 (m, 1H), 0.89 (t, J=6.4 Hz, 6H).

4-76. (3S)-3-(4'-cyclopropyl-4-fluoro-2',5,6'-trimethyl-[1,1'-biphenyl]-3-yl)-3-(2-(5-(2-(dimethylamino)ethyl)-3-fluoro-4-methyl-2-oxopyridin-1(2H)-yl)-4-methylpentanamido)propanoic Acid (Diastereomeric Compounds DW-P1 and DW-P2)

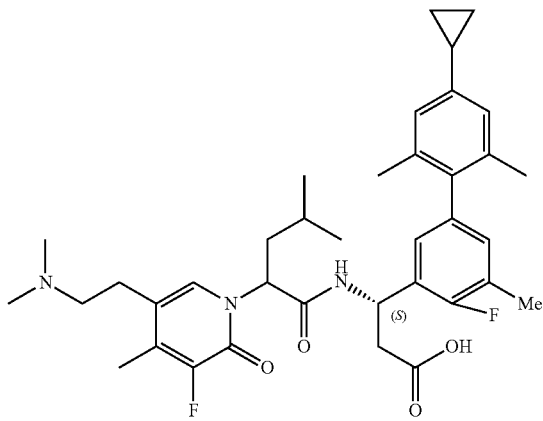

DW-P1 ESI 636.3 (M+H)+. 1H NMR (400 MHz, MeOD) δ 7.47 (s, 1H), 6.94-6.78 (m, 3H), 6.57 (d, J=12.7 Hz, 1H), 5.74-5.57 (m, 1H), 5.46 (t, J=5.9 Hz, 1H), 3.25-3.10 (m, 2H), 2.92 (t, J=6.9 Hz, 2H), 2.75 (s, 6H), 2.70-2.52 (m, 2H), 2.30-2.25 (m, 9H), 1.99-1.88 (m, 5H), 1.46-1.39 (m, 2H), 0.97-0.86 (m, 6H), 0.72-0.43 (m, 4H).

DW-P2 ESI 636.3 (M+H)+. 1H NMR (400 MHz, MeOD) δ 7.42 (d, J=11.3 Hz, 1H), 6.97 (t, J=8.2 Hz, 2H), 6.89 (s, 1H), 6.59 (s, 1H), 5.72-5.52 (m, 2H), 3.32-3.22 (m, 2H), 2.98-2.90 (m, 2H), 2.85 (s, 6H), 2.67-2.38 (m, 2H), 2.32-2.25 (m, 9H), 2.00-1.98 (m, 4H), 1.83-1.67 (m, 1H), 1.51-1.26 (m, 2H), 0.90 (d, J=6.6 Hz, 6H), 0.70-0.48 (m, 4H).

4-77. (3S)-3-(4-fluoro-2',4',5,6'-tetramethyl-[1,1'-biphenyl]-3-y)-3-(2-(3-fluoro-5-(2-(3-methoxyazetidin-1-yl)ethyl)-4-methyl-2-oxopyridin-1(2H)-yl)-4-methylpentanamido)propanoic Acid (Diastereomeric Compounds DX-P1 and DX-P2)

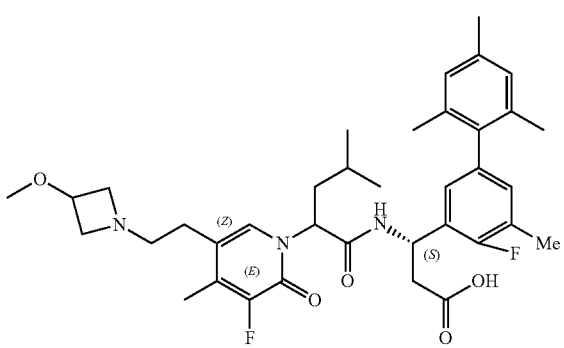

DX-P1 ESI 652.3 (M+H)+. 1H NMR (400 MHz, MeOD) δ 7.26 (s, 1H), 6.84-6.68 (m, 4H), 5.54-5.45 (m, 1H), 5.41 (t, J=6.3 Hz, 1H), 4.14-3.93 (m, 3H), 3.64-3.54 (m, 1H), 3.52-3.50 (m, 1H), 3.25-3.16 (m, 5H), 2.74-2.55 (m, 4H), 2.18 (s, 6H), 2.12 (d, J=4.0 Hz, 3H), 1.88-1.74 (m, 8H), 1.29-1.25 (m, 1H), 0.83-0.78 (m, 6H).

DX-P2 ESI 652.3 (M+H)+. 1H NMR (400 MHz, MeOD) δ 7.20 (s, 1H), 6.85-6.72 (m, 4H), 5.61-5.43 (m, 2H), 4.36-4.08 (m, 3H), 3.84-3.61 (m, 2H), 3.32-3.22 (m, 5H), 2.82-2.78 (m, 1H), 2.64-2.56 (m, 1H), 2.51-2.47 (m, 1H), 2.39-2.32 (m, 1H), 2.23-2.13 (m, 6H), 2.10 (d, J=2.7 Hz, 3H), 1.90-1.73 (m, 8H), 1.68-1.51 (m, 1H), 1.32-1.20 (m, 1H), 0.79-0.74 (m, 6H).

4-78. (3S)-3-(2-(5-(2-(azetidin-1-yl)ethyl)-2-oxo-4-(trifluoromethyl)pyridin-1(2H)-yl)-4-methylpentanamido)-3-(4,4'-difluoro-2',5,5'-trimethylbiphenyl-3-yl)propanoic Acid (Diastereomeric Compounds DY-P1 and DY-P2)

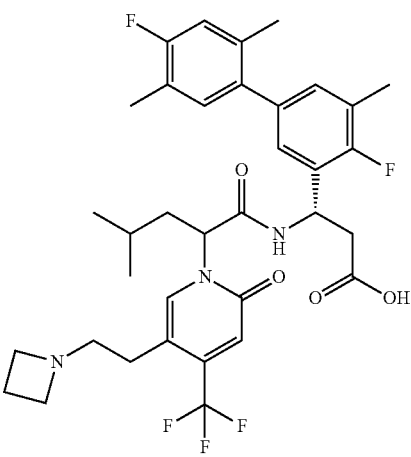 [SMILES: Cc1cc(-c2cc(C)c(F)c([C@H](CC(=O)O)NC(=O)C(CC(C)C)n3cc(CCN4CCC4)c(C(F)(F)F)cc3=O)c2)c(C)cc1F]

DY-P1 ESI 662.2 (M+H)$^+$. 1H NMR (400 MHz, MeOD) δ 7.84 (s, 1H), 7.03-7.00 (m, 3H), 6.93 (d, J=10.6 Hz, 1H), 6.81 (s, 1H), 5.70-5.63 (m, 1H), 5.59 (t, J=6.7 Hz, 1H), 4.02 (t, J=8.2 Hz, 4H), 3.30 (s, 2H), 2.86 (t, J=6.9 Hz, 2H), 2.71 (d, J=6.8 Hz, 2H), 2.42-2.39 (m, 2H), 2.30 (d, J=1.4 Hz, 3H), 2.25 (s, 3H), 2.15 (s, 3H), 2.02-2.19 (m, 2H), 1.48-1.39 (m, 1H), 0.96-0.90 (m, 6H).

DY-P2 ESI 662.2 (M+H)$^+$. 1H NMR (400 MHz, MeOD) δ 7.73 (s, 1H), 7.09-7.06 (m, 2H), 7.04 (d, J=8.1 Hz, 1H), 6.99-6.88 (m, 2H), 5.75-5.70 (m, 1H), 5.64 (t, J=7.7 Hz, 1H), 4.15 (t, J=8.0 Hz, 4H), 3.42-3.40 (m, 2H), 2.95 (d, J=16.2 Hz, 1H), 2.82-2.80 (m, 1H), 2.64-2.60 (m, 1H), 2.55-2.43 (m, 3H), 2.34 (s, 3H), 2.26 (s, 3H), 2.20 (s, 3H), 2.04-1.97 (m, 1H), 1.71-1.68 (m, 1H), 1.43-1.38 (m, 1H), 0.92 (t, J=6.3 Hz, 6H).

4-79. (3S)-3-(2-(5-(2-(azetidin-1-yl)ethyl)-2-oxo-4-(trifluoromethyl)pyridin-1(2H)-yl)-4-methylpentanamido)-3-(4-fluoro-4'-methoxy-2',5,5'-trimethyl-[1,1'-biphenyl]-3-yl)propanoic Acid (Diastereomeric Compounds DZ-P1 and DZ-P2)

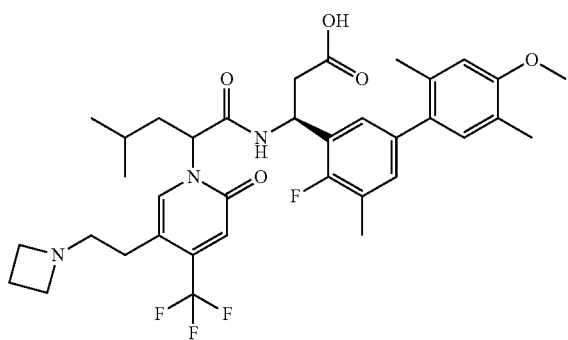 [SMILES: COc1cc(C)c(-c2cc(C)c(F)c([C@H](CC(=O)O)NC(=O)C(CC(C)C)n3cc(CCN4CCC4)c(C(F)(F)F)cc3=O)c2)cc1C]

DZ-P1 ESI 674.3 (M+H)$^+$. $^1$H NMR (400 MHz, MeOD) δ 7.83 (s, 1H), 7.03 (t, J=7.3 Hz, 2H), 6.90 (s, 1H), 6.83 (s, 1H), 6.78 (s, 1H), 5.67 (t, J=8.0 Hz, 1H), 5.59 (t, J=6.7 Hz, 1H), 3.99 (t, J=8.2 Hz, 4H), 3.86 (s, 3H), 3.29 (d, J=3.5 Hz, 2H), 2.85 (t, J=6.7 Hz, 2H), 2.71 (d, J=6.7 Hz, 2H), 2.44-2.34 (m, 2H), 2.29 (d, J=1.6 Hz, 3H), 2.18 (s, 6H), 2.02 (t, J=7.5 Hz, 2H), 1.46-1.39 (m, 1H), 0.96 (t, J=6.2 Hz, 6H).

DZ-P2 ESI 674.3 (M+H)$^+$. $^1$H NMR (400 MHz, MeOD) δ 7.74 (s, 1H), 7.14-7.03 (m, 2H), 6.93 (s, 2H), 6.80 (s, 1H), 5.80-5.71 (m, 1H), 5.64 (t, J=7.6 Hz, 1H), 4.14 (t, J=8.0 Hz, 4H), 3.86 (s, 3H), 3.50-3.36 (m, 2H), 2.95 (d, J=15.7 Hz, 1H), 2.87-2.78 (m, 1H), 2.67-2.60 (m, 1H), 2.57-2.42 (m, 3H), 2.33 (d, J=1.6 Hz, 3H), 2.20 (d, J=19.2 Hz, 6H), 2.05-1.96 (m, 1H), 1.73-1.65 (m, 1H), 1.47-1.37 (m, 1H), 0.92 (t, J=6.7 Hz, 6H).

4-80. (3S)-3-(2-(5-(2-(azetidin-1-yl)ethyl)-2-oxo-4-(trifluoromethyl)pyridin-1(2H)-yl)-4-methylpentanamido)-3-(4'-cyano-4,5'-difluoro-2',5-dimethylbiphenyl-3-yl)propanoic Acid (Diastereomeric Compounds EA-P1 and EA-P2)

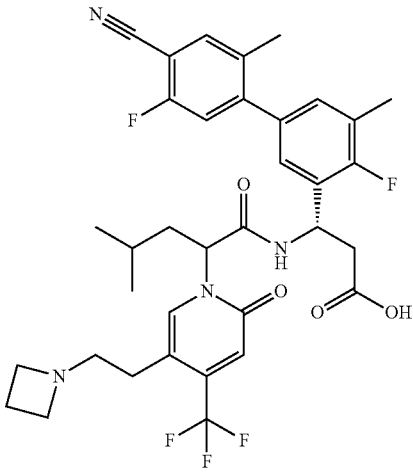 [SMILES: Cc1cc(C#N)c(F)cc1-c1cc(C)c(F)c([C@H](CC(=O)O)NC(=O)C(CC(C)C)n2cc(CCN3CCC3)c(C(F)(F)F)cc2=O)c1]

EA-P1 ESI 673.3 (M+H)$^+$. $^1$H NMR (500 MHz, MeOD) δ 7.86 (s, 1H), 7.67 (d, J=6.6 Hz, 1H), 7.24-7.07 (m, 3H), 6.79 (d, J=7.4 Hz, 1H), 5.78-5.50 (m, 2H), 4.10 (t, J=8.1 Hz, 4H), 3.41-3.34 (m, 2H), 2.92-2.65 (m, 4H), 2.61-2.40 (m, 2H), 2.32 (s, 3H), 2.23 (s, 3H), 2.15-1.86 (m, 2H), 1.54-1.38 (m, 1H), 0.97 (t, J=6.6 Hz, 6H).

EA-P2 ESI 673.3 (M+H)$^+$. $^1$H NMR (500 MHz, MeOD) δ 7.75-7.59 (m, 2H), 7.25-7.16 (m, 3H), 6.93 (s, 1H), 5.80-5.55 (m, 2H), 4.16 (t, J=7.9 Hz, 4H), 3.50-3.37 (m, 2H), 3.04-2.77 (m, 2H), 2.72-2.43 (m, 4H), 2.36 (s, 3H), 2.28 (s, 3H), 2.06-1.96 (m, 1H), 1.83-1.64 (m, 1H), 1.53-1.29 (m, 1H), 0.97-0.89 (m, 6H).

4-81. (3S)-3-(2-(5-(2-(azetidin-1-yl)ethyl)-2-oxo-4-(trifluoromethyl)pyridin-1(2H)-yl)-4-methylpentanamido)-3-(5'-cyano-4,4'-difluoro-2',5-dimethyl-[1,1'-biphenyl]-3-yl)propanoic Acid (Diastereomeric Compounds EB-P1 and EB-P2)

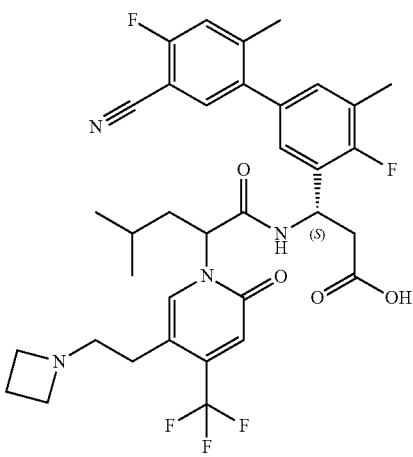

EB-P1 ESI 673.3 (M+H)$^+$. $^1$H NMR (400 MHz, MeOD) δ 7.85 (s, 1H), 7.55 (d, J=6.7 Hz, 1H), 7.32 (d, J=10.3 Hz,

1H), 7.10 (d, J=6.4 Hz, 2H), 6.81 (s, 1H), 5.65-5.55 (m, 2H), 4.03 (t, J=8.0 Hz, 4H), 3.32-3.26 (m, 2H), 2.84 (t, J=7.0 Hz, 2H), 2.78-2.67 (m, 2H), 2.51-2.36 (m, 2H), 2.36-2.25 (m, 6H), 2.14-1.92 (m, 2H), 1.52-1.36 (m, 1H), 0.97 (t, J=6.1 Hz, 6H).

EB-P2 ESI 673.3 (M+H)+. 1H NMR (400 MHz, MeOD) δ 7.74 (s, 1H), 7.57 (d, J=6.7 Hz, 1H), 7.34 (d, J=10.2 Hz, 1H), 7.14 (d, J=6.7 Hz, 2H), 6.93 (s, 1H), 5.76-5.71 (m, 1H), 5.63 (t, J=7.7 Hz, 1H), 4.13 (t, J=7.9 Hz, 4H), 3.49-3.35 (m, 2H), 3.00-2.87 (m, 1H), 2.88-2.75 (m, 1H), 2.68-2.60 (m, 1H), 2.57-2.42 (m, 3H), 2.39-2.28 (m, 6H), 2.05-1.95 (m, 1H), 1.79-1.63 (m, 1H), 1.48-1.37 (m, 1H), 0.92 (t, J=6.6 Hz, 6H).

4-82. (3S)-3-(2-(5-(2-(dimethylamino)ethyl)-3-fluoro-2-oxo-4-(trifluoromethyl)pyridin-1(2H)-yl)-4-methylpentanamido)-3-(4-fluoro-2',5',6'-trimethylbiphenyl-3-yl)propanoic Acid (Diastereomeric Compounds EC-P1 and EC-P2)

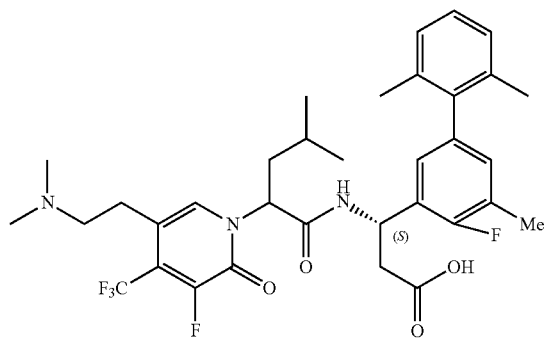

EC-P1 ESI 650.2 (M+H)+. 1H NMR (500 MHz, MeOD) δ 7.70 (s, 1H), 7.12 (t, J=7.5 Hz, 1H), 7.08-7.02 (m, 2H), 6.89-6.85 (m, 2H), 5.69 (t, J=8.0 Hz, 1H), 5.61-5.54 (m, 1H), 3.09-3.02 (m, 2H), 2.99 (d, J=7.3 Hz, 2H), 2.74-2.70 (m, 8H), 2.30 (s, 3H), 2.05-1.94 (m, 5H), 1.86 (s, 3H), 1.44 (m, 1H), 0.94-0.90 (m, 6H).

EC-P2 ESI 650.2 (M+H)+. 1H NMR (500 MHz, MeOD) δ 7.62 (s, 1H), 7.18-7.07 (m, 3H), 6.94 (t, J=6.8 Hz, 2H), 5.73-5.70 (m, 1H), 5.61 (t, J=7.6 Hz, 1H), 3.31-3.18 (m, 2H), 3.11-2.95 (m, 2H), 2.84 (s, 6H), 2.65-2.60 (m, 1H), 2.52-2.48 (m, 1H), 2.35-2.32 (m, 3H), 2.08-1.94 (m, 7H), 1.74-1.64 (m, 1H), 1.42-1.39 (m, 1H), 0.90 (d, J=6.6 Hz, 6H).

4-83. (3S)-3-(2-(5-(2-(dimethylamino)ethyl)-3-fluoro-2-oxo-4-(trifluoromethyl)pyridin-1(2H)-yl)-4-methylpentanamido)-3-(4-fluoro-2',4',5,6'-tetramethylbiphenyl-3-yl)propanoic Acid (Diastereomeric Compounds ED-P1 and ED-P2)

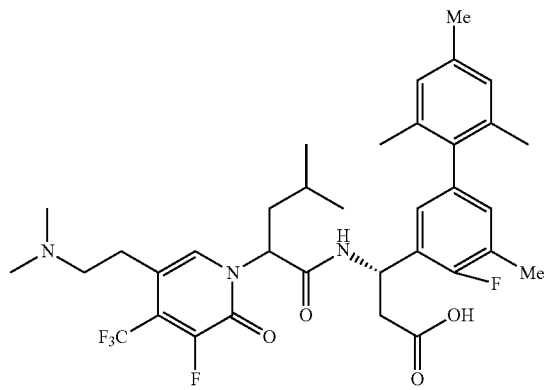 [SMILES: Cc1cc(C)c(-c2cc(C)c(F)c([C@H](CC(=O)O)NC(=O)C(CC(C)C)n3cc(CCN(C)C)c(C(F)(F)F)c(F)c3=O)c2)c(C)c1]

ED-P1 ESI 664.2 (M+H)+. 1H NMR (400 MHz, MeOD) δ 7.69 (s, 1H), 6.96-6.77 (m, 4H), 5.72-5.66 (m, 1H), 5.56 (s, 1H), 3.09-2.90 (m, 4H), 2.71 (d, J=4.8 Hz, 8H), 2.29 (s, 6H), 2.08-1.91 (m, 5H), 1.82 (s, 3H), 1.44 (s, 1H), 0.95-0.90 (m, 6H).

ED-P2 ESI 664.2 (M+H)+. 1H NMR (400 MHz, MeOD) δ 7.62 (d, J=12.1 Hz, 1H), 6.97-6.85 (m, 4H), 5.72-5.69 (m, 1H), 5.62 (t, J=7.6 Hz, 1H), 3.22 (qd, J=13.0, 6.1 Hz, 2H), 3.13-2.89 (m, 2H), 2.82 (s, 6H), 2.64-2.60 (m, 1H), 2.49-2.45 (m, 1H), 2.36-2.23 (m, 6H), 2.04-1.90 (m, 7H), 1.74-1.64 (m, 1H), 1.41-1.38 (m, 1H), 0.90-0.86 (m, 6H).

4-84. (3S)-3-(4,4'-difluoro-2',5,6'-trimethylbiphenyl-3-yl)-3-(2-(5-(2-(3-methoxyazetidin-1-yl)ethyl)-2-oxo-4-(trifluoromethyl)pyridin-1(2H)-yl)-4-methylpentanamido)propanoic Acid (Diastereomeric Compounds EE-P1 and EE-P2)

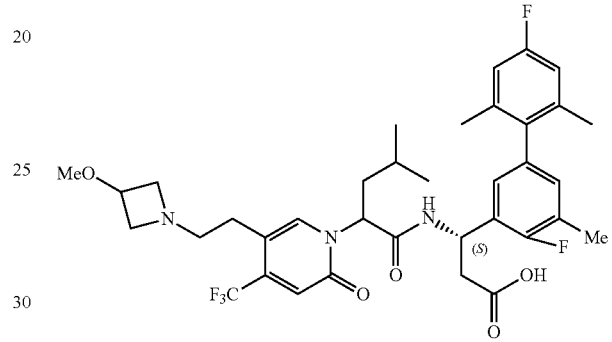

EE-P1 ESI 692.2 (M+H)+. 1H NMR (400 MHz, MeOD) δ 7.84 (s, 1H), 6.96-6.68 (m, 5H), 5.75-5.48 (m, 2H), 4.26-4.01 (m, 3H), 3.74-3.52 (m, 2H), 3.31 (s, 3H), 3.14 (t, J=6.8 Hz, 2H), 2.87-2.63 (m, 4H), 2.30 (s, 3H), 2.05-1.92 (m, 5H), 1.85 (s, 3H), 1.54-1.36 (m, 1H), 1.07-0.87 (m, 6H).

EE-P2 ESI 692.2 (M+H)+. 1H NMR (400 MHz, MeOD) δ 7.74 (s, 1H), 7.04-6.78 (m, 5H), 5.80-5.70 (m, 1H), 5.62 (t, J=7.7 Hz, 1H), 4.49-4.21 (m, 3H), 4.01-3.74 (m, 2H), 3.46-3.35 (m, 5H), 3.03-2.77 (m, 2H), 2.68-2.44 (m, 2H), 2.34 (d, J=1.7 Hz, 3H), 2.12-1.90 (m, 7H), 1.74-1.57 (m, 1H), 1.53-1.32 (m, 1H), 0.99-0.83 (m, 6H).

4-85. (3S)-3-(2-(5-(2-(dimethylamino)ethyl)-2-oxo-4-(trifluoromethyl)pyridin-1(2H)-yl)pentanamido)-3-(4-fluoro-2',4',5,6'-tetramethyl-[1,1'-biphenyl]-3-yl)propanoic Acid (Diastereomeric Compounds EF-P1 and EF-P2)

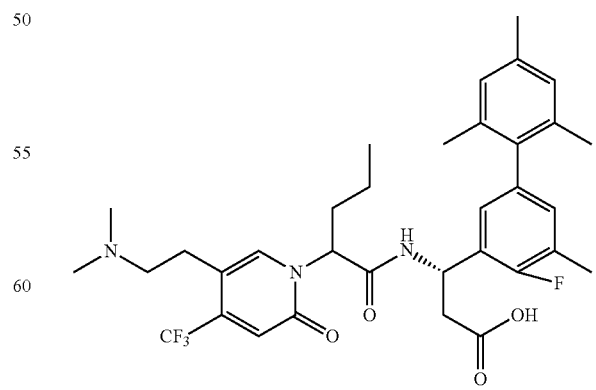

EF-P1 ESI 632.2 (M+H)+. 1H NMR (500 MHz, MeOD) δ 7.88 (s, 1H), 6.92-6.79 (m, 4H), 6.74 (s, 1H), 5.66-5.45 (m, 2H), 3.11-2.85 (m, 5H), 2.78-2.68 (m, 7H), 2.32-2.22 (m,

6H), 2.18-2.08 (m, 1H), 2.06-1.92 (m, 4H), 1.78 (s, 3H), 1.41-1.24 (m, 2H), 0.97 (t, J=7.4 Hz, 3H).

EF-P2 ESI 632.2 (M+H)+. 1H NMR (500 MHz, MeOD) δ 7.82 (s, 1H), 6.90 (d, J=7.1 Hz, 5H), 5.79-5.64 (m, 1H), 5.52 (t, J=7.6 Hz, 1H), 3.30-3.15 (m, 2H), 3.00 (t, J=6.6 Hz, 2H), 2.83 (s, 6H), 2.69-2.59 (m, 1H), 2.58-2.44 (m, 1H), 2.31 (d, J=9.7 Hz, 6H), 2.13-2.01 (m, 1H), 1.97 (s, 6H), 1.91-1.73 (m, 1H), 1.39-1.02 (m, 2H), 0.91 (t, J=7.4 Hz, 3H).

4-86. (3S)-3-(2-(5-(2-(dimethylamino)ethyl)-4-methyl-2-oxopyridin-1(2H)-yl)-5-methylhexanamido)-3-(4-fluoro-2',4',5,6'-tetramethylbiphenyl-3-yl)propanoic Acid (Diastereomeric Compounds EF2-P1 and EF2-P2)

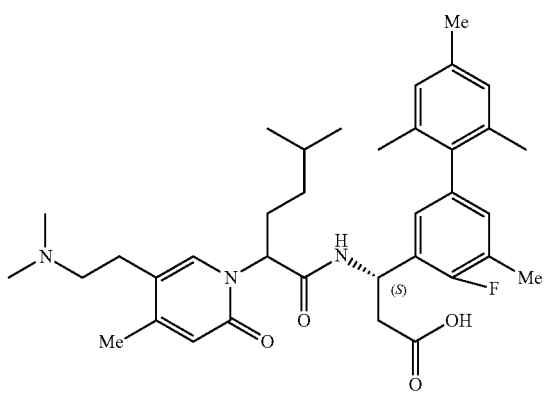

EF2-P1 ESI 606.3 (M+H)+. 1H NMR (400 MHz, MeOD) δ 7.57 (s, 1H), 6.90 (s, 2H), 6.85-6.80 (m, 2H), 6.34 (s, 1H), 5.48 (t, J=6.0 Hz, 1H), 5.42-5.37 (s, 1H), 3.24-3.02 (m, 2H), 2.89-2.85 (m, 2H), 2.76 (s, 6H), 2.71-2.60 (m, 2H), 2.30 (d, J=4.9 Hz, 6H), 2.25 (s, 3H), 2.22-2.14 (m, 1H), 1.95 (s, 4H), 1.87 (s, 3H), 1.60-1.53 (m, 1H), 1.25-1.14 (m, 1H), 1.12-1.00 (m, 1H), 0.89-0.87 (m, 6H).

EF2-P2 ESI 606.3 (M+H)+. 1H NMR (400 MHz, MeOD) δ 7.54 (s, 1H), 6.98-6.78 (m, 4H), 6.44 (s, 1H), 5.66-5.63 (m, 1H), 5.42 (t, J=7.7 Hz, 1H), 3.31-3.28 (m, 1H), 3.26-3.14 (m, 1H), 2.99-2.88 (m, 2H), 2.84 (s, 6H), 2.64-2.59 (m, 1H), 2.50-2.43 (m, 1H), 2.39-2.28 (m, 6H), 2.27 (s, 3H), 2.16-2.07 (m, 1H), 1.96 (s, 6H), 1.89-1.74 (m, 1H), 1.57-1.50 (m, 1H), 1.15-1.11 (m, 1H), 1.08-0.97 (m, 1H), 0.85 (t, J=6.5 Hz, 6H).

4-87. (3S)-3-(4,4'-difluoro-2',5,6'-trimethylbiphenyl-3-yl)-3-(2-(5-(2-(dimethylamino)ethyl)-4-methyl-2-oxopyridin-1(2H)-yl)-5-methylhexanamido)propanoic Acid (Diastereomeric Compounds EG-P1 and EG-P2)

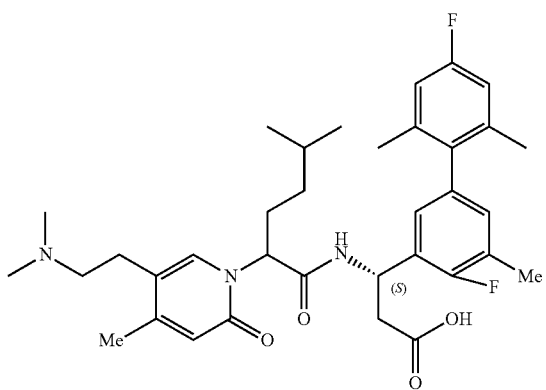

EG-P1 ESI 610.3 (M+H)+. 1H NMR (400 MHz, MeOD) δ 7.58 (s, 1H), 6.84 (t, J=9.1 Hz, 4H), 6.32 (s, 1H), 5.50 (t, J=6.2 Hz, 1H), 5.44-5.33 (m, 1H), 3.24-3.06 (m, 2H), 2.90-2.84 (m, 2H), 2.78 (s, 6H), 2.73-2.62 (m, 2H), 2.28 (d, J=14.1 Hz, 6H), 2.22-2.11 (m, 1H), 2.00-1.96 (m, 4H), 1.89 (s, 3H), 1.60-1.54 (m, 1H), 1.29-1.15 (m, 1H), 1.10-1.03 (m, 1H), 0.89-0.87 (m, 6H).

EG-P2 ESI 610.3 (M+H)+. 1H NMR (400 MHz, MeOD) δ 7.54 (s, 1H), 6.90 (d, J=6.9 Hz, 2H), 6.84 (d, J=9.6 Hz, 2H), 6.44 (s, 1H), 5.66-5.62 (m, 1H), 5.43 (t, J=7.6 Hz, 1H), 3.38-3.35 (m, 1H), 3.24-3.20 (m, 1H), 3.00-2.89 (m, 2H), 2.85 (s, 6H), 2.64-2.59 (m, 1H), 2.50-2.44 (m, 1H), 2.33 (d, J=4 Hz, 3H), 2.28 (s, 3H), 2.17-2.07 (m, 1H), 2.01 (s, 6H), 1.87-1.77 (m, 1H), 1.57-1.51 (m, 1H), 1.20-1.09 (m, 1H), 1.08-0.97 (m, 1H), 0.85 (t, J=6.4 Hz, 6H).

4-88. (3S)-3-(4,4'-difluoro-2',5,6'-trimethyl-[1,1'-biphenyl]-3-yl)-3-(2-(3-fluoro-5-(2-(3-methoxyazetidin-1-yl)ethyl)-4-methyl-2-oxopyridin-1(2H)-yl)-4-methylpentanamido)propanoic Acid (Diastereomeric Compounds EH-P1 and EH-P2)

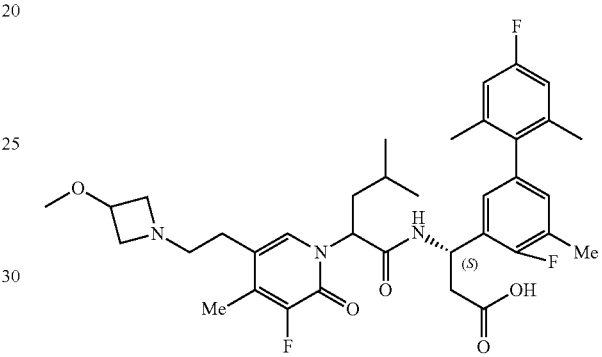

EH-P1 ESI 656.3 (M+H)+. 1H NMR (400 MHz, MeOD) δ 7.40 (s, 1H), 6.95-6.72 (m, 4H), 5.71-5.47 (m, 2H), 4.27-4.16 (m, 2H), 4.16-4.07 (m, 1H), 3.81-3.69 (m, 1H), 3.70-3.58 (m, 1H), 3.30 (s, 3H), 3.25 (t, J=6.8 Hz, 2H), 2.88-2.63 (m, 4H), 2.37-2.16 (m, 6H), 2.06-1.82 (m, 8H), 1.49-1.28 (m, 1H), 0.97-0.90 (m, 6H).

EH-P2 ESI 656.3 (M+H)+. 1H NMR (400 MHz, MeOD) δ 7.33 (s, 1H), 6.96-6.89 (m, 2H), 6.84 (d, J=9.7 Hz, 2H), 5.72-5.58 (m, 2H), 4.39-4.14 (m, 3H), 3.85-3.65 (m, 2H), 3.31-3.20 (m, 5H), 2.93-2.78 (m, 1H), 2.77-2.55 (m, 2H), 2.54-2.45 (m, 1H), 2.33 (d, J=1.7 Hz, 3H), 2.22 (d, J=2.7 Hz, 3H), 2.06-1.86 (m, 7H), 1.81-1.66 (m, 1H), 1.344-1.32 (m, 1H), 0.90 (d, J=6.6 Hz, 6H).

4-89. (3S)-3-(5-chloro-4-fluoro-2',4',6'-trimethylbiphenyl-3-yl)-3-(2-(5-(2-(dimethylamino)ethyl)-3-fluoro-2-oxo-4-(trifluoromethyl)pyridin-1(2H)-yl)-4-methylpentanamido)propanoic Acid (Diastereomeric Compounds EI-P1 and EI-P2)

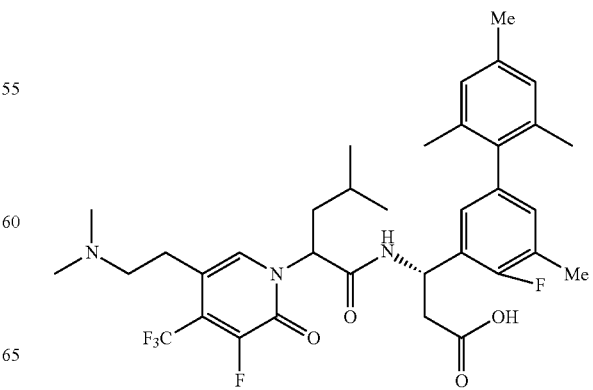

EI-P1 ESI 684.2 (M+H)⁺. 1H NMR (500 MHz, MeOD) δ 7.65 (s, 1H), 7.13 (d, J=6.3 Hz, 1H), 7.08 (d, J=6.1 Hz, 1H), 6.93 (s, 2H), 5.66 (d, J=5.4 Hz, 2H), 3.13-2.89 (m, 4H), 2.70 (s, 6H), 2.67-2.62 (m, 1H), 2.62-2.53 (m, 1H), 2.30 (s, 3H), 1.98 (d, J=6.9 Hz, 7H), 1.74-1.70 (m, 1H), 1.40-1.33 (m, 1H), 0.89 (d, J=5.6 Hz, 6H).

EI-P2 ESI 684.2 (M+H)⁺. 1H NMR (500 MHz, MeOD) δ 7.67 (s, 1H), 7.10 (d, J=6.9 Hz, 1H), 7.02 (d, J=6.1 Hz, 1H), 6.91 (d, J=13.0 Hz, 2H), 5.68 (t, J=8.1 Hz, 1H), 5.55 (t, J=7.0 Hz, 1H), 3.08 (s, 2H), 2.98 (d, J=7.7 Hz, 2H), 2.73 (d, J=9.7 Hz, 8H), 2.30 (s, 3H), 2.04-1.93 (m, 5H), 1.83 (s, 3H), 1.44-1.40 (m, 1H), 0.96-0.92 (m, 6H).

4-90. (3S)-3-(2-(5-(2-(azetidin-1-yl)ethyl)-2-oxo-4-(trifluoromethyl)pyridin-1(2H)-yl)-4-methylpentanamido)-3-(4'-cyano-4-fluoro-2',5,5'-trimethyl-[1,1'-biphenyl]-3-yl)propanoic Acid (Diastereomeric Compounds EJ-P1 and EJ-P2)

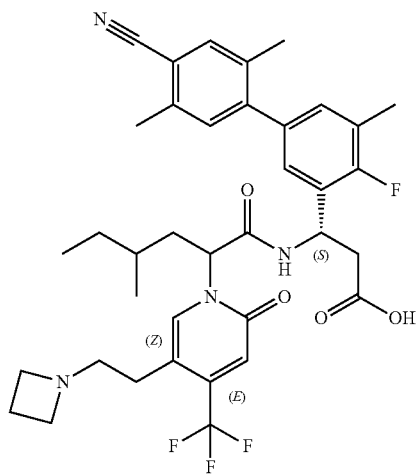

EJ-P1 ESI 669.3 (M+H)⁺. ¹H NMR (400 MHz, MeOD) δ 7.72 (s, 1H), 7.45 (s, 1H), 7.10 (s, 1H), 7.06-6.92 (m, 2H), 6.65 (s, 1H), 5.57-5.40 (m, 2H), 3.92 (t, J=8.1 Hz, 4H), 2.73-2.70 (m, 2H), 2.60 (d, J=7.6 Hz, 2H), 2.40 (s, 3H), 23.0-2.33 (m, 2H), 2.36-2.30 (m, 2H), 2.19 (s, 3H), 2.09 (s, 3H), 1.94-1.88 (m, 2H), 1.35-1.21 (m, 1H), 0.86-0.83 (m, 6H).

EJ-P2 ESI 669.3 (M+H)⁺. ¹H NMR (400 MHz, MeOD) δ 7.61 (s, 1H), 7.47 (s, 1H), 7.13 (s, 1H), 7.10-6.98 (m, 2H), 6.80 (s, 1H), 5.65-5.62 (m, 1H), 5.52 (t, J=7.7 Hz, 1H), 4.04 (t, J=8.1 Hz, 4H), 3.40-3.25 (m, 2H), 2.86-2.64 (m, 2H), 2.54-2.49 (m, 1H), 2.45-2.30 (m, 6H), 2.23 (d, J=1.5 Hz, 3H), 2.14 (s, 3H), 1.95-1.81 (m, 1H), 1.63-1.52 (m, 1H), 1.31-1.26 (m, 1H), 0.84-0.78 (m, 6H).

4-91. (3S)-3-(4-fluoro-4'-methoxy-2',5,6'-trimethyl-[1,1'-biphenyl]-3-yl)-3-(2-(5-(2-(3-methoxyazetidin-1-yl)ethyl)-2-oxo-4-(trifluoromethyl)pyridin-1(2H)-yl)-4-methylpentanamido)propanoic Acid (Diastereomeric Compounds EK-P1 and EK-P2)

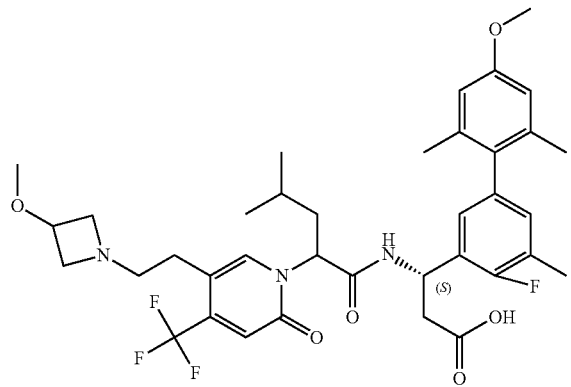

EK-P1 ESI 704.4 (M+H)⁺. ¹H NMR (400 MHz, MeOD) δ 7.85 (s, 1H), 6.86 (t, J=6.2 Hz, 2H), 6.77 (s, 1H), 6.65 (s, 1H), 6.62 (s, 1H), 5.67 (t, J=8.0 Hz, 1H), 5.61-5.56 (m, 1H), 4.25-4.09 (m, 3H), 3.79 (s, 3H), 3.71-3.61 (m, 2H), 3.31 (s, 3H), 3.17 (t, J=6.8 Hz, 2H), 2.81 (t, J=6.9 Hz, 2H), 2.76-2.69 (m, 2H), 2.28 (s, 3H), 2.04-1.97 (m, 5H), 1.82 (s, 3H), 1.48-1.41 (m, 1H), 0.98-0.93 (m, 6H).

EK-P2 ESI 704.4 (M+H)⁺. ¹H NMR (400 MHz, MeOD) δ 7.75 (s, 1H), 6.96-6.90 (m, 3H), 6.67 (s, 2H), 5.76-5.72 (m, 1H), 5.63 (t, J=7.7 Hz, 1H), 4.44-4.26 (m, 3H), 3.98-3.92 (m, 1H), 3.88-3.83 (m, 1H), 3.80 (s, 3H), 3.42-3.35 (m, 5H), 2.97-2.80 (m, 2H), 2.67-2.62 (m, 1H), 2.56-2.50 (m, 1H), 2.33 (d, J=1.6 Hz, 3H), 2.04-1.94 (m, 7H), 1.73-1.64 (m, 1H), 1.47-1.39 (m, 1H), 0.92-0.89 (m, 6H).

4-92. (3S)-3-(4'-cyano-4-fluoro-2',5,6'-trimethyl-[1,1'-biphenyl]-3-yl)-3-(2-(5-(2-(dimethylamino)ethyl)-2-oxo-4-(trifluoromethyl)pyridin-1(2H)-yl)-4-methylpentanamido)propanoic Acid (Diastereomeric Compounds EL-P1 and EL-P2)

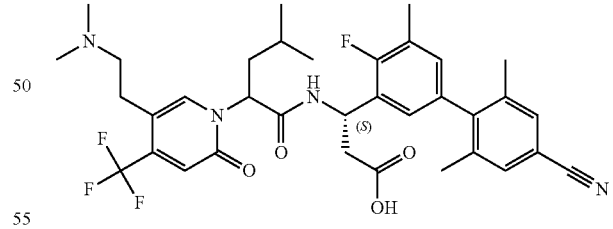

EL-P1 ESI 657.4 (M+H)⁺. ¹H NMR (400 MHz, MeOD) δ 7.88 (s, 1H), 7.45 (d, J=21.6 Hz, 2H), 6.88 (d, J=5.6 Hz, 2H), 6.71 (s, 1H), 5.72-5.47 (m, 2H), 3.08-2.85 (m, 4H), 2.79-2.57 (m, 8H), 2.30 (d, J=1.4 Hz, 3H), 2.11-1.93 (m, 5H), 1.88 (s, 3H), 1.50-1.37 (m, 1H), 1.06-0.86 (m, 6H).

EL-P2 ESI 657.4 (M+H)⁺. ¹H NMR (400 MHz, MeOD) δ 7.84 (s, 1H), 7.49 (s, 2H), 7.02-6.74 (m, 3H), 5.75-5.53 (m, 2H), 3.25-3.06 (m, 2H), 2.98 (t, J=6.9 Hz, 2H), 2.78 (s, 6H), 2.70-2.48 (m, 2H), 2.34 (d, J=1.4 Hz, 3H), 2.14-1.86 (m, 7H), 1.79-1.62 (m, 1H), 1.46-1.31 (m, 1H), 0.95-0.82 (m, 6H).

4-93. (3S)-3-(4'-chloro-4-fluoro-2',5,6'-trimethylbiphenyl-3-yl)-3-(2-(5-(2-(dimethylamino)ethyl)-2-oxo-4-(trifluoromethyl)pyridin-1(2H)-yl)-4-methylpentanamido)propanoic Acid (Diastereomeric Compounds EM-P1 and EM-P2)

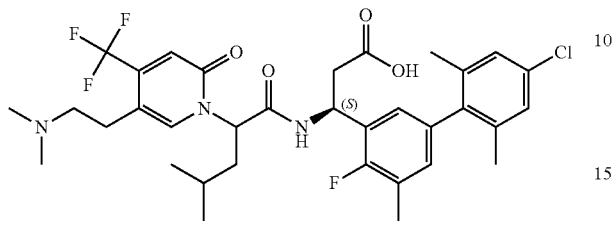

EM-P1 ESI 666.3 (M+H)⁺. 1H NMR (400 MHz, MeOD) δ 7.91 (s, 1H), 7.08 (d, J=24.1 Hz, 2H), 6.91-6.80 (m, 2H), 6.72 (s, 1H), 5.68 (t, J=8.0 Hz, 1H), 5.59-5.48 (m, 1H), 3.18-3.02 (m, 2H), 2.95 (t, J=7.0 Hz, 2H), 2.82-2.63 (m, 8H), 2.29 (s, 3H), 2.04-1.91 (m, 5H), 1.79 (s, 3H), 1.58-1.30 (m, 1H), 1.04-0.86 (m, 6H).

EM-P2 ESI 666.3 (M+H)⁺. 1H NMR (400 MHz, MeOD) δ 7.88 (s, 1H), 7.13 (s, 2H), 6.94-6.83 (m, 3H), 5.81-5.68 (m, 1H), 5.62 (t, J=7.7 Hz, 1H), 3.30-3.16 (m, 2H), 3.01 (t, J=6.8 Hz, 2H), 2.83 (s, 6H), 2.72-2.45 (m, 2H), 2.33 (d, J=1.1 Hz, 3H), 1.98 (d, 7H), 1.75-1.63 (m, 1H), 1.51-1.33 (m, 1H), 0.87 (d, J=6.6 Hz, 6H).

4-94. ((3S)-3-(4-fluoro-2',5,6'-trimethylbiphenyl-3-yl)-3-(2-(5-(2-((R)-3-fluoropyrrolidin-1-yl)ethyl)-4-methyl-2-oxopyridin-1(2H)-yl)-4-methylpentanamido)propanoic Acid (Diastereomeric Compounds EN-P1 and EN-P2)

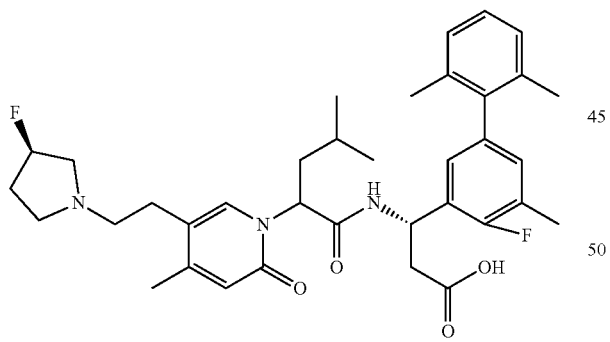

EN-P1 ESI 622.2 (M+H)⁺. ¹H NMR (500 MHz, MeOD) δ 7.54 (s, 1H), 7.16-7.02 (m, 3H), 6.87-6.78 (m, 2H), 6.27 (s, 1H), 5.73-5.50 (m, 2H), 5.34-5.15 (m, 1H), 3.31-3.23 (m, 1H), 3.22-3.00 (m, 2H), 2.94-2.80 (m, 3H), 2.78-2.59 (m, 4H), 2.36-2.09 (m, 8H), 2.01-1.91 (m, 5H), 1.83 (s, 3H), 1.50-1.37 (m, 1H), 0.97-0.89 (m, 6H).

EN-P2 ESI 622.2 (M+H)⁺. ¹H NMR (500 MHz, MeOD) δ 7.56 (s, 1H), 7.22-7.02 (m, 3H), 6.91 (d, J=6.8 Hz, 2H), 6.42 (s, 1H), 5.65-5.57 (m, 2H), 5.41-5.24 (m, 1H), 3.62-3.35 (m, 3H), 3.31-3.09 (m, 3H), 2.94-2.74 (m, 2H), 2.68-2.49 (m, 2H), 2.39-2.22 (m, 8H), 2.10-1.89 (m, 7H), 1.82-1.70 (m, 1H), 1.49-1.31 (m, 1H), 0.95-0.85 (m, 6H).

4-95. (3S)-3-(4-fluoro-2',4',5,6'-tetramethyl-[1,1'-biphenyl]-3-yl)-3-(2-(5-(2-(3-fluoroazetidine-1-yl)ethyl)-2-oxopyridin-1(2H)-yl)-4-methylpentanamido)propanoic Acid (Diastereomeric Compounds EO-P1 and EO-P2)

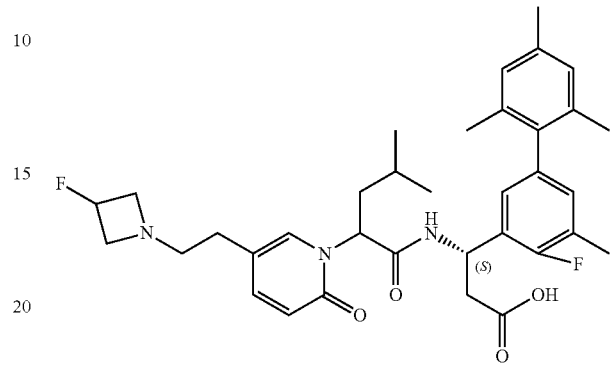

EO-P1 ESI 608.3 (M+H)⁺. ¹H NMR (400 MHz, MeOD) δ 7.52 (s, 1H), 7.39 (d, J=9.0 Hz, 1H), 6.96-6.79 (m, 3H), 6.73 (s, 1H), 6.43 (d, J=9.5 Hz, 1H), 5.74-5.46 (m, 2H), 5.14 (d, J=57.6 Hz, 1H), 3.77 (s, 2H), 3.50 (s, 2H), 2.88 (s, 2H), 2.79-2.60 (m, 2H), 2.51 (s, 2H), 2.29 (d, J=14.1 Hz, 6H), 1.96 (d, J=12.7 Hz, 5H), 1.80 (s, 3H), 1.42 (s, 1H), 1.03-0.79 (m, 6H).

EO-P2 ESI 608.3 (M+H)⁺. ¹H NMR (400 MHz, MeOD) δ 7.60-7.40 (m, 2H), 6.90 (d, J=7.8 Hz, 4H), 6.57 (d, J=9.2 Hz, 1H), 5.70-5.57 (m, 2H), 5.32 (d, J=57.4 Hz, 1H), 4.51-4.26 (m, 2H), 4.14-3.87 (m, 2H), 3.39 (d, J=5.3 Hz, 2H), 2.85-2.44 (m, 4H), 2.35-2.17 (m, 6H), 2.04-1.86 (m, 7H), 1.86-1.73 (m, 1H), 1.48-1.33 (m, 1H), 0.90 (t, J=6.3 Hz, 6H).

4-96. (3S)-3-(4,4'-difluoro-2',5,6'-trimethyl-[1,1'-biphenyl]-3-yl)-3-(2-(5-(2-(3-fluoroazetidine-1-yl)ethyl)-2-oxopyridin-1(2H)-yl)-4-methylpentanamido)propanoic Acid (Diastereomeric Compounds EP-P1 and EP-P2)

EP-P1 ESI 612.2 (M+H)⁺. ¹H NMR (400 MHz, MeOD) δ 7.54 (s, 1H), 7.43 (dd, J=9.2, 2.3 Hz, 1H), 6.87-6.82 (m, 3H), 6.76 (d, J=6.7 Hz, 1H), 6.46 (d, J=9.3 Hz, 1H), 5.63 (d, J=7.9 Hz, 1H), 5.54-5.43 (m, 1H), 5.20 (d, J=57.2 Hz, 1H), 4.09-3.88 (m, 2H), 3.71-3.55 (m, 2H), 3.10-3.02 (m, 2H), 2.80-2.53 (m, 4H), 2.29 (s, 3H), 2.03-1.92 (m, 5H), 1.87 (s, 3H), 1.50-1.36 (m, 1H), 0.97-0.92 (m, 6H).

EP-P2 ESI 612.2 (M+H)+. 1H NMR (400 MHz, MeOD) δ 7.41 (s, 1H), 7.38-7.35 (m, 1H), 6.79 (t, J=6.1 Hz, 2H), 6.73 (d, J=9.7 Hz, 2H), 6.45 (d, J=9.3 Hz, 1H), 5.53-5.48 (m, 2H), 5.20 (d, J=57.2 Hz, 1H), 4.39-4.14 (m, 2H), 3.99-3.87 (m, 2H), 3.32-3.25 (m, 2H), 2.67-2.48 (m, 3H), 2.40-2.34 (m, 1H), 2.21 (d, J=1.7 Hz, 3H), 1.90-1.81 (m, 7H), 1.72-1.64 (m, 1H), 1.33-1.22 (m, 1H), 0.79 (t, J=6.6 Hz, 6H).

4-97. (3S)-3-(4,4'-difluoro-2',5,6'-trimethyl-[1,1'-biphenyl]-3-yl)-3-(2-(3-fluoro-5-(2-(3-fluoroazetidine-1-yl)ethyl)-2-oxopyridin-1(2H)-yl)-4-methylpentanamido)propanoic Acid (Diastereomeric Compounds EQ-P1 and EQ-P2)

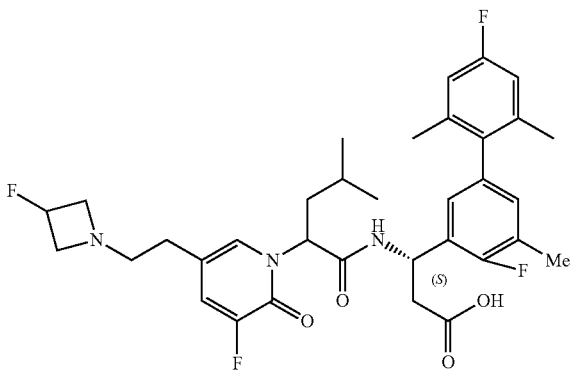

EQ-P1 ESI 630.2 (M+H)+. 1H NMR (400 MHz, MeOD) δ 7.30 (s, 1H), 7.25-7.22 (m, 1H), 6.77-6.75 (m, 1H), 6.72-6.69 (m, 3H), 5.55 (t, J=8.0 Hz, 1H), 5.40-5.37 (m, 1H), 5.18-5.01 (m, 1H), 3.99-3.82 (m, 2H), 3.66-3.48 (m, 2H), 3.06-2.99 (m, 2H), 2.66-2.50 (m, 4H), 2.18 (d, J=1.5 Hz, 3H), 1.89-1.81 (m, 5H), 1.78 (s, 3H), 1.34-1.27 (m, 1H), 0.85-0.78 (m, 6H).

EQ-P2 ESI 630.2 (M+H)+. 1H NMR (400 MHz, MeOD) δ 7.27-7.23 (m, 2H), 6.80 (d, J=6.9 Hz, 2H), 6.73 (d, J=9.6 Hz, 2H), 5.56-5.49 (m, 2H), 5.28-5.11 (m, 2H), 4.33-4.18 (m, 2H), 3.97-3.83 (m, 2H), 3.27-3.22 (m, 2H), 2.64-2.35 (m, 4H), 2.21 (d, J=1.9 Hz, 3H), 1.89-1.82 (m, 7H), 1.69-1.62 (m, 1H), 1.31-1.21 (m, 1H), 0.83-0.78 (m, 6H).

4-98. (3S)-3-(4,5-difluoro-2',6'-dimethyl-[1,1'-biphenyl]-3-yl)-3-(2-(5-(2-(dimethylamino)ethyl)-2-oxopyridin-1(2H)-yl)-4-methylpentanamido)propanoic Acid (Diastereomeric Compounds ER-P1 and ER-P2)

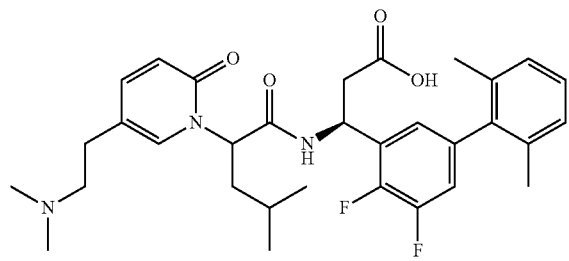 [SMILES: Cc1cccc(C)c1-c1cc(F)c(F)c([C@H](CC(=O)O)NC(=O)C(CC(C)C)n2cc(CCN(C)C)ccc2=O)c1]

ER-P1 ESI 568.2 (M+H)+. 1H NMR (500 MHz, MeOD) δ 7.64 (d, J=2.0 Hz, 1H), 7.54-7.51 (m, 1H), 7.18 (t, J=7.5 Hz, 1H), 7.11 (t, J=6.8 Hz, 2H), 6.99-6.90 (m, 1H), 6.78 (d, J=5.9 Hz, 1H), 6.52 (d, J=9.3 Hz, 1H), 5.61-5.56 (m, 1H), 5.42 (t, J=5.6 Hz, 1H), 3.32-3.19 (s, 1H), 3.24-3.10 (m, 1H), 2.88-2.80 (m, 2H), 2.73 (s, 6H), 2.70-2.64 (m, 1H), 2.59-2.53 (m, 1H), 2.06-1.89 (m, 8H), 1.50-1.36 (m, 1H), 0.97-0.90 (m, 6H).

ER-P2 ESI 568.2 (M+H)+. 1H NMR (500 MHz, MeOD) δ 1H NMR (500 MHz, MeOD) δ 7.65 (d, J=2.1 Hz, 1H), 7.54-7.50 (m, 1H), 7.22-7.13 (m, 1H), 7.14-7.07 (m, 2H), 7.01-6.90 (m, 1H), 6.88 (d, J=5.8 Hz, 1H), 6.54 (d, J=9.3 Hz, 1H), 5.66-5.52 (m, 2H), 3.38-3.34 (m, 1H), 3.28-3.21 (m, 1H), 2.98-2.86 (m, 1H), 2.86-2.73 (m, 7H), 2.64-2.59 (m, 1H), 2.51-2.44 (m, 1H), 2.08-1.91 (m, 7H), 1.92-1.81 (m, 1H), 1.49-1.35 (m, 1H), 0.93-0.88 (m, 6H).

4-99. (3S)-3-(2-(5-(2-(dimethylamino)ethyl)-2-oxopyridin-1(2H)-yl)-4-methylpentanamido)-3-(4,4',5-trifluoro-2',6'-dimethyl-[1,1'-biphenyl]-3-yl)propanoic Acid (Diastereomeric Compounds ES-P1 and ES-P2)

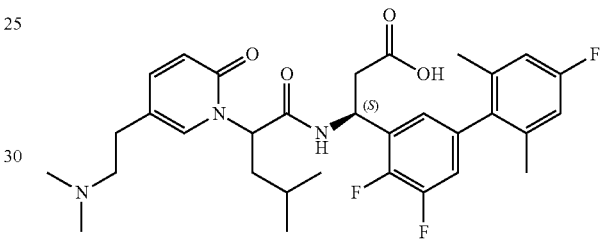

ES-P1 ESI 586.2 (M+H)+. 1H NMR (500 MHz, MeOD) δ 7.65 (s, 1H), 7.57-7.48 (m, 1H), 6.99-6.90 (m, 1H), 6.87 (d, J=8.8 Hz, 2H), 6.79 (d, J=5.8 Hz, 1H), 6.52 (d, J=9.4 Hz, 1H), 5.56 (s, 1H), 5.42 (t, J=5.6 Hz, 1H), 3.32-3.27 (m, 1H), 3.23-3.16 (m, 1H), 2.93-2.80 (m, 2H), 2.75 (s, 6H), 2.70-2.62 (m, 1H), 2.59-2.52 (m, 1H), 2.10-1.91 (m, 8H), 1.44 (s, 1H), 0.98-0.87 (m, 6H).

ES-P2 ESI 586.2 (M+H)+. 1H NMR (500 MHz, MeOD) δ 7.65 (d, J=2.1 Hz, 1H), 7.56-7.50 (m, 1H), 7.01-6.94 (m, 1H), 6.90-6.81 (m, 3H), 6.55 (d, J=9.3 Hz, 1H), 5.64-5.54 (m, 2H), 3.45-3.36 (m, 1H), 3.31-3.24 (m, 1H), 2.99-2.90 (m, 1H), 2.90-2.78 (m, 7H), 2.64-2.55 (m, 1H), 2.51-2.41 (m, 1H), 2.07-1.95 (m, 7H), 1.92-1.83 (m, 1H), 1.46-1.36 (m, 1H), 0.96-0.86 (m, 6H).

4-100. (3S)-3-(4,5-difluoro-2',6'-dimethyl-[1,1'-biphenyl]-3-yl)-3-(2-(5-(2-(3-fluoroazetidine-1-yl)ethyl)-2-oxopyridin-1(2H)-yl)-4-methylpentanamido)propanoic Acid (Diastereomeric Compounds ET-P1 and ET-P2)

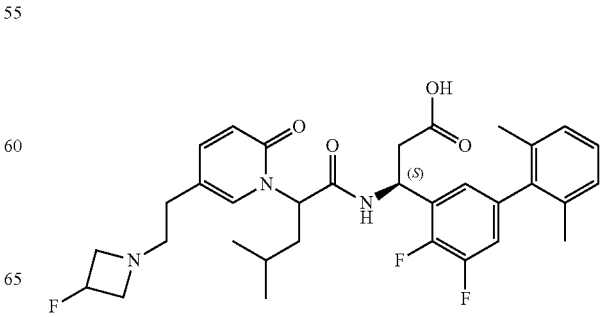

ET-P1 ESI 598.2 (M+H)⁺. ¹H NMR (500 MHz, MeOD) δ 7.54 (d, J=1.9 Hz, 1H), 7.46-7.40 (m, 1H), 7.21-7.14 (m, 1H), 7.11 (d, J=7.3 Hz, 2H), 6.99-6.90 (m, 1H), 6.81 (d, J=5.9 Hz, 1H), 6.47 (d, J=9.3 Hz, 1H), 5.62 (t, J=8.1 Hz, 1H), 5.51 (t, J=6.1 Hz, 1H), 5.31-5.14 (m, 1H), 4.17-3.96 (m, 2H), 3.82-3.67 (m, 2H), 3.21-3.11 (m, 2H), 2.78-2.58 (m, 4H), 2.03-1.89 (m, 8H), 1.47-1.40 (m, 1H), 0.97-0.88 (m, 6H).

ET-P2 ESI 598.2 (M+H)⁺. ¹H NMR (500 MHz, MeOD) δ 7.53 (d, J=2.0 Hz, 1H), 7.49-7.42 (m, 1H), 7.16 (d, J=7.4 Hz, 1H), 7.11 (d, J=7.7 Hz, 2H), 7.03-6.94 (m, 1H), 6.92 (d, J=5.9 Hz, 1H), 6.55 (d, J=9.3 Hz, 1H), 5.68-5.60 (m, 2H), 5.41-5.22 (m, 1H), 4.47-4.27 (m, 2H), 4.09-3.94 (m, 2H), 3.37 (s, 2H), 2.79-2.62 (m, 3H), 2.60-2.50 (m, 1H), 2.03 (d, J=2.2 Hz, 6H), 1.98-1.91 (m, 1H), 1.84-1.76 (m, 1H), 1.47-1.37 (m, 1H), 0.91 (t, J=6.1 Hz, 6H).

4-101. (3S)-3-(4-fluoro-2',5,6'-trimethyl-[1,1'-biphenyl]-3-yl)-3-(2-(5-(2-(3-fluoroazetidine-1-yl)ethyl)-4-methyl-2-oxopyridin-1(2H)-yl)-4-methylpentanamido)propanoic Acid (Diastereomeric Compounds EU-P1 and EU-P2)

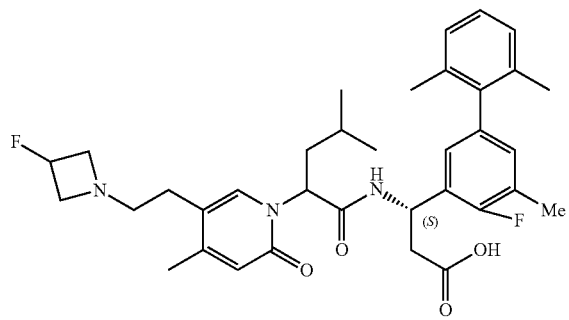

EU-P1 ESI 608.2 (M+H)⁺. ¹H NMR (500 MHz, MeOD) δ 8.45 (s, 0.47HCOOH), 7.54 (s, 1H), 7.15-7.05 (m, 3H), 6.89-6.81 (m, 2H), 6.30 (s, 1H), 5.68-5.48 (m, 2H), 5.40-5.14 (m, 1H), 4.35-4.13 (m, 2H), 4.06-3.86 (m, 2H), 3.26-3.20 (m, 2H), 2.88-2.65 (m, 4H), 2.29 (s, 3H), 2.23 (s, 3H), 2.01-1.89 (m, 5H), 1.85 (s, 3H), 1.48-1.38 (m, 1H), 0.98-0.91 (m, 6H).

EU-P2 ESI 608.2 (M+H)⁺. ¹H NMR (500 MHz, MeOD) δ 8.45 (s, 0.23HCOOH), 7.46 (s, 1H), 7.20-7.02 (m, 3H), 6.93 (d, J=5.0 Hz, 2H), 6.44 (s, 1H), 5.75-5.54 (m, 2H), 5.34 (d, J=57.3 Hz, 1H), 4.48-4.35 (m, 2H), 4.16-3.96 (m, 2H), 3.42-3.34 (m, 2H), 2.90-2.82 (m, 1H), 2.74-2.63 (m, 2H), 2.60-2.52 (m, 1H), 2.33 (s, 3H), 2.25 (s, 3H), 2.07-1.85 (m, 7H), 1.82-1.70 (m, 1H), 1.44-1.34 (m, 1H), 0.91-0.87 (m, 6H).

4-102. (3S)-3-(2-(5-((dimethylamino)methyl)-2-oxo-4-(trifluoromethyl)pyridin-1(2H)-yl)-4-methylpentanamido)-3-(4-fluoro-2',5,6'-trimethyl-[1,1'-biphenyl]-3-yl)propanoic Acid (Diastereomeric Compounds EV-P1 and EV-P2)

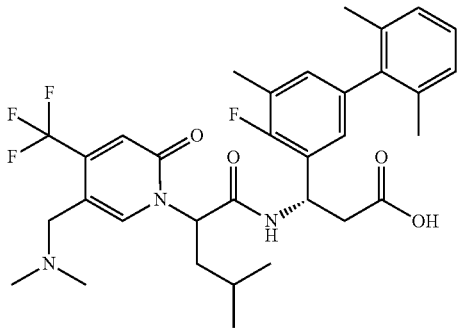 [SMILES: Cc1cc(-c2c(C)cccc2C)cc([C@H](CC(=O)O)NC(=O)C(CC(C)C)n2cc(CN(C)C)c(C(F)(F)F)cc2=O)c1F]

EV-P1 ESI 618.2 (M+H)⁺. ¹H NMR (400 MHz, MeOD) δ 8.07 (s, 1H), 7.15-7.00 (m, 3H), 6.94-6.83 (m, 2H), 6.77 (s, 1H), 5.75 (t, J=8.1 Hz, 1H), 5.63-5.52 (m, 1H), 3.83-3.59 (m, 2H), 2.82-2.72 (m, 2H), 2.52 (s, 6H), 2.29 (d, J=1.3 Hz, 3H), 2.05-1.95 (m, 5H), 1.80 (s, 3H), 1.49-1.37 (m, 1H), 1.01-0.91 (m, 6H).

EV-P2 ESI 618.2 (M+H)⁺. ¹H NMR (400 MHz, MeOD) δ 8.09 (s, 1H), 7.18-7.00 (m, 3H), 7.00-6.84 (m, 3H), 5.81-5.70 (m, 1H), 5.63-5.46 (m, 1H), 4.10 (d, J=14.4 Hz, 1H), 3.87 (d, J=14.4 Hz, 1H), 2.79-2.55 (m, 8H), 2.34 (d, J=1.5 Hz, 3H), 2.05-1.93 (m, 7H), 1.71-1.61 (m, 1H), 1.48-1.39 (m, 1H), 0.93-0.82 (m, 6H).

4-103. (3S)-3-(4,4'-difluoro-2',5,6'-trimethyl-[1,1'-biphenyl]-3-yl)-3-(2-(5-((dimethylamino)methyl)-2-oxo-4-(trifluoromethyl)pyridin-1(2H)-yl)-4-methylpentanamido)propanoic Acid (Diastereomeric Compounds EW-P1 and EW-P2)

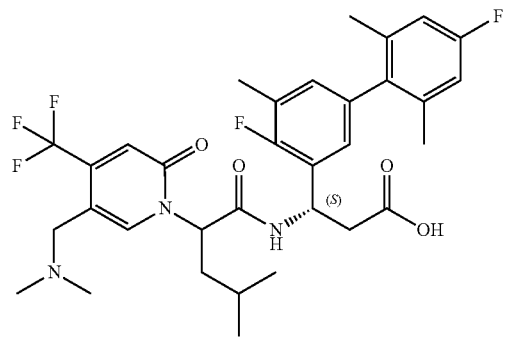

EW-P1 ESI 636.1 (M+H)⁺. ¹H NMR (400 MHz, MeOD) δ 8.06 (s, 1H), 6.95-6.72 (m, 5H), 5.75 (t, J=8.1 Hz, 1H), 5.62-5.56 (m, 1H), 3.79-3.65 (m, 2H), 2.86-2.65 (m, 2H), 2.52 (s, 6H), 2.29 (s, 3H), 2.04-1.93 (m, 5H), 1.81 (s, 3H), 1.50-1.38 (m, 1H), 0.96 (t, J=7.4 Hz, 6H).

EW-P2 ESI 636.1 (M+H)⁺. ¹H NMR (400 MHz, MeOD) δ 8.08 (s, 1H), 6.95-6.88 (m, 3H), 6.85 (d, J=9.6 Hz, 2H), 5.76-5.70 (m, 1H), 5.55 (t, J=7.5 Hz, 1H), 4.08 (d, J=14.4

Hz, 1H), 3.85 (d, J=14.4 Hz, 1H), 2.79-2.52 (m, 8H), 2.34 (s, 3H), 2.03-1.93 (m, 7H), 1.70-1.61 (m, 1H), 1.50-1.38 (m, 1H), 0.95-0.80 (m, 6H).

4-104. (3S)-3-(2-(5-((dimethylamino)methyl)-2-oxo-4-(trifluoromethyl)pyridin-1(2H)-yl)-4-methylpentanamido)-3-(4-fluoro-2',4',5,6'-tetramethyl-[1,1'-biphenyl]-3-yl)propanoic Acid (Diastereomeric Compounds EX-P1 and EX-P2)

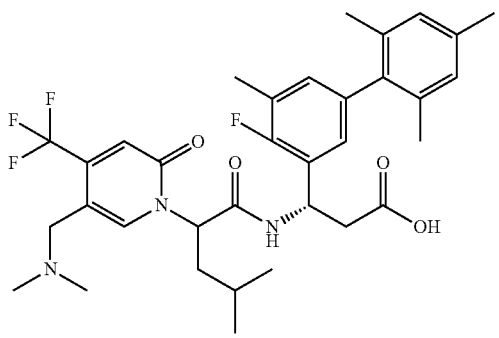

EX-P1 ESI 632.2 (M+H)$^+$. $^1$H NMR (400 MHz, MeOD) δ 8.05 (s, 1H), 6.92-6.82 (m, 4H), 6.76 (s, 1H), 5.75 (t, J=8.1 Hz, 1H), 5.63-5.50 (m, 1H), 3.78-3.62 (m, 2H), 2.88-2.65 (m, 2H), 2.50 (s, 6H), 2.29 (d, J=3.7 Hz, 6H), 2.03-1.89 (m, 5H), 1.76 (s, 3H), 1.52-1.36 (m, 1H), 0.96 (t, J=7.2 Hz, 6H).

EX-P2 ESI 632.2 (M+H)$^+$. $^1$H NMR (400 MHz, MeOD) δ 8.09 (s, 1H), 6.95-6.83 (m, 5H), 5.81-5.68 (m, 1H), 5.54 (t, J=7.4 Hz, 1H), 4.09 (d, J=14.4 Hz, 1H), 3.85 (d, J=14.3 Hz, 1H), 2.81-2.52 (m, 8H), 2.32 (d, J=9.8 Hz, 6H), 1.97 (t, J=9.1 Hz, 7H), 1.71-1.58 (m, 1H), 1.50-1.34 (m, 1H), 0.88 (d, J=6.4 Hz, 6H).

4-105. (3S)-3-(4,5-difluoro-2',4',6'-trimethyl-[1,1'-biphenyl]-3-yl)-3-(2-(5-((dimethylamino)methyl)-2-oxo-4-(trifluoromethyl)pyridin-1(2H)-yl)-4-methylpentanamido)propanoic Acid (Diastereomeric Compounds EY-P1 and EY-P2)

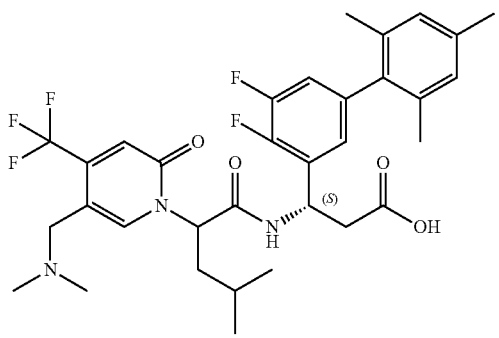

EY-P1 ESI 636.2 (M+H)$^+$. $^1$H NMR (400 MHz, MeOD) δ 7.99 (s, 1H), 6.92-6.84 (m, 4H), 6.72 (s, 1H), 5.82-5.68 (m, 1H), 5.61-5.55 (m, 1H), 3.61-3.48 (m, 2H), 2.83-2.65 (m, 2H), 2.38 (s, 6H), 2.30 (s, 3H), 2.03-1.92 (m, 5H), 1.73 (s, 3H), 1.49-1.37 (m, 1H), 0.99-0.93 (m, 6H).

EY-P2 ESI 636.2 (M+H)$^+$. $^1$H NMR (400 MHz, MeOD) δ 8.08 (s, 1H), 7.02-6.84 (m, 5H), 5.77-5.72 (m, 1H), 5.59-5.52 (m, 1H), 4.08 (d, J=14.4 Hz, 1H), 3.85 (d, J=14.4 Hz, 1H), 2.79-2.75 (m, 1H), 2.70-2.54 (m, 7H), 2.31 (s, 3H), 2.02-1.87 (m, 7H), 1.74-1.57 (m, 1H), 1.49-1.37 (m, 1H), 0.91-0.86 (m, 6H).

4-106. (3S)-3-(2-(5-(2-(dimethylamino)ethyl)-3-fluoro-2-oxopyridin-1(2H)-yl)-4-methylpentanamido)-3-(4,4',5-trifluoro-2',6'-dimethyl-[1,1'-biphenyl]-3-yl)propanoic Acid (Diastereomeric Compounds EZ-P1 and EZ-P2)

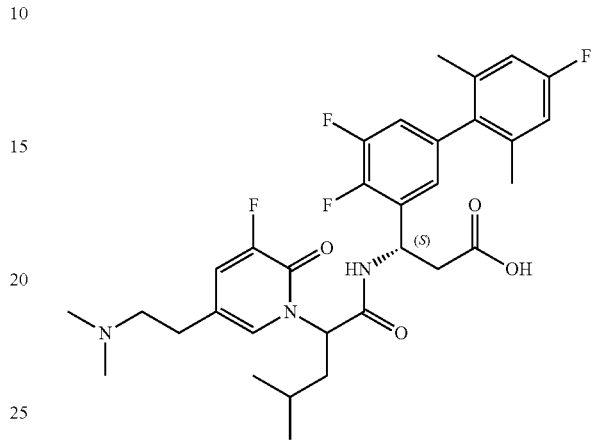

EZ-P1 ESI 604.2 (M+H)$^+$. $^1$H NMR (400 MHz, MeOD) δ 7.44 (s, 1H), 7.34-7.30 (m, 1H), 6.96-6.75 (m, 4H), 5.76-5.71 (m, 1H), 5.60-5.48 (m, 1H), 2.76-2.55 (m, 6H), 2.39 (s, 6H), 2.07-1.90 (m, 5H), 1.84 (s, 3H), 1.49-1.33 (m, 1H), 0.98-0.92 (m, 6H).

EZ-P2 ESI 604.2 (M+H)$^+$. $^1$H NMR (400 MHz, MeOD) δ 7.50 (s, 1H), 7.46-7.10 (m, 1H), 7.04-6.93 (m, 1H), 6.91-6.84 (m, 3H), 5.67-5.57 (m, 2H), 3.47-3.37 (m, 1H), 3.31-3.21 (m, 1H), 3.02-2.91 (m, 1H), 2.90-2.79 (m, 7H), 2.64-2.57 (m, 1H), 2.50-2.42 (m, 1H), 2.07-1.92 (m, 7H), 1.90-1.78 (m, 1H), 1.47-1.31 (m, 1H), 0.94-0.89 (m, 6H).

4-107. (3S)-3-(4,5-difluoro-2',4',6'-trimethyl-[1,1'-biphenyl]-3-yl)-3-(2-(5-(2-(dimethylamino)ethyl)-3-fluoro-2-oxopyridin-1(2H)-yl)-4-methylpentanamido)propanoic Acid (Diastereomeric Compounds FA-P1 and FA-P2)

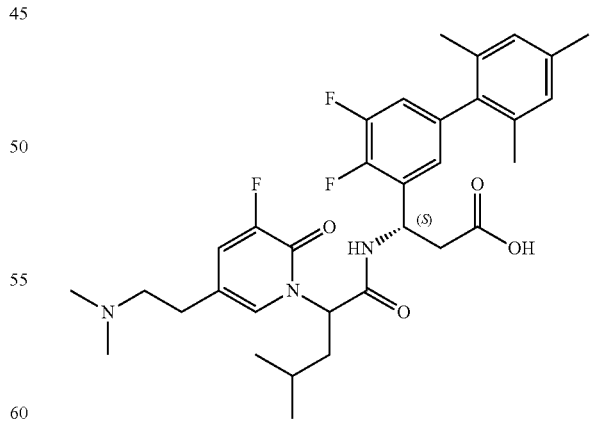

FA-P1 ESI 600.2 (M+H)$^+$. $^1$H NMR (400 MHz, MeOD) δ 7.49-7.44 (m, 2H), 6.92 (t, J=8.2 Hz, 3H), 6.76 (d, J=6.0 Hz, 1H), 5.65-5.61 (m, 1H), 5.40 (t, J=5.6 Hz, 1H), 3.19-3.15 (m, 2H), 2.90-2.84 (m, 3H), 2.75-2.63 (m, 7H), 2.57-2.52 (m, 1H), 2.31 (s, 3H), 2.03-1.87 (m, 9H), 1.46-1.40 (m, 1H), 0.98-0.91 (m, 6H).

FA-P2 ESI 600.2 (M+H)+. 1H NMR (400 MHz, MeOD) δ 7.37-7.29 (m, 2H), 6.87-6.71 (m, 4H), 5.57-5.42 (m, 2H), 3.34-3.24 (m, 1H), 3.18-3.07 (m, 1H), 2.87-2.81 (m, 1H), 2.73-2.70 (m, 7H), 2.50-2.45 (m, 1H), 2.36-2.30 (m, 1H), 2.19 (s, 3H), 1.96-1.80 (m, 7H), 1.74-1.63 (m, 1H), 1.30-1.25 (m, 1H), 0.81-0.79 (m, 6H).

4-108. (3S)-3-(2-(5-(2-(3-fluoroazetidine-1-yl)ethyl)-4-methyl-2-oxopyridin-1(2H)-yl)-4-methylpentanamido)-3-(4,4',5-trifluoro-2',6'-dimethylbiphenyl-3-yl)propanoic Acid (Diastereomeric Compounds FB-P1 and FB-P2)

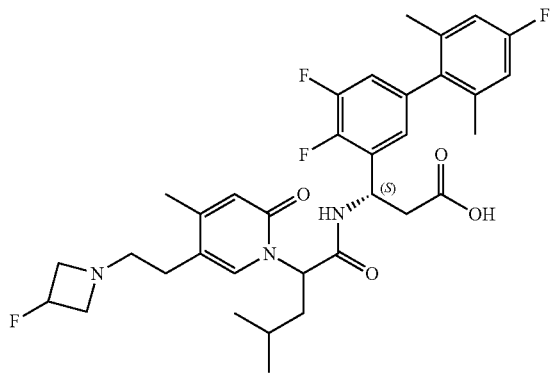

FB-P1 ESI 630.2 (M+H)+. 1H NMR (400 MHz, MeOD) δ 7.49 (s, 1H), 6.99-6.89 (m, 1H), 6.89-6.76 (m, 3H), 6.29 (s, 1H), 5.66-5.50 (m, 2H), 5.40-5.10 (m, 1H), 4.14-3.90 (m, 2H), 3.86-3.55 (m, 2H), 3.03 (s, 2H), 2.86-2.53 (m, 4H), 2.23 (s, 3H), 2.06-1.90 (m, 5H), 1.86 (s, 3H), 1.49-1.32 (m, 1H), 1.02-0.84 (m, 6H).

FB-P2 ESI 630.2 (M+H)+. 1H NMR (400 MHz, MeOD) δ 7.49 (s, 1H), 7.09-6.86 (m, 4H), 6.44 (s, 1H), 5.72-5.55 (m, 2H), 5.30 (d, J=57.8 Hz, 1H), 4.28 (s, 2H), 3.93 (s, 2H), 3.19 (s, 2H), 2.87-2.50 (m, 4H), 2.25 (s, 3H), 2.04 (s, 6H), 1.93-1.73 (m, 2H), 1.47-1.28 (m, 1H), 0.91-0.85 (m, 6H).

4-109. (3S)-3-(5-chloro-4,4'-difluoro-2',6'-dimethylbiphenyl-3-yl)-3-(2-(5-(2-(dimethylamino)ethyl)-2-oxo-4-(trifluoromethyl)pyridin-1(2H)-yl)-4-methylpentanamido)propanoic Acid (Diastereomeric Compounds FC-P1 and FC-P2)

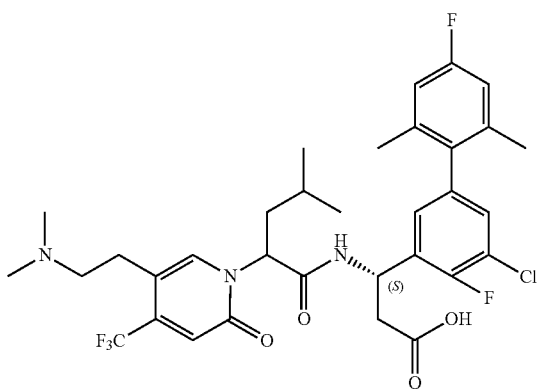

FC-P1 ESI 670.2 (M+H)+. 1H NMR (400 MHz, MeOD) δ 7.90 (s, 1H), 7.13-7.11 (m, 1H), 7.04-7.02 (m, 1H), 6.88-6.81 (m, 2H), 6.74 (s, 1H), 5.69-5.65 (m, 1H), 5.57-5.53 (m, 1H), 3.16-3.10 (m, 2H), 2.97-2.94 (m, 2H), 2.80 (s, 6H), 2.74-2.71 (m, 2H), 2.02-1.98 (m, 5H), 1.84 (s, 3H), 1.47-1.40 (m, 1H), 0.98-0.93 (m, 6H).

FC-P2 ESI 670.2 (M+H)+. 1H NMR (400 MHz, MeOD) δ 7.86 (s, 1H), 7.20-7.18 (m, 1H), 7.07 (d, J=6.1 Hz, 1H), 6.88 (d, J=11.2 Hz, 3H), 5.73-5.67 (m, 1H), 5.63 (t, J=7.6 Hz, 1H), 3.30-3.18 (m, 2H), 3.01 (t, J=6.9 Hz, 2H), 2.85 (s, 6H), 2.69-2.60 (m, 1H), 2.58-2.52 (m, 1H), 2.03-1.95 (m, 7H), 1.77-1.70 (m, 1H), 1.41-1.36 (m, 1H), 0.91-0.89 (m, 6H).

4-110. (3S)-3-(5-chloro-4,4'-difluoro-2',6'-dimethylbiphenyl-3-yl)-3-(2-(5-(2-(3-fluoroazetidine-1-yl)ethyl)-4-methyl-2-oxopyridin-1(2H)-yl)-4-methylpentanamido)propanoic Acid (Diastereomeric Compounds FD-P1 and FD-P2)

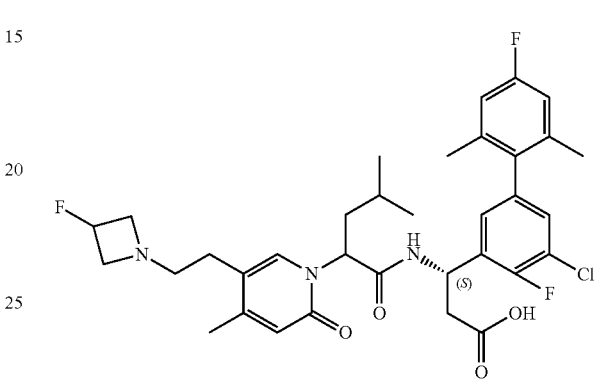

FD-P1 ESI 646.2 (M+H)+. 1H NMR (400 MHz, MeOD) δ 7.50 (s, 1H), 7.15-7.13 (m, 1H), 6.99-6.97 (m, 1H), 6.88-6.85 (m, 2H), 6.29 (s, 1H), 5.64-5.49 (m, 2H), 5.32-5.18 (m, 1H), 4.11-4.07 (m, 2H), 3.85-3.72 (m, 2H), 3.10 (t, J=6.9 Hz, 2H), 2.82-2.62 (m, 4H), 2.24 (s, 3H), 2.09-1.90 (m, 5H), 1.89 (d, J=8.2 Hz, 3H), 1.43-1.38 (m, 1H), 0.96-0.92 (m, 6H).

FD-P2 ESI 646.2 (M+H)+. 1H NMR (400 MHz, MeOD) δ 7.45 (s, 1H), 7.21-7.18 (m, 1H), 7.08-7.06 (m, 1H), 6.89 (d, J=9.6 Hz, 2H), 6.43 (s, 1H), 5.73-5.53 (m, 2H), 5.43-5.25 (m, 1H), 4.44-4.41 (m, 2H), 4.16-4.01 (m, 2H), 3.39-3.36 (m, 2H), 2.91-2.87 (m, 1H), 2.73-2.62 (m, 2H), 2.52-2.49 (m, 1H), 2.25 (s, 3H), 2.03 (s, 6H), 1.98-1.88 (m, 1H), 1.81-1.72 (m, 1H), 1.44-1.33 (m, 1H), 0.91-0.89 (m, 6H).

4-111. (3S)-3-(2-(5-(2-(dimethylamino)ethyl)-2-oxo-4-(trifluoromethyl)pyridin-1(2H)-yl)-4-methylpentanamido)-3-(4,4',5-trifluoro-2',6'-dimethylbiphenyl-3-yl)propanoic Acid (Diastereomeric Compounds FE-P1 and FE-P2)

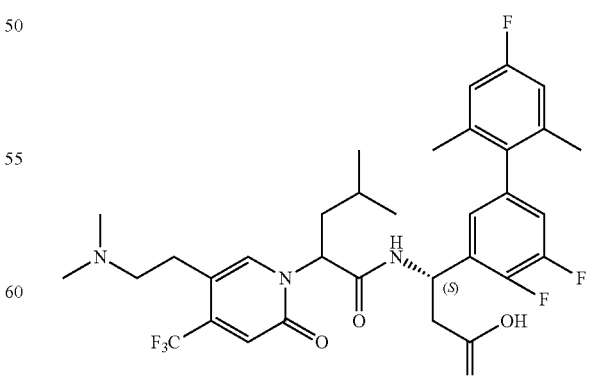

FE-P1 ESI 654.2 (M+H)+. 1H NMR (400 MHz, MeOD) δ 7.89 (s, 1H), 6.98-6.78 (m, 4H), 6.75 (s, 1H), 5.69-5.65 (m, 1H), 5.59-5.56 (m, 1H), 3.15-3.06 (m, 2H), 2.95 (d, J=6.2

Hz, 2H), 2.77 (s, 6H), 2.74-2.71 (m, 2H), 2.13-1.91 (m, 5H), 1.85 (s, 3H), 1.50-1.40 (m, 1H), 0.98-0.94 (m, 6H).
FE-P2 ESI 654.2 (M+H)+. 1H NMR (400 MHz, MeOD) δ 7.86 (s, 1H), 7.05-6.96 (m, 1H), 6.95-6.83 (m, 4H), 5.73-5.69 (m, 1H), 5.63 (t, J=7.7 Hz, 1H), 3.28-3.14 (m, 2H), 2.99 (t, J=7.0 Hz, 2H), 2.82 (s, 6H), 2.69-2.64 (m, 1H), 2.62-2.52 (m, 1H), 2.03 (d, J=2.1 Hz, 6H), 1.99-1.94 (m, 1H), 1.77-1.72 (m, 1H), 1.45-1.31 (m, 1H), 0.91-0.89 (m, 6H).

4-112. (3S)-3-(5-chloro-4,4'-difluoro-2',6'-dimethyl-biphenyl-3-yl)-3-(2-(5-(2-(3-fluoroazetidine-1-yl)ethyl)-2-oxopyridin-1(2H)-yl)-4-methylpentanamido)propanoic Acid (Diastereomeric Compounds FF-P1 and FF-P2)

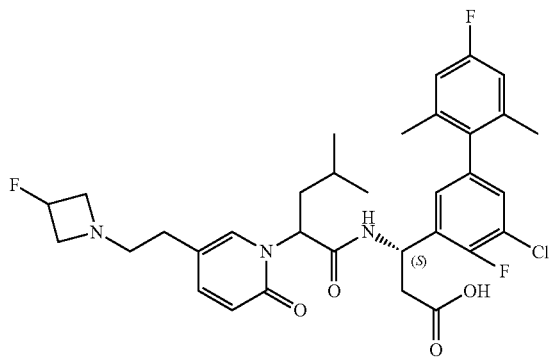

FF-P1 ESI 632.2 (M+H)+. 1H NMR (400 MHz, MeOD) δ 7.59 (s, 1H), 7.46-7.43 (m, 1H), 7.15-7.13 (m, 1H), 7.00-6.92 (m, 1H), 6.87 (d, J=9.6 Hz, 2H), 6.45 (d, J=9.3 Hz, 1H), 5.68-5.57 (m, 1H), 5.51 (t, J=6.2 Hz, 1H), 5.38-5.16 (m, 1H), 4.25-4.04 (m, 2H), 3.96-3.76 (m, 2H), 3.25-3.13 (m, 2H), 2.83-2.58 (m, 4H), 2.08-1.92 (m, 5H), 1.88 (s, 3H), 1.47-1.40 (m, 1H), 0.97-0.92 (m, 6H).
FF-P2 ESI 632.2 (M+H)+. 1H NMR (400 MHz, MeOD) δ 7.54 (s, 1H), 7.49 (d, J=8.8 Hz, 1H), 7.20-7.18 (m, 1H), 7.04 (d, J=4.5 Hz, 1H), 6.88 (d, J=9.6 Hz, 2H), 6.56 (d, J=9.1 Hz, 1H), 5.71-5.57 (m, 2H), 5.34 (d, J=59.0 Hz, 1H), 4.40 (s, 2H), 4.08 (s, 2H), 3.42 (s, 1H), 2.70 (d, J=52.7 Hz, 3H), 2.52 (s, 1H), 2.03 (d, J=3.5 Hz, 6H), 1.99-1.93 (m, 2H), 1.88-1.76 (m, 1H), 1.49-1.31 (m, 1H), 0.91 (t, J=6.7 Hz, 6H).

4-113. (3S)-3-(4,4'-difluoro-2',5,6'-trimethylbiphenyl-3-yl)-3-(2-(5-(2-(dimethylamino)ethyl)-3-fluoro-2-oxopyridin-1(2H)-yl)-4-methylpentanamido)propanoic Acid (Diastereomeric Compounds FG-P1 and FG-P2)

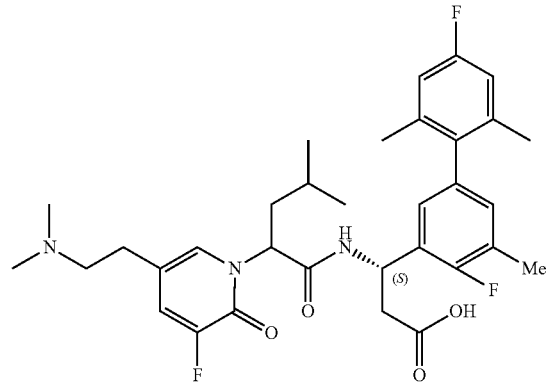

FG-P1 ESI 600.3 (M+H)+. 1H NMR (400 MHz, MeOD) δ 7.52 (s, 1H), 7.47-7.44 (m, 1H), 6.91-6.81 (m, 3H), 6.78 (d, J=6.8 Hz, 1H), 5.64-5.60 (m, 1H), 5.40 (t, J=5.6 Hz, 1H), 3.36 (d, J=6.1 Hz, 1H), 3.24-3.12 (m, 1H), 2.97-2.77 (m, 2H), 2.73 (s, 6H), 2.70-2.61 (m, 1H), 2.57-2.52 (m, 1H), 2.30 (d, J=1.6 Hz, 3H), 2.12-1.96 (m, 5H), 1.95 (s, 3H), 1.52-1.37 (m, 1H), 0.97-0.91 (m, 6H).
FG-P2 ESI 600.2 (M+H)+. 1H NMR (400 MHz, MeOD) δ 7.50 (s, 1H), 7.45-7.42 (m, 1H), 6.89 (t, J=6.1 Hz, 2H), 6.84 (d, J=9.6 Hz, 2H), 5.66-5.62 (m, 1H), 5.59-5.56 (m, 1H), 3.47-3.36 (m, 1H), 3.30-3.25 (m, 1H), 3.00-2.94 (m, 1H), 2.90-2.77 (m, 7H), 2.61-2.56 (m, 1H), 2.46-2.40 (m, 1H), 2.32 (d, J=1.8 Hz, 3H), 2.09-1.94 (m, 7H), 1.87-1.79 (m, 1H), 1.48-1.37 (m, 1H), 0.93-0.90 (m, 6H).

4-114. (3S)-3-(5-chloro-4,4'-difluoro-2',6'-dimethyl-biphenyl-3-yl)-3-(2-(5-(2-(dimethylamino)ethyl)-3-fluoro-2-oxopyridin-1(2H)-yl)-4-methylpentanamido)propanoic Acid (Diastereomeric Compounds FH-P1 and FH-P2)

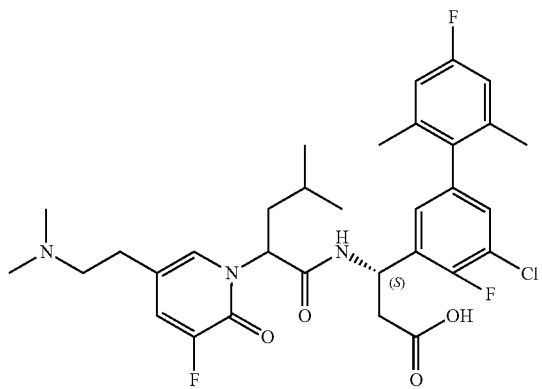

FH-P1 ESI 620.2 (M+H)+. 1H NMR (400 MHz, MeOD) δ 7.53 (s, 1H), 7.46-7.43 (m, 1H), 7.15-7.12 (m, 1H), 6.95-6.93 (m, 1H), 6.87 (d, J=9.6 Hz, 2H), 5.65-5.61 (m, 1H), 5.42 (t, J=5.8 Hz, 1H), 3.31-3.26 (m, 1H), 3.20-3.15 (m, 1H), 2.96-2.81 (m, 2H), 2.75 (s, 6H), 2.70-2.65 (m, 1H), 2.59-2.54 (m, 1H), 2.19-1.78 (m, 8H), 1.46-1.40 (m, 1H), 0.97-0.91 (m, 6H).
FH-P2 ESI 620.2 (M+H)+. H NMR (400 MHz, MeOD) δ 7.50 (s, 1H), 7.45-7.42 (m, 1H), 7.18-7.16 (m, 1H), 7.04-7.02 (m, 1H), 6.88 (d, J=9.6 Hz, 2H), 5.67-5.63 (m, 1H), 5.59-5.56 (m, 1H), 3.46-3.36 (m, 1H), 3.29-3.22 (m, 1H), 2.98-2.92 (m, 1H), 2.86-2.84 (m, 1H), 2.82 (s, 6H), 2.62-2.58 (m, 1H), 2.51-2.41 (m, 1H), 2.03 (d, J=1.5 Hz, 6H), 1.97 (t, J=7.1 Hz, 1H), 1.90-1.78 (m, 1H), 1.41-1.36 (m, 1H), 0.97-0.74 (m, 6H).

4-115. (3S)-3-(4,4'-difluoro-2',5,6'-trimethylbiphenyl-3-yl)-3-(2-(5-(2-(dimethylamino)ethyl)-4-methyl-2-oxopyridin-1(2H)-yl)-4-methylpentanamido)propanoic Acid (Diastereomeric Compounds FI-P1 and FI-P2)

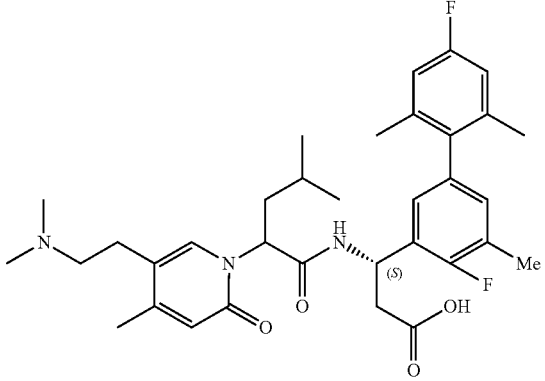

FI-P1 ESI 596.3 (M+H)⁺. ¹H NMR (400 MHz, MeOD) δ 7.59 (s, 1H), 6.83 (t, J=7.2 Hz, 4H), 6.32 (s, 1H), 5.70-5.56 (m, 1H), 5.54-5.47 (m, 1H), 3.21-3.06 (m, 2H), 2.95-2.83 (m, 2H), 2.79 (s, 6H), 2.73-2.55 (m, 2H), 2.35-2.20 (m, 6H), 2.07-1.91 (m, 5H), 1.85 (s, 3H), 1.50-1.29 (m, 1H), 1.02-0.83 (m, 6H).

FI-P2 ESI 596.3 (M+H)⁺. ¹H NMR (400 MHz, MeOD) δ 7.57 (s, 1H), 6.99-6.78 (m, 4H), 6.43 (s, 1H), 5.71-5.53 (m, 2H), 3.28-3.06 (m, 2H), 2.97-2.85 (m, 2H), 2.81 (s, 6H), 2.66-2.56 (m, 1H), 2.56-2.40 (m, 1H), 2.36-2.24 (m, 6H), 2.05-1.89 (m, 7H), 1.86-1.72 (m, 1H), 1.43-1.28 (m, 1H), 0.89 (t, J=5.2 Hz, 6H).

4-116. (3S)-3-(4'-chloro-4-fluoro-2',5,6'-trimethylbiphenyl-3-yl)-3-(2-(5-(2-(dimethylamino)ethyl)-4-methyl-2-oxopyridin-1(2H)-yl)-4-methylpentanamido)propanoic Acid (Diastereomeric Compounds FJ-P1 and FJ-P2)

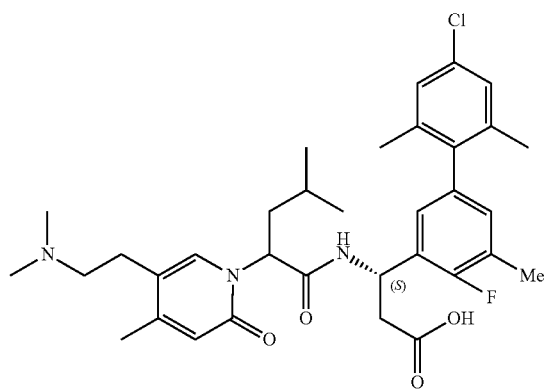

FJ-P1 ESI 612.2 (M+H)⁺. ¹H NMR (400 MHz, MeOD) δ 7.58 (s, 1H), 7.11 (d, J=2.5 Hz, 2H), 6.92-6.76 (m, 2H), 6.32 (s, 1H), 5.61-5.41 (m, 2H), 3.25-3.05 (m, 2H), 2.88 (t, J=7.3 Hz, 2H), 2.78 (s, 6H), 2.71-2.54 (m, 2H), 2.28 (d, J=13.0 Hz, 6H), 2.05-1.92 (m, 5H), 1.88 (s, 3H), 1.48-1.32 (m, 1H), 1.04-0.85 (m, 6H).

FJ-P2 ESI 612.2 (M+H)⁺. ¹H NMR (400 MHz, MeOD) δ 7.55 (s, 1H), 7.13 (s, 2H), 6.93-6.84 (m, 2H), 6.42 (s, 1H), 5.70-5.54 (m, 2H), 3.24-3.11 (m, 2H), 2.99-2.76 (m, 8H), 2.64-2.42 (m, 2H), 2.36-2.20 (m, 6H), 2.03-1.90 (m, 7H), 1.83-1.72 (m, 1H), 1.47-1.28 (m, 1H), 0.90 (t, J=6.2 Hz, 6H).

4-117. (3S)-3-(2-(5-(2-(dimethylamino)ethyl)-3-fluoro-2-oxopyridin-1(2H)-yl)-4-methylpentanamido)-3-(4-fluoro-2',4',5,6'-tetramethyl-[1,1'-biphenyl]-3-yl)propanoic Acid (Diastereomeric Compounds FK-P1 and FK-P2)

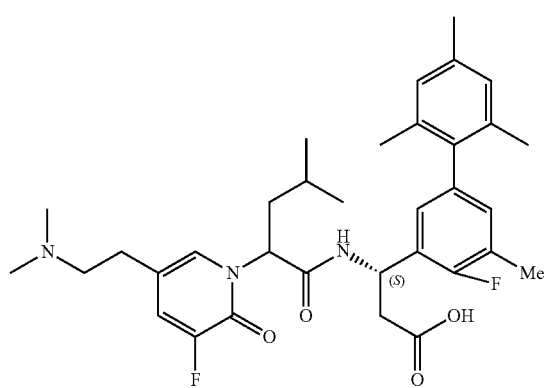

FK-P1 ESI 596.3 (M+H)⁺. ¹H NMR (400 MHz, MeOD) δ 7.59-7.37 (m, 2H), 6.96-6.64 (m, 4H), 5.76-5.58 (m, 1H), 5.39 (t, J=5.5 Hz, 1H), 3.42-3.25 (m, 1H), 3.23-3.06 (m, 1H), 2.96-2.76 (m, 2H), 2.73-2.46 (m, 8H), 2.41-2.22 (m, 6H), 2.05-1.88 (m, 8H), 1.44 (m, J=13.7, 6.7 Hz, 1H), 0.93 (m, J=17.3, 6.6 Hz, 6H).

FK-P2 ESI 596.3 (M+H)⁺. ¹H NMR (400 MHz, MeOD) δ 7.51 (s, 1H), 7.42 (m, J=10.3, 2.1 Hz, 1H), 6.89 (m, J=7.0, 4.6 Hz, 4H), 5.62 (m, J=14.0, 9.4, 5.4 Hz, 2H), 3.43-3.30 (m, 1H), 3.23 (s, 1H), 2.93 (m, J=9.6, 4.9 Hz, 1H), 2.87-2.75 (m, 7H), 2.59 (m, J=14.9, 4.0 Hz, 1H), 2.44 (m, J=14.8, 10.1 Hz, 1H), 2.34-2.22 (m, 6H), 2.05-1.91 (m, 7H), 1.84-1.72 (m, 1H), 1.46-1.22 (m, 1H), 0.91 (m, J=6.6, 3.1 Hz, 6H).

4-118. (3S)-3-(4-fluoro-2',4',5,6'-tetramethyl-[1,1'-biphenyl]-3-yl)-3-(2-(3-fluoro-5-(2-((R)-3-fluoropyrrolidin-1-yl)ethyl)-2-oxopyridin-1(2H)-yl)-4-methylpentanamido)propanoic Acid (Diastereomeric Compounds FL-P1 and FL-P2)

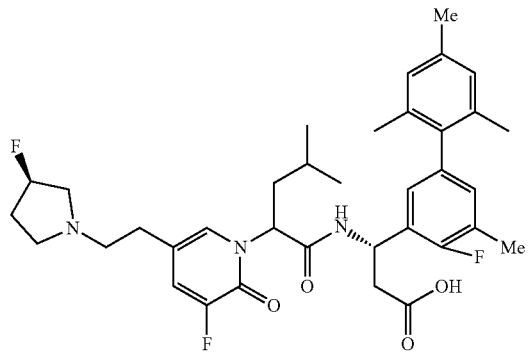 [SMILES: Cc1cc(C)c(-c2cc(C)c(F)c([C@H](CC(=O)O)NC(=O)C(CC(C)C)n3cc(CCN4CC[C@@H](F)C4)cc(F)c3=O)c2)c(C)c1]

FL-P1 ESI 640.2 (M+H)⁺. 1H NMR (400 MHz, MeOD) δ 7.50 (s, 1H), 7.41-7.31 (m, 1H), 6.91 (s, 2H), 6.85 (d, J=7.0 Hz, 1H), 6.79 (d, J=6.7 Hz, 1H), 5.70 (s, 1H), 5.49 (s, 1H), 5.24 (d, J=53.7 Hz, 1H), 3.26-3.00 (m, 5H), 2.88-2.56 (m, 4H), 2.41-2.13 (m, 9H), 2.07-1.90 (m, 5H), 1.85 (s, 3H), 1.53-1.26 (m, 1H), 1.05-0.80 (m, 6H).

FL-P2 ESI 640.2 (M+H)⁺. 1H NMR (500 MHz, MeOD) δ 7.49 (s, 1H), 7.47-7.36 (m, 1H), 6.90 (d, J=8.8 Hz, 4H), 5.67 (t, J=7.7 Hz, 1H), 5.61-5.52 (m, 1H), 5.33 (d, J=54.6 Hz, 1H), 3.73-3.38 (m, 5H), 3.28 (s, 1H), 2.97-2.76 (m, 2H), 2.65-2.43 (m, 2H), 2.41-2.19 (m, 6H), 2.07-1.88 (m, 7H), 1.84-1.73 (m, 1H), 1.51-1.20 (m, 1H), 0.91 (d, J=6.5 Hz, 6H).

4-119. (3S)-3-(2-(5-(2-(dimethylamino)ethyl)-3-methyl-2-oxopyridin-1(2H)-yl)-4-methylpentanamido)-3-(4-fluoro-2',4',5',6'-tetramethyl-[1,1'-biphenyl]-3-yl)propanoic Acid (Diastereomeric Compounds FM-P1 and FM-P2)

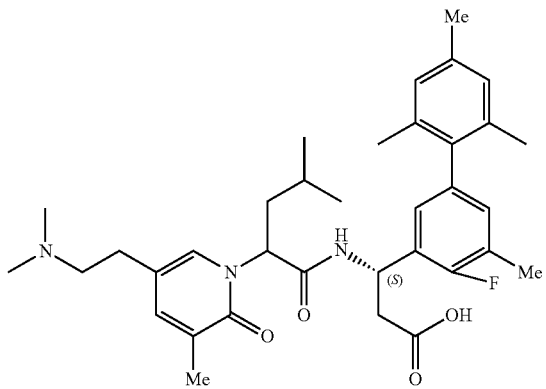

FM-P1 ESI 592.3 (M+H)⁺. ¹H NMR (400 MHz, MeOD) δ 7.35 (S, 1H), 7.32 (S, 1H), 6.80 (d, J=8.4 Hz, 2H), 6.73 (d, J=5.5 Hz, 1H), 6.59 (d, J=6.7 Hz, 1H), 5.48-5.46 (m, 1H), 5.23 (t, J=5.1 Hz, 1H), 3.08-2.98 (m, 1H), 2.68-2.67 (m, 2H), 2.56 (s, 6H), 2.51-2.35 (m, 3H), 2.25-2.11 (m, 6H), 1.97-1.74 (m, 1H), 1.36-1.24 (m, 1H), 0.88-0.76 (m, 6H).

FM-P2 ESI 592.3 (M+H)⁺. ¹H NMR (400 MHz, MeOD) δ 7.40 (s, 1H), 7.29 (s, 1H), 6.78-6.74 (m, 3H), 6.67 (d, J=7.0 Hz, 1H), 5.52-5.48 (m, 1H), 5.42-5.39 (m, 1H), 3.33-3.27 (m, 1H), 3.20-3.14 (m, 1H), 2.85-2.61 (m, 8H), 2.49-2.44 (m, 1H), 2.33-2.27 (m, 1H), 2.18 (s, 6H), 1.97-1.67 (m, 1H), 1.38-1.24 (m, 1H), 0.82-0.77 (m, 6H).

4-120. (3S)-3-(4,4'-difluoro-2',6'-dimethyl-5-(trifluoromethyl)-[1,1'-biphenyl]-3-yl)-3-(2-(5-(2-(dimethylamino)ethyl)-3-fluoro-2-oxopyridin-1(2H)-yl)-4-methylpentanamido)propanoic Acid (Diastereomeric Compounds FN-P1 and FN-P2)

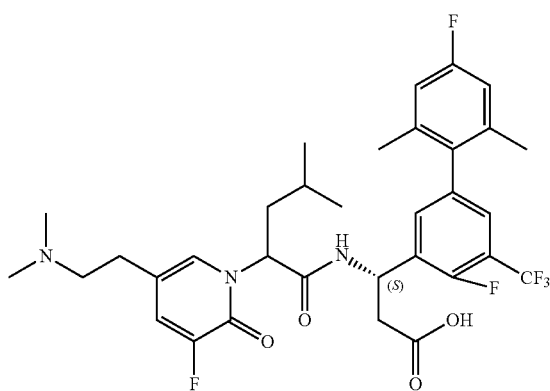

FN-P1 ESI 654.3 (M+H)⁺. ¹H NMR (400 MHz, MeOD) δ 7.55 (s, 1H), 7.50-7.37 (m, 1H), 7.40-7.25 (m, 2H), 6.89 (d, J=9.6 Hz, 2H), 5.73-5.55 (m, 1H), 5.47 (t, J=5.9 Hz, 1H), 3.27-3.13 (m, 1H), 2.98-2.82 (m, 3H), 2.78 (s, 6H), 2.73-2.64 (m, 1H), 2.63-2.50 (m, 1H), 2.13-1.97 (m, 5H), 1.93 (s, 3H), 1.42 (s, 1H), 1.11-0.79 (m, 6H).

FN-P2 ESI 654.3 (M+H)⁺. ¹H NMR (400 MHz, MeOD) δ 7.51 (s, 1H), 7.48-7.41 (m, 1H), 7.38 (t, J=6.0 Hz, 2H), 6.90 (d, J=9.6 Hz, 2H), 5.76-5.43 (m, 2H), 3.42 (d, J=10.1 Hz, 1H), 3.28 (d, J=12.8 Hz, 1H), 2.96 (d, J=9.5 Hz, 1H), 2.85 (d, J=7.2 Hz, 6H), 2.74-2.54 (m, 1H), 2.55-2.34 (m, 1H), 2.15-1.93 (m, 6H), 1.93-1.72 (m, 1H), 1.52-1.27 (m, 1H), 0.92 (t, J=6.5 Hz, 6H).

4-121. (3S)-3-(4-fluoro-2',4',5',6'-tetramethylbiphenyl-3-yl)-3-(2-(3-fluoro-5-(2-(3-fluoroazetidine-1-yl)ethyl)-2-oxopyridin-1(2H)-yl)-4-methylpentanamido)propanoic Acid (Diastereomeric Compounds FO-P1 and FO-P2)

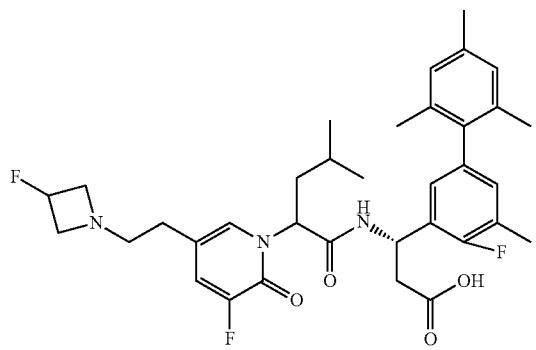 [SMILES: Cc1cc(C)c(-c2cc(C)c(F)c([C@H](CC(=O)O)NC(=O)C(CC(C)C)n3cc(CCN4CC(F)C4)cc(F)c3=O)c2)c(C)c1]

FO-P1 ESI 626.3 (M+H)⁺. ¹H NMR (400 MHz, MeOD) δ 7.45-7.33 (m, 2H), 6.96-6.85 (m, 3H), 6.83-6.75 (m, 1H), 5.69 (t, J=8.1 Hz, 1H), 5.52-5.45 (m, 1H), 5.30-5.10 (m, 1H), 4.23-4.09 (m, 1H), 4.02-3.89 (m, 1H), 3.78-3.62 (m, 2H), 3.26-3.16 (m, 2H), 2.78-2.56 (m, 4H), 2.36-2.25 (m, 6H), 2.00-1.92 (m, 5H), 1.88 (s, 3H), 1.48-1.39 (m, 1H), 0.98-0.86 (m, 6H).

FO-P2 ESI 626.3 (M+H)⁺. ¹H NMR (400 MHz, MeOD) δ 7.45-7.35 (m, 2H), 6.97-6.86 (m, 4H), 5.76-5.62 (m, 2H), 5.42-5.20 (m, 1H), 4.49-4.28 (m, 2H), 4.12-3.95 (m, 2H), 3.44-3.36 (m, 2H), 2.78-2.63 (m, 2H), 2.67-2.52 (m, 1H), 2.61-2.52 (m, 1H), 2.37-2.25 (m, 6H), 2.01-1.91 (m, 7H), 1.85-1.69 (m, 1H), 1.43-1.36 (m, 1H), 0.96-0.85 (m, 6H).

4-122. (3S)-3-(2'-chloro-4,4'-difluoro-5,6'-dimethyl-[1,1'-biphenyl]-3-yl)-3-(2-(3-fluoro-5-(2-(3-fluoroazetidine-1-yl)ethyl)-2-oxopyridin-1(2H)-yl)-4-methylpentanamido)propanoic Acid (Diastereomeric Compounds FP-P1 and FP-P2)

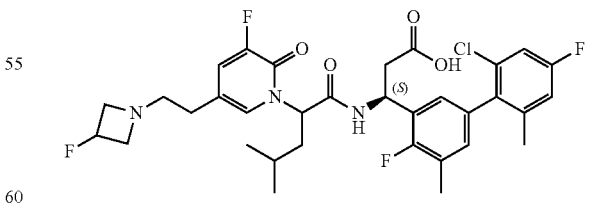

FP-P1 ESI 650.2 (M+H)⁺. ¹H NMR (400 MHz, MeOD)⁶ 7.43-7.34 (m, 2H), 7.17-7.13 (m, 1H), 7.06-7.01 (m, 1H), 6.89-6.85 (m, 1H), 5.72-5.67 (m, 1H), 5.54-5.49 (m, 1H), 5.32-5.09 (m, 1H), 4.21-3.65 (m, 4H), 3.19-3.10 (m, 2H), 2.78-2.60 (m, 4H), 2.31 (s, 3H), 2.08-1.92 (m, 5H), 1.49-1.39 (m, 1H), 0.97-0.93 (m, 6H).

FP-P2 ESI 650.2 (M+H)⁺. ¹H NMR (400 MHz, MeOD) δ 7.39-7.36 (m, 2H), 7.15 (d, J=8.5 Hz, 1H), 7.08-6.96 (m, 3H), 5.73-5.61 (m, 2H), 5.41-5.22 (m, 1H), 4.48-4.28 (m, 2H), 4.11-3.94 (m, 2H), 3.42-3.33 (m, 2H), 2.80-2.47 (m, 4H), 2.34 (d, J=1.8 Hz, 3H), 2.09 (d, J=2.7 Hz, 3H), 2.03-1.90 (m, 1H), 1.83-1.72 (m, 1H), 1.44-1.30 (m, 1H), 0.94-0.89 (m, 6H).

4-123. (3S)-3-(2-(3-fluoro-5-(2-(3-fluoroazetidine-1-yl)ethyl)-2-oxopyridin-1(2H)-yl)-4-methylpentanamido)-3-(2',4,4'-trifluoro-5,6'-dimethylbiphenyl-3-yl)propanoic Acid (Diastereomeric Compounds FQ-P1 and FQ-P2)

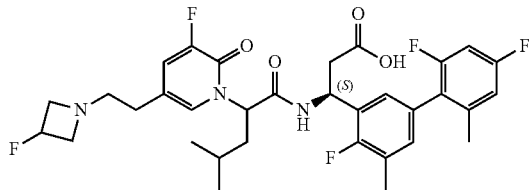

FQ-P1 ESI 634.2 (M+H)⁺. ¹H NMR (400 MHz, MeOD) δ 7.43 (s, 1H), 7.36 (d, J=10.3 Hz, 1H), 7.02 (d, J=6.8 Hz, 1H), 6.98-6.89 (m, 2H), 6.85 (t, J=9.2 Hz, 1H), 5.69 (t, J=8.1 Hz, 1H), 5.53-5.50 (m, 1H), 5.30-5.08 (m, 1H), 4.09-3.99 (m, 2H), 3.77-3.63 (m, 2H), 3.15-3.12 (m, 2H), 2.79-2.69 (m, 2H), 2.66-2.62 (m, 2H), 2.31 (s, 3H), 2.09 (s, 3H), 1.97 (t, J=7.6 Hz, 2H), 1.51-1.37 (m, 1H), 0.98-0.93 (m, 6H).

FQ-P2 ESI 634.2 (M+H)⁺. ¹H NMR (400 MHz, MeOD) δ 7.43-7.32 (m, 2H), 7.06 (d, J=6.7 Hz, 2H), 6.93 (d, J=9.3 Hz, 1H), 6.88-6.83 (m, 1H), 5.74-5.59 (m, 2H), 5.39-5.24 (m, 1H), 4.42-4.32 (m, 2H), 4.10-3.88 (m, 2H), 3.40-3.37 (m, 2H), 2.81-2.71 (m, 2H), 2.65-2.60 (m, 1H), 2.55-2.48 (m, 1H), 2.34 (d, J=1.6 Hz, 3H), 2.16 (s, 3H), 2.03-1.93 (m, 1H), 1.86-1.75 (m, 1H), 1.45-1.33 (m, 1H), 0.93-0.91 (m, 6H).

4-124. (3S)-3-(2-(5-(2-(azetidin-1-yl)ethyl)-2-oxo-4-(trifluoromethyl)pyridin-1(2H)-yl)-4-methylpentanamido)-3-(2'-cyclopropyl-4,4'-difluoro-5,6'-dimethyl-[1,1'-biphenyl]-3-yl)propanoic Acid (Diastereomeric Compounds FR-P1 and FR-P2)

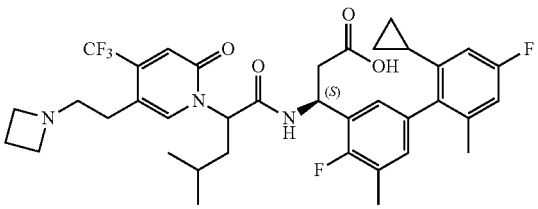

FR-P1 ESI 688.2 (M+H)⁺. ¹H NMR (400 MHz, MeOD) δ 7.84 (s, 1H), 6.95 (dd, J=19.9, 7.2 Hz, 2H), 6.86-6.64 (m, 2H), 6.55-6.23 (m, 1H), 5.75-5.49 (m, 2H), 3.85 (t, J=7.7 Hz, 4H), 3.33 (m, J=3.2, 1.6 Hz, 2H), 3.13 (m, J=6.8 Hz, 2H), 2.90-2.58 (m, 2H), 2.51-2.21 (m, 5H), 2.01 (d, J=5.3 Hz, 4H), 1.87 (s, 1H), 1.40 (d, J=6.4 Hz, 1H), 1.07-0.85 (m, 6H), 0.75 (m, J=8.6, 3.5 Hz, 1H), 0.66-0.43 (m, 3H).

FR-P2 ESI 688.2 (M+H)⁺. ¹H NMR (400 MHz, MeOD) δ 7.74 (d, J=11.5 Hz, 1H), 6.94 (m, J=46.9, 28.6, 8.1 Hz, 4H), 6.50 (d, J=10.4 Hz, 1H), 5.78 (m, J=11.0, 3.1 Hz, 1H), 5.62 (m, J=7.3 Hz, 1H), 4.13 (m, J=8.0 Hz, 4H), 3.50-3.32 (m, 2H), 2.94 (d, J=16.3 Hz, 1H), 2.81 (d, J=7.7 Hz, 2H), 2.68-2.61 (m, 1H), 2.57-2.42 (m, 3H), 2.34 (d, J=1.1 Hz, 3H), 2.05-1.79 (m, 4H), 1.65 (m, J=13.9, 7.1 Hz, 1H), 1.50-1.30 (m, 2H), 0.88 (d, J=6.6 Hz, 6H), 0.74 (m, J=14.0, 7.3 Hz, 2H), 0.60 (m, J=6.4, 5.0 Hz, 2H).

4-125. (3S)-3-((3R)-2-(5-(2-(dimethylamino)ethyl)-2-oxo-4-(trifluoromethyl)pyridin-1(2H)-yl)-3-methylpentanamido)-3-(4-fluoro-2',4',5,6'-tetramethylbiphenyl-3-yl)propanoic Acid (Diastereomeric Compounds FS-P1 and FS-P2)

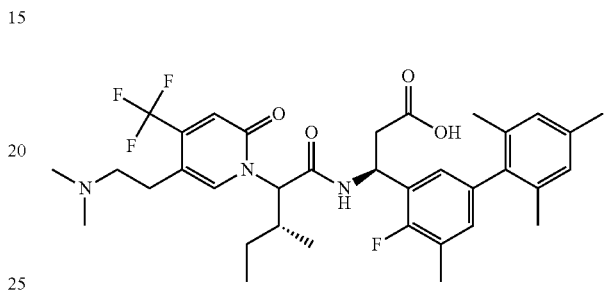

FS-P1 ESI 646.2 (M+H)⁺. ¹H NMR (400 MHz, MeOD) δ 7.94 (s, 1H), 6.89 (s, 1H), 6.82-6.75 (m, 3H), 6.66 (s, 1H), 5.65-5.53 (m, 1H), 5.33 (d, J=11.3 Hz, 1H), 3.05-2.83 (m, 5H), 2.82-2.62 (m, 6H), 2.40-2.18 (m, 8H), 2.03-1.88 (m, 3H), 1.78-1.67 (m, 1H), 1.63 (s, 3H), 1.38-1.21 (m, 3H), 1.07-0.96 (m, 3H), 0.75 (d, J=6.5 Hz, 3H).

FS-P2 ESI 646.2 (M+H)⁺. ¹H NMR (400 MHz, MeOD) δ 7.92 (s, 1H), 6.91-6.72 (m, 5H), 5.69-5.52 (m, 1H), 5.21 (d, J=10.9 Hz, 1H), 3.14-2.79 (m, 3H), 2.68 (s, 6H), 2.55-2.36 (m, 2H), 2.22-2.06 (m, H), 1.84 (d, J=3.6 Hz, 4H), 1.32-0.99 (m, 3H), 0.93-0.61 (m, 7H).

4-126. (3S)-3-(2',6'-dichloro-4-fluoro-4',5-dimethyl-biphenyl-3-yl)-3-(2-(5-(2-(dimethylamino)ethyl)-2-oxo-4-(trifluoromethyl)pyridin-1(2H)-yl)-3-methylbutanamido)propanoic Acid (Diastereomeric Compounds FT-P1 and FT-P2)

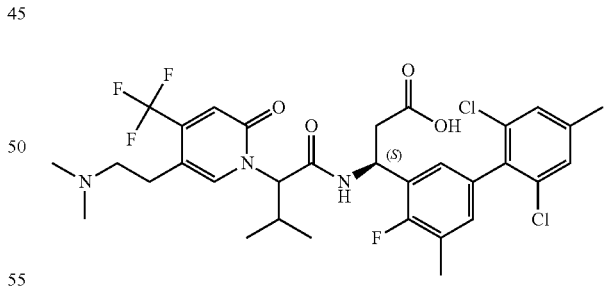

FT-P1 ESI 672.1 (M+H)⁺. ¹H NMR (400 MHz, MeOD) δ: 7.91 (s, 1H), 7.27 (d, J=6.0 Hz, 1H), 7.14 (d, J=5.2 Hz, 1H), 6.90 (t, J=6.0 Hz, 2H), 6.67 (d, J=5.6 Hz, 1H), 5.64-5.60 (m, 1H), 5.29 (d, J=11.2 Hz, 1H), 2.97-2.85 (m, 4H), 2.78-2.61 (m, 8H), 2.46-2.40 (m, 1H), 2.36 (s, 3H), 2.27 (s, 3H), 1.16 (d, J=6.4 Hz, 3H), 0.78 (d, J=6.4 Hz, 3H).

FT-P2 ESI 672.2 (M+H)⁺. ¹H NMR (400 MHz, MeOD) δ: 8.01 (s, 1H), 7.30 (s, 2H), 7.09-7.07 (m, 1H), 7.00 (d, J=7.2 Hz, 1H), 6.90 (s, 1H), 5.78-5.74 (m, 1H), 5.23 (d, J=11.2 Hz, 1H), 3.27-3.20 (m, 1H), 3.17-3.11 (m, 1H), 3.09-3.01 (m, 1H), 2.99-2.93 (m, 1H), 2.78 (s, 6H), 2.61-

2.50 (m, 2H), 2.47-2.37 (m, 4H), 2.31 (d, J=1.2 Hz, 3H), 0.94 (d, J=6.4 Hz, 3H), 0.71 (d, J=6.8 Hz, 3H).

4-127. (3S)-3-(2-(5-(2-(azetidin-1-yl)ethyl)-2-oxo-4-(trifluoromethyl)pyridin-1(2H)-yl)-4-methylpentanamido)-3-(2'-cyclopropyl-4-fluoro-4',5,6'-trimethyl-[1,1'-biphenyl]-3-yl)propanoic Acid (Diastereomeric Compounds FU-P1 and FU-P2)

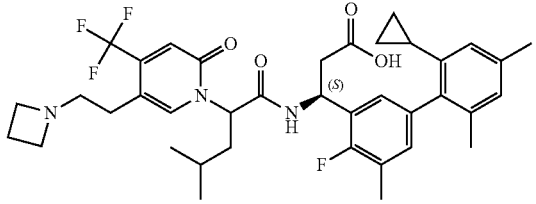

FU-P1 ESI 684.3 (M+H)⁺. ¹H NMR (400 MHz, MeOD) δ 7.84 (s, 1H), 6.97-6.78 (m, 4H), 6.58 (s, 1H), 5.69-5.59 (m, 2H), 3.97-3.94 (m, 4H), 3.26-3.21 (m, 2H), 2.86-2.81 (m, 2H), 2.72-2.68 (m, 2H), 2.46-2.38 (m, 2H), 2.29 (d, J=4.9 Hz, 6H), 2.03-1.97 (m, 3H), 1.85 (s, 2H), 1.48-1.31 (m, 2H), 0.98-0.91 (m, 6H), 0.67 (d, J=8.4 Hz, 1H), 0.59-0.44 (m, 3H).

FU-P2 ESI 684.3 (M+H)⁺. ¹H NMR (400 MHz, MeOD) δ 7.73 (d, J=10.5 Hz, 1H), 7.02-6.96 (m, 2H), 6.91 (s, 1H), 6.90 (s, 1H), 6.59 (s, 1H), 5.78-5.75 (m, 1H), 5.64-5.59 (m, 1H), 4.14-4.10 (m, 4H), 3.47-3.38 (m, 2H), 2.97-2.92 (m, 1H), 2.85-2.75 (m, 1H), 2.69-2.60 (m, 1H), 2.55-2.45 (m, 3H), 2.34 (s, 3H), 2.29 (s, 3H), 2.05-1.96 (m, 4H), 1.71-1.61 (m, 1H), 1.49-1.39 (m, 2H), 0.90 (d, J=6.6 Hz, 6H), 0.70-0.66 (m, 2H), 0.58-0.55 (m, 2H).

4-128. (3S)-3-(2',6'-dichloro-4-fluoro-5-methylbiphenyl-3-yl)-3-(2-(5-(2-(dimethylamino)ethyl)-2-oxo-4-(trifluoromethyl)pyridin-1(2H)-yl)-4-methyl-pentanamido)propanoic Acid (Diastereomeric Compounds FV-P1 and FV-P2)

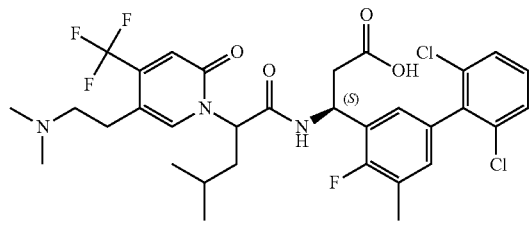

FV-P1 ESI 672.2 (M+H)⁺. ¹H NMR (400 MHz, MeOD) δ: 7.89 (s, 1H), 7.46 (d, J=8.0 Hz, 1H), 7.39 (d, J=7.2 Hz, 1H), 7.32 (t, J=8.0 Hz, 1H), 7.00-6.96 (m, 2H), 6.75 (s, 1H), 5.72-5.68 (m, 1H), 5.60-5.56 (m, 1H), 3.10-3.01 (m, 2H), 2.94-2.92 (m, 2H), 2.74-2.65 (m, 8H), 2.27 (d, J=1.2 Hz, 3H), 2.01-1.93 (m, 2H), 1.47-1.41 (m, 1H), 0.95 (d, J=6.4 Hz, 3H), 0.93 (d, J=6.4 Hz, 3H).

FV-P2 ESI 672.2 (M+H)⁺. ¹H NMR (400 MHz, MeOD) δ: 7.91-5.88 (m, 1H), 7.47 (d, J=8.0 Hz, 2H), 7.35-7.31 (m, 1H), 7.08-7.02 (m, 2H), 6.89 (s, 1H), 5.78-5.74 (m, 1H), 5.64 (t, J=7.6 Hz, 1H), 3.27-3.15 (m, 2H), 3.06-2.95 (m, 2H), 2.80 (s, 6H), 2.65-2.60 (m, 1H), 2.55-2.49 (m, 1H), 2.32 (s, 3H), 1.99-1.92 (m, 1H), 1.71-1.64 (m, 1H), 1.41-1.34 (m, 1H), 0.86-0.84 (m, 6H).

4-129. (3S)-3-(2-(5-(2-(azetidin-1-yl)ethyl)-2-oxo-4-(trifluoromethyl)pyridin-1(2H)-yl)-4-methylpentanamido)-3-(4-fluoro-2',5,6'-trimethyl-4'-(trifluoromethyl)biphenyl-3-yl)propanoic Acid (Diastereomeric Compounds FW-P1 and FW-P2)

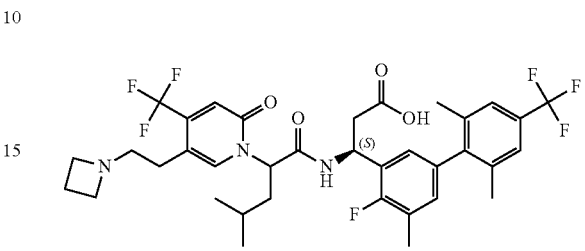

FW-P1 ESI 712.2 (M+H)⁺. ¹H NMR (400 MHz, MeOD) δ: 7.88 (s, 1H), 7.39 (s, 1H), 7.35 (s, 1H), 6.91 (t, J=6.2 Hz, 2H), 6.70 (s, 1H), 5.66-5.57 (m, 2H), 4.04 (t, J=8.2 Hz, 4H), 3.29 (t, J=7.4 Hz, 2H), 2.84 (t, J=7.2 Hz, 2H), 2.78-2.67 (m, 2H), 2.48-2.40 (m, 2H), 2.30 (d, J=1.2 Hz, 3H), 2.08 (s, 3H), 2.03-1.99 (m, 2H), 1.91 (s, 3H), 1.47-1.40 (m, 1H), 0.95 (d, J=6.8 Hz, 3H), 0.93 (d, J=6.4 Hz, 3H).

FW-P2 ESI 712.2 (M+H)⁺. ¹H NMR (400 MHz, MeOD) δ: 7.74 (s, 1H), 7.41 (s, 2H), 6.98 (s, 1H), 6.96 (s, 1H), 6.90 (s, 1H), 5.79-5.76 (m, 1H), 5.60 (t, J=8.0 Hz, 1H), 4.15 (t, J=8.0 Hz, 4H), 3.48-3.42 (m, 1H), 3.38-3.33 (m, 1H), 2.98-2.91 (m, 1H), 2.84-2.77 (m, 1H), 2.69-2.64 (m, 1H), 2.55-2.45 (m, 3H), 2.35 (d, J=1.6 Hz, 3H), 2.09 (s, 3H), 2.08 (s, 3H), 2.03-1.96 (m, 1H), 1.69-1.62 (m, 1H), 1.46-1.36 (m, 1H), 0.89 (d, J=1.6 Hz, 3H), 0.87 (d, J=2.0 Hz, 3H).

4-130. (3S)-3-(2'-chloro-4-fluoro-5,6'-dimethyl-[1,1'-biphenyl]-3-yl)-3-(2-(5-(2-(dimethylamino)ethyl)-2-oxo-4-(trifluoromethyl)pyridin-1(2H)-yl)-4-methylpentanamido)propanoic Acid (Diastereomeric Compounds FX-P1 and FX-P2)

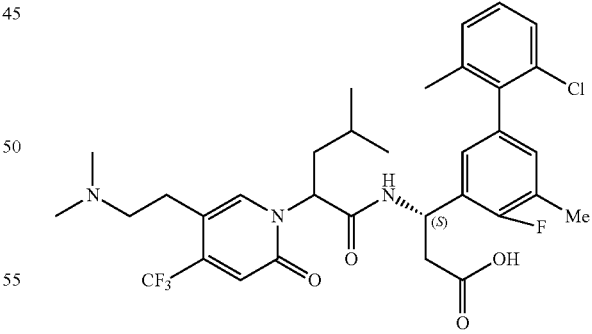

FX-P1 ESI 652.2 (M+H)⁺. ¹H NMR (400 MHz, MeOD) δ 7.90 (d, J=4.5 Hz, 1H), 7.37-7.09 (m, 3H), 6.93 (m, J=10.9, 4.9 Hz, 2H), 6.75 (d, J=6.5 Hz, 1H), 5.68 (m, J=30.2, 23.4 Hz, 2H), 3.00 (d, J=50.0 Hz, 4H), 2.73 (d, J=14.3 Hz, 8H), 2.30 (s, 3H), 2.13-1.83 (m, 5H), 1.45 (d, J=6.4 Hz, 1H), 0.96 (m, J=12.9, 6.6, 2.5 Hz, 6H).

FX-P2 ESI 652.2 (M+H)⁺. ¹H NMR (400 MHz, MeOD) δ 7.88 (s, 1H), 7.34-7.09 (m, 3H), 7.11-6.51 (m, 3H), 5.69 (m, J=21.6, 10.6, 4.3 Hz, 2H), 3.15 (s, 2H), 2.98 (s, 2H), 2.88-2.53 (m, 8H), 2.34 (s, 3H), 2.08 (d, J=5.6 Hz, 3H), 1.98-1.81 (m, 1H), 1.78 (s, 1H), 1.40 (s, 1H), 0.89 (m, J=6.4, 4.6 Hz, 6H).

4-131. (3S)-3-(2-(5-(2-(azetidin-1-yl)ethyl)-2-oxo-4-(trifluoromethyl)pyridin-1(2H)-yl)-4-methylpentanamido)-3-(2',4-difluoro-5,6'-dimethylbiphenyl-3-yl)propanoic Acid (Diastereomeric Compounds FY-P1 and FY-P2)

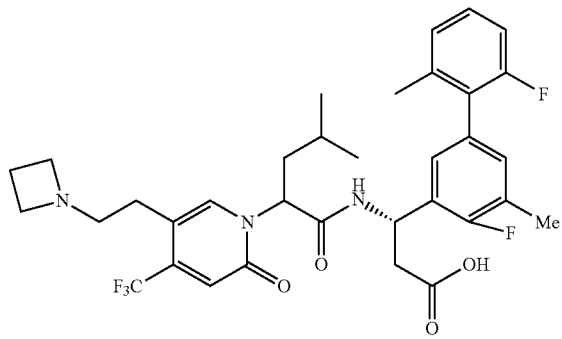 [SMILES: Cc1cc(-c2c(C)cccc2F)cc([C@H](CC(=O)O)NC(=O)C(CC(C)C)n2cc(CCN3CCC3)c(C(F)(F)F)cc2=O)c1F]

FY-P1 ESI 648.2 (M+H)⁺. 1H NMR (400 MHz, MeOD) δ 7.84 (s, 1H), 7.30-7.23 (m, 1H), 7.16-7.09 (m, 1H), 7.06-6.92 (m, 3H), 6.81 (s, 1H), 5.71-5.60 (m, 2H), 4.01 (t, J=8.1 Hz, 4H), 3.29 (s, 2H), 2.86 (t, J=6.8 Hz, 2H), 2.72 (d, J=6.6 Hz, 2H), 2.46-2.36 (m, 2H), 2.36-2.31 (m, 3H), 2.10 (s, 3H), 2.00 (t, J=7.6 Hz, 2H), 1.51-1.42 (m, 1H), 0.98-0.93 (m, 6H).

FY-P2 ESI 648.2 (M+H)⁺. ¹H NMR (400 MHz, MeOD) δ 7.75 (s, 1H), 7.31-7.19 (m, 1H), 7.15-7.04 (m, 3H), 6.99 (t, J=8.8 Hz, 1H), 6.92 (s, 1H), 5.81-5.75 (m, 1H), 5.64 (t, J=7.6 Hz, 1H), 4.14 (t, J=8.0 Hz, 4H), 3.49-3.35 (m, 2H), 2.94 (d, J=15.7 Hz, 1H), 2.87-2.75 (m, 1H), 2.69-2.56 (m, 1H), 2.57-2.43 (m, 3H), 2.35 (d, J=1.5 Hz, 3H), 2.17 (d, J=8.1 Hz, 3H), 2.04-1.95 (m, 1H), 1.72-1.62 (m, 1H), 1.46-1.32 (m, 1H), 0.97-0.91 (m, 6H).

4-132. (3S)-3-(3',4-difluoro-2',4',5,6'-tetramethylbiphenyl-3-yl)-3-(2-(5-(2-(dimethylamino)ethyl)-2-oxo-4-(trifluoromethyl)pyridin-1(2H)-yl)-4-methylpentanamido)propanoic Acid (Diastereomeric Compounds FZ-P1 and FZ-P2)

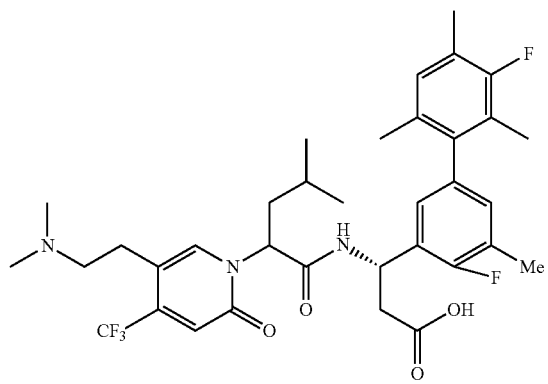 [SMILES: Cc1cc(-c2c(C)cc(C)c(F)c2C)cc([C@H](CC(=O)O)NC(=O)C(CC(C)C)n2cc(CCN(C)C)c(C(F)(F)F)cc2=O)c1F]

FZ-P1 ESI 664.2 (M+H)⁺. ¹H NMR (400 MHz, MeOD) δ 7.85 (s, 1H), 7.01-6.79 (m, 4H), 5.78-5.58 (m, 2H), 3.29-3.07 (m, 2H), 3.04-2.89 (m, 2H), 2.81 (s, 6H), 2.70-2.42 (m, 2H), 2.33 (s, 3H), 2.26 (s, 3H), 2.13-1.83 (m, 7H), 1.81-1.60 (m, 1H), 1.52-1.30 (m, 1H), 1.02-0.81 (m, 6H).

FZ-P2 ESI 664.2 (M+H)⁺. ¹H NMR (400 MHz, MeOD) δ 7.91 (s, 1H), 6.99-6.68 (m, 4H), 5.82-5.50 (m, 2H), 3.19-2.89 (m, 4H), 2.83-2.54 (m, 8H), 2.38-2.22 (m, 6H), 2.13-1.80 (m, 5H), 1.72 (d, J=14.7 Hz, 3H), 1.51-1.36 (m, 1H), 1.06-0.84 (m, 6H).

4-133. (3S)-3-(2-(5-(2-(azetidin-1-yl)ethyl)-2-oxo-4-(trifluoromethyl)pyridin-1(2H)-yl)-4-methylpentanamido)-3-(4'-cyano-4-fluoro-2',5,6'-trimethylbiphenyl-3-yl)propanoic Acid (Diastereomeric Compounds GA-P1 and GA-P2)

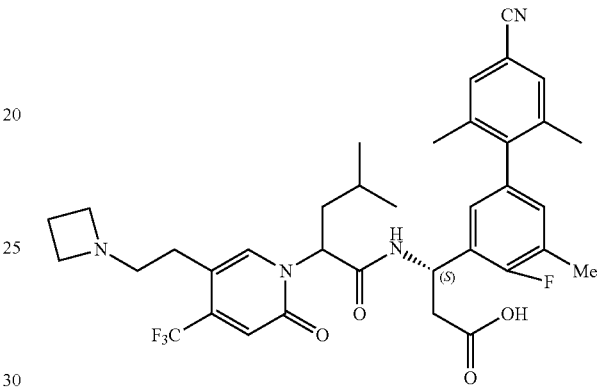

GA-P1 ESI 669.2 (M+H)⁺. ¹H NMR (400 MHz, MeOD) δ 7.84 (s, 1H), 7.47 (d, J=10.3 Hz, 2H), 6.91 (d, J=6.7 Hz, 2H), 6.75 (s, 1H), 5.59 (d, J=7.7 Hz, 2H), 4.06 (t, J=8.1 Hz, 4H), 3.31-3.27 (m, 2H), 2.98-2.85 (m, 2H), 2.79-2.64 (m, 2H), 2.58-2.39 (m, 2H), 2.31 (s, 3H), 2.14-1.88 (m, 8H), 1.54-1.27 (m, 1H), 1.10-0.80 (m, 6H).

GA-P2 ESI 669.2 (M+H)⁺. ¹H NMR (400 MHz, MeOD) δ 7.74 (s, 1H), 7.50 (s, 2H), 7.06-6.84 (m, 3H), 5.90-5.71 (m, 1H), 5.61 (t, J=7.6 Hz, 1H), 4.10 (s, 4H), 3.36 (s, 2H), 3.09-2.74 (m, 2H), 2.74-2.60 (m, 1H), 2.55-2.39 (m, 3H), 2.35 (s, 3H), 2.13-1.89 (m, 7H), 1.75-1.62 (m, 1H), 1.50-1.35 (m, 1H), 0.98-0.81 (m, 6H).

4-134. (3S)-3-(2'-cyano-4-fluoro-5,6'-dimethylbiphenyl-3-yl)-3-(2-(5-(2-(dimethylamino)ethyl)-2-oxo-4-(trifluoromethyl)pyridin-1(2H)-yl)-4-methylpentanamido)propanoic Acid (Diastereomeric Compounds GB-P1 and GB-P2)

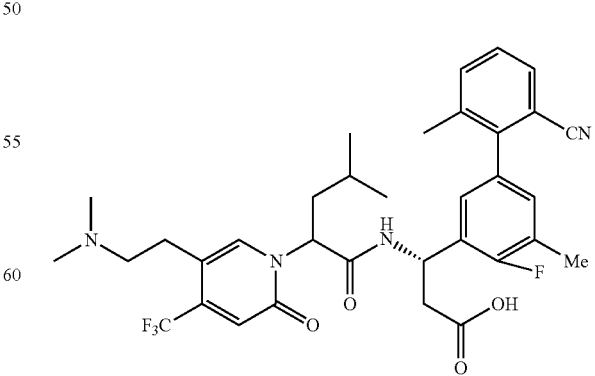

GB-P1 ESI 643.2 (M+H)⁺. ¹H NMR (400 MHz, MeOD) δ 7.89 (s, 1H), 7.59 (s, 2H), 7.43 (t, J=7.7 Hz, 1H), 7.06 (s, 2H), 6.71 (d, J=26.7 Hz, 1H), 5.73 (s, 1H), 5.60 (d, J=7.3 Hz,

1H), 3.10 (s, 2H), 2.93 (d, J=8.3 Hz, 2H), 2.80-2.69 (m, 8H), 2.32 (s, 3H), 2.19 (s, 2H), 2.00 (s, 3H), 1.49-1.42 (m, 1H), 1.00-0.92 (m, 6H).

GB-P1 ESI 643.2 (M+H)⁺. ¹H NMR (400 MHz, MeOD) δ 7.81 (s, 1H), 7.66-7.52 (m, 2H), 7.45 (t, J=7.7 Hz, 1H), 7.13 (d, J=6.4 Hz, 2H), 6.90 (s, 1H), 5.77-5.59 (m, 2H), 3.23 (s, 2H), 3.01 (s, 2H), 2.83 (s, 6H), 2.69-2.53 (m, 1H), 2.58-2.49 (m, 1H), 2.37 (d, J=1.6 Hz, 3H), 2.19 (s, 3H), 2.05-1.96 (m, 1H), 1.81 (s, 1H), 1.42-1.36 (m, 1H), 0.99-0.91 (m, 6H).

4-135. (3S)-3-(2-(5-(2-(azetidin-1-yl)ethyl)-2-oxo-4-(trifluoromethyl)pyridin-1(2H)-yl)-4-methylpentanamido)-3-(4-fluoro-2'-methoxy-5,6'-dimethylbiphenyl-3-yl)propanoic Acid (Diastereomeric Compounds GC-P1 and GC-P2)

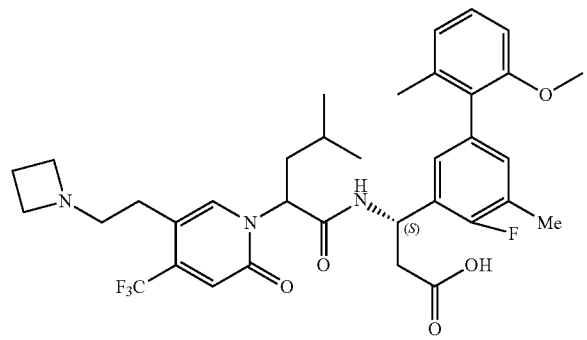

GC-P1 ESI 660.2 (M+H)⁺. ¹H NMR (400 MHz, MeOD) δ 7.82 (s, 1H), 7.21 (t, J=8.0 Hz, 1H), 6.99-6.82 (m, 5H), 5.70-5.62 (m, 2H), 4.01-3.96 (m, 4H), 3.66 (s, 3H), 3.30-3.27 (m, 2H), 2.88-2.85 (m, 2H), 2.71 (d, J=7.4 Hz, 2H), 2.45-2.39 (m, 2H), 2.29 (s, 3H), 2.02-1.93 (m, 5H), 1.45-1.38 (m, 1H), 0.97-0.93 (m, 6H).

GC-P2 ESI 660.2 (M+H)⁺. ¹H NMR (400 MHz, MeOD) δ 7.73 (s, 1H), 7.22 (t, J=8.0 Hz, 1H), 7.00-6.87 (m, 5H), 5.79-5.75 (m, 1H), 5.62 (t, J=7.6 Hz, 1H), 4.13 (t, J=7.9 Hz, 4H), 3.68 (s, 3H), 3.49-3.35 (m, 2H), 2.97-2.91 (d, J=16.1 Hz, 1H), 2.85-2.77 (m, 1H), 2.66-2.62 (m, 1H), 2.56-2.42 (m, 3H), 2.32 (d, J=1.7 Hz, 3H), 2.04 (s, 3H), 2.02-1.97 (m, 1H), 1.72-1.60 (m, 1H), 1.49-1.36 (m, 1H), 0.91 (d, J=6.5 Hz, 6H).

4-136. (3S)-3-(2'-cyclopropyl-4-fluoro-4',5,6'-trimethyl-[1,1'-biphenyl]-3-yl)-3-(2-(5-(2-(dimethylamino)ethyl)-4-methyl-2-oxopyridin-1(2H)-yl)-4-methylpentanamido)propanoic Acid (Diastereomeric Compounds GD-P1 and GD-P2)

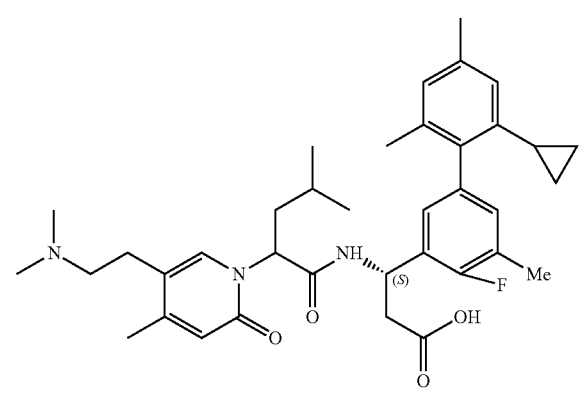

GD-P1 ESI 618.3 (M+H)⁺. ¹H NMR (400 MHz, MeOD) δ 7.57 (d, J=1.8 Hz, 1), 6.91-6.84 (m, 3H), 6.57 (d, J=11.0 Hz, 1H), 6.38 (d, J=8.9 Hz, 1H), 5.59 (d, J=5.8 Hz, 1H), 5.46 (t, J=5.9 Hz, 1H), 3.22-3.06 (m, 2H), 2.87 (t, J=7.1 Hz, 2H), 2.74 (s, 6H), 2.71-2.56 (m, 2H), 2.27 (d, J=13.3 Hz, 9H), 2.04-1.87 (m, 5H), 1.48-1.38 (m, 2H), 0.95-0.89 (m, 6H), 0.72-0.67 (m, 1H), 0.63-0.55 (m, 1H), 0.53-0.48 (m, 2H).

GD-P2 ESI 618.3 (M+H)⁺. ¹H NMR (400 MHz, MeOD) δ 7.54 (d, J=10.5 Hz, 1H), 6.98-6.89 (m, 2H), 6.89 (s, 1H), 6.59 (s, 1H), 6.44 (d, J=5.1 Hz, 1H), 5.65-5.56 (m, 2H), 3.34-3.26 (m, 2H), 3.20-3.13 (m, 2H), 2.94-2.88 (m, 2H), 2.81 (d, J=2.0 Hz, 6H), 2.64-2.57 (m, 1H), 2.48-2.41 (m, 1H), 2.32-2.246 (m, 9H), 1.99-1.92 (m, 4H), 1.81-1.74 (m, 1H), 1.49-1.33 (m, 1H), 0.92-0.85 (m, 6H), 0.68-0.63 (m, 2H), 0.58-0.51 (m, 2H).

4-137. (3S)-3-(4'-cyclopropyl-4-fluoro-2',5,6'-trimethyl-[1,1'-biphenyl]-3-yl)-3-(2-(5-(2-(dimethylamino)ethyl)-4-methyl-2-oxopyridin-1(2H)-yl)-4-methylpentanamido)propanoic Acid (Diastereomeric Compounds GE-P1 and GE-P2)

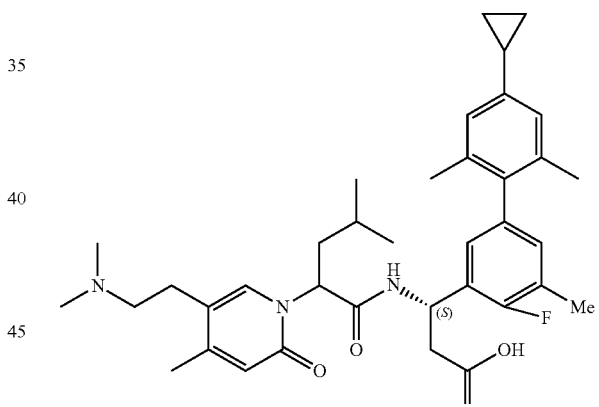

GE-P1 ESI 618.3 (M+H)⁺. ¹H NMR (400 MHz, MeOD) δ 7.46 (s, 1H), 6.84-6.65 (m, 3H), 6.45 (d, J=11.2 Hz, 1H), 6.27 (d, J=8.7 Hz, 1H), 5.48-5.46 (m, 1H), 5.33 (d, J=5.6 Hz, 1H), 3.15-2.95 (m, 2H), 2.78-2.74 (m, 3H), 2.60 (d, J=25.4 Hz, 6H), 2.58-2.40 (m, 2H), 2.17 (s, 6H), 2.13 (s, 3H), 1.95-1.73 (m, 5H), 1.34-1.28 (m, 2H), 0.86-0.73 (m, 6H), 0.62-0.32 (m, 4H).

GE-P2 ESI 618.3 (M+H)⁺. ¹H NMR (400 MHz, MeOD) δ 7.43 (s, 1H), 7.40 (s, 1H), 6.84 (t, J=6.2 Hz, 2H), 6.77 (s, 1H), 6.47 (s, 1H), 6.32 (d, J=5.5 Hz, 1H), 5.52-5.44 (m, 2H), 3.09-3.06 (m, 1H), 2.88-2.67 (m, 8H), 2.51-2.45 (m, 1H), 2.37-2.29 (m, 1H), 2.24-2.09 (m, 9H), 1.85-1.81 (m, 4H), 1.70-1.59 (m, 1H), 1.39-1.16 (m, 2H), 0.78-0.76 (m, 6H), 0.54 (t, J=7.6 Hz, 2H), 0.45 (d, J=4.5 Hz, 2H).

4-138. (3S)-3-(2'-chloro-4,4'-difluoro-5,6'-dimethyl-[1,1'-biphenyl]-3-yl)-3-(2-(5-(2-(dimethylamino)ethyl)-2-oxo-4-(trifluoromethyl)pyridin-1(2H)-yl)-4-methylpentanamido)propanoic Acid (Diastereomeric Compounds GF-P1 and GF-P2)

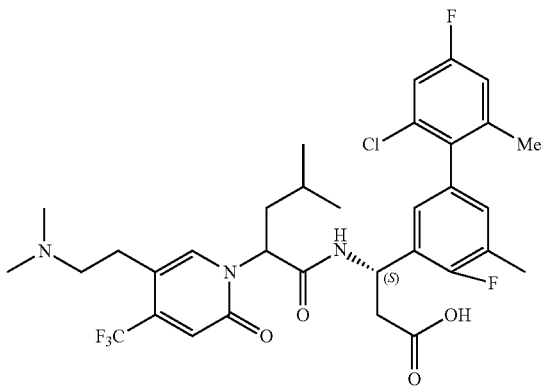

GF-P1 ESI 670.2 (M+H)⁺. ¹H NMR (400 MHz, MeOD) δ 7.90 (d, J=3.1 Hz, 1H), 7.14-6.92 (m, 4H), 6.76 (d, J=5.6 Hz, 1H), 5.72-5.65 (m, 1H), 5.60-5.56 (m, 1H), 3.10-2.87 (m, 4H), 2.76-2.66 (m, 8H), 2.30 (s, 3H), 2.09-1.91 (m, 5H), 1.47-1.41 (m, 1H), 1.00-0.92 (m, 6H).

GF-P2 ESI 670.2 (M+H)⁺. ¹H NMR (400 MHz, MeOD) δ 7.84 (s, 1H), 7.16-7.12 (m, 1H), 7.07-6.95 (m, 3H), 6.91 (d, J=2.7 Hz, 1H), 5.74-5.59 (m, 2H), 3.32-3.21 (m, 2H), 3.03-2.99 (m, 2H), 2.84 (d, J=2.9 Hz, 6H), 2.67-2.49 (m, 2H), 2.34 (d, J=1.6 Hz, 3H), 2.03-1.90 (m, 1H), 1.76-1.67 (m, 1H), 1.46-1.37 (m, 1H), 0.92-0.89 (m, 6H).

4-139. (3S)-3-(2',6'-dichloro-4-fluoro-4',5-dimethyl-[1,1'-biphenyl]-3-yl)-3-(2-(5-(2-(dimethylamino)ethyl)-2-oxo-4-(trifluoromethyl)pyridin-1(2H)-yl)-4-methylpentanamido)propanoic Acid (Diastereomeric Compounds GG-P1 and GG-P2)

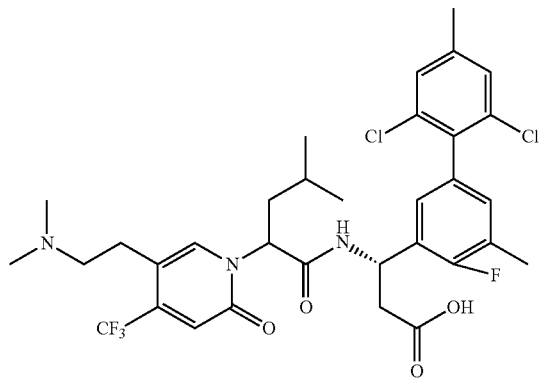 [SMILES: Cc1cc(Cl)c(-c2cc(C)c(F)c([C@H](CC(=O)O)NC(=O)C(CC(C)C)n3cc(CCN(C)C)c(C(F)(F)F)cc3=O)c2)c(Cl)c1]

GG-P1 ESI 686.1 (M+H)⁺. ¹H NMR (400 MHz, MeOD) δ 7.90 (s, 1H), 7.31 (s, 1H), 7.23 (s, 1H), 7.02-6.91 (m, 2H), 6.76 (s, 1H), 5.76-5.66 (m, 1H), 5.63-5.53 (m, 1H), 3.15-3.04 (m, 2H), 2.94 (t, J=11.0 Hz, 2H), 2.80-2.66 (m, 8H), 2.38 (s, 3H), 2.29 (d, J=1.3 Hz, 3H), 2.04-1.92 (m, 2H), 1.51-1.42 (m, 1H), 1.01-0.90 (m, 6H).

GG-P2 ESI 686.1 (M+H)⁺. ¹H NMR (400 MHz, MeOD) δ 7.88 (s, 1H), 7.32 (s, 2H), 7.09-6.99 (m, 2H), 6.91 (s, 1H), 5.79-5.71 (m, 1H), 5.65 (t, J=7.7 Hz, 1H), 3.30-3.15 (m, 2H), 3.00 (t, J=6.8 Hz, 2H), 2.81 (s, 6H), 2.67-2.50 (m, 2H), 2.39 (s, 3H), 2.33 (d, J=1.5 Hz, 3H), 2.02-1.92 (m, 1H), 1.73-1.65 (m, 1H), 1.44-1.36 (m, 1H), 0.91-0.85 (m, 6H).

4-140. (3S)-3-(2-(5-(2-(dimethylamino)ethyl)-4-methyl-2-oxopyridin-1(2H)-yl)-4-methylpentanamido)-3-(4-fluoro-2',5,6'-trimethyl-4'-(trifluoromethyl)biphenyl-3-yl)propanoic Acid (Diastereomeric Compounds GH-P1 and GH-P2)

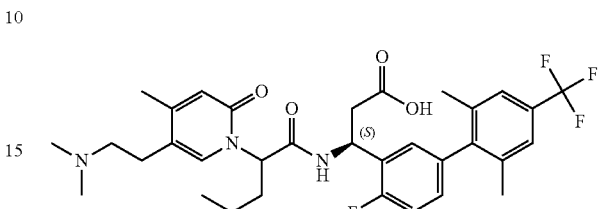

GH-P1 ESI 646.3 (M+H)⁺. ¹H NMR (400 MHz, MeOD) δ: 7.59 (s, 1H), 7.40 (s, 1H), 7.38 (s, 1H), 6.89 (d, J=6.8 Hz, 1H), 6.84 (d, J=6.4 Hz, 1H), 6.28 (s, 1H), 5.55 (t, J=5.6 Hz, 1H), 5.49 (t, J=6.0 Hz, 1H), 3.16-3.08 (m, 2H), 2.87 (t, J=7.2 Hz, 2H), 2.78 (s, 6H), 2.73-2.68 (m, 1H), 2.65-2.60 (m, 1H), 2.31 (s, 3H), 2.25 (s, 3H), 2.08 (s, 3H), 2.01-1.90 (m, 5H), 1.45-1.38 (m, 1H), 0.94 (d, J=6.4 Hz, 3H), 0.91 (d, J=6.8 Hz, 3H).

GH-P2 ESI 646.3 (M+H)⁺. ¹H NMR (400 MHz, MeOD) δ: 7.55 (s, 1H), 7.41 (s, 2H), 6.95-6.93 (m, 1H), 6.90 (d, J=6.4 Hz, 1H), 6.41 (s, 1H), 5.63-5.60 (m, 1H), 5.58-5.56 (m, 1H), 3.38-3.36 (m, 1H), 3.25-3.19 (m, 1H), 2.95-2.90 (m, 2H), 2.85 (s, 6H), 2.64-2.59 (m, 1H), 2.50-2.44 (m, 1H), 2.34 (d, J=1.6 Hz, 3H), 2.26 (s, 3H), 2.08 (s, 6H), 2.00-1.93 (m, 1H), 1.83-1.76 (m, 1H), 1.42-1.35 (m, 1H), 0.89 (t, J=6.4 Hz, 6H).

4-141. (3S)-3-(4'-cyclopropyl-4-fluoro-2',5,6'-trimethyl-[1,1'-biphenyl]-3-yl)-3-(2-(5-(2-(dimethylamino)ethyl)-3-fluoro-4-methyl-2-oxopyridin-1(2H)-yl)-4-methylpentanamido)propanoic Acid (Diastereomeric Compounds GI-P1 and GI-P2)

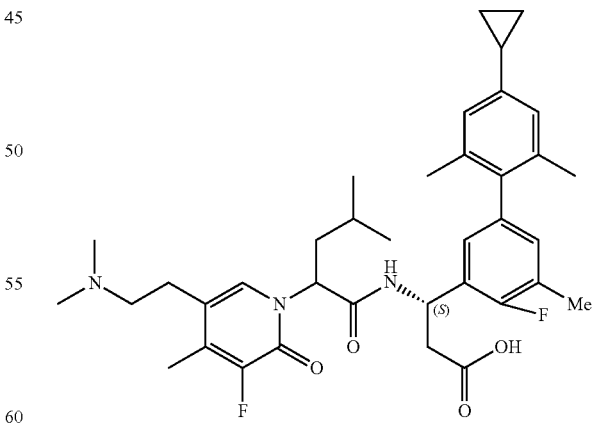

GI-P1 ESI 636.3 (M+H)⁺. ¹H NMR (400 MHz, MeOD) δ 7.47 (s, 1H), 6.94-6.78 (m, 3H), 6.57 (d, J=12.7 Hz, 1H), 5.74-5.57 (m, 1H), 5.46 (t, J=5.9 Hz, 1H), 3.25-3.10 (m, 2H), 2.92 (t, J=6.9 Hz, 2H), 2.75 (s, 6H), 2.70-2.52 (m, 2H), 2.30-2.25 (m, 9H), 1.99-1.88 (m, 5H), 1.46-1.39 (m, 2H), 0.97-0.86 (m, 6H), 0.72-0.43 (m, 4H).

GI-P2 ESI 636.3 (M+H)⁺. ¹H NMR (400 MHz, MeOD) δ 7.42 (d, J=11.3 Hz, 1H), 6.97 (t, J=8.2 Hz, 2H), 6.89 (s, 1H), 6.59 (s, 1H), 5.72-5.52 (m, 2H), 3.32-3.22 (m, 2H), 2.98-2.90 (m, 2H), 2.85 (s, 6H), 2.67-2.38 (m, 2H), 2.32-2.25 (m, 9H), 2.00-1.98 (m, 4H), 1.83-1.67 (m, 1H), 1.51-1.26 (m, 2H), 0.90 (d, J=6.6 Hz, 6H), 0.70-0.48 (m, 4H).

4-142. (3S)-3-(4-fluoro-2',4',5,6'-tetramethyl-[1,1'-biphenyl]-3-yl)-3-(2-(3-fluoro-5-(2-(3-methoxyazetidin-1-yl)ethyl)-4-methyl-2-oxopyridin-1(2H)-yl)-4-methylpentanamido)propanoic Acid (Diastereomeric Compounds GJ-P1 and GJ-P2)

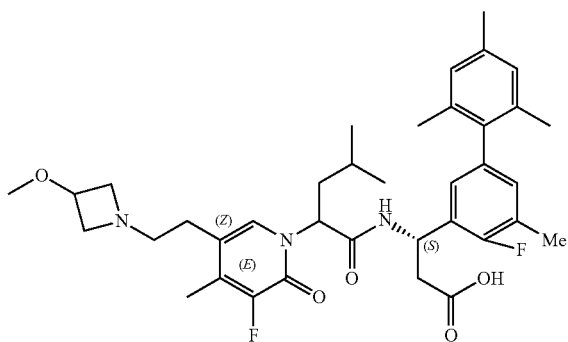

GJ-P1 ESI 652.3 (M+H)⁺. ¹H NMR (400 MHz, MeOD) δ 7.26 (s, 1H), 6.84-6.68 (m, 4H), 5.54-5.45 (m, 1H), 5.41 (t, J=6.3 Hz, 1H), 4.14-3.93 (m, 3H), 3.64-3.54 (m, 1H), 3.52-3.50 (m, 1H), 3.25-3.16 (m, 5H), 2.74-2.55 (m, 4H), 2.18 (s, 6H), 2.12 (d, J=4.0 Hz, 3H), 1.88-1.74 (m, 8H), 1.29-1.25 (m, 1H), 0.83-0.78 (m, 6H).

GJ-P2 ESI 652.3 (M+H)⁺. ¹H NMR (400 MHz, MeOD) δ 7.20 (s, 1H), 6.85-6.72 (m, 4H), 5.61-5.43 (m, 2H), 4.36-4.08 (m, 3H), 3.84-3.61 (m, 2H), 3.32-3.22 (m, 5H), 2.82-2.78 (m, 1H), 2.64-2.56 (m, 1H), 2.51-2.47 (m, 1H), 2.39-2.32 (m, 1H), 2.23-2.13 (m, 6H), 2.10 (d, J=2.7 Hz, 3H), 1.90-1.73 (m, 8H), 1.68-1.51 (m, 1H), 1.32-1.20 (m, 1H), 0.79-0.74 (m, 6H).

4-143. (3S)-3-(2-(5-(2-(azetidin-1-yl)ethyl)-2-oxo-4-(trifluoromethyl)pyridin-1(2H)-yl)-4-methylpentanamido)-3-(4,4'-difluoro-2',5,5'-trimethylbiphenyl-3-yl)propanoic Acid (Diastereomeric Compounds GK-P1 and GK-P2)

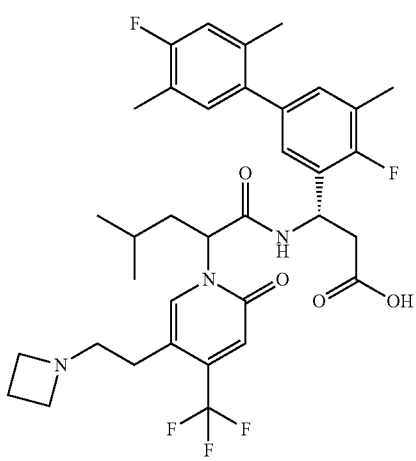 [SMILES: Cc1cc(-c2cc(C)c(F)c([C@H](CC(=O)O)NC(=O)C(CC(C)C)n3cc(CCN4CCC4)c(C(F)(F)F)cc3=O)c2)c(C)cc1F]

GK-P1 ESI 662.2 (M+H)⁺. ¹H NMR (400 MHz, MeOD) δ 7.84 (s, 1H), 7.03-7.00 (m, 3H), 6.93 (d, J=10.6 Hz, 1H), 6.81 (s, 1H), 5.70-5.63 (m, 1H), 5.59 (t, J=6.7 Hz, 1H), 4.02 (t, J=8.2 Hz, 4H), 3.30 (s, 2H), 2.86 (t, J=6.9 Hz, 2H), 2.71 (d, J=6.8 Hz, 2H), 2.42-2.39 (m, 2H), 2.30 (d, J=1.4 Hz, 3H), 2.25 (s, 3H), 2.15 (s, 3H), 2.02-2.19 (m, 2H), 1.48-1.39 (m, 1H), 0.96-0.90 (m, 6H).

GK-P2 ESI 662.2 (M+H)⁺. ¹H NMR (400 MHz, MeOD) δ 7.73 (s, 1H), 7.09-7.06 (m, 2H), 7.04 (d, J=8.1 Hz, 1H), 6.99-6.88 (m, 2H), 5.75-5.70 (m, 1H), 5.64 (t, J=7.7 Hz, 1H), 4.15 (t, J=8.0 Hz, 4H), 3.42-3.40 (m, 2H), 2.95 (d, J=16.2 Hz, 1H), 2.82-2.80 (m, 1H), 2.64-2.60 (m, 1H), 2.55-2.43 (m, 3H), 2.34 (s, 3H), 2.26 (s, 3H), 2.20 (s, 3H), 2.04-1.97 (m, 1H), 1.71-1.68 (m, 1H), 1.43-1.38 (m, 1H), 0.92 (t, J=6.3 Hz, 6H).

4-144. (3S)-3-(2-(5-(2-(azetidin-1-yl)ethyl)-2-oxo-4-(trifluoromethyl)pyridin-1(2H)-yl)-4-methylpentanamido)-3-(4-fluoro-4'-methoxy-2',5,5'-trimethyl-[1,1'-biphenyl]-3-y)propanoic Acid (Diastereomeric Compounds GL-P1 and GL-P2)

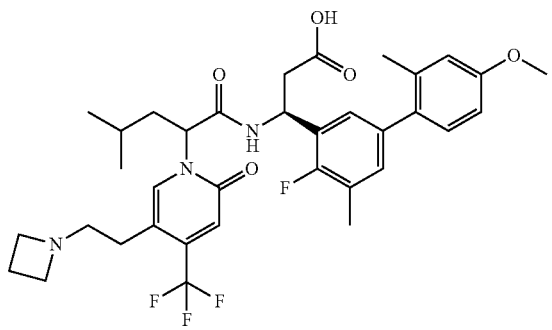 [SMILES: COc1ccc(-c2cc(C)c(F)c([C@H](CC(=O)O)NC(=O)C(CC(C)C)n3cc(CCN4CCC4)c(C(F)(F)F)cc3=O)c2)c(C)c1]

GL-P1 ESI 674.3 (M+H)⁺. ¹H NMR (400 MHz, MeOD) δ 7.83 (s, 1H), 7.03 (t, J=7.3 Hz, 2H), 6.90 (s, 1H), 6.83 (s, 1H), 6.78 (s, 1H), 5.67 (t, J=8.0 Hz, 1H), 5.59 (t, J=6.7 Hz, 1H), 3.99 (t, J=8.2 Hz, 4H), 3.86 (s, 3H), 3.29 (d, J=3.5 Hz, 2H), 2.85 (t, J=6.7 Hz, 2H), 2.71 (d, J=6.7 Hz, 2H), 2.44-2.34 (m, 2H), 2.29 (d, J=1.6 Hz, 3H), 2.18 (s, 6H), 2.02 (t, J=7.5 Hz, 2H), 1.46-1.39 (m, 1H), 0.96 (t, J=6.2 Hz, 6H).

GL-P2 ESI 674.3 (M+H)⁺. ¹H NMR (400 MHz, MeOD) δ 7.74 (s, 1H), 7.14-7.03 (m, 2H), 6.93 (s, 2H), 6.80 (s, 1H), 5.80-5.71 (m, 1H), 5.64 (t, J=7.6 Hz, 1H), 4.14 (t, J=8.0 Hz, 4H), 3.86 (s, 3H), 3.50-3.36 (m, 2H), 2.95 (d, J=15.7 Hz, 1H), 2.87-2.78 (m, 1H), 2.67-2.60 (m, 1H), 2.57-2.42 (m, 3H), 2.33 (d, J=1.6 Hz, 3H), 2.20 (d, J=19.2 Hz, 6H), 2.05-1.96 (m, 1H), 1.73-1.65 (m, 1H), 1.47-1.37 (m, 1H), 0.92 (t, J=6.7 Hz, 6H).

4-145. (3S)-3-(2-(5-(2-(azetidin-1-yl)ethyl)-2-oxo-4-(trifluoromethyl)pyridin-1(2H)-yl)-4-methylpentanamido)-3-(4'-cyano-4,5'-difluoro-2',5-dimethylbiphenyl-3-yl)propanoic Acid (Diastereomeric Compounds GM-P1 and GM-P2)

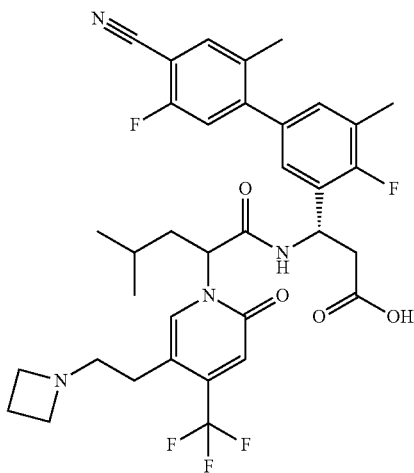 [SMILES: Cc1cc(C#N)c(F)cc1-c1cc(C)c(F)c([C@H](CC(=O)O)NC(=O)C(CC(C)C)n2cc(CCN3CCC3)c(C(F)(F)F)cc2=O)c1]

GM-P1 ESI 673.3 (M+H)⁺. ¹H NMR (500 MHz, MeOD) δ 7.86 (s, 1H), 7.67 (d, J=6.6 Hz, 1H), 7.24-7.07 (m, 3H), 6.79 (d, J=7.4 Hz, 1H), 5.78-5.50 (m, 2H), 4.10 (t, J=8.1 Hz, 4H), 3.41-3.34 (m, 2H), 2.92-2.65 (m, 4H), 2.61-2.40 (m, 2H), 2.32 (s, 3H), 2.23 (s, 3H), 2.15-1.86 (m, 2H), 1.54-1.38 (m, 1H), 0.97 (t, J=6.6 Hz, 6H).

GM-P2 ESI 673.3 (M+H)⁺. ¹H NMR (500 MHz, MeOD) δ 7.75-7.59 (m, 2H), 7.25-7.16 (m, 3H), 6.93 (s, 1H), 5.80-5.55 (m, 2H), 4.16 (t, J=7.9 Hz, 4H), 3.50-3.37 (m, 2H), 3.04-2.77 (m, 2H), 2.72-2.43 (m, 4H), 2.36 (s, 3H), 2.28 (s, 3H), 2.06-1.96 (m, 1H), 1.83-1.64 (m, 1H), 1.53-1.29 (m, 1H), 0.97-0.89 (m, 6H).

4-146. (3S)-3-(2-(5-(2-(azetidin-1-yl)ethyl)-2-oxo-4-(trifluoromethyl)pyridin-1(2H)-yl)-4-methylpentanamido)-3-(5'-cyano-4,4'-difluoro-2',5-dimethyl-[1,1'-biphenyl]-3-yl)propanoic Acid (Diastereomeric Compounds GN-P1 and GN-P2)

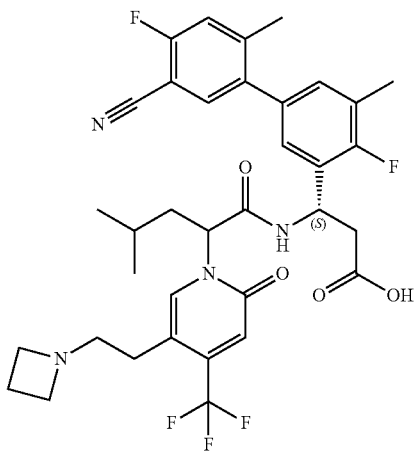

GN-P1 ESI 673.3 (M+H)⁺. ¹H NMR (400 MHz, MeOD) δ 7.85 (s, 1H), 7.55 (d, J=6.7 Hz, 1H), 7.32 (d, J=10.3 Hz, 1H), 7.10 (d, J=6.4 Hz, 2H), 6.81 (s, 1H), 5.65-5.55 (m, 2H), 4.03 (t, J=8.0 Hz, 4H), 3.32-3.26 (m, 2H), 2.84 (t, J=7.0 Hz, 2H), 2.78-2.67 (m, 2H), 2.51-2.36 (m, 2H), 2.36-2.25 (m, 6H), 2.14-1.92 (m, 2H), 1.52-1.36 (m, 1H), 0.97 (t, J=6.1 Hz, 6H).

GN-P2 ESI 673.3 (M+H)⁺. ¹H NMR (400 MHz, MeOD) δ 7.74 (s, 1H), 7.57 (d, J=6.7 Hz, 1H), 7.34 (d, J=10.2 Hz, 1H), 7.14 (d, J=6.7 Hz, 2H), 6.93 (s, 1H), 5.76-5.71 (m, 1H), 5.63 (t, J=7.7 Hz, 1H), 4.13 (t, J=7.9 Hz, 4H), 3.49-3.35 (m, 2H), 3.00-2.87 (m, 1H), 2.88-2.75 (m, 1H), 2.68-2.60 (m, 1H), 2.57-2.42 (m, 3H), 2.39-2.28 (m, 6H), 2.05-1.95 (m, 1H), 1.79-1.63 (m, 1H), 1.48-1.37 (m, 1H), 0.92 (t, J=6.6 Hz, 6H).

4-147. (3S)-3-(2-(5-(2-(dimethylamino)ethyl)-3-fluoro-2-oxo-4-(trifluoromethyl)pyridin-1(2H)-yl)-4-methylpentanamido)-3-(4-fluoro-2',5,6'-trimethylbiphenyl-3-yl)propanoic Acid (Diastereomeric Compounds GO-P1 and GO-P2)

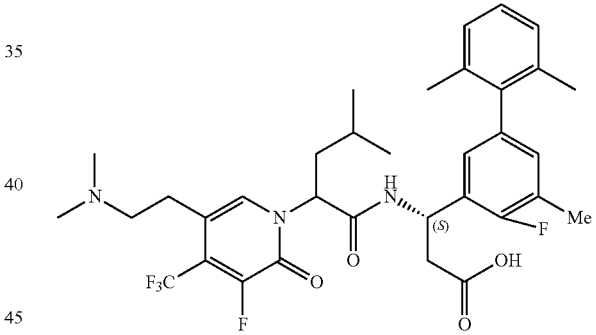

GO-P1 ESI 650.2 (M+H)+. ¹H NMR (500 MHz, MeOD) δ 7.70 (s, 1H), 7.12 (t, J=7.5 Hz, 1H), 7.08-7.02 (m, 2H), 6.89-6.85 (m, 2H), 5.69 (t, J=8.0 Hz, 1H), 5.61-5.54 (m, 1H), 3.09-3.02 (m, 2H), 2.99 (d, J=7.3 Hz, 2H), 2.74-2.70 (m, 8H), 2.30 (s, 3H), 2.05-1.94 (m, 5H), 1.86 (s, 3H), 1.44 (m, 1H), 0.94-0.90 (m, 6H).

GO-P2 ESI 650.2 (M+H)+. ¹H NMR (500 MHz, MeOD) δ 7.62 (s, 1H), 7.18-7.07 (m, 3H), 6.94 (t, J=6.8 Hz, 2H), 5.73-5.70 (m, 1H), 5.61 (t, J=7.6 Hz, 1H), 3.31-3.18 (m, 2H), 3.11-2.95 (m, 2H), 2.84 (s, 6H), 2.65-2.60 (m, 1H), 2.52-2.48 (m, 1H), 2.35-2.32 (m, 3H), 2.08-1.94 (m, 7H), 1.74-1.64 (m, 1H), 1.42-1.39 (m, 1H), 0.90 (d, J=6.6 Hz, 6H).

4-148. (3S)-3-(2-(5-(2-(dimethylamino)ethyl)-3-fluoro-2-oxo-4-(trifluoromethyl)pyridin-1(2H)-yl)-4-methylpentanamido)-3-(4-fluoro-2',4',5,6'-tetramethylbiphenyl-3-yl)propanoic Acid (Diastereomeric Compounds GP-P1 and GP-P2)

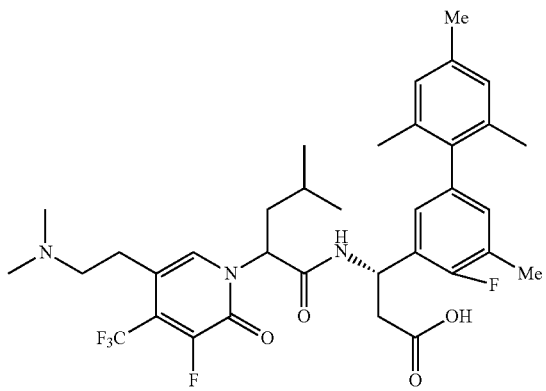 [SMILES: Cc1cc(C)c(-c2cc(C)c(F)c([C@H](CC(=O)O)NC(=O)C(CC(C)C)n3cc(CCN(C)C)c(C(F)(F)F)c(F)c3=O)c2)c(C)c1]

GP-P1 ESI 664.2 (M+H)+. 1H NMR (400 MHz, MeOD) δ 7.69 (s, 1H), 6.96-6.77 (m, 4H), 5.72-5.66 (m, 1H), 5.56 (s, 1H), 3.09-2.90 (m, 4H), 2.71 (d, J=4.8 Hz, 8H), 2.29 (s, 6H), 2.08-1.91 (m, 5H), 1.82 (s, 3H), 1.44 (s, 1H), 0.95-0.90 (m, 6H).

GP-P2 ESI 664.2 (M+H)+. 1H NMR (400 MHz, MeOD) δ 7.62 (d, J=12.1 Hz, 1H), 6.97-6.85 (m, 4H), 5.72-5.69 (m, 1H), 5.62 (t, J=7.6 Hz, 1H), 3.22 (qd, J=13.0, 6.1 Hz, 2H), 3.13-2.89 (m, 2H), 2.82 (s, 6H), 2.64-2.60 (m, 1H), 2.49-2.45 (m, 1H), 2.36-2.23 (m, 6H), 2.04-1.90 (m, 7H), 1.74-1.64 (m, 1H), 1.41-1.38 (m, 1H), 0.90-0.86 (m, 6H).

4-149. (3S)-3-(4,4'-difluoro-2',5,6'-trimethylbiphenyl-3-yl)-3-(2-(5-(2-(3-methoxyazetidin-1-yl)ethyl)-2-oxo-4-(trifluoromethyl)pyridin-1(2H)-yl)-4-methylpentanamido)propanoic Acid (Diastereomeric Compounds GQ-P1 and GQ-P2)

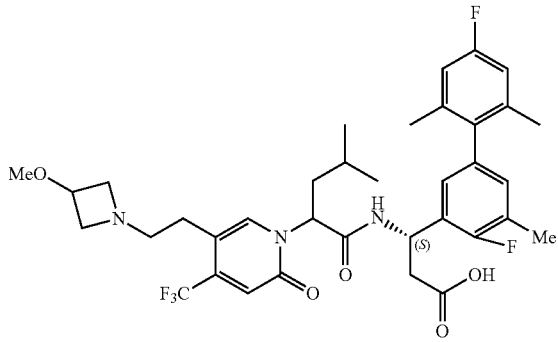

GQ-P1 ESI 692.2 (M+H)+. 1H NMR (400 MHz, MeOD) δ 7.84 (s, 1H), 6.96-6.68 (m, 5H), 5.75-5.48 (m, 2H), 4.26-4.01 (m, 3H), 3.74-3.52 (m, 2H), 3.31 (s, 3H), 3.14 (t, J=6.8 Hz, 2H), 2.87-2.63 (m, 4H), 2.30 (s, 3H), 2.05-1.92 (m, 5H), 1.85 (s, 3H), 1.54-1.36 (m, 1H), 1.07-0.87 (m, 6H).

GQ-P2 ESI 692.2 (M+H)+. 1H NMR (400 MHz, MeOD) δ 7.74 (s, 1H), 7.04-6.78 (m, 5H), 5.80-5.70 (m, 1H), 5.62 (t, J=7.7 Hz, 1H), 4.49-4.21 (m, 3H), 4.01-3.74 (m, 2H), 3.46-3.35 (m, 5H), 3.03-2.77 (m, 2H), 2.68-2.44 (m, 2H), 2.34 (d, J=1.7 Hz, 3H), 2.12-1.90 (m, 7H), 1.74-1.57 (m, 1H), 1.53-1.32 (m, 1H), 0.99-0.83 (m, 6H).

4-150. (3S)-3-(2-(5-(2-(dimethylamino)ethyl)-2-oxo-4-(trifluoromethyl)pyridin-1(2H)-yl)pentanamido)-3-(4-fluoro-2',4',5,6'-tetramethyl-[1,1'-biphenyl]-3-yl)propanoic Acid (Diastereomeric Compounds GR-P1 and GR-P2)

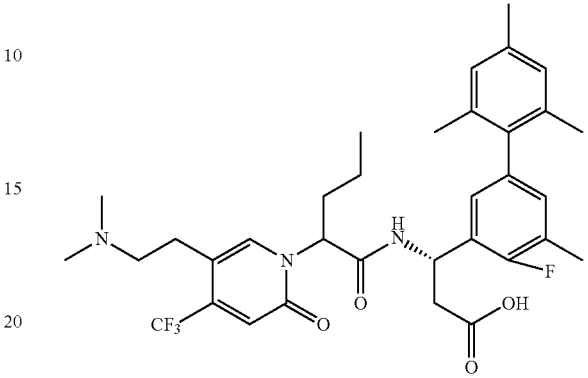

GR-P1 ESI 632.2 (M+H)+. 1H NMR (500 MHz, MeOD) δ 7.88 (s, 1H), 6.92-6.79 (m, 4H), 6.74 (s, 1H), 5.66-5.45 (m, 2H), 3.11-2.85 (m, 5H), 2.78-2.68 (m, 7H), 2.32-2.22 (m, 6H), 2.18-2.08 (m, 1H), 2.06-1.92 (m, 4H), 1.78 (s, 3H), 1.41-1.24 (m, 2H), 0.97 (t, J=7.4 Hz, 3H).

GR-P2 ESI 632.2 (M+H)+. 1H NMR (500 MHz, MeOD) δ 7.82 (s, 1H), 6.90 (d, J=7.1 Hz, 5H), 5.79-5.64 (m, 1H), 5.52 (t, J=7.6 Hz, 1H), 3.30-3.15 (m, 2H), 3.00 (t, J=6.6 Hz, 2H), 2.83 (s, 6H), 2.69-2.59 (m, 1H), 2.58-2.44 (m, 1H), 2.31 (d, J=9.7 Hz, 6H), 2.13-2.01 (m, 1H), 1.97 (s, 6H), 1.91-1.73 (m, 1H), 1.39-1.02 (m, 2H), 0.91 (t, J=7.4 Hz, 3H).

4-151. (3S)-3-(2-(5-(2-(dimethylamino)ethyl)-4-methyl-2-oxopyridin-1(2H)-yl)-5-methylhexanamido)-3-(4-fluoro-2',4',5,6'-tetramethylbiphenyl-3-yl)propanoic Acid (Diastereomeric Compounds GS-P1 and GS-P2)

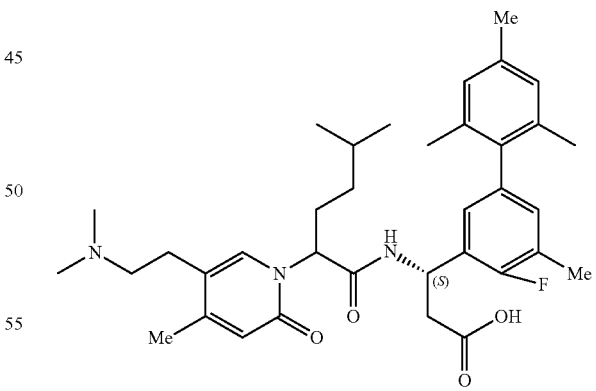

GS-P1 ESI 606.3 (M+H)+. 1H NMR (400 MHz, MeOD) δ 7.57 (s, 1H), 6.90 (s, 2H), 6.85-6.80 (m, 2H), 6.34 (s, 1H), 5.48 (t, J=6.0 Hz, 1H), 5.42-5.37 (s, 1H), 3.24-3.02 (m, 2H), 2.89-2.85 (m, 2H), 2.76 (s, 6H), 2.71-2.60 (m, 2H), 2.30 (d, J=4.9 Hz, 6H), 2.25 (s, 3H), 2.22-2.14 (m, 1H), 1.95 (s, 4H), 1.87 (s, 3H), 1.60-1.53 (m, 1H), 1.25-1.14 (m, 1H), 1.12-1.00 (m, 1H), 0.89-0.87 (m, 6H).

GS-P2 ESI 606.3 (M+H)+. 1H NMR (400 MHz, MeOD) δ 7.54 (s, 1H), 6.98-6.78 (m, 4H), 6.44 (s, 1H), 5.66-5.63 (m,

1H), 5.42 (t, J=7.7 Hz, 1H), 3.31-3.28 (m, 1H), 3.26-3.14 (m, 1H), 2.99-2.88 (m, 2H), 2.84 (s, 6H), 2.64-2.59 (m, 1H), 2.50-2.43 (m, 1H), 2.39-2.28 (m, 6H), 2.27 (s, 3H), 2.16-2.07 (m, 1H), 1.96 (s, 6H), 1.89-1.74 (m, 1H), 1.57-1.50 (m, 1H), 1.15-1.11 (m, 1H), 1.08-0.97 (m, 1H), 0.85 (t, J=6.5 Hz, 6H).

4-152. (3S)-3-(4,4'-difluoro-2',5,6'-trimethylbiphenyl-3-yl)-3-(2-(5-(2-(dimethylamino)ethyl)-4-methyl-2-oxopyridin-1(2H)-yl)-5-methylhexanamido)propanoic Acid (Diastereomeric Compounds GT-P1 and GT-P2)

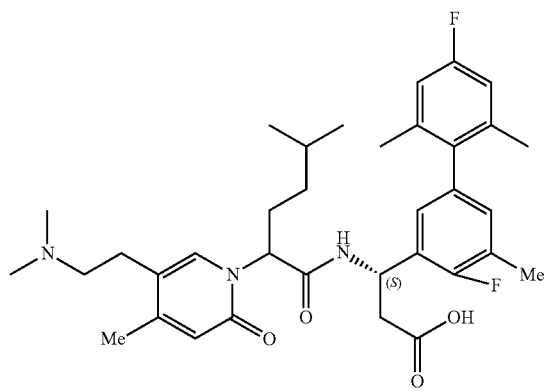

GT-P1 ESI 610.3 (M+H)+. 1H NMR (400 MHz, MeOD) δ 7.58 (s, 1H), 6.84 (t, J=9.1 Hz, 4H), 6.32 (s, 1H), 5.50 (t, J=6.2 Hz, 1H), 5.44-5.33 (m, 1H), 3.24-3.06 (m, 2H), 2.90-2.84 (m, 2H), 2.78 (s, 6H), 2.73-2.62 (m, 2H), 2.28 (d, J=14.1 Hz, 6H), 2.22-2.11 (m, 1H), 2.00-1.96 (m, 4H), 1.89 (s, 3H), 1.60-1.54 (m, 1H), 1.29-1.15 (m, 1H), 1.10-1.03 (m, 1H), 0.89-0.87 (m, 6H).

GT-P2 ESI 610.3 (M+H)+. 1H NMR (400 MHz, MeOD) δ 7.54 (s, 1H), 6.90 (d, J=6.9 Hz, 2H), 6.84 (d, J=9.6 Hz, 2H), 6.44 (s, 1H), 5.66-5.62 (m, 1H), 5.43 (t, J=7.6 Hz, 1H), 3.38-3.35 (m, 1H), 3.24-3.20 (m, 1H), 3.00-2.89 (m, 2H), 2.85 (s, 6H), 2.64-2.59 (m, 1H), 2.50-2.44 (m, 1H), 2.33 (d, J=4 Hz, 3H), 2.28 (s, 3H), 2.17-2.07 (m, 1H), 2.01 (s, 6H), 1.87-1.77 (m, 1H), 1.57-1.51 (m, 1H), 1.20-1.09 (m, 1H), 1.08-0.97 (m, 1H), 0.85 (t, J=6.4 Hz, 6H).

4-153. (3S)-3-(4,4'-difluoro-2',5,6'-trimethyl-[1,1'-biphenyl]-3-yl)-3-(2-(3-fluoro-5-(2-(3-methoxyazetidin-1-yl)ethyl)-4-methyl-2-oxopyridin-1(2H)-yl)-4-methylpentanamido)propanoic Acid (Diastereomeric Compounds GU-P1 and GU-P2)

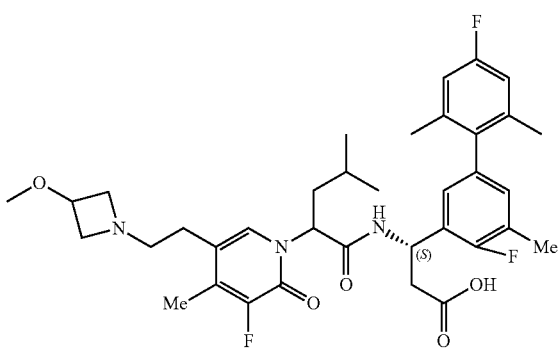

GU-P1 ESI 656.3 (M+H)+. 1H NMR (400 MHz, MeOD) δ 7.40 (s, 1H), 6.95-6.72 (m, 4H), 5.71-5.47 (m, 2H), 4.27-4.16 (m, 2H), 4.16-4.07 (m, 1H), 3.81-3.69 (m, 1H), 3.70-3.58 (m, 1H), 3.30 (s, 3H), 3.25 (t, J=6.8 Hz, 2H), 2.88-2.63 (m, 4H), 2.37-2.16 (m, 6H), 2.06-1.82 (m, 8H), 1.49-1.28 (m, 1H), 0.97-0.90 (m, 6H).

GU-P2 ESI 656.3 (M+H)+. 1H NMR (400 MHz, MeOD) δ 7.33 (s, 1H), 6.96-6.89 (m, 2H), 6.84 (d, J=9.7 Hz, 2H), 5.72-5.58 (m, 2H), 4.39-4.14 (m, 3H), 3.85-3.65 (m, 2H), 3.31-3.20 (m, 5H), 2.93-2.78 (m, 1H), 2.77-2.55 (m, 2H), 2.54-2.45 (m, 1H), 2.33 (d, J=1.7 Hz, 3H), 2.22 (d, J=2.7 Hz, 3H), 2.06-1.86 (m, 7H), 1.81-1.66 (m, 1H), 1.344-1.32 (m, 1H), 0.90 (d, J=6.6 Hz, 6H).

4-154. (3S)-3-(5-chloro-4-fluoro-2',4',6'-trimethylbiphenyl-3-yl)-3-(2-(5-(2-(dimethylamino)ethyl)-3-fluoro-2-oxo-4-(trifluoromethyl)pyridin-1(2H)-yl)-4-methylpentanamido)propanoic Acid (Diastereomeric Compounds GV-P1 and GV-P2)

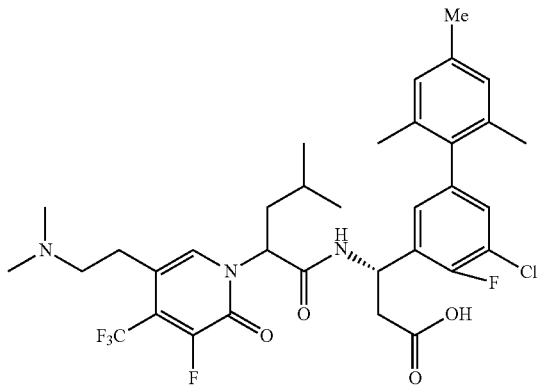 [SMILES: Cc1cc(C)c(-c2cc(Cl)c(F)c([C@H](CC(=O)O)NC(=O)C(CC(C)C)n3cc(CCN(C)C)c(C(F)(F)F)c(F)c3=O)c2)c(C)c1]

GV-P1 ESI 684.2 (M+H)+. 1H NMR (500 MHz, MeOD) δ 7.65 (s, 1H), 7.13 (d, J=6.3 Hz, 1H), 7.08 (d, J=6.1 Hz, 1H), 6.93 (s, 2H), 5.66 (d, J=5.4 Hz, 2H), 3.13-2.89 (m, 4H), 2.70 (s, 6H), 2.67-2.62 (m, 1H), 2.62-2.53 (m, 1H), 2.30 (s, 3H), 1.98 (d, J=6.9 Hz, 7H), 1.74-1.70 (m, 1H), 1.40-1.33 (m, 1H), 0.89 (d, J=5.6 Hz, 6H).

GV-P2 ESI 684.2 (M+H)+. 1H NMR (500 MHz, MeOD) δ 7.67 (s, 1H), 7.10 (d, J=6.9 Hz, 1H), 7.02 (d, J=6.1 Hz, 1H), 6.91 (d, J=13.0 Hz, 2H), 5.68 (t, J=8.1 Hz, 1H), 5.55 (t, J=7.0 Hz, 1H), 3.08 (s, 2H), 2.98 (d, J=7.7 Hz, 2H), 2.73 (d, J=9.7 Hz, 8H), 2.30 (s, 3H), 2.04-1.93 (m, 5H), 1.83 (s, 3H), 1.44-1.40 (m, 1H), 0.96-0.92 (m, 6H).

4-155. (3S)-3-(2-(5-(2-(azetidin-1-yl)ethyl)-2-oxo-4-(trifluoromethyl)pyridin-1(2H)-yl)-4-methylpentanamido)-3-(4'-cyano-4-fluoro-2',5,5'-trimethyl-[1,1'-biphenyl]-3-yl)propanoic Acid (Diastereomeric Compounds GW-P1 and GW-P2)

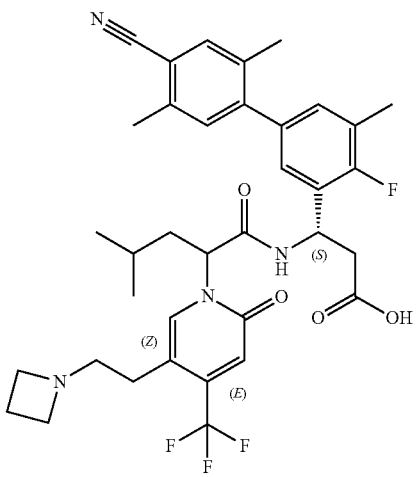

GW-P1 ESI 669.3 (M+H)⁺. ¹H NMR (400 MHz, MeOD) δ 7.72 (s, 1H), 7.45 (s, 1H), 7.10 (s, 1H), 7.06-6.92 (m, 2H), 6.65 (s, 1H), 5.57-5.40 (m, 2H), 3.92 (t, J=8.1 Hz, 4H), 2.73-2.70 (m, 2H), 2.60 (d, J=7.6 Hz, 2H), 2.40 (s, 3H), 23.0-2.33 (m, 2H), 2.36-2.30 (m, 2H), 2.19 (s, 3H), 2.09 (s, 3H), 1.94-1.88 (m, 2H), 1.35-1.21 (m, 1H), 0.86-0.83 (m, 6H).

GW-P2 ESI 669.3 (M+H)⁺. ¹H NMR (400 MHz, MeOD) δ 7.61 (s, 1H), 7.47 (s, 1H), 7.13 (s, 1H), 7.10-6.98 (m, 2H), 6.80 (s, 1H), 5.65-5.62 (m, 1H), 5.52 (t, J=7.7 Hz, 1H), 4.04 (t, J=8.1 Hz, 4H), 3.40-3.25 (m, 2H), 2.86-2.64 (m, 2H), 2.54-2.49 (m, 1H), 2.45-2.30 (m, 6H), 2.23 (d, J=1.5 Hz, 3H), 2.14 (s, 3H), 1.95-1.81 (m, 1H), 1.63-1.52 (m, 1H), 1.31-1.26 (m, 1H), 0.84-0.78 (m, 6H).

4-156. (3S)-3-(4-fluoro-4'-methoxy-2',5,6'-trimethyl-[1,1'-biphenyl]-3-yl)-3-(2-(5-(2-(3-methoxyazetidin-1-yl)ethyl)-2-oxo-4-(trifluoromethyl)pyridin-1(2H)-yl)-4-methylpentanamido)propanoic Acid (Diastereomeric Compounds GX-P1 and GX-P2)

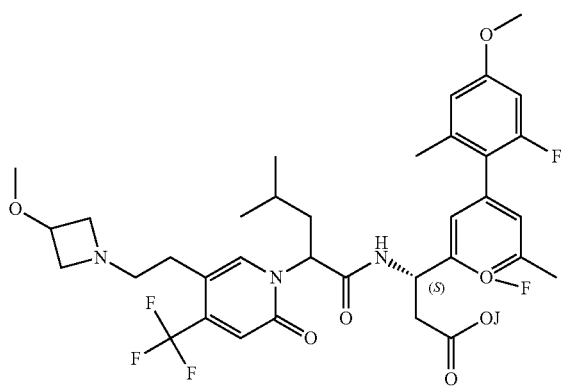

GX-P1 ESI 704.4 (M+H)⁺. ¹H NMR (400 MHz, MeOD) δ 7.85 (s, 1H), 6.86 (t, J=6.2 Hz, 2H), 6.77 (s, 1H), 6.65 (s, 1H), 6.62 (s, 1H), 5.67 (t, J=8.0 Hz, 1H), 5.61-5.56 (m, 1H), 4.25-4.09 (m, 3H), 3.79 (s, 3H), 3.71-3.61 (m, 2H), 3.31 (s, 3H), 3.17 (t, J=6.8 Hz, 2H), 2.81 (t, J=6.9 Hz, 2H), 2.76-2.69 (m, 2H), 2.28 (s, 3H), 2.04-1.97 (m, 5H), 1.82 (s, 3H), 1.48-1.41 (m, 1H), 0.98-0.93 (m, 6H).

GX-P2 ESI 704.4 (M+H)⁺. ¹H NMR (400 MHz, MeOD) δ 7.75 (s, 1H), 6.96-6.90 (m, 3H), 6.67 (s, 2H), 5.76-5.72 (m, 1H), 5.63 (t, J=7.7 Hz, 1H), 4.44-4.26 (m, 3H), 3.98-3.92 (m, 1H), 3.88-3.83 (m, 1H), 3.80 (s, 3H), 3.42-3.35 (m, 5H), 2.97-2.80 (m, 2H), 2.67-2.62 (m, 1H), 2.56-2.50 (m, 1H), 2.33 (d, J=1.6 Hz, 3H), 2.04-1.94 (m, 7H), 1.73-1.64 (m, 1H), 1.47-1.39 (m, 1H), 0.92-0.89 (m, 6H).

4.157. (3S)-3-(4'-cyano-4-fluoro-2',5,6'-trimethyl-[1,1'-biphenyl]-3-yl)-3-(2-(5-(2-(dimethylamino)ethyl)-2-oxo-4-(trifluoromethyl)pyridin-1(2H)-yl)-4-methylpentanamido)propanoic Acid (Diastereomeric Compounds GY-P1 and GY-P2)

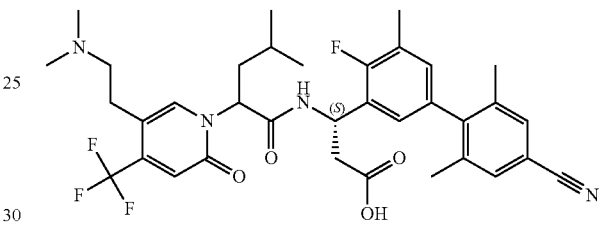

GY-P1 ESI 657.4 (M+H)⁺. ¹H NMR (400 MHz, MeOD) δ 7.88 (s, 1H), 7.45 (d, J=21.6 Hz, 2H), 6.88 (d, J=5.6 Hz, 2H), 6.71 (s, 1H), 5.72-5.47 (m, 2H), 3.08-2.85 (m, 4H), 2.79-2.57 (m, 8H), 2.30 (d, J=1.4 Hz, 3H), 2.11-1.93 (m, 5H), 1.88 (s, 3H), 1.50-1.37 (m, 1H), 1.06-0.86 (m, 6H).

GY-P2 ESI 657.4 (M+H)⁺. ¹H NMR (400 MHz, MeOD) δ 7.84 (s, 1H), 7.49 (s, 2H), 7.02-6.74 (m, 3H), 5.75-5.53 (m, 2H), 3.25-3.06 (m, 2H), 2.98 (t, J=6.9 Hz, 2H), 2.78 (s, 6H), 2.70-2.48 (m, 2H), 2.34 (d, J=1.4 Hz, 3H), 2.14-1.86 (m, 7H), 1.79-1.62 (m, 1H), 1.46-1.31 (m, 1H), 0.95-0.82 (m, 6H).

4-158. (3S)-3-(4'-chloro-4-fluoro-2',5,6'-trimethylbiphenyl-3-yl)-3-(2-(5-(2-(dimethylamino)ethyl)-2-oxo-4-(trifluoromethyl)pyridin-1(2H)-yl)-4-methylpentanamido)propanoic Acid (Diastereomeric Compounds GZ-P1 and GZ-P2)

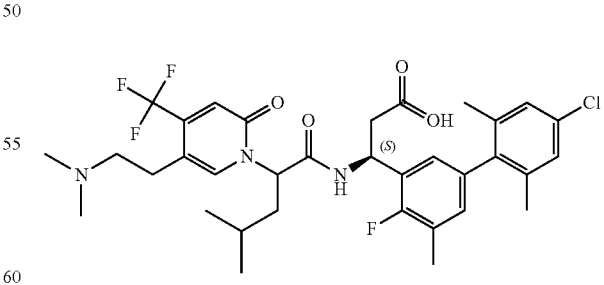

GZ-P1 ESI 666.3 (M+H)⁺. ¹H NMR (400 MHz, MeOD) δ 7.91 (s, 1H), 7.08 (d, J=24.1 Hz, 2H), 6.91-6.80 (m, 2H), 6.72 (s, 1H), 5.68 (t, J=8.0 Hz, 1H), 5.59-5.48 (m, 1H), 3.18-3.02 (m, 2H), 2.95 (t, J=7.0 Hz, 2H), 2.82-2.63 (m, 8H), 2.29 (s, 3H), 2.04-1.91 (m, 5H), 1.79 (s, 3H), 1.58-1.30 (m, 1H), 1.04-0.86 (m, 6H).

GZ-P2 ESI 666.3 (M+H)+. 1H NMR (400 MHz, MeOD) δ 7.88 (s, 1H), 7.13 (s, 2H), 6.94-6.83 (m, 3H), 5.81-5.68 (m, 1H), 5.62 (t, J=7.7 Hz, 1H), 3.30-3.16 (m, 2H), 3.01 (t, J=6.8 Hz, 2H), 2.83 (s, 6H), 2.72-2.45 (m, 2H), 2.33 (d, J=1.1 Hz, 3H), 1.98 (d, 7H), 1.75-1.63 (m, 1H), 1.51-1.33 (m, 1H), 0.87 (d, J=6.6 Hz, 6H).

4-159. ((3S)-3-(4-fluoro-2',5,6'-trimethylbiphenyl-3-yl)-3-(2-(5-(2-((R)-3-fluoropyrrolidin-1-yl)ethyl)-4-methyl-2-oxopyridin-1(2H)-yl)-4-methylpentanamido)propanoic Acid (Diastereomeric Compounds HA-P1 and HA-P2)

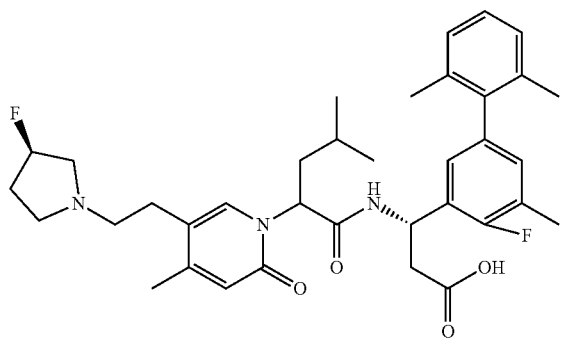 [SMILES: Cc1cc(=O)n(C(CC(C)C)C(=O)N[C@@H](CC(=O)O)c2cc(-c3c(C)cccc3C)cc(C)c2F)cc1CCN1CC[C@@H](F)C1]

HA-P1 ESI 622.2 (M+H)+. 1H NMR (500 MHz, MeOD) δ 7.54 (s, 1H), 7.16-7.02 (m, 3H), 6.87-6.78 (m, 2H), 6.27 (s, 1H), 5.73-5.50 (m, 2H), 5.34-5.15 (m, 1H), 3.31-3.23 (m, 1H), 3.22-3.00 (m, 2H), 2.94-2.80 (m, 3H), 2.78-2.59 (m, 4H), 2.36-2.09 (m, 8H), 2.01-1.91 (m, 5H), 1.83 (s, 3H), 1.50-1.37 (m, 1H), 0.97-0.89 (m, 6H).
HA-P2 ESI 622.2 (M+H)+. 1H NMR (500 MHz, MeOD) δ 7.56 (s, 1H), 7.22-7.02 (m, 3H), 6.91 (d, J=6.8 Hz, 2H), 6.42 (s, 1H), 5.65-5.57 (m, 2H), 5.41-5.24 (m, 1H), 3.62-3.35 (m, 3H), 3.31-3.09 (m, 3H), 2.94-2.74 (m, 2H), 2.68-2.49 (m, 2H), 2.39-2.22 (m, 8H), 2.10-1.89 (m, 7H), 1.82-1.70 (m, 1H), 1.49-1.31 (m, 1H), 0.95-0.85 (m, 6H).

4-160. (3S)-3-(4-fluoro-2',4',5,6'-tetramethyl-[1,1'-biphenyl]-3-yl)-3-(2-(5-(2-(3-fluoroazetidine-1-yl)ethyl)-2-oxopyridin-1(2H)-yl)-4-methylpentanamido)propanoic Acid (Diastereomeric Compounds HB-P1 and HB-P2)

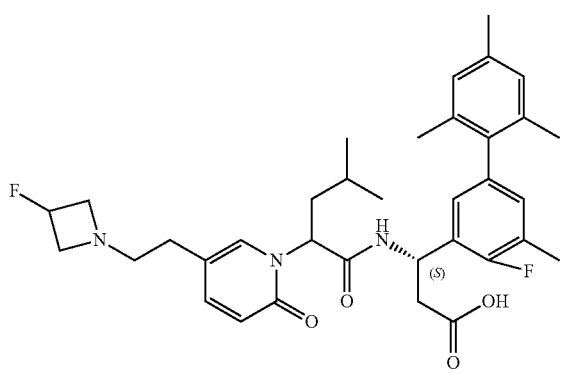

HB-P1 ESI 608.3 (M+H)+. 1H NMR (400 MHz, MeOD) δ 7.52 (s, 1H), 7.39 (d, J=9.0 Hz, 1H), 6.96-6.79 (m, 3H), 6.73 (s, 1H), 6.43 (d, J=9.5 Hz, 1H), 5.74-5.46 (m, 2H), 5.14 (d, J=57.6 Hz, 1H), 3.77 (s, 2H), 3.50 (s, 2H), 2.88 (s, 2H), 2.79-2.60 (m, 2H), 2.51 (s, 2H), 2.29 (d, J=14.1 Hz, 6H), 1.96 (d, J=12.7 Hz, 5H), 1.80 (s, 3H), 1.42 (s, 1H), 1.03-0.79 (m, 6H).
HB-P2 ESI 608.3 (M+H)+. 1H NMR (400 MHz, MeOD) δ 7.60-7.40 (m, 2H), 6.90 (d, J=7.8 Hz, 4H), 6.57 (d, J=9.2 Hz, 1H), 5.70-5.57 (m, 2H), 5.32 (d, J=57.4 Hz, 1H), 4.51-4.26 (m, 2H), 4.14-3.87 (m, 2H), 3.39 (d, J=5.3 Hz, 2H), 2.85-2.44 (m, 4H), 2.35-2.17 (m, 6H), 2.04-1.86 (m, 7H), 1.86-1.73 (m, 1H), 1.48-1.33 (m, 1H), 0.90 (t, J=6.3 Hz, 6H).

4-161. (3S)-3-(4,4'-difluoro-2',5,6'-trimethyl-[1,1'-biphenyl]-3-yl)-3-(2-(5-(2-(3-fluoroazetidine-1-yl)ethyl)-2-oxopyridin-1(2H)-yl)-4-methylpentanamido)propanoic Acid (Diastereomeric Compounds HC-P1 and HC-P2)

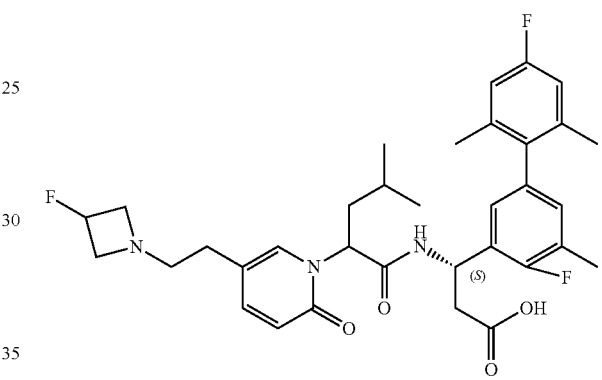

HC-P1 ESI 612.2 (M+H)+. 1H NMR (400 MHz, MeOD) δ 7.54 (s, 1H), 7.43 (dd, J=9.2, 2.3 Hz, 1H), 6.87-6.82 (m, 3H), 6.76 (d, J=6.7 Hz, 1H), 6.46 (d, J=9.3 Hz, 1H), 5.63 (d, J=7.9 Hz, 1H), 5.54-5.43 (m, 1H), 5.20 (d, J=57.2 Hz, 1H), 4.09-3.88 (m, 2H), 3.71-3.55 (m, 2H), 3.10-3.02 (m, 2H), 2.80-2.53 (m, 4H), 2.29 (s, 3H), 2.03-1.92 (m, 5H), 1.87 (s, 3H), 1.50-1.36 (m, 1H), 0.97-0.92 (m, 6H).
HC-P2 ESI 612.2 (M+H)+. 1H NMR (400 MHz, MeOD) δ 7.41 (s, 1H), 7.38-7.35 (m, 1H), 6.79 (t, J=6.1 Hz, 2H), 6.73 (d, J=9.7 Hz, 2H), 6.45 (d, J=9.3 Hz, 1H), 5.53-5.48 (m, 2H), 5.20 (d, J=57.2 Hz, 1H), 4.39-4.14 (m, 2H), 3.99-3.87 (m, 2H), 3.32-3.25 (m, 2H), 2.67-2.48 (m, 3H), 2.40-2.34 (m, 1H), 2.21 (d, J=1.7 Hz, 3H), 1.90-1.81 (m, 7H), 1.72-1.64 (m, 1H), 1.33-1.22 (m, 1H), 0.79 (t, J=6.6 Hz, 6H).

Introduction to the In Vitro Assays Described in Examples 5-7

Three in vitro assays were used to examine the $\alpha_4\beta_7$ mechanistic process used by cells: 1) ligand:receptor affinity, 2) the avidity of those interactions on a cell's surface, and 3) how those interactions fare under an imposing force. In Example 5, a Fluorescence Polarization (FP) assay is used to measure compound activity through binding competition with the fluorescein-labeled peptide. In Example 6, the potency of compounds against $\alpha_4\beta_7$ is measured in the cell-based ligand binding assay (LBA), using RPMI 8866 cells incubated with the compound samples in competition with soluble MAdCAM-1 ligand. In Example 7, activity of compounds is evaluated in a cell adhesion assay that mechanistically tests what occurs in vivo when trafficking cells utilize $\alpha_4\beta_7$ to adhere to MAdCAM-1 expressing HEVs of the gut during the extravasation process. In the cell adhesion assay of Example 7, a MAdCAM1-(Fc) is coated on plastic, and $\alpha_4\beta_7$ expressing cells (RPMI-8866) are allowed to adhere to the coated surface in the presence of the test compounds. Next, the force of washing with buffer is applied to cells thereby testing the strength of that adhesion. Unattached cells are removed and the remaining adherent cells are quantified.

Example 5: Fluorescence Polarization Assays of Compounds for $\alpha_4\beta_7$ Binding Fluorescence Polarization (FP) assays were used to measure compound activity through binding competition with the fluorescein-labeled peptide CRSDTLCGE{Lys(FITC)}. In the assay, 6.5 nM of integrin $\alpha_4\beta_7$ was incubated with the test compound in 2 mM manganese chloride, 0.1 mM calcium chloride, 20 mM HEPES buffer at pH 7.3, 150 mM sodium chloride, 0.01% Triton X-100, 2% DMSO, and 3 nM of the fluorescein-labeled peptide. Running the assays in 384-well plates, the integrin protein was pre-incubated with the test compounds for 15 minutes at 22° C. before the fluorescein-labeled peptide was added. After the fluorescein-labeled peptide was added, the assay was incubated at 22° C. for 1 hour and fluorescence polarization was measured. $IC_{50}$ values were determined by non-linear regression, four-parameter curve fitting.

Figure 3:
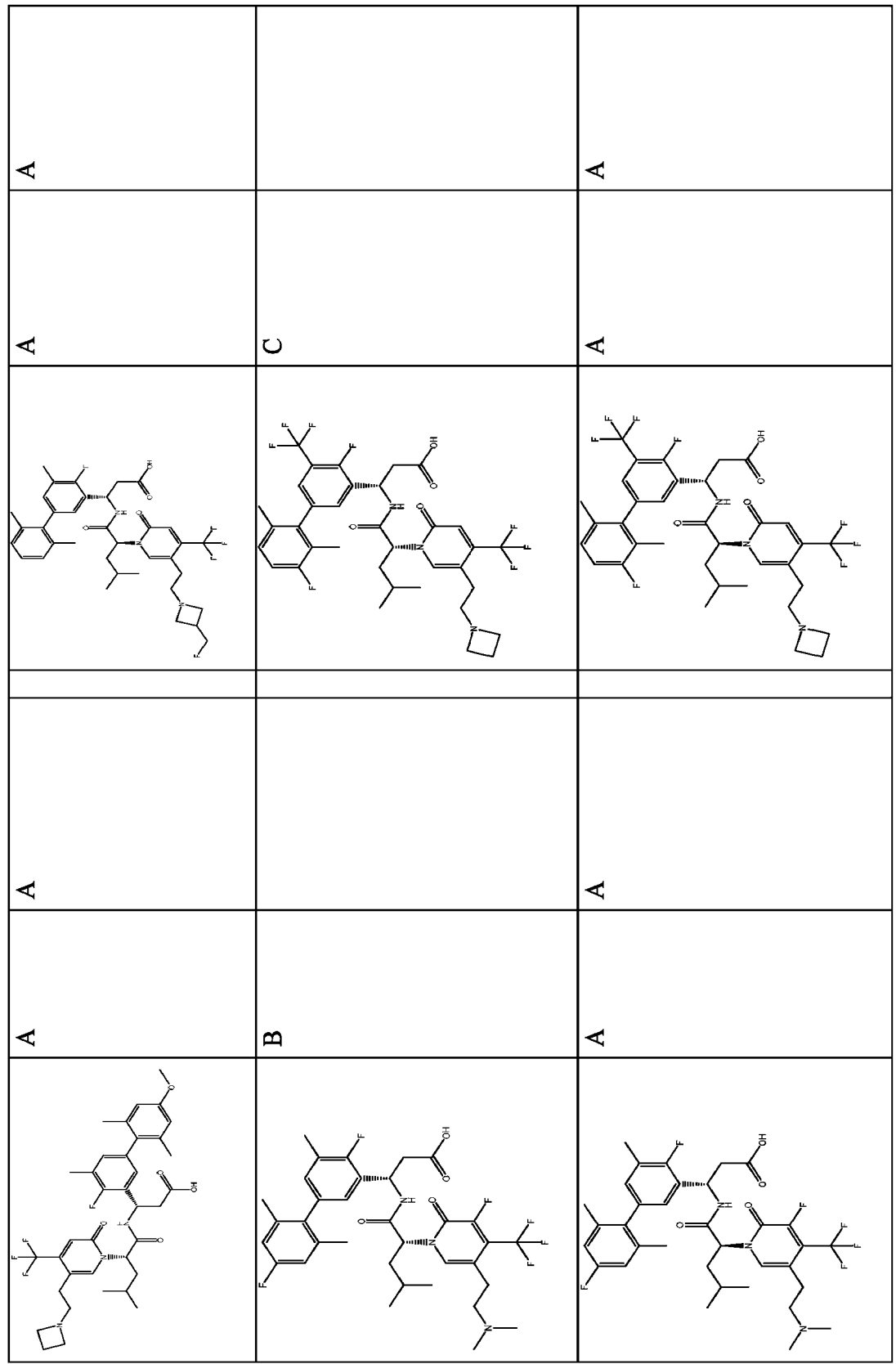
FIG. 3 is a table (Table 5) summarizing in vitro inhibition of $\alpha_4\beta_7$ integrin by exemplary compounds (i.e., data obtained from the fluorescence polarization assay of Example 5, and the ligand binding assay of Example 6).
Figure 3:
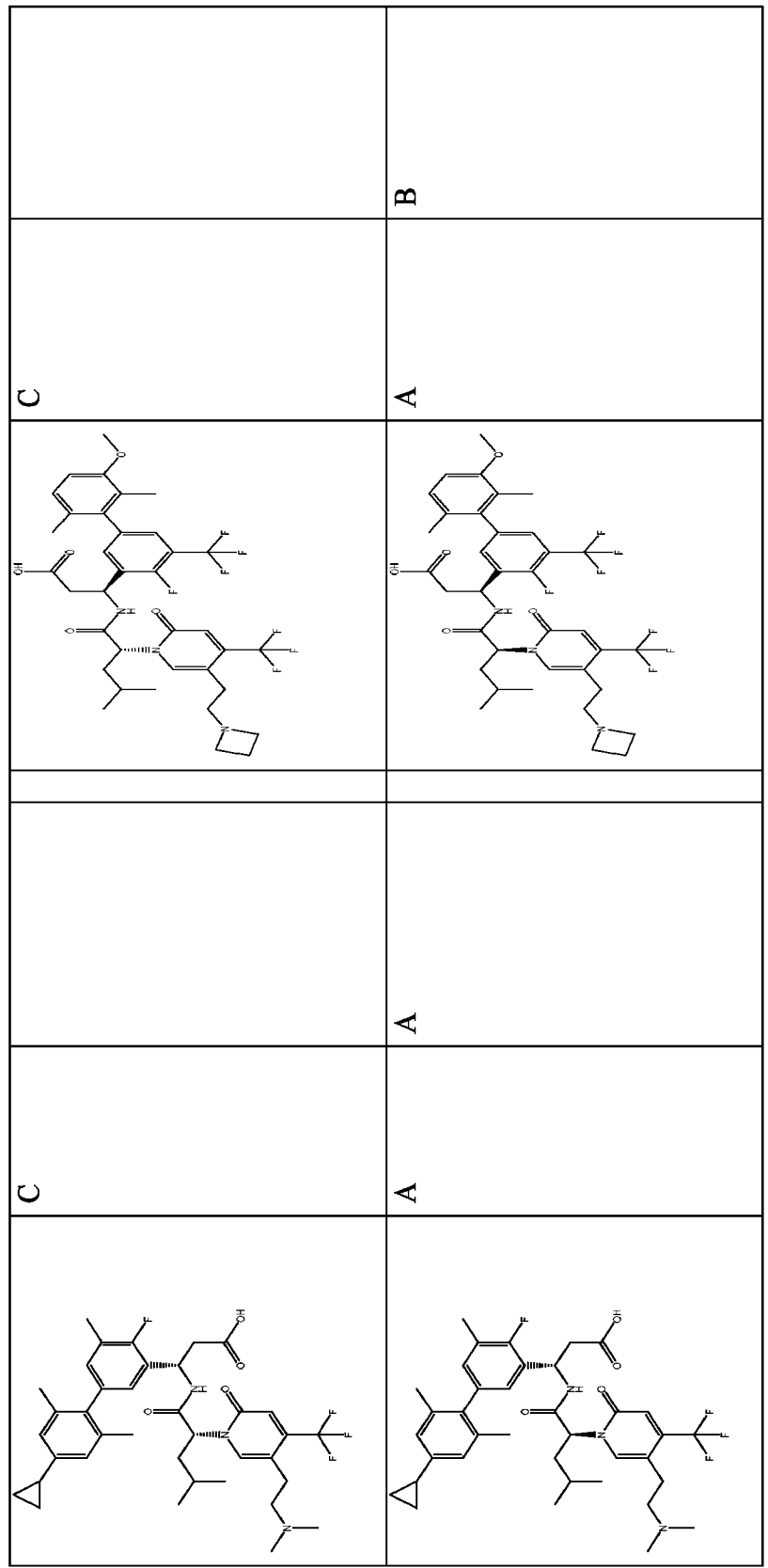
Figure 3:
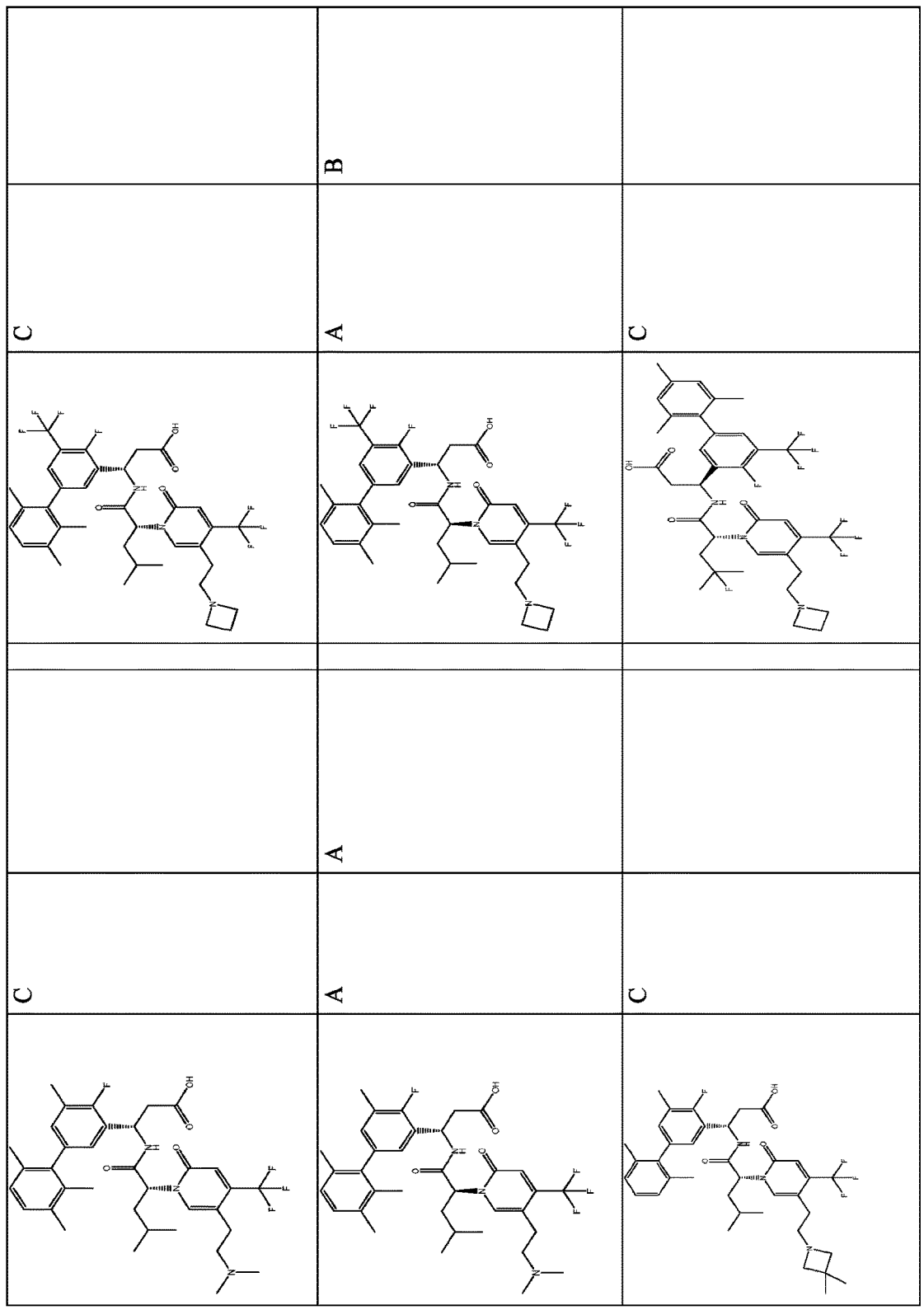
Figure 3:
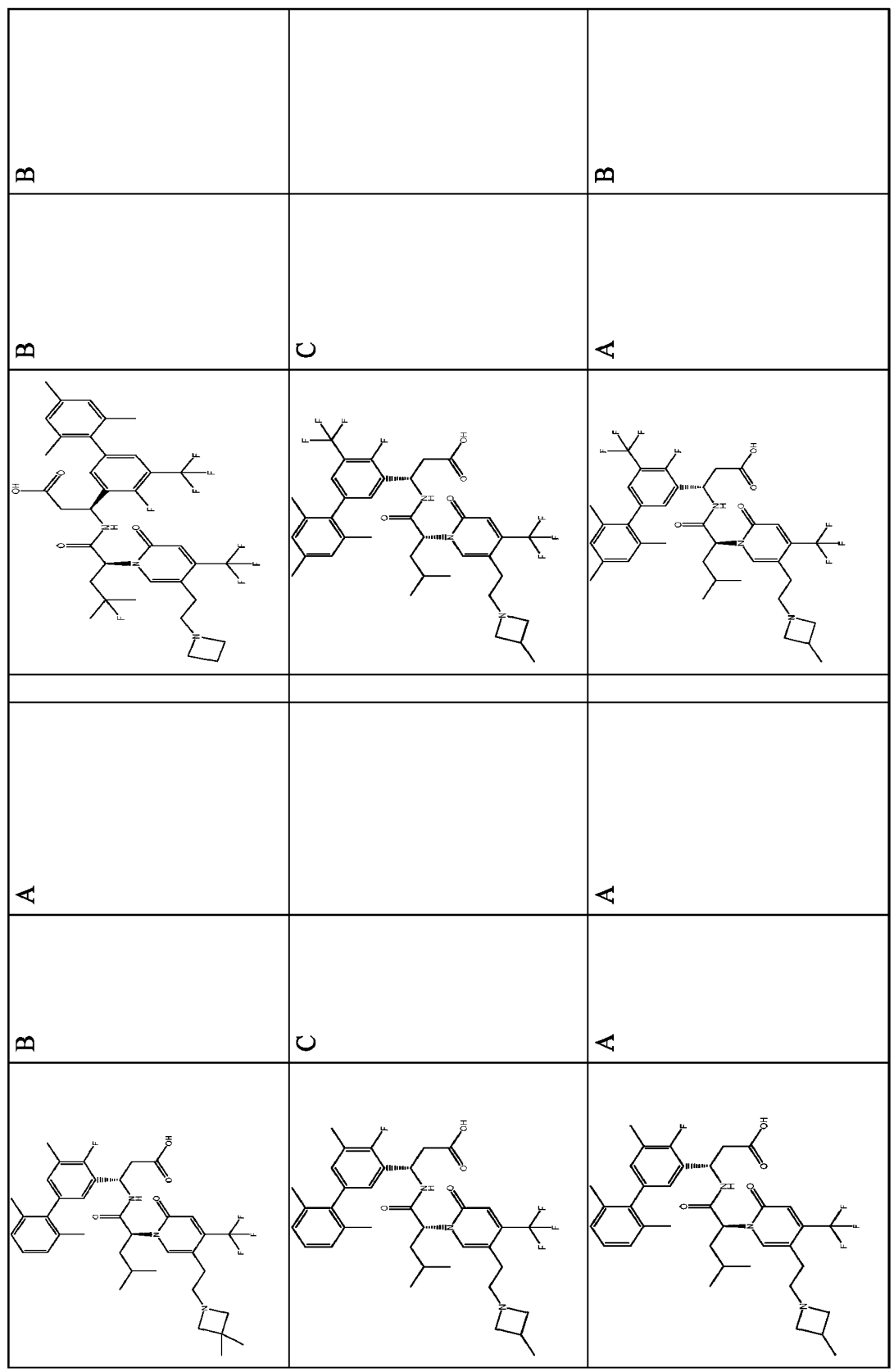
Figure 3:
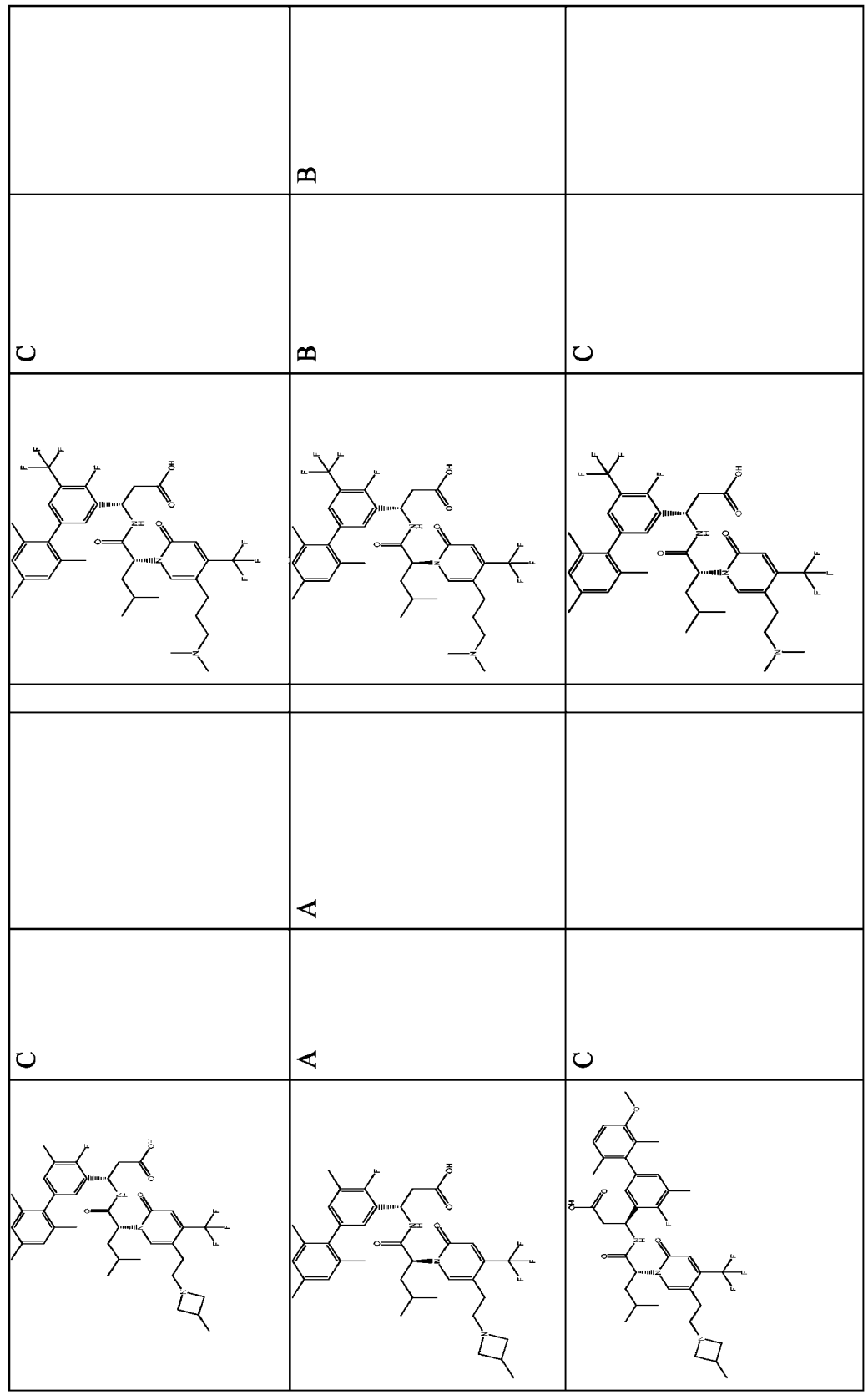
Figure 3:
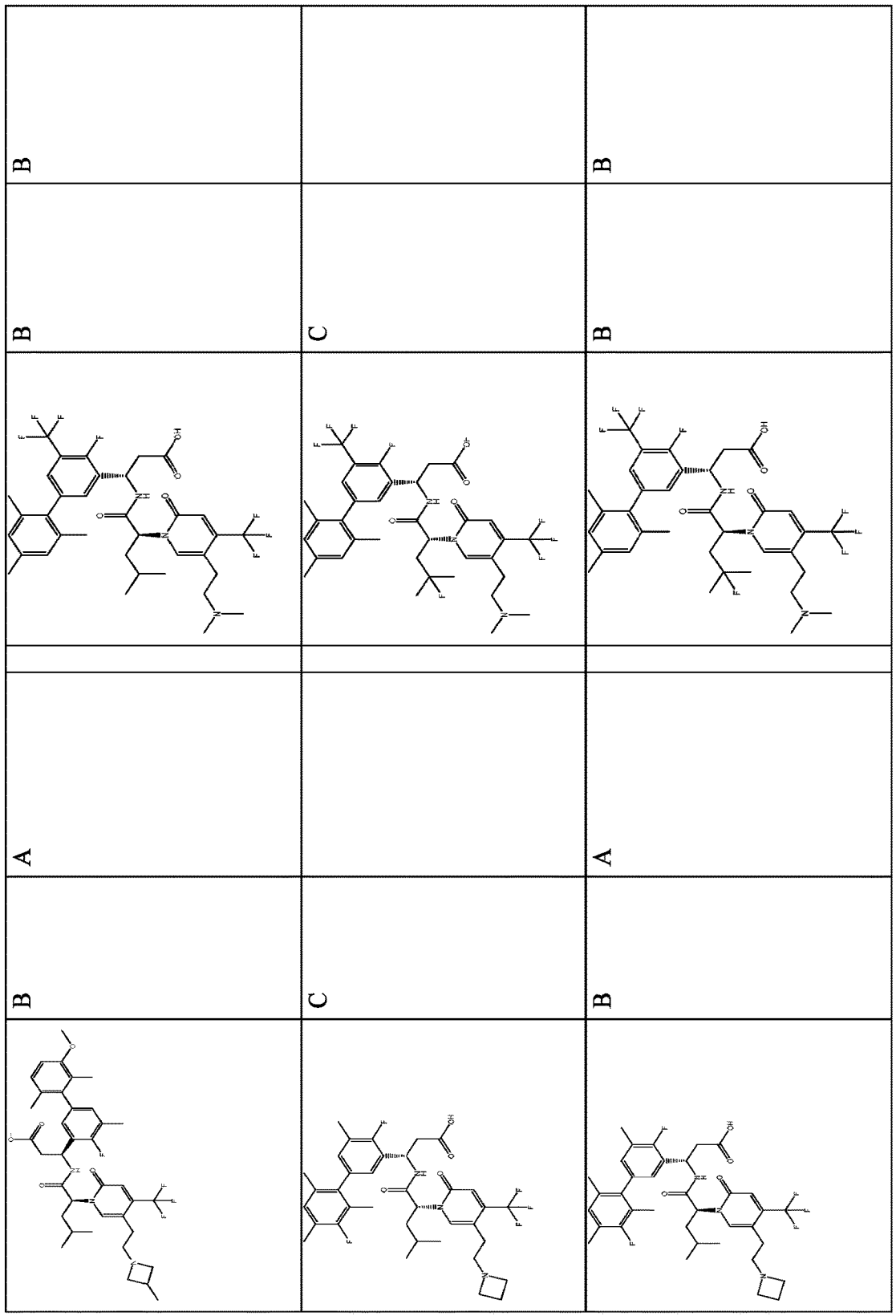
Figure 3:
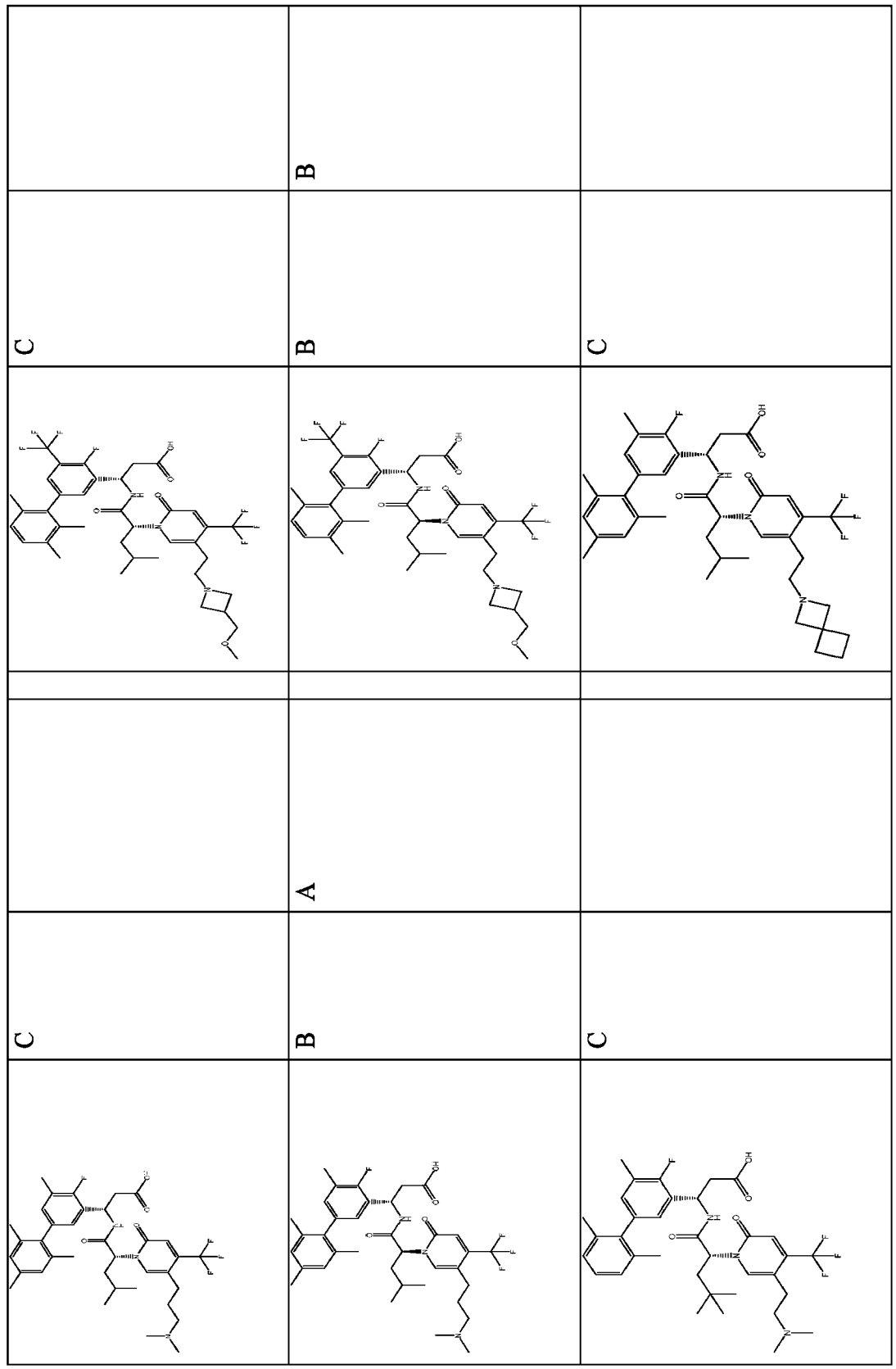
Figure 3:
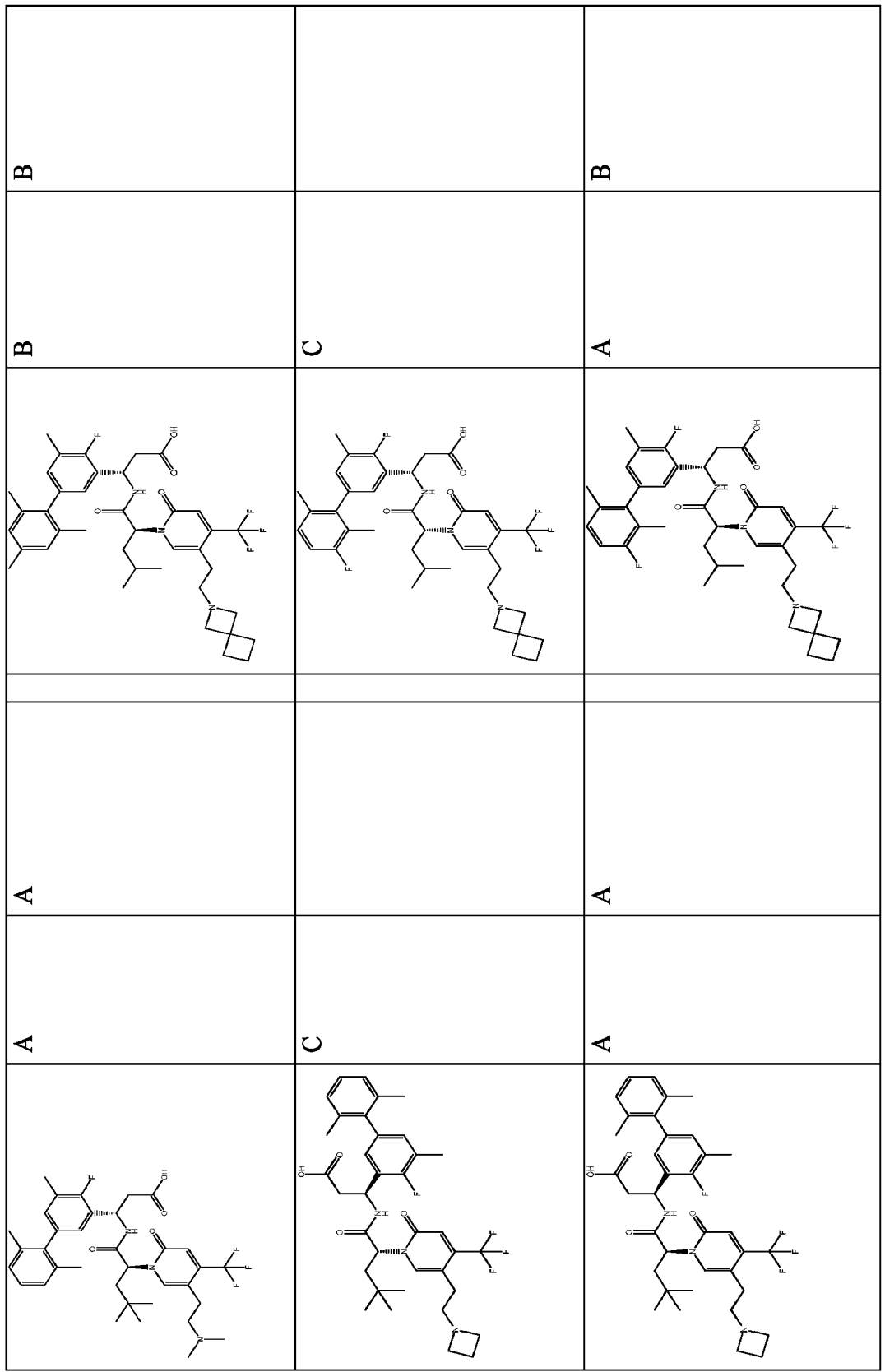
Figure 3:
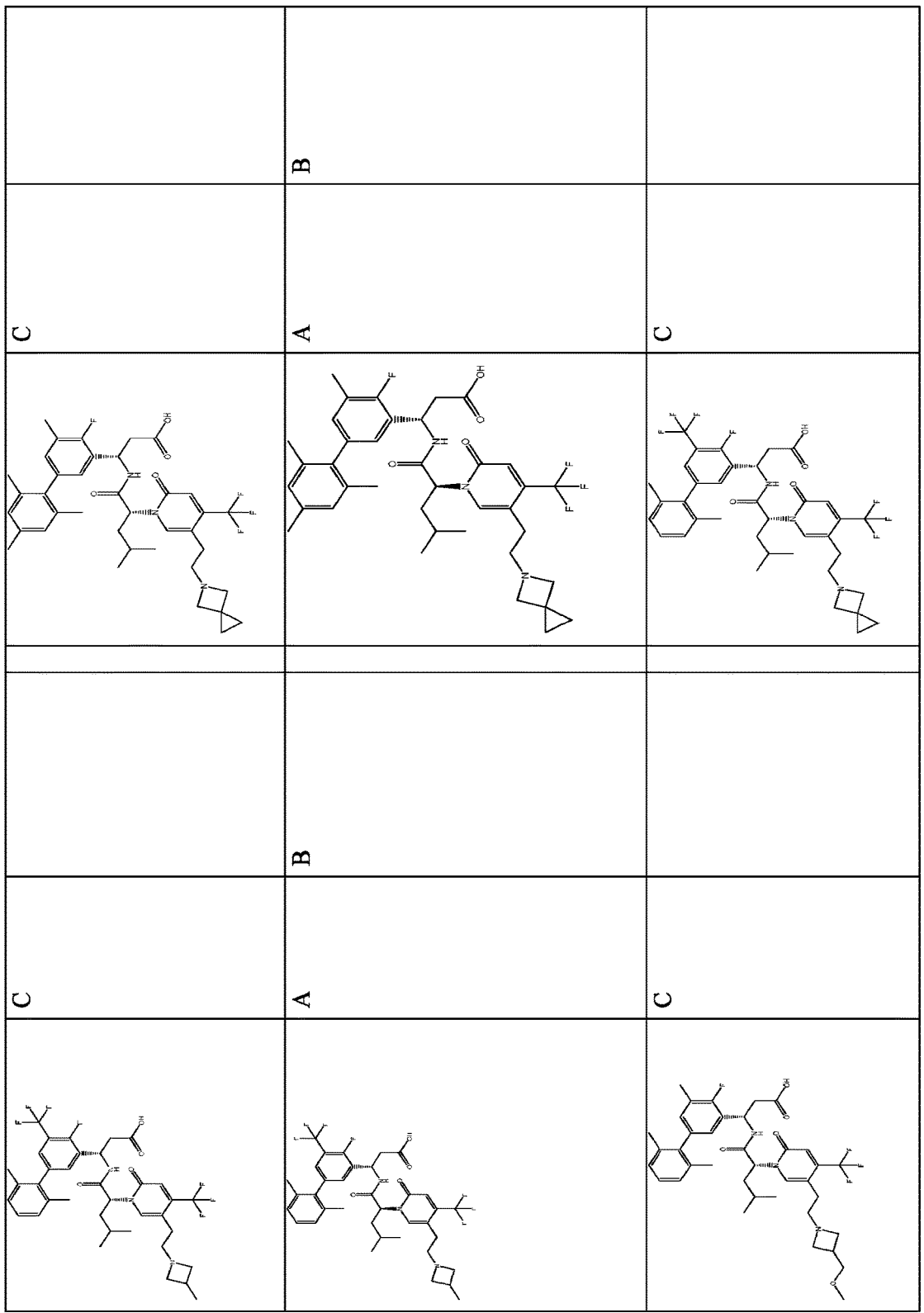
Figure 3:
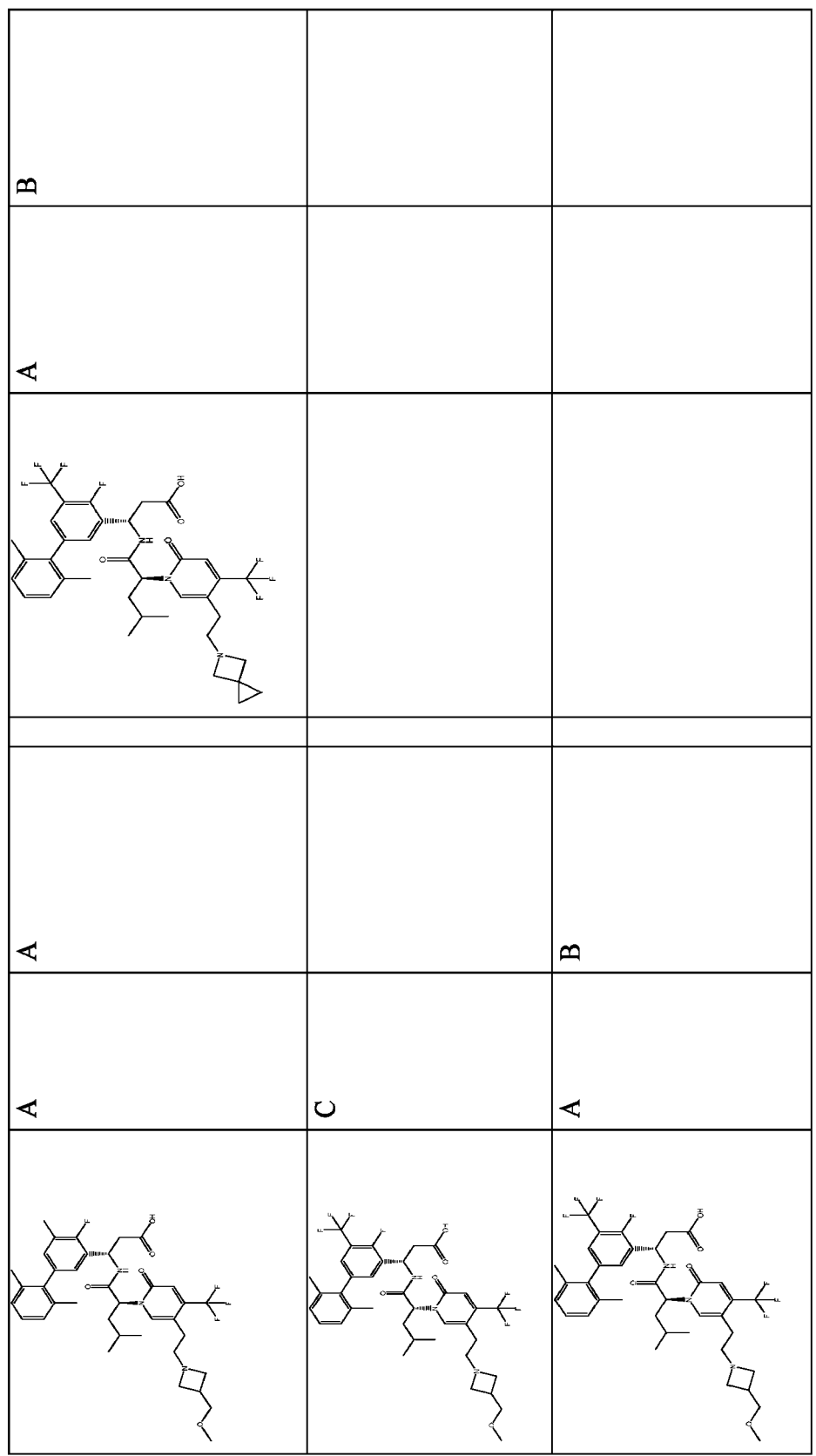
Figure 4:
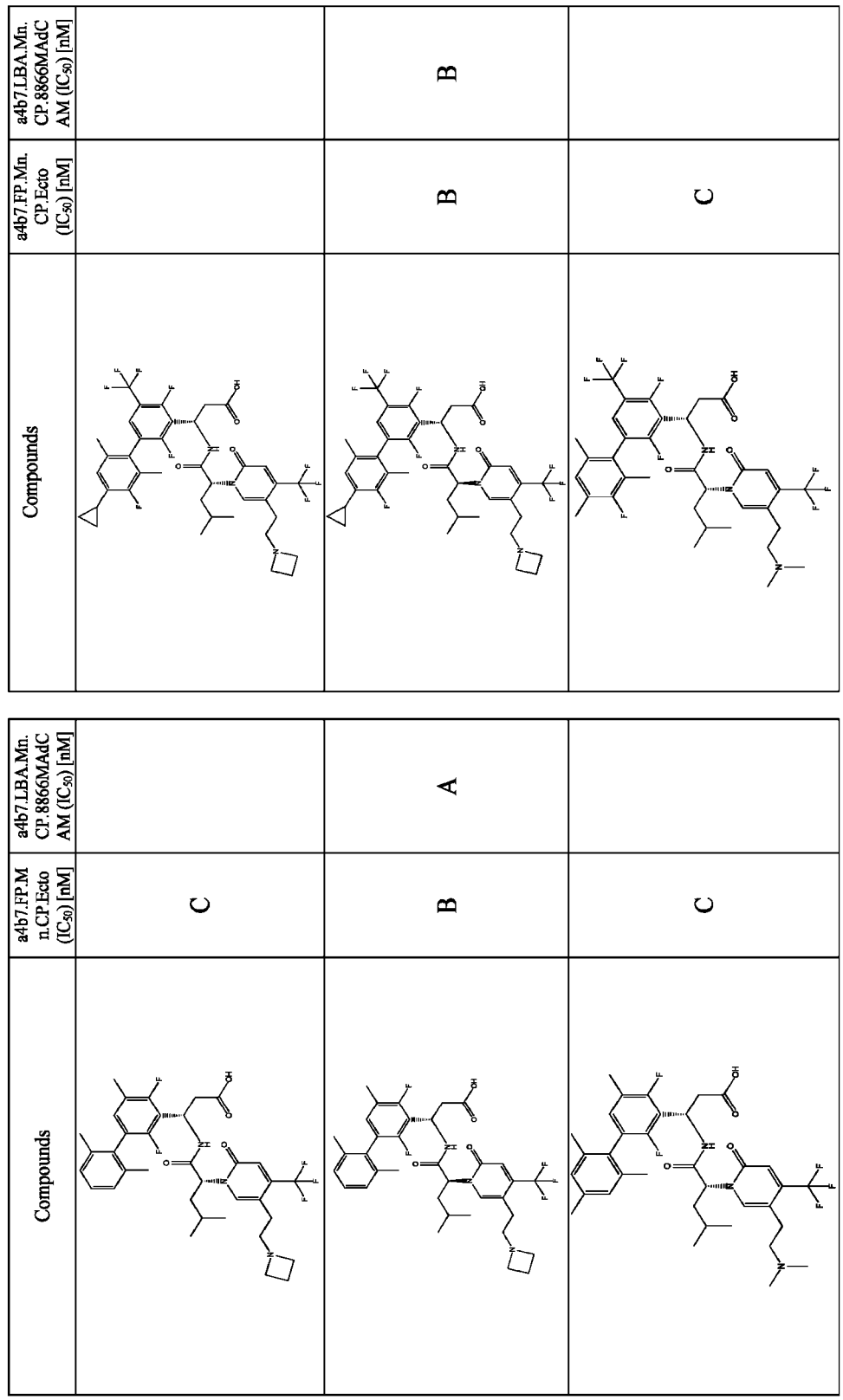
FIG. 4 is a table (Table 6) summarizing in vitro inhibition of $\alpha_4\beta_7$ integrin by exemplary compounds (i.e., data obtained from the fluorescence polarization assay of Example 5, and the ligand binding assay of Example 6).
Figure 4:
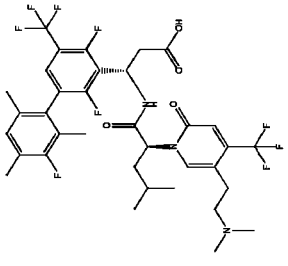
Figure 4:
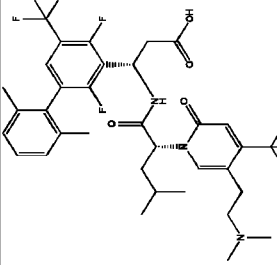
Figure 4:
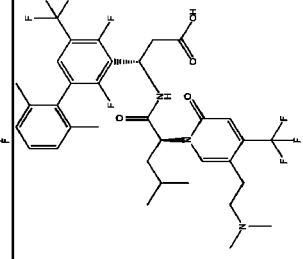
Figure 4:
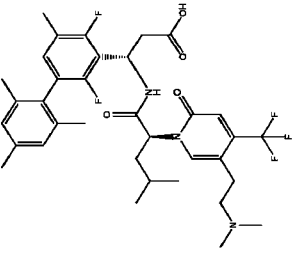
Figure 4:
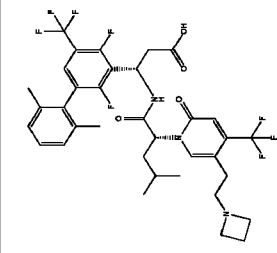
Figure 4:
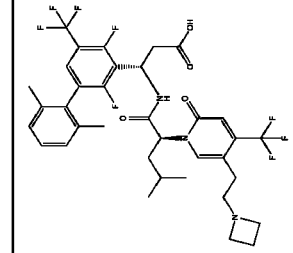
Figure 4:
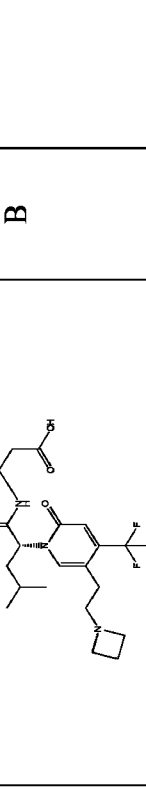
Figure 4:
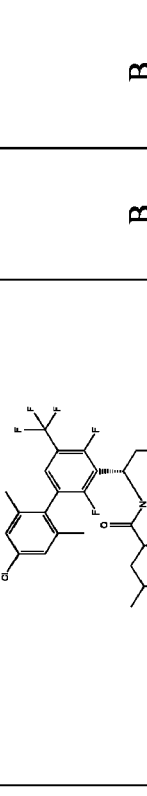
Figure 4:
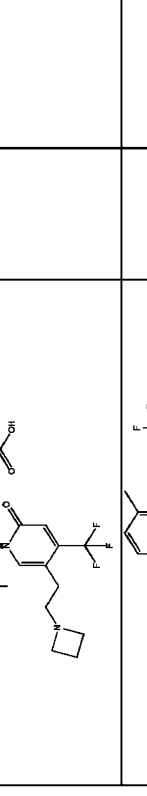
Figure 4:
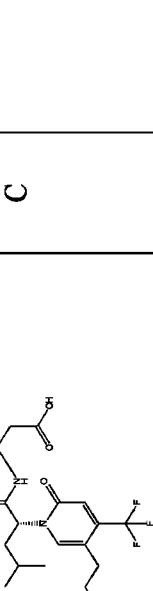
Figure 4:
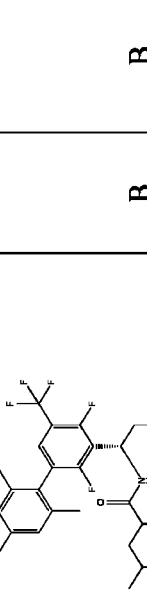
Figure 4:
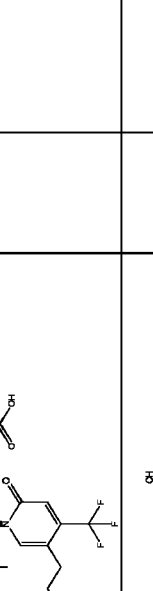
Figure 4:
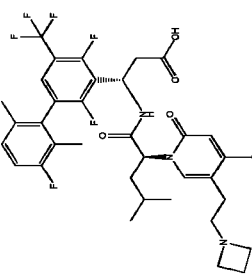
Figure 4:
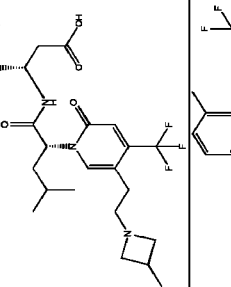
Figure 4:
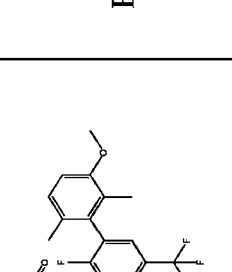
Figure 4:
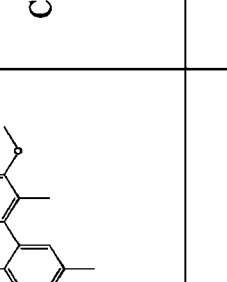
Figure 4:
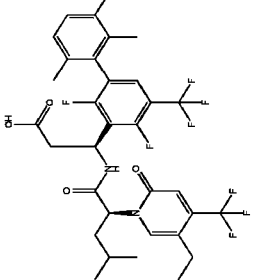
Figure 4:
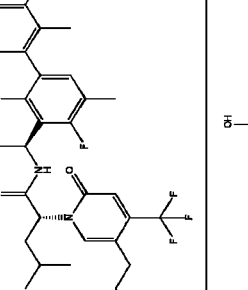
Figure 4:
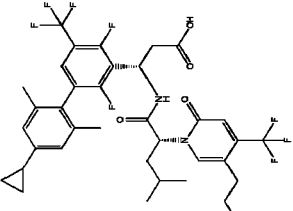
Figure 4:
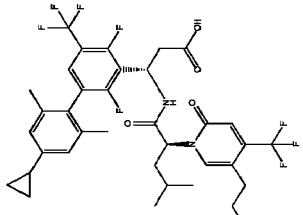
Figure 4:
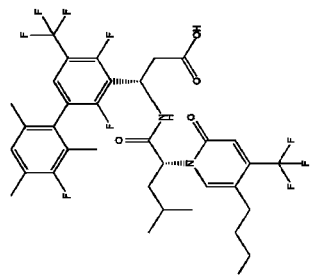
Figure 4:
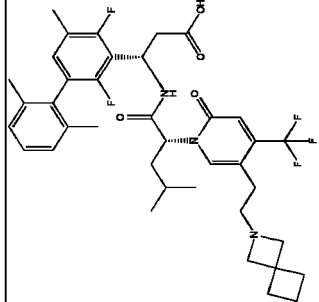
Figure 4:
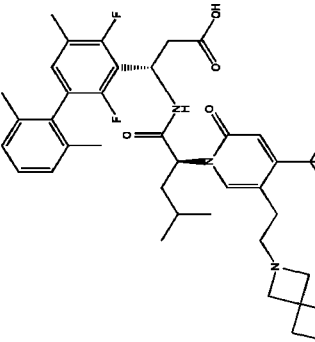
Figure 4:
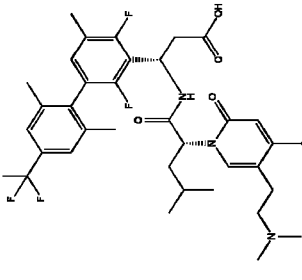
Figure 4:
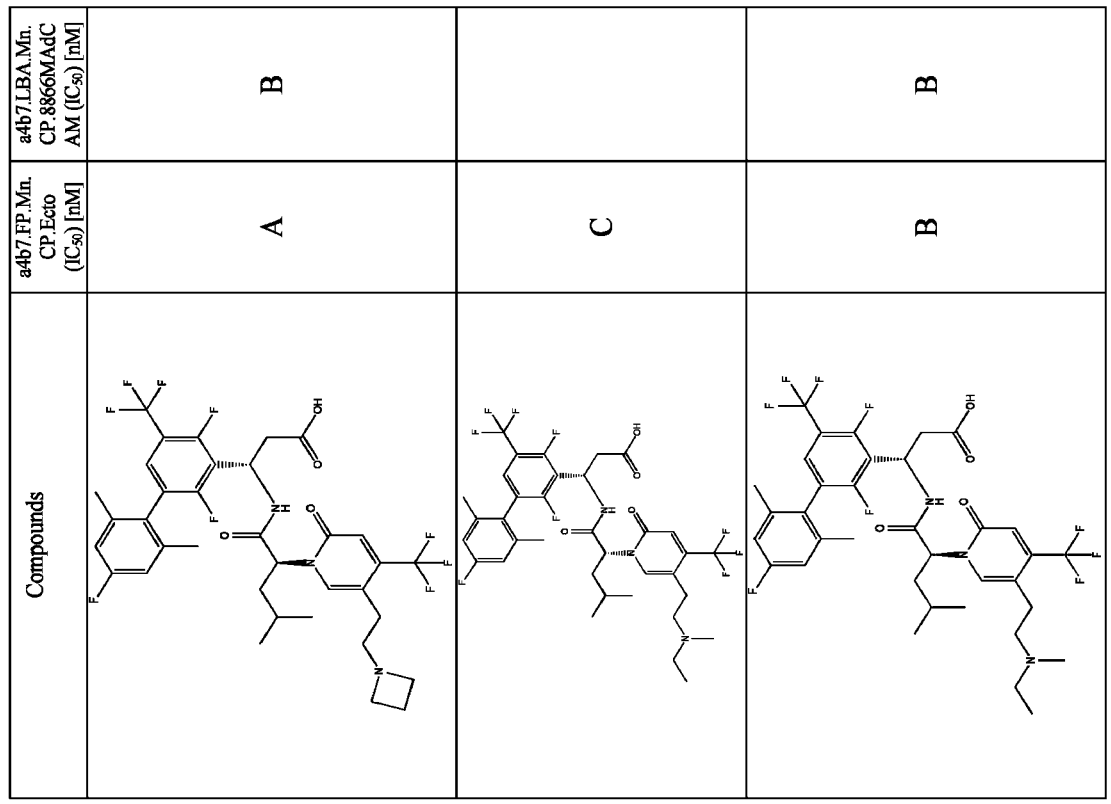
Figure 4:
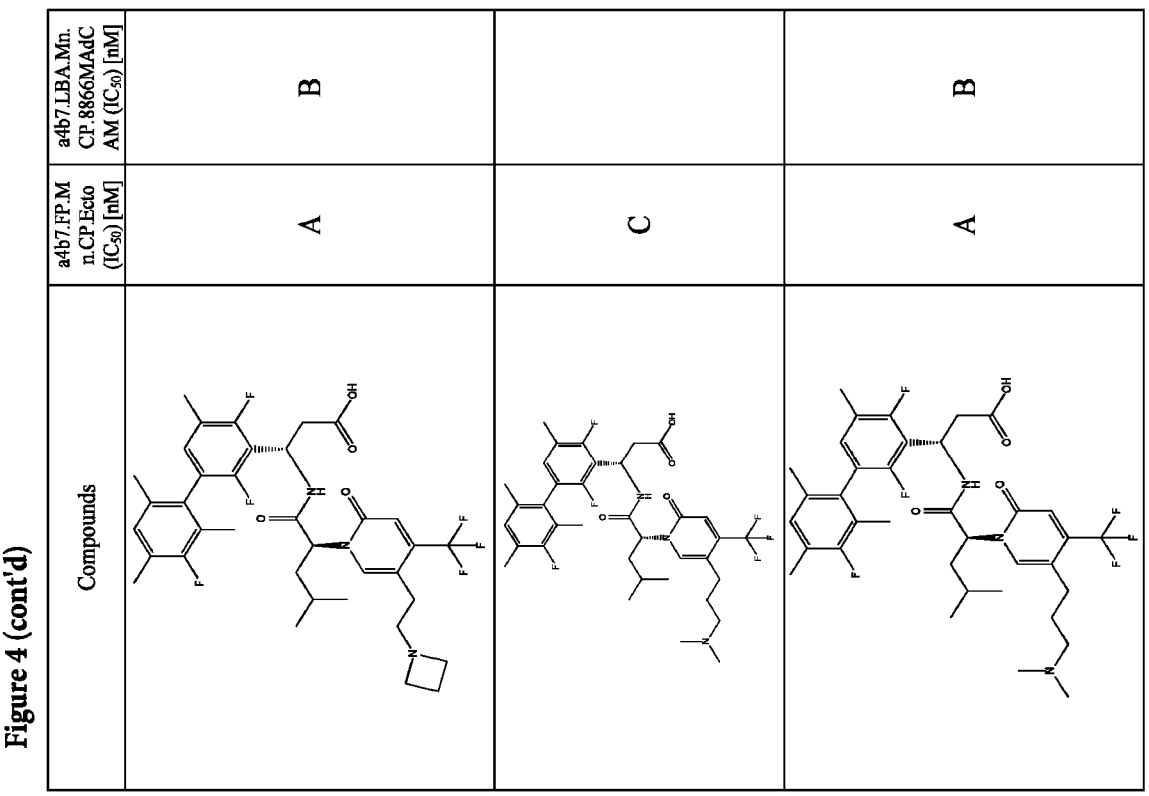
Figure 4:
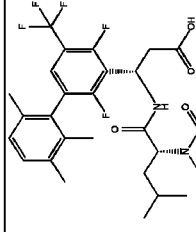
Figure 4:
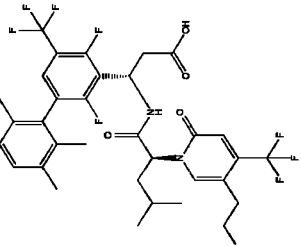
Figure 4:
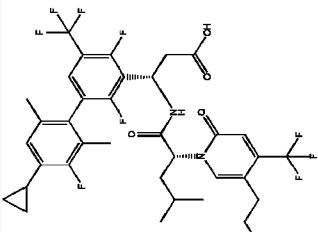
Figure 4:
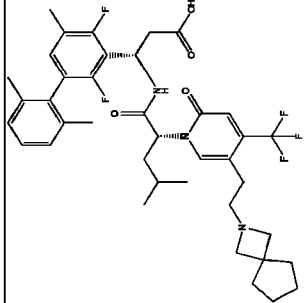
Figure 4:
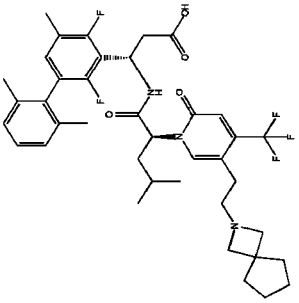
Figure 4:
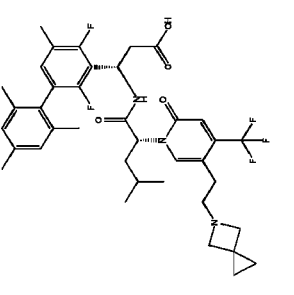
Figure 4:

Figure 4:

Figure 4:
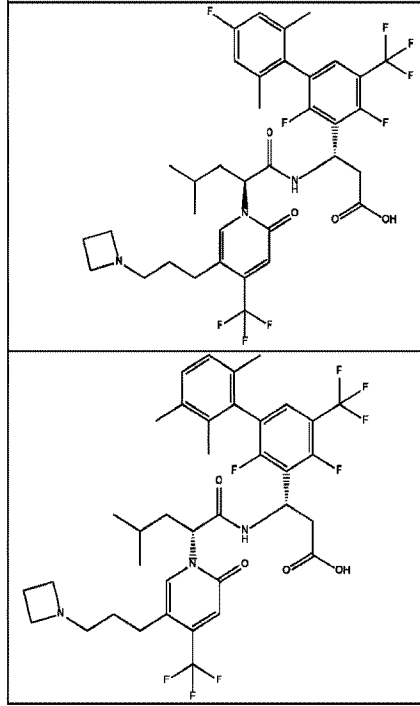
Figure 4:

Figure 4:
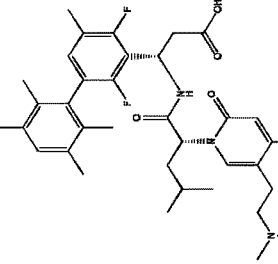
Figure 4:
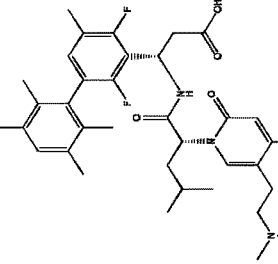
Figure 4:
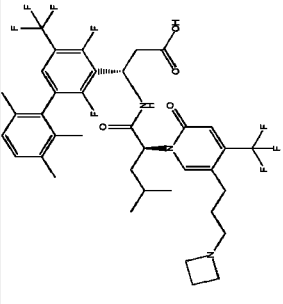
Figure 4:
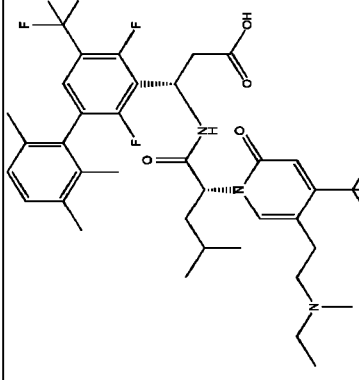
Figure 4:
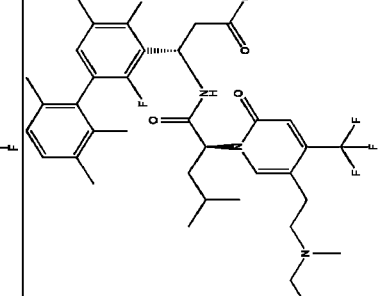
Figure 4:
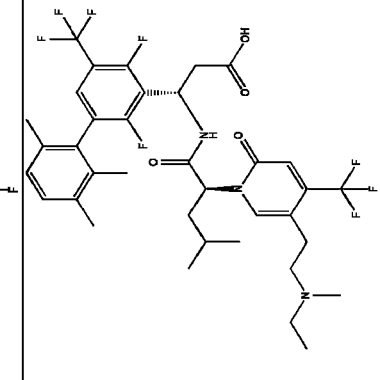
Figure 4:
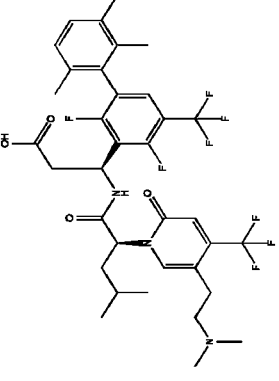
Figure 4:
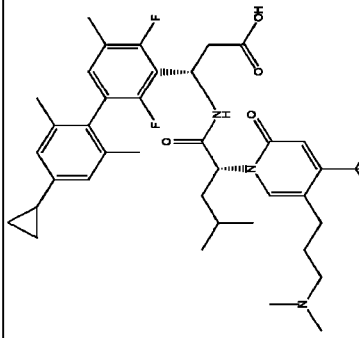
Figure 4:
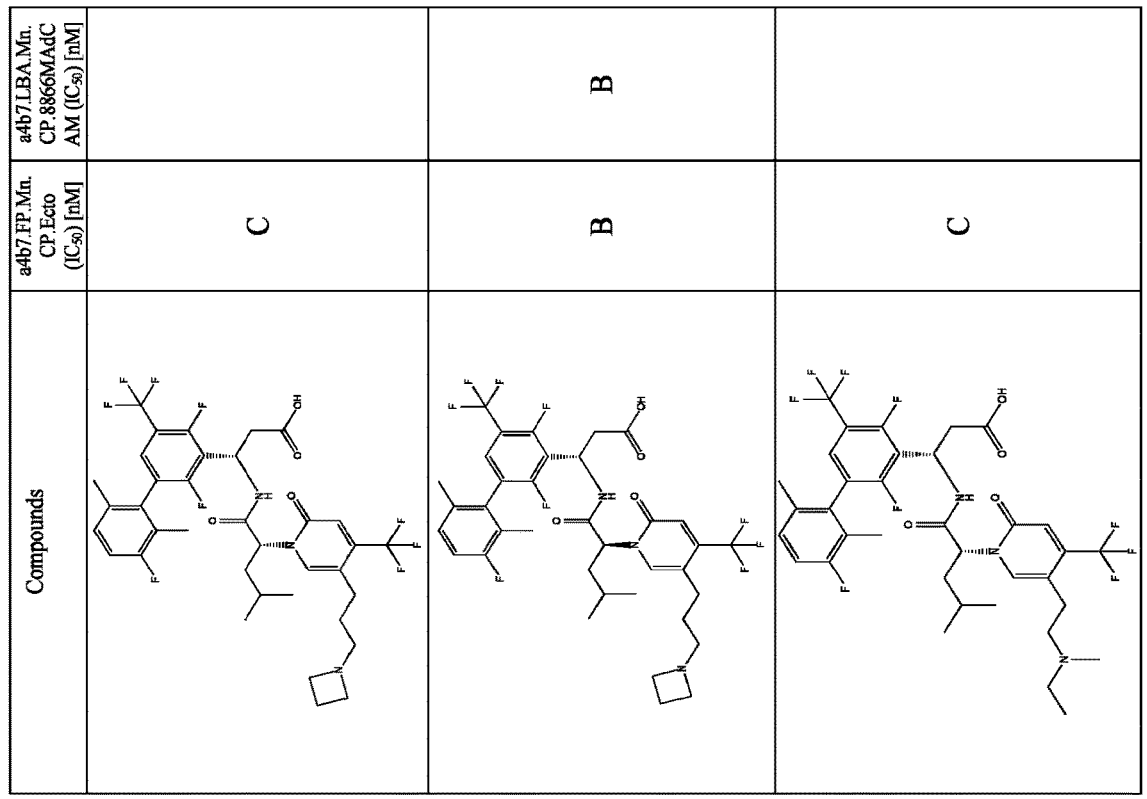
Figure 4:
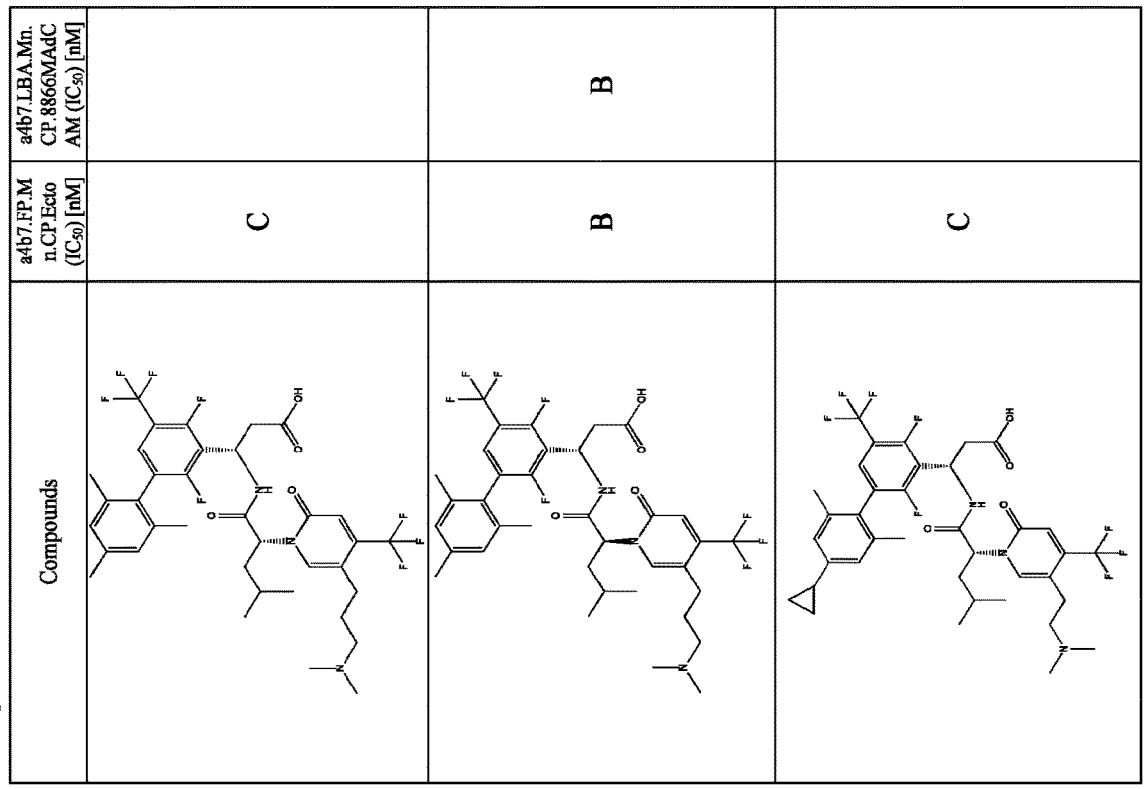
Figure 4:
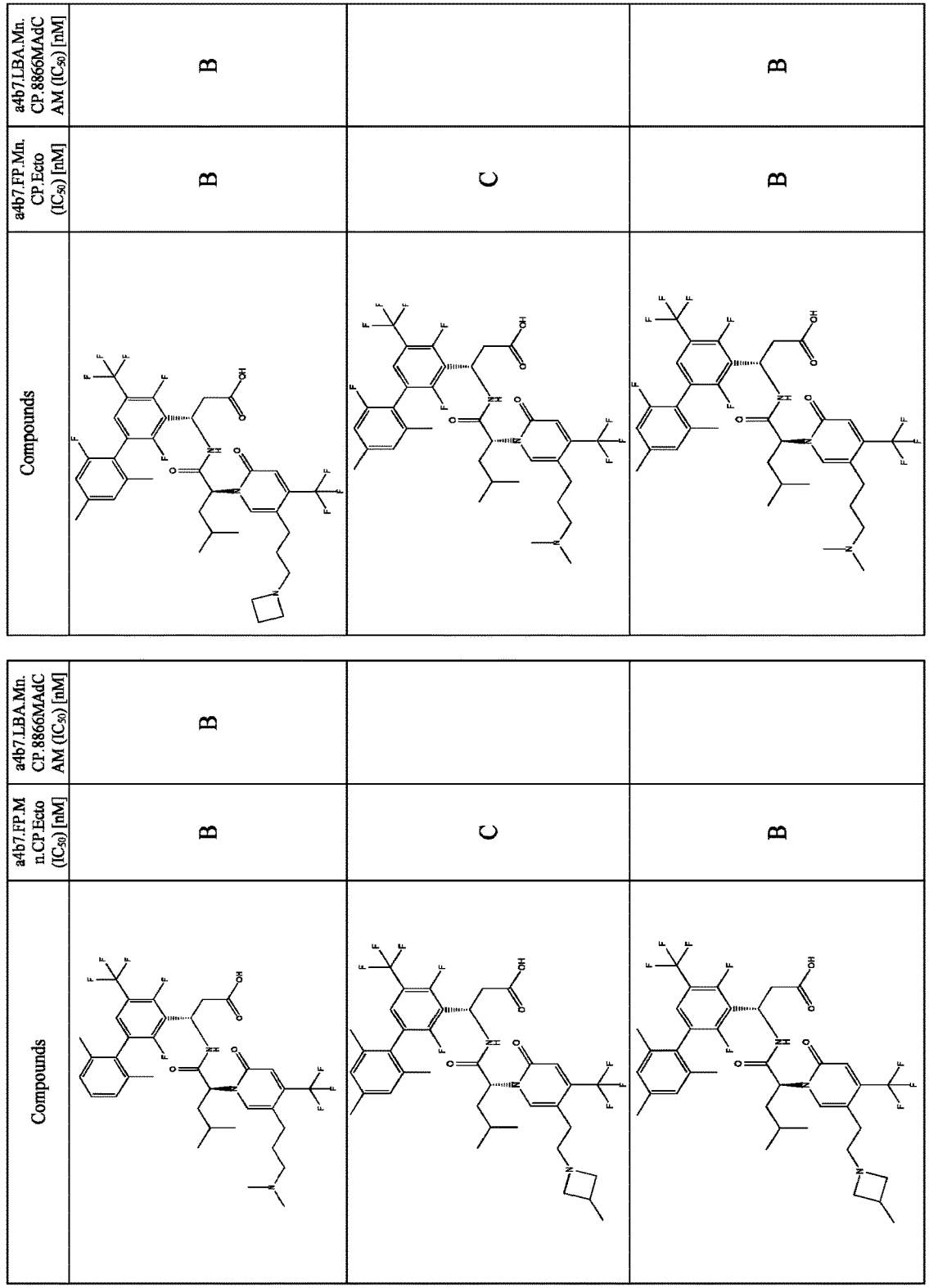
Figure 4:
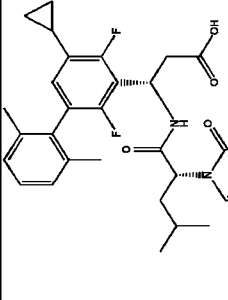
Figure 4:
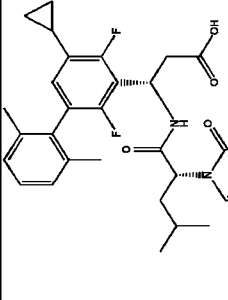
Figure 4:
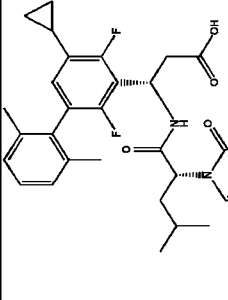
Figure 4:
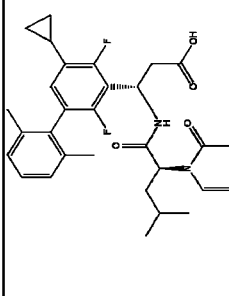
Figure 4:
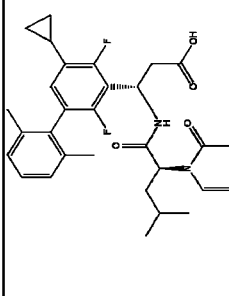
Figure 4:
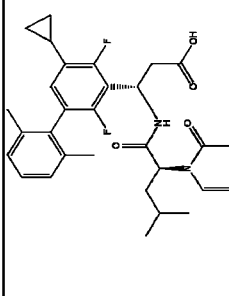
Figure 4:
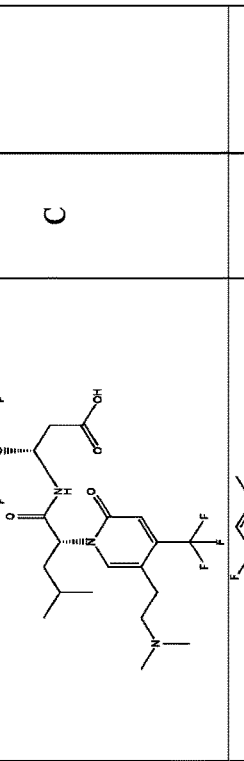
Figure 4:
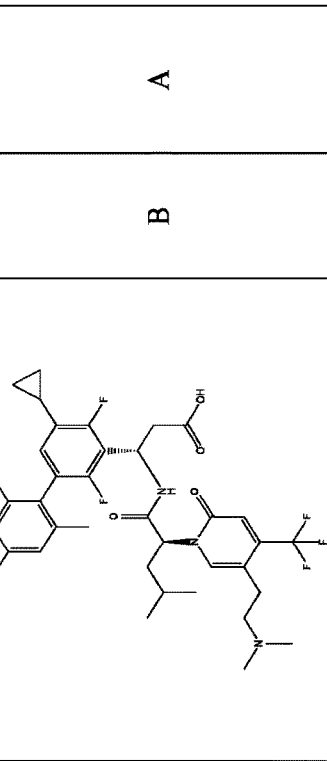
Figure 4:
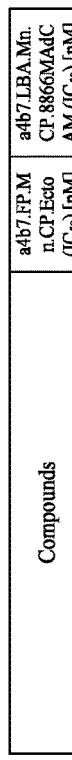
Figure 4:
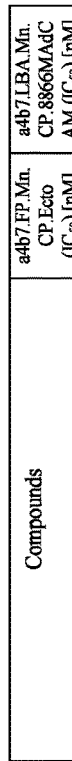
Figure 4:
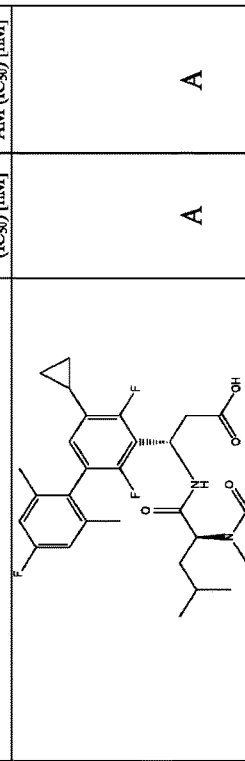
Figure 4:
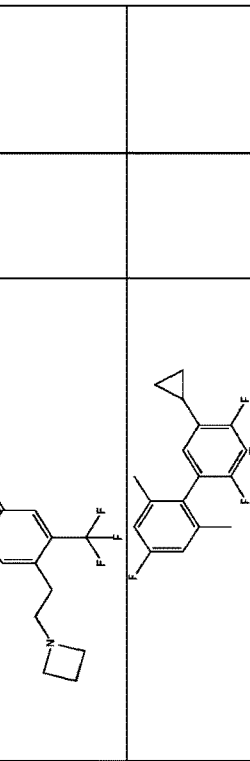
Figure 4:
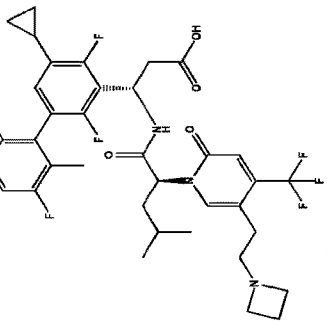
Figure 4:
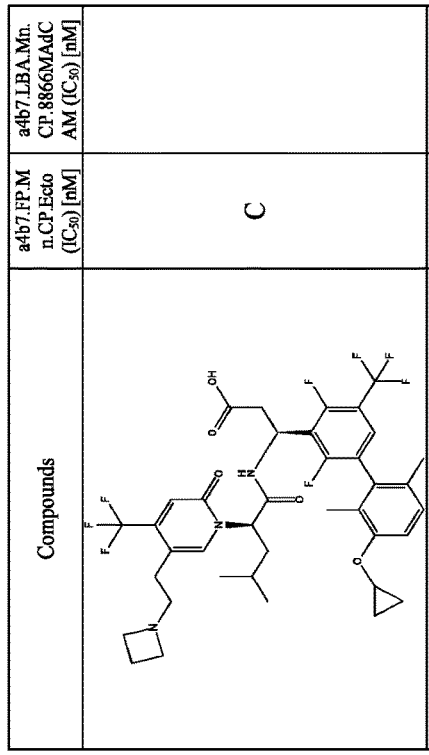
Figure 4:
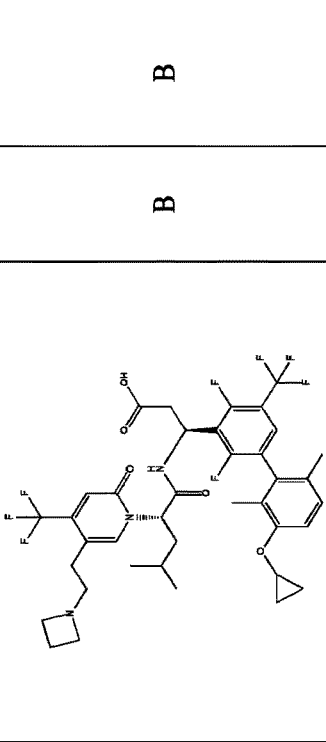
Figure 4:
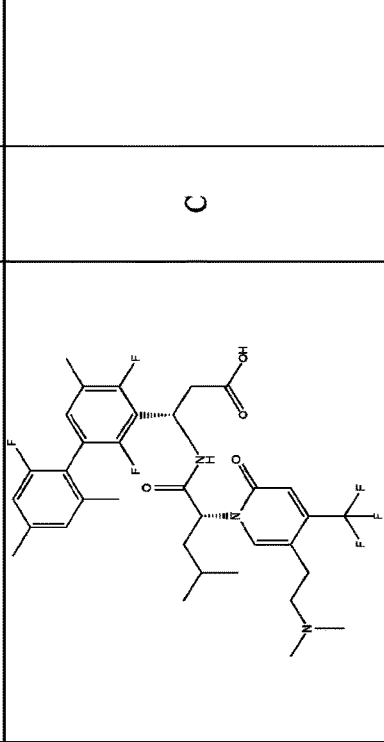
Figure 4:
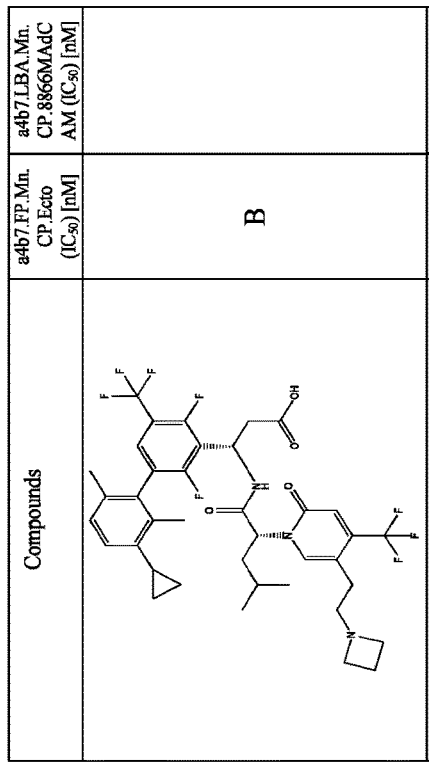
Figure 4:
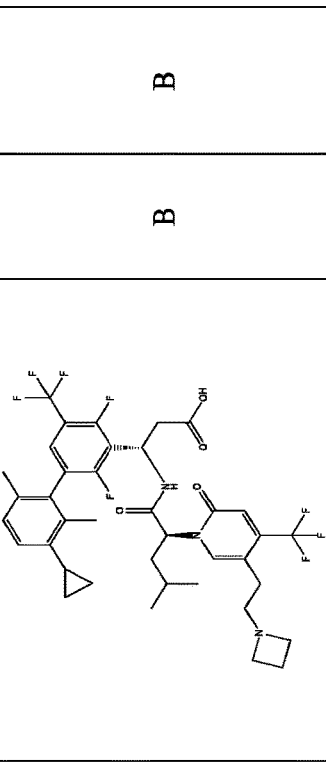
Figure 4:
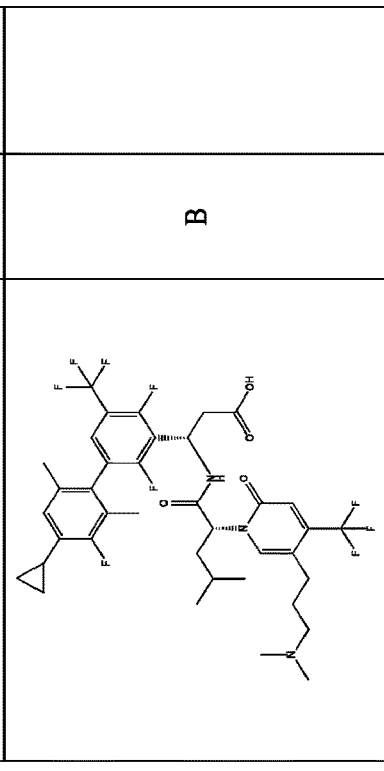
Figure 4:
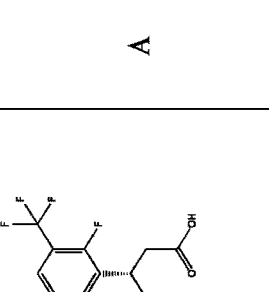
Figure 4:
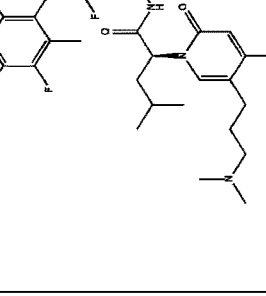
Figure 4:
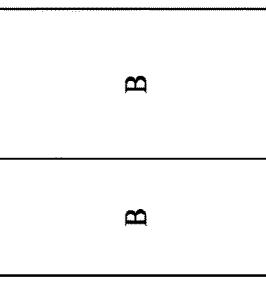
Figure 4:
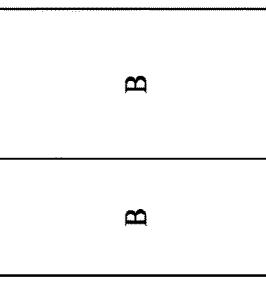
Figure 4:
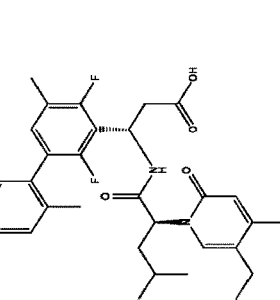
Figure 4:
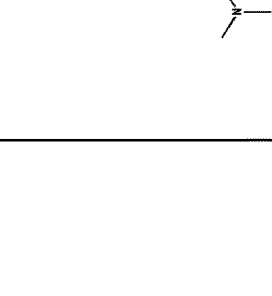
Figure 4:
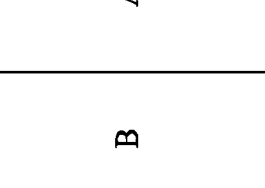
Figure 4:
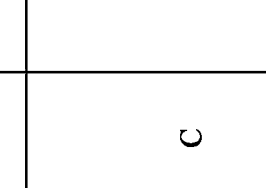
Figure 4:
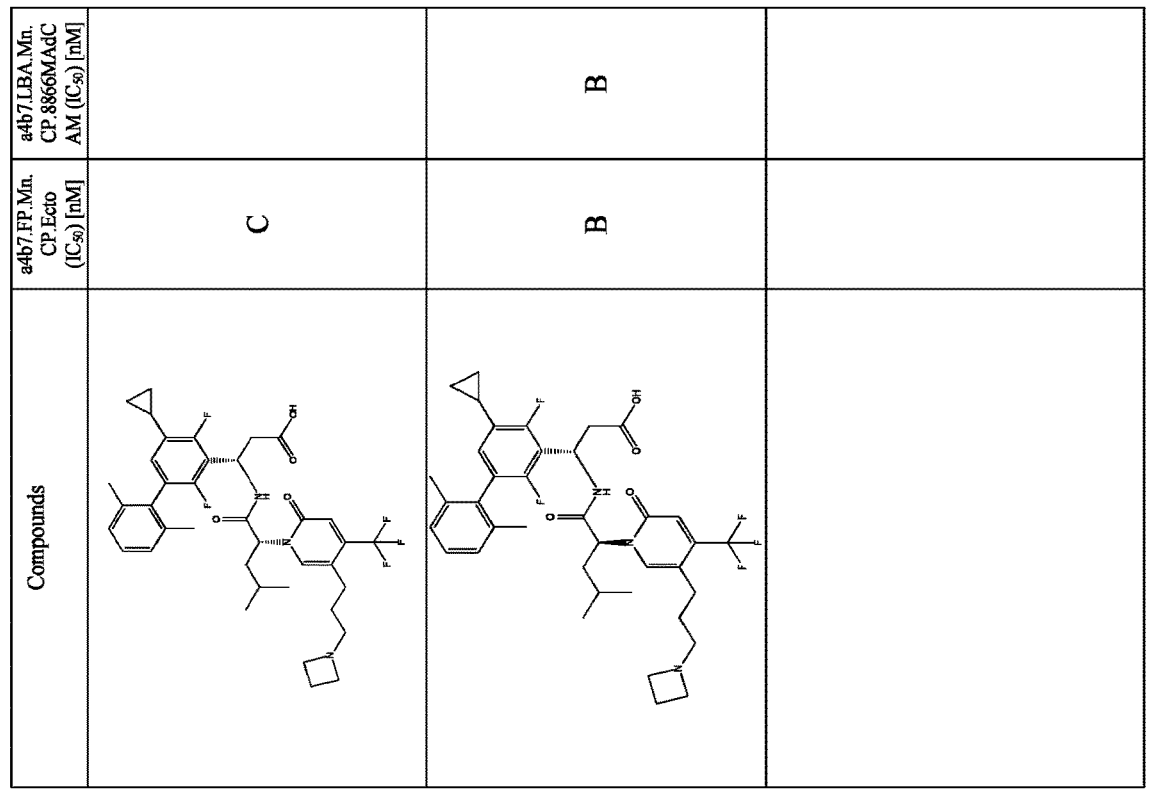
Figure 4:
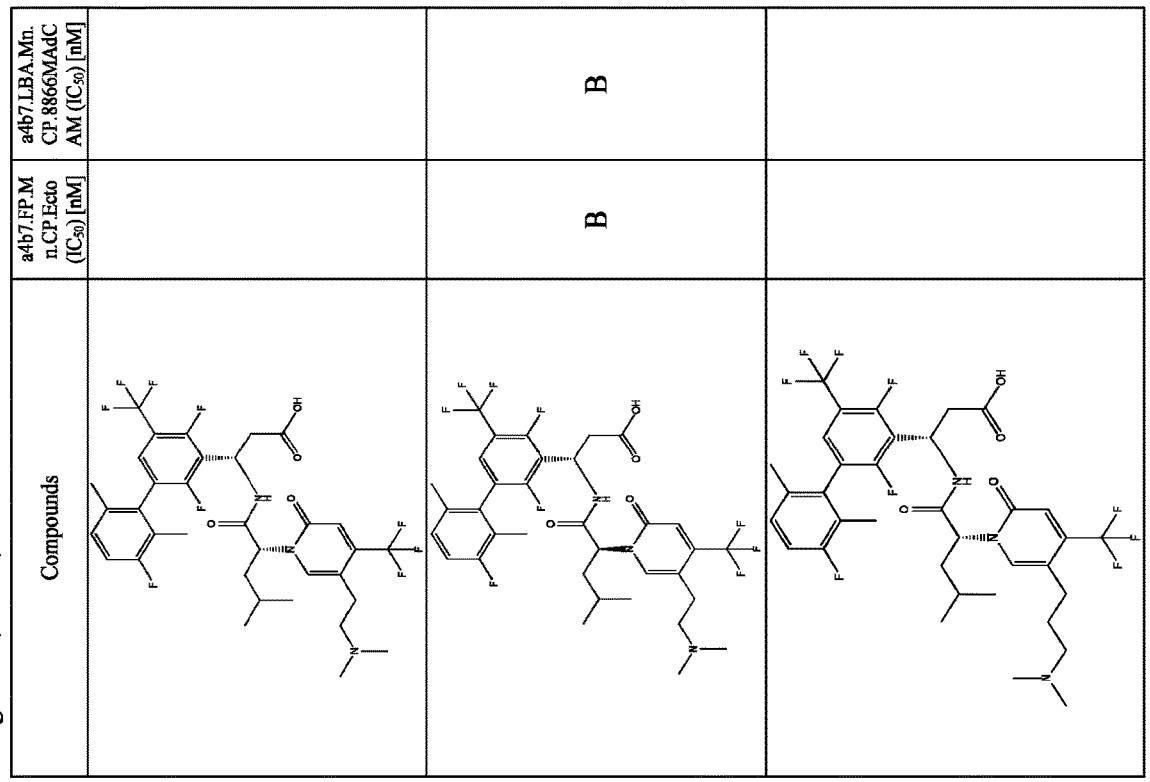
Figure 4:
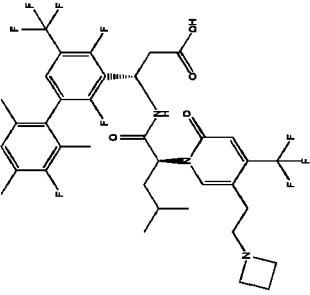
Figure 4:
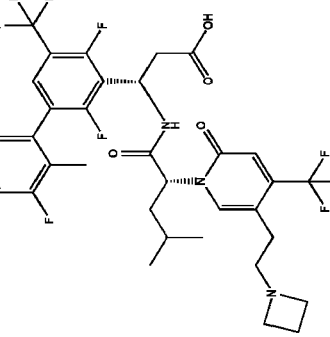
Figure 4:
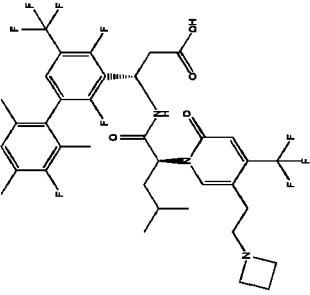

An $\alpha_4\beta_7$ inhibition potency measurement for compounds including certain compounds in FIG. 1, FIG. 3 and FIG. 4 was made using the FP assay of Example 5. In FIG. 1, the $IC_{50}$ value obtained using the FP assay of Example 5 is provided as a numerical range (A: <5.55 nM; B: 5.55-500 nM; C: >500 nM in FIG. 1). In FIG. 3 and FIG. 4, the $IC_{50}$ value obtained using the FP assay of Example 5 is provided as a numerical range (A: <5 nM; B: 5-500 nM; C: >500 nM in FIG. 3 and FIG. 4).

An $\alpha_4\beta_7$ inhibition potency measurement was also performed using the FP assay of Example 5 for compounds in Table 3A, Table 3B and (comparative) Table 4 below, with results provided as a numerical range of the resulting $IC_{50}$ value (A: ≤10 nM; B: >10-500 nM; C: >500 nM in Table 3A, Table 3B and Table 4).

Example 6: Ligand Binding Assays

To measure the potency of compounds against $\alpha_4\beta_7$ in the cell-based ligand binding assay (LBA), RPMI 8866 cells were incubated with the compound samples in a volume of 10 μl at room temperature for 15 minutes in buffer containing 50 mM HEPES pH 7.3, 150 mM sodium chloride, 1% bovine serum albumin, 3 mM manganese chloride, 0.15 mM calcium chloride, 15 mM glucose, 1.5% dimethyl sulfoxide, and 0.025% e780 fixable viability dye. 5 ul of 33 nM MAdCAM-1-Fc fluorescently labeled with Dylight 650 in 50 mM HEPES pH 7.3, 150 mM sodium chloride, and 1% bovine serum albumin was added to the cells. The samples were incubated for 45 minutes at room temperature, fixed with 0.8% formaldehyde for 30 minutes at room temperature, and washed with 50 mM Tris pH 7.5, 150 mM NaCl, 1 mM EDTA, and 1% bovine serum albumin. Fluorescence intensity for each cell was measured via flow cytometry. Dead cells were excluded from further analysis based on staining with the 780 fixable viability dye. Median fluorescence intensity for Dylight 650 was determined for each sample and concentration-response curves were analyzed for IC50 values using 4-parameter non-linear regression analysis.

An $\alpha_4\beta_7$ ligand binding assay measurement was performed with the ligand binding assay of Example 6 for compounds listed in FIG. 1, FIG. 3 and FIG. 4. In FIG. 1, FIG. 3 and FIG. 4, the $IC_{50}$ value obtained using the LB assay of Example 6 is provided by numerical range (A: <5 nM; B: 5-500 nM; C: >500 nM in FIG. 1, FIG. 3 and FIG. 4).

An $\alpha_4\beta_7$ ligand binding assay measurement was also performed using the ligand binding assay of Example 6 for compounds in Table 3A, Table 3B and (comparative) Table 4 below, with the resulting $IC_{50}$ value provided as a numerical range (A: ≤10 nM; B: >10-500 nM; C: >500 nM in Table 3A, Table 3B and Table 4).

Example 7: Cell Adhesion Assay

Example 7 describes a cell adhesion assay. The $\alpha_4\beta_7$ cell adhesion measurement from the assay of Example 7 was obtained from compounds in the Table 3A and Table 3B below, as well as for the comparative compounds in Table 4, with results presented as a numerical range of the resulting $IC_{50}$ value (A: <5 nM; B: 5 to <10 nM; $C_{10-50}$ nM; D: >50 nM; E: >100 nM and F >500 nM for Table 3A, Table 3B and Table 4).

To each well of a 96 well plate, 100 ug of recombinant human MAdCAM in 100 ul PBS is added and incubated overnight at 4° C. After incubation MAdCAM is removed by aspiration and 200 ul of PBS+1% BSA is added to block the plate for 2 hours at 37° C. and 5% CO2. During this incubation dilution curves of compound are made in 100% DMSO in 96 well V bottom plates. 1.75 ul of diluted compounds are then transferred to a new 96 well U bottom plate containing 20 ul of assay media (phosphate free DMEM+25 mM HEPES+1% BSA). To this an additional 155 ul of assay media is added with mixing by pipetting up and down. This mixture is allowed to incubate for 15 minutes at 37° C. and 5% CO2. After incubation 175 ul of assay media containing 2e6/mL RPMI8866 cells is added to compound containing wells without mixing and plate is allowed to incubate for another 15 minutes at 37° C. and 5% CO2. During this incubation MAdCAM coated plates are removed from incubator and washed twice with 200 ul PBS+0.1% BSA. After cells have incubated with compound for 15 minutes they are mixed by pipetting up and down and 100 ul of mixture is transferred to the washed MAdCAM coated plates in triplicate. This plate is then incubated at 37° C. and 5% CO2 for 1 hour. After incubation plates are washed twice with 200 ul and once with 50 ul of phenol free RPMI+1% BSA. A final 50 ul of phenol free RPMI+1% BSA is added to wells after last wash. Next 50 ul of Promega cell titer glow is added to the wells. Plate is incubated on shaker for 2 minutes at 200 RPM followed by another 8 minutes off shaker before having the luminescence read on a Biotek Citation 5 plate reader. Raw data is converted to % inhibition compared to bottom of curve and analyzed using a 4-parameter non linear curve in Prism to determine $IC_{50}$ and $IC_{90}$.

TABLE 3A
Selected Exemplary Compounds.
| Compound | Example | FP Assay (Example 5) | LB Assay (Example 6) | CA Assay (Example 7) |
| --- | --- | --- | --- | --- |
| 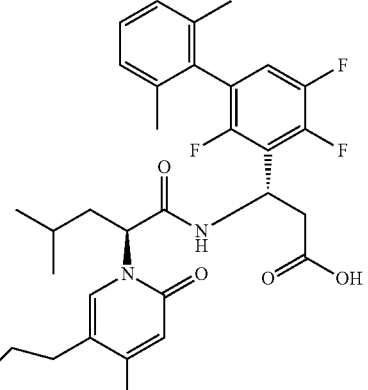 | 3-1 (D-P2) | A | A | A |
| 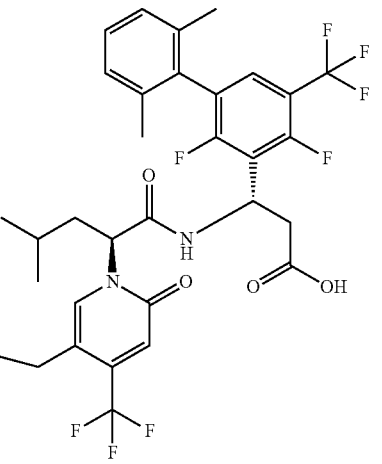 | 3-4 (G-P2) | A | A | A |
| 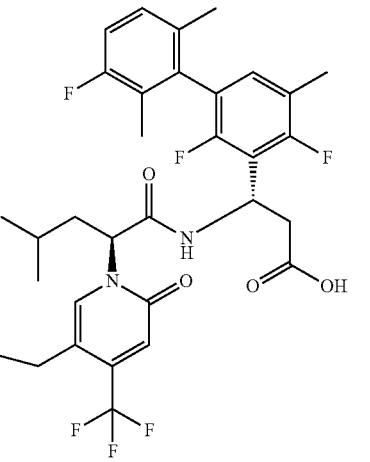 | 3-27 (AF-P2) | A | A | A |

TABLE 3A-continued

Selected Exemplary Compounds.

| Compound | Example | FP Assay (Example 5) | LB Assay (Example 6) | CA Assay (Example 7) |
|---|---|---|---|---|
| | 3-28 (AG-P2) | A | A | A |
| | 3-32 (AK-P2) | A | A | A |
| | 3-18 (W-P2) | A | A | A |

TABLE 3A-continued
Selected Exemplary Compounds.
| Compound | Example | FP Assay (Example 5) | LB Assay (Example 6) | CA Assay (Example 7) |
|---|---|---|---|---|
| 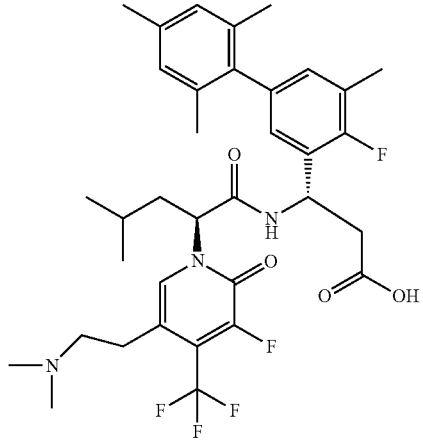 [SMILES: Cc1cc(C)c(-c2cc(C)c(F)c([C@H](CC(=O)O)NC(=O)[C@H](CC(C)C)n3cc(CCN(C)C)c(C(F)(F)F)c(F)c3=O)c2)c(C)c1] | 3-24 (AC-P2) | A | A | A |
| 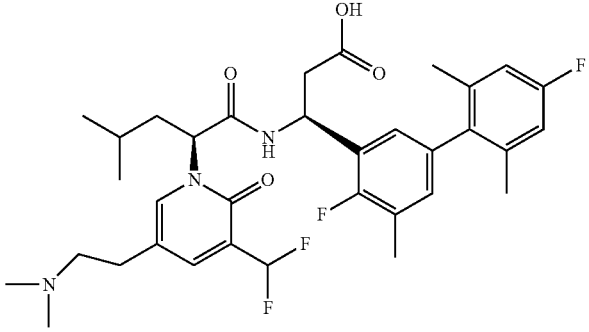 [SMILES: Cc1cc(-c2c(C)cc(F)cc2C)cc([C@H](CC(=O)O)NC(=O)[C@H](CC(C)C)n2cc(CCN(C)C)cc(C(F)F)c2=O)c1F] | 3-6 (I-P2) | A | A | A |
| 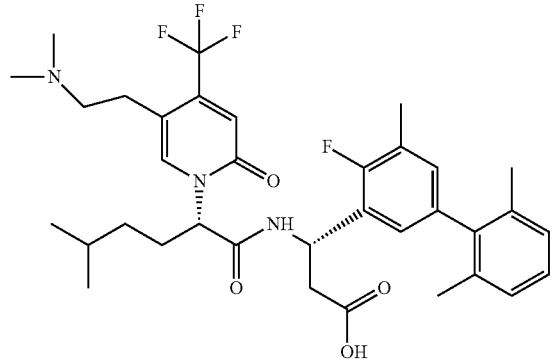 [SMILES: Cc1cc(-c2c(C)cccc2C)cc([C@H](CC(=O)O)NC(=O)[C@H](CCC(C)C)n2cc(CCN(C)C)c(C(F)(F)F)cc2=O)c1F] | 3-7 (J-P2) | A | A | A |

TABLE 3A-continued

Selected Exemplary Compounds.

| Compound | Example | FP Assay (Example 5) | LB Assay (Example 6) | CA Assay (Example 7) |
|---|---|---|---|---|
| [structure] | 3-43 (AV-P2) | A | A | A |
| [structure] | 3-42 (AU-P2) | A | A | A |

TABLE 3B

Selected Exemplary Compounds.

| Compound | Example | FP Assay (Example 5) | LB Assay (Example 6) | CA Assay (Example 7) |
|---|---|---|---|---|
| [structure] | 3-57 (HM-P2) | A | A | A |

TABLE 3B-continued
Selected Exemplary Compounds.
| Compound | Example | FP Assay (Example 5) | LB Assay (Example 6) | CA Assay (Example 7) |
|---|---|---|---|---|
| 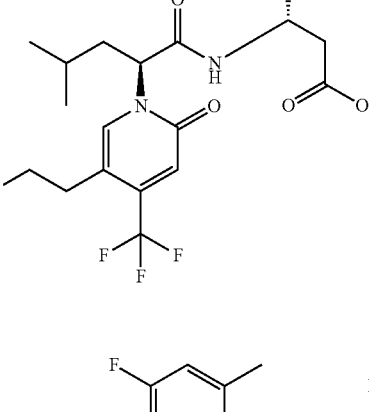 | 3-52 (HH-P2) | A | A | B |
| 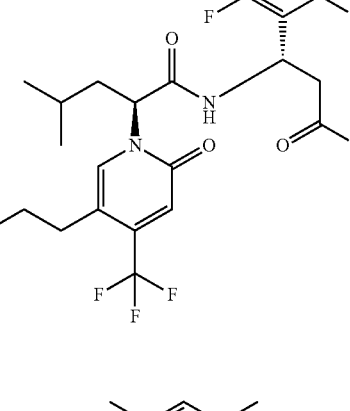 | 3-67 (HW-P2) | A | A | A |
| 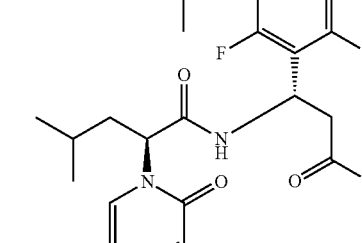 | 3-93 (IW-P2) | A | B | B |

TABLE 3B-continued
Selected Exemplary Compounds.
| Compound | Example | FP Assay (Example 5) | LB Assay (Example 6) | CA Assay (Example 7) |
|---|---|---|---|---|
| 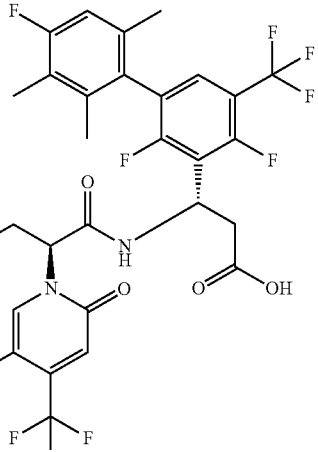 | 3-142 (KT-P2) | A | B | A. |
| 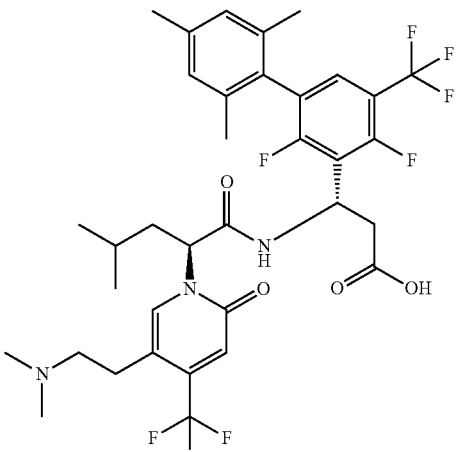 | 3-76 (IF-P2) | A | B | A |
| 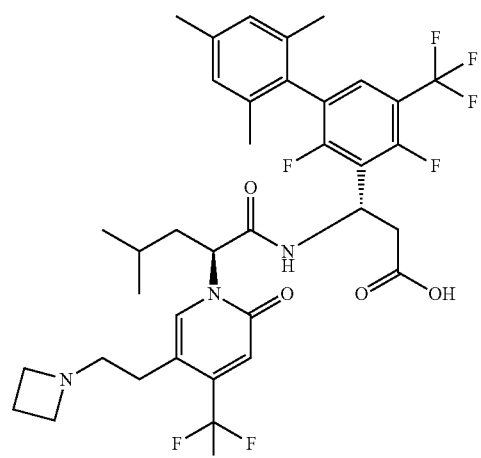 | 3-77 (IG-P2) | A | B | A |

TABLE 3B-continued

Selected Exemplary Compounds.

| Compound | Example | FP Assay (Example 5) | LB Assay (Example 6) | CA Assay (Example 7) |
|---|---|---|---|---|
| | 3-70 (HZ-P2) | A | B | B |
| | 3-65 (HU-P2) | A | B | B |
| | 3-64 (HT-P2) | A | B | A |

TABLE 4
| No. | Comparator Compound | FP Assay (Example 5) | LB Assay (Example 6) | CA Assay (Example 7) |
|---|---|---|---|---|
| C-1 | 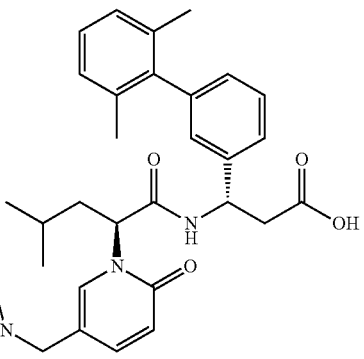 | A | A | D |
| C-2 | 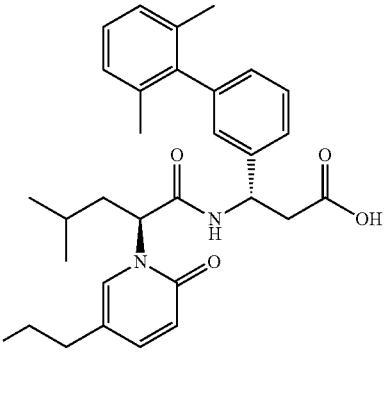 | A | A | B |
| C-3 | 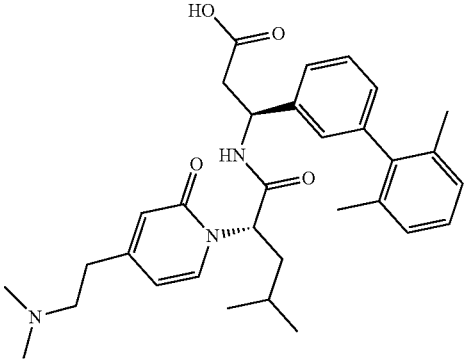 [SMILES: Cc1cccc(C)c1-c1cccc([C@H](CC(=O)O)NC(=O)[C@H](CC(C)C)n2ccc(CCN(C)C)cc2=O)c1] | A | A | C |
| C-4 | 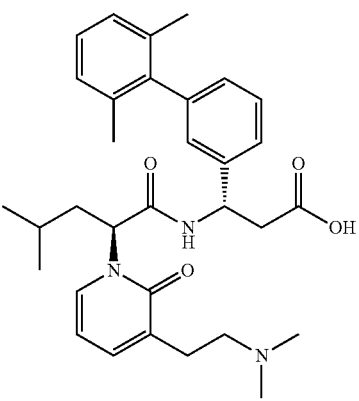 [SMILES: Cc1cccc(C)c1-c1cccc([C@H](CC(=O)O)NC(=O)[C@H](CC(C)C)n2cccc(CCN(C)C)c2=O)c1] | A | B | E |

TABLE 4-continued

Comparative Compounds

| No. | Comparator Compound | FP Assay (Example 5) | LB Assay (Example 6) | CA Assay (Example 7) |
|---|---|---|---|---|
| C-5 | | A | A | C |
| C-6 | | A | A | C |
| C-7 | | A | A | C |
| C-8 | | A | | D |

TABLE 4-continued

| | Comparative Compounds | | | |
|---|---|---|---|---|
| No. | Comparator Compound | FP Assay (Example 5) | LB Assay (Example 6) | CA Assay (Example 7) |
| C-9 | | A | B | D |
| C-10 | | | B | E |
| C-11 | | A | B | F |

TABLE 4-continued

| | Comparative Compounds | | | |
|---|---|---|---|---|
| No. | Comparator Compound | FP Assay (Example 5) | LB Assay (Example 6) | CA Assay (Example 7) |
| C-12 | | A | B | F |
| C-13 | | A | B | F |
| C-14 | | A | B | F |

TABLE 4-continued
Comparative Compounds
| No. | Comparator Compound | FP Assay (Example 5) | LB Assay (Example 6) | CA Assay (Example 7) |
|---|---|---|---|---|
| C-15 | 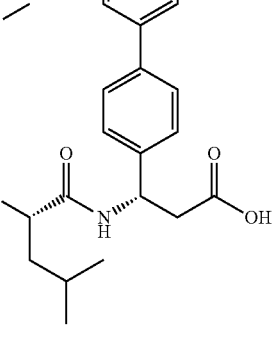 | B | B | F |
| C-16 | 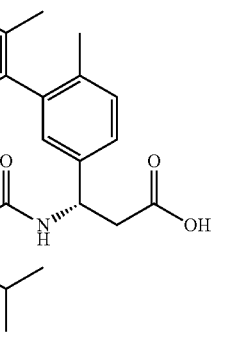 | B | | F |
| C-17 | 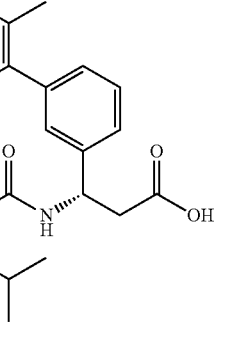 | B | | F |
| C-18 | 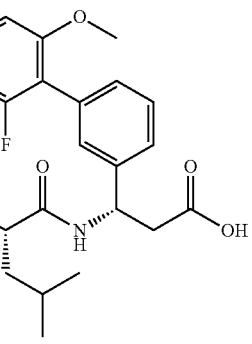 | B | | F |

TABLE 4-continued
| | Comparative Compounds | | | |
|---|---|---|---|---|
| No. | Comparator Compound | FP Assay (Example 5) | LB Assay (Example 6) | CA Assay (Example 7) |
| C-19 | 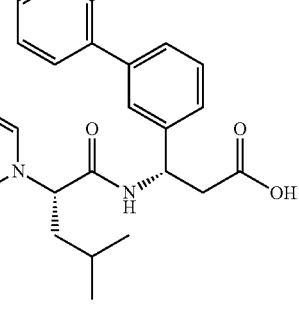 | B | | F |
| C-20 | 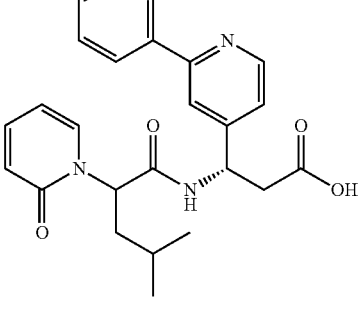 | B | | F |
| C-21 | 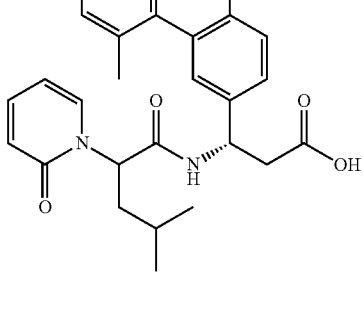 | B | | F |
| C-22 | 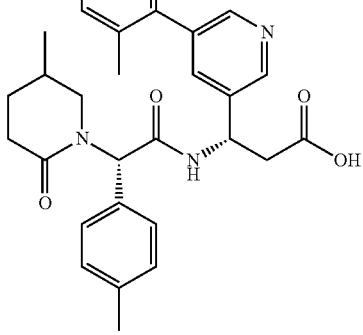 | A | B | F |

TABLE 4-continued

Comparative Compounds

| No. | Comparator Compound | FP Assay (Example 5) | LB Assay (Example 6) | CA Assay (Example 7) |
|---|---|---|---|---|
| C-23 | | B | | F |
| C-24 | | A | | F |
| C-25 | | B | B | F |
| C-26 | | B | | |

TABLE 4-continued

Comparative Compounds

| No. | Comparator Compound | FP Assay (Example 5) | LB Assay (Example 6) | CA Assay (Example 7) |
|---|---|---|---|---|
| C-27 | | | C | |
| C-28 | | B | B | |
| C-29 | | A | | E |
| C-30 | | | C | |

INCORPORATION BY REFERENCE

All of the U.S. patents and U.S. and PCT patent application publications cited herein are hereby incorporated by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

We claim:

1. A pharmaceutical composition, comprising a compound or a pharmaceutically acceptable salt thereof selected from the group consisting of:

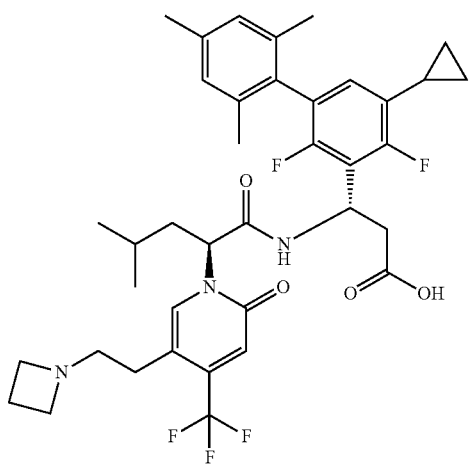

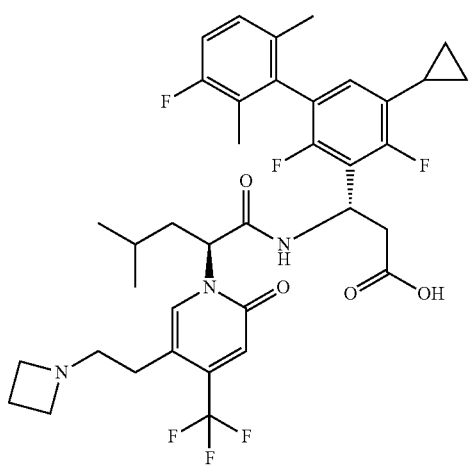

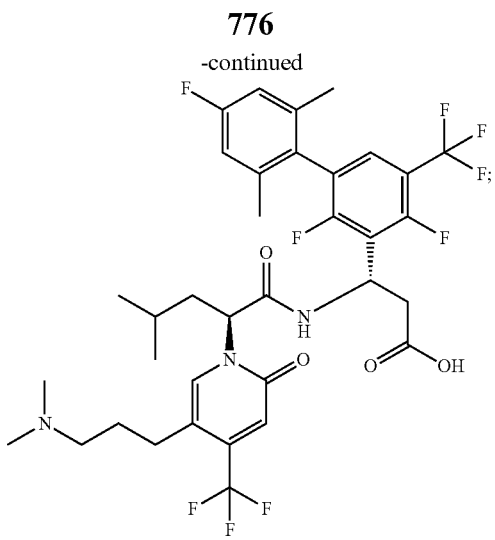

-continued

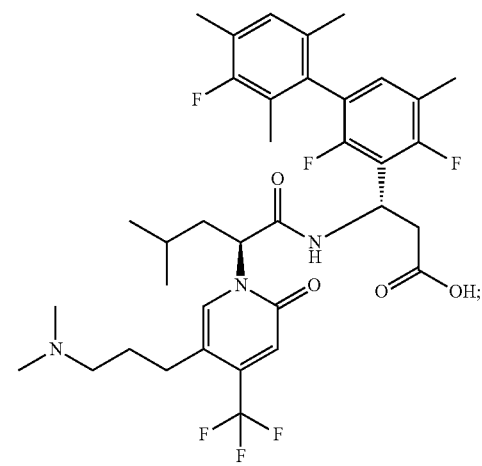

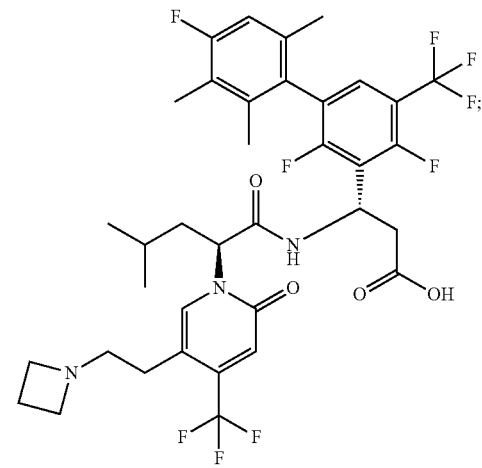

777
-continued
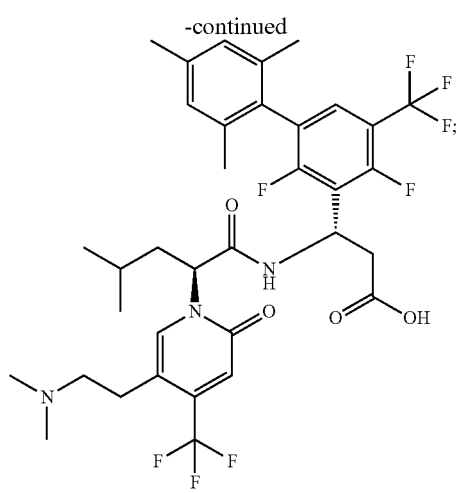
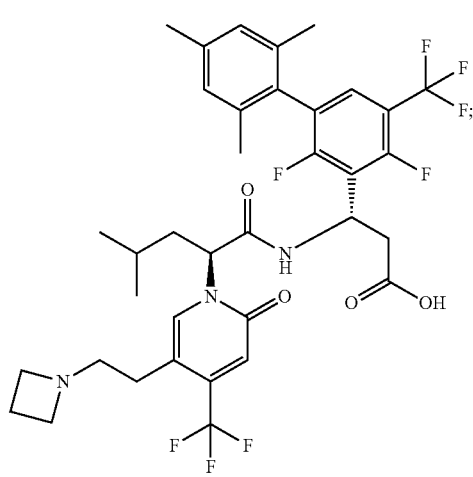
778
-continued
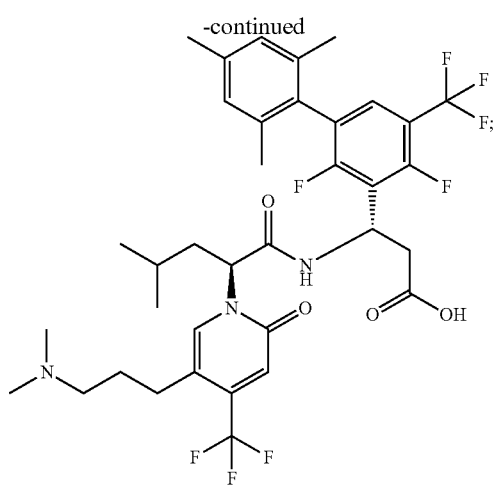
and
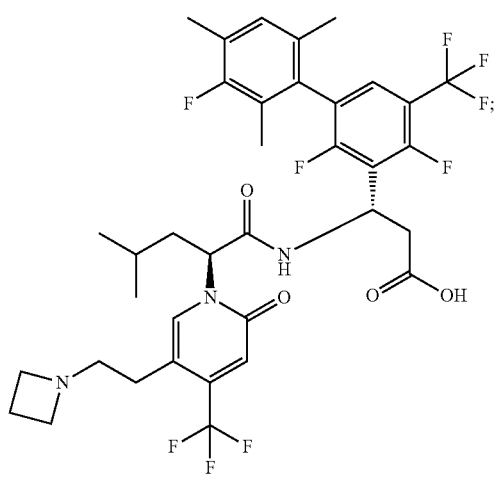 [SMILES: Cc1cc(C)c(-c2cc(C(F)(F)F)c(F)c([C@H](CC(=O)O)NC(=O)[C@H](CC(C)C)n3cc(CCN4CCC4)c(C(F)(F)F)cc3=O)c2F)c(C)c1F]
and
a pharmaceutically acceptable excipient.

2. The pharmaceutical composition of claim 1, wherein the compound is

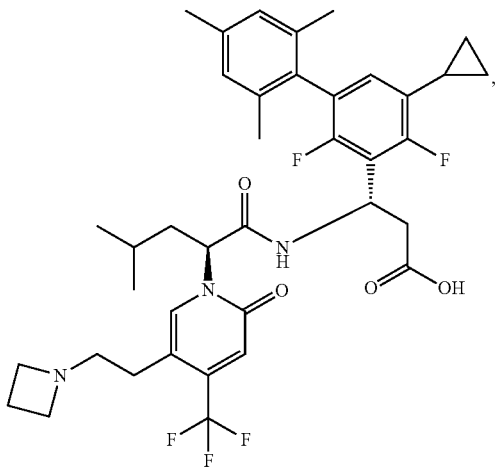 [SMILES: Cc1cc(C)c(-c2cc(C3CC3)c(F)c([C@H](CC(=O)O)NC(=O)[C@H](CC(C)C)n3cc(CCN4CCC4)c(C(F)(F)F)cc3=O)c2F)c(C)c1]

or a pharmaceutically acceptable salt thereof.

3. The pharmaceutical composition of claim 1, wherein the compound is

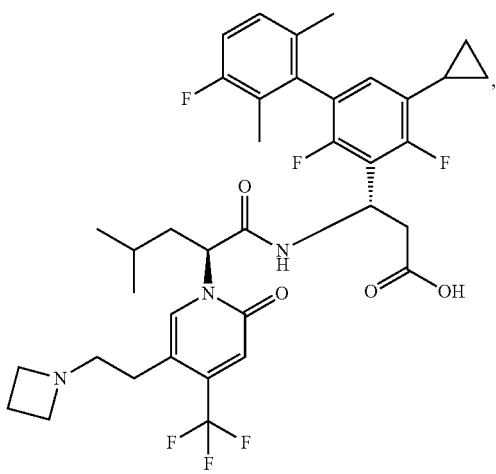 [SMILES: Cc1ccc(F)c(C)c1-c1cc(C2CC2)c(F)c([C@H](CC(=O)O)NC(=O)[C@H](CC(C)C)n2cc(CCN3CCC3)c(C(F)(F)F)cc2=O)c1F]

or a pharmaceutically acceptable salt thereof.

4. The pharmaceutical composition of claim 1, wherein the compound is

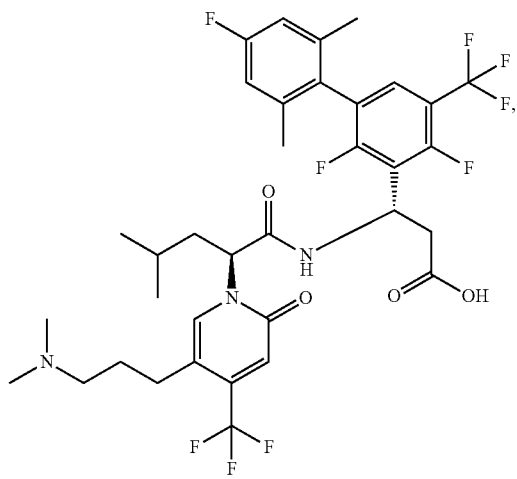 [SMILES: Cc1cc(F)cc(C)c1-c1cc(C(F)(F)F)c(F)c([C@H](CC(=O)O)NC(=O)[C@H](CC(C)C)n2cc(CCCN(C)C)c(C(F)(F)F)cc2=O)c1F]

or a pharmaceutically acceptable salt thereof.

5. The pharmaceutical composition of claim 1, wherein the compound is

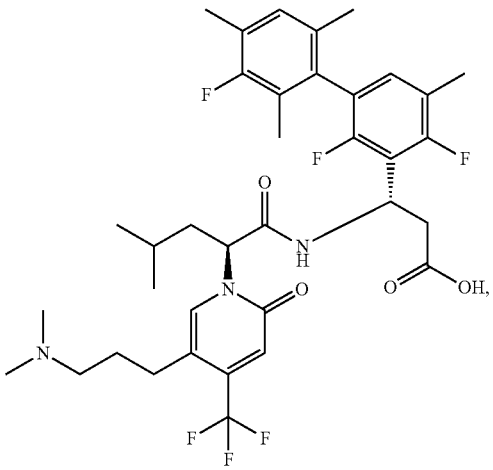

or a pharmaceutically acceptable salt thereof.

6. The pharmaceutical composition of claim 1, wherein the compound is

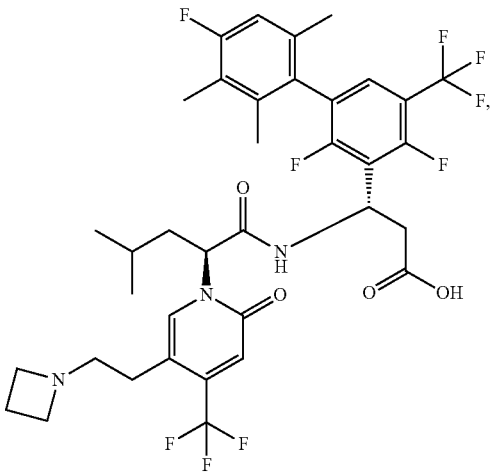 [SMILES: Cc1cc(F)c(C)c(C)c1-c1cc(C(F)(F)F)c(F)c([C@H](CC(=O)O)NC(=O)[C@H](CC(C)C)n2cc(CCN3CCC3)c(C(F)(F)F)cc2=O)c1F]

or a pharmaceutically acceptable salt thereof.

7. The pharmaceutical composition of claim 1, wherein the compound is

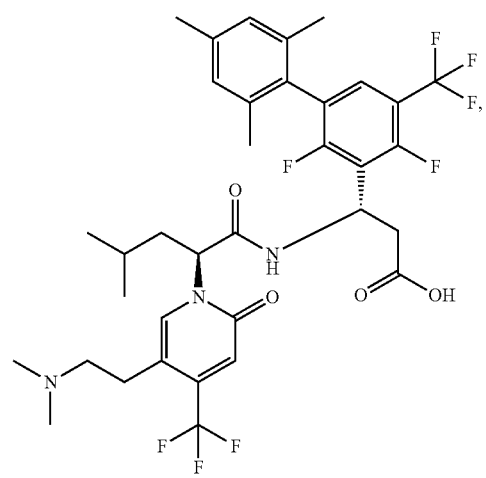 [SMILES: Cc1cc(C)c(-c2cc(C(F)(F)F)c(F)c([C@H](CC(=O)O)NC(=O)[C@H](CC(C)C)n3cc(CCN(C)C)c(C(F)(F)F)cc3=O)c2F)c(C)c1]

or a pharmaceutically acceptable salt thereof.

8. The pharmaceutical composition of claim 1, wherein the compound is

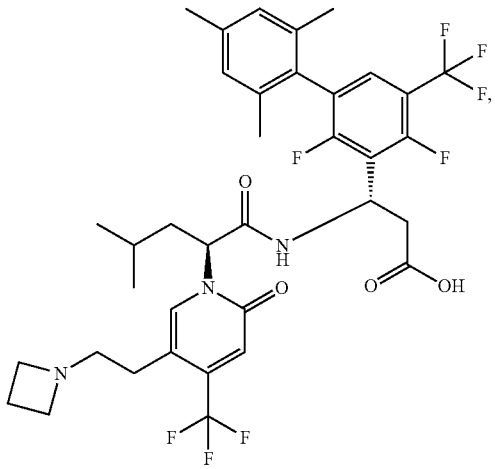 [SMILES: Cc1cc(C)c(-c2cc(C(F)(F)F)c(F)c([C@H](CC(=O)O)NC(=O)[C@H](CC(C)C)n3cc(CCN4CCC4)c(C(F)(F)F)cc3=O)c2F)c(C)c1]

or a pharmaceutically acceptable salt thereof.

9. The pharmaceutical composition of claim 1, wherein the compound is

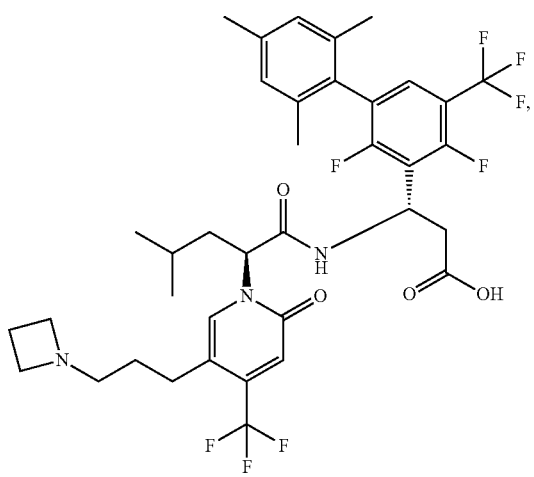 [SMILES: Cc1cc(C)c(-c2cc(C(F)(F)F)c(F)c([C@H](CC(=O)O)NC(=O)[C@H](CC(C)C)n3cc(CCCN4CCC4)c(C(F)(F)F)cc3=O)c2F)c(C)c1]

or a pharmaceutically acceptable salt thereof.

10. The pharmaceutical composition of claim 1, wherein the compound is

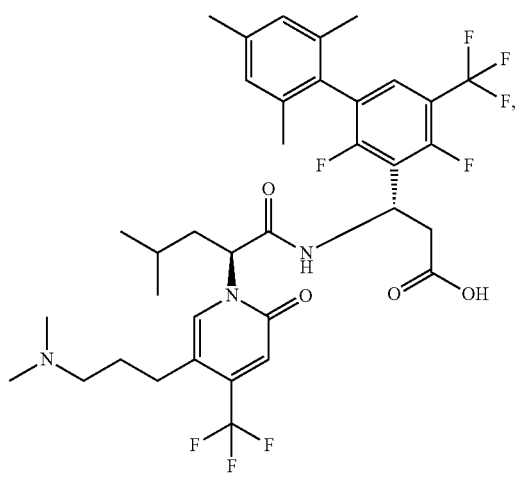 [SMILES: Cc1cc(C)c(-c2cc(C(F)(F)F)c(F)c([C@H](CC(=O)O)NC(=O)[C@H](CC(C)C)n3cc(CCCN(C)C)c(C(F)(F)F)cc3=O)c2F)c(C)c1]

or a pharmaceutically acceptable salt thereof.

11. The pharmaceutical composition of claim 1, wherein the compound is

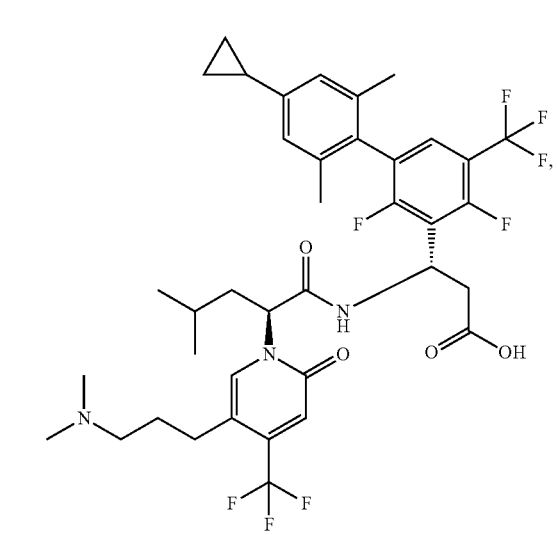 [SMILES: Cc1cc(C2CC2)cc(C)c1-c1cc(C(F)(F)F)c(F)c([C@H](CC(=O)O)NC(=O)[C@H](CC(C)C)n2cc(CCCN(C)C)c(C(F)(F)F)cc2=O)c1F]

or a pharmaceutically acceptable salt thereof.

12. The pharmaceutical composition of claim 1, wherein the compound is

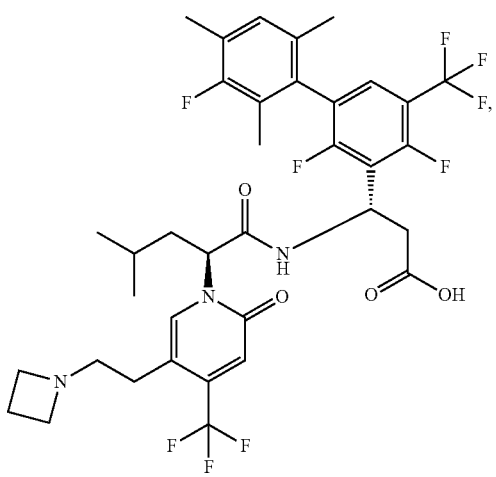 [SMILES: Cc1cc(C)c(-c2cc(C(F)(F)F)c(F)c([C@H](CC(=O)O)NC(=O)[C@H](CC(C)C)n3cc(CCN4CCC4)c(C(F)(F)F)cc3=O)c2F)c(C)c1F]

or a pharmaceutically acceptable salt thereof.

13. A compound selected from the group consisting of:
(S)-3-((S)-2-(5-(2-(azetidin-1-yl)ethyl)-2-oxo-4-(trifluoromethyl)pyridin-1(2H)-yl)-4-methylpentanamido)-3-(5-cyclopropyl-2,4-difluoro-2',4',6'-trimethyl-[1,1'-biphenyl]-3-yl)propanoic acid;
(3S)-3-((S)-2-(5-(2-(azetidin-1-yl)ethyl)-2-oxo-4-(trifluoromethyl)pyridin-1(2H)-yl)-4-methylpentanamido)-3-(5-cyclopropyl-2,3',4-trifluoro-2',6'-dimethyl-[1,1'-biphenyl]-3-yl)propanoic acid;
(S)-3-((S)-2-(5-(3-(dimethylamino)propyl)-2-oxo-4-(trifluoromethyl)pyridin-1(2H)-yl)-4-methylpentanamido)-3-(2,4,4'-trifluoro-2',6'-dimethyl-5-(trifluoromethyl)-[1,1'-biphenyl]-3-yl)propanoic acid;
(3S)-3-((S)-2-(5-(3-(dimethylamino)propyl)-2-oxo-4-(trifluoromethyl)pyridin-1(2H)-yl)-4-methylpentanamido)-3-(2,3',4-trifluoro-2',4',5,6'-tetramethyl-[1,1'-biphenyl]-3-yl)propanoic acid;
(3S)-3-((S)-2-(5-(2-(azetidin-1-yl)ethyl)-2-oxo-4-(trifluoromethyl)pyridin-1(2H)-yl)-4-methylpentanamido)-3-(2,4,4'-trifluoro-2',3',6'-trimethyl-5-(trifluoromethyl)-[1,1'-biphenyl]-3-yl)propanoic acid;
(S)-3-(2,4-difluoro-2',4',6'-trimethyl-5-(trifluoromethyl)-[1,1'-biphenyl]-3-yl)-3-((S)-2-(5-(2-(dimethylamino)ethyl)-2-oxo-4-(trifluoromethyl)pyridin-1(2H)-yl)-4-methylpentanamido)propanoic acid;
(S)-3-((S)-2-(5-(2-(azetidin-1-yl)ethyl)-2-oxo-4-(trifluoromethyl)pyridin-1(2H)-yl)-4-methylpentanamido)-3-(2,4-difluoro-2',4',6'-trimethyl-5-(trifluoromethyl)-[1,1'-biphenyl]-3-yl)propanoic acid;
(S)-3-((S)-2-(5-(3-(azetidin-1-yl)propyl)-2-oxo-4-(trifluoromethyl)pyridin-1(2H)-yl)-4-methylpentanamido)-3-(2,4-difluoro-2',4',6'-trimethyl-5-(trifluoromethyl)-[1,1'-biphenyl]-3-yl)propanoic acid;
(S)-3-(2,4-difluoro-2',4',6'-trimethyl-5-(trifluoromethyl)-[1,1'-biphenyl]-3-yl)-3-((S)-2-(5-(3-(dimethylamino)propyl)-2-oxo-4-(trifluoromethyl)pyridin-1(2H)-yl)-4-methylpentanamido)propanoic acid;
(S)-3-(4'-cyclopropyl-2,4-difluoro-2',6'-dimethyl-5-(trifluoromethyl)-[1,1'-biphenyl]-3-yl)-3-((S)-2-(5-(3-(dimethylamino)propyl)-2-oxo-4-(trifluoromethyl)pyridin-1(2H)-yl)-4-methylpentanamido)propanoic acid; and
(3S)-3-((S)-2-(5-(2-(azetidin-1-yl)ethyl)-2-oxo-4-(trifluoromethyl)pyridin-1(2H)-yl)-4-methylpentanamido)-3-(2,3',4-trifluoro-2',4',6'-trimethyl-5-(trifluoromethyl)-[1,1'-biphenyl]-3-yl)propanoic acid,
or a pharmaceutically acceptable salt thereof.

14. The compound of claim 13, wherein the compound is (S)-3-((S)-2-(5-(2-(azetidin-1-yl)ethyl)-2-oxo-4-(trifluoromethyl)pyridin-1(2H)-yl)-4-methylpentanamido)-3-(5-cyclopropyl-2,4-difluoro-2',4',6'-trimethyl-[1,1'-biphenyl]-3-yl)propanoic acid,
or a pharmaceutically acceptable salt thereof.

15. The compound of claim 13, wherein the compound is (3S)-3-((S)-2-(5-(2-(azetidin-1-yl)ethyl)-2-oxo-4-(trifluoromethyl)pyridin-1(2H)-yl)-4-methylpentanamido)-3-(5-cyclopropyl-2,3',4-trifluoro-2',6'-dimethyl-[1,1'-biphenyl]-3-yl)propanoic acid,
or a pharmaceutically acceptable salt thereof.

16. The compound of claim 13, wherein the compound is (S)-3-((S)-2-(5-(3-(dimethylamino)propyl)-2-oxo-4-(trifluoromethyl)pyridin-1(2H)-yl)-4-methylpentanamido)-3-(2,4,4'-trifluoro-2',6'-dimethyl-5-(trifluoromethyl)-[1,1'-biphenyl]-3-yl)propanoic acid,
or a pharmaceutically acceptable salt thereof.

17. The compound of claim 13, wherein the compound is (3S)-3-((S)-2-(5-(3-(dimethylamino)propyl)-2-oxo-4-(trifluoromethyl)pyridin-1(2H)-yl)-4-methylpentanamido)-3-(2,3',4-trifluoro-2',4',5,6'-tetramethyl-[1,1'-biphenyl]-3-yl)propanoic acid,
or a pharmaceutically acceptable salt thereof.

18. The compound of claim 13, wherein the compound is (3S)-3-((S)-2-(5-(2-(azetidin-1-yl)ethyl)-2-oxo-4-(trifluoromethyl)pyridin-1(2H)-yl)-4-methylpentanamido)-3-(2,4,4'-trifluoro-2',3',6'-trimethyl-5-(trifluoromethyl)-[1,1'-biphenyl]-3-yl)propanoic acid,
or a pharmaceutically acceptable salt thereof.

19. The compound of claim 13, wherein the compound is (S)-3-(2,4-difluoro-2',4',6'-trimethyl-5-(trifluoromethyl)-[1,1'-biphenyl]-3-yl)-3-((S)-2-(5-(2-(dimethylamino)ethyl)-2-oxo-4-(trifluoromethyl)pyridin-1(2H)-yl)-4-methylpentanamido)propanoic acid,
or a pharmaceutically acceptable salt thereof.

20. The compound of claim 13, wherein the compound is (S)-3-((S)-2-(5-(2-(azetidin-1-yl)ethyl)-2-oxo-4-(trifluoromethyl)pyridin-1(2H)-yl)-4-methylpentanamido)-3-(2,4-difluoro-2',4',6'-trimethyl-5-(trifluoromethyl)-[1,1'-biphenyl]-3-yl)propanoic acid,
or a pharmaceutically acceptable salt thereof.

21. The compound of claim 13, wherein the compound is (S)-3-((S)-2-(5-(3-(azetidin-1-yl)propyl)-2-oxo-4-(trifluoromethyl)pyridin-1(2H)-yl)-4-methylpentanamido)-3-(2,4-difluoro-2',4',6'-trimethyl-5-(trifluoromethyl)-[1,1'-biphenyl]-3-yl)propanoic acid,
or a pharmaceutically acceptable salt thereof.

22. The compound of claim 13, wherein the compound is (S)-3-(2,4-difluoro-2',4',6'-trimethyl-5-(trifluoromethyl)-[1,1'-biphenyl]-3-yl)-3-((S)-2-(5-(3-(dimethylamino)propyl)-2-oxo-4-(trifluoromethyl)pyridin-1(2H)-yl)-4-methylpentanamido)propanoic acid,
or a pharmaceutically acceptable salt thereof.

23. The compound of claim 13, wherein the compound is (S)-3-(4'-cyclopropyl-2,4-difluoro-2',6'-dimethyl-5-(trifluoromethyl)-[1,1'-biphenyl]-3-yl)-3-((S)-2-(5-(3-(dimethylamino)propyl)-2-oxo-4-(trifluoromethyl)pyridin-1(2H)-yl)-4-methylpentanamido)propanoic acid,
or a pharmaceutically acceptable salt thereof.

24. The compound of claim 13, wherein the compound is (3S)-3-((S)-2-(5-(2-(azetidin-1-yl)ethyl)-2-oxo-4-(trifluoromethyl)pyridin-1(2H)-yl)-4-methylpentanamido)-3-(2,3',4-trifluoro-2',4',6'-trimethyl-5-(trifluoromethyl)-[1,1'-biphenyl]-3-yl)propanoic acid,
or a pharmaceutically acceptable salt thereof.

\* \* \* \* \*